US008791132B2

(12) United States Patent  (10) Patent No.: US 8,791,132 B2
Protter et al.  (45) Date of Patent: Jul. 29, 2014

(54) COMPOUNDS AND METHODS FOR TREATMENT OF HYPERTENSION

(75) Inventors: Andrew Asher Protter, Palo Alto, CA (US); Sarvajit Chakravarty, Mountain View, CA (US); Rajendra Parasmal Jain, Pune (IN); Michael John Green, Half Moon Bay, CA (US)

(73) Assignee: Medivation Technologies, Inc., San Francisco, CA (US)

( * ) Notice: Subject to any disclaimer, the term of this patent is extended or adjusted under 35 U.S.C. 154(b) by 104 days.

(21) Appl. No.: 13/400,031

(22) Filed: Feb. 17, 2012

(65) Prior Publication Data

US 2013/0053366 A1 Feb. 28, 2013

Related U.S. Application Data

(60) Provisional application No. 61/444,642, filed on Feb. 18, 2011, provisional application No. 61/444,655, filed on Feb. 18, 2011, provisional application No. 61/444,659, filed on Feb. 18, 2011, provisional application No. 61/469,664, filed on Mar. 30, 2011, provisional application No. 61/529,745, filed on Aug. 31, 2011, provisional application No. 61/529,816, filed on Aug. 31, 2011, provisional application No. 61/562,927, filed on Nov. 22, 2011, provisional application No. 61/562,938, filed on Nov. 22, 2011.

(51) Int. Cl.
*A61K 31/04* (2006.01)
(52) U.S. Cl.
USPC .......................................................... 514/292
(58) Field of Classification Search
USPC .......................................................... 514/292
See application file for complete search history.

(56) References Cited

U.S. PATENT DOCUMENTS

| 6,187,785 | B1 | 2/2001 | Zefirov et al. |
| 6,653,304 | B2 * | 11/2003 | Leftheris et al. ........... 514/232.8 |
| 7,071,206 | B2 | 7/2006 | Zefirov et al. |
| 8,338,408 | B2 | 12/2012 | Hung et al. |
| 8,338,447 | B2 | 12/2012 | Hung et al. |
| 8,546,381 | B2 | 10/2013 | Hung et al. |
| 8,569,287 | B2 | 10/2013 | Hung et al. |
| 2001/0020028 | A1 | 9/2001 | Zefirov et al. |
| 2002/0115682 | A1 | 8/2002 | Zefirov et al. |
| 2003/0225058 | A1 | 12/2003 | Frank et al. |
| 2004/0044022 | A1 | 3/2004 | Zefirov, Jr. et al. |
| 2006/0140866 | A1 | 6/2006 | Zefirov et al. |
| 2007/0015746 | A1 | 1/2007 | Martin et al. |
| 2007/0117834 | A1 | 5/2007 | Hung |
| 2007/0117835 | A1 | 5/2007 | Hung |
| 2007/0179174 | A1 | 8/2007 | Bachurin et al. |
| 2007/0225316 | A1 | 9/2007 | Bachurin et al. |
| 2008/0234310 | A1 | 9/2008 | Bachurin et al. |
| 2010/0022580 | A1 | 1/2010 | Hung et al. |
| 2010/0099700 | A1 | 4/2010 | Hung |
| 2010/0125085 | A1 * | 5/2010 | Gant et al. ................ 514/292 |
| 2010/0130528 | A1 * | 5/2010 | Gant ......................... 514/292 |
| 2010/0152108 | A1 | 6/2010 | Hung et al. |
| 2010/0152163 | A1 | 6/2010 | Hung et al. |
| 2010/0152225 | A1 | 6/2010 | Hung |
| 2010/0178277 | A1 | 7/2010 | Hung et al. |
| 2010/0216814 | A1 | 8/2010 | Hung et al. |
| 2010/0286188 | A1 | 11/2010 | Bachurin et al. |
| 2011/0112132 | A1 | 5/2011 | Bachurin et al. |
| 2011/0237582 | A1 | 9/2011 | Jain et al. |
| 2011/0245272 | A1 | 10/2011 | Jain et al. |
| 2011/0269777 | A1 | 11/2011 | Bachurin et al. |
| 2012/0101121 | A1 | 4/2012 | Bachurin et al. |
| 2012/0136008 | A1 | 5/2012 | Jain et al. |
| 2012/0172377 | A1 | 7/2012 | Jain et al. |
| 2013/0053367 | A1 | 2/2013 | Protter et al. |
| 2013/0079352 | A1 | 3/2013 | Hung et al. |
| 2013/0123277 | A1 | 5/2013 | Jain et al. |
| 2013/0131054 | A1 | 5/2013 | Hung et al. |
| 2013/0131077 | A1 | 5/2013 | Hung et al. |
| 2013/0137705 | A1 | 5/2013 | Jain et al. |
| 2013/0172320 | A1 | 7/2013 | Chakravarty et al. |
| 2013/0172366 | A1 | 7/2013 | Jain et al. |
| 2013/0184269 | A1 | 7/2013 | Hung et al. |
| 2013/0184303 | A1 | 7/2013 | Jain et al. |
| 2013/0184304 | A1 | 7/2013 | Jain et al. |
| 2013/0184306 | A1 | 7/2013 | Hung et al. |
| 2013/0190293 | A1 | 7/2013 | Chakravarty et al. |

(Continued)

FOREIGN PATENT DOCUMENTS

WO WO-2005/005951 A2 6/2005
WO WO-2005/005951 A3 6/2005

(Continued)

OTHER PUBLICATIONS

Keay, Exp Brain Res vol. 80, pp. 148-156, 1990.*
Berge, S.M. et al. (Jan. 1977). "Pharmaceutical Salts," *J. Pharm. Sci.* 66(1):1-19.
Burke, S.L. et al. (2011). "Effects of Chronic Sympatho-Inhibition on Renal Excretory Function in Renovascular Hypertension," *J Hypertension* 29(5):945-952.
Cheng, Y. et al. (Sep. 15, 1973). "Relationship Between the Inhibition Constant ($K_I$) and the Concentration of Inhibitor Which Causes 50 Per Cent Inhibition ($I_{50}$) of an Enzymatic Reaction," *Biochem Pharmacol* 22(18):3099-3108.

(Continued)

*Primary Examiner* — D M Seaman
(74) *Attorney, Agent, or Firm* — Morrison & Foerster LLP

(57) ABSTRACT

Hydrogenated pyrido[4,3-b]indoles, pyrido[3,4-b]indoles and azepino[4,5-b]indoles are described. The compounds may bind to and are adrenergic receptor $\alpha_{2B}$ antagonists. The compounds may also bind to and antagonize adrenergic receptor $\alpha_{1B}$. The compounds may find use in therapy, e.g., to (i) reduce blood pressure and/or (ii) promote renal blood flow and/or (iii) decrease or inhibit sodium reabsorption. The compounds may also be used to treat diseases or conditions that are, or are expected to be, responsive to a decrease in blood pressure. Use of the compounds to treat cardiovascular and renal disorders is particularly described.

62 Claims, 30 Drawing Sheets

(56) References Cited

U.S. PATENT DOCUMENTS

| | | |
|---|---|---|
| 2013/0190294 A1 | 7/2013 | Protter et al. |
| 2013/0190295 A1 | 7/2013 | Hung et al. |
| 2013/0190303 A1 | 7/2013 | Hung et al. |
| 2013/0190304 A1 | 7/2013 | Hung et al. |
| 2013/0190308 A1 | 7/2013 | Jain et al. |
| 2013/0190322 A1 | 7/2013 | Hung et al. |
| 2013/0190323 A1 | 7/2013 | Hung et al. |
| 2013/0190328 A1 | 7/2013 | Jain et al. |
| 2013/0190331 A1 | 7/2013 | Jain et al. |
| 2013/0190344 A1 | 7/2013 | Jain et al. |
| 2013/0190347 A1 | 7/2013 | Hung et al. |
| 2013/0190348 A1 | 7/2013 | Hung et al. |
| 2013/0190359 A1 | 7/2013 | Jain et al. |
| 2013/0203746 A1 | 8/2013 | Hung et al. |
| 2013/0210803 A1 | 8/2013 | Chakravarty et al. |
| 2013/0217675 A1 | 8/2013 | Chakravarty et al. |
| 2013/0225558 A1 | 8/2013 | Chakravarty et al. |
| 2014/0024643 A1 | 1/2014 | Hung et al. |

FOREIGN PATENT DOCUMENTS

| | | |
|---|---|---|
| WO | WO-2007/041697 A2 | 4/2007 |
| WO | WO-2007/041697 A3 | 4/2007 |
| WO | WO-2007/087425 A1 | 8/2007 |
| WO | WO-2008/036400 A2 | 3/2008 |
| WO | WO-2008/036400 A3 | 3/2008 |
| WO | WO-2008/036410 A2 | 3/2008 |
| WO | WO-2008/036410 A3 | 3/2008 |
| WO | WO-2008/051599 A2 | 5/2008 |
| WO | WO-2008/051599 A3 | 5/2008 |
| WO | WO-2008/069963 A1 | 6/2008 |
| WO | WO-2008/073231 A1 | 6/2008 |
| WO | WO-2008/147551 A1 | 12/2008 |
| WO | WO-2009/005771 A1 | 1/2009 |
| WO | WO-2009/017836 A1 | 2/2009 |
| WO | WO-2009/039420 A1 | 3/2009 |
| WO | WO-2009/039420 A9 | 3/2009 |
| WO | WO-2009/055828 A1 | 4/2009 |
| WO | WO-2009/094668 A1 | 7/2009 |
| WO | WO-2009/094668 A8 | 7/2009 |
| WO | WO-2009/094668 C1 | 7/2009 |
| WO | WO-2009/111540 A1 | 9/2009 |
| WO | WO-2009/120717 A2 | 10/2009 |
| WO | WO-2009/120717 A3 | 10/2009 |
| WO | WO-2009/120720 A1 | 10/2009 |
| WO | WO-2009/135091 A1 | 11/2009 |
| WO | WO-2010/051501 A1 | 5/2010 |
| WO | WO-2010/051503 A1 | 5/2010 |
| WO | WO-2010/127177 A1 | 11/2010 |
| WO | WO-2011/014695 A1 | 2/2011 |
| WO | WO-2011/019417 A1 | 2/2011 |
| WO | WO-2011/038161 A1 | 3/2011 |
| WO | WO-2011/038162 A1 | 3/2011 |
| WO | WO-2011/038163 A1 | 3/2011 |
| WO | WO-2011/038164 A1 | 3/2011 |
| WO | WO-2011/103430 A1 | 8/2011 |
| WO | WO-2011/103433 A1 | 8/2011 |
| WO | WO-2011/103448 A1 | 8/2011 |
| WO | WO-2011/103460 A1 | 8/2011 |
| WO | WO-2011/103485 A1 | 8/2011 |
| WO | WO-2011/103487 A1 | 8/2011 |
| WO | WO-2012/112961 A1 | 8/2012 |
| WO | WO-2012/112962 A1 | 8/2012 |
| WO | WO-2012/112963 A1 | 8/2012 |
| WO | WO-2012/112964 A2 | 8/2012 |
| WO | WO-2012/112965 A1 | 8/2012 |
| WO | WO-2012/112966 A1 | 8/2012 |
| WO | WO 2012/154261 A1 | 11/2012 |

OTHER PUBLICATIONS

Duprez, D.A. (2008). "Systolic Hypertension in the Elderly: Addressing an Unmet Need," *Am J. Med* 121:179-184.

Franklin, S. S. et al. (2011). "The Significance of Low DBP in US Adults with Isolated Systolic Hypertension," *J Hypertension* 29(6):1101-1108.

García-Sáinz, J.A. et al. (Jul. 31, 1992). "Species Heterogeneity of Hepatic $\alpha_1$-Adrenoceptors: $\alpha1_A$-, $\alpha1_B$- and $\alpha1_C$-Subtypes," *Biochemical and Biophysical Research Communications* 186(2):760-767.

Giorgetti, M. et al. (2010). "Cognition-Enhancing Properties of Dimebon in a Rat Novel Object Recognition Task Are Unlikely to Be Associated With Acetylcholinsterase Inhibition or *N*-Methyl-D-Aspartate Receptor Antagonism," *The Journal of Pharmacology and Experimental Therapeutics* 333(3):748-757.

International Search Report mailed on May 31, 2012, for PCT Application No. PCT/US2012/025755, filed on Feb. 17, 2012, 4 pages.

International Search Report mailed on Aug. 3, 2012, for PCT Application No. PCT/US2012/25753, filed on Feb. 17, 2012, 5 pages.

Meister, B. et al. (1994). Patterns of Messenger RNA Expression for Adrenergic Receptor Subtypes in the Rat Kidney, *J Pharmacol Exp Therapeutics* 268(3):1606-1611.

Michel, A.D. et al. (1989). "Identification of a Single $\alpha_1$-Adrenoceptor Corresponding to the $\alpha$1A-Subtype in Rat Submaxillary Gland," *Br J Pharmacol* 98:883-889.

Perrin, R.J. et al. (2003). Epitope Mapping and Specificity of the Anti-$\alpha$-Synuclein Monoclonal Antibody Syn-1 in Mouse Brain and Cultured Cell Lines *Neurosci Lett* 349:133-135.

Regard, J.B. et al. (Oct. 31, 2008). "Anatomical Profiling of G Protein-Coupled Receptor Expression," *Cell* 135:561-571.

Uhlén, S. et al. (1994). "The Novel *Alpha*-2 Adrenergic RadioLigand [$^3$H]-MK912 is *Alpha*-2C Selective Among Human *Alpha*-2A, *Alpha*-2B and *Alpha*-2C Adrenoceptors," *Journal of Pharmacology and Experimental Therapeutics* 271(3):1558-1565.

Uhlén, S. et al. (1998). "[$^3$H]RS79948-197 Binding to Human, Rat, Guinea Pig and Pig $\alpha_{2A}$-, $\alpha_{2B}$- and $\alpha_{2C}$-Adrenoceptors. Comparison with MK912, RX821002, Rauwolscine and Yohimbine," *European Journal of Pharmacology* 343:93-101.

Vekrellis, K. et al. (2009). "Inducible Over-Expressing of $\alpha$-Synuclein in Human Neuronal Cells Leads to Caspase-Dependent Non-Apoptotic Death," *J Neurochem* 109:1348-1362.

U.S. Appl. No. 13/789,361, filed Mar. 7, 2013, by Protter et al.
U.S. Appl. No. 13/791,648, filed Mar. 8, 2013, by Hung et al.
U.S. Appl. No. 13/791,750, filed Mar. 8, 2013, by Hung et al.
U.S. Appl. No. 14/000,171, filed Aug. 16, 2013, by Protter et al.
U.S. Appl. No. 14/000,176, filed Aug. 16, 2013, by Protter et al.
U.S. Appl. No. 14/000,179, filed Aug. 16, 2013, by Chakravarty et al.
U.S. Appl. No. 14/000,184, filed Aug. 16, 2013, by Protter et al.
U.S. Appl. No. 14/000,197, filed Aug. 16, 2013, by Protter et al.
U.S. Appl. No. 14/033,234, filed Sep. 20, 2013, by Hung et al.
U.S. Appl. No. 14/048,656, filed Oct. 8, 2013, by Hung et al.

Final Office Action mailed on Oct. 25, 2013, for U.S. Appl. No. 13/318,124, filed on Jan. 10, 2012, 16 pages.

Non-Final Office Action mailed on Jul. 11, 2013, for U.S. Appl. No. 13/318,124, filed on Jan. 10, 2012, 10 pages.

Non-Final Office Action mailed on Sep. 23, 2013, for U.S. Appl. No. 13/791,862, filed on Mar. 8, 2013, 10 pages.

Written Opinion mailed on May 31, 2012, for PCT Application No. PCT/US2012/025755, filed on Feb. 17, 2012, 8 pages.

* cited by examiner

COMPOUNDS AND METHODS FOR TREATMENT OF HYPERTENSION

CROSS-REFERENCE TO RELATED APPLICATIONS

This application claims priority to U.S. Provisional Patent Application No. 61/444,642 filed Feb. 18, 2011, U.S. Provisional Patent Application No. 61/444,655 filed Feb. 18, 2011, U.S. Provisional Patent Application No. 61/444,659 filed Feb. 18, 2011, U.S. Provisional Patent Application No. 61/469,664 filed Mar. 30, 2011, U.S. Provisional Patent Application No. 61/529,745 filed Aug. 31, 2011, U.S. Provisional Patent Application No. 61/529,816 filed Aug. 31, 2011, U.S. Provisional Patent Application No. 61/562,927 filed Nov. 22, 2011 and U.S. Provisional Patent Application No. 61/562,938 filed Nov. 22, 2011, the disclosures of each of which are incorporated herein by reference in their entireties.

BACKGROUND OF THE INVENTION

Hypertension is a serious condition that can damage vital organs, such as the heart and kidneys, and other parts of the body, such as the central nervous system. Individuals who have hypertension may have, or be at risk of developing, dangerous diseases such as coronary heart disease and kidney failure. Hypertension, which is the leading modifiable risk factor for cardiovascular disease mortality, causes more than 7 million deaths every year worldwide.

Hypertension is the most common chronic medical condition in developed countries as well as the most common indication for physician visits and prescription medication use. Hypertension affects more than 50 million individuals in the United States and over one billion individuals worldwide, and overall prevalence may continue to increase with the advancing age of the population.

Unfortunately, despite the importance of blood pressure control and the availability of multiple classes of antihypertensive agents, the treatment of hypertension remains suboptimal. Data from the most recent National Health and Nutrition Examination Survey demonstrate that only 34% of patients with hypertension have blood pressures at their therapeutic goal. Additionally, it was shown that the majority of patients with hypertension will require two or more antihypertensive agents to achieve their goal blood pressure. Even with optimal compliance with multiple antihypertensive agents of different classes, a significant fraction of patients will not be able to achieve their goal blood pressure. The overall prevalence of resistant hypertension, defined as elevated blood pressure in spite of the use of three or more antihypertensive agents, is unknown, but small studies suggest that it ranges from 5%-16% in primary care settings to greater than 50% in nephrology clinics. Given data suggesting that increasing age and obesity are important risk factors for the development of resistant hypertension, it is expected that the overall prevalence of this condition is likely to increase due to demographic changes in the population.

Systolic blood pressure tends to increase with age and systolic hypertension is an important health issue, prominent in the elderly (Duprez, *Am. J. Med.* 121:179-184 (2008)). It has been suggested that this occurs as large vessels such as the aorta lose their elasticity with age and is less able to buffer the pulsative nature of cardiac output. There exists a need for a treatment for patients in such clinical setting, for example, patients with systolic hypertension accompanied with low diastolic pressure (Franklin et al. *J. Hypertension* 29:1101-1108 (2011)).

Metabolic syndrome is a cluster of disorders including obesity, hypertension, hypertrigleridemia, hypercholesterolemia and elevated blood sugar. Individuals with this spectrum of disorders are at increased risk of diabetes, heart disease and stroke. Agents capable of treating more than one of these disorders are desirable.

Hypertensive emergencies are defined as severe elevations in blood pressure associated with resultant organ damage (i.e. pulmonary edema, renal impairment, visual impairment, intracranial hemorrhage, or encephalopathy). The treatment of hypertensive emergencies involves aggressive and controlled blood pressure lowering in a highly monitored intensive care setting using intravenous blood pressure lowering agents. Therapeutic agents and method of treatment is needed to gradually lower blood pressure and minimize damage of end organs such as the brain, kidney, heart, and eye.

The frequency of chronic kidney disease also continues to increase worldwide as does the prevalence of end-stage renal disease. Although chronic kidney disease is often caused by hypertension, other factors such as a decrease in renal blood flow and increase in sodium retention or reabsorption can lead to renal diseases. Increased age and diabetes can also contribute to renal disease. Especially the elderly, which are a growing segment of the world population, are at increased risk for renal disease. The presence of chronic kidney disease is also associated with a large increase in cardiovascular morbidity and mortality. Consequently, the identification and reduction of chronic kidney disease has become a vital public health priority.

Thus, there remains a need for new and useful agents that are capable of (i) reducing an individual's blood pressure and/or (ii) promoting renal blood flow and/or (iii) inhibiting or decreasing sodium reabsorption.

BRIEF SUMMARY OF THE INVENTION

Hydrogenated pyrido[4,3-b]indoles, pyrido[3,4-b]indoles and azepino[4,5-b]indoles are described. Compositions and kits comprising the compounds are also provided, as are methods of using and making the compounds. Compounds provided herein may find use in treating a disease or condition that is, or is believed to be responsive to any one or more of: (i) a decrease in blood pressure; (ii) an increase in renal blood flow and (iii) a decrease or inhibition of sodium reabsorption. In one aspect, compounds provided herein are selective adrenergic receptor $\alpha_{2B}$ antagonists that may find use in treating a disease or condition that is, or is believed to be responsive to any one or more of: (i) a decrease in blood pressure; (ii) an increase in renal blood flow and (iii) a decrease or inhibition of sodium reabsorption. Compounds provided may also find use in treating diseases and/or conditions such as hypertension, congestive heart failure or a renal disease or condition.

In another aspect, compounds that promote mitochondrial health and cellular viability are also described. The compounds provided herein are selective adrenergic receptor $\alpha_{2B}$ antagonists that may find use in treating a disease or condition that is associated with dysfunction of mitochondria in a renal or cardiac cell. Compounds provided may also find use in treating diseases and/or conditions selected from the group consisting of acute renal failure, chronic renal failure, coronary ischemia, acute congestive heart failure, chronic congestive heart failure, coronary artery disease, sleep apnea, respiratory distress, hypertension, and peripheral vascular disease.

In one aspect, provided is a method of lowering blood pressure in an individual in need thereof comprising admin istering to the individual an effective amount of a compound of the formula (I):

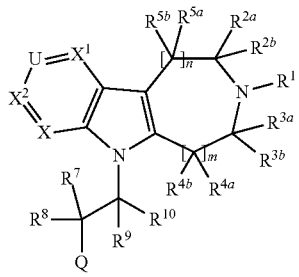

or a salt, solvate or N-oxide thereof, wherein:

$R^1$ is H; $C_1$-$C_5$ alkyl optionally substituted with 1 to 3 substituents independently selected from the group consisting of halo, hydroxyl, carboxyl, $SO_3H$, $SR^{1a}$, $S(O)R^{1a}$, $SO_2R^{1a}$ and perhaloalkyl; $C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{3a}$ to form a propylene (—$CH_2CH_2CH_2$—) moiety or a butylene (—$CH_2CH_2CH_2CH_2$—) moiety; or is taken together with $R^{4a}$ or $R^{5a}$, where present, to form an ethylene (—$CH_2CH_2$—) moiety or a propylene (—$CH_2CH_2CH_2$—) moiety;

$R^{1a}$ is H or optionally substituted $C_1$-$C_5$ alkyl;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—$CH_2CH_2CH_2$—) moiety or a butylene (—$CH_2CH_2CH_2CH_2$—) moiety; or is taken together with $R^{3a}$ to form an ethylene (—$CH_2CH_2$—) moiety or a propylene (—$CH_2CH_2CH_2$—) moiety; or is taken together with $R^{4a}$, where present, to form a methylene (—$CH_2$—) moiety or an ethylene (—$CH_2CH_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—$CH_2CH_2CH_2$—) moiety or a butylene (—$CH_2CH_2CH_2CH_2$—) moiety; or is taken together with $R^{2a}$ to form an ethylene (—$CH_2CH_2$—) moiety or a propylene (—$CH_2CH_2CH_2$—) moiety; or is taken together with $R^{5a}$, where present, to form a methylene (—$CH_2$—) moiety or an ethylene (—$CH_2CH_2$—) moiety;

$R^{4a}$, where present, is H; halo; hydroxyl; cyano; carboxyl; —OC(O)N($R^{14a}$)$R^{15a}$; —C(O)N($R^{14a}$)$R^{15a}$; optionally substituted $C_1$-$C_5$ alkyl; optionally substituted $C_2$-$C_5$ alkenyl; or optionally substituted aryl; or is taken together with $R^{3a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{2a}$ to form a methylene (—$CH_2$—) moiety or an ethylene (—$CH_2CH_2$—) moiety; or is taken together with $R^{5a}$, where present, to form a methylene (—$CH_2$—) moiety;

$R^{5a}$, where present, is H H; halo; hydroxyl; cyano; carboxyl; —OC(O)N($R^{14a}$)$R^{15a}$; —C(O)N($R^{14a}$)$R^{15a}$; optionally substituted $C_1$-$C_5$ alkyl; optionally substituted $C_2$-$C_5$ alkenyl; or optionally substituted aryl; or is taken together with $R^{2a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{3a}$ to form a methylene (—$CH_2$—) moiety or an ethylene (—$CH_2CH_2$—) moiety; or is taken together with $R^{4a}$, where present, to form a methylene (—$CH_2$—) moiety;

each $R^{2b}$ and $R^{3b}$ is independently H, optionally substituted $C_1$-$C_5$ alkyl, optionally substituted $C_2$-$C_5$ alkenyl, or optionally substituted aryl;

each $R^{4b}$ and $R^{5b}$, where present, is independently H, halo, optionally substituted $C_1$-$C_5$ alkyl, optionally substituted $C_2$-$C_5$ alkenyl, or optionally substituted aryl;

each n and m is 1, or n is 0 and m is 1, or n is 1 and m is 0;

each $X^1$, $X^2$, X and U is independently N or $CR^6$;

each $R^6$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; azido; aminoacyl, carboxyl; carbonylalkoxy; N($R^{11}$)$R^{12}$; $SR^{13}$, S(O)$R^{13}$; $SO_2R^{13}$; —OC(O)N($R^{14}$)$R^{15}$; —C(O)N($R^{14}$)$R^{15}$; optionally substituted —OC(O)-aryl; optionally substituted —OC(O)-heteroaryl; —OC(O)$C_1$-$C_6$ alkyl optionally substituted with amino or carboxyl; or —O$C_1$-$C_5$ alkyl optionally substituted with carboxyl; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene;

each $R^{14a}$, and $R^{15a}$ is independently H or optionally substituted $C_1$-$C_5$ alkyl; and Q is optionally substituted cycloalkyl, optionally substituted aryl, or optionally substituted heteroaryl.

In some embodiments, the individual has high blood pressure. In other embodiments, the method reduces one or more of any of the following: systolic blood pressure, diastolic blood pressure, mean arterial blood pressure, and pulse pressure of the individual, following administration of the compound. In other embodiments, the method does not substantially increase heart rate of the individual. In yet other embodiments, the individual has one or more risk factors for developing high blood pressure.

Provided is also a method of (i) increasing renal blood flow, and/or (ii) decreasing sodium reabsorption, in an individual in need thereof comprising administering to the individual an effective amount of a compound of the formula (I) or any variations detailed herein. In some embodiments, the method results in one or more of any of the following: increase in renal blood flow, decrease in sodium reabsorption, increase in urine sodium content and/or increase in urine volume, reduction in edema, reduction in elevated blood urea nitrogen to creatinine (BUN/Cr) ratio, and decrease in creatinine levels.

In some embodiments, the individual has or is at risk of developing acute or chronic congestive heart failure, acute decompensated congestive heart failure, acute or chronic renal failure, or acute or chronic renal failure due to renal insufficiency.

Provided is also a method of treating a disease or condition that is responsive to any one or more of: (i) a decrease in blood pressure; (ii) an increase in renal blood flow; and (iii) a decrease of sodium reabsorption, comprising administering to an individual in need thereof an effective amount of a compound of the formula (I) or any variations detailed herein. In some embodiments, the disease or condition is hypertension. In certain embodiments, the disease or condition is treatment-resistant hypertension, or hypertensive emergency. In yet other embodiments, the disease or condition is a cardiac or renal disease or condition.

In some embodiments, the compound used in the methods described above is a compound of formula (A-III):

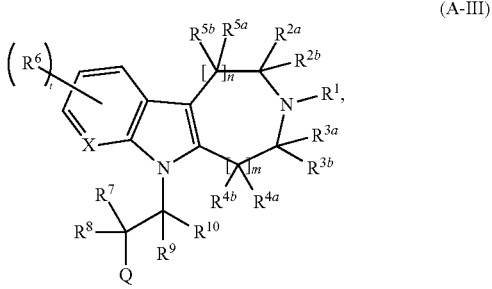

(A-III)

or a salt, solvate or N-oxide thereof, wherein:

$R^1$ is H; $C_1$-$C_5$ alkyl optionally substituted with 1 to 3 substituents independently selected from the group consisting of halo, hydroxyl, carboxyl and perhaloalkyl; $C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{3a}$ to form a propylene (—CH$_2$CH$_2$CH$_2$—) moiety or a butylene (—CH$_2$CH$_2$CH$_2$CH$_2$—) moiety; or is taken together with $R^{4a}$ or $R^{5a}$, where present, to form an ethylene (—CH$_2$CH$_2$—) moiety or a propylene (—CH$_2$CH$_2$CH$_2$—) moiety;

each n and m is 1, or n is 0 and m is 1, or n is 1 and m is 0;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—CH$_2$CH$_2$CH$_2$—) moiety or a butylene (—CH$_2$CH$_2$CH$_2$CH$_2$—) moiety; or is taken together with $R^{3a}$ to form an ethylene (—CH$_2$CH$_2$—) moiety or a propylene (—CH$_2$CH$_2$CH$_2$—) moiety; or is taken together with $R^{4a}$, where present, to form a methylene (—CH$_2$—) moiety or an ethylene (—CH$_2$CH$_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—CH$_2$CH$_2$CH$_2$—) moiety or a butylene (—CH$_2$CH$_2$CH$_2$CH$_2$—) moiety; or is taken together with $R^{2a}$ to form an ethylene (—CH$_2$CH$_2$—) moiety or a propylene (—CH$_2$CH$_2$CH$_2$—) moiety; or is taken together with $R^{5a}$, where present, to form a methylene (—CH$_2$—) moiety or an ethylene (—CH$_2$CH$_2$—) moiety;

$R^{4a}$ is H; optionally substituted $C_1$-$C_5$ alkyl; optionally substituted $C_2$-$C_5$ alkenyl; or optionally substituted aryl; or is taken together with $R^{3a}$ to form a propylene (—CH$_2$CH$_2$CH$_2$—) moiety or a butylene (—CH$_2$CH$_2$CH$_2$CH$_2$—) moiety; or is taken together with $R^1$ to form an ethylene (—CH$_2$CH$_2$—) moiety or a propylene (—CH$_2$CH$_2$CH$_2$—) moiety; or is taken together with $R^{2a}$ to form a methylene (—CH$_2$—) moiety or an ethylene (—CH$_2$CH$_2$—) moiety; or is taken together with $R^{5a}$, where present, to form a methylene (—CH$_2$—) moiety;

$R^{5a}$ is H; optionally substituted $C_1$-$C_5$ alkyl; optionally substituted $C_2$-$C_5$ alkenyl; or optionally substituted aryl; or is taken together with $R^{2a}$ to form a propylene (—CH$_2$CH$_2$CH$_2$—) moiety or a butylene (—CH$_2$CH$_2$CH$_2$CH$_2$—) moiety; or is taken together with $R^1$ to form an ethylene (—CH$_2$CH$_2$—) moiety or a propylene (—CH$_2$CH$_2$CH$_2$—) moiety; or is taken together with $R^{3a}$ to form a methylene (—CH$_2$—) moiety or an ethylene (—CH$_2$CH$_2$—) moiety; or is taken together with $R^{4a}$, where present, to form a methylene (—CH$_2$—) moiety;

each $R^{2b}$, $R^{3b}$, $R^{4b}$ and $R^{5b}$ is independently H, optionally substituted $C_1$-$C_5$ alkyl, optionally substituted $C_2$-$C_5$ alkenyl, or optionally substituted aryl;

X is N or $CR^{6a}$;

t is 1, 2 or 3;

each $R^6$ and $R^{6a}$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; $N(R^{11})R^{12}$; $SR^{13}$; $S(O)R^{13}$; $SO_2R^{13}$; —OC(O)N($R^{14}$)$R^{15}$; OC(O)-aryl; —OC(O)-heteroaryl; or —OC(O)$C_1$-$C_5$ alkyl optionally substituted with amino; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl; or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl; or is taken together with $R^8$ to form a bond;

each $R^{11}$ and $R^{12}$ is independently H or optionally substituted $C_1$-$C_5$ alkyl; or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some embodiments, the compound used in the methods described above is a compound of formula (A-III), wherein any one or more of provisions (1) to (34) apply:

(1) X is $CR^{6a}$, wherein each $R^{6a}$ is independently H, halo or $C_1$-$C_5$ alkyl;

(2) each $R^6$ is independently H, halo or $C_1$-$C_5$ alkyl;

(3) X is N;

(4) $R^1$ is H or $C_1$-$C_5$ alkyl;

(5) $R^{2a}$ and $R^{3a}$ is H;

(6) $R^7$ is H or $C_1$-$C_5$ alkyl;

(8) $R^8$ is H, hydroxyl, $N(R^{11})R^{12}$ or —$OC(O)C_1$-$C_5$ alkyl;

(9) $R^7$ is H or $C_1$-$C_5$ alkyl, and $R^8$ is H, hydroxyl, $N(R^{11})R^{12}$ or —$OC(O)C_1$-$C_5$ alkyl;

(10) $R^7$ is H, and $R^8$ is H, hydroxyl, $N(R^{11})R^{12}$ or —$OC(O)C_1$-$C_5$ alkyl;

(11) $R^7$ is $C_1$-$C_5$ alkyl, and $R^8$ is H, hydroxyl, $N(R^{11})R^{12}$ or —$OC(O)C_1$-$C_5$ alkyl;

(12) $R^7$ is H or $C_1$-$C_5$ alkyl, and $R^8$ is H or hydroxyl;

(13) $R^7$ is H or $C_1$-$C_5$ alkyl, and $R^8$ is hydroxyl;

(14) $R^7$ is H, and $R^8$ is hydroxyl;

(15) $R^7$ is methyl, and $R^8$ is hydroxyl;

(16) $R^7$ is H, and $R^8$ is $NH_2$;

(17) $R^7$ is H, and $R^8$ is —$OC(O)C_1$-$C_5$ alkyl;

(18) $R^9$ is H or $C_1$-$C_5$ alkyl;

(19) $R^{10}$ is H or $C_1$-$C_5$ alkyl;

(20) each $R^9$ and $R^{10}$ is H;

(21) one of $R^9$ and $R^{10}$ is H and the other is $C_1$-$C_5$ alkyl;

(22) Q is: unsubstituted pyridyl; unsubstituted pyrimidyl; unsubstituted pyrazinyl; unsubstituted phenyl; unsubstituted imidazolyl; unsubstituted triazolyl; pyridyl substituted with 1 to 3 substituents independently selected form the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl; pyrimidyl substituted with 1 to 3 substituents independently selected form the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl; pyrazinyl substituted with 1 to 3 substituents independently selected form the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl; or phenyl substituted with 1 to 3 substituents independently selected form the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl; imidazolyl substituted with 1 to 3 substituents independently selected form the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl; or triazolyl substituted with 1 to 3 substituents independently selected form the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl;

(23) X is $CR^{6a}$, wherein $R^{6a}$ is H, halo or $C_1$-$C_5$ alkyl; and each $R^6$ is independently H, halo or $C_1$-$C_5$ alkyl;

(24) wherein $R^1$ is H or $C_1$-$C_5$ alkyl, $R^7$ is H or $C_1$-$C_5$ alkyl, and $R^8$ is H, hydroxyl, $N(R^{11})R^{12}$ or —$OC(O)C_1$-$C_5$ alkyl;

(25) wherein $R^1$ is H or $C_1$-$C_5$ alkyl, $R^7$ is H or $C_1$-$C_5$ alkyl, and $R^8$ is H or hydroxyl;

(26) $R^1$ is H or $C_1$-$C_5$ alkyl, $R^7$ is H or $C_1$-$C_5$ alkyl, and $R^8$ is hydroxyl;

(27) wherein $R^1$ is $CH_3$, $R^7$ is H, $R^8$ is hydroxyl, n is zero and m is 1;

(28) $R^1$ is $CH_3$, $R^7$ is methyl, $R^8$ is hydroxyl, n is zero and m is 1;

(29) X is $CR^{6a}$, wherein $R^{6a}$ is H, halo or $C_1$-$C_5$ alkyl; each $R^6$ is independently H, halo or $C_1$-$C_5$ alkyl; $R^1$ is H or $C_1$-$C_5$ alkyl, $R^7$ is H or $C_1$-$C_5$ alkyl, $R^8$ is H, hydroxyl, $N(R^{11})R^{12}$ or —$OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl;

(30) n is 0 and m is 1; $R^1$ is H or $CH_3$; $R^7$ is H or $CH_3$; and $R^8$ is H or hydroxyl;

(31) X is N; $R^1$ is H or $C_1$-$C_5$ alkyl, $R^7$ is H or $C_1$-$C_5$ alkyl, $R^8$ is H, hydroxyl, $N(R^{11})R^{12}$ or —$OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl;

(32) n is 0 and m is 1; $R^1$ is H or $CH_3$; $R^7$ is H or $CH_3$; and $R^8$ is H or hydroxyl;

(33) n is 0 and m is 1; $R^1$ is taken together with $R^{2a}$ to form a propylene (—$CH_2CH_2CH_2$—) moiety; X is $CR^{6a}$, wherein $R^{6a}$ is H, halo or $C_1$-$C_5$ alkyl; each $R^6$ is independently H, halo or $C_1$-$C_5$ alkyl; $R^7$ is H or $C_1$-$C_5$ alkyl, $R^8$ is H, hydroxyl, $N(R^{11})R^{12}$ or —$OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —$C(O)NR^{16}R^{17}$, wherein each $R^{16}$ and $R^{17}$ is independently H or optionally substituted $C_1$-$C_5$ alkyl; and

(34) $R^7$ is H or $CH_3$; and $R^8$ is H or hydroxyl.

In some embodiments, the compound used in the methods described herein is a compound of formula (A-IIIA) detailed herein, wherein any one or more of provisions (35)-(45) apply:

(35) X is CH;

(36) X is N;

(37) $R^1$ is H or $CH_3$;

(38) $R^{2a}$ is H or is taken together with $R^1$ to form a propylene (—$CH_2CH_2CH_2$—) moiety;

(39) each $R^6$ and $R^{6a}$ is independently H, halo or $C_1$-$C_5$ alkyl;

(40) $R^7$ is H or $CH_3$;

(41) $R^8$ is hydroxyl;

(42) Q is: unsubstituted pyridyl; unsubstituted pyrimidyl; unsubstituted pyrazinyl; unsubstituted phenyl; pyridyl substituted with halo, $CH_3$, $CF_3$, $CONH_2$, OH, or $OCH_3$; pyrimidyl substituted with halo, $CH_3$, $CF_3$, $CONH_2$, OH, or $OCH_3$; pyrazinyl substituted with halo, $CH_3$, $CF_3$, $CONH_2$, OH, or $OCH_3$; or phenyl substituted with halo, $CH_3$, $CF_3$, $CONH_2$, OH, or $OCH_3$;

(43) Q is: unsubstituted pyridyl; unsubstituted pyrimidyl; unsubstituted pyrazinyl; unsubstituted phenyl; unsubstituted imidazolyl; unsubstituted triazolyl; pyridyl substituted with halo, $CH_3$, $CF_3$, $CONH_2$, OH, or $OCH_3$; pyrimidyl substituted with halo, $CH_3$, $CF_3$, $CONH_2$, OH, or $OCH_3$; pyrazinyl substituted with halo, $CH_3$, $CF_3$, $CONH_2$, OH, or $OCH_3$; or phenyl substituted with halo, $CH_3$, $CF_3$, $CONH_2$, OH, or $OCH_3$;

(44) X is CH; $R^1$ is H or $CH_3$; each $R^6$ is independently H, halo or $C_1$-$C_5$ alkyl; $R^7$ is H or $CH_3$; $R^8$ is hydroxyl; and Q is unsubstituted pyridyl, or pyridyl substituted with halo, $CH_3$, $CF_3$, $CONH_2$, OH, or $OCH_3$; and

(45) $R^1$ is $CH_3$; $R^6$ is $CH_3$; and Q is unsubstituted pyridyl.

In some embodiments, the compound is an adrenergic receptor $\alpha_{2B}$ antagonist. In other embodiments, the compound is also an adrenergic receptor $\alpha_{1B}$ antagonist. In yet other embodiments, the compound is also adrenergic receptor $\alpha_{1D}$ antagonist.

Further provided is a kit comprising (i) a compound of formula (I) or any variations detailed herein, or a pharmaceutically acceptable salt thereof, and (ii) instructions for use according to the method described above. Also provided is a kit comprising a compound of formula (A-IIIA) or any variations detailed herein, or a pharmaceutically acceptable salt thereof, and (ii) instructions for use according to the method described above.

Also provided is use of a compound detailed herein, such as a compound of formula (I) or any variations thereof, or a salt, solvate or N-oxide thereof, in lowering blood pressure, increasing renal blood flow, and/or decreasing or inhibiting sodium reabsorption. Further provided are uses of a compound detailed herein, such as a compound of formula (I) or any variations thereof, or a salt, solvate or N-oxide thereof, for the manufacturing of a medicament for the treatment of a disease or condition that is responsive to any one or more of: (i) a decrease in blood pressure; (ii) an increase in renal blood flow; and (iii) a decrease of sodium reabsorption.

DETAILED DESCRIPTION OF THE INVENTION

Definitions

Figure 1:
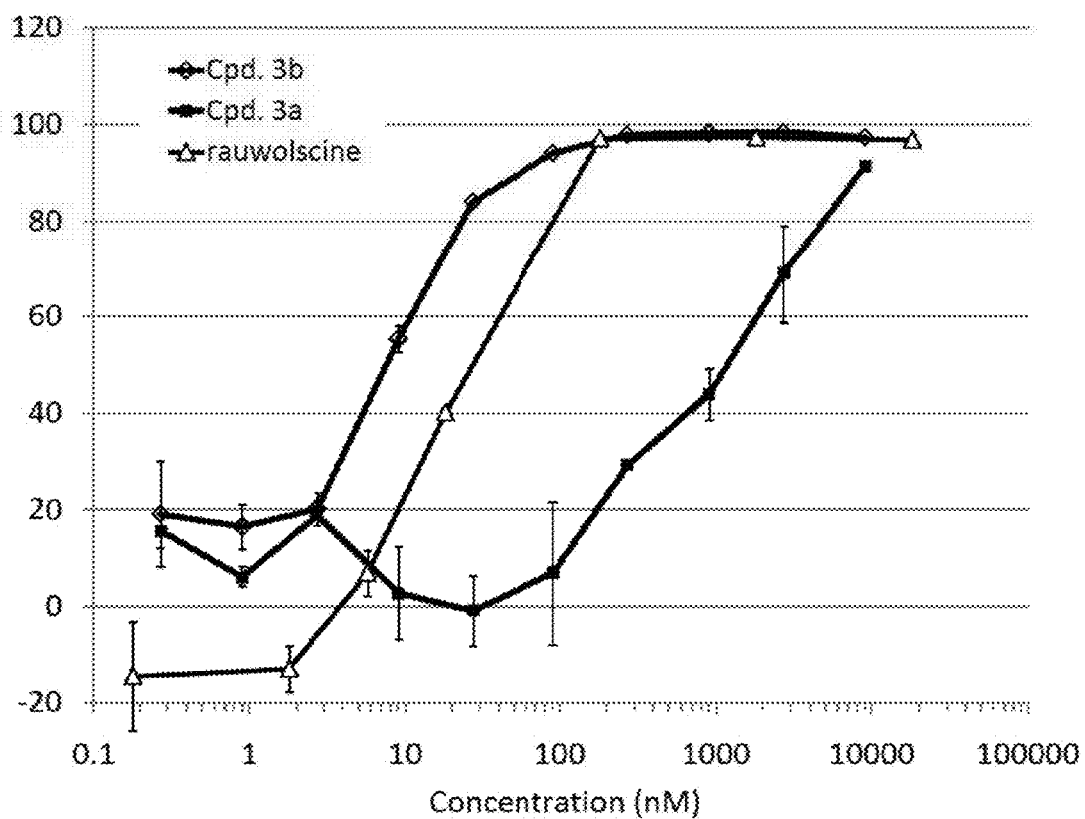
FIG. 1 illustrates the $\alpha_{2B}$ antagonist activity of Compound Nos. 3a and 3b in the cell-based Aequorin Assay. The word "Compound" may be abbreviated as "Cpd." in the figures.
Figure 2:
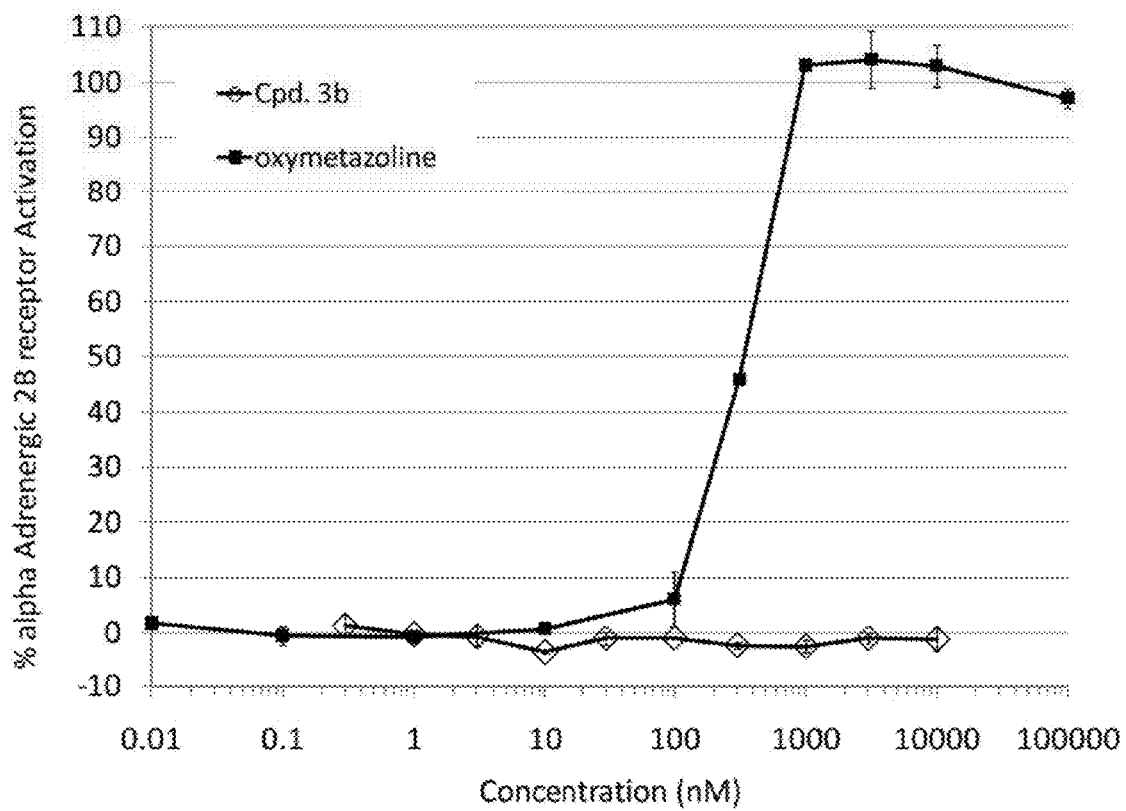
FIG. 2 illustrates the $\alpha_{2B}$ antagonist activity of Compound No. 3b in the Aequorin Antagonist Activity Assay.

Unless clearly indicated otherwise, the terms "a", "an", and the like, refer to one or more.

It is also understood and clearly conveyed by this disclosure that reference to "the compound" or "a compound" includes and refers to any compounds (e.g., selective adrenergic receptor $\alpha_{2B}$ antagonists) or pharmaceutically acceptable salt or other form thereof as described herein.

Reference to "about" a value or parameter herein includes (and describes) embodiments that are directed to that value or parameter per se. For example, description referring to "about X" includes description of "X".

Unless clearly indicated otherwise, "an individual" as used herein intends a mammal, including but not limited to a human. The invention may find use in both human medicine and in the veterinary context.

As used herein, an "at risk" individual is an individual who is at risk of developing a disease or condition. An individual "at risk" may or may not have a detectable disease or condition, and may or may not have displayed detectable disease prior to the treatment methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s).

As used herein, "treatment" or "treating" is an approach for obtaining a beneficial or desired result, including clinical results.

As used herein, "delaying" development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

As used herein, the term "effective amount" intends such amount of a compound of the invention which should be effective in a given therapeutic form. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any of the co-administered compounds may optionally be lowered due to the combined action (e.g., additive or synergistic effects) of the compounds.

As used herein, "unit dosage form" refers to physically discrete units, suitable as unit dosages, each unit containing a predetermined quantity of active ingredient, or compound which may be in a pharmaceutically acceptable carrier.

As used herein, by "pharmaceutically acceptable" is meant a material that is not biologically or otherwise undesirable, e.g., the material may be incorporated into a pharmaceutical composition administered to an individual without causing significant undesirable biological effects or interacting in a deleterious manner with any of the other components of the composition in which it is contained. Pharmaceutically acceptable carriers or excipients have preferably thus in some embodiments met the required standards of toxicological and manufacturing testing and/or are included on the Inactive Ingredient Guide prepared by the U.S. Food and Drug administration.

"Pharmaceutically acceptable salts" are those salts which retain at least some of the biological activity of the free (non-salt) compound and which can be administered as drugs or pharmaceuticals to an individual. Such salts, for example, include: (1) acid addition salts, formed with inorganic acids such as hydrochloric acid, hydrobromic acid, sulfuric acid, nitric acid, phosphoric acid, and the like; or formed with organic acids such as acetic acid, oxalic acid, propionic acid, succinic acid, maleic acid, tartaric acid and the like; (2) salts formed when an acidic proton present in the parent compound either is replaced by a metal ion, e.g., an alkali metal ion, an alkaline earth metal ion, or an aluminum ion; or coordinates with an organic base. Acceptable organic bases include ethanolamine, diethanolamine, triethanolamine and the like. Acceptable inorganic bases include aluminum hydroxide, calcium hydroxide, potassium hydroxide, sodium carbonate, sodium hydroxide, and the like. Further examples of pharmaceutically acceptable salts include those listed in Berge et al., Pharmaceutical Salts, *J. Pharm. Sci.* 1977 January; 66(1):1-19. Pharmaceutically acceptable salts can be prepared in situ in the manufacturing process, or by separately reacting a purified compound of the invention in its free acid or base form with a suitable organic or inorganic base or acid, respectively, and isolating the salt thus formed during subsequent purification. It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are often formed during the process of crystallization. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The term "excipient" as used herein includes an inert or inactive substance that may be used in the production of a drug or pharmaceutical, such as a tablet containing a compound detailed herein, or a pharmaceutically acceptable salt thereof, as an active ingredient. Various substances may be embraced by the term excipient, including without limitation any substance used as a binder, disintegrant, coating, compression/encapsulation aid, cream or lotion, lubricant, solutions for parenteral administration, materials for chewable tablets, sweetener or flavoring, suspending/gelling agent, or wet granulation agent. Binders include, e.g., carbomers, povidone, xanthan gum, etc.; coatings include, e.g., cellulose acetate phthalate, ethylcellulose, gellan gum, maltodextrin, enteric coatings, etc.; compression/encapsulation aids include, e.g., calcium carbonate, dextrose, fructose dc (dc="directly compressible"), honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams or lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

An inverse agonist is a compound that binds to a receptor and inhibits the activity of the receptor in the absence of an agonist. An inverse agonist requires that the receptor have some constitutive basal activity in the absence of an agonist. While an agonist increases activity of the receptor over basal level an inverse agonist reduces receptor activity below basal level.

"Alkyl" refers to and includes saturated linear, branched, or cyclic univalent hydrocarbon structures and combinations thereof. Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"). When an alkyl residue having a specific number of carbons is named, all geometric isomers having that number of carbons are intended to be encompassed and described; thus, for example, "butyl" is meant to include n-butyl, sec-butyl, isobutyl, tert-butyl and cyclobutyl; "propyl" includes n-propyl, iso-propyl and cyclopropyl. This term is exemplified by groups such as methyl, t-butyl, n-heptyl, octyl, cyclohexylmethyl, cyclopropyl and the like. Cycloalkyl is a subset of alkyl and can consist of one ring, such as cyclohexyl, or multiple rings, such as adamantyl. A cycloalkyl comprising more than one ring may be fused, spiro or bridged, or combinations thereof. A preferred cycloalkyl is a saturated cyclic hydrocarbon having from 3 to 13 annular carbon atoms. A more preferred cycloalkyl is a saturated cyclic hydrocarbon having from 3 to 8 annular carbon atoms (a "$C_3$-$C_8$ cycloalkyl"). Examples of cycloalkyl groups include adamantyl, decahydronaphthalenyl, cyclopropyl, cyclobutyl, cyclopentyl, cyclohexyl and the like.

"Alkylene" refers to the same residues as alkyl, but having bivalency. Examples of alkylene include methylene (—$CH_2$—), ethylene (—$CH_2CH_2$—), propylene (—$CH_2CH_2CH_2$—), butylene (—$CH_2CH_2CH_2CH_2$—) and the like.

"Alkenyl" refers to an unsaturated hydrocarbon group having at least one site of olefinic unsaturation (i.e., having at least one moiety of the formula C=C) and preferably having from 2 to 10 carbon atoms and more preferably 2 to 8 carbon atoms. Examples of alkenyl include but are not limited to —$CH_2$—CH=CH—$CH_3$ and —$CH_2$—$CH_2$-cyclohexenyl, where the ethyl group of the latter example can be attached to the cyclohexenyl moiety at any available position on the ring. Cycloalkenyl is a subset of alkenyl and can consist of one ring, such as cyclohexyl, or multiple rings, such as norbornenyl. A more preferred cycloalkenyl is an unsaturated cyclic hydrocarbon having from 3 to 8 annular carbon atoms (a "$C_3$-$C_8$ cycloalkenyl"). Examples of cycloalkenyl groups include cyclopropenyl, cyclobutenyl, cyclopentenyl, cyclohexenyl and the like.

"Alkynyl" refers to an unsaturated hydrocarbon group having at least one site of acetylenic unsaturation (i.e., having at least one moiety of the formula C≡C) and preferably having from 2 to 10 carbon atoms and more preferably 2 to 8 carbon atoms and the like.

"Substituted alkyl" refers to an alkyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkenyl" refers to alkenyl group having from 1 to 5 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted alkynyl" refers to alkynyl groups having from 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted heterocyclyl, substituted or unsubstituted aralkyl, aminosulfonyl, sulfonylamino, sulfonyl, oxo, carbonylalkylenealkoxy and the like.

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, alkynyl-C(O)—, substituted alkynyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Acyloxy" refers to the groups H—C(O)O—, alkyl-C(O)O—, substituted alkyl-C(O)O—, alkenyl-C(O)O—, substituted alkenyl-C(O)O—, alkynyl-C(O)O—, substituted alkynyl-C(O)O—, cycloalkyl-C(O)O—, substituted cycloalkyl-C(O)O—, aryl-C(O)O—, substituted aryl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Heterocycle", "heterocyclic", or "heterocyclyl" refers to a saturated or an unsaturated non-aromatic group having a single ring or multiple condensed rings, and having from 1 to 10 annular carbon atoms and from 1 to 4 annular heteroatoms, such as nitrogen, sulfur or oxygen, and the like. A heterocycle comprising more than one ring may be fused, spiro or bridged, or any combination thereof. In fused ring systems, one or more of the rings can be aryl or heteroaryl. A heterocycle having more than one ring where at least one ring is aromatic may be connected to the parent structure at either a non-aromatic ring position or at an aromatic ring position. In one variation, a heterocycle having more than one ring where at least one ring is aromatic is connected to the parent structure at a non-aromatic ring position.

"Substituted heterocyclic" or "substituted heterocyclyl" refers to a heterocycle group which is substituted with from 1 to 3 substituents including, but not limited to, substituents such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted aralkyl, aminosulfonyl, sulfonylamino, sulfonyl, oxo, carbonylalkylenealkoxy and the like. In one variation, a substituted heterocycle is a heterocycle substituted with an additional ring, wherein the additional ring may be aromatic or non-aromatic.

"Aryl" or "Ar" refers to an unsaturated aromatic carbocyclic group having a single ring (e.g., phenyl) or multiple condensed rings (e.g., naphthyl or anthryl) which condensed rings may or may not be aromatic. In one variation, the aryl group contains from 6 to 14 annular carbon atoms. An aryl group having more than one ring where at least one ring is non-aromatic may be connected to the parent structure at either an aromatic ring position or at a non-aromatic ring position. In one variation, an aryl group having more than one ring where at least one ring is non-aromatic is connected to the parent structure at an aromatic ring position.

"Heteroaryl" or "HetAr" refers to an unsaturated aromatic carbocyclic group having from 1 to 10 annular carbon atoms and at least one annular heteroatom, including but not limited to heteroatoms such as nitrogen, oxygen and sulfur. A heteroaryl group may have a single ring (e.g., pyridyl, furyl) or multiple condensed rings (e.g., indolizinyl, benzothienyl) which condensed rings may or may not be aromatic. A heteroaryl group having more than one ring where at least one ring is non-aromatic may be connected to the parent structure at either an aromatic ring position or at a non-aromatic ring position. In one variation, a heteroaryl group having more than one ring where at least one ring is non-aromatic is connected to the parent structure at an aromatic ring position.

"Substituted aryl" refers to an aryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Substituted heteroaryl" refers to a heteroaryl group having 1 to 5 substituents including, but not limited to, groups such as alkoxy, substituted alkoxy, acyl, acyloxy, carbonylalkoxy, acylamino, substituted or unsubstituted amino, aminoacyl, aminocarbonylamino, aminocarbonyloxy, aryl, substituted aryl, heteroaryl, substituted heteroaryl, aryloxy, substituted aryloxy, cyano, halo, hydroxyl, nitro, carboxyl, thiol, thioalkyl, substituted or unsubstituted alkyl, substituted or unsubstituted alkenyl, substituted or unsubstituted alkynyl, substituted or unsubstituted heterocyclyl, substituted or unsubstituted aralkyl, aminosulfonyl, sulfonylamino, sulfonyl, oxo, carbonylalkylenealkoxy and the like.

"Aralkyl" refers to a residue in which an aryl moiety is attached to an alkyl residue and wherein the aralkyl group may be attached to the parent structure at either the aryl or the alkyl residue. Preferably, an aralkyl is connected to the parent structure via the alkyl moiety. In one variation, an aralkyl is a fused ring system where at least one cycloalkyl moiety is fused with at least one aryl moiety. A "substituted aralkyl" refers to a residue in which an aryl moiety is attached to a substituted alkyl residue and wherein the aralkyl group may be attached to the parent structure at either the aryl or the alkyl residue. When an aralkyl is connected to the parent structure via the alkyl moiety, it may also be referred to as an "alkaryl". More particular alkaryl groups are those having 1 to 3 carbon atoms in the alkyl moiety (a "$C_1$-$C_3$ alkaryl").

"Alkoxy" refers to the group alkyl-O—, which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. Similarly, alkenyloxy refers to the group "alkenyl-O—" and alkynyloxy refers to the group "alkynyl-O—". "Substituted alkoxy" refers to the group substituted alkyl-O.

"Unsubstituted amino" refers to the group —$NH_2$.

"Substituted amino" refers to the group —$NR_aR_b$, where either (a) each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, provided that both $R_a$ and $R_b$ groups are not H; or (b) $R_a$ and $R_b$ are joined together with the nitrogen atom to form a heterocyclic or substituted heterocyclic ring.

"Acylamino" refers to the group —$C(O)NR_aR_b$ where $R_a$ and $R_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic or $R_a$ and $R_b$ groups can be joined together with the nitrogen atom to form a heterocyclic or substituted heterocyclic ring.

"Aminoacyl" refers to the group —$NR_aC(O)R_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic or substituted heterocyclic. Preferably, $R_a$ is H or alkyl.

"Aminosulfonyl" refers to the groups —$NRSO_2$-alkyl, —$NRSO_2$ substituted alkyl, —$NRSO_2$-alkenyl, —$NRSO_2$-substituted alkenyl, —$NRSO_2$-alkynyl, —$NRSO_2$— substituted alkynyl, —$NRSO_2$-cycloalkyl, —$NRSO_2$-substituted cycloalkyl, —$NRSO_2$-aryl, —$NRSO_2$-substituted aryl, —$NRSO_2$-heteroaryl, —$NRSO_2$— substituted heteroaryl, —$NRSO_2$-heterocyclic, and —$NRSO_2$— substituted heterocyclic, where R is H or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Sulfonylamino" refers to the groups —$SO_2NH_2$, —$SO_2NR$-alkyl, —$SO_2NR$-substituted alkyl, —$SO_2NR$-alkenyl, —$SO_2NR$-substituted alkenyl, —$SO_2NR$-alkynyl, —$SO_2NR$-substituted alkynyl, —$SO_2NR$-aryl, —$SO_2NR$-substituted aryl, —$SO_2NR$-heteroaryl, —$SO_2NR$-substituted heteroaryl, —$SO_2NR$-heterocyclic, and —$SO_2NR$-substituted heterocyclic, where R is H or alkyl, or —$SO_2NR_2$, where the two R groups are taken together and with the nitrogen atom to which they are attached to form a heterocyclic or substituted heterocyclic ring.

"Sulfonyl" refers to the groups —$SO_2$-alkyl, —$SO_2$-substituted alkyl, —$SO_2$-alkenyl, —$SO_2$-substituted alkenyl, —$SO_2$-alkynyl, —$SO_2$-substituted alkynyl, —$SO_2$-aryl, —$SO_2$-substituted aryl, —$SO_2$-aralkyl, —$SO_2$-substituted aralkyl, —$SO_2$-heteroaryl, —$SO_2$-substituted heteroaryl, —$SO_2$-heterocyclic, and —$SO_2$-substituted heterocyclic.

"Aminocarbonylalkoxy" refers to the group —$NR_aC(O)OR_b$ where each $R_a$ and $R_b$ group is independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic and substituted heterocyclyl.

"Carbonylalkylenealkoxy" refers to the group —$C(O)$—$(CH_2)_n$—OR where R is a substituted or unsubstituted alkyl and n is an integer from 1 to 100, more preferably n is an integer from 1 to 10 or 1 to 5.

"Halo" or "halogen" refers to elements of the Group 17 series having atomic number 9 to 85. Preferred halo groups include the radicals of fluorine, chlorine, bromine and iodine. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halogen; thus 4-chloro-3-fluorophenyl is within the scope of dihaloaryl. An alkyl group in which each H is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—OCF$_3$).

"Carbonyl" refers to the group C=O.
"Cyano" refers to the group —CN.
"Oxo" refers to the moiety =O.
"Nitro" refers to the group —NO$_2$.
"Thioalkyl" refers to the groups —S-alkyl.
"Alkylsulfonylamino" refers to the groups —R$^1$SO$_2$NR$_a$R$_b$ where R$_a$ and R$_b$ are independently selected from the group consisting of H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, or the R$_a$ and R$_b$ groups can be joined together with the nitrogen atom to form a heterocyclic or substituted heterocyclic ring and R$^1$ is an alkyl group.

"Carbonylalkoxy" refers to as used herein refers to the groups —C(O)O-alkyl, —C(O)O-substituted alkyl, —C(O)O-aryl, —C(O)O-substituted aryl, —C(O)O-alkenyl, —C(O)O-substituted alkenyl, —C(O)O-alkynyl, —C(O)O-substituted alkynyl, —C(O)O-heteroaryl, —C(O)O-substituted heteroaryl, —C(O)O-heterocyclic or —C(O)O-substituted heterocyclic.

"Geminal" refers to the relationship between two moieties that are attached to the same atom. For example, in the residue —CH$_2$—CHR$^1$R$^2$, R$^1$ and R$^2$ are geminal and R$^1$ may be referred to as a geminal R group to R$^2$.

"Vicinal" refers to the relationship between two moieties that are attached to adjacent atoms. For example, in the residue —CHR$^1$—CH$_2$R$^2$, R$^1$ and R$^2$ are vicinal and R$^1$ may be referred to as a vicinal R group to R$^2$.

Receptor Binding Profile

In some embodiments, compounds that bind to and are antagonists of the adrenergic receptor $\alpha_{2B}$, but which are not antagonists of the adrenergic receptor $\alpha_{2A}$, and pharmaceutically acceptable salts thereof, are provided. The compounds may find use in therapy for decreasing blood pressure in an individual and in treating diseases or conditions which are responsive to (i) a decrease in blood pressure and/or (ii) an increase in renal blood flow and/or (iii) a decrease or inhibition of sodium reabsorption or sodium retention. Thus, an individual who has a disease or condition that is responsive to (i) a decrease in blood pressure and/or (ii) an increase in renal blood flow and/or (iii) a decrease or inhibition of sodium reabsorption or sodium retention will experience one or more beneficial or desirable results upon administration of a compound provided herein, or pharmaceutically acceptable salt thereof. In one aspect, the beneficial or desirable result is a reduction in the individual's mean arterial blood pressure for a period of time following administration of the compound or pharmaceutically acceptable salt thereof. In another aspect, the beneficial or desirable result is a reduction in the individual's systolic blood pressure for a period of time following administration of the compound or pharmaceutically acceptable salt thereof. In a further aspect, the beneficial or desirable result is an increase in renal blood flow (e.g., by altering the vascular tone of renal efferent and afferent arterioles) for a period of time following administration of the compound or pharmaceutically acceptable salt thereof. In another aspect, the beneficial or desirable result is a decrease or inhibition in sodium reabsorption (e.g., thereby exerting a natriuretic and diuretic effect) for a period of time following administration of the compound or pharmaceutically acceptable salt thereof. In another aspect, the beneficial or desirable result is an increase in urine sodium and/or urine volume for a period of time following administration of the compound or pharmaceutically acceptable salt thereof. In one variation, the compounds may find use in therapy in treating diseases or conditions which are responsive to (i) a decrease in blood pressure and (ii) an increase in renal blood flow. In one variation, the compounds my find use in therapy in treating diseases or conditions which are responsive to (i) a decrease in blood pressure and (ii) a decrease or inhibition of sodium reabsorption. In one variation, the compounds may find use in treating diseases or conditions which are responsive to (i) an increase in renal blood flow and (ii) a decrease or inhibition of sodium reabsorption. In one variation, the compounds may find use in therapy in treating diseases or conditions which are responsive to (i) a decrease in blood pressure and (ii) an increase in renal blood flow and (iii) a decrease or inhibition of sodium reabsorption.

Compounds that bind to and are antagonists of the adrenergic receptor $\alpha_{2B}$ should reduce an individual's blood pressure. However, compounds that antagonize the adrenergic receptor $\alpha_{2A}$ in some instances may actually increase an individual's blood pressure. Thus, compounds that antagonize the adrenergic receptor $\alpha_{2B}$ but do not antagonize the adrenergic receptor $\alpha_{2A}$ (compounds referred to herein as "selective adrenergic receptor $\alpha_{2B}$ antagonists") are desirable agents in therapy. Selective adrenergic receptor $\alpha_{2B}$ antagonists find further use in therapy of cardiovascular and renal indications. The selective adrenergic receptor $\alpha_{2B}$ antagonists provided herein (i) bind to and are antagonists of the adrenergic receptor $\alpha_{2B}$, and (ii) are not antagonists of the adrenergic receptor $\alpha_{2A}$.

The selective adrenergic receptor $\alpha_{2B}$ antagonists may in some variations also bind to and be agonists of the adrenergic receptor $\alpha_{2A}$. The selective adrenergic receptor $\alpha_{2B}$ antagonists may also be used in conjunction with other agents that are agonists of the adrenergic receptor $\alpha_{2A}$.

The selective adrenergic receptor $\alpha_{2B}$ antagonists may in some variations also bind to and be antagonists of the adrenergic receptor $\alpha_{1B}$. The selective adrenergic receptor $\alpha_{2B}$ antagonists may also be used in conjunction with other agents that are antagonists of the adrenergic receptor $\alpha_{1B}$ The selective adrenergic receptor $\alpha_{2B}$ antagonists may in some variations also bind to and be antagonists of the adrenergic receptor $\alpha_{1D}$. The selective adrenergic receptor $\alpha_{2B}$ antagonists may also be used in conjunction with other agents that are antagonists of the adrenergic receptor $\alpha_{1D}$ The selective adrenergic receptor $\alpha_{2B}$ antagonists may in some variations both (i) bind to and be agonists of the adrenergic receptor $\alpha_{2A}$ and (ii) bind to and be antagonists of the adrenergic receptor $\alpha_{1B}$ and/or $\alpha_{1D}$.

In one variation, a selective adrenergic receptor $\alpha_{2B}$ antagonist exhibits (i) equal to or greater than about 60% inhibition of $\alpha_{2B}$ ligand binding at 0.03 μM and antagonist activity to adrenergic receptor $\alpha_{2B}$ and (ii) equal to or less than about 30% inhibition of $\alpha_{2A}$ ligand binding at 0.1 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.03 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.1 μM and absence of antagonist activity to adrenergic receptor $\alpha_{2A}$. In one variation, a selective adrenergic receptor $\alpha_{2B}$ antagonist exhibits (i) equal to or greater than about 60% inhibition of $\alpha_{2B}$ ligand binding at 0.1 μM and antagonist activity to adrenergic receptor $\alpha_{2B}$ and (ii) equal to or less than about 30% inhibition of $\alpha_{2A}$ ligand binding at 0.1 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.1 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.1 μM and absence of antagonist activity to adrenergic receptor $\alpha_{2A}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 μM and antagonist activity to adrenergic receptor $\alpha_{2B}$, and (ii) equal to or less than about 25% inhibition of $\alpha_{2A}$ ligand binding at 0.1 μM and absence of antagonist activity to adrenergic receptor $\alpha_{2A}$.

In one variation, a selective adrenergic receptor $\alpha_{2B}$ antagonist exhibits (i) equal to or greater than about 60% inhibition of $\alpha_{2B}$ ligand binding at 0.03 μM and antagonist activity to adrenergic receptor $\alpha_{2B}$ and (ii) equal to or less than about 30% inhibition of $\alpha_{2A}$ ligand binding at 0.03 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.03 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.03 μM and absence of antagonist activity to adrenergic receptor $\alpha_{2A}$. In one variation, a selective adrenergic receptor $\alpha_{2B}$ antagonist exhibits (i) equal to or greater than about 60% inhibition of $\alpha_{2B}$ ligand binding at 0.1 μM and antagonist activity to adrenergic receptor $\alpha_{2B}$ and (ii) equal to or less than about 30% inhibition of $\alpha_{2A}$ ligand binding at 0.03 μM and absence of antagonist activity to adrenergic receptor $\alpha_{2A}$. In one variation, a selective adrenergic receptor $\alpha_{2B}$ antagonist exhibits (i) equal to or greater than about any one of 60%, 65%, 70%, 75%, 80%, 85%, 90%, or 95%, or between about 60% and about 90%, between about 70% and about 90%, or between about 80% and about 100% inhibition of $\alpha_{2B}$ ligand binding at 0.1 μM and antagonist activity to adrenergic receptor $\alpha_{2B}$, and (ii) equal to or less than about any one of 30%, 25%, 20%, 15%, 10%, or 5%, or between about 0% and about 30%, between about 10% and about 30%, or between about 20% and about 30% inhibition of $\alpha_{2A}$ ligand binding at 0.03 μM and absence of antagonist activity to adrenergic receptor $\alpha_{2A}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 μM and antagonist activity to adrenergic receptor $\alpha_{2B}$, and (ii) equal to or less than about 25% inhibition of $\alpha_{2A}$ ligand binding at 0.03 μM and absence of antagonist activity to adrenergic receptor $\alpha_{2A}$.

In another variation, a selective adrenergic receptor $\alpha_{2B}$ antagonist has a Ki ratio of $\alpha_{2A}$ to $\alpha_{2B}$ that is greater than about any one of 5 or 15 or 50. Ki is the binding affinity from the Cheng-Prusoff equation: $Ki=IC_{50}/(1+[S]/Kd)$, wherein [S] is the concentration of the radioligand and Kd is dissociation constant (affinity) of the radioligand for the protein (Cheng, Y., Prusoff, W. H., Biochem. Pharmacol. 22:3099-3108, 1973). It is understood that the Ki ratio of $\alpha_{2A}$ to $\alpha_{2B}$ may be combined with any binding and/or other activity profile details described herein for selective adrenergic receptor $\alpha_{2B}$ antagonists the same as if each were specifically and individually listed. For example, in one variation, a selective adrenergic receptor $\alpha_{2B}$ antagonist may exhibit (i) equal to or greater than about 65% inhibition of $\alpha_{2B}$ ligand binding at 0.03 μM and antagonist activity to adrenergic receptor $\alpha_{2B}$, and (ii) equal to or less than about 25% inhibition of $\alpha_{2A}$ ligand binding at 0.1 μM and absence of antagonist activity to adrenergic receptor $\alpha_{2A}$; and a Ki ratio of $\alpha_{2A}$ to $\alpha_{2B}$ that is greater than about any one of 5 or 15 or 50.

The selective adrenergic receptor $\alpha_{2B}$ antagonists may in some variations also bind to and be antagonists of the adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about 60% inhibition of $\alpha_{1B}$ ligand binding at 0.03 μM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ ligand binding at 0.03 μM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.1 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about 60% inhibition of $\alpha_{1B}$ ligand binding at 0.1 μM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 μM and absence of antagonist activity to adrenergic receptor $\alpha_{2A}$, and (iii) equal to or greater than about 60% inhibition of $\alpha_{1B}$ ligand binding at 0.1 μM and antagonist activity to adrenergic receptor $\alpha_{1B}$. In one variation, the selective adrenergic receptor $\alpha_{2B}$ antagonists may exhibit (i) equal to or greater than about 60% inhibition of $\alpha_{2B}$ ligand binding at 0.03 μM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ ligand binding at 0.1 µM and antagonist activity to adrenergic receptor $\alpha_{1B}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein and any of the adrenergic receptor $\alpha_{1B}$ binding profiles, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, (ii) equal to or less than about 25% inhibition of $\alpha_{2A}$ ligand binding at 0.1 µM and absence of antagonist activity to adrenergic receptor $\alpha_{2A}$, and (iii) equal to or greater than about 65% inhibition of $\alpha_{1B}$ ligand binding at 0.03 µM and antagonist activity to adrenergic receptor $\alpha_{1B}$. The selective adrenergic receptor $\alpha_{2B}$ antagonists may also be used in conjunction with other agents that antagonize the adrenergic receptor $\alpha_{1B}$. Administration in conjunction with another compound includes administration in the same or different composition, either sequentially, simultaneously, or continuously.

The selective adrenergic receptor $\alpha_{2B}$ antagonists may in some variations also bind to and be antagonists of the adrenergic receptor $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1D}$ ligand binding at 0.03 µM and antagonist activity to adrenergic receptor $\alpha_{1D}$. In another variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, (iii) equal to or greater than about 60% inhibition of $\alpha_{1B}$ ligand binding at 0.03 µM and antagonist activity to adrenergic receptor $\alpha_{1B}$ and (iv) equal to or greater than about 60% inhibition of $\alpha_{1D}$ ligand binding at 0.03 µM and antagonist activity to adrenergic receptor $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1D}$ and/or $\alpha_{1B}$ ligand binding at 0.03 µM and antagonist activity to adrenergic receptor $\alpha_{1D}$ and/or $\alpha_{1B}$. In one variation, the selective adrenergic receptor $\alpha_{2B}$ antagonists may exhibit (i) equal to or greater than about 60% inhibition of $\alpha_{2B}$ ligand binding at 0.1 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ and/or $\alpha_{1D}$ ligand binding at 0.1 µM and antagonist activity to adrenergic receptor $\alpha_{1B}$ and/or $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about 60% inhibition of $\alpha_{1B}$ and/or $\alpha_{1D}$ ligand binding at 0.1 µM and antagonist activity to adrenergic receptor $\alpha_{1B}$ and/or $\alpha_{1D}$. In one variation, the selective adrenergic receptor $\alpha_{2B}$ antagonists may exhibit (i) equal to or greater than about 60% inhibition of $\alpha_{2B}$ ligand binding at 0.03 µM and antagonist activity to adrenergic receptor $\alpha_{2B}$, (ii) equal to or less than about 30% inhibition of $\alpha_{2A}$ ligand binding at 0.1 µM and absence of antagonist activity to adrenergic receptor $\alpha_{2A}$, and (iii) equal to or greater than about any one of 60%, 65%, 70%, 75%, 80%, 85%, 90%, or 95%, or between about 60% and 90%, between about 70% and 90%, or between about 80% and about 100% inhibition of $\alpha_{1B}$ and/or $\alpha_{1D}$ ligand binding at 0.1 µM and antagonist activity to adrenergic receptor $\alpha_{1B}$ and/or $\alpha_{1D}$. It is understood and clearly conveyed herein that a selective adrenergic receptor $\alpha_{2B}$ antagonist can exhibit any of the adrenergic receptor $\alpha_{2B}$ binding profiles described herein in combination with any of the adrenergic receptor $\alpha_{2A}$ binding profiles described herein and any of the adrenergic receptor $\alpha_{1B}$ and/or $\alpha_{1D}$ binding profiles, as if each and every combination were listed separately. For example, a selective adrenergic receptor $\alpha_{2B}$ antagonist may exhibit (i) equal to or greater than about 65% inhibition of $\alpha_{2B}$ ligand binding at 0.03 µM and antagonist activity to adrenergic receptor $\alpha_{2B}$, (ii) equal to or less than about 25% inhibition of $\alpha_{2A}$ ligand binding at 0.1 µM and absence of antagonist activity to adrenergic receptor $\alpha_{2A}$, and (iii) equal to or greater than about 65% inhibition of $\alpha_{1D}$ ligand binding at 0.03 µM and antagonist activity to adrenergic receptor $\alpha_{1D}$. The selective adrenergic receptor $\alpha_{2B}$ antagonists may also be used in conjunction with other agents that antagonize the adrenergic receptor $\alpha_{1D}$. Administration in conjunction with another compound includes administration in the same or different composition, either sequentially, simultaneously, or continuously.

In some instances, compounds provided herein bind to and are antagonists of adrenergic receptor $\alpha_{2B}$ and may also be antagonists for the adrenergic receptor $\alpha_{2A}$. In such instances, it is preferable that the compound is more potent at inhibiting the adrenergic receptor $\alpha_{2B}$ compared to the adrenergic receptor $\alpha_{2A}$. In one variation, the compound inhibit both the adrenergic receptor $\alpha_{2B}$ and the adrenergic receptor $\alpha_{2A}$, and wherein the compound has limited or no brain bioavailability and so cannot easily activate adrenergic $\alpha_{2A}$ receptors in the brain. In one variation, the compound inhibits both the adrenergic receptor $\alpha_{2B}$ and the adrenergic receptor $\alpha_{2A}$, and wherein the compound has brain bioavailability. In some other instances, compounds provided herein bind to and are antagonists of adrenergic receptor $\alpha_{2B}$ and may be inverse agonists for the adrenergic receptor $\alpha_{2A}$. In some embodiments, the compound (1) binds to and is an antagonist of adrenergic receptor $\alpha_{2B}$, and (2) binds to and is an antagonist and/or inverse agonist of the adrenergic receptor $\alpha_{2A}$. In some embodiments, the compound (1) binds to and is an antagonist of adrenergic receptor $\alpha_{2B}$, (2) binds to and is an antagonist and/or inverse agonist of the adrenergic receptor $\alpha_{2A}$, and (3) binds to and is antagonist of the adrenergic receptor $\alpha_{1B}$ and/or the adrenergic receptor $\alpha_{1D}$. It is understood and clearly conveyed herein that an adrenergic receptor $\alpha_{2B}$ antagonist can exhibit any of the adrenergic receptor $\alpha_{2B}$ binding profiles (in terms of % inhibition at a given concentration and/or in terms of $K_i$) described herein in combination with any of the adrenergic receptor $\alpha_{1B}$ and/or $\alpha_{1D}$ binding profiles, as if each and every combination were listed separately.

The binding properties to adrenergic receptors of compounds disclosed herein may be assessed by methods known in the art, such as competitive binding assays. In one variation, compounds are assessed by the binding assays detailed herein. In one variation, inhibition of binding of a ligand to a receptor is measured by the assays described herein. In another variation, inhibition of binding of a ligand is measured in an assay known in the art.

Functional Assay Profile

Antagonist activity to the adrenergic receptor $\alpha_{2B}$ receptor may be assessed by methods known in the art, such as standard $\alpha_{2B}$ receptor cell membrane-based or intact cell-based activity assays. For example, the GTPγS binding or Aequorin-based assays may be used. In one variation, the selective adrenergic receptor $\alpha_{2B}$ antagonists exhibit an $IC_{50}$ value equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)) in an $\alpha_{2B}$ antagonist assay. In one variation, a selective adrenergic receptor $\alpha_{2B}$ antagonist exhibits an $IC_{50}$ value in an $\alpha_{2B}$ antagonist assay equal to or less than about 10 nM at a given concentration of agonist (e.g., concentration corresponding to $EC_{80}$ of oxymetazoline (for Aequorin assay) or guanfacine (for GTPγS assay)) in an $\alpha_{2B}$ antagonist assay. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of oxymetazoline corresponding to its $EC_{80}$ concentration as obtained by assay protocols described herein. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of oxymetazoline between about 50 nM and about 5000 nM. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of about 480 nM oxymetazoline. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of guanfacine between about 50 nM and about 5000 nM. In one variation, a selective adrenergic receptor $\alpha_{2B}$ antagonist exhibits an $IC_{50}$ value in an $\alpha_{2B}$ antagonist assay equal to or less than about any one of 100 nM, 30 nM or 10 nM at a concentration of about 500 nM guanfacine, which in a particular variation is 504 nM guanfacine.

The absence of antagonist activity to the adrenergic receptor $\alpha_{2A}$ may be assessed by methods known in the art, such as standard $\alpha_{2A}$ receptor intact cell-based activity assays. For example, the Aequorin-based assay may be used. It is understood and clearly conveyed that absence of antagonist activity to the adrenergic receptor $\alpha_{2A}$ intends activity that is sufficiently reduced, but not necessarily eliminated or undetectable, at the adrenergic receptor $\alpha_{2A}$. In one variation, a compound will exhibit an undetectable amount of antagonist activity to the adrenergic receptor $\alpha_{2A}$. In another variation, a compound will lack antagonist activity to the adrenergic receptor $\alpha_{2A}$ if it exhibits an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304). In one variation, the adrenergic receptor $\alpha_{2A}$ exhibits an $IC_{50}$ value in an $\alpha_{2A}$ antagonist assay that is greater than about 200 nM at a given concentration of agonist (e.g., concentration corresponding to $EC_{80}$ of UK14304). In one variation, a selective adrenergic receptor $\alpha_{2B}$ antagonist exhibits an $IC_{50}$ value in an $\alpha_{2A}$ antagonist assay greater than about any one of 50 nM, 100 nM or 200 nM at a concentration of UK14304 corresponding to its $EC_{80}$ concentration as obtained by assay protocols described herein. In one variation, a selective adrenergic receptor $\alpha_{2B}$ antagonist exhibits an $IC_{50}$ value in an $\alpha_{2A}$ antagonist assay greater than about any one of 50 nM, 100 nM or 200 nM at a concentration of UK14304 between about 0.4 nM and about 40 nM. In one variation, a selective adrenergic receptor $\alpha_{2B}$ antagonists exhibits an $IC_{50}$ value in an $\alpha_{2A}$ antagonist assay greater than about any one of 50 nM, 100 nM or 200 nM at a concentration of about 5 nM UK14304, which in a particular variation is 4.57 nM UK14304. Alternatively, a compound that does not bind the $\alpha_{2A}$ receptor will be neither an agonist nor antagonist of the $\alpha_{2A}$ receptor.

In some variations, regardless of $IC_{50}$ values obtained from $\alpha_{2B}$ and $\alpha_{2A}$ assays, a compound may nonetheless be a selective adrenergic receptor $\alpha_{2B}$ antagonist if it exhibits a Ki ratio of $\alpha_{2A}$ to $\alpha_{2B}$ that is higher than about any one of 5, 10, or 15. For example, where a compound exhibits an $IC_{50}$ value between about 50-100 nM in an $\alpha_{2B}$ antagonist assay at a given concentration of agonist (e.g., concentration corresponding to $EC_{80}$ of oxymetazoline) and an $IC_{50}$ value between about 50 and 100 nM in an $\alpha_{2A}$ antagonist assay at a given concentration of agonist (e.g., concentration corresponding to $EC_{80}$ of UK14304), the compound is considered, in one variation, a selective adrenergic receptor $\alpha_{2B}$ antagonist if it exhibits a Ki ratio of $\alpha_{2A}$ to $\alpha_{2B}$ higher than about any one of 5, 10, or 15.

Antagonist activity to adrenergic receptor $\alpha_{1B}$ may be assessed by methods known in the art, such as standard $\alpha_{1B}$ receptor intact cell-based activity assays, including the Aequorin-based assay. In one variation, a selective adrenergic receptor $\alpha_{2B}$ antagonist will also antagonize the adrenergic receptor $\alpha_{1B}$ and exhibit an $IC_{50}$ value equal to or less than about any one of 100 nM or 30 nM or 10 nM at a given concentration of agonist (e.g., concentration corresponding to $EC_{80}$ of cirazoline) in an adrenergic receptor $\alpha_{1B}$ antagonist assay. In one variation, a selective adrenergic receptor $\alpha_{2B}$ antagonist will also antagonize the adrenergic receptor $\alpha_{1B}$ and exhibit an $IC_{50}$ value equal or less than about 10 nM at a given concentration of agonist (e.g., concentration corresponding to $EC_{80}$ of cirazoline) in an adrenergic receptor $\alpha_{1B}$ antagonist assay. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of cirazoline corresponding to its $EC_{80}$ concentration as obtained by assay protocols described herein. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of cirazoline between about 2.3 nM and about 230 nM. In one variation, the selective adrenergic receptor $\alpha_{2B}$ antagonists exhibit an $IC_{50}$ value in an $\alpha_{1B}$ antagonist assay equal to or less than about any one of 100 nM, 30 nM or 10 nM at a concentration of about 25 nM cirazoline, which in a particular variation is 23.56 nM cirazoline.

Antagonist activity to adrenergic receptor $\alpha_{1D}$ may be assessed by methods known in the art, such as standard $\alpha_{1D}$ receptor intact cell-based activity assays, including the Aequorin-based assay. In one variation, a selective adrenergic receptor $\alpha_{2B}$ antagonist will also antagonize the adrenergic receptor $\alpha_{1D}$ and exhibit an $IC_{50}$ value equal to or less than about any one of 100 nM or 30 nM or 10 nM at a given concentration of agonist (e.g., concentration corresponding to $EC_{80}$ of cirazoline) in an adrenergic receptor $\alpha_{1D}$ antagonist assay. In one variation, a selective adrenergic receptor $\alpha_{2B}$ antagonist will also antagonize the adrenergic receptor $\alpha_{1D}$ and exhibit an $IC_{50}$ value equal or less than about 10 nM at a given concentration of agonist (e.g., concentration corresponding to $EC_{80}$ of cirazoline) in an adrenergic receptor $\alpha_{1D}$ antagonist assay. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of cirazoline corresponding to its $EC_{80}$ concentration as obtained by assay protocols described herein. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of cirazoline between about 2.3 nM and about 230 nM. In one variation, the selective adrenergic receptor $\alpha_{2B}$ antagonists exhibit an $IC_{50}$ value in an $\alpha_{1D}$ antagonist assay equal to or less than about any one of 100 nM, 30 nM or 10 nM at a concentration of about 25 nM cirazoline, which in a particular variation is 23.56 nM cirazoline.

In one variation, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 µM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304). In some variations, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 µM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), and (iii) equal to or greater than about 60% inhibition of $\alpha_{1B}$ ligand binding at 0.03 µM and an $IC_{50}$ value in an $\alpha_{1B}$ antagonist assay equal or less than about any one of 100 nM or 30 nM or 10 nM at a given concentration of agonist (e.g., concentration corresponding to $EC_{80}$ of cirazoline). In some variations, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 µM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), and (iii) equal to or greater than about 60% inhibition of $\alpha_{1D}$ ligand binding at 0.03 µM and an $IC_{50}$ value in an $\alpha_{1D}$ antagonist assay equal or less than about any one of 100 nM or 30 nM or 10 nM at a given concentration of agonist (e.g., concentration corresponding to $EC_{80}$ of cirazoline). In some variations, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than about any one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) equal to or less than about 30% inhibition of $\alpha_{2A}$ ligand binding at 0.1 µM and an $IC_{50}$ value in an $\alpha_{2A}$ antagonist assay that is greater than about any one of 50 nM, 100 nM or 200 nM at a given concentration of agonist (e.g., concentration corresponding to $EC_{80}$ of UK14304), (iii) equal to or greater than about 60% inhibition of $\alpha_{1B}$ ligand binding at 0.03 µM and an $IC_{50}$ value in an $\alpha_{1B}$ antagonist assay equal or less than about any one of 100 nM or 30 nM or 10 nM at a given concentration of agonist (e.g., concentration corresponding to $EC_{80}$ of cirazoline); and (iv) equal to or greater than about 60% inhibition of $\alpha_{1D}$ ligand binding at 0.03 µM and an $IC_{50}$ value in an $\alpha_{1D}$ antagonist assay equal or less than about any one of 100 nM or 30 nM or 10 nM at a given concentration of agonist (e.g., concentration corresponding to $EC_{80}$ of cirazoline).

In another variation, the selective adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than any about one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) binding to and agonist activity to adrenergic receptor $\alpha_{2A}$.

In another variation, the adrenergic receptor $\alpha_{2B}$ antagonists exhibit (i) equal to or greater than about 60% inhibition of $\alpha_{2B}$ ligand binding at 0.03 µM and an $IC_{50}$ value in an $\alpha_{2B}$ antagonist assay equal to or less than any about one of 100 nM, 30 nM or 10 nM at a given concentration of agonist (e.g., concentration corresponding to $EC_{80}$ of oxymetazoline (for Aequorin assay) or guanfacine (for GTPγS assay)), and (ii) greater than or equal to about 30% inhibition of $\alpha_{2A}$ ligand binding at 0.1 µM and $IC_{50}$ value in an adrenergic receptor $\alpha_{2A}$ antagonist assay equal to or less than about any one of 100 nM, 30 nM or 10 nM at a concentration of UK14304 (for Aequorin assay) corresponding to its $EC_{80}$ concentration obtained by assay protocols described herein.

It is understood and clearly conveyed herein that compounds provided herein, including selective adrenergic receptor $\alpha_{2B}$ antagonists provided herein can exhibit any of the binding profiles and any of the antagonist or agonist activity profiles detailed herein, the same as if each and every combination were individually listed. For example, in one variation, the selective adrenergic receptor $\alpha_{2B}$ antagonists exhibit (i) greater than about 65% inhibition of $\alpha_{2B}$ ligand binding at 0.03 µM and an $IC_{50}$ value in an $\alpha_{2B}$ antagonist assay equal to or less than about 10 nM at a concentration of oxymetazoline corresponding to its $EC_{80}$ concentration as obtained by assay protocols described herein, and (ii) less than about 25% inhibition of $\alpha_{2A}$ ligand binding at 0.1 µM and an $IC_{50}$ value in an $\alpha_{2A}$ antagonist assay that is greater than 200 nM at a concentration of UK14304 corresponding to its $EC_{80}$ concentration as obtained by assay protocols described herein, and (iii) equal to or greater than about 60% inhibition of $\alpha_{1B}$ ligand binding at 0.03 µM and an $IC_{50}$ value in an $\alpha_{1B}$ antagonist assay equal or less than about 10 nM at a concentration of cirazoline corresponding to its $EC_{80}$ concentration as obtained by assay protocols described herein. In one aspect, such a compound will also exhibit a Ki ratio of $\alpha_{2A}$ to $\alpha_{2B}$ that is greater than about any one of 5 or 15 or 50.

Medical Use

Without being bound by theory, it is believed that the compounds provided herein are capable of (i) reducing blood pressure and/or (ii) promoting renal blood flow and/or (iii) decreasing or inhibiting sodium reabsorption. In some embodiments, the compounds are adrenergic receptor $\alpha_{2B}$ antagonists (e.g., selective adrenergic receptor $\alpha_{2B}$ antagonists). In some embodiments, it is believed that the selective adrenergic receptor $\alpha_{2B}$ antagonists provided herein are capable of (i) reducing blood pressure and/or (ii) promoting renal blood flow and/or (iii) decreasing or inhibiting sodium reabsorption without concomitantly antagonizing the $\alpha_{2A}$ receptor, which would reduce or potentially eliminate the beneficial blood pressure lowering and renal effects modulated by antagonizing $\alpha_{2B}$. Furthermore, the selective adrenergic receptor $\alpha_{2B}$ antagonists provided herein may be capable of decreasing blood pressure sensitivity to salt, decreasing sodium retention, decreasing vasoconstriction in small arteries and veins, increasing insulin secretion, increasing basal metabolic rate, decreasing platelet aggregation and/or enhancing mitochondrial function. However, in certain cases where the compound has strong antagonist activities against adrenergic receptor $\alpha_{2B}$ and/or adrenergic receptor $\alpha_{1B}$, some antagonist activity against adrenergic receptor $\alpha_{2A}$ may be tolerated and even beneficial.

Compounds provided herein may be capable of mediating control of the renal function. Adrenergic $\alpha_{2B}$ receptors are located within the kidney. Regard et al. (Cell 2008; 135:561) have demonstrated that the gene for the adrenergic $\alpha_{2B}$ receptor is most abundantly expressed in the kidney. Meister et al. (J. Pharmacol. Exp. Therapeutics 1994; 268:1605) have shown by in situ hypbridization that expression predominates in the medulla outer stripe with extensions into the cortical S3 segment of the proximal tubules. Adrenergic $\alpha_{2B}$ receptor antagonists provided herein may be capable of disrupting sodium reabsorption resulting in natriuresis and diuresis. Methods to determine effects of adrenergic $\alpha_{2B}$ antagonists on renal function in a rabbit model of hypertension have been described by Burke et al. (J Hypertens 29:945-952).

In addition to reducing blood pressure, compounds disclosed herein, including adrenergic $\alpha_{2B}$ antagonists, are capable of a reduction in blood volume that might result from diueresis and/or the movement of fluid from the vascular space to the extravascular space. Reduction of blood volume results in increase in hematocrit levels which can be measured by methods known in the art, for example, by estimation of erythrocyte volume fraction. Characterization of the effect of $\alpha_{2B}$ antagonists on renal function are determined by measuring urine volume, urine sodium and urine potassium using methods described by Burke et al. (Effects of chronic sympatho-inhibition on renal excretory function in renovascular hypertension Sandra L. Burke, Roger G. Evans and Geoffrey A. Head. Journal of Hypertens 29:945-952 (2011).

The compounds detailed herein are expected to find use in therapy, particularly in cardiac and renal diseases and conditions, in addition to hypertension and other conditions in which a (i) reduction in blood pressure and/or (ii) increase in renal blood flow and/or (iii) decrease in sodium reabsorption would be beneficial. In the methods provided herein, an effective amount of a compound detailed herein is administered to an individual. Methods of using compounds as described herein to (i) reduce blood pressure and/or (ii) promote renal blood flow and/or (iii) decrease or inhibit sodium reabsorption in an individual in need thereof are provided. The compounds may also find use in treating a disease or condition that is, or is expected to be, responsive to (i) a reduction in an individual's blood pressure and/or (ii) an increase in renal blood flow and/or (iii) a decrease or inhibition of sodium reabsorption. The individual may be a human who has been diagnosed with or is suspected of having high blood pressure or a disease or condition that is, or is expected to be, responsive to (i) a reduction in an individual's blood pressure and/or (ii) an increase in renal blood flow and/or (iii) a decrease or inhibition of sodium reabsorption. The individual may be a human who exhibits one or more symptoms associated with high blood pressure or a disease or condition that is, or is expected to be, responsive to (i) a reduction in an individual's blood pressure and/or (ii) an increase in renal blood flow and/or (iii) a decrease or inhibition of sodium reabsorption. The individual may be a human who is genetically or otherwise predisposed to developing high blood pressure or a disease or condition that is, or is expected to be, responsive to (i) a reduction in an individual's blood pressure and/or (ii) an increase in renal blood flow and/or (iii) a decrease or inhibition of sodium reabsorption. In one variation, the compounds may find use in treating metabolic syndrome. In some embodiments, the compounds are adrenergic receptor $\alpha_{2B}$ antagonists. In one variation, the adrenergic receptor $\alpha_{2B}$ antagonists are selective adrenergic receptor $\alpha_{2B}$ antagonists. In one variation, a compound that is an adrenergic receptor $\alpha_{2B}$ antagonist also showing adrenergic receptor $\alpha_{2A}$ antagonist and/or inverse agonist activity may find use reducing blood pressure in an individual with hypertension who is also suffering from obesity, type-2 diabetes and/or metabolic syndrome. Thus, provided is a method for lowering blood pressure in hypertensive patients with a disease or condition that is responsive to treatment using an antagonist or inverse agonist of adrenergic receptor $\alpha_{2A}$, such as obesity and/or type-2 diabetes and/or metabolic syndrome.

Compounds detailed herein may be used in a method of treating a disease or condition that is responsive to (i) a reduction in an individual's blood pressure and/or (ii) an increase in renal blood flow and/or (iii) a decrease or inhibition of sodium reabsorption. For example, the compounds may find use in treating hypertension, including treatment-resistant hypertension. In some embodiments, the compounds may be used in a method of treating hypertension in an individual not suffering from obesity or type-2 diabetes. In some embodiments, the compounds are adrenergic receptor $\alpha_{2B}$ antagonists. In some embodiments, the compounds are selective adrenergic receptor $\alpha_{2B}$ antagonists.

In one aspect, the disease or indication is a cardiac or renal disease or indication for which (i) a reduction in an individual's blood pressure and/or (ii) an increase in renal blood flow and/or (iii) a decrease or inhibition of sodium reabsorption would be, or would be expected to be, beneficial. Such cardiac indications include, but are not limited to, heart failure, such as compensated heart failure, decompensated heart failure, acute decompensated congestive heart failure and chronic congestive heart failure, coronary heart disease, cardiac arrhythmias, myocardial ischemia, and hypertrophy. Such renal indications include, but are not limited to, renal failure such as chronic renal failure, acute renal failure and endstage renal failure, renal ischemia and chronic kidney disease. Other indications for which (i) a reduction in an individual's blood pressure and/or (ii) an increase in renal blood flow and/or (iii) a decrease or inhibition of sodium reabsorption would be, or would be expected to be, beneficial include but are not limited to sleep apnea and ischemic attacks.

Compounds detailed herein may also ameliorate symptoms of a disease or condition that have a cardiac or renal component in which (i) a reduction in an individual's blood pressure and/or (ii) an increase in renal blood flow and/or (iii) a decrease or inhibition of sodium reabsorption would be, or would be expected to be, beneficial. For example, the compounds may reduce elevated blood pressure, improve shortness of breath, reduce tachycardia, reduce edema, reduce elevated blood urea nitrogen to creatinine (BUN/Cr) ratio, improve creatinine levels, improve the ability to lie flat, reduce the incidence or severity of high blood pressure, reduce the risk and/or number of acute cardiac events (e.g., acute decompensation or myocardial infarction) an individual experiences over a period of time (e.g., one year, 2 years, 5 years, etc.), reduce the incidence of acute heart failure an individual experiences over a period of time (e.g., one year, 2 years, 5 years, etc.), reduce the severity and/or incidence of pulmonary congestion and/or reduce the risk of stroke, reduce shortness of breath and/or tachycardia in individuals after myocardial infarction, improve left ventricular ejection fraction (LVEF) post infarct and/or lower weight and blood pressure in obese individuals (e.g., men and women) with prehypertension. In some embodiments, the compounds are adrenergic receptor $\alpha_{2B}$ antagonists. In some embodiments, the compounds are selective adrenergic receptor $\alpha_{2B}$ antagonists.

Compounds detailed herein (such as the adrenergic receptor $\alpha_{2B}$ antagonists detailed herein) may find use in the treatment of hypertensive emergencies. Provided is a method of treating hypertensive emergencies, comprising administering intravenously an effective amount of an adrenergic receptor $\alpha_{2B}$ antagonist to an individual in need thereof. In some embodiments, the method comprises administering intravenously an effective amount of an adrenergic receptor $\alpha_{2B}$ antagonist to an individual in need thereof in a highly monitored intensive care setting, wherein the administration results in aggressive and controlled blood pressure lowering in the individual. In some embodiments, intravenous administration of an adrenergic receptor $\alpha_{2B}$ antagonist in an individual results in gradually lowering of blood pressure in the individual and minimizing damage of end organs such as the brain, kidney, heart, and eye. Particularly useful in the treatment of hypertensive emergencies or crisis are parenteral formulations of an adrenergic receptor $\alpha_{2B}$ antagonist detailed herein. In one variation, the compound is an adrenergic receptor $\alpha_{2B}$ antagonist. In some variations, the compound is a selective adrenergic receptor $\alpha_{2B}$ antagonist. In one variation, the adrenergic receptor $\alpha_{2B}$ antagonist also exhibits adrenergic receptor $\alpha_{2A}$ antagonist and/or inverse agonist activity.

In one variation, a method of decreasing the severity and/or incidence of shortness of breath, tachycardia, edema, and/or the inability to lie flat is provided, comprising administering an effective amount of a compound detailed herein to an individual who has or is suspected of having heart failure (e.g., compensated heart failure and decompensated heart failure). In another variation, a method of decreasing the severity and/or incidence of elevated BUN/Cr, and/or edema is provided comprising administering an effective amount of a compound detailed herein to an individual who has or is suspected of having renal failure (e.g., acute or chronic renal failure). In another variation, a method of reducing blood pressure in an individual is provided comprising administering an effective amount of a compound detailed herein to an individual who has or is suspected of having hypertension (e.g., treatment-resistant hypertension). In another variation, a method of decreasing the severity and/or incidence of shortness of breath, tachycardia, and/or improving LVEF post infarct in an individual is provided comprising administering an effective amount of a compound detailed herein to an individual who has experienced myocardial infarction (e.g., an individual who has recently experienced myocardial infarction such as within 30 minutes, 1, 3, 6, 12, or 24 hours of treatment). In some of the variations, the adrenergic receptor $\alpha_{2B}$ antagonist is a selective adrenergic receptor $\alpha_{2B}$ antagonist. In some of the variations, the adrenergic receptor $\alpha_{2B}$ antagonist also exhibits antagonist activity for the adrenergic receptor $\alpha_{2A}$. In some embodiments, the compounds are adrenergic receptor $\alpha_{2B}$ antagonists. In some embodiments, the compounds are selective adrenergic receptor $\alpha_{2B}$ antagonists.

In one variation, provided is method for lowering the blood pressure in an individual in need thereof comprising administering to the individual a compound described herein, or a pharmaceutically acceptable salt thereof. Administration of an adrenergic receptor $\alpha_{2B}$ antagonist detailed herein lowers the blood pressure in the individual from a level considered above the desired level for such individual. The blood pressure lowering therapy such as administration of compounds detailed herein is intended to help hypertensive individuals reach their blood pressure goals defined by their individual cardiovascular risk factors. For example, for otherwise healthy individuals without diabetes or known cardiovascular disease, goal blood pressure is less than about 140/90 mmHg; for patients with known cardiovascular disease (e.g., prior myocardial infarction, peripheral vascular disease) goal blood pressure is less than about 130-135/85 mmHg; for patients with diabetes, goal blood pressure is less than about 130/80 mmHg.

In one variation, compounds provided herein may have any one or more of the following beneficial effects on an individual: (1) reduce arterial blood pressure (e.g., in an individual with hypertension, certain forms of heart failure and/or renal failure); (2) reduce pulse pressure (e.g., in an individual with hypertension, certain forms of heart failure and/or renal failure); (3) tachycardia-preserved baroreceptor activity (e.g., in an individual whose systolic blood pressure is expected to or does fall in response to an $\alpha_{2B}$ antagonist), which may suggest a lack of orthostatic hypotension; and (4) bradycardia-reduced cardiac work load and added reduction on blood pressure reduction by further reducing cardiac output (e.g., in an individual who has been administered a therapy that is an $\alpha_{2B}$ and $\alpha_{1B}$ mixed antagonist).

In another variation, compounds provided herein may exert their therapeutic effect with no or reduced side-effects, such as when compared to other therapies used in the treatment of the same or similar indication. In one aspect, compounds provided herein exhibit no or reduced side effects upon administration to an individual, wherein the side effects may be any one or more of: (i) reduced libido, (ii) orthostatic hypotension, (iii) muscle weakness, (iv) fatigue, (v) erectile dysfunction, (vi) constipation, (vii) depression, (viii) dizziness, (ix) dry mouth, (x) impaired thinking, (xi) weight gain, (xii) persistent cough, (xiii) chest pain, (xiv) headache, (xv) fluid retention, (xvi) racing pulse, and (xvii) emesis.

In one aspect, compounds are provided that do not bind appreciably any one or more of the histamine, dopamine and serotonin receptors. In any of the methods detailed herein, in one variation the individual does not have a cognitive disorder, psychotic disorder, neurotransmitter-mediated disorder and/or neuronal disorder. As used herein, the term "cognitive disorders" refers to and intends diseases and conditions that are believed to involve or be associated with or do involve or are associated with progressive loss of structure and/or function of neurons, including death of neurons, and where a central feature of the disorder may be the impairment of cognition (e.g., memory, attention, perception and/or thinking). These disorders include pathogen-induced cognitive dysfunction, e.g., HIV associated cognitive dysfunction and Lyme disease associated cognitive dysfunction. Examples of cognitive disorders include Alzheimer's Disease, Huntington's Disease, Parkinson's Disease, schizophrenia, amyotrophic lateral sclerosis (ALS), autism, mild cognitive impairment (MCI), stroke, traumatic brain injury (TBI) and age-associated memory impairment (AAMI). As used herein, the term "psychotic disorders" refers to and intends mental diseases or conditions that are believed to cause or do cause abnormal thinking and perceptions. Psychotic disorders are characterized by a loss of reality which may be accompanied by delusions, hallucinations (perceptions in a conscious and awake state in the absence of external stimuli which have qualities of real perception, in that they are vivid, substantial, and located in external objective space), personality changes and/or disorganized thinking. Other common symptoms include unusual or bizarre behavior, as well as difficulty with social interaction and impairment in carrying out the activities of daily living. Exemplary psychotic disorders are schizophrenia, bipolar disorders, psychosis, anxiety and depression. As used herein, the term "neurotransmitter-mediated disorders" refers to and intends diseases or conditions that are believed to involve or be associated with or do involve or are associated with abnormal levels of neurotransmitters such as histamine, serotonin, dopamine, norepinephrine or impaired function of aminergic G protein-coupled receptors. Exemplary neurotransmitter-mediated disorders include spinal cord injury, diabetic neuropathy, allergic diseases and diseases involving geroprotective activity such as age-associated hair loss (alopecia), age-associated weight loss and age-associated vision disturbances (cataracts). Abnormal neurotransmitter levels are associated with a wide variety of diseases and conditions including, but not limited to Alzheimer's disease, Parkinson's Disease, autism, Guillain-Barré syndrome, mild cognitive impairment, schizophrenia, anxiety, multiple sclerosis, stroke, traumatic brain injury, spinal cord injury, diabetic neuropathy, fibromyalgia, bipolar disorders, psychosis, depression and a variety of allergic diseases. As used herein, the term "neuronal disorders" refers to and intends diseases or conditions that are believed to involve, or be associated with, or do involve or are associated with neuronal cell death and/or impaired neuronal function or decreased neuronal function. Exemplary neuronal indications include neurodegenerative diseases and disorders such as Alzheimer's disease, Huntington's disease, amyotrophic lateral sclerosis (ALS), Parkinson's disease, canine cognitive dysfunction syndrome (CCDS), Lewy body disease, Menkes disease, Wilson disease, Creutzfeldt-Jakob disease, Fahr disease, an acute or chronic disorder involving cerebral circulation, such as ischemic or hemorrhagic stroke or other cerebral hemorrhagic insult, age-associated memory impairment (AAMI), mild cognitive impairment (MCI), injury-related mild cognitive impairment (MCI), post-concussion syndrome, post-traumatic stress disorder, adjuvant chemotherapy, traumatic brain injury (TBI), neuronal death mediated ocular disorder, macular degeneration, age-related macular degeneration, autism, including autism spectrum disorder, Asperger syndrome, and Rett syndrome, an avulsion injury, a spinal cord injury, myasthenia gravis, Guillain-Barré syndrome, multiple sclerosis, diabetic neuropathy, fibromyalgia, neuropathy associated with spinal cord injury, schizophrenia, bipolar disorder, psychosis, anxiety or depression.

Individuals who have high blood pressure, or a disease or condition that is, or is expected to be, responsive to (i) a reduction in an individual's blood pressure and/or (ii) an increase in renal blood flow and/or (iii) a decrease or inhibition of sodium reabsorption may benefit from the compounds detailed herein, including the adrenergic receptor $\alpha_{2B}$ antagonists (e.g., the selective adrenergic receptor $\alpha_{2B}$ antagonist) detailed herein.

An individual who does not have high blood pressure or a disease or condition that is, or is expected to be, responsive to (i) a reduction in an individual's blood pressure and/or (ii) an increase in renal blood flow and/or (iii) a decrease or inhibition of sodium reabsorption may nevertheless benefit from the compounds detailed herein if the individual has one or more risk factors for high blood pressure, or a disease or condition that is, or is expected to be, responsive to (i) a reduction in an individual's blood pressure and/or (ii) an increase in renal blood flow and/or (iii) a decrease or inhibition of sodium reabsorption. Risk factors for developing high blood pressure may include gender, race, ethnicity, age, family history, weight and/or lifestyle. For example, African-Americans, men (particularly if over age 45), woman over age 55, anyone over age 60, pre-hypertension individuals (individuals with a blood pressure of 120-130/80-89 mmHg), individuals who are overweight or obese, individuals with sleep apnea (such as obstructive sleep apnea), individuals who smoke, individuals who have a high salt diet, individuals who have a low potassium diet, individuals with chronic heavy alcohol use, individuals with a sedentary lifestyle, individuals with moderate to high stress, individuals with compromised renal function or renal failure and individuals with close relatives who have high blood pressure are each at an increased risk of developing high blood pressure themselves, or diseases or conditions associated with high blood pressure. Individuals with more than one such risk factor are particularly susceptible to developing high blood pressure. Risk factors for developing kidney disease may include diabetes, high blood pressure (hypertension), cardiovascular diseases, smoking, obesity, high cholesterol, a family history of kidney disease, and/or age 65 or older. Members of certain ethnic groups are also at higher risk for kidney disease including people of Aboriginal, Asian, south Asian, Pacific Island, African/Caribbean, American Indian and Hispanic origin.

Cell Viability and Mitochondrial Health

Methods of promoting cellular viability by promoting mitochondrial health are provided, the methods comprising contacting the cell with a compound detailed herein. The methods are applicable to various cells, such as neuronal and non-neuronal cells. In one variation, the cell is a non-neuronal cell, such as a renal or cardiac cell (e.g., myocardial muscle cell). In one aspect, methods of promoting cellular viability are provided wherein the cell is one whose viability would be, or would be expected to be, promoted by nutrient influx and/or oxygenation. Methods of promoting cellular viability in a cell experiencing, or exhibiting symptoms of, mitochondrial stress are also provided.

Methods of treating a disease or condition that is, or is expected to be, responsive to promoting mitochondrial health and cell viability are also described, the methods comprising administering to an individual in need thereof an effective amount of a compound provided herein. In one variation, the disease or condition is one which is associated with dysfunction of mitochondria in a non-neuronal cell. In a particular variation, the disease or condition is one which is associated with dysfunction of mitochondria in a renal or cardiac cell (e.g., myocardial muscle cell). In another variation, the disease or condition is one which would benefit from cellular (e.g., renal or cardiac) nutrient influx and/or oxygenation.

Thus, individuals who have a disease or condition that is associated with, or believed to be associated with, mitochondrial dysfunction may benefit from the compounds detailed herein, or pharmaceutically acceptable salts thereof. An individual who has a disease or condition that is associated with mitochondrial dysfunction should experience one or more beneficial or desirable results upon administration of an effective amount of a compound provided herein, or pharmaceutically acceptable salt thereof. In one aspect, the beneficial or desirable result is an increase in nutrient influx and/or oxygenation of a cell. In another aspect, the beneficial or desirable result is a reduction in the number and/or severity of symptoms associated with a disease or condition that is associated with mitochondrial dysfunction.

In one variation, a method of treating a renal or cardiac condition is provided, comprising administering to an individual in need thereof a compound as detailed herein. Such conditions include, but are not limited to, renal failure, such as acute renal failure and chronic renal failure, coronary (e.g., myocardial) ischemia, heart failure, such as acute and chronic congestive heart failure (including the muscle fatigue associated with these conditions), and coronary artery disease. Methods of treating other diseases and conditions are also described, such as methods of treating sleep apnea, acute respiratory distress syndrome (adult and infant) and peripheral vascular disease. The compounds as provided herein may also be used in a method of delaying the onset and/or development of a disease or condition associated with mitochondrial dysfunction, comprising administering a compound as provided herein, or a pharmaceutical salt thereof, to an individual who is at risk of developing a disease or condition associated with mitochondrial dysfunction.

Compounds that do not bind appreciably to neurotransmitter receptors but nevertheless enhance mitochondrial function, e.g., when administered to cells in the setting of mitochondrial stress (e.g., excess intracellular calcium), may be used in the methods herein to promote cell survival. In one aspect, the compounds exhibit the ability to enhance mitochondrial function by protecting against cell death mediated by mitochondrial dysfunction in an assay detailed herein. Thus, it is understood and clearly conveyed that enhancing mitochondrial function includes protecting a cell against cell death mediated by mitochondrial dysfunction. The compounds may also be assessed in assays known in the art.

It is understood and clearly conveyed that the binding and activity profiles detailed herein (e.g., in the disclosure above) in one variation apply to the formulae provided herein (e.g., the formulae for use in the methods). In one aspect, selective adrenergic receptor $\alpha_{2B}$ antagonists are of the formula (I), (A-I), (A-IIA), (A-IIB), (A-IIC), (A-IID), (A-IIA-1), (A-IIB-1), (A-IIC-1), (A-IID-1), (A-III), (A-IIIA), (A-IIIB), (A-IIIC), (A-IIID), (A-IIIE), (A-IIIE-1), (A-IIIE-2), (A-IIIE-3), (A-IIIE-4), (A-IIIE-5), (A-IIIE-6), (A-IIIE-7), (A-IIIE-8), (A-IIIF), (A-IIIF-1), (A-IIIF-2), (A-IIIF-3), (A-IIIF-4), (A-IIIG-1), (A-IIIG-2), (A-IIIG-3), (A-IIIH), (A-IIIH-1), (A-IIIH-2), (A-IIIH-3), (A-IIIH-4), (A-IIIA'), (A-IV), (A-V), (A-VI), (A-VIIA), (A-VIIB), (A-VIIC), (A-VIID), (A-VIIE), (A-VIIF), (A-VIIIA-1), (A-VIIIA-2), (A-VIIIA-3), (A-VIIIA-4), (A-VIIIA-5), (A-VIIIA-6), (A-VIIIA-7), (A-IXA), (A-IXB), (A-IXC), (A-IXD), (B-I), (B-IA), (B-IB), (B-IC), (B-ID), (C-I), (C-IA), (C-IB), (C-IA-1), (C-IA-2), (C-IA-3), (C-IA-4), (C-IA-5), (C-IA-6), (C-IA-7), (C-IB), (C-IB-1), (C-IB-2), (C-IB-3), (C-IC-1), (C-II), (C-IIA), (C-IIB), (C-IIIA), (C-IIIB), (C-IIIC), (C-IIID), (CIII-E), (C-IIIF), (C-IVA), (C-IVB), (C-IVC), (C-IVD), (C-IVE), (C-IVF), (C-IVG), (C-VA), (C-VB), (D-I), (D-IIA), (D-IIB), (D-IIA-1), (D-IIA-2), (D-IIIA), (D-IIIB), (E-I), (E-IIA), (E-IIB), (F-I), (F-IIB), (F-IIA-1), (F-IIA-2), (G-I), (G-IIA), (G-IIB), (G-IIA-1), (G-IIA-2), (H-IA), (H-IB), (H-IC), (H-ID), (H-IA-1), (H-IB-1), (H-IC-1), (H-ID-1), (H-IE-1), (H-IF-1), (J), (J-IA), (J-IB), (J-IC), (J-ID), (J-IA-1), (J-IB-1), (J-IC-1), (J-ID-1), (K-IA), (K-IB), (K-IC), (K-ID), (K-IE) or (K-IF), or any variations detailed herein.

Compounds of the Invention

Compounds according to the invention are detailed herein, including in the Brief Summary of the Invention and elsewhere. The invention includes the use of all of the compounds described herein, including any and all stereoisomers, including geometric isomers (cis/trans or E/Z isomers), tautomers, salts, N-oxides, and solvates of the compounds described herein, as well as methods of making such compounds.

In one aspect, provided is a compound of formula (I):

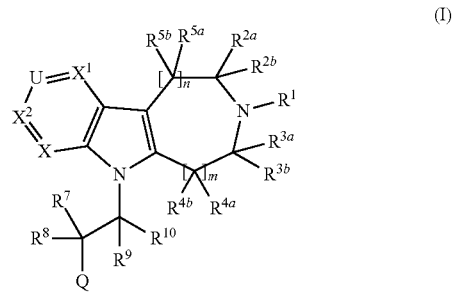

or a salt, solvate or N-oxide thereof, wherein:

$R^1$ is H; $C_1$-$C_5$ alkyl optionally substituted with 1 to 3 substituents independently selected from the group consisting of halo, hydroxyl, carboxyl, $SO_3H$, $SR^{1a}$, $S(O)R^{1a}$, $SO_2R^{1a}$ and perhaloalkyl; $C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{1a}$ to form a propylene (—$CH_2CH_2CH_2$—) moiety or a butylene (—$CH_2CH_2CH_2CH_2$—) moiety; or is taken together with $R^{4a}$ or $R^{5a}$, where present, to form an ethylene (—$CH_2CH_2$—) moiety or a propylene (—$CH_2CH_2CH_2$—) moiety;

$R^{1a}$ is H or optionally substituted $C_1$-$C_5$ alkyl;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—$CH_2CH_2CH_2$—) moiety or a butylene (—$CH_2CH_2CH_2CH_2$—) moiety; or is taken together with $R^{3a}$ to form an ethylene (—$CH_2CH_2$—) moiety or a propylene (—$CH_2CH_2CH_2$—) moiety; or is taken together with $R^{4a}$, where present, to form a methylene (—$CH_2$—) moiety or an ethylene (—$CH_2CH_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—$CH_2CH_2CH_2$—) moiety or a butylene (—$CH_2CH_2CH_2CH_2$—) moiety; or is taken together with $R^{2a}$ to form an ethylene (—$CH_2CH_2$—) moiety or a propylene (—$CH_2CH_2CH_2$—) moiety; or is taken together with $R^{5a}$, where present, to form a methylene (—$CH_2$—) moiety or an ethylene (—$CH_2CH_2$—) moiety;

$R^{4a}$, where present, is H; halo; hydroxyl; cyano; carboxyl; —OC(O)N($R^{14a}$)$R^{15a}$; —C(O)N($R^{14a}$)$R^{15a}$; optionally substituted $C_1$-$C_5$ alkyl; optionally substituted $C_2$-$C_5$ alkenyl; or optionally substituted aryl; or is taken together with $R^{3a}$ to form a propylene (—$CH_2CH_2CH_2$—) moiety or a butylene (—$CH_2CH_2CH_2CH_2$—) moiety; or is taken together with $R^1$ to form an ethylene (—CH$_2$CH$_2$—) moiety or a propylene (—CH$_2$CH$_2$CH$_2$—) moiety; or is taken together with R$^{2a}$ to form a methylene (—CH$_2$—) moiety or an ethylene (—CH$_2$CH$_2$—) moiety; or is taken together with R$^{5a}$, where present, to form a methylene (—CH$_2$—) moiety;

R$^{5a}$, where present, is H; halo; hydroxyl; cyano; carboxyl; —OC(O)N(R$^{14a}$)R$^{15a}$; —C(O)N(R$^{14a}$)R$^{15a}$; optionally substituted C$_1$-C$_5$ alkyl; optionally substituted C$_2$-C$_5$ alkenyl; or optionally substituted aryl; or is taken together with R$^{2a}$ to form a propylene (—CH$_2$CH$_2$CH$_2$—) moiety or a butylene (—CH$_2$CH$_2$CH$_2$CH$_2$—) moiety; or is taken together with R$^1$ to form an ethylene (—CH$_2$CH$_2$—) moiety or a propylene (—CH$_2$CH$_2$CH$_2$—) moiety; or is taken together with R$^{3a}$ to form a methylene (—CH$_2$—) moiety or an ethylene (—CH$_2$CH$_2$—) moiety; or is taken together with R$^{4a}$, where present, to form a methylene (—CH$_2$—) moiety;

each R$^{2b}$ and R$^{3b}$ is independently H, optionally substituted C$_1$-C$_5$ alkyl, optionally substituted C$_2$-C$_5$ alkenyl, or optionally substituted aryl;

each R$^{4b}$ and R$^{5b}$, where present, is independently H, halo, optionally substituted C$_1$-C$_5$ alkyl, optionally substituted C$_2$-C$_5$ alkenyl, or optionally substituted aryl;

each n and m is 1, or n is 0 and m is 1, or n is 1 and m is 0;

each X$^1$, X$^2$, X and U is independently N or CR$^6$;

each R$^6$ is independently H; hydroxyl; halo; C$_1$-C$_5$ alkyl optionally substituted with 1 to 3 substituents independently selected from the group consisting of halo, hydroxyl, carboxyl and perhaloalkyl; C$_2$-C$_5$ alkenyl; optionally substituted C$_1$-C$_5$ alkoxy; or optionally substituted —C(O)C$_1$-C$_5$ alkyl;

R$^7$ is H; halo; optionally substituted C$_1$-C$_5$ alkyl; or optionally substituted aryl; or is taken together with R$^8$ and the carbon atom to which they are attached to form a dioxolane ring or a carbonyl moiety; or is taken together with R$^9$ to form a C$_3$-C$_5$ alkylene when R$^8$ and R$^{10}$ are taken together to form a bond;

R$^8$ is H; halo; hydroxyl; azido; aminoacyl; carboxyl; carbonylalkoxy; N(R$^{11}$)R$^{12}$; SR$^{13}$, S(O)R$^{13}$; SO$_2$R$^{13}$; —OC(O)N(R$^{14}$)R$^{15}$; —C(O)N(R$^{14}$)R$^{15}$; optionally substituted —OC(O)-aryl; optionally substituted —OC(O)-heteroaryl; —OC(O)C$_1$-C$_6$ alkyl optionally substituted with amino or carboxyl; or —OC$_1$-C$_5$ alkyl optionally substituted with carboxyl; or is taken together with R$^7$ and the carbon atom to which they are attached to form a dioxolane ring or a carbonyl moiety; or is taken together with R$^{10}$ to form a bond;

R$^9$ is H or optionally substituted C$_1$-C$_5$ alkyl, or is taken together with R$^7$ to form a C$_3$-C$_5$ alkylene when R$^8$ and R$^{10}$ are taken together to form a bond;

R$^{10}$ is H or optionally substituted C$_1$-C$_5$ alkyl, or is taken together with R$^8$ to form a bond;

each R$^{11}$ and R$^{12}$ is independently H or optionally substituted C$_1$-C$_5$ alkyl, or R$^{11}$ and R$^{12}$ are taken together to form C$_3$-C$_5$ alkylene;

R$^{13}$ is H or optionally substituted C$_1$-C$_5$ alkyl;

each R$^{14}$ and R$^{15}$ is independently H or optionally substituted C$_1$-C$_5$ alkyl; or R$^{14}$ and R$^{15}$ are taken together to form a C$_3$-C$_5$ alkylene;

each R$^{14a}$, and R$^{15a}$ is independently H or optionally substituted C$_1$-C$_5$ alkyl; and Q is optionally substituted cycloalkyl, optionally substituted aryl, or optionally substituted heteroaryl.

It should be understood that when two substituents are taken together to form a bond, an additional bond is formed. For example, as shown below, when R$^y$ and R$^w$ are taken together to form a bond, an additional bond is formed such that R$^x$ and R$^z$ is a double bond.

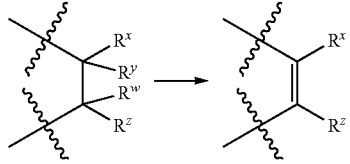

In some variations, one of X$^1$, X$^2$, X and U is N, and the other three of X$^1$, X$^2$, X and U are independently CR$^6$. In other variations, two of X$^1$, X$^2$, X and U is N, and the other two of X$^1$, X$^2$, X and U are independently CR$^6$. In yet other variations, each X$^1$, X$^2$, X and U is independently CR$^6$.

In some variations, R$^1$ is H, optionally substituted C$_1$-C$_5$ alkyl, or optionally substituted C$_3$-C$_8$ cycloalkyl, wherein the C$_1$-C$_5$ alkyl or the C$_3$-C$_8$ cycloalkyl is independently unsubstituted or substituted with hydroxyl. In some variations, R$^1$ is unsubstituted C$_2$-C$_5$ alkenyl. In other variations, the C$_1$-C$_5$ alkyl is substituted with SO$_3$H. In some variations, R$^1$ is methyl, ethyl, n-propyl, or i-propyl. In some variations, R$^1$ is CF$_3$, or CH$_2$CF$_3$. In some variations R$^1$ is H. In some variations, R$^1$ is hydroxyethyl, hydroxypropyl, or hydroxybutyl. In some variations, R$^1$ is cyclobutyl, or cyclopropyl. In some variations, R$^1$ is CH$_2$CH$_2$—SO$_3$H. In some variations, R$^1$ is CH$_2$CH=CH$_2$.

In some variations, R$^{4a}$ is halo; hydroxyl; cyano; carboxyl; —OC(O)N(R$^{14a}$)R$^{15a}$; —C(O)N(R$^{14a}$)R$^{15a}$; optionally substituted C$_1$-C$_5$ alkyl. In some embodiments, R$^{4a}$ is optionally substituted C$_1$-C$_5$ alkyl. In other embodiments, R$^{4a}$ is monohaloalkyl, dihaloalkyl, or perhaloalkyl. In one embodiment, R$^{4a}$ is CF$_3$, CHF$_2$, or CH$_2$F. In another embodiment, R$^{4a}$ is CCl$_3$, CHCl$_2$, or CH$_2$Cl. In some variations, R$^{4a}$ is halo. In some variations, R$^{4a}$ and R$^{4b}$ are each halo. In certain variations, each R$^{4a}$ and R$^{4b}$ is fluoro or chloro. In one variation, each R$^{4a}$ and R$^{4b}$ is fluoro. In one variation, each R$^{4a}$ and R$^{4b}$ is chloro.

In some variations, R$^{5a}$ is halo; hydroxyl; cyano; carboxyl; —OC(O)N(R$^{14a}$)R$^{15a}$; —C(O)N(R$^{14a}$)R$^{15a}$; optionally substituted C$_1$-C$_5$ alkyl. In some embodiments, R$^{5a}$ is optionally substituted C$_1$-C$_5$ alkyl. In other embodiments, R$^{5a}$ is monohaloalkyl, dihaloalkyl, or perhaloalkyl. In one embodiment, R$^{5a}$ is CF$_3$, CHF$_2$, or CH$_2$F. In another embodiment, R$^{5a}$ is CCl$_3$, CHCl$_2$, or CH$_2$Cl. In some variations, R$^{5a}$ is halo. In some variations, R$^{5a}$ and R$^{5b}$ are each halo. In certain variations, each R$^{5a}$ and R$^{5b}$ is fluoro or chloro. In one variation, each R$^{5a}$ and R$^{5b}$ is fluoro. In one variation, each R$^{5a}$ and R$^{5b}$ is chloro.

In some variations, R$^7$ is a C$_1$-C$_5$ alkyl optionally substituted with 1 to 3 substituents independently selected from the group consisting of halo, hydroxyl, —N(R$^{7a}$)(R$^{7b}$), —C(O)N(R$^{7a}$)(R$^{7b}$), —C(O)OR$^{7a}$, and —C(O)R$^{7a}$. In other variations, R$^7$ is an optionally substituted C$_3$-C$_8$ cycloalkyl. In some variations, R$^8$ is hydroxyl or NH$_2$. In some variations, R$^8$ is —OC(O)C$_1$-C$_5$ alkyl optionally substituted with amino or carboxyl. In some variations, R$^8$ is taken together with R$^{10}$ to form a bond. In some variations, R$^9$ is H or CH$_3$. In some variations, in R$^{10}$ is H or CH$_3$. In some variations, each R$^9$ and R$^{10}$ is H. In some variations, R$^{10}$ is an optionally substituted C$_3$-C$_8$ cycloalkyl. In other variations, R$^{11}$ or R$^{12}$ is an optionally substituted C$_3$-C$_8$ cycloalkyl.

In some variations, Q is unsubstituted aryl; unsubstituted heteroaryl; aryl substituted with 1 to 3 substituents independently selected from the group consisting of halo, hydroxyl, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl, $N(R^{16})(R^{17})$, —$C(O)OR^{18}$, $SR^{18}$, $S(O)R^{18}$ and $SO_2R^{18}$; or heteroaryl substituted with 1 to 3 substituents independently selected from the group consisting of halo, hydroxyl, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl, $N(R^{16})(R^{17})$, —$C(O)OR^{18}$, $SR^{18}$, $S(O)R^{18}$ and $SO_2R^{18}$, wherein each $R^{16}$ and $R^{17}$ is independently H or optionally substituted $C_1$-$C_5$ alkyl, or $R^{16}$ and $R^{17}$ are taken together to form $C_3$-$C_5$ alkylene, and wherein $R^{18}$ is an optionally substituted $C_1$-$C_5$ alkyl.

In one embodiment of the compound of formula (I):

$R^1$ is H; $C_1$-$C_5$ alkyl optionally substituted with 1 to 3 substituents independently selected from halo, hydroxyl, carboxyl and perhaloalkyl; $C_3$-$C_8$ cycloalkyl optionally substituted with 1 to 3 substituents independently selected from halo, hydroxyl, carboxyl and perhaloalkyl; $C_2$-$C_5$ alkenyl optionally substituted with 1 to 3 substituents independently selected from halo, hydroxyl, carboxyl and perhaloalkyl; or —$C(O)O$—$C_1$-$C_5$ alkyl, or is taken together with $R^{2a}$ or $R^{1a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{4a}$ is selected from the group consisting of halo, hydroxyl, cyano, carboxyl, —$OC(O)N(R^{14a})R^{15a}$, —$C(O)N(R^{14a})R^{15a}$, and optionally substituted $C_1$-$C_5$ alkyl;

each $R^{2b}$ and $R^{3b}$ is independently H;

$R^{4b}$ is H, halo, optionally substituted $C_1$-$C_5$ alkyl;

n is 0 and m is 1;

each $X^1$, $X^2$, and U is CH;

X is independently N or $CR^{6a}$;

each $R^6$ and $R^{6a}$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —$C(O)C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; azido; aminoacyl, carboxyl; carbonylalkoxy; $N(R^{11})R^{12}$; $SR^{13}$, $S(O)R^{13}$; $SO_2R^{13}$; —$OC(O)N(R^{14})R^{15}$; —$C(O)N(R^{14})R^{15}$; optionally substituted —$OC(O)$-aryl; optionally substituted —$OC(O)$-heteroaryl; —$OC(O)C_1$-$C_6$ alkyl optionally substituted with amino or carboxyl; or —$OC_1$-$C_5$ alkyl optionally substituted with carboxyl; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is cycloalkyl, aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some embodiments, $R^{4a}$ is an optionally substituted $C_1$-$C_5$ alkyl. In certain embodiments, $R^{4a}$ is a monohaloalkyl, a dihaloalkyl, or perhaloalkyl. In some variations, $R^{4a}$ is halo, hydroxyl, and cyano. In some variations, $R^{4a}$ is halo. In some variations, $R^{4a}$ and $R^{4b}$ are each halo. In certain variations, each $R^{4a}$ and $R^{4b}$ is fluoro or chloro. In one variation, each $R^{4a}$ and $R^{4b}$ is fluoro.

In certain embodiments, with respect to the compounds of formula (I), X is $CR^6$, $R^8$ is —$OC(O)C_1$-$C_5$ alkyl substituted with carboxyl, and the compound is Compound No. 25, 54, 130, 146, 147, 338, II-15, II-16, or II-19.

In certain embodiments, with respect to the compounds of formula (I), $R^8$ is azido, and the compound is Compound No. II-261, II-266, II-276, II-298, V-1, V-2, V-3, V-21, V-22, or V-23.

In one embodiment, the compound is of formula (A-I):

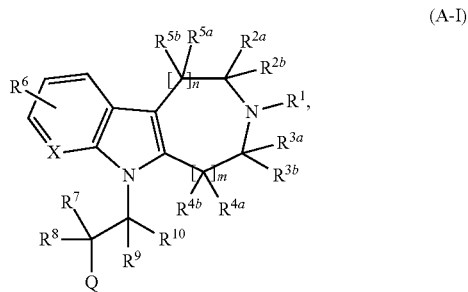

(A-I)

or a salt, solvate or N-oxide thereof, wherein:

$R^1$ is H, $C_1$-$C_5$ alkyl or cycloalkyl optionally substituted with 1 to 3 halogen atoms or hydroxyl, $C_2$-$C_5$ alkenyl, or —$C(O)OR^{11}$;

each $R^{2a}$, $R^{2b}$, $R^{3a}$, $R^{3b}$, $R^{4a}$, $R^{4b}$, $R^{5a}$ and $R^{5b}$ is independently H or optionally substituted $C_1$-$C_5$ alkyl;

each n and m is 1, or n is 0 and m is 1, or n is 1 and m is 0;

or $R^1$ and $R^{2a}$, or $R^1$ and $R^{3a}$, or $R^{2a}$ and $R^{5a}$, or $R^{3a}$ and $R^{4a}$, where present, are taken together to form a propylene (—$CH_2CH_2CH_2$—) moiety or a butylene (—$CH_2CH_2CH_2CH_2$—) moiety, or $R^1$ and $R^{4a}$, or $R^1$ and $R^{5a}$, or $R^{2a}$ and $R^{3a}$, where present, are taken together to form an ethylene (—$CH_2CH_2$—) moiety or a propylene (—$CH_2CH_2CH_2$—) moiety, or $R^{2a}$ and $R^{4a}$, or $R^{3a}$ and $R^{5a}$, where present, are taken together to form a methylene (—$CH_2$—) moiety or an ethylene (—$CH_2CH_2$—) moiety, or $R^{4a}$ and $R^{5a}$, where present, are taken together to form a methylene (—$CH_2$—) moiety;

X is N or $CR^{6a}$;

each $R^6$ and $R^{6a}$ is independently H, halogen, $C_1$-$C_5$ alkyl optionally substituted with 1 to 3 halogen atoms, hydroxyl, optionally substituted $C_1$-$C_5$ alkoxy or optionally substituted —$C(O)C_1$-$C_5$ alkyl;

each $R^7$, $R^9$ and $R^{10}$ is independently H or optionally substituted $C_1$-$C_5$ alkyl;

$R^8$ is H, hydroxyl, $N(R^{11})R^{12}$, $SR^{13}$, $S(O)R^{13}$, $SO_2R^{13}$, or —OC(O)$C_1$-$C_5$ alkyl optionally substituted with amino;

or $R^7$ and $R^8$ are taken together with the carbon atom to which they are attached to form a dioxolane ring or a carbonyl moiety;

or $R^{10}$ and $R^8$ are taken together to form a bond;

or $R^9$ and $R^7$ are taken together to form an alkylene bridge of 3-5 carbon atoms when $R^{10}$ and $R^8$ are taken together to form a bond;

each $R^{11}$, $R^{12}$ and $R^{13}$ is independently H or optionally substituted $C_1$-$C_5$ alkyl; and Q is aryl or heteroaryl optionally substituted with 1 to 3 substituents including halogen, $C_1$-$C_5$ alkyl or cycloalkyl, halo-substituted $C_1$-$C_5$ alkyl or cycloalkyl, $C_1$-$C_5$ alkoxy or cycloalkoxy, —CN or —C(O)N($R^a$)$R^b$ where each $R^a$ and $R^b$ is independently H or $C_1$-$C_5$ alkyl.

In another embodiment, the compound is of the formula (A-IIA), (A-IIB), (A-IIC) or (A-IID):

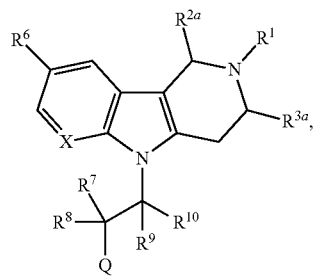

(A-IIA)

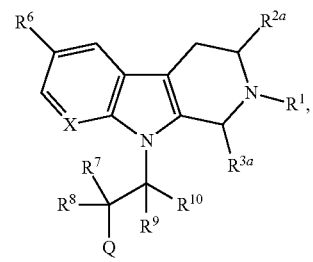

(A-IIB)

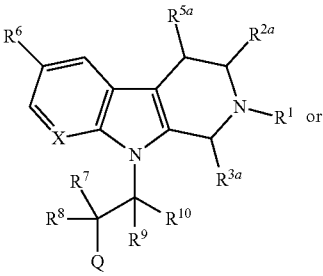

(A-IIC)

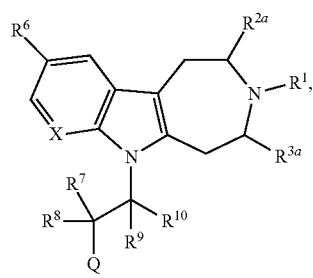

(A-IID)

or a salt, solvate or N-oxide thereof, wherein:

$R^1$ is H, $C_1$-$C_5$ alkyl or cycloalkyl optionally substituted with 1 to 3 halogen atoms or hydroxyl, $C_2$-$C_5$ alkenyl, or —C(O)OR$^{11}$;

each $R^{2a}$, $R^{3a}$ or $R^{5a}$ is independently H or optionally substituted $C_1$-$C_5$ alkyl;

or $R^1$ and $R^{2a}$, or $R^1$ and $R^{3a}$ are taken together to form a propylene (—CH$_2$CH$_2$CH$_2$—) moiety or a butylene (—CH$_2$CH$_2$CH$_2$CH$_2$—) moiety;

X is N or CR$^{6a}$;

each $R^6$ and $R^{6a}$ is independently H, halogen, $C_1$-$C_5$ alkyl optionally substituted with 1 to 3 halogen atoms, hydroxyl, optionally substituted $C_1$-$C_5$ alkoxy or optionally substituted —C(O)$C_1$-$C_5$ alkyl;

each $R^7$, $R^9$ and $R^{10}$ is independently H or optionally substituted $C_1$-$C_5$ alkyl;

$R^8$ is H, hydroxyl, $N(R^{11})R^{12}$, $SR^{13}$, $S(O)R^{13}$, $SO_2R^{13}$, or —OC(O)$C_1$-$C_5$ alkyl optionally substituted with amino;

or $R^7$ and $R^8$ are taken together with the carbon atom to which they are attached to form a dioxolane ring or a carbonyl moiety;

or $R^{10}$ and $R^8$ are taken together to form a bond;

or $R^9$ and $R^7$ are taken together to form an alkylene bridge of 3 to 5 carbon atoms when $R^{10}$ and $R^8$ are taken together to form a bond;

each $R^{11}$, $R^{12}$ and $R^{13}$ is independently H or optionally substituted $C_1$-$C_5$ alkyl; and Q is aryl or heteroaryl optionally substituted with 1 to 3 substituents including halogen, $C_1$-$C_5$ alkyl or cycloalkyl, halo-substituted $C_1$-$C_5$ alkyl or cycloalkyl, $C_1$-$C_5$ alkoxy or cycloalkoxy, —CN, —CO$_2$H or —C(O)N($R^a$)$R^b$, wherein each $R^a$ and $R^b$ is independently H or $C_1$-$C_5$ alkyl.

In some embodiments, the compound is of formula (A-IIA). In some variations, X is CR$^{6a}$, wherein R$^{6a}$ is H. In some variations, R$^6$ is H. In other variations, R$^1$ is H or CH$_3$. In yet other variations, R$^7$ is H or CH$_3$. In yet other variations, R$^8$ is hydroxyl. In yet other variations, Q is optionally substituted pyridyl, optionally substituted pyrimidyl, optionally substituted pyrazinyl, or optionally substituted phenyl.

In some embodiments, the compound is of formula (A-IIB). In some variations, X is CR$^{6a}$, wherein R$^{6a}$ is H. In some variations, R$^6$ is H. In other variations, R$^1$ is H or CH$_3$. In yet other variations, R$^7$ is H or CH$_3$. In yet other variations, R$^8$ is hydroxyl. In yet other variations, Q is optionally substituted pyridyl, optionally substituted pyrimidyl, optionally substituted pyrazinyl, or optionally substituted phenyl.

In one embodiment, the compound is of formula (A-IA):

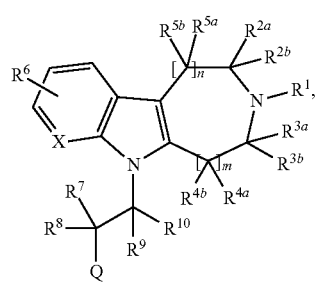

(A-IA)

or a salt, solvate or N-oxide thereof, wherein:

$R^1$ is H, $C_1$-$C_5$ alkyl or cycloalkyl optionally substituted with 1 to 3 halogen atoms or hydroxyl, $C_2$-$C_5$ alkenyl, or —C(O)OR$^{11}$;

each $R^{2a}$, $R^{2b}$, $R^{3a}$, $R^{3b}$, $R^{4a}$, $R^{4b}$, $R^{5a}$ and $R^{5b}$ is independently H or optionally substituted $C_1$-$C_5$ alkyl;

each n and m is 1, or n is 0 and m is 1, or n is 1 and m is 0;

or $R^1$ and $R^{2a}$, or $R^1$ and $R^{3a}$, or $R^{2a}$ and $R^{5a}$, or $R^{3a}$ and $R^{4a}$, where present, are taken together to form a propylene (—CH₂CH₂CH₂—) moiety or a butylene (—CH₂CH₂CH₂CH₂—) moiety, or R¹ and R⁴ᵃ, or R¹ and R⁵ᵃ, or R²ᵃ and R³ᵃ, where present, are taken together to form an ethylene (—CH₂CH₂—) moiety or a propylene (—CH₂CH₂CH₂—) moiety, or R²ᵃ and R⁴ᵃ, or R³ᵃ and R⁵ᵃ, where present, are taken together to form a methylene (—CH₂—) moiety or an ethylene (—CH₂CH₂—) moiety, or R⁴ᵃ and R⁵ᵃ, where present, are taken together to form a methylene (—CH₂—) moiety;

X is N or CR⁶ᵃ;

each R⁶ and R⁶ᵃ is independently H, halogen, C₁-C₅ alkyl optionally substituted with 1 to 3 halogen atoms, hydroxyl, optionally substituted C₁-C₅ alkoxy or optionally substituted —C(O)C₁-C₅ alkyl;

each R⁷, R⁹ and R¹⁰ is independently H or optionally substituted C₁-C₅ alkyl;

R⁸ is N(R¹¹)R¹², SR¹³, S(O)R¹³, SO₂R¹³, or —OC(O)C₁-C₅ alkyl optionally substituted with amino;

each R¹¹, R¹² and R¹³ is independently H or optionally substituted C₁-C₅ alkyl; and Q is aryl or heteroaryl optionally substituted with 1 to 3 substituents including halogen, C₁-C₅ alkyl or cycloalkyl, halo-substituted C₁-C₅ alkyl or cycloalkyl, C₁-C₅ alkoxy or cycloalkoxy, —CN, —CO₂H or —C(O)N(Rᵃ)Rᵇ, wherein each Rᵃ and Rᵇ is independently H or C₁-C₅ alkyl.

In one aspect, the present invention provides compounds according to formula (A-IB), (A-IC) or (A-ID):

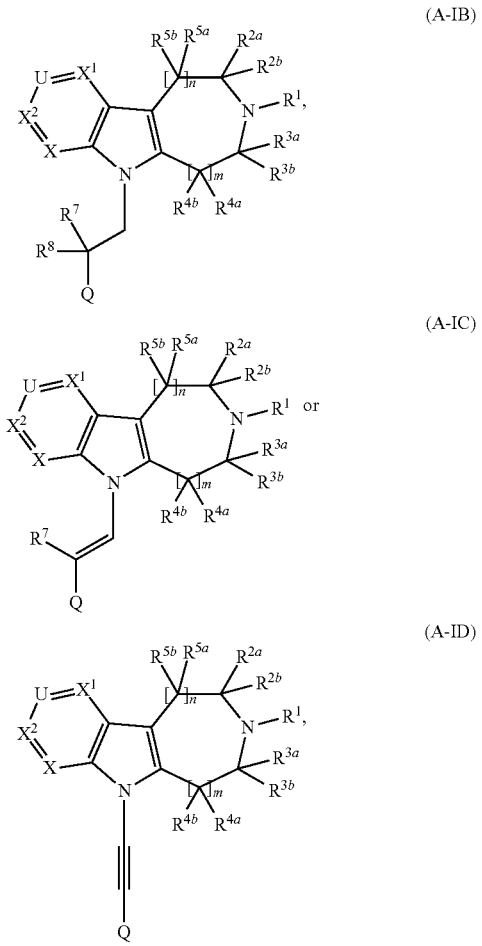

wherein Q, R¹, R²ᵃ, R²ᵇ, R³ᵃ, R³ᵇ, R⁴ᵃ, R⁴ᵇ, R⁵ᵃ, R⁵ᵇ, R⁶, R⁷, R⁸, m, and n are as described for formula (A-I), above; and each X¹, U, X² and X is independently CR⁶.

In certain embodiments, with respect to the compounds of formula (A-IB), R⁷ is optionally substituted cycloalkyl; R⁸ is OH; R¹ is methyl; n is 0; each of R²ᵇ, R³ᵃ, R³ᵇ, R⁴ᵇ, R⁹, and R¹⁰ is H; each R²ᵃ and R⁴ᵃ is H; or R²ᵃ taken together with R⁴ᵃ, when present, to form an ethylene (—CH₂CH₂—) moiety; each X¹, X² and X is CH, U is CR⁶, and R⁶ is methyl or chloro; and Q is other than unsubstituted phenyl, phenyl substituted with F, or unsubstituted pyridyl.

In certain embodiments, with respect to the compounds of formula (A-IB), R⁷ is C₁-C₅ alkyl substituted with acylamino. In one embodiment, R⁷ is CH₂—CON(H)CH₃; R¹ is methyl or ethyl; n is 0; each of R²ᵇ, R³ᵃ, R³ᵇ, R⁴ᵇ, R⁹ and R¹⁰ is H; each R²ᵃ and R⁴ᵃ is H; or R²ᵃ taken together with R⁴ᵃ, when present, to form an ethylene (—CH₂CH₂—) moiety; each X¹, X² and X is CH, U is CR⁶, and R⁶ is methyl or chloro; and Q is other than phenyl substituted with fluoro, chloro, methoxy, or difluoro, unsubstituted pyridyl, pyridyl substituted with methyl, or unsubstituted pyrimidinyl In certain embodiments, with respect to the compounds of formula (A-IB), R⁷ is C₁-C₅ alkyl substituted with —C(O)OR⁷ᵃ, wherein R⁷ᵃ is H or optionally substituted C₁-C₅ alkyl; R¹ is methyl or ethyl; n is 0; each of R²ᵇ, R³ᵃ, R³ᵇ and R⁴ᵇ is H; each R²ᵃ and R⁴ᵃ is H, or R²ᵃ taken together with R⁴ᵃ, when present, to form an ethylene (—CH₂CH₂—) moiety; each X¹, X² and X is CH, U is CR⁶, and R⁶ is methyl or chloro; and Q is other than phenyl substituted with fluoro, chloro, methoxy, or difluoro, unsubstituted pyridyl, pyridyl substituted with methyl, or unsubstituted pyrimidinyl.

In certain embodiments, with respect to the compounds of formula (A-IB), R⁷ is C₁-C₅ alkyl substituted with 1 to 3 halo; R⁷ is CF₃,'R⁸ is OH; R¹ is methyl; n is 0, each of R²ᵇ, R³ᵃ, R³ᵇ and R⁴ᵇ is H; each R²ᵃ and R⁴ᵃ is H; or R²ᵃ taken together with R⁴ᵃ, when present, to form an ethylene (—CH₂CH₂—) moiety; each X¹, X² and X is CH, U is CR⁶, and R⁶ is methyl; and Q is other than phenyl substituted with fluoro.

In certain embodiments, with respect to the compounds of formula (A-IB), R⁷ is optionally substituted phenyl; R⁸ is OH; R¹ is methyl or ethyl; n is 0; each of R²ᵇ, R³ᵃ, R³ᵇ and R⁴ᵇ is H; each R²ᵃ and R⁴ᵃ is H; or R²ᵃ taken together with R⁴ᵃ, when present, to form an ethylene (—CH₂CH₂—) moiety; each X¹, X² and X is CH, U is CR⁶, and R⁶ is methyl or chloro; and Q is other than unsubstituted phenyl, phenyl substituted with fluoro or unsubstituted pyridyl.

In certain embodiments, with respect to the compounds of formula (A-IB), R⁸ is halo. In one embodiment, R⁸ is fluoro or chloro; R¹ is methyl, ethyl, isopropyl, or cyclopropyl; n is 0; each of R²ᵇ, R³ᵃ, R³ᵇ and R⁴ᵇ is H; each R²ᵃ and R⁴ᵃ is H; or R²ᵃ taken together with R⁴ᵃ, when present, to form an ethylene (—CH₂CH₂—) moiety; R⁷ is H or methyl; each X¹, X² and X is CH, U is CR⁶, and R⁶ is methyl or chloro; and Q is other than unsubstituted phenyl, phenyl substituted with methoxy, chloro, fluoro, difluoro, unsubstituted pyridyl, pyridyl substituted with methyl, or unsubstituted pyrimidinyl.

In certain embodiments, with respect to the compounds of formula (A-IB), R⁸ is —C(O)N(R¹⁴)R¹⁵; and each R¹⁴ and R¹⁵ is independently H or optionally substituted C₁-C₅ alkyl; or R¹⁴ and R¹⁵ are taken together to form a C₃-C₅ alkylene; R¹ is methyl; n is 0; each of R²ᵇ, R³ᵃ, R³ᵇ and R⁴ᵇ is H; each R²ᵃ and R⁴ᵃ is H; or R²ᵃ taken together with R⁴ᵃ, when present, to form an ethylene (—CH₂CH₂—) moiety; each X¹, X² and X is CH, U is CR⁶, and R⁶ is methyl; and Q is other than cyclobutyl.

In certain embodiments, with respect to the compounds of formula (A-IB), R⁸ is —OC(O)N(R¹⁴)R¹⁵, —OC(O)-aryl, —OC(O)-heteroaryl, —OC(O)C₁-C₅ alkyl optionally substituted with amino, —OC(O)C₁-C₅ alkyl substituted with carboxyl, or —OC$_1$-C$_5$ alkyl optionally substituted with carboxyl; and each R$^{14}$ and R$^{15}$ is independently H or optionally substituted C$_1$-C$_5$ alkyl, or R$^{14}$ and R$^{15}$ are taken together to form a C$_3$-C$_5$ alkylene.

In certain embodiments, with respect to the compounds of formula (A-IC), Q is optionally substituted 5-membered heteroaryl; n is 0; R$^7$ is fluoro or methyl; R$^1$ is methyl; each of R$^{2a}$, R$^{2b}$, R$^{3a}$, R$^{3b}$, R$^{4a}$ and R$^{4b}$ is H; each X$^1$, X$^2$ and X is CH, U is CR$^6$, and R$^6$ is methyl or chloro; and Q is other than unsubstituted thienyl or unsubstituted thiazolyl.

In certain embodiments, with respect to the compounds of formula (A-IC), Q is optionally substituted pyridyl, each of R$^{2a}$, R$^{2b}$, R$^{3a}$, R$^{3b}$, R$^{4a}$ and R$^{4b}$ is H; each X$^1$, X$^2$ and X is CH, U is CR$^6$, and R$^6$ is H, halo, optionally substituted C$_1$-C$_5$ alkyl, or optionally substituted C$_1$-C$_5$ alkoxy; and Q is other than unsubstituted pyridyl, or pyridyl substituted with methyl, chloro, bromo, methoxy, or dimethyl.

In certain embodiments, with respect to the compounds of formula (A-IC), Q is optionally substituted pyrimidinyl; R$^1$ is methyl; each of R$^{2a}$, R$^{2b}$, R$^{3a}$, R$^{3b}$, R$^{4a}$ and R$^{4b}$ is H; each X$^1$, X$^2$ and X is CH, U is CR$^6$, and R$^6$ is methyl or chloro; and Q is other than unsubstituted pyrimidin-4-yl, pyrimidin-4-yl substituted with methyl, unsubstituted pyrimidin-5-yl, or pyrimidin-5-yl substituted with methyl.

In certain embodiments, with respect to the compounds of formula (A-ID), each of R$^{2b}$, R$^{3a}$, R$^{3b}$, R$^{4b}$, R$^{5a}$ and R$^{5b}$ is H; each R$^{2a}$ and R$^{4a}$ is H; or R$^{2a}$ taken together with R$^{4a}$, where present, an ethylene (—CH$_2$CH$_2$—) moiety; U is CR$^6$, and R$^6$ is selected from the group consisting of CF$_3$, methyl, Cl, CONHCH$_3$, COOH, COOCH$_3$, H and F; then R$^1$ is other than methyl.

In certain embodiments, with respect to the compounds of formula (A-ID), each of R$^{2b}$, R$^{3a}$, R$^{3b}$, R$^{4b}$, R$^{5a}$ and R$^{5b}$ is H; each R$^{2a}$ and R$^{4a}$ is H; or R$^{2a}$ taken together with R$^{4a}$, where present, an ethylene (—CH$_2$CH$_2$—) moiety; X is CR$^6$, and R$^6$ is F; then R$^1$ is other than methyl.

In certain embodiments, with respect to the compounds of formula (A-IB), (A-IC), or (A-ID), n is 0. In certain embodiments, with respect to the compounds of formula (A-IB), (A-IC), or (A-ID), n is 1. In certain embodiments, with respect to the compounds of formula (A-IB), (A-IC), or (A-ID), m is 0. In certain embodiments, with respect to the compounds of formula (A-IB), (A-IC), or (A-ID), m is 1.

In certain embodiments, with respect to the compounds of formula (A-IB), (A-IC), or (A-ID), each R$^{2a}$, R$^{2b}$, R$^{3a}$, R$^{3b}$, R$^{4a}$, R$^{4b}$, R$^{5a}$, and R$^{5b}$ is H.

In certain embodiments, with respect to the compounds of formula (A-IB), (A-IC), or (A-ID), R$^{2a}$ together with R$^1$ form a butylene or propylene moiety.

In certain embodiments, with respect to the compounds of formula (A-IB), (A-IC), or (A-ID), R$^{2a}$ together with R$^{3a}$ form a propylene or ethylene moiety.

In certain embodiments, with respect to the compounds of formula (A-IB), (A-IC), or (A-ID), R$^{2a}$ together with R$^{4a}$ form a propylene or ethylene moiety.

In certain embodiments, with respect to the compounds of formula (A-IB), (A-IC), or (A-ID), R$^{5a}$ together with R$^{3a}$ form a methylene or ethylene moiety.

In certain embodiments, with respect to the compounds of formula (A-IB), (A-IC), or (A-ID), R$^{2a}$ together with R$^{4a}$ form a methylene or ethylene moiety.

In certain embodiments, with respect to the compounds of formula (A-IB), (A-IC), or (A-ID), R$^{3a}$ together with R$^1$ form a butylene or propylene moiety.

In one embodiment, the present invention provides compounds according to formula (A-IE):

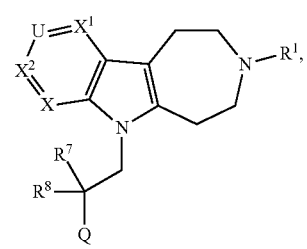

(A-IE)

wherein X$^1$, U, X$^2$, X, Q, R$^1$, R$^6$, R$^7$ and R$^8$ are as described for formula (A-IB).

In another embodiment, the compound is of the formula (A-IIA-1), (A-IIB-1), (A-IIC-1) or (A-IID-1):

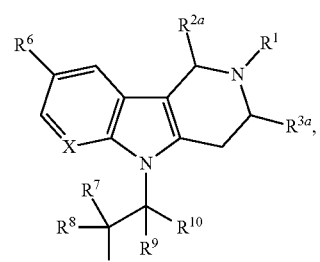

(A-IIA-1)

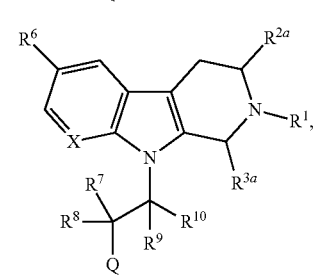

(A-IIB-1)

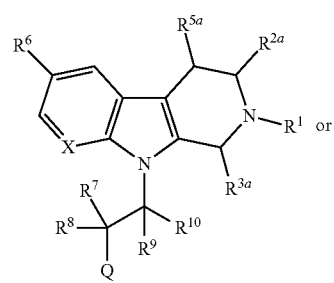

(A-IIC-1) or

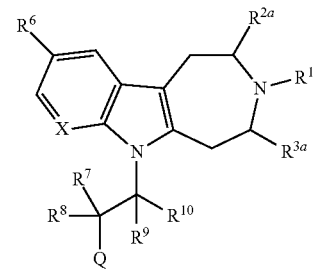

(A-IID-1)

or a salt, solvate or N-oxide thereof, wherein:

R$^1$ is H, C$_1$-C$_5$ alkyl or cycloalkyl optionally substituted with 1 to 3 halogen atoms or hydroxyl, C$_2$-C$_5$ alkenyl, or —C(O)OR$^{11}$;

each $R^{2a}$, $R^{3a}$ or $R^{5a}$ is independently H or optionally substituted $C_1$-$C_5$ alkyl;

or $R^1$ and $R^{2a}$, or $R^1$ and $R^{3a}$ are taken together to form a propylene (—$CH_2CH_2CH_2$—) moiety or a butylene (—$CH_2CH_2CH_2CH_2$—) moiety;

X is N or $CR^{6a}$;

each $R^6$ and $R^{6a}$ is independently H, halogen, $C_1$-$C_5$ alkyl optionally substituted with 1 to 3 halogen atoms, hydroxyl, optionally substituted $C_1$-$C_5$ alkoxy or optionally substituted —C(O)$C_1$-$C_5$ alkyl;

each $R^7$, $R^9$ and $R^{10}$ is independently H or optionally substituted $C_1$-$C_5$ alkyl;

$R^8$ is H, azido, hydroxyl, $N(R^{11})R^{12}$, $SR^{13}$, $S(O)R^{13}$, $SO_2R^{13}$, or —OC(O)$C_1$-$C_5$ $C_5$ alkyl optionally substituted with amino;

each $R^{11}$, $R^{12}$ and $R^{13}$ is independently H or optionally substituted $C_1$-$C_5$ alkyl; and Q is aryl or heteroaryl optionally substituted with 1 to 3 substituents including halogen, $C_1$-$C_5$ alkyl or cycloalkyl, halo-substituted $C_1$-$C_5$ alkyl or cycloalkyl, $C_1$-$C_5$ alkoxy or cycloalkoxy, —CN or —C(O)$N(R^a)R^b$ where each $R^a$ and $R^b$ is independently H or $C_1$-$C_5$ alkyl.

In one variation, each $R^6$ and $R^{6a}$ is independently H, $CH_3$ or Cl.

In one variation, $R^8$ is H, hydroxyl, $N(R^{11})R^{12}$, $SR^{13}$, $S(O)R^{13}$, $SO_2R^{13}$, or —OC(O)$C_1$-$C_5$ alkyl optionally substituted with amino, where $R^{11}$, $R^{12}$ and $R^{13}$ are each independently H or optionally substituted $C_1$-$C_5$ alkyl. In a particular variation, $R^8$ is H, OH, $NH_2$, —OC(O)CH($NH_2$)—$CH_3$, —OC(O)CH($NH_2$)—CH($CH_3$)$_2$, and —OC(O)CH($NH_2$)—$CH_3$—CH($CH_3$)$_2$.

In one variation, $R^{10}$ and $R^8$ are taken together to form a bond.

In one variation, $R^{10}$ and $R^8$ are taken together to form a bond, and $R^7$ and $R^9$ are taken together to form an alkylene bridge of 3 to 5 carbon atoms.

In one embodiment, the compound is of formula (A-IIA-1). In some variations, X is $CR^{6a}$, wherein $R^{6a}$ is H. In other variations, $R^6$ is H. In other variations, $R^1$ is H or $CH_3$. In yet other variations, $R^7$ is H or $CH_3$. In yet other variations, $R^8$ is hydroxyl or $NH_2$. In yet other variations, Q is optionally substituted pyridyl, optionally substituted pyrimidyl, optionally substituted pyrazinyl, or optionally substituted phenyl.

In another embodiment, the compound is of formula (A-IID-1). In some variations, X is $CR^6$, wherein $R^6$ is H. In other variations, $R^1$ is H or $CH_3$. In yet other variations, $R^7$ is H or $CH_3$. In yet other variations, $R^8$ is hydroxyl or $NH_2$. In yet other variations, Q is optionally substituted pyridyl, optionally substituted pyrimidyl, optionally substituted pyrazinyl, or optionally substituted phenyl.

In another embodiment, the compound is of formula (A-III):

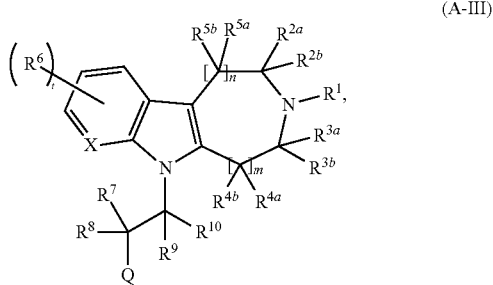

(A-III)

or a salt, solvate or N-oxide thereof, wherein:

$R^1$ is H; $C_1$-$C_5$ alkyl optionally substituted with 1 to 3 substituents independently selected from the group consisting of halo, hydroxyl, carboxyl and perhaloalkyl; $C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{3a}$ to form a propylene (—$CH_2CH_2CH_2$—) moiety or a butylene (—$CH_2CH_2CH_2CH_2$—) moiety; or is taken together with $R^{4a}$ or $R^{5a}$, where present, to form an ethylene (—$CH_2CH_2$—) moiety or a propylene (—$CH_2CH_2CH_2$—) moiety;

each n and m is 1, or n is 0 and m is 1, or n is 1 and m is 0;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—$CH_2CH_2CH_2$—) moiety or a butylene (—$CH_2CH_2CH_2CH_2$—) moiety; or is taken together with $R^{3a}$ to form an ethylene (—$CH_2CH_2$—) moiety or a propylene (—$CH_2CH_2CH_2$—) moiety; or is taken together with $R^{4a}$, where present, to form a methylene (—$CH_2$—) moiety or an ethylene (—$CH_2CH_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—$CH_2CH_2CH_2$—) moiety or a butylene (—$CH_2CH_2CH_2CH_2$—) moiety; or is taken together with $R^{2a}$ to form an ethylene (—$CH_2CH_2$—) moiety or a propylene (—$CH_2CH_2CH_2$—) moiety; or is taken together with $R^{5a}$, where present, to form a methylene (—$CH_2$—) moiety or an ethylene (—$CH_2CH_2$—) moiety;

$R^{4a}$ is H; optionally substituted $C_1$-$C_5$ alkyl; optionally substituted $C_2$-$C_5$ alkenyl; or optionally substituted aryl; or is taken together with $R^{3a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{2a}$ to form a methylene (—$CH_2$—) moiety or an ethylene (—$CH_2CH_2$—) moiety; or is taken together with $R^{5a}$, where present, to form a methylene (—$CH_2$—) moiety;

$R^{5a}$ is H; optionally substituted $C_1$-$C_5$ alkyl; optionally substituted $C_2$-$C_5$ alkenyl; or optionally substituted aryl; or is taken together with $R^{2a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{3a}$ to form a methylene (—$CH_2$—) moiety or an ethylene (—$CH_2CH_2$—) moiety; or is taken together with $R^{4a}$, where present, to form a methylene (—$CH_2$—) moiety;

each $R^{2b}$, $R^{3b}$, $R^{4b}$ and $R^{5b}$ is independently H, optionally substituted $C_1$-$C_5$ alkyl, optionally substituted $C_2$-$C_5$ alkenyl, or optionally substituted aryl;

X is N or $CR^{6a}$;

t is 1, 2 or 3;

each $R^6$ and $R^{6a}$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; $N(R^{11})R^{12}$; $SR^{13}$, $S(O)R^{13}$; $SO_2R^{13}$; —OC(O)N($R^{14}$)$R^{15}$; OC(O)-aryl; —OC(O)-heteroaryl; or —OC(O)$C_1$-$C_5$ alkyl optionally substituted with amino; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl; or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl; or is taken together with $R^8$ to form a bond;

each $R^{11}$ and $R^{12}$ is independently H or optionally substituted $C_1$-$C_5$ alkyl; or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some variations, Q is unsubstituted aryl; unsubstituted heteroaryl; aryl substituted with halo, $CH_3$, $CF_3$, or $OCH_3$; or heteroaryl substituted with halo, $CH_3$, $CF_3$, or $OCH_3$. In other variations, Q is unsubstituted pyridyl; unsubstituted pyrimidyl; unsubstituted pyrazinyl; unsubstituted phenyl; pyridyl substituted with halo, $CH_3$, $CF_3$, $CONH_2$, OH, or $OCH_3$; pyrimidyl substituted with halo, $CH_3$, $CF_3$, $CONH_2$, OH, or $OCH_3$; pyrazinyl substituted with halo, $CH_3$, $CF_3$, $CONH_2$, OH, or $OCH_3$; or phenyl substituted with halo, $CH_3$, $CF_3$, $CONH_2$, OH, or $OCH_3$.

In one variation, the compound is of the formula (A-III), wherein Q, X, m, n, t, $R^1$, $R^{2a}$, $R^{2b}$, $R^{3a}$, $R^{3b}$, $R^{4a}$, $R^{4b}$, $R^{5a}$, $R^{5b}$, $R^6$, $R^{6a}$, $R^{11}$, $R^{12}$, $R^{13}$, $R^{14}$ and $R^{15}$ are as defined for the formula (A-III), $R^7$ is H, halo, optionally substituted $C_1$-$C_5$ alkyl, $R^8$ is H, halo, hydroxyl, $N(R^{11})R^{12}$, $SR^{13}$, $S(O)R^{13}$, $SO_2R^{13}$, —OC(O)N($R^{14}$)$R^{15}$, or —OC(O)$C_1$-$C_5$ alkyl optionally substituted with amino, and each $R^9$ and $R^{10}$ is independently H or optionally substituted $C_1$-$C_5$ alkyl; or a salt, solvate or N-oxide thereof.

In some variations of the compound of the formula (A-III), $R^1$ is $C_1$-$C_5$ alkyl (e.g., methyl), each $R^{2a}$ and $R^{3a}$ is H, $R^6$ is methyl or chloro, and X is $CR^{6a}$ where $R^{6a}$ is methyl or chloro. In some of these variations, t is 1, 2 or 3. In some of these variations, $R^7$ is H or $C_1$-$C_5$ alkyl (e.g., methyl) and $R^8$ is H or hydroxyl. In some of these variations, each $R^7$ and $R^8$ is H. In some of these variations, $R^9$ is H or $C_1$-$C_5$ alkyl (e.g., methyl) and $R^{10}$ is H. In some of these variations, each $R^9$ and $R^{10}$ is H. In some of these variations, each $R^7$, $R^8$, $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl. In some of these variations, Q is phenyl substituted with —C(O)NR$^{16}$R$^{17}$, wherein each R$^{16}$ and R$^{17}$ is H. In some of these variations, Q is 4-carbamoylphenyl.

In some variations, X is $CR^{6a}$, wherein $R^{6a}$ is H, halo or $C_1$-$C_5$ alkyl; and each $R^6$ is independently H, halo or $C_1$-$C_5$ alkyl. In other variations, X is N. In some variations, $R^1$ is H or $C_1$-$C_5$ alkyl. In some variations, $R^7$ is H or $C_1$-$C_5$ alkyl, and $R^8$ is H, hydroxyl, $N(R^{11})R^{12}$ or —OC(O)$C_1$-$C_5$ alkyl. In other variations, $R^7$ is H or $C_1$-$C_5$ alkyl, and $R^8$ is H or hydroxyl. In yet other variations, $R^7$ is H or $C_1$-$C_5$ alkyl, and $R^8$ is hydroxyl. In yet other variations, $R^7$ is H, $R^8$ is hydroxyl, n is zero and m is 1. In certain variations, $R^7$ is methyl, $R^8$ is hydroxyl, n is zero and m is 1.

In some variations, Q is unsubstituted pyridyl; unsubstituted pyrimidyl; unsubstituted pyrazinyl; unsubstituted phenyl; unsubstituted imidazolyl; unsubstituted triazolyl; pyridyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl; pyrimidyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl; pyrazinyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl; phenyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl; imidazolyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl; or triazolyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl.

In certain variations, X is $CR^{6a}$, wherein $R^{6a}$ is H, halo or $C_1$-$C_5$ alkyl; each $R^6$ is independently H, halo or $C_1$-$C_5$ alkyl; $R^7$ is H or $C_1$-$C_5$ alkyl; $R^8$ is H, hydroxyl, $N(R^{11})R^{12}$ or —OC(O)$C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl. In some variations, n is 0 and m is 1; $R^7$ is H or $CH_3$; and $R^8$ is H or hydroxyl.

In yet other variations, X is N; $R^7$ is H or $C_1$-$C_5$ alkyl; $R^8$ is H, hydroxyl, $N(R^{11})R^{12}$ or —OC(O)$C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl. In some variations, n is 0 and m is 1; $R^7$ is H or $CH_3$; and $R^8$ is H or hydroxyl.

In some variations, n is 0 and m is 1; $R^1$ is taken together with $R^{2a}$ to form a propylene (—$CH_2CH_2CH_2$—) moiety; X is $CR^{6a}$, wherein $R^{6a}$ is H, halo or $C_1$-$C_5$ alkyl; each $R^6$ is independently H, halo or $C_1$-$C_5$ alkyl; $R^7$ is H or $C_1$-$C_5$ alkyl;

$R^8$ is H, hydroxyl, $N(R^{11})R^{12}$ or $—OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl. In some variations, $R^7$ is H or $CH_3$; and $R^8$ is H or hydroxyl.

In some variations, the compound is Compound No. 3a, 3b, 39a, 4a, 5b, 13b, 14a, 41a, 74a, 26a, 26b, 27a, 29b, 31a, 127a, 129d, 134b, 144b, 148, 173a, 174a, 150a, 176a, IV-210a, 151a, II-4-b, II-132b, 148b, 141b, 154b, II-135b, II-138, II-139, II-140, II-244a, II-7, II-146a, II-152a, II-227c, II-220, II-148a, II-13a, II-212a, II-260a or II-260b, or a salt, solvate or N-oxide thereof.

In one aspect, compounds provided herein used in the methods described above is a compound of formula (A-III), wherein any one or more of the following conditions applies: (1) X is $CR^{6a}$, wherein each $R^{6a}$ is independently H, halo or $C_1$-$C_5$ alkyl; (2) each $R^6$ is independently H, halo or $C_1$-$C_5$ alkyl; (3) X is N; (4) $R^1$ is H or $C_1$-$C_5$ alkyl; (5) $R^{2a}$ and $R^{3a}$ is H; (6) $R^7$ is H or $C_1$-$C_5$ alkyl; (8) $R^8$ is H, hydroxyl, $N(R^{11})R^{12}$ or $—OC(O)C_1$-$C_5$ alkyl; (9) $R^7$ is H or $C_1$-$C_5$ alkyl, and $R^8$ is H, hydroxyl, $N(R^{11})R^{12}$ or $—OC(O)C_1$-$C_5$ alkyl; (10) $R^7$ is H, and $R^8$ is H, hydroxyl, $N(R^{11})R^{12}$ or $—OC(O)C_1$-$C_5$ alkyl; (11) $R^7$ is $C_1$-$C_5$ alkyl, and $R^8$ is H, hydroxyl, $N(R^{11})R^{12}$ or $—OC(O)C_1$-$C_5$ alkyl; (12) $R^7$ is H or $C_1$-$C_5$ alkyl, and $R^8$ is H or hydroxyl; (13) $R^7$ is H or $C_1$-$C_5$ alkyl, and $R^8$ is hydroxyl; (14) $R^7$ is H, and $R^8$ is hydroxyl; (15) $R^7$ is methyl, and $R^8$ is hydroxyl; (16) $R^7$ is H, and $R^8$ is $NH_2$; (17) $R^7$ is H, and $R^8$ is $—OC(O)C_1$-$C_5$ alkyl; (18) $R^9$ is H or $C_1$-$C_5$ alkyl; (19) $R^{10}$ is H or $C_1$-$C_5$ alkyl; (20) each $R^9$ and $R^{10}$ is H; (21) one of $R^9$ and $R^{10}$ is H and the other is $C_1$-$C_5$ alkyl; (22) Q is: unsubstituted pyridyl; unsubstituted pyrimidyl; unsubstituted pyrazinyl; unsubstituted phenyl; unsubstituted imidazolyl; unsubstituted triazolyl; pyridyl substituted with 1 to 3 substituents independently selected form the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; pyrimidyl substituted with 1 to 3 substituents independently selected form the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; pyrazinyl substituted with 1 to 3 substituents independently selected form the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; or phenyl substituted with 1 to 3 substituents independently selected form the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; imidazolyl substituted with 1 to 3 substituents independently selected form the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; or triazolyl substituted with 1 to 3 substituents independently selected form the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; (23) X is $CR^{6a}$, wherein $R^{6a}$ is H, halo or $C_1$-$C_5$ alkyl; and each $R^6$ is independently H, halo or $C_1$-$C_5$ alkyl; (24) wherein $R^1$ is H or $C_1$-$C_5$ alkyl, $R^7$ is H or $C_1$-$C_5$ alkyl, and $R^8$ is H, hydroxyl, $N(R^{11})R^{12}$ or $—OC(O)C_1$-$C_5$ alkyl; (25) wherein $R^1$ is H or $C_1$-$C_5$ alkyl, $R^7$ is H or $C_1$-$C_5$ alkyl, and $R^8$ is H or hydroxyl; (26) $R^1$ is H or $C_1$-$C_5$ alkyl, $R^7$ is H or $C_1$-$C_5$ alkyl, and $R^8$ is hydroxyl; (27) wherein $R^1$ is $CH_3$, $R^7$ is H, $R^8$ is hydroxyl, n is zero and m is 1; (28) $R^1$ is $CH_3$, $R^7$ is methyl, $R^8$ is hydroxyl, n is zero and m is 1; (29) X is $CR^{6a}$, wherein $R^{6a}$ is H, halo or $C_1$-$C_5$ alkyl; each $R^6$ is independently H, halo or $C_1$-$C_5$ alkyl; $R^1$ is H or $C_1$-$C_5$ alkyl, $R^7$ is H or $C_1$-$C_5$ alkyl, $R^8$ is H, hydroxyl, $N(R^{11})R^{12}$ or $—OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; (30) n is 0 and m is 1; $R^1$ is H or $CH_3$; $R^7$ is H or $CH_3$; and $R^8$ is H or hydroxyl; (31) X is N; $R^1$ is H or $C_1$-$C_5$ alkyl, $R^7$ is H or $C_1$-$C_5$ alkyl, $R^8$ is H, hydroxyl, $N(R^{11})R^{12}$ or $—OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; (32) n is 0 and m is 1; $R^1$ is H or $CH_3$; $R^7$ is H or $CH_3$; and $R^8$ is H or hydroxyl; (33) n is 0 and m is 1; $R^1$ is taken together with $R^{2a}$ to form a propylene ($—CH_2CH_2CH_2—$) moiety; X is $CR^{6a}$, wherein $R^{6a}$ is H, halo or $C_1$-$C_5$ alkyl; each $R^6$ is independently H, halo or $C_1$-$C_5$ alkyl; $R^7$ is H or $C_1$-$C_5$ alkyl, $R^8$ is H, hydroxyl, $N(R^{11})R^{12}$ or $—OC(O)C_1$-$C_5$ alkyl; each $R^9$ and $R^{10}$ is hydrogen; and Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and $—C(O)NR^{16}R^{17}$, wherein each $R^{16}$ and $R^{17}$ is independently H or optionally substituted $C_1$-$C_5$ alkyl; (34) $R^7$ is H or $CH_3$; and $R^8$ is H or hydroxyl.

In another embodiment, the compound of formula (A-III) has the formula (A-IIIA):

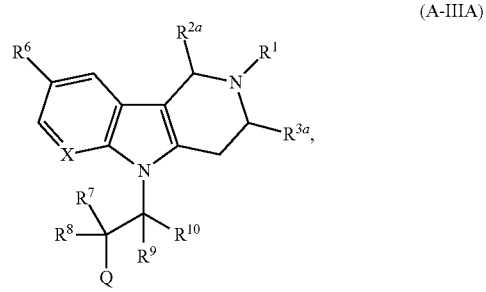

(A-IIIA)

or a salt, solvate or N-oxide thereof, wherein:

$R^1$ is H; $C_1$-$C_5$ alkyl optionally substituted with 1 to 3 substituents independently selected from halo, hydroxyl, carboxyl and perhaloalkyl; $C_3$-$C_8$ cycloalkyl optionally substituted with 1 to 3 substituents independently selected from halo, hydroxyl, carboxyl and perhaloalkyl; $C_2$-$C_5$ alkenyl optionally substituted with 1 to 3 substituents independently selected from halo, hydroxyl, carboxyl and perhaloalkyl; or $—C(O)O—C_1$-$C_5$ alkyl, or is taken together with $R^{2a}$ or $R^{3a}$ to form a propylene ($—CH_2CH_2CH_2—$) moiety or a butylene ($—CH_2CH_2CH_2CH_2—$) moiety;

$R^{2a}$ is H, optionally substituted $C_1$-$C_5$ alkyl, optionally substituted alkenyl or optionally substituted aryl, or is taken together with $R^1$ to form a propylene ($—CH_2CH_2CH_2—$) moiety or a butylene ($—CH_2CH_2CH_2CH_2—$) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some variations, Q is unsubstituted aryl; unsubstituted heteroaryl; aryl substituted with halo, $CH_3$, $CF_3$, or $OCH_3$; or heteroaryl substituted with halo, $CH_3$, $CF_3$, or $OCH_3$. In other variations, Q is unsubstituted pyridyl; unsubstituted pyrimidyl; unsubstituted pyrazinyl; unsubstituted phenyl; pyridyl substituted with halo, $CH_3$, $CF_3$, or $OCH_3$; pyrimidyl substituted with halo, $CH_3$, $CF_3$, or $OCH_3$; pyrazinyl substituted with halo, $CH_3$, $CF_3$, or $OCH_3$; or phenyl substituted with halo, $CH_3$, $CF_3$, or $OCH_3$.

In one variation, the compound is of the formula (A-IIIA), wherein Q, X, $R^1$, $R^{2a}$, $R^{3a}$, $R^6$, $R^{6a}$, $R^{11}$, $R^{12}$, $R^{13}$, $R^{14}$ and $R^{15}$ are as defined for the formula (A-IIIA); $R^7$ is H, halo, optionally substituted $C_1$-$C_5$ alkyl; $R^8$ is H, halo, hydroxyl, $N(R^{11})R^{12}$, $SR^{13}$, $S(O)R^{13}$, $SO_2R^{13}$, —OC(O)N($R^{14}$)$R^{15}$, or —OC(O)$C_1$-$C_5$ alkyl optionally substituted with amino; and each $R^9$ and $R^{10}$ is independently H or optionally substituted $C_1$-$C_5$ alkyl.

In some variations of the compound of the formula (A-IIIA), each $R^{2a}$ and $R^{3a}$ is H. In some variations, $R^1$ is $C_1$-$C_5$ alkyl (e.g., methyl). In some variations, each $R^6$ and $R^{6a}$ is independently halo (e.g., chloro) or $C_1$-$C_5$ alkyl (e.g., methyl). In some variations, each $R^6$ and $R^{6a}$ is independently halo (e.g., chloro or fluoro). In some variations, each $R^6$ or $R^{6a}$ is chloro. In some variations, each $R^6$ and $R^{6a}$ is independently $C_1$-$C_5$ alkyl (e.g., methyl). In some variations, X is $CR^{6a}$, wherein $R^{6a}$ is H or halo. In some variations, X is $CR^{6a}$, wherein $R^{6a}$ is H. In some variations, X is $CR^{6a}$, wherein $R^{6a}$ is chloro. In some variations, X is $CR^{6a}$, wherein $R^{6a}$ is halo (e.g., chloro or fluoro). In some variations, $R^6$ is H or halo. In some variations, $R^6$ is H. In some variations, $R^6$ is chloro. In some variations, $R^6$ is halo (e.g., chloro or fluoro). In some variations, $R^7$ is H or $C_1$-$C_5$ alkyl (e.g., methyl). In some variations, X is N. In some variations, $R^7$ is H. In some variations, $R^7$ is $C_1$-$C_5$ alkyl (e.g., methyl). In some variations, $R^8$ is H, hydroxyl, $N(R^{11})R^{12}$ or —OC(O)$C_1$-$C_5$ alkyl. In some variations, $R^8$ is H or hydroxyl. In some variations, $R^8$ is $N(R^{11})R^{12}$ where each $R^{11}$ and $R^{12}$ is H. In some variations, $R^8$ is —OC(O)$C_1$-$C_5$ alkyl (e.g., —OC(O)-t-butyl). In some variations, $R^7$ is H or $C_1$-$C_5$ alkyl (e.g., methyl) and $R^8$ is H, hydroxyl, $N(R^{11})R^{12}$ or —OC(O)$C_1$-$C_5$ alkyl. In some variations, $R^7$ is H; and $R^8$ is H, hydroxyl, $N(R^{11})R^{12}$ or —OC(O)$C_1$-$C_5$ alkyl. In some variations, $R^7$ is $C_1$-$C_5$ alkyl (e.g., methyl); and $R^8$ is H, hydroxyl, $N(R^{11})R^{12}$ or —OC(O)$C_1$-$C_5$ alkyl. In some variations, $R^7$ is H or $C_1$-$C_5$ alkyl (e.g., methyl); and $R^8$ is H or hydroxyl. In some variations, $R^7$ is H or $C_1$-$C_5$ alkyl (e.g., methyl); and $R^8$ is hydroxyl. In some variations, $R^7$ is H; and $R^8$ is hydroxyl. In some variations, $R^7$ is methyl; and $R^8$ is hydroxyl. In some variations, $R^7$ is H; and $R^8$ is $N(R^{11})R^{12}$, wherein each $R^{11}$ and $R^{12}$ is H. In some variations, $R^7$ is H; and $R^8$ is —OC(O)$C_1$-$C_5$ alkyl (e.g., —OC(O)-t-butyl). In some variations, $R^9$ is H or $C_1$-$C_5$ alkyl (e.g., methyl). In some variations, $R^{10}$ is H or $C_1$-$C_5$ alkyl (e.g., methyl). In some variations, each $R^9$ and $R^{10}$ is H. In some variations, one of $R^9$ and $R^{10}$ is H and the other of $R^9$ and $R^{10}$ is $C_1$-$C_5$ alkyl (e.g., methyl). In some variations, Q is an unsubstituted heteroaryl (e.g., pyridyl). In some variations, Q is an unsubstituted pyridyl group which may be attached to the parent structure at any position (e.g., 2-pyridyl, 3-pyridyl or 4-pyridyl). In some variations, Q is 3-pyridyl or 4-pyridyl. In some variations, Q is heteroaryl substituted with a substituent selected form the group consisting of halo (e.g., fluoro or chloro), $C_1$-$C_5$ alkyl (e.g., methyl), halo-substituted $C_1$-$C_5$ alkyl (e.g., $CF_3$) and carboxyl. In some variations, Q is heteroaryl substituted with halo (e.g., fluoro or chloro) or $C_1$-$C_5$ alkyl (e.g., methyl). In some variations, Q is heteroaryl substituted with $C_1$-$C_5$ alkyl (e.g., methyl). In some variations, Q is a pyridyl optionally substituted with a methyl where the pyridyl group may be attached to the parent structure at any position and the methyl group may be attached to the pyridyl group at any open position (e.g., 6-methyl-3-pyridyl and 3-methyl-4-pyridyl). In some variations, Q is phenyl substituted with a substituent selected form the group consisting of halo (e.g., fluoro or chloro), $C_1$-$C_5$ alkyl (e.g., methyl), halo-substituted $C_1$-$C_5$ alkyl (e.g., $CF_3$), carboxyl and —C(O)$NR^{16}R^{17}$ where each $R^{16}$ and $R^{17}$ is independently H or optionally substituted $C_1$-$C_5$ alkyl. In some variations, Q is phenyl substituted with a halo group (e.g., fluorophenyl). In some variations, Q is 4-fluorophenyl. In some variations, Q is phenyl substituted with —C(O)$NR^{16}R^{17}$ where each $R^{16}$ and $R^{17}$ is H.

In some variations of the compound of the formula (A-IIIA), $R^1$ is $C_1$-$C_5$ alkyl (e.g., methyl), each $R^{2a}$ and $R^{3a}$ is H, $R^6$ is methyl or chloro, and X is CH. In some of these variations, $R^7$ is H or $C_1$-$C_5$ alkyl (e.g., methyl) and $R^8$ is hydroxyl. In some of these variations, $R^7$ is H and $R^8$ is hydroxyl. In some of these variations, $R^7$ is methyl and $R^8$ is hydroxyl. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is hydroxyl, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, phenyl substituted with a halo group (e.g., fluorophenyl). In some of these variations, Q is 4-fluorophenyl. In some of these variations, Q is phenyl substituted with —C(O)$NR^{16}R^{17}$ where each $R^{16}$ and $R^{17}$ is H. In some of these variations, Q is 4-carbamoylphenyl.

In some variations of the compound of the formula (A-IIIA), $R^1$ is $C_1$-$C_5$ alkyl (e.g., methyl), each $R^{2a}$ and $R^{3a}$ is H, $R^6$ is methyl or chloro, and X is CH. In some variations, $R^7$ is H and $R^8$ is $N(R^{11})R^{12}$, wherein each $R^{11}$ and $R^{12}$ is H. In some variations, $R^7$ is H and $R^8$ is —OC(O)$C_1$-$C_5$ alkyl (e.g., —OC(O)-t-butyl). In some of these variations, $R^9$ is H or $C_1$-$C_5$ alkyl (e.g., methyl); and $R^{10}$ is H. In some of these variations, each $R^9$ and $R^{10}$ is H. In some of these variations, $R^7$ is H, $R^8$ is $NH_2$, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl. In some of these variations, Q is phenyl substituted with —C(O)$NR^{16}R^{17}$, wherein each $R^{16}$ and $R^{17}$ is H. In some of these variations, Q is 4-carbamoylphenyl.

In some variations of the compound of the formula (A-IIIA), $R^1$ and $R^{2a}$ are taken together to form a propylene (—$CH_2CH_2CH_2$—) moiety and $R^{3a}$ is H. In some of these variations, X is N. In some of these variations, X is CH. In some of these variations, $R^6$ is $C_1$-$C_5$ alkyl (e.g., methyl) or halo (e.g., chloro). In some of these variations, $R^6$ is methyl or chloro. In some of these variations, $R^7$ is H or $C_1$-$C_5$ alkyl (e.g., methyl) and $R^8$ is H or hydroxyl. In some of these variations, $R^7$ is H and $R^8$ is hydroxyl. In some of these variations, $R^7$ is methyl and $R^8$ is hydroxyl. In some of these variations, each $R^7$ and $R^8$ is H. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is H or hydroxyl, and each $R^9$ and $R^{10}$ is H. In some of these variations, each $R^7$, $R^8$, $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl. In some of these variations, Q is phenyl substituted with —C(O)$NR^{16}R^{17}$, wherein each $R^{16}$ and $R^{17}$ is H. In some of these variations, Q is 4-carbamoylphenyl.

In some variations, X is CH. In other variations, X is N. In yet other variations, $R^1$ is H or $CH_3$. In yet other variations, $R^{2a}$ is H or is taken together with $R^1$ to form a propylene (—$CH_2CH_2CH_2$—) moiety. In some variations, each $R^6$ and $R^{6a}$ is independently H, halo or $C_1$-$C_5$ alkyl. In yet other variations, $R^7$ is H or $CH_3$. In one variation, $R^8$ is hydroxyl.

In some variations, Q is: unsubstituted pyridyl; unsubstituted pyrimidyl; unsubstituted pyrazinyl; unsubstituted phenyl; unsubstituted imidazolyl; unsubstituted triazolyl; pyridyl substituted with halo, $CH_3$, $CF_3$, $CONH_2$, OH, or $OCH_3$; pyrimidyl substituted with halo, $CH_3$, $CF_3$, $CONH_2$, OH, or $OCH_3$; pyrazinyl substituted with halo, $CH_3$, $CF_3$, $CONH_2$, OH, or $OCH_3$; or phenyl substituted with halo, $CH_3$, $CF_3$, $CONH_2$, OH, or $OCH_3$.

In some variations, X is CH; each $R^6$ is independently H, halo or $C_1$-$C_5$ alkyl; $R^7$ is H or $CH_3$; $R^8$ is hydroxyl; and Q is unsubstituted pyridyl, or pyridyl substituted with halo, $CH_3$, $CF_3$, $CONH_2$, OH, or $OCH_3$.

In some variations, the compound is Compound No. 3a, 3b, 39a, 4a, 5b, 74a, 26a, 26b, 27a, 29b, 31a, 127a, 129d, 134b, 144b, 148, 173a, 174a, 150a, 176a, IV-210a, 151a, II-4b, II-132b, 148b, 141b, II-135b, II-138, II-139, II-140, II-244a, II-7, II-146a, II-151b, II-152a, II-227c, II-220, II-148a, II-13a, II-212a, II-260a and II-260b, or a salt, solvate or N-oxide thereof.

In another embodiment, the compound of formula (A-III) has the formula (A-IIIB):

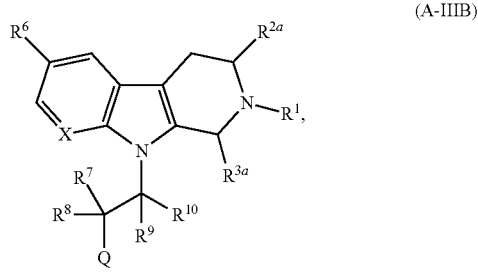

(A-IIIB)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents independently selected from halo, hydroxyl, carboxyl and perhaloalkyl, or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some variations, Q is unsubstituted aryl; unsubstituted heteroaryl; aryl substituted with halo, $CH_3$, $CF_3$, or $OCH_3$; or heteroaryl substituted with halo, $CH_3$, $CF_3$, or $OCH_3$. In other variations, Q is unsubstituted pyridyl; unsubstituted pyrimidyl; unsubstituted pyrazinyl; unsubstituted phenyl; pyridyl substituted with halo, $CH_3$, $CF_3$, $CONH_2$, OH, or $OCH_3$; pyrimidyl substituted with halo, $CH_3$, $CF_3$, $CONH_2$, OH, or $OCH_3$; pyrazinyl substituted with halo, $CH_3$, $CF_3$, $CONH_2$, OH, or $OCH_3$; or phenyl substituted with halo, $CH_3$, $CF_3$, $CONH_2$, OH, or $OCH_3$.

In some variations of the compound of the formula (A-IIIB), $R^1$ is $C_1$-$C_5$ alkyl (e.g., methyl), each $R^{2a}$ and $R^{3a}$ is H, $R^6$ is methyl or chloro, and X is CH. In some of these variations, $R^7$ is H or $C_1$-$C_5$ alkyl (e.g., methyl) and $R^8$ is hydroxyl. In some of these variations, $R^7$ is H and $R^8$ is hydroxyl. In some of these variations, $R^7$ is methyl and $R^8$ is hydroxyl. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is hydroxyl, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl.

In another embodiment, the compound of formula (A-III) has the formula (A-IIIC):

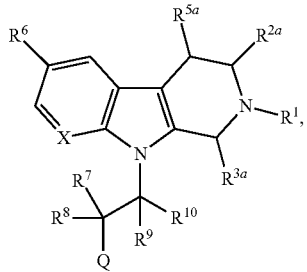

(A-IIIC)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents selected from halo, hydroxyl, carboxyl and perhaloalkyl, or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{5a}$ is H, optionally substituted $C_1$-$C_5$ alkyl, optionally substituted alkenyl or optionally substituted aryl;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —$C(O)C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, —$OC(O)N(R^{14})R^{15}$, —OC(O)-aryl, —OC(O)-heteroaryl, or —$OC(O)C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some variations, Q is unsubstituted aryl; unsubstituted heteroaryl; aryl substituted with halo, $CH_3$, $CF_3$, or $OCH_3$; or heteroaryl substituted with halo, $CH_3$, $CF_3$, or $OCH_3$. In other variations, Q is unsubstituted pyridyl; unsubstituted pyrimidyl; unsubstituted pyrazinyl; unsubstituted phenyl; pyridyl substituted with halo, $CH_3$, $CF_3$, or $OCH_3$; pyrimidyl substituted with halo, $CH_3$, $CF_3$, or $OCH_3$; pyrazinyl substituted with halo, $CH_3$, $CF_3$, or $OCH_3$; or phenyl substituted with halo, $CH_3$, $CF_3$, or $OCH_3$.

In one variation, the compound is of the formula (A-IIIC), wherein Q, X, $R^1$, $R^{2a}$, $R^{3a}$, $R^{5a}$, $R^6$, $R^{6a}$, $R^{11}$, $R^{12}$, $R^{13}$, $R^{14}$ and $R^{15}$ are as defined for the formula (A-IIIC), $R^7$ is H, halo, optionally substituted $C_1$-$C_5$ alkyl, $R^8$ is H, halo, hydroxyl, $N(R^{11})R^{12}$, $SR^{13}$, $S(O)R^{13}$, $SO_2R^{13}$, —$OC(O)N(R^{14})R^{15}$ or —$OC(O)C_1$-$C_5$ alkyl optionally substituted with amino, and each $R^9$ and $R^{10}$ is independently H or optionally substituted $C_1$-$C_5$ alkyl; or a salt, solvate or N-oxide thereof.

In another embodiment, the compound of formula (A-III) has the formula (A-IIID):

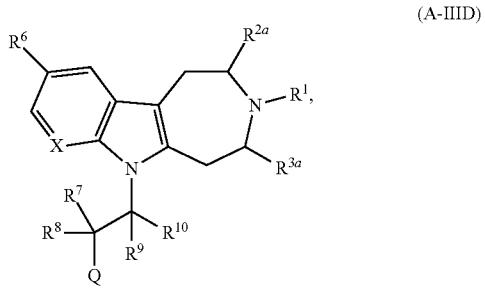

(A-IIID)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, —$OC(O)N(R^{14})R^{15}$, —OC(O)-aryl, —OC(O)-heteroaryl, or —$OC(O)C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some variations, Q is unsubstituted aryl; unsubstituted heteroaryl; aryl substituted with halo, $CH_3$, $CF_3$, or $OCH_3$; or heteroaryl substituted with halo, $CH_3$, $CF_3$, or $OCH_3$. In other variations, Q is unsubstituted pyridyl; unsubstituted pyrimidyl; unsubstituted pyrazinyl; unsubstituted phenyl; pyridyl substituted with halo, $CH_3$, $CF_3$, $CONH_2$, OH, or $OCH_3$; pyrimidyl substituted with halo, $CH_3$, $CF_3$, $CONH_2$, OH, or $OCH_3$; pyrazinyl substituted with halo, $CH_3$, $CF_3$, $CONH_2$, OH, or $OCH_3$; or phenyl substituted with halo, $CH_3$, $CF_3$, $CONH_2$, OH, or $OCH_3$.

In one variation, the compound is of the formula (A-IIID), wherein Q, X, $R^1$, $R^{2a}$, $R^{3a}$, $R^6$, $R^{6a}$, $R^{11}$, $R^{12}$, $R^{13}$, $R^{14}$ and $R^{15}$ are as defined for the formula (A-IIID), $R^7$ is H, halo, optionally substituted $C_1$-$C_5$ alkyl, $R^8$ is H, halo, hydroxyl, $N(R^{11})R^{12}$, $SR^{13}$, $S(O)R^{13}$, $SO_2R^{13}$, —$OC(O)N(R^{14})R^{15}$, or —$OC(O)C_1$-$C_5$ alkyl optionally substituted with amino, and each $R^9$ and $R^{10}$ is independently H or optionally substituted $C_1$-$C_5$ alkyl; or a salt, solvate or N-oxide thereof.

In some variations of the compound of the formula (A-IIID), $R^1$ is $C_1$-$C_5$ alkyl (e.g., methyl), each $R^{2a}$ and $R^{3a}$ is H, $R^6$ is methyl or chloro, and X is CH. In some of these variations, $R^7$ is H or $C_1$-$C_5$ alkyl (e.g., methyl) and $R^8$ is H or hydroxyl. In some of these variations, $R^7$ is H and $R^8$ is hydroxyl. In some of these variations, $R^7$ is methyl and $R^8$ is hydroxyl. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is hydroxyl, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl.

In certain embodiments, with respect to the compounds of formula (IIID), X is CH, $R^7$ is H or methyl, $R^8$ is H or OH, Q is phenyl, unsubstituted or substituted with F, Cl, or methoxy; and $R^6$ is other than methyl or chloro.

In another embodiment, the compound of formula (A-III) has the formula (A-IIIE):

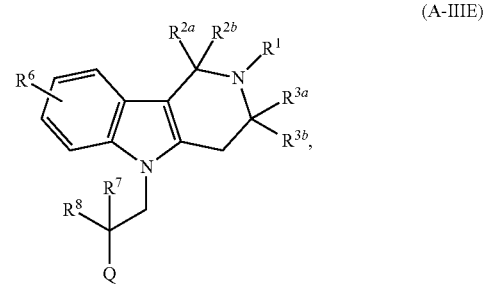

(A-IIIE)

or a salt, solvate or N-oxide thereof, wherein:

$R^1$ is H; $C_1$-$C_5$ alkyl optionally substituted with 1 to 3 substituents independently selected from halo, hydroxyl, carboxyl and perhaloalkyl; $C_3$-$C_8$ cycloalkyl optionally substituted with 1 to 3 substituents independently selected from halo, hydroxyl, carboxyl and perhaloalkyl; $C_2$-$C_5$ alkenyl optionally substituted with 1 to 3 substituents independently selected from halo, hydroxyl, carboxyl and perhaloalkyl, or —C(O)O—$C_1$-$C_5$ alkyl; or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H; optionally substituted $C_1$-$C_5$ alkyl; optionally substituted alkenyl; or optionally substituted aryl; or is taken together with $R^1$ to form a propylene (—$CH_2CH_2CH_2$—) moiety or a butylene (—$CH_2CH_2CH_2CH_2$—) moiety;

$R^{3a}$ is H; optionally substituted $C_1$-$C_5$ alkyl; optionally substituted alkenyl; or optionally substituted aryl; or is taken together with $R^1$ to form a propylene (—$CH_2CH_2CH_2$—) moiety or a butylene (—$CH_2CH_2CH_2CH_2$—) moiety;

each $R^{2b}$ and $R^{3b}$ is independently H or optionally substituted $C_1$-$C_5$ alkyl;

$R^6$ is H; hydroxyl; halo; $C_1$-$C_5$ alkyl optionally substituted with 1 to 3 substituents independently selected from halo, hydroxyl, carboxyl and perhaloalkyl; optionally substituted $C_1$-$C_5$ alkoxy or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety;

$R^8$ is H; halo; hydroxyl; $N(R^{11})R^{12}$; $SR^{13}$; $S(O)R^{13}$; $SO_2R^{13}$; —OC(O)N($R^{14}$)$R^{15}$; —OC(O)-aryl; —OC(O)-heteroaryl; or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In some variations of the compound of formula (A-IIIE), $R^1$ is $C_1$-$C_5$ alkyl optionally substituted with 1 to 3 substituents independently selected from halo, hydroxyl, carboxyl and perhaloalkyl. In certain variations, $R^1$ is $C_1$-$C_5$ alkyl substituted with a hydroxyl. In other variations, $R^1$ is methyl. In yet other variations, $R^1$ is H.

In some variations of the compound of formula (A-IIIE), $R^6$ is halo, $C_1$-$C_5$ alkyl, or perhaloalkyl. In certain variations, $R^6$ is methyl or isopropyl. In other variations of the compound of formula (A-IIIE), each $R^{2a}$, $R^{2b}$, $R^{3a}$ and $R^{3b}$ is H. In yet other variations of the compound of formula (A-IIIE), $R^7$ is an optionally substituted H or an unsubstituted $C_1$-$C_5$ alkyl, and $R^8$ is hydroxyl. In certain variations, $R^7$ is methyl, and $R^8$ is hydroxyl.

In yet other variations of the compound of formula (A-IIIE), Q is cycloalkyl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; aryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino. In other variations, Q is an optionally substituted pyridyl, an optionally substituted pyrimidyl, an optionally substituted pyrazinyl, or an optionally substituted phenyl, wherein each of the pyridyl, pyrimidyl, pryazinyl and phenyl is independently unsubstituted or substituted with 1 to 3 substituents independently selected from halo, carboxyl, alkoxy and $C_1$-$C_5$ alkyl. In one variation, Q is an unsubstituted pyridyl. In another variation, Q is an unsubstituted pyrimidyl. In yet another variation, Q is an unsubstituted pyrazinyl. In yet another variation, Q is an unsubstituted phenyl. In yet another variation, Q is a phenyl substituted with 1 to 3 substituents independently selected from the group consisting of halo or $C_1$-$C_5$ alkyl. In one variation, Q is fluoro-phenyl.

In another embodiment, the compound is of the formula (A-IIIE-1), (A-IIIE-2), (A-IIIE-3) or (A-IIIE-4):

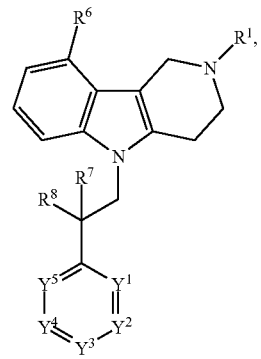

(A-IIIE-1)

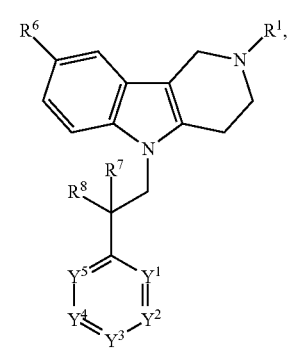

(A-IIIE-2)

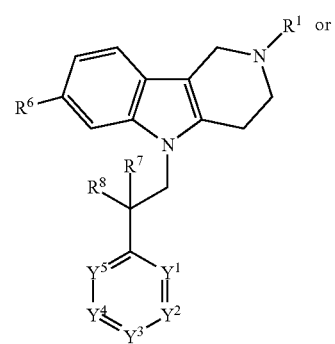

(A-IIIE-3)

-continued (A-IIIE-4)

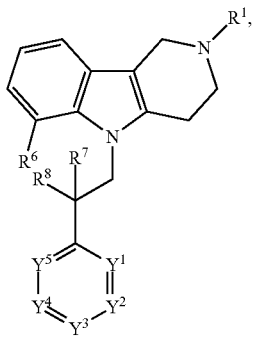

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, $N(R^{11})R^{12}$, $SR^{13}$, $S(O)R^{13}$, $SO_2R^{13}$, —OC(O)$N(R^{14})R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and each $Y^1$, $Y^2$, $Y^3$, $Y^4$ and $Y^5$ is independently N or $CR^4$ such that no more than two of $Y^1$, $Y^2$, $Y^3$, $Y^4$ and $Y^5$ are N, wherein $R^4$ is H, halo, $CH_3$, $CF_3$, or $OCH_3$.

In some variations of the compound of the formula (A-IIIE-1), (A-IIIE-2), (A-IIIE-3) or (A-IIIE-4), one of $Y^1$, $Y^2$, $Y^3$, $Y^4$ and $Y^5$ is N and the other four of $Y^1$, $Y^2$, $Y^3$, $Y^4$ and $Y^5$ are independently $CR^4$, and wherein $R^4$ is H, halo, $CH_3$, $CF_3$, or $OCH_3$. In other variations, $Y^5$ is CH, and each $Y^1$, $Y^2$, $Y^3$ and $Y^4$ is independently N or $CR^4$ such that two of $Y^1$, $Y^2$, $Y^3$ and $Y^4$ are N, and wherein $R^4$ is H, halo, $CH_3$, $CF_3$, or $OCH_3$. In some variations, $R^4$ is halo. In other variations, $R^4$ is $CH_3$. In one embodiment, $R^4$ is F. In another embodiment, $R^4$ is Cl. In some embodiments, any two of $Y^1$, $Y^2$, $Y^3$, $Y^4$ and $Y^5$ are $CR^4$, and each $R^4$ is independently Cl or F. In one embodiment, each $R^4$ is Cl. In another embodiment, each $R^4$ is F.

In some embodiments, the compound is of formula (A-IIIE-1), when each $R^7$ and $R^8$ is H; $R^1$ is H or methyl; $R^6$ is methyl or chloro; each $Y^1$, $Y^2$, $Y^4$ and $Y^5$ is $CR^4$, and $Y^3$ is CH, CF, or CCl; then at least one of $Y^1$, $Y^2$, $Y^4$ and $Y^5$ is other than CH.

In certain embodiments, with respect to the compounds of formula (A-IIIE-1), the compound is Compound No. 214.

In some embodiments, the compound is of formula (A-IIIE-2). In some variations, X is CH. In other variations, $R^1$ is H or $CH_3$. In yet other variations, $R^7$ is H or $CH_3$. In yet other variations, $R^8$ is hydroxyl. In some variations, one of $Y^1$, $Y^2$, $Y^3$, $Y^4$ and $Y^5$ is N, and the other four of $Y^1$, $Y^2$, $Y^3$, $Y^4$ and $Y^5$ are independently $CR^4$ (e.g., optionally substituted pyridyl). In other variations, two of $Y^1$, $Y^2$, $Y^3$, $Y^4$ and $Y^5$ is N, and the other three of $Y^1$, $Y^2$, $Y^3$, $Y^4$ and $Y^5$ are independently $CR^4$ (e.g., optionally substituted pyrimidyl or optionally substituted pyrazinyl). In yet other variations, each $Y^1$, $Y^2$, $Y^3$, $Y^4$ and $Y^5$ is $CR^4$ (e.g., optionally substituted phenyl). In certain variations, $R^4$ is H, halo, $CH_3$, $CF_3$, or $OCH_3$. In one embodiment, $R^4$ is F. In another embodiment, $R^4$ is Cl. In some embodiments, any two of $Y^1$, $Y^2$, $Y^3$, $Y^4$ and $Y^5$ are $CR^4$, wherein each $R^4$ is independently Cl or F. In one embodiment, each $R^4$ is Cl. In another embodiment, each $R^4$ is F.

In some embodiments, the compound is of formula (A-IIIE-2), $R^7$ is optionally substituted cycloalkyl, $R^8$ is OH, $R^1$ is methyl, $R^6$ is methyl or chloro, each $Y^1$, $Y^2$, $Y^3$, $Y^4$ and $Y^5$ is $CR^4$ wherein at least one $R^4$ is other than H or fluoro. In another embodiment, one of $Y^1$, $Y^2$, $Y^3$, $Y^4$ and $Y^5$ is N and the rest are independently $CR^4$, wherein at least one $R^4$ is other than H.

In some embodiments, the compound is of formula (A-IIIE-2), $R^7$ is $C_1$-$C_5$ alkyl, substituted with acylamino, $R^8$ is $CH_2$—CON(H)$CH_3$, $R^1$ is methyl or ethyl, $R^6$ is methyl or chloro, each $Y^1$, $Y^2$, $Y^3$, $Y^4$ and $Y^5$ is $CR^4$, wherein at least one $R^4$ is other than H, fluoro, chloro, methoxy, or difluoro. In another embodiment, one of $Y^1$, $Y^2$, $Y^3$, $Y^4$ and $Y^5$ is N and the rest are independently $CR^4$, wherein at least one $R^4$ is other than H or methyl. In another embodiment, two of $Y^1$, $Y^2$, $Y^3$, $Y^4$ and $Y^5$ are N and the rest are independently $CR^4$, wherein at least one $R^4$ is other than H.

In some embodiments, the compound is of formula (A-IIIE-2), $R^7$ is $C_1$-$C_5$ alkyl, substituted with —C(O)$OR^{7a}$, $R^{7a}$ is H or optionally substituted $C_1$-$C_5$ alkyl, $R^1$ is methyl or ethyl, $R^6$ is methyl or chloro, each $Y^1$, $Y^2$, $Y^3$, $Y^4$ and $Y^5$ is $CR^4$, wherein at least one $R^4$ is other than H, fluoro, chloro, methoxy, or difluoro. In another embodiment, one of $Y^1$, $Y^2$, $Y^3$, $Y^4$ and $Y^5$ is N and the rest are independently $CR^4$, wherein at least one $R^4$ is other than H, or methyl. In another embodiment, two of $Y^1$, $Y^2$, $Y^3$, $Y^4$ and $Y^5$ are N and the rest are independently $CR^4$, wherein at least one $R^4$ is other than H.

In some embodiments, the compound is of formula (A-IIIE-2), $R^7$ is $C_1$-$C_5$ alkyl, substituted with 1-3 halo, $R^7$ is $CF_3$, $R^8$ is OH, $R^1$ is methyl, $R^6$ is methyl, each $Y^1$, $Y^2$, $Y^3$, $Y^4$ and $Y^5$ is $CR^4$, wherein at least one $R^4$ is other than H or fluoro.

In some embodiments, the compound is of formula (A-IIIE-2), $R^7$ is optionally substituted phenyl, $R^8$ is OH, $R^1$ is methyl or ethyl, $R^6$ is methyl or chloro, each $Y^1$, $Y^2$, $Y^3$, $Y^4$ and $Y^5$ is $CR^4$, wherein at least one $R^4$ is other than H, or fluoro. In another embodiment, one of $Y^1$, $Y^2$, $Y^3$, $Y^4$ and $Y^5$ is N and the rest are independently $CR^4$, wherein at least one $R^4$ is other than H.

In some embodiments, the compound is of formula (A-IIIE-2), $R^8$ is halo. In one embodiment, $R^8$ is fluoro or chloro, $R^1$ is methyl, ethyl, isopropyl, or cyclopropyl, $R^6$ is methyl or chloro, each $Y^1$, $Y^2$, $Y^3$, $Y^4$ and $Y^5$ is $CR^4$, wherein at least one $R^4$ is other than H, fluoro, chloro, methoxy, or difluoro. In another embodiment, one of $Y^1$, $Y^2$, $Y^3$, $Y^4$ and $Y^5$ is N and the rest are independently $CR^4$, wherein at least one $R^4$ is other than H, or methyl. In another embodiment, two of $Y^1$, $Y^2$, $Y^3$, $Y^4$ and $Y^5$ are N and the rest are independently $CR^4$, wherein at least one $R^4$ is other than H.

In certain embodiments, with respect to the compounds of formula (A-IIIE-2), each $R^7$ and $R^8$ is H, and the compound is Compound No. 60, 61, 84-86, 89, 91, 117, 180, 184, 200, 201, 202, 204, 206-210, 213, 217-19, 297-299, 317, 319-320, or 332, or a salt, solvate or N-oxide thereof.

In certain embodiments, with respect to the compounds of formula (I), each $R^7$ and $R^8$ is H, and the compound is Compound No. II-39 or II-40.

In certain embodiments, with respect to the compounds of formula (A-IIIE-2), $R^7$ is H, $R^8$ is OH, each $Y^1$, $Y^2$, $Y^3$, $Y^4$ and $Y^5$ is $CR^4$, and the compound is Compound No. 30, 52, 66, 67, 139, 142, 183, or 203.

In certain embodiments, with respect to the compounds of formula (A-IIIE-2), $R^7$ is H, $R^8$ is OH, each $Y^1$, $Y^2$, $Y^3$, $Y^4$ and $Y^5$ is $CR^4$, and the compound is Compound No. II-88 or II-192.

In certain embodiments, with respect to the compounds of formula (A-IIIE-2), $R^7$ is H, $R^8$ is OH, each $Y^1$, $Y^3$, $Y^4$ and $Y^5$ is $CR^4$, $Y^2$ is N, and the compound is Compound No. 7, 21, 51, 59, 62, 140, or 144.

In certain embodiments, with respect to the compounds of formula (A-IIIE-2), $R^7$ is H, $R^8$ is OH, each $Y^1$, $Y^3$, $Y^4$ and $Y^5$ is $CR^4$, $Y^2$ is N, and the compound is Compound No. II-57, II-92, II-94, II-190 or II-191.

In certain embodiments, with respect to the compounds of formula (A-IIIE-2), $R^7$ is H, $R^8$ is OH, each $Y^1$, $Y^3$, $Y^4$ and $Y^5$ is $CR^4$, $Y^2$ is N, and the compound is Compound No. III-1.

In certain embodiments, with respect to the compounds of formula (A-IIIE-2), $R^7$ is H, $R^8$ is OH, each $Y^1$, $Y^2$, $Y^4$ and $Y^5$ is $CR^4$, $Y^3$ is N, and the compound is Compound No. 3, 4, 6, 11, 23, 49, 63, 69-72, 81, 133, or 135.

In certain embodiments, with respect to the compounds of formula (A-IIIE-2), $R^7$ is H, $R^8$ is OH, each $Y^1$, $Y^2$, $Y^3$ and $Y^5$ is $CR^4$, $Y^2$ is N, and the compound is Compound No. II-60, II-63, II-64, II-65, II-67, II-68, II-75, II-83, II-84, II-90, II-93, or II-97.

In certain embodiments, with respect to the compounds of formula (A-IIIE-2), $R^7$ is methyl, $R^8$ is OH, each $Y^1$, $Y^2$, $Y^3$, $Y^4$ and $Y^5$ is $CR^4$, and the compound is Compound No. 90, 98, or 254.

In certain embodiments, with respect to the compounds of formula (A-IIIE-2), $R^7$ is methyl, $R^8$ is OH, each $Y^1$, $Y^2$, $Y^3$, $Y^4$ and $Y^5$ is $CR^4$, and the compound is Compound No. II-36, 47, 163, 189, 194 to 203, or II-205.

In certain embodiments, with respect to the compounds of formula (A-IIIE-2), $R^7$ is methyl, $R^8$ is OH, each $Y^1$, $Y^2$, $Y^3$, $Y^4$ and $Y^5$ is $CR^4$, and the compound is Compound No. III-36, III-47, III-50, or III-51.

In certain embodiments, with respect to the compounds of formula (A-IIIE-2), $R^7$ is methyl, $R^8$ is OH, each $Y^1$, $Y^2$, $Y^4$ and $Y^5$ is $CR^4$, $Y^3$ is N, and the compound is Compound No. 1, 2, or 253.

In certain embodiments, with respect to the compounds of formula (A-IIIE-2), $R^7$ is methyl, $R^8$ is OH, each $Y^1$, $Y^2$, $Y^4$ and $Y^5$ is $CR^4$, $Y^3$ is N, and the compound is Compound No. II-58, II-168, II-172, II-173, II-181, II-182, or III-49.

In certain embodiments, with respect to the compounds of formula (A-IIIE-2), $R^7$ is methyl, $R^8$ is OH, each $Y^1$, $Y^3$, $Y^4$ and $Y^5$ is $CR^4$, $Y^2$ is N, and the compound is Compound No. 5, 29, 31, 56, 64, 93, 143, 169, 174, or 179.

In certain embodiments, with respect to the compounds of formula (A-IIIE-2), $R^7$ is methyl, $R^8$ is OH, each $Y^1$, $Y^3$, $Y^4$ and $Y^5$ is $CR^4$, $Y^2$ is N, and the compound is Compound No. II-80, 105, 118, 123, 124, 136, 141, 145, 148, 154, 193, 220, 269, II-280, or III-48.

In certain embodiments, with respect to the compounds of formula (A-IIIE-2), $R^8$ is $N(R^{11})R^{12}$, and the compound is Compound No. 27, 149 to 152, or 157.

In certain embodiments, with respect to the compounds of formula (A-IIIE-2), $R^8$ is $N(R^{11})R^{12}$, and the compound is Compound No. II-1, II-8 to II-14, or II-260.

In certain embodiments, with respect to the compounds of formula (A-IIIE-2), $R^7$ is other than H or methyl, $R^8$ is OH, and the compound is Compound No. 33 to 35, 223, or 263.

In certain embodiments, with respect to the compounds of formula (A-IIIE-2), $R^7$ is other than H or methyl, $R^8$ is OH, and the compound is Compound No. II-160, II-162, II-166, II-167, II-174, II-186, II-206, II-255, II-257, II-259, II-264, II-265, II-278, or III-52.

In certain embodiments, with respect to the compounds of formula (A-IIIE-2), $R^7$ is methyl, $R^8$ is H, and the compound is Compound No. 255, 288, or 289.

In certain embodiments, with respect to the compounds of formula (A-IIIE-2), $R^7$ is substituted $C_1$-$C_5$ alkyl, $R^8$ is H, and the compound is Compound No. II-216 to II-218, II-221 to II-231, II-232, or III-224 to III-253.

In certain embodiments, with respect to the compounds of formula (A-IIIE-2), the compound is Compound No. 25, 54, 68, 83, 94, 102, 130, 141, 146, 147, 260, or 338.

In certain embodiments, with respect to the compounds of formula (A-IIIE-2), the compound is Compound No. II-15, II-16, II-19, II-207-II-213, II-256, II-258, II-262, II-263, II-274, II-277, II-295, II-296, II-299, or V-14.

In some embodiments, the compound is of formula (A-IIIE-3), when each $R^7$ and $R^8$ is H; $R^1$ is methyl; $R^6$ is chloro; each $Y^1$, $Y^2$, $Y^4$ and $Y^5$ is $CR^4$, and $Y^3$ is CH, CF, or CCl; then at least one of $Y^1$, $Y^2$, $Y^4$ and $Y^5$ is other than CH.

In certain embodiments, with respect to the compounds of formula (A-IIIE-3), the compound is Compound No. 40, 53, 65, 119, 215, 315, II-169, or II-184.

In some embodiments, the compound is of formula (A-IIIE-4), when each $R^7$ and $R^8$ is H, or $R^7$ taken together with $R^8$ form a —$CH_2$ moiety, $R^1$ is methyl; $R^6$ is F, Cl, $CF_3$, ethenyl, or propenyl; each $Y^1$, $Y^2$, $Y^4$ and $Y^5$ is $CR^4$, and $Y^3$ is CH, CF or CCl; then at least one of $Y^1$, $Y^2$, $Y^4$ and $Y^5$ is other than CH.

In certain embodiments, with respect to the compounds of formula (A-IIIE-4), the compound is Compound No. 32, 44, 45, 48, 57, 82, 216, II-170, or II-183.

In another embodiment, the compound is of the formula (A-IIIE-5), (A-IIIE-6), (A-IIIE-7) or (A-IIIE-8):

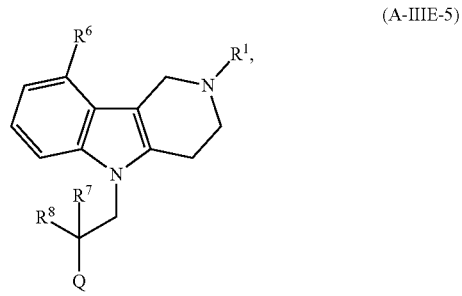

(A-IIIE-5)

-continued (A-IIIE-6)

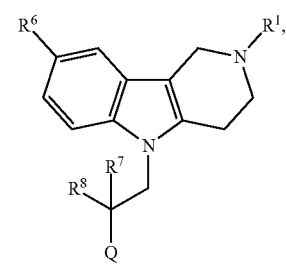

(A-IIIE-7)

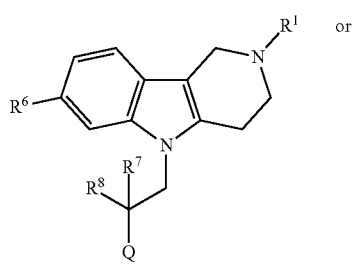

or (A-IIIE-8)

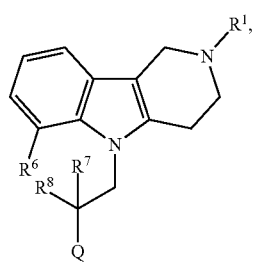

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, N($R^{11}$)$R^{12}$, S$R^{13}$, S(O)$R^{13}$, SO$_2$$R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene;

Q is

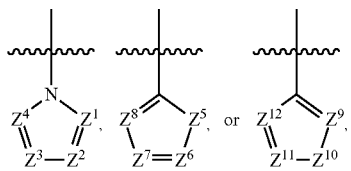

wherein each $Z^1$, $Z^2$, $Z^3$ and $Z^4$ is independently N or C$R^4$ such that no more than two of $Z^1$, $Z^2$, $Z^3$ and $Z^4$ are N, wherein $R^4$ is H, halo, CH$_3$, CF$_3$, or OCH$_3$;

each $Z^5$ and $Z^{10}$ is independently O, S or N$R^{4a}$, wherein $R^{4a}$ is H or CH$_3$; and each $Z^6$, $Z^7$, $Z^8$, $Z^9$, $Z^{11}$ and $Z^{12}$ is independently N or C$R^4$, wherein $R^4$ is H, halo, CH$_3$, CF$_3$, or OCH$_3$.

In other embodiments, the compound is of formula (A-IIIE-6). In other variations, $R^1$ is H or CH$_3$. In yet other variations, $R^7$ is H or CH$_3$. In yet other variations, $R^8$ is hydroxyl.

In some variations, Q is

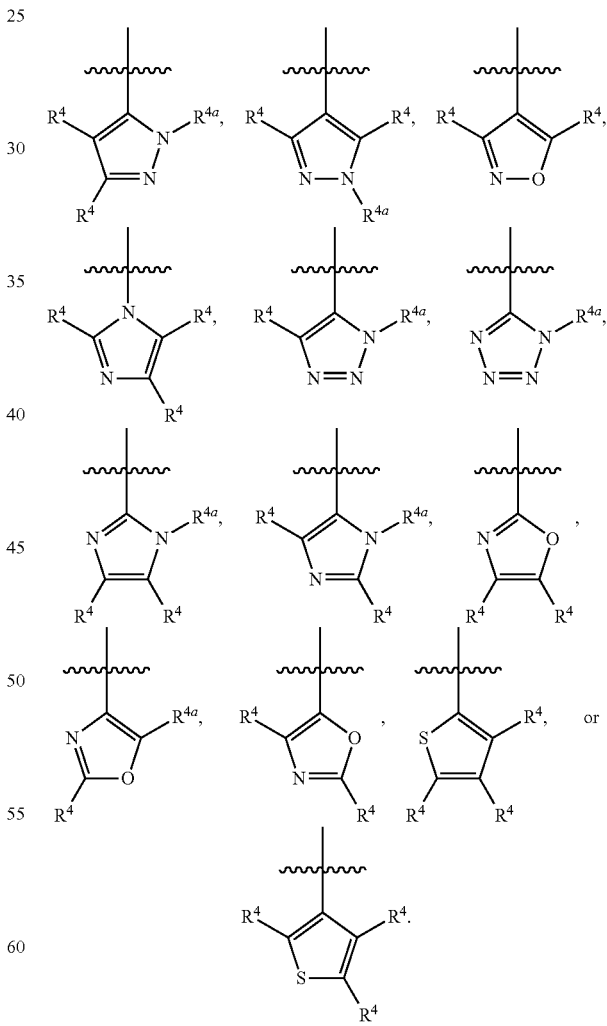

In some variations, $R^4$ is H, halo, CH$_3$, CF$_3$, or OCH$_3$.

In some variations of the compound of formula (A-IIIE-1), (A-IIIE-2), (A-IIIE-3), (A-IIIE-4), (A-IIIE-5), (A-IIIE-6), (A-IIIE-7) or (A-IIIE-8), $R^1$ is $C_1$-$C_5$ alkyl optionally substituted with 1 to 3 substituents independently selected from halo, hydroxyl, carboxyl and perhaloalkyl. In certain variations, $R^1$ is $C_1$-$C_5$ alkyl substituted with a hydroxyl. In other variations, $R^1$ is methyl. In some variations, $R^6$ is halo, $C_1$-$C_5$ alkyl or perhaloalkyl. In certain variations, $R^6$ is methyl or isopropyl. In yet other variations of the compound of formula (A-IIIE-1), (A-IIIE-2), (A-IIIE-3), (A-IIIE-4), (A-IIIE-5), (A-IIIE-6), (A-IIIE-7) or (A-IIIE-8), $R^7$ is an optionally substituted or an unsubstituted $C_1$-$C_5$ alkyl, and $R^8$ is hydroxyl. In certain variations, $R^7$ is methyl, and $R^8$ is hydroxyl.

In some embodiments, the compound is of formula (A-IIIE-6), when each $R^7$ and $R^8$ is H, $R^6$ is H, methyl, Cl, F, $CF_3$, or methoxy; then $R^1$ is other than methyl or cyclopropyl.

In certain embodiments, with respect to the compounds of formula (A-IIIE-6), the compound is Compound No. 131, 307, 308, 318, 326, II-106, or II-142.

In another embodiment, the compound is of the formula (A-IIIF):

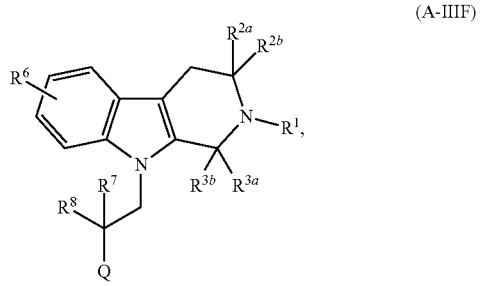

(A-IIIF)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

each $R^{2b}$ and $R^{3b}$ is independently H or optionally substituted $C_1$-$C_5$ alkyl;

$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, N($R^{11}$)$R^{12}$, S$R^{13}$, S(O)$R^{13}$, SO$_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In another embodiment, the compound is of the formula (A-IIIF-1), (A-IIIF-2), (A-IIIF-3) or (A-IIIF-4):

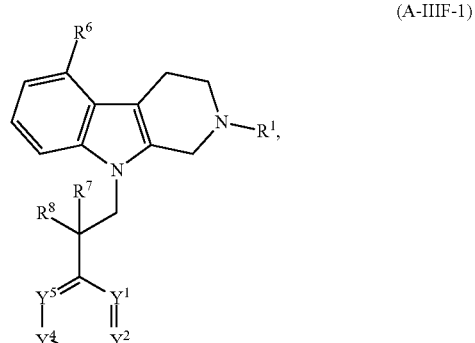

(A-IIIF-1)

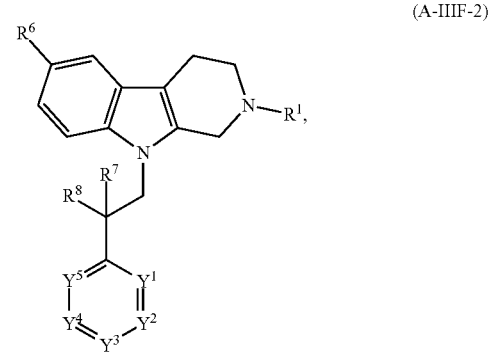

(A-IIIF-2)

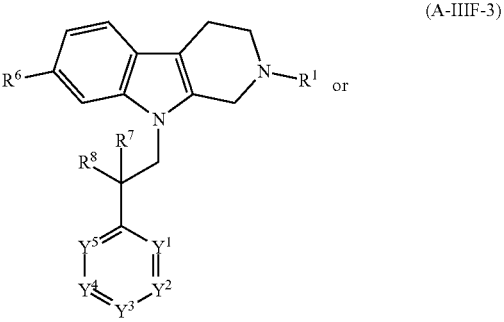

(A-IIIF-3) or

-continued (A-IIIF-4)

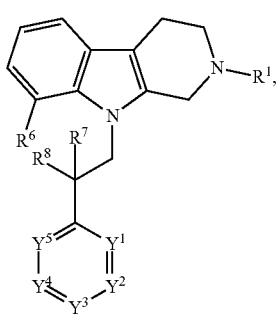

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, N($R^{11}$)$R^{12}$, $SR^{13}$, S(O)$R^{13}$, $SO_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and each $Y^1$, $Y^2$, $Y^3$, $Y^4$ and $Y^5$ is independently N or $CR^4$ such that no more than two of $Y^1$, $Y^2$, $Y^3$, $Y^4$ and $Y^5$ are N, wherein $R^4$ is H, halo, $CH_3$, $CF_3$, or $OCH_3$.

In some variations, one of $Y^1$, $Y^2$, $Y^3$, $Y^4$ and $Y^5$ is N and the other four of $Y^1$, $Y^2$, $Y^3$, $Y^4$ and $Y^5$ are independently $CR^4$, and wherein $R^4$ is H, halo, $CH_3$, $CF_3$, or $OCH_3$. In other variations, $Y^5$ is CH, and each $Y^1$, $Y^2$, $Y^3$ and $Y^4$ is independently N or $CR^4$ such that two of $Y^1$, $Y^2$, $Y^3$ and $Y^4$ are N, and wherein $R^4$ is H, halo, $CH_3$, $CF_3$, or $OCH_3$. In some variations, $R^4$ is halo. In other variations, $R^4$ is $CH_3$. In one embodiment, $R^4$ is F. In another embodiment, $R^4$ is Cl. In some embodiments, any two of $Y^1$, $Y^2$, $Y^3$, $Y^4$ and $Y^5$ are $CR^4$, and each $R^4$ is independently Cl or F. In one embodiment, each $R^4$ is Cl. In another embodiment, each $R^4$ is F.

In some embodiments, the compound is of formula (A-IIIF-1), when $R^7$ is methyl, $R^8$ is OH, $R^1$ is methyl, $R^6$ is chloro; then $Y^3$ is other than N.

In some embodiments, the compound is of formula (A-IIIF-2), when each $Y^1$, $Y^2$, $Y^3$, $Y^4$ and $Y^5$ is independently $CR^4$; and $R^1$ is methyl, ethyl, iso-propyl, or cyclopropyl; then $R^6$ is other than Cl or methyl.

In some embodiments, the compound is of formula (A-IIIF-2), $R^7$ is optionally substituted cycloalkyl, $R^8$ is OH, $R^1$ is methyl, $R^6$ is methyl or chloro, each $Y^1$, $Y^2$, $Y^3$, $Y^4$ and $Y^5$ is $CR^4$, wherein at least one $R^4$ is other than H or fluoro. In another embodiment, one of $Y^1$, $Y^2$, $Y^3$, $Y^4$ and $Y^5$ is N and the rest are independently $CR^4$, wherein at least one $R^4$ is other than H.

In some embodiments, the compound is of formula (A-IIIF-2), $R^7$ is $C_1$-$C_5$ alkyl, substituted with acylamino. In one embodiment, $R^7$ is $CH_2$—CON(H)$CH_3$, $R^1$ is methyl or ethyl, $R^6$ is methyl or chloro, each $Y^1$, $Y^2$, $Y^3$, $Y^4$ and $Y^5$ is $CR^4$, wherein at least one $R^4$ is other than H, fluoro, chloro, methoxy, or difluoro. In another embodiment, one of $Y^1$, $Y^2$, $Y^3$, $Y^4$ and $Y^5$ is N and the rest are independently $CR^4$, wherein at least one $R^4$ is other than H, or methyl. In another embodiment, two of $Y^1$, $Y^2$, $Y^3$, $Y^4$ and $Y^5$ are N and the rest are independently $CR^4$, wherein at least one $R^4$ is other than H.

In some embodiments, the compound is of formula (A-IIIF-2), $R^7$ is $C_1$-$C_5$ alkyl, substituted with —C(O)$OR^{7a}$, $R^{7a}$ is H or optionally substituted $C_1$-$C_5$ alkyl, $R^1$ is methyl or ethyl, $R^6$ is methyl or chloro, each $Y^1$, $Y^2$, $Y^3$, $Y^4$ and $Y^5$ is $CR^4$, wherein at least one $R^4$ is other than H, fluoro, chloro, methoxy, or difluoro. In another embodiment, one of $Y^1$, $Y^2$, $Y^3$, $Y^4$ and $Y^5$ is N and the rest are independently $CR^4$, wherein at least one $R^4$ is other than H, or methyl. In another embodiment, two of $Y^1$, $Y^2$, $Y^3$, $Y^4$ and $Y^5$ are N and the rest are independently $CR^4$, wherein at least one $R^4$ is other than H.

In some embodiments, the compound is of formula (A-IIIF-2), $R^7$ is $C_1$-$C_5$ alkyl, substituted with 1-3 halo, $R^7$ is $CF_3$, $R^8$ is OH, $R^1$ is methyl, $R^6$ is methyl, each $Y^1$, $Y^2$, $Y^3$, $Y^4$ and $Y^5$ is $CR^4$, wherein at least one $R^4$ is other than H or fluoro.

In some embodiments, the compound is of formula (A-IIIF-2), $R^7$ is optionally substituted phenyl, $R^8$ is OH, $R^1$ is methyl or ethyl, $R^6$ is methyl or chloro, each $Y^1$, $Y^2$, $Y^3$, $Y^4$ and $Y^5$ is $CR^4$, wherein at least one $R^4$ is other than H, or fluoro. In another embodiment, one of $Y^1$, $Y^2$, $Y^3$, $Y^4$ and $Y^5$ is N and the rest are independently $CR^4$, wherein at least one $R^4$ is other than H.

In some embodiments, the compound is of formula (A-IIIF-2), and $R^8$ is halo. In one embodiment, $R^8$ is fluoro or chloro, $R^1$ is methyl, ethyl, isopropyl, or cyclopropyl, $R^6$ is methyl or chloro, each $Y^1$, $Y^2$, $Y^3$, $Y^4$ and $Y^5$ is $CR^4$, wherein at least one $R^4$ is other than H, fluoro, chloro, methoxy, or difluoro. In another embodiment, one of $Y^1$, $Y^2$, $Y^3$, $Y^4$ and $Y^5$ is N and the rest are independently $CR^4$, wherein at least one $R^4$ is other than H, or methyl. In another embodiment, two of $Y^1$, $Y^2$, $Y^3$, $Y^4$ and $Y^5$ are N and the rest are independently $CR^4$, wherein at least one $R^4$ is other than H.

In certain embodiments, with respect to the compounds of formula (A-IIIF-2), $R^8$ is OH, each $Y^1$, $Y^2$, $Y^3$, $Y^4$ and $Y^5$ is $CR^4$, and the compound is Compound No. 18 or 20.

In certain embodiments, with respect to the compounds of formula (A-IIIF-2), $R^8$ is OH, each $Y^1$, $Y^2$, $Y^3$, $Y^4$ and $Y^5$ is $CR^4$, and the compound is Compound No. II-20, II-48, II-49, II-52, II-53, II-55, II-156, II-157, or II-158.

In certain embodiments, with respect to the compounds of formula (A-IIIF-2), $R^8$ is OH, each $Y^1$, $Y^2$, $Y^3$, $Y^4$ and $Y^5$ is $CR^4$, and the compound is Compound No. III-6, III-7, III-8, III-64-68, III-74, III-78, III-92, III-95 to III-97, or III-98.

In certain embodiments, with respect to the compounds of formula (A-IIIF-2), each $Y^1$, $Y^2$, $Y^3$, $Y^4$ and $Y^5$ is $CR^4$, and the compound is Compound No. III-189-191, III-196, III-256 to III-257, or III-258.

In certain embodiments, with respect to the compounds of formula (A-IIIF-2), $R^8$ is OH, each $Y^1$, $Y^3$, $Y^4$ and $Y^5$ is $CR^4$, $Y^2$ is N, and the compound is Compound No. 14, 28, 43, 128, 196, II-87, or III-93.

In certain embodiments, with respect to the compounds of formula (I) or (A-IIIF-2), each $Y^1, Y^3, Y^4$ and $Y^5$ is $CR^4$, $Y^2$ is N, and the compound is Compound No. II-249, III-192, or III-194.

In certain embodiments, with respect to the compounds of formula (I) or (A-IIIF-2), $R^8$ is OH, each $Y^1, Y^2, Y^4$ and $Y^5$ is $CR^4$, $Y^3$ is N, and the compound is Compound No. 8, 19, 41, III-69, III-75 to III-82, III-87 to III-88, III-90, or III-94.

In certain embodiments, with respect to the compounds of formula (A-IIIF-2), each $Y^1, Y^2, Y^4$ and $Y^5$ is $CR^4$, $Y^3$ is N, and the compound is Compound No. 153, III-187, III-188, III-195 or III-197.

In some embodiments, the compound is of formula (A-IIIF-3), when each $R^7$ and $R^8$ is H; $R^1$ is methyl; $R^6$ is chloro; each $Y^1, Y^2, Y^4$ and $Y^5$ is $CR^4$, and $Y^3$ is CH, CF or CCl; then at least one of $Y^1, Y^2, Y^4$ and $Y^5$ is other than CH.

In some embodiments, the compound is of formula (A-IIIF-4), when each $R^7$ and $R^8$ is H, or $R^7$ taken together with $R^8$ form a —$CH_2$ moiety, $R^1$ is methyl' $R^6$ is F, Cl, $CF_3$, ethenyl, or propenyl; each $Y^1, Y^2, Y^4$ and $Y^5$ is $CR^4$, and $Y^3$ is CH, CF or CCl; then at least one of $Y^1, Y^2, Y^4$ and $Y^5$ is other than CH.

In some embodiments, the compound is of formula (A-IIIF-3), when $R^7$ is H or methyl; $R^8$ is OH; $R^6$ is chloro or iso-propyl; $Y^2$ or $Y^3$ is N; then $R^1$ is other than methyl.

In certain embodiments, with respect to the compounds of formula (A-IIIF-3), the compound is Compound No. III-4, III-71, or III-90.

In some embodiments, the compound is of formula (A-IIIF-4), when $R^7$ is H or methyl, $R^8$ is OH, $R^1$ is methyl, $R^6$ is Cl, F, or methoxy; then $Y^3$ is other than N.

In certain embodiments, with respect to the compounds of formula (A-IIIF-4), the compound is Compound No. III-5, III-70, III-72, or III-89.

In another embodiment, the compound is of the formula (A-IIIG-1), (A-IIIG-2) or (A-IIIG-3):

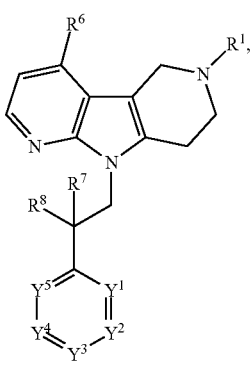
(A-IIIG-1)

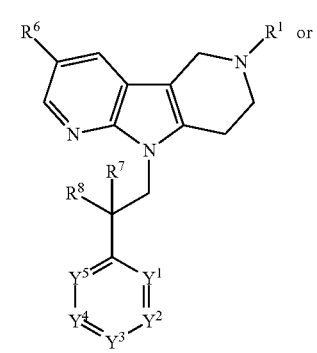
(A-IIIG-2)

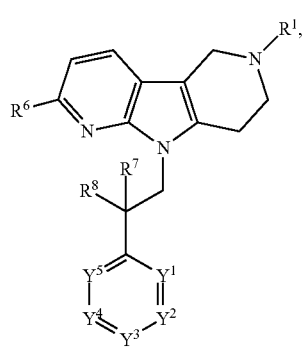
(A-IIIG-3)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, N($R^{11}$)$R^{12}$, S$R^{13}$, S(O)$R^{13}$, SO$_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and each $Y^1, Y^2, Y^3, Y^4$ and $Y^5$ is independently N or $CR^4$ such that no more than two of $Y^1, Y^2, Y^3, Y^4$ and $Y^5$ are N, wherein $R^4$ is H, halo, $CH_3$, $CF_3$, or $OCH_3$.

In some embodiments, the compound is of the formula (A-IIIG-2). In some variations, $R^1$ is H or $CH_3$. In other variations, $R^7$ is H or $CH_3$. In yet other variations, $R^8$ is hydroxyl or $NH_2$. In yet other variations, each $R^7$ and $R^8$ is H. In yet other variations, one of $Y^1, Y^2, Y^3, Y^4$ and $Y^5$ is N and the other four of $Y^1, Y^2, Y^3, Y^4$ and $Y^5$ are independently $CR^4$, and wherein $R^4$ is H, halo, $CH_3$, $CF_3$, or $OCH_3$. In other variations, $Y^5$ is CH, and each $Y^1, Y^2, Y^3$ and $Y^4$ is independently N or $CR^4$ such that two of $Y^1, Y^2, Y^3$ and $Y^4$ are N, and wherein $R^4$ is H, halo, $CH_3$, $CF_3$, or $OCH_3$. In some variations, $R^4$ is halo. In other variations, $R^4$ is $CH_3$. In one embodiment, $R^4$ is F. In another embodiment, $R^4$ is Cl. In some embodiments, any two of $Y^1, Y^2, Y^3, Y^4$ and $Y^5$ are $CR^4$, and each $R^4$ is independently Cl or F. In one embodiment, each $R^4$ is Cl. In another embodiment, each $R^4$ is F.

In some embodiments, the compound is of the formula (A-IIIG-1), (A-IIIG-2), or (A-IIIG-3), $R^6$ is H, $R^1$ is methyl, each of $R^7$ and $R^8$ is H, each $Y^1, Y^2, Y^3, Y^4$ and $Y^5$ is $CR^4$ wherein at least one $R^4$ is other than H.

In certain embodiments, with respect to the compounds of formula (A-IIIG-2), R⁸ is OH, and the compound is Compound No. 55, 136, 138, 145, II-99, II-100, II-108, II-109, II-111, or II-114.

In certain embodiments, with respect to the compounds of formula (A-IIIG-2), the compound is Compound No. 156, 159, II-110, II-119, II-240, or V-2.

In another embodiment, the compound is of the formula (A-IIIH):

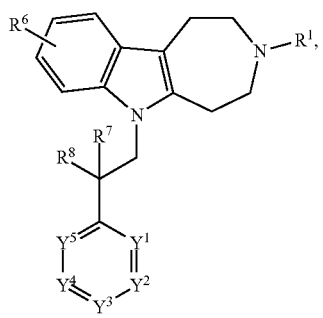

(A-IIIH)

or a salt, solvate or N-oxide thereof, wherein:

R¹ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

R⁶ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

R⁷ is H, halo, optionally substituted $C_1$-$C_5$ alkyl, or optionally substituted aryl, or is taken together with R⁸ and the carbon atom to which they are attached to form a dioxolane ring or a carbonyl moiety;

R⁸ is H, halo, hydroxyl, N(R¹¹)R¹², SR¹³, S(O)R¹³, SO₂R¹³, —OC(O)N(R¹⁴)R¹⁵, —OC(O)-aryl, —OC(O)-heteroaryl, or —OC(O)$C_1$-$C_5$ alkyl optionally substituted with amino, or is taken together with R⁷ and the carbon atom to which they are attached to form a dioxolane ring or a carbonyl moiety;

each R¹¹ and R¹² is independently H or optionally substituted $C_1$-$C_5$ alkyl, or R¹¹ and R¹² are taken together to form $C_3$-$C_5$ alkylene;

R¹³ is H or optionally substituted $C_1$-$C_5$ alkyl;

each R¹⁴ and R¹⁵ is independently H or optionally substituted $C_1$-$C_5$ alkyl; or R¹⁴ and R¹⁵ are taken together to form a $C_3$-$C_5$ alkylene; and each Y¹, Y², Y³, Y⁴ and Y⁵ is independently N or CR⁴ such that no more than two of Y¹, Y², Y³, Y⁴ and Y⁵ are N, wherein R⁴ is H, halo, CH₃, CF₃, or OCH₃.

In certain embodiments, with respect to the compounds of formula (A-IIIH), the compound is Compound No. 13, 15, 92, 154, 172, 221, or 339.

In certain embodiments, with respect to the compounds of formula (A-IIIH), the compound is Compound No. II-22, II-24 to II-35, II-37, II-38, II-41 to II-46, II-51, II-134, II-135, II-155, II-159, II-246, or II-289.

In certain embodiments, with respect to the compounds of formula (A-IIIH), the compound is Compound No. III-9-46, III-209 to III-220, III-320 to III-351, or III-352.

In certain embodiments, with respect to the compounds of formula (A-IIIH), the compound is Compound No. V-21.

In another embodiment, the compound is of the formula (A-IIIH-1), (A-IIIH-2), (A-IIIH-3) or (A-IIIH-4):

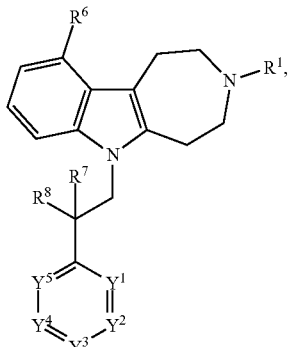

(A-IIIH-1)

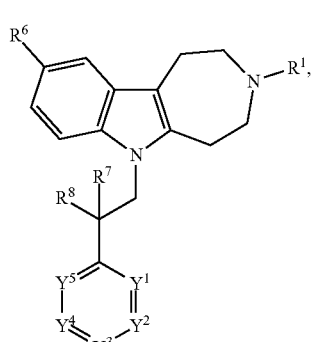

(A-IIIH-2)

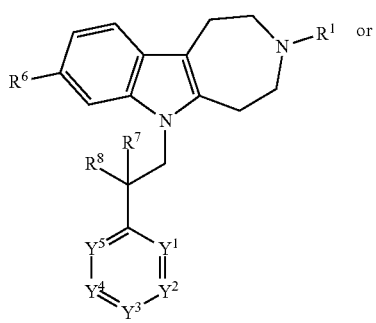

(A-IIIH-3) or

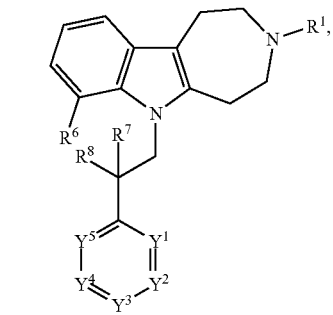

(A-IIIH-4)

or a salt, solvate or N-oxide thereof, wherein:

R¹ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 independently substituents selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, N($R^{11}$)$R^{12}$, S$R^{13}$, S(O)$R^{13}$, S$O_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and each $Y^1$, $Y^2$, $Y^3$, $Y^4$ and $Y^5$ is independently N or C$R^4$ such that no more than two of $Y^1$, $Y^2$, $Y^3$, $Y^4$ and $Y^5$ are N, wherein $R^4$ is H, halo, $CH_3$, $CF_3$, or $OCH_3$.

In some variations, $R^1$ is H or $CH_3$. In other variations, $R^7$ is H or $CH_3$. In yet other variations, $R^8$ is hydroxyl or $NH_2$. In yet other variations, each $R^7$ and $R^8$ is H. In some variations, each $Y^1$, $Y^2$, $Y^3$, $Y^4$ and $Y^5$ is independently N or C$R^4$ such that no more than two of $Y^1$, $Y^2$, $Y^3$, $Y^4$ and $Y^5$ are N, wherein $R^4$ is H, halo, $CH_3$, $CF_3$, or $OCH_3$. one of $Y^1$, $Y^2$, $Y^3$, $Y^4$ and $Y^5$ is N and the other four of $Y^1$, $Y^2$, $Y^3$, $Y^4$ and $Y^5$ are independently C$R^4$, and wherein $R^4$ is H, halo, $CH_3$, $CF_3$, or $OCH_3$. In other variations, $Y^5$ is CH, and each $Y^1$, $Y^2$, $Y^3$ and $Y^4$ is independently N or C$R^4$ such that two of $Y^1$, $Y^2$, $Y^3$ and $Y^4$ are N, and wherein $R^4$ is H, halo, $CH_3$, $CF_3$, or $OCH_3$. In some variations, $R^4$ is halo. In other variations, $R^4$ is $CH_3$. In one embodiment, $R^4$ is F. In another embodiment, $R^4$ is Cl. In some embodiments, any two of $Y^1$, $Y^2$, $Y^3$, $Y^4$ and $Y^5$ are C$R^4$, and each $R^4$ is independently Cl or F. In one embodiment, each $R^4$ is Cl. In another embodiment, each $R^4$ is F.

In certain embodiments, with respect to the compounds of formula (A-IIIH-2), $R^6$ is methyl or chloro, $R^7$ is H or methyl, $R^8$ is H or OH, $Y^1$ or $Y^2$ is independently C—H, C—F, C—Cl, or C-methoxy, and $Y^3$ is other than CH, CF, CCl, or C—$OCH_3$.

In certain embodiments, with respect to the compounds of formula (A-IIIH-2), $R^6$ is Cl or methyl, $R^7$ is methyl, $R^8$ is hydroxyl, and the compound is Compound No. 221.

In certain embodiments, with respect to the compounds of formula (A-IIIH-2), $R^6$ is Cl or methyl, $R^7$ is methyl, $R^8$ is hydroxyl, and the compound is Compound No. II-24, II-25, or II-26.

In certain embodiments, with respect to the compounds of formula (A-IIIH-2), $R^6$ is Cl or methyl, $R^7$ is methyl, $R^8$ is hydroxyl, and the compound is Compound No. III-11 to III-20, III-22, III-26 to III-38, or III-44 to III-46.

In one aspect, provided is a compoud of formula (A-IIIA'):

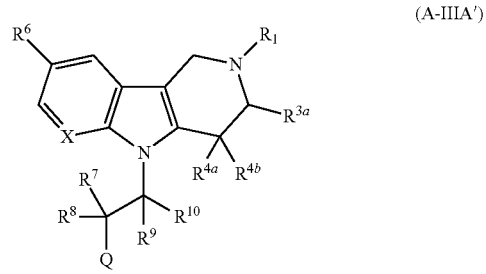

(A-IIIA')

or a salt, solvate or N-oxide thereof, wherein:
X, $R^1$, $R^{3a}$, $R^6$, $R^7$, $R^8$, $R^9$, $R^{10}$ and Q are as defined for formula (A-IIIA), $R^{4a}$ is selected from the group consisting of hydrogen; halo; hydroxyl; cyano; carboxyl; —OC(O)N($R^{14a}$)$R^{15a}$; and —C(O)N($R^{14a}$)$R^{15a}$;

$R^{4b}$ is selected from the group consisting of hydrogen, halo, and optionally substituted $C_1$-$C_5$ alkyl;

In one embodiment, when $R^{4b}$ is hydrogen, $R^{4a}$ is other than hydrogen. In some variations, $R^{4a}$ is halo. In some variations, $R^{4a}$ is chloro. In some variations, $R^{4a}$ is fluoro. In some variations, each $R^{4a}$ and $R^{4b}$ is halo.

In one aspect, provided is a compound of formula (A-IV):

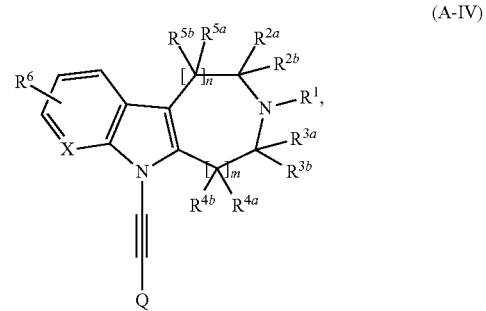

(A-IV)

or a salt, solvate or N-oxide thereof, wherein:
$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents selected from halo, hydroxyl, carboxyl and perhaloalkyl, or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety, or is taken together with $R^{4a}$ or $R^{5a}$, where present, to form an ethylene (—$CH_2CH_2$—) moiety or a propylene (—$CH_2CH_2CH_2$—) moiety;

each n and m is 1, or n is 0 and m is 1, or n is 1 and m is 0;

$R^{2a}$ is H, optionally substituted $C_1$-$C_5$ alkyl, optionally substituted alkenyl or optionally substituted aryl, or is taken together with $R^1$ or $R^{5a}$, where present, to form a propylene (—$CH_2CH_2CH_2$—) moiety or a butylene (—$CH_2CH_2CH_2CH_2$—) moiety, or is taken together with $R^{3a}$ to form an ethylene (—$CH_2CH_2$—) moiety or a propylene (—$CH_2CH_2CH_2$—) moiety, taken together with $R^{4a}$, where present, to form a methylene (—$CH_2$—) moiety or an ethylene (—$CH_2CH_2$—) moiety;

$R^{3a}$ is H, optionally substituted $C_1$-$C_5$ alkyl, optionally substituted alkenyl or optionally substituted aryl, or is taken together with $R^1$ or $R^{4a}$, where present, to form a propylene (—$CH_2CH_2CH_2$—) moiety or a butylene (—$CH_2CH_2CH_2CH_2$—) moiety, or is taken together with $R^{2a}$ to form an ethylene (—$CH_2CH_2$—) moiety or a propylene (—$CH_2CH_2CH_2$—) moiety, taken together with $R^{5a}$, where present, to form a methylene (—$CH_2$—) moiety or an ethylene (—$CH_2CH_2$—) moiety;

$R^{4a}$ is H, optionally substituted $C_1$-$C_5$ alkyl, optionally substituted alkenyl or optionally substituted aryl, or is taken together with $R^{3a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{2a}$ to form a methylene (—$CH_2$—) moiety or an ethylene (—$CH_2CH_2$—) moiety, or is taken together with $R^{5a}$, where present, to form a methylene (—$CH_2$—) moiety;

$R^{5a}$ is H, optionally substituted $C_1$-$C_5$ alkyl, optionally substituted alkenyl or optionally substituted aryl, or is taken together with $R^{2a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{3a}$ to form a methylene (—$CH_2$—) moiety or an ethylene (—$CH_2CH_2$—) moiety, or is taken together with $R^{4a}$, where present, to form a methylene (—$CH_2$—) moiety;

each $R^{2b}$, $R^{3b}$, $R^{4b}$ and $R^{5b}$ is independently H, optionally substituted $C_1$-$C_5$ alkyl, optionally substituted alkenyl or optionally substituted aryl;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —$C(O)C_1$-$C_5$ alkyl; and Q is cycloalkyl, aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one variation, the compound is of the formula (A-IV), wherein m, n and $R^1$ are as defined for the formula (A-IV);

$R^{2a}$ is H or optionally substituted $C_1$-$C_5$ alkyl, or is taken together with $R^1$ or $R^{5a}$, where present, to form a propylene (—$CH_2CH_2CH_2$—) moiety or a butylene (—$CH_2CH_2CH_2CH_2$—) moiety, or is taken together with $R^{3a}$ to form an ethylene (—$CH_2CH_2$—) moiety or a propylene (—$CH_2CH_2CH_2$—) moiety, taken together with $R^{4a}$, where present, to form a methylene (—$CH_2$—) moiety or an ethylene (—$CH_2CH_2$—) moiety;

$R^{3a}$ is H or optionally substituted $C_1$-$C_5$ alkyl, or is taken together with $R^1$ or $R^{4a}$, where present, to form a propylene (—$CH_2CH_2CH_2$—) moiety or a butylene (—$CH_2CH_2CH_2CH_2$—) moiety, or is taken together with $R^{2a}$ to form an ethylene (—$CH_2CH_2$—) moiety or a propylene (—$CH_2CH_2CH_2$—) moiety, taken together with $R^{5a}$, where present, to form a methylene (—$CH_2$—) moiety or an ethylene (—$CH_2CH_2$—) moiety;

$R^{4a}$ is H or optionally substituted $C_1$-$C_5$ alkyl, or is taken together with $R^{3a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{2a}$ to form a methylene (—$CH_2$—) moiety, or is taken together with $R^{5a}$, where present, to form a methylene (—$CH_2$—) moiety;

$R^{5a}$ is H or optionally substituted $C_1$-$C_5$ alkyl, or is taken together with $R^{2a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{3a}$ to form a methylene (—$CH_2$—) moiety or an ethylene (—$CH_2CH_2$—) moiety, or is taken together with $R^{4a}$, where present, to form a methylene (—$CH_2$—) moiety;

each $R^{2b}$, $R^{3b}$, $R^{4b}$ and $R^{5b}$ is independently H or optionally substituted $C_1$-$C_5$ alkyl;

X is N or $CR^{6a}$;

each $R^6$ and $R^{6a}$ is independently H, hydroxyl, halogen, $C_1$-$C_5$ alkyl optionally substituted with 1 to 3 halogen atoms, optionally substituted $C_1$-$C_5$ alkoxy or optionally substituted —$C(O)C_1$-$C_5$ alkyl;

Q is aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —$NHC(O)CH_3$ and —$C(O)NR^{16}R^{17}$; and each $R^{16}$ and $R^{17}$ is independently H or optionally substituted $C_1$-$C_5$ alkyl.

In one embodiment, the compound is of formula (A-IV), each of $R^{2b}$, $R^{3a}$, $R^{3b}$, $R^{4b}$, $R^{5a}$ and $R^{5b}$ is H; each $R^{2a}$ and $R^{4a}$ is H, or $R^{2a}$ is taken together with $R^{4a}$, when present, to form an ethylene (—$CH_2CH_2$—) moiety; each $R^6$ and $R^{6a}$ is independently $CF_3$, methyl, Cl, $CONHCH_3$, COOH, $COOCH_3$, or F; X is $CR^6$; and $R^1$ is other than methyl. In another embodiment, X is $CR^6$, $R^6$ is F; and $R^1$ is other than methyl.

In one aspect, provided is a compound of formula (A-V):

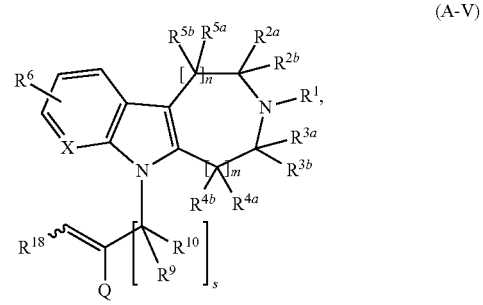

(A-V)

or a salt, solvate or N-oxide thereof, wherein:

$R^1$ is H, $C_1$-$C_5$ alkyl optionally substituted with 1 to 3 halogen atoms or hydroxyl, cycloalkyl optionally substituted with 1 to 3 halogen atoms or hydroxyl, $C_2$-$C_5$ alkenyl, or —$C(O)OR^{11}$, or is taken together with $R^{2a}$ or $R^{3a}$ to form a propylene (—$CH_2CH_2CH_2$—) moiety or a butylene (—$CH_2CH_2CH_2CH_2$—) moiety, or is taken together with $R^{4a}$ or $R^{5a}$, where present, to form an ethylene (—$CH_2CH_2$—) moiety or a propylene (—$CH_2CH_2CH_2$—) moiety;

each n and m is 1, or n is 0 and m is 1, or n is 1 and m is 0;

$R^{2a}$ is H, optionally substituted $C_1$-$C_5$ alkyl, optionally substituted alkenyl or optionally substituted aryl, or is taken together with $R^1$ or $R^{5a}$, where present, to form a propylene (—$CH_2CH_2CH_2$—) moiety or a butylene (—$CH_2CH_2CH_2CH_2$—) moiety, or is taken together with $R^{3a}$ to form an ethylene (—$CH_2CH_2$—) moiety or a propylene (—$CH_2CH_2CH_2$—) moiety, taken together with $R^{4a}$, where present, to form a methylene (—$CH_2$—) moiety or an ethylene (—$CH_2CH_2$—) moiety;

$R^{3a}$ is H, optionally substituted $C_1$-$C_5$ alkyl, optionally substituted alkenyl or optionally substituted aryl, or is taken together with $R^1$ or $R^{4a}$, where present, to form a propylene (—$CH_2CH_2CH_2$—) moiety or a butylene (—$CH_2CH_2CH_2CH_2$—) moiety, or is taken together with $R^{2a}$ to form an ethylene (—$CH_2CH_2$—) moiety or a propylene (—$CH_2CH_2CH_2$—) moiety, taken together with $R^{5a}$, where present, to form a methylene (—$CH_2$—) moiety or an ethylene (—$CH_2CH_2$—) moiety;

$R^{4a}$ is H, optionally substituted $C_1$-$C_5$ alkyl, optionally substituted alkenyl or optionally substituted aryl, or is taken together with $R^{3a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{2a}$ to form a methylene (—$CH_2$—) moiety or an ethylene (—$CH_2CH_2$—) moiety, or is taken together with $R^{5a}$, where present, to form a methylene (—$CH_2$—) moiety;

$R^{5a}$ is H, optionally substituted $C_1$-$C_5$ alkyl, optionally substituted alkenyl or optionally substituted aryl, or is taken together with $R^{2a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{3a}$ to form a methylene (—$CH_2$—) moiety or an ethylene (—$CH_2CH_2$—) moiety, or is taken together with $R^{4a}$, where present, to form a methylene (—$CH_2$—) moiety;

each $R^{2b}$, $R^{3b}$, $R^{4b}$ and $R^{5b}$ is independently H, optionally substituted $C_1$-$C_5$ alkyl, optionally substituted alkenyl or optionally substituted aryl;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

s is 0 or 1;

each $R^9$ and $R^{10}$, where present, is independently H or optionally substituted $C_1$-$C_5$ alkyl;

$R^{18}$ is H or optionally substituted $C_1$-$C_5$ alkyl, and ⁓ indicates the presence of either an (E) or (Z) double bond configuration; and Q is cycloalkyl, aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one variation, the compound is of the formula (A-V), wherein m, n and $R^1$ are as defined for the formula (A-V);

$R^{2a}$ is H or optionally substituted $C_1$-$C_5$ alkyl, or is taken together with $R^1$ or $R^{5a}$, where present, to form a propylene (—$CH_2CH_2CH_2$—) moiety or a butylene (—$CH_2CH_2CH_2CH_2$—) moiety, or is taken together with $R^{3a}$ to form an ethylene (—$CH_2CH_2$—) moiety or a propylene (—$CH_2CH_2CH_2$—) moiety, taken together with $R^{4a}$, where present, to form a methylene (—$CH_2$—) moiety or an ethylene (—$CH_2CH_2$—) moiety;

$R^{3a}$ is H or optionally substituted $C_1$-$C_5$ alkyl, or is taken together with $R^1$ or $R^{4a}$, where present, to form a propylene (—$CH_2CH_2CH_2$—) moiety or a butylene (—$CH_2CH_2CH_2CH_2$—) moiety, or is taken together with $R^{2a}$ to form an ethylene (—$CH_2CH_2$—) moiety or a propylene (—$CH_2CH_2CH_2$—) moiety, taken together with $R^{5a}$, where present, to form a methylene (—$CH_2$—) moiety or an ethylene (—$CH_2CH_2$—) moiety;

$R^{4a}$ is H or optionally substituted $C_1$-$C_5$ alkyl, or is taken together with $R^{3a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{2a}$ to form a methylene (—$CH_2$—) moiety or an ethylene (—$CH_2CH_2$—) moiety, or is taken together with $R^{5a}$, where present, to form a methylene (—$CH_2$—) moiety;

$R^{5a}$ is H or optionally substituted $C_1$-$C_5$ alkyl, or is taken together with $R^{2a}$ to form a propylene (—$CH_2CH_2CH_2$—) moiety or a butylene (—$CH_2CH_2CH_2CH_2$—) moiety, or is taken together with $R^1$ to form an ethylene (—$CH_2CH_2$—) moiety or a propylene (—$CH_2CH_2CH_2$—) moiety, or is taken together with $R^{3a}$ to form a methylene (—$CH_2$—) moiety or an ethylene (—$CH_2CH_2$—) moiety, or is taken together with $R^{4a}$, where present, to form a methylene (—$CH_2$—) moiety;

each $R^{2b}$, $R^{3b}$, $R^{4b}$ and $R^{5b}$ is independently H or optionally substituted $C_1$-$C_5$ alkyl;

X is N or $CR^{6a}$;

each $R^6$ and $R^{6a}$ is independently H, hydroxyl, halogen, $C_1$-$C_5$ alkyl optionally substituted with 1-3 halogen atoms, optionally substituted $C_1$-$C_5$ alkoxy or optionally substituted —C(O)$C_1$-$C_5$ alkyl;

s is 0 or 1;

each $R^9$ and $R^{10}$, where present, is independently H or optionally substituted $C_1$-$C_5$ alkyl;

$R^{18}$ is H or optionally substituted $C_1$-$C_5$ alkyl, and ⁓ indicates the presence of either an (E) or (Z) double bond configuration;

Q is aryl or heteroaryl optionally substituted with 1-3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)$CH_3$ and —C(O)$NR^{16}R^{17}$; and each $R^{16}$ and $R^{17}$ is independently H or optionally substituted $C_1$-$C_5$ alkyl.

In certain embodiments, with respect to the compounds of formula (A-V), the compound is Compound No. 116, 121, or 132.

In one aspect, provided is a compound of formula (A-VI):

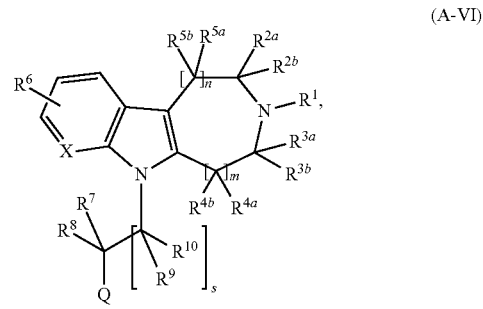

(A-VI)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety, or is taken together with $R^{4a}$ or $R^{5a}$, where present, to form an ethylene ($-CH_2CH_2-$) moiety or a propylene ($-CH_2CH_2CH_2-$) moiety;

each n and m is 1, or n is 0 and m is 1, or n is 1 and m is 0;

$R^{2a}$ is H, optionally substituted $C_1-C_5$ alkyl, optionally substituted alkenyl or optionally substituted aryl, or is taken together with $R^1$ or $R^{5a}$, where present, to form a propylene ($-CH_2CH_2CH_2-$) moiety or a butylene ($-CH_2CH_2CH_2CH_2-$) moiety, or is taken together with $R^{3a}$ to form an ethylene ($-CH_2CH_2-$) moiety or a propylene ($-CH_2CH_2CH_2-$) moiety, taken together with $R^{4a}$, where present, to form a methylene ($-CH_2-$) moiety or an ethylene ($-CH_2CH_2-$) moiety;

$R^{3a}$ is H, optionally substituted $C_1-C_5$ alkyl, optionally substituted alkenyl or optionally substituted aryl, or is taken together with $R^1$ or $R^{4a}$, where present, to form a propylene ($-CH_2CH_2CH_2-$) moiety or a butylene ($-CH_2CH_2CH_2CH_2-$) moiety, or is taken together with $R^{2a}$ to form an ethylene ($-CH_2CH_2-$) moiety or a propylene ($-CH_2CH_2CH_2-$) moiety, taken together with $R^{5a}$, where present, to form a methylene ($-CH_2-$) moiety or an ethylene ($-CH_2CH_2-$) moiety;

$R^{4a}$ is H, optionally substituted $C_1-C_5$ alkyl, optionally substituted alkenyl or optionally substituted aryl, or is taken together with $R^{3a}$ to form a propylene ($-CH_2CH_2CH_2-$) moiety or a butylene ($-CH_2CH_2CH_2CH_2-$) moiety, or is taken together with $R^1$ to form an ethylene ($-CH_2CH_2-$) moiety or a propylene ($-CH_2CH_2CH_2-$) moiety, or is taken together with $R^{2a}$ to form a methylene ($-CH_2-$) moiety or an ethylene ($-CH_2CH_2-$) moiety, or is taken together with $R^{5a}$, where present, to form a methylene ($-CH_2-$) moiety;

$R^{5a}$ is H, optionally substituted $C_1-C_5$ alkyl, optionally substituted alkenyl or optionally substituted aryl, or is taken together with $R^{2a}$ to form a propylene ($-CH_2CH_2CH_2-$) moiety or a butylene ($-CH_2CH_2CH_2CH_2-$) moiety, or is taken together with $R^1$ to form an ethylene ($-CH_2CH_2-$) moiety or a propylene ($-CH_2CH_2CH_2-$) moiety, or is taken together with $R^{3a}$ to form a methylene ($-CH_2-$) moiety or an ethylene ($-CH_2CH_2-$) moiety, or is taken together with $R^{4a}$, where present, to form a methylene ($-CH_2-$) moiety;

each $R^{2b}$, $R^{3b}$, $R^{4b}$ and $R^{5b}$ is independently H, optionally substituted $C_1-C_5$ alkyl, optionally substituted alkenyl or optionally substituted aryl;

X is N or $CR^{6a}$;

each $R^6$ and $R^{6a}$ is independently H, hydroxyl, halo, $C_1-C_5$ alkyl optionally substituted with 1 to 3 substituents independently selected from halo, hydroxyl, carboxyl and perhaloalkyl, optionally substituted $C_1-C_5$ alkoxy or optionally substituted $-C(O)C_1-C_5$ alkyl;

$R^7$ is H, halo, optionally substituted $C_1-C_5$ alkyl, or optionally substituted aryl, or is taken together with $R^8$ and the carbon atom to which they are attached to form a dioxolane ring or a carbonyl moiety, or is taken together with $R^9$, where present, to form a $C_3-C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, $-OC(O)N(R^{14})R^{15}$, $-OC(O)$-aryl, $-OC(O)$-heteroaryl, or $-OC(O)C_1-C_5$ alkyl optionally substituted with amino, or is taken together with $R^7$ and the carbon atom to which they are attached to form a dioxolane ring or a carbonyl moiety, or is taken together with $R^{10}$, where present, to form a bond;

s is 0 or 1;

each $R^9$ and $R^{10}$, where present, is independently H or optionally substituted $C_1-C_5$ alkyl;

each $R^{11}$, $R^{12}$, $R^{13}$, $R^{14}$ and $R^{15}$ is independently H or optionally substituted $C_1-C_5$ alkyl; and Q is acylamino, carbonylalkoxy, acyloxy, aminoacyl, aminocarbonylalkoxy or aminoaryl.

In one variation, the compound is of the formula (A-VI), wherein m, n, Q and $R^1$ are defined for the formula (A-VI);

$R^{2a}$ is H or optionally substituted $C_1-C_5$ alkyl, or is taken together with $R^1$ or $R^{5a}$, where present, to form a propylene ($-CH_2CH_2CH_2-$) moiety or a butylene ($-CH_2CH_2CH_2CH_2-$) moiety, or is taken together with $R^{3a}$ to form an ethylene ($-CH_2CH_2-$) moiety or a propylene ($-CH_2CH_2CH_2-$) moiety, taken together with $R^{4a}$, where present, to form a methylene ($-CH_2-$) moiety or an ethylene ($-CH_2CH_2-$) moiety;

$R^{3a}$ is H or optionally substituted $C_1-C_5$ alkyl, or is taken together with $R^1$ or $R^{4a}$, where present, to form a propylene ($-CH_2CH_2CH_2-$) moiety or a butylene ($-CH_2CH_2CH_2CH_2-$) moiety, or is taken together with $R^{2a}$ to form an ethylene ($-CH_2CH_2-$) moiety or a propylene ($-CH_2CH_2CH_2-$) moiety, taken together with $R^{5a}$, where present, to form a methylene ($-CH_2-$) moiety or an ethylene ($-CH_2CH_2-$) moiety;

$R^{4a}$ is H or optionally substituted $C_1-C_5$ alkyl, or is taken together with $R^{3a}$ to form a propylene ($-CH_2CH_2CH_2-$) moiety or a butylene ($-CH_2CH_2CH_2CH_2-$) moiety, or is taken together with $R^1$ to form an ethylene ($-CH_2CH_2-$) moiety or a propylene ($-CH_2CH_2CH_2-$) moiety, or is taken together with $R^{2a}$ to form a methylene ($-CH_2-$) moiety or an ethylene ($-CH_2CH_2-$) moiety, or is taken together with $R^{5a}$, where present, to form a methylene ($-CH_2-$) moiety;

$R^{5a}$ is H or optionally substituted $C_1-C_5$ alkyl, or is taken together with $R^{2a}$ to form a propylene ($-CH_2CH_2CH_2-$) moiety or a butylene ($-CH_2CH_2CH_2CH_2-$) moiety, or is taken together with $R^1$ to form an ethylene ($-CH_2CH_2-$) moiety or a propylene ($-CH_2CH_2CH_2-$) moiety, or is taken together with $R^{3a}$ to form a methylene ($-CH_2-$) moiety or an ethylene ($-CH_2CH_2-$) moiety, or is taken together with $R^{4a}$, where present, to form a methylene ($-CH_2-$) moiety;

each $R^{2b}$, $R^{3b}$, $R^{4b}$ and $R^{5b}$ is independently H or optionally substituted $C_1-C_5$ alkyl;

X is N or $CR^{6a}$;

each $R^6$ and $R^{6a}$ is independently H, hydroxyl, halogen, $C_1-C_5$ alkyl optionally substituted with 1-3 halogen atoms, optionally substituted $C_1-C_5$ alkoxy or optionally substituted $-C(O)C_1-C_5$ alkyl;

$R^7$ is H or optionally substituted $C_1-C_5$ alkyl;

$R^8$ is H, halo, hydroxyl, $N(R^{11})R^{12}$, $SR^{13}$, $S(O)R^{13}$, $SO_2R^{13}$, $-OC(O)N(R^{14})R^{15}$, or $-OC(O)C_1-C_5$ alkyl optionally substituted with amino;

s is 0 or 1;

each $R^9$ and $R^{10}$, where present, is independently H or optionally substituted $C_1-C_5$ alkyl; and each $R^{11}$, $R^{12}$, $R^{13}$, $R^{14}$ and $R^{15}$ is independently H or optionally substituted $C_1-C_5$ alkyl.

In another embodiment, the compound is of formula (A-VIIA), (A-VIIB), (A-VIIC), (A-VIID), (A-VIIE) or (A-VIIF):

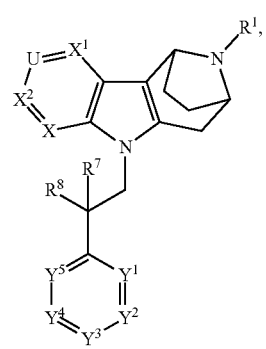

(A-VIIA)

-continued (A-VIIB)
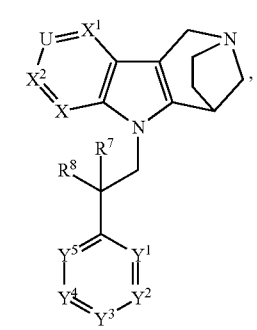

(A-VIIC)
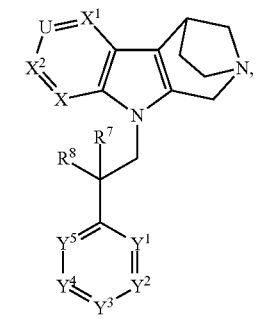

(A-VIID)
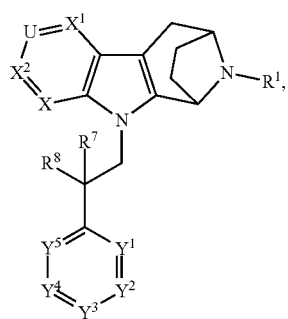

(A-VIIE)
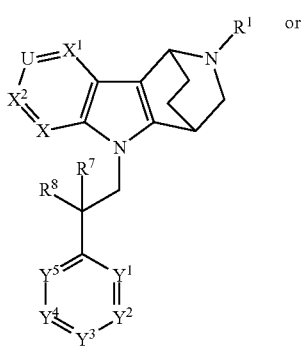

(A-VIIF)
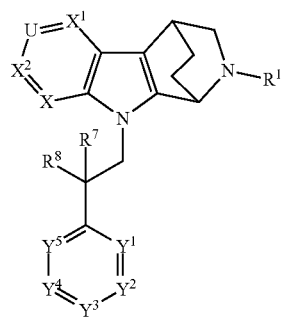

or a salt, solvate or N-oxide thereof, wherein:
$R^1$, where present, is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

each $X^1$, $X^2$, X and U is independently N or $CR^6$;

each $R^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, $N(R^{11})R^{12}$, $SR^{13}$, $S(O)R^{13}$, $SO_2R^{13}$, $OC(O)N(R^{14})R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and each $Y^1$, $Y^2$, $Y^3$, $Y^4$ and $Y^5$ is independently N or $CR^4$ such that no more than two of $Y^1$, $Y^2$, $Y^3$, $Y^4$ and $Y^5$ are N, wherein $R^4$ is H, halo, $CH_3$, $CF_3$, or $OCH_3$.

In certain embodiments, with respect to the compounds of formula (A-VIIA), $R^8$ is OH, and the compound is Compound No. II-107, II-164, II-165, III-2, III-102-107, III-114, III-131, III-135, III-137, or III-138.

In certain embodiments, with respect to the compounds of formula (A-VIIA), each $X^1$, $X^2$, X and U is independently $CR^6$; and the compound is Compound No. 211, III-100, III-200-202, III-207, III-289 to III-296, III-307, III-309, III-316, III-318, or III-319.

In certain embodiments, with respect to the compounds of formula (A-VIIA), each $X^1$, $X^2$, X and U is independently $CR^6$, each $Y^1$, $Y^3$, $Y^4$ and $Y^5$ is independently $CR^4$, $Y^2$ is N, and the compound is Compound No. III-132, III-133, III-203, III-205, III-294, III-299, III-303, III-306, III-312, or III-315.

In certain embodiments, with respect to the compounds of formula (A-VIIA), each $X^1$, $X^2$, X and U is independently $CR^6$, each $Y^1$, $Y^2$, $Y^4$ and $Y^5$ is independently $CR^4$, $Y^3$ is N, and the compound is Compound No. 73, 154, II-66, III-101, III-108 to III-113, III-115 to III-121, III-125 to III-130, III-134, III-138, III-198, III-199, III-206 to III-208, III-297, III-298, III-301, III-302, III-305, III-308, III-311, III-314, or III-317.

In certain embodiments, with respect to the compounds of formula (A-VIIA), each $X^1$, $X^2$, and X is $CR^6$; U is N, and the compound is Compound No. III-2.

In certain embodiments, with respect to the compounds of formula (A-VIIB), each $X^1$, $X^2$, X and U is independently $CR^6$, $R^8$ is OH, and the compound is Compound No. III-59.

In certain embodiments, with respect to the compounds of formula (A-VIIC), each $X^1$, $X^2$, X and U is independently $CR^6$, $R^8$ is OH, each $Y^1$, $Y^2$, $Y^4$ and $Y^5$ is independently $CR^4$, $Y^3$ is N, and the compound is Compound No. 36, 38, or II-69.

In certain embodiments, with respect to the compounds of formula (A-VIID), each $X^1$, $X^2$, X and U is independently $CR^6$, $R^8$ is OH, and the compound is Compound No. III-58.

In certain embodiments, with respect to the compounds of formula (A-VIIE), each $X^1$, $X^2$, X and U is independently $CR^6$, $R^8$ is OH, and the compound is Compound No. III-60.

In certain embodiments, with respect to the compounds of formula (A-VIIE), each $X^1$, $X^2$, X and U is independently $CR^6$, $R^8$ is OH, and the compound is Compound No. III-56.

In another embodiment, the compound is of formula (A-VIIIA) or (A-VIIIB):

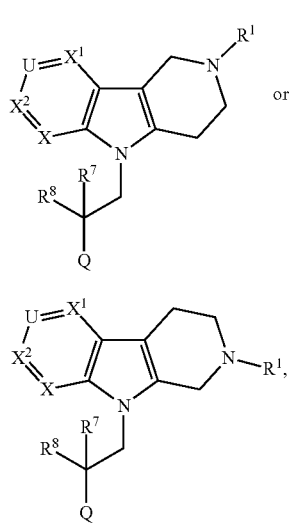

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

each $X^1$, $X^2$, X and U is independently N or $CR^6$;

each $R^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, N($R^{11}$)$R^{12}$, $SR^{13}$, $S(O)R^{13}$, $SO_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is aryl or heteroaryl, wherein the aryl or heteroaryl is independently optionally substituted with 1 to 3 substituents including halogen, $C_1$-$C_5$ alkyl or cycloalkyl, halo-substituted $C_1$-$C_5$ alkyl or cycloalkyl, $C_1$-$C_5$ alkoxy or cycloalkoxy, —CN or —C(O)N($R^a$)$R^b$, and wherein each $R^a$ and $R^b$ is independently H or $C_1$-$C_5$ alkyl.

In some variations of the compounds of formula (A-VIIIA) or (A-VIIIB), one of $X^1$, $X^2$, X and U is N, and the other three of $X^1$, $X^2$, X and U is $CR^6$. In other variations, two of $X^1$, $X^2$, X and U is N, and the other two of $X^1$, $X^2$, X and U is $CR^6$. In some variations, $R^7$ is a $C_1$-$C_5$ alkyl optionally substituted with 1 to 3 substituents independently selected from the group consisting of halo, hydroxyl, —N($R^{7a}$)($R^{7b}$), —C(O)N($R^{7a}$)($R^{7b}$), —C(O)O$R^{7a}$, —C(O)$R^{7a}$. In other variations, $R^7$ is an optionally substituted $C_3$-$C_8$ cycloalkyl. In some variations, $R^{10}$ is an optionally substituted $C_3$-$C_8$ cycloalkyl. In other variations, $R^{11}$ or $R^{12}$ is an optionally substituted $C_3$-$C_8$ cycloalkyl. In some variations, Q is optionally substituted pyridyl, optionally substituted pyrimidyl, optionally substituted pyrazinyl, or optionally substituted phenyl.

In some variations of the compounds of formula (A-VIIIA), $X^1$ is N; each $X^2$ and X is $CR^6$, wherein each $R^6$ is H; U is $CR^6$, wherein each $R^6$ is H or methyl; $R^1$ is methyl; each $R^7$ and $R^8$ is H; and Q is other than unsubstituted pyridyl, or pyridyl substituted with methyl or $CF_3$.

In some variations of the compounds of formula (A-VIIIA), U is N, each $X^1$, $X^2$ and X is $CR^6$, wherein each $R^6$ is H; $R^1$ is methyl; $R^7$ is H or methyl; $R^8$ is H, OH or methyl; and Q is other than unsubstituted phenyl, phenyl substituted with chloro, unsubstituted pyridyl, or pyridyl substituted with methyl or $CF_3$.

In some variations of the compounds of formula (A-VIIIA), $X^2$ is N, each $X^2$ and X is $CR^6$, wherein each $R^6$ is H; U is $CR^6$, wherein $R^6$ is H or methyl; $R^1$ is methyl; each of $R^7$ and $R^8$ is H; and Q is other than unsubstituted phenyl, unsubstituted pyridyl, or pyridyl substituted with $CF_3$.

In some variations of the compounds of formula (A-VIIIA), X is N, each $X^1$, U and $X^2$ is $CR^6$, wherein each $R^6$ is H; $R^1$ is methyl; each of $R^7$ and $R^8$ is H; and Q is other than unsubstituted phenyl.

In some variations of the compounds of formula (A-VIIIA), each X and U is N, each $X^1$ and $X^2$ is $CR^6$, wherein each $R^6$ is H; $R^1$ is methyl; each of $R^7$ and $R^8$ is H; and Q is other than unsubstituted phenyl.

In some variations of the compounds of formula (A-VIIIA), the compound is according to formula (A-VIIIA-1), (A-VIIIA-2), (A-VIIIA-3), (A-VIIIA-4), (A-VIIIA-5), (A-VIIIA-6), or (A-VIIIA-7):

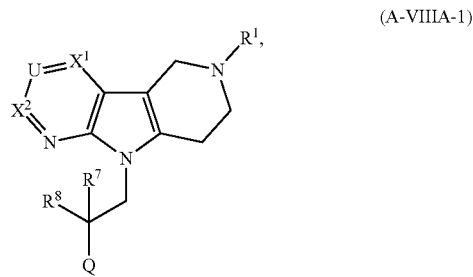

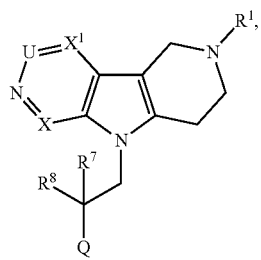
(A-VIIIA-2)

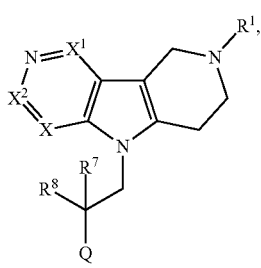
(A-VIIIA-3)

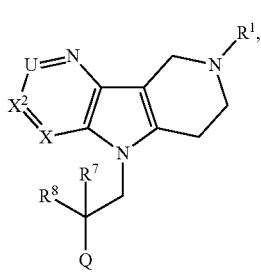
(A-VIIIA-4)

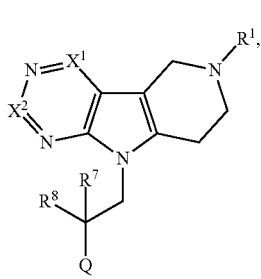
(A-VIIIA-5)

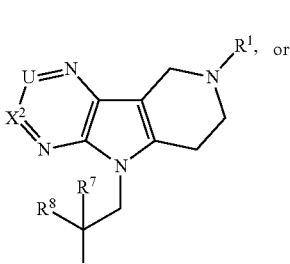
(A-VIIIA-6)

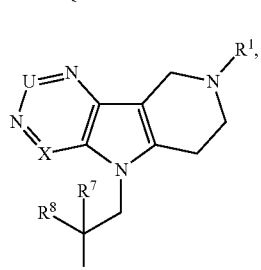
(A-VIIIA-7)

or a salt, solvate or N-oxide thereof, wherein Q, $R^1$, $R^6$, $R^7$, and $R^8$, are as described for formula (A-VIIIA), and each $X^1$, U, $X^2$, or X (where present) is independently $CR^6$.

In one embodiment, the compound is according to formula (A-VIIIA-1), each $X^1$, U and $X^2$ is $CR^6$, wherein each $R^6$ is H; $R^1$ is methyl; each of $R^7$ and $R^8$ is H; and Q is other than unsubstituted phenyl.

In one embodiment, the compound is according to formula (A-VIIIA-2), each $X^1$ and X is $CR^6$, wherein each $R^6$ is H; U is $CR^6$, wherein $R^6$ is H or methyl; $R^1$ is methyl; each of $R^7$ and $R^8$ is H; and Q is other than unsubstituted phenyl, unsubstituted pyridyl, or pyridyl substituted with $CF_3$.

In one embodiment, the compound is according to formula (A-VIIIA-3), each $X^1$, $X^2$ and X is $CR^6$, wherein each $R^6$ is H; $R^1$ is methyl; $R^7$ is H or methyl; $R^8$ is H, OH or methyl; and Q is other than unsubstituted phenyl, phenyl substituted with chloro, unsubstituted pyridyl, or pyridyl substituted with methyl or $CF_3$.

In one embodiment, the compound is according to formula (A-VIIIA-4), each $X^2$ and X is $CR^6$, wherein each $R^6$ is H; U is $CR^6$, wherein $R^6$ is H or methyl; $R^1$ is methyl; each $R^7$ and $R^8$ is H; and Q is other than unsubstituted pyridyl, or pyridyl substituted with methyl or $CF_3$.

In one embodiment, the compound is according to formula (A-VIIIA-5), each $X^1$ and $X^2$ is $CR^6$, wherein each $R^6$ is H; $R^1$ is methyl; each of $R^7$ and $R^8$ is H; and Q is other than unsubstituted phenyl.

In one embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), each $X^1$, U, $X^2$, or X (where present) is independently $CR^6$, and each $R^6$ is H. In another embodiment, each $R^6$ is independently selected from H, $C_1$-$C_5$ alkyl, and halo $C_1$-$C_5$ alkyl. In certain embodiments, each $R^6$ is independently selected from H, methyl, ethyl, fluoro, chloro, $CH_2F$, and $CF_3$.

In one embodiment, with respect to the compounds of formula (A-VIIIA-1), (A-VIIIA-2), (A-VIIIA-4), (A-VIIIA-6), or (A-VIIIA-7), each $X^1$, $X^2$, or X (where present) is CH, U is $CR^6$, and $R^6$ is selected from H, $C_1$-$C_5$ alkyl, and halo $C_1$-$C_5$ alkyl. In certain embodiments, each $R^6$ is independently selected from methyl, ethyl, fluoro, chloro, $CH_2F$, and $CF_3$.

In one embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), each $R^7$ and $R^8$ is H. In another embodiment, $R^7$ is H or methyl, and $R^8$ is H, OH or methyl.

In one embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), Q is optionally substituted phenyl.

In another embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), Q is phenyl substituted with $C_1$-$C_5$ alkyl, halo, halo $C_1$-$C_5$ alkyl, or $C_1$-$C_5$ alkoxy.

In another embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), Q is phenyl substituted with methyl, ethyl, fluoro, chloro, methoxy, or $CF_3$.

In another embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), Q is optionally substituted pyridyl, or optionally substituted pyrimidinyl.

In another embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), Q is pyridyl substituted with $C_1$-$C_5$ alkyl, halo, halo or $C_1$-$C_5$ alkyl.

In another embodiment, with respect to the compounds of formula (A-VIIIA-1), (A-VIIIA-2), (A-VIIIA-3), (A-VIIIA-4), (A-VIIIA-5), (A-VIIIA-6), or (A-VIIIA-7), Q is pyridyl substituted with methyl, ethyl, fluoro, chloro, or $CF_3$.

In one embodiment, provided are compounds of formula (A-IXA), (A-IXB), (A-IXC) or (A-IXD):

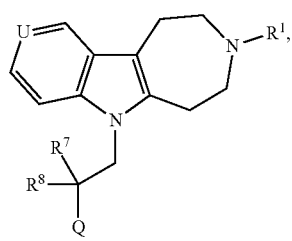

(A-IXA)

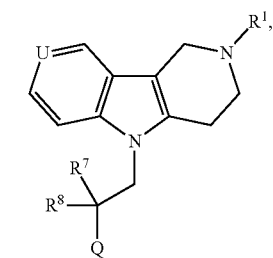

(A-IXB)

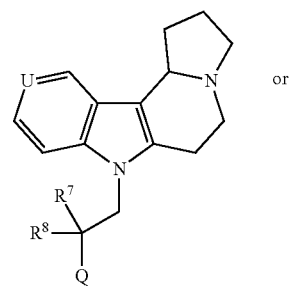

(A-IXC)

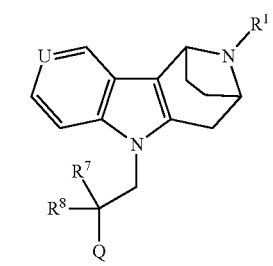

(A-IXD)

wherein U, Q, $R^1$, $R^6$, $R^7$, and $R^8$ are as described for formula (A-I).

In certain embodiments, $R^8$ is azido. In certain embodiments, $R^8$ is $N(R^{11})R^{12}$. In certain embodiments, each $R^{11}$ and $R^{12}$ is independently H or optionally substituted $C_1$-$C_5$ alkyl, or $R^{11}$ and $R^{12}$ are taken together to form $C_3$-$C_5$ alkylene. In certain embodiments, $R^7$ is H or methyl, $R^8$ is azido, or $N(R^{11})R^{12}$, and each $R^{11}$ and $R^{12}$ is independently H or optionally substituted $C_1$-$C_5$ alkyl, or $R^{11}$ and $R^{12}$ are taken together to form $C_3$-$C_5$ alkylene. In certain embodiments, $R^8$ is $SR^{13}$, $S(O)R^{13}$, or $SO_2R^{13}$; and $R^{13}$ is independently H or optionally substituted $C_1$-$C_5$ alkyl. In one embodiment, $R^{13}$ is methyl, ethyl, i-propyl, n-propyl, n-butyl, or t-butyl. In certain embodiments, $R^7$ is $C_1$-$C_5$ alkyl, substituted with amino or substituted amino. In certain embodiments, $R^7$ is $C_1$-$C_5$ alkyl, substituted with OH or optionally substituted $C_1$-$C_5$ alkoxy. In certain embodiments, $R^7$ is $C_1$-$C_5$ alkyl, substituted with —$C(O)N(R^{7a})R^{7b}$; and each $R^{7a}$ and $R^{7b}$ is independently H or optionally substituted $C_1$-$C_5$ alkyl, or $R^{7a}$ and $R^{7b}$ are taken together to form $C_3$-$C_5$ alkylene. In certain embodiments, $R^7$ is $C_1$-$C_5$ alkyl, substituted with acyl.

In certain embodiments, $R^8$ is halo. In one embodiment, with respect to the compounds of formula (A-IXB) or (A-IXC), when $R^8$ is fluoro or chloro, $R^1$ is methyl, ethyl, i-propyl, or cyclopropyl, $R^7$ is H or methyl, U is $CR^6$, and $R^6$ is methyl or chloro, then Q is other than unsubstituted phenyl, phenyl substituted with methoxy, chloro, fluoro, difluoro, unsubstituted pyridyl, pyridyl substituted with methyl, or unsubstituted pyrimidinyl.

In certain embodiments, $R^7$ is optionally substituted cycloalkyl. In one embodiment, with respect to the compounds of formula (A-IXB) or (A-IXC), when $R^7$ is optionally substituted cycloalkyl, $R^8$ is OH, $R^1$ is methyl, U is $CR^6$, and $R^6$ is methyl or chloro, then Q is other than unsubstituted phenyl, phenyl substituted with fluoro, or unsubstituted pyridyl. In one embodiment, $R^7$ is optionally substituted cyclopropyl, cyclobutyl, cyclopentyl or cyclohexyl. In certain embodiments, $R^7$ is $C_1$-$C_5$ alkyl, substituted with acylamino.

In one embodiment, with respect to the compounds of formula (A-IXB) or (A-IXC), when $R^7$ is $CH_2$—$CON(H)CH_3$, $R^1$ is methyl or ethyl, U is $CR^6$, and $R^6$ is methyl or chloro, then Q is other than phenyl substituted with fluoro, chloro, methoxy, or difluoro, unsubstituted pyridyl, pyridyl substituted with methyl, or unsubstituted pyrimidinyl.

In certain embodiments, $R^7$ is $C_1$-$C_5$ alkyl, substituted with —$C(O)OR^{7a}$, and $R^{7a}$ is H or optionally substituted $C_1$-$C_5$ alkyl.

In one embodiment, $R^7$ is $C_1$-$C_5$ alkyl, substituted with —$C(O)OR^{7a}$, $R^{7a}$ is H or optionally substituted $C_1$-$C_5$ alkyl, $R^1$ is methyl or ethyl, U is $CR^6$, and $R^6$ is methyl or chloro; and Q is other than phenyl substituted with F, chloro, methoxy, or difluoro, unsubstituted pyridyl, pyridyl substituted with methyl, or unsubstituted pyrimidinyl.

In certain embodiments, $R^7$ is $C_1$-$C_5$ alkyl, substituted with 1-3 halo.

In one embodiment, with respect to the compounds of formula (A-IXB), $R^7$ is $CF_3$, $R^8$ is OH, $R^1$ is methyl, U is $CR^6$, and $R^6$ is methyl; and Q is other than phenyl substituted with fluoro. In one particular embodiment, $R^7$ is $CF_3$.

In certain embodiments, $R^8$ is —$C(O)N(R^{14})R^{15}$; and each $R^{14}$ and $R^{15}$ is independently H or optionally substituted $C_1$-$C_5$ alkyl, or $R^{14}$ and $R^{15}$ are taken together to form a $C_3$-$C_5$ alkylene.

In one particular embodiment, $R^8$ is —$C(O)N(R^{14})R^{15}$; and each $R^{14}$ and $R^{15}$ is independently H or methyl, $R^1$ is methyl, U is $CR^6$, and $R^6$ is methyl; and Q is other than cyclobutyl.

In certain embodiments, $R^8$ is —$OC(O)N(R^{14})R^{15}$, —$OC(O)$-aryl, —$OC(O)$-heteroaryl, —$OC(O)C_1$-$C_5$ alkyl optionally substituted with amino, —$OC(O)C_1$-$C_5$ alkyl substituted with carboxyl, or —$OC_1$-$C_5$ alkyl optionally substituted with carboxyl; and each $R^{14}$ and $R^{15}$ is independently H or optionally substituted $C_1$-$C_5$ alkyl, or $R^{14}$ and $R^{15}$ are taken together to form a $C_3$-$C_5$ alkylene.

In certain embodiments, $R^7$ is optionally substituted phenyl. In one particular embodiment, $R^7$ is optionally substituted phenyl, $R^8$ is OH, $R^1$ is methyl or ethyl, U is $CR^6$, and $R^6$ is methyl or chloro; and Q is other than unsubstituted phenyl, phenyl substituted with fluoro or unsubstituted pyridyl.

In certain embodiments, $R^8$ is OH. In some embodiments, $R^8$ is OH, and $R^7$ is other than H, or $C_1$-$C_4$ alkyl.

In some embodiments, compounds of the formula (B-I) are provided:

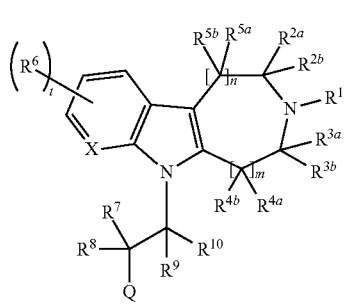

(B-I)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents selected from halo, hydroxyl, carboxyl and perhaloalkyl, or —C(O)O—$C_1$-$C_5$ alkyl, or is taken together with $R^{2a}$ or $R^{3a}$ to form a propylene (—CH$_2$CH$_2$CH$_2$—) moiety or a butylene (—CH$_2$CH$_2$CH$_2$CH$_2$—) moiety, or is taken together with $R^{4a}$ or $R^{5a}$, where present, to form an ethylene (—CH$_2$CH$_2$—) moiety or a propylene (—CH$_2$CH$_2$CH$_2$—) moiety;

each n and m is 1, or n is 0 and m is 1, or n is 1 and m is 0;

$R^{2a}$ is H, optionally substituted $C_1$-$C_5$ alkyl, optionally substituted alkenyl or optionally substituted aryl, or is taken together with $R^1$ or $R^{5a}$, where present, to form a propylene (—CH$_2$CH$_2$CH$_2$—) moiety or a butylene (—CH$_2$CH$_2$CH$_2$CH$_2$—) moiety, or is taken together with $R^{3a}$ to form an ethylene (—CH$_2$CH$_2$—) moiety or a propylene (—CH$_2$CH$_2$CH$_2$—) moiety, taken together with $R^{4a}$, where present, to form a methylene (—CH$_2$—) moiety or an ethylene (—CH$_2$CH$_2$—) moiety;

$R^{3a}$ is H, optionally substituted $C_1$-$C_5$ alkyl, optionally substituted alkenyl or optionally substituted aryl, or is taken together with $R^1$ or $R^{4a}$, where present, to form a propylene (—CH$_2$CH$_2$CH$_2$—) moiety or a butylene (—CH$_2$CH$_2$CH$_2$CH$_2$—) moiety, or is taken together with $R^{2a}$ to form an ethylene (—CH$_2$CH$_2$—) moiety or a propylene (—CH$_2$CH$_2$CH$_2$—) moiety, taken together with $R^{5a}$, where present, to form a methylene (—CH$_2$—) moiety or an ethylene (—CH$_2$CH$_2$—) moiety;

$R^{4a}$ is H, optionally substituted $C_1$-$C_5$ alkyl, optionally substituted alkenyl or optionally substituted aryl, or is taken together with $R^{3a}$ to form a propylene (—CH$_2$CH$_2$CH$_2$—) moiety or a butylene (—CH$_2$CH$_2$CH$_2$CH$_2$—) moiety, or is taken together with $R^1$ to form an ethylene (—CH$_2$CH$_2$—) moiety or a propylene (—CH$_2$CH$_2$CH$_2$—) moiety, or is taken together with $R^{2a}$ to form a methylene (—CH$_2$—) moiety or an ethylene (—CH$_2$CH$_2$—) moiety, or is taken together with $R^{5a}$, where present, to form a methylene (—CH$_2$—) moiety;

$R^{5a}$ is H, optionally substituted $C_1$-$C_5$ alkyl, optionally substituted alkenyl or optionally substituted aryl, or is taken together with $R^{2a}$ to form a propylene (—CH$_2$CH$_2$CH$_2$—) moiety or a butylene (—CH$_2$CH$_2$CH$_2$CH$_2$—) moiety, or is taken together with $R^1$ to form an ethylene (—CH$_2$CH$_2$—) moiety or a propylene (—CH$_2$CH$_2$CH$_2$—) moiety, or is taken together with $R^{3a}$ to form a methylene (—CH$_2$—) moiety or an ethylene (—CH$_2$CH$_2$—) moiety, or is taken together with $R^{4a}$, where present, to form a methylene (—CH$_2$—) moiety;

each $R^{2b}$, $R^{3b}$, $R^{4b}$ and $R^{5b}$ is independently H, optionally substituted $C_1$-$C_5$ alkyl, optionally substituted alkenyl or optionally substituted aryl;

X is N or $CR^{6a}$;

t is 1, 2 or 3;

each $R^6$ and $R^{6a}$ is independently H, hydroxyl, halo, $C_1$-$C_5$ alkyl optionally substituted with 1-3 substituents selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl;

$R^8$ is azido, acylamino, carboxyl, carbonylalkoxy, —OC(O)$C_1$-$C_5$ alkyl substituted with carboxyl, or —O$C_1$-$C_5$ alkyl optionally substituted with carboxyl;

each $R^9$ and $R^{10}$ is independently H or optionally substituted $C_1$-$C_5$ alkyl; and Q is cycloalkyl, aryl or heteroaryl optionally substituted with 1-3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one variation, Q, X, m, n, t, $R^1$, $R^{2a}$, $R^{2b}$, $R^{3a}$, $R^{3b}$, $R^{4a}$, $R^{4b}$, $R^{5a}$, $R^{5b}$, $R^6$, $R^{6a}$, $R^7$, $R^9$ and $R^{10}$ are as defined for the formula (B-I), and $R^8$ is azido, acylamino, —OC(O)$C_1$-$C_5$ alkyl substituted with carboxyl, or —O$C_1$-$C_5$ alkyl substituted with carboxyl, or a salt, solvate or N-oxide thereof. In another variation, Q, X, m, n, t, $R^1$, $R^{2a}$, $R^{2b}$, $R^{3a}$, $R^{3b}$, $R^{4a}$, $R^{4b}$, $R^{5a}$, $R^{5b}$, $R^6$, $R^{6a}$, $R^7$, $R^9$ and $R^{10}$ are as defined for the formula (B-I), and $R^8$ is carboxyl, or carbonylalkoxy, or a salt, solvate or N-oxide thereof.

In one variation, Q is cycloalkyl, aryl or heteroaryl optionally substituted with 1-3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)CH$_3$ and —C(O)NR$^{11}$R$^{12}$ where each $R^{11}$ and $R^{12}$ is independently H or optionally substituted $C_1$-$C_5$ alkyl.

In some variations, $R^1$ is $C_1$-$C_5$ alkyl (e.g., methyl), each $R^{2a}$ and $R^{3a}$ is H, $R^6$ is methyl or chloro, and X is $CR^{6a}$ where $R^{6a}$ is methyl or chloro. In some of these variations, t is 1, 2 or 3. In some of these variations, $R^7$ is H or $C_1$-$C_5$ alkyl (e.g., methyl). In some of these variations, $R^7$ is H. In some of these variations, $R^9$ is H or $C_1$-$C_5$ alkyl (e.g., methyl) and $R^{10}$ is H. In some of these variations, each $R^9$ and $R^{10}$ is H. In some of these variations, each $R^7$, $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl. In some of these variations, Q is phenyl substituted with —C(O)NR$^{11}$R$^{12}$ where each $R^{11}$ and $R^{12}$ is H. In some of these variations, Q is 4-carbamoylphenyl.

In another embodiment, the compound of formula (B-I) has the formula (B-IA):

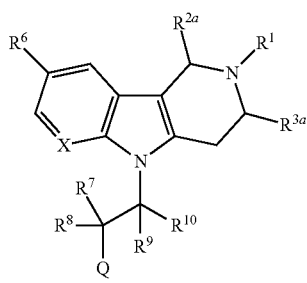

(B-IA)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents selected from halo, hydroxyl, carboxyl and perhaloalkyl, or —C(O)O—$C_1$-$C_5$ alkyl, or is taken together with $R^{2a}$ or $R^{3a}$ to form a propylene (—CH$_2$CH$_2$CH$_2$—) moiety or a butylene (—CH$_2$CH$_2$CH$_2$CH$_2$—) moiety;

$R^{2a}$ is H, optionally substituted $C_1$-$C_5$ alkyl, optionally substituted alkenyl or optionally substituted aryl, or is taken together with $R^1$ to form a propylene (—CH$_2$CH$_2$CH$_2$—) moiety or a butylene (—CH$_2$CH$_2$CH$_2$CH$_2$—) moiety;

$R^{3a}$ is H, optionally substituted $C_1$-$C_5$ alkyl, optionally substituted alkenyl or optionally substituted aryl, or is taken together with $R^1$ to form a propylene (—CH$_2$CH$_2$CH$_2$—) moiety or a butylene (—CH$_2$CH$_2$CH$_2$CH$_2$—) moiety;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl;

$R^8$ is azido, acylamino, carboxyl, carbonylalkoxy, —OC(O)$C_1$-$C_5$ alkyl substituted with carboxyl or —O$C_1$-$C_5$ alkyl optionally substituted with carboxyl;

each $R^9$ and $R^{10}$ is independently H or optionally substituted $C_1$-$C_5$ alkyl; and Q is cycloalkyl, aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one variation, the compound is of the formula (B-IA), wherein Q, X, $R^1$, $R^{2a}$, $R^{3a}$, $R^6$, $R^{6a}$, $R^7$, $R^9$ and $R^{10}$ are as defined for the formula (B-IA), and $R^8$ is azido, acylamino, —OC(O)$C_1$-$C_5$ alkyl substituted with carboxyl, or —O$C_1$-$C_5$ alkyl substituted with carboxyl, or a salt, solvate or N-oxide thereof. In another variation, Q, X, $R^1$, $R^{2a}$, $R^{3a}$, $R^6$, $R^{6a}$, $R^7$, $R^9$ and $R^{10}$ are as defined for the formula (B-IA), and $R^8$ is carboxyl, or carbonylalkoxy.

In some variations of the compound of the formula (B-IA), each $R^{2a}$ and $R^{3a}$ is H. In some variations, $R^1$ is $C_1$-$C_5$ alkyl (e.g., methyl). In some variations, each $R^6$ and $R^{6a}$ is independently halo (e.g., chloro) or $C_1$-$C_5$ alkyl (e.g., methyl). In some variations, each $R^6$ and $R^{6a}$ is independently halo (e.g., chloro or fluoro). In some variations, $R^6$ and $R^{6a}$ is chloro. In some variations, each $R^6$ and $R^{6a}$ is independently $C_1$-$C_5$ alkyl (e.g., methyl). In some variations, X is $CR^{6a}$ where $R^{6a}$ is H or halo. In some variations, X is $CR^{6a}$ where $R^{6a}$ is H. In some variations, X is $CR^{6a}$ where $R^{6a}$ is chloro. In some variations, X is $CR^{6a}$ where $R^{6a}$ is halo (e.g., chloro or fluoro). In some variations, $R^6$ is H or halo. In some variations, $R^6$ is H. In some variations, $R^6$ is chloro. In some variations, $R^6$ is halo (e.g., chloro or fluoro). In some variations, $R^7$ is H or $C_1$-$C_5$ alkyl (e.g., methyl). In some variations, X is N. In some variations, $R^7$ is H. In some variations, $R^7$ is $C_1$-$C_5$ alkyl (e.g., methyl). In some variations, $R^8$ is azido. In some variations, $R^8$ is carboxyl, —OC(O)$C_1$-$C_5$ alkyl substituted with carboxyl, or —O$C_1$-$C_5$ alkyl optionally substituted with carboxyl. In some variations, $R^8$ is acylamino. In some variations, $R^7$ is H or $C_1$-$C_5$ alkyl (e.g., methyl) and $R^8$ is azido, acylamino, —OC(O)$C_1$-$C_5$ alkyl substituted with carboxyl or —O$C_1$-$C_5$ alkyl optionally substituted with carboxyl. In some variations, $R^7$ is H and $R^8$ is azido, acylamino, —OC(O)$C_1$-$C_5$ alkyl substituted with carboxyl or —O$C_1$-$C_5$ alkyl optionally substituted with carboxyl. In some variations, $R^9$ is H or $C_1$-$C_5$ alkyl (e.g., methyl). In some variations, $R^{10}$ is H or $C_1$-$C_5$ alkyl (e.g., methyl). In some variations, each $R^9$ and $R^{10}$ is H. In some variations, one of $R^9$ and $R^{10}$ is H and the other is $C_1$-$C_5$ alkyl (e.g., methyl). In some variations, Q is an unsubstituted heteroaryl (e.g., pyridyl). In some variations, Q is an unsubstituted pyridyl group which may be attached to the parent structure at any position (e.g., 2-pyridyl, 3-pyridyl or 4-pyridyl). In some variations, Q is 3-pyridyl or 4-pyridyl. In some variations, Q is heteroaryl substituted with a substituent selected form the group consisting of halo (e.g., fluoro or chloro), $C_1$-$C_5$ alkyl (e.g., methyl), halo-substituted $C_1$-$C_5$ alkyl (e.g., CF$_3$) and carboxyl. In some variations, Q is heteroaryl substituted with halo (e.g., fluoro or chloro) or $C_1$-$C_5$ alkyl (e.g., methyl). In some variations, Q is heteroaryl substituted with $C_1$-$C_5$ alkyl (e.g., methyl). In some variations, Q is a pyridyl optionally substituted with a methyl where the pyridyl group may be attached to the parent structure at any position and the methyl group may be attached to the pyridyl group at any open position (e.g., 6-methyl-3-pyridyl and 3-methyl-4-pyridyl). In some variations, Q is phenyl substituted with a substituent selected form the group consisting of halo (e.g., fluoro or chloro), $C_1$-$C_5$ alkyl (e.g., methyl), halo-substituted $C_1$-$C_5$ alkyl (e.g., CF$_3$), carboxyl and —C(O)NR$^{11}$R$^{12}$ where each R$^{11}$ and R$^{12}$ is independently H or optionally substituted $C_1$-$C_5$ alkyl. In some variations, Q is phenyl substituted with a halo group (e.g., fluorophenyl). In some variations, Q is 4-fluorophenyl. In some variations, Q is phenyl substituted with —C(O)NR$^{11}$R$^{12}$ where each R$^{11}$ and R$^{12}$ is H.

In some variations of the compound of the formula (B-IA), $R^1$ is $C_1$-$C_5$ alkyl (e.g., methyl), each $R^{2a}$ and $R^{3a}$ is H, $R^6$ is methyl or chloro, and X is CH. In some of these variations, $R^7$ is H or $C_1$-$C_5$ alkyl (e.g., methyl) and $R^8$ is azido. In some of these variations, $R^7$ is H and $R^8$ is azido, acylamino, —OC(O)$C_1$-$C_5$ alkyl substituted with carboxyl or —O$C_1$-$C_5$ alkyl optionally substituted with carboxyl. In some of these variations, $R^7$ is methyl and $R^8$ is azido, acylamino, —OC(O)$C_1$-$C_5$ alkyl substituted with carboxyl or —O$C_1$-$C_5$ alkyl optionally substituted with carboxyl. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is azido, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, phenyl substituted with a halo group (e.g., fluorophenyl). In some of these variations, Q is 4-fluorophenyl. In some of these variations, Q is phenyl substituted with —C(O)NR$^{11}$R$^{12}$ where each R$^{11}$ and R$^{12}$ is H. In some of these variations, Q is 4-carbamoylphenyl.

In some variations of the compound of the formula (B-IA), R$^1$ is C$_1$-C$_5$ alkyl (e.g., methyl), each R$^{2a}$ and R$^{3a}$ is H, R$^6$ is methyl or chloro, and X is CH. In some variations, R$^7$ is H and R$^8$ is azido, acylamino, —OC(O)C$_1$-C$_5$ alkyl substituted with carboxyl or —OC$_1$-C$_5$ alkyl optionally substituted with carboxyl. In some variations, R$^7$ is H and R$^8$ is azido, acylamino, —OC(O)C$_1$-C$_5$ alkyl substituted with carboxyl or —OC$_1$-C$_5$ alkyl optionally substituted with carboxyl. In some of these variations, R$^9$ is H or C$_1$-C$_5$ alkyl (e.g., methyl) and R$^{10}$ is H. In some of these variations, each R$^9$ and R$^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl. In some of these variations, Q is phenyl substituted with —C(O)NR$^{11}$R$^{12}$ where each R$^{11}$ and R$^{12}$ is H. In some of these variations, Q is 4-carbamoylphenyl.

In some variations of the compound of the formula (B-IA), R$^1$ and R$^{2a}$ are taken together to form a propylene (—CH$_2$CH$_2$CH$_2$—) moiety and R$^{1a}$ is H. In some of these variations, X is N. In some of these variations, X is CH. In some of these variations, R$^6$ is C$_1$-C$_5$ alkyl (e.g., methyl) or halo (e.g., chloro). In some of these variations, R$^6$ is methyl or chloro. In some of these variations, R$^7$ is H or C$_1$-C$_5$ alkyl (e.g., methyl) and R$^8$ is azido, acylamino, —OC(O)C$_1$-C$_5$ alkyl substituted with carboxyl or —OC$_1$-C$_5$ alkyl optionally substituted with carboxyl. In some of these variations, R$^7$ is H and R$^8$ is azido, acylamino, —OC(O)C$_1$-C$_5$ alkyl substituted with carboxyl or —OC$_1$-C$_5$ alkyl optionally substituted with carboxyl. In some of these variations, R$^7$ is methyl and R$^8$ is azido, acylamino, —OC(O)C$_1$-C$_5$ alkyl substituted with carboxyl or —OC$_1$-C$_5$ alkyl optionally substituted with carboxyl. In some of these variations, R$^9$ is H or C$_1$-C$_5$ alkyl (e.g., methyl) and R$^{10}$ is H. In some of these variations, each R$^9$ and R$^{10}$ is H. In some of these variations, R$^7$ is H or C$_1$-C$_5$ alkyl (e.g., methyl), R$^8$ is azido, and each R$^9$ and R$^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl. In some of these variations, Q is phenyl substituted with —C(O)NR$^{11}$R$^{12}$ where each R$^{11}$ and R$^{12}$ is H. In some of these variations, Q is 4-carbamoylphenyl.

In certain embodiments, with respect to the compounds of formula (B-IA), X is CR$^6$, R$^8$ is azido, and the compound is Compound No. II-261, II-266, II-276, II-298, V-1, V-3, V-22, or V23.

In certain embodiments, with respect to the compounds of formula (B-IA), X is CR$^6$, R$^8$ is acylamino, carboxyl, or carbonylalkoxy, and the compound is Compound No. II-258, II-262, II-263, or II-277.

In certain embodiments, with respect to the compounds of formula (B-IA), X is CR$^6$, R$^8$ is —OC(O)C$_1$-C$_5$ alkyl substituted with carboxyl, and the compound is Compound No. V-18.

In certain embodiments, with respect to the compounds of formula (B-IA), X is CR$^6$, R$^8$ is —OC$_1$-C$_5$ alkyl optionally substituted with carboxyl, and the compound is Compound No. II-256, II-274, II-281, V-14 or V-15.

In another embodiment, the compound of formula (B-I) has the formula (B-IB):

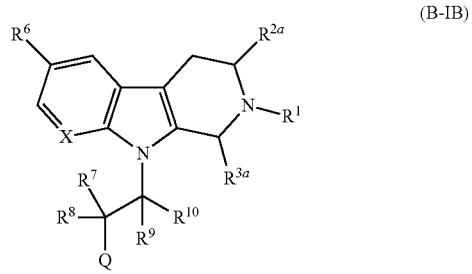

(B-IB)

or a salt, solvate or N-oxide thereof, wherein:

R$^1$ is H, C$_1$-C$_5$ alkyl optionally substituted with 1 to 3 substituents independently selected from halo, hydroxyl, carboxyl and perhaloalkyl, C$_3$-C$_8$ cycloalkyl optionally substituted with 1 to 3 substituents independently selected from halo, hydroxyl, carboxyl and perhaloalkyl, C$_2$-C$_5$ alkenyl optionally substituted with 1-3 substituents selected from halo, hydroxyl, carboxyl and perhaloalkyl, or —C(O)O—C$_1$-C$_5$ alkyl, or is taken together with R$^{2a}$ or R$^{3a}$ to form a propylene (—CH$_2$CH$_2$CH$_2$—) moiety or a butylene (—CH$_2$CH$_2$CH$_2$CH$_2$—) moiety;

R$^{2a}$ is H, optionally substituted C$_1$-C$_5$ alkyl, optionally substituted alkenyl or optionally substituted aryl, or is taken together with R$^1$ to form a propylene (—CH$_2$CH$_2$CH$_2$—) moiety or a butylene (—CH$_2$CH$_2$CH$_2$CH$_2$—) moiety;

R$^{3a}$ is H, optionally substituted C$_1$-C$_5$ alkyl, optionally substituted alkenyl or optionally substituted aryl, or is taken together with R$^1$ to form a propylene (—CH$_2$CH$_2$CH$_2$—) moiety or a butylene (—CH$_2$CH$_2$CH$_2$CH$_2$—) moiety;

X is N or CR$^{6a}$;

each R$^6$ and R$^{6a}$ is independently H, hydroxyl, halo, C$_1$-C$_5$ alkyl optionally substituted with 1 to 3 substituents independently selected from halo, hydroxyl, carboxyl and perhaloalkyl, optionally substituted C$_1$-C$_5$ alkoxy or optionally substituted —C(O)C$_1$-C$_5$ alkyl;

R$^7$ is H, halo, optionally substituted C$_1$-C$_5$ alkyl, or optionally substituted aryl;

R$^8$ is azido, acylamino, carboxyl, carbonylalkoxy, —OC(O)C$_1$-C$_5$ alkyl substituted with carboxyl, or —OC$_1$-C$_5$ alkyl optionally substituted with carboxyl;

each R$^9$ and R$^{10}$ is independently H or optionally substituted C$_1$-C$_5$ alkyl; and Q is cycloalkyl, aryl or heteroaryl optionally substituted with 1 to 3 substituents independently selected from the group consisting of halo, C$_1$-C$_5$ alkyl, C$_3$-C$_8$ cycloalkyl, halo-substituted C$_1$-C$_5$ alkyl, halo-substituted C$_3$-C$_8$ cycloalkyl, C$_1$-C$_5$ alkoxy, C$_3$-C$_8$ cycloalkoxy, cyano, carboxyl, aminoacyl and acylamino.

In one variation, the compound is of the formula (B-IB), wherein Q, X, R$^1$, R$^{2a}$, R$^{3a}$, R$^6$, R$^{6a}$, R$^7$, R$^9$ and R$^{10}$ are as defined for the formula (B-IB), and R$^8$ is azido, acylamino, —OC(O)C$_1$-C$_5$ alkyl substituted with carboxyl, or —OC$_1$-C$_5$ alkyl substituted with carboxyl, or a salt, solvate or N-oxide thereof. In another variation, Q, X, $R^1$, $R^{2a}$, $R^{3a}$, $R^6$, $R^{6a}$, $R^7$, $R^9$ and $R^{10}$ are as defined for the formula (B-IB), and $R^8$ is carboxyl, or carbonylalkoxy.

In some variations of the compound of the formula (B-IB), $R^1$ is $C_1$-$C_5$ alkyl (e.g., methyl),
each $R^{2a}$ and $R^{3a}$ is H, $R^6$ is methyl or chloro, and X is CH. In some of these variations, $R^7$ is H or $C_1$-$C_5$ alkyl (e.g., methyl) and $R^8$ is azido. In some of these variations, $R^7$ is H and $R^8$ is azido, acylamino, —OC(O)$C_1$-$C_5$ alkyl substituted with carboxyl or —O$C_1$-$C_5$ alkyl optionally substituted with carboxyl. In some of these variations, $R^7$ is methyl and $R^8$ is azido, acylamino, —OC(O)$C_1$-$C_5$ alkyl substituted with carboxyl or —O$C_1$-$C_5$ alkyl optionally substituted with carboxyl. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is azido, acylamino, —OC(O)$C_1$-$C_5$ alkyl substituted with carboxyl or —O$C_1$-$C_5$ alkyl substituted with carboxyl, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl.

In another embodiment, the compound of formula (B-I) has the formula (B-IC):

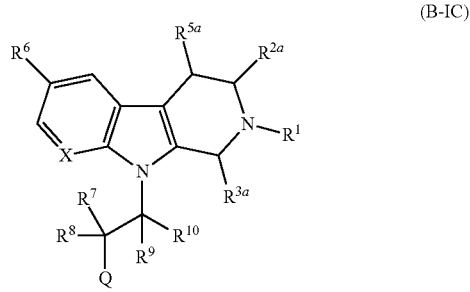

(B-IC)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents selected from halo, hydroxyl, carboxyl and perhaloalkyl, or —C(O)O—$C_1$-$C_5$ alkyl, or is taken together with $R^{2a}$ or $R^{3a}$ to form a propylene (—CH$_2$CH$_2$CH$_2$—) moiety or a butylene (—CH$_2$CH$_2$CH$_2$CH$_2$—) moiety;

$R^{2a}$ is H, optionally substituted $C_1$-$C_5$ alkyl, optionally substituted alkenyl or optionally substituted aryl, or is taken together with $R^1$ to form a propylene (—CH$_2$CH$_2$CH$_2$—) moiety or a butylene (—CH$_2$CH$_2$CH$_2$CH$_2$—) moiety;

$R^{3a}$ is H, optionally substituted $C_1$-$C_5$ alkyl, optionally substituted alkenyl or optionally substituted aryl, or is taken together with $R^1$ to form a propylene (—CH$_2$CH$_2$CH$_2$—) moiety or a butylene (—CH$_2$CH$_2$CH$_2$CH$_2$—) moiety;

$R^{5a}$ is H, optionally substituted $C_1$-$C_5$ alkyl, optionally substituted alkenyl or optionally substituted aryl;

X is N or CR$^{6a}$;

each $R^6$ and $R^{6a}$ is independently H, hydroxyl, halo, $C_1$-$C_5$ alkyl optionally substituted with 1-3 substituents selected from halo, hydroxyl, carboxyl and perhaloalkyl, optionally substituted $C_1$-$C_5$ alkoxy or optionally substituted —C(O) $C_1$-$C_5$ alkyl;

$R^7$ is H, halo, optionally substituted $C_1$-$C_5$ alkyl, or optionally substituted aryl;

$R^8$ is azido, acylamino, carboxyl, carbonylalkoxy, —OC(O)$C_1$-$C_5$ alkyl substituted with carboxyl or —O$C_1$-$C_5$ alkyl optionally substituted with carboxyl;

each $R^9$ and $R^{10}$ is independently H or optionally substituted $C_1$-$C_5$ alkyl; and Q is cycloalkyl, aryl or heteroaryl optionally substituted with 1-3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one variation, the compound is of the formula (B-IC), wherein Q, X, $R^1$, $R^{2a}$, $R^{3a}$, $R^{5a}$, $R^6$, $R^{6a}$, $R^7$, $R^9$ and $R^{10}$ are as defined for the formula (B-IC), and $R^8$ is azido, acylamino, —OC(O)$C_1$-$C_5$ alkyl substituted with carboxyl, or —O$C_1$-$C_5$ alkyl substituted with carboxyl, or a salt, solvate or N-oxide thereof. In another variation, Q, X, $R^1$, $R^{2a}$, $R^{3a}$, $R^{5a}$, $R^6$, $R^{6a}$, $R^7$, $R^9$ and $R^{10}$ are as defined for the formula (B-IC), and $R^8$ is carboxyl, or carbonylalkoxy.

In another embodiment, the compound of formula (B-I) has the formula (B-ID):

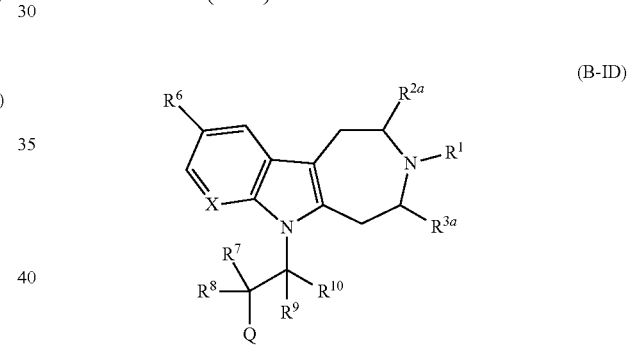

(B-ID)

or a salt, solvate or N-oxide thereof, wherein:

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1-3 substituents selected from halo, hydroxyl, carboxyl and perhaloalkyl, or —C(O)O—$C_1$-$C_5$ alkyl, or is taken together with $R^{2a}$ or $R^{3a}$ to form a propylene (—CH$_2$CH$_2$CH$_2$—) moiety or a butylene (—CH$_2$CH$_2$CH$_2$CH$_2$—) moiety;

$R^{2a}$ is H, optionally substituted $C_1$-$C_5$ alkyl, optionally substituted alkenyl or optionally substituted aryl, or is taken together with $R^1$ to form a propylene (—CH$_2$CH$_2$CH$_2$—) moiety or a butylene (—CH$_2$CH$_2$CH$_2$CH$_2$—) moiety;

$R^{3a}$ is H, optionally substituted $C_1$-$C_5$ alkyl, optionally substituted alkenyl or optionally substituted aryl, or is taken together with $R^1$ to form a propylene (—CH$_2$CH$_2$CH$_2$—) moiety or a butylene (—CH$_2$CH$_2$CH$_2$CH$_2$—) moiety;

X is N or CR$^{6a}$;

each $R^6$ and $R^{6a}$ is independently H; hydroxyl; halo; $C_1$-$C_5$ alkyl optionally substituted with 1 to 3 substituents independently selected from halo, hydroxyl, carboxyl and perhaloalkyl; optionally substituted $C_1$-$C_5$ alkoxy; or optionally substituted —C(O)$C_1$-$C_5$ alkyl;

$R^7$ is H, halo, optionally substituted $C_1$-$C_5$ alkyl, or optionally substituted aryl;

$R^8$ is azido, acylamino, carboxyl, carbonylalkoxy, —OC(O)$C_1$-$C_5$ alkyl substituted with carboxyl, or —O$C_1$-$C_5$ alkyl optionally substituted with carboxyl;

each $R^9$ and $R^{10}$ is independently H or optionally substituted $C_1$-$C_5$ alkyl; and Q is cycloalkyl, aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one variation, the compound is of the formula (B-ID), wherein Q, X, $R^1$, $R^{2a}$, $R^{3a}$, $R^6$ and $R^{6a}$ are as defined for the formula (B-ID), $R^7$ is H, halo, or optionally substituted $C_1$-$C_5$ alkyl;

$R^8$ is azido, acylamino, —OC(O)$C_1$-$C_5$ alkyl substituted with carboxyl or —O$C_1$-$C_5$ alkyl substituted with carboxyl; and each $R^9$ and $R^{10}$ is independently H or optionally substituted $C_1$-$C_5$ alkyl, or a salt, solvate or N-oxide thereof.

In some variations of the compound of the formula (B-ID), $R^1$ is $C_1$-$C_5$ alkyl (e.g., methyl), each $R^{2a}$ and $R^{3a}$ is H, $R^6$ is methyl or chloro, and X is CH. In some of these variations, $R^7$ is H or $C_1$-$C_5$ alkyl (e.g., methyl) and $R^8$ is azido, acylamino, —OC(O)$C_1$-$C_5$ alkyl substituted with carboxyl or —O$C_1$-$C_5$ alkyl optionally substituted with carboxyl. In some of these variations, $R^7$ is H and $R^8$ is azido, acylamino, —OC(O)$C_1$-$C_5$ alkyl substituted with carboxyl or —O$C_1$-$C_5$ alkyl optionally substituted with carboxyl. In some of these variations, $R^7$ is methyl and $R^8$ is azido, acylamino, —OC(O)$C_1$-$C_5$ alkyl substituted with carboxyl or —O$C_1$-$C_5$ alkyl optionally substituted with carboxyl. In some of these variations, $R^9$ is H or $C_1$-$C_5$ alkyl (e.g., methyl) and $R^{10}$ is H. In some of these variations, each $R^9$ and $R^{10}$ is H. In some of these variations, $R^7$ is H or $C_1$-$C_5$ alkyl (e.g., methyl), $R^8$ is azido, and each $R^9$ and $R^{10}$ is H. In some of these variations, Q is an unsubstituted pyridyl group which may be attached to the parent structure at any position (e.g., 2-pyridyl, 3-pyridyl or 4-pyridyl). In some of these variations, Q is 3-pyridyl or 4-pyridyl. In some of these variations, Q is pyridyl substituted a methyl (e.g., 6-methyl-3-pyridyl and 3-methyl-4-pyridyl). In some of these variations, Q is phenyl substituted with a halo group (e.g., fluorophenyl). In some of these variations, Q is 4-fluorophenyl.

In one particular embodiment, the compound is of the formula (B-IA), (B-IB), (B-IC) or (B-ID), or a salt, solvate or N-oxide thereof, wherein:

$R^1$ is H, $C_1$-$C_5$ alkyl optionally substituted with 1 to 3 substituents independently selected from halo and hydroxyl, $C_3$-$C_8$ cycloalkyl optionally substituted with 1 to 3 substituents independently selected from halo and hydroxyl, $C_2$-$C_5$ alkenyl optionally substituted with 1 to 3 substituents independently selected from halo and hydroxyl, or —C(O)O—$C_1$-$C_5$ alkyl;

each $R^{2a}$, $R^{3a}$ or $R^{5a}$ (where applicable) is independently H or optionally substituted $C_1$-$C_5$ alkyl;

or $R^1$ and $R^{2a}$, or $R^1$ and $R^{3a}$ are taken together to form a propylene (—CH$_2$CH$_2$CH$_2$—) moiety or a butylene (—CH$_2$CH$_2$CH$_2$CH$_2$—) moiety;

X is N or CR$^{6a}$;

each $R^6$ and $R^{6a}$ is independently H; halogen; $C_1$-$C_5$ alkyl optionally substituted with 1 to 3 substituents selected from halogen atoms and hydroxyl; optionally substituted $C_1$-$C_5$ alkoxy; or optionally substituted —C(O)$C_1$-$C_5$ alkyl;

each $R^7$, $R^9$ and $R^{10}$ is independently H or optionally substituted $C_1$-$C_5$ alkyl;

$R^8$ is azido, acylamino, —OC(O)$C_1$-$C_5$ alkyl substituted with carboxyl or —O$C_1$-$C_5$ alkyl optionally substituted with carboxyl; and Q is aryl or heteroaryl optionally substituted with 1 to 3 substituents including halogen, $C_1$-$C_5$ alkyl or cycloalkyl, halo-substituted $C_1$-$C_5$ alkyl or cycloalkyl, $C_1$-$C_5$ alkoxy or cycloalkoxy, —CN, —CO$_2$H or —C(O)N(R$^a$)R$^b$ where each R$^a$ and R$^b$ is independently H or $C_1$-$C_5$ alkyl.

In certain embodiments of the compounds of any formula detailed herein, where applicable, such as compounds of the formulae (B-I), (B-IA), (B-IB), (B-IC) and (B-ID), $R^1$ is H, $C_1$-$C_5$ alkyl (e.g., methyl) or —C(O)OR$^{11}$ where R$^{11}$ is $C_1$-$C_5$ alkyl. It is understood that any descriptions of $R^1$ may be combined with any descriptions of other moieties (e.g., X, $R^6$, $R^{6a}$, $R^7$, $R^8$, $R^9$, $R^{10}$ and Q) the same as if each and every combination were specifically and individually listed.

In certain embodiments of the compounds of any formula detailed herein, where applicable, such as compounds of the formulae (B-I), (B-IA), (B-IB), (B-IC) and (B-ID), each $R^6$ and $R^{6a}$ is independently H, CH$_3$ or Cl. It is understood that any descriptions of $R^6$ or $R^{6a}$ may be combined with any descriptions of other moieties (e.g., X, $R^1$, $R^7$, $R^8$, $R^9$, $R^{10}$ and Q) the same as if each and every combination were specifically and individually listed.

In certain embodiments of the compounds of any formula detailed herein, where applicable, such as compounds of the formulae (B-I), (B-IA), (B-IB), (B-IC) and (B-ID), X is N. In certain embodiments of the compounds of the formulae (B-I), (B-IA), (B-IB), (B-IC) and (B-ID), X is CR$^{6a}$. In some of these embodiments, R$^{6a}$ is H, CH$_3$ or Cl. It is understood that any descriptions of X, $R^6$ and $R^{6a}$ may be combined with any descriptions of other moieties (e.g., $R^1$, $R^7$, $R^8$, $R^9$, $R^{10}$ and Q) the same as if each and every combination were specifically and individually listed.

In certain embodiments of the compounds any formula detailed herein, where applicable, such as compounds of the formulae (B-I), (B-IA), (B-IB), (B-IC) and (B-ID), $R^8$ is azido. In another variation, $R^8$ is carboxyl. In another variation, $R^8$ is carbonylalkoxy. In another variation, $R^8$ is —OC(O)$C_1$-$C_5$ alkyl substituted with carboxyl (e.g., —OC(O)CH$_2$CO$_2$H, —OC(O)CH$_2$CH$_2$CO$_2$H, or —OC(O)CH$_2$CH$_2$CH$_2$CO$_2$H). In one variation, $R^8$ is —O$C_1$-$C_5$ alkyl optionally substituted with carboxyl. In another variation, $R^8$ is —O$C_1$-$C_5$ alkyl substituted with carboxyl (e.g., —OCH$_2$CO$_2$H, —OCH$_2$CH$_2$CO$_2$H, or —OCH$_2$CH$_2$CH$_2$CO$_2$H). In yet another variation, $R^8$ is —O$C_1$-$C_5$ alkyl. In another variation, $R^8$ is acylamino of the formula —C(O)NR$^{13}$R$^{14}$ where each R$^{13}$ and R$^{14}$ is independently H or optionally substituted $C_1$-$C_5$ alkyl (e.g., —C(O)NH$_2$, —C(O)NHCH$_3$ or —C(O)N(CH$_3$)$_2$). In some variations, $R^8$ is acylamino of the formula —C(O)NR$^{13}$R$^{14}$ where R$^{13}$ and R$^{14}$ are joined with the nitrogen to which they are attached to form a heterocycle (e.g., —C(O)-pyrrolidinyl). It is understood that any descriptions of $R^8$ may be combined with any descriptions of other moieties (e.g., X, $R^1$, $R^6$, $R^{6a}$, $R^7$, $R^9$, $R^{10}$ and Q) the same as if each and every combination were specifically and individually listed.

In certain embodiments of the compounds of any formula detailed herein, where applicable, such as compounds of the formulae (B-I), (B-IA), (B-IB), (B-IC) and (B-ID), Q is aryl or heteroaryl optionally substituted with 1, 2 or 3 substituents independently selected form the group consisting of halo (e.g., fluoro or chloro), $C_1$-$C_5$ alkyl (e.g., methyl), halo-substituted $C_1$-$C_5$ alkyl (e.g., CF$_3$), carboxyl and —C(O)NR$^{11}$R$^{12}$. In some variations, Q is unsubstituted heteroaryl. In some variations, Q is aryl or heteroaryl substituted with a substituent selected form the group consisting of halo (e.g., fluoro or chloro), $C_1$-$C_5$ alkyl (e.g., methyl), halo-substituted $C_1$-$C_5$ alkyl (e.g., CF$_3$), carboxyl and —C(O)NR$^{11}$R$^{12}$. In some variations, Q is aryl or heteroaryl optionally substituted with 2 substituents independently selected form the group consisting of halo (e.g., fluoro or chloro), $C_1$-$C_5$ alkyl (e.g., methyl), halo-substituted $C_1$-$C_5$ alkyl (e.g., $CF_3$), carboxyl and —C(O)$NR^{11}R^{12}$. In some variations, Q is aryl or heteroaryl optionally substituted with 3 substituents independently selected form the group consisting of halo (e.g., fluoro or chloro), $C_1$-$C_5$ alkyl (e.g., methyl), halo-substituted $C_1$-$C_5$ alkyl (e.g., $CF_3$), carboxyl and —C(O)$NR^{11}R^{12}$ (e.g., —C(O)$NH_2$). It is understood that any descriptions of Q may be combined with any descriptions of other moieties (e.g., X, $R^1$, $R^6$, $R^{6a}$, $R^7$, $R^8$, $R^9$ and $R^{10}$) the same as if each and every combination were specifically and individually listed.

In certain embodiments, with respect to the compounds of formula (B-ID), the compound is Compound No. V-21.

In some embodiments, compounds of the formula (C-I) are provided:

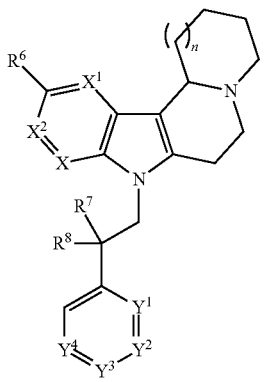

(C-I)

or a salt, solvate or N-oxide thereof, wherein:

$R^6$ is H; halo; $C_1$-$C_5$ alkyl optionally substituted with 1 to 3 substituents independently selected from halogen atoms or hydroxyl; $C_2$-$C_5$ alkenyl; or —C(O)$OR^{11}$; or cycloalkyl optionally substituted with 1 to 3 halogen atoms or hydroxyl, $C_2$-$C_5$ alkenyl, or —C(O)$OR^{11}$;

$R^7$ is H or optionally substituted $C_1$-$C_5$ alkyl;

$R^8$ is H, hydroxyl, —OC(O)$C_1$-$C_5$ alkyl optionally substituted with amino, $N(R^{11})R^{12}$, $SR^{13}$, S(O)$R^{13}$ or $SO_2R^{13}$;

each $R^{11}$, $R^{12}$ and $R^{13}$ is independently H or optionally substituted $C_1$-$C_5$ alkyl;

each $X^1$, $X^2$ and X is N or CH such that no more than two of $X^1$, $X^2$ and X are N;

each $Y^1$, $Y^2$, $Y^3$ and $Y^4$ is N or $CR^4$ such that no more than two of $Y^1$, $Y^2$, $Y^3$ and $Y^4$ are N, and wherein $R^4$ is H, halo, $CH_3$, $CF_3$, or $OCH_3$; and n is 0 or 1.

In one variation of formula (C-I), one or more of the following apply (i) n is 1; (ii) $R^6$ is other than Cl when n is 0, each $R^7$ and $R^8$ is H, each $X^1$, $X^2$, X, $Y^1$, $Y^2$ and $Y^4$ is CH and $Y^3$ is CF; (iii) $R^6$ is other than H when n is 0 and (iv) $R^6$ is other than $CH_3$ when n is 0, each $R^7$ and $R^8$ is H, each $X^1$, $X^2$, $Y^1$ and $Y^4$ is CH; each X and $Y^2$ is N and $Y^3$ is $CCH_3$. In one such variation, $R^6$ is a fluoro-containing moiety, such as —$CF_3$, —$CHF_2$, —$CH_2F$, or —$CH_2F$. In another variation, compounds of the formula (C-I) are provided, wherein the compounds are other than compounds (A)-(G) in Table A.

In one variation, compounds of formula (C-I) are embraced, provided that at least one of $X^1$, $X^2$ and X is CH. In another variation, at least two of $X^1$, $X^2$ and X is CH. In one aspect, when at least one or when at least two of $X^1$, $X^2$ and X is CH, one or more of the following apply (i) n is 1 and (ii) $R^6$ is other than H, $C_1$ or $CH_3$. In another variation, when $X^2$ is N then X is CH. In another variation, when $X^2$ is CH then X is N. In one aspect, when $X^2$ is CH and X is N, then one or more of the following apply (i) n is 1 and (ii) $R^6$ is other than H or $CH_3$.

In another variation of formula (C-I), $R^6$ is halo, $CH_3$, $CH_2F$, $CHF_2$, $CF_3$ or $CD_3$.

In another variation of formula (C-I), $R^7$ is H or $CH_3$. In one variation, $R^7$ is H, $CH_3$, $CF_3$, $CH_2F$, $CHF_2$ or $CH_2OH$.

In another variation of formula (C-I), $R^8$ is H or OH. In one variation, $R^8$ is —OC(O)$C_1$-$C_5$ alkyl optionally substituted with amino, $N(R^{11})R^{12}$, $SR^{13}$, S(O)$R^{13}$ or $SO_2R^{13}$. In one variation, $R^8$ is $N(R^{11})R^{12}$. In one variation, $R^8$ is $SR^{13}$, S(O)$R^{13}$ or $SO_2R^{13}$.

In another variation of formula (C-I), at least one of $Y^1$, $Y^2$, $Y^3$ and $Y^4$ is N. In another variation, $Y^1$ and $Y^3$ are each N. In another variation, $Y^2$ and $Y^4$ are each N. In another variation, $Y^1$ and $Y^4$ are each N.

In another variation of formula (C-I), $Y^1$, $Y^2$ and $Y^4$ are each H, and $Y^3$ is $CR^4$, wherein $R^4$ is halo, $CH_3$, $CF_3$ or $OCH_3$.

In another variation of formula (C-I), $R^6$ is F, Cl, Br, $CD_3$ or $CH_2F$; $X^1$, $X^2$ and X are each N or CH; $Y^2$ and $Y^3$ are each N or $CR^4$, wherein $R^4$ is $CH_3$ or $CF_3$; $R^8$ is H or hydroxyl; and n is 0 or 1. In another variation, of formula (C-I), $R^6$ is F, Cl, Br, $CD_3$ or $CH_2F$; $R^7$ is H, $CH_3$, $CF_3$, $CH_2F$, $CHF_2$ or $CH_2OH$; $X^1$, $X^2$ and X are each N or CH; $Y^2$ and $Y^3$ are each N or $CR^4$, wherein $R^4$ is $CH_3$ or $CF_3$; $R^8$ is H or hydroxyl; and n is 0 or 1. In one such variation, $Y^1$ and $Y^4$ are both CH.

In certain embodiments, with respect to the compounds of formula (C-I), n is 0, $R^6$ is Cl, $R^7$ and $R^8$ are both H, each $X^1$, $X^2$, X, $Y^1$, $Y^2$ and $Y^4$ is CH and $Y^3$ is other than CF.

In one embodiment, the compound is of formula (C-IA) or (C-IB):

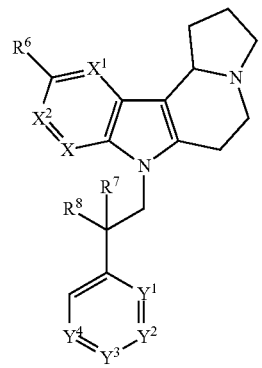

(C-IA)

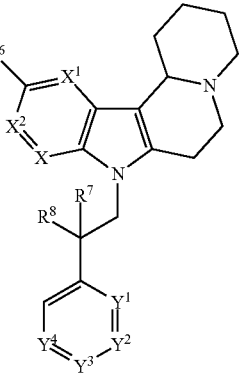

(C-IB)

wherein $R^6$, $R^7$, $R^8$, $X^1$, $X^2$, X, $Y^1$, $Y^2$, $Y^3$ and $Y^4$ are as described for formula (C-I). In one variation of formula (C-IA), one or more of the following apply (i) $R^6$ is other than Cl when n is 0, each $R^7$ and $R^8$ is H, each $X^1$, $X^2$, X, $Y^1$, $Y^2$ and $Y^4$ is CH and $Y^3$ is CF; (ii) $R^6$ is other than H when n is 0 and (iii) $R^6$ is other than $CH_3$ when n is 0, each $R^7$ and $R^8$ is H, each $X^1$, $X^2$, $Y^1$ and $Y^4$ is CH; each X and $Y^2$ is N and $Y^3$ is $CCH_3$. In one such variation, $R^6$ is a fluoro-containing moiety, such as —$CH_2F$. In another variation, compounds of the formula (C-IA) and (C-IB) are provided, wherein the compounds are other than compounds (A)-(G) in Table A.

In certain embodiments, with respect to the compounds of formula (C-IA), $X^1$ is N, and the compound is Compound No. IV-3, IV-29 to IV-38, IV-109 to IV-118, IV-151, IV-152, IV-154 to W-158, or IV-230 to IV-238.

In certain embodiments, with respect to the compounds of formula (C-IA), $X^2$ is N, and the compound is Compound No. II-5 or II-275.

In certain embodiments, with respect to the compounds of formula (C-IB), X is N, and the compound is Compound No. IV-8, IV-49 to IV-58, IV-169 to IV-177, or IV-178.

In certain embodiments, with respect to the compounds of formula (C-IB), $X^1$ is N, and the compound is Compound No. IV-69 to IV-78, IV-189 to W-197, or IV-198.

In certain embodiments, with respect to the compounds of formula (C-IB), each of X, $X^1$, and $X^2$ is independently is $CR^6$, and the compound is Compound No. 47.

In specific variations, compounds of formula (C-IA) have the structure:

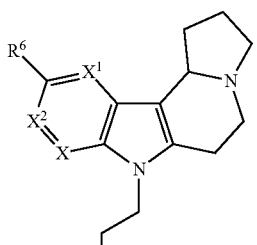

(C-IA-1)

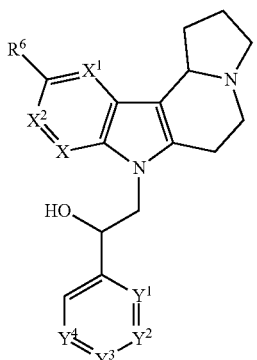

(C-IA-2)

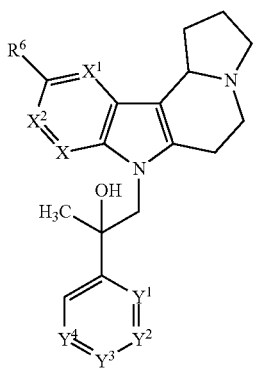

(C-IA-3)

or a salt or solvate thereof, wherein $R^6$, $X^1$, $X^2$, X, $Y^1$, $Y^2$, $Y^3$ and $Y^4$ are defined as for formula (C-I).

In certain embodiments, with respect to the compounds of formula (C-IA-1), each of X, $X^1$, and $X^2$ is independently is $CR^6$, and the compound is Compound No. 197.

In certain embodiments, with respect to the compounds of formula (C-IA-1), each of X, $X^1$, and $X^2$ is independently is $CR^6$, and the compound is No. Compound II-290, IV-6, or IV-7.

In certain embodiments, with respect to the compounds of formula (C-IA-1), X is N, and the compound is Compound No. 74, 134, or 336.

In certain embodiments, with respect to the compounds of formula (C-IA-1), X is N, and the compound is Compound No. II-238, II-243 to II-245, II-268, or II-297.

In certain embodiments, with respect to the compounds of formula (C-IA-1), X is N, and the compound is Compound No. IV-2, IV-4, IV-9, IV-11 to IV-18, IV-89, IV-93 to IV-97, or IV-98.

In certain embodiments, with respect to the compounds of formula (C-IA-1), $X^1$ is N, and the compound is Compound No. IV-29 to IV-38, IV-109 to IV-117, or IV-118 (Table IV).

In certain embodiments, with respect to the compounds of formula (C-IA-2), the compound is Compound No. II-129, II-168, or II-198.

In certain embodiments, with respect to the compounds of formula (C-IA-2), the compound is Compound No. IV-129 to IV-133, IV-149 to IV-152, IV-154 to IV-158, IV-209, IV-211 to IV-216, IV-219, IV-221, IV-229, IV-230, IV-232, IV-234, IV-236, IV-239, IV-241, IV-242, or IV-244 (Table IV).

In certain embodiments, with respect to the compounds of formula (C-IA-3), each of X, $X^1$, and $X^2$ is independently is $CR^6$, and the compound is Compound No. 176.

In certain embodiments, with respect to the compounds of formula (C-IA-3), each of X, $X^1$, and $X^2$ is independently is $CR^6$, and the compound is Compound No. II-121, II-127, II-128, II-130, II-291, II-294, or IV-7.

In certain embodiments, with respect to the compounds of formula (C-IA-3), X is N, and the compound is Compound No. 26 or 148.

In certain embodiments, with respect to the compounds of formula (C-IA-3), X is N, and the compound is Compound No. II-149.

In certain embodiments, with respect to the compounds of formula (C-IA-3), X is N, and the compound is Compound No. IV-134 to IV-138, IV-210, IV-217, or IV-218.

In certain embodiments, with respect to the compounds of formula (C-IA-3), $X^1$ is N, and the compound is Compound No. II-17.

In certain embodiments, with respect to the compounds of formula (C-IA-3), $X^1$ is N, and the compound is Compound No. IV-231, IV-233, IV-235, IV-237, or IV-238.

In other variations, compounds of formula (C-IA) have the structure:

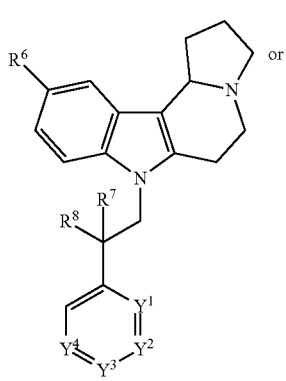

(C-IA-4)

or

-continued (C-IA-5)

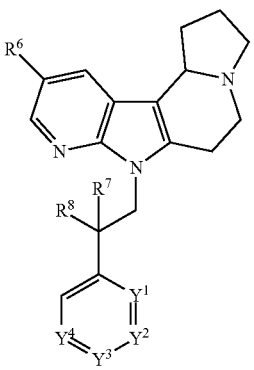

or a salt or solvate thereof, wherein $R^6$, $R^7$, $R^8$, $Y^1$, $Y^2$, $Y^3$ and $Y^4$ are defined as for formula (C-I). In one variation, $R^7$ and $R^8$ are both H.

In certain embodiments, with respect to the compounds of formula (C-IA-4), each $Y^1$, $Y^2$, $Y^3$ and $Y^4$ is independently $CR^4$; and the compound is Compound No. II-120, II-121, II-266, II-271, or II-279.

In certain embodiments, with respect to the compounds of formula (C-IA-4), each $Y^1$, $Y^2$, $Y^3$ and $Y^4$ is independently $CR^4$; and the compound is Compound No. W-6, IV-7, or IV-9.

In certain embodiments, with respect to the compounds of formula (C-IA-4), one of $Y^1$, $Y^2$, $Y^3$ and $Y^4$ is N, and the rest of $Y^1$, $Y^2$, $Y^3$ and $Y^4$ are independently $CR^4$; and the compound is Compound No. 129, 168, 197, or 198.

In certain embodiments, with respect to the compounds of formula (C-IA-4), one of $Y^1$, $Y^2$, $Y^3$ and $Y^4$ is N, and the rest of $Y^1$, $Y^2$, $Y^3$ and $Y^4$ are independently $CR^4$; and the compound is Compound No. II-125, II-127, II-128, II-130, II-131, II-281, II-282, II-284, II-290, II-291, or II-293.

In certain embodiments, with respect to the compounds of formula (C-IA-4), one of $Y^1$, $Y^2$, $Y^3$ and $Y^4$ is N, and the rest of $Y^1$, $Y^2$, $Y^3$ and $Y^4$ are independently $CR^4$; and the compound is Compound No. IV-4, IV-5, IV-15, or IV-18.

In certain embodiments, with respect to the compounds of formula (C-IA-4), two of $Y^1$, $Y^2$, $Y^3$ and $Y^4$ are N, and the rest of $Y^1$, $Y^2$, $Y^3$ and $Y^4$ are independently $CR^4$; and the compound is Compound No. 176.

In certain embodiments, with respect to the compounds of formula (C-IA-4), two of $Y^1$, $Y^2$, $Y^3$ and $Y^4$ are N, and the rest of $Y^1$, $Y^2$, $Y^3$ and $Y^4$ are independently $CR^4$; and the compound is Compound No. II-6, II-7, II-261, II-276, or II-294.

In certain embodiments, with respect to the compounds of formula (C-IA-5), each $Y^1$, $Y^2$, $Y^3$ and $Y^4$ is independently $CR^4$; and the compound is Compound No. 336.

In certain embodiments, with respect to the compounds of formula (C-IA-5), each $Y^1$, $Y^2$, $Y^3$ and $Y^4$ is independently $CR^4$; and the compound is Compound No. II-149. In certain embodiments, with respect to the compounds of formula (C-IA-5), each $Y^1$, $Y^2$, $Y^3$ and $Y^4$ is independently $CR^4$; and the compound is Compound No. II-149a, II-149b, II-149c, or II-149d.

In certain embodiments, with respect to the compounds of formula (C-IA-5), each $Y^1$, $Y^2$, $Y^3$ and $Y^4$ is independently $CR^4$; and the compound is Compound No. W-1, IV-9, IV-11 to IV-18, IV-129, IV-130 to IV-137, or IV-138.

In certain embodiments, with respect to the compounds of formula (C-IA-5), one or two of $Y^1$, $Y^2$, $Y^3$ and $Y^4$ is N, and the rest of $Y^1$, $Y^2$, $Y^3$ and $Y^4$ are independently $CR^4$; and the compound is Compound No. 26, 74, 134, 137, or 148.

In certain embodiments, with respect to the compounds of formula (C-IA-5), one or two of $Y^1$, $Y^2$, $Y^3$ and $Y^4$ is N, and the rest of $Y^1$, $Y^2$, $Y^3$ and $Y^4$ are independently $CR^4$; and the compound is Compound No. II-79, II-238, II-243, II-244, II-245, II-268, or II-297.

In certain embodiments, with respect to the compounds of formula (C-IA-5), one or two of $Y^1$, $Y^2$, $Y^3$ and $Y^4$ is N, and the rest of $Y^1$, $Y^2$, $Y^3$ and $Y^4$ are independently $CR^4$; and the compound is Compound No. IV-2, IV-4, IV-89, IV-91, IV-93 to IV-98, IV-209, IV-210, IV-211, IV-213 to IV-217, or IV-218.

In other variations, compounds of formula (C-IA) have the structure:

(C-IA-6)

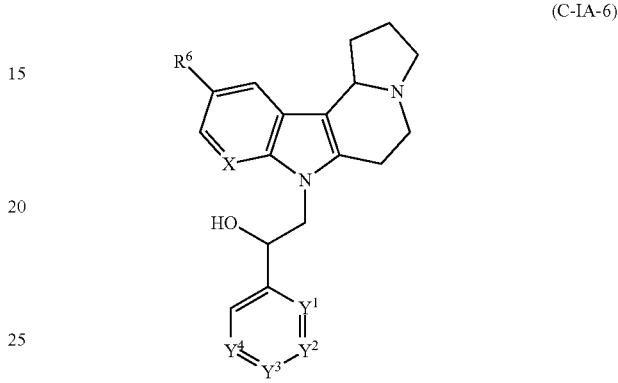

or a salt or solvate thereof, wherein X is C or N; and $R^6$, $Y^1$, $Y^2$, $Y^3$ and $Y^4$ are defined as for formula (C-I).

In certain embodiments, with respect to the compounds of formula (C-IA-6), the compound is Compound No. 129, 168, or 198.

In certain embodiments, with respect to the compounds of formula (C-IA-6), the compound is Compound No. II-79, II-120, II-125, II-131, or II-293.

In certain embodiments, with respect to the compounds of formula (C-IA-6), the compound is Compound No. IV-129 to IV-133, IV-209, IV-211, IV-213 to IV-215, or IV-216.

In other variations, compounds of formula (C-IA) have the structure:

(C-IA-7)

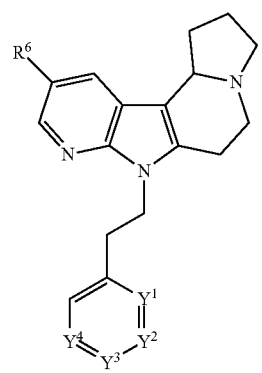

or a salt or solvate thereof, wherein $R^6$, $Y^1$, $Y^2$, $Y^3$ and $Y^4$ are defined as for formula (C-I).

In certain embodiments, with respect to the compounds of formula (C-IA-7); the compound is Compound No. 74, 134, 137, or 336.

In certain embodiments, with respect to the compounds of formula (C-IA-7); the compound is Compound No. II-238, II-243, II-244, II-245, or II-297.

In certain embodiments, with respect to the compounds of formula (C-IA-7); the compound is Compound No. IV-2, IV-4, IV-9, IV-11, IV-13 to IV18, IV-89, IV-91, IV-93 to IV-97, or IV-98.

In one variation of formula (C-IA-1) one or more of the following apply: (i) $R^6$ is other than Cl when each $X^1$, $X^2$, X, $Y^1$, $Y^2$ and $Y^4$, a Y is CH and $Y^3$ is CF; (ii) $R^6$ is other than H when each $X^1$, $X^2$, X, $Y^1$, $Y^2$ and $Y^4$ is CH and $Y^3$ is CF; (iii) $R^6$ is other than H when each $X^1$, $X^2$, $Y^1$ and $Y^4$ is CH; each X and $Y^2$ is N and $Y^3$ is $CCH_3$; and (iv) $R^6$ is other than $CH_3$ when each $X^1$, $X^2$, $Y^1$ and $Y^4$ is CH; each X and $Y^2$ is N and $Y^3$ is $CCH_3$.

In one variation of formula (C-IA-2), $R^6$ is other than H when each $X^1$, $X^2$, $Y^1$, $Y^2$ and $Y^4$ is CH; each X and $Y^3$ is N.

In one variation of formula (C-IA-3), $R^6$ is other than H when each $X^1$, $X^2$, X, $Y^1$, $Y^2$ and $Y^4$ is CH and $Y^3$ is N.

In certain embodiments, with respect to the compounds of formula (C-IA), (C-IA-1), (C-IA-3), or (C-IA-7), n is 0, $R^6$ is Cl, $R^7$ and $R^8$ are both H, each $X^1$, $X^2$, X, $Y^1$, $Y^2$ and $Y^4$ is CH and $Y^3$ is other than CF.

In specific variations, compounds of formula (C-IB) have the structure:

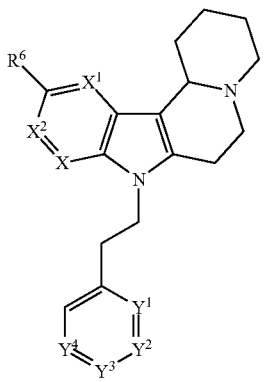

(C-IB-1)

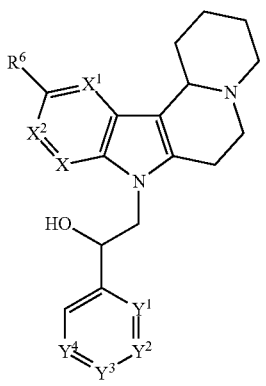

(C-IB-2)

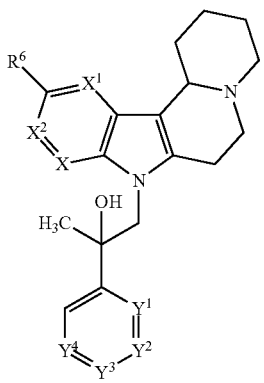

(C-IB-3)

or a salt or solvate thereof, wherein $R^6$, $X^1$, $X^2$, X, $Y^1$, $Y^2$, $Y^3$ and $Y^4$ are defined as for formula (C-I).

In certain embodiments, with respect to the compounds of formula (C-IB-1); the compound is Compound No. IV-8, IV-49 to IV-87, or IV-88.

In certain embodiments, with respect to the compounds of formula (C-IB-2); the compound is Compound No. 47.

In certain embodiments, with respect to the compounds of formula (C-IB-2); the compound is Compound No. IV-179 to IV-188, IV-199 to IV-207, or IV-208.

In certain embodiments, with respect to the compounds of formula (C-IB-3); the compound is Compound No. IV-169 to IV-178, IV-190 to IV-197, or IV-198.

In one embodiment, the compound is of formula (C-IC-1):

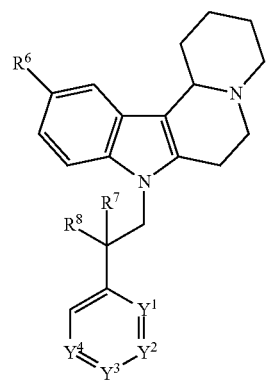

(C-IC-1)

or a salt or solvate thereof, wherein $R^6$, $X^1$, $X^2$, X, $Y^1$, $Y^2$, $Y^3$ and $Y^4$ are defined as for formula (C-I).

In one embodiment, the compound is of formula (C-II):

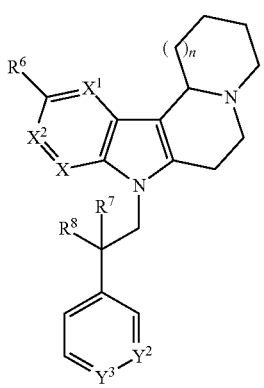

(C-II)

wherein $R^6$, $R^7$, $R^8$, $X^1$, $X^2$, X, $Y^2$ and $Y^3$ are as described for formula (C-I). In one variation of formula (C-II), one or more of the following apply (i) n is 1 and (ii) $R^6$ is other than Cl when n is 0, each $R^7$ and $R^8$ is H, each $X^1$, $X^2$, X, $Y^1$, $Y^2$ and $Y^4$ is CH and $Y^3$ is CF; (iii) $R^6$ is other than H when n is 0 and (iv) $R^6$ is other than $CH_3$ when n is 0, each $R^7$ and $R^8$ is H, each $X^1$, $X^2$, $Y^1$ and $Y^4$ is CH; each X and $Y^2$ is N and $Y^3$ is $CCH_3$. In one such variation, $R^6$ is a fluoro-containing moiety, such as $-CH_2F$. In another variation, compounds of the formula (C-II) are provided, wherein the compounds are other than compounds (A)-(G) in Table A.

In one embodiment, the compound is of formula (C-IIA) or (C-IIB):

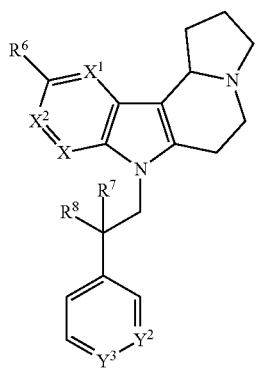
(C-IIA)

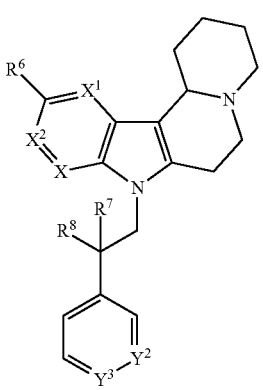
(C-IIB)

wherein $R^6$, $R^7$, $R^8$, $X^1$, $X^2$, X, $Y^2$, and $Y^3$ are as described for formula (C-I). In one variation of formula (C-IIA), one or more of the following apply (i) $R^6$ is other than Cl when n is 0, each $R^7$ and $R^8$ is H, each $X^1$, $X^2$, X, $Y^2$ is CH and $Y^3$ is CF; (ii) $R^6$ is other than H when n is 0 and (iii) $R^6$ is other than $CH_3$ when n is 0, each $R^7$ and $R^8$ is H, each $X^1$ and $X^2$ is CH; each X and $Y^2$ is N and $Y^3$ is $CCH_3$. In one variation, the compound of formula (C-IIA) is selected from Compounds (A)-(G), presented in Table A. In another variation, the compound of formula (C-IIA) is other than Compounds (A)-(G) in Table A. It is understood that each of compounds (A)-(G) may exist as individual isomers, e.g., isomer A1 and isomer A2 for compound A.

TABLE A

Representative Compounds of formula (C-IIA)

| Compound | $R^6$ | $R^7$ | $R^8$ | $X^1$ | $X^2$ | X | $Y^2$ | $Y^3$ |
|---|---|---|---|---|---|---|---|---|
| A | Cl | H | H | CH | CH | CH | CH | CF |
| B | H | H | H | CH | CH | CH | CH | CH |
| C | H | $CH_3$ | OH | CH | CH | CH | CH | N |
| D | $CH_3$ | H | H | CH | CH | N | N | $CCH_3$ |
| E | H | H | H | CH | CH | N | N | $CCH_3$ |
| F | H | H | H | CH | CH | N | N | $CCF_3$ |
| G | H | H | OH | CH | CH | N | CH | N |

In one embodiment, the compound is of formulae (C-IIIA): (C-IIIF):

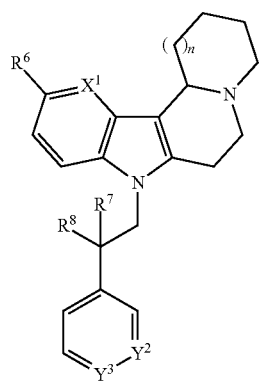
(C-IIIA)

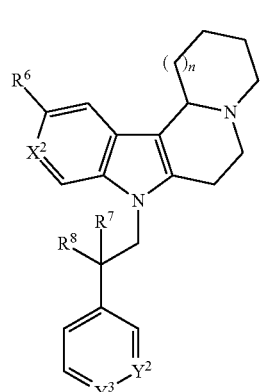
(C-IIIB)

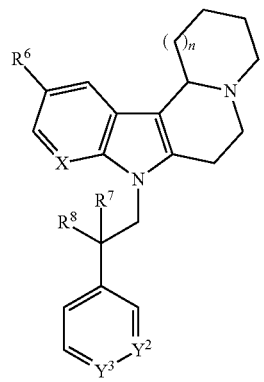
C-(IIIC)

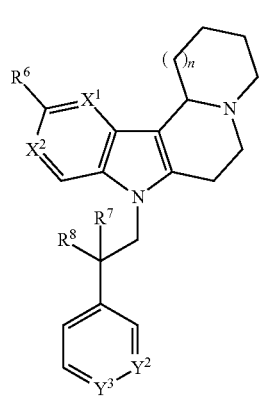
(C-IIID)

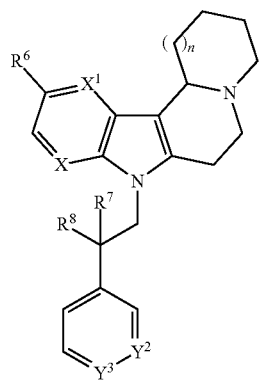
(C-IIIE)

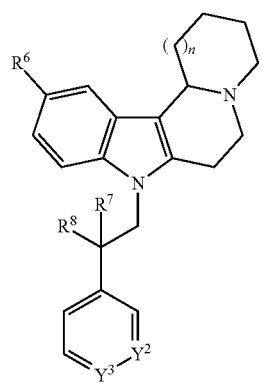
(C-IIIF)

wherein $R^6$, $R^7$, $R^8$, $X^1$, $X^2$, X, $Y^2$, $Y^3$ and n are as described for formula (C-I). In one variation, the compound is of formula (C-IIIA), (C-IIIB), (C-IIIC), (C-IIID), (CIII-E) or (C-IIIF), wherein n is 0. In one variation compound is of formulae (C-IIIA), (C-IIIB), (C-IIIC), (C-IIID), (CIII-E) or (C-IIIF), wherein n is 0, and wherein one or more of the following provisions apply: (i) $R^6$ is other than Cl when n is 0, each $R^7$ and $R^8$ is H, each $X^1$, $X^2$, X, $Y^1$, $Y^2$ and $Y^4$ is CH. and $Y^3$ is CF; (ii) $R^6$ is other than H when n is 0 and (iii) $R^6$ is other than $CH_3$ when n is 0, each $R^7$ and $R^8$ is H, each $X^1$, $X^2$, $Y^1$ and $Y^4$ is CH; each X and $Y^2$ is N and $Y^3$ is $CCH_3$. In another variation, the compound is of formulae (C-IIIA), (C-IIIB), (C-IIIC), (C-IIID), (CIII-E) or (C-IIIF), wherein n is 1.

In another embodiment the compound is according to formula (C-IVA), (C-IVB), (C-IVC), (C-IVD), (C-IVE), (C-IVF) or (C-IVG):

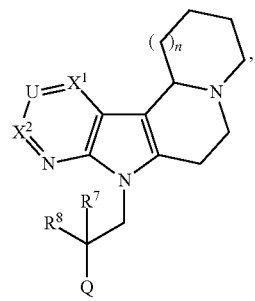
(C-IVA)

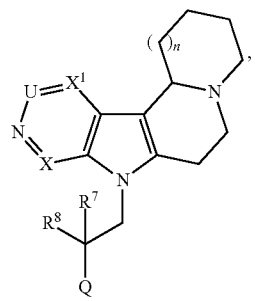
(C-IVB)

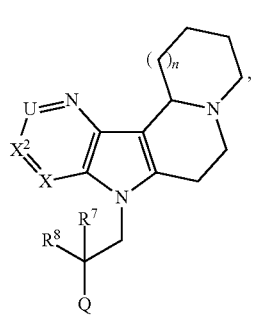
(C-IVC)

(C-IVD)

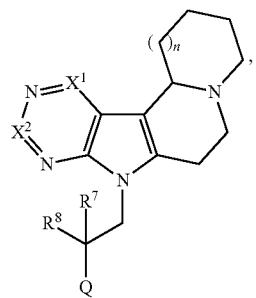
(C-IVE)

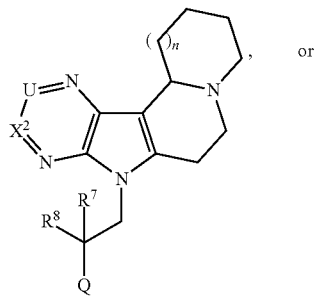
(C-IVF) or

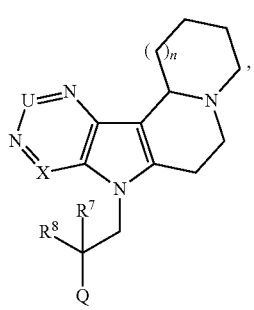

(C-IVG)

or a salt, solvate or N-oxide thereof, wherein:
n is 0 or 1;
each $X^1$, U, $X^2$, or X, where present, is independently $CR^6$;
$R^6$ is H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;
$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;
$R^8$ is H, halo, hydroxyl, $N(R^{11})R^{12}$, $SR^{13}$, $S(O)R^{13}$, $SO_2R^{13}$, —OC(O)$N(R^{14})R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety; and
Q is cycloalkyl, aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

In one embodiment, with respect to the compounds of formula (C-IVA), (C-IVB), (C-IVC), (C-IVD), (C-IVE), (C-IVF), or (C-IVG), each $X^1$, U, $X^2$, or X is independently $CR^6$, and each $R^6$ is H. In another embodiment, each $R^6$ is independently selected from H, $C_1$-$C_5$ alkyl, and halo $C_1$-$C_5$ alkyl. In certain embodiments, each $R^6$ is independently selected from H, methyl, ethyl, fluoro, chloro, $CH_2F$, and $CF_3$.

In one embodiment, with respect to the compounds of formula (C-IVA), (C-IVB), (C-IVD), (C-IVF) or (C-IVG), each $X^1$, $X^2$ and X (where present) is $CR^6$, wherein $R^6$ is H; U is $CR^6$, wherein $R^6$ is selected from H, $C_1$-$C_5$ alkyl and halo $C_1$-$C_5$ alkyl. In certain embodiments, each $R^6$ is independently selected from methyl, ethyl, fluoro, chloro, $CH_2F$, and $CF_3$.

In one embodiment, with respect to the compounds of formula (C-IVA), (C-IVB), (C-IVC), (C-IVD), (C-IVE), (C-IVF) or (C-IVG), each $R^7$ and $R^8$ is H. In another embodiment, $R^7$ is H or methyl, and $R^8$ is H, OH or methyl.

In certain embodiments, with respect to the compounds of formula (C-IVA), (C-IVB), (C-IVC), (C-IVD), (C-IVE), (C-IVF) or (C-IVG), $R^7$ is H; and $R^8$ is OH, $NH_2$, $CF_3$ or methyl.

In one embodiment, with respect to the compounds of formula (C-IVA), (C-IVB), (C-IVC), (C-IVD), (C-IVE), (C-IVF) or (C-IVG), Q is optionally substituted phenyl.

In another embodiment, with respect to the compounds of formula (C-IVA), (C-IVB), (C-IVC), (C-IVD), (C-IVE), (C-IVF) or (C-IVG), Q is phenyl substituted with $C_1$-$C_5$ alkyl, halo, halo $C_1$-$C_5$ alkyl or $C_1$-$C_5$ alkoxy.

In another embodiment, with respect to the compounds of formula (C-IVA), (C-IVB), (C-IVC), (C-IVD), (C-IVE), (C-IVF), or (C-IVG), Q is phenyl substituted with methyl, ethyl, fluoro, chloro, methoxy or $CF_3$. In certain embodiments, Q is phenyl substituted with 4-methyl, 4-ethyl, 4-fluoro, 4-chloro, 4-methoxy, or 4-$CF_3$.

In another embodiment, with respect to the compounds of formula (C-IVA), (C-IVB), (C-IVC), (C-IVD), (C-IVE), (C-IVF), or (C-IVG), Q is optionally substituted pyridyl, or optionally substituted pyrimidinyl.

In another embodiment, with respect to the compounds of formula (C-IVA), (C-IVB), (C-IVC), (C-IVD), (C-IVE), (C-IVF), or (C-IVG), Q is pyridyl substituted with $C_1$-$C_5$ alkyl, halo, halo or $C_1$-$C_5$ alkyl.

In another embodiment, with respect to the compounds of formula (C-IVA), (C-IVB), (C-IVC), (C-IVD), (C-IVE), (C-IVF), or (C-IVG), Q is pyridyl substituted with methyl, ethyl, fluoro, chloro, or $CF_3$.

In one embodiment, with respect to the compounds of formula (C-IVA), (C-IVB), (C-IVC), (C-IVD), (C-IVE), (C-IVF), or (C-IVG), n is 0. In another embodiment, n is 1.

In certain embodiments, with respect to the compounds of formula (C-IVA), (C-IVB), (C-IVC), (C-IVD), (C-IVE), (C-IVF) or (C-IVG), the compound is any one of compounds listed in Table IV. In another embodiment, with respect to the compounds of formula (C-IVA), (C-IVB), (C-IVC), (C-IVD), (C-IVE), (C-IVF), or (C-IVG), the compound is any one of compounds listed in Table IV, provided that the compound is other than Compound No. W-2, IV-4, IV-5, IV-6, or IV-7.

In certain embodiments, with respect to the compounds of formula (C-IVA), n is 0, Q is optionally substituted 4-pyridyl, and the compound is Compound No. II-79, II-89, II-209, or II-244.

In certain embodiments, with respect to the compounds of formula (C-IVA), n is 0, Q is optionally substituted 3-pyridyl, and the compound is Compound No. 26, 74, 134, 137, 148, II-238, II-243, II-268, II-297, IV-2, IV-4, IV-97 to IV-98, IV-210, IV-217, or IV-218.

In certain embodiments, with respect to the compounds of formula (C-IVA), n is 0, Q is optionally substituted 2-pyridyl, and the compound is Compound No. W-91, IV-95, IV-96, IV-211, IV-215, or IV-216.

In certain embodiments, with respect to the compounds of formula (C-IVA), n is 0, Q is optionally substituted pyrimidyl, and the compound is Compound No. IV-93 or IV-213.

In certain embodiments, with respect to the compounds of formula (C-IVA), n is 0, Q is optionally substituted pyrazinyl, and the compound is Compound No. II-245, IV-94, or IV-214.

In certain embodiments, with respect to the compounds of formula (C-IVA), n is 0, Q is optionally substituted phenyl, and the compound is Compound No. 336, II-149, IV-1, IV-9, IV-11 to W-18, IV-129 to IV-137, or IV-138.

In certain embodiments, with respect to the compounds of formula (C-IVA), n is 1, Q is optionally substituted phenyl, and the compound is Compound No. W-49 to IV-58, or IV-178.

In certain embodiments, with respect to the compounds of formula (C-IVA), n is 1, Q is optionally substituted 3-pyridyl, and the compound is Compound No. W-8.

In certain embodiments, with respect to the compounds of formula (C-IVB), n is 0, and the compound is Compound No. II-5 or II-275.

In certain embodiments, with respect to the compounds of formula (C-IVD), n is 0, and the compound is Compound IV-3, IV-29 to IV-38, IV-109 to IV-118, IV-149 to IV-158, IV-229 to IV-237, or IV-238.

In certain embodiments, with respect to the compounds of formula (C-IVD), n is 1, and the compound is Compound No. IV-69 to IV-78, IV-189 to W-197, or IV-198.

In certain embodiments, with respect to the compounds of formula (C-IVF), the compound is Compound No. IV-19 to IV-21, IV-25 to IV-28, IV-59 to IV-68, IV-100 to IV-108, IV-139 to IV-148, IV-179 to IV-188, IV-219 to IV-227 or IV-228.

In certain embodiments, with respect to the compounds of formula (C-IVG), the compound is Compound No. IV-10, IV-39 to IV-48, IV-79 to IV-88, IV-90, IV-92, IV-119 to IV-128, IV-159 to IV-168, IV-199 to VI-208, IV-212, IV-239 to IV-243, or IV-244.

In one embodiment, compounds of formula (C-VA) or (C-VB) are provided:

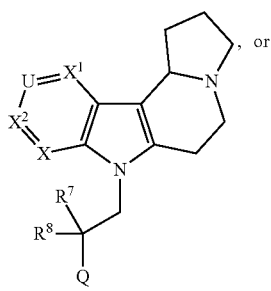

(C-VA)

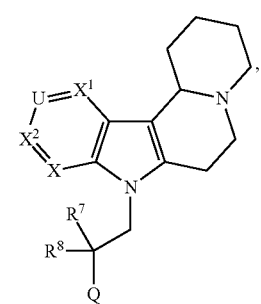

(C-VB)

or a salt, solvate or N-oxide thereof, wherein:

each $X^1$, $X^2$, X and U is independently N or $CR^6$;

each $R^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;

$R^8$ is H, halo, hydroxyl, $N(R^{11})R^{12}$, $SR^{13}$, $S(O)R^{13}$, $SO_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;

Q is aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)$CH_3$ and —C(O)$NR^{16}R^{17}$; and each $R^{16}$ and $R^{17}$ is independently H or optionally substituted $C_1$-$C_5$ alkyl.

In some embodiments, compounds of the formula (D-I) are provided:

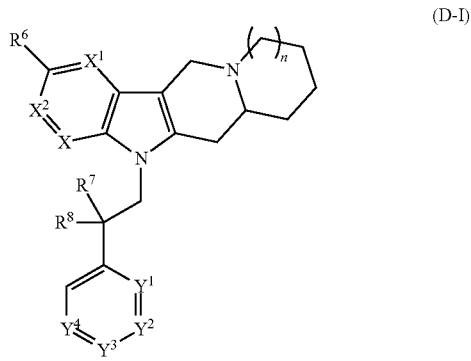

(D-I)

or a salt, solvate or N-oxide thereof, wherein:

$R^6$ is H, halo, $C_1$-$C_5$ alkyl or cycloalkyl optionally substituted with 1 to 3 halogen atoms or hydroxyl, $C_2$-$C_5$ alkenyl, or —C(O)$OR^{11}$;

$R^7$ is H or optionally substituted $C_1$-$C_5$ alkyl;

$R^8$ is H, hydroxyl, —OC(O)$C_1$-$C_5$ alkyl optionally substituted with amino, $N(R^{11})R^{12}$, $SR^{13}$, $S(O)R^{13}$ or $SO_2R^{13}$;

each $R^{11}$, $R^{12}$ and $R^{13}$ is independently H or optionally substituted $C_1$-$C_5$ alkyl;

each $X^1$, $X^2$ and X is N or CH such that no more than two of $X^1$, $X^2$ and X are N;

each $Y^1$, $Y^2$, $Y^3$ and $Y^4$ is N or $CR^4$ such that no more than two of $Y^1$, $Y^2$, $Y^3$ and $Y^4$ are N, and wherein $R^4$ is H, halo, $CH_3$, $CF_3$, or $OCH_3$; and n is 0 or 1.

In one variation, the compound is of formula (D-IIA) or (D-IIB):

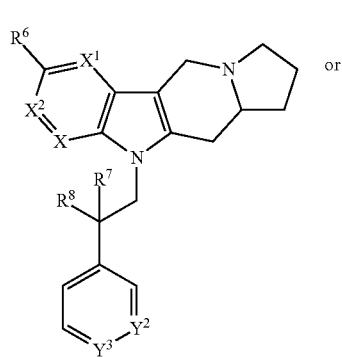

(D-IIA)

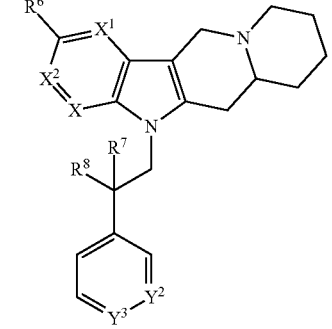

(D-IIB)

or a salt or solvate thereof, wherein $R^6$, $X^1$, $X^2$, X, $Y^2$ and $Y^3$ are defined as for formula (D-I).

In other variations, compounds of formula (D-IIA) have the structure:

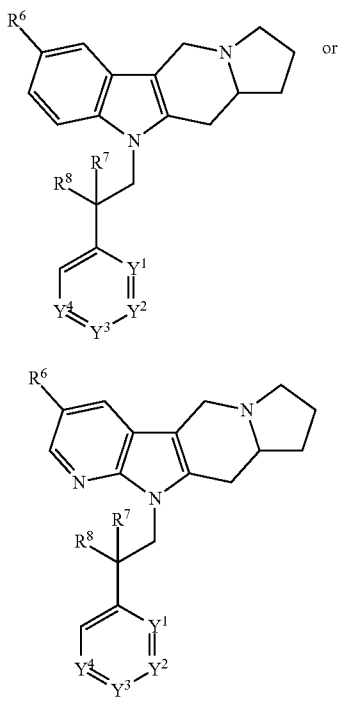

(D-IIA-1)

or

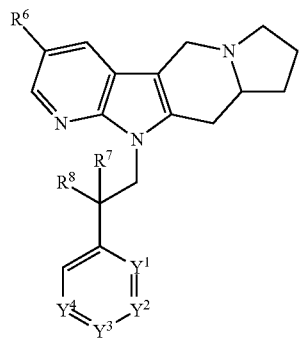

(D-IIA-2)

or a salt or solvate thereof, wherein $R^6$, $R^7$, $R^8$, $Y^1$, $Y^2$, $Y^3$ and $Y^4$ are defined as for formula (D-I).

In certain embodiments, with respect to the compounds of formula (D-IIB), the compound is Compound No. 75.

In certain embodiments, with respect to the compounds of formula (D-IIA-1), the compound is Compound No. 76, III-122, III-356, III-358, or III-359.

In certain embodiments, with respect to the compounds of formula (D-IIA-2), the compound is Compound No. 37, II-86, II-234, II-235, II-236, or II-239.

In one embodiment, compounds of formula (D-IIIA) or (D-IIIB) are provided:

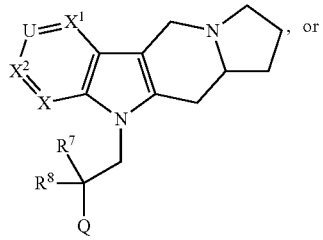

(D-IIIA)

or

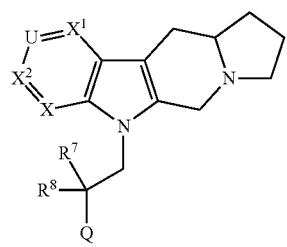

(D-IIIB)

or a salt, solvate or N-oxide thereof, wherein:
each $X^1$, $X^2$, X and U is independently N or $CR^6$;
each $R^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;
$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety;
$R^8$ is H, halo, hydroxyl, $N(R^{11})R^{12}$, $SR^{13}$, $S(O)R^{13}$, $SO_2R^{13}$, —OC(O)ON($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety;
Q is aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)$CH_3$ and —C(O)$NR^{16}R^{17}$; and
each $R^{16}$ and $R^{17}$ is independently H or optionally substituted $C_1$-$C_5$ alkyl.

In certain embodiments, with respect to the compounds of formula (D-IIIA), each $X^1$, U, $X^2$, and X is independently $CR^6$, and the compound is Compound 75, or 76 (Table I); or III-122, III-125, III-126, III-131, III-134, III-135, III-203, III-207, III-208, III-301, III-305, III-314, III-356, III-358, or III-359.

In certain embodiments, with respect to the compounds of formula (D-IIIA), each $X^1$, U, and $X^2$ is independently $CR^6$, X is N, and the compound is Compound No. 37, II-86, II-234, II-235, II-236, or II-239.

In certain embodiments, with respect to the compounds of formula (D-IIIB), the compound is Compound No. III-54, III-353, or III-354.

In some embodiments, compounds of the formula (E-I) are provided:

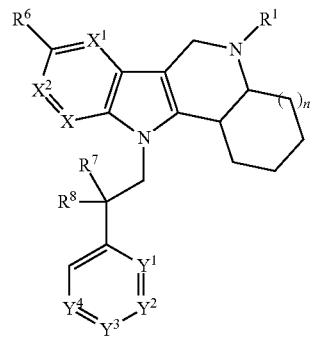

(E-I)

or a salt, solvate or N-oxide thereof, wherein:
$R^1$ is H, $C_1$-$C_5$ alkyl or cycloalkyl optionally substituted with 1 to 3 halogen atoms or hydroxyl, $C_2$-$C_5$ alkenyl, or —C(O)$OR^{11}$;
$R^6$ is H, halo, $C_1$-$C_5$ alkyl or cycloalkyl optionally substituted with 1 to 3 halogen atoms or hydroxyl, $C_2$-$C_5$ alkenyl, or —C(O)$OR^{11}$;
$R^7$ is H or optionally substituted $C_1$-$C_5$ alkyl;
$R^8$ is H, hydroxyl, —OC(O)$C_1$-$C_5$ alkyl optionally substituted with amino, $N(R^{11})R^{12}$, $SR^{13}$, $S(O)R^{13}$ or $SO_2R^{13}$;
each $R^{11}$, $R^{12}$ and $R^{13}$ is independently H or optionally substituted $C_1$-$C_5$ alkyl;
each $X^1$, $X^2$ and X is N or CH such that no more than two of $X^1$, $X^2$ and X are N;

each $Y^1$, $Y^2$, $Y^3$ and $Y^4$ is N or $CR^4$ such that no more than two of $Y^1$, $Y^2$, $Y^3$ and $Y^4$ are N, and wherein $R^4$ is H, halo, $CH_3$, $CF_3$, or $OCH_3$; and n is 0 or 1.

In one variation, the compound is of formula (E-IIA) or (E-IIB):

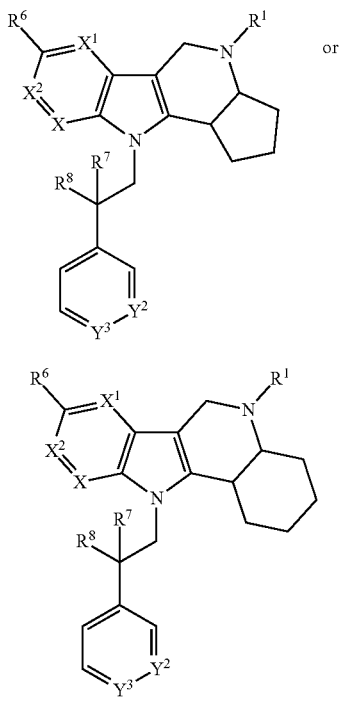

(E-IIA)

(E-IIB)

or a salt or solvate thereof, wherein $R^1$, $R^6$, $X^1$, $X^2$, X, $Y^2$ and $Y^3$ are defined as for formula (E-I).

In other variations, compounds of formula (E-IIA) have the structure:

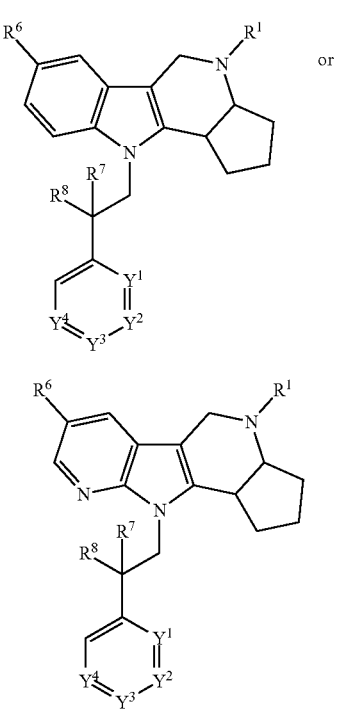

(E-IIA-1)

(E-IIA-2)

or a salt or solvate thereof, wherein $R^1$, $R^6$, $R^7$, $R^8$, $Y^1$, $Y^2$, $Y^3$ and $Y^4$ are defined as for formula (E-I).

In certain embodiments, with respect to the compounds of formula (E-IIA), the compound is Compound No. III-61.

In some embodiments, compounds of the formula (F-I) are provided:

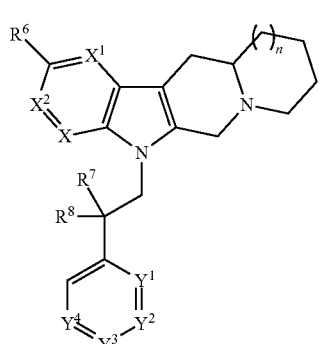

(F-I)

or a salt, solvate or N-oxide thereof, wherein:

$R^6$ is H, halo, $C_1$-$C_5$ alkyl or cycloalkyl optionally substituted with 1 to 3 halogen atoms or hydroxyl, $C_2$-$C_5$ alkenyl, or —C(O)$OR^{11}$;

$R^7$ is H or optionally substituted $C_1$-$C_5$ alkyl;

$R^8$ is H, hydroxyl, —OC(O)$C_1$-$C_5$ alkyl optionally substituted with amino, $N(R^{11})R^{12}$, $SR^{13}$, $S(O)R^{13}$ or $SO_2R^{13}$;

each $R^{11}$, $R^{12}$ and $R^{13}$ is independently H or optionally substituted $C_1$-$C_5$ alkyl;

each $X^1$, $X^2$ and X is N or CH such that no more than two of $X^1$, $X^2$ and X are N;

each $Y^1$, $Y^2$, $Y^3$ and $Y^4$ is N or $CR^4$ such that no more than two of $Y^1$, $Y^2$, $Y^3$ and $Y^4$ are N, and wherein $R^4$ is H, halo, $CH_3$, $CF_3$, or $OCH_3$; and n is 0 or 1.

In one variation, the compound is of formula (F-IIA) or (F-IIB):

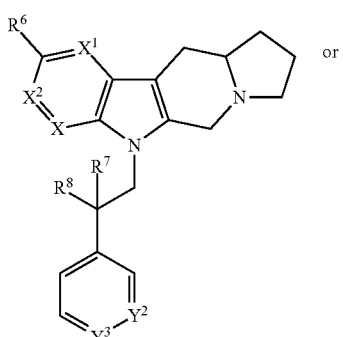

(F-IIA)

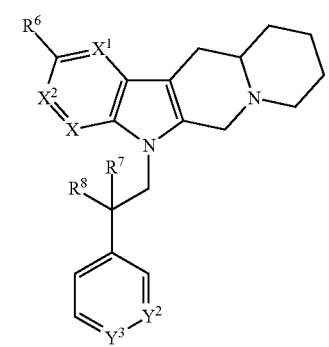

(F-IIB)

or a salt or solvate thereof, wherein $R^6$, $X^1$, $X^2$, X, $Y^2$ and $Y^3$ are defined as for formula (F-I).

In other variations, compounds of formula (F-IIA) have the structure:

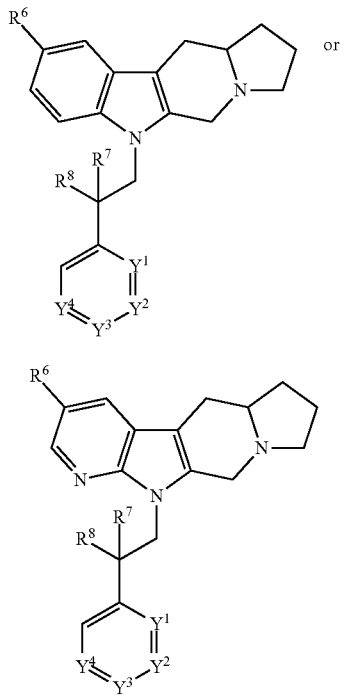

(F-IIA-1)

or (F-IIA-2)

or a salt or solvate thereof, wherein $R^6$, $R^7$, $R^8$, $Y^1$, $Y^2$, $Y^3$ and $Y^4$ are defined as for formula (F-I).

In certain embodiments, with respect to the compounds of formula (F-IIA), the compound is Compound No. III-54, III-353, or III-354.

In some embodiments, compounds of the formula (G-I) are provided:

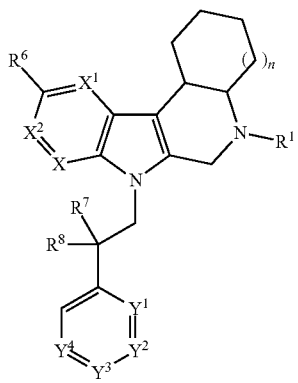

(G-I)

or a salt, solvate or N-oxide thereof, wherein:

$R^1$ is H, $C_1$-$C_5$ alkyl or cycloalkyl optionally substituted with 1 to 3 halogen atoms or hydroxyl, $C_2$-$C_5$ alkenyl, or —C(O)OR$^{11}$;

$R^6$ is H, halo, $C_1$-$C_5$ alkyl or cycloalkyl optionally substituted with 1 to 3 halogen atoms or hydroxyl, $C_2$-$C_5$ alkenyl, or —C(O)OR$^{11}$;

$R^7$ is H or optionally substituted $C_1$-$C_5$ alkyl;

$R^8$ is H, hydroxyl, —OC(O)$C_1$-$C_5$ alkyl optionally substituted with amino, N(R$^{11}$)R$^{12}$, SR$^{13}$, S(O)R$^{13}$ or SO$_2$R$^{13}$;

each $R^{11}$, $R^{12}$ and $R^{13}$ is independently H or optionally substituted $C_1$-$C_5$ alkyl;

each $X^1$, $X^2$ and X is N or CH such that no more than two of $X^1$, $X^2$ and X are N;

each $Y^1$, $Y^2$, $Y^3$ and $Y^4$ is N or CR$^4$ such that no more than two of $Y^1$, $Y^2$, $Y^3$ and $Y^4$ are N, and wherein $R^4$ is H, halo, CH$_3$, CF$_3$, or OCH$_3$; and n is 0 or 1.

In one variation, the compound is of formula (G-IIA) or (G-IIB):

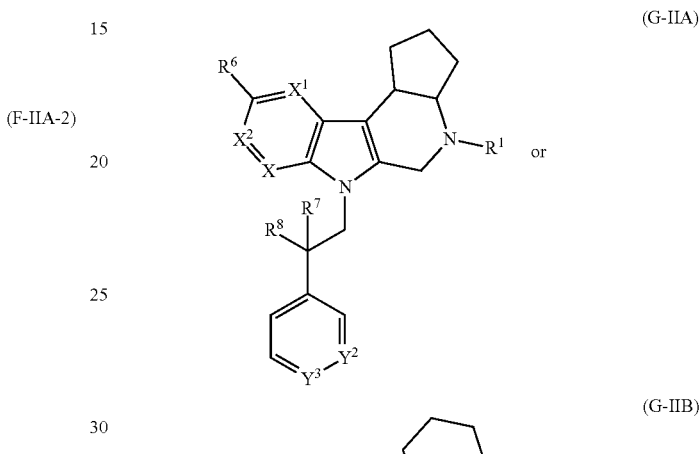

(G-IIA)

or (G-IIB)

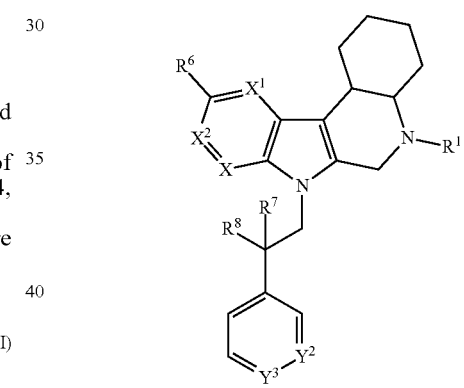

or a salt or solvate thereof, wherein $R^1$, $R^6$, $X^1$, $X^2$, X, $Y^2$ and $Y^3$ are defined as for formula (G-I).

In other variations, compounds of formula (G-IIA) have the structure:

(G-IIA-1)

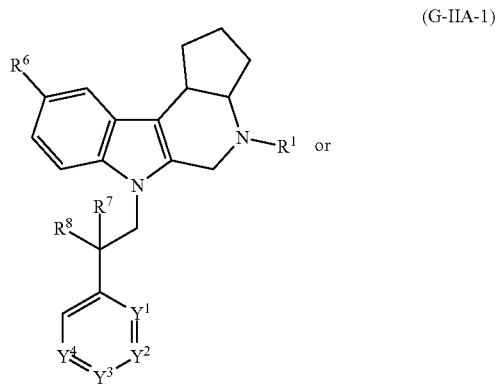

or (G-IIA-2)

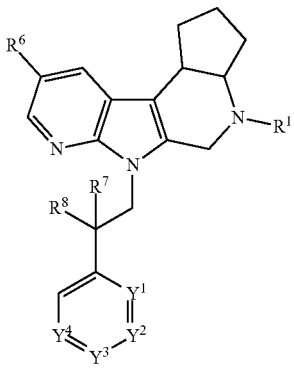

or a salt or solvate thereof, wherein $R^6$, $R^7$, $R^8$, $Y^1$, $Y^2$, $Y^3$ and $Y^4$ are defined as for formula (G-I).

In certain embodiments, with respect to the compounds of formula (G-I), n is 0, $R^8$ is OH, and the compound is Compound No. III-57.

In one embodiment, compounds of formula (H-IA), (H-IB), (H-IC) or (H-ID) are provided:

(H-IA)

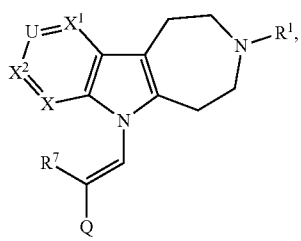

(H-IB)

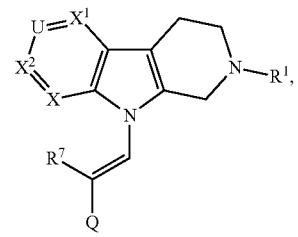

(H-IC)

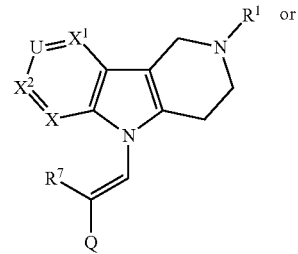

(H-ID)

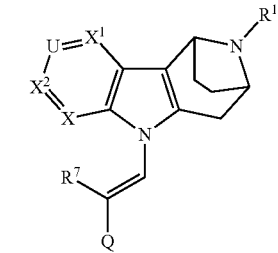

or a salt, solvate or N-oxide thereof, wherein:
each $X^1$, $X^2$, X and U is independently N or $CR^6$;

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

each $R^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl;

Q is aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)$CH_3$ and —C(O)$NR^{16}R^{17}$; and each $R^{16}$ and $R^{17}$ is independently H or optionally substituted $C_1$-$C_5$ alkyl.

In certain embodiments, with respect to the compounds of formula (H-IA), (H-IB), (H-IC), or (H-ID), each $X^1$, $X^2$ and X is independently $CR^6$; wherein each $R^6$ is independently halo, $C_1$-$C_5$-alkyl, halo $C_1$-$C_5$-alkyl, perhalo $C_1$-$C_5$-alkyl, or $C_1$-$C_5$-alkoxy. In certain embodiments, each $X^1$, $X^2$ and X is independently $CR^6$; wherein each $R^6$ is independently fluoro, chloro, methyl, ethyl, $CF_3$, or methoxy. In certain embodiments, U is $CR^6$, wherein $R^6$ is $CF_3$, methyl, chloro, CONH$CH_3$, COOH, COO$CH_3$, H, or fluoro; provided that $R^1$ is other than methyl.

In one embodiment, compounds of formula (H-IA-1), (H-IB-1), (H-IC-1) or (H-ID-1) are provided:

(H-IA-1)

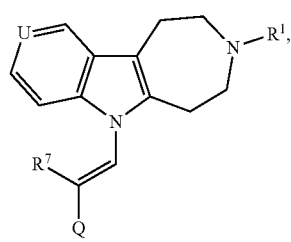

(H-IB-1)

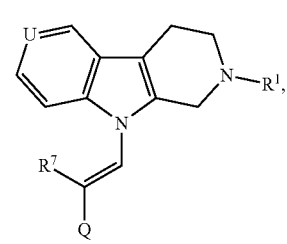

(H-IC-1)

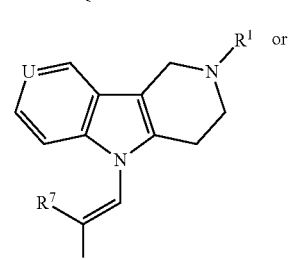

-continued (H-ID-1)

or a salt, solvate or N-oxide thereof, wherein:
U is N or CR$^6$;
R$^1$ is H, C$_1$-C$_5$ alkyl optionally substituted with 1 to 3 substituents independently selected from halo, hydroxyl, carboxyl and perhaloalkyl, C$_3$-C$_8$ cycloalkyl optionally substituted with 1 to 3 substituents independently selected from halo, hydroxyl, carboxyl and perhaloalkyl, C$_2$-C$_5$ alkenyl optionally substituted with 1 to 3 substituents independently selected from halo, hydroxyl, carboxyl and perhaloalkyl, or —C(O)O—C$_1$-C$_5$ alkyl;
R$^6$ is independently H, hydroxyl, halo, C$_1$-C$_5$ alkyl optionally substituted with 1 to 3 substituents independently selected from halo, hydroxyl, carboxyl and perhaloalkyl, optionally substituted C$_1$-C$_5$ alkoxy or optionally substituted —C(O)C$_1$-C$_5$ alkyl;
R$^7$ is H, halo, optionally substituted C$_1$-C$_5$ alkyl, or optionally substituted aryl;
Q is aryl or heteroaryl optionally substituted with 1 to 3 substituents independently selected from the group consisting of halo, C$_1$-C$_5$ alkyl, C$_3$-C$_8$ cycloalkyl, halo-substituted C$_1$-C$_5$ alkyl, halo-substituted C$_3$-C$_8$ cycloalkyl, C$_1$-C$_5$ alkoxy, C$_3$-C$_8$ cycloalkoxy, cyano, carboxyl, —NHC(O)CH$_3$ and —C(O)NR$^{16}$R$^{17}$; and
each R$^{16}$ and R$^{17}$ is independently H or optionally substituted C$_1$-C$_5$ alkyl.

In certain embodiments, with respect to the compounds of formula (H-IA), (H-IB), (H-IC) or (H-ID), (H-IA-1), (H-IB-1), (H-IC-1) or (H-ID-1), Q is an optionally substituted 5-membered heteroaryl; R$^7$ is F or methyl; R$^1$ is methyl; each X$^1$, X$^2$ and X (when present) is CR$^6$, wherein each R$^6$ is H; U is CR$^6$, wherein R$^6$ is methyl or Cl; and Q is other than unsubstituted thienyl or unsubstituted thiazolyl.

In certain embodiments, with respect to the compounds of (H-IA), (H-IB), (H-IC) or (H-ID), (H-IA-1), (H-IB-1), (H-IC-1) or (H-ID-1), Q is optionally substituted pyridyl; each X$^1$, X$^2$ and X (when present) is CR$^6$, wherein each R$^6$ is H; U is CR$^6$, wherein R$^6$ is H, halo, optionally substituted C$_1$-C$_5$ alkyl, or optionally substituted C$_1$-C$_5$ alkoxy; and Q is other than unsubstituted pyridyl, or pyridyl substituted with methyl, Cl, Br, OCH$_3$, or di-methyl.

In certain embodiments, with respect to the compounds of formula (H-IA), (H-IB), (H-IC) or (H-ID), (H-IA-1), (H-IB-1), (H-IC-1) or (H-ID-1), Q is optionally substituted pyrimidinyl; R$^1$ is methyl; each X$^1$, X$^2$ and X (when present) is CR$^6$, wherein each R$^6$ is H; U is CR$^6$, wherein R$^6$ is methyl or Cl; and Q is other than unsubstituted pyrimidin-4-yl, pyrimidin-4-yl substituted with methyl, unsubstituted pyrimidin-5-yl, or pyrimidin-5-yl substituted with methyl.

In certain embodiments, with respect to the compounds of formula (H-IA-1), the compound is Compound No. 99, 106, 222, 226-230, 232-235, 238, 240-241, 244-249, or 251.

In certain embodiments, with respect to the compounds of formula (H-IB-1), the compound is Compound No. 224 or 239.

In certain embodiments, with respect to the compounds of formula (H-IC-1), Q is optionally substituted pyridyl, and the compound is Compound No. 78, 79, 100, 103, 105, 111, 112, 122, 124, 125, 126, 185, 186, 188, 250, 257, 259, 266, 269, 312, 329, or 331.

In certain embodiments, with respect to the compounds of formula (H-IC-1), Q is optionally substituted pyrimidyl, and the compound is Compound No. 101, 187, or 279.

In certain embodiments, with respect to the compounds of formula (H-IC-1), Q is optionally substituted pyridyl, and the compound is Compound No. II-2, II-3, II-59, II-76, II-77, II-96, or II-101.

In certain embodiments, with respect to the compounds of formula (H-IC-1), Q is optionally substituted 5-membered heteroaryl, and the compound is Compound No. 78, 108-110, 110, 115, 189, 273, 275, 277, 278, 285, or 287.

In certain embodiments, with respect to the compounds of formula (H-IC-1), Q is optionally substituted 9-membered heteroaryl, and the compound is Compound No. 282, 283, 284, 290, or 293.

In certain embodiments, with respect to the compounds of formula (H-IC-1), Q is optionally substituted quinolinyl or isoquinolinyl, and the compound is Compound No. 292, 311, 316, or 323.

In certain embodiments, with respect to the compounds of formula (H-IC), X is N, and the compound is Compound No. 78, 124, or 335.

In certain embodiments, with respect to the compounds of formula (H-IE-1), the compound is Compound No. 193 or 194. In certain embodiments, with respect to the compounds of formula (H-IE-1), the compound is Compound No. 193a, 193b, 194a, or 194b.

In certain embodiments, with respect to the compounds of formula (H-IF-1), the compound is Compound No. 199. In certain embodiments, with respect to the compounds of formula (H-IF-1), the compound is Compound No. 199a or 199b.

In certain embodiments, with respect to the compounds of formula (H-IIB-1), the compound is Compound No. 333.

In certain embodiments, with respect to the compounds of formula (H-IIC-1), the compound is Compound No. 242, 256, 264, 313, 321, 328, 330, or 334.

In certain embodiments, with respect to the compounds of formula (H-IID-1), the compound is Compound No. 95.

In certain embodiments, with respect to the compounds of formula (H-IA-1), (H-IB-1), (H—IC-1) or (H-ID-1) U is CR$^6$, and R$^6$ is CF$_3$, methyl, chloro, —CONHCH$_3$, —COOH, —COOCH$_3$, H, or fluoro; and R$^1$ is other than methyl.

In certain embodiments, with respect to the compounds of formula (H-IA), (H-IB), (H-IC) or (H-ID), (H-IA-1), (H-IB-1), (H-IC-1) or (H-ID-1), R$^7$ is H, halo, or C$_1$-C$_5$ alkyl substituted with halo. In one embodiment, R$^7$ is H, methyl, or CF$_3$.

In another aspect, provided is a compound of formula (J):

(J)

wherein:
R$^1$ is H; C$_1$-C$_5$ alkyl optionally substituted with 1 to 3 substituents independently selected from the group consisting of halo, hydroxyl, carboxyl, SO$_3$H, SR$^{1a}$, S(O)R$^{1a}$, $SO_2R^{1a}$ and perhaloalkyl; $C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{1a}$ to form a propylene (—$CH_2CH_2CH_2$—) moiety or a butylene (—$CH_2CH_2CH_2CH_2$—) moiety; or is taken together with $R^{4a}$ or $R^{5a}$, where present, to form an ethylene (—$CH_2CH_2$—) moiety or a propylene (—$CH_2CH_2CH_2$—) moiety;

$R^{1a}$ is H or optionally substituted $C_1$-$C_5$ alkyl;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—$CH_2CH_2CH_2$—) moiety or a butylene (—$CH_2CH_2CH_2CH_2$—) moiety; or is taken together with $R^{3a}$ to form an ethylene (—$CH_2CH_2$—) moiety or a propylene (—$CH_2CH_2CH_2$—) moiety; or is taken together with $R^{4a}$, where present, to form a methylene (—$CH_2$—) moiety or an ethylene (—$CH_2CH_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—$CH_2CH_2CH_2$—) moiety or a butylene (—$CH_2CH_2CH_2CH_2$—) moiety; or is taken together with $R^{2a}$ to form an ethylene (—$CH_2CH_2$—) moiety or a propylene (—$CH_2CH_2CH_2$—) moiety; or is taken together with $R^{5a}$, where present, to form a methylene (—$CH_2$—) moiety or an ethylene (—$CH_2CH_2$—) moiety;

$R^{4a}$ is H; optionally substituted $C_1$-$C_5$ alkyl; optionally substituted $C_2$-$C_5$ alkenyl; or optionally substituted aryl; or is taken together with $R^{3a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{2a}$ to form a methylene (—$CH_2$—) moiety or an ethylene (—$CH_2CH_2$—) moiety; or is taken together with $R^{5a}$, where present, to form a methylene (—$CH_2$—) moiety;

$R^{5a}$ is H; optionally substituted $C_1$-$C_5$ alkyl; optionally substituted $C_2$-$C_5$ alkenyl; or optionally substituted aryl; or is taken together with $R^{2a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{3a}$ to form a methylene (—$CH_2$—) moiety or an ethylene (—$CH_2CH_2$—) moiety; or is taken together with $R^{4a}$, where present, to form a methylene (—$CH_2$—) moiety;

each $R^{2b}$, $R^{3b}$, $R^{4b}$ and $R^{5b}$ is independently H, optionally substituted $C_1$-$C_5$ alkyl, optionally substituted $C_2$-$C_5$ alkenyl, or optionally substituted aryl;

each n and m is 1, or n is 0 and m is 1, or n is 1 and m is 0;

each $X^1$, $X^2$, X and U is independently N or $CR^6$;

each $R^6$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

Q is optionally substituted cycloalkyl, optionally substituted aryl, or optionally substituted heteroaryl.

In one embodiment, compounds of formula (J-IA), (J-IB), (J-IC) or (J-ID):

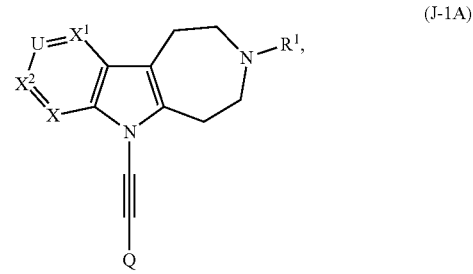

(J-1A)

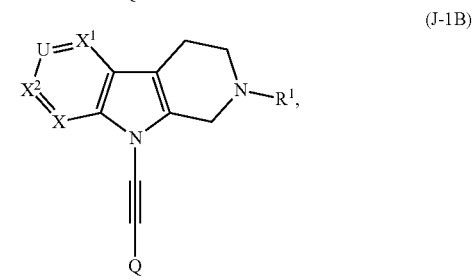

(J-1B)

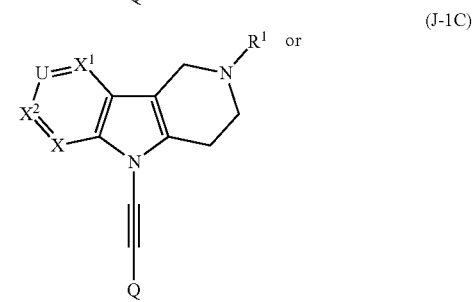

(J-1C)

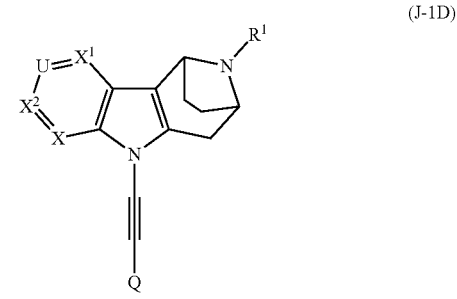

(J-1D)

or a salt, solvate or N-oxide thereof, wherein:

each $X^1$, $X^2$, X and U is independently N or $CR^6$;

$R^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

each $R^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

Q is aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)CH$_3$ and —C(O)NR$^{16}$R$^{17}$; and each R$^{16}$ and R$^{17}$ is independently H or optionally substituted $C_1$-$C_5$ alkyl.

In certain embodiments, with respect to the compounds of formula (J-IA), (J-IB), (J-IC) or (J-ID), each $X^1$, $X^2$ and X is independently CR$^6$; wherein each R$^6$ is independently halo, $C_1$-$C_5$-alkyl, halo $C_1$-$C_5$-alkyl, perhalo $C_1$-$C_5$-alkyl, or $C_1$-$C_5$-alkoxy. In certain embodiments, each $X^1$, $X^2$ and X is independently CR$^6$; wherein each R$^6$ is independently fluoro, chloro, methyl, ethyl, CF$_3$, or methoxy. In certain embodiments, U is CR$^6$, wherein R$^6$ is CF$_3$, methyl, chloro, CONHCH$_3$, COOH, COOCH$_3$, H, or fluoro; provided that R$^1$ is other than methyl.

In certain embodiments, with respect to the compounds of formula (J-IA), (J-IB), (J-IC) or (J-ID), X is CR$^6$, wherein R$^6$ is fluoro; and R$^1$ is other than methyl.

In one embodiment, compound is according to formula (J-IA-1), (J-IB-1), (J-IC-1) or (J-ID-1) are provided:

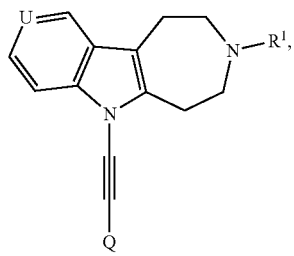

(J-IA-1)

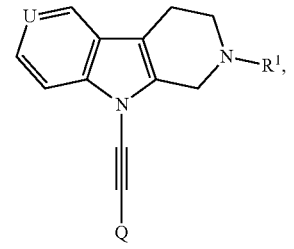

(J-IB-1)

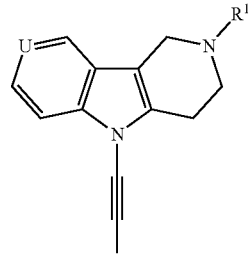

(J-IC-1)

or

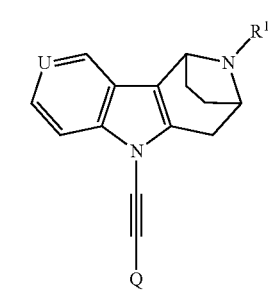

(J-ID-1)

or a salt, solvate or N-oxide thereof, wherein:

U is N or CR$^6$;

R$^1$ is H, $C_1$-$C_5$ alkyl optionally substituted with 1 to 3 substituents independently selected from halo, hydroxyl, carboxyl and perhaloalkyl, $C_3$-$C_8$ cycloalkyl optionally substituted with 1 to 3 substituents independently selected from halo, hydroxyl, carboxyl and perhaloalkyl, $C_2$-$C_5$ alkenyl optionally substituted with 1 to 3 substituents independently selected from halo, hydroxyl, carboxyl and perhaloalkyl, or —C(O)O—$C_1$-$C_5$ alkyl;

R$^6$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)C$_1$-$C_5$ alkyl;

Q is aryl or heteroaryl optionally substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, —NHC(O)CH$_3$ and —C(O)NR$^{16}$R$^{17}$; and each R$^{16}$ and R$^{17}$ is independently H or optionally substituted $C_1$-$C_5$ alkyl.

In another embodiment, the compound is of the formula (K-IA), (K-IB), (K-IC) or (K-ID):

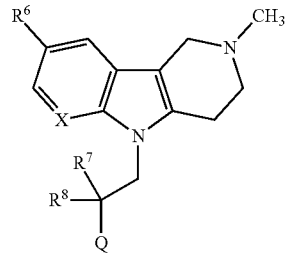

(K-IA)

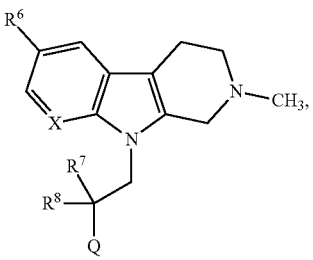

(K-IB)

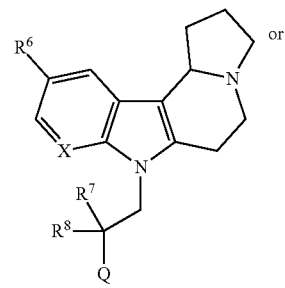

(K-IC)

or

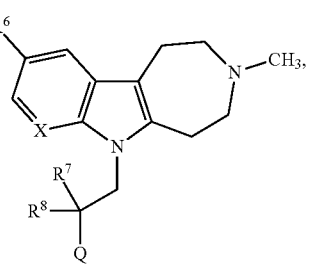

(K-ID)

or a salt, solvate or N-oxide thereof, wherein:

X is N or CH;

R$^6$ is $C_1$, CF$_3$, or methyl;

R⁷ is independently H or methyl;
R⁸ is H; azido; F; OH; NH₂; N(CH₃)H; N(CH₃)₂; NH-cyclopropyl; or NH-cyclobutyl; OC(O)N(CH₃)₂; or 3,3-dimethyl-2-hydroxybutyl; and
Q is unsubstituted 3-pyridyl; 3-pyridyl substituted with methyl, Cl, or CONH₂; unsubstituted 4-pyridyl; 4-pyridyl substituted with OH; unsubstituted pyrazinyl; unsubstituted imidazolyl; or unsubstituted triazolyl.

In certain embodiments, with respect to the compounds of formula (K-IA), (K-IB), (K-IC) or (K-ID); R⁷ is H, and R⁸ is OH. In one embodiment, the compound is Compound 3, 4, 13, 39, 41, 129, or 144 (Table I); or II-132, II-138, II-139, or II-140 (Table II).

In certain embodiments, with respect to the compounds of formula (K-IA), (K-IB), (K-IC) or (K-ID); R⁷ is methyl, and R⁸ is OH. In one embodiment, the compound is Compound 5, 14, 26, 29, 31, 148, 173, 174, or 176 (Table I); or II-148 (Table II).

In certain embodiments, with respect to the compounds of formula (K-IA), (K-IB), (K-IC) or (K-ID); R⁸ is NH₂, N(CH₃)H, N(CH₃)₂, NH-cyclopropyl, or NH-cyclobutyl. In one embodiment, the compound is Compound 27, 150, 151, or 154 (Table I); or II-4, II-7, II-13, or II-260 (Table II).

In certain embodiments, with respect to the compounds of formula (K-IA), (K-IB), (K-IC) or (K-ID); each R⁷ and R⁸ is H. In one embodiment, the compound is Compound 74, 134, or II-244 (Table I and II).

In certain embodiments, with respect to the compounds of formula (K-IA), (K-IB), (K-IC) or (K-ID); R⁷Me, and R⁸ is F. In one embodiment, the compound is Compound II-212 (Table II).

In certain embodiments, with respect to the compounds of formula (K-IA), (K-IB), (K-IC) or (K-ID); R⁸ is —OC(O)N(CH₃)₂. In one embodiment, the compound is Compound 141.

In certain embodiments, with respect to the compounds of formula (K-IA), (K-IB), (K-IC) or (K-ID); R⁷ is 3,3-dimethyl-2-hydroxybutyl. In one embodiment, the compound is Compound II-227 (Table II).

In another embodiment, the compound is of the formula (K-IE), or (K-IF):

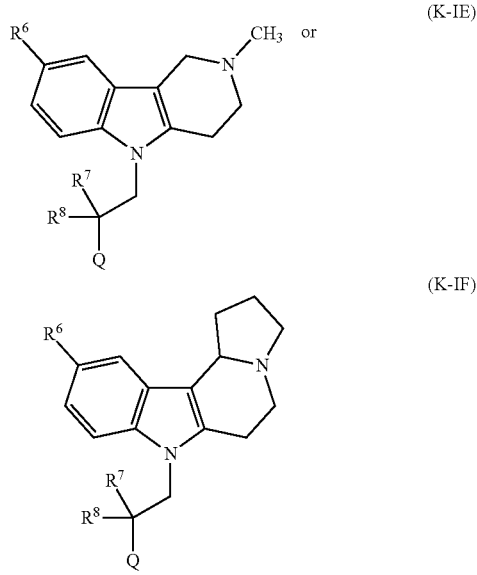

or a salt, solvate or N-oxide thereof, wherein:
R⁶ is Cl, or methyl;
R⁷ is H or methyl;
R⁸ is OH; N(CH₃)₂; or OC(O)-t-Bu; and
Q is phenyl substituted with F; unsubstituted 3-pyridyl; 3-pyridyl substituted with methyl; unsubstituted 4-pyridyl; or unsubstituted pyrazinyl.

In certain embodiments, with respect to the compounds of formula (K-IE), or (K-IF); R⁷ is H, and R⁸ is OH. In one embodiment, the compound is Compound 129 (Table I); or II-131 (Table II).

In certain embodiments, with respect to the compounds of formula (K-IE), or (K-IF); R⁷ is methyl, and R⁸ is OH. In one embodiment, the compound is II-121, II-127, II-128, or II-130 (Table II).

In certain embodiments, with respect to the compounds of formula (K-IE), or (K-IF), R⁸ is N(CH₃)₂. In one embodiment, the compound is Compound II-6 (Table II).

In certain embodiments, with respect to the compounds of formula (K-IE), or (K-IF); R⁸ is OC(O)-t-Bu. In one embodiment, the compound is Compound 130 (Table I).

In one embodiment, the compound is Compound II-123 (Table II).

In one embodiment, the compound is Compound 325 (Table I).

In certain embodiments, with respect to the compounds of formula (A-IIIE-2), (A-IIIE-6), (A-IIIF-2), (A-IIIG-2), (A-IIIH-2), (C-IA-4), or (C-IA-5), and R¹ is methyl.

In certain embodiments, with respect to the compounds of formula (A-IIIE-2), (A-IIIE-6), (A-IIIF-2), (A-IIIG-2), (A-IIIH-2), (C-IA-4), or (C-IA-5), and R⁶ is methyl, chloro, or trifluoromethyl.

In certain embodiments, with respect to the compounds of formula (A-IIIE-2), (A-IIIE-6), (A-IIIF-2), (A-IIIG-2), (A-IIIH-2), (C-IA-4), or (C-IA-5), and R⁷ is H, methyl, cyclopropyl, cyclobutyl, or 3,3-dimethyl-2-hydroxybutyl.

In certain embodiments, with respect to the compounds of formula (A-IIIE-2), (A-IIIE-6), (A-IIIF-2), (A-IIIG-2), (A-IIIH-2), (C-IA-4), or (C-IA-5), and R⁸ is H, F, OH, —N(CH₃)₂, or —OC(O)N(CH₃)₂.

In certain embodiments, with respect to the compounds of formula (A-IIIE-2), (A-IIIF-2), (A-IIIG-2), (A-IIIH-2), (C-IA-4), or (C-IA-5), and Y² is N. In one embodiment, Y² is N, and one of Y¹, Y³, or Y⁴ is methyl.

In certain embodiments, with respect to the compounds of formula (A-IIIE-2), (A-IIIF-2), (A-IIIG-2), (A-IIIH-2), (C-IA-4), or (C-IA-5), and Y³ is N. In one embodiment, Y³ is N, and one of Y¹, Y², or Y⁴ is methyl.

In certain embodiments, with respect to the compounds of formula (A-IIIE-2), (A-IIIF-2), (A-IIIG-2), (A-IIIH-2), (C-IA-4), or (C-IA-5), and each of Y¹ and Y⁴ is N.

In certain embodiments, with respect to the compounds of formula (A-IIIE-6), and Q is triazolyl, or imidazolyl.

In certain embodiments, with respect to the compounds of formula (A-IIIE-2), (A-IIIE-6), (A-IIIF-2), (A-IIIG-2), (A-IIIH-2), (C-IA-4), or (C-IA-5), R⁷ is H, R⁸ is OH, and the compound is Compound No. 3, 4, 13, 39, 41, 127, 144, II-132, II-138, II-139, or II-140.

In certain embodiments, with respect to the compounds of formula (I), (A-IIIE-2), (A-IIIE-6), (A-IIIF-2), (A-IIIG-2), (A-IIIH-2), (C-IA-4), or (C-IA-5), R⁷ is methyl, R⁸ is OH, and the compound is Compound No. 5, 14, 26, 29, 31, 148, 173, 174, 176, II-148, II-151, II-152, or II-220.

In certain embodiments, with respect to the compounds of formula (I), (A-IIIE-2), (A-IIIE-6), (A-IIIF-2), (A-IIIG-2), (A-IIIH-2), (C-IA-4), or (C-IA-5), R⁸ is NH₂, N(CH₃)H, N(CH₃)₂, NH-cyclopropyl, or NH-cyclobutyl, and the compound is Compound No. 27, 150, 151, 154, II-4, II-7, 11-13, or II-260.

In certain embodiments, with respect to the compounds of formula (I), (A-IIIE-2), (A-IIIE-6), (A-IIIF-2), (A-IIIG-2), (A-IIIH-2), (C-IA-4), or (C-IA-5), each R⁷ and R⁸ is H, and the compound is Compound No. 74, 134, or II-244.

In certain embodiments, with respect to the compounds of formula (I), (A-IIIE-2), (A-IIIE-6), (A-IIIF-2), (A-IIIG-2), (A-IIIH-2), (C-IA-4), or (C-IA-5), $R^7$Me, and $R^8$ is F, and the compound is Compound No. II-212.

In certain embodiments, with respect to the compounds of formula (I), (A-IIIE-2), (A-IIIE-6), (A-IIIF-2), (A-IIIG-2), (A-IIIH-2), (C-IA-4), or (C-IA-5), $R^8$ is —OC(O)N(CH$_3$)$_2$, and the compound is Compound No. 141.

In certain embodiments, with respect to the compounds of formula (A-IIIE-2), (A-IIIE-6), (A-IIIF-2), (A-IIIG-2), (A-IIIH-2), (C-IA-4), or (C-IA-5), and $R^7$ is 3,3-dimethyl-2-hydroxybutyl, and the compound is Compound No. II-227.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), Q is optionally substituted phenyl.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), Q is phenyl substituted with $C_1$-$C_5$ alkyl, halo, halo $C_1$-$C_5$ alkyl, or $C_1$-$C_5$ alkoxy.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), Q is phenyl substituted with methyl, ethyl, F, Cl, OCH$_3$, or CF$_3$.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), Q is optionally substituted pyridyl, or optionally substituted pyrimidinyl.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (H-IIB, (J-IC) or (J-ID), (J-IA-1), (J-IB-1), (J-IC-1) or (J-ID-1), Q is pyridyl substituted with $C_1$-$C_5$ alkyl, halo, halo or $C_1$-$C_5$ alkyl.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or -1), Q is pyridyl substituted with methyl, ethyl, F, Cl, or CF$_3$.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), $R^1$ is H; unsubstituted $C_1$-$C_5$alkyl; $C_1$-$C_5$ alkyl substituted with OH or SO$_3$H; cycloalkyl; or $C_2$-$C_5$ alkenyl.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), $R^1$ is H; unsubstituted $C_1$-$C_5$alkyl; $C_1$-$C_5$ alkyl substituted with up to three halogen atoms; cycloalkyl; or $C_2$-$C_5$ alkenyl.

In one embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), $R^1$ is methyl, ethyl, hydroxyethyl, hydroxypropyl, hydroxybutyl, cyclobutyl, cyclopropyl, CF$_3$, CH$_2$CF$_3$ or CH$_2$CH$_2$—SO$_3$H.

In one particular embodiment, with respect to the compounds of formula (A-IB), (A-IC), (A-ID), (A-IE), (A-VIIIA), (A-VIIIB), (C-VA), (C-VB), (D-IIIA), (D-IIIB), (H-IA), (H-IB), (H-IC) or (H-ID), (H-IA-1), (H-IB-1), (H-IC-1), (H-ID-1), (J-IA), (J-IB), (J-IC) or (J-ID), (J-IA-1), (J-IB-1), (J-IC-1) or (J-ID-1), $R^1$ is methyl.

In one embodiment, with respect to the compounds of formula (I); $R^{4a}$ is F. In another embodiment, each $R^{4a}$ and $R^{4b}$ is F. In a particular embodiment, the compound is Compound II-267 or II-280.

In certain embodiments, with respect to the compounds of formula (A-IIIE-2); when $R^1$ is methyl, $R^{4a}$ is F, $R^{4b}$ is H, $R^6$ is Cl, each $R^7$ and $R^8$ is H, and $Y^3$ is C—CF$_3$; then $Y^2$ is other than N.

In certain embodiments, with respect to the compounds of formula (A-IIIE-2); when $R^1$ is methyl, each $R^{4a}$ and $R^{4b}$ is F, H, $R^6$ is methyl, each $R^7$ and $R^8$ is H, and $Y^3$ is C—CH$_3$; then $Y^2$ is other than N.

In certain embodiments, with respect to the compounds of formula (A-IIIE-2); when $R^1$ is methyl, each $R^{4a}$ and $R^{4b}$ is F, H, $R^6$ is Cl or methyl, each $R^7$ and $R^8$ is H, and $Y^3$ is C—F; then $Y^2$ is other than CH.

In one embodiment, the invention relates to Compound No. 87, and uses thereof. In another embodiment, the invention relates to Compound No. 88, and uses thereof. In yet another embodiment, the invention relates to Compound No. 120, and uses thereof. In a further embodiment, the invention relates to Compound No. 324, and uses thereof.

In one embodiment, the invention relates to Compound No. 338, and uses thereof. In another embodiment, the invention relates to Compound No. II-1, and uses thereof.

In one embodiment, the invention relates to Compounds 25a, 25b, 27a, 27b, 54a and 54b, and uses thereof. In another embodiment, the invention relates to Compounds 25, 25a, 25b, 27, 27a, 27b, 54a, 54b, 130a, 130b, 141, 147 and 149-160, and uses thereof.

In another embodiment, the invention relates to Compounds 3a-5a, 3b-5b, 6,7a-9a, 7b-9b, 8-9, 39, 51, 55, 63-68, 70-73, 77-82, 91-92, 10a-31a, 10b-31b, 37c-37d, 39a-59a, 39b-59b, 69a-b, 74a-b, 75a-d and 76a-d, and uses thereof.

In another embodiment, the invention relates to Compounds 6, 9-12, 14, 16-21, 23-25, 27-28, 39-40, 42, 44-45, 48-49, 51-59, 63-72, 75-82, 108-122, 124-126, 128-131, 133-176; 1a-25a, 27a-31a, 36a-45a, 48a-49a, 51a-59a, 62a-67a, 69a-73a, 75a-76a, 81a-82a, 93a, 95a-98a, 102a, 127a-128a, 130a-131a, 133a, 135a-136a, 138a-179a; 1b-25b, 27b-31b, 36b-45b, 48b-49b, 51b-59b, 62b-67b, 69b-73b, 75b-76b, 81b-82b, 93b, 95b-98b, 102b, 127b-128b, 130b-131b, 133b, 135b-136b, 138b-179b; 36c-h, 37c-d, 38c-h, 70c-d, 73c-h, 75c-d, 76c-d, 95c-d, 97c-d, 127c-d, 148c-d, 155c-h, 161c-d, 162c-d, 163c-d, 164c-d, 168c-d, 176c-d and 177c-d, and uses thereof.

In another embodiment, the invention relates to Compounds 3, 3b, 4a, 5b and 39a. In another embodiment, the invention relates to Compounds 3, 3a, 3b, 5, 5a, 5b, 13b, 14a, 15b, 26a, 26b, 27a, 29a, 31a, 74a, 93a, 127a, 130a, 130b, 133b, 134b, 137a, 139a, 141, 144b, 147, 150a and 154, and uses thereof.

In another embodiment, the invention relates to Compound Nos. 3, 39, 4, 5, 13, 14, 41, 74, 26, 27, 29, 31, 127, 129, 134, 144, 148, 173, 174, 150, 176, IV-210, 151, II-4, II-132, 141, 154, II-135, II-138, II-139, II-140, V-22, II-244, II-7, II-146, II-151, II-152, II-227, II-220, II-148, II-13, II-212, II-260 and II-260b, and uses thereof. In another embodiment, the invention relates to Compound Nos. 3a, 3b, 39a, 4a, 5b, 13b, 14a, 41a, 74a, 26a, 26b, 27a, 29b, 31a, 127a, 129d, 134b, 144b, 148, 173a, 174a, 150a, 176a, IV-210a, 151a, II-4b, II-132b, 148b, 141b, 154b, II-135b, II-138, II-139, II-140, V-22, II-244a, II-7, II-146a, II-151b, II-152a, II-227c, II-220, II-148a, II-13a, II-212a, II-260a and II-260b, and uses thereof.

In one embodiment, the invention relates to Compound Nos. 3a, 3b, 4a, 4b, 5a, 5b, 6, 7a, 7b, 8a, 8b, 9, 9a, 9b, 10, 10a, 10b, 11, 11a, 11b, 12, 12a, 12b, 13a, 13b, 14, 14a, 14b, 15a, 15b, 16, 16a, 16b, 17, 17a, 17b, 18, 18a, 18b, 19, 19a, 19b, 20, 20a, 20b, 21, 21a, 21b, 22, 22a, 22b, 23, 23a, 23b, 24, 24a, 24b, 25, 25a, 25b, 26, 26a, 26b, 26c, 26d, 27, 27a, 27b, 28, 28a, 28b, 29a, 29b, 30a, 30b, 31a, 31b, 36, 37, 37c, 37d, 39, 39a, 39b, 40, 40a, 40b, 41, 41a, 41b, 42, 42a, 42b, 43a, 43b, 44, 44a, 44b, 45, 45a, 45b, 47a, 47b, 47c, 47d, 48a, 48b, 49a, 49b, 51, 51a, 51b, 52, 52a, 52b, 53, 53a, 53b, 54, 54, 54a, 54b, 55, 55a, 55b, 56, 56a, 56b, 57, 57a, 57b, 58, 58a, 58b, 59, 59a, 59b, 63, 63a, 63b, 64, 65, 66, 67, 68, 69, 69a, 69b, 70, 71, 72, 75, 75a, 75b, 75c, 75d, 76, 76a, 76b, 76c, 76d, 77, 78, 79, 80, 81, 82, 90a, 90b, 108, 109, 110, 111, 112, 113, 114, 115, 116, 117, 118, 119, 120, 121, 122, 124, 125, 126, 127, 127a, 127b, 128a, 128b, 129a, 129b, 129c, 129d, 130a, 130b, 131a, 131b, 133a, 133b, 134a, 134b, 135a, 135b, 136a, 136b, 137a, 137b, 138a, 138b, 139, 139a, 139b, 140, 140a, 140b, 141, 141a, 141b, 142, 142a, 142b, 143, 143a, 143b, 144, 144a, 144b, 145, 146, 146a, 146b, 147, 147a, 147b, 148, 148a, 148b, 148c, 148d, 149, 149a, 149b, 150, 150a, 150b, 151, 151a, 151b, 152, 152a, 152b, 153, 154, 154a, 154b, 155, 155a, 155b, 156, 157, 158, 159, 159a, 159b, 160, 160a, 160b, 168, 169, 170, 171, 172a, 172b, 173, 173a, 173b, 174, 174a, 174b, 175, 175a, 175b, 176, 176a, 176b, 177, 178, 179, 189, 190, 191, 193, 193a, 193b, 194a, 194b, 196, 196a, 196b, 197, 197a, 197b, 198, 198a, 198b, 198c, 198d, 199a, 199b, 203a, 203b, 211a, 211b, 221a, 221b, 223a, 223b, 225a, 225b, 231a, 231b, 253a, 253b, 255a, 255b, 257a, 257b, 269, 270, 271, 272a, 272b, 273, 274, 274a, 274b, 275, 276, 277, 278, 279, 280, 281, 282, 283, 284, 285, 286, 287, 288a, 288b, 289a, 289b, 290, 291, 292, 293, 294, 295, 296, 297, 298, 299, 300, 301, 302, 303, 304, 305, 306, 307, 308, 309, 310, 311, 312, 313, 314, 314a, 314b, 315, 316, 317, 318, 319, 320, 321, 322, 323, 324, 325, 326, 327, 328, 329, 330, 331, 332, 333, 334, 335, 336, 336a, 336b, 338, 338a, 338b, 339a, 339b, II-1a, II-1b, II-2, II-3, II-4-a, II-4b, II-5, II-6a, II-6b, II-7, II-7a, II-7b, II-8, II-9, II-10, II-11, II-11a, II-11b, II-12, II-12a, II-12b, II-13, II-13a, II-13b, II-14a, II-14b, II-15a, II-15b, II-16a, II-16b, II-17, II-18, II-19, II-39, II-40, II-49a, II-49b, II-57a, II-57b, II-58, II-59, II-60, II-61, II-62, II-63, II-64, II-65, II-67, II-68, II-70, II-71, II-75, II-76, II-77, II-78, II-80, II-81, II-82, II-83, II-84, II-88, II-89, II-90, II-91, II-92, II-93a, II-93b, II-94a, II-94b, II-95a, II-95b, II-96, II-97, II-98a, II-98b, II-99a, II-99b, II-100a, II-100b, II-101, II-102, II-103, II-104, II-105, II-106a, II-106b, II-108a, II-108b, II-109a, II-109b, II-110, II-111, II-112a, II-112b, II-113a, II-113b, II-114a, II-114b, II-115a, II-115b, II-115c, II-115d, II-116, II-117, II-118a, II-118b, II-119, II-120a, II-120b, II-121a, II-121b, II-122, II-123a, II-123b, II-124a, II-124b, II-125a, II-125b, II-125c, II-125d, II-126, II-127a, II-127b, II-128a, II-128b, II-129, II-130, II-130a, II-130b, II-131, II-132a, II-132b, II-133, II-134a, II-134b, II-135a, II-135b, II-136a, II-136b, II-137, II-138, II-139, II-140, II-141, II-142, II-143, II-144, II-145, II-146a, II-146b, II-146c, II-146d, II-147a, II-147b, II-147c, II-147d, II-148, II-148a, II-148b, II-149a, II-149b, II-149c, II-149d, II-150, II-151a, II-151b, II-152a, II-152b, II-152c, II-152d, II-153, II-154, II-209, II-210, II-211, II-212, II-212a, II-212b, II-213, II-215, II-220, II-221, II-222, II-223, II-224, II-224a, II-224b, II-225, II-226, II-227a, II-227b, II-227c, II-227d, II-229, II-230, II-231, II-232, II-240, II-241, II-242, II-243, II-244a, II-244b, II-245, II-246, II-247, II-248, II-249, II-250, II-251, II-252, II-253, II-255a, II-255b, II-256, II-257, II-258, II-259, II-260a, II-260b, II-261, II-261a, II-261b, II-262, II-263, II-264, II-265a, II-265b, II-266, II-267, II-268, II-269, II-270, II-271, II-272, II-273, II-274, II-275, II-276, II-277, II-278, II-279, II-280, II-281, II-282a, II-282b, II-282c, II-282d, II-283, II-284, II-285, II-286, II-287, II-288, II-289, II-290a, II-290b, II-291a, II-291b, II-291c, II-291d, II-292, II-293a, II-293b, II-293c, II-293d, II-294a, II-294b, II-294c, II-294d, II-295, II-296a, II-296b, II-297, II-298, II-299, IV-8, IV-8a, IV-8b, IV-93a, IV-93b, IV-209a, IV-209b, IV-209c, IV-209d, IV-210a, IV-210b, IV-210c, IV-210d, V-1, V-1a, V-1b, V-2, V-2a, V-2b, V-3, V-3a, V-3b, V-14, V-14a, V-14b, V-15, V-15a, V-15b, V-15c, V-15d, V-18, V-18a, V-18b, V-18c, V-18d, V-21, V-21a, V-21b, V-22, V-22a, V-22b, V-23, V-23a and V-23b, and uses thereof.

In another embodiment, the invention relates to Compounds described in Table 1, and uses thereof. In another embodiment, the invention relates to one or more of the Compounds described in Table 2, and uses thereof.

In another embodiment, the invention relates to one or more of the Compounds described in Table 3, and uses thereof.

In another embodiment, the invention relates to one or more of the Compounds described in Table 4, and uses thereof.

In another embodiment, the invention relates to one or more of the Compounds described in Table 5, and uses thereof.

In one embodiment, the invention embraces compounds detailed herein provided that the compound is other than dimebon and metabolites of dimebon. In another embodiment, the invention embraces dimebon or a salt thereof for uses detailed herein. In another embodiment, the invention embraces a dimebon metabolite or salt thereof for uses detailed herein, such as use in therapy, e.g., to (i) reduce blood pressure and/or (ii) promote renal blood flow and/or (iii) decrease or inhibit sodium reabsorption.

The embodiments and variations described herein are suitable for compounds of any formulae detailed herein, where applicable.

Representative examples of compounds detailed herein, including intermediates and final compounds according to the invention are depicted in the tables below. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the invention embraces all salts and solvates of the compounds depicted here, as well as the non-salt and non-solvate form of the compound, as is well understood by the skilled artisan. In some embodiments, the salts of the compounds of the invention are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. For example, when a 2-hydroxypyridyl moiety is depicted, the corresponding 2-pyridone tautomer is also intended. The tautomeric forms specifically depicted may or may not be the predominant forms in solution or when used according to the methods described herein.

The invention also includes any or all of the stereochemical forms, including any enantiomeric or diasteriomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

Pharmaceutical compositions of any of the compounds detailed herein are embraced by this invention. Thus, the invention includes pharmaceutical compositions comprising a compound of the invention or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions according to the invention may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. In one variation, "substantially pure" intends a composition that contains no more than 35% impurity, wherein the impurity denotes a compound other than the compound comprising the majority of the composition or a salt thereof. Taking compound 1 as an example, a composition of substantially pure compound 1 intends a composition that contains no more than 35% impurity, wherein the impurity denotes a compound other than compound 1 or a salt thereof. In one variation, a composition of substantially pure compound or a salt thereof is provided wherein the composition contains no more than 25% impurity. In another variation, a composition of substantially pure compound or a salt thereof is provided wherein the composition contains or no more than 20% impurity. In still another variation, a composition of substantially pure compound or a salt thereof is provided wherein the composition contains or no more than 10% impurity. In a further variation, a composition of substantially pure compound or a salt thereof is provided wherein the composition contains or no more than 5% impurity. In another variation, a composition of substantially pure compound or a salt thereof is provided wherein the composition contains or no more than 3% impurity. In still another variation, a composition of substantially pure compound or a salt thereof is provided wherein the composition contains or no more than 1% impurity. In a further variation, a composition of substantially pure compound or a salt thereof is provided wherein the composition contains or no more than 0.5% impurity. In yet other variations, a composition of substantially pure compound means that the composition contains no more than 15% or preferably no more than 10% or more preferably no more than 5% or even more preferably no more than 3% and most preferably no more than 1% impurity, which impurity may be the compound in a different stereochemical form. For instance, a composition of substantially pure (S) compound means that the composition contains no more than 15% or no more than 10% or no more than 5% or no more than 3% or no more than 1% of the (R) form of the compound.

In one variation, the compounds herein are synthetic compounds prepared for administration to an individual. In another variation, compositions are provided containing a compound in substantially pure form. In another variation, the invention embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

Kits comprising a compound of the invention, or a salt or solvate thereof, and suitable packaging are provided. In one embodiment, a kit further comprises instructions for use. In one aspect, a kit comprises a compound of the invention, or a salt or solvate thereof, and instructions for use of the compounds in the treatment of a disease or condition for which a reduction in blood pressure and/or promoting renal blood flow and/or inhibiting or decreasing sodium reabsorption is expected to be or is beneficial.

Articles of manufacture comprising a compound of the invention, or a salt or solvate thereof, in a suitable container are provided. The container may be a vial, jar, ampoule, preloaded syringe, i.v. bag, and the like.

In one aspect, a compounds detailed herein as provided herein exhibits the ability to cross the blood-brain barrier. In another aspect, a compounds detailed herein as provided herein is not able to cross the blood-brain barrier. In one aspect, a compounds detailed herein as provided herein exerts its therapeutic effect in the brain only. In one aspect, a compounds detailed herein as provided herein exerts its therapeutic effect in the periphery only. In one aspect, a compounds detailed herein as provided herein exerts its therapeutic effect both in the brain and peripherally. In some embodiments, the adrenergic receptor $\alpha_{2B}$ antagonist is a selective adrenergic receptor $\alpha_{2B}$ antagonist. In some embodiments, the adrenergic receptor $\alpha_{2B}$ antagonist also exhibits adrenergic receptor $\alpha_{2A}$ antagonist and/or inverse agonist activity.

Blood brain barrier permeability can be measured in rodents or dog by administering the compound orally or intravenously, recovering a blood and brain tissue sample at different time points and comparing how much compound is in each sample. Blood fraction is typically processed to plasma for determination of compound content. Brain exposure can be described from the ratio of brain to plasma levels of drug. In one varioation, a compound that poorly crosses the blood brain barrier has a brain to plasma ratio of compound of about 0.1 or less. In another variation, the compound has a brain to plasma ratio of about 0.2 or less, about 0.3 or less, about 0.4 or less, about 0.5 or less, about 0.8 or less, or about 1.0 or less.

Preferably, the compounds detailed herein are orally bioavailable. However, the compounds may also be formulated for parenteral (e.g., intravenous) administration. In some settings, parenteral administration of an adrenergic receptor $\alpha_{2B}$ antagonists (e.g., selective adrenergic receptor $\alpha_{2B}$ antagonist) may be desired. For example, intra-renal delivery may offer treatment options for acute and chronic renal failure, end stage renal failure and acute decompensated congestive heart failure. Parenteral formulation may be preferred in the treatment of hypertensive urgency and emergency. In some embodiments, the adrenergic receptor $\alpha_{2B}$ antagonist is a selective adrenergic receptor $\alpha_{2B}$ antagonist. In some embodiments, the adrenergic receptor $\alpha_{2B}$ antagonist also exhibits adrenergic receptor $\alpha_{2A}$ antagonist and/or inverse agonist activity.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., reducing the blood pressure of an individual, promoting renal blood flow and/or decreasing or inhibiting sodium reabsorption.

Methods as provided herein may comprise administering to an individual a pharmacological composition that contains an effective amount of a compound and a pharmaceutically acceptable carrier. The effective amount of the compound may in one aspect be a dose of between about 0.01 and about 100 mg.

The compound may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein can be used in the preparation of a formulation, such as a pharmaceutical formulation, by combining the compound or compounds as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in *Remington's Pharmaceutical Sciences*, Mack Publishing Company, Philadelphia, Pa., 20th ed. (2000), which is incorporated herein by reference.

Compounds as described herein may be administered to individuals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

The compound may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

Compositions comprising a compound provided herein are also described. In one variation, the composition comprises a compound and a pharmaceutically acceptable carrier or excipient. In another variation, a composition of substantially pure compound is provided.

The invention further provides kits for carrying out the methods of the invention, which comprises one or more compounds described herein or a pharmacological composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for any one or more of the following uses: treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention also provides compositions (including pharmacological compositions) as described herein for the use in treating, preventing, and/or delaying the onset and/or development of hypertension and/or a disease or condition which is responsive, or expected to be responsive, to (i) a reduction in an individual's blood pressure and/or (ii) an increase in renal blood flow and/or (iii) a decrease or inhibition of sodium reabsorption and other methods described herein. In certain embodiments, the composition comprises a pharmaceutical formulation which is present in a unit dosage form. As used herein, the term "unit dosage form" refers to a formulation that contains a predetermined dose of a compound as disclosed herein and optionally a second pharmaceutically active compound useful for treatment of a disease or condition detailed herein (e.g., hypertension).

For compounds bearing one or more chiral centers, each unique stereoisomer has a compound number bearing a suffix "a", "b", etc. As examples, racemic compound V-1, bearing one chiral center, can be resolved into its individual enantiomers V-1a and V-1b.

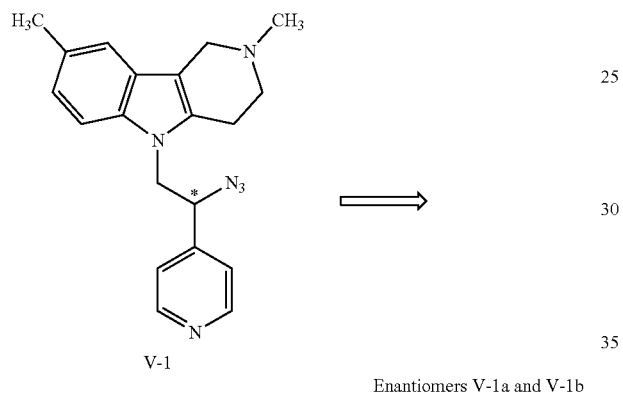

Enantiomers V-1a and V-1b

\* = chiral center

Similarly, racemic compound V-4, bearing two chiral centers, can be resolved into its individual diastereomers V-4a, V-4b, V-4c and V-4d.

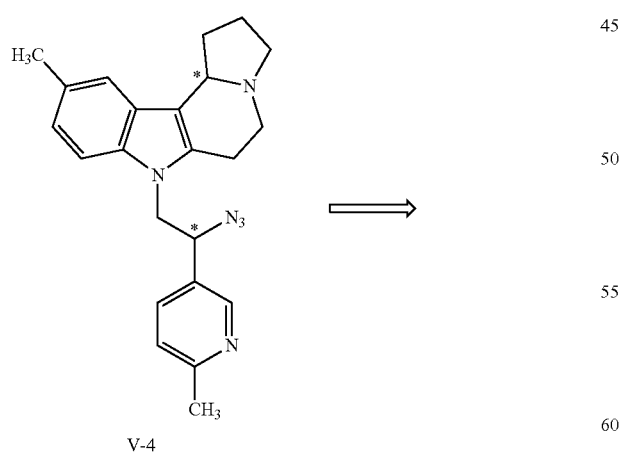

Diastereomers V-4a, V-4b, V-4c and V-4d

\* = chiral center

Representative compounds of the invention are shown in Tables 1-5.

TABLE 1

Representative Compounds of the Invention

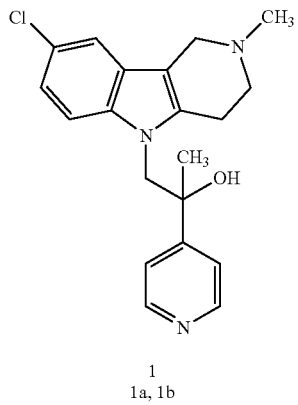

1
1a, 1b

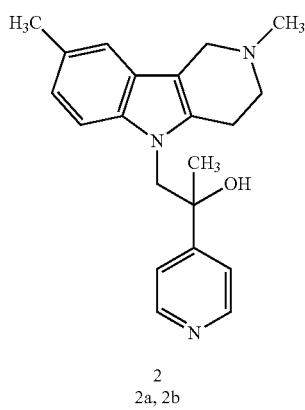

2
2a, 2b

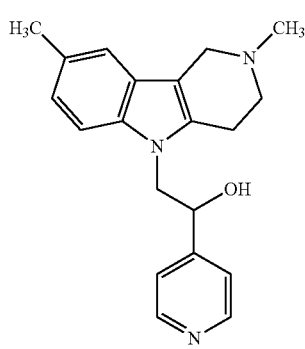

3
3a, 3b

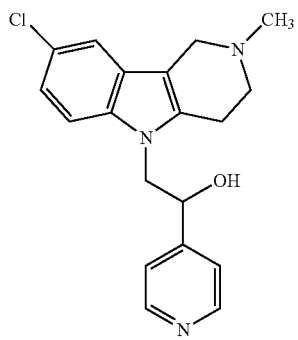 [SMILES: CN1CCc2c(c3cc(Cl)ccc3n2CC(O)c2ccncc2)C1]

4
4a, 4b

TABLE 1-continued

Representative Compounds of the Invention 5
5a, 5b 6
6a, 6b 7
7a, 7b 8
8a, 8b 9
9a, 9b 10
10a, 10b 11
11a, 11b 12
12a, 12b TABLE 1-continued
Representative Compounds of the Invention
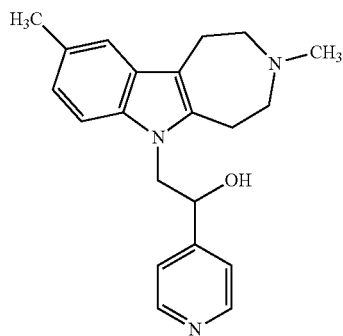
13
13a, 13b
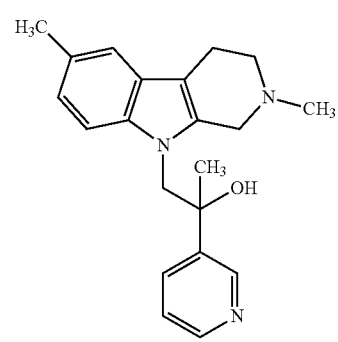
14
14a, 14b
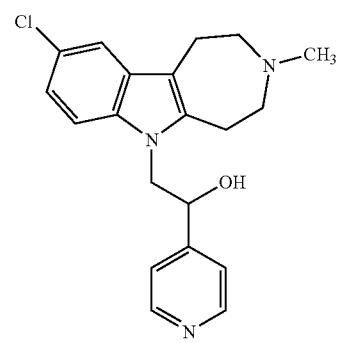 [SMILES: CN1CCc2c(n(CC(O)c3ccncc3)c3ccc(Cl)cc23)CC1]
15
15a, 15b
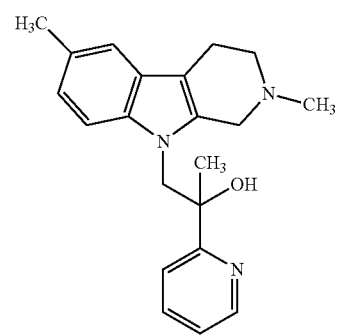
16
16a, 16b
TABLE 1-continued
Representative Compounds of the Invention
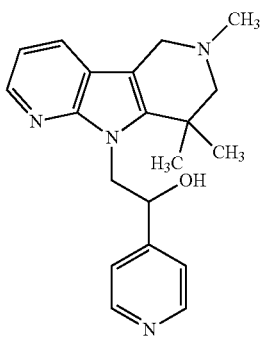 [SMILES: CN1Cc2c(n(CC(O)c3ccncc3)c3ncccc23)C(C)(C)C1]
17
17a, 17b
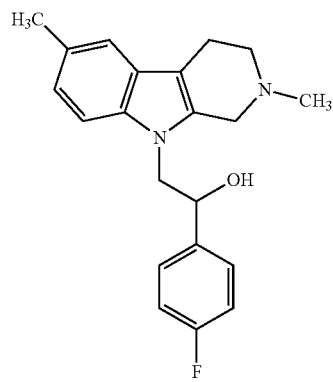
18
18a, 18b
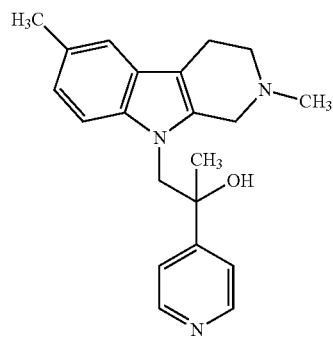
19
19a, 19b TABLE 1-continued Representative Compounds of the Invention 20
20a, 20b 21
21a, 21b 22
22a, 22b 23
23a, 23b 24
24a, 24b 25
25a, 25b, 25c, 25d 26
26a, 26b, 26c, 26d 27
27a, 27b TABLE 1-continued
Representative Compounds of the Invention
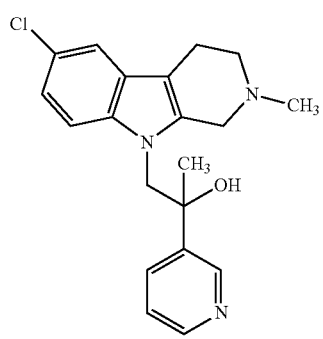 [SMILES: CN1CCc2c(n(CC(C)(O)c3cccnc3)c3ccc(Cl)cc23)C1]
28
28a, 28b
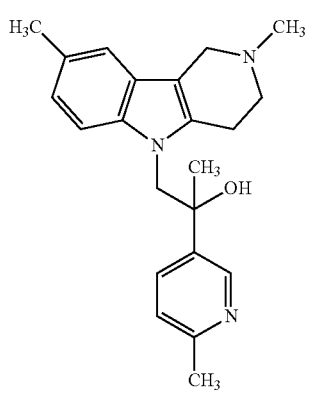
29
29a, 29b
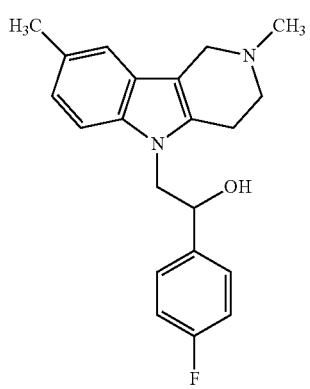
30
30a, 30b
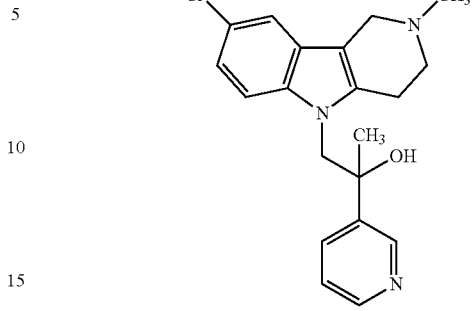
31
31a, 31b
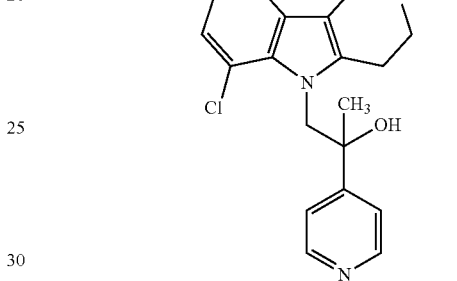
32
32a, 32b
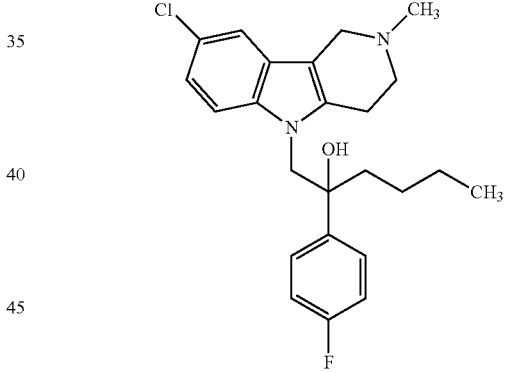
33
33a, 33b
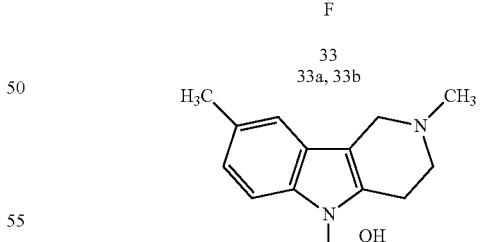
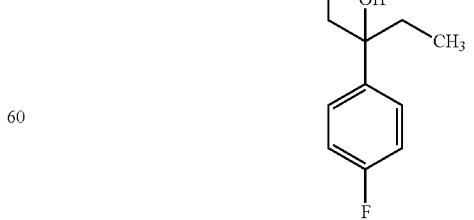
34
34a, 34b TABLE 1-continued
Representative Compounds of the Invention
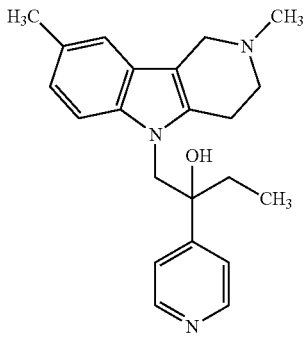
35
35a, 35b
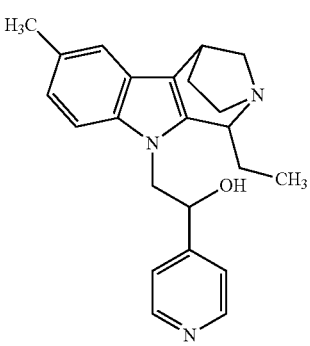 [SMILES: CCC1c2c(c3cc(C)ccc3n2CC(O)c2ccncc2)C2CCN1C2]
36
36a, 36b, 36c, 36d
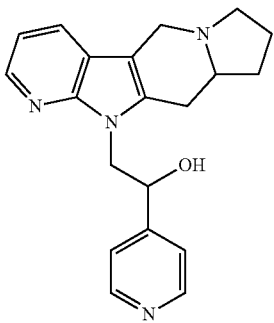 [SMILES: OC(Cn1c2c(c3cccnc31)CN1CCCC1C2)c1ccncc1]
37
37a, 37b, 37c, 37d
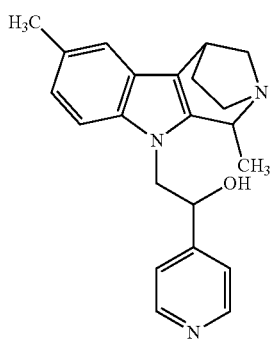 [SMILES: Cc1ccc2c(c1)c1c(n2CC(O)c2ccncc2)C(C)N2CCC1C2]
38
38a, 38b, 38c, 38d, 38e,
38f, 38g, 38h
TABLE 1-continued
Representative Compounds of the Invention
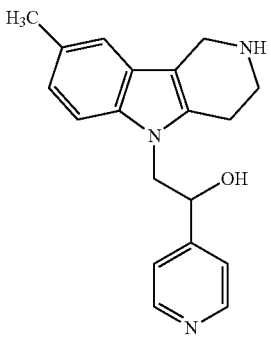 [SMILES: Cc1ccc2c(c1)c1c(n2CC(O)c2ccncc2)CCNC1]
39
39a, 39b
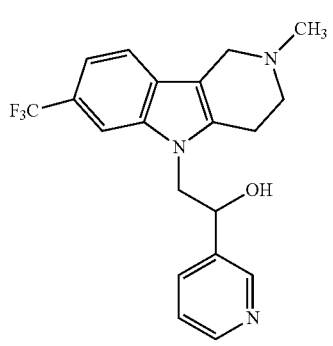 [SMILES: CN1CCc2c(c3ccc(C(F)(F)F)cc3n2CC(O)c2cccnc2)C1]
40
40a, 40b
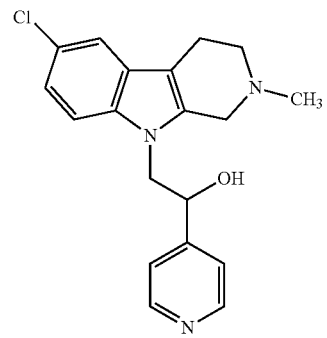 [SMILES: CN1CCc2c(n(CC(O)c3ccncc3)c3ccc(Cl)cc23)C1]
41
41a, 41b
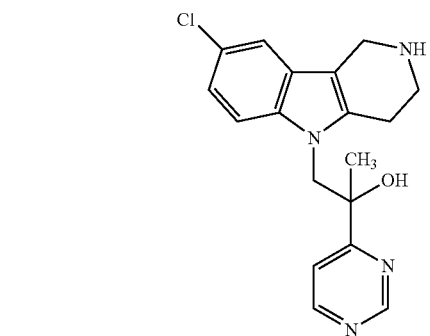 [SMILES: CC(O)(Cn1c2c(c3cc(Cl)ccc31)CNCC2)c1ccncn1]
42
42a, 42b TABLE 1-continued
Representative Compounds of the Invention
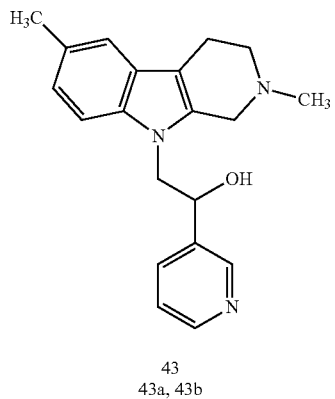
43
43a, 43b
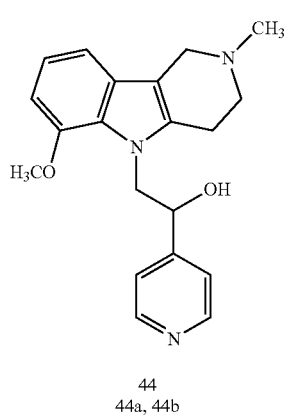
44
44a, 44b
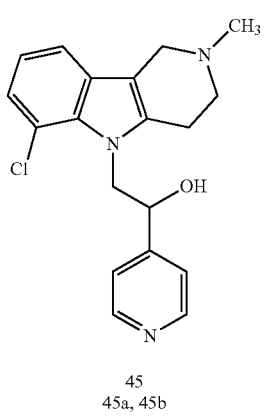
45
45a, 45b
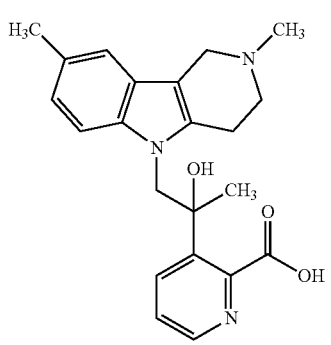 [SMILES: Cc1ccc2c(c1)c1c(n2CC(C)(O)c2cccnc2C(=O)O)CCN(C)C1]
46
46a, 46b
TABLE 1-continued
Representative Compounds of the Invention
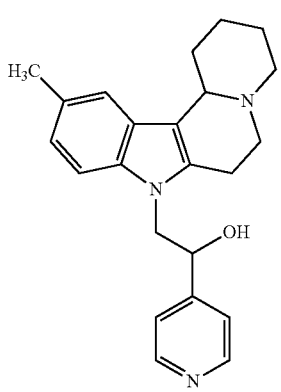 [SMILES: Cc1ccc2c(c1)c1c(n2CC(O)c2ccncc2)CCN2CCCCC12]
47
47a, 47b, 47c, 47d
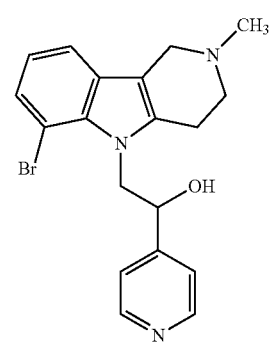
48
48a, 48b
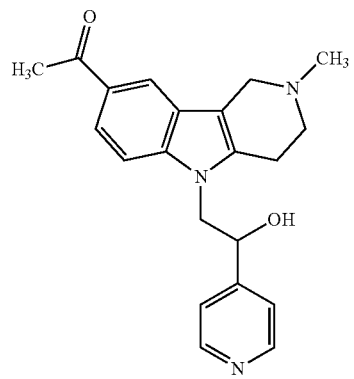
49
49a, 49b TABLE 1-continued
Representative Compounds of the Invention
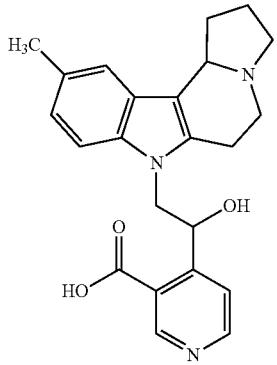 [SMILES: Cc1ccc2c(c1)c1c(n2CC(O)c2ccncc2C(=O)O)CCN2CCCC12]
50
50a, 50b, 50c, 50d
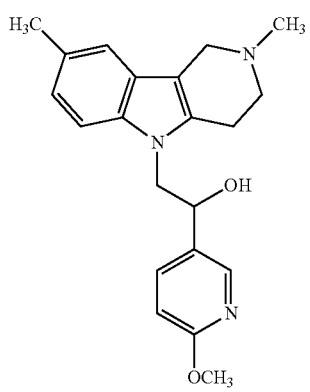
51
51a, 51b
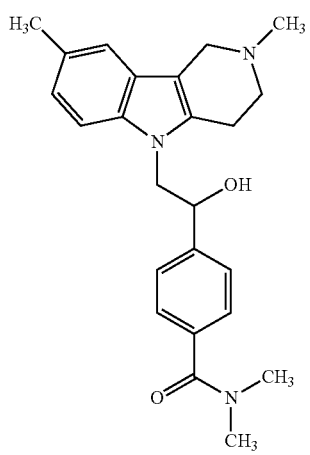
52
52a, 52b
TABLE 1-continued
Representative Compounds of the Invention
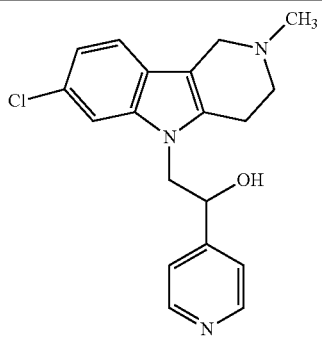
53
53a, 53b
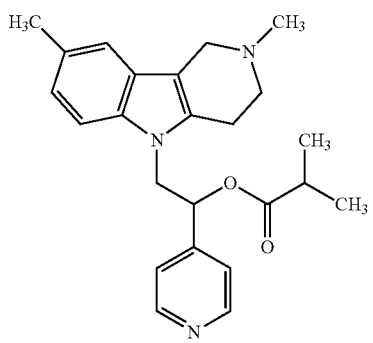 [SMILES: Cc1ccc2c(c1)c1c(n2CC(OC(=O)C(C)C)c2ccncc2)CCN(C)C1]
54
54a, 54b
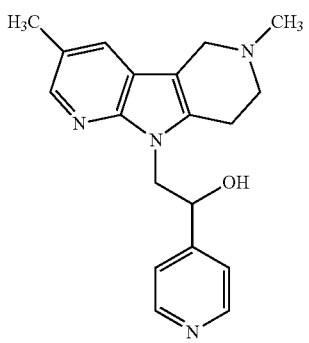
55
55a, 55b
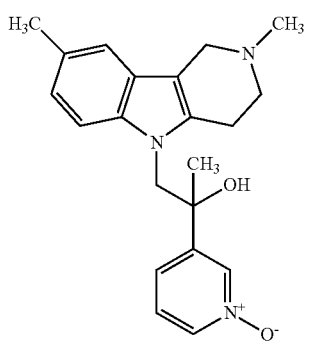
56
56a, 56b TABLE 1-continued
Representative Compounds of the Invention
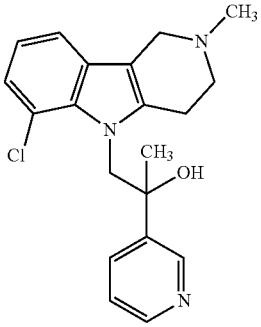 [SMILES: CN1CCc2c(c3cccc(Cl)c3n2CC(C)(O)c2cccnc2)C1]
57
57a, 57b
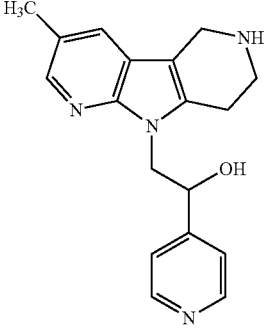
58
58a, 58b
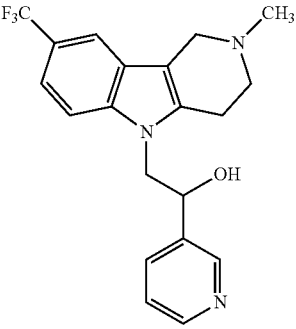 [SMILES: CN1CCc2c(c3cc(C(F)(F)F)ccc3n2CC(O)c2cccnc2)C1]
59
59a, 59b
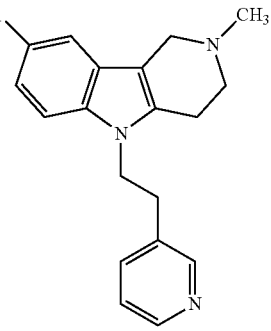
60
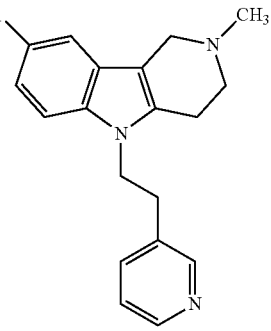
61
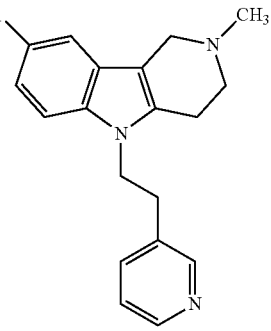
62
62a, 62b
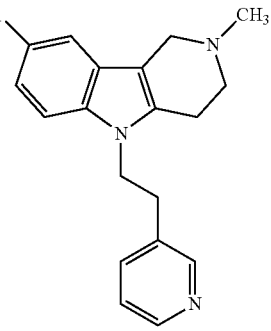
63
63a, 63b
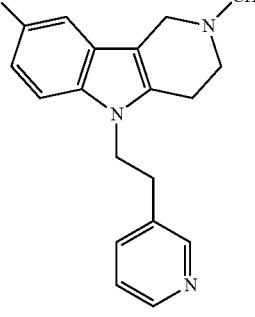
64
64a, 64b TABLE 1-continued
Representative Compounds of the Invention
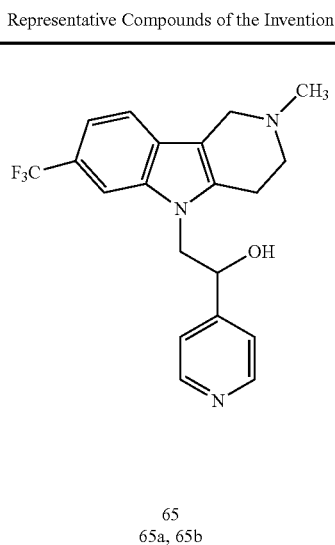
65
65a, 65b
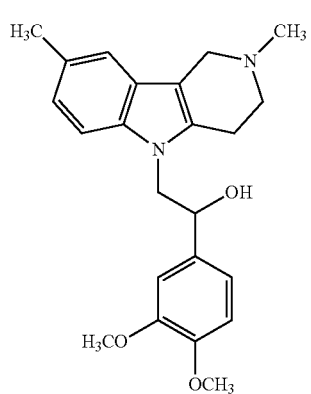
66
66a, 66b
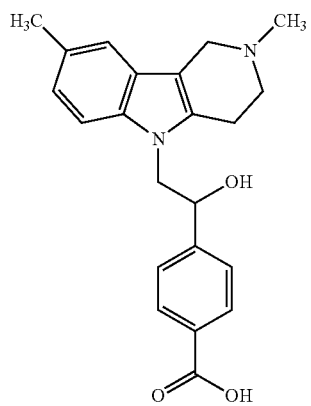
67
67a, 67b
TABLE 1-continued
Representative Compounds of the Invention
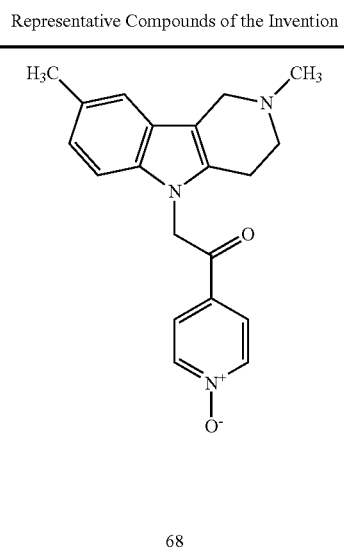
68
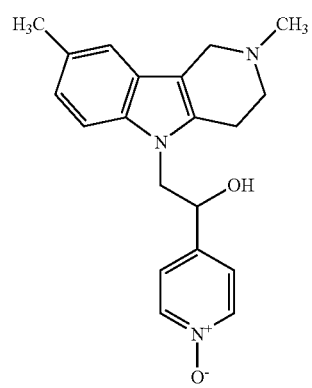
69
69a, 69b
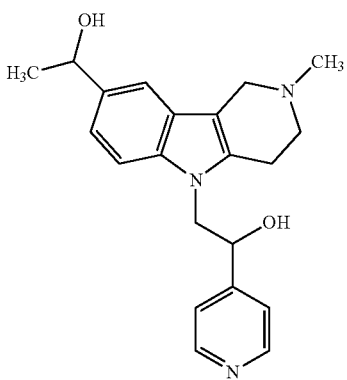 [SMILES: CC(O)c1ccc2c(c1)c1c(n2CC(O)c2ccncc2)CCN(C)C1]
70
70a, 70b, 70c, 70d TABLE 1-continued
Representative Compounds of the Invention
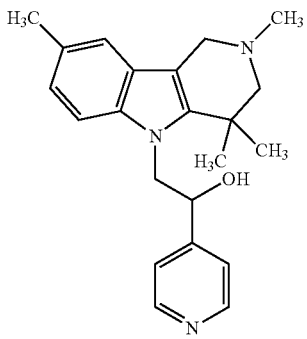
71
71a, 71b
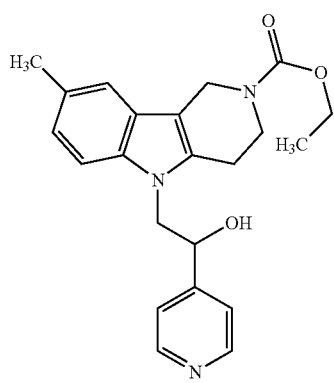 [SMILES: CCOC(=O)N1CCc2c(c3cc(C)ccc3n2CC(O)c2ccncc2)C1]
72
72a, 72b
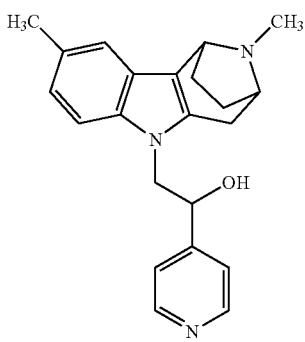
73
73a, 73b, 73c, 73d
TABLE 1-continued
Representative Compounds of the Invention
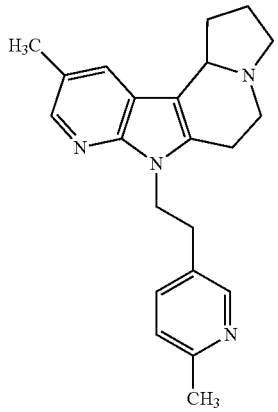
74
74a, 74b
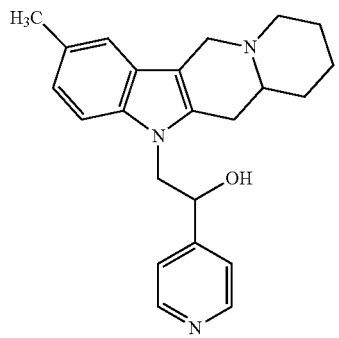 [SMILES: Cc1ccc2c(c1)c1c(n2CC(O)c2ccncc2)CC2CCCCN2C1]
75
75a, 75b, 75c, 75d
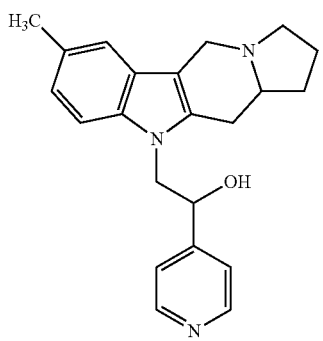 [SMILES: Cc1ccc2c(c1)c1c(n2CC(O)c2ccncc2)CC2CCCN2C1]
76
76a, 76b, 76c, 76d
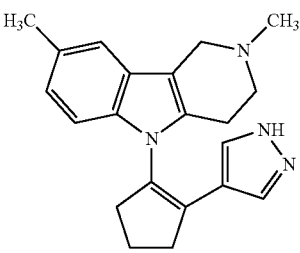 [SMILES: Cc1ccc2c(c1)c1c(n2C2=C(c3cn[nH]c3)CCC2)CCN(C)C1]
77

TABLE 1-continued

Representative Compounds of the Invention

78

79

80

81
81a, 81b 82
82a, 82b

83

84

85

TABLE 1-continued
Representative Compounds of the Invention
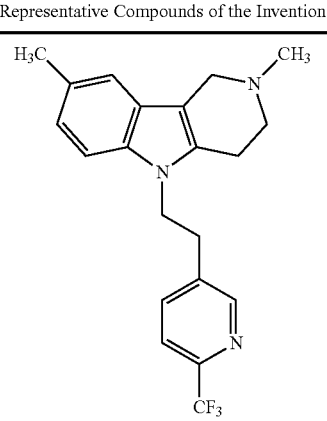
86
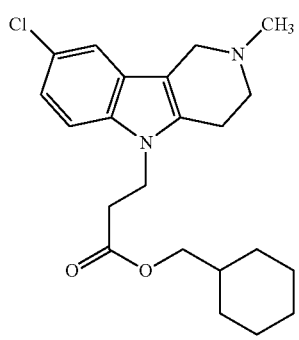 [SMILES: CN1CCc2c(c3cc(Cl)ccc3n2CCC(=O)OCC2CCCCC2)C1]
87
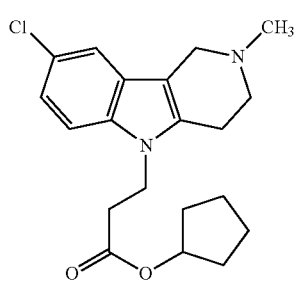 [SMILES: CN1CCc2c(c3cc(Cl)ccc3n2CCC(=O)OC2CCCC2)C1]
88
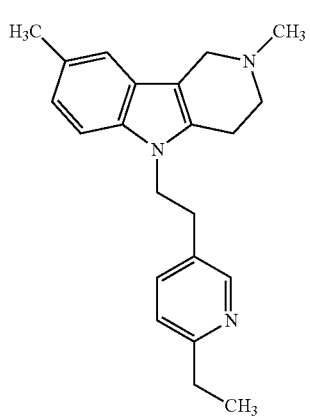
89
TABLE 1-continued
Representative Compounds of the Invention
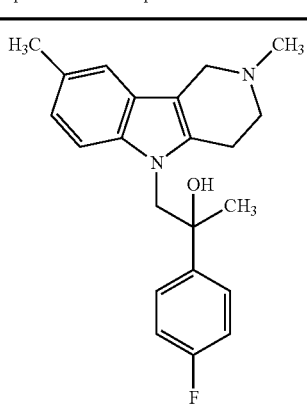
90
90a, 90b
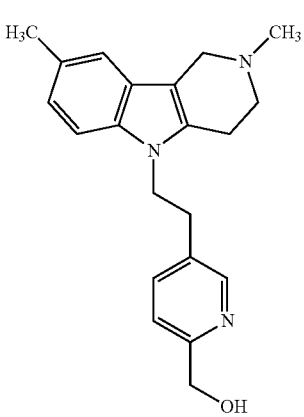
91
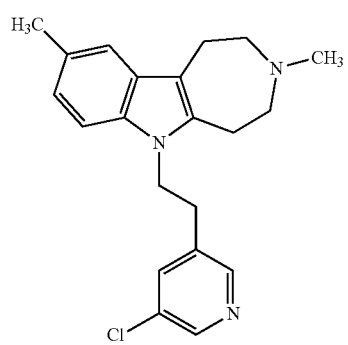
92

TABLE 1-continued
Representative Compounds of the Invention
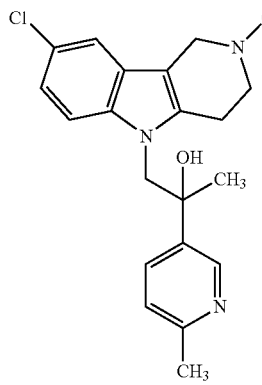
93
93a, 93b
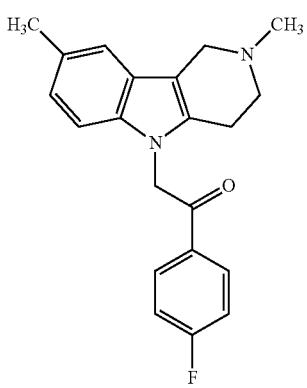
94
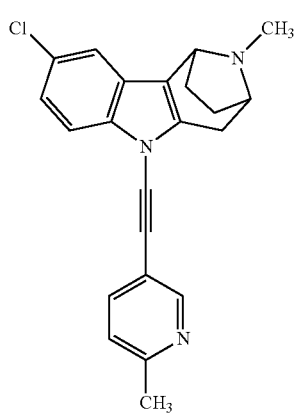 [SMILES: Cc1ccc(C#Cn2c3c(c4cc(Cl)ccc42)C2CCC(C3)N2C)cn1]
95
95a, 95b
TABLE 1-continued
Representative Compounds of the Invention
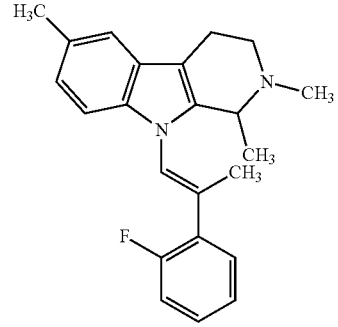
96
96a, 96b
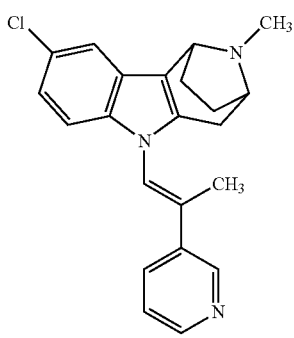 [SMILES: C/C(=C\n1c2c(c3cc(Cl)ccc31)C1CCC(C2)N1C)c1cccnc1]
97
97a, 97b
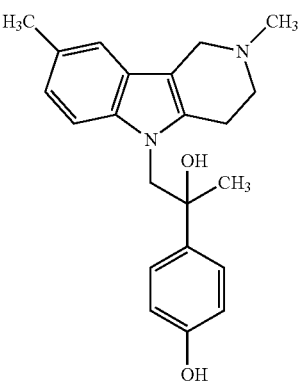
98
98a, 98b
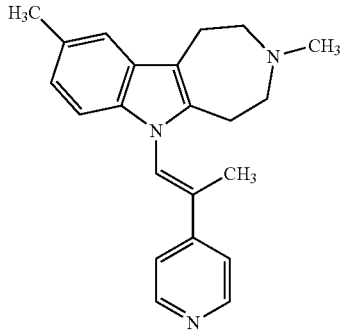
99

TABLE 1-continued
Representative Compounds of the Invention
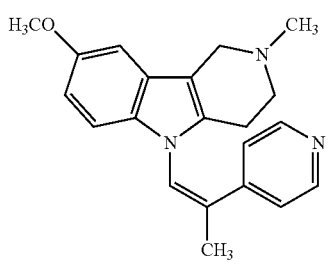 [SMILES: COc1ccc2c(c1)c1c(n2/C=C(/C)c2ccncc2)CCN(C)C1]
100
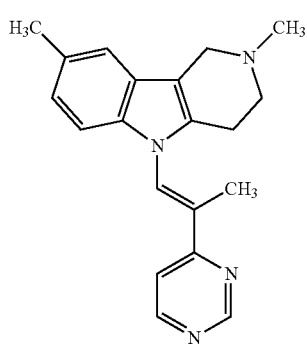
101
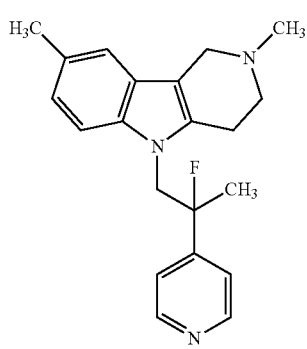
102
102a, 102b
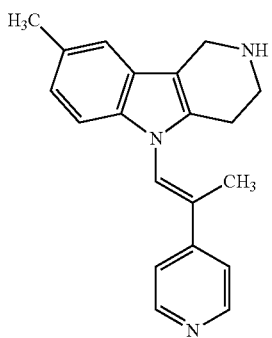
103
TABLE 1-continued
Representative Compounds of the Invention
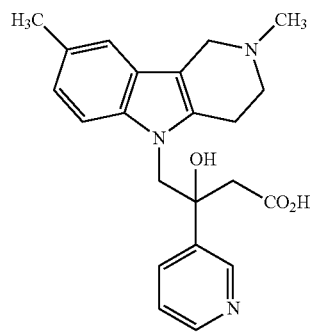
104
104a, 104b
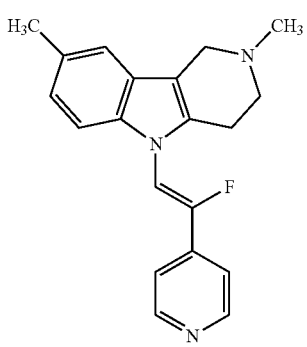
105
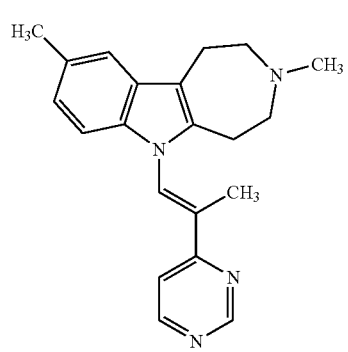
106
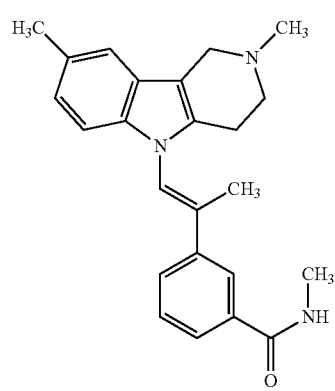
107

TABLE 1-continued
Representative Compounds of the Invention
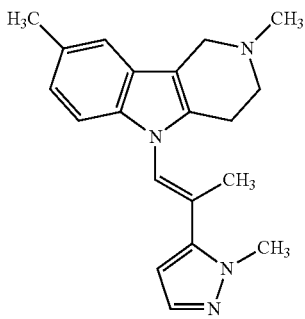
108
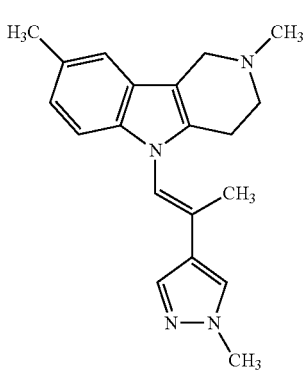
109
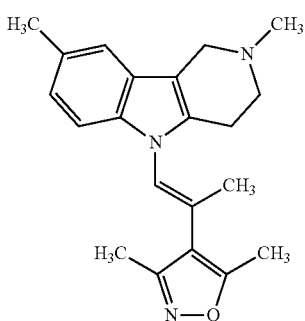
110
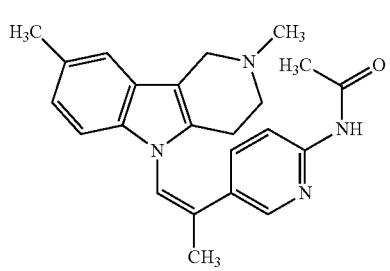 [SMILES: CC(=O)Nc1ccc(/C(C)=C\n2c3c(c4cc(C)ccc42)CN(C)CC3)cn1]
111
TABLE 1-continued
Representative Compounds of the Invention
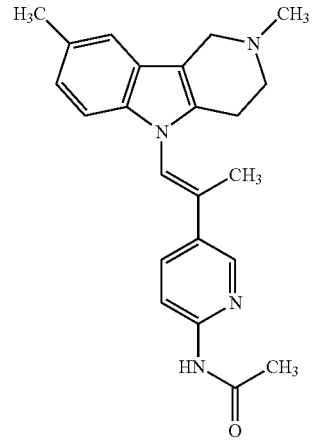
112
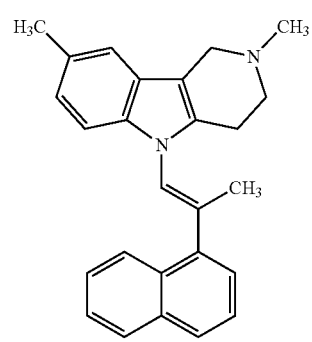
113
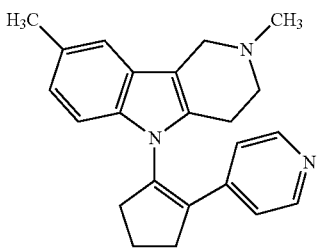 [SMILES: Cc1ccc2c(c1)c1c(n2C2=C(c3ccncc3)CCC2)CCN(C)C1]
114
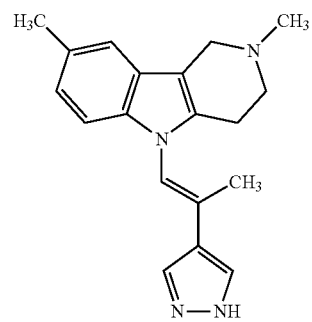
115

TABLE 1-continued
Representative Compounds of the Invention
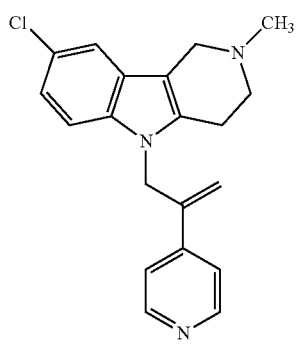 [SMILES: C=C(Cn1c2c(c3cc(Cl)ccc31)CN(C)CC2)c1ccncc1]
116
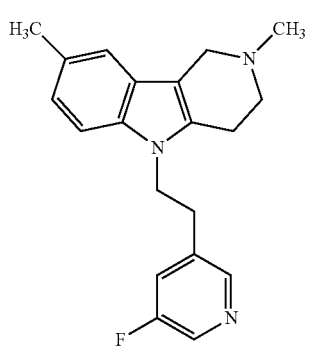
117
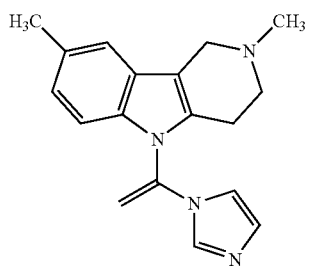
118
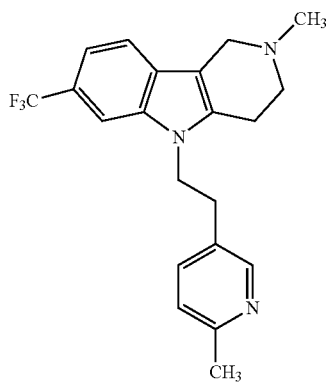 [SMILES: Cc1ccc(CCn2c3c(c4ccc(C(F)(F)F)cc42)CN(C)CC3)cn1]
119
TABLE 1-continued
Representative Compounds of the Invention
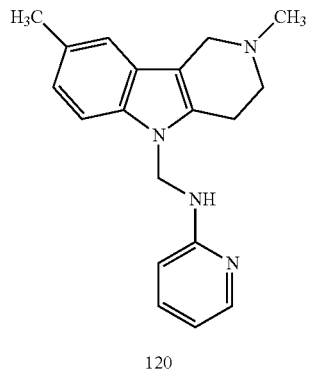
120
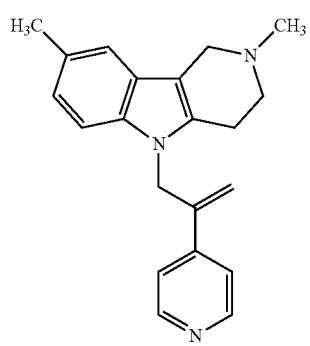
121
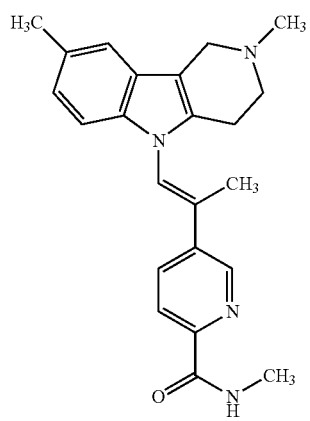
122
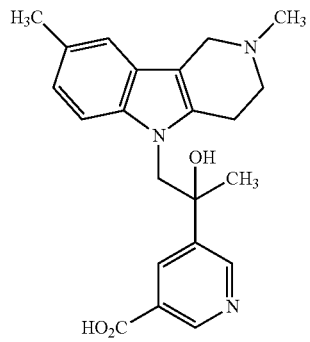
123
123a, 123b TABLE 1-continued
Representative Compounds of the Invention
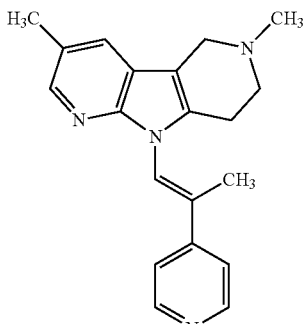
124
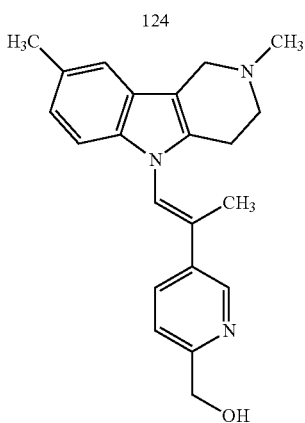
125
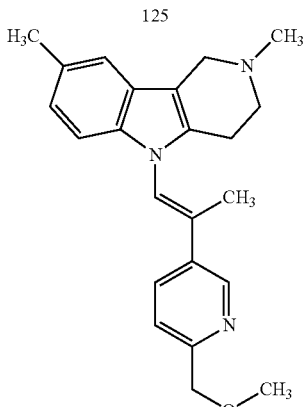
126
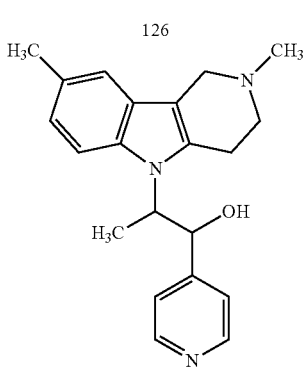
127
127a, 127b, 127c, 127d
TABLE 1-continued
Representative Compounds of the Invention
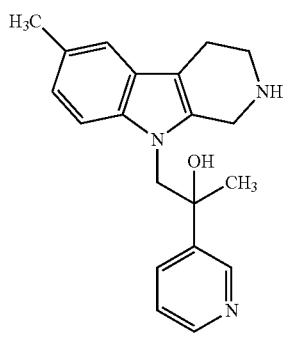 [SMILES: Cc1ccc2c(c1)c1c(n2CC(C)(O)c2cccnc2)CNCC1]
128
128a, 128b
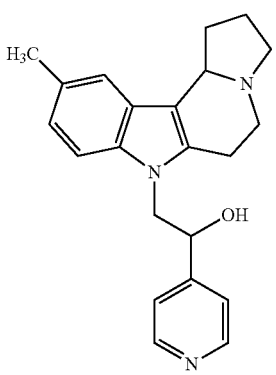 [SMILES: Cc1ccc2c(c1)c1c(n2CC(O)c2ccncc2)CCN2CCCC12]
129
129a, 129b, 129c, 129d
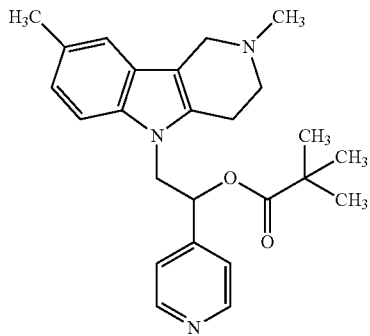
130
130a, 130b TABLE 1-continued
Representative Compounds of the Invention
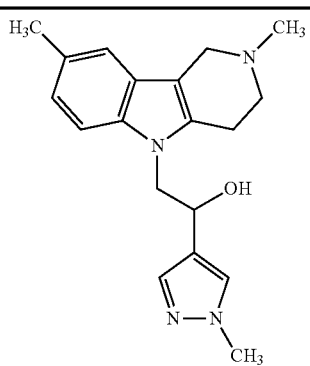
131
131a, 131b
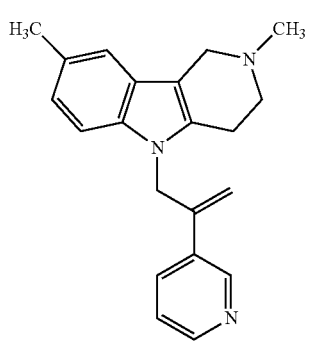
132
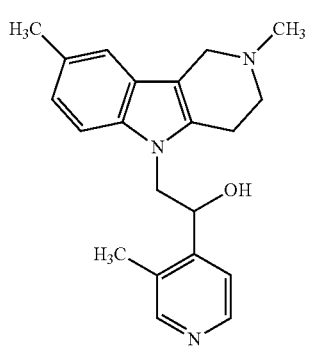
133
133a, 133b
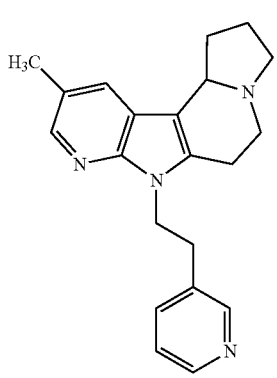 [SMILES: Cc1cnc2c(c1)c1c(n2CCc2cccnc2)CCN2CCCC12]
134
134a, 134b
TABLE 1-continued
Representative Compounds of the Invention
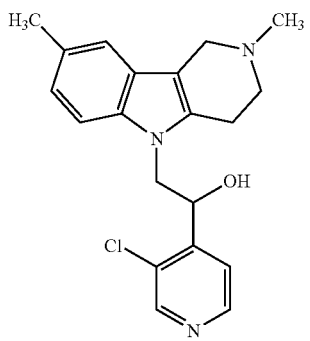
135
135a, 135b
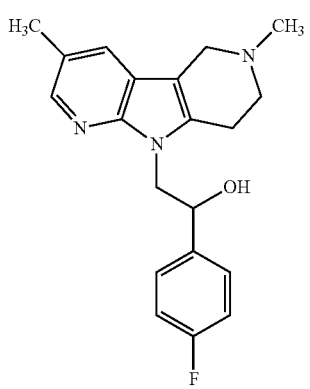
136
136a, 136b
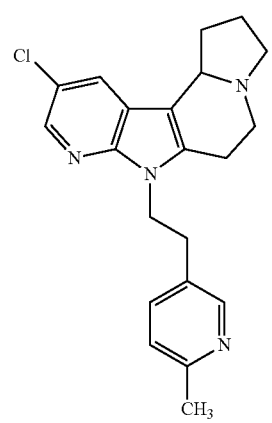 [SMILES: Cc1ccc(CCn2c3c(c4cc(Cl)cnc42)C2CCCN2CC3)cn1]
137
137a, 137b TABLE 1-continued
Representative Compounds of the Invention
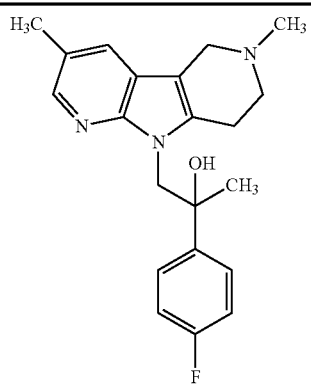
138
138a, 138b
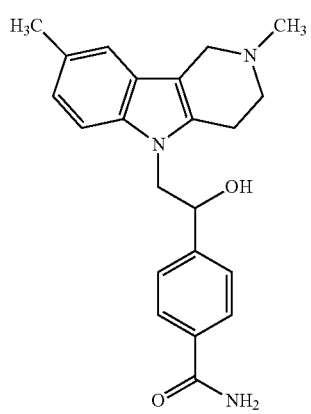
139
139a, 139b
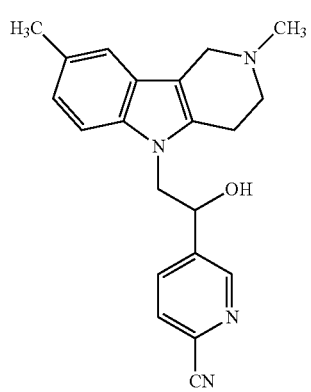
140
140a, 140b
TABLE 1-continued
Representative Compounds of the Invention
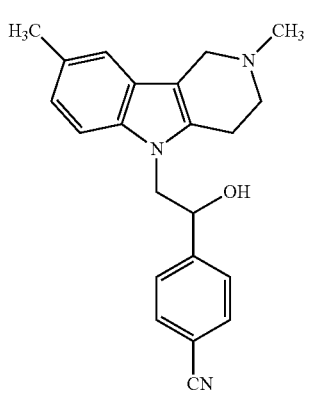
141
141a, 141b
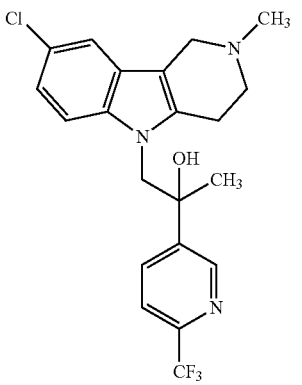
142
142, 142b
143
143a, 143b TABLE 1-continued
Representative Compounds of the Invention
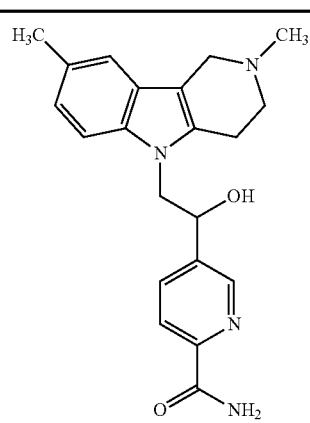
144
144a, 144b
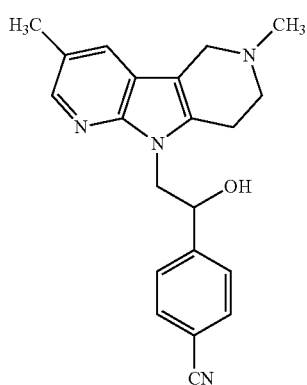
145
145a, 145b
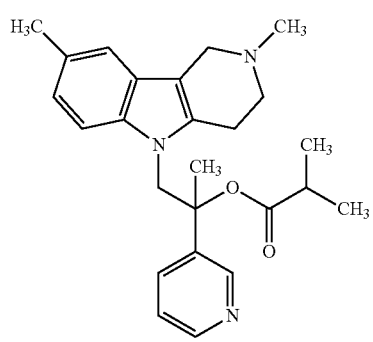 [SMILES: Cc1ccc2c(c1)c1c(n2CC(C)(OC(=O)C(C)C)c2cccnc2)CCN(C)C1]
146
146a, 146b
TABLE 1-continued
Representative Compounds of the Invention
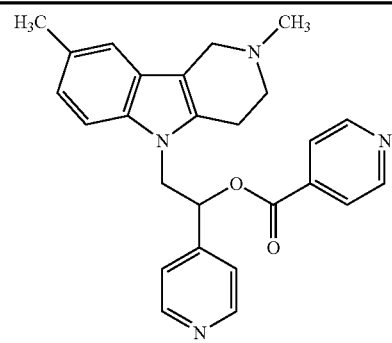
147
147a, 147b
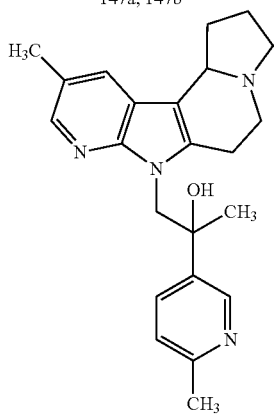
148
148a, 148b, 148a, 148d
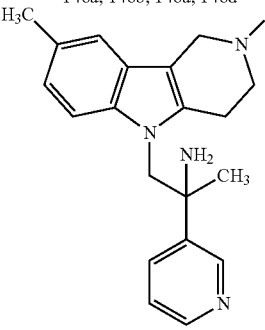
149
149a, 149b
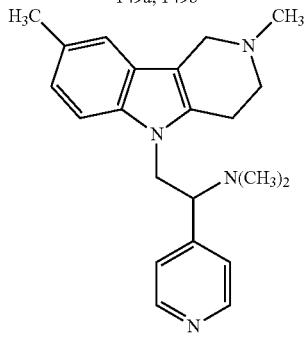
150
150a, 150b TABLE 1-continued Representative Compounds of the Invention 151
151a, 151b 152
152a, 152b 153
153a, 153b 154
154a, 154b 155
155a, 155b, 155c, 155d 156
156a, 156b 157
157a, 157b 158
158a, 158b TABLE 1-continued Representative Compounds of the Invention 159
159a, 159b 160
160a, 160b 161
161a, 161b, 161c, 161d 162
162a, 162b, 162c, 162d 163
163a, 163b, 163c, 163d 164
164a, 164b, 164c, 164d 165
165a, 165b TABLE 1-continued Representative Compounds of the Invention 166
166a, 166b 167
167a, 167b 168
168a, 168b, 168c, 168d 169
169a, 169b 170
170a, 170b 171
171a, 171b 172
172a, 172b 173
173a, 173b TABLE 1-continued
Representative Compounds of the Invention
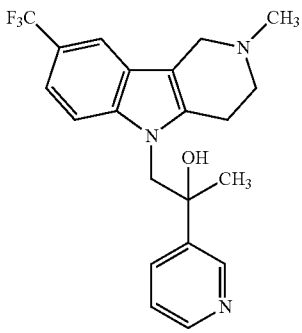 [SMILES: CN1CCc2c(c3cc(C(F)(F)F)ccc3n2CC(C)(O)c2cccnc2)C1]
174
174a, 174b
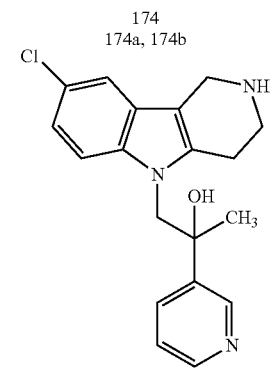
175
175a, 175b
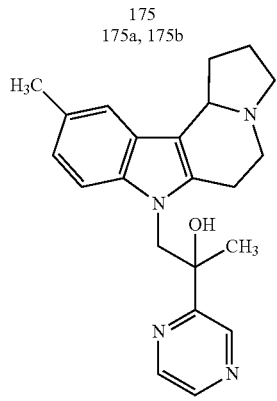
176
176a, 176b, 176c, 176d
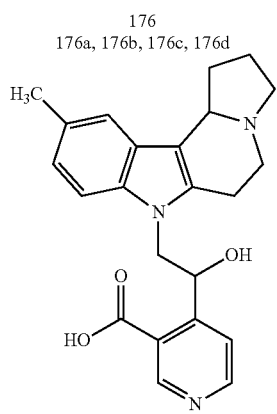
177
177a, 177b, 177c, 177d
TABLE 1-continued
Representative Compounds of the Invention
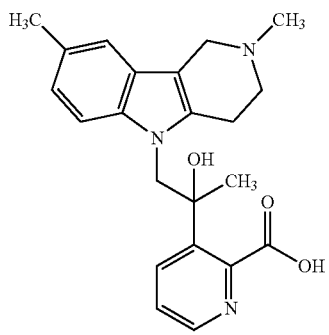 [SMILES: Cc1ccc2c(c1)c1c(n2CC(C)(O)c2cccnc2C(=O)O)CCN(C)C1]
178
178a, 178b
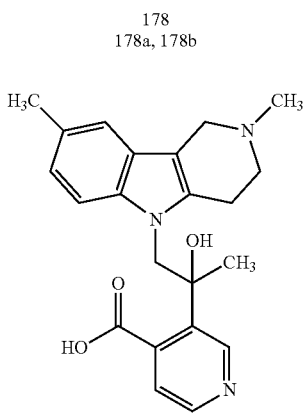
179
179a, 179b
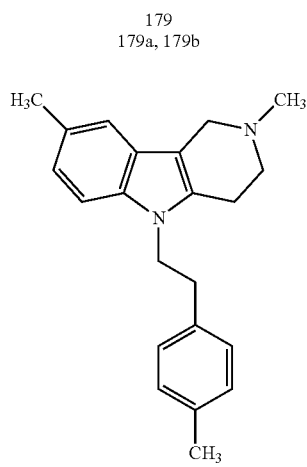
180

TABLE 1-continued
Representative Compounds of the Invention
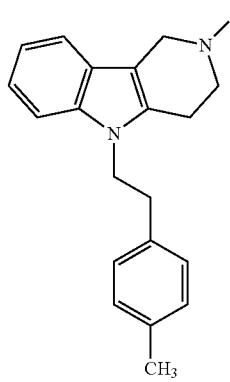
181
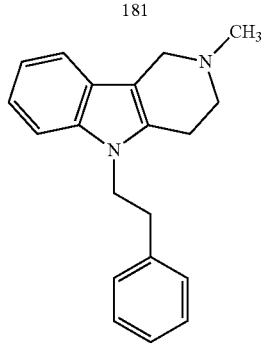
182
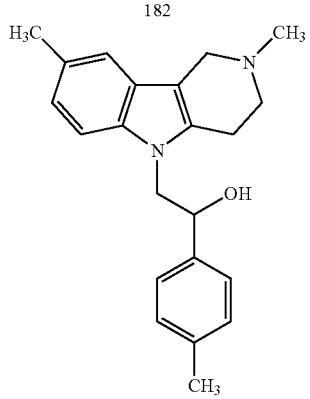
183
183a, 183b
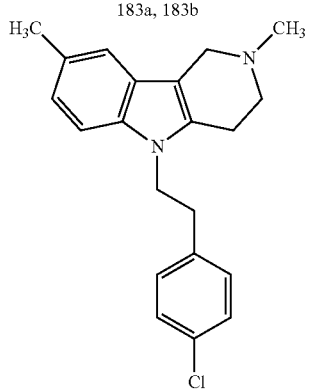
184
TABLE 1-continued
Representative Compounds of the Invention
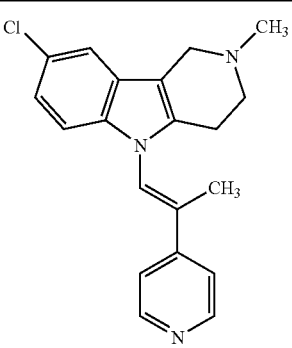
185
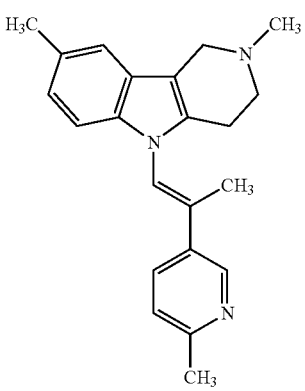
186
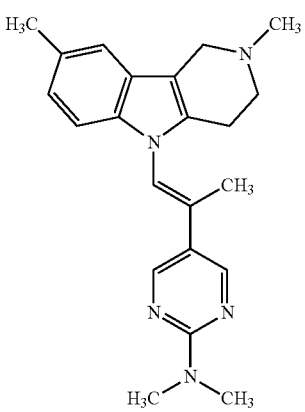
187

TABLE 1-continued
Representative Compounds of the Invention
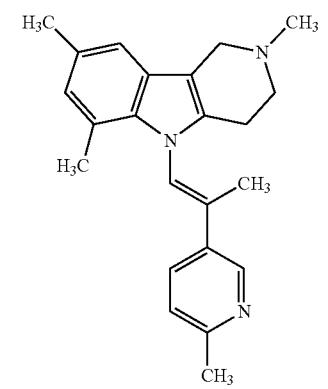
188
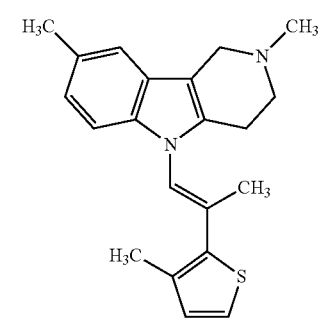
189
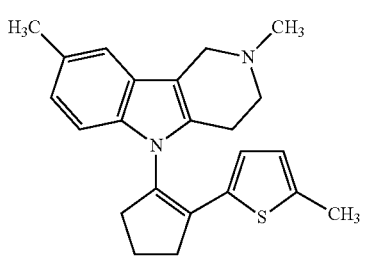
190
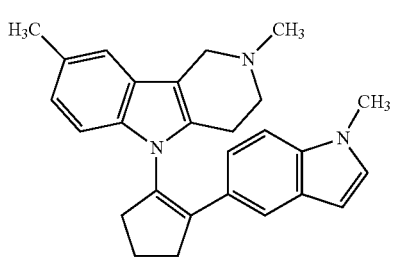 [SMILES: Cc1ccc2c(c1)c1c(n2C2=C(c3ccc4c(ccn4C)c3)CCC2)CCN(C)C1]
191
TABLE 1-continued
Representative Compounds of the Invention
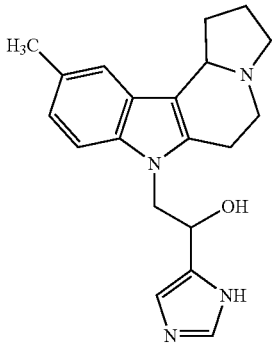 [SMILES: Cc1ccc2c(c1)c1c(n2CC(O)c2cnc[nH]2)CCN2CCCC12]
192
192a, 192b, 192c, 192d
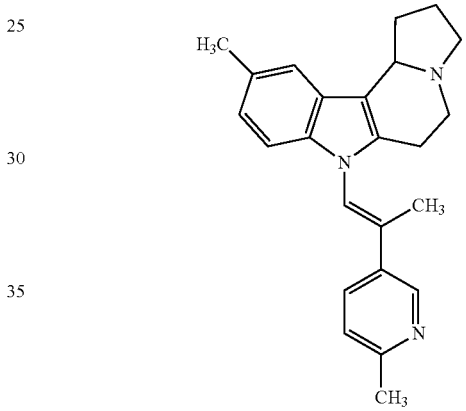
193
193a, 193b
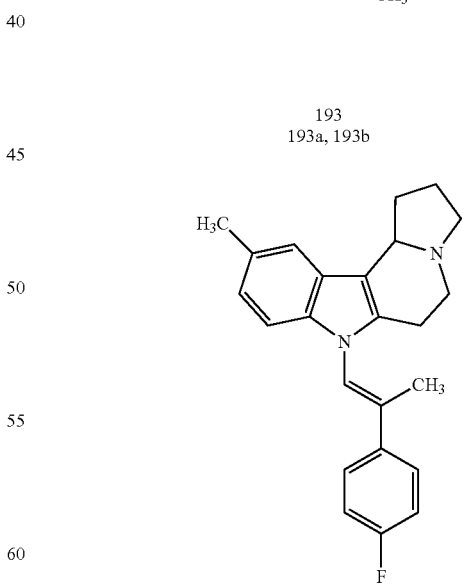
194
194a, 194b TABLE 1-continued
Representative Compounds of the Invention
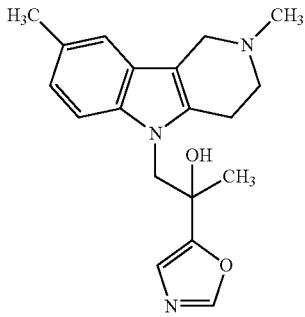
195
195a, 195b
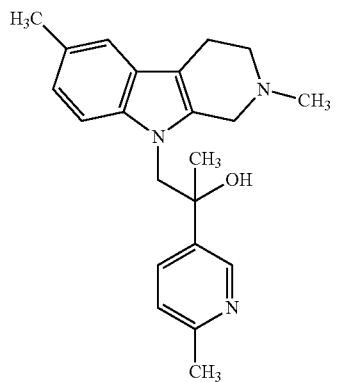
196
196a, 196b
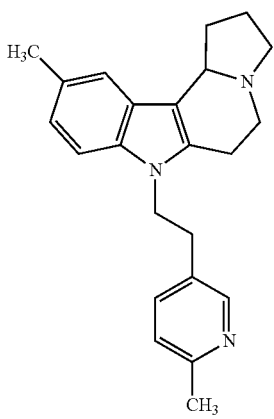 [SMILES: Cc1ccc2c(c1)c1c(n2CCc2ccc(C)nc2)CCN2CCCC12]
197
197a, 197b
TABLE 1-continued
Representative Compounds of the Invention
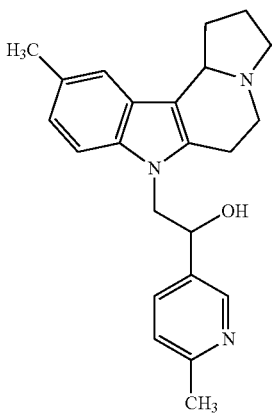 [SMILES: Cc1ccc2c(c1)c1c(n2CC(O)c2ccc(C)nc2)CCN2CCCC12]
198
198a, 198b, 198c, 198d
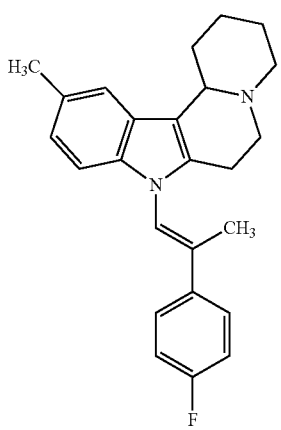 [SMILES: C/C(=C\n1c2c(c3cc(C)ccc31)C1CCCCN1CC2)c1ccc(F)cc1]
199
199a, 199b
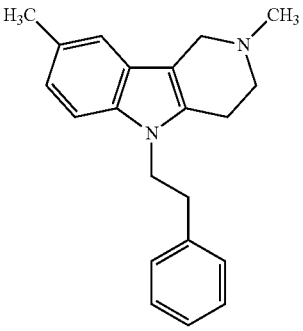
200

TABLE 1-continued
Representative Compounds of the Invention
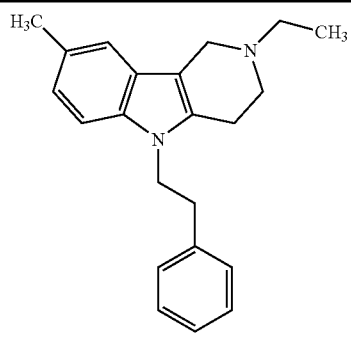
201
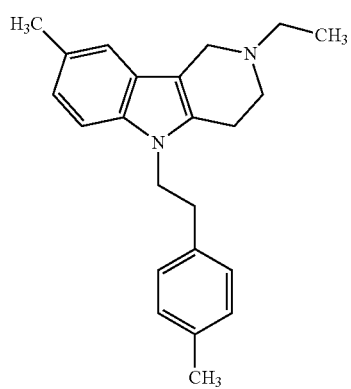 [SMILES: CCN1CCc2c(c3cc(C)ccc3n2CCc2ccc(C)cc2)C1]
202
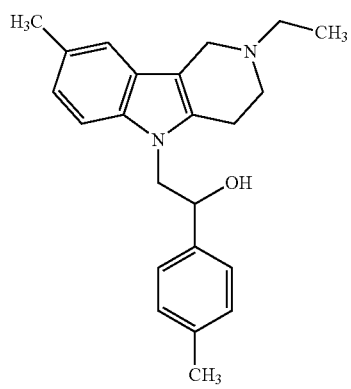 [SMILES: CCN1CCc2c(c3cc(C)ccc3n2CC(O)c2ccc(C)cc2)C1]
203
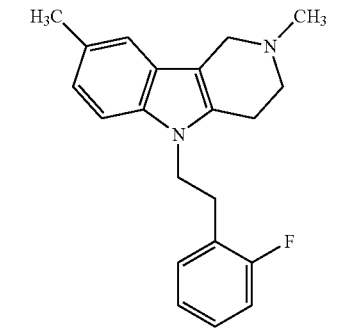
204
TABLE 1-continued
Representative Compounds of the Invention
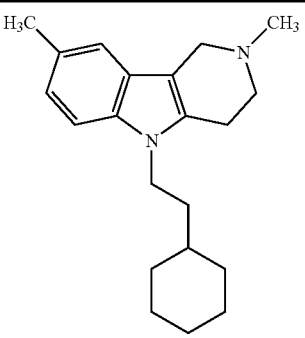
205
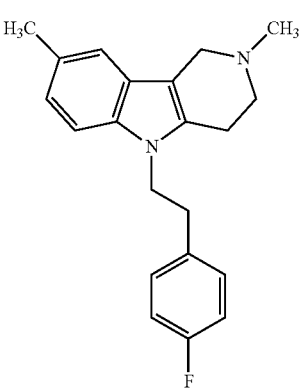
206
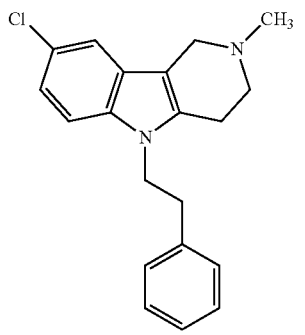 [SMILES: CN1CCc2c(c3cc(Cl)ccc3n2CCc2ccccc2)C1]
207
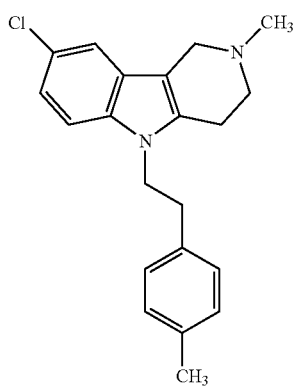 [SMILES: Cc1ccc(CCn2c3c(c4cc(Cl)ccc42)CN(C)CC3)cc1]
208

TABLE 1-continued
Representative Compounds of the Invention
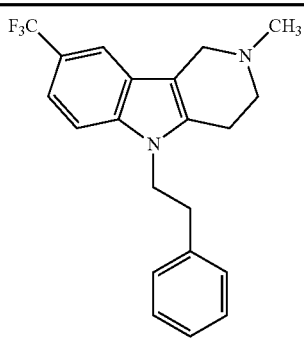
209
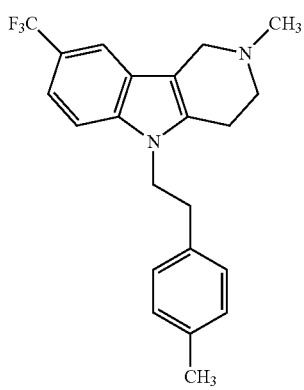 [SMILES: Cc1ccc(CCn2c3c(c4cc(C(F)(F)F)ccc42)CN(C)CC3)cc1]
210
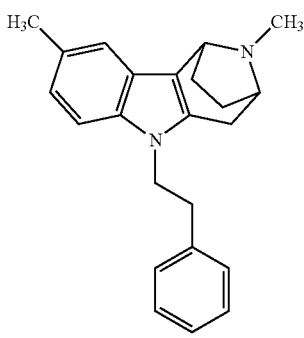
211
211a, 211b
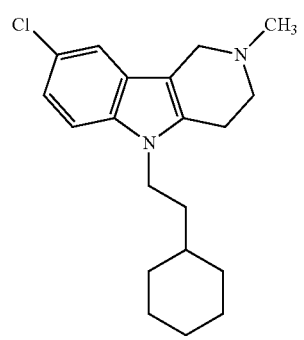 [SMILES: CN1CCc2c(c3cc(Cl)ccc3n2CCC2CCCCC2)C1]
212
TABLE 1-continued
Representative Compounds of the Invention
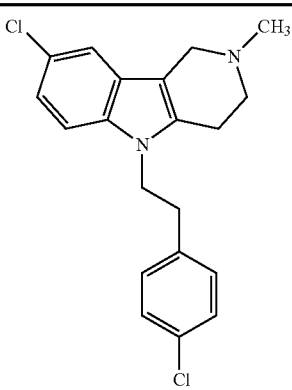
213
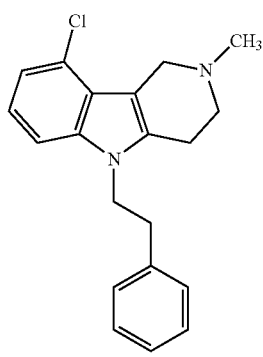 [SMILES: CN1CCc2c(c3c(Cl)cccc3n2CCc2ccccc2)C1]
214
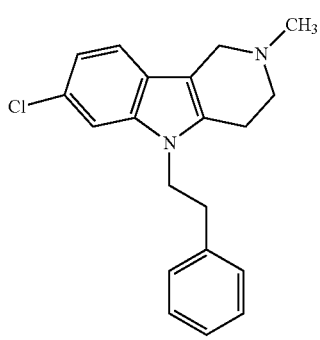 [SMILES: CN1CCc2c(c3ccc(Cl)cc3n2CCc2ccccc2)C1]
215
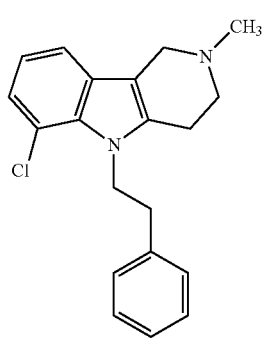 [SMILES: CN1CCc2c(c3cccc(Cl)c3n2CCc2ccccc2)C1]
216

TABLE 1-continued
Representative Compounds of the Invention
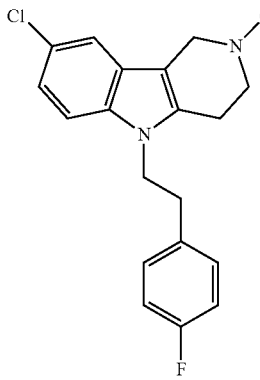
217
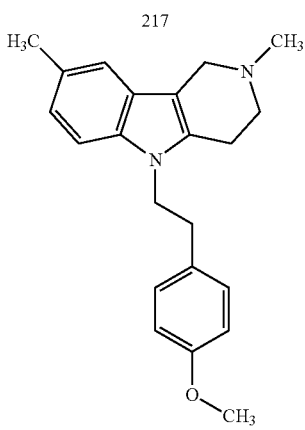
218
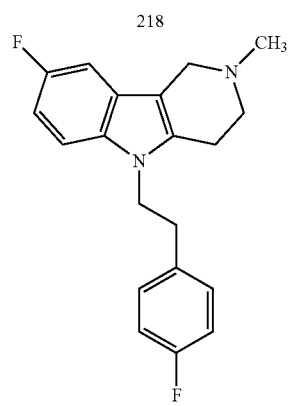
219
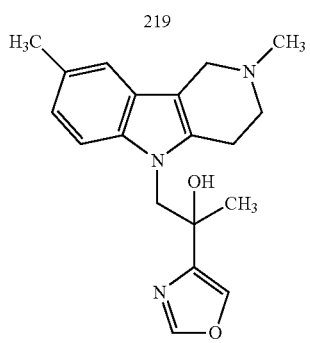
220
220a, 220b
TABLE 1-continued
Representative Compounds of the Invention
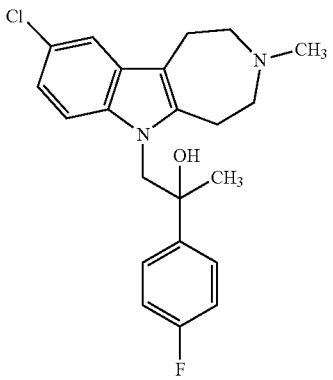 [SMILES: CN1CCc2c(n(CC(C)(O)c3ccc(F)cc3)c3ccc(Cl)cc23)CC1]
221
221a, 221b
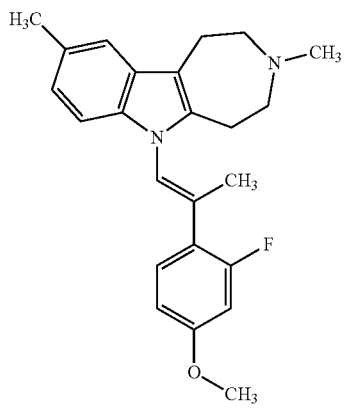
222
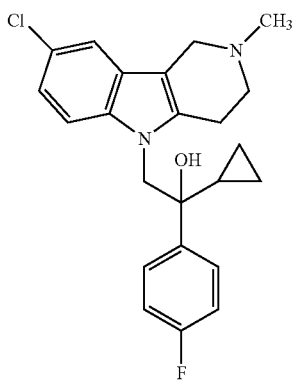 [SMILES: CN1CCc2c(c3cc(Cl)ccc3n2CC(O)(c2ccc(F)cc2)C2CC2)C1]
223
223a, 223b TABLE 1-continued
Representative Compounds of the Invention
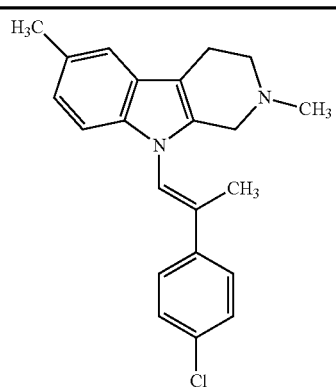
224
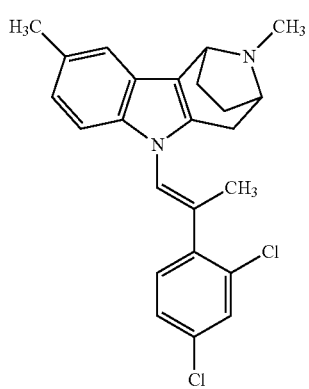
225
225a, 225b
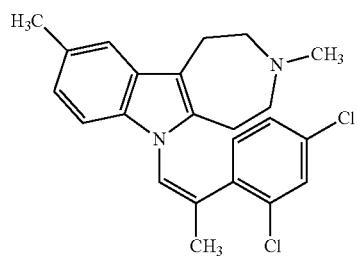 [SMILES: C/C(=C/n1c2c(c3cc(C)ccc31)CCN(C)CC2)c1ccc(Cl)cc1Cl]
226
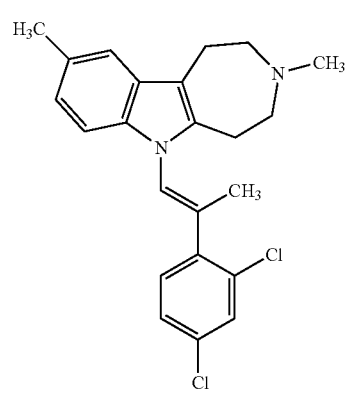
227
TABLE 1-continued
Representative Compounds of the Invention
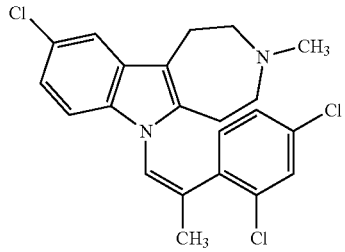 [SMILES: C/C(=C/n1c2c(c3cc(Cl)ccc31)CCN(C)CC2)c1ccc(Cl)cc1Cl]
228
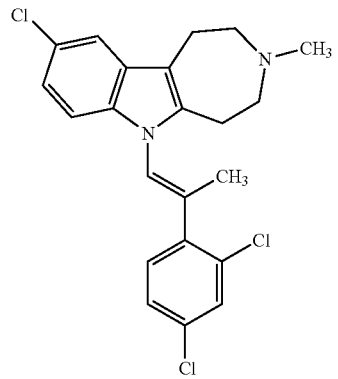 [SMILES: C/C(=C\n1c2c(c3cc(Cl)ccc31)CCN(C)CC2)c1ccc(Cl)cc1Cl]
229
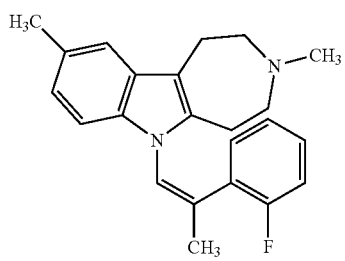
230
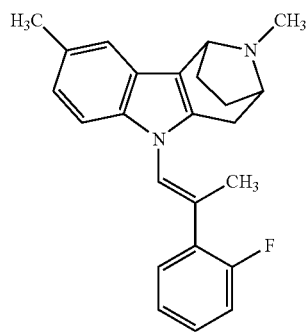
231
231a, 231b TABLE 1-continued
Representative Compounds of the Invention
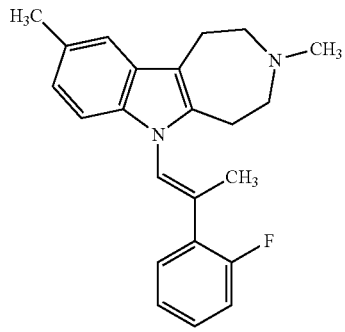
232
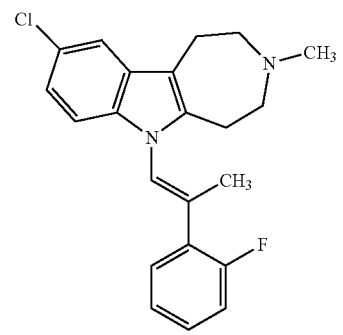 [SMILES: C/C(=C\n1c2c(c3cc(Cl)ccc31)CCN(C)CC2)c1ccccc1F]
233
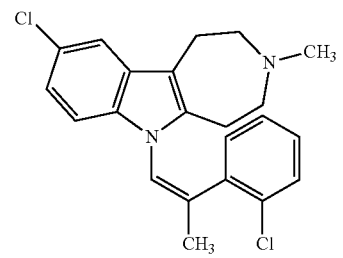 [SMILES: C/C(=C/n1c2c(c3cc(Cl)ccc31)CCN(C)CC2)c1ccccc1Cl]
234
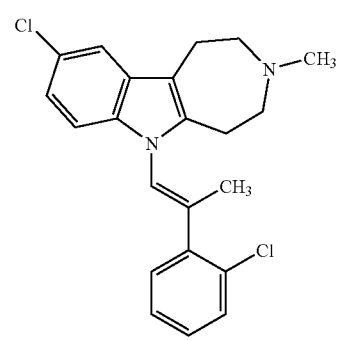
235
TABLE 1-continued
Representative Compounds of the Invention
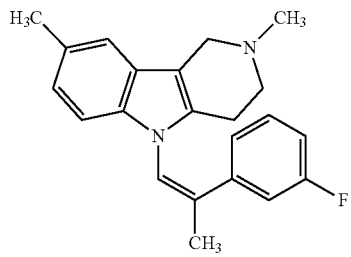 [SMILES: C/C(=C/n1c2c(c3cc(C)ccc31)CN(C)CC2)c1cccc(F)c1]
236
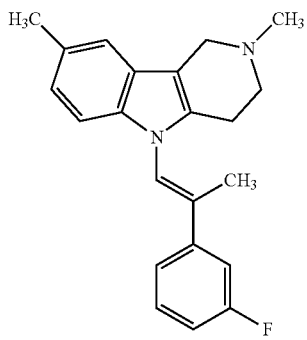
237
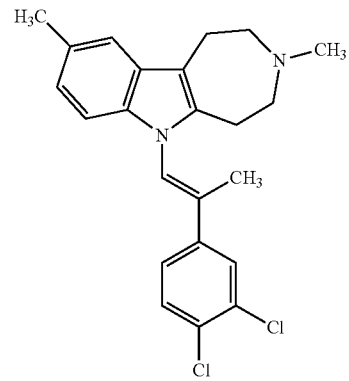
238
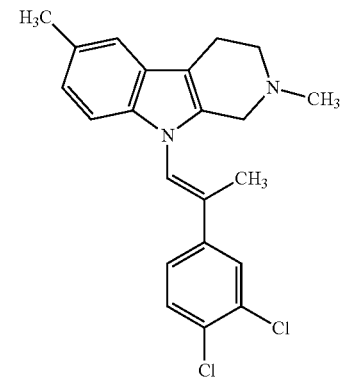
239

TABLE 1-continued
Representative Compounds of the Invention
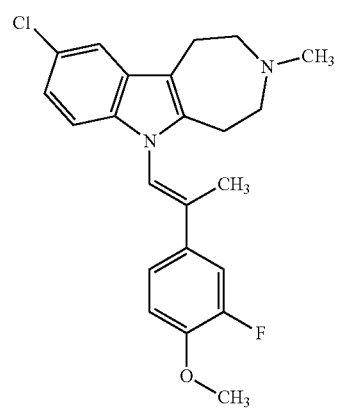 [SMILES: COc1ccc(/C(C)=C/n2c3c(c4cc(Cl)ccc42)CCN(C)CC3)cc1F]
240
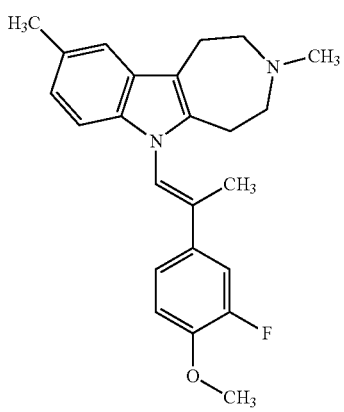
241
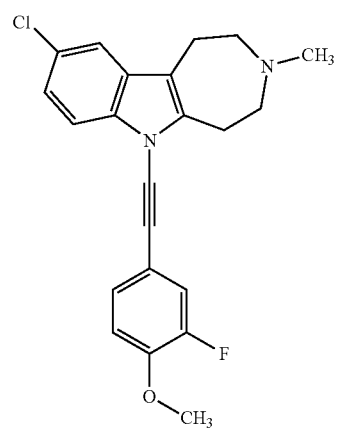 [SMILES: COc1ccc(C#Cn2c3c(c4cc(Cl)ccc42)CCN(C)CC3)cc1F]
242
TABLE 1-continued
Representative Compounds of the Invention
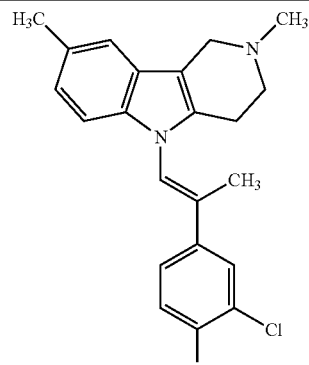
243
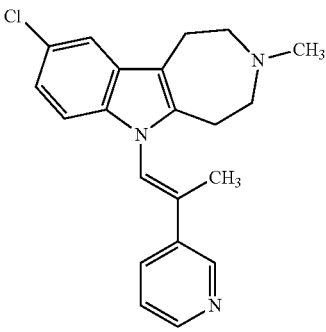 [SMILES: C/C(=C\n1c2c(c3cc(Cl)ccc31)CCN(C)CC2)c1cccnc1]
244
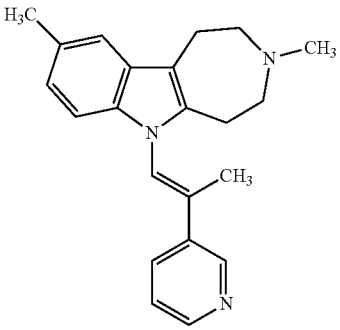
245
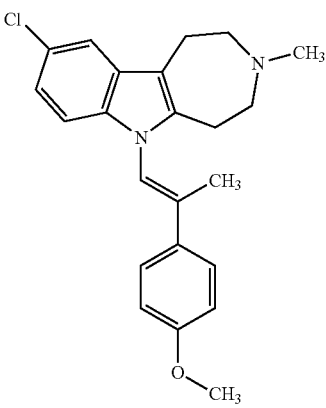 [SMILES: COc1ccc(/C(C)=C/n2c3c(c4cc(Cl)ccc42)CCN(C)CC3)cc1]
246

TABLE 1-continued
Representative Compounds of the Invention
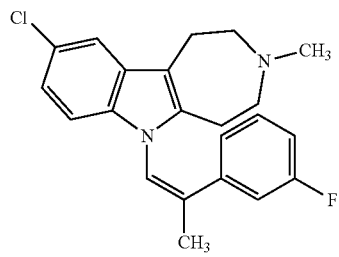 [SMILES: C/C(=C/n1c2c(c3cc(Cl)ccc31)CCN(C)CC2)c1cccc(F)c1]
247
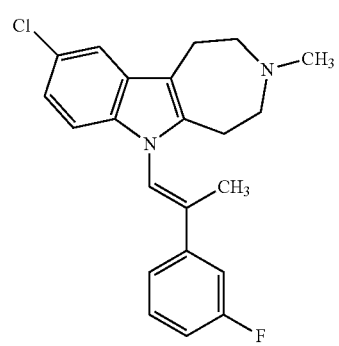 [SMILES: C/C(=C\n1c2c(c3cc(Cl)ccc31)CCN(C)CC2)c1cccc(F)c1]
248
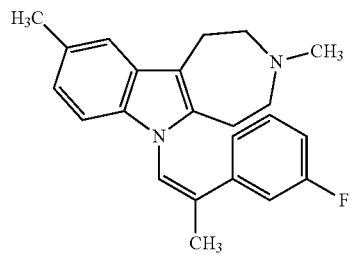 [SMILES: C/C(=C/n1c2c(c3cc(C)ccc31)CCN(C)CC2)c1cccc(F)c1]
249
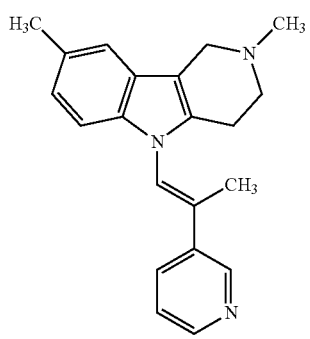
250
TABLE 1-continued
Representative Compounds of the Invention
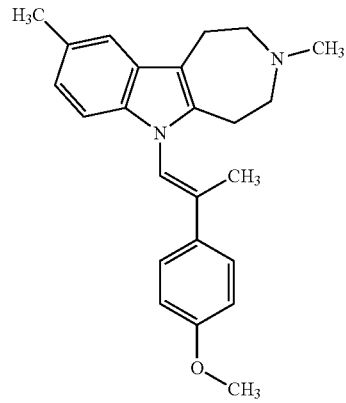
251
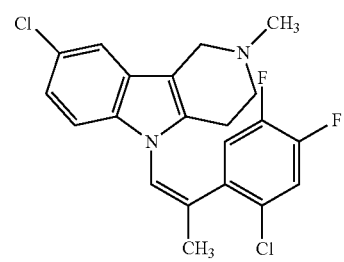 [SMILES: C/C(=C/n1c2c(c3cc(Cl)ccc31)CN(C)CC2)c1cc(F)c(F)cc1Cl]
252
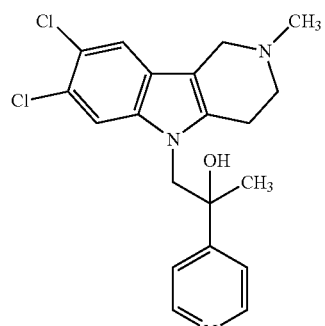
253
253a, 253b
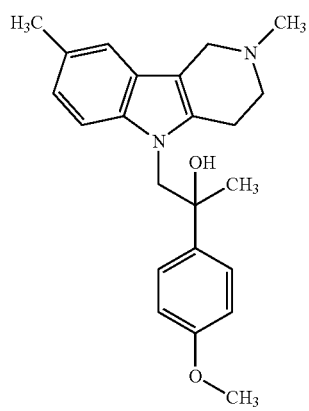
254
254a, 254b TABLE 1-continued
Representative Compounds of the Invention
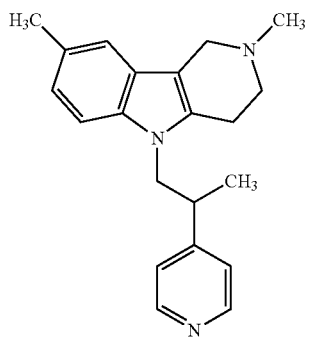
255
255a, 255b
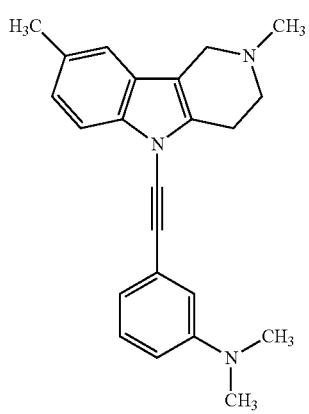
256
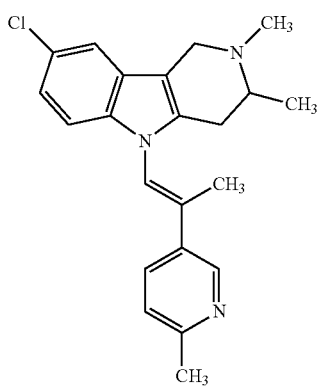 [SMILES: C/C(=C\n1c2c(c3cc(Cl)ccc31)CN(C)C(C)C2)c1ccc(C)nc1]
257
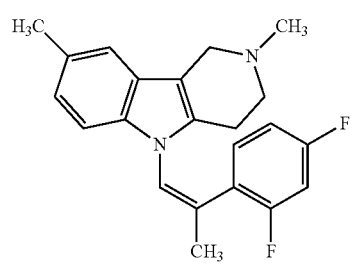 [SMILES: C/C(=C/n1c2c(c3cc(C)ccc31)CN(C)CC2)c1ccc(F)cc1F]
258
TABLE 1-continued
Representative Compounds of the Invention
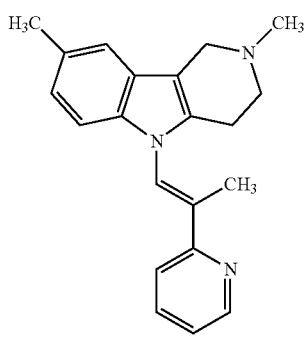
259
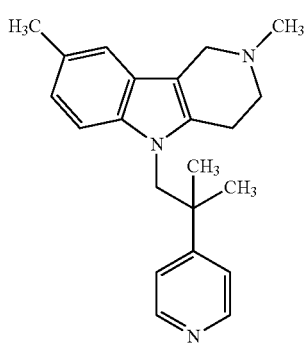
260
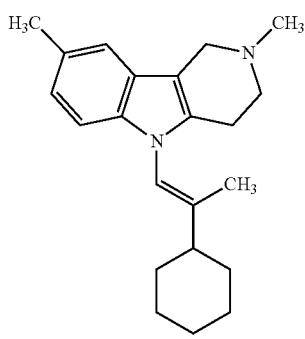
261
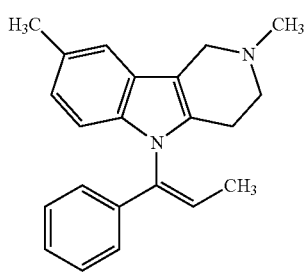
262

TABLE 1-continued
Representative Compounds of the Invention
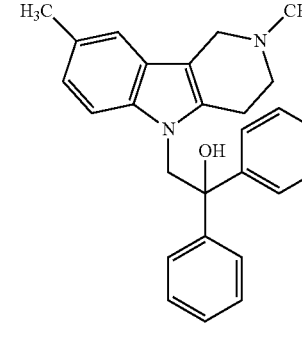
263
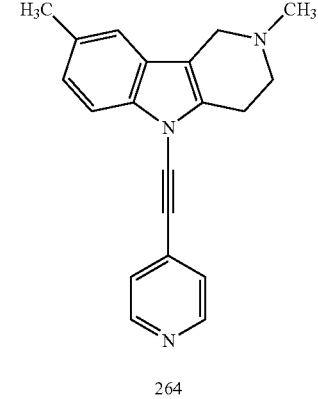
264
265
266
TABLE 1-continued
Representative Compounds of the Invention
267
268
269
270

TABLE 1-continued

Representative Compounds of the Invention

271

272
272a, 272b

273

274
274a, 274b

275

276

277

278

279

TABLE 1-continued
Representative Compounds of the Invention
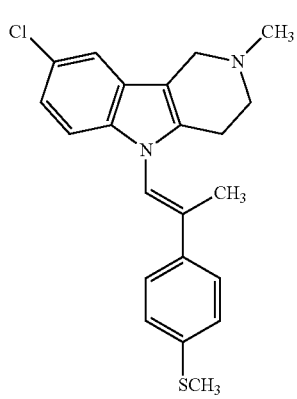 [SMILES: CSc1ccc(/C(C)=C/n2c3c(c4cc(Cl)ccc42)CN(C)CC3)cc1]
280
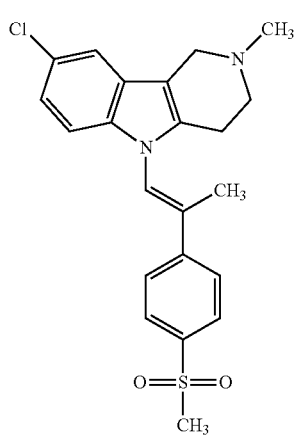 [SMILES: C/C(=C\n1c2c(c3cc(Cl)ccc31)CN(C)CC2)c1ccc(S(C)(=O)=O)cc1]
281
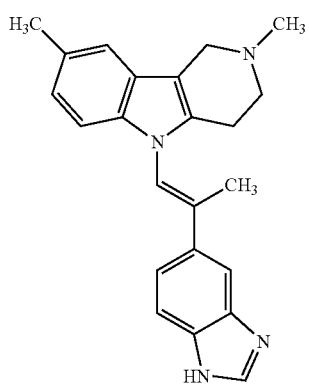
282
TABLE 1-continued
Representative Compounds of the Invention
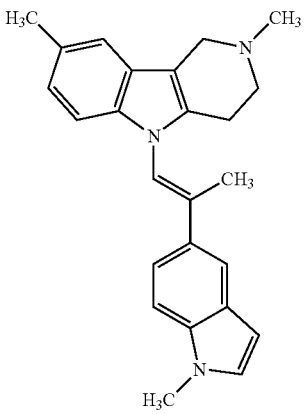
283
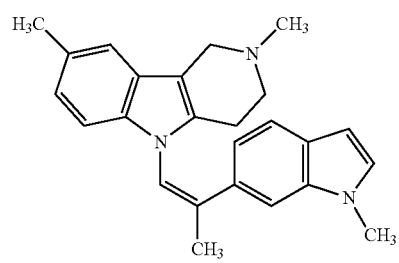 [SMILES: C/C(=C/n1c2c(c3cc(C)ccc31)CN(C)CC2)c1ccc2ccn(C)c2c1]
284
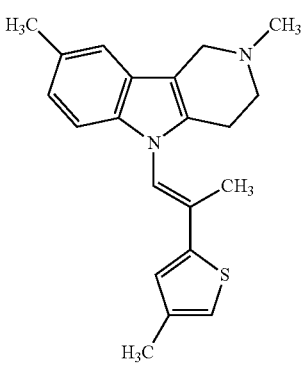
285
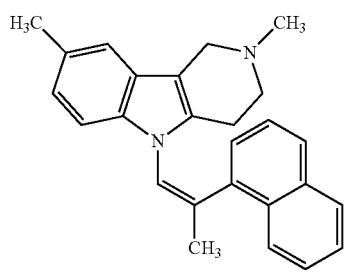 [SMILES: C/C(=C/n1c2c(c3cc(C)ccc31)CN(C)CC2)c1cccc2ccccc12]
286

TABLE 1-continued
Representative Compounds of the Invention
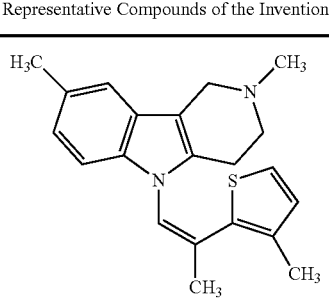
287
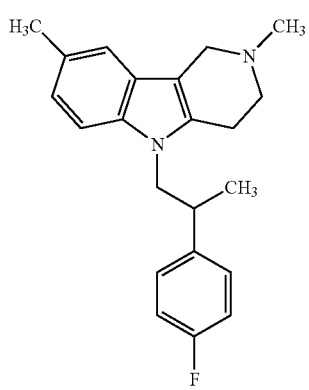
288
288a, 288b
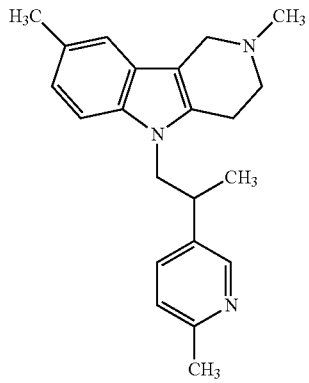
289
289a, 289b
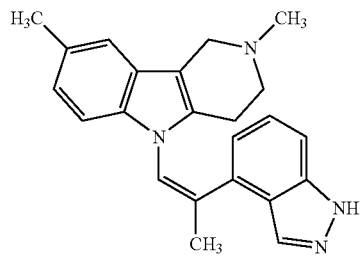
290
TABLE 1-continued
Representative Compounds of the Invention
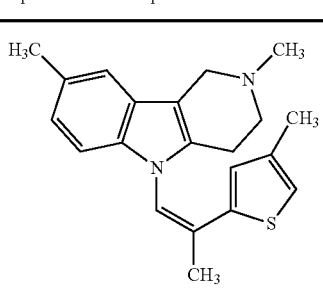
291
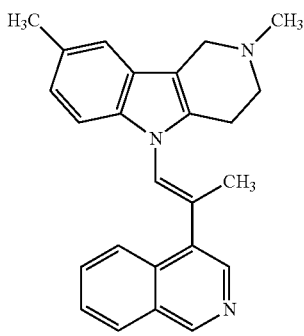
292
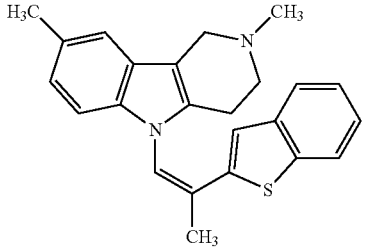 [SMILES: C/C(=C/n1c2c(c3cc(C)ccc31)CN(C)CC2)c1cc2ccccc2s1]
293
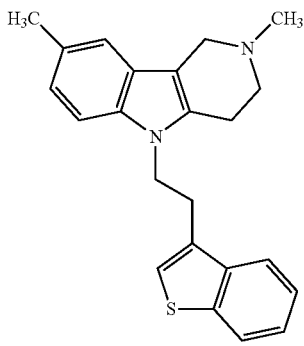 [SMILES: Cc1ccc2c(c1)c1c(n2CCc2csc3ccccc23)CCN(C)C1]
294

TABLE 1-continued

Representative Compounds of the Invention

295

296

297

298

299

300

301

302

303

TABLE 1-continued
Representative Compounds of the Invention
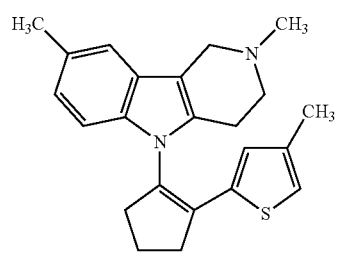
304
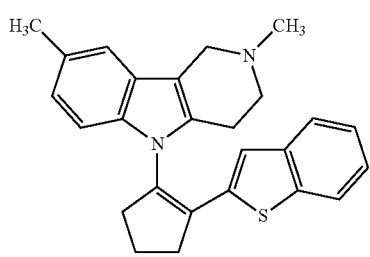 [SMILES: Cc1ccc2c(c1)c1c(n2C2=C(c3cc4ccccc4s3)CCC2)CCN(C)C1]
305
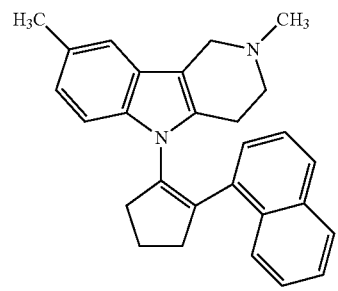 [SMILES: Cc1ccc2c(c1)c1c(n2C2=C(c3cccc4ccccc34)CCC2)CCN(C)C1]
306
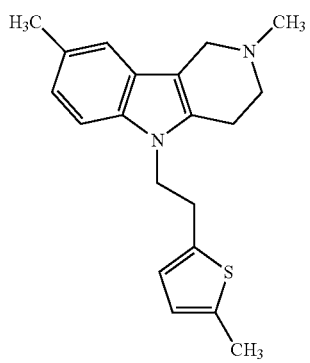
307
TABLE 1-continued
Representative Compounds of the Invention
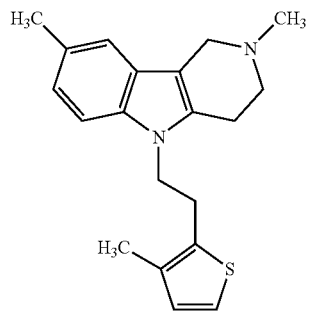
308
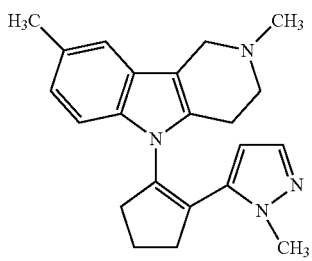 [SMILES: Cc1ccc2c(c1)c1c(n2C2=C(c3ccnn3C)CCC2)CCN(C)C1]
309
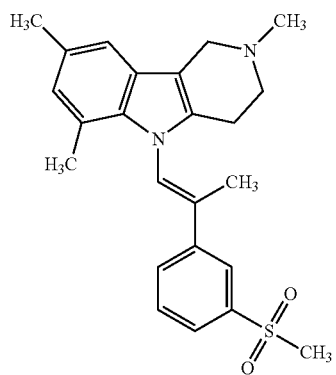
310
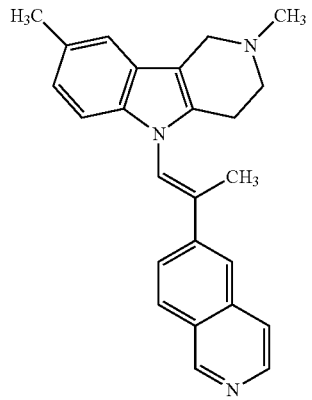
311

TABLE 1-continued

Representative Compounds of the Invention

TABLE 1-continued

Representative Compounds of the Invention

320

321

322

TABLE 1-continued

Representative Compounds of the Invention

323

324

325

TABLE 1-continued
Representative Compounds of the Invention
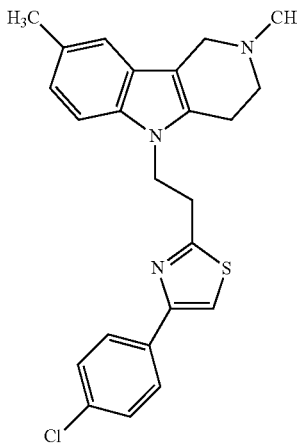
326
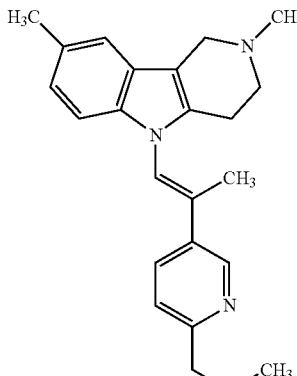
329
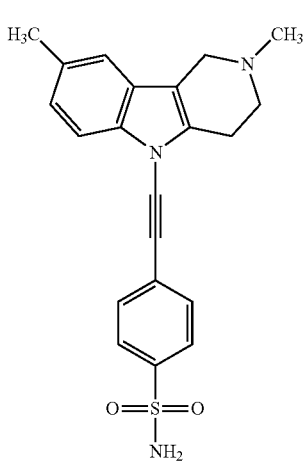
330
327
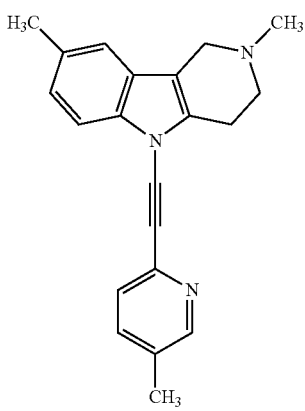
328
TABLE 1-continued
Representative Compounds of the Invention
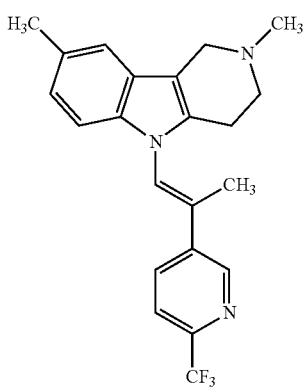
331

TABLE 1-continued
Representative Compounds of the Invention
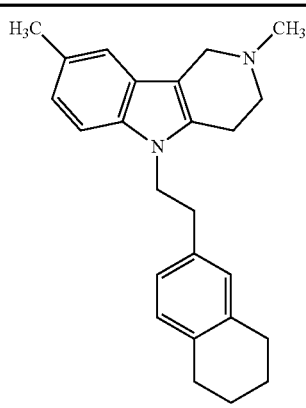
331
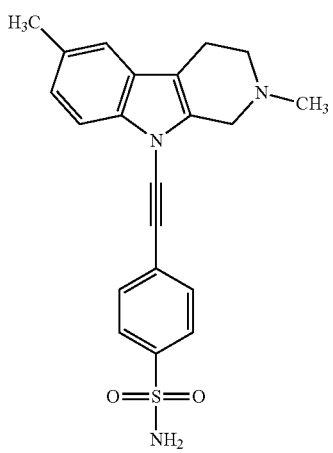
332
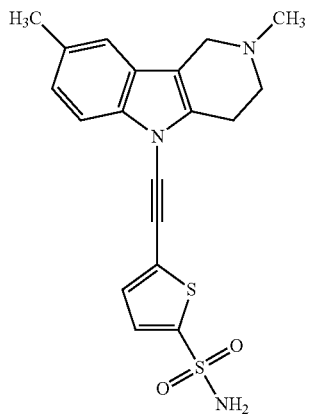
333
TABLE 1-continued
Representative Compounds of the Invention
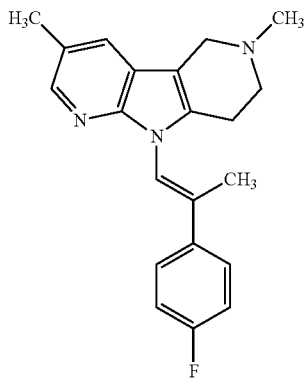
334
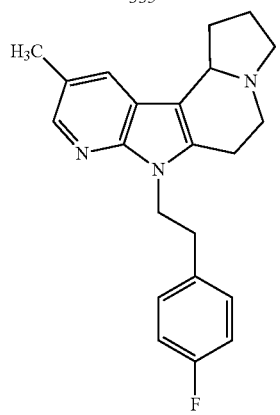
335
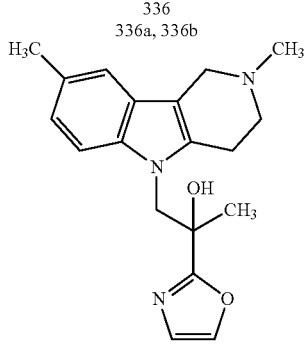
336
336a, 336b
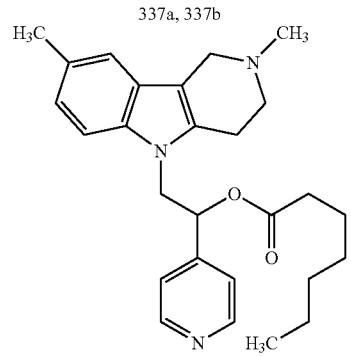
337
337a, 337b
338
338a, 338b TABLE 1-continued
Representative Compounds of the Invention
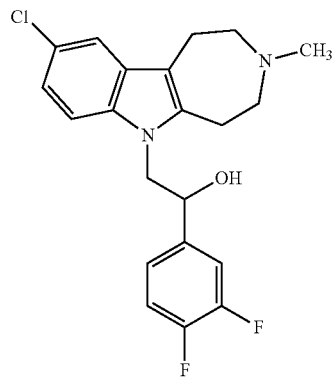 [SMILES: CN1CCc2c(n(CC(O)c3ccc(F)c(F)c3)c3ccc(Cl)cc23)CC1]
339
339a, 339b
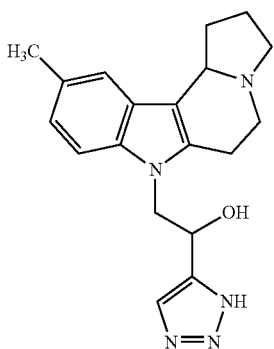
340
340a, 340b, 340c, 340d
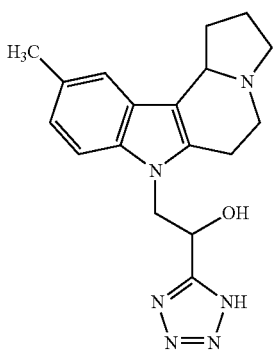 [SMILES: Cc1ccc2c(c1)c1c(n2CC(O)c2nnn[nH]2)CCN2CCCC12]
341
341a, 341b, 341c, 341d
TABLE 1-continued
Representative Compounds of the Invention
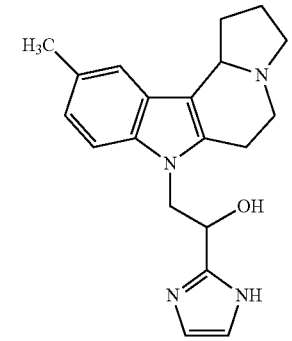 [SMILES: Cc1ccc2c(c1)c1c(n2CC(O)c2ncc[nH]2)CCN2CCCC12]
342
342a, 342b, 342c, 342d
TABLE 2
Representative Compounds of the Invention
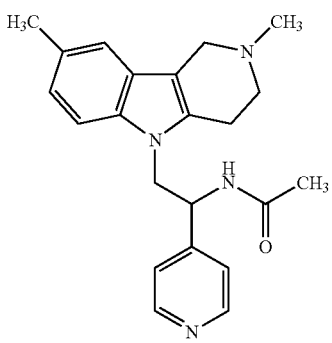 [SMILES: CC(=O)NC(Cn1c2c(c3cc(C)ccc31)CN(C)CC2)c1ccncc1]
II-1
II-1a, II-1b
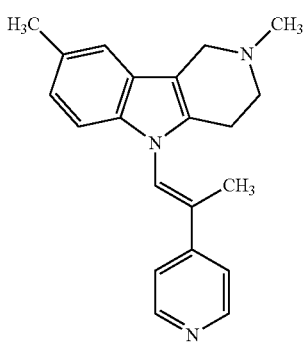
II-2

TABLE 2-continued
Representative Compounds of the Invention
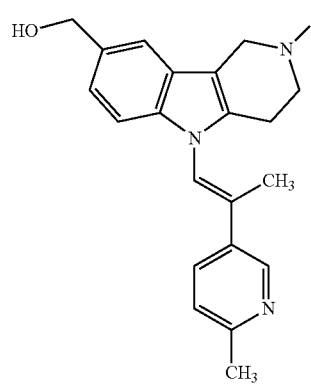
II-3
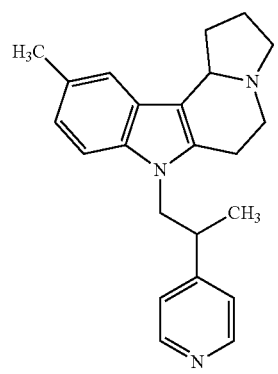
II-4a, II-4b, II-4c, II-4d
II-4
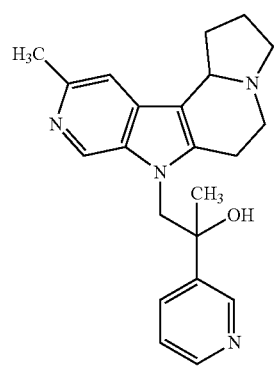
II-5a, II-5 II-5c, II-5d
II-5
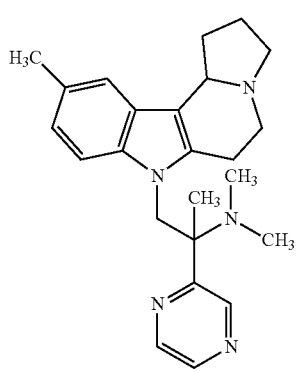 [SMILES: Cc1ccc2c(c1)c1c(n2CC(C)(c2cnccn2)N(C)C)CCN2CCCC12]
II-6a, II-6b, II-6c, II-6d
II-6
TABLE 2-continued
Representative Compounds of the Invention
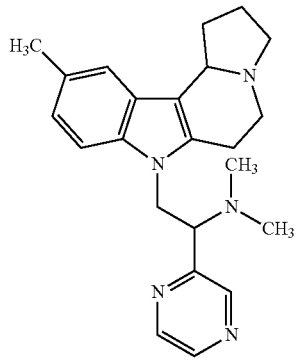 [SMILES: Cc1ccc2c(c1)c1c(n2CC(c2cnccn2)N(C)C)CCN2CCCC12]
II-7a, II-7b, II-7c, II-7d
II-7
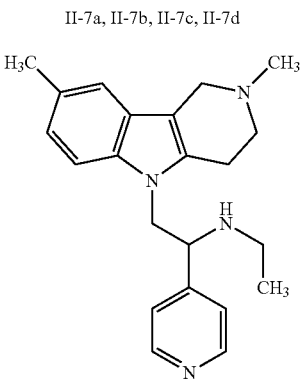
II-8a, II-8b
II-8
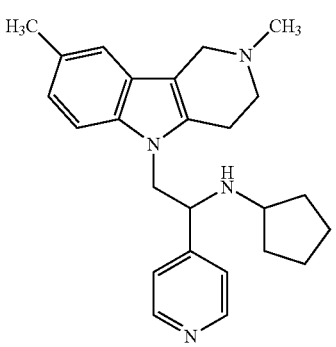 [SMILES: Cc1ccc2c(c1)c1c(n2CC(NC2CCCC2)c2ccncc2)CCN(C)C1]
II-9a, II-9b
II-9
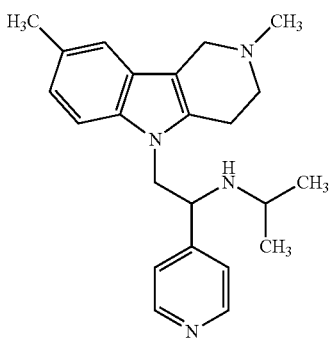 [SMILES: Cc1ccc2c(c1)c1c(n2CC(NC(C)C)c2ccncc2)CCN(C)C1]
II-10a, II-10b
II-10

TABLE 2-continued

Representative Compounds of the Invention

II-11
II-11a, II-11b

II-12
II-12a, II-12b

II-13
II-13a, II-13b

II-14
II-14a, II-14b

II-15
II-15a, II-15b

II-16
II-16a, II-16b

II-17
II-17a, II-17b, II-17c, II-17d

TABLE 2-continued
Representative Compounds of the Invention
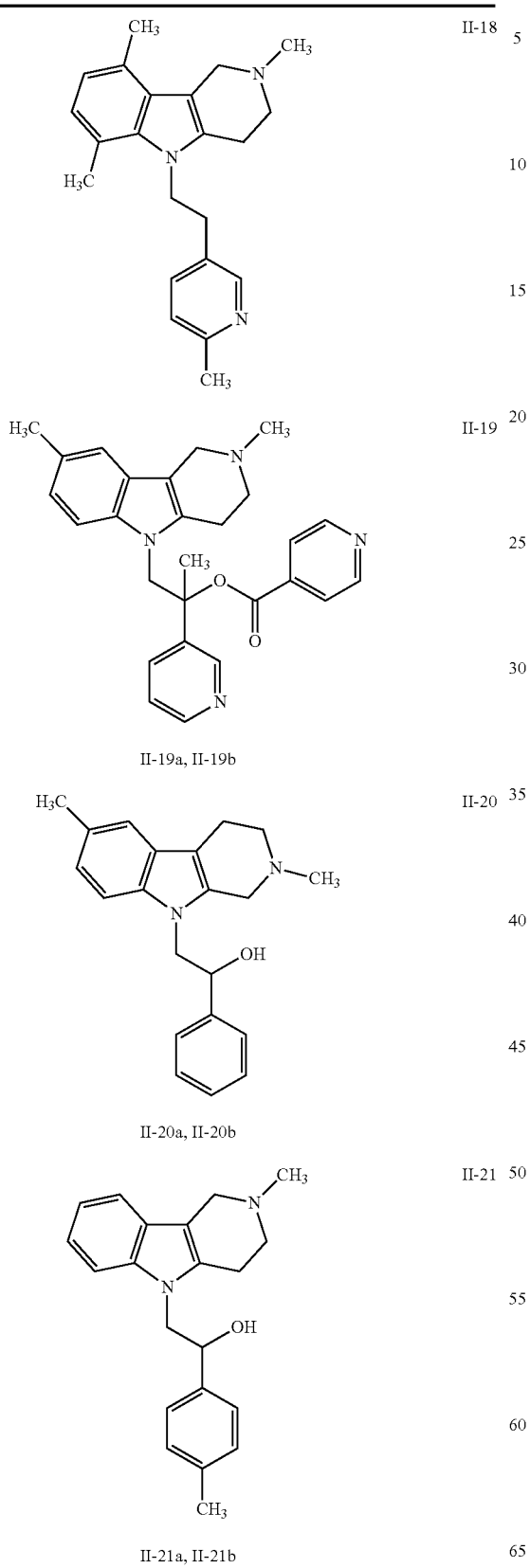
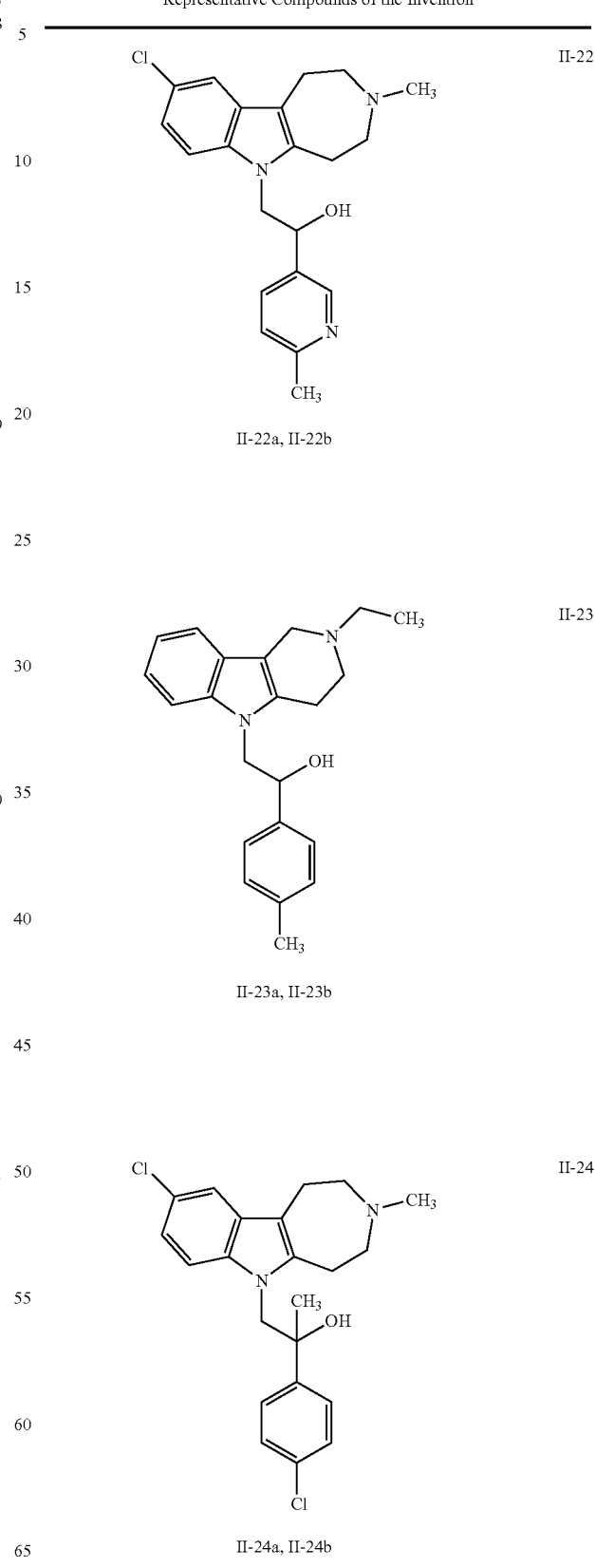

TABLE 2-continued
Representative Compounds of the Invention
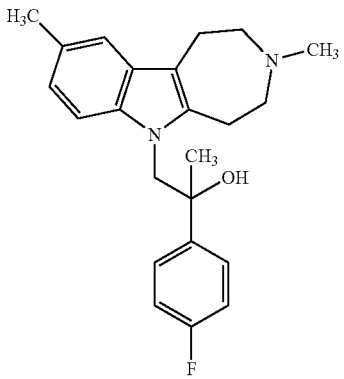
II-25
II-25a, II-25b
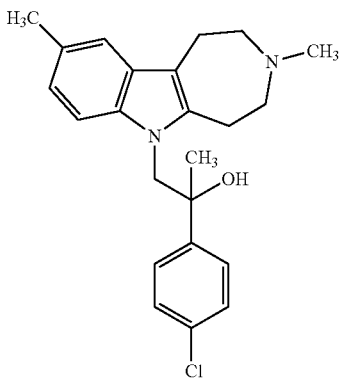
II-26
II-26a, II-26b
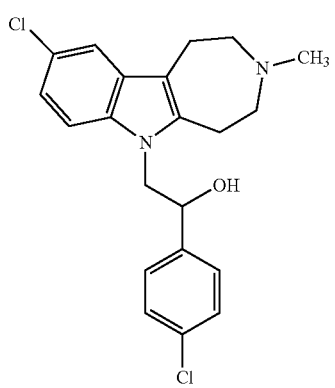 [SMILES: CN1CCc2c(n(CC(O)c3ccc(Cl)cc3)c3ccc(Cl)cc23)CC1]
II-27
II-27a, II-27b
TABLE 2-continued
Representative Compounds of the Invention
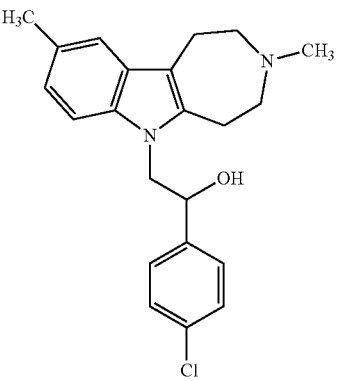
II-28
II-28a, II-28b
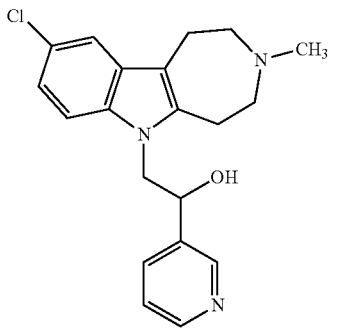 [SMILES: CN1CCc2c(n(CC(O)c3cccnc3)c3ccc(Cl)cc23)CC1]
II-29
II-29a, II-29b
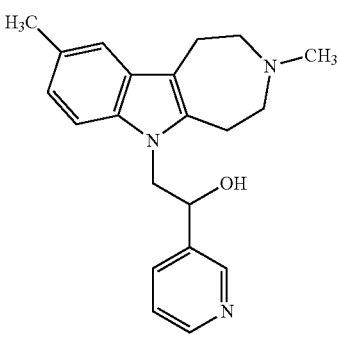
II-30
II-30a, II-30b
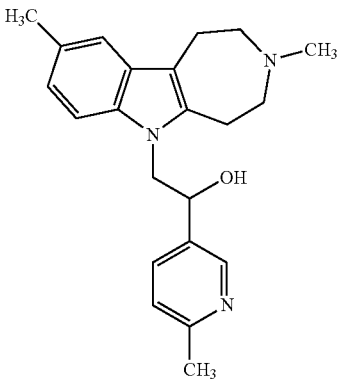
II-31
II-31a, II-31b TABLE 2-continued Representative Compounds of the Invention II-32, II-32a, II-32b II-33, II-33a, II-33b II-34, II-34a, II-34b II-35, II-35a, II-35b II-36, II-36a, II-36b II-37, II-37a, II-37b II-38, II-38a, II-38b

II-39

TABLE 2-continued
Representative Compounds of the Invention
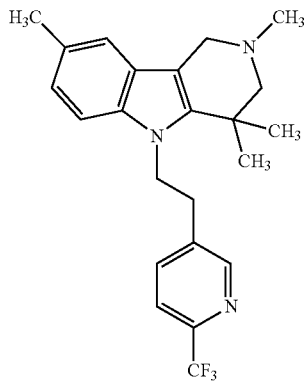
II-40
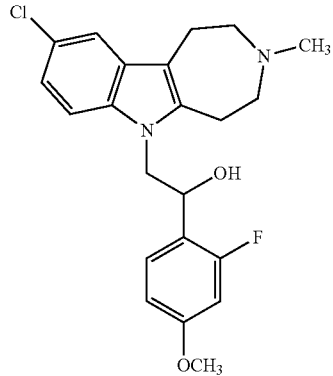
II-43
II-43a, II-43b
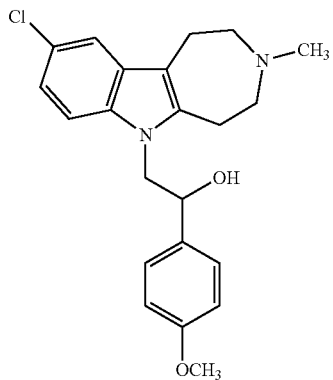 [SMILES: COc1ccc(C(O)Cn2c3c(c4cc(Cl)ccc42)CCN(C)CC3)cc1]
II-41
II-41a, II-41b
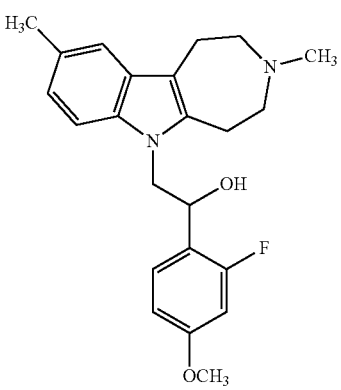
II-44
II-44a, II-44b
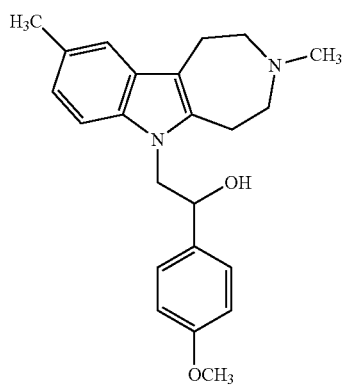
II-42
II-42a, II-42b
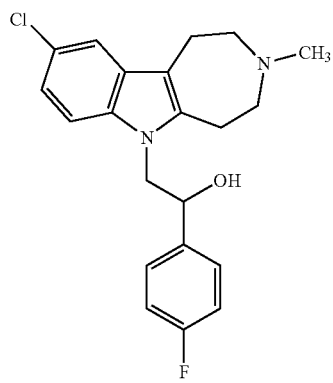 [SMILES: CN1CCc2c(n(CC(O)c3ccc(F)cc3)c3ccc(Cl)cc23)CC1]
II-45
II-45a, II-45b TABLE 2-continued Representative Compounds of the Invention II-46, II-46a, II-46b II-47, II-47a, II-47b II-48, II-48a, II-48b II-49, II-49a, II-49b II-50, II-50a, II-50b II-51, II-51a, II-51b II-52, II-52a, II-52b TABLE 2-continued
Representative Compounds of the Invention
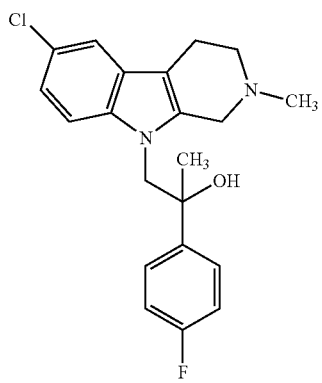 [SMILES: CN1CCc2c(n(CC(C)(O)c3ccc(F)cc3)c3ccc(Cl)cc23)C1]
II-53
II-53a, II-53b
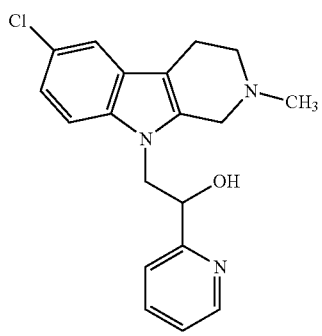 [SMILES: CN1CCc2c(n(CC(O)c3ccccn3)c3ccc(Cl)cc23)C1]
II-54
II-54a, II-54b
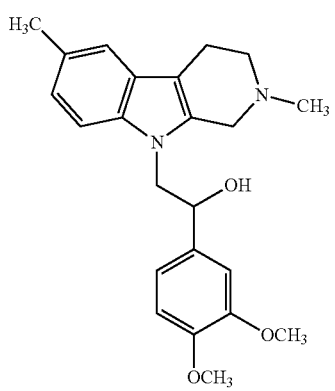
II-55
II-55a, II-55b
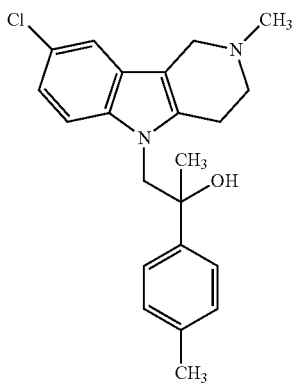 [SMILES: Cc1ccc(C(C)(O)Cn2c3c(c4cc(Cl)ccc42)CN(C)CC3)cc1]
II-56
II-56a, II-56b
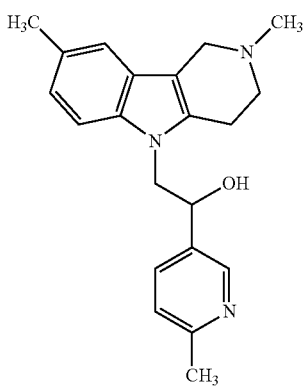
II-57
II-57a, II-57b
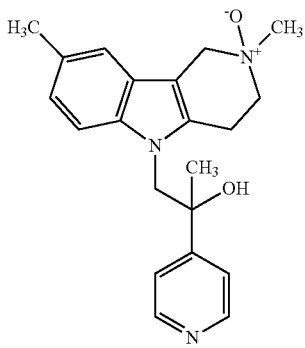
II-58
II-58a, II-58b TABLE 2-continued
Representative Compounds of the Invention
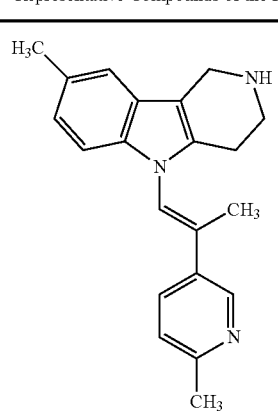
II-59
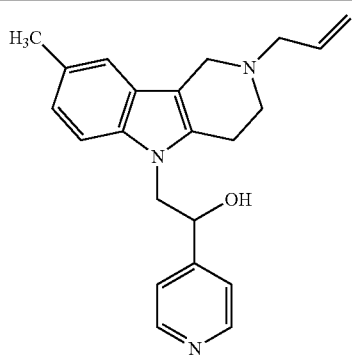
II-63
II-63a, II-63b
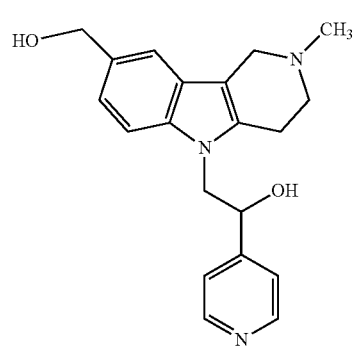 [SMILES: CN1CCc2c(c3cc(CO)ccc3n2CC(O)c2ccncc2)C1]
II-60
II-60a, II-60b
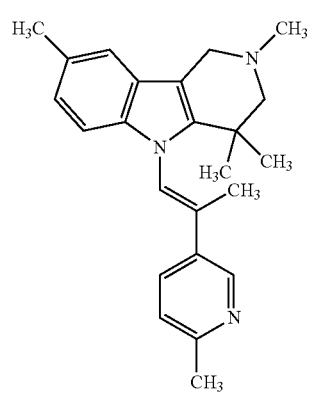
II-61
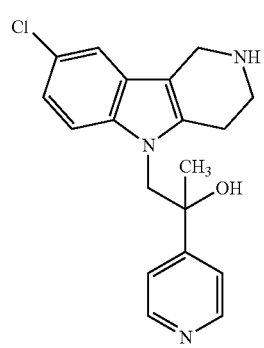 [SMILES: CC(O)(Cn1c2c(c3cc(Cl)ccc31)CNCC2)c1ccncc1]
II-62
II-62a, II-62b

TABLE 2-continued
Representative Compounds of the Invention
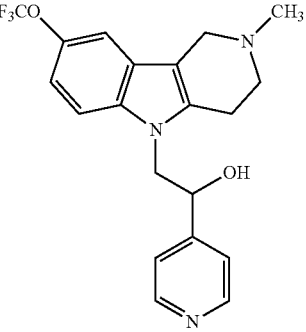 [SMILES: CN1CCc2c(c3cc(OC(F)(F)F)ccc3n2CC(O)c2ccncc2)C1]
II-67
II-67a, II-67b
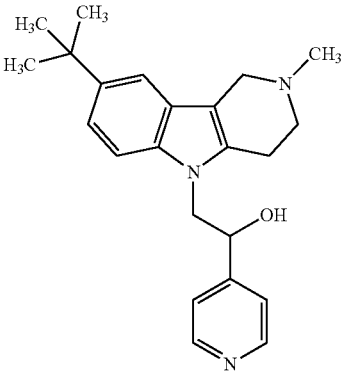 [SMILES: CN1CCc2c(c3cc(C(C)(C)C)ccc3n2CC(O)c2ccncc2)C1]
II-68
II-68a, II-68b
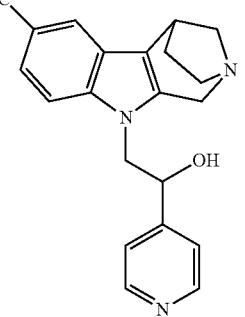
II-69
II-69a, II-69b, II-69c, II-69d
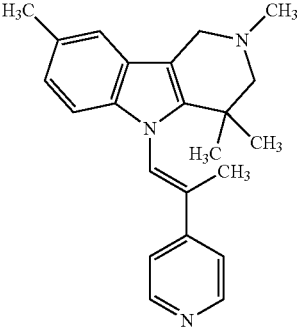
II-70
TABLE 2-continued
Representative Compounds of the Invention
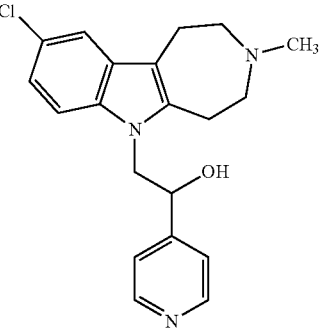
II-71
II-71a, II-71b
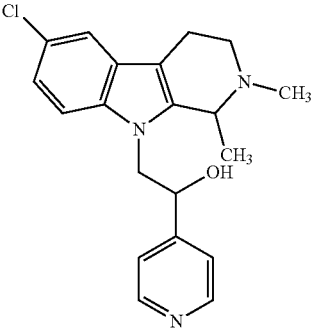 [SMILES: CC1c2c(c3cc(Cl)ccc3n2CC(O)c2ccncc2)CCN1C]
II-72
II-72a, II-72b, II-72c, II-72d
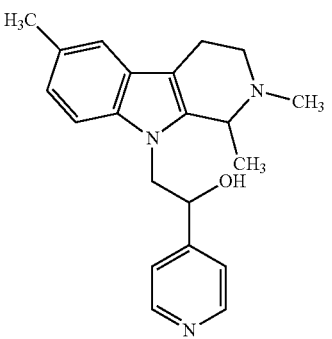
II-73
II-73a, II-73b, II-73c, II-73d
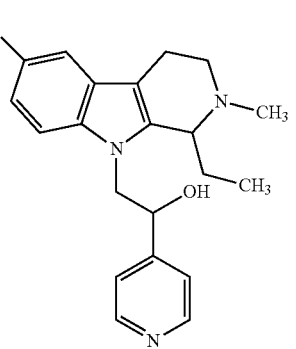
II-74
II-74a, II-74b, II-74c, II-74d TABLE 2-continued
Representative Compounds of the Invention
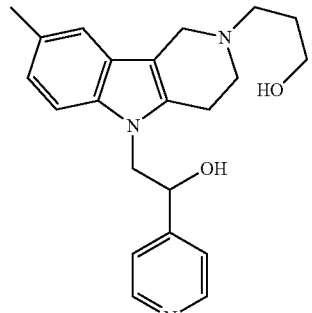
II-75
II-75a, II-75b
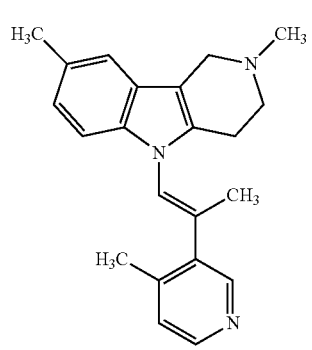
II-76
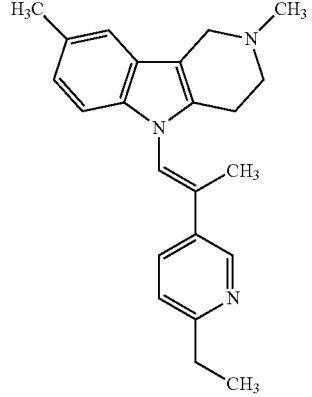
II-77
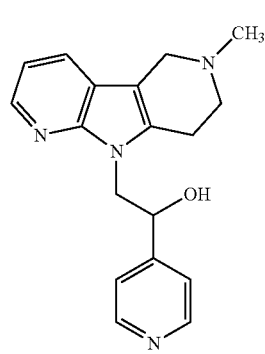 [SMILES: CN1CCc2c(c3cccnc3n2CC(O)c2ccncc2)C1]
II-78
II-78a, II-78b
TABLE 2-continued
Representative Compounds of the Invention
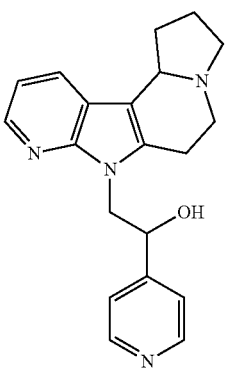 [SMILES: OC(Cn1c2c(c3cccnc31)C1CCCN1CC2)c1ccncc1]
II-79
II-79a, II-79b, II-79c, II-79d
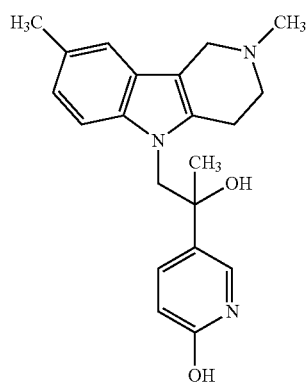
II-80
II-80a, II-80b
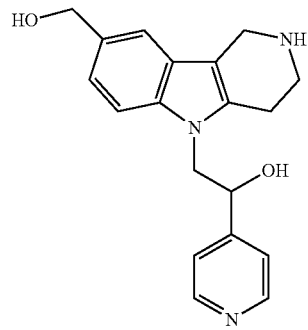 [SMILES: OCc1ccc2c(c1)c1c(n2CC(O)c2ccncc2)CCNC1]
II-81
II-81a, II-81b
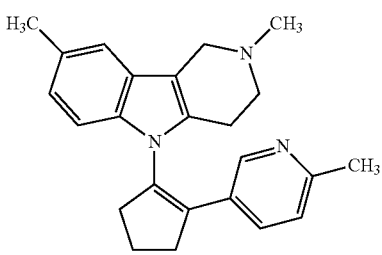
II-82

TABLE 2-continued
Representative Compounds of the Invention
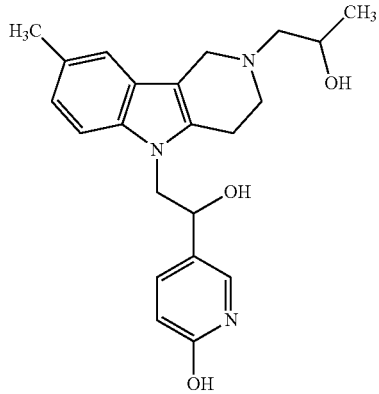 [SMILES: Cc1ccc2c(c1)c1c(n2CC(O)c2ccc(O)nc2)CCN(CC(C)O)C1]
II-83
II-83a, II-83b, II-83c, II-83d
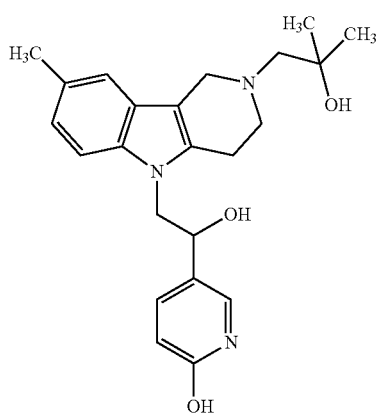 [SMILES: Cc1ccc2c(c1)c1c(n2CC(O)c2ccc(O)nc2)CCN(CC(C)(C)O)C1]
II-84
II-84a, II-84b
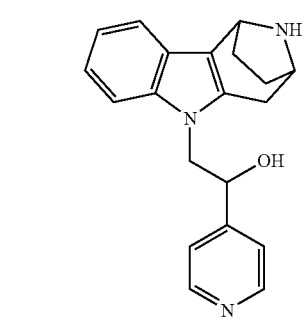 [SMILES: OC(Cn1c2c(c3ccccc31)C1CCC(C2)N1)c1ccncc1]
II-85
II-85a, II-85b, II-85c, II-85d
TABLE 2-continued
Representative Compounds of the Invention
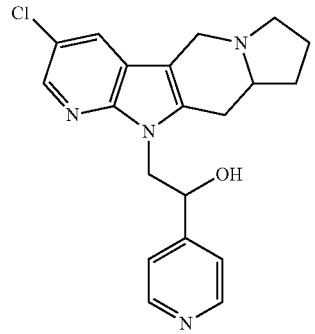 [SMILES: OC(Cn1c2c(c3cc(Cl)cnc31)CN1CCCC1C2)c1ccncc1]
II-86
II-86a, II-86b, II-86c, II-86d
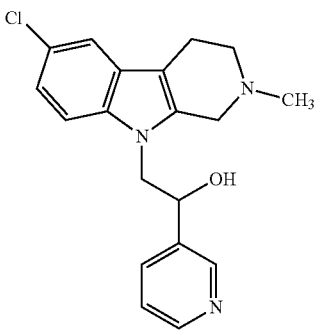 [SMILES: CN1CCc2c(n(CC(O)c3cccnc3)c3ccc(Cl)cc23)C1]
II-87
II-87a, II-87b
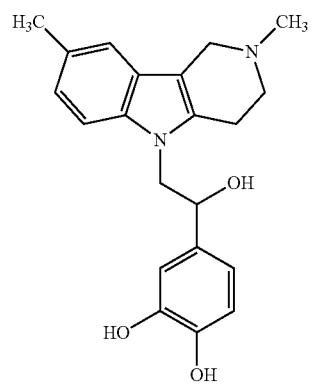
II-88
II-88a, II-88b
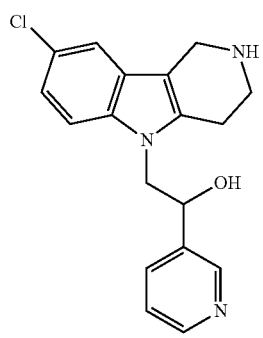 [SMILES: OC(Cn1c2c(c3cc(Cl)ccc31)CNCC2)c1cccnc1]
II-89
II-89a, II-89b TABLE 2-continued
Representative Compounds of the Invention
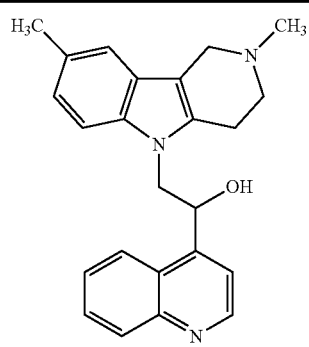
II-90
II-90a, II-90b
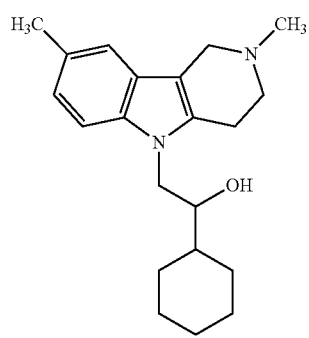
II-91
II-91a, II-91b
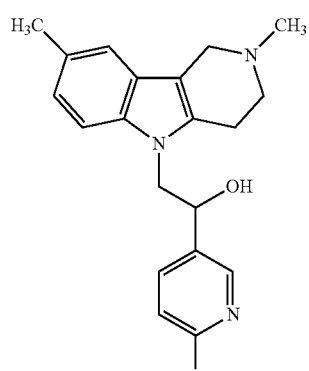
II-92
II-92a, II-92b
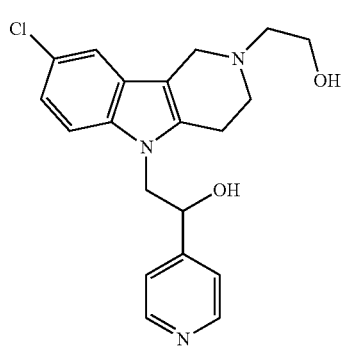 [SMILES: OCCN1CCc2c(c3cc(Cl)ccc3n2CC(O)c2ccncc2)C1]
II-93
II-93a, II-93b
TABLE 2-continued
Representative Compounds of the Invention
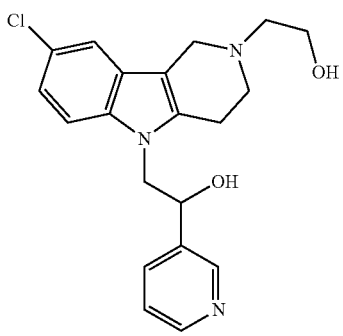 [SMILES: OCCN1CCc2c(c3cc(Cl)ccc3n2CC(O)c2cccnc2)C1]
II-94
II-94a, II-94b
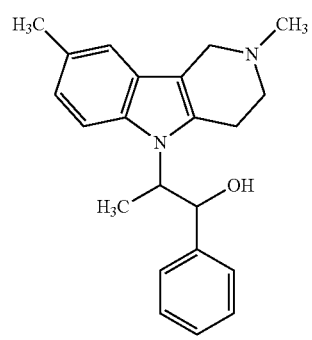
II-95
II-95a, II-95b, II-95c, II-95d
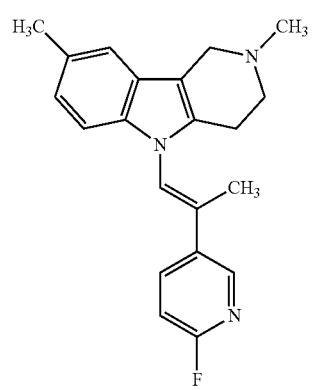
II-96
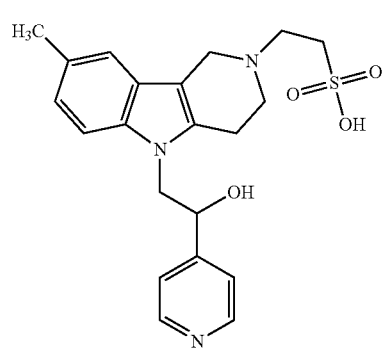 [SMILES: Cc1ccc2c(c1)c1c(n2CC(O)c2ccncc2)CCN(CCS(=O)(=O)O)C1]
II-97
II-97a, II-97b TABLE 2-continued
Representative Compounds of the Invention
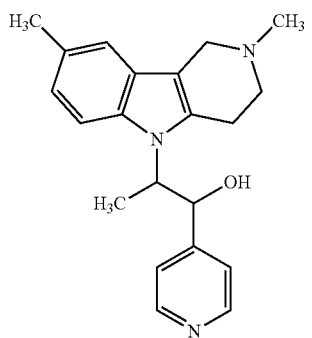
II-98
II-98a, II-98b, II-98c, II-98d
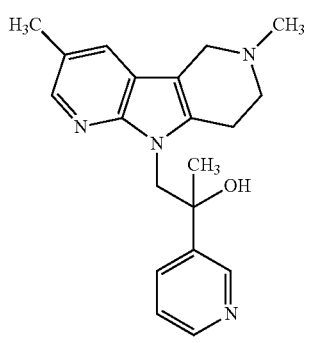
II-99
II-99a, II-99b
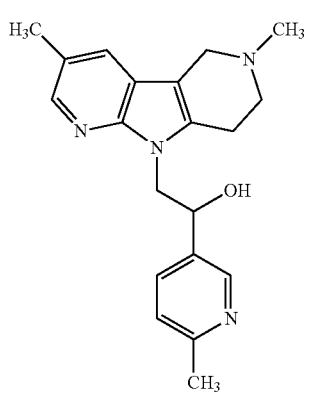
II-100
II-100a, II-100b
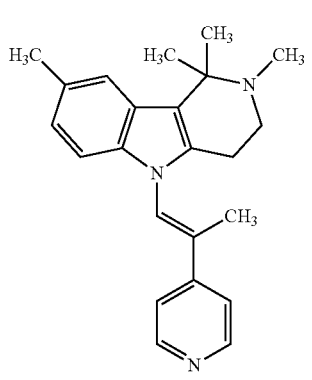
II-101
TABLE 2-continued
Representative Compounds of the Invention
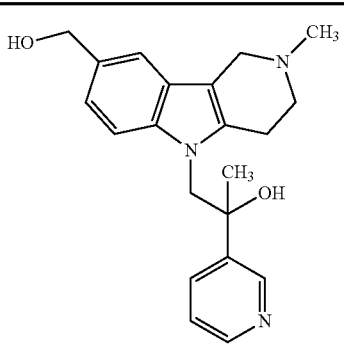
II-102
II-102a, II-102b
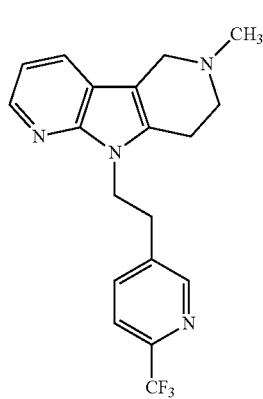 [SMILES: CN1CCc2c(c3cccnc3n2CCc2ccc(C(F)(F)F)nc2)C1]
II-103
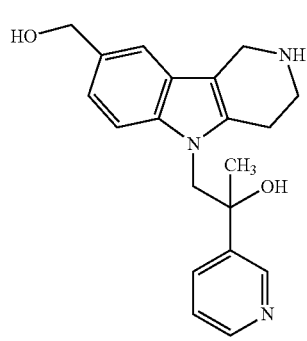 [SMILES: CC(O)(Cn1c2c(c3cc(CO)ccc31)CNCC2)c1cccnc1]
II-104
II-104a, II-104b
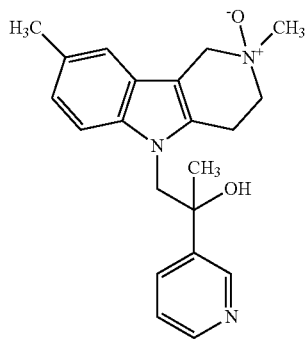
II-105
II-105a, II-105b TABLE 2-continued
Representative Compounds of the Invention
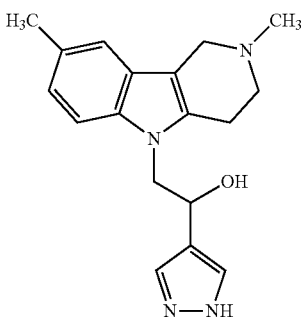
II-106
II-106a, II-106b
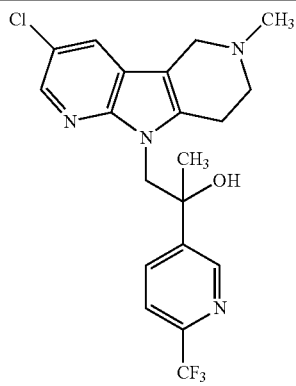
II-109
II-109a, II-109b
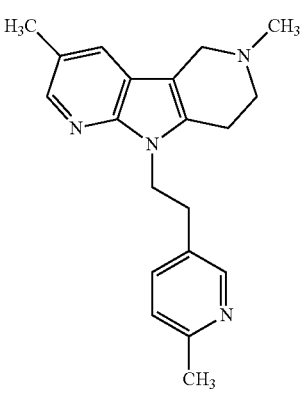
II-110
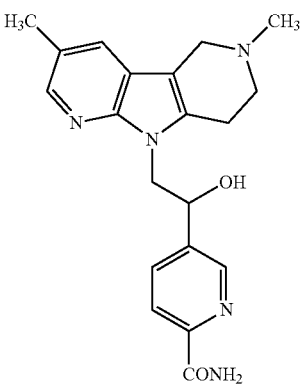
II-111
II-111a, II-111b
II-107
II-107a, II-107b, II-107c, II-107d
II-108
II-108a, II-108b
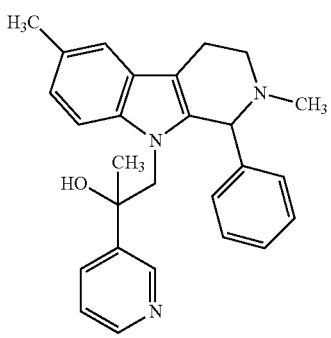
II-112
II-112a, II-112b, II-112c, II-112d TABLE 2-continued
Representative Compounds of the Invention
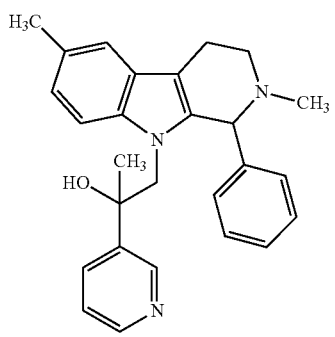
II-113
II-113a, II-113b, II-113c, II-113d
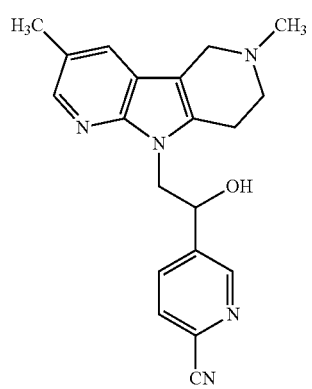
II-114
II-114a, II-114b
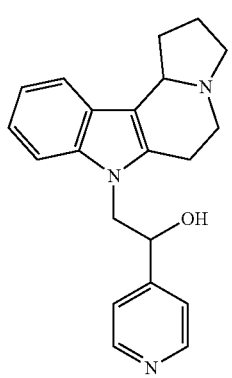 [SMILES: OC(Cn1c2c(c3ccccc31)C1CCCN1CC2)c1ccncc1]
II-115
II-115a, II-115b, II-115c, II-115d
TABLE 2-continued
Representative Compounds of the Invention
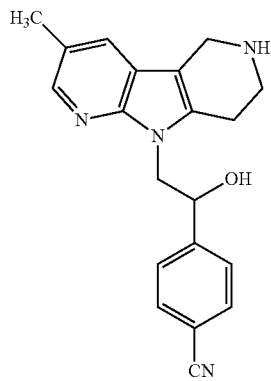 [SMILES: Cc1cnc2c(c1)c1c(n2CC(O)c2ccc(C#N)cc2)CCNC1]
II-116
II-116a, II-116b
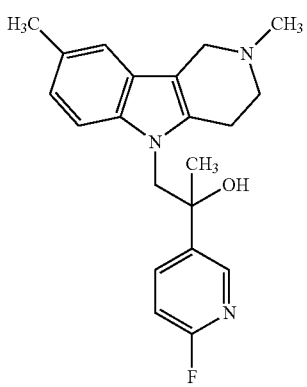
II-117
II-117a, II-117b
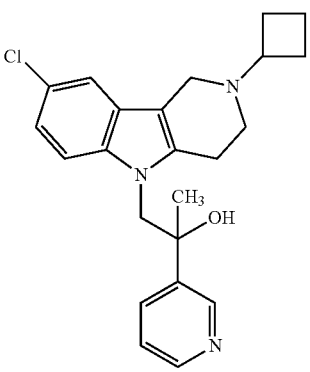 [SMILES: CC(O)(Cn1c2c(c3cc(Cl)ccc31)CN(C1CCC1)CC2)c1cccnc1]
II-118
II-118a, II-118b TABLE 2-continued Representative Compounds of the Invention

II-119

II-120

II-120a, II-120b, II-120c, II-120d

II-121

II-121a, II-121b, II-121c, II-121d

II-122

II-122a, II-122b, II-122c, II-122d

II-123

II-123a, II-123b

II-124

II-124a, II-124b

II-125

II-125a, II-125b, II-125c, II-125d

TABLE 2-continued
Representative Compounds of the Invention
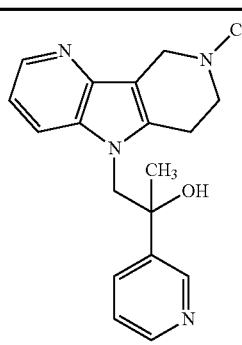
II-126
II-126a, II-126b
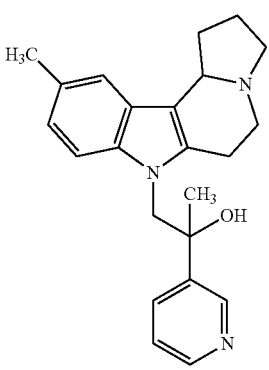 [SMILES: Cc1ccc2c(c1)c1c(n2CC(C)(O)c2cccnc2)CCN2CCCC12]
II-127
II-127a, II-127b, II-127c, II-127d
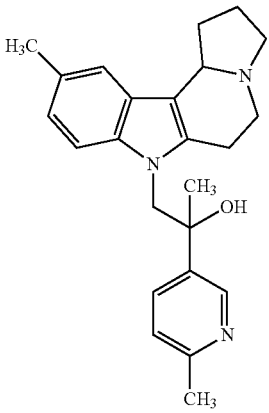 [SMILES: Cc1ccc2c(c1)c1c(n2CC(C)(O)c2ccc(C)nc2)CCN2CCCC12]
II-128
II-128a, II-128b, II-128c, II-128d
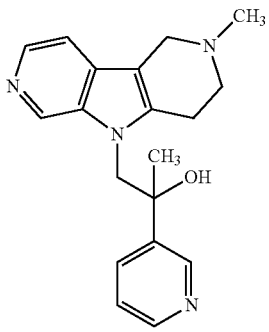 [SMILES: CN1CCc2c(c3ccncc3n2CC(C)(O)c2cccnc2)C1]
II-129
II-129a, II-129b
TABLE 2-continued
Representative Compounds of the Invention
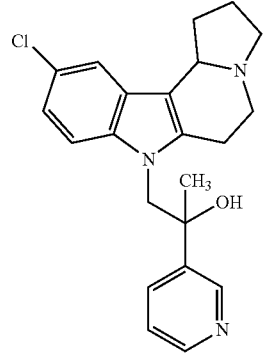 [SMILES: CC(O)(Cn1c2c(c3cc(Cl)ccc31)C1CCCN1CC2)c1cccnc1]
II-130
II-130a, II-130b, II-130c, II-130d
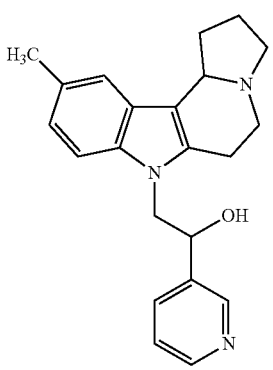
II-131
II-131a, II-131b, II-131c, II-131d
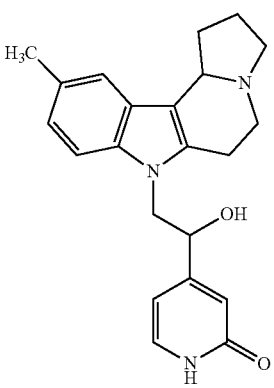 [SMILES: Cc1ccc2c(c1)c1c(n2CC(O)c2cc[nH]c(=O)c2)CCN2CCCC12]
II-132
II-132a, II-132b, II-132c, II-132d TABLE 2-continued
Representative Compounds of the Invention
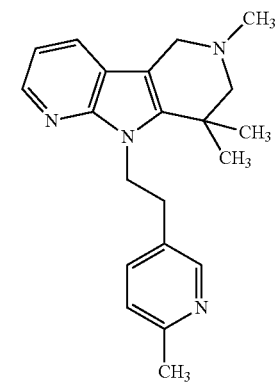 [SMILES: Cc1ccc(CCn2c3c(c4cccnc42)CN(C)CC3(C)C)cn1]
II-133
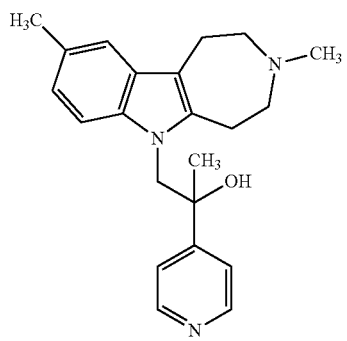
II-134
II-134a, II-134b
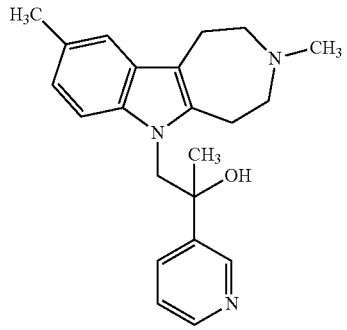
II-135
II-135a, II-135b
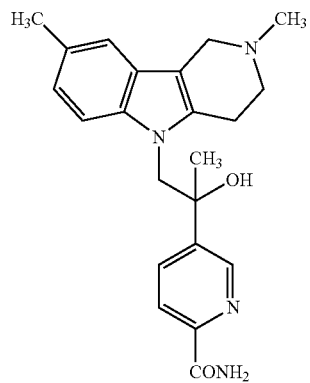
II-136
II-136a, II-136b
TABLE 2-continued
Representative Compounds of the Invention
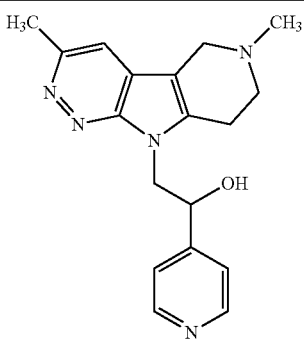
II-137
II-137a, II-137b
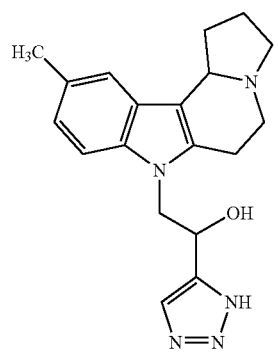 [SMILES: Cc1ccc2c(c1)c1c(n2CC(O)c2cnc[nH]2)CCN2CCCC12]
II-138
II-138a, II-138b, II-138c, II-138d
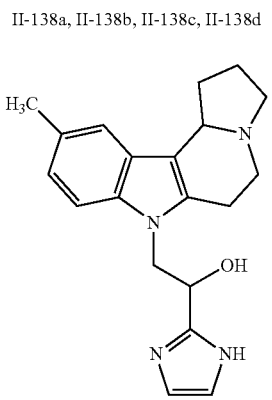
II-139
II-139a, II-139b, II-139c, II-139d
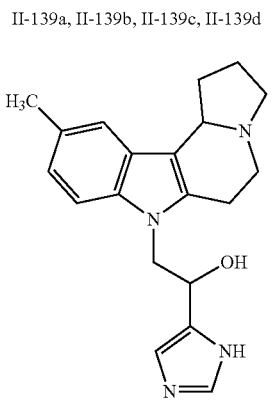
II-140
II-140a, II-140b, II-140c, II-140d TABLE 2-continued Representative Compounds of the Invention

| Compound | ID |
|---|---|
| (structure) | II-141, II-141a, II-141b |
| (structure) | II-142, II-142a, II-142b |
| (structure) | II-143, II-143a, II-143b |
| (structure) | II-144 |
| (structure) | II-145, II-145a, II-145b |
| (structure) | II-146, II-146a, II-146b, II-146c, II-146d |
| (structure) | II-147, II-147a, II-147b, II-147c, II-147d |
| (structure) | II-148, II-148a, II-148b |

TABLE 2-continued
Representative Compounds of the Invention
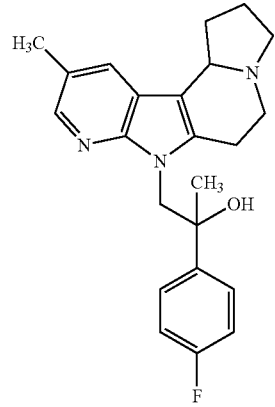 [SMILES: Cc1cnc2c(c1)c1c(n2CC(C)(O)c2ccc(F)cc2)CCN2CCCC12]
II-149
II-149a, II-149b, II-149c, II-149d
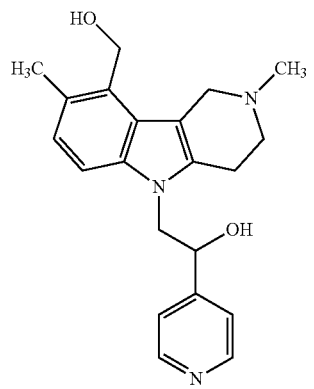
II-150
II-150a, II-150b, II-150c, II-150d
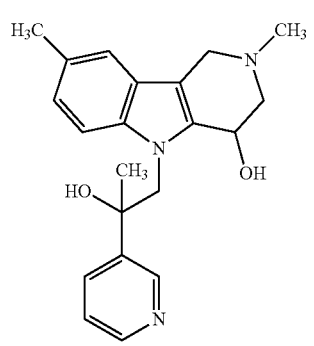
II-151
II-151a, II-151b, II-151c, II-151d
TABLE 2-continued
Representative Compounds of the Invention
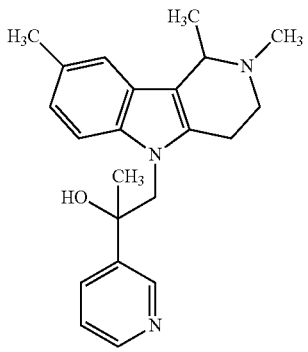
II-152
II-152a, II-152b, II-152c, II-152d
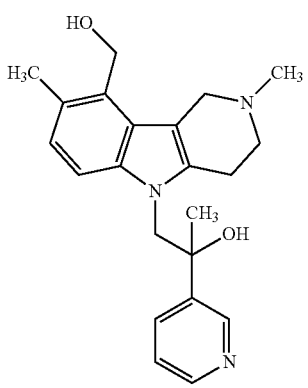
II-153
II-153a, II-153b
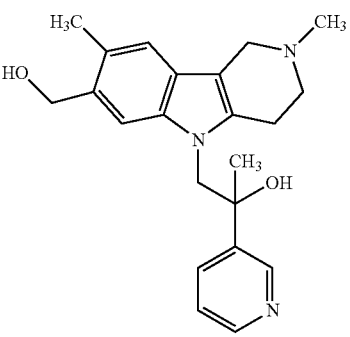 [SMILES: Cc1cc2c3c(n(CC(C)(O)c4cccnc4)c2cc1CO)CCN(C)C3]
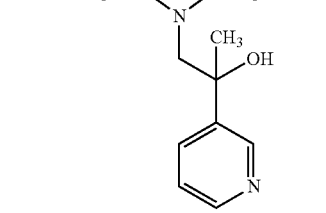
II-154
II-154a, II-154b
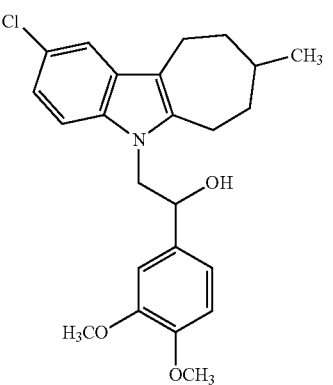 [SMILES: COc1ccc(C(O)Cn2c3c(c4cc(Cl)ccc42)CCC(C)CC3)cc1OC]
II-155
II-155a, II-155b TABLE 2-continued
Representative Compounds of the Invention
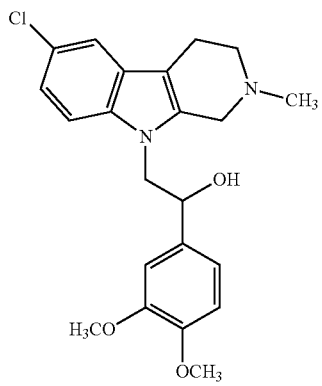 [SMILES: COc1ccc(C(O)Cn2c3c(c4cc(Cl)ccc42)CCN(C)C3)cc1OC]
II-156
II-156a, II-156b
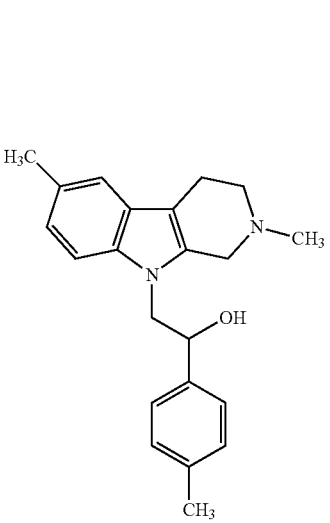
II-157
II-157a, II-157b
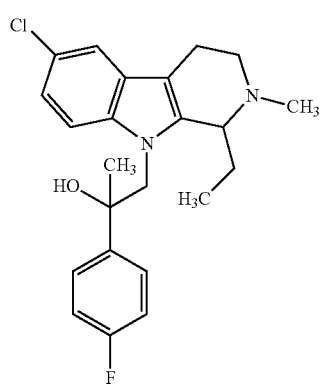 [SMILES: CCC1c2c(c3cc(Cl)ccc3n2CC(C)(O)c2ccc(F)cc2)CCN1C]
II-158
II-158a, II-158b
TABLE 2-continued
Representative Compounds of the Invention
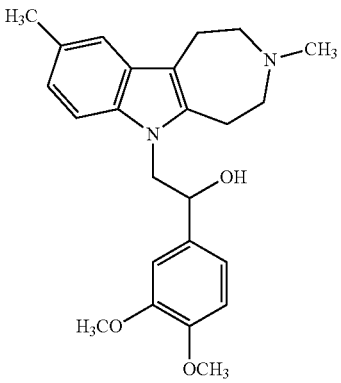
II-159
II-159a, II-159b
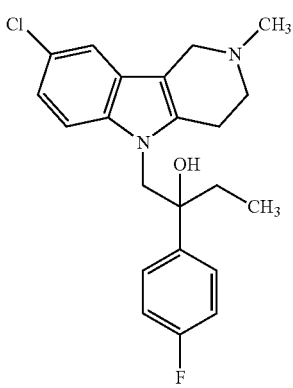 [SMILES: CCC(O)(Cn1c2c(c3cc(Cl)ccc31)CN(C)CC2)c1ccc(F)cc1]
II-160
II-160a, II-160b
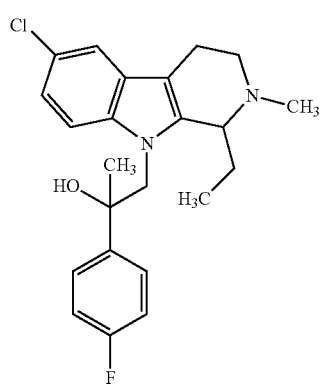 [SMILES: CCC1c2c(c3cc(Cl)ccc3n2CC(C)(O)c2ccc(F)cc2)CCN1C]
II-161
II-161a, II-161b, II-161c, II-161d

TABLE 2-continued
Representative Compounds of the Invention
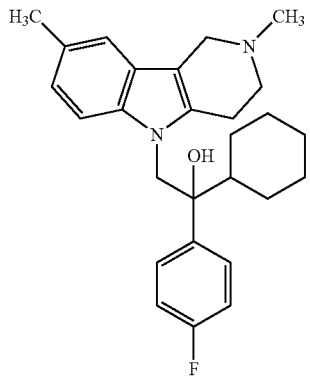 [SMILES: Cc1ccc2c(c1)c1c(n2CC(O)(c2ccc(F)cc2)C2CCCCC2)CCN(C)C1]
II-162
II-162a, II-162b
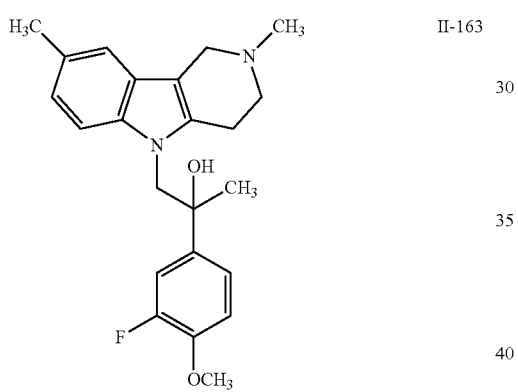
II-163
II-163a, II-163b
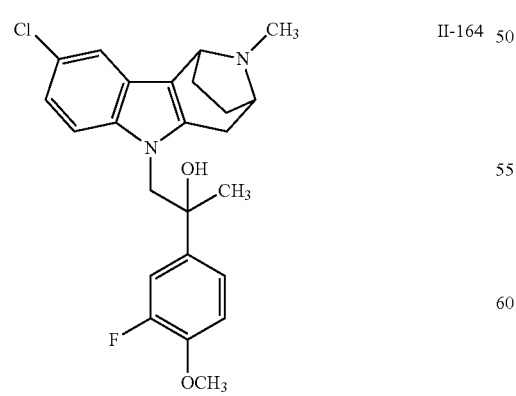
II-164
II-164a, II-164b, II-164c, II-164d
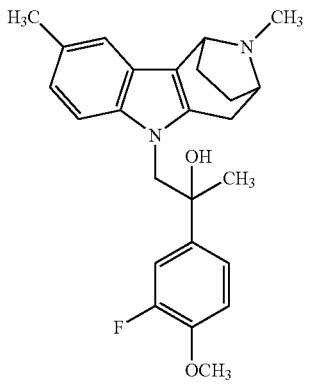
II-165
II-165a, II-165b, II-165c, II-165d
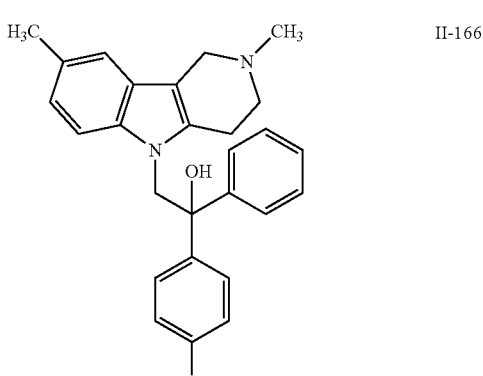
II-166
II-166a, II-166b
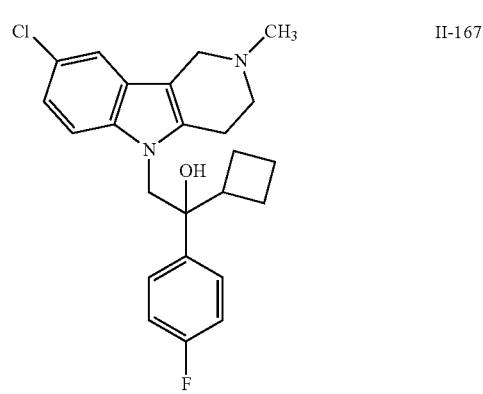
II-167
II-167a, II-167b TABLE 2-continued
Representative Compounds of the Invention
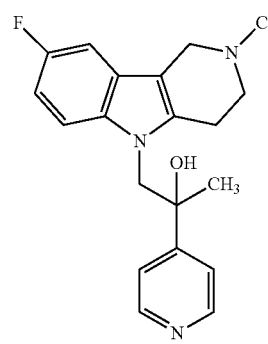
II-168
II-168a, II-168b
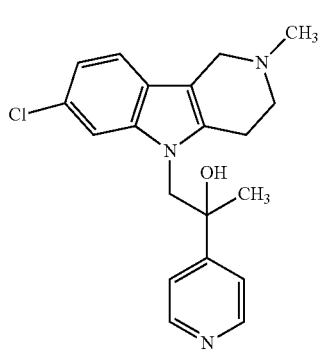 [SMILES: CN1CCc2c(c3ccc(Cl)cc3n2CC(C)(O)c2ccncc2)C1]
II-169
II-169a, II-169b
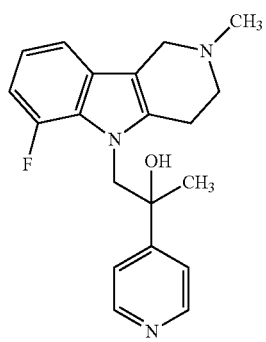 [SMILES: CN1CCc2c(c3cccc(F)c3n2CC(C)(O)c2ccncc2)C1]
II-170
II-170a, II-170b
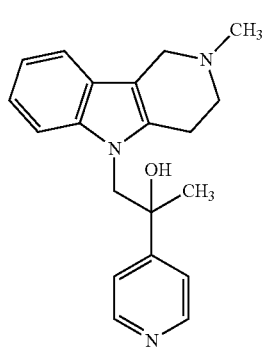 [SMILES: CN1CCc2c(c3ccccc3n2CC(C)(O)c2ccncc2)C1]
II-171
II-171a, II-171b
TABLE 2-continued
Representative Compounds of the Invention
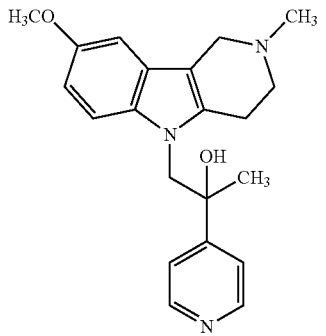 [SMILES: COc1ccc2c(c1)c1c(n2CC(C)(O)c2ccncc2)CCN(C)C1]
II-172
II-172a, II-172b
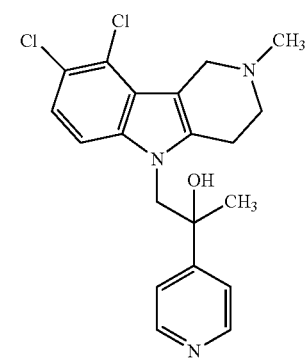 [SMILES: CN1CCc2c(c3c(Cl)c(Cl)ccc3n2CC(C)(O)c2ccncc2)C1]
II-173
II-173a, II-173b
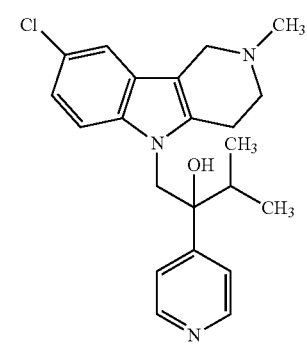 [SMILES: CC(C)C(O)(Cn1c2c(c3cc(Cl)ccc31)CN(C)CC2)c1ccncc1]
II-174
II-174a, II-174b
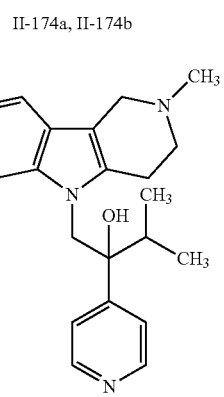
II-175
II-175a, II-175b TABLE 2-continued
Representative Compounds of the Invention
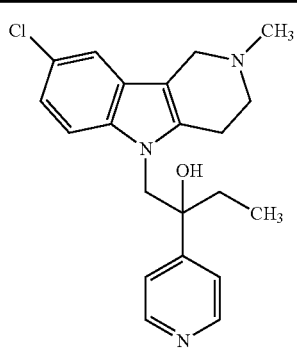
II-176
II-176a, II-176b
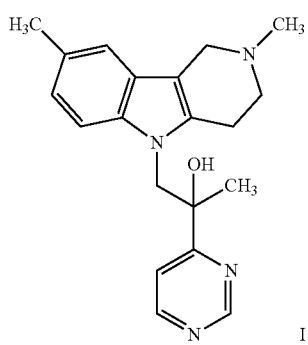
I-177
II-177a, II-177b
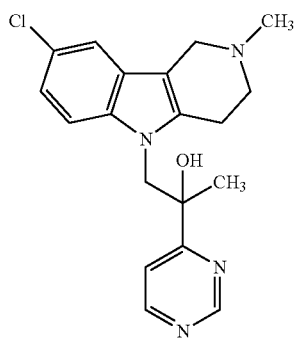 [SMILES: CN1CCc2c(c3cc(Cl)ccc3n2CC(C)(O)c2ccncn2)C1]
II-178
II-178a, II-178b
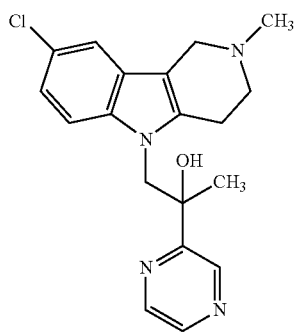 [SMILES: CN1CCc2c(c3cc(Cl)ccc3n2CC(C)(O)c2cnccn2)C1]
II-179
II-179a, II-179b
TABLE 2-continued
Representative Compounds of the Invention
II-180
II-180a, II-180b
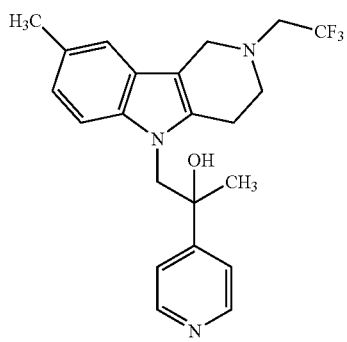 [SMILES: Cc1ccc2c(c1)c1c(n2CC(C)(O)c2ccncc2)CCN(CC(F)(F)F)C1]
II-181
II-181a, II-181b
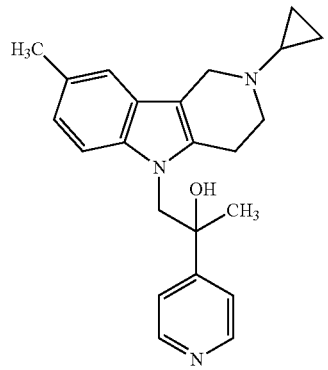 [SMILES: Cc1ccc2c(c1)c1c(n2CC(C)(O)c2ccncc2)CCN(C2CC2)C1]
II-182
II-182a, II-182b
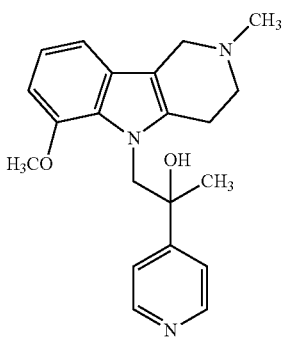 [SMILES: COc1cccc2c3c(n(CC(C)(O)c4ccncc4)c12)CCN(C)C3]
II-183
II-183a, II-183b TABLE 2-continued
Representative Compounds of the Invention
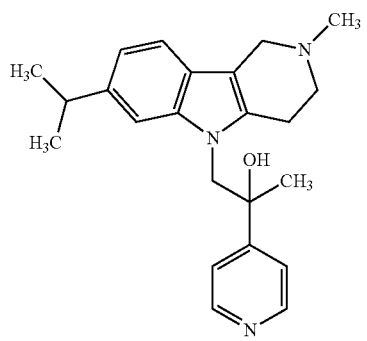 [SMILES: CC(C)c1ccc2c3c(n(CC(C)(O)c4ccncc4)c2c1)CCN(C)C3]
II-184
II-184a, II-184b
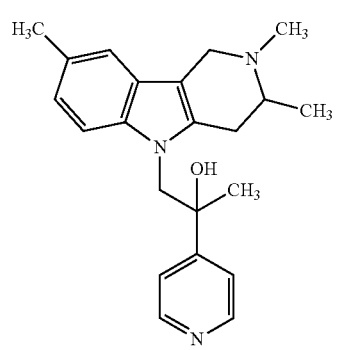
II-185
II-185a, II-185b, II-185c, II-185d
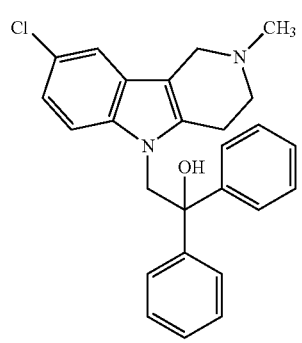 [SMILES: CN1CCc2c(c3cc(Cl)ccc3n2CC(O)(c2ccccc2)c2ccccc2)C1]
II-186
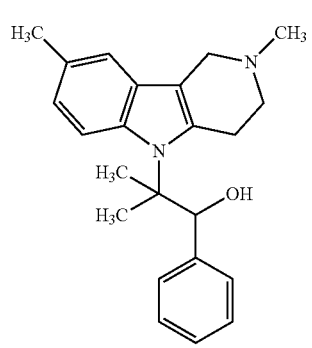
II-187
II-187a, II-187b
TABLE 2-continued
Representative Compounds of the Invention
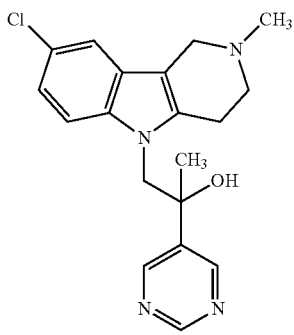 [SMILES: CN1CCc2c(c3cc(Cl)ccc3n2CC(C)(O)c2cncnc2)C1]
II-188
II-188a, II-188b
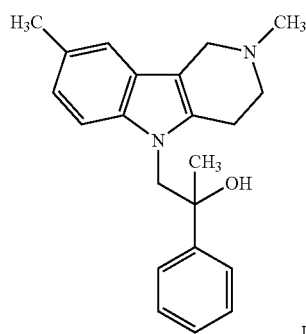
I-189
I
II-189a, II-189b
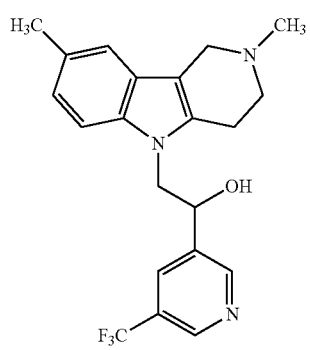
II-190
II-190a, II-190b
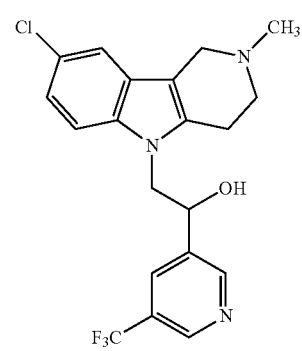 [SMILES: CN1CCc2c(c3cc(Cl)ccc3n2CC(O)c2cncc(C(F)(F)F)c2)C1]
II-191
II-191a, II-191b TABLE 2-continued
Representative Compounds of the Invention
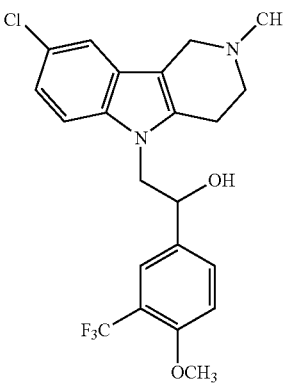
II-192
II-192a, II-192b
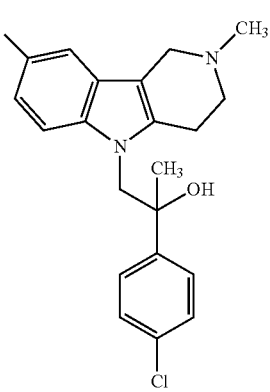
II-195
II-195a, II-195b
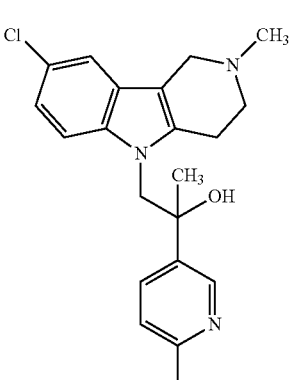
II-193
II-193a, II-193b
II-196
II-196a, II-196b
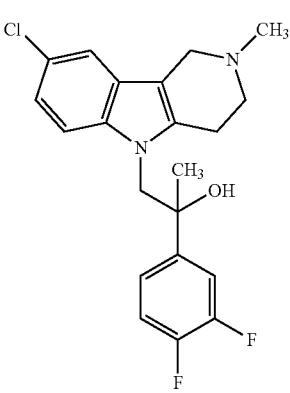 [SMILES: CN1CCc2c(c3cc(Cl)ccc3n2CC(C)(O)c2ccc(Cl)c(F)c2)C1]
II-194
II-194a, II-194b
II-197
II-197a, II-197b TABLE 2-continued
Representative Compounds of the Invention
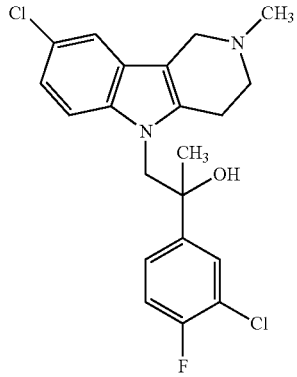 [SMILES: CN1CCc2c(c3cc(Cl)ccc3n2CC(C)(O)c2ccc(F)c(Cl)c2)C1]
II-198
II-198a, II-198b
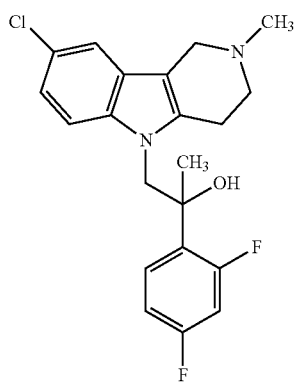 [SMILES: CN1CCc2c(c3cc(Cl)ccc3n2CC(C)(O)c2ccc(F)cc2F)C1]
II-199
II-199a, II-199b
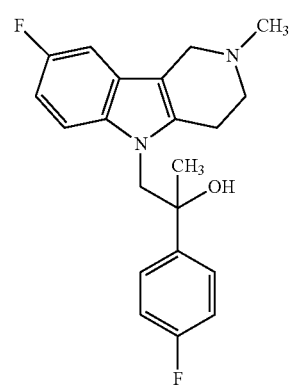 [SMILES: CN1CCc2c(c3cc(F)ccc3n2CC(C)(O)c2ccc(F)cc2)C1]
II-200
II-200a, II-200b
TABLE 2-continued
Representative Compounds of the Invention
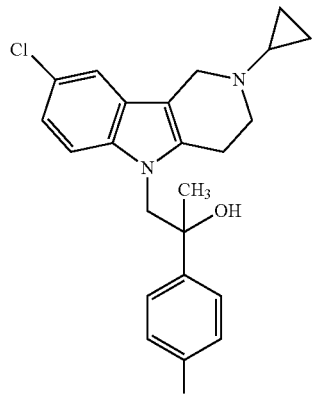
II-201
II-201a, II-201b
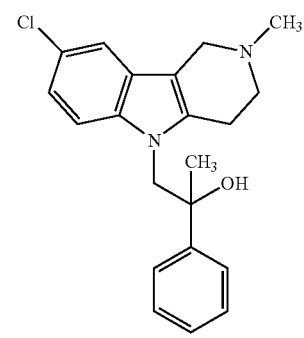 [SMILES: CN1CCc2c(c3cc(Cl)ccc3n2CC(C)(O)c2ccccc2)C1]
II-202
II-202a, II-202b
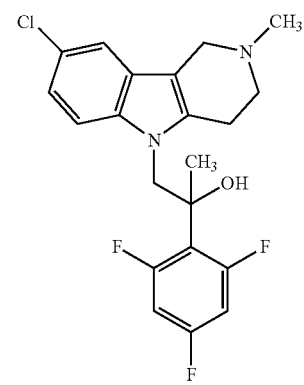 [SMILES: CN1CCc2c(c3cc(Cl)ccc3n2CC(C)(O)c2c(F)cc(F)cc2F)C1]
II-203
II-203a, II-203b TABLE 2-continued
Representative Compounds of the Invention
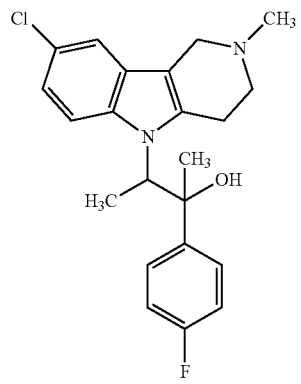 [SMILES: CC(n1c2c(c3cc(Cl)ccc31)CN(C)CC2)C(C)(O)c1ccc(F)cc1]
II-204
II-204a, II-204b
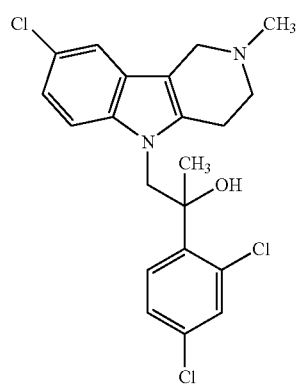
II-205
II-205a, II-205b
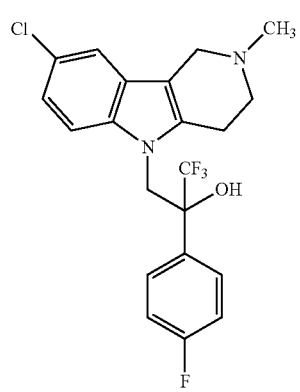 [SMILES: CN1CCc2c(c3cc(Cl)ccc3n2CC(O)(c2ccc(F)cc2)C(F)(F)F)C1]
II-206
II-206a, II-206b
TABLE 2-continued
Representative Compounds of the Invention
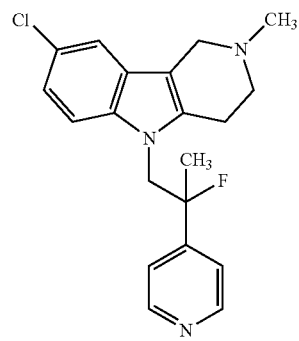 [SMILES: CN1CCc2c(c3cc(Cl)ccc3n2CC(C)(F)c2ccncc2)C1]
II-207
II-207a, II-207b
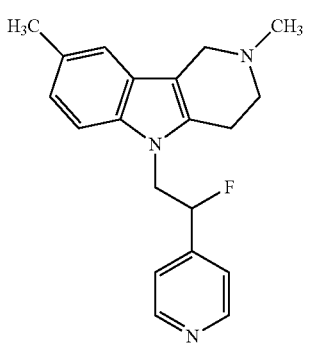
II-208
II-208a, II-208b
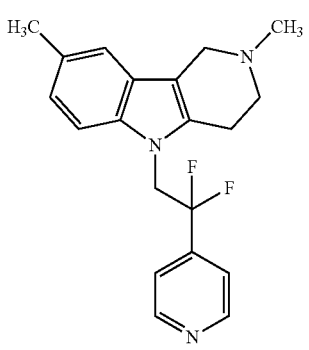
II-209
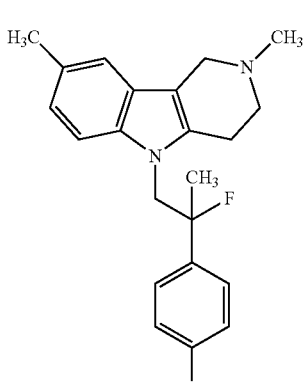
II-210
II-210a, II-210b TABLE 2-continued
Representative Compounds of the Invention
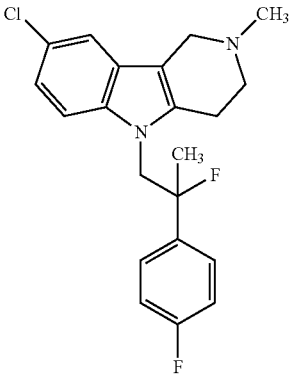 [SMILES: CN1CCc2c(c3cc(Cl)ccc3n2CC(C)(F)c2ccc(F)cc2)C1] II-211
II-211a, II-211b
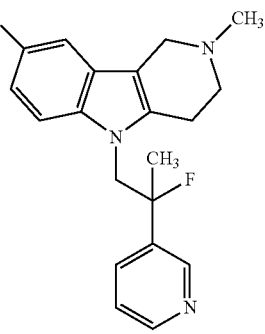 II-212
II-212a, II-212b
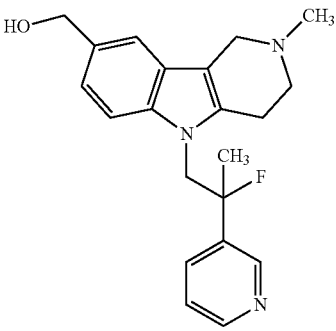 [SMILES: CN1CCc2c(c3cc(CO)ccc3n2CC(C)(F)c2cccnc2)C1] II-213
II-213a, II-213b
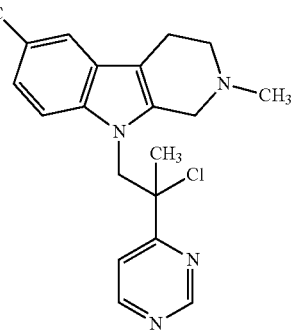 II-214
II-214a, II-214b
TABLE 2-continued
Representative Compounds of the Invention
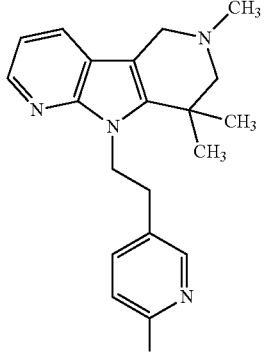 II-215
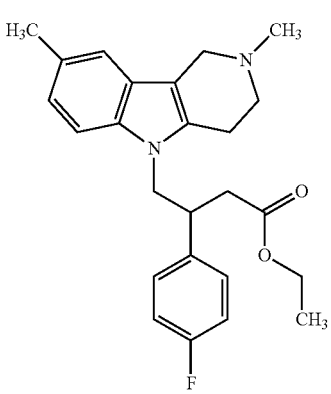 [SMILES: CCOC(=O)CC(Cn1c2c(c3cc(C)ccc31)CN(C)CC2)c1ccc(F)cc1] II-216
II-216a, II-216b
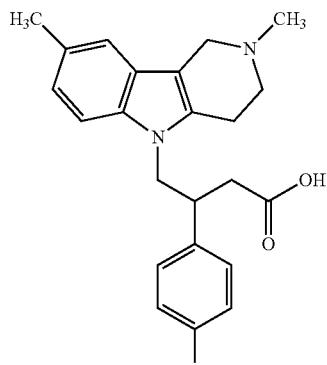 II-217
II-217a, II-217b TABLE 2-continued
Representative Compounds of the Invention
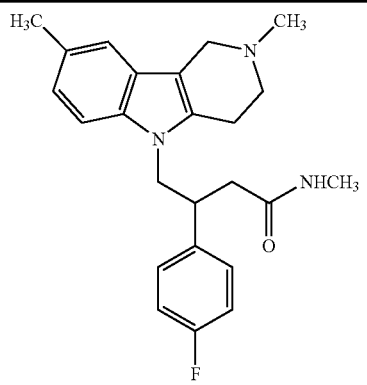
II-218
II-218a, II-218b
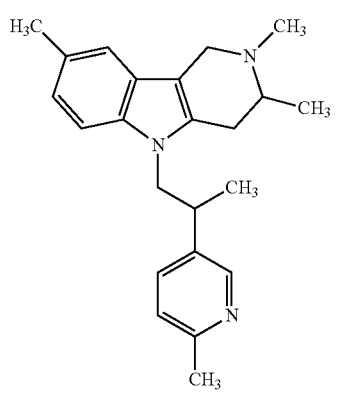
II-219
II-219a, II-219b, II-219c, II-219d
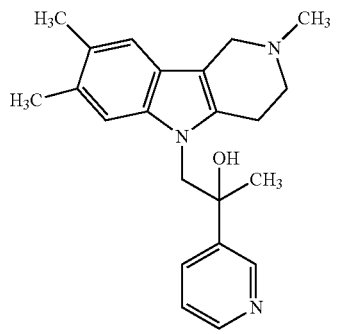
II-220
II-220a, II-220b
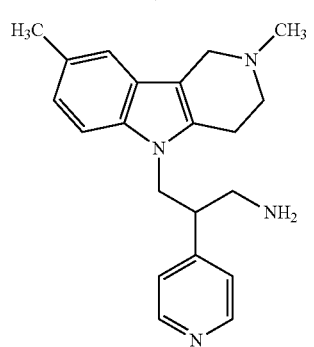
II-221
II-221a, II-221b
TABLE 2-continued
Representative Compounds of the Invention
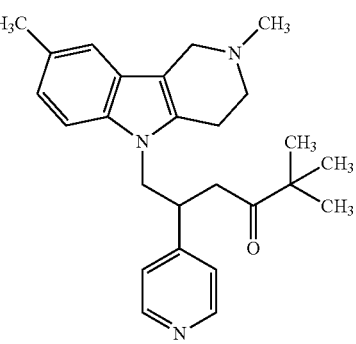
II-222
II-222a, II-222b
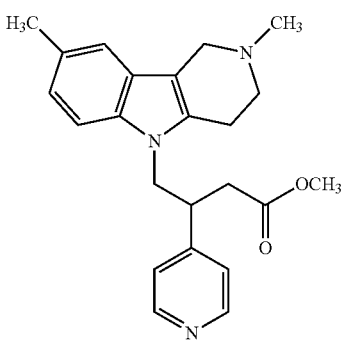 [SMILES: COC(=O)CC(Cn1c2c(c3cc(C)ccc31)CN(C)CC2)c1ccncc1]
II-223
II-223a, II-223b
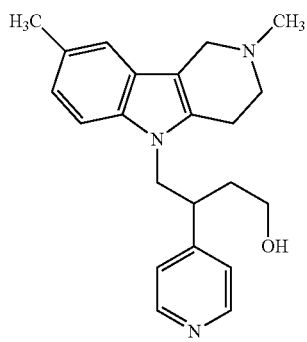
II-224
II-224a, II-224b
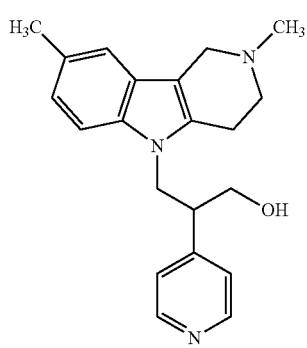
II-225
II-225a, II-225b TABLE 2-continued
Representative Compounds of the Invention
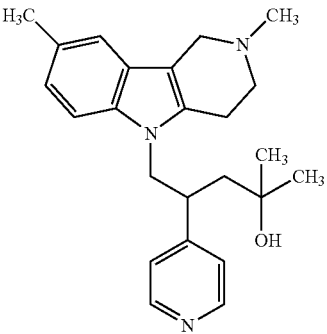 [SMILES: Cc1ccc2c(c1)c1c(n2CC(CC(C)(C)O)c2ccncc2)CCN(C)C1]
II-226
II-226a, II-226b
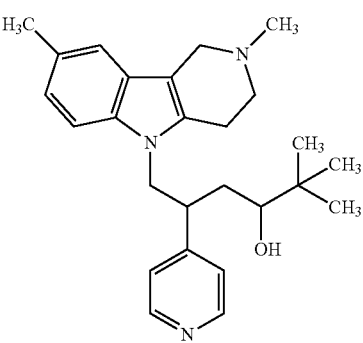 [SMILES: Cc1ccc2c(c1)c1c(n2CC(CC(O)C(C)(C)C)c2ccncc2)CCN(C)C1]
II-227
II-227a, II-227b, II-227c, II-227d
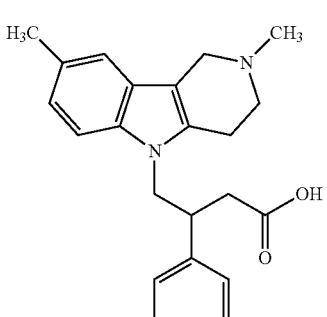
II-228
II-228a, II-228b
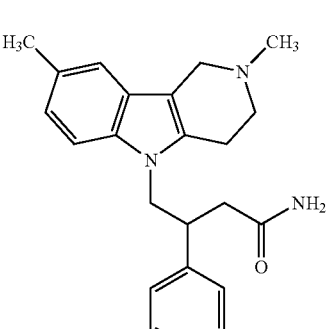
II-229
II-229a, II-229b
TABLE 2-continued
Representative Compounds of the Invention
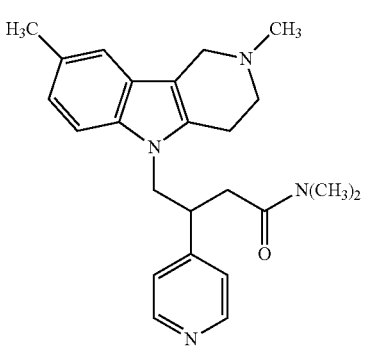 [SMILES: Cc1ccc2c(c1)c1c(n2CC(CC(=O)N(C)C)c2ccncc2)CCN(C)C1]
II-230
II-230a, II-230b
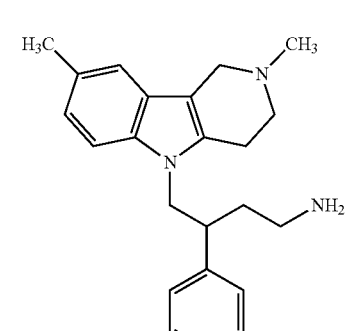
II-231
II-231a, II-231b
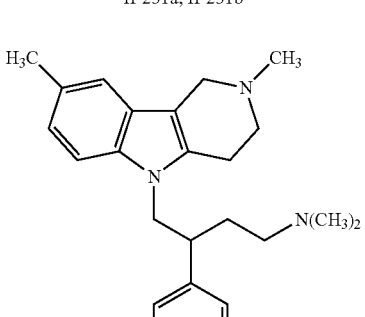
II-232
II-232a, II-232b
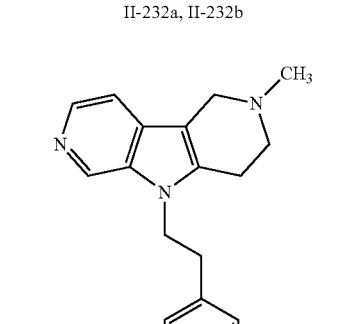
II-233

TABLE 2-continued
Representative Compounds of the Invention
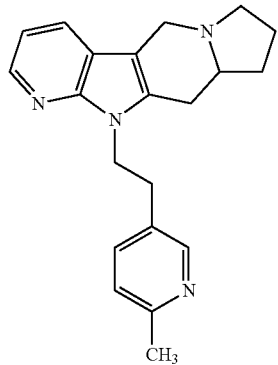 [SMILES: Cc1ccc(CCn2c3c(c4cccnc42)CN2CCCC2C3)cn1]
II-234a, II-234b
II-234
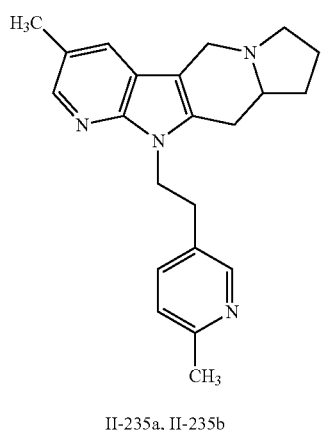
II-235a, II-235b
II-235
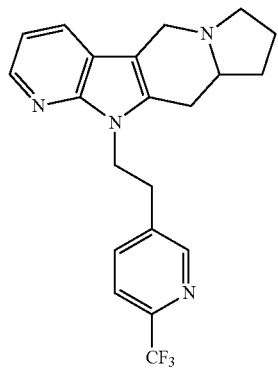 [SMILES: FC(F)(F)c1ccc(CCn2c3c(c4cccnc42)CN2CCCC2C3)cn1]
II-236a, II-236b
II-236
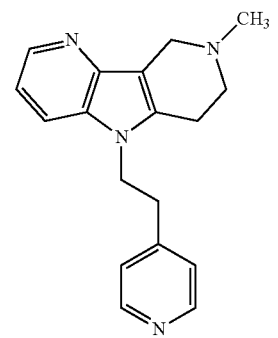 [SMILES: CN1CCc2c(c3ncccc3n2CCc2ccncc2)C1]
II-237
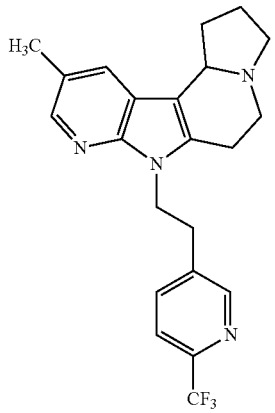 [SMILES: Cc1cnc2c(c1)c1c(n2CCc2ccc(C(F)(F)F)nc2)CCN2CCCC12]
II-238a, II-238b
II-238
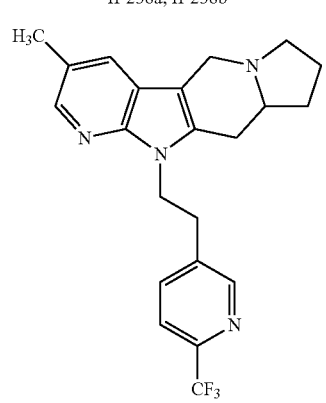
II-239a, II-239b
II-239
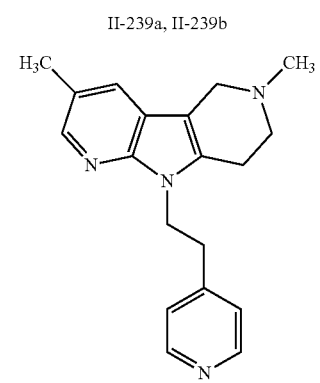
II-240
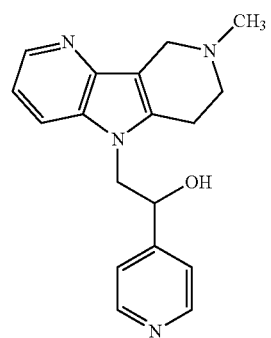 [SMILES: CN1CCc2c(c3ncccc3n2CC(O)c2ccncc2)C1]
II-241a, II-241b
II-241

TABLE 2-continued
Representative Compounds of the Invention
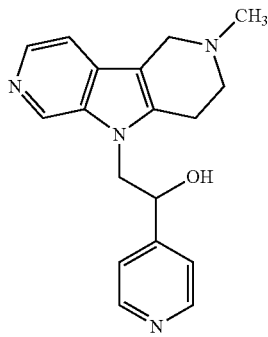 [SMILES: CN1CCc2c(c3ccncc3n2CC(O)c2ccncc2)C1]
II-242
II-242a, II-242b
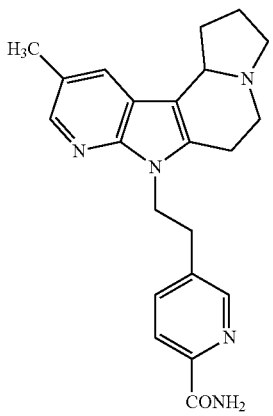
II-243
II-243a, II-243b
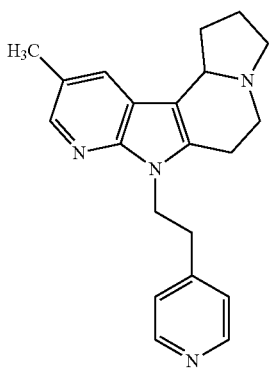 [SMILES: Cc1cnc2c(c1)c1c(n2CCc2ccncc2)CCN2CCCC12]
II-244
II-244a, II-244b
TABLE 2-continued
Representative Compounds of the Invention
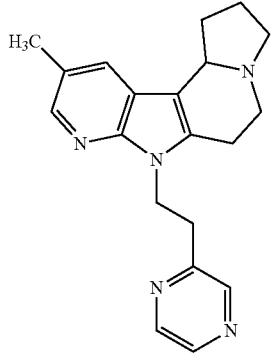 [SMILES: Cc1cnc2c(c1)c1c(n2CCc2cnccn2)CCN2CCCC12]
II-245
II-245a, II-245b
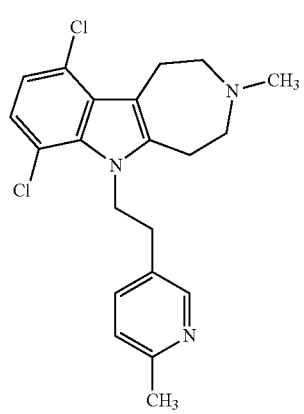 [SMILES: Cc1ccc(CCn2c3c(c4c(Cl)ccc(Cl)c42)CCN(C)CC3)cn1]
II-246
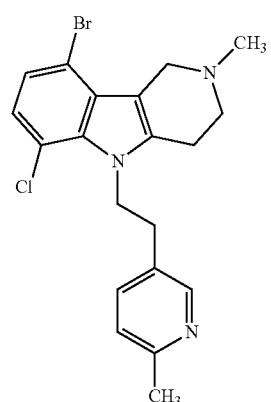
II-247
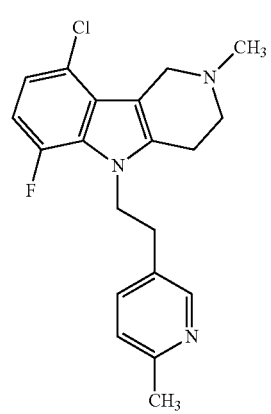 [SMILES: Cc1ccc(CCn2c3c(c4c(Cl)ccc(F)c42)CN(C)CC3)cn1]
II-248

TABLE 2-continued
Representative Compounds of the Invention
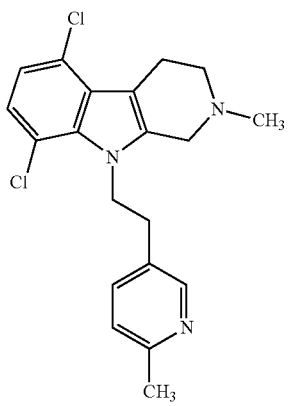 [SMILES: Cc1ccc(CCn2c3c(c4c(Cl)ccc(Cl)c42)CCN(C)C3)cn1] II-249
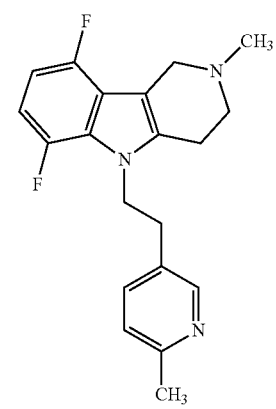 II-250
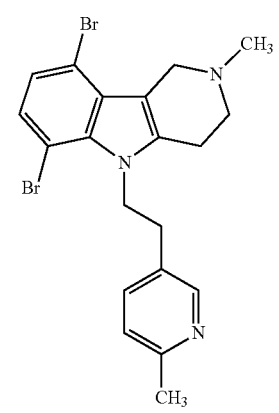 [SMILES: Cc1ccc(CCn2c3c(c4c(Br)ccc(Br)c42)CN(C)CC3)cn1] II-251
TABLE 2-continued
Representative Compounds of the Invention
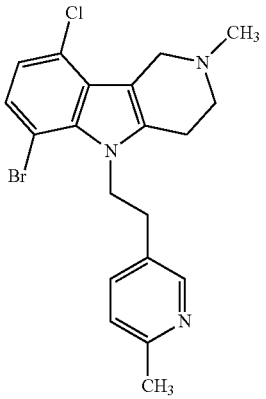 [SMILES: Cc1ccc(CCn2c3c(c4c(Cl)ccc(Br)c42)CN(C)CC3)cn1] II-252
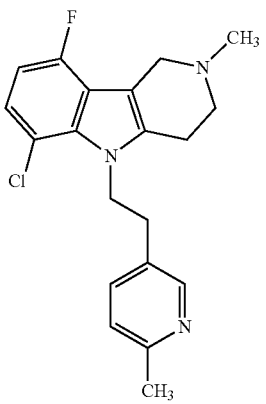 [SMILES: Cc1ccc(CCn2c3c(c4c(F)ccc(Cl)c42)CN(C)CC3)cn1] II-253
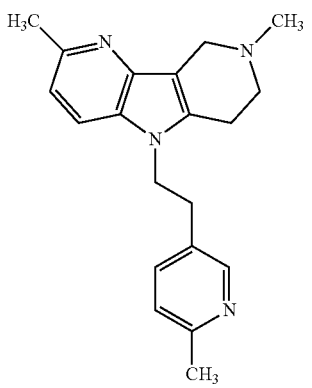 II-254
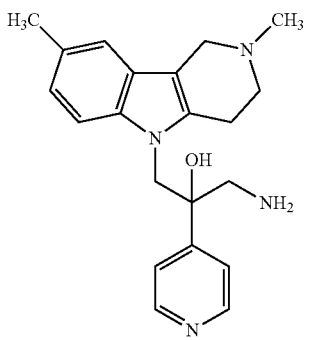 II-255
II-255a, II-255b

TABLE 2-continued
Representative Compounds of the Invention
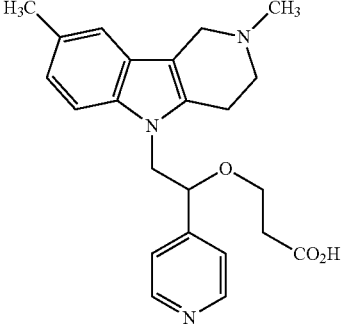 [SMILES: Cc1ccc2c(c1)c1c(n2CC(OCCC(=O)O)c2ccncc2)CCN(C)C1] II-256
II-256a, II-256b
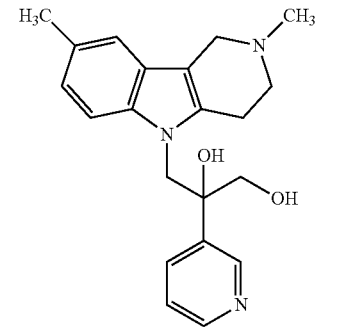 II-257
II-257a, II-257b
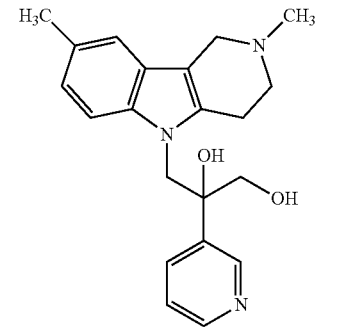 II-258
II-258a, II-258b
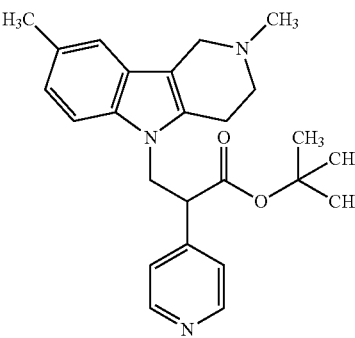 II-259
II-259a, II-259b
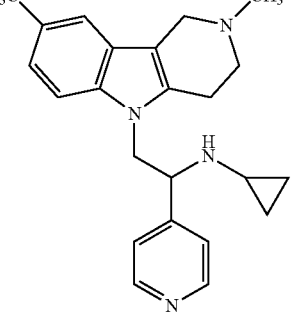 II-260
II-260a, II-260b
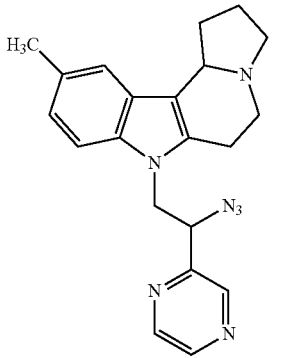 [SMILES: Cc1ccc2c(c1)c1c(n2CC(N=[N+]=[N-])c2cnccn2)CCN2CCCC12] II-261
II-261a, II-261b, II-261c, II-261d
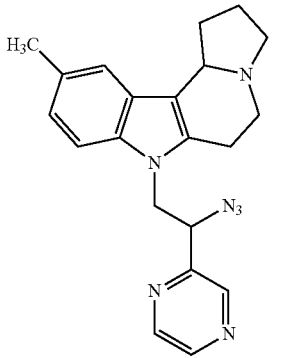 [SMILES: Cc1ccc2c(c1)c1c(n2CC(N=[N+]=[N-])c2cnccn2)CCN2CCCC12] II-262
II-262a, II-262b
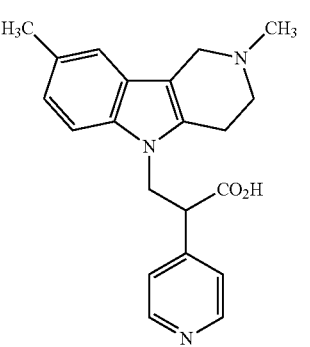 II-263
II-263a, II-263b

TABLE 2-continued
Representative Compounds of the Invention
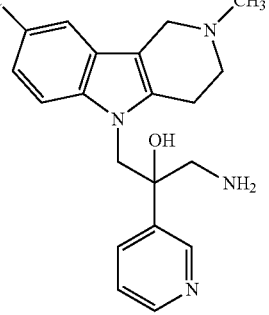 II-264
II-264a, II-264b
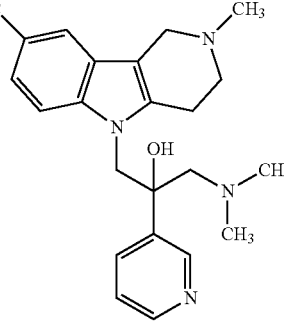 II-265
II-265a, II-265b
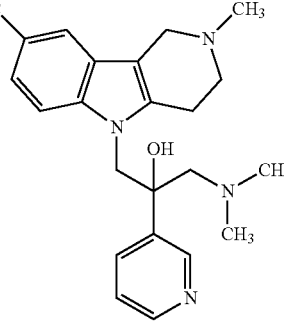 II-266
II-266a, II-266b, II-266c, II-266d
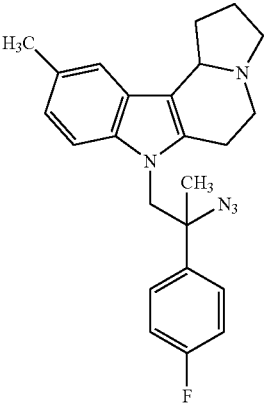 II-267
II-267a, II-267b
TABLE 2-continued
Representative Compounds of the Invention
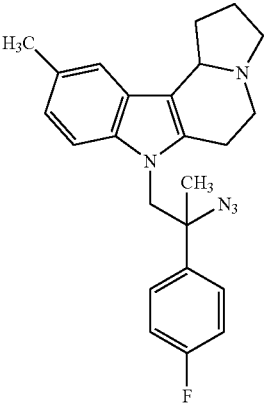 II-268
II-268a, II-268b
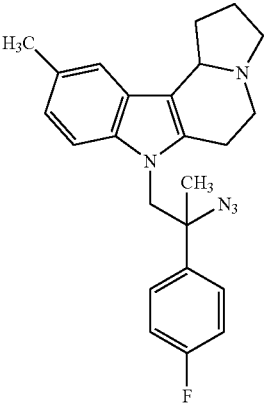 II-269
II-269a, II-269b
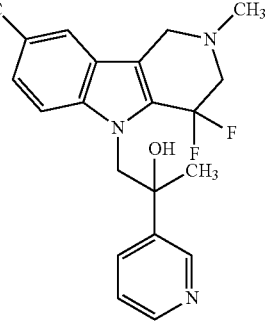 II-270
II-270a, II-270b

TABLE 2-continued

Representative Compounds of the Invention

II-271, II-271a, II-271b, II-271c, II-271d

II-272

II-273

II-274, II-274a, II-274b

II-275, II-275a, II-275b, II-275c, II-275d

II-276, II-276a, II-276b, II-276c, II-276d

II-277, II-277a, II-277b

II-278, II-278a, II-278b

TABLE 2-continued
Representative Compounds of the Invention
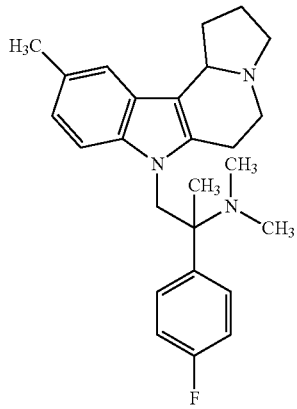 [SMILES: Cc1ccc2c(c1)c1c(n2CC(C)(c2ccc(F)cc2)N(C)C)CCN2CCCC12]
II-279
II-279a, II-279b, II-279c, II-279d
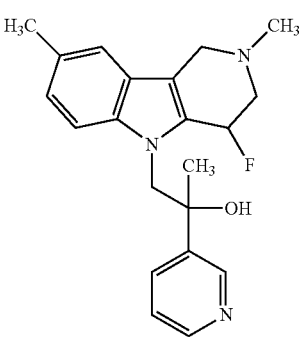
II-280
II-280a, II-280b, II-280c, II-280d
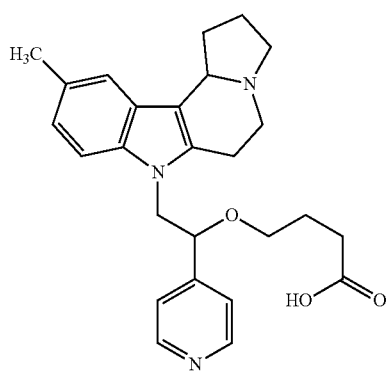 [SMILES: Cc1ccc2c(c1)c1c(n2CC(OCCCC(=O)O)c2ccncc2)CCN2CCCC12]
II-281
II-281a, II-281b, II-281c, II-281d
TABLE 2-continued
Representative Compounds of the Invention
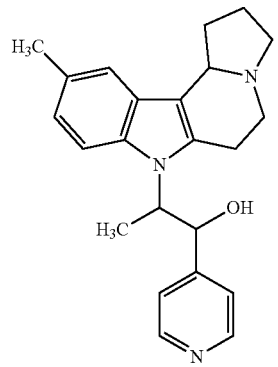 [SMILES: Cc1ccc2c(c1)c1c(n2C(C)C(O)c2ccncc2)CCN2CCCC12]
II-282
II-282a, II-282b, II-282c, II-282d,
II-282e, II-282f, II-282g, II-282h
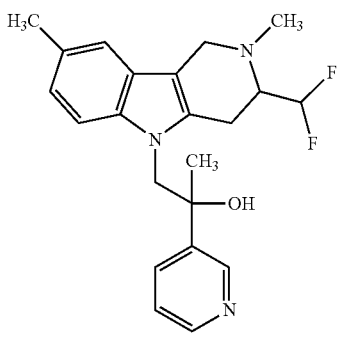 [SMILES: Cc1ccc2c(c1)c1c(n2CC(C)(O)c2cccnc2)CC(C(F)F)N(C)C1]
II-283
II-283a, II-283b, II-283c, II-283d
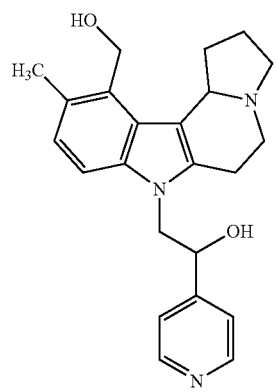 [SMILES: Cc1ccc2c(c1CO)c1c(n2CC(O)c2ccncc2)CCN2CCCC12]
II-284
II-284a, II-284b, II-284c, II-284d TABLE 2-continued
Representative Compounds of the Invention
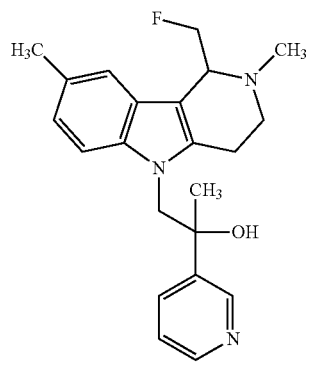
II-285
II-285a, II-285b, II-285c, II-285d
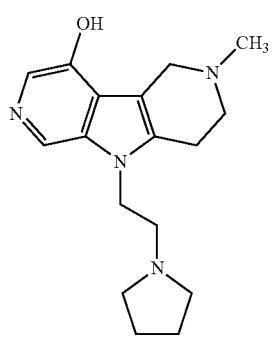 [SMILES: CN1CCc2c(c3c(O)cncc3n2CCN2CCCC2)C1]
II-286
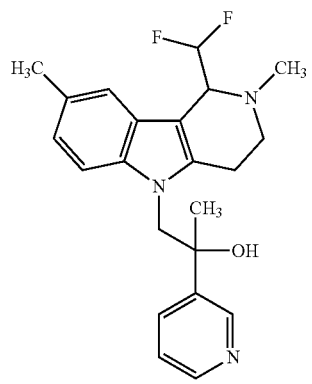
II-287
II-287a, II-287b, II-287c, II-287d
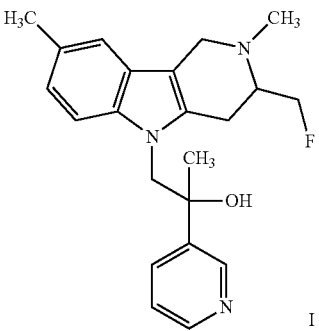
II-288
II-288a, II-288b, II-288c, II-288d
TABLE 2-continued
Representative Compounds of the Invention
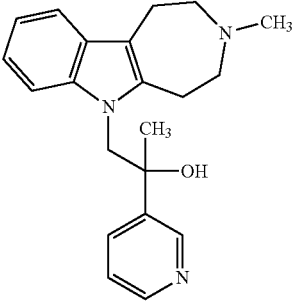 [SMILES: CN1CCc2c(n(CC(C)(O)c3cccnc3)c3ccccc23)CC1]
II-289
II-289a, II-289b
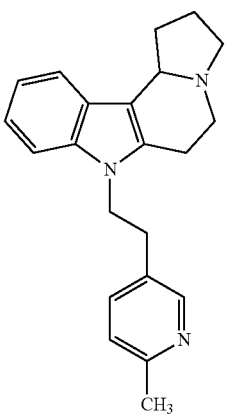 [SMILES: Cc1ccc(CCn2c3c(c4ccccc42)C2CCCN2CC3)cn1]
II-290
II-290a, II-290b
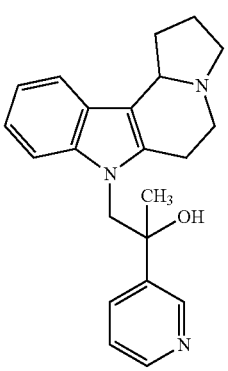 [SMILES: CC(O)(Cn1c2c(c3ccccc31)C1CCCN1CC2)c1cccnc1]
II-291
II-291a, II-291b, II-291c, II-291d
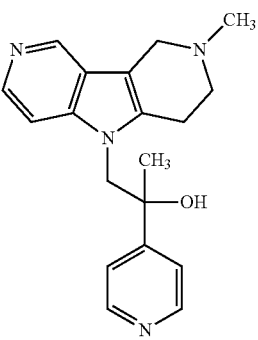 [SMILES: CN1CCc2c(c3cnccc3n2CC(C)(O)c2ccncc2)C1]
II-292
II-292a, II-292b TABLE 2-continued
Representative Compounds of the Invention
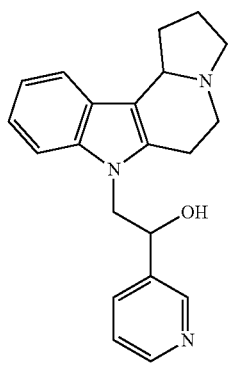 [SMILES: OC(Cn1c2c(c3ccccc31)C1CCCN1CC2)c1cccnc1]
II-293
II-293a, II-293b, II-293c, II-293d
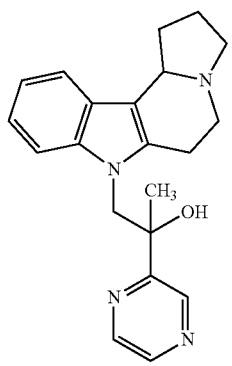 [SMILES: CC(O)(Cn1c2c(c3ccccc31)C1CCCN1CC2)c1cnccn1]
II-294
II-294a, II-294b, II-294c, II-294d
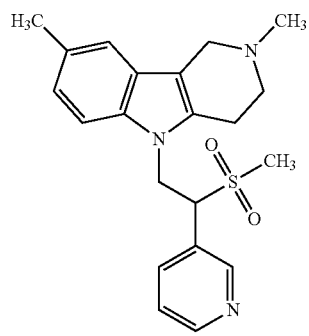
II-295
II-295a, II-295b
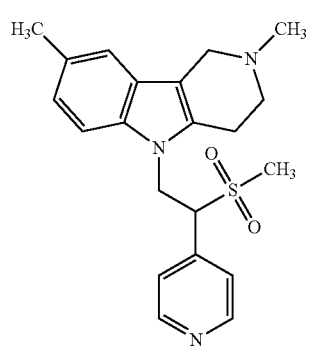
II-296
II-296a, II-296b
TABLE 2-continued
Representative Compounds of the Invention
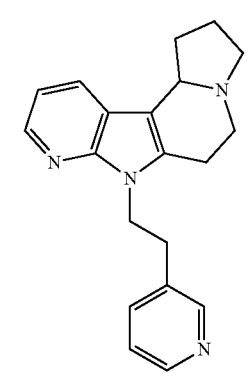 [SMILES: c1cncc(CCn2c3c(c4cccnc42)C2CCCN2CC3)c1]
II-297
II-297a, II-297b
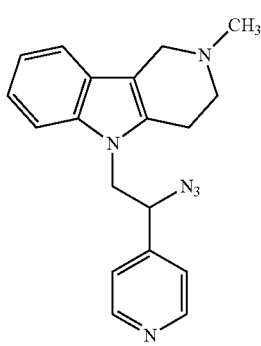 [SMILES: CN1CCc2c(c3ccccc3n2CC(N=[N+]=[N-])c2ccncc2)C1]
II-298
II-298a, II-298b
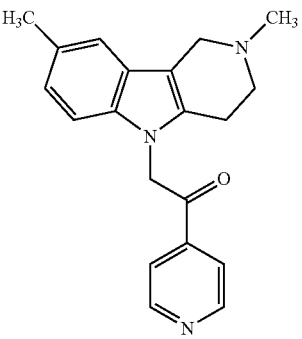
II-299

TABLE 3
Representative Compounds of the Invention.
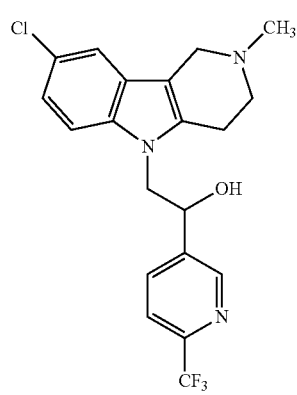
III-1
III-1a,
III-1b
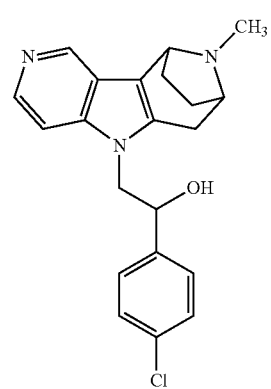
III-2
III-2a,
III-2b,
III-2c,
III-2d
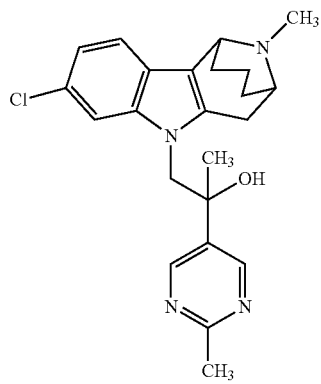
III-3
III-3a,
III-3b,
III-3c,
III-3d
TABLE 3-continued
Representative Compounds of the Invention.
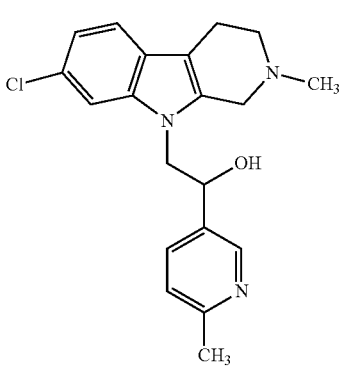
III-4
III-4a,
III-4b
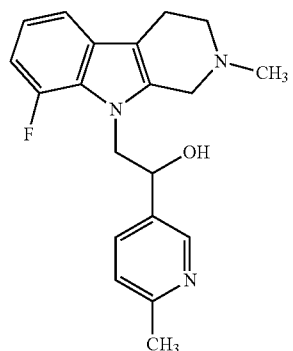
III-5
III-5a,
III-5b
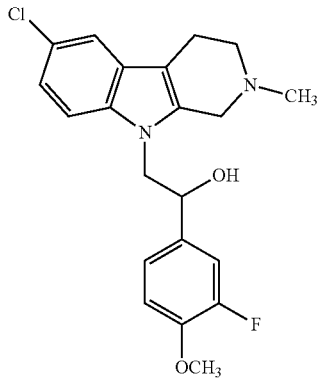
III-6
III-6a,
III-6b TABLE 3-continued
Representative Compounds of the Invention.
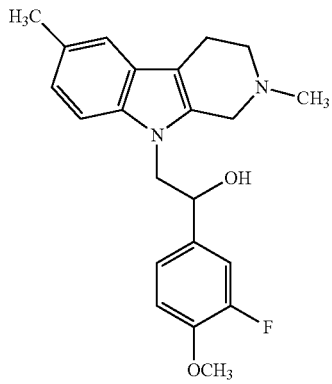
III-7
III-7a,
III-7b
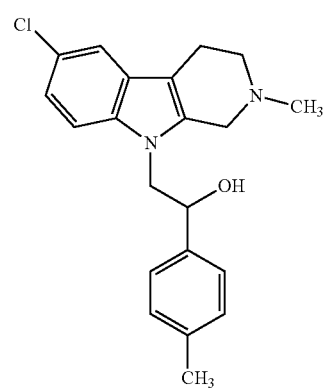
III-8
III-8a,
III-8b
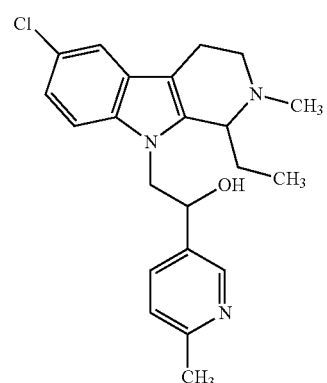
III-9
III-9a,
III-9b,
III-9c,
III-9d
TABLE 3-continued
Representative Compounds of the Invention.
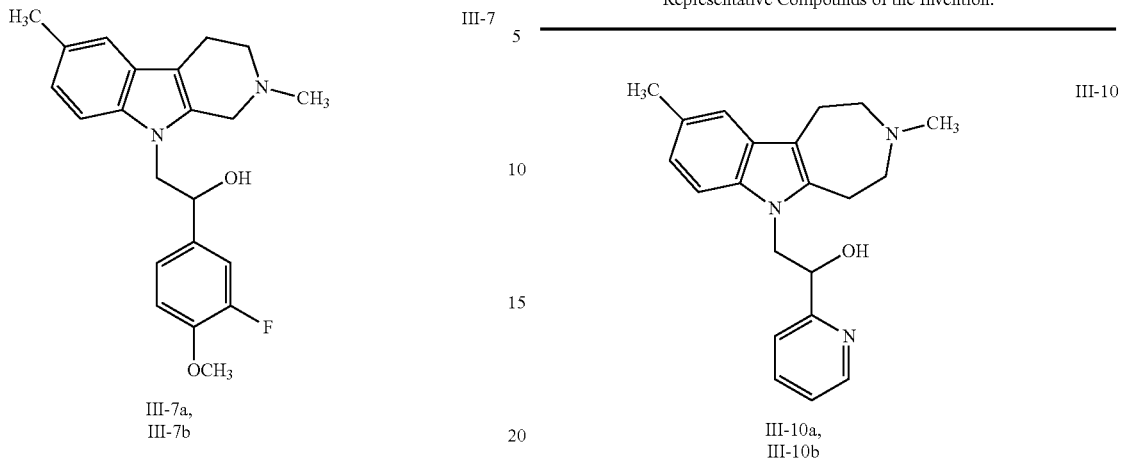
III-10
III-10a,
III-10b
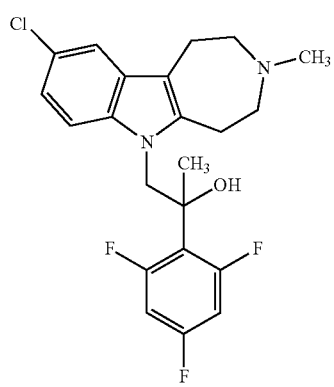
III-11
III-11a,
III-11b
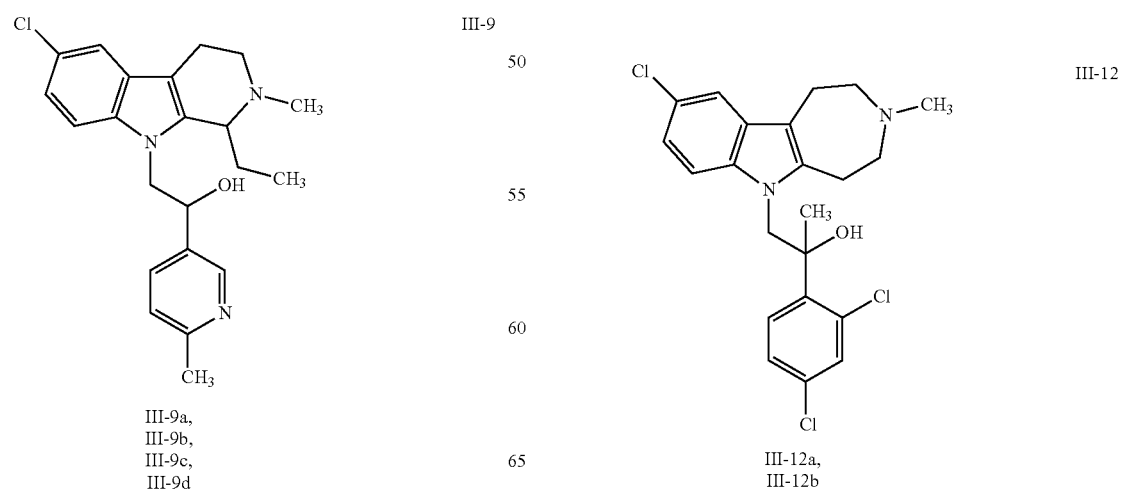
III-12
III-12a,
III-12b TABLE 3-continued Representative Compounds of the Invention.

| III-13 | III-16 |
| III-13a, III-13b | III-16a, III-16b |

| III-14 | III-17 |
| III-14a, III-14b | III-17a, III-17b |

| III-15 | III-18 |
| III-15a, III-15b | III-18a, III-18b |

TABLE 3-continued
Representative Compounds of the Invention.
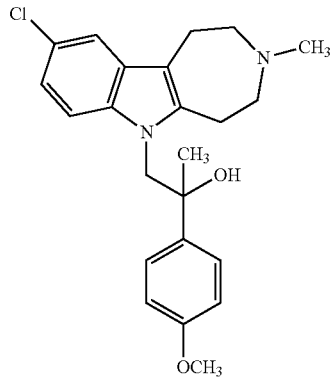
III-19a,
III-19b
III-19
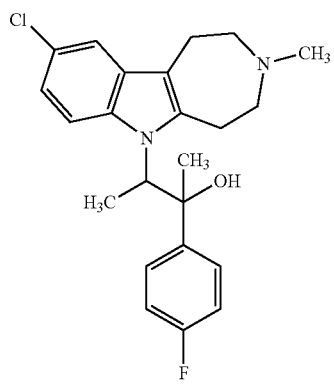
III-20a,
III-20b,
III-20c,
III-20d
III-20
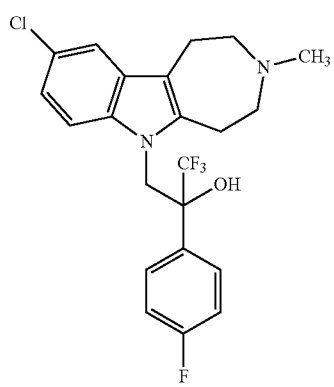
III-21a,
III-21b
III-21
TABLE 3-continued
Representative Compounds of the Invention.
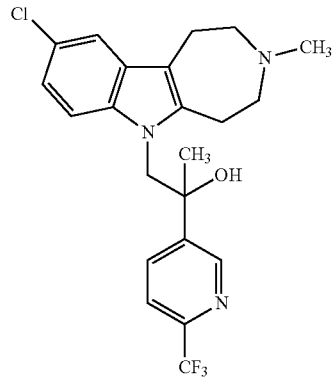
III-22a,
III-22b
III-22
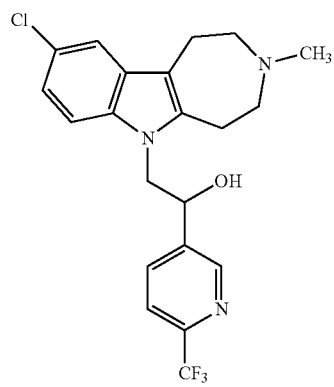
III-23a,
III-23b
III-23
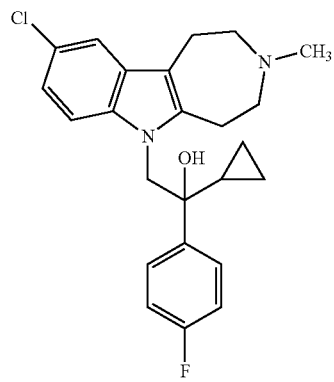
III-24a,
III-24b
III-24

TABLE 3-continued
Representative Compounds of the Invention.
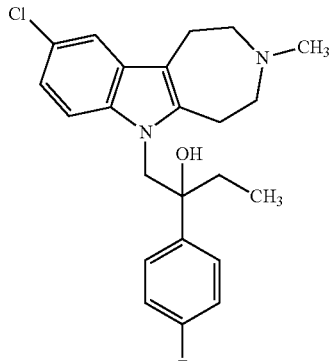
III-25a,
III-25b
III-25
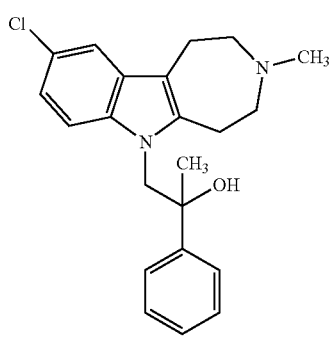
III-26a,
III-26b
III-26
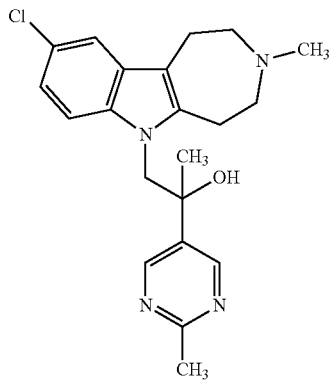
III-27a,
III-27b
III-27
TABLE 3-continued
Representative Compounds of the Invention.
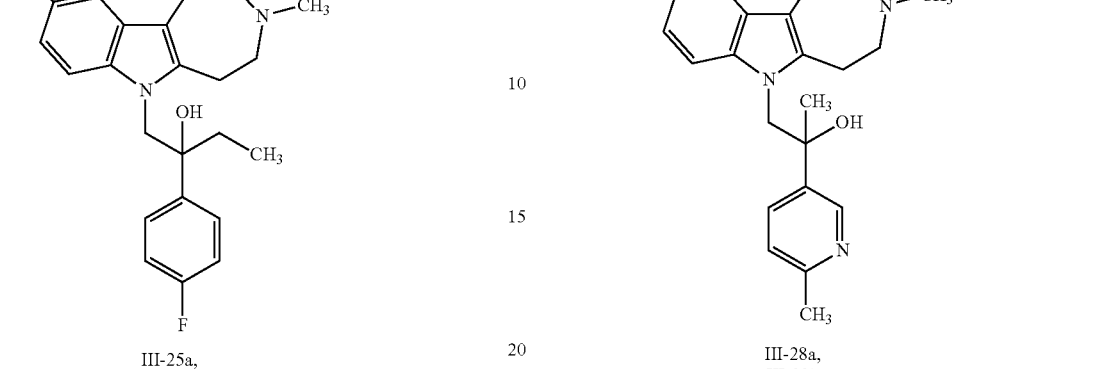
III-28a,
III-28b
III-28
III-29a,
III-29b
III-29
III-30a,
III-30b
III-30

TABLE 3-continued

Representative Compounds of the Invention.

III-31: 8-methyl substituted tetracyclic indole-azepine with N-CH3, N-linked CH2-C(CH3)(OH)-aryl where aryl = 2,4-difluorophenyl.
III-31a, III-31b III-32: same scaffold with aryl = 3,4-dichlorophenyl.
III-32a, III-32b III-33: same scaffold with aryl = 3,4-difluorophenyl.
III-33a, III-33b III-34: same scaffold with aryl = 3-chloro-4-fluorophenyl.
III-34a, III-34b III-35: same scaffold with aryl = 3-fluoro-4-methoxyphenyl.
III-35a, III-35b III-36: same scaffold with aryl = 4-chloro-3-fluorophenyl.
III-36a, III-36b TABLE 3-continued
Representative Compounds of the Invention.
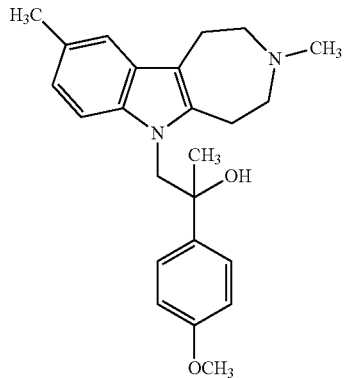
III-37a,
III-37b
III-37
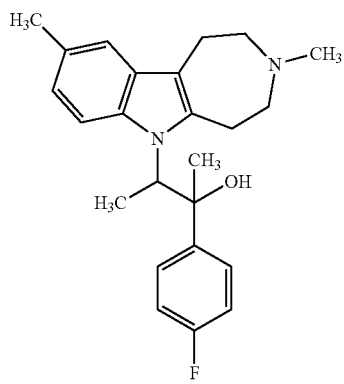
III-38a,
III-38b,
III-38c,
III-38d
III-38
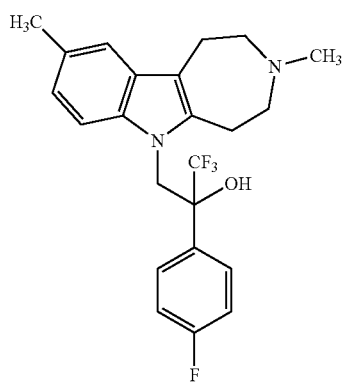
III-39a,
III-39b
III-39
TABLE 3-continued
Representative Compounds of the Invention.
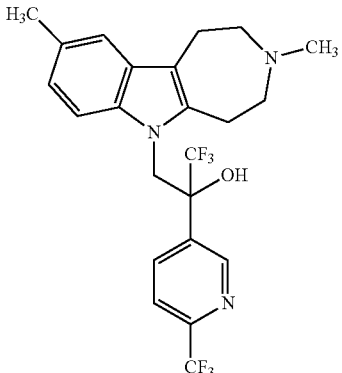
III-40a,
III-40b
III-40
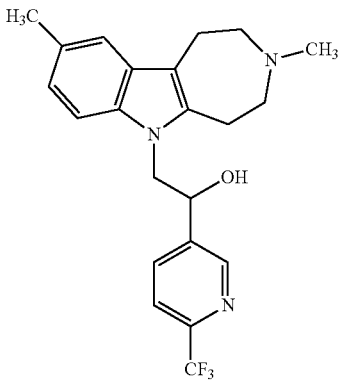
III-41a,
III-41b
III-41
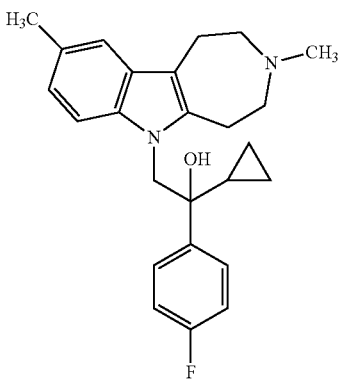
III-42a,
III-42b
III-42

TABLE 3-continued
Representative Compounds of the Invention.
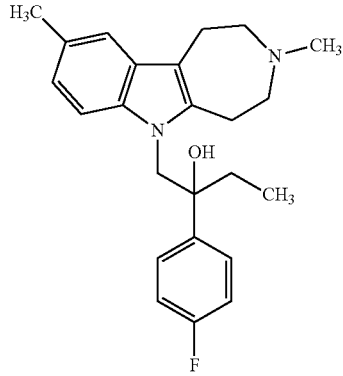 III-43
III-43a,
III-43b
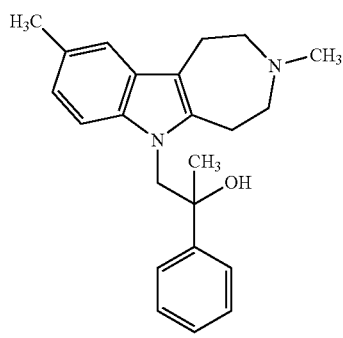 III-44
III-44a,
III-44b
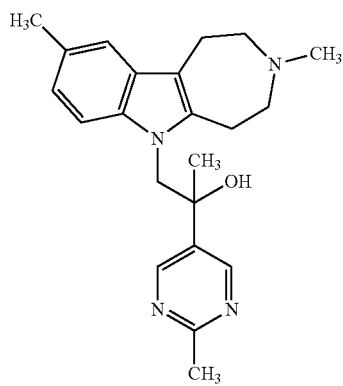 III-45
III-45a,
III-45b
TABLE 3-continued
Representative Compounds of the Invention.
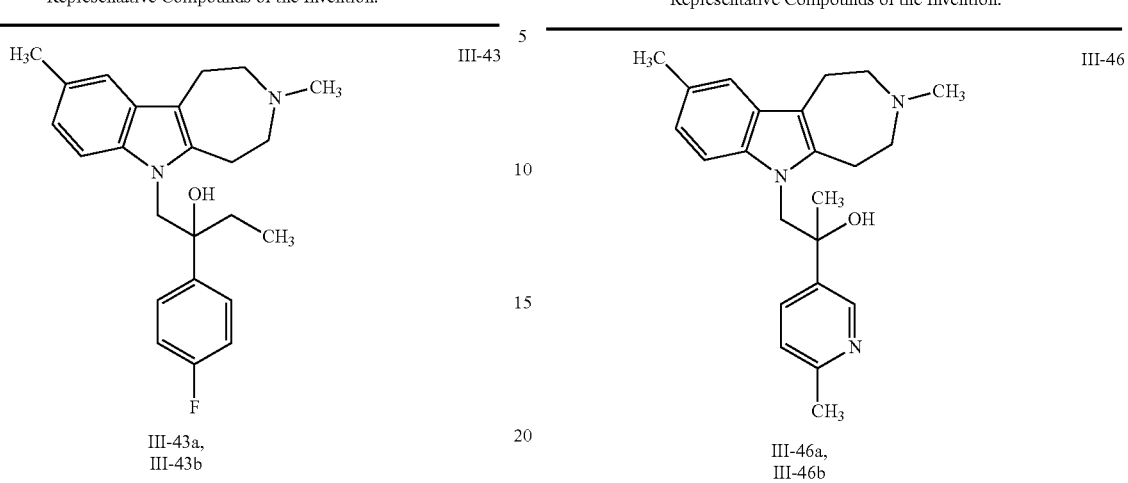 III-46
III-46a,
III-46b
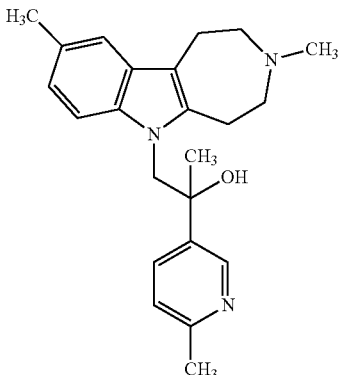 III-47
III-47a,
III-47b
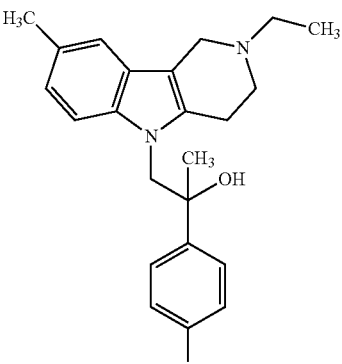 III-48
III-48a,
III-48b TABLE 3-continued
Representative Compounds of the Invention.
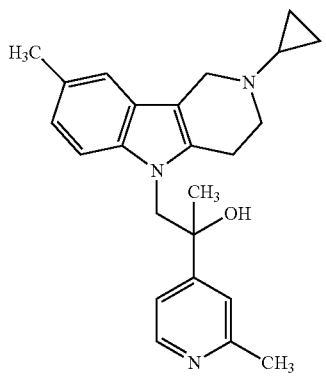
III-49a,
III-49b
III-49
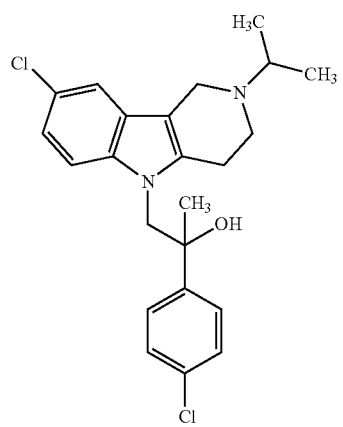
III-50a,
III-50b
III-50
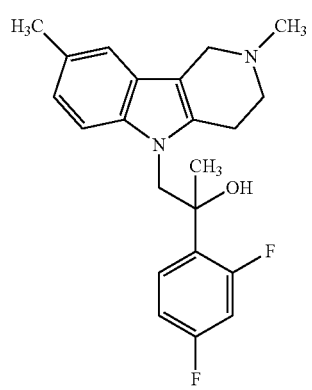
III-51a,
III-51b
III-51
TABLE 3-continued
Representative Compounds of the Invention.
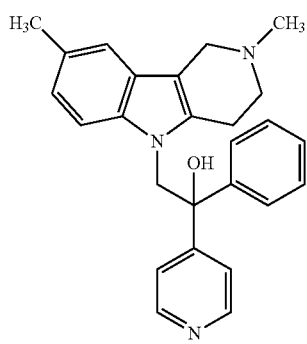
III-52a,
III-52b
III-52
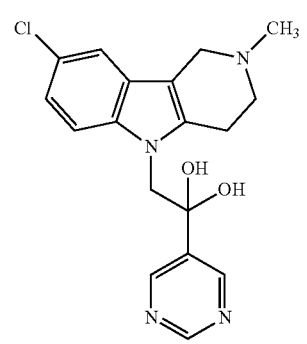
III-53a,
III-53b
III-53
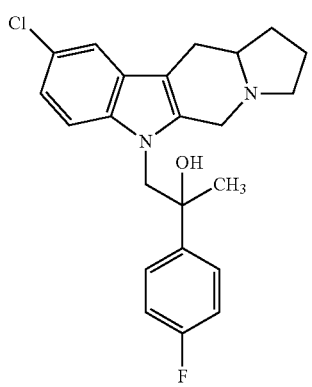
III-54a,
III-54b,
III-54c,
III-54d
III-54

TABLE 3-continued
Representative Compounds of the Invention.
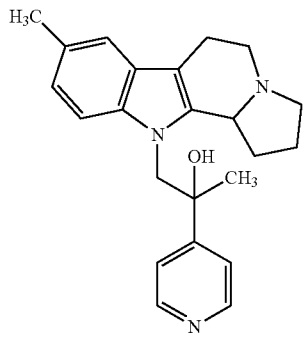
III-55
III-55a,
III-55b,
III-55c,
III-55d
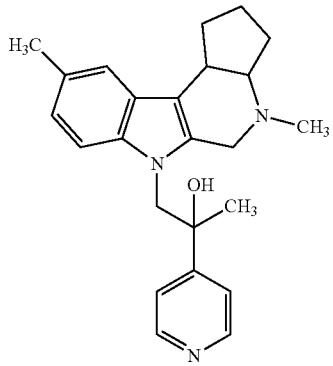
III-56
III-56a,
III-56b,
III-56c,
III-56d
III-57
III-57a,
III-57b,
III-57c,
III-57d
TABLE 3-continued
Representative Compounds of the Invention.
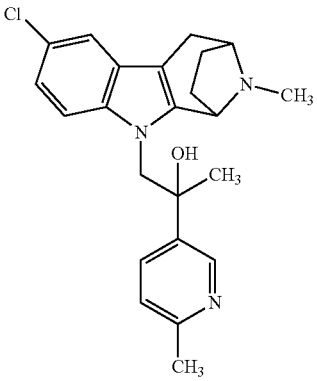
III-58
III-58a,
III-58b,
III-58c,
III-58d
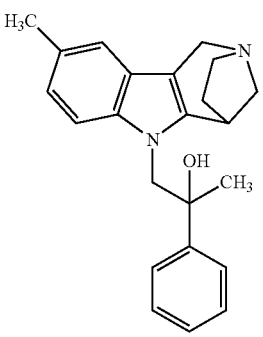
III-59
III-59a,
III-59b,
III-59c,
III-59d
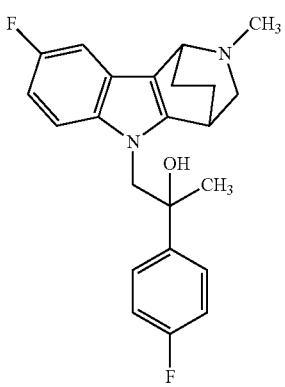
III-60
III-60a,
III-60b,
III-60c,
III-60d TABLE 3-continued
Representative Compounds of the Invention.
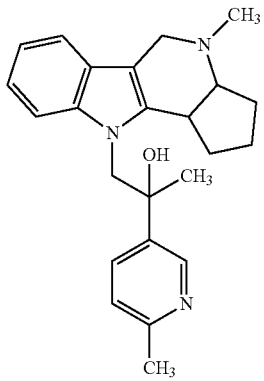
III-61
III-61a,
III-61b,
III-61c,
III-61d
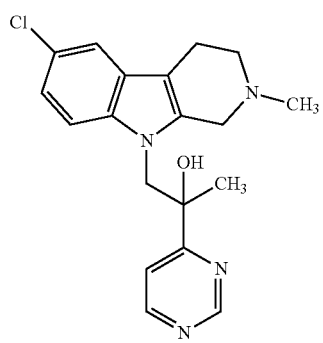
III-62
III-62a,
III-62b
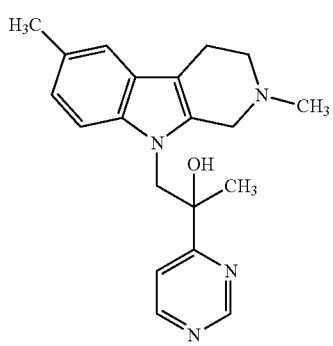
III-63
III-63a,
III-63b
TABLE 3-continued
Representative Compounds of the Invention.
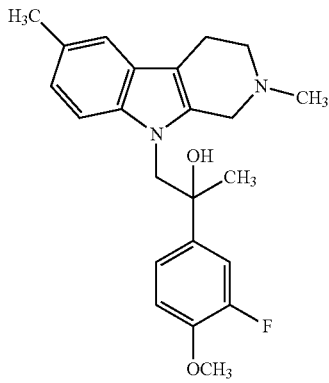
III-64
III-64a,
III-64b
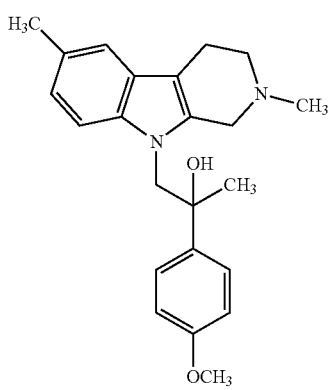
III-65
III-65a,
III-65b
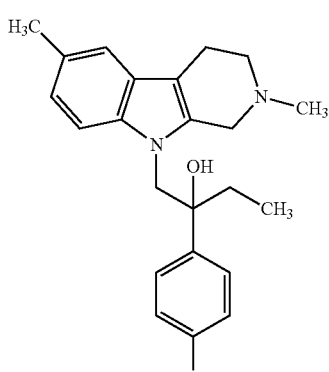
III-66
III-66a,
III-66b TABLE 3-continued
Representative Compounds of the Invention.
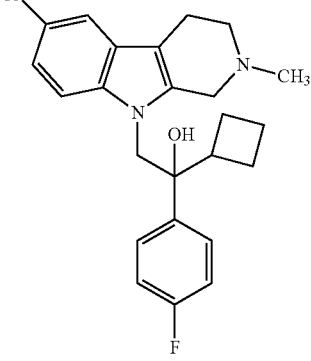
III-67
III-67a,
III-67b
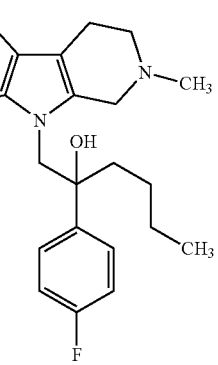
III-68
III-68a,
III-68b
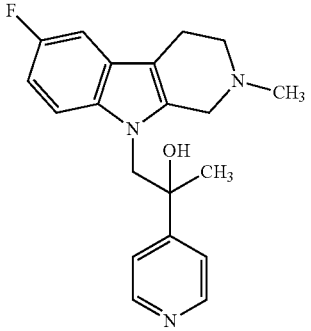
III-69
III-69a,
III-69b
TABLE 3-continued
Representative Compounds of the Invention.
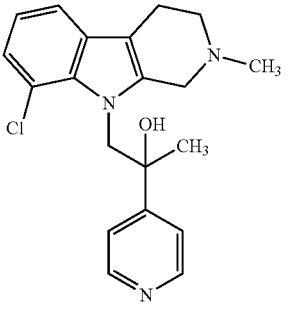
III-70
III-70a,
III-70b
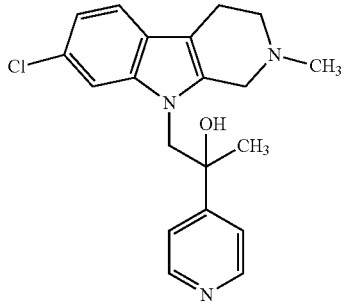
III-71
III-71a,
III-71b
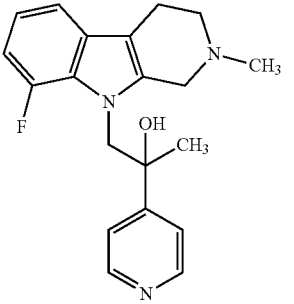
III-72
III-72a,
III-72b
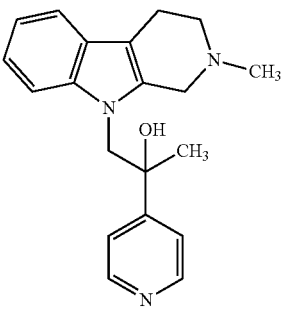
III-73
III-73a,
III-73b TABLE 3-continued
Representative Compounds of the Invention.
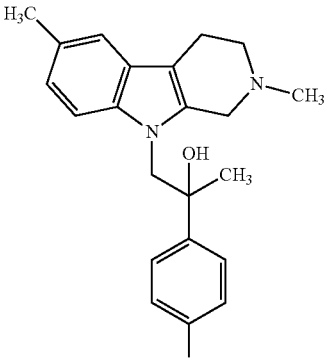
III-74
III-74a,
III-74b
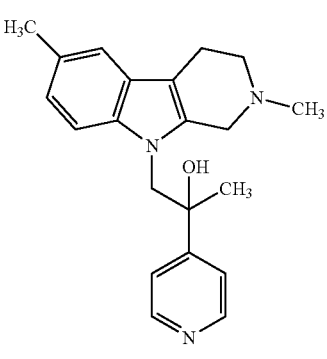
III-75
III-75a,
III-75b
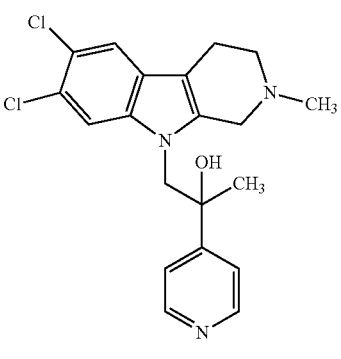
III-76
III-76a,
III-76b
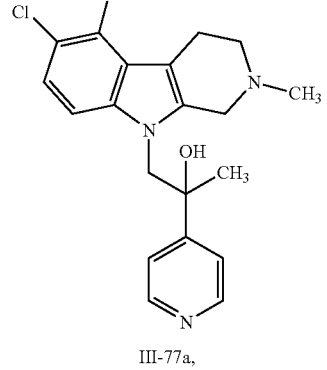
III-77
III-77a,
III-77b
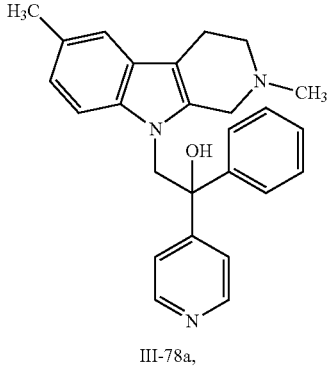
III-78
III-78a,
III-78b
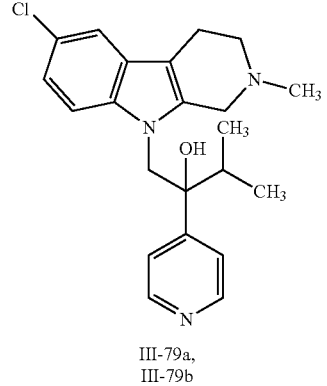 [SMILES: CC(C)C(O)(Cn1c2c(c3cc(Cl)ccc31)CCN(C)C2)c1ccncc1]
III-79
III-79a,
III-79b
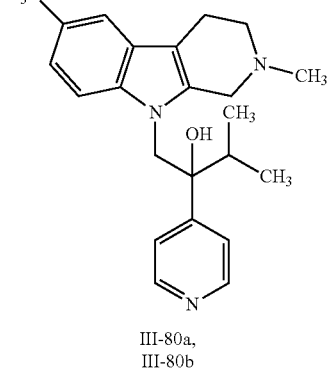
III-80
III-80a,
III-80b TABLE 3-continued
Representative Compounds of the Invention.
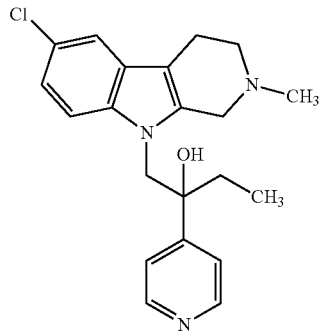
III-81a,
III-81b
III-81
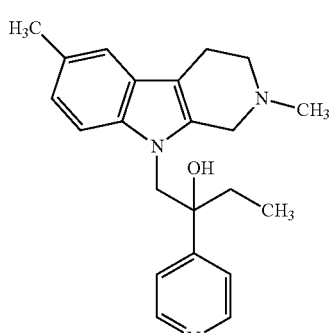
III-82a,
III-82b
III-82
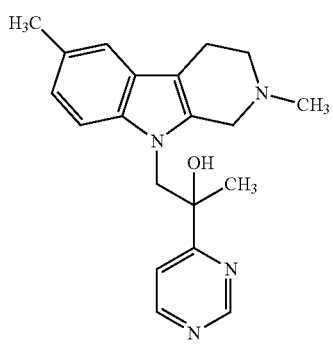
III-83a,
III-83b
III-83
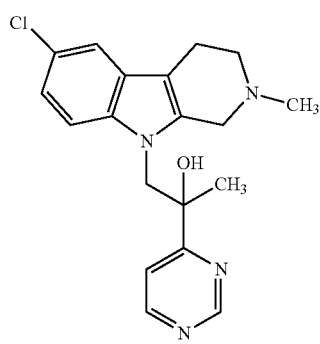
III-84a,
III-84b
III-84
TABLE 3-continued
Representative Compounds of the Invention.
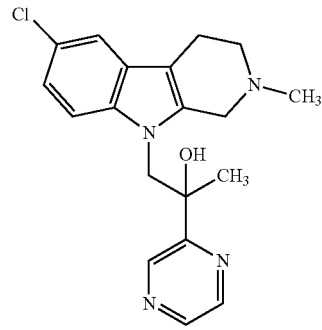
III-85a,
III-85b
III-85
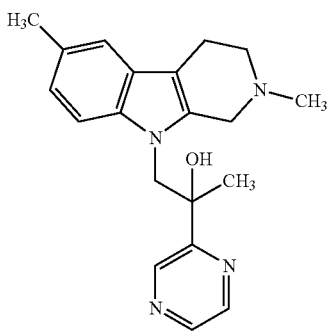
III-86a,
III-86b
III-86
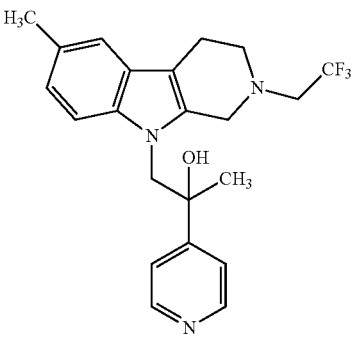
III-87a,
III-87b
III-87
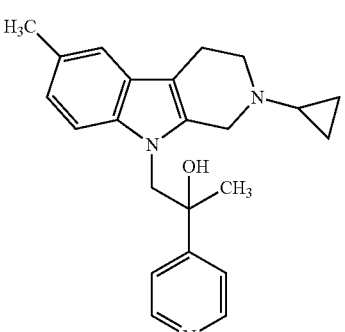
III-88a,
III-88b
III-88

TABLE 3-continued
Representative Compounds of the Invention.
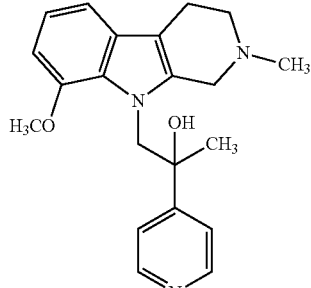
III-89a,
III-89b
III-89
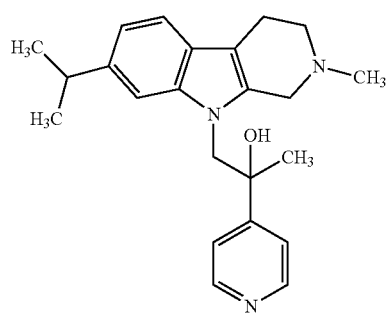
III-90a,
III-90b
III-90
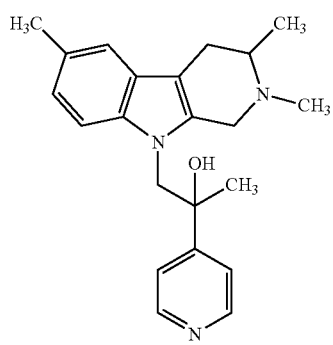
III-91a,
III-91b,
III-91c,
III-91d
III-91
TABLE 3-continued
Representative Compounds of the Invention.
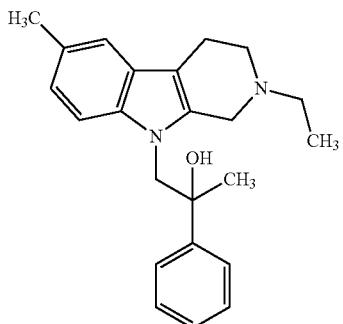
III-92a,
III-92b
III-92
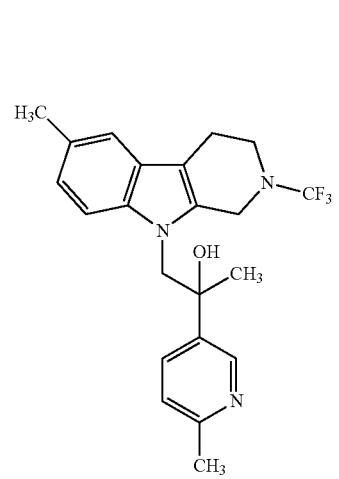
III-93a,
III-93b
III-93
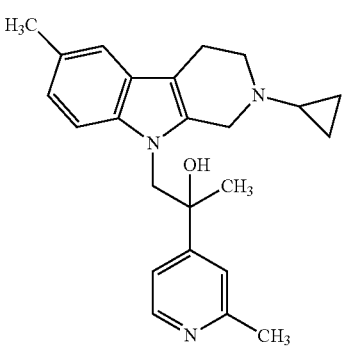
III-94a,
III-94b
III-94

TABLE 3-continued
Representative Compounds of the Invention.
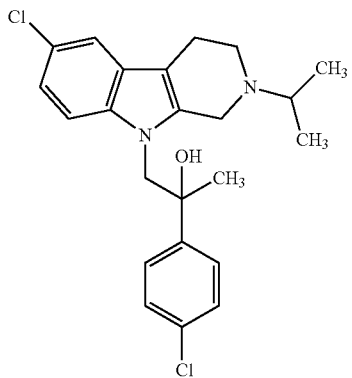
III-95a,
III-95b
III-95
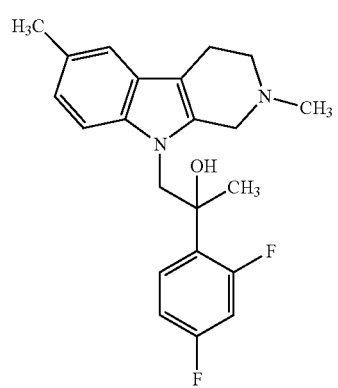
III-96a,
III-96b
III-96
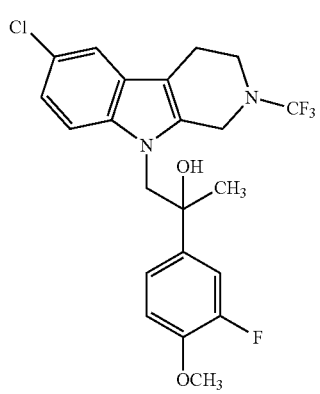
III-97a,
III-97b
III-97
TABLE 3-continued
Representative Compounds of the Invention.
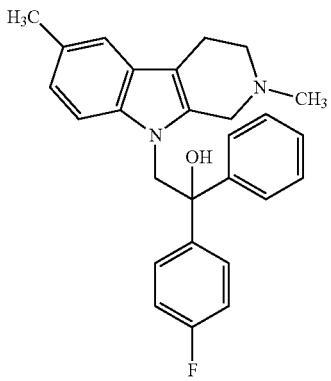
III-98a,
III-98b
III-98
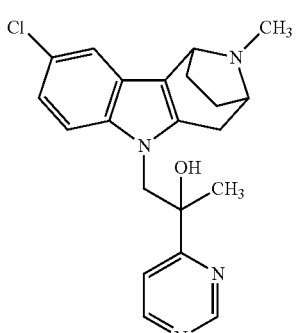
III-99a,
III-99b,
III-99c,
III-99d
III-99
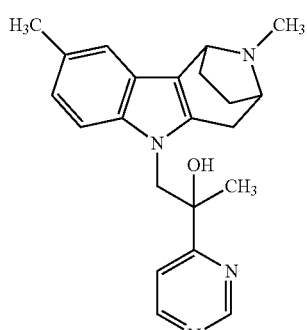
III-100a,
III-100b,
III-100c,
III-100d
III-100

TABLE 3-continued
Representative Compounds of the Invention.
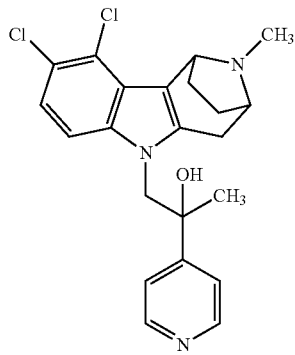
III-101
III-101a,
III-101b,
III-101c,
III-101d
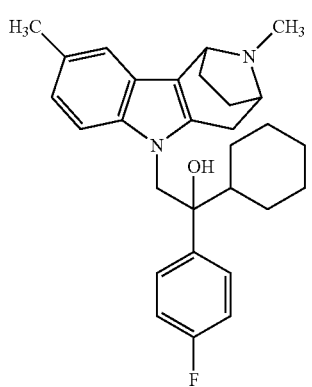
III-102
III-102a,
III-102b,
III-102c,
III-102d
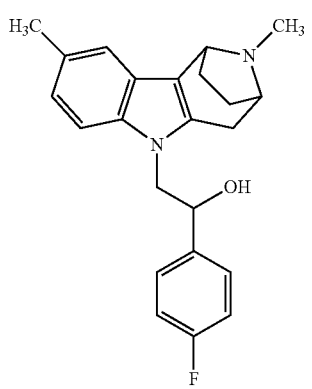
III-103
III-103a,
III-103b,
III-103c,
III-103d
TABLE 3-continued
Representative Compounds of the Invention.
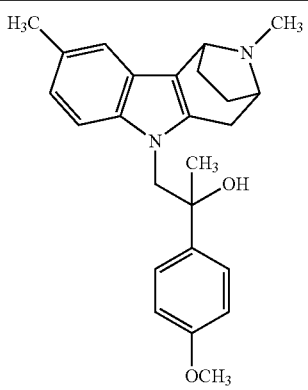
III-104
III-104a,
III-104b,
III-104c,
III-104d
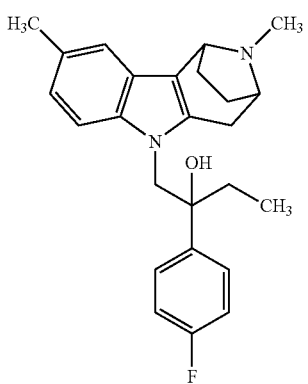
III-105
III-105a,
III-105b,
III-105c,
III-105d
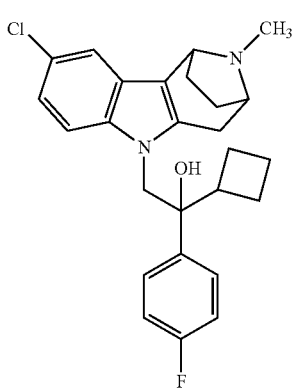
III-106
III-106a,
III-106b,
III-106c,
III-106d TABLE 3-continued
Representative Compounds of the Invention.
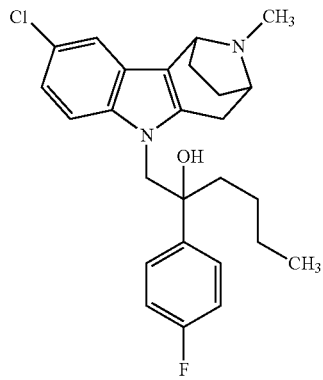
III-107
III-107a,
III-107b,
III-107c,
III-107d
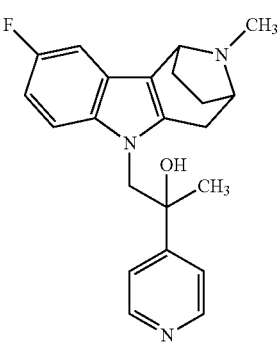
III-108
III-108a,
III-108b,
III-108c,
III-108d
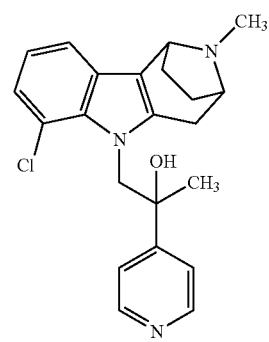
III-109
III-109a,
III-109b,
III-109c,
III-109d
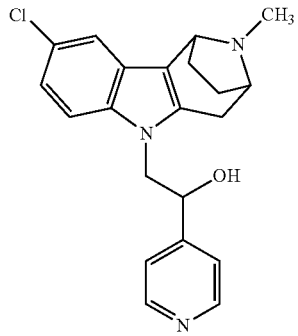
III-110
III-110a,
III-110b,
III-110c,
III-110d
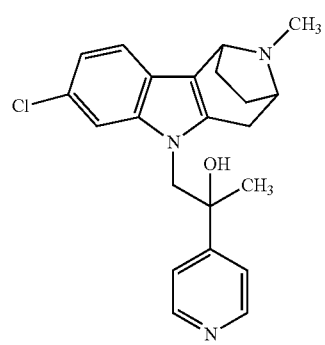
III-111
III-111a,
III-111b,
III-111c,
III-111d
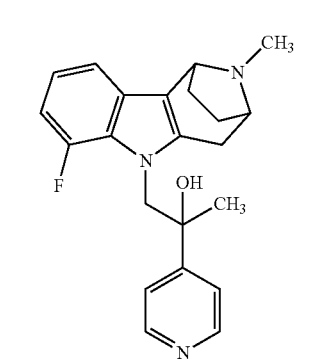
III-112
III-112a,
III-112b,
III-112c,
III-112d

TABLE 3-continued
Representative Compounds of the Invention.
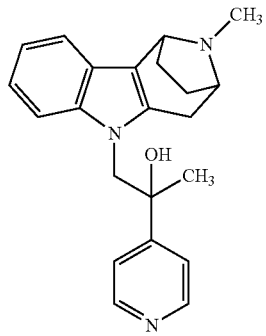
III-113
III-113a,
III-113b,
III-113c,
III-113d
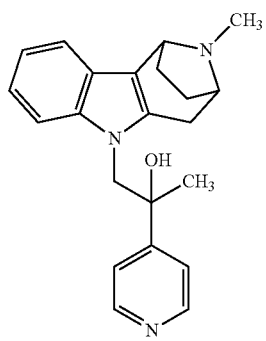
III-114
III-114a,
III-114b,
III-114c,
III-114d
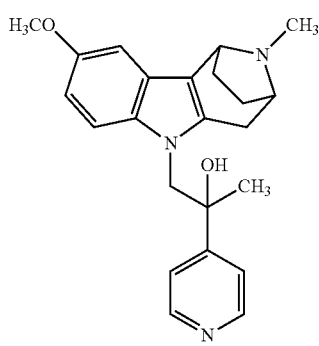
III-115
III-115a,
III-115b,
III-115c,
III-115d
TABLE 3-continued
Representative Compounds of the Invention.
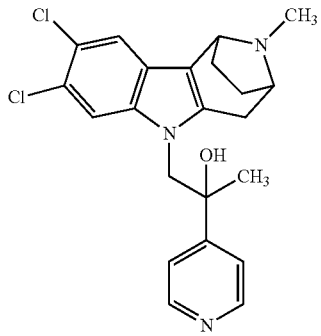
III-116
III-116a,
III-116b,
III-116c,
III-116d
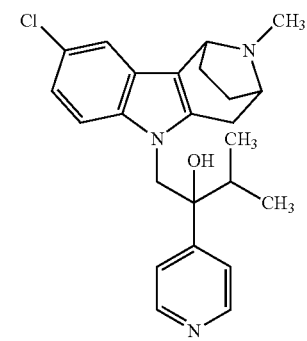
III-117
III-117a,
III-117b,
III-117c,
III-117d
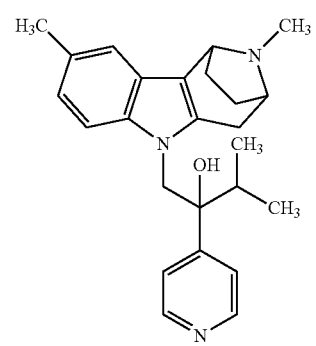
III-118
III-118a,
III-118b,
III-118c,
III-118d TABLE 3-continued
Representative Compounds of the Invention.
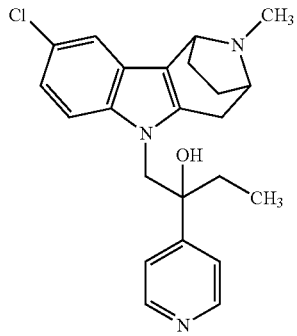
III-119
III-119a,
III-119b,
III-119c,
III-119d
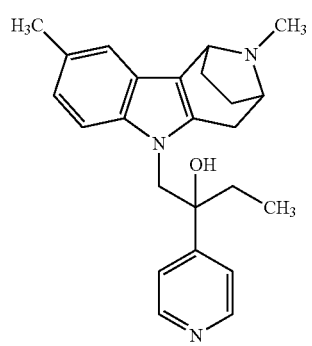
III-120
III-120a,
III-120b,
III-120c,
III-120d
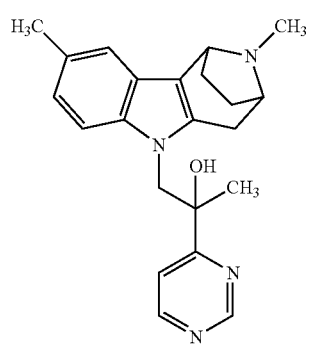
III-121
III-121a,
III-121b,
III-121c,
III-121d
TABLE 3-continued
Representative Compounds of the Invention.
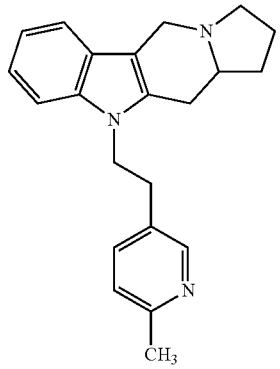
III-122
III-122a,
III-122b,
III-122c,
III-122d
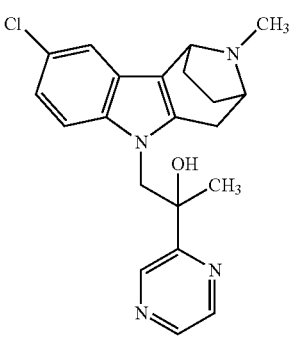
III-123
III-123a,
III-123b,
III-123c,
III-123d
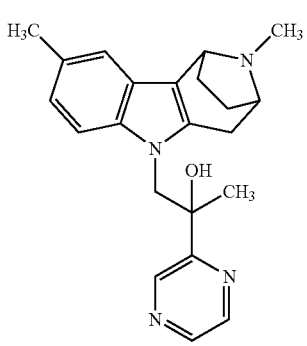
III-124
III-124a,
III-124b,
III-124c,
III-124d TABLE 3-continued
Representative Compounds of the Invention.
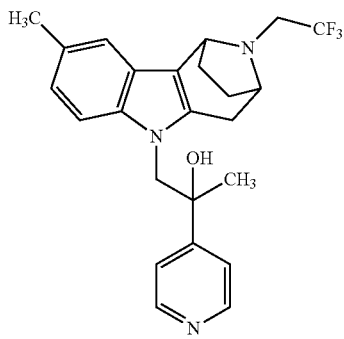
III-125
III-125a,
III-125b,
III-125c,
III-125d
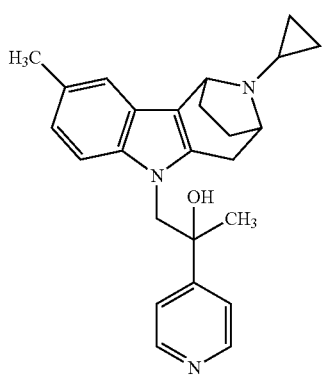
III-126
III-126a,
III-126b,
III-126c,
III-126d
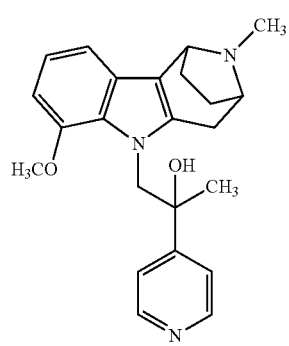
III-127
III-127a,
III-127b,
III-127c,
III-127d
TABLE 3-continued
Representative Compounds of the Invention.
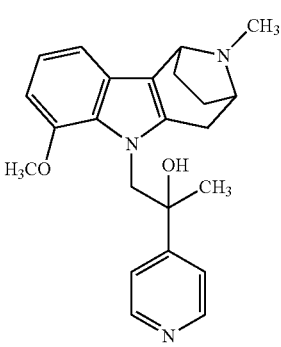
III-128
III-128a,
III-128b,
III-128c,
III-128d
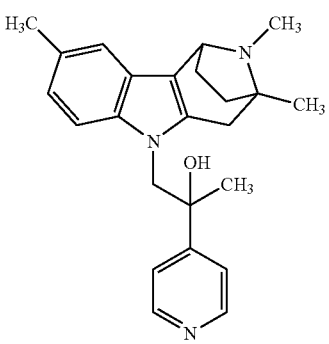
III-129
III-129a,
III-129b,
III-129c,
III-129d
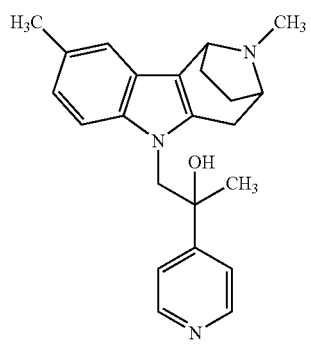
III-130
III-130a,
III-130b,
III-130c,
III-130d TABLE 3-continued
Representative Compounds of the Invention.
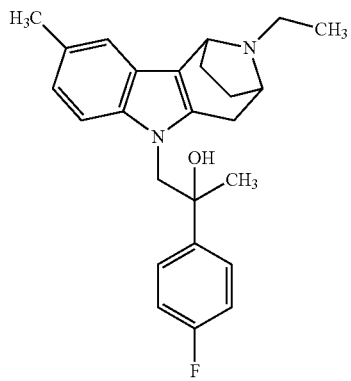
III-131
III-131a,
III-131b,
III-131c,
III-131d
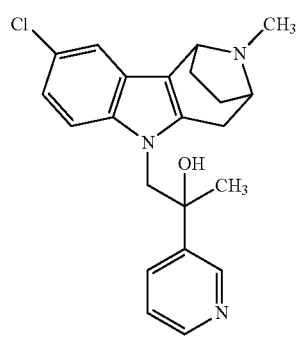
III-132
III-132a,
III-132b,
III-132c,
III-132d
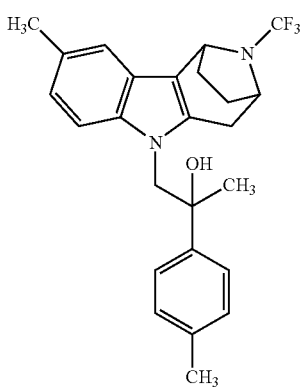
III-133
III-133a,
III-133b,
III-133c,
III-133d
TABLE 3-continued
Representative Compounds of the Invention.
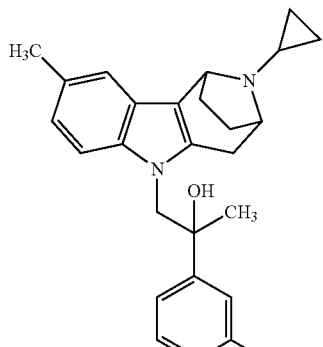
III-134
III-134a,
III-134b,
III-134c,
III-134d
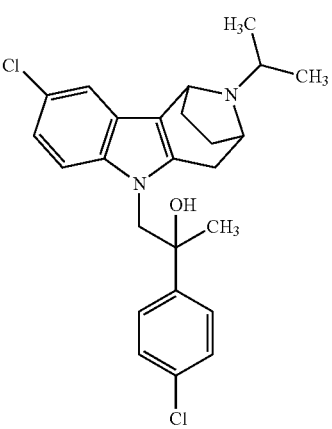
III-135
III-135a,
III-135b,
III-135c,
III-135d
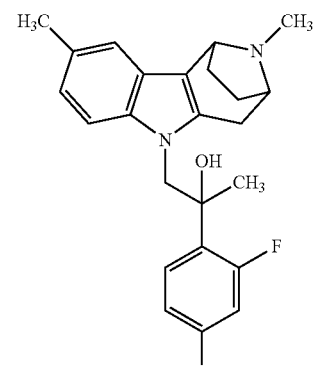
III-136
III-136a,
III-136b,
III-136c,
III-136d

TABLE 3-continued
Representative Compounds of the Invention.
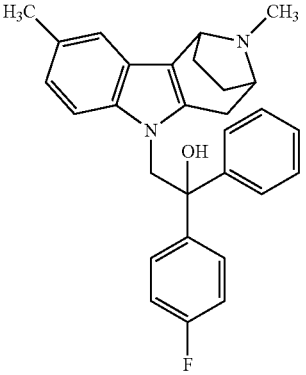 III-137
III-137a,
III-137b,
III-137c,
III-137d
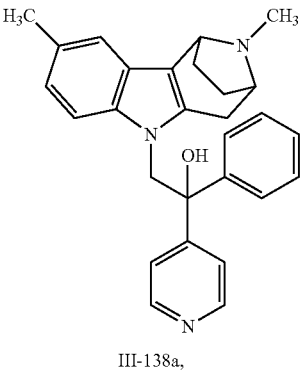 III-138
III-138a,
III-138b,
III-138c,
III-138d
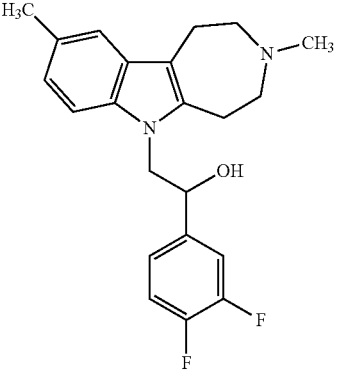 III-139
III-139a,
III-139b
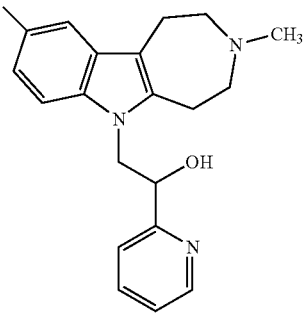 III-140
III-140a,
III-140b
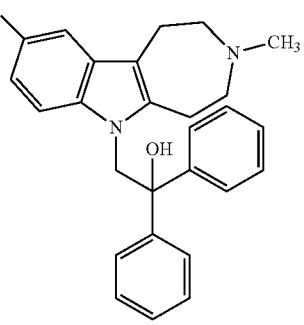 III-141
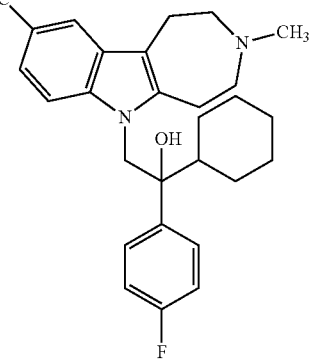 III-142
III-142a,
III-142b
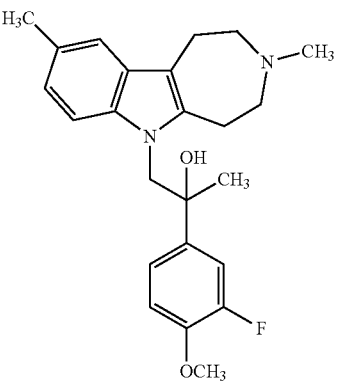 III-143
III-143a,
III-143b

TABLE 3-continued
Representative Compounds of the Invention.
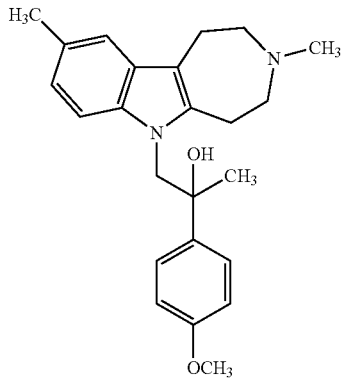
III-144
III-144a,
III-144b
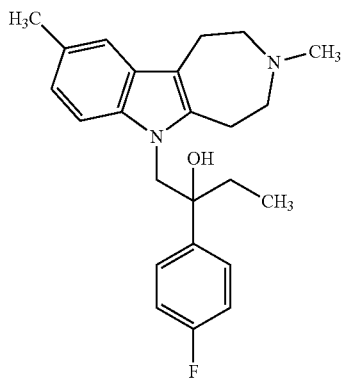
III-145
III-145a,
III-145b
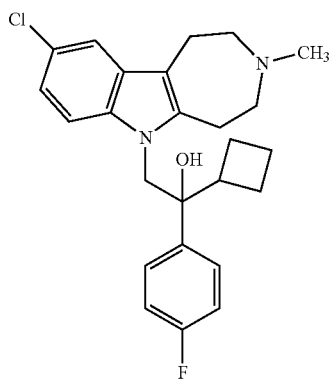
III-146
III-146a,
III-146b
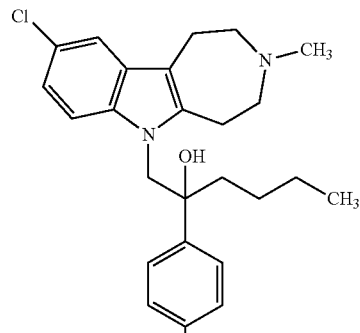
III-147
III-147a,
III-147b
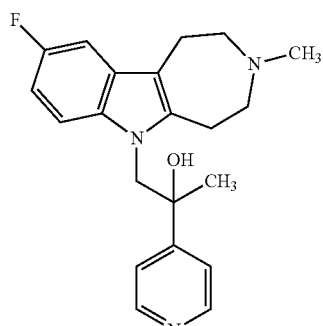
III-148
III-148a,
III-148b
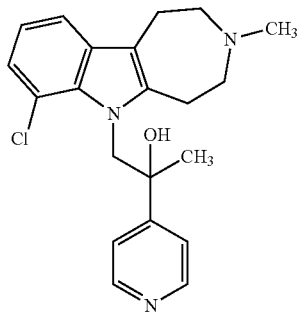
III-149
III-149a,
III-149b
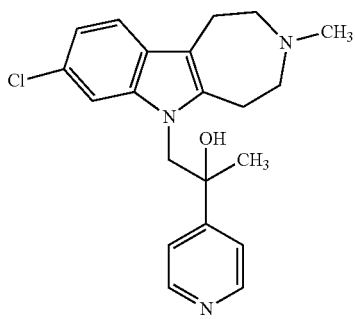
III-150
III-150a,
III-150b TABLE 3-continued
Representative Compounds of the Invention.
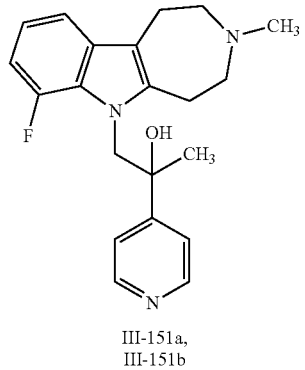 [SMILES: CN1CCc2c(n(CC(C)(O)c3ccncc3)c3c(F)cccc23)CC1]
III-151
III-151a,
III-151b
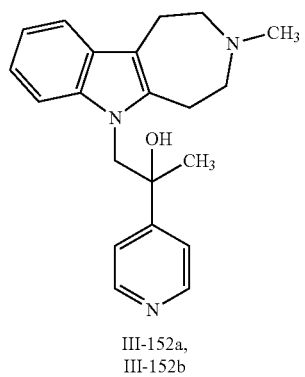 [SMILES: CN1CCc2c(n(CC(C)(O)c3ccncc3)c3ccccc23)CC1]
III-152
III-152a,
III-152b
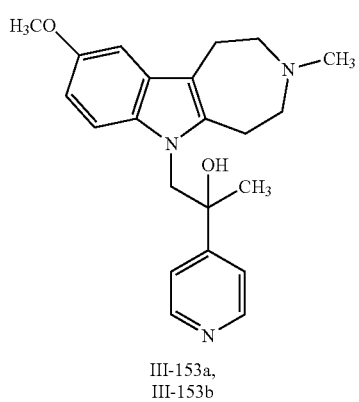 [SMILES: COc1ccc2c(c1)c1c(n2CC(C)(O)c2ccncc2)CCN(C)CC1]
III-153
III-153a,
III-153b
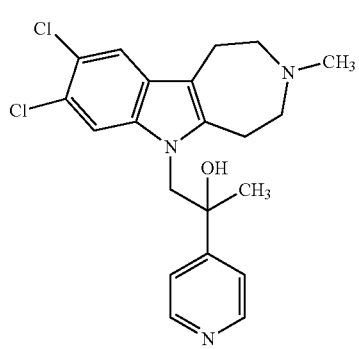
III-154
III-154a,
III-154b
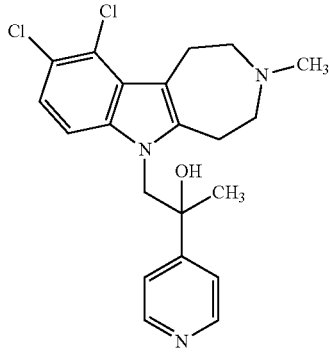
III-155
III-155a,
III-155b
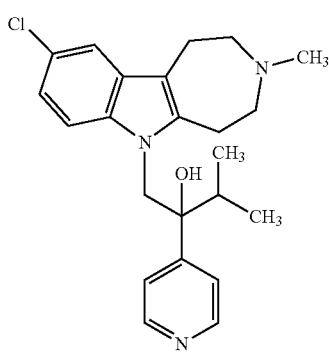
III-156
III-156a,
III-156b
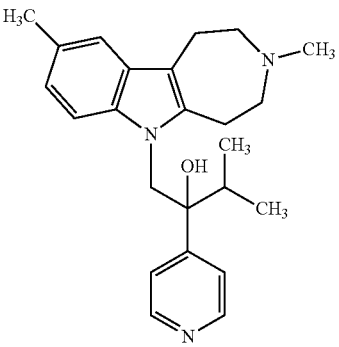
III-157
III-157a,
III-157b TABLE 3-continued
Representative Compounds of the Invention.
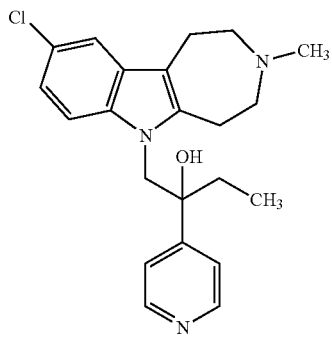
III-158
III-158a,
III-158b
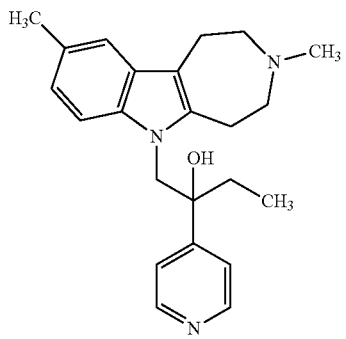
III-159
III-159a,
III-159b
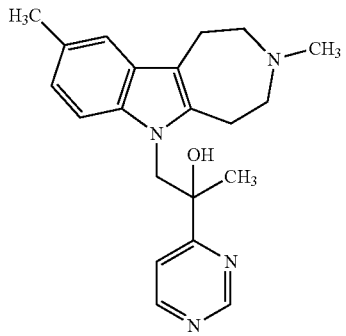
III-160
III-160a,
III-160b
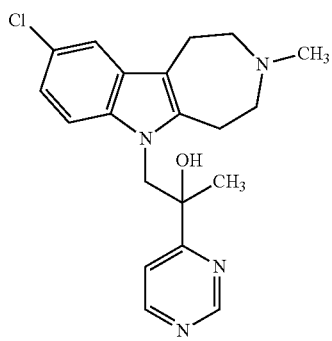
III-161
III-161a,
III-161b
TABLE 3-continued
Representative Compounds of the Invention.
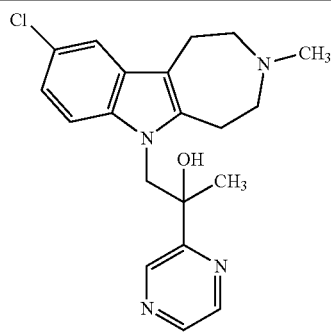
III-162
III-162a,
III-162b
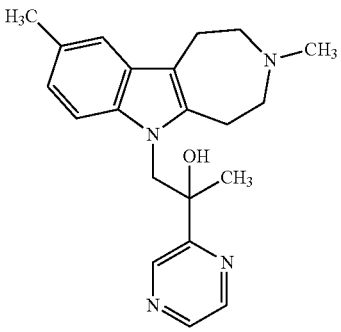
III-163
III-163a,
III-163b
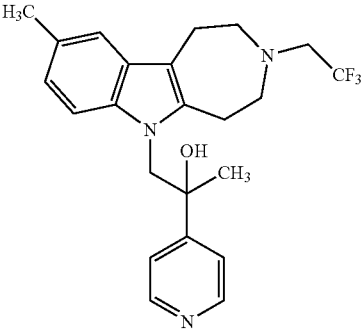
III-164
III-164a,
III-164b
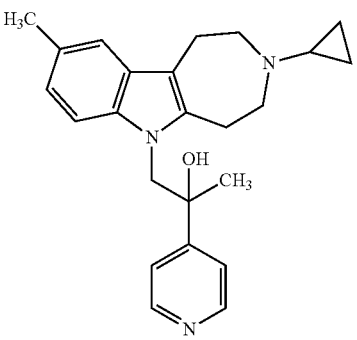
III-165
III-165a,
III-165b

TABLE 3-continued

Representative Compounds of the Invention.

III-166

III-166a,
III-166b

III-167

III-167a,
III-167b

III-168

III-168a,
III-168b,
III-168c,
III-168d

TABLE 3-continued

Representative Compounds of the Invention.

III-169

III-169a,
III-169b

III-170

III-170a,
III-170b

III-171

III-171a,
III-171b

TABLE 3-continued
Representative Compounds of the Invention.
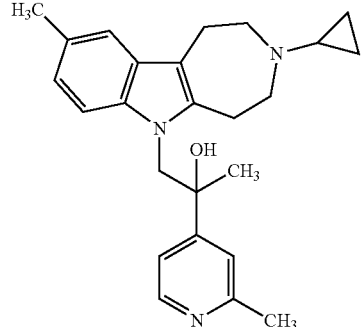
III-172
III-172a,
III-172b
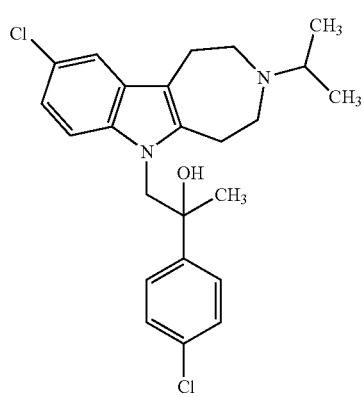
III-173
III-173a,
III-173b
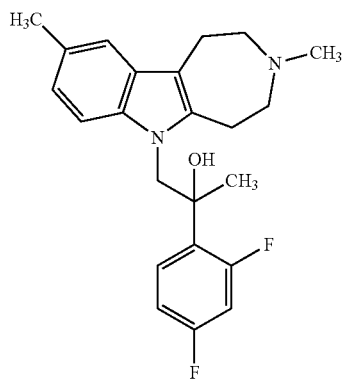
III-174
III-174a,
III-174b
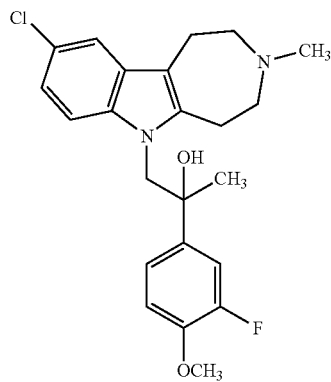
III-175
III-175a,
III-175b
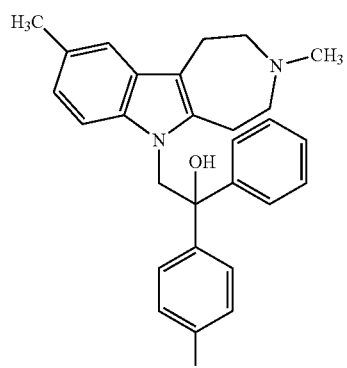
III-176
III-176a,
III-176b
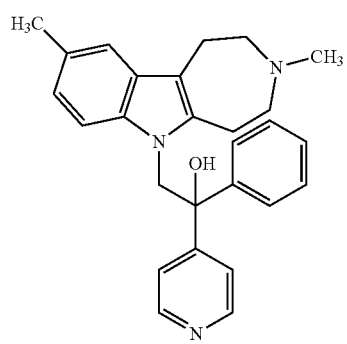
III-177
III-177a,
III-177b TABLE 3-continued
Representative Compounds of the Invention.
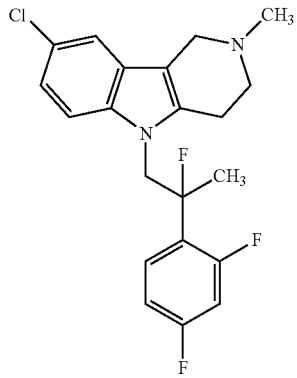
III-178
III-178a,
III-178b
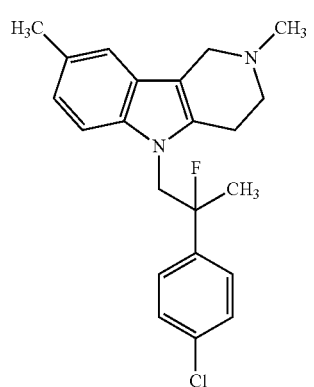
III-179
III-179a,
III-179b
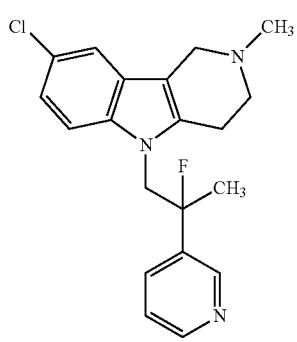
III-180
III-180a,
III-180b
TABLE 3-continued
Representative Compounds of the Invention.
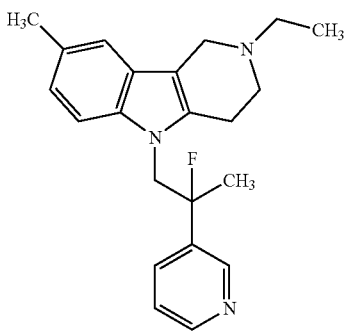
III-181
III-181a,
III-181b
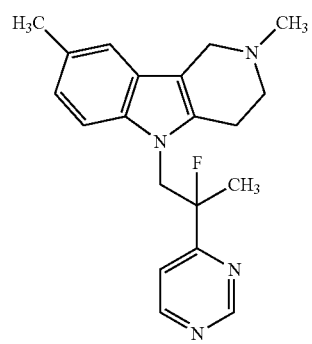
III-182
III-182a,
III-182b
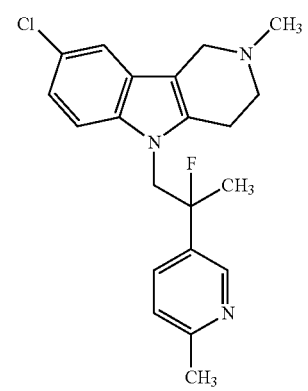
III-183
III-183a,
III-183b

TABLE 3-continued
Representative Compounds of the Invention.
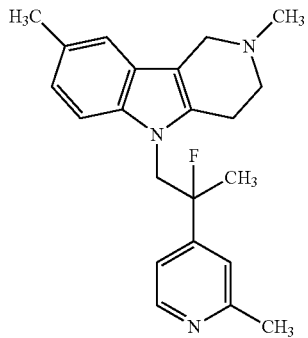
III-184
III-184a,
III-184b
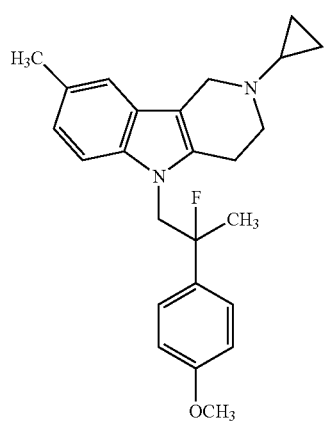
III-185
III-185a,
III-185b
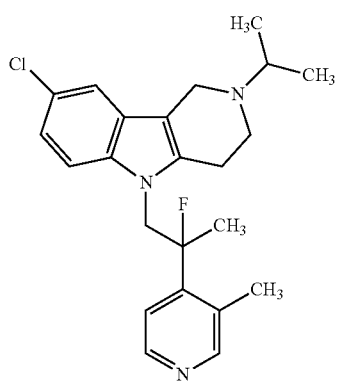
III-186
III-186a,
III-186b
TABLE 3-continued
Representative Compounds of the Invention.
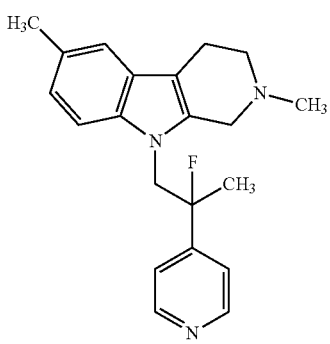
III-187
III-187a,
III-187b
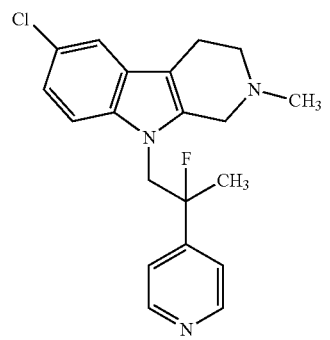
III-188
III-188a,
III-188b
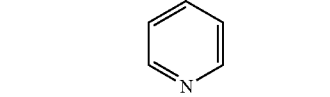
III-189
III-189a,
III-189b TABLE 3-continued
Representative Compounds of the Invention.
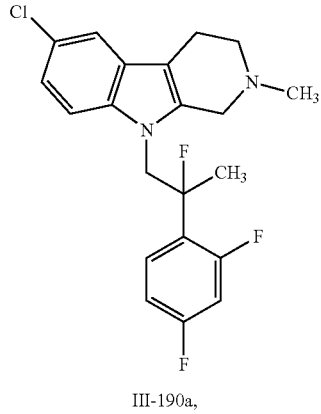
III-190a,
III-190b
III-190
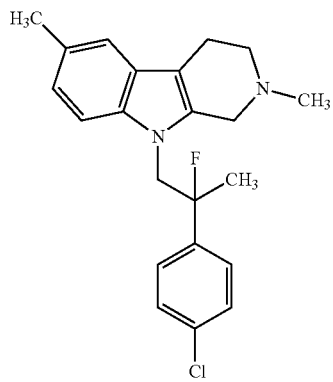
III-191a,
III-191b
III-191
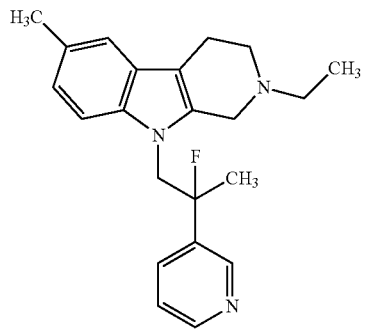
III-192a,
III-192b
III-192
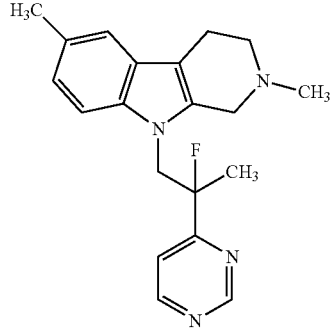
III-193a,
III-193b
III-193
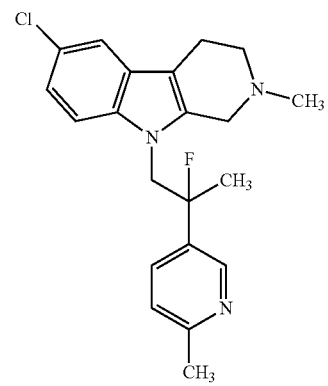
III-194a,
III-194b
III-194
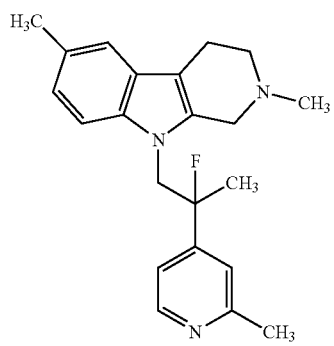
III-195a,
III-195b
III-195

TABLE 3-continued
Representative Compounds of the Invention.
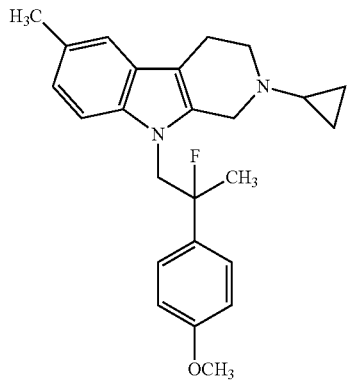
III-196
III-196a,
III-196b
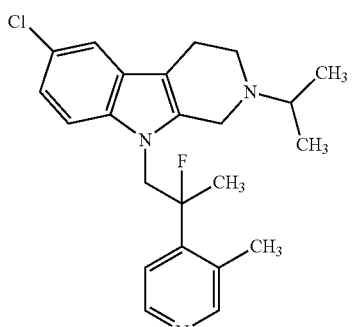
III-197
III-197a,
III-197b
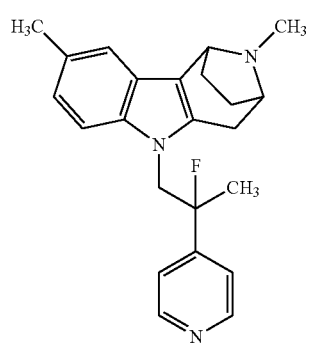
III-198
III-198a,
III-198b,
III-198c,
III-198d
TABLE 3-continued
Representative Compounds of the Invention.
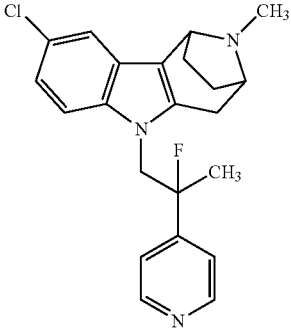
III-199
III-199a,
III-199b,
III-199c,
III-199d
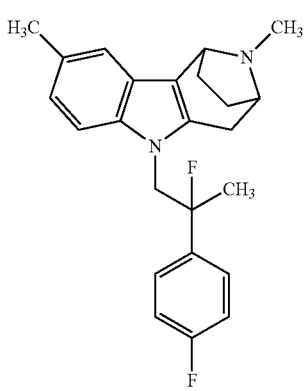
III-200
III-200a,
III-200b,
III-200c,
III-200d
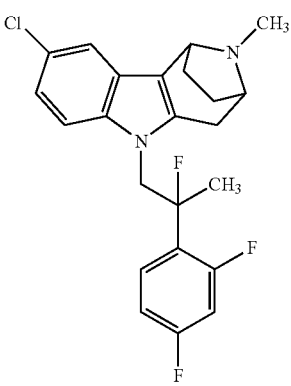
III-201
III-201a,
III-201b,
III-201c,
III-201d TABLE 3-continued
Representative Compounds of the Invention.
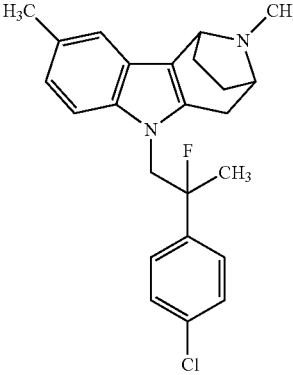
III-202
III-202a,
III-202b,
III-202c,
III-202d
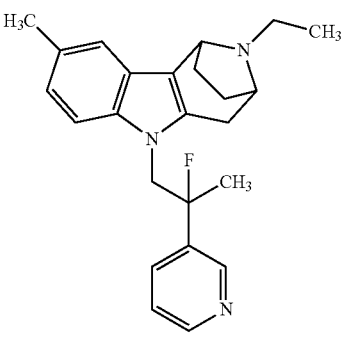
III-203
III-203a,
III-203b,
II-203c,
III-203d
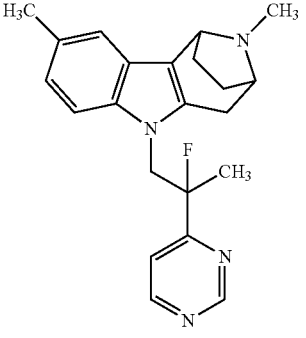
III-204
III-204a,
III-204b,
III-204c,
III-204d
TABLE 3-continued
Representative Compounds of the Invention.
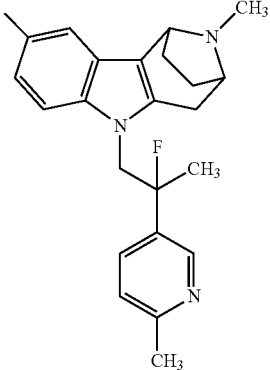
III-205
III-205a,
III-205b,
III-205c,
III-205d
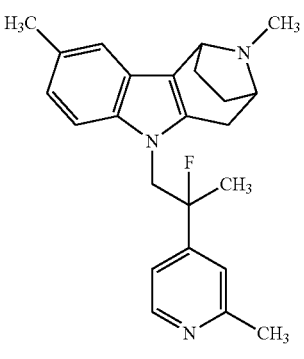
III-206
III-206a,
III-206b,
III-206c,
III-207d
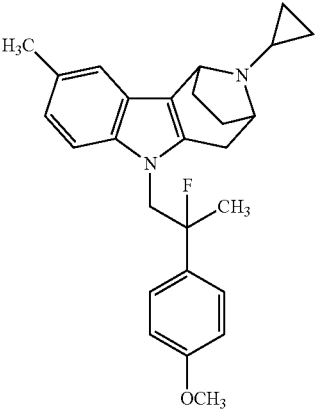
III-207
III-207a,
III-207b,
III-207c,
III-207d TABLE 3-continued
Representative Compounds of the Invention.
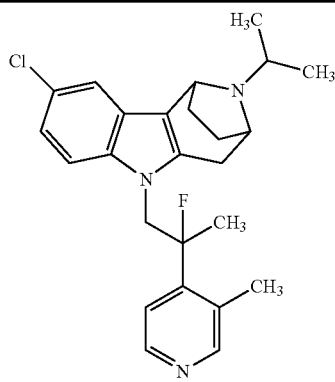
III-208
III-208a,
III-208b,
III-208c,
III-208d
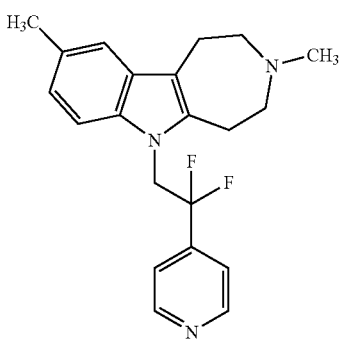
III-209
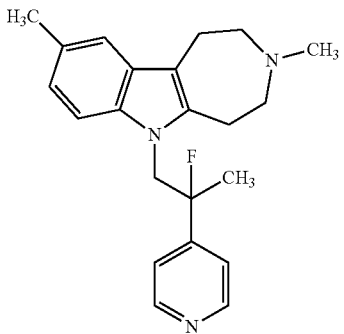
III-210
III-210a,
III-210b
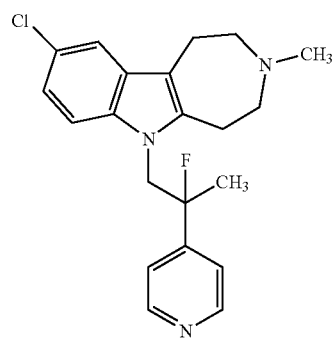
III-211
III-211a,
III-211b
TABLE 3-continued
Representative Compounds of the Invention.
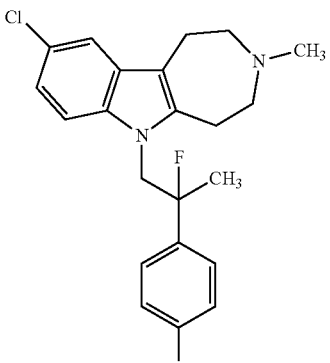
III-212
III-212a,
III-212b
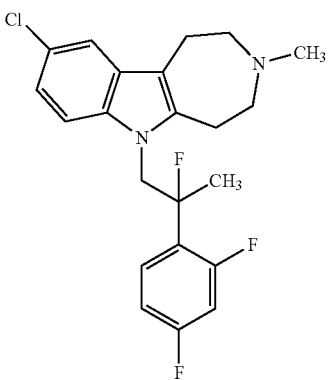
III-213
III-213a,
III-213b
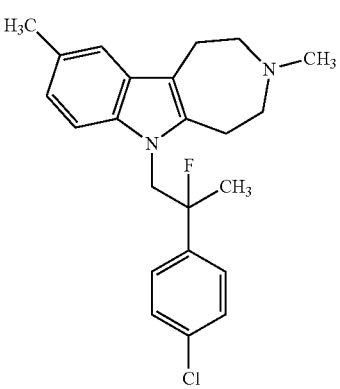
III-214
III-214a,
III-214b TABLE 3-continued Representative Compounds of the Invention.

III-215, III-215a, III-215b

III-216, III-216a, III-216b

III-217, III-217a, III-217b

III-218, III-218a, III-218b

III-219, III-219a, III-219b

III-220, III-220a, III-220b

TABLE 3-continued
Representative Compounds of the Invention.
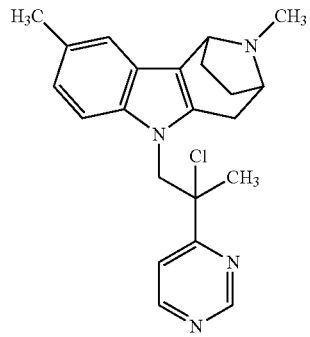
III-221
III-221a,
III-221b,
III-221c,
III-221d
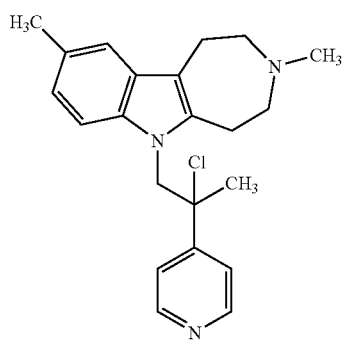
III-222
III-222a,
III-222b
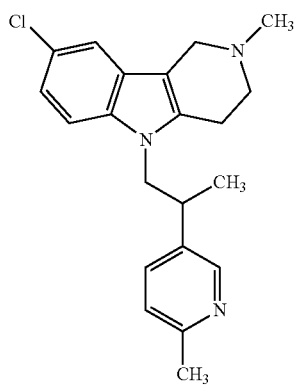
III-223
III-223a,
III-223b
TABLE 3-continued
Representative Compounds of the Invention.
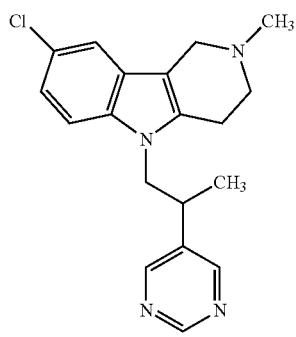
III-224
III-224a,
III-224b
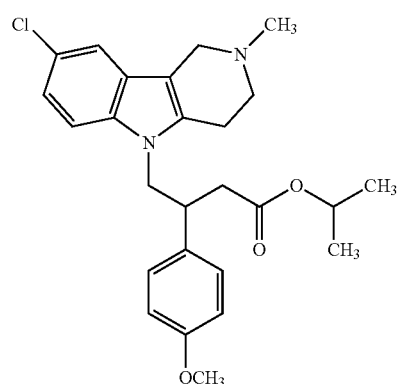
III-225
III-225a,
III-225b
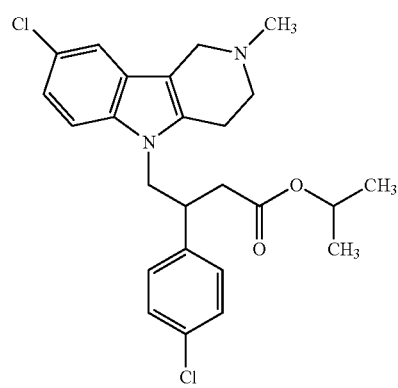
III-226
III-226a,
III-226b TABLE 3-continued
Representative Compounds of the Invention.
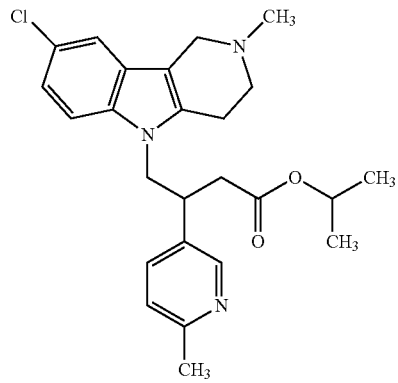
III-227
III-227a,
III-227b
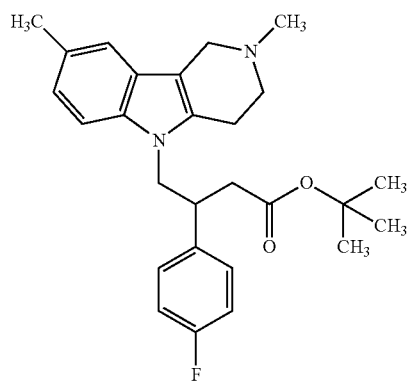
III-228
III-228a,
III-228b
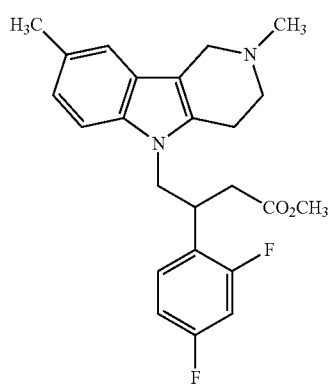
III-229
III-229a,
III-229b
TABLE 3-continued
Representative Compounds of the Invention.
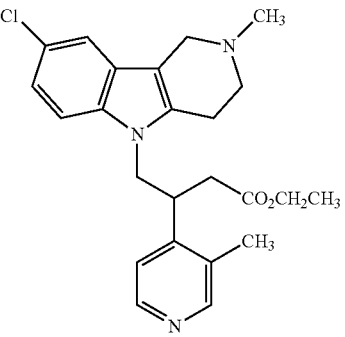
III-230
III-230a,
III-230b
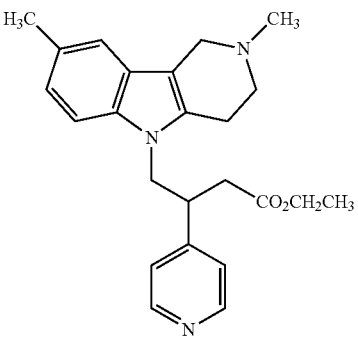
III-231
III-231a,
III-231b
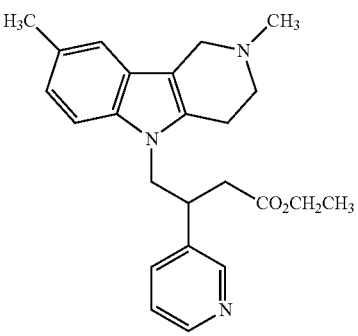
III-232
III-232a,
III-232b
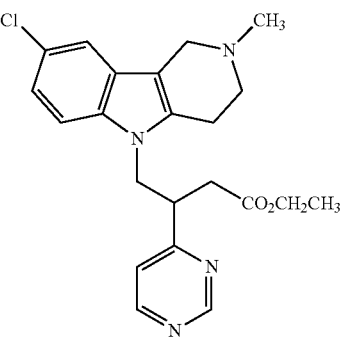
III-233
III-233a,
III-233b TABLE 3-continued
Representative Compounds of the Invention.
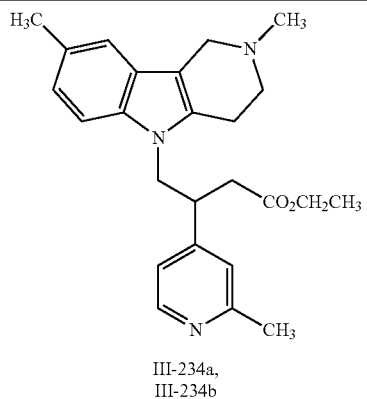
III-234a,
III-234b
III-234
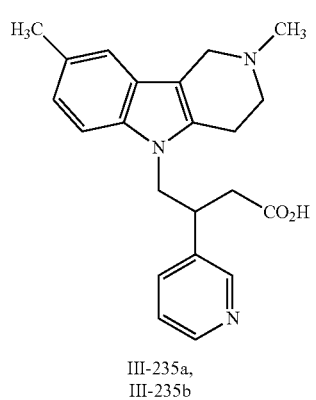
III-235a,
III-235b
III-235
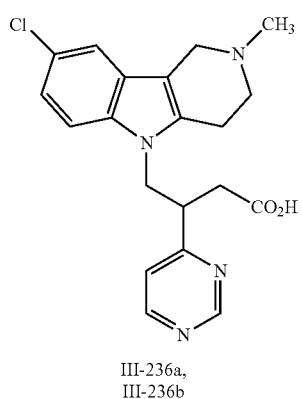 [SMILES: CN1CCc2c(c3cc(Cl)ccc3n2CC(CC(=O)O)c2ccncn2)C1]
III-236a,
III-236b
III-236
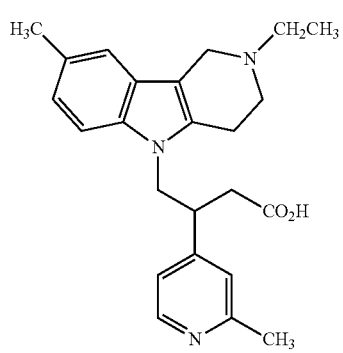
III-237a,
III-237b
III-237
TABLE 3-continued
Representative Compounds of the Invention.
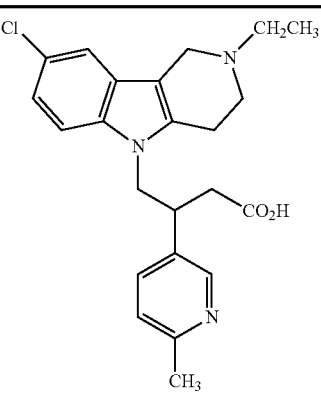
III-238a,
III-238b
III-238
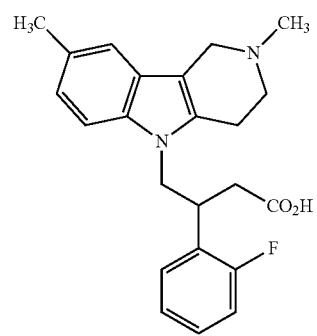
III-239a,
III-239b
III-239
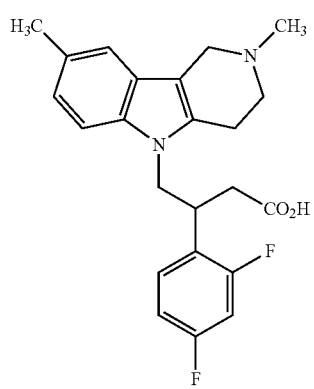
III-240a,
III-240b
III-240

TABLE 3-continued
Representative Compounds of the Invention.
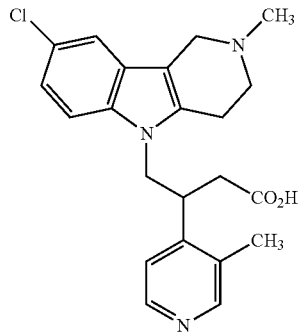
III-241
III-241a,
III-241b
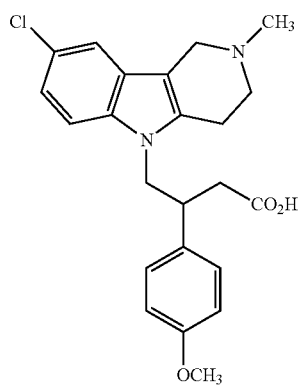
III-242
III-242a,
III-242b
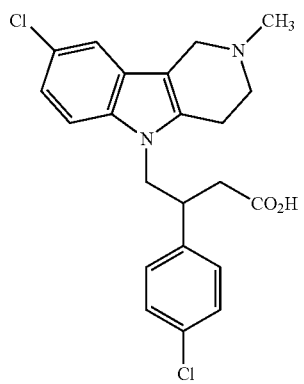
III-243
III-243a,
III-243b
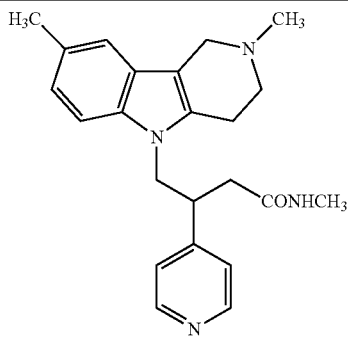
III-244
III-244a,
III-244b
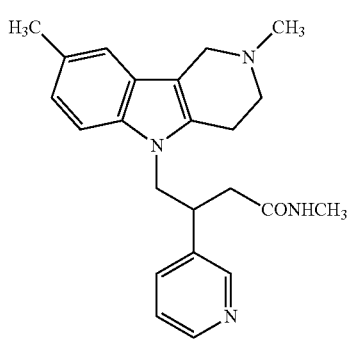
III-245
III-245a,
III-245b
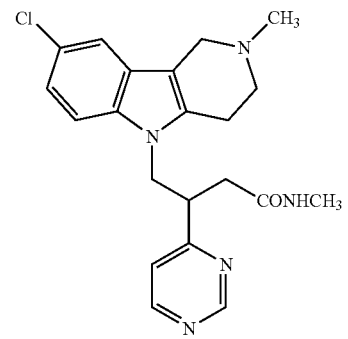
III-246
III-246a,
III-246b
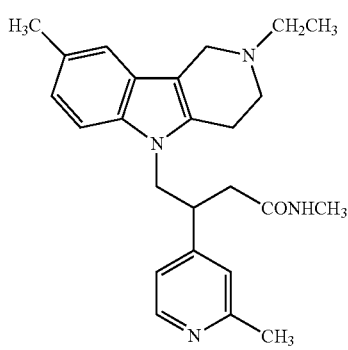
III-247
III-247a,
III-247b

TABLE 3-continued
Representative Compounds of the Invention.
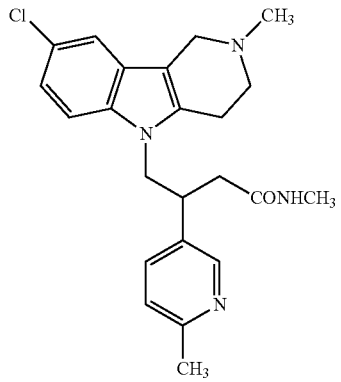
III-248
III-248a,
III-248b
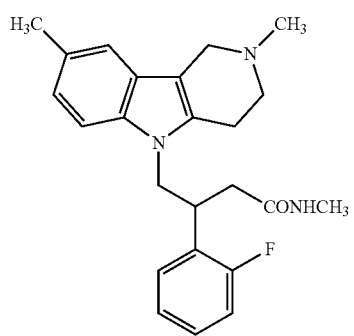
III-249
III-249a,
III-249b
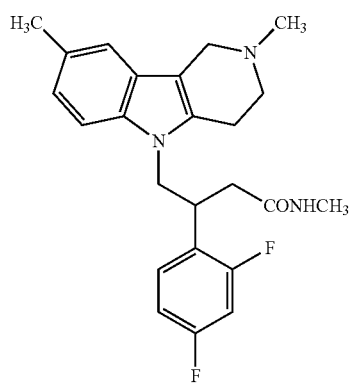
III-250
III-250a,
III-250b
TABLE 3-continued
Representative Compounds of the Invention.
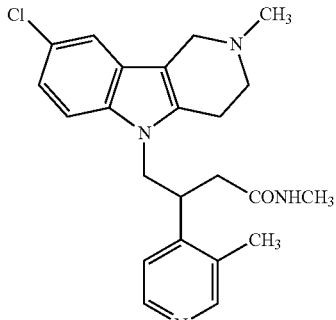
III-251
III-251a,
III-251b
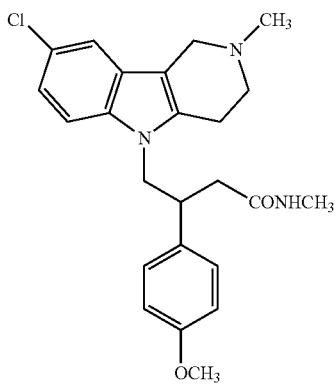
III-252
III-252a,
III-252b
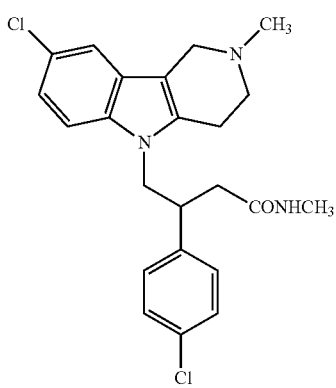
III-253
III-253a,
III-253b TABLE 3-continued
Representative Compounds of the Invention.
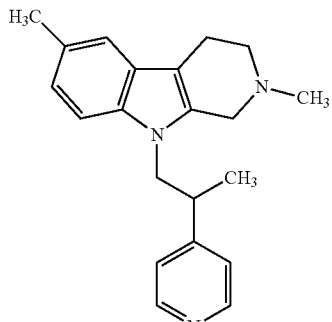
III-254a,
III-254b
III-254
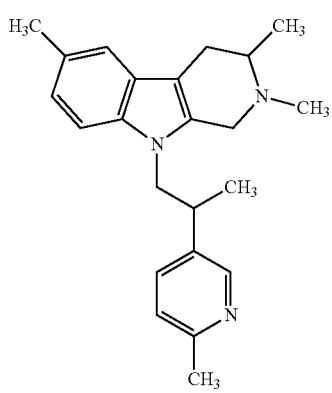
III-255a,
III-255b,
III-255c,
III-255d
III-255
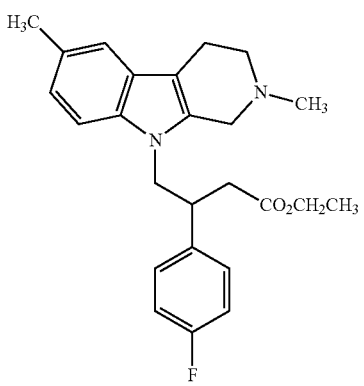
III-256a,
III-256b
III-256
TABLE 3-continued
Representative Compounds of the Invention.
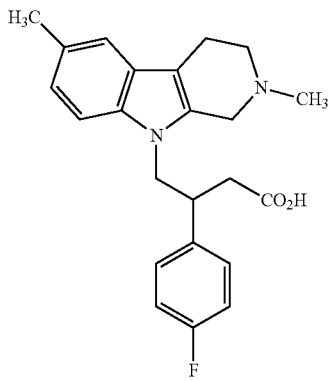
III-257a,
III-257b
III-257
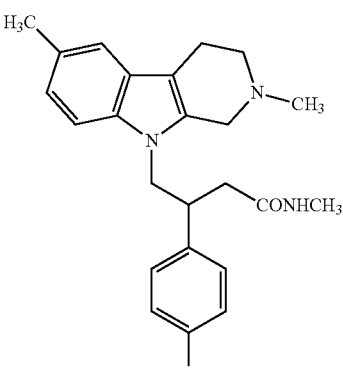
III-258a,
III-258b
III-258
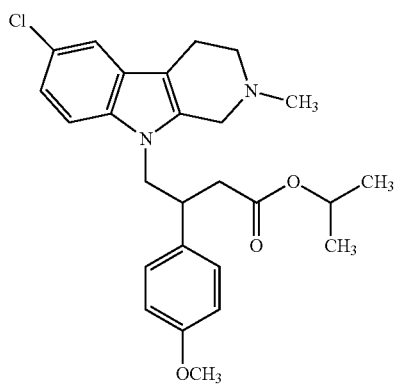
III-259a,
III-259b
III-259

TABLE 3-continued
Representative Compounds of the Invention.
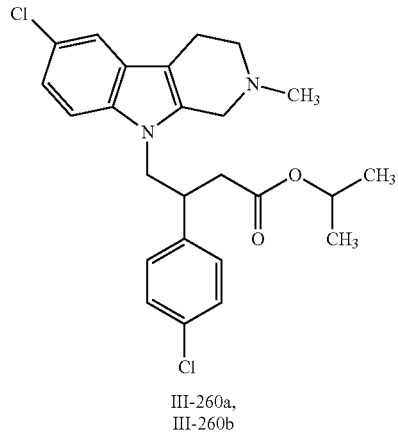 [SMILES: CC(C)OC(=O)CC(Cn1c2c(c3cc(Cl)ccc31)CCN(C)C2)c1ccc(Cl)cc1]
III-260a,
III-260b
III-260
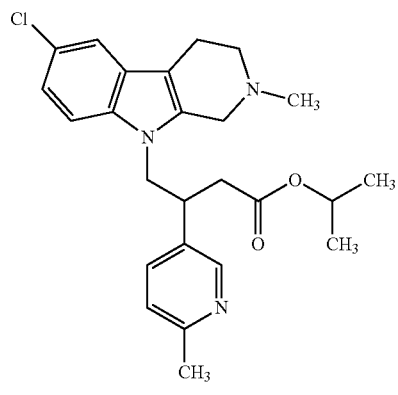
III-261a,
III-261b
III-261
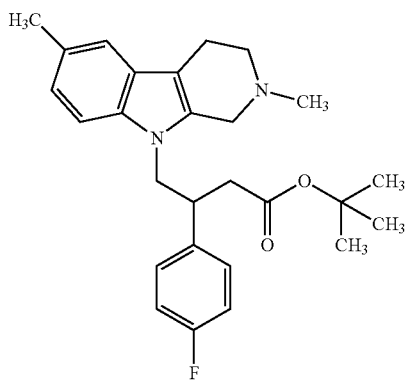
III-262a,
III-262b
III-262
TABLE 3-continued
Representative Compounds of the Invention.
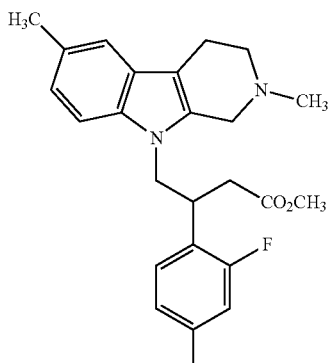
III-263a,
III-263b
III-263
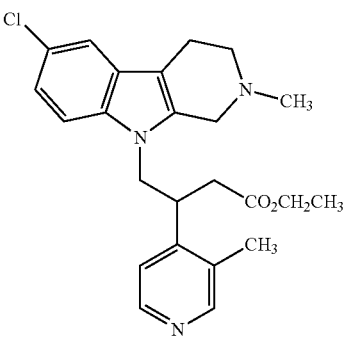
III-264a,
III-264b
III-264
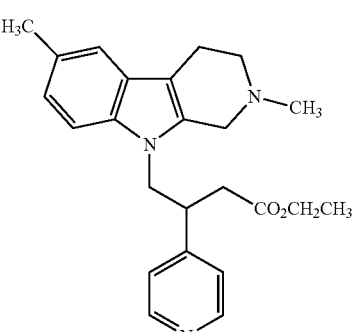
III-265a,
III-265b
III-265

TABLE 3-continued
Representative Compounds of the Invention.
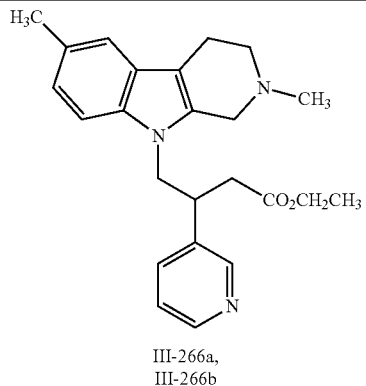
III-266
III-266a,
III-266b
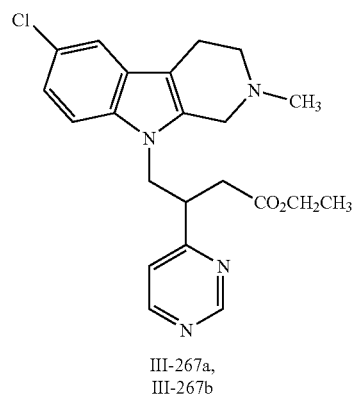
III-267
III-267a,
III-267b
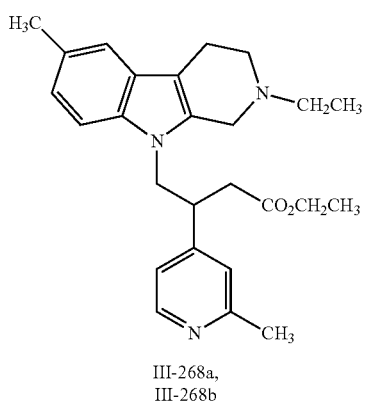
III-268
III-268a,
III-268b
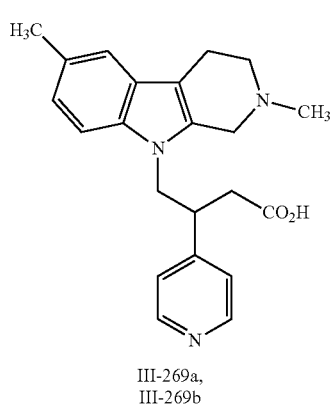
III-269
III-269a,
III-269b
TABLE 3-continued
Representative Compounds of the Invention.
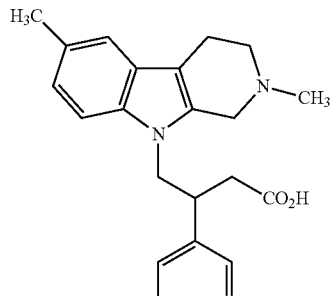
III-270
III-270a,
III-270b
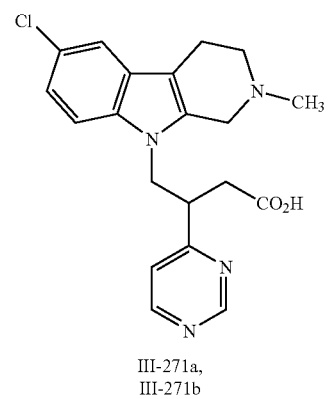 [SMILES: CN1CCc2c(n(CC(CC(=O)O)c3ccncn3)c3ccc(Cl)cc23)C1]
III-271
III-271a,
III-271b
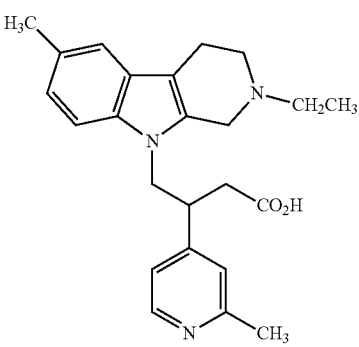
III-272
III-272a,
III-272b TABLE 3-continued
Representative Compounds of the Invention.
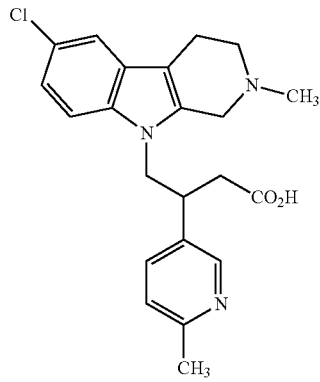
III-273
III-273a,
III-274b
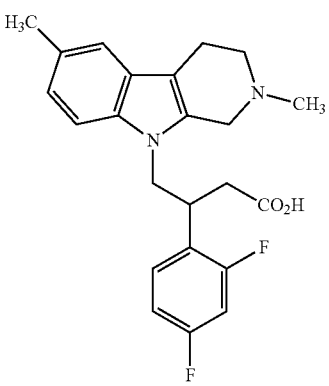
III-274
III-274a,
III-274b
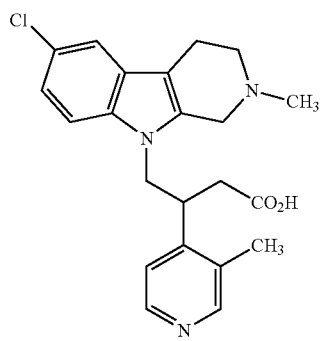
III-275
III-275a,
III-275b
TABLE 3-continued
Representative Compounds of the Invention.
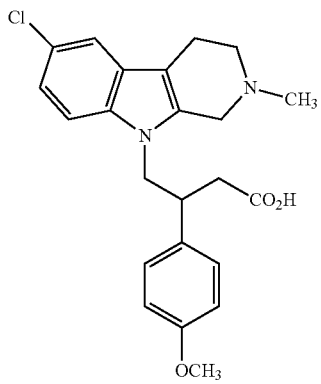
III-276
III-276a,
III-276b
III-277
III-277a,
III-277b
III-278
III-278a,
III-278b TABLE 3-continued
Representative Compounds of the Invention.
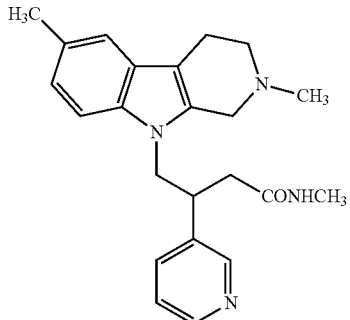
III-279
III-279a,
III-279b
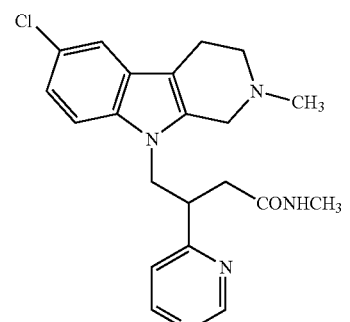
III-280
III-280a,
III-280b
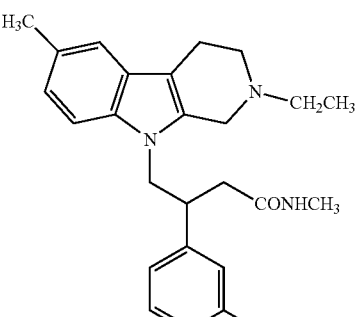
III-281
III-281a,
III-281b
TABLE 3-continued
Representative Compounds of the Invention.
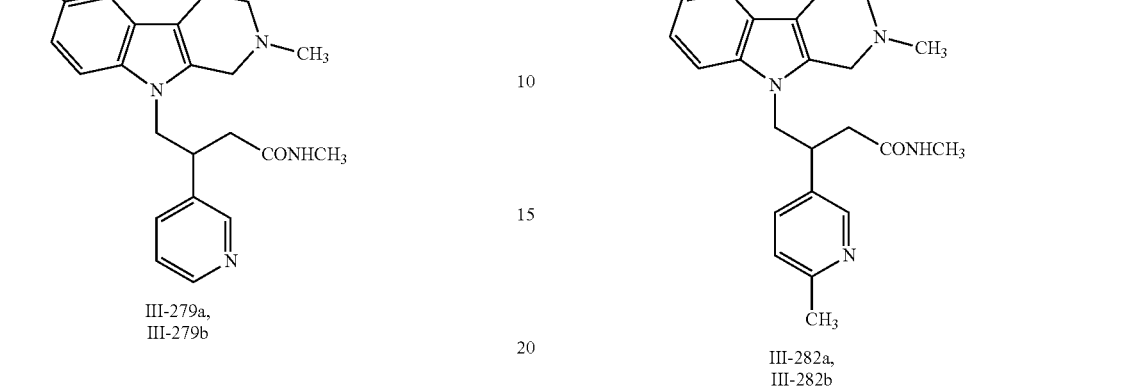
III-282
III-282a,
III-282b
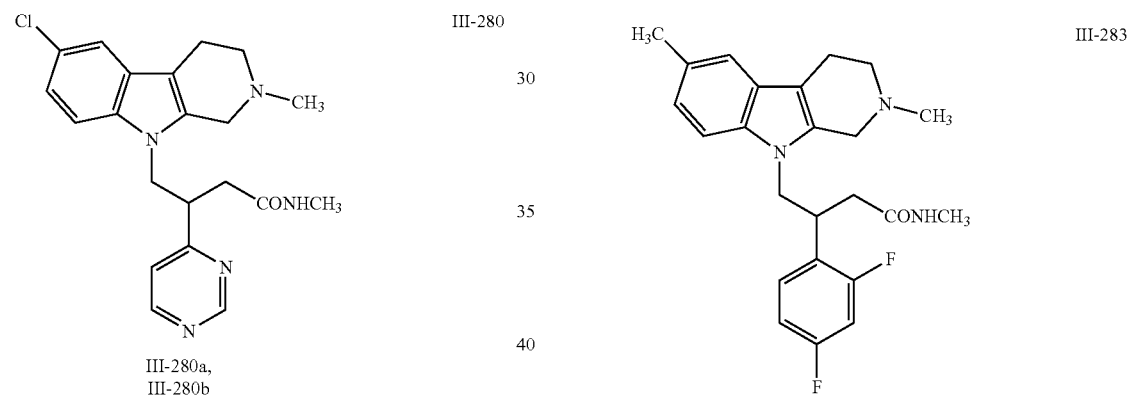
III-283
III-283a,
III-283b
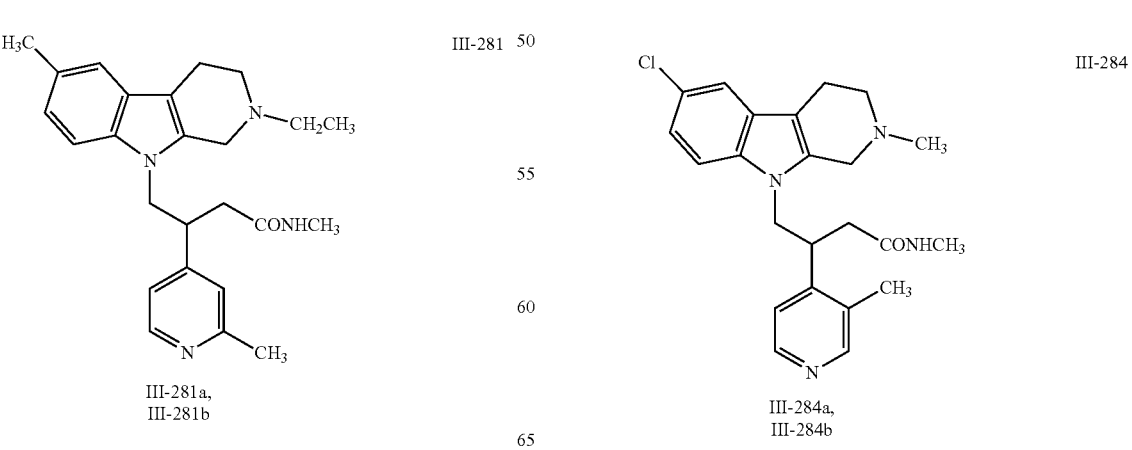
III-284
III-284a,
III-284b TABLE 3-continued
Representative Compounds of the Invention.
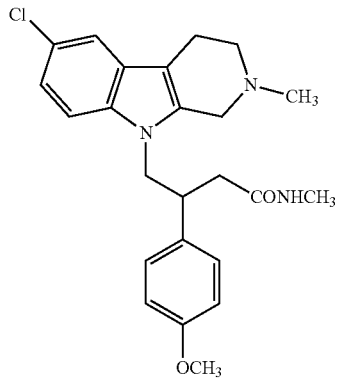
III-285a,
III-285b
III-285
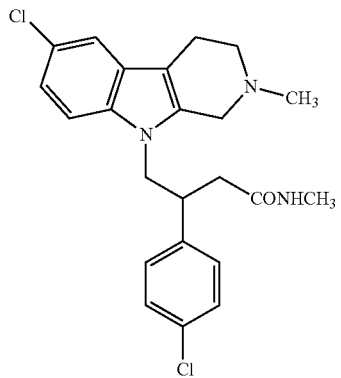
III-286a,
III-286b
III-286
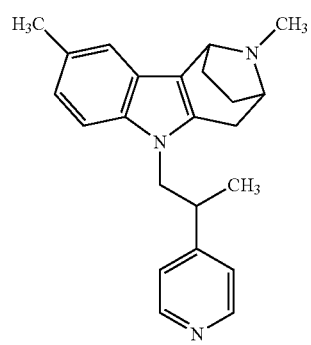
III-287a,
III-287b,
III-287c,
III-287d
III-287
TABLE 3-continued
Representative Compounds of the Invention.
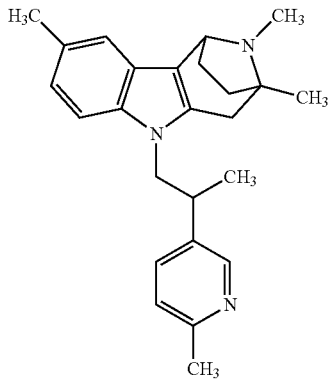
III-288a,
III-288b,
III-288c,
III-288d
III-288
III-289
III-289a,
III-289b,
III-289c,
III-289d
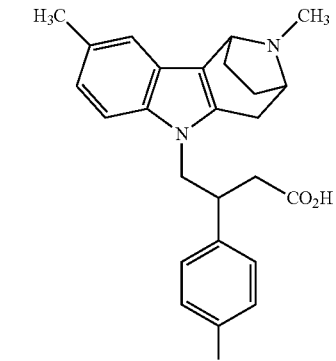
III-290a,
III-290b,
III-290c,
III-290d
III-290

TABLE 3-continued
Representative Compounds of the Invention.
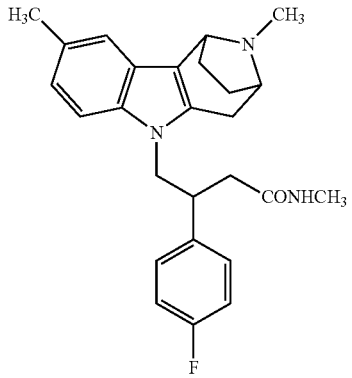
III-291
III-291a,
III-291b,
III-291c,
III-291d
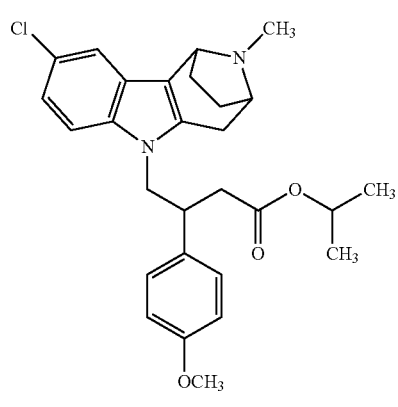
III-292
III-292a,
III-292b,
III-292c,
III-292d
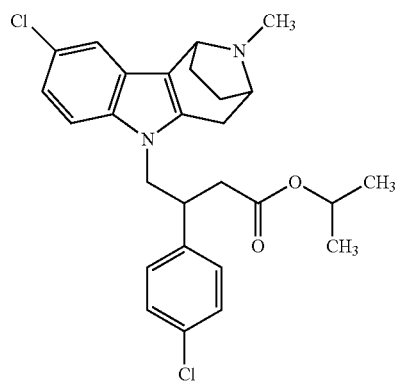
III-293
III-293a,
III-293b,
III-293c,
III-293d
TABLE 3-continued
Representative Compounds of the Invention.
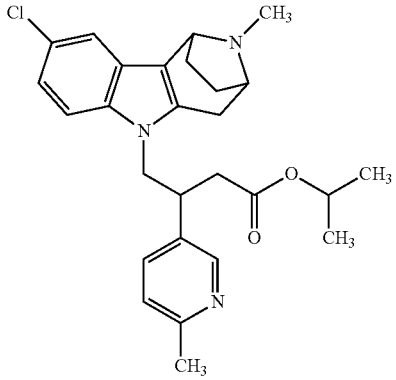
III-294
III-294a,
III-294b,
III-294c,
III-294d
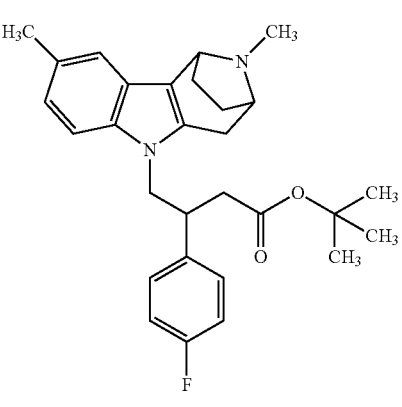
III-295
III-295a,
III-295b,
III-295c,
III-295d
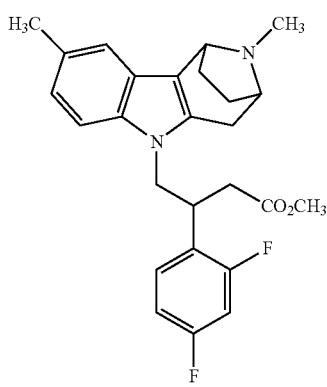
III-296
III-296a,
III-296b,
III-296c,
III-296d TABLE 3-continued
Representative Compounds of the Invention.
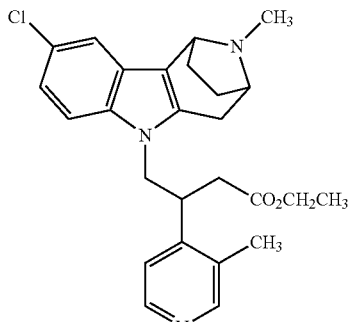
III-297
III-297a,
III-297b,
III-297c,
III-297d
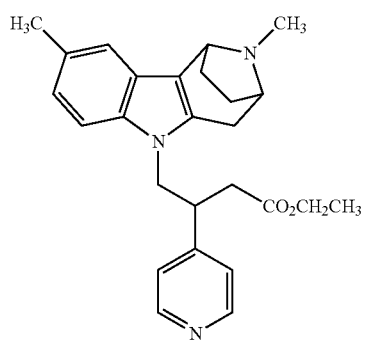
III-298
III-298a,
III-298b,
III-298c,
III-298d
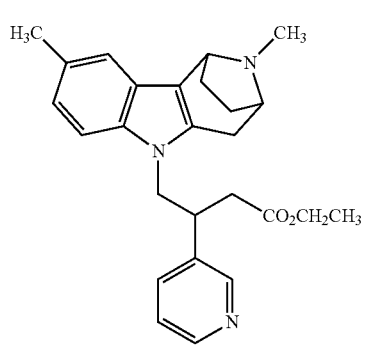
III-299
III-299a,
III-299b,
III-299c,
III-299d
TABLE 3-continued
Representative Compounds of the Invention.
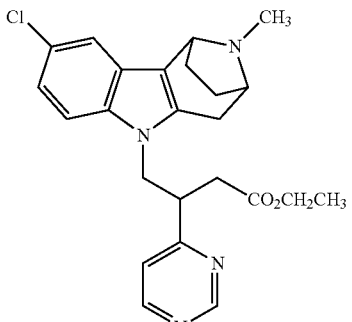
III-300
III-300a,
III-300b,
III-300c,
III-300d
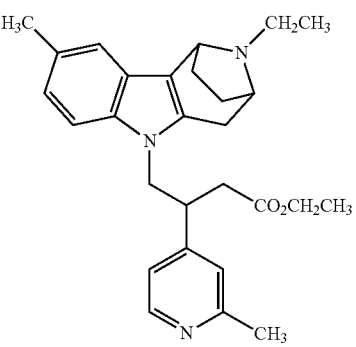
III-301
III-301a,
III-301b,
III-301c,
III-301d
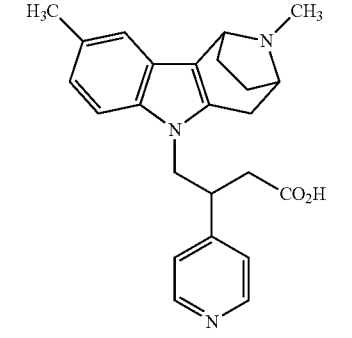
III-302
III-302a,
III-302b,
III-302c,
III-302d TABLE 3-continued
Representative Compounds of the Invention.
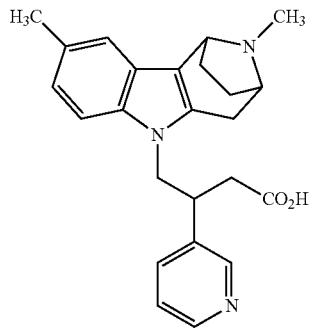
III-303
III-303a,
III-303b,
III-303c,
III-303d
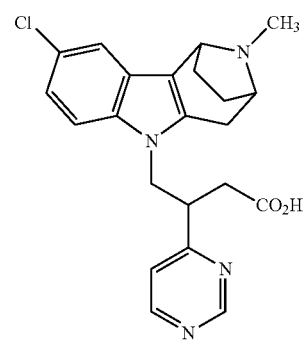
III-304
III-304a,
III-304b,
III-304c,
III-304d
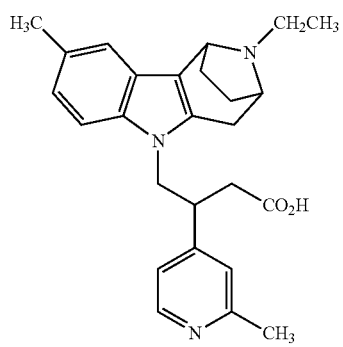
III-305
III-305a,
III-305b,
III-305c,
III-305d
TABLE 3-continued
Representative Compounds of the Invention.
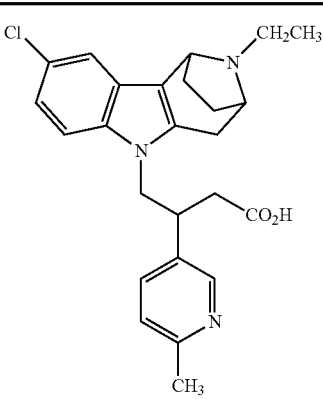
III-306
III-306a,
III-306b,
III-306c,
III-306d
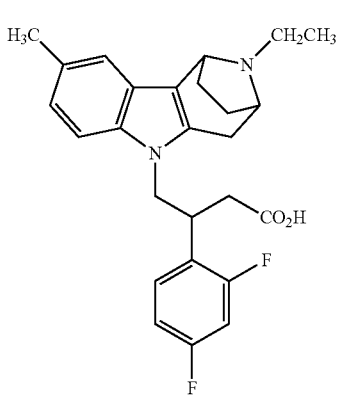
III-307
III-307a,
III-307b,
III-307c,
III-307d
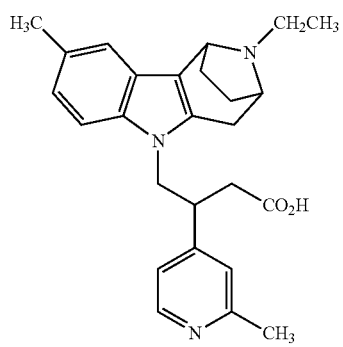
III-308
III-308a,
III-308b,
III-308c,
III-308d TABLE 3-continued Representative Compounds of the Invention.

III-309
III-309a,
III-309b,
III-309c,
III-309d

III-310
III-310a,
III-310b,
III-310c,
III-310d

III-311
III-311a,
III-311b,
III-311c,
III-311d

III-312
III-312a,
III-312b,
III-312c,
III-312d

III-313
III-313a,
III-313b,
III-313c,
III-313d

III-314
III-314a,
III-314b,
III-314c,
III-314d

TABLE 3-continued

Representative Compounds of the Invention.

| Compound | Stereoisomers |
|---|---|
| III-315 | III-315a, III-315b, III-315c, III-315d |
| III-316 | III-316a, III-316b, III-316c, III-316d |
| III-317 | III-317a, III-317b, III-317c, III-317d |
| III-318 | III-318a, III-318b, III-318c, III-318d |
| III-319 | III-319a, III-319b, III-319c, III-319d |
| III-320 | III-320a, III-320b |

TABLE 3-continued
Representative Compounds of the Invention.
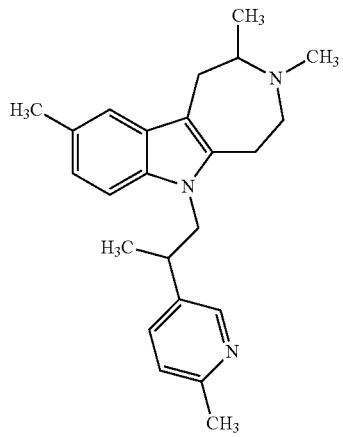
III-321
III-321a,
III-321b,
III-321c,
III-321d
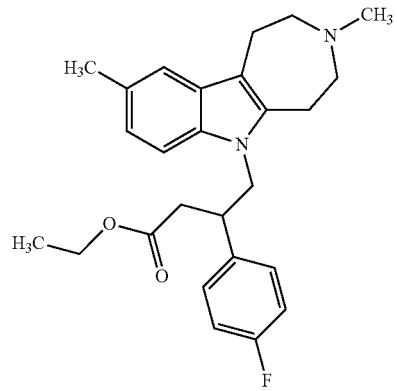
III-322
III-322a,
III-322b
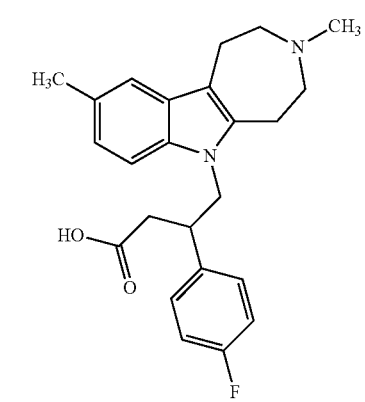
III-323
III-323a,
III-323b
TABLE 3-continued
Representative Compounds of the Invention.
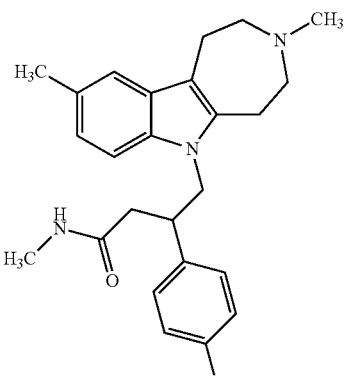
III-324
III-324a,
III-324b
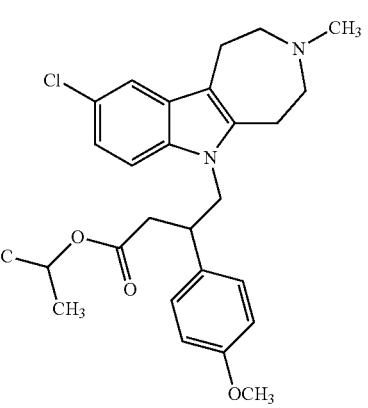
III-325
III-325a,
III-325b
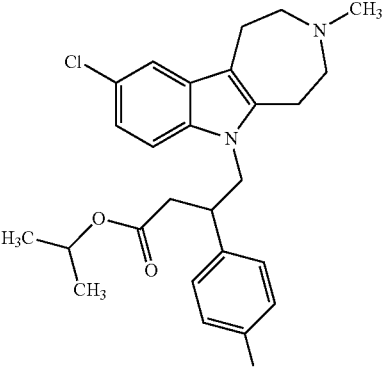
III-326
III-326a,
III-326b

TABLE 3-continued
Representative Compounds of the Invention.
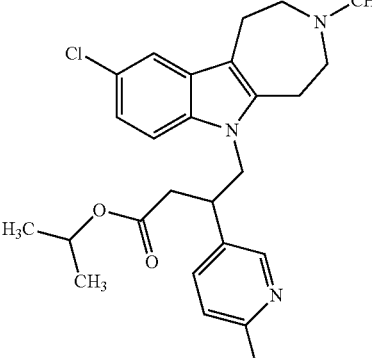
III-327
III-327a,
III-327b
III-328
III-328a,
III-328b
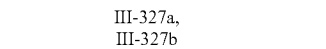
III-329
III-329a,
III-329b
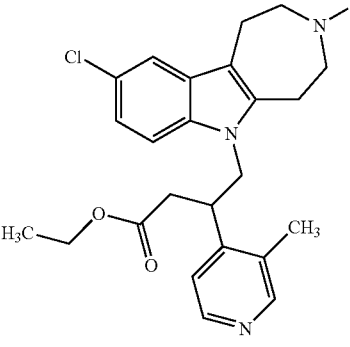
III-330
III-330a,
III-330b
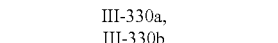
III-331
III-331a,
III-331b
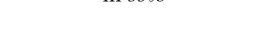
III-332
III-332a,
III-332b TABLE 3-continued Representative Compounds of the Invention.

III-333, III-333a, III-333b

III-334, III-334a, III-334b

III-335, III-335a, III-335b

III-336, III-336a, III-336b

III-337, III-337a, III-337b

III-338, III-338a, III-338b

TABLE 3-continued
Representative Compounds of the Invention.
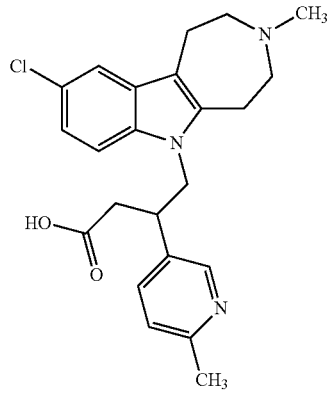
III-339a,
III-339b
III-339
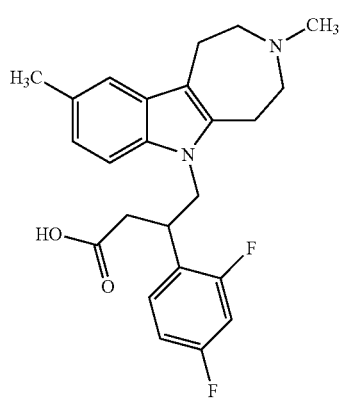
III-340a,
III-340b
III-340
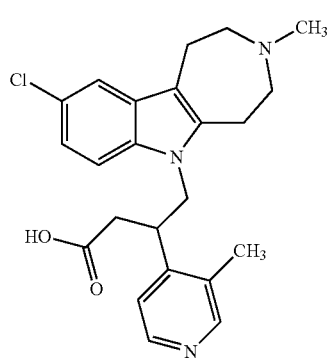
III-341a,
III-341b
III-341
TABLE 3-continued
Representative Compounds of the Invention.
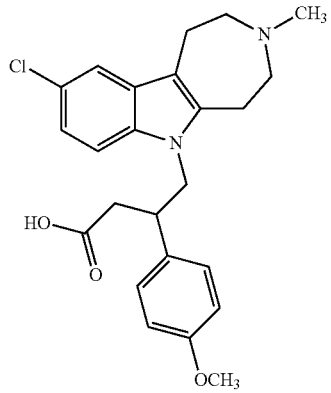
III-342a,
III-342b
III-342
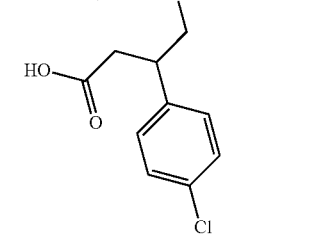
III-343a,
III-343b
III-343
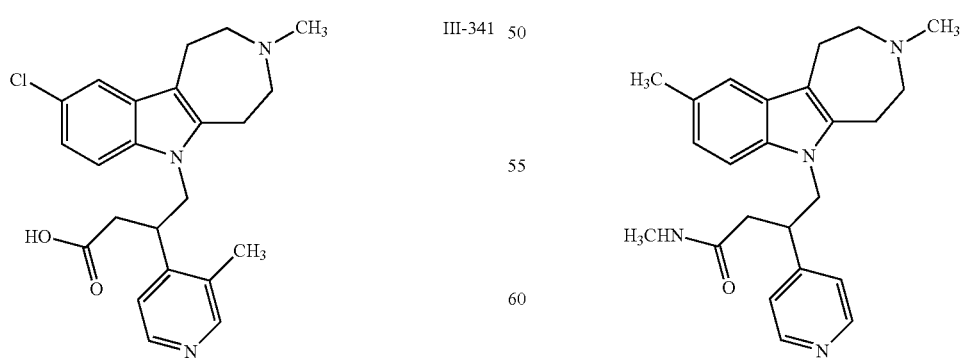
III-344a,
III-344b
III-344

TABLE 3-continued
Representative Compounds of the Invention.
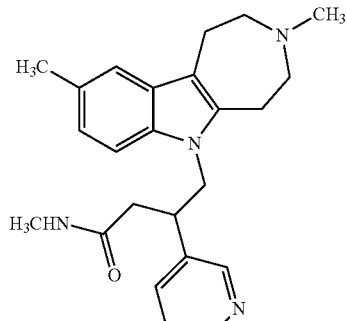
III-345
III-345a,
III-345b
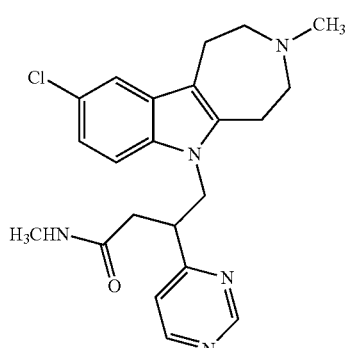
III-346
III-346a,
III-346b
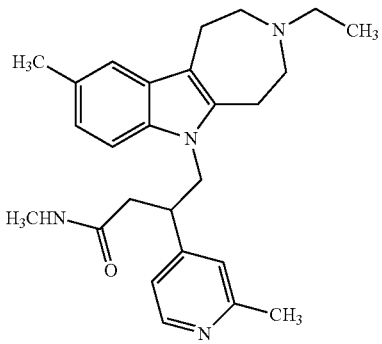
III-347
III-347a,
III-347b
TABLE 3-continued
Representative Compounds of the Invention.
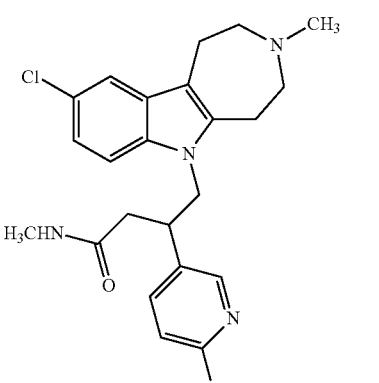
III-348
III-348a,
III-348b
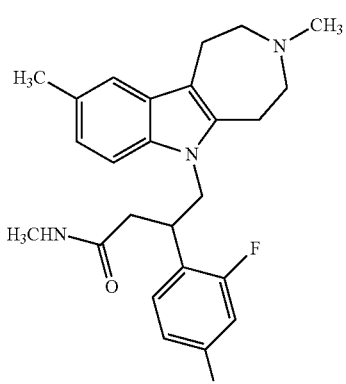
III-349
III-349a,
III-349b
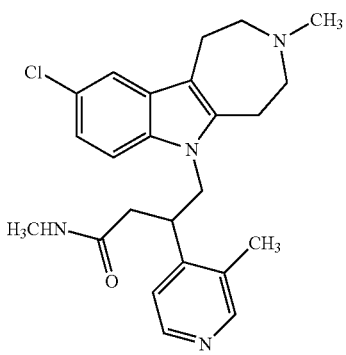
III-350
III-350a,
III-350b TABLE 3-continued
Representative Compounds of the Invention.
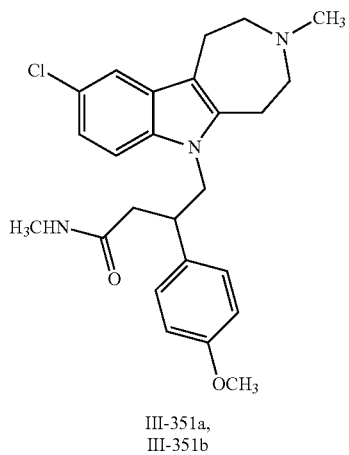
III-351a,
III-351b
III-351
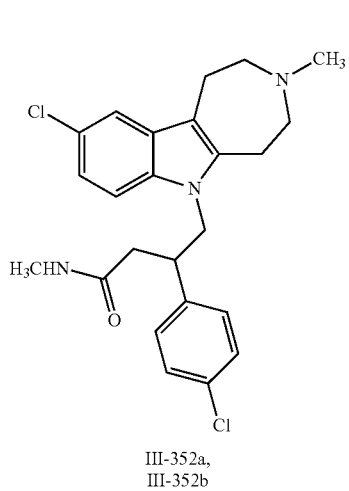
III-352a,
III-352b
III-352
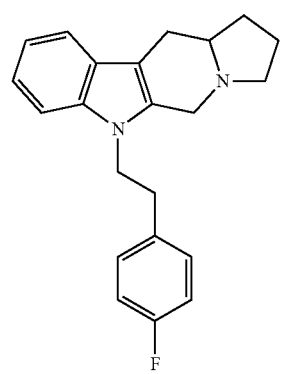
III-353a,
III-353b
III-353
TABLE 3-continued
Representative Compounds of the Invention.
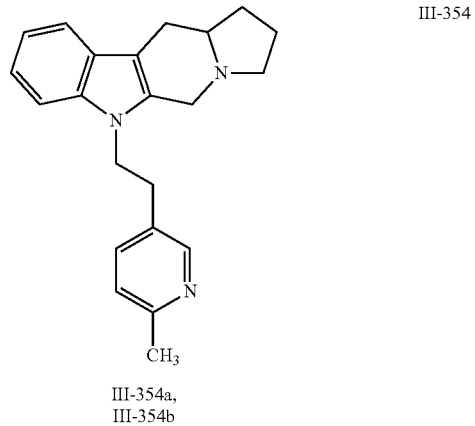
III-354a,
III-354b
III-354
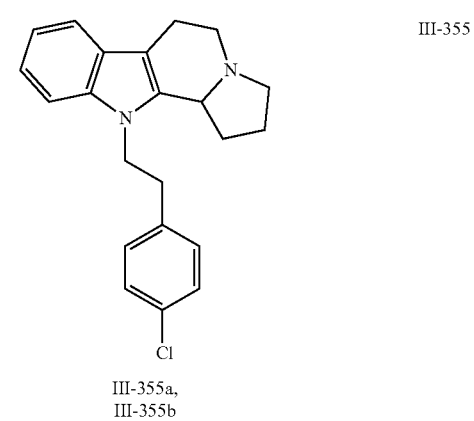
III-355a,
III-355b
III-355
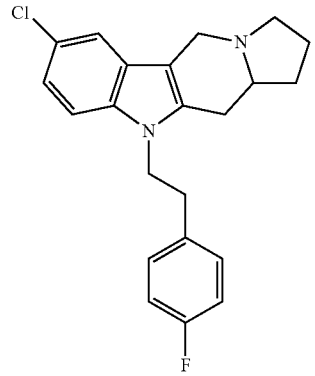
III-356a,
III-356b
III-356

TABLE 3-continued
Representative Compounds of the Invention.
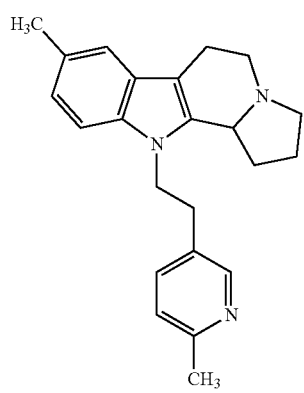
III-357
III-357a,
III-357b
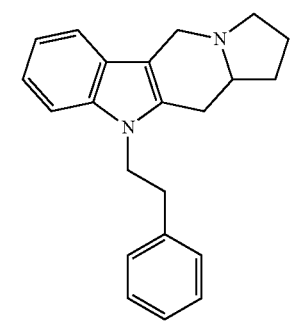
III-358
III-358a,
III-358b
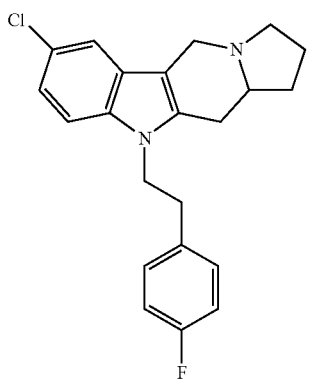
III-359
III-359a,
III-359b
TABLE 4
Representative Compounds of the Invention
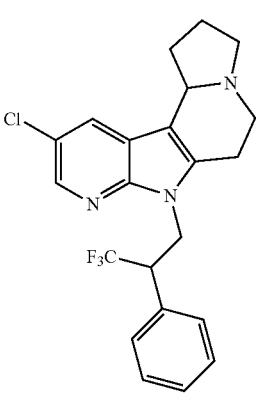 [SMILES: FC(F)(F)C(Cn1c2c(c3cc(Cl)cnc31)C1CCCN1CC2)c1ccccc1]
IV-1
IV-1a, IV-1b
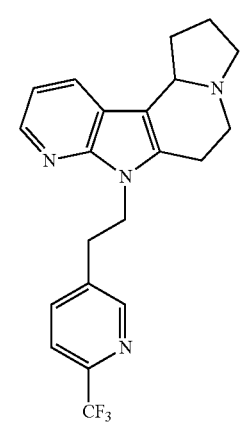 [SMILES: FC(F)(F)c1ccc(CCn2c3c(c4cccnc42)C2CCCN2CC3)cn1]
IV-2
IV-2a, IV-2b
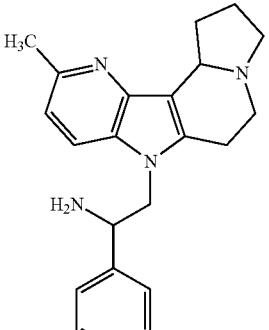
IV-3
IV-3a, IV-3b, IV-3c, IV-3d TABLE 4-continued
Representative Compounds of the Invention
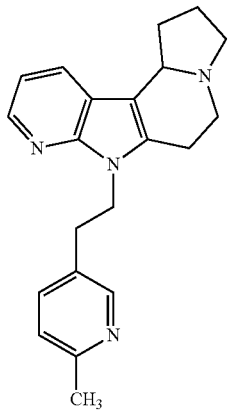
IV-4
IV-4a, IV-4b
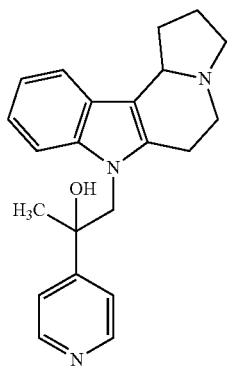 [SMILES: CC(O)(Cn1c2c(c3ccccc31)C1CCCN1CC2)c1ccncc1]
IV-5
IV-5a, IV-5b, IV-5c, IV-5d
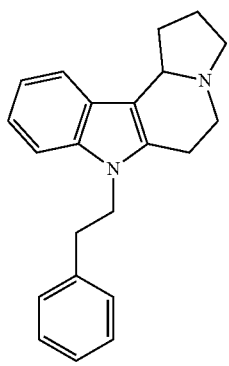 [SMILES: c1ccc(CCn2c3c(c4ccccc42)C2CCCN2CC3)cc1]
IV-6
IV-6a, IV-6b
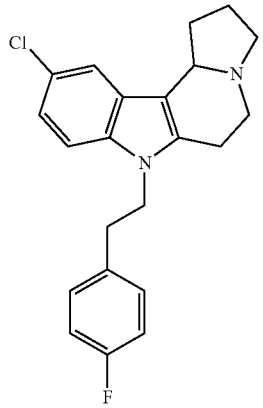 [SMILES: Fc1ccc(CCn2c3c(c4cc(Cl)ccc42)C2CCCN2CC3)cc1]
IV-7
IV-7a, IV-7b
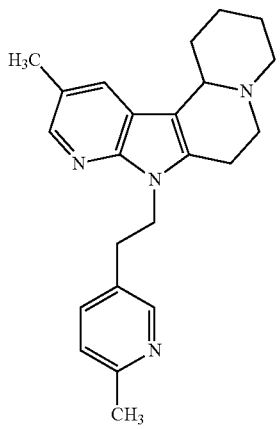 [SMILES: Cc1cnc2c(c1)c1c(n2CCc2ccc(C)nc2)CCN2CCCCC12]
IV-8
IV-8a, IV-8b
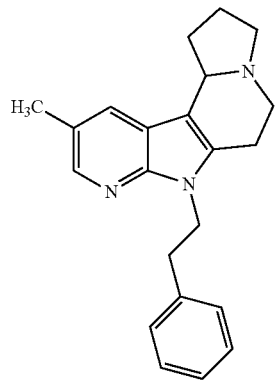 [SMILES: Cc1cnc2c(c1)c1c(n2CCc2ccccc2)CCN2CCCC12]
IV-9
IV-9a, IV-9b TABLE 4-continued
Representative Compounds of the Invention
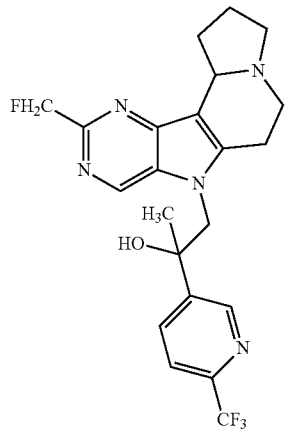
IV-10
IV-10a, IV-10b, IV-10c, IV-10d
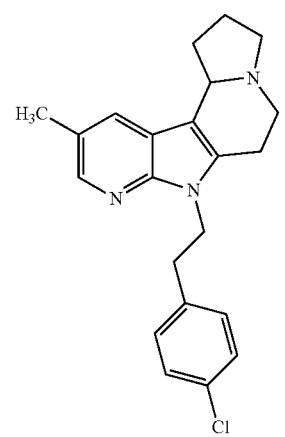 [SMILES: Cc1cnc2c(c1)c1c(n2CCc2ccc(Cl)cc2)CCN2CCCC12]
IV-11
IV-11a, IV-11b
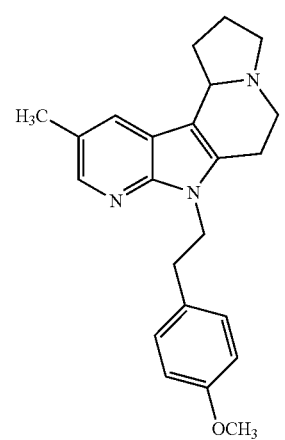 [SMILES: COc1ccc(CCn2c3c(c4cc(C)cnc42)C2CCCN2CC3)cc1]
IV-12
IV-12a, IV-12b
TABLE 4-continued
Representative Compounds of the Invention
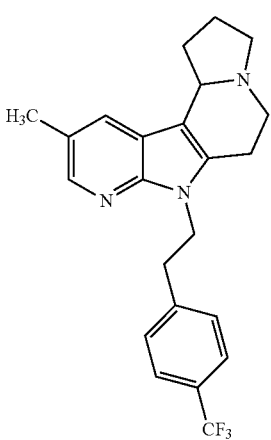 [SMILES: Cc1cnc2c(c1)c1c(n2CCc2ccc(C(F)(F)F)cc2)CCN2CCCC12]
IV-13
IV-13a, IV-13b
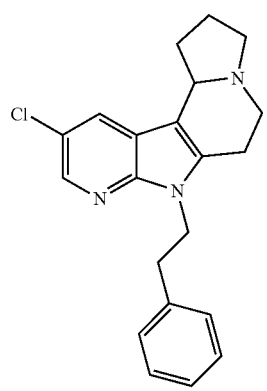 [SMILES: Clc1cnc2c(c1)c1c(n2CCc2ccccc2)CCN2CCCC12]
IV-14
IV-14a, IV-14b
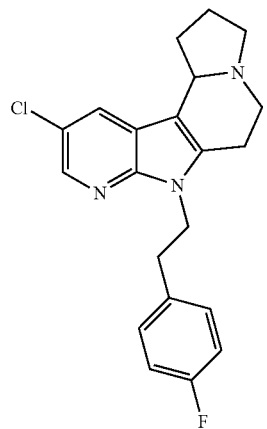 [SMILES: Fc1ccc(CCn2c3c(c4cc(Cl)cnc42)C2CCCN2CC3)cc1]
IV-15
IV-15a, IV-15b TABLE 4-continued
Representative Compounds of the Invention
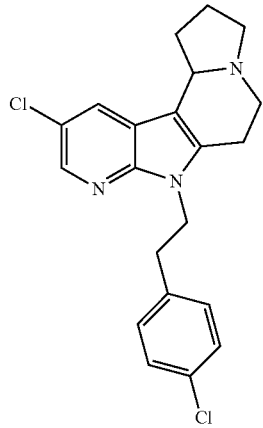 [SMILES: Clc1ccc(CCn2c3c(c4cc(Cl)cnc42)C2CCCN2CC3)cc1]
IV-16
IV-16a, IV-16b
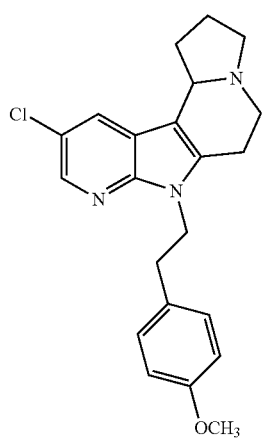 [SMILES: COc1ccc(CCn2c3c(c4cc(Cl)cnc42)C2CCCN2CC3)cc1]
IV-17
IV-17a, IV-17b
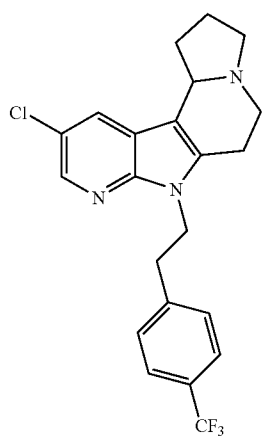 [SMILES: FC(F)(F)c1ccc(CCn2c3c(c4cc(Cl)cnc42)C2CCCN2CC3)cc1]
IV-18
IV-18a, IV-18b
TABLE 4-continued
Representative Compounds of the Invention
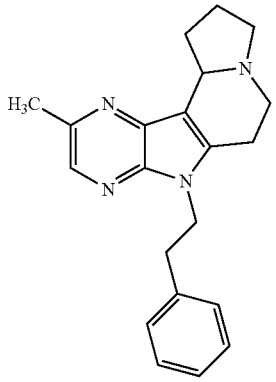 [SMILES: Cc1cnc2c(n1)c1c(n2CCc2ccccc2)CCN2CCCC12]
IV-19
IV-19a, IV-19b
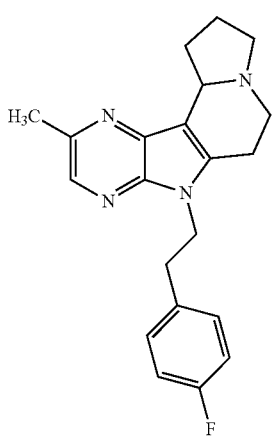
IV-20
IV-20a, IV-20b
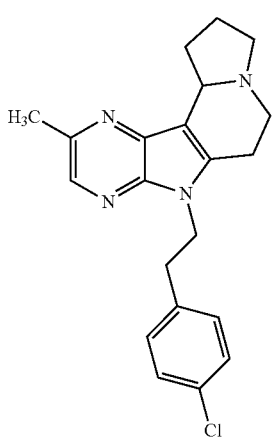 [SMILES: Cc1cnc2c(n1)c1c(n2CCc2ccc(Cl)cc2)CCN2CCCC12]
IV-21
IV-21a, IV-21b TABLE 4-continued
Representative Compounds of the Invention
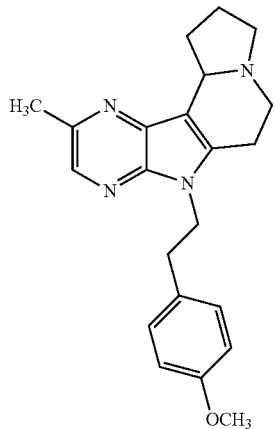 [SMILES: COc1ccc(CCn2c3c(c4nc(C)cnc42)C2CCCN2CC3)cc1]
IV-22
IV-22a, IV-22b
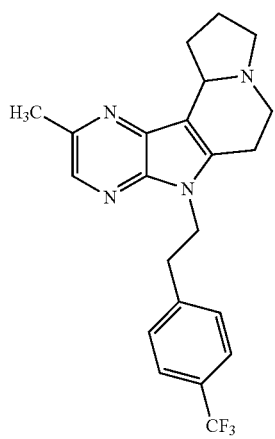
IV-23
IV-23a, IV-23b
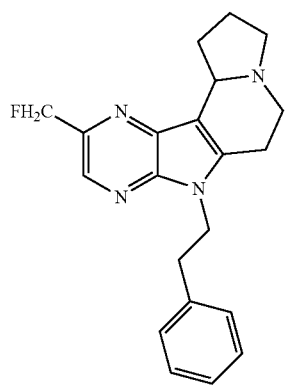
IV-24
IV-24a, IV-24b
TABLE 4-continued
Representative Compounds of the Invention
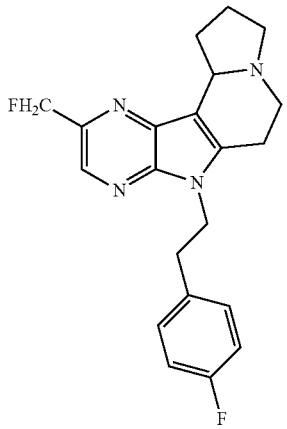
IV-25
IV-25a, IV-25b
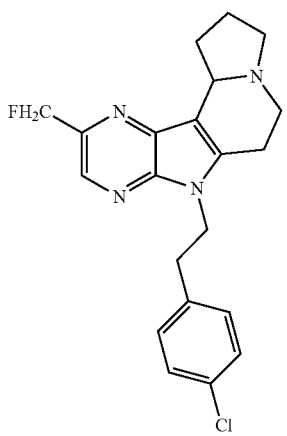
IV-26
IV-26a, IV-26b
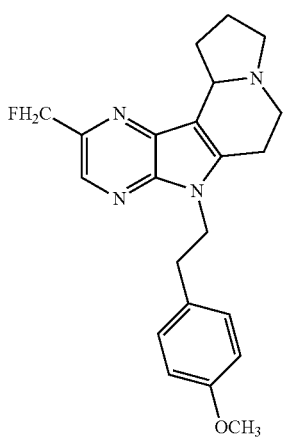
IV-27
IV-27a, IV-27b TABLE 4-continued
Representative Compounds of the Invention
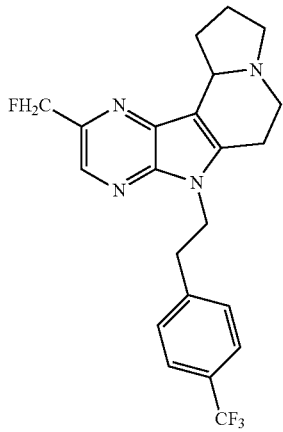
IV-28
IV-28a, IV-28b
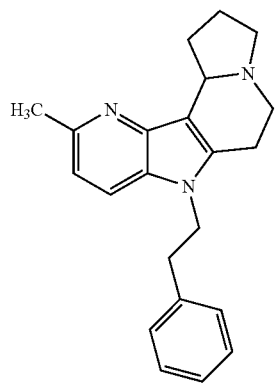 [SMILES: Cc1ccc2c(n1)c1c(n2CCc2ccccc2)CCN2CCCC12]
IV-29
IV-29a, IV-29b
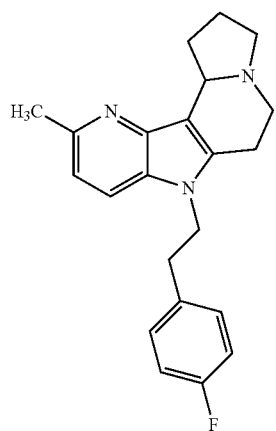 [SMILES: Cc1ccc2c(n1)c1c(n2CCc2ccc(F)cc2)CCN2CCCC12]
IV-30
IV-30a, IV-30b
TABLE 4-continued
Representative Compounds of the Invention
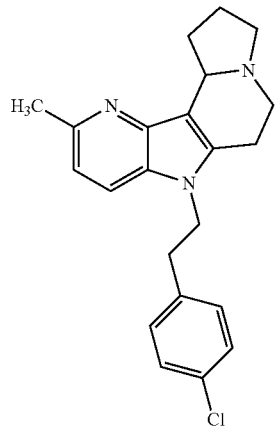 [SMILES: Cc1ccc2c(n1)c1c(n2CCc2ccc(Cl)cc2)CCN2CCCC12]
IV-31
IV-31a, IV-31b
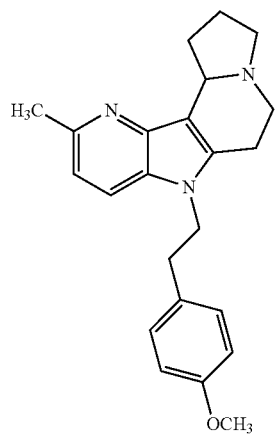
IV-32
IV-32a, IV-32b
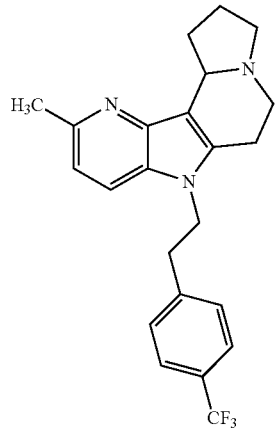
IV-33
IV-33a, IV-33b TABLE 4-continued
Representative Compounds of the Invention
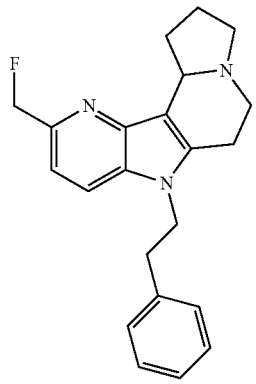 [SMILES: FCc1ccc2c(n1)c1c(n2CCc2ccccc2)CCN2CCCC12]
IV-34
IV-34a, IV-34b
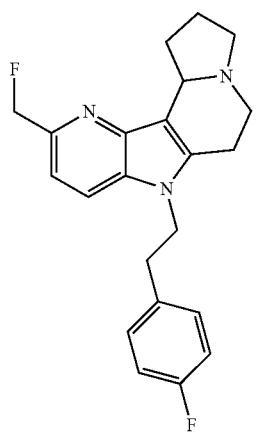 [SMILES: FCc1ccc2c(n1)c1c(n2CCc2ccc(F)cc2)CCN2CCCC12]
IV-35
IV-35a, IV-35b
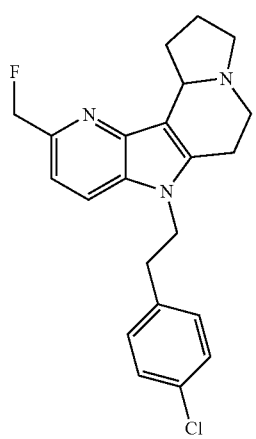 [SMILES: FCc1ccc2c(n1)c1c(n2CCc2ccc(Cl)cc2)CCN2CCCC12]
IV-36
IV-36a, IV-36b
TABLE 4-continued
Representative Compounds of the Invention
IV-37
IV-37a, IV-37b
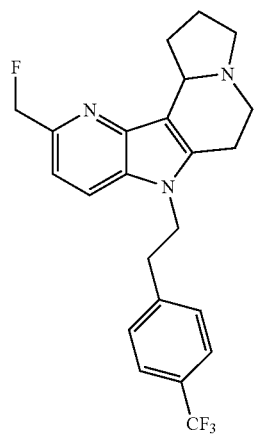
IV-38
IV-38a, IV-38b
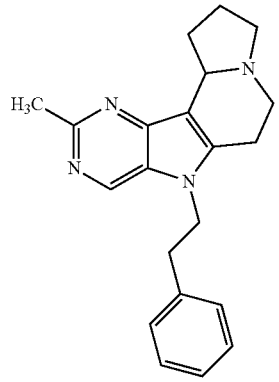 [SMILES: Cc1ncc2c(n1)c1c(n2CCc2ccccc2)CCN2CCCC12]
IV-39
IV-39a, IV-39b TABLE 4-continued
Representative Compounds of the Invention
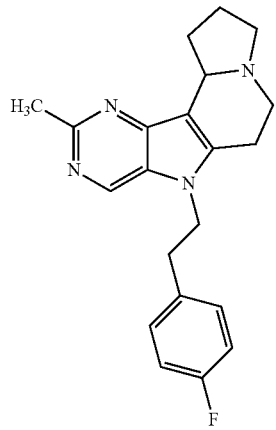 [SMILES: Cc1ncc2c(n1)c1c(n2CCc2ccc(F)cc2)CCN2CCCC12]
IV-40
IV-40a, IV-40b
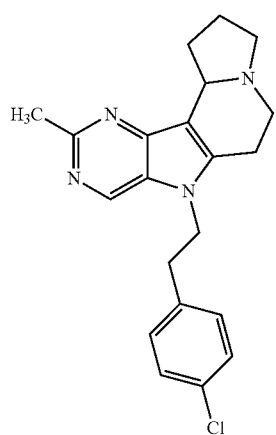 [SMILES: Cc1ncc2c(n1)c1c(n2CCc2ccc(Cl)cc2)CCN2CCCC12]
IV-41
IV-41a, IV-41b
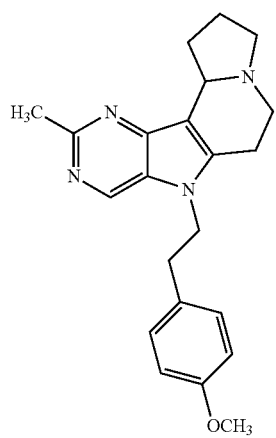 [SMILES: COc1ccc(CCn2c3c(c4nc(C)ncc42)C2CCCN2CC3)cc1]
IV-42
IV-42a, IV-42b
TABLE 4-continued
Representative Compounds of the Invention
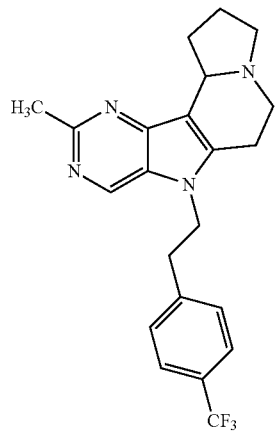 [SMILES: Cc1ncc2c(n1)c1c(n2CCc2ccc(C(F)(F)F)cc2)CCN2CCCC12]
IV-43
IV-43a, IV-43b
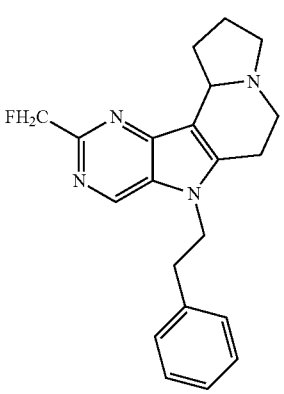
IV-44
IV-44a, IV-44b
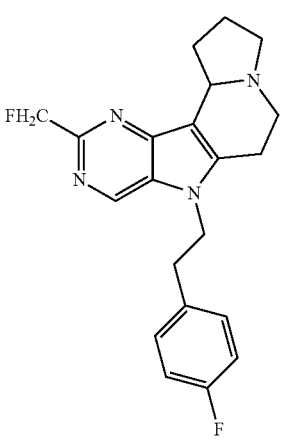
IV-45
IV-45a, IV-45b TABLE 4-continued
Representative Compounds of the Invention
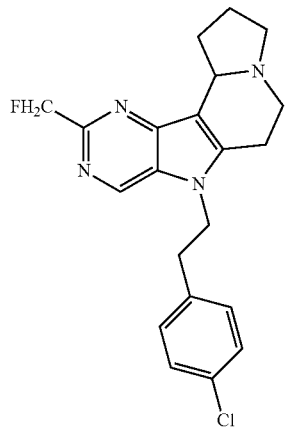
IV-46
IV-46a, IV-46b
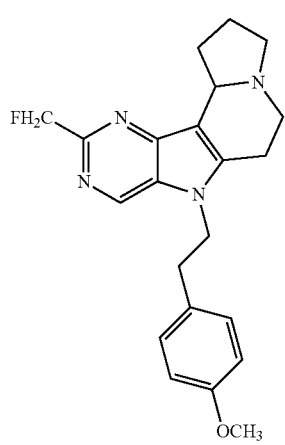
IV-47
IV-47a, IV-47b
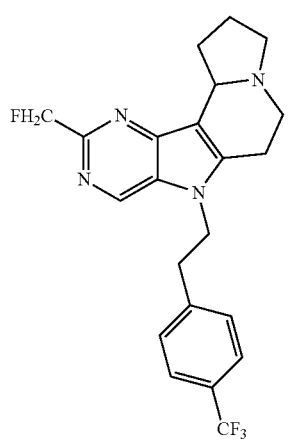
IV-48
IV-48a, IV-48b
TABLE 4-continued
Representative Compounds of the Invention
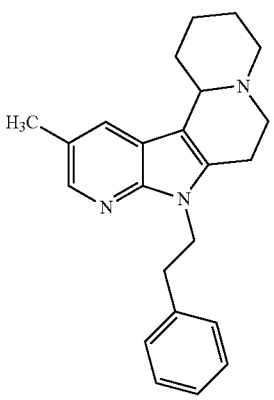
IV-49
IV-49a, IV-49b
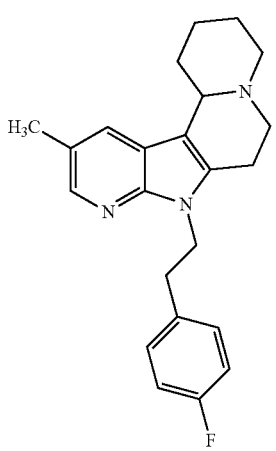 [SMILES: Cc1cnc2c(c1)c1c(n2CCc2ccc(F)cc2)CCN2CCCCC12]
IV-50
IV-50a, IV-50b
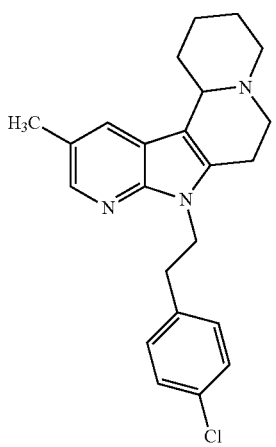 [SMILES: Cc1cnc2c(c1)c1c(n2CCc2ccc(Cl)cc2)CCN2CCCCC12]
IV-51
IV-51a, IV-51b TABLE 4-continued
Representative Compounds of the Invention
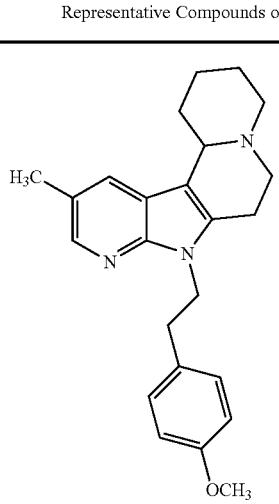
IV-52
IV-52a, IV-52b
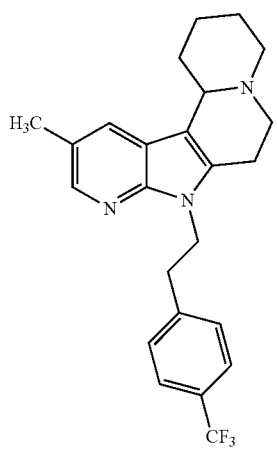 [SMILES: Cc1cnc2c(c1)c1c(n2CCc2ccc(C(F)(F)F)cc2)CCN2CCCCC12]
IV-53
IV-53a, IV-53b
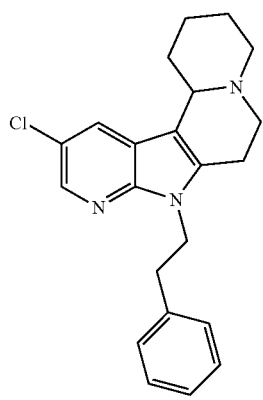 [SMILES: Clc1cnc2c(c1)c1c(n2CCc2ccccc2)CCN2CCCCC12]
IV-54
IV-54a, IV-54b
TABLE 4-continued
Representative Compounds of the Invention
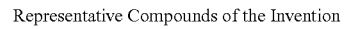
IV-55
IV-55a, IV-55b
IV-56
IV-56a, IV-56b
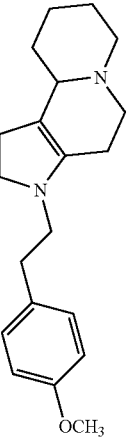
IV-57
IV-57a, IV-57b TABLE 4-continued
Representative Compounds of the Invention
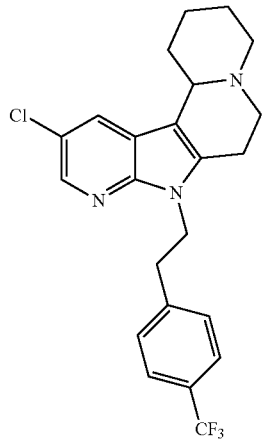 [SMILES: FC(F)(F)c1ccc(CCn2c3c(c4cc(Cl)cnc42)C2CCCCN2CC3)cc1]
IV-58
IV-58a, IV-58b
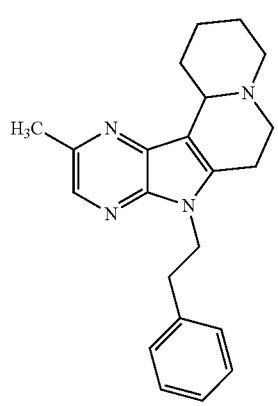 [SMILES: Cc1cnc2c(n1)c1c(n2CCc2ccccc2)CCN2CCCCC12]
IV-59
IV-59a, IV-59b
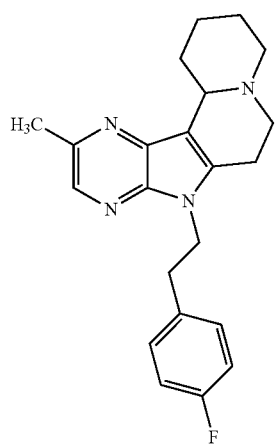 [SMILES: Cc1cnc2c(n1)c1c(n2CCc2ccc(F)cc2)CCN2CCCCC12]
IV-60
IV-60a, IV-60b
TABLE 4-continued
Representative Compounds of the Invention
IV-61
IV-61a, IV-61b
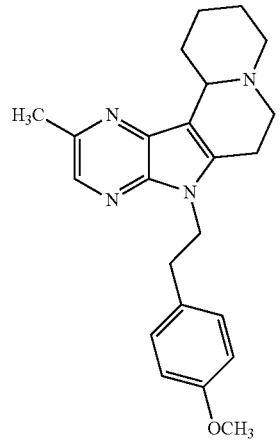
IV-62
IV-62a, IV-62b
IV-63
IV-63a, IV-63b TABLE 4-continued
Representative Compounds of the Invention
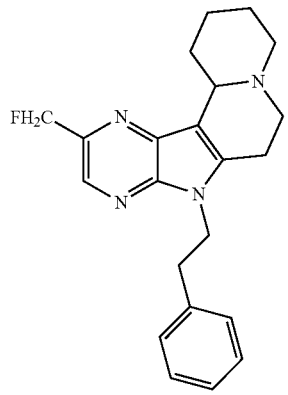
IV-64
IV-64a, IV-64b
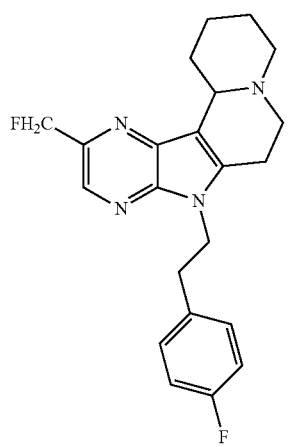
IV-65
IV-65a, IV-65b
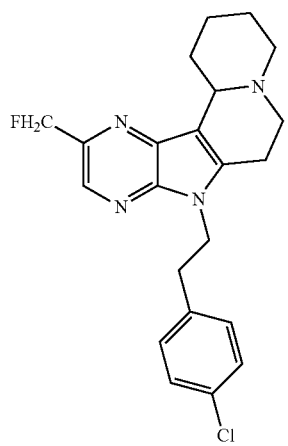
IV-66
IV-66a, IV-66b
TABLE 4-continued
Representative Compounds of the Invention
IV-67
IV-67a, IV-67b
IV-68
IV-68a, IV-68b
IV-69
IV-69a, IV-69b TABLE 4-continued
Representative Compounds of the Invention
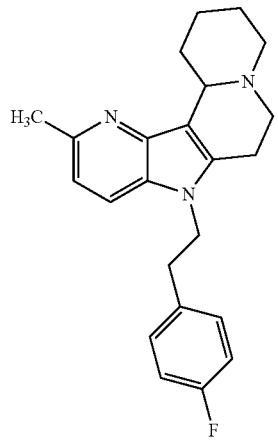
IV-70
IV-70a, IV-70b
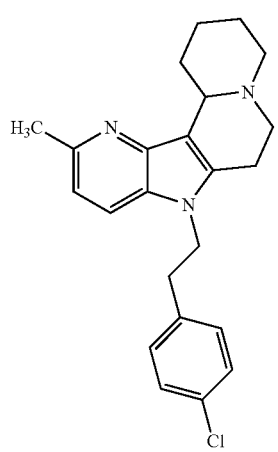 [SMILES: Cc1ccc2c(n1)c1c(n2CCc2ccc(Cl)cc2)CCN2CCCCC12]
IV-71
IV-71a, IV-71b
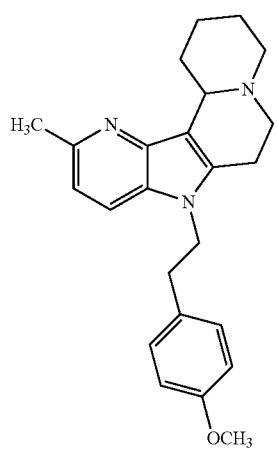 [SMILES: COc1ccc(CCn2c3c(c4nc(C)ccc42)C2CCCCN2CC3)cc1]
IV-72
IV-72a, IV-72b
TABLE 4-continued
Representative Compounds of the Invention
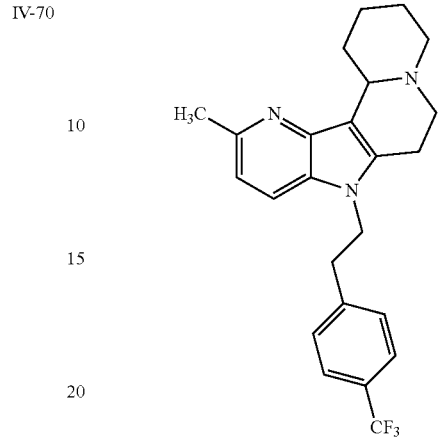
IV-73
IV-73a, IV-73b
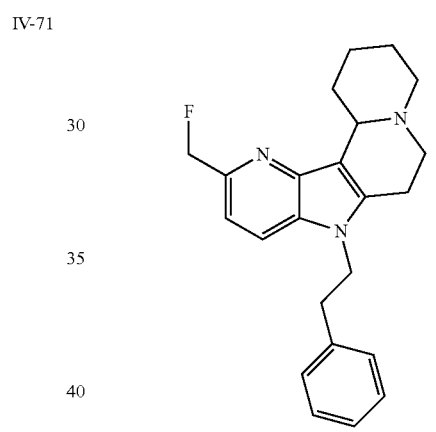
IV-74
IV-74a, IV-74b
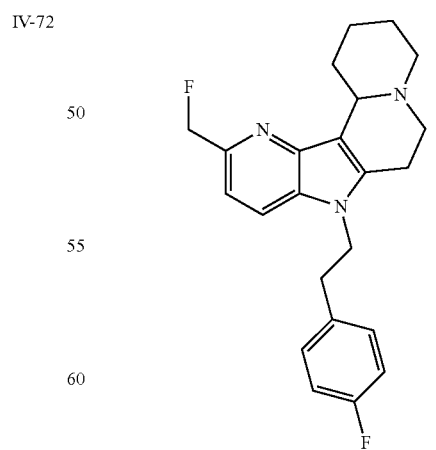
IV-75
IV-75a, IV-75b TABLE 4-continued
Representative Compounds of the Invention
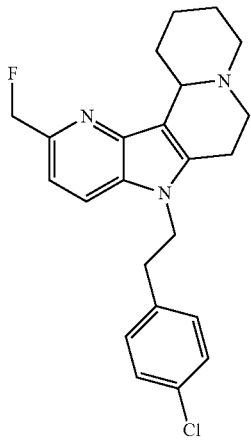 [SMILES: FCc1ccc2c(n1)c1c(n2CCc2ccc(F)cc2)CCN2CCCCC12]
IV-76
IV-76a, IV-76b
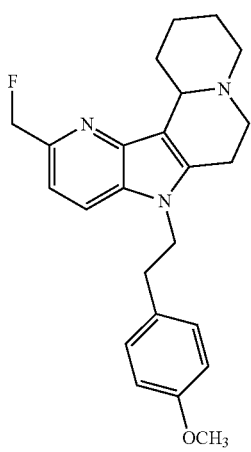 [SMILES: COc1ccc(CCn2c3c(c4nc(CF)ccc42)C2CCCCN2CC3)cc1]
IV-77
IV-77a, IV-77b
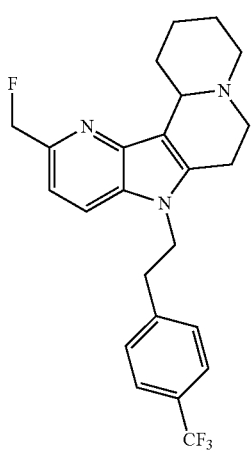 [SMILES: FCc1ccc2c(n1)c1c(n2CCc2ccc(C(F)(F)F)cc2)CCN2CCCCC12]
IV-78
IV-78a, IV-78b
TABLE 4-continued
Representative Compounds of the Invention
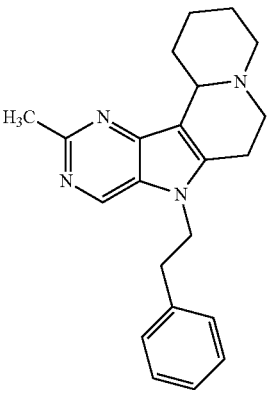 [SMILES: Cc1ncc2c(n1)c1c(n2CCc2ccccc2)CCN2CCCCC12]
IV-79
IV-79a, IV-79b
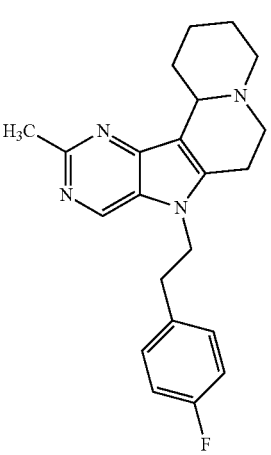 [SMILES: Cc1ncc2c(n1)c1c(n2CCc2ccc(F)cc2)CCN2CCCCC12]
IV-80
IV-80a, IV-80b
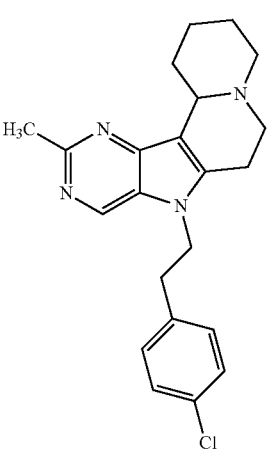 [SMILES: Cc1ncc2c(n1)c1c(n2CCc2ccc(Cl)cc2)CCN2CCCCC12]
IV-81
IV-81a, IV-81b TABLE 4-continued
Representative Compounds of the Invention
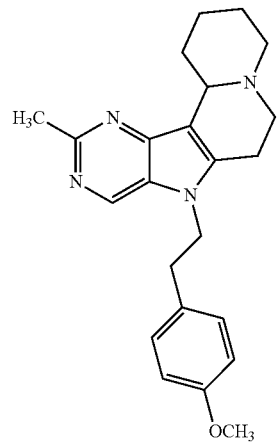
IV-82
IV-82a, IV-82b
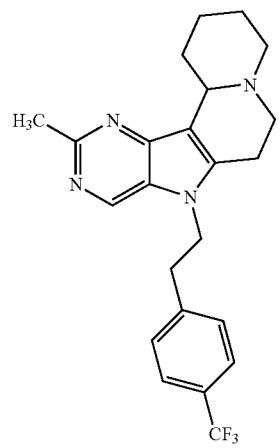 [SMILES: Cc1ncc2c(n1)c1c(n2CCc2ccc(C(F)(F)F)cc2)CCN2CCCCC12]
IV-83
IV-83a, IV-83b
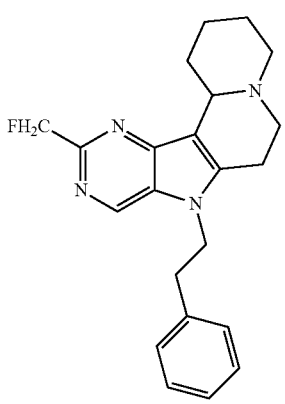
IV-84
IV-84a, IV-84b
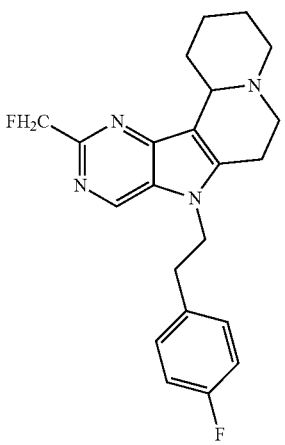
IV-85
IV-85a, IV-85b
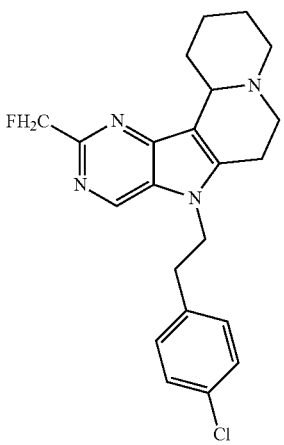
IV-86
IV-86a, IV-86b
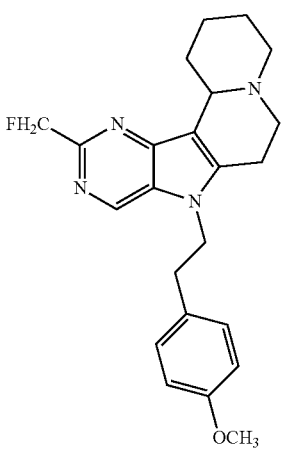
IV-87
IV-87a, IV-87b TABLE 4-continued
Representative Compounds of the Invention
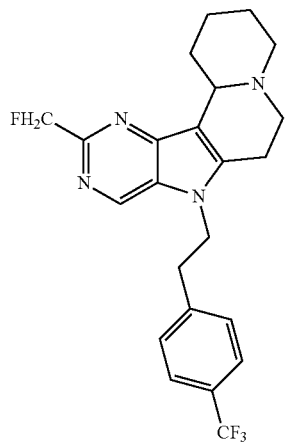
IV-88
IV-88a, IV-88b
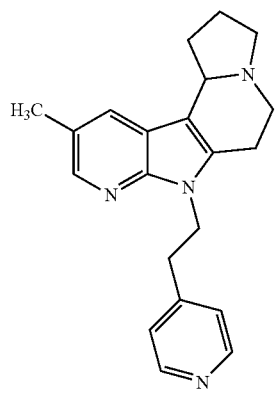 [SMILES: Cc1cnc2c(c1)c1c(n2CCc2ccncc2)CCN2CCCC12]
IV-89
IV-89a, IV-89b
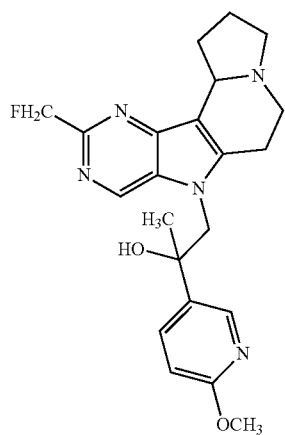
IV-90
IV-90a, IV-90b, IV-90c, IV-90d
TABLE 4-continued
Representative Compounds of the Invention
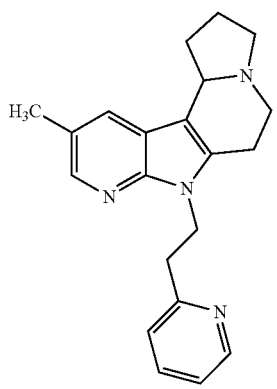 [SMILES: Cc1cnc2c(c1)c1c(n2CCc2ccccn2)CCN2CCCC12]
IV-91
IV-91a, IV-91b
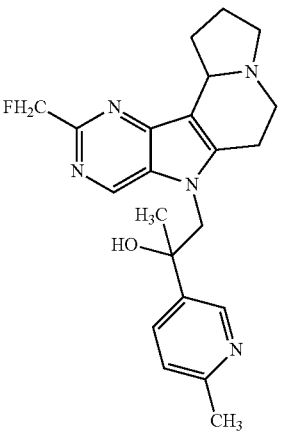
IV-92
IV-92a, IV-92b, IV-92c, IV-92d
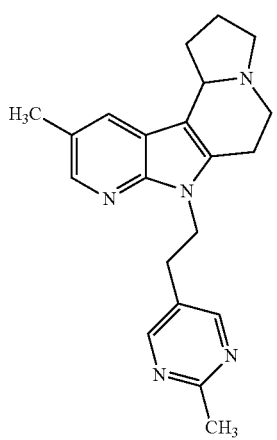 [SMILES: Cc1cnc2c(c1)c1c(n2CCc2cnc(C)nc2)CCN2CCCC12]
IV-93
IV-93a, IV-93b TABLE 4-continued
Representative Compounds of the Invention
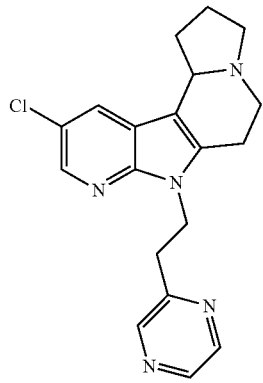 [SMILES: Clc1cnc2c(c1)c1c(n2CCc2cnccn2)CCN2CCCC12]
IV-94
IV-94a, IV-94b
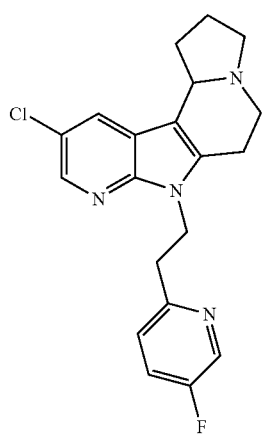 [SMILES: Fc1ccc(CCn2c3c(c4cc(Cl)cnc42)C2CCCN2CC3)nc1]
IV-95
IV-95a, IV-95b
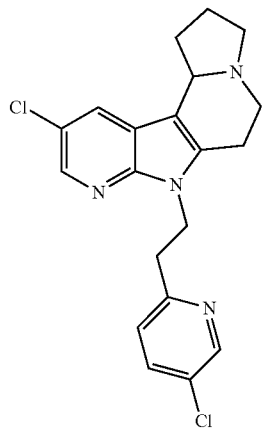 [SMILES: Clc1ccc(CCn2c3c(c4cc(Cl)cnc42)C2CCCN2CC3)nc1]
IV-96
IV-96a, IV-96b
TABLE 4-continued
Representative Compounds of the Invention
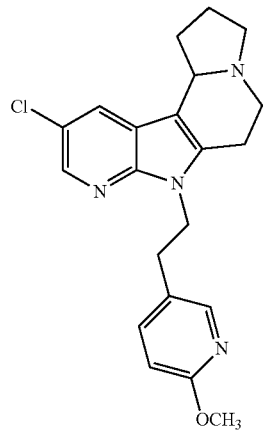 [SMILES: COc1ccc(CCn2c3c(c4cc(Cl)cnc42)C2CCCN2CC3)cn1]
IV-97
IV-97a, IV-97b
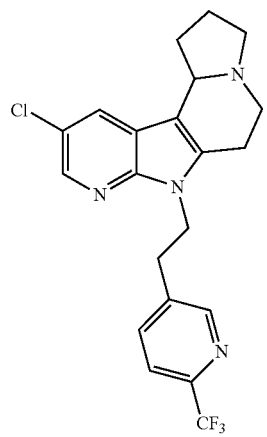 [SMILES: FC(F)(F)c1ccc(CCn2c3c(c4cc(Cl)cnc42)C2CCCN2CC3)cn1]
IV-98
IV-98a, IV-98b
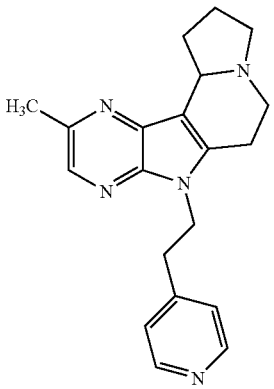 [SMILES: Cc1cnc2c(n1)c1c(n2CCc2ccncc2)CCN2CCCC12]
IV-99
IV-99a, IV-99b TABLE 4-continued
Representative Compounds of the Invention
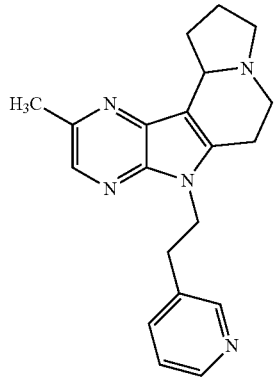 [SMILES: Cc1cnc2c(n1)c1c(n2CCc2cccnc2)CCN2CCCC12]
IV-100
IV-100a, IV-100b
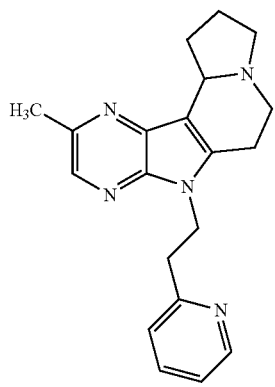 [SMILES: Cc1cnc2c(n1)c1c(n2CCc2ccccn2)CCN2CCCC12]
IV-101
IV-101a, IV-101b
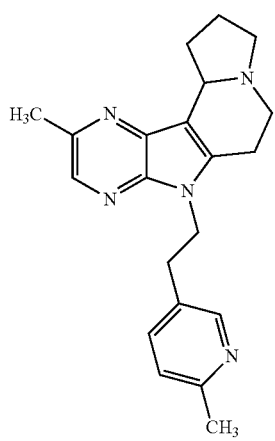 [SMILES: Cc1ccc(CCn2c3c(c4nc(C)cnc42)C2CCCN2CC3)cn1]
IV-102
IV-102a, IV-102b
TABLE 4-continued
Representative Compounds of the Invention
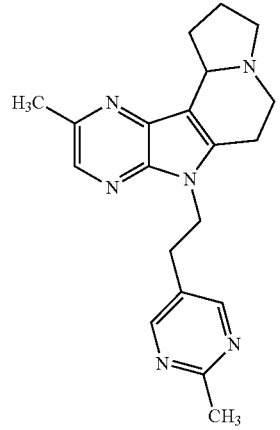 [SMILES: Cc1cnc2c(n1)c1c(n2CCc2cnc(C)nc2)CCN2CCCC12]
IV-103
IV-103a, IV-103b
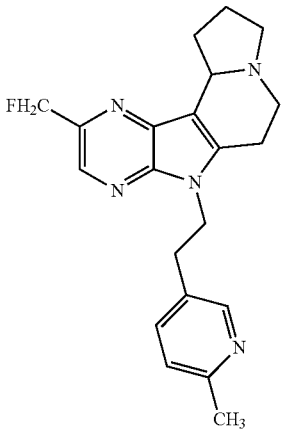
IV-104
IV-104a, IV-104b
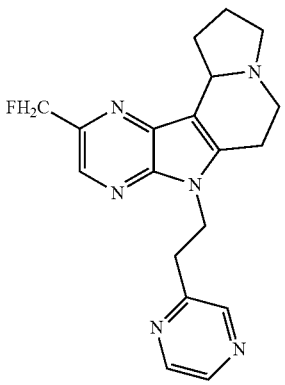
IV-105
IV-105a, IV-105b TABLE 4-continued
Representative Compounds of the Invention
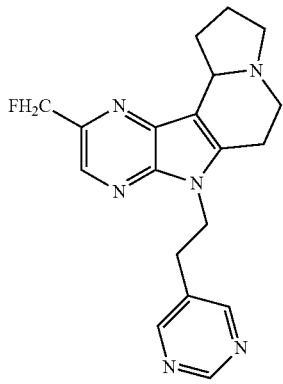
IV-106
IV-106a, IV-106b
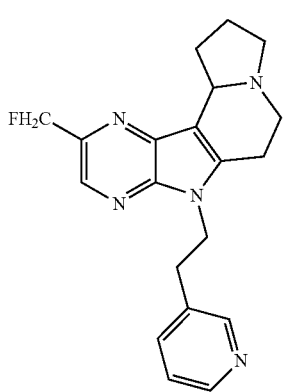
IV-107
IV-107a, IV-107b
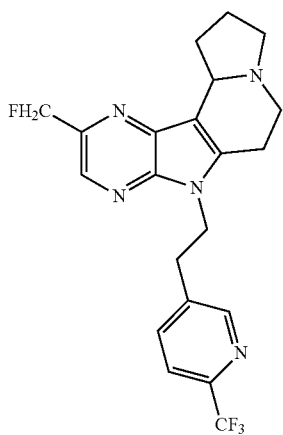
IV-108
IV-108a, IV-108b
TABLE 4-continued
Representative Compounds of the Invention
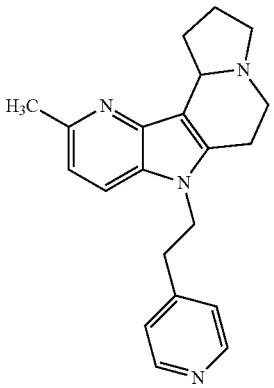 [SMILES: Cc1ccc2c(n1)c1c(n2CCc2ccncc2)CCN2CCCC12]
IV109
IV-109a, IV-109b
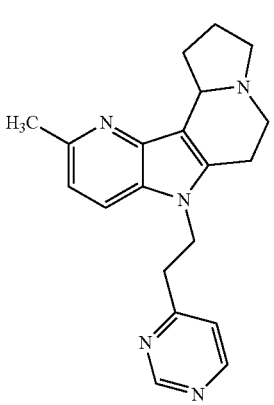
IV-110
IV-110a, IV-110b
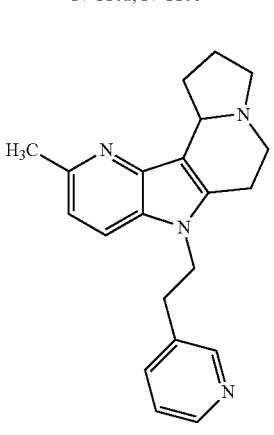
IV-111
IV-111a, IV-111b TABLE 4-continued
Representative Compounds of the Invention
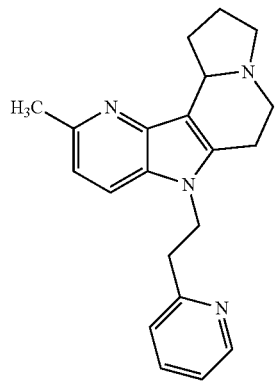 [SMILES: Cc1ccc2c(n1)c1c(n2CCc2ccccn2)CCN2CCCC12]
IV-112
IV-112a, IV-112b
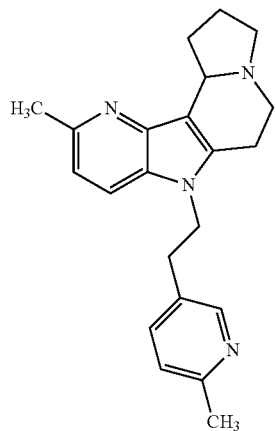 [SMILES: Cc1ccc(CCn2c3c(c4nc(C)ccc42)C2CCCN2CC3)cn1]
IV-113
IV-113a, IV-113b
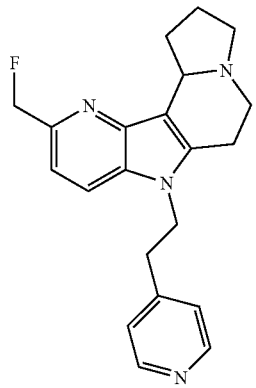 [SMILES: FCc1ccc2c(n1)c1c(n2CCc2ccncc2)CCN2CCCC12]
IV-114
IV-114a, IV-114b
TABLE 4-continued
Representative Compounds of the Invention
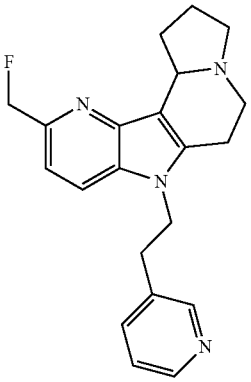 [SMILES: FCc1ccc2c(n1)c1c(n2CCc2cccnc2)CCN2CCCC12]
IV-115
IV-115a, IV-115b
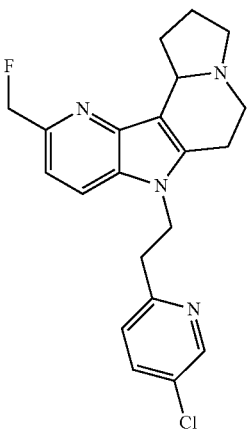 [SMILES: FCc1ccc2c(n1)c1c(n2CCc2ccc(Cl)cn2)CCN2CCCC12]
IV-116
IV-116a, IV-116b
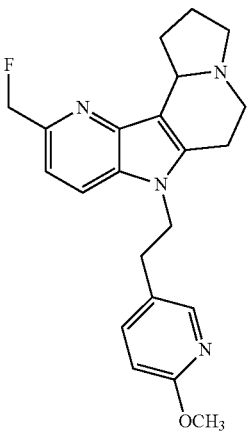
IV-117
IV-117a, IV-117b TABLE 4-continued
Representative Compounds of the Invention
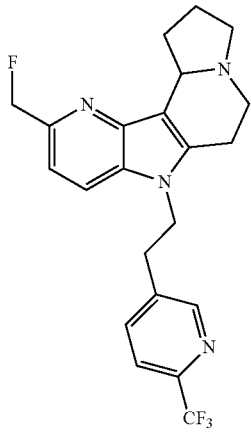 [SMILES: FCc1ccc2c(n1)c1c(n2CCc2ccc(C(F)(F)F)nc2)CCN2CCCC12]
IV-118
IV-118a, IV-118b
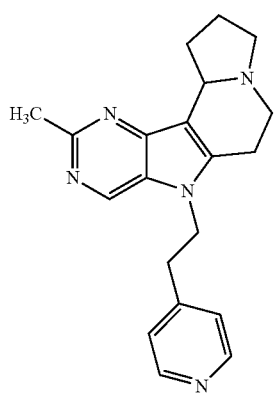
IV-119
IV-119a, IV-119b
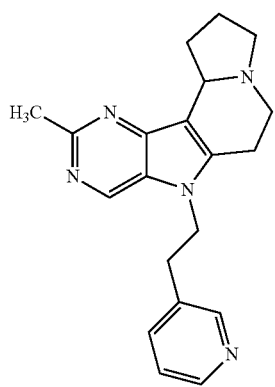 [SMILES: Cc1ncc2c(n1)c1c(n2CCc2cccnc2)CCN2CCCC12]
IV-120
IV-120a, IV-120b
TABLE 4-continued
Representative Compounds of the Invention
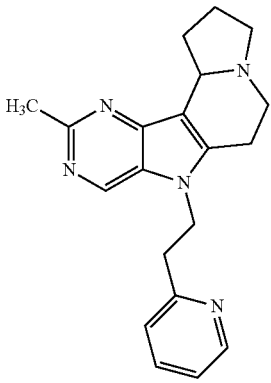 [SMILES: Cc1ncc2c(n1)c1c(n2CCc2ccccn2)CCN2CCCC12]
IV-121
IV-121a, IV-121b
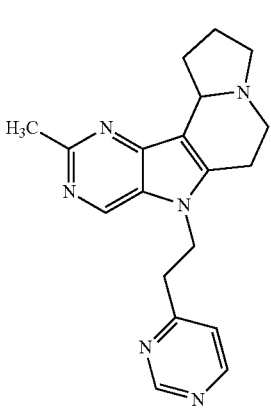 [SMILES: Cc1ncc2c(n1)c1c(n2CCc2ccncn2)CCN2CCCC12]
IV-122
IV-122a, IV-122b
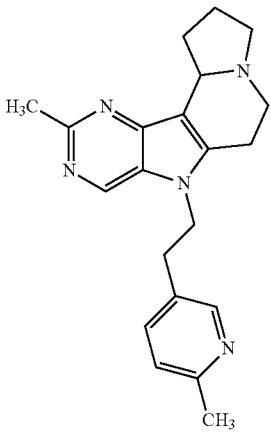
IV-123
IV-123a, IV-123b TABLE 4-continued
Representative Compounds of the Invention
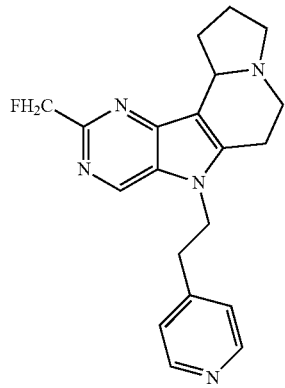
IV-124
IV-124a, IV-124b
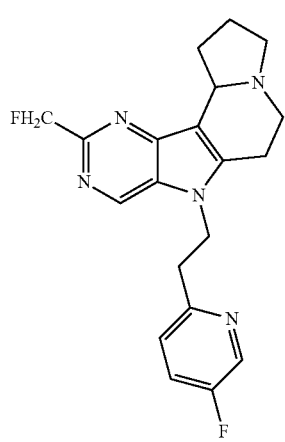
IV-125
IV-125a, IV-125b
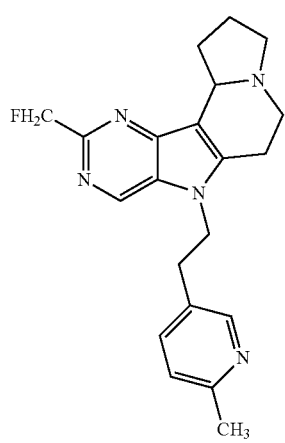
IV-126
IV-126a, IV-126b
TABLE 4-continued
Representative Compounds of the Invention
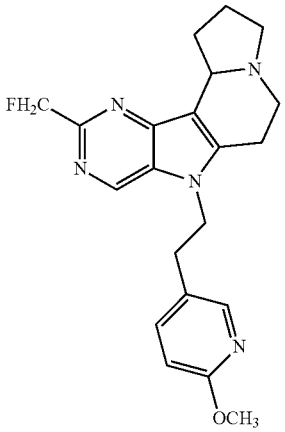
IV-127
IV-127a, IV-127b
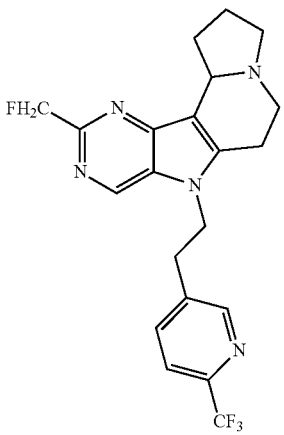
IV-128
IV-128a, IV-128b
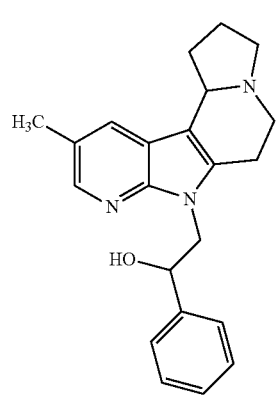 [SMILES: Cc1cnc2c(c1)c1c(n2CC(O)c2ccccc2)CCN2CCCC12]
IV-129
IV-129a, IV-129b, IV-129c, IV-129d TABLE 4-continued
Representative Compounds of the Invention
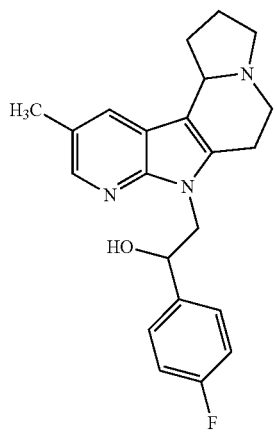 [SMILES: Cc1cnc2c(c1)c1c(n2CC(O)c2ccc(F)cc2)CCN2CCCC12]
IV-130
IV-130a, IV-130b, IV-130c, IV-130d
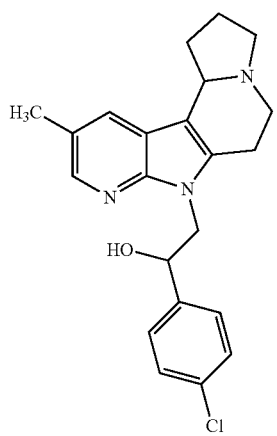 [SMILES: Cc1cnc2c(c1)c1c(n2CC(O)c2ccc(Cl)cc2)CCN2CCCC12]
IV-131
IV-131a, IV-131b, IV-131c, IV-131d
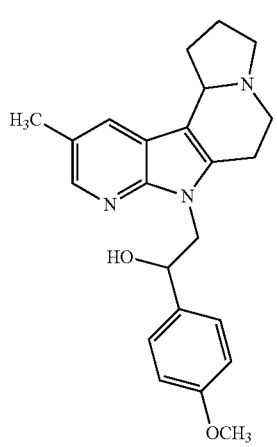 [SMILES: COc1ccc(C(O)Cn2c3c(c4cc(C)cnc42)C2CCCN2CC3)cc1]
IV-132
IV-132a, IV-132b, IV-132c, IV-132d
TABLE 4-continued
Representative Compounds of the Invention
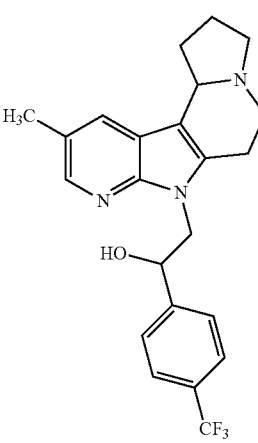
IV-133
IV-133a, IV-133b, IV-133c, IV-133d
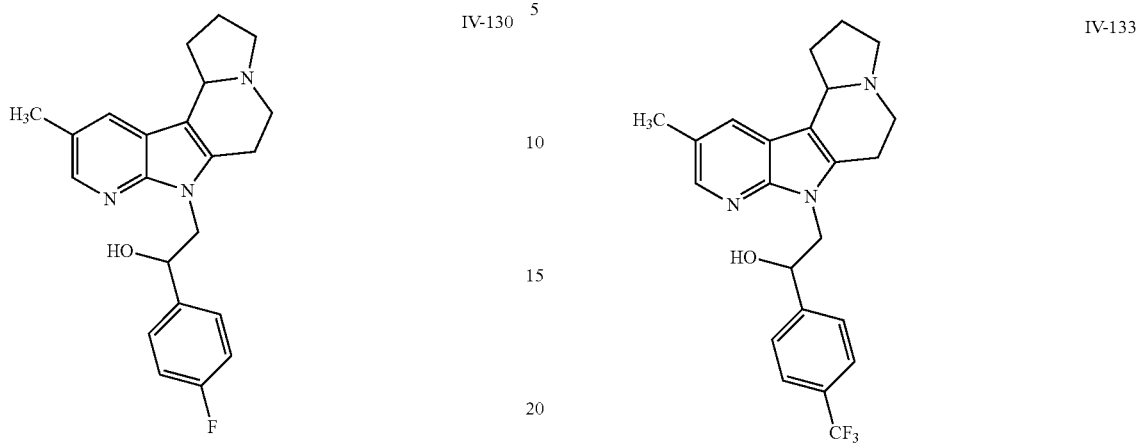
IV-134
IV-134a, IV-134b, IV-134c, IV-134d
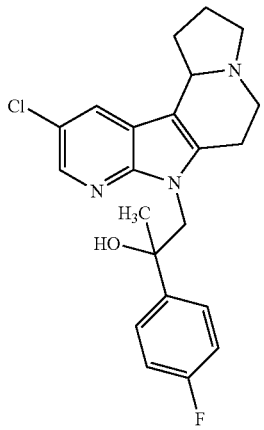 [SMILES: CC(O)(Cn1c2c(c3cc(Cl)cnc31)C1CCCN1CC2)c1ccc(F)cc1]
IV-135
IV-135a, IV-135b, IV-135c, IV-135d TABLE 4-continued
Representative Compounds of the Invention
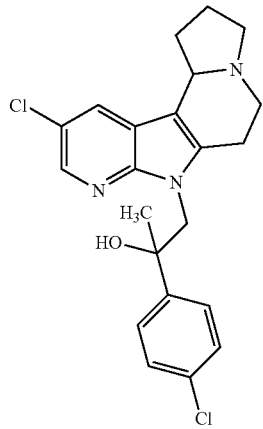 [SMILES: CC(O)(Cn1c2c(c3cc(Cl)cnc31)C1CCCN1CC2)c1ccc(Cl)cc1]
IV-136
IV-136a, IV-136b, IV-136c, IV-136d
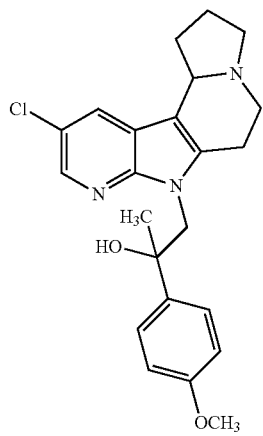 [SMILES: COc1ccc(C(C)(O)Cn2c3c(c4cc(Cl)cnc42)C2CCCN2CC3)cc1]
IV-137
IV-137a, IV-137b, IV-137c, IV-137d
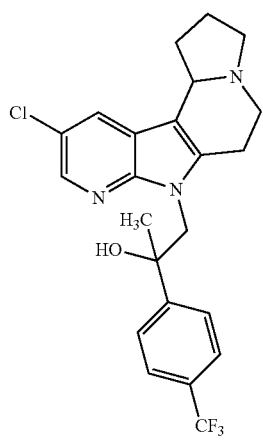 [SMILES: CC(O)(Cn1c2c(c3cc(Cl)cnc31)C1CCCN1CC2)c1ccc(C(F)(F)F)cc1]
IV-138
IV-138a, IV-138b, IV-138c, IV-138d
TABLE 4-continued
Representative Compounds of the Invention
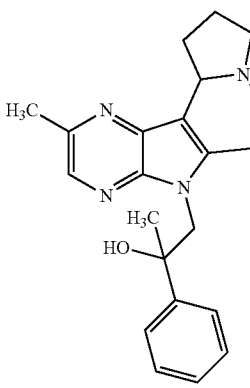
IV-139
IV-139a, IV-139b, IV-139c, IV-139d
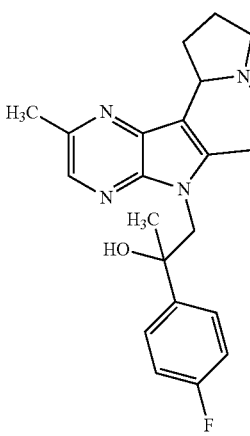
IV-140
IV-140a, IV-140b, IV-140c, IV-140d
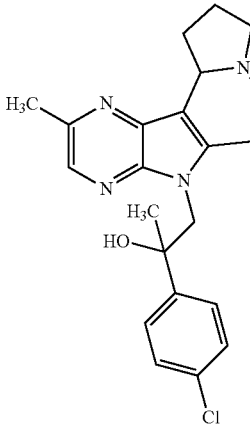
IV-141
IV-141a, IV-141b, IV-141c, IV-141d TABLE 4-continued
Representative Compounds of the Invention
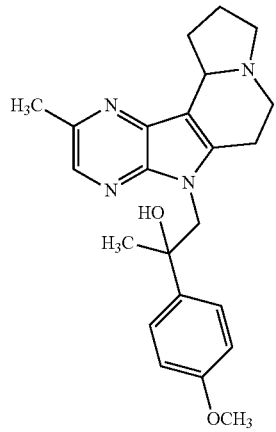 [SMILES: COc1ccc(C(C)(O)Cn2c3c(c4nc(C)cnc42)C2CCCN2CC3)cc1]
IV-142
IV-142a, IV-142b, IV-142c, IV-142d
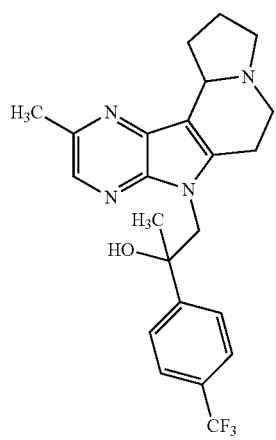 [SMILES: Cc1cnc2c(n1)c1c(n2CC(C)(O)c2ccc(C(F)(F)F)cc2)CCN2CCCC12]
IV-143
IV-143a, IV-143b, IV-143c, IV-143d
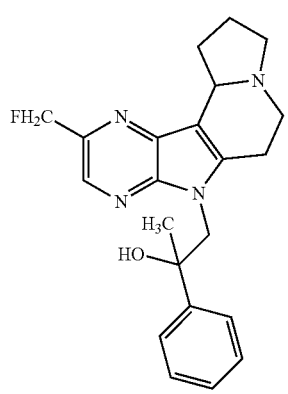
IV-144
IV-144a, IV-144b, IV-144c, IV-144d
TABLE 4-continued
Representative Compounds of the Invention
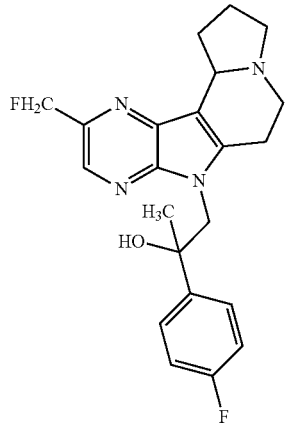
IV-145
IV-145a, IV-145b, IV-145c, IV-145d
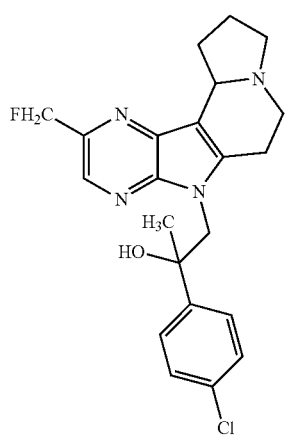
IV-146
IV-146a, IV-146b, IV-146c, IV-146d
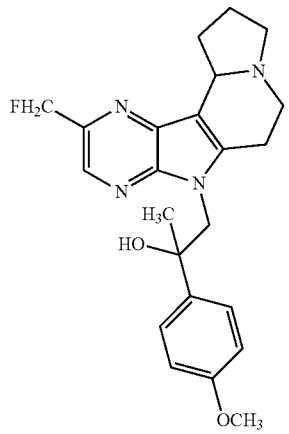
IV-147
IV-147a, IV-147b, IV-147c, IV-147d

TABLE 4-continued
Representative Compounds of the Invention
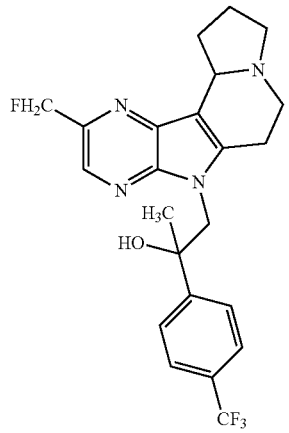
IV-148
IV-148a, IV-148b, IV-148c, IV-148d
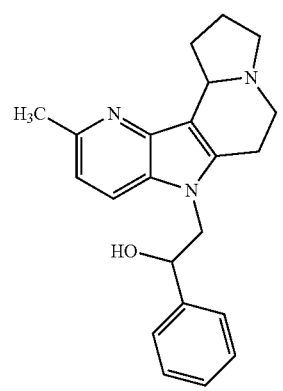 [SMILES: Cc1ccc2c(n1)c1c(n2CC(O)c2ccccc2)CCN2CCCC12]
IV-149
IV-149a, IV-149b, IV-149c, IV-149d
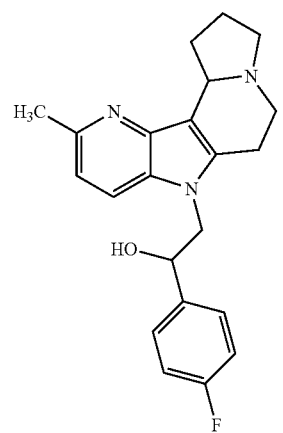 [SMILES: Cc1ccc2c(n1)c1c(n2CC(O)c2ccc(F)cc2)CCN2CCCC12]
IV-150
IV-150a, IV-150b, IV-150c, IV-150d
TABLE 4-continued
Representative Compounds of the Invention
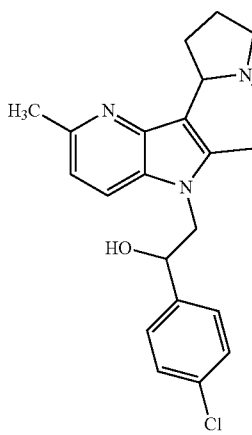
IV-151
IV-151a, IV-151b, IV-151c, IV-151d
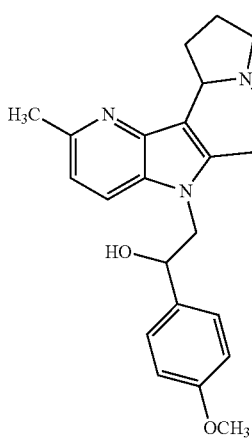
IV-152
IV-152a, IV-152b, IV-152c, IV-152d
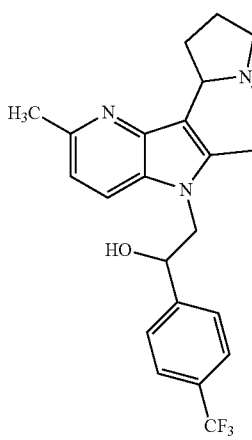
IV-153
IV-153a, IV-153b, IV-153c, IV-153d TABLE 4-continued
Representative Compounds of the Invention
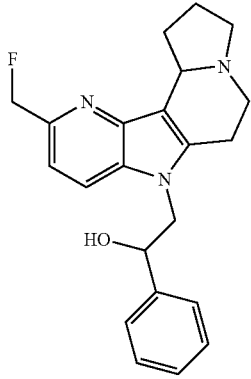 [SMILES: OC(Cn1c2c(c3nc(CF)ccc31)C1CCCN1CC2)c1ccccc1]
IV-154
IV-154a, IV-154b, IV-154c, IV-154d
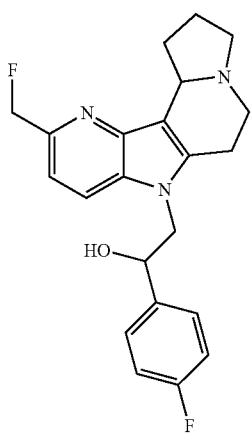
IV-155
IV-155a, IV-155b, IV-155c, IV-155d
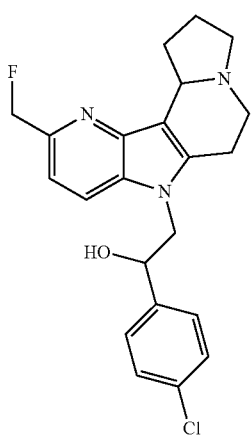 [SMILES: OC(Cn1c2c(c3nc(CF)ccc31)C1CCCN1CC2)c1ccc(F)cc1]
IV-156
IV-156a, IV-156b, IV-156c, IV-156d
TABLE 4-continued
Representative Compounds of the Invention
IV-157
IV-157a, IV-157b, IV-157c, IV-157d
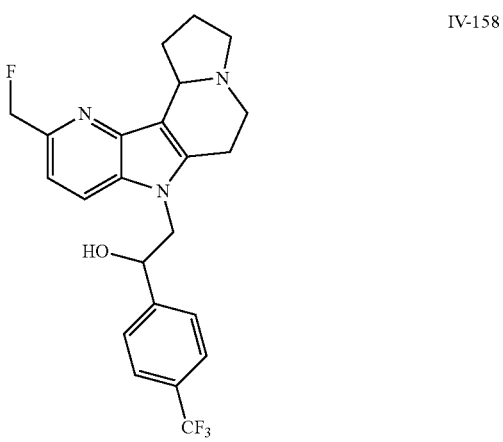
IV-158
IV-158a, IV-158b, IV-158c, IV-158d
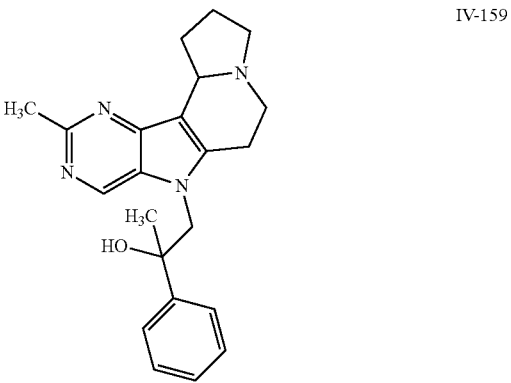
IV-159
IV-159a, IV-159b, IV-159c, IV-159d TABLE 4-continued
Representative Compounds of the Invention
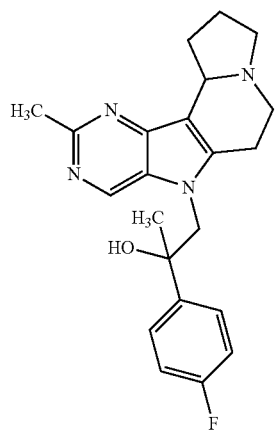 [SMILES: Cc1ncc2c(n1)c1c(n2CC(C)(O)c2ccc(F)cc2)CCN2CCCC12]
IV-160
IV-160a, IV-160b, IV-160c, IV-160d
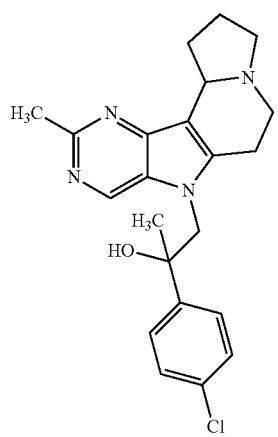 [SMILES: Cc1ncc2c(n1)c1c(n2CC(C)(O)c2ccc(Cl)cc2)CCN2CCCC12]
IV-161
IV-161a, IV-161b, IV-161c, IV-161d
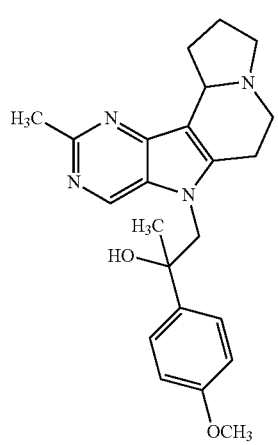 [SMILES: COc1ccc(C(C)(O)Cn2c3c(c4nc(C)ncc42)C2CCCN2CC3)cc1]
IV-152
IV-162a, IV-162b, IV-162c, IV-162d
TABLE 4-continued
Representative Compounds of the Invention
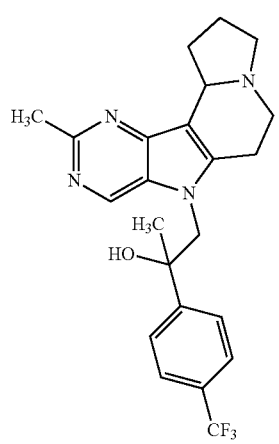
IV-163
IV-163a, IV-163b, IV-163c, IV-163d
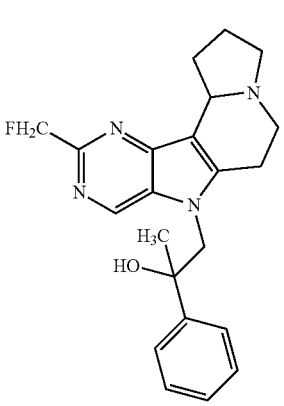
IV-164
IV-164a, IV-164b, IV-164c, IV-164d
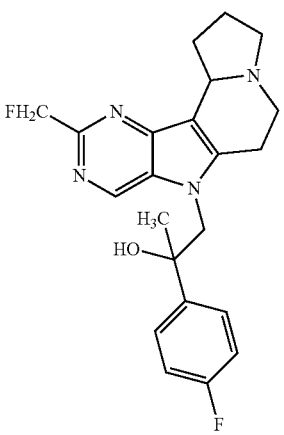
IV-165
IV-165a, IV-165b, IV-165c, IV-165d TABLE 4-continued
Representative Compounds of the Invention
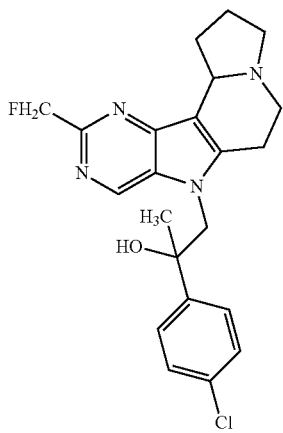
IV-166
IV-166a, IV-166b, IV-166c, IV-166d
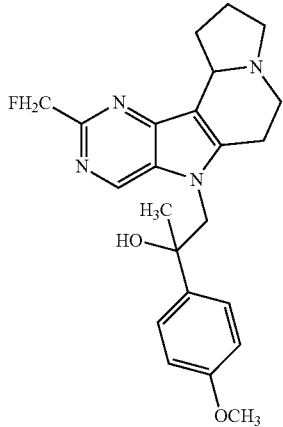
IV-167
IV-167a, IV-167b, IV-167c, IV-167d
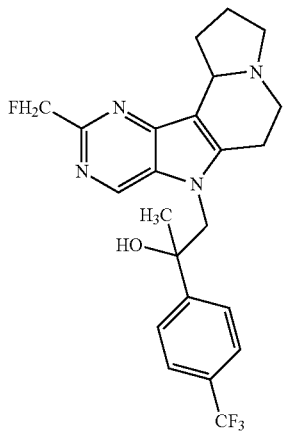
IV-168
IV-168a, IV-168b, IV-168c, IV-168d
TABLE 4-continued
Representative Compounds of the Invention
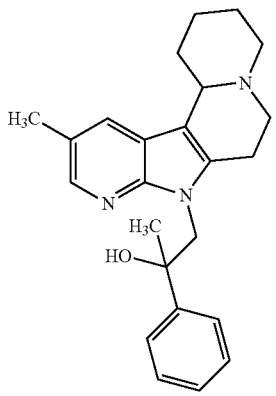 [SMILES: Cc1cnc2c(c1)c1c(n2CC(C)(O)c2ccccc2)CCN2CCCCC12]
IV-169
IV-169a, IV-169b, IV-169c, IV-169d
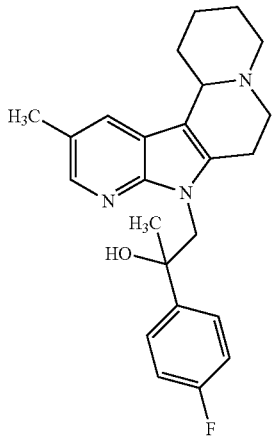 [SMILES: Cc1cnc2c(c1)c1c(n2CC(C)(O)c2ccc(F)cc2)CCN2CCCCC12]
IV-170
IV-170a, IV-170b, IV-170c, IV-170d
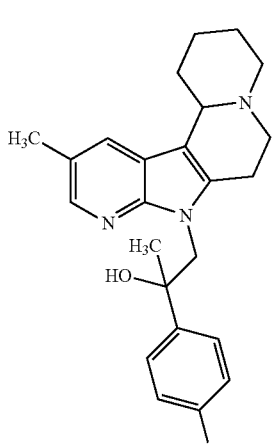
IV-171
IV-171a, IV-171b, IV-171c, IV-171d TABLE 4-continued
Representative Compounds of the Invention
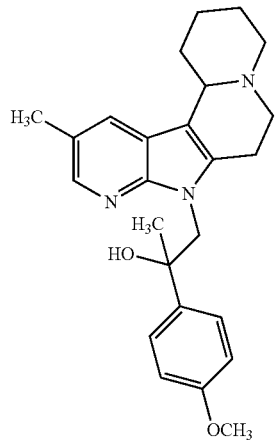 [SMILES: COc1ccc(C(C)(O)Cn2c3c(c4cc(C)cnc42)C2CCCCN2CC3)cc1]
IV-172
IV-172a, IV-172b, IV-172c, IV-172d
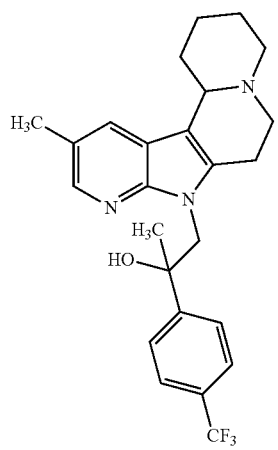 [SMILES: Cc1cnc2c(c1)c1c(n2CC(C)(O)c2ccc(C(F)(F)F)cc2)CCN2CCCCC12]
IV-173
IV-173a, IV-173b, IV-173c, IV-173d
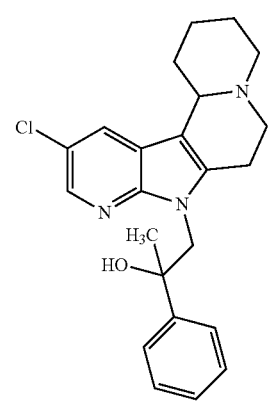 [SMILES: CC(O)(Cn1c2c(c3cc(Cl)cnc31)C1CCCCN1CC2)c1ccccc1]
IV-174
IV-174a, IV-174b, IV-174c, IV-174d
TABLE 4-continued
Representative Compounds of the Invention
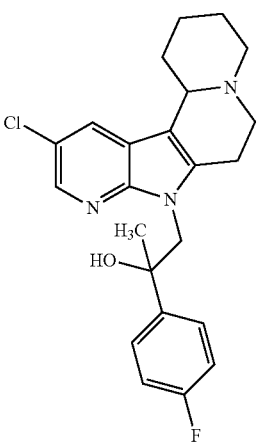 [SMILES: CC(O)(Cn1c2c(c3cc(Cl)cnc31)C1CCCCN1CC2)c1ccc(F)cc1]
IV-175
IV-175a, IV-175b, IV-175c, IV-175d
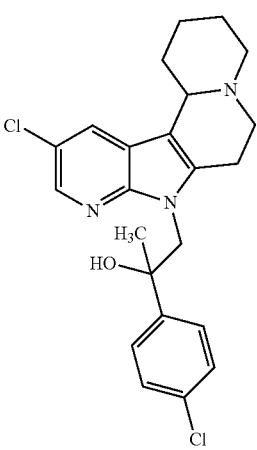 [SMILES: CC(O)(Cn1c2c(c3cc(Cl)cnc31)C1CCCCN1CC2)c1ccc(Cl)cc1]
IV-176
IV-176a, IV-176b, IV-176c, IV-176d
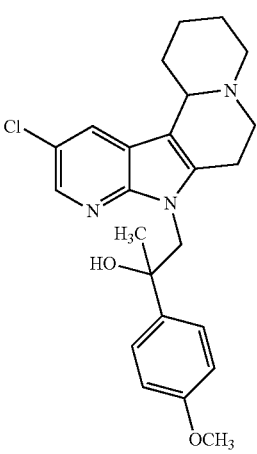 [SMILES: COc1ccc(C(C)(O)Cn2c3c(c4cc(Cl)cnc42)C2CCCCN2CC3)cc1]
IV-177
IV-177a, IV-177b, IV-177c, IV-177d TABLE 4-continued
Representative Compounds of the Invention
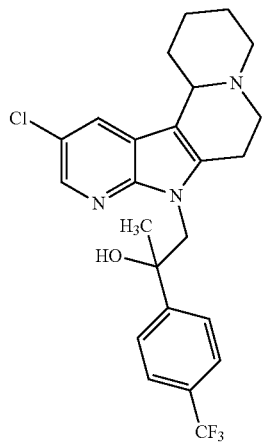 [SMILES: CC(O)(Cn1c2c(c3cc(Cl)cnc31)C1CCCCN1CC2)c1ccc(C(F)(F)F)cc1]
IV-178
IV-178a, IV-178b, IV-178c, IV-178d
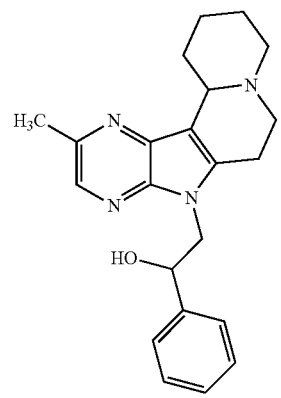 [SMILES: Cc1cnc2c(n1)c1c(n2CC(O)c2ccccc2)CCN2CCCCC12]
IV-179
IV-179a, IV-179b, IV-179c, IV-179d
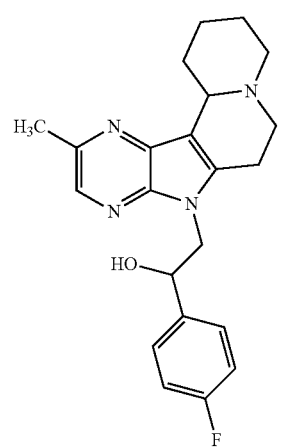 [SMILES: Cc1cnc2c(n1)c1c(n2CC(O)c2ccc(F)cc2)CCN2CCCCC12]
IV-180
IV-180a, IV-180b, IV-180c, IV-180d
TABLE 4-continued
Representative Compounds of the Invention
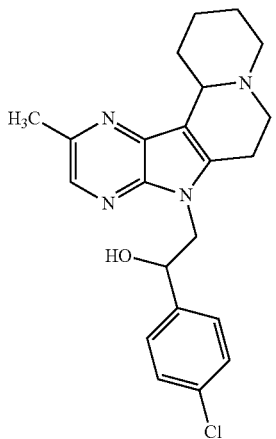
IV-181
IV-181a, IV-181b, IV-181c, IV-181d
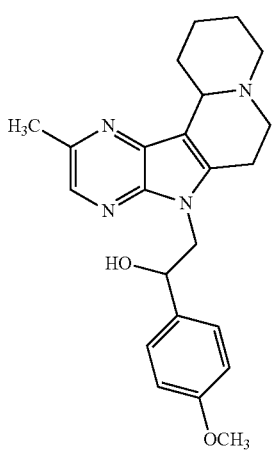 [SMILES: COc1ccc(C(O)Cn2c3c(c4nc(C)cnc42)C2CCCCN2CC3)cc1]
IV-182
IV-182a, IV-182b, IV-182c, IV-182d
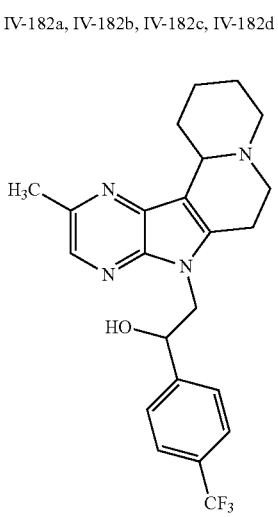
IV-183
IV-183a, IV-183b, IV-183c, IV-183d TABLE 4-continued
Representative Compounds of the Invention
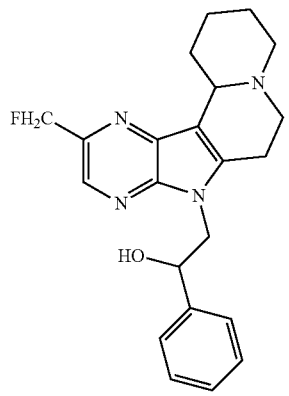
IV-184
IV-184a, IV-184b, IV-184c, IV-184d
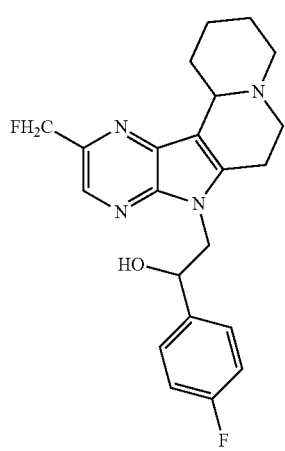
IV-185
IV-185a, IV-185b, IV-185c, IV-185d
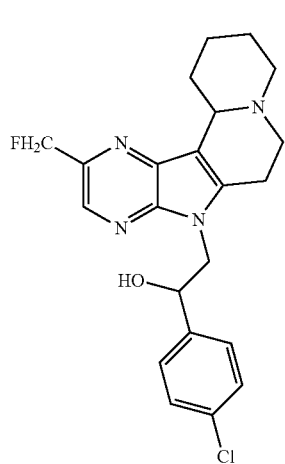
IV-186
IV-186a, IV-186b, IV-186c, IV-186d
TABLE 4-continued
Representative Compounds of the Invention
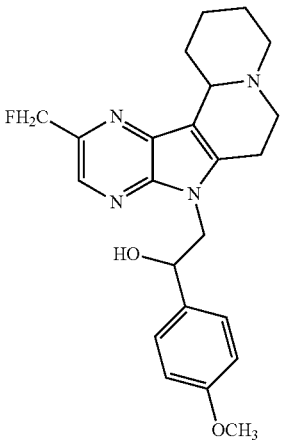
IV-187
IV-187a, IV-187b, IV-187c, IV-187d
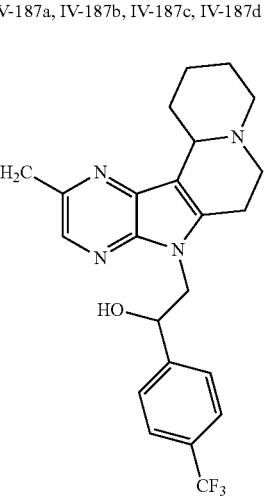
IV-188
IV-188a, IV-188b, IV-188c, IV-188d
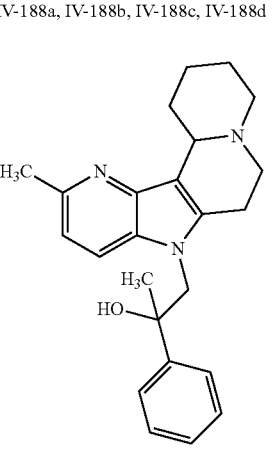
IV-189
IV-189a, IV-189b, IV-189c, IV-189d TABLE 4-continued
Representative Compounds of the Invention
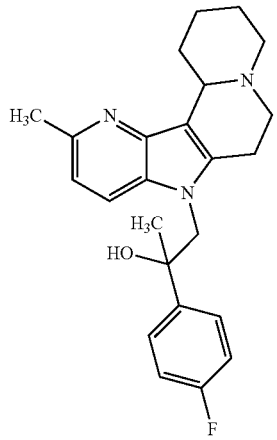 [SMILES: Cc1ccc2c(n1)c1c(n2CC(C)(O)c2ccc(F)cc2)CCN2CCCCC12]
IV-190
IV-190a, IV-190b, IV-190c, IV-190d
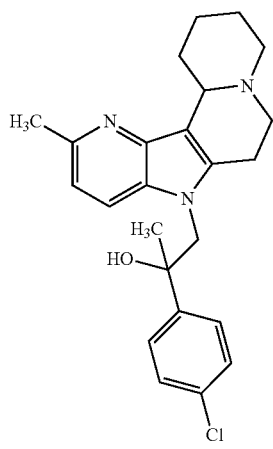
IV-191
IV-191a, IV-191b, IV-191c, IV-191d
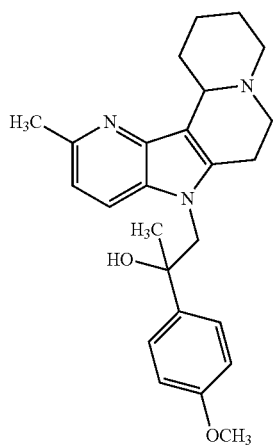 [SMILES: COc1ccc(C(C)(O)Cn2c3c(c4nc(C)ccc42)C2CCCCN2CC3)cc1]
IV-192
IV-192a, IV-192b, IV-192c, IV-192d
TABLE 4-continued
Representative Compounds of the Invention
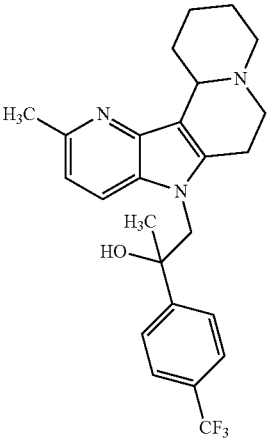 [SMILES: Cc1ccc2c(n1)c1c(n2CC(C)(O)c2ccc(C(F)(F)F)cc2)CCN2CCCCC12]
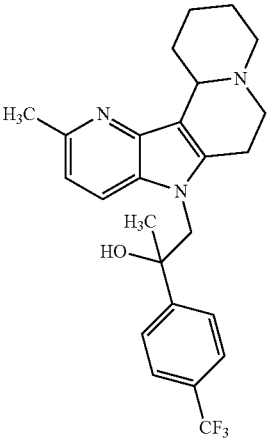 [SMILES: Cc1ccc2c(n1)c1c(n2CC(C)(O)c2ccc(C(F)(F)F)cc2)CCN2CCCCC12]
IV-193
IV-193a, IV-193b, IV-193c, IV-193d
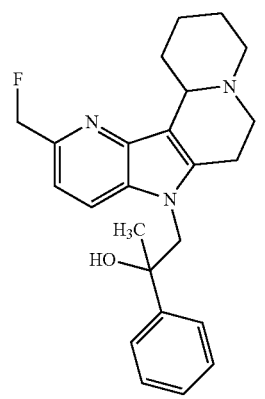 [SMILES: CC(O)(Cn1c2c(c3nc(CF)ccc31)C1CCCCN1CC2)c1ccccc1]
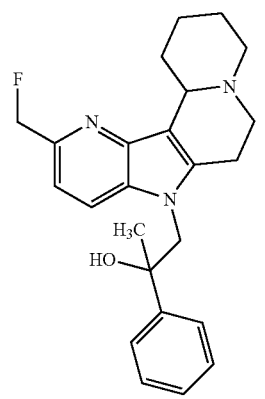
IV-194
IV-194a, IV-194b, IV-194c, IV-194d
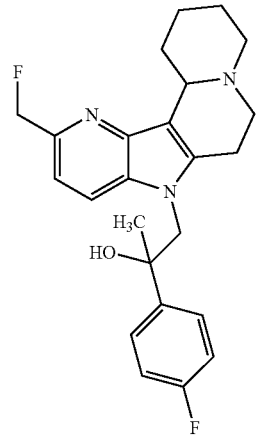 [SMILES: CC(O)(Cn1c2c(c3nc(CF)ccc31)C1CCCCN1CC2)c1ccc(F)cc1]
IV-195
IV-195a, IV-195b, IV-195c, IV-195d

TABLE 4-continued
Representative Compounds of the Invention
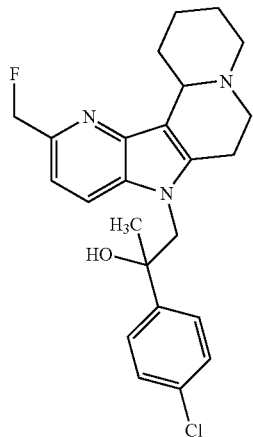 [SMILES: CC(O)(Cn1c2c(c3nc(CF)ccc31)C1CCCCN1CC2)c1ccc(Cl)cc1]
IV-196
IV-196a, IV-196b, IV-196c, IV-196d
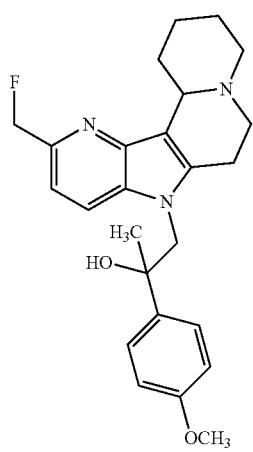 [SMILES: COc1ccc(C(C)(O)Cn2c3c(c4nc(CF)ccc42)C2CCCCN2CC3)cc1]
IV-197
IV-197a, IV-197b, IV-197c, IV-197d
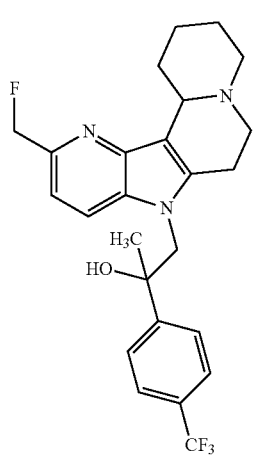 [SMILES: CC(O)(Cn1c2c(c3nc(CF)ccc31)C1CCCCN1CC2)c1ccc(C(F)(F)F)cc1]
IV-198
IV-198a, IV-198b, IV-198c, IV-198d
TABLE 4-continued
Representative Compounds of the Invention
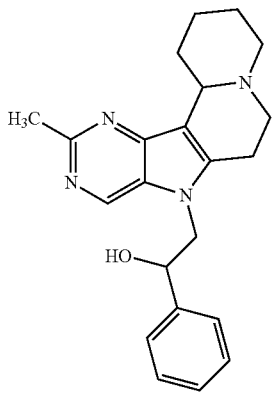 [SMILES: Cc1ncc2c(n1)c1c(n2CC(O)c2ccccc2)CCN2CCCCC12]
IV-199
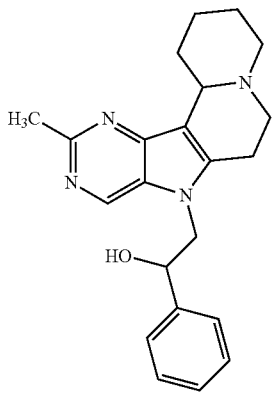 [SMILES: Cc1ncc2c(n1)c1c(n2CC(O)c2ccccc2)CCN2CCCCC12]
IV-199a, IV-199b, IV-199c, IV-199d
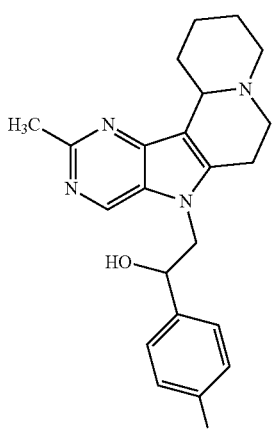
IV-200
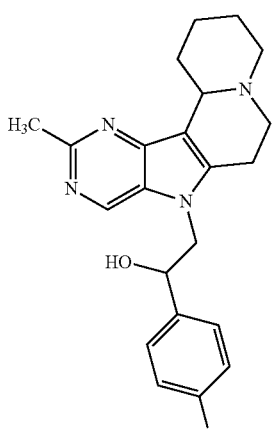
IV200a, IV-200b, IV-200c, IV-200d
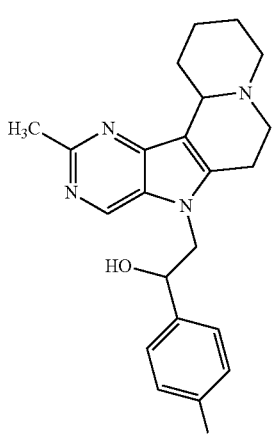
IV-201
IV-201a, IV-201b, IV-201c, IV-201d

TABLE 4-continued
Representative Compounds of the Invention
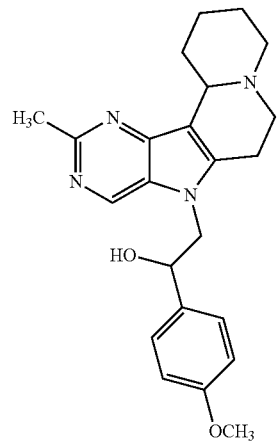 [SMILES: COc1ccc(C(O)Cn2c3c(c4nc(C)ncc42)C2CCCCN2CC3)cc1]
IV-202
IV-202a, IV-202b, IV-202c, IV-202d
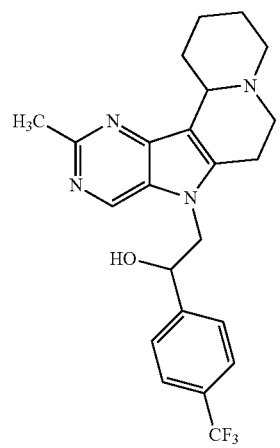 [SMILES: Cc1ncc2c(n1)c1c(n2CC(O)c2ccc(C(F)(F)F)cc2)CCN2CCCCC12]
IV-203
IV-203a, IV-203b, IV-203c, IV-203d
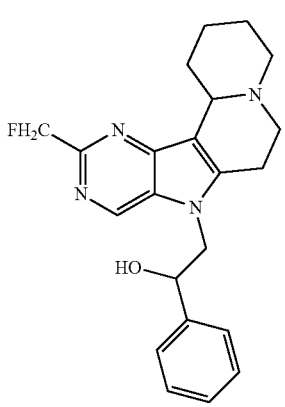
IV-204
IV-204a, IV-204b, IV-204c, IV-204d
TABLE 4-continued
Representative Compounds of the Invention
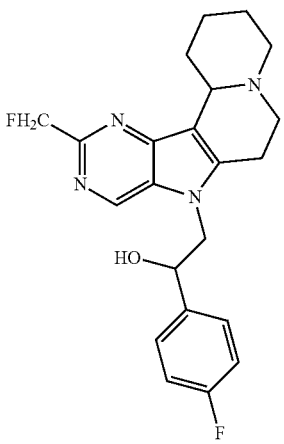
IV-205
IV-205a, IV-205b, IV-205c, IV-205d
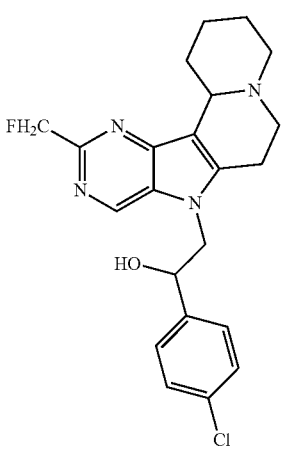
IV-206
IV-206a, IV-206b, IV-206c, IV-206d
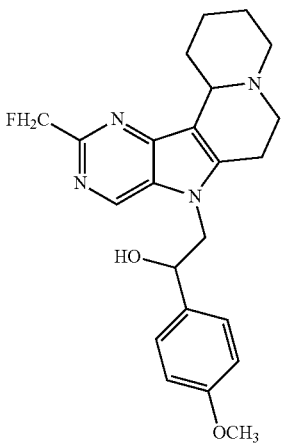
IV-207
IV-207a, IV-207b, IV-207c, IV-207d TABLE 4-continued
Representative Compounds of the Invention
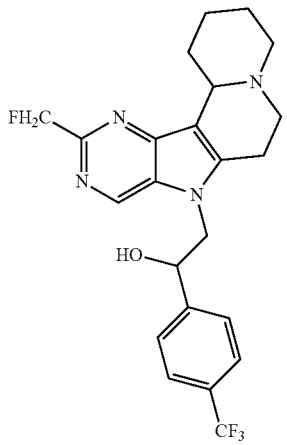
IV-208
IV-208a, IV-208b, IV-208c, IV-208d
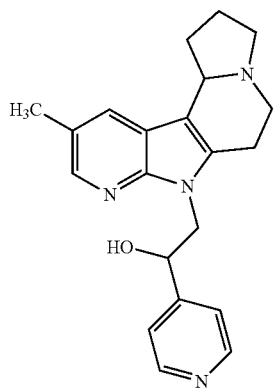 [SMILES: Cc1cnc2c(c1)c1c(n2CC(O)c2ccncc2)CCN2CCCC12]
IV-209
IV-209a, IV-209b, IV-209c, IV-209d
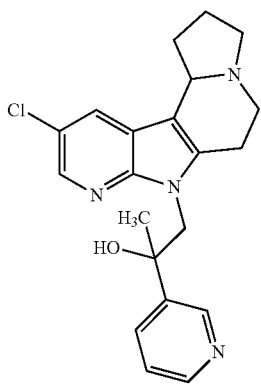 [SMILES: CC(O)(Cn1c2c(c3cc(Cl)cnc31)C1CCCN1CC2)c1cccnc1]
IV-210
IV-210a, IV-210b, IV-210c, IV-210d
TABLE 4-continued
Representative Compounds of the Invention
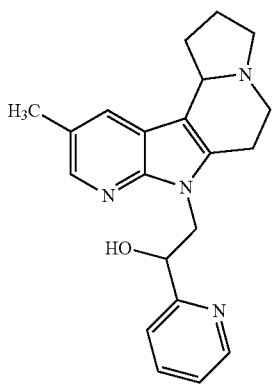 [SMILES: Cc1cnc2c(c1)c1c(n2CC(O)c2ccccn2)CCN2CCCC12]
IV-211
IV-211a, IV-211b, IV-211c, IV-211d
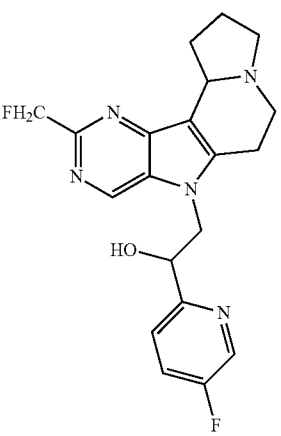
IV-212
IV-212a, IV-212b, IV-212c, IV-212d
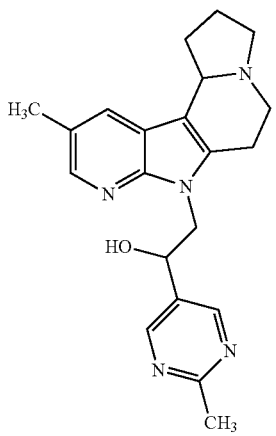 [SMILES: Cc1cnc2c(c1)c1c(n2CC(O)c2cnc(C)nc2)CCN2CCCC12]
IV-213
IV-213a, IV-213b, IV-213c, IV-213d

TABLE 4-continued
Representative Compounds of the Invention
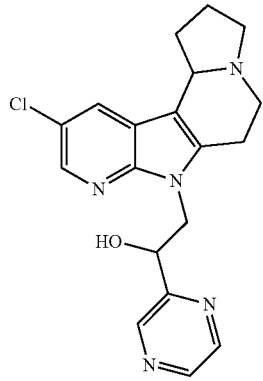 [SMILES: OC(Cn1c2c(c3cc(Cl)cnc31)C1CCCN1CC2)c1cnccn1]
IV-214
IV-214a, IV-214b, IV-214c, IV-214d
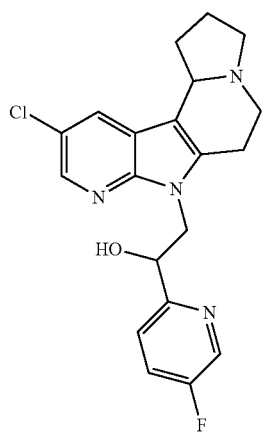 [SMILES: OC(Cn1c2c(c3cc(Cl)cnc31)C1CCCN1CC2)c1ccc(F)cn1]
IV-215
IV-215a, IV-215b, IV-215c, IV-215d
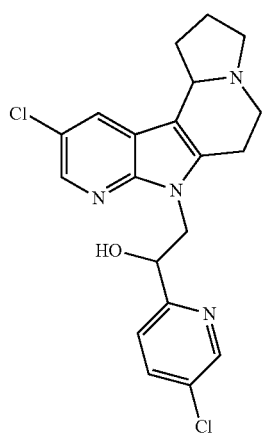 [SMILES: OC(Cn1c2c(c3cc(Cl)cnc31)C1CCCN1CC2)c1ccc(Cl)cn1]
IV-216
IV-216a, IV-216b, IV-216c, IV-216d
TABLE 4-continued
Representative Compounds of the Invention
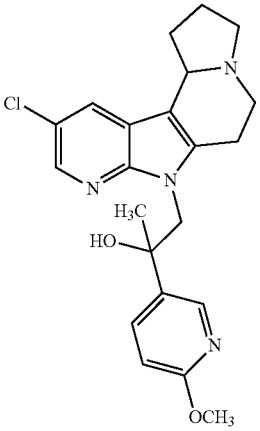
IV-217
IV-217a, IV-217b, IV-217c, IV-217d
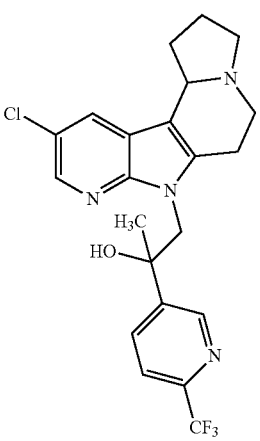 [SMILES: CC(O)(Cn1c2c(c3cc(Cl)cnc31)C1CCCN1CC2)c1ccc(C(F)(F)F)nc1]
IV-218
IV-218a, IV-218b, IV-218c, IV-218d
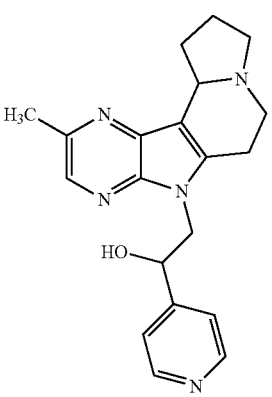
IV-219
IV-219a, IV-219b, IV-219c, IV-219d TABLE 4-continued
Representative Compounds of the Invention
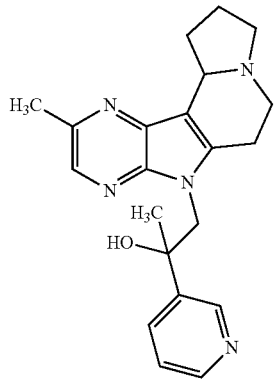 [SMILES: Cc1cnc2c(n1)c1c(n2CC(C)(O)c2cccnc2)CCN2CCCC12]
IV-220
IV-220a, IV-220b, IV-220c, IV-220d
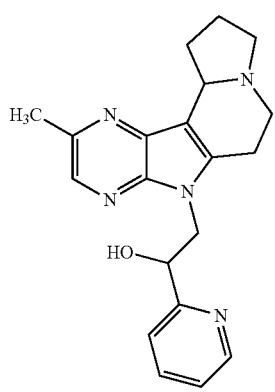 [SMILES: Cc1cnc2c(n1)c1c(n2CC(O)c2ccccn2)CCN2CCCC12]
IV-221
IV-221a, IV-221b, IV-221c, IV-221d
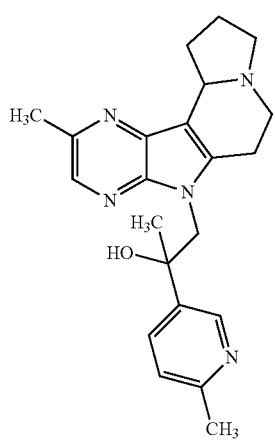
IV-222
IV-222a, IV-222b, IV-222c, IV-222d
TABLE 4-continued
Representative Compounds of the Invention
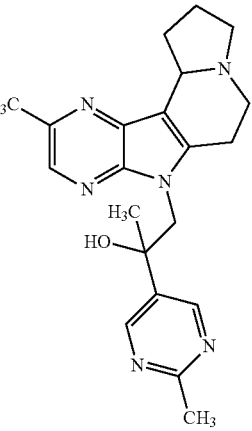
IV-223
IV-223a, IV-223b, IV-223c, IV-223d
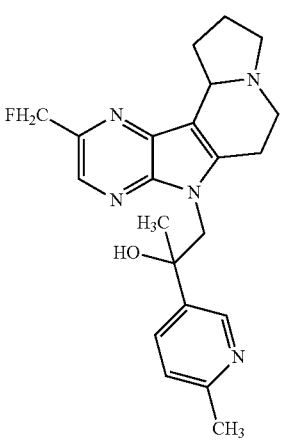
IV-224
IV-224a, IV-224b, IV-224c, IV-224d
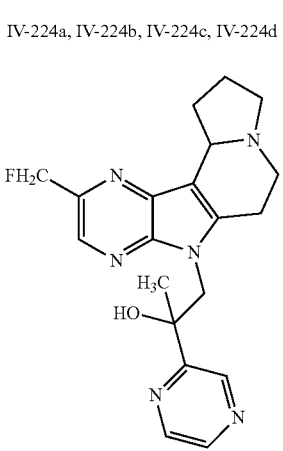
IV-225
IV-225a, IV-225b, IV-225c, IV-225d

TABLE 4-continued
Representative Compounds of the Invention
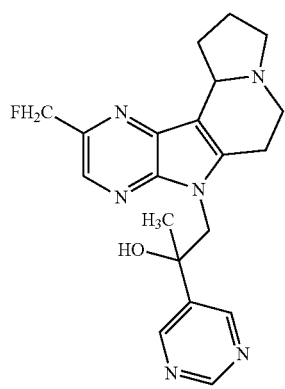
IV-226
IV-226a, IV-226b, IV-226c, IV-226d
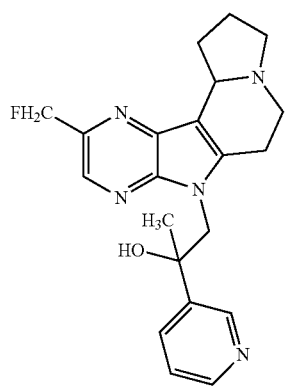
IV-227
IV-227a, IV-227b, IV-227c, IV-227d
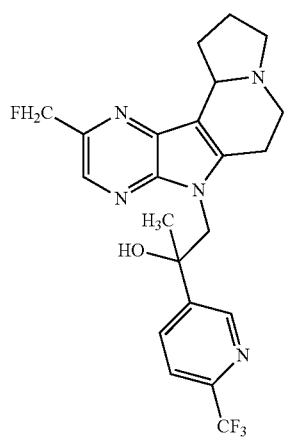
IV-228
IV-228a, IV-228b, IV-228c, IV-228d
TABLE 4-continued
Representative Compounds of the Invention
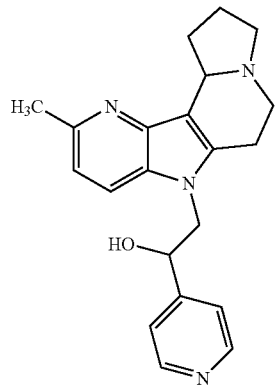 [SMILES: Cc1ccc2c(n1)c1c(n2CC(O)c2ccncc2)CCN2CCCC12]
IV-229
IV-229a, IV-229b, IV-229c, IV-229d
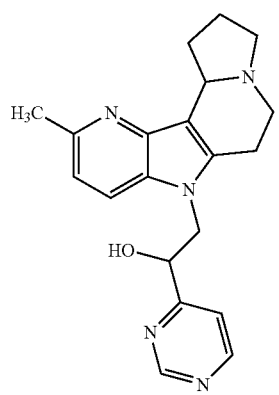 [SMILES: Cc1ccc2c(n1)c1c(n2CC(O)c2ccncn2)CCN2CCCC12]
IV-230
IV-230a, IV-230b, IV-230c, IV-230d
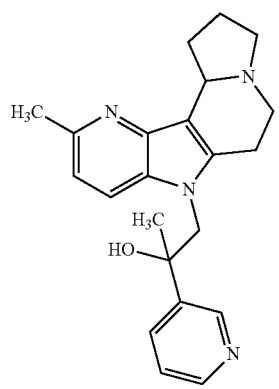 [SMILES: Cc1ccc2c(n1)c1c(n2CC(C)(O)c2cccnc2)CCN2CCCC12]
IV-231
IV-231a, IV-231b, IV-231c, IV-231d TABLE 4-continued
Representative Compounds of the Invention
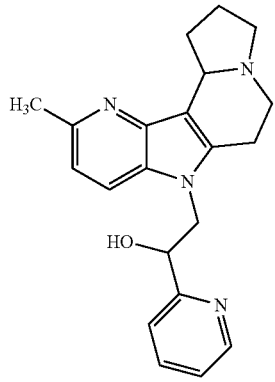 [SMILES: Cc1ccc2c(n1)c1c(n2CC(O)c2ccccn2)CCN2CCCC12]
IV-232
IV-232a, IV-232b, IV-232c, IV-232d
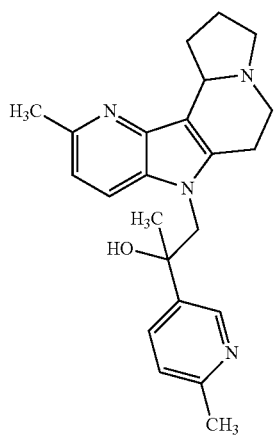
IV-233
IV-233a, IV-233b, IV-233c, IV-233d
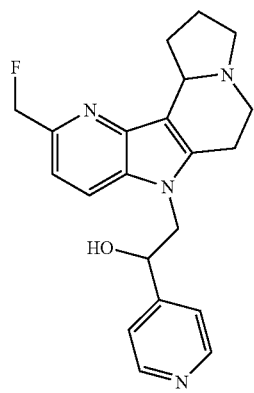 [SMILES: OC(Cn1c2c(c3nc(CF)ccc31)C1CCCN1CC2)c1ccncc1]
IV-234
IV-234a, IV-234b, IV-234c, IV-234d
TABLE 4-continued
Representative Compounds of the Invention
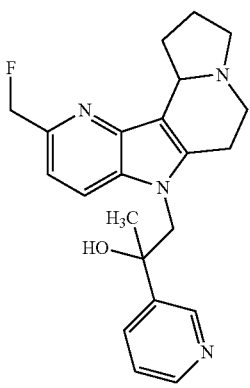 [SMILES: CC(O)(Cn1c2c(c3nc(CF)ccc31)C1CCCN1CC2)c1cccnc1]
IV-235
IV-235a, IV-235b, IV-235c, IV-235d
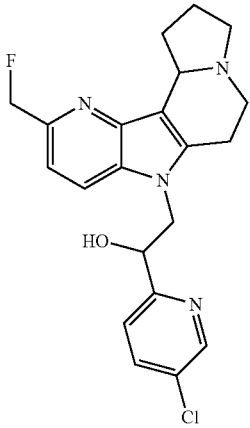
IV-236
IV-236a, IV-236b, IV-236c, IV-236d
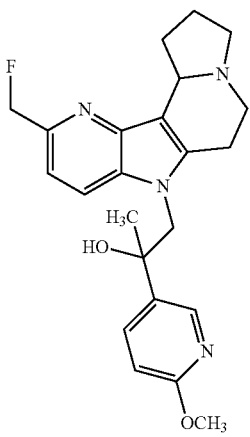 [SMILES: COc1ccc(C(C)(O)Cn2c3c(c4nc(CF)ccc42)C2CCCN2CC3)cn1]
IV-237
IV-237a, IV-237b, IV-237c, IV-237d TABLE 4-continued
Representative Compounds of the Invention
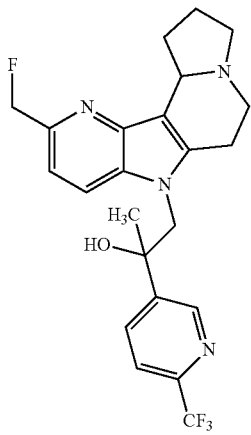 [SMILES: CC(O)(Cn1c2c(c3nc(CF)ccc31)C1CCCN1CC2)c1ccc(C(F)(F)F)nc1]
IV-238
IV-238a, IV-238b, IV-238c, IV-238d
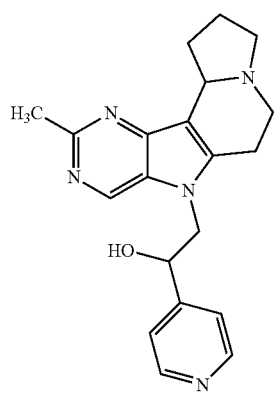 [SMILES: Cc1ncc2c(n1)c1c(n2CC(O)c2ccncc2)CCN2CCCC12]
IV-239
IV-239a, IV-239b, IV-239c, IV-239d
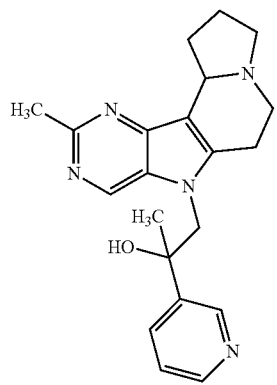
IV-240
IV-240a, IV-240b, IV-240c, IV-240d
TABLE 4-continued
Representative Compounds of the Invention
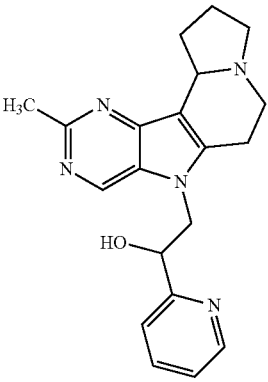 [SMILES: Cc1ncc2c(n1)c1c(n2CC(O)c2ccccn2)CCN2CCCC12]
IV-241
IV-241a, IV-241b, IV-241c, IV-241d
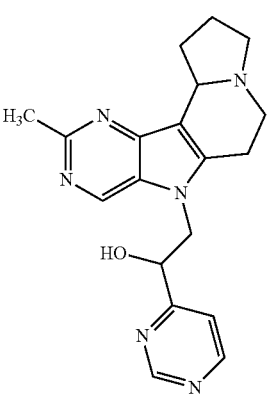 [SMILES: Cc1ncc2c(n1)c1c(n2CC(O)c2ccncn2)CCN2CCCC12]
IV-242
IV-242a, IV-242b, IV-242c, IV-242d
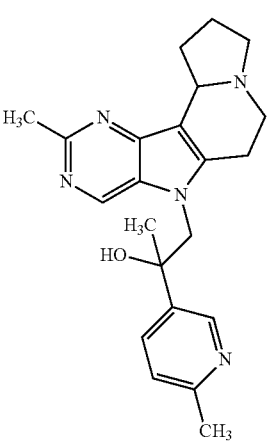
IV-243
IV-243a, IV-243b, IV-243c, IV-243d TABLE 4-continued
Representative Compounds of the Invention
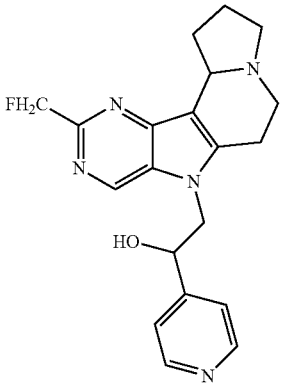
IV-244
IV-244a, IV-244b, IV-244c, IV-244d
TABLE 5
Representative Compounds of the Invention
V-1
V-1a, V-1b
V-2
V-2a, V-2b
TABLE 5-continued
Representative Compounds of the Invention
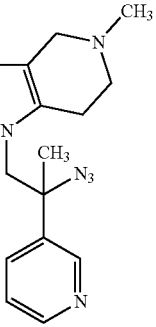
V-3
V-3a, V-3b
V-4
V-4a, V-4b, V-4c, V-4d
V-5
V-5a, V-5b, V-5c, V-5d TABLE 5-continued
Representative Compounds of the Invention
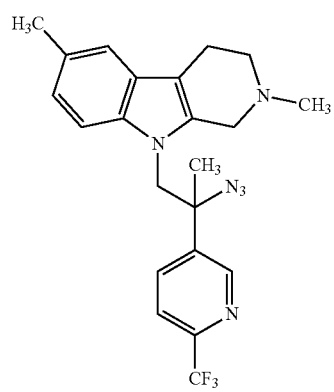
V-6
V-6a, V-6b
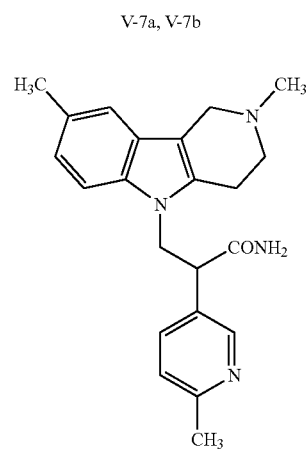
V-7
V-7a, V-7b
TABLE 5-continued
Representative Compounds of the Invention
V-8
V-8a, V-8b
V-9
V-9a, V-9b
V-10
V-10a, V-10b
V-11
V-11a, V-11b TABLE 5-continued
Representative Compounds of the Invention
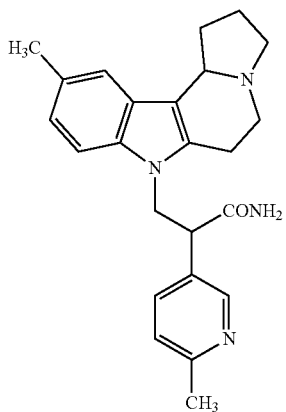 [SMILES: Cc1ccc2c(c1)c1c(n2CC(C(N)=O)c2ccc(C)nc2)CCN2CCCC12]
V-12a, V-12b, V-12c, V-12d
V-12
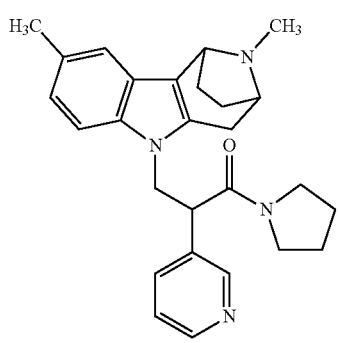 [SMILES: Cc1ccc2c(c1)c1c(n2CC(C(=O)N2CCCC2)c2cccnc2)CC2CCC1N2C]
V-13a, V-13b, V-13c, V-13d
V-13
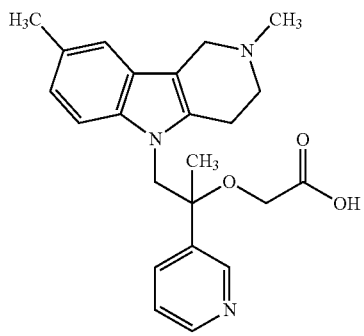 [SMILES: Cc1ccc2c(c1)c1c(n2CC(C)(OCC(=O)O)c2cccnc2)CCN(C)C1]
V-14a, V-14b
V-14
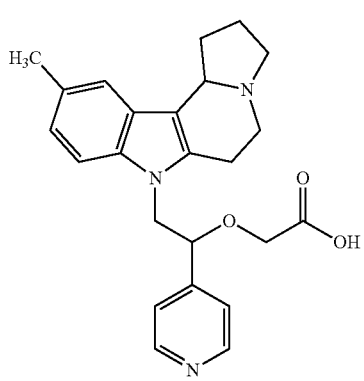 [SMILES: Cc1ccc2c(c1)c1c(n2CC(OCC(=O)O)c2ccncc2)CCN2CCCC12]
V-15a, V-15b, V-15c, V-15d
V-15
TABLE 5-continued
Representative Compounds of the Invention
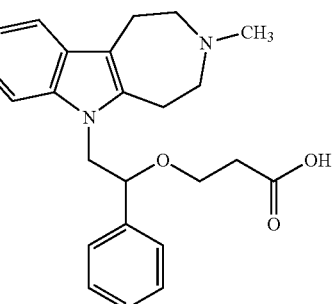
V-16a, V-16b
V-16
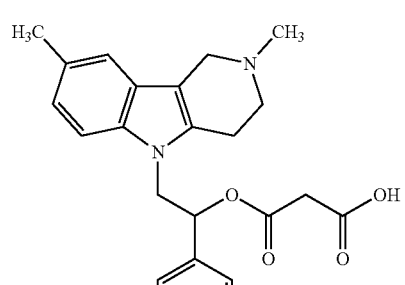
V-17a, V-17b
V-17
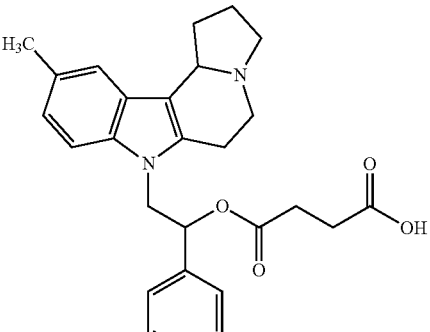
V-18a, V-18b, V-18c, V-18d
V-18
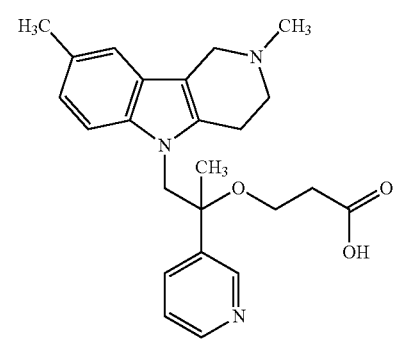 [SMILES: Cc1ccc2c(c1)c1c(n2CC(C)(OCCC(=O)O)c2cccnc2)CCN(C)C1]
V-19a, V-19b
V-19

TABLE 5-continued

Representative Compounds of the Invention

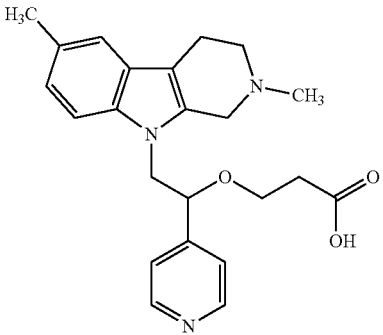 [SMILES: Cc1ccc2c(c1)c1c(n2CC(OCCC(=O)O)c2ccncc2)CN(C)CC1]

V-20

V-20a, V-20b

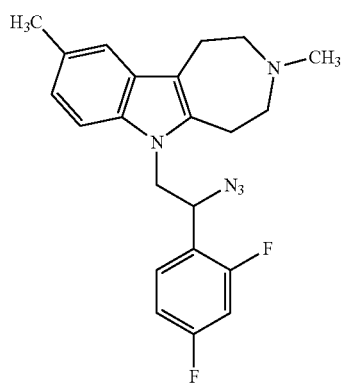

V-21

V-21a, V-21b

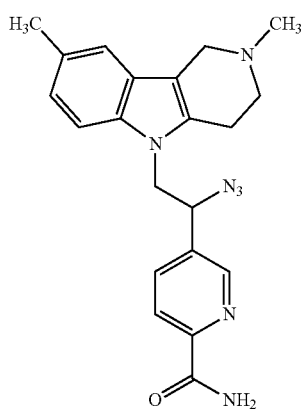

V-22

V-22a, V-22b

TABLE 5-continued

Representative Compounds of the Invention

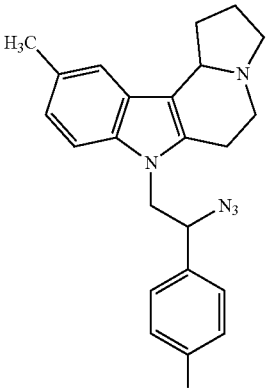

V-23

V-23a, V-23b, V-23c, V-23d

General Synthetic Methods

The compounds of the invention may be prepared by a number of processes as generally described below and more specifically in the Examples hereinafter. In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

General Protocol for Chiral Preparative HPLC Separation of Racemic Compounds

For chiral separations, samples were dissolved in MeOH and EtOH according to the solubility of sample and filtered through 0.22μ. PTFE filters. The columns used were CHIRALPAK-AD; 20*250 mm, 10μ and CHIRALCEL-ODH; 20*250 mm, 5μ. A flow rate of 12 mL/min-17 mL/min was used according to the resolution. Alkanes such as n-Pentane, Hexane and Heptane (40%-95%) and alcohols such as EtOH, Isopropyl alcohol and t-Butanol (5%-60%) were used as mobile phase. In some cases alcohol combinations i.e. (EtOH+MeOH), (EtOH+IPA), (IPA+MeOH), (t-Butanol+MeOH), (t-Butanol+EtOH) were used instead of a single alcohol. Diethyl amine (up to 0.3%) was used as modifier in the mobile phase.

Example H1: General Method for the Chiral HPLC Separation and Characterization of Compounds that were Synthesized Initially as a Mixture of Enantiomers Crude or in some cases partially purified (normal or reverse phase HPLC) mixtures of enantiomers were analyzed by analytical chiral HPLC methods. Once adequate separation was achieved, larger quantities of the mixtures were separated using preparative scale columns as shown below for Compound Nos. 138a and 138b. Separation was followed by removal of solvents on a rotary evaporator to accomplish the isolation of the individual single enantiomers. In some cases where appropriate, after removal of solvent, the samples were lyophilized. After isolation, each individual enantiomer was further analyzed by analytical (reverse phase and chiral) HPLC, LCMS and NMR. When final products were converted to salts, final characterization of the compounds was carried out after conversion to the salt for each enantiomer.

Analytical Chiral HPLC of Compound Nos. 138a and 138b.
Column: Chiralcel OD-H; Column ID: 4.6*250 mm, 5μ. Mobile Phase:Hexane: (EtOH:MeOH 80:20)–93:7. Flow rate: 1 mL/min. Retention Time: Compound No. 138a-9.939 min. Compound No. 138b-13.660 min.

Chiral Preparative Data of Compound Nos. 138a and 138b.
Column: Chiralcel OD-H. Column ID: 20*250 mm, 5μ. Mobile Phase:Hexane: (EtOH:MeOH 80:20)–95:5. Flow rate: 15 mL/min. Solubility: 30 mg/mL in MeOH.
Example H2: General Method for the Chiral HPLC Separation and Characterization of Compounds that were Synthesized Initially as a Mixture of Diastereomers:

Crude or in some cases partially purified (normal or reverse phase HPLC) mixtures of diastereomers were analyzed by analytical chiral HPLC methods. Once adequate separation was achieved, larger quantities of the mixtures were separated using preparative scale columns as shown below for Compound Nos. II-149a-d. Separation was followed by removal of solvents on a rotary evaporator to accomplish the isolation of the individual single diastereomers. In some cases where appropriate, after removal of solvent, the samples were lyophilized. Once each individual diastereomer was isolated they were further analyzed by analytical (reverse phase and chiral) HPLC, LCMS and NMR. When final products were converted to salts, final characterization of the compounds was carried out after conversion to the salt for each diastereomer.

Analytical Chiral HPLC Data of Compound Nos. II-149a-d.
Column: Chiral Pak AD-H. Column ID: 4.6*250 mm, 5μ. Mobile Phase:Hexane (0.2% diethylamine):Isopropanol–93:7. Flow rate: 1 mL/min. Retention Time: Compound No. II-149a-15.470 min. Compound No. II-149b-19.808 min. Compound No. II-149c-33.280 min. Compound No. II-149d-39.585 min.

Chiral Preparative Data of Compound Nos. II-149a-d.
Column: Chiral PAK-AD-H. Column ID: 20*250 mm, 5μ. Mobile Phase:Hexane (0.2% diethylamine):Isopropanol–93:7. Flow rate: 15 mL/min. Solubility: 40 mg/mL in MeOH.

The following abbreviations are used herein: thin layer chromatography (TLC); hour (h); minute (min); second (sec); ethanol (EtOH); dimethylsulfoxide (DMSO); N,N-dimethylformamide (DMF); trifluoroacetic acid (TFA); tetrahydrofuran (THF); Normal (N); aqueous (aq.); methanol (MeOH); dichloromethane (DCM); ethyl acetate (EtOAc); Retention factor (Rf); room temperature (RT).

Compounds detailed herein may be prepared by those of skill in the art by referral to General Methods and Examples described in published PCT applications WO2009/055828 (see e.g., General Methods 1-24 and Examples 1-325), WO2010/127177 (General Methods 1-3 and Examples 1-58), WO2009/120720 (General Methods 1-15C and Examples 1-134), WO2009/120717 (General Methods 1-17 and Examples 1-134), WO2010/051501 (General Methods 1-10 and Examples 1-450) and WO2010/051503 (General Methods 1-15 and Examples 1-111), WO2011/019417 (General Methods 1-9 and Examples 1-10), WO2011/038164 (General Methods 1-19), WO2011/038162 (General Methods 1-21 and Examples 1-6), WO2011/038163 (General Methods 1-19 and Examples 1-49) and WO2011/038161 (General Methods 1-15B and Examples 1-22). The PCT publications described above are incorporated herein by reference in their entireties. Particular examples of each of the General Methods and Examples are provided in the Examples below.

General Method 1

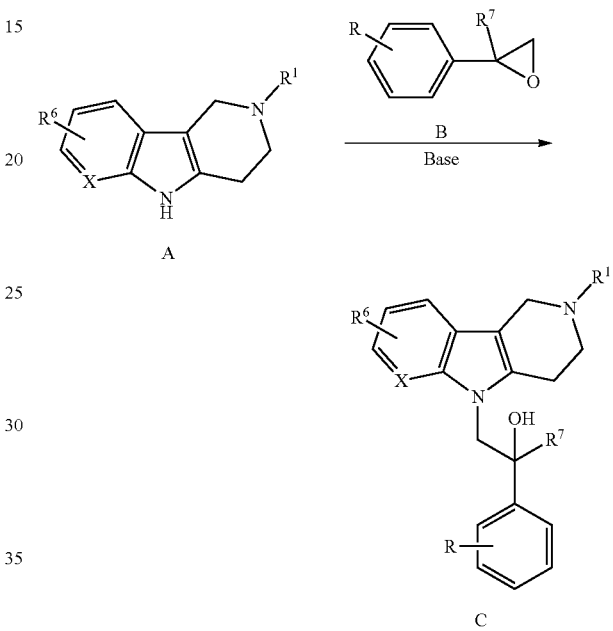

In certain examples of formula (I) provided herein, and as similarly described in the publications presented above, alcohols of the type C can be prepared by treating appropriately functionalized carboline A with functionalized epoxide B, in the presence of a base. A selection of bases effective for this reaction will be apparent to those skilled in the art, such as for example, sodium hydride, sodium tert-butoxide, potassium tert-butoxide, lithium tert-butoxide, lithium diisopropylamide, lithium hexamethyldisilazide, sodium ethoxide, sodium methoxide, and the like. In some instances, one or more of the bases may be used interchangeably; for example, other bases such as sodium tert-butoxide, potassium tert-butoxide, lithium tert-butoxide, lithium diisopropylamide, lithium hexamethyldisilazide, sodium ethoxide or sodium methoxide may be substituted where sodium hydride is specifically described. It is understood that modifications to the specific materials shown are intended, e.g., where Compound B can be a heteroaryl group such as pyridyl, and Compound A can comprise structures such as pyrido[3,4-b]indoles, azepino[4,5-b]indoles, and indolizino[7,8-b]indoles, and the like.

The following Examples are provided to illustrate but not to limit the invention.

All references disclosed herein are incorporated herein by reference in their entireties.

EXAMPLES

Example 1

Preparation of Compound Nos. 1, 1a and 1b

Sodium hydride (1-3 equiv.) was added to a solution of 8-chloro-2,3,4,5-tetrahydro-2-methyl-1H-pyrido[4,3-b]indole (1.0 equiv.) in DMF and heated to 120° C. for 1 h with stirring. The reaction mixture was cooled to 0° C. and 4-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over anhydrous sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CDCl$_3$, oxalate salt) δ (ppm): 8.42 (d, 2H), 7.35-7.20 (m, 3H), 7.00-6.90 (m, 2H), 4.10 (q, 2H), 3.50 (q, 2H), 2.95-2.68 (m, 4H), 2.42(s, 3H), 1.55 (s, 3H). Separation by chiral HPLC provides enantiomers 1a and 1b.

Example 2

Preparation of Compound Nos. 2, 2a and 2b

Sodium hydride (1-3 equiv.) was added to a solution of 2,3,4,5-tetrahydro-2,8-dimethyl-1H-pyrido[4,3-b]indole (1.0 equiv.) in DMF, and heated to 120° C. for 1 h with stirring. The reaction mixture was cooled to 0° C. and 4-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over anhydrous sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CD$_3$OD, oxalate salt) δ (ppm): 8.38 (d, 2H), 7.50 (d, 2H), 7.15 (s, 1H), 7.06 (d, 1H), 6.86 (d, 1H), 4.45 (m, 2H), 4.31 (m, 1H), 4.22 (m, 1H), 3.61 (m, 2H), 3.19 (m, 1H), 3.06 (s, 3H), 2.78 (m, 2H), 2.35 (s, 3H), 1.60 (s, 3H). Separation by chiral HPLC provides enantiomers 2a and 2b.

Example 3

Preparation of Compound Nos. 3, 3a and 3b

Sodium hydride (2.4 g, 100 mmol) was washed with hexane and dried under vacuum. To this was added DMF (15 mL) and cooled to 0° C. Then to this was added 2,8-dimethyl-2,3,4,5-tetrahydro-1H-pyrido[4,3-b]indole (4 g, 20 mmol) and the mixture stirred at 0° C. for 30 min. Then 4-oxiranyl-pyridine (2.90 g, 23.96 mmol) was dissolved in 5 mL DMF and added dropwise to the mixture, which was then left stirred at RT overnight. The reaction was monitored by TLC. The reaction mixture was poured into ice water and extracted with EtOAc (3×). The combined organic layer was washed with water, dried over anhydrous sodium sulfate and concentrated. The resultant solid material was washed with hexane and crystallized from EtOH and ether. $^1$H NMR (DMSO-d6, HCl salt) δ (ppm): 8.70 (d, 2H), 7.70 (d, 2H), 7.38 (m, 1H), 7.20 (s, 1H), 6.90 (d, 1H), 5.05 (m, 1H), 4.58 (m, 1H), 4.30 (m, 1H), 4.20 (m, 2H), 3.70 (m, 2H), 3.20 (m, 4H), 2.90 (s, 1H), 2.38 (s, 3H). Separation by chiral HPLC provided enantiomers 3a and 3b. Optical rotations: Compound 3a; (−)31.32 (c 1, Chloroform, 94.1% HPLC purity); Compound 3b, (+)28.24 (c 1, Chloroform, 98.05% HPLC purity).

Example 4

Preparation of Compound Nos. 4, 4a, and 4b

Sodium hydride (2.72 g, 113.33 mmol) was washed with hexane and dried under vacuum. To this was added DMF (15 mL) and the mixture cooled to 0° C. 8-Chloro-2-methyl-2,3,4,5-tetrahydro-1H-pyrido[4,3-b]indole (5 g, 22.72 mmol) was added and the mixture stirred at 0° C. for 30 min, followed by 4-oxiranyl-pyridine (3.3 g, 27.27 mmol) dissolved in 5 mL DMF added dropwise. The reaction mixture was stirred at RT overnight. The reaction was monitored by TLC. The reaction mixture was poured into ice water and the product extracted into EtOAc (3×). The combined organic layers were washed with water, dried over anhydrous sodium sulfate and concentrated. The resultant solid material was washed with hexane and crystallized from EtOH and ether. $^1$H NMR (CD$_3$OD, HCl salt) δ (ppm): 8.80 (d, 2H), 8.18 (d, 2H), 7.50 (s, 1H), 7.30 (m, 1H), 7.10 (d, 1H), 5.30 (m, 1H), 4.70 (m, 1H), 4.50 (m, 1H), 4.40 (m, 2H), 3.90 (m, 1H), 3.60 (m, 2H), 3.40 (m, 2H), 3.10 (s, 3H). Separation by chiral HPLC provided enantiomers 4a and 4b. Optical rotations: Compound 4a, (+)47.31 (c 0.58, Chloroform, 96.26% HPLC purity); Compound 4b, (−) 43.75 (c 0.55, Chloroform, 98.59% HPLC purity).

Example 5

Preparation of Compound Nos. 5, 5a and 5b

To a solution of 2,3,4,5-tetrahydro-2,8-dimethyl-1H-pyrido[4,3-b]indole (290 mg, 1.4 mmol) in DMF (6 mL) was added sodium hydride (38 mg, 1.6 mmol) and the solution was stirred at 120° C. for 1 h. The reaction mixture was cooled to 0° C. and 3-(2-methyloxiran-2-yl)pyridine (400 mg, 2.96 mmol) was added dropwise over a period of 5 min. The reaction mixture was stirred at 120° C. for 2 h, quenched with ice-water (15 mL) and extracted with EtOAc (60 mL). The organic layer was washed with water, brine, dried over anhydrous sodium sulfate and concentrated under reduced pressure. The residue was purified by flash column chromatography (5-15% MeOH/EtOAc) to yield 1-(1,2,3,4-tetrahydro-2,8-dimethylpyrido[4,3-b]indol-5-yl)-2-(pyridin-3-yl)propan-2-ol. Separation by chiral HPLC provided enantiomers 5a and 5b. $^1$H NMR (CDCl$_3$, freebase) δ (ppm): 8.79 (s, 1H), 8.42 (d, 1H), 7.56 (d, 1H), 7.04 (s, 1H), 6.9 (m, 2H), 6.8 (d, 1H), 4.17 (dd, 2H), 3.42 (s, 2H), 2.8 (t, 2H), 2.62 (t, 2H), 2.42 (s, 3H), 2.39 (s, 3H), 1.61 (s, 3H). Optical rotations: Compound 5a, (−)39.27 (c 0.43, Chloroform, 99.69% HPLC purity); Compound 5b, (+)58.97 (c 0.58, Chloroform, 99.49% HPLC purity).

Example 6

Preparation of Compound Nos. 6, 6a and 6b

To a solution of 2-methyl-8-(trifluoromethyl)-2,3,4,5-tetrahydro-1H-pyrido[4,3-b]indole (1.0 g, 3.937 mmol) in DMF (10 mL) was added sodium hydride (472 mg, 11.81 mmol) in portions at RT. After stirring at RT for 15 min, the suspension was allowed to cool to 0° C. and 4-(oxiran-2-yl)pyridine (762 mg, 6.299 mmol) was added dropwise into the reaction mixture, which was stirred at RT overnight. The reaction mixture was poured into ice-cooled water and extracted with EtOAc (3×50 mL). The organic layer was washed with water (2×50 mL), dried over anhydrous sodium sulfate and concentrated. The solid obtained was re-crystallized in DCM-diethyl ether to yield 2-(2-methyl-8-(trifluoromethyl)-3,4-dihydro-1H-pyrido[4,3-b]indol-5(2H)-yl)-1-(pyridin-4-yl)ethanol. $^1$H NMR (CDCl$_3$, freebase) δ (ppm): 8.59 (d, 2H), 7.4 (s, 1H), 7.39 (d, 1H), 7.3 (d, 1H), 7.19 (d, 2H), 4.68 (m, 1H), 4.1 (m, 2H), 3.4 (dd, 2H), 2.82 (m, 1H), 2.74 (bs, 2H), 2.6 (m, 1H), 2.4 (s, 3H). Separation by chiral HPLC provides enantiomers 6a and 6b.

Example 7

Preparation of Compound Nos. 7, 7a and 7b

Chloro carboline (500 mg, 2.27 mmol) was taken in DMF. NaH (180 mg, 4.5 mmol) was added at RT and stirred for 10-15 min. Neat epoxide (450 mg, 3.7 mmol) was added dropwise at RT. The reaction was stirred at RT for 4 h and the reaction was monitored by LCMS. After completion, the reaction mixture was poured on ice water and extracted with EtOAc, dried and concentrated. The residue was purified by HPLC. 465 mg of product as a white solid (TFA salt). TLC: 5% MeOH-DCM, Rf 0.1 was observed. $^1$H NMR (CD$_3$OD, TFA salt) δ (ppm): 8.80 (s, 2H), 8.40 (s, 1H), 7.9 (t, 1H), 7.40 (s, 1H), 7.20 (d, 1H), 7.0 (d, 1H), 5.25 (bs, 1H), 4.7 (d, 1H), 4.4 (m, 2H), 4.3 (d, 1H), 3.9 (bs, 1H), 3.5 (bs, 1H), 3.3 (m, 2H), 3.10 (s, 3H). Separation by chiral HPLC provided enantiomers 7a and 7b. Optical rotations: Compound 7a, (−)21.05 (c 0.52, Chloroform, 89.7% HPLC purity); Compound 7b, (+)6.85 (c 0.69, Chloroform, 95.74% HPLC purity).

Example 8

Preparation of Compound Nos. 8, 8a and 8b

To a solution of 2,6-dimethyl-2,3,4,9-tetrahydro-1H-pyrido[3,4-b]indole (1.0 g, 5.00 mmol) in DMF (20 mL) was added sodium hydride (600 mg, 15 mmol), the suspension stirred at RT for 10 min. A solution of 4-(oxiran-2-yl)pyridine (1.21 g, 10 mmol) in DMF (5 mL) was added slowly into the reaction mixture which was stirred at RT overnight. The progress of reaction was monitored by TLC and LCMS. The reaction mass was poured into ice cold water (200 mL) slowly and extracted with EtOAc (3×200 mL). The organic layer was washed with water (4×300 mL), dried over anhydrous sodium sulfate and concentrated. The residue obtained was washed with hexane (2×15 mL) and triturated with diethyl ether (50 mL) to yield the desired product. $^1$H NMR (CDCl$_3$, freebase) δ (ppm): 8.62 (d, 2H), 7.31 (d, 2H), 7.28 (s, 1H), 7.21 (d, 1H), 7.02 (d, 1H), 5.05 (m, 1H), 4.14 (dd, 1H), 4.078 (dd, 1H), 3.74 (d, 1H), 3.37 (d, 1H), 2.83 (m, 3H), 2.72 (m, 1H), 2.51 (s, 3H), 2.46 (s, 3H). Separation by chiral HPLC provided enantiomers 8a and 8b.

Example 9

Preparation of Compound Nos. 9, 9a and 9b 2-(2-Allyl-8-methyl-1,2,3,4-tetrahydro-pyrido[4,3-b]indol-5-yl)-1-pyridin-3-yl-ethanol (1.0 g, 2.8 mmol) was dissolved in DCM and the solution was purged with nitrogen for 5 min. 1,3-Dimethylbarbituric acid (1.34 g, 8.6 mmol) and Pd(PPh$_3$)$_4$ (66.5 mg, 0.056 mmol) were added and the reaction mixture was stirred at RT for 3 h. The reaction mixture was concentrated under reduced pressure, and the residue was basified with saturated aqueous potassium carbonate, and extracted with EtOAc (3×50 mL). The combined organic layer was washed with saturated aqueous potassium carbonate (6×20 mL), dried over anhydrous sodium sulfate and concentrated. The crude product was purified by reverse phase chromatography to obtain 50 mg of 2-(8-methyl-1,2,3,4-tetrahydro-pyrido[4,3-b]indol-5-yl)-1-pyridin-3-yl-ethanol. $^1$H NMR (CDCl$_3$, freebase) δ (ppm): 8.47 (s, 1H), 8.41 (d, 1H), 7.59 (d, 1H), 7.19 (m, 3H), 7.10 (s, 1H), 7.00 (d, 1H), 5.0 (t, 1H), 4.10 q (d, 2H), 3.92 q (d, 2H), 3.10 (m, 2H), 2.90 (m, 2H), 2.47 (m, 1H), 2.42 (s, 3H). This racemate was separated by chiral semi-preparative HPLC to obtain enantiomers 9a and 9b.

Example 10

Preparation of Compound Nos. 10, 10a and 10b 2-(2-Allyl-8-chloro-1,2,3,4-tetrahydro-pyrido[4,3-b]indol-5-yl)-1-pyridin-4-yl-ethanol (4.0 g, 10.87 mmol) was dissolved in DCM (350 mL) and nitrogen was purged for 10 min into the reaction mixture. 1,3-Dimethyl barbituric acid (5.08 g, 32.62 mmol) and Pd(PPh$_3$)$_4$ (251 mg, 0.217 mmol) was added and stirred for 2 h at RT. After consumption of starting material, the reaction mixture was diluted with saturated potassium carbonate (200 mL) and extracted with DCM (2×100 mL). The combined organic layer was dried over anhydrous sodium sulfate and concentrated, and the crude mixture crystallized in MeOH (5 mL) and ether (50 mL) to obtain 2.2 g of 2-(8-chloro-1,2,3,4-tetrahydro-pyrido[4,3-b]indol-5-yl)-1-pyridin-4-yl-ethanol. $^1$H NMR (CDCl$_3$, freebase) δ (ppm): 8.58 (d, 2H), 7.37 (s, 1H), 7.25 (d, 2H), 7.23 (d, 1H), 7.13 (d, 1H), 5.0 (t, 1H), 4.15 (d, 2H), 3.99 (s, 2H), 3.19 (m, 2H), 2.81 (m, 1H), 2.53 (m, 1H). Separation by chiral HPLC provided enantiomers 10a and 10b. Optical rotations: Compound 10a, (−)34.60 (c 0.55, Chloroform, 99.16% HPLC purity); Compound 10b, (+)31.78 (c 0.53, Chloroform, 92.71% HPLC purity).

Example 11

Preparation of Compound Nos. 11, 11a and 11b

3-[8-Chloro-5-(2-hydroxy-2-pyridin-4-yl-ethyl)-1,3,4,5-tetrahydro-pyrido[4,3-b]indol-2-yl]-propionic acid methyl ester (200 mg, 0.484 mmol) was dissolved in dry THF (5 mL), and cooled to −78° C. Methyl magnesium chloride (0.2 mL, 1.93 mmol) was added dropwise and stirred for 15 min and allowed to RT and stirred for 2 h. After consumption of starting material, 2 mL MeOH was added into the reaction, which was then concentrated, and the residue diluted with water (20 mL) and extracted with EtOAc (3×30 mL). The combined organic layer was dried over anhydrous sodium sulfate and concentrated, and the crude product purified by reverse phase chromatography to obtain 50 mg of 4-[8-chloro-5-(2-hydroxy-2-pyridin-4-yl-ethyl)-1,3,4,5-tetrahydro-pyrido[4,3-b]indol-2-yl]-2-methyl-butan-2-ol. $^1$H NMR (CDCl$_3$, freebase) δ (ppm): 8.48 (d, 2H), 7.35 (s, 1H), 7.18 (d, 2H), 7.16 (d, 1H), 7.10 (d, 1H), 4.90 (t, 1H), 4.05 (m, 2H), 3.68 (m, 2H), 2.87 (m, 3H), 2.79 (m, 2H), 2.49 (m, 1H), 1.72 (t, 2H), 1.24 (s, 6H). Separation by chiral HPLC provided enantiomers 11a and 11b. Optical rotations: Compound 11a, (−)25.66 (c 0.56, Chloroform, 96.42% HPLC purity); Compound 11b, (+)24.07 (c 0.56, Chloroform, 98.39% HPLC purity).

Example 12

Preparation of Compound Nos. 12, 12a and 12b 1-(6-Allyl-3-chloro-5,6,7,8-tetrahydro-1,6,9-triaza-fluoren-9-yl)-2-pyridin-4-yl-propan-2-ol (260 mg, 0.680 mmol) was dissolved in DCM (7 mL) and N$_2$ was purged into the reaction mixture. 1,3-Dimethyl barbituric acid (318 mg, 2.04 mmol) and Pd(PPh$_3$)$_4$ (15 mg, 0.013 mmol) was added and the mixture stirred for 45 min at RT. After consumption of starting material, the reaction mixture was diluted with saturated potassium carbonate and extracted with DCM (3×50 mL). The combined organic layer was dried over anhydrous sodium sulfate and concentrated, and the crude product was purified by reverse phase chromatography to obtain 100 mg of 1-(3-chloro-5,6,7,8-tetrahydro-1,6,9-triaza-fluoren-9-yl)-2-pyridin-4-yl-propan-2-ol. $^1$H NMR (CDCl$_3$, freebase) δ (ppm): 8.51 (d, 2H), 8.14 (s, 1H), 7.67 (s, 1H), 7.33 (d, 2H), 4.39 (d, 1H), 4.36 (d, 1H), 3.93 q (d, 2H), 3.16 (m, 2H), 2.62 (m, 1H), 2.40 (m, 1H), 1.57 (s, 3H). Separation by chiral HPLC provided enantiomers 12a and 12b. Optical rotations: Compound 12a, (+)121.78 (c 0.53, Chloroform, 97.32% HPLC purity); Compound 12b, (−)118.34 (c 0.54, Chloroform, 99.01% HPLC purity).

Example 13

Preparation of Compound Nos. 13, 13a and 13b 3,9-Dimethyl-1,2,3,4,5,6-hexahydroazepino[4,5-b]indole (300 mg, 1.40 mmol) was taken into DMF (6 mL). To a solution of sodium hydride (50%) (100 mg, 4.22 mmol) was added in portions at RT and stirred at RT for 10 min. A solution of 4-(oxiran-2-yl)pyridine (254 mg, 2.11 mmol) in DMF (1 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(3,9-dimethyl-2,3,4,5-tetrahydroazepino[4,5-b]indol-6(1H)-yl)-1-(pyridin-4-yl)ethanol as the TFA salt (250 mg). Separation by chiral HPLC provided enantiomers 13a and 13b. Optical rotations: Compound 13a, (−)5.03 (c 0.56, Chloroform, 99.17% HPLC purity); Compound 13b, (+)5.70 (c 0.56, Chloroform, 99.35% HPLC purity).

Example 14

Preparation of Compound Nos. 14, 14a and 14b 2,6-Dimethyl-2,3,4,9-tetrahydro-1H-β-carboline (1 g, 5 mmol) was dissolved in 15 mL DMF and stirred for 10 min at 0° C. Sodium hydride (600 mg, 15 mmol) was added portionwise at RT and stirred for 10 min. 3-(2-Methyl-oxiranyl)-pyridine (1.01 g, 7.5 mmol) was added dropwise at the same temperature and the mixture stirred for 12 h at RT. The reaction was monitored by TLC & LCMS. After consumption of starting material, the reaction mixture was quenched with ice water and extracted with EtOAc (3×100 mL). The combined organic layer was washed with water (4×100 mL). The organic layer was dried over anhydrous sodium sulfate and concentrated and the residue was crystallized in EtOH and ether to obtain 375 mg of 1-(2,6-dimethyl-1,2,3,4-tetrahydro-β-carbolin-9-yl)-2-pyridin-3-yl-propan-2-ol. $^1$H NMR (CDCl$_3$, freebase) δ (ppm): 8.76 (d, 1H), 8.55 (dd, 1H), 7.703 (d, 1H), 7.24 (s, 1H), 7.23 (dd, 1H), 7.15 (d, 1H), 6.95 (d, 1H), 4.13 (d, 1H), 4.08 (d, 1H), 3.38 (dd, 2H), 2.79 (q, 2H), 2.74 (q, 2H), 2.46 (s, 3H), 2.43 (s, 3H), 1.64 (s, 3H). Separation by chiral HPLC provided enantiomers 14a and 14b. Optical rotations: Compound 14a, (+)31.28 (c 0.58, Chloroform, 96.04% HPLC purity); Compound 14b, (−)27.23 (c 0.57, Chloroform, 96.09% HPLC purity).

Example 15

Preparation of Compound Nos. 15, 15a and 15b

9-Chloro-3-methyl-1,2,3,4,5,6-hexahydroazepino[4,5-b]indole (300 mg, 1.27 mmol) was taken into DMF (6 mL). Sodium hydride (50%) (92 mg, 3.83 mmol) was added in portions at RT and the mixture was stirred at RT for 10 min. A solution of 4-(oxiran-2-yl)pyridine (232 mg, 1.9 mmol) in DMF (1 mL) was added dropwise for 10 min. and stirred for 14 h at RT. The reaction was monitored by TLC and LCMS. The reaction mixture was quenched with ice water, extracted in ethyl acetate. The organic layer was dried over anhydrous sodium sulfate and evaporated under reduced pressure. The crude product was purified by reverse phase chromatography to get pure product 2-(9-chloro-3-methyl-2,3,4,5-tetrahydroazepino[4,5-b]indol-6(1H)-yl)-1-(pyridin-4-yl)ethanol as the TFA salt (230 mg). $^1$HNMR (DMSO-d6, TFA salt) δ (ppm): 8.65 (m, 2H), 7.80-7.45 (m, 3H), 7.40 (m, 1H), 7.0 (m, 1H), 6.0 (m, 1H), 4.95 (m, 1H), 4.40 (m, 2H), 3.40 (m, 3H), 3.20 (m, 4H), 2.92 (s, 3H). Separation by chiral HPLC provided enantiomers 15a and 15b.

Example 16

Preparation of Compound Nos. 16, 16a and 16b 2,6-Dimethyl-2,3,4,9-tetrahydro-1H-β-carboline (500 mg, 2.5 mmol) was dissolved in 20 mL DMF and stirred for 10 min at RT. Sodium hydride (180 mg, 7.5 mmol) was added portionwise at RT and the mixture stirred for 10 min. 2-(2-Methyl-oxiranyl)-pyridine (472 mg, 3.5 mmol) was added dropwise at the same temperature and stirred for 12 h at RT. The reaction was monitored by TLC & LCMS. After consumption of starting material, the reaction mixture was quenched with ice water and extracted with EtOAc (3×100 mL). The combined organic layer was washed with water (3×100 mL). The organic layer was dried over anhydrous sodium sulfate and concentrated and the residue was crystallized in hexane to obtain 115 mg of 1-(2,6-dimethyl-1,2,3,4-tetrahydro-β-carbolin-9-yl)-2-pyridin-2-yl-propan-2-ol. $^1$HNMR (CDCl$_3$, freebase) δ (ppm): 8.51 (d,1H), 7.65 (t,1H), 7.29 (d, 1H), 7.22 (d,1H), 7.20 (s,1H), 6.95 (d,1H), 6.85 (d, 1H), 4.9 (bs,1H), 4.18 (s, 2H), 3.21 (dd, 2H), 2.77 (m, 2H), 2.69 (m, 2H), 2.42 (d, 6H), 1.63 (s, 3H). Separation by chiral HPLC provided enantiomers 16a and 16b. Optical rotations: Compound 16a, (−)5.77(c 0.52, Chloroform, 98.11% HPLC purity); Compound 16b, (+)5.85 (c 0.51, Chloroform, 98.06% HPLC purity).

Example 17

Preparation of Compound Nos. 17, 17a and 17b 6,8,8-Trimethyl-6,7,8,9-tetrahydro-5H-1,6,9-triaza-fluorene (100 mg, 0.465 mmol) was dissolved in DMF (2 mL) and sodium hydride (56 mg, 1.39 mmol) was added portionwise under nitrogen. 4-Oxiranyl-pyridine (113 mg, 0.933 mmol) was added dropwise at RT and stirred for 12 h. After consumption of starting material (by monitoring TLC and LCMS), the reaction mixture was poured in to ice water and extracted with EtOAc (2×25 mL). The combined organic layer was washed with water (5×10 mL), the organic layer was dried over anhydrous sodium sulfate and concentrated, and the crude product purified by reverse phase chromatography to obtain 15 mg of 1-pyridin-4-yl-2-(6,8,8-trimethyl-5,6,7,8-tetrahydro-1,6,9-triaza-fluoren-9-yl)-ethanol.
$^1$HNMR (CDCl$_3$, freebase) δ (ppm): 8.63 (d, 2H), 8.22 (d, 1H), 7.75 (d, 1H), 7.45 (d, 2H), 7.09 (dd, 1H), 5.17 (d, 1H), 4.53 (dd, 1H), 4.47 (d, 1H), 3.71 (d, 1H), 3.44 (d, 1H), 2.5 (s, 3H), 2.49 (d, 1H), 2.44 (d, 1H), 1.47 (s, 3H), 1.32 (s, 3H). Separation by chiral HPLC provided enantiomers 17a and 17b. Optical rotations: Compound 17a, (+)50.54 (c 0.56, Chloroform, 99.31% HPLC purity); Compound 17b, (−)51.38 (c 0.55, Chloroform, 95.62% HPLC purity).

Example 18

Preparation of Compound Nos. 18, 18a and 18b 2,6-Dimethyl-2,3,4,9-tetrahydro-1H-β-carboline (500 mg, 2.5 mmol) was dissolved in 5 mL DMF and sodium hydride (250 mg, 6.24 mmol) was added portionwise at 0° C. and the mixture stirred for 10 min. 2-(4-Fluoro-phenyl)-oxirane (450 mg, 3.26 mmol) was added dropwise at same temperature and stirred for 12 h at RT. The reaction was monitored by TLC & LCMS. After consumption of starting material, the reaction mixture was quenched with ice cold water. The resultant solid was filtered and washed with water (100 mL) and hexane (100 mL), and the crude product was crystallized in EtOH:hexane (5:95 ratio) to obtain 300 mg of 2-(2,6-dimethyl-1,2,3,4-tetrahydro-β-carbolin-9-yl)-1-(4-fluoro-phenyl)-ethanol. $^1$H NMR (CDCl$_3$, Free base) δ (ppm): 7.30 (m, 2H), 7.20 (d, 1H), 7.05 (m, 3H), 7.0 (d, 1H), 5.0 (t, 1H), 4.05 (d, 2H), 3.62 (d, 1H), 3.30 (d, 1H), 2.80 (m, 3H), 2.70 (m, 1H), 2.50 (s, 3H), 2.44 (s, 3H). Separation by chiral HPLC provided enantiomers 18a and 18b. Optical rotations: Compound 18a, (−)6.97 (c 0.56, Chloroform, 89.35% HPLC purity); Compound 18b, (+)13.03 (c 0.51, Chloroform, 99.51% HPLC purity).

Example 19

Preparation of Compound Nos. 19, 19a and 19b 2,6-Dimethyl-2,3,4,9-tetrahydro-1H-β-carboline (500 mg, 2.5 mmol) was dissolved in 10 mL DMF and stirred for 10 min at 0° C. Sodium hydride (300 mg, 7.5 mmol) was added portionwise at RT and stirred for 10 min. 4-(2-Methyl-oxiranyl)-pyridine (472 mg, 3.5 mmol) was added dropwise at the same temperature and stirred for 4 h at RT. The reaction was monitored by TLC & LCMS. After consumption of starting material, the reaction mixture was quenched with ice water and extracted with EtOAc (2×60 mL). The combined organic layer was washed with water (5×75 mL), dried over anhydrous sodium sulfate and concentrated and the residue was crystallized in EtOH and hexane to obtain 175 mg of 1-(2,6-dimethyl-1,2,3,4-tetrahydro-β-carbolin-9-yl)-2-pyridin-4-yl-propan-2-ol. $^1$H NMR (CDCl$_3$, Free base) δ (ppm): 8.58 (d, 2H), 7.40 (d, 2H), 7.25 (s, 1H), 7.16 (d, 1H), 6.92 (d, 1H), 4.18-4.0 (dd, 2H), 3.50-3.38 (dd, 2H), 2.80 (m, 2H), 2.70 (m, 2H), 2.44 (s, 3H), 2.42 (s, 3H), 1.58 (s, 3H). Separation by chiral HPLC provided enantiomers 19a and 19b. Optical rotations: Compound 19a, (+)22.35 (c 0.58, Chloroform, 98.36% HPLC purity); Compound 19b, (−)22.43 (c 0.55, Chloroform, 99.09% HPLC purity).

Example 20

Preparation of Compound Nos. 20, 20a and 20b 2,6-Dimethyl-2,3,4,9-tetrahydro-1H-β-carboline (1.0 g, 5.0 mmol) was dissolved in 15 mL DMF and sodium hydride (600 mg, 15 mmol) was added portionwise at 0° C. and stirred for 10 min. 2-(4-Methoxy-phenyl)-oxirane (900 mg, 6.0 mmol) was added dropwise at the same temperature and stirred for 12 h at RT. The reaction was monitored by TLC & LCMS. After consumption of starting material, the reaction mixture was quenched with ice cold water and filtered through a Celite bed. A cake of compound was formed which was dissolved in MeOH and DCM. This was again filtered through a Celite bed and the filtrate concentrated. The solid thus obtained was crystallized in ether & hexane to get 600 mg of 2-(2,6-dimethyl-1,2,3,4-tetrahydro-β-carbolin-9-yl)-1-(4-methoxy-phenyl)-ethanol. $^1$H NMR (CDCl$_3$, freebase) δ (ppm): 7.27 (m, 3H), 7.24 (d, 1H), 7.00 (d, 1H), 6.98 (d, 2H), 4.98 (t, 1H), 4.09 (d, 2H), 3.81 (s, 3H), 3.67 (d, 1H), 3.32 (d, 1H), 2.79 (m, 3H), 2.7 (m, 1H), 2.49 (s, 3H), 2.45 (s, 3H). Separation by chiral HPLC provided enantiomers 20a and 20b. Optical rotations: Compound 20a, (−)10.20 (c 0.58, Chloroform, 99.61% HPLC purity); Compound 20b, (+)10.00 (c 0.59, Chloroform, 96.54% HPLC purity).

Example 21

Preparation of Compound Nos. 21, 21a and 21b 2-(8-Methyl-3,4-dihydro-1H-pyrido[4,3-b]indol-5(2H)-yl)-1-(pyridin-3-yl)ethanol (1.6 g) was dissolved in acetone (40 mL) followed by the addition of potassium carbonate (2.16 g) and 2-bromoethanol (1.29 g). The reaction mixture was heated at 80° C. for 2 h. The reaction was monitored by TLC and LCMS. The reaction mixture was cooled to RT and evaporated under reduced pressure. The residue was diluted with water and extracted with DCM, dried over anhydrous sodium sulfate, and evaporated under reduced pressure to obtain crude product. The crude product was purified by reverse phase column chromatography to obtain desired product. $^1$H NMR (CDCl$_3$, freebase) δ (ppm): 8.33 (d, 1H), 8.24 (s, 1H), 7.56 (d, 1H), 7.16 (m, 2H), 7.11 (s, 1H), 6.99 (d, 1H), 4.82 (dd, 1H), 4.03 (dd, 1H), 3.98 (dd, 1H), 3.75 (d, 1H), 3.70 (m, 2H), 3.64 (d, 1H), 2.90 (m, 3H), 2.74 (m, 2H), 2.5 (dd, 1H), 2.44 (s, 3H). Separation by chiral HPLC provided enantiomers 21a and 21b. Optical rotations: Compound 21a, (−)12.41 (c 0.56, Chloroform, 97.75% HPLC purity); Compound 21b, (+)12.71 (c 0.56, Chloroform, 97.37% HPLC purity).

Example 22

Preparation of Compound Nos. 22, 22a and 22b

Sodium hydride (54 mg, 2.2 mmol) was dissolved in N,N-dimethylformamide (7.5 mL) and stirred for 10 min. 2,6-

Dimethyl-2,3,4,9-tetrahydro-1H-pyrido[3,4-b]indole (150 mg, 0.75 mmol) was added to the solution and stirred for 10 min, followed by addition of 2-(oxiran-2-yl)pyridine (133 mg, 1.1 mmol) and stirred overnight at RT. The progress of the reaction was monitored by TLC and LCMS. The reaction mixture was quenched with ice water, extracted with ethyl acetate. The organic layer was washed with brine, dried over anhydrous sodium sulfate and evaporated under reduced pressure. The crude product was purified by reverse phase chromatography to get pure title compound as the TFA salt (27 mg). $^1$H NMR (DMSO) δ (ppm): 10.30-10.10 (m, 1H), 8.70-8.55 (m, 1H), 7.95-7.50 (m, 2H), 7.45-7.05 (m, 2H), 7.00-6.75 (m, 2H), 4.95-4.70 (m, 1H), 4.60-4.40 (m, 2H), 4.20-3.60 (m, 4H), 3.55-3.35 (m, 2H), 3.00 (s, 3H), 2.38 (s, 3H). Separation by chiral HPLC provided enantiomers 22a and 22b. Optical rotations: Compound 22a, (−)58.57 (c 0.57, Chloroform, 98.5% HPLC purity); Compound 22b, (+)31.73 (c 0.52, Chloroform, 96.24% HPLC purity).

Example 23

Preparation of Compound Nos. 23, 23a and 23b

To a stirred solution of 2-(2,3,4,5-tetrahydro-2-methyl-1H-pyrido[4,3-b]indol-8-yl)propan-2-ol (942 mg, 3.86 mmol) in DMF (5 mL) was added sodium hydride (60%, 464 mg, 11.58 mmol). After stirring for 10 min, the reaction mixture was cooled to 0° C. and a solution of 4-(oxiran-2-yl) pyridine (700 mg, 5.8 mmol) in DMF (2 mL) was added. The reaction mixture was allowed to warm to RT and stirring was continued for 16 h. The progress of reaction was monitored by LCMS and NMR. The reaction mixture was quenched with ice water and extracted with EtOAc. The organic layer was washed with water, dried over anhydrous sodium sulfate and concentrated under reduced pressure. The residue obtained was crystallized from ether to yield 2-(2,3,4,5-tetrahydro-5-(2-hydroxy-2-(pyridin-4-yl)ethyl)-2-methyl-1H-pyrido[4,3-b]indol-8-yl)propan-2-ol (500 mg) as yellow solid. $^1$H NMR (CDCl$_3$, freebase) δ (ppm): 8.37 (d, 2H), 7.36 (s, 1H), 7.20 (d, 1H), 7.11 (d, 2H), 7.04 (d, 1H), 4.82 (t, 1H), 4.05 (d, 2H), 3.49 (d, 1H), 3.4 (d, 1H), 2.9 (m, 1H), 2.85 (m, 1H), 2.64 (m, 2H), 2.40 (s, 3H), 1.65 (s, 6H). Separation by chiral HPLC provided enantiomers 23a and 23b. Optical rotations: Compound 23a, (−)52.54 (c 0.55, Chloroform, 95.4% HPLC purity); Compound 23b, (+)29.08 (c 0.56, Chloroform, 98.94% HPLC purity).

Example 24

Preparation of Compound Nos. 24, 24a and 24b

To a solution of carboline (320 mg, 1.49 mmol) in DMF (4 mL) was added sodium hydride (169 mg, 4.23 mmol). After stirring for 5 min, a solution of 3-(2-methyloxiran-2-yl)pyridine (285 mg, 2.11 mmol) in DMF was added to the reaction mixture, which was stirred at RT for 16 h. The reaction mixture was quenched with ice-water and extracted with EtOAc. The organic layer was dried over anhydrous sodium sulfate, concentrated and residue obtained was submitted for reverse phase HPLC purification. $^1$H NMR (CDCl$_3$, freebase) δ (ppm): 8.72 (s, 1H), 8.52 (d, 1H), 7.69 (d, 1H), 7.21 (m, 3H), 6.95 (d, 1H), 4.21 (q, 2H), 4.00 (s, 2H), 3.11 (t, 2H), 2.48 (m, 2H), 2.43 (s, 3H), 1.65 (s, 3H). Separation by chiral HPLC provided enantiomers 24a and 24b. Optical rotations: Compound 24a, (+)25.89 (c 0.58, Chloroform, 96.39% HPLC purity); Compound 24b, (−)26.65 (c 0.56, Chloroform, 93.46% HPLC purity).

Example 25

Preparation of Compound Nos. 25, 25a and 25b

To an ice-cooled stirred solution of the Boc protected ester (75 mg) in DCM (1 mL) was added cold 20% TFA-DCM solution (5 mL). After stirring for 30 min at 0° C., the reaction mixture was stirred at RT for 2 h. The solvent was removed under reduced pressure to yield title compound as the TFA salt. HPLC provided enantiomers 25a and 25b. Compound No. 25a: $^1$H NMR (CD$_3$OD, Di-TFA salt) δ (ppm): 8.74 (t, 2H), 7.84 (t, 2H), 7.29 (s, 1H), 7.03 (t, 1H), 6.4 (m, 1H), 4.66 (m, 3H), 4.32 (d, 1H), 3.98 (m, 2H), 3.5 (m, 1H), 3.2 (m, 1H), 3.11 (s, 3H), 3.06 (m, 1H), 2.4 (s, 3H), 2.38 (m, 1H), 0.95 (d, 3H), 0.91 (d,3H). Compound No. 25b: $^1$H NMR (CD$_3$OD, Di-TFA salt) δ (ppm): 8.806 (d, 2H), 8.05 (t, 2H), 7.63 (t, 1H), 7.03 (d, 1H), 6.35 (s, 1H), 4.66 (m, 3H), 4.32 (m, 1H), 4.12 (dd, 1H), 3.97 (m, 1H), 3.59 (m, 1H), 3.30 (m, 2H), 3.27 (s, 3H), 3.25 (m, 1H) 2.41 (s, 3H), 1.95 (m, 1H), 0.88 (d, 3H), 0.59 (d, 3H).

Example 26

Preparation of Compound Nos. 26, 26a, 26b, 26c and 26d

To a stirred solution of 6-aza-8-methyl tetracyclic carboline (320 mg, 1.4 mmol) in DMF (4 mL) was added sodium hydride (169 mg, 4.2 mmol). After stirring for 5 min, a solution of 3-(2-methyloxiran-2-yl)pyridine (285 mg, 2.14 mmol) in DMF (1 mL) was added and the reaction mixture stirred at RT for 16 h. The progress of reaction was monitored by TLC and LCMS. The reaction mixture was quenched with ice-water and extracted with EtOAc. The organic layer was dried over anhydrous sodium sulfate and concentrated under reduced pressure. The residue was purified by reverse phase HPLC to yield title compound (574 mg). $^1$H NMR (CDCl$_3$, freebase) δ (ppm): 8.64 (s, 1H), 8.42 (d, 1H), 8.03 (s, 1H), 7.7 (d, 1H), 7.53 (s, 1H), 7.14 (dd, 1H), 4.45 (d, 1H), 4.26 (d, 2H), 4.14 (t, 1H), 3.25 (d, 1H), 3.01 (m, 1H), 2.84 (m, 1H), 2.63 (q, 1H), 2.46 (m, 2H), 2.42 (s, 3H), 2.34 (m, 1H), 1.85 (m, 2H), 1.68 (m, 1H), 1.64 (s, 3H). Separation by chiral HPLC provided enantiomers 26a, 26b 26c and 26d.

Example 27

Preparation of Compound Nos. 27, 27a and 27b

To a solution of 5-(2-azido-2-(pyridin-4-yl)ethyl)-2,3,4,5-tetrahydro-2,8-dimethyl-1H-pyrido[4,3-b]indole (2.4 g, 6.93 mmol) in EtOH-water (25-2.5 mL) were added zinc dust (1.8 g, 27.7 mmol) and ammonium chloride (1.5 g, 27.74 mmol) and the reaction mixture stirred at 80° C. for 45 min. The reaction mixture was filtered and the filtrate was concentrated under reduced pressure. The residue was basified with aq. ammonia and extracted with EtOAc. The organic layer was dried over anhydrous sodium sulfate and evaporated to yield 2-(1,2,3,4-tetrahydro-2,8-dimethylpyrido[4,3-b]indol-5-yl)-1-(pyridin-4-yl)ethanamine (1.2 g). $^1$H NMR (CDCl$_3$, freebase) δ (ppm): 8.56 (d, 2H), 7.28 (d, 2H), 7.21 (m, 2H), 7.00 (d, 1H), 4.48 (t, 1H), 4.08 (m, 2H), 3.65 (q, 2H), 2.83 (m, 2H), 2.72 (m, 1H), 2.56 (m, 1H), 2.53 (s, 3H), 2.44 (s, 3H). Separation by chiral HPLC provided enantiomers 27a and 27b.

Example 28

Preparation of Compound Nos. 28, 28a and 28b

To a stirred solution of 6-chloro-2,3,4,9-tetrahydro-2-methyl-1H-pyrido[3,4-b]indole (550 mg, 2.5 mmol) in DMF (5 mL) was added sodium hydride (300 mg, 7.5 mmol). After stirring for 5 min, a solution of 3-(2-methyloxiran-2-yl)pyridine (506 mg, 3.75 mmol) in DMF (1 mL) was added and the reaction mixture stirred at RT for 16 h. The progress of reaction was monitored by TLC and LCMS. The reaction mixture was quenched with ice-water and extracted with EtOAc. The organic layer was dried over anhydrous sodium sulfate and concentrated under reduced pressure. The solid was crystallized from ether to yield the title compound (300 mg). $^1$H NMR (CDCl$_3$, freebase) δ (ppm): 8.68 (s, 1H), 8.49 (d, 1H), 7.54 (d, 1H), 7.32 (s, 1H), 7.0 (t, 1H), 6.94 (s, 1H), 4.10 (d, 1H), 4.04 (d, 1H), 3.59 (d, 1H), 3.34 (d, 1H), 2.65 (m, 4H), 2.42 (s, 3H), 1.63 (s, 3H). Separation by chiral HPLC provided enantiomers 28a and 28b. Optical rotations: Compound 28a, (+)26.78 (c 0.54, Chloroform, 98.11% HPLC purity); Compound 28b, (−)20.39 (c 0.59, Chloroform, 93.42% HPLC purity).

Example 29

Preparation of Compound Nos. 29, 29a and 29b

A mixture of compound 2,3,4,5-tetrahydro-2,8-dimethyl-1H-pyrido[4,3-b]indole (1.5 g, 7.5 mmol, 1 equiv.) and NaH (252 mg, 10.5 mmol, 1.4 equiv.) in DMF (30 mL) were heated to 120° C. for 1 h. The reaction mixture was cooled to RT and 2-methyl-5-(2-methyloxiran-2-yl)pyridine (2.46 g, 16.5 mmol, 2.2 equiv.) in DMF (17 mL) was added dropwise over 12 min. The temperature was again raised to 120° C. and stirred for 3 h. The reaction mixture was cooled to RT and water (5 mL) was added, diluted with EtOAc (700 mL) and the organic layer was washed with water (3×100 mL) and then with brine, dried over anhydrous sodium sulfate and concentrated under vacuum. The compound was purified by column chromatography over 230-400 mesh silica gel using a gradient of 10-20% MeOH in EtOAc. Yield: 2.3 g (87%). $^1$H NMR (DMSO-d6, oxalate salt) δ (ppm): 8.52 (bs, 1H), 7.73-7.71 (d, 1H), 7.31-7.29 (d, 1H), 7.17-7.15 (m, 2H), 6.88-6.86 (d, 1H), 4.34 (bs, 2H), 4.24-4.40 (dd, 2H), 3.47 (bs, 2H), 2.98 (bs, 2H), 2.91 (s, 3H), 2.42 (s, 3H), 2.35 (s, 3H), 1.48 (s, 3H). Separation by chiral HPLC provided enantiomers 29a and 29b.

Example 30

Preparation of Compound Nos. 30, 30a and 30b

Activated magnesium turnings (480 mg, 20 g/atom) and 2-3 crystals of iodine were stirred under anhydrous conditions. The excess of iodine was removed by heating with a heat gun. The magnesium turnings were now yellow in color. To this was added diethyl ether (15 mL) at 0° C. and stirred for 15 min. (until the color of the magnesium becomes white). To this was added cyclopentyl bromide (480 mg, 20 g/atom) dropwise with constant stirring. The reaction mixture was stirred until a dark grey-colored solution was obtained. Into a separate flask was placed the starting material 2-(2,8-dimethyl-3,4-dihydro-1H-pyrido[4,3-b]indol-5(2H)-yl)-1-(4-fluorophenyl)ethanone (168 mg, 5 mmol) in THF under anhydrous conditions. The solution of the prepared cyclopentylmagnesium bromide (5 mL) was added dropwise. After addition, the mixture was allowed to come to RT and stirred at RT for 2 h. The reaction was monitored by TLC and NMR. The reaction was quenched with ice water and the product extracted into EtOAc. The organic extracts were concentrated and the residue purified by silica gel column chromatography (#100-200 mesh) using 0-3% MeOH:DCM as eluent. (Note: The desired compound was not formed but reduction of keto group occurred to yield the hydroxy compound). $^1$H NMR (DMSO-d6, oxalate salt) δ (ppm): 7.55 (m, 3H), 7.18 (m, 3H), 6.95 (d, 1H), 4.85 (s, 1H), 4.30 (m, 2H), 4.15 (m, 2H), 3.60 (m, 2H), 3.10 (m, 3H), 2.90 (s, 3H), 2.40 (s, 3H). Separation by chiral HPLC provided enantiomers 30a and 30b.

Example 31

Preparation of Compound Nos. 31, 31a and 31b

Sodium hydride (1-3 equiv.) was added to a solution of 8-chloro-2,3,4,5-tetrahydro-2-methyl-1H-pyrido[4,3-b]indole (1.0 equiv.) in DMF, and heated to 120° C. for 1 h with stirring. The reaction mixture was cooled to 0° C. and 3-(2-methyloxiran-2-yl)pyridine (2-7.5 equiv.) was added dropwise over 5 min. The temperature was raised to 120° C. and stirred for 2 h. The reaction mixture was cooled to RT and partitioned between EtOAc and water. The organic layer was separated and the aqueous layer was extracted with EtOAc. The combined organic layers were washed with water and followed by brine, dried over anhydrous sodium sulfate and concentrated under vacuum to provide the crude product. The product was purified by flash column chromatography over silica gel (230-400 mesh, deactivated with 1% triethylamine/hexane) using a gradient of 5 to 15% MeOH/EtOAc to yield the free base. The pure compound was converted to its oxalate salt. The analytical sample was prepared by dissolving free base in THF and treatment with 1 equiv. of oxalic acid dihydrate. $^1$H NMR (CD$_3$OD, oxalate salt) δ (ppm): 8.43 (s, 1H), 8.34 (d, 1H), 7.87 (d, 1H), 7.37 (s, 1H), 7.30 (m, 1H), 6.97 (m, 1H), 6.93 (d, 1H), 4.48 (m, 2H), 4.32 (m, 2H), 3.71 (m, 2H), 3.12 (s, 3H), 2.81 (m, 2H), 1.70 (s, 3H). Separation by chiral HPLC provided enantiomers 31a and 31b.

Example 32

Preparation of Compound Nos. 32, 32a and 32b

A flask was charged with 6-chloro-2-methyl-2,3,4,5-tetrahydro-1H-pyrido[4,3-b]indole (1.0 g, 4.5 mmol) in DMF (10 mL) and stirred for 5 min. To this was added NaH (60% in hexane) (220 mg, 6.8 mmol) and stirred at RT for 10 min., followed by 4-(2-methyloxiran-2-yl)pyridine (1.08 g, 9 mmol) and stirred at RT for 16 h. The progress of reaction was monitored by TLC. The mixture was poured into ice water and filtered. The filtrate was washed with water and concentrated. The residue was recrystallized from ether to get pure product. $^1$H NMR (DMSO-d6, HCl salt) δ (ppm): 8.70 (d, 2H), 7.90 (d, 2H), 7.40 (m, 1H), 7.0 (m, 2H), 6.0 (m, 1H), 4.80 (m, 1H), 4.60 (m, 2H), 4.25 (m, 2H), 3.80 (m, 2H), 2.90 (s, 3H), 1.60 (s, 3H). Separation by chiral HPLC provided enantiomers 32a and 32b.

Example 33

Preparation of Compound Nos. 33, 33a and 33b

8-Chloro-2,3,4,5-tetrahydro-2-methyl-1H-pyrido[4,3-b] indole (1.3 g, 5 mmol) was dissolved in DMF (10 mL) and stirred for 5 min. Sodium hydride (709 mg, 17.7 mmol) was then added to it portionwise under nitrogen. This was followed by addition of 2-butyl-2-(4-fluorophenyl)oxirane (3.4 g, 17.7 mmol) at RT and the reaction mixture was stirred for 18 h. After completion of reaction, the reaction mixture was poured into ice water and the product extracted with EtOAc. The organic layer was washed with water, dried over anhydrous sodium sulfate and concentrated under reduced pressure to give the crude product which was purified by silica gel (#100-200 mesh) column chromatography using 1% MeOH in DCM as eluent. The pure compound was converted into the oxalate salt. $^1$HNMR (CDCl$_3$, Oxalate salt) δ (ppm): 7.30 (m, 3H), 7.10 (d, 1H), 6.95 (m, 3H), 4.20 (m, 1H), 4.0 (m, 1H), 3.62 (m, 2H), 2.70 (m, 3H), 2.50 (s, 3H), 2.20 (m, 1H), 2.0 (m, 1H), 1.80 (m, 1H), 1.22 (m, 3H), 1.0 (m, 1H), 0.80 (t, 3H). Separation by chiral HPLC provided enantiomers 33a and 33b.

Example 34

Preparation of Compound Nos. 34, 34a and 34b 2-(2,8-Dimethyl-3,4-dihydro-1H-pyrido[4,3-b]indol-5 (2H)-yl)-1-(4-fluorophenyl)ethanone (168 mg, 5 mmol) was dissolved in 10 mL anhydrous THF. Ethyl magnesium bromide (1.5 mL, 0.0015 mol) was then added dropwise at RT under nitrogen. The reaction mixture was stirred at RT for 2 h. The reaction was monitored by LCMS. On completion of the reaction, water (3 mL) was added to the reaction mixture and the product extracted with EtOAc (3×). The combined organic layers were washed with water, dried over anhydrous sodium sulfate, and the solvent evaporated under reduced pressure to obtain the crude product, which was purified by HPLC. The pure compound was isolated as the TFA salt. $^1$HNMR (CD$_3$OD, TFA salt) δ (ppm): 7.38 (m, 2H), 7.18 (d, 1H), 7.10 (m, 1H), 7.0 (m, 2H), 6.85 (d, 1H), 4.60 (m, 1H), 4.30 (m, 2H), 3.75 (m, 1H), 3.42 (m, 1H), 3.10 (s, 3H), 2.90 (m, 2H), 2.42 (d, 1H), 2.38 (s, 3H), 2.20 (m, 1H), 1.80 (m, 2H), 0.8 (t, 3H). Separation by chiral HPLC provided enantiomers 34a and 34b.

Example 35

Preparation of Compound Nos. 35, 35a and 35b

A flask was charged with sodium hydride (0.640 g, 50-60%) in dry DMF (10 mL) at 0° C. and to this was added 2,8-dimethyl-2,3,4,4a,5,9b-hexahydro-1H-pyrido[4,3-b]indole (0.8 g). The mixture was stirred at RT for 30 min and then 4-(2-ethyloxiran-2-yl)pyridine (0.834 g) dissolved in DMF (2 mL) was added, which was stirred at RT for 12 h. The reaction mixture was diluted with ice-water and extracted with EtOAc (3×30 mL). The combined organic layers were washed with brine, dried over anhydrous sodium sulfate and evaporated. The crude product was triturated with diethyl ether to obtain the desired compound. $^1$HNMR (DMSO, Oxalate salt) δ (ppm): 8.45 (d, 2H), 7.42 (d, 2H), 7.30 (d, 1H), 7.10 (s, 1H), 6.82 (d, 1H), 4.30 (d, 1H), 4.18 (d, 1H), 3.60 (s, 2H), 3.50 (m, 2H), 3.38 (m, 1H), 3.0 (m, 2H), 2.90 (s, 3H), 3.32 (s, 3H), 2.10 (m, 1H), 0.6 (t, 3H). Separation by chiral HPLC provided enantiomers 35a and 35b.

Example 36

Preparation of Compound Nos. 36, 36a-36d

To a solution of 1-ethyl-7-methyl-3,4,5,10-tetrahydro-1H-2,5-methanoazepino[3,4-b]indole (1000 mg, 4.17 mmol) in DMF (10 mL) was added sodium hydride (500 mg, 12.498 mmol) portionwise. After stirring at RT for 5 min, 4-(oxiran-2-yl)pyridine (630 mg, 5.00 mmol) was added dropwise into the reaction mixture, which was stirred at RT overnight. The reaction mixture was quenched with ice-water and the solid mass was filtered. The residue was washed with water (2×10 mL), hexane (2×50 mL) and purified by reverse phase HPLC to yield the title compound. Separation by chiral HPLC provided enantiomers 36a and 36b.

Example 37

Preparation of Compound Nos. 37, 37a, 37c and 37d

To a solution of 2,3,4,9,10,10a-hexahydro-1H-3a,8,9-triaza-cyclopenta[b]fluorene (1 g, 0.0046 mol) in DMF (20 mL) was added NaH (60%, 0.552 g, 0.0138 mol) portionwise followed by 4-(oxiran-2-yl)pyridine (0.709 g, 0.0056 mol). The reaction mixture was stirred at RT overnight. The progress of reaction mixture was monitored by LCMS. The reaction mixture was quenched with ice cold water (300 mL) and extracted with EtOAc (3×100 mL). The combined organic layer was washed with water (10×100 mL) followed by brine (2×100 mL), dried over anhydrous sodium sulfate and concentrated. The residue was purified by silica gel column chromatography followed by reverse phase HPLC to obtain the desired compound. $^1$H NMR (CDCl$_3$, freebase) δ (ppm): 8.56 (d, 2H), 8.21 (d, 1H), 7.74 (d, 1H), 7.32 (d, 2H), 7.06 (dd, 1H), 5.16 (dd, 1H), 4.44 (dd, 1H), 4.31 (dd, 1H), 4.2 (d, 1H), 3.32 (m, 2H), 2.85 (d, 1H), 2.5 (m, 1H), 2.39 (q, 2H), 2.11 (m, 1H), 1.93 (m, 2H). Separation by chiral HPLC provided enantiomers 37a, 37b, 37c and 37d.

Example 38

Preparation of Compound Nos. 38, 38a-38h

To a solution of 1,7-dimethyl-3,4,5,10-tetrahydro-1H-2,5-methanoazepino[3,4-b]indole (1 g, 4.42 mmol) in DMF (10 mL) was added sodium hydride (530 mg, 13.24 mmol) portionwise under nitrogen. After stirring for 10 min at 0° C., 4-oxiranyl-pyridine (1.07 g, 8.84 mmol) was added dropwise at 0° C. into the reaction mixture and stirring continued for 12 h at RT. After completion, the reaction mixture was poured into ice water and extracted with EtOAc (2×100 mL). The combined organic layers were washed with water (5×50 mL), dried over anhydrous sodium sulfate and concentrated to obtain 1.2 g of product. $^1$H NMR (CD$_3$OD, Formate salt) δ (ppm): 8.42 (d, 2H), 7.8 (d, 2H), 7.22 (s, 1H), 6.78 (t, 2H), 5.67 (q, 1H), 5.4 (m, 1H), 4.77 (dd, 1H), 4.4 (dd, 1H), 3.82 (d, 1H), 3.7-3.8 (m, 3H), 3.6 (d, 1H), 2.4 (m, 1H), 2.3 (s, 3H), 2.18 (m, 1H), 1.97 (d, 3H). Separation by chiral HPLC provided enantiomers 38a and 38b.

Example 39

Preparation of Compound Nos. 39, 39a and 39b 2-(2-Allyl-8-methyl-1,2,3,4-tetrahydro-pyrido[4,3-b]indol-5-yl)-1-pyridin-4-yl-ethanol (740 mg, 2.132 mmol) was dissolved in 40 mL DCM, and purged with nitrogen for 5 min. Pd(PPh$_3$)$_4$ (50 mg, 0.0432 mmol) and 1,3-dimethylbarbituric acid (998 mg, 6.397 mmol) were added and the reaction mixture was stirred at RT for 30 min. The reaction mixture was diluted with saturated aqueous potassium carbonate (20 mL) solution and extracted with DCM (2×20 mL). The combined organic layer was dried over anhydrous sodium sulfate and concentrated. The residue was purified by column chromatography over neutral alumina (eluent 50% MeOH in DCM) to obtain 400 mg of 2-(8-methyl-1,2,3,4-tetrahydro-pyrido[4,3-b]indol-5-yl)-1-pyridin-4-yl-ethanol. $^1$H NMR (CD$_3$OD, freebase) δ (ppm): 8.71 (d, 2H), 8.04 (d, 2H), 7.22 (s, 1H), 7.13 (d, 1H), 6.94 (d, 1H), 5.33 (t, 1H), 4.42 (m, 4H), 3.63 (t, 2H), 3.28 d (t, 1H), 3.22 (m 1H), 2.38 (s, 3H). This racemate was separated by chiral semi-preparative HPLC to obtain enantiomers 39a and 39b.

Example 40

Preparation of Compound Nos. 40, 40a and 40b

To a solution of 2-methyl-7-(trifluoromethyl)-2,3,4,5-tetrahydro-1H-pyrido[4,3-b]indole (500 mg, 1.96 mmol) in DMF (5 mL) was added sodium hydride (60%, 236 mg, 5.9 mmol) at RT under $N_2$. After stirring for 10 min, a solution of 3-(oxiran-2-yl)pyridine (356 mg, 2.9 mmol) in DMF (1 mL) was added into the reaction mixture, which was stirred at RT for 16 h. The progress of reaction was monitored by TLC, LCMS and NMR. After completion, the reaction mixture was quenched with ice water and extracted with EtOAc. The organic layer was washed with water, dried over anhydrous sodium sulfate and concentrated under reduced pressure. The residue was purified by reverse phase HPLC to obtain the desired compounds 40a and 40b.

Example 41

Preparation of Compound Nos. 41, 41a and 41b

To a solution of 6-chloro-2-methyl-2,3,4,9-tetrahydro-1H-pyrido[3,4-b]indole (1.0 g, 4.55 mmol) in DMF (20 mL), sodium hydride (546 mg, 13.65 mmol) was added and the suspension stirred at RT for 10 min. A solution of 4-(oxiran-2-yl)pyridine (1.10 g, 9.1 mmol) in DMF (5 mL) was added slowly into the reaction mixture, which was stirred at RT overnight. The progress of reaction was monitored by TLC and LCMS. The reaction mass was poured into ice cold water (200 mL) slowly and extracted with EtOAc (3×200 mL). The organic layer was washed with water (4×300 mL), dried over anhydrous sodium sulfate and concentrated. The residue was purified by silica gel column chromatography using 7% MeOH-DCM as eluent. The residue obtain was triturated with diethyl ether (20 mL) to yield the desired product. $^1$H NMR (CDCl$_3$, freebase) δ (ppm): 8.42-8.58 (d, 2H), 7.4 (s, 1H), 7.26 (d, 2H), 7.15 (d, 1H), 7.11 (d, 1H), 4.9 (dd, 1H), 4.08 (dd, 1H), 4.04 (dd, 1H), 3.73 (d, 1H), 3.48 (s, 1H), 3.3 (d, 1H), 2.69 (m, 1H), 2.68 (m, 3H), 2.45 (s, 3H). Separation by chiral HPLC provided enantiomers 41a and 41b.

Example 42

Preparation of Compound Nos. 42, 42a and 42b 1-(2-Allyl-8-chloro-1,2,3,4-tetrahydro-pyrido[4,3-b]indol-5-yl)-2-pyrimidin-4-yl-propan-2-ol (300 mg, 0.785 mmol) was dissolved in DCM (6 mL) and $N_2$ was purged for 5 min into the reaction mixture. 1,3-Dimethylbarbituricacid (367 mg, 2.356 mmol) and Pd(PPh$_3$)$_4$ (18 mg, 0.0157 mmol) was added and the mixture stirred for 1 h at RT. After consumption of starting material, the reaction mixture was diluted with saturated potassium carbonate (50 mL) and extracted with DCM (2×40 mL). The combined organic layer was dried over anhydrous sodium sulfate and concentrated, crude was purified by reverse phase chromatography to obtain 97 mg of 1-(8-chloro-1,2,3,4-tetrahydro-pyrido[4,3-b]indol-5-yl)-2-pyrimidin-4-yl-propan-2-ol. $^1$H NMR (CDCl$_3$, freebase) δ (ppm): 9.13 (s, 1H), 8.45 (d, 1H), 7.31 (d, 1H), 7.25 (s, 1H), 6.94 (s, 2H), 4.3 (q, 2H), 3.93 (q, 2H), 3.13 (m, 2H), 2.78 (d, 1H), 2.57 (d, 1H), 1.6 (s, 3H). Separation by chiral HPLC provided enantiomers 42a and 42b.

Example 43

Preparation of Compound Nos. 43, 43a and 43b

To a solution of 2,8-dimethyl-2,3,4,5-tetrahydro-1H-pyrido[4,3-b]indole (1 g, 5 mmol) in 10 mL DMF, was added sodium hydride (600 mg, 15 mmol) portionwise under nitrogen at 0° C. and stirred for 10 min. 3-Oxiranyl-pyridine (908 mg, 15.0 mmol) was added dropwise under nitrogen and the reaction mixture stirred at RT for 12 h. After the complete conversion of starting material (TLC and LCMS), the reaction mixture was poured in ice-cold water and extracted with EtOAc (2×100 mL). The combined organic layer was washed with water (5×50 mL), dried over anhydrous sodium sulfate, and concentrated. The crude mixture was purified by reverse phase chromatography to obtain 290 mg of 2-(2,6-dimethyl-1,2,3,4-tetrahydro-β-carbolin-9-yl)-1-pyridin-3-yl-ethanol. $^1$H NMR (CDCl$_3$, freebase) δ (ppm): 8.62 (s, 1H), 8.57 (d, 1H), 7.67 (d, 1H), 7.3 (m, 2H), 7.19 (d, 1H), 7.01 (d, 1H), 5.09 (t, 1H), 4.13 (m, 2H), 3.70 (d, 1H), 3.36 (d, 1H), 2.79 (m, 3H), 2.703 (m, 1H), 2.5 (s, 3H), 2.45 (s, 3H). Separation by chiral HPLC provided enantiomers 43a and 43b.

Example 44

Preparation of Compound Nos. 44, 44a and 44b

Sodium hydride (60%) (555 mg, 13.88 mmol) was added portionwise to a solution of 6-methoxy-2-methyl-2,3,4,5-tetrahydro-1H-pyrido[4,3-b]indole (1.0 g, 4.629 mmol) in DMF (10 mL) and stirred at RT for 15 min, the suspension was allowed to cool at 0° C. 4-(Oxiran-2-yl)pyridine (896 mg, 7.407 mmol) was added dropwise and reaction mixture was stirred at RT for 48 h. The reaction mixture was poured in to ice-cooled water and extracted with EtOAc (3×50 mL), and the organic layer was washed with water (2×50 mL), dried over anhydrous sodium sulfate and concentrated in vacuo, afforded crude was purified by reverse phase HPLC to afford 2-(6-methoxy-2-methyl-3,4-dihydro-1H-pyrido[4,3-b]indol-5(2H)-yl)-1-(pyridin-4-yl)ethanol (165 mg) as the formate salt. $^1$H NMR (CDCl$_3$, freebase) δ (ppm): 8.60 (d, 2H), 7.31 (d, 2H), 7.02 (m, 2H), 6.66 (d, 1H), 5.08 (dd, 1H), 4.66 (dd, 1H), 4.12 (dd, 1H), 3.99 (s, 3H), 3.60 (d, 1H), 3.56 (d, 1H), 2.9 (m, 1H), 2.81 (m, 1H), 2.72 (m, 1H), 2.64 (m, 1H), 2.55 (s, 3H). Separation by chiral HPLC provided enantiomers 44a and 44b.

Example 45

Preparation of Compound Nos. 45, 45a and 45b

To a stirred solution of 6-chloro-2,3,4,5-tetrahydro-2-methyl-1H-pyrido[4,3-b]indole (1 g, 4.54 mmol) in DMF (8 mL) was added sodium hydride (60%, 545 mg, 13.6 mmol). After stirring for 10 min, a solution of 4-(oxiran-2-yl)pyridine (825 mg, 6.8 mmol) in DMF (2 mL) was added into the reaction mixture, which was stirred at RT for 16 h. The reaction mixture was poured into ice-cold water and extracted with EtOAc. The organic layer was washed with water, dried over anhydrous sodium sulfate and concentrated under reduced pressure. $^1$H NMR (CDCl$_3$, freebase) δ (ppm): 8.54 (d, 2H), 7.31 (d, 2H), 7.19 (d, 1H), 7.11 (d, 1H), 7.01 (t, 1H), 5.04 (dd, 1H), 4.81 (dd, 1H), 3.99 (dd, 1H), 3.27 (dd, 2H), 3.11 (m, 1H), 2.84 (m, 1H), 2.51 (m, 2H), 2.32 (s, 3H). Separation by chiral HPLC provided enantiomers 45a and 45b.

Example 46

Preparation of Compound Nos. 47, 47a, 47b, 47c and 47d

To a solution of 11-methyl-1,2,3,4,6,7,8,12c-octahydro-indolo[3,2-a]quinolizine (800 mg, 3.33 mmol) in 12 mL DMF was added sodium hydride (400 mg, 13.2 mmol) under nitrogen at RT and stirred for 20 min. 4-Oxiranyl-pyridine (685 mg, 5.66 mmol) was added dropwise under nitrogen and the reaction mixture stirred at RT for 18 h. After complete conversion of starting material (TLC and LCMS), the reaction mixture was poured in ice-cold water and extracted with EtOAc (3×80 mL). The combined organic layer was washed with water (5×50 mL), dried over anhydrous sodium sulfate, concentrated and the crude product was recrystallized in EtOH (1 mL) and ether (50 mL) to obtain 700 mg of desired product. $^1$H NMR (CDCl$_3$, freebase) δ (ppm): 8.53 (d, 2H), 7.36 (s, 1H), 7.21 (d, 2H), 7.12 (d, 1H), 6.94 (d, 1H), 4.99 (t, 1H), 4.1 (m, 2H), 3.35 (d, 1H), 3.13 (t, 1H), 3.0 (m, 2H), 2.63 (d, 1H), 2.56 (m, 1H), 2.46 (s, 3H), 2.4 (d, 1H), 1.8 (d, 1H), 1.7 (m, 1H), 1.5 (m, 2H). Separation by chiral HPLC provided enantiomers 47a 47b, 47c and 47d.

Example 47

Preparation of Compound Nos. 48, 48a and 48b

To a stirred solution of 6-bromo-2,3,4,5-tetrahydro-2-methyl-1H-pyrido[4,3-b]indole (1 g, 3.77 mmol) in DMF (8 mL) was added sodium hydride (60%, 452 mg, 11.32 mmol). After stirring for 10 min, a solution of 4-(oxiran-2-yl)pyridine (684 mg, 5.66 mmol) in DMF (2 mL) was added into the reaction mixture, which was stirred at RT for 16 h. The reaction mixture was poured into ice-cold water and extracted with EtOAc. The organic layer was washed with water, dried over anhydrous sodium sulfate and concentrated under reduced pressure. The residue was dissolved in DCM and pure product precipitated out as a white solid. $^1$H NMR (CDCl$_3$, freebase) δ (ppm): 8.57 (d, 2H), 7.36 (d, 2H), 7.33 (d, 1H), 7.27 (d, 1H), 6.95 (t, 1H), 5.17 (dd, 1H), 4.96 (dd, 1H), 4.04 (dd, 1H), 3.34 (dd, 2H), 3.1 (m, 1H), 2.85 (m, 1H), 2.55 (m, 2H), 2.38 (s, 3H). Separation by chiral HPLC provided enantiomers 48a and 48b.

Example 48

Preparation of Compound Nos. 49, 49a and 49b

To a stirred solution of 1-(2,3,4,5-tetrahydro-2-methyl-1H-pyrido[4,3-b]indol-8-yl)ethanone (80 mg, 0.35 mmol) in DMF (2 mL) was added sodium hydride (60%, 42 mg, 1.05 mmol). After stirring for 10 min, a solution of 4-(oxiran-2-yl)pyridine (62 mg, 0.51 mmol) in DMF (1 mL) was added into the reaction mixture, and stirred at RT for 4 h. The reaction mixture was quenched with ice water and extracted with EtOAc. The organic layer was washed with water, dried over anhydrous sodium sulfate and concentrated under reduced pressure. The residue obtain was purified by crystallization with ether to yield 1-(2,3,4,5-tetrahydro-5-(2-hydroxy-2-(pyridin-4-yl)ethyl)-2-methyl-1H-pyrido[4,3-b]indol-8-yl)ethanone (6 mg). $^1$H NMR (CDCl$_3$, freebase) δ (ppm): 8.5 (d, 2H), 7.95 (s, 1H), 7.73 (d, 1H), 7.26 (d, 2H), 7.12 (d, 1H), 4.78 (t, 1H), 4.8 (d, 2H), 3.49 (m, 2H), 2.90 (m, 1H), 2.8 (q, 2H), 2.79 (s, 3H), 2.6 (m, 1H), 2.37 (s, 3H). Separation by chiral HPLC provided enantiomers 49a and 49b.

Example 49

Preparation of Compound Nos. 51, 51a and 51b 2,8-Dimethyl-2,3,4,5-tetrahydro-1H-pyrido[4,3-b]indole (1.0 g, 5.0 mmol) was dissolved in DMF (8 mL). Sodium hydride (600 mg, 15 mmol) was added portionwise under nitrogen at 0° C.

2-Methoxy-5-oxiranyl-pyridine (1.130 g, 7.5 mmol) was diluted in DMF (2 mL) was added dropwise under nitrogen atmosphere and the reaction mixture stirred at RT for 3 h. By monitoring TLC & NMR after consumption of starting material, the reaction mixture was then quenched with ice water and extracted with EtOAc (3×40 mL). The combined organic layer was washed with water (4×30 mL) and dried over anhydrous sodium sulfate and concentrated to obtain 1.0 g of 2-(2,8-dimethyl-1,2,3,4-tetrahydro-pyrido[4,3-b]indol-5-yl)-1-(6-methoxy-pyridin-3-yl)-ethanol. $^1$H NMR (CDCl$_3$, freebase) δ (ppm): 8.11 (s, 1H), 7.55 (d, 1H), 7.18 (s, 1H), 7.16 (d, 1H), 6.98 (d, 1H), 6.72 (d, 1H), 4.98 (t, 1H), 4.11 (m, 2H), 3.93 (s, 3H), 3.60 (q, 2H), 2.88 (d, 1H), 2.78 (m, 2H), 2.69 (d, 1H), 2.51 (s, 3H), 2.44 (s, 3H). Separation by chiral HPLC provided enantiomers 51a and 51b.

Example 50

Preparation of Compound Nos. 52, 52a and 52b

To a stirred solution of 2,3,4,5-tetrahydro-2,8-dimethyl-1H-pyrido[4,3-b]indole (250 mg, 1.25 mmol) in DMF (5 mL) was added sodium hydride (60%, 150 mg, 3.75 mmol). After stirring for 10 min, a solution of ethyl 4-(oxiran-2-yl)benzoate (480 mg, 2.5 mmol) in DMF (1 mL) was added to the reaction mixture, which was stirred at RT for 16 h. The reaction mixture was quenched with ice water and extracted with EtOAc. The organic layer was dried over anhydrous sodium sulfate, evaporated and residue was purified by reverse phase HPLC. $^1$H NMR (CDCl$_3$, freebase) δ (ppm): 7.28 (m, 4H), 7.12 (s, 1H), 7.04 (d, 1H), 6.88 (d, 1H), 4.91 (t, 1H), 4.09 (d, 2H), 3.58 (q, 2H), 3.1 (s, 3H), 2.92 (s, 3H), 2.87 (m, 1H), 2.80 (m, 2H), 2.68 (d, 1H), 2.47 (s, 3H), 2.41 (s, 3H). Separation by chiral HPLC provided enantiomers 52a and 52b.

Example 51

Preparation of Compound Nos. 53, 53a and 53b

To a stirred solution of 7-chloro-2-methyl-2,3,4,5-tetrahydro-1H-pyrido[4,3-b]indole (0.5 g, 2.265 mmol) in anhydrous DMF was added sodium hydride (271 mg, 3 eq.) portionwise followed by 4-(oxiran-2-yl)pyridine (548 mg, 4.5 mmol) at RT. The reaction mixture was stirred for 12 h. The reaction mixture was quenched with ice water and extracted with EtOAc, the organic layer washed with water, dried on anhydrous sodium sulfate, concentrated under vacuum to obtain crude product that was triturated with diethyl ether to obtain 2-(7-chloro-2-methyl-3,4-dihydro-1H-pyrido[4,3-b]indol-5(2H)-yl)-1-(pyridin-4-yl)ethanol as solid. $^1$H NMR (CDCl$_3$, freebase) δ (ppm): 8.53 (d, 2H), 7.2 (m, 3H), 7.14 (d, 1H), 7.05 (d, 1H), 4.82 (t, 1H), 4.03 (d, 2H), 3.4 (q, 2H), 2.85

(m, 1H), 2.76 (m, 1H), 2.64 (m, 2H), 2.37 (s, 3H). Separation by chiral HPLC provided enantiomers 53a and 53b.

Example 52

Preparation of Compound Nos. 54, 54a and 54b

To a solution of 2-(1,2,3,4-tetrahydro-2,8-dimethylpyrido[4,3-b]indol-5-yl)-1-(pyridin-4-yl)ethanol (500 mg, 1.55 mmol) and isobutyric acid (274 mg, 3.1 mmol) in DCM (100 mL) were added EDC.HCl (657 mg, 3.4 mmol), DMAP (19 mg, 0.16 mmol) and TEA (346 mg, 3.4 mmol). The reaction mixture was stirred at RT for 16 h and washed with water. The organic layer was dried over anhydrous sodium sulfate and concentrated under reduced pressure. The residue was purified by silica gel column chromatography (4% MeOH-DCM) followed by reverse phase purification to yield 2-(1,2,3,4-tetrahydro-2,8-dimethylpyrido[4,3-b]indol-5-yl)-1-(pyridin-4-yl)ethyl isobutyrate (310 mg). $^1$H NMR (CDCl$_3$, freebase) δ (ppm): 8.53 (d, 2H), 7.2 (d, 1H), 7.18 (s, 1H), 7.04 (d, 2H), 6.97 (d, 1H), 5.98 (t, 1H), 4.4 (dd, 1H), 4.14 (dd, 1H), 3.64 (q, 2H), 2.73 (m, 2H), 2.6 (m, 1H), 2.49 (s, 3H), 2.43 (s, 3H), 2.37 (m, 1H), 1.15 (d, 3H), 1.09 (d, 3H). Separation by chiral HPLC provided enantiomers 54a and 54b.

Example 53

Preparation of Compound Nos. 55, 55a and 55b 3,6-Dimethyl-6,7,8,9-tetrahydro-5H-1,6,9-triaza-fluorene (250 mg, 1.243 mmol) was dissolved in DMF (3 mL) and cooled to 0° C. Sodium hydride (149 mg, 3.729 mmol) was added portionwise and the mixture stirred at the same temperature for 10 min. 4-Oxiranyl-pyridine (240 mg, 1.990 mmol) was diluted in DMF (1 mL) and added dropwise in the reaction mixture at 0° C. The reaction mixture was stirred at RT for 12 h. The desired product was detected by LCMS. The reaction mixture was poured in ice cold water and extracted with EtOAc (3×25 mL). The combined organic layer was washed with water (5×30 mL), dried over anhydrous sodium sulfate and concentrated under reduced pressure. The crude product was purified by reverse phase chromatography to obtain 18 mg of 2-(3,6-dimethyl-5,6,7,8-tetrahydro-1,6,9-triaza-fluoren-9-yl)-1-pyridin-4-yl-ethanol. $^1$H NMR (CDCl$_3$, freebase) δ (ppm): 8.48 (d, 2H), 7.95 (s, 1H), 7.43 (s, 1H), 7.18 (d, 2H) 5.06 (d, 1H), 4.37 (d, 1H), 4.24 (dd, 1H), 3.45 (q, 2H), 2.29 (t, 2H), 2.55 (t, 2H), 2.45 (s, 3H), 2.38 (s, 3H). Separation by chiral HPLC provided enantiomers 55a and 55b.

Example 54

Preparation of Compound Nos. 56, 56a and 56b

To a solution of 2-(1,2,3,4-tetrahydro-2,8-dimethylpyrido[4,3-b]indol-5-yl)-1-(pyridin-4-yl)ethanol (900 mg, 4.5 mmol) in DMF (4 mL) was added sodium hydride (540 mg, 13.5 mmol). After stirring for 10 min at RT, a solution of 3-(2-methyloxiran-2-yl)pyridine-N-oxide (1 g, 6.75 mmol) was added to the reaction mixture, and stirred at RT for 16 h. The reaction mixture was cooled to 0° C., quenched with ice water and extracted with EtOAc. The organic layer was washed with water, dried over anhydrous sodium sulfate and evaporated. The residue was triturated with ether to yield the title compound as yellow solid (220 mg). $^1$H NMR (CD$_3$OD, freebase) δ (ppm): 8.27 (s, 1H), 8.12 (d, 1H), 7.58 (d, 1H), 7.32 (t, 1H), 7.07 (s, 1H), 6.94 (d, 1H), 6.79 (d, 1H) 4.14 (q, 2H), 3.63 (s, 2H), 2.88 (m, 1H), 2.82 (s, 2H), 2.79 (m, 1H), 2.51 (s, 3H), 2.331(s, 3H), 1.62 (s, 3H). Separation by chiral HPLC provided enantiomers 56a and 56b.

Example 55

Preparation of Compound Nos. 57, 57a and 57b

6-Chloro-2-methyl-2,3,4,5-tetrahydro-1H-pyrido[4,3-b]indole (1 g, 4.5 mmol) was dissolved in 15 mL DMF and stirred for 5 min at RT. Sodium hydride (540 mg, 13.5 mmol) was added portionwise at RT under nitrogen. 3-(2-Methyloxiranyl)-pyridine (800 mg, 5.9 mmol) was diluted in 5 mL DMF and added dropwise at the same temperature and stirred for 16 h at RT. The reaction was monitored by TLC & LCMS. After consumption of starting material, the reaction mixture was quenched with ice water (30 mL) and filtered. The residue was crystallized in EtOH (1 mL) and ether (40 mL) and purified by reverse phase chromatography to obtain 620 mg of 1-(6-chloro-2-methyl-1,2,3,4-tetrahydro-pyrido[4,3-b]indol-5-yl)-2-pyridin-3-yl-propan-2-ol. $^1$H NMR (CDCl$_3$, freebase) δ (ppm): 8.77 (s, 1H), 8.5 (d, 1H), 8.45 (s, 1H), 7.71 b(s, 1H), 7.17 b(s, 1H), 7.06 (d, 1H), 6.97 (t, 1H), 5.12 b(s, 1H), 4.3 b (s, 1H), 3.78 (m, 1H), 3.62 (m, 1H), 3.14 (m, 1H), 2.63 (m, 2H), 2.57 (s, 3H), 2.5 b(s, 2H), 1.53 (s, 3H). Separation by chiral HPLC provided enantiomers 57a and 57b.

Example 56

Preparation of Compound Nos. 58, 58a and 58b

To a degassed solution of 2-(6-allyl-3-methyl-5,6,7,8-tetrahydro-1,6,9-triaza-fluoren-9-yl)-1-pyridin-4-yl-ethanol (300 mg, 0.862 mmol) and 1,3 dimethyl barbituric acid (403 mg, 2.586 mmol) in DCM (7 mL) was added and Pd(PPh$_3$)$_4$ (20 mg, 0.0172 mmol) and the reaction mixture stirred at RT for 1 h. The progress of reaction was monitored by TLC and LCMS. The reaction mixture was diluted with 20% aq potassium carbonate solution and extracted with DCM (3×25 mL). The combined organic layer was washed with 20% aq potassium carbonate solution, dried over anhydrous sodium sulfate and concentrated to yield 2-(3-methyl-5,6,7,8-tetrahydro-1,6,9-triaza-fluoren-9-yl)-1-pyridin-4-yl-ethanol. $^1$H NMR (CDCl$_3$, freebase) δ (ppm):8.5 (d, 2H), 8.03 (s, 1H), 7.51(s, 1H), 7.22 (d, 2H) 5.14 (d, 1H), 4.4 (dd, 1H), 4.27 (dd, 1H), 3.93 (q, 2H), 3.13 (m, 2H), 2.54 (dd, 1H), 2.42 (s, 3H), 2.3 (dd, 1H). Separation by chiral HPLC provided enantiomers 58a and 58b.

Example 57

Preparation of Compound Nos. 59, 59a and 59b

To a solution of 2-methyl-8-(trifluoromethyl)-2,3,4,5-tetrahydro-1H-pyrido[4,3-b]indole (200 mg, 0.78 mmol) in DMF (3 mL) was added sodium hydride (60%, 94 mg, 2.3 mmol) at RT under N$_2$. After stirring for 10 min, a solution of 3-(oxiran-2-yl)pyridine (142 mg, 1.17 mmol) in DMF (1 mL) was added into the reaction mixture, which was stirred at RT for 16 h. The progress of reaction was monitored by TLC, LCMS and NMR. After completion, the reaction mixture was quenched with ice water and extracted with EtOAc. The organic layer was washed with water, dried over anhydrous sodium sulfate and concentrated under reduced pressure. The residue was purified by reverse phase HPLC to obtain the desired compounds. 59a: $^1$H NMR (CDCl$_3$, freebase) δ (ppm): 8.51 (s, 1H), 8.35 (d, 1H), 7.51 (s, 1H), 7.42 (d, 1H), 7.32 (d, 1H), 7.21 (d, 1H), 7.07 (t, 1H), 4.94 (t, 1H), 4.20 (dd, 1H), 4.09 (dd, 1H), 3.49 (q, 2H), 2.9 (d, 1H), 2.76 (m, 3H), 2.41 (s, 3H). 59b: $^1$H NMR (CDCl$_3$, freebase) δ (ppm): 8.51 (s, 1H), 8.35 (d, 1H), 7.51 (s, 1H), 7.42 (d, 1H), 7.32 (d, 1H), 7.21 (d, 1H), 7.07 (t, 1H), 4.94 (t, 1H), 4.20 (dd, 1H), 4.09 (dd, 1H), 3.49 (q, 2H), 2.9 (d, 1H), 2.76 (m, 3H), 2.41 (s, 3H). Separation by chiral HPLC provided enantiomers 59a and 59b. Optical rotations: Compound 59a, (−)16.42 (c 0.54, Chloroform, 99.96% HPLC purity); Compound 59b, (+)11.20 (c 0.54, Chloroform, 99.01% HPLC purity).

Example 58

Preparation of Compound No. 60

To a solution of 8-chloro-2-methyl-2,3,4,5-tetrahydro-1H-pyrido[4,3-b]indole (0.2 g, 0.9 mmol) in N-methyl-2-pyrolidone (1.5 mL) was added powdered potassium hydroxide (0.507 g, 9.0 mmol). The reaction mixture was stirred for 10 min at RT. 3-Vinyl pyridine (0.3 g, 2.8 mmol) was added and the reaction mixture was stirred at 100° C. for 18 h. After consumption of starting material (TLC), the reaction mixture was diluted with water (15 mL) and extracted with EtOAc (3×100 mL). The organic layer was dried over anhydrous sodium sulfate and concentrated under reduced pressure. The crude product was purified by column chromatography over silica gel (eluent 8% MeOH: DCM) followed by preparative TLC to obtain the desired compound as a yellow oil (0.032 g, 11% yield). $^1$H NMR (DMSO, Oxalate salt) δ (ppm): 8.4 (d, 1H), 8.3 (s, 1H), 7.57 (d, 2H), 7.49 (d, 1H), 7.26 (m, 1H), 7.10 (d, 1H), 4.45 (m, 4H), 3.5 (bs, 2H), 3.0 (t, 2H), 2.95 (m, 2H), 2.90 (s, 3H).

Example 59

Preparation of Compound No. 61

To a solution of 2,8-dimethyl-2,3,4,5-tetrahydro-1H-pyrido[4,3-b]indole (0.1 g, 0.49 mmol) in N-methyl-2-pyrrolidone (0.5 mL) was added powdered potassium hydroxide (0.274 g, 4.9 mmol) and the reaction mixture was stirred for 10 min at RT. 3-Vinyl pyridine (0.26 g, 2.49 mmol) was added and stirring was continued for further 18 h at 100° C. After consumption of starting material (TLC), the reaction mixture was diluted with water (15 mL) and extracted with EtOAc (3×50 mL). The organic layer was dried over anhydrous sodium sulfate and concentrated under reduced pressure. The crude product was purified by silica gel chromatography (eluent 7% MeOH: DCM) followed by preparative TLC, to obtain desired compound as yellow oil (0.040 g, 26% yield).

$^1$H NMR (DMSO, Oxalate salt) δ (ppm): 8.4 (s, 1H), 8.3 (s, 1H), 7.55 (s, 2H), 7.35 (d, 1H), 7.25 (bs, 1H), 7.2 (s, 1H), 4.35 (bs, 4H), 3.5 (bs, 2H), 3.0 (m, 2H), 2.9 (m, 5H), 2.45 (s, 3H).

Example 60

Preparation of Compound Nos. 62, 62a and 62b

Carboline (500 mg, 2.5 mmol) was dissolved in DMF (5 mL). To this solution was added NaH (60%, 180 mg, 4.5 mmol) at RT and the reaction mixture was stirred for 10-15 min. after which 3-(oxiran-2-yl)pyridine (450 mg, 3.7 mmol) was added. The reaction mixture was stirred at RT for 4 h and the reaction was monitored by LCMS. After completion, the reaction mixture was poured on ice water and extracted with EtOAc. The organic layer was dried on sodium sulfate and concentrated under reduced pressure. The residue was purified by HPLC to obtain 420 mg of product as a white solid (TFA salt). TLC (silica gel) 5:95 MeOH:DCM, Rf 0.1 was observed. $^1$H NMR (CD$_3$OD, TFA salt) δ (ppm): 8.60 (d, 2H), 8.20 (bs, 1H), 7.85 (bs, 1H), 7.20 (s, 1H), 7.0 (d, 1H), 6.9 (d, 1H), 5.2 (bs, 1H), 4.8 (d, 2H), 4.4 (m, 4H), 3.9 (bs, 1H), 3.60 (bs, 2H), 3.10 (s, 3H), 2.40 (s, 3H). Separation by chiral HPLC provides enantiomers 62a and 62b.

Example 61

Preparation of Compound Nos. 63, 63a and 63b 2-(2,8-Dimethyl-1,2,3,4-tetrahydro-pyrido[4,3-b]indol-5-yl)-1-pyridin-4-yl-ethanol (200 mg.0.62 mmol) was dissolved in 10 mL DCM and m-CPBA (128 mg, 0.74 mmol) was diluted in DCM and added dropwise at RT. After consumption of starting material by monitoring TLC & LCMS reaction mixture was complete, the mixture was concentrated and the crude product was purified by reverse phase chromatography, to obtain 120 mg of 2-(2,8-dimethyl-2-oxy-1,2,3,4-tetrahydro-pyrido[4,3-b]indol-5-yl)-1-pyridin-4-yl-ethanol. Separation by chiral HPLC provided enantiomers 63a and 63b. 63a: $^1$H NMR (CD$_3$OD, TFA salt) δ (ppm): 8.56 (d, 2H), 7.9 (t, 2H), 7.22 (s, 1H), 7.2 (d, 1H), 7.0 (d, 1H), 5.23 (dd, 1H), 5.08 (d, 1H), 5.0 (d, 1H), 4.4 (m, 2H), 4.2 (d, 2H), 3.68 (s, 3H), 3.44 (m, 1H), 3.3 (m, 1H), 2.4 (s, 3H). 63b: $^1$H NMR (CD$_3$OD, Free base) δ (ppm): 8.44 d (2H), 7.38 d (2H), 7.24 d (1H), 7.25 s (1H), 7.00 d (1H), 5.07 t (1H), 4.77 d (1H), 4.56 d (1H), 4.27 m (2H), 3.86 t (2H), 3.39 m (1H), 3.34 s (3H), 2.82 d t (1H), 2.4 s (3H).

Example 62

Preparation of Compound Nos. 64, 64a and 64b 2,8-Dimethyl-2,3,4,5-tetrahydro-1H-pyrido[4,3-b]indole (500 mg, 2.5 mmol) was dissolved in 5 mL DMF and stirred for 10 min at RT. Sodium hydride (300 mg, 7.5 mmol) was added portionwise at 0° C. and the reaction mixture was stirred for 10 min. 2-Methoxy-5-(2-methyl-oxiranyl)-pyridine (566 mg, 3.75 mmol) was diluted in DMF (2 mL) and added dropwise at the same temperature and stirred for 12 h. After consumption of starting material, the reaction mixture was quenched with ice water and extracted with EtOAc (3×30 mL). The combined organic layer was washed with water (7×30 mL), dried over anhydrous sodium sulfate and concentrated. The residue was purified by column chromatography over silica gel (eluent: 15% MeOH in DCM) and further crystallized in ether-hexane to obtain 190 mg of 1-(2,8-dimethyl-1,2,3,4-tetrahydro-pyrido[4,3-b]indol-5-yl)-2-(6-methoxy-pyridin-3-yl)-propan-2-ol. $^1$H NMR (CDCl$_3$, freebase) δ (ppm): 8.22 (s, 1H), 7.5 (d, 1H), 7.1 (s, 1H), 7.0 (d, 1H), 6.83 (d, 1H), 6.5 (d, 1H), 4.1 (m, 2H), 3.91 (s, 3H), 3.5 (m, 2H), 2.63-2.81 (m, 4H), 2.41 (s, 3H), 2.39 (s, 3H), 1.58 (s, 3H). Separation by chiral HPLC provides enantiomers 64a and 64b.

Example 63

Preparation of Compound Nos. 65, 65a and 65b

To a solution of 2-methyl-7-(trifluoromethyl)-2,3,4,5-tetrahydro-1H-pyrido[4,3-b]indole (1.0 g, 3.937 mmol) in DMF (5 mL) was added NaH (472 mg, 11.81 mmol) in portions at 0° C. After stirring the reaction mixture at 0° C. for 15 min, a solution of 4-(oxiran-2-yl)pyridine (714 mg, 5.90 mmol) in DMF (1 mL) was dropwise added into the reaction mixture at the same temperature and stirring was continued at RT overnight. The progress of reaction was monitored by TLC, LCMS and NMR. After consumption of starting material, ice water was added into the reaction mixture and the product was extracted with EtOAc (3×50 mL). The organic layer was washed with water (5×50 mL), dried over anhydrous sodium sulfate and concentrated. The residue was purified by silica gel chromatography to yield 2-(2-methyl-7-(trifluoromethyl)-3,4-dihydro-1H-pyrido[4,3-b]indol-5(2H)-yl)-1-(pyridin-4-yl)ethanol. $^1$H NMR (CDCl$_3$, freebase) δ (ppm): 8.54 (d, 2H), 7.5 (s, 1H), 7.37 (d, 1H), 7.3 (d, 1H), 7.18 (d, 2H), 4.78 (m, 1H), 4.17 (m, 2H), 3.5 (m, 2H), 2.8 (m, 1H), 2.7 (m, 2H), 2.63 (m, 1H), 2.4 (s, 3H). Separation by chiral HPLC provides enantiomers 65a and 65b.

Example 64

Preparation of Compound Nos. 66, 66a and 66b

To a solution of 2,8-dimethyl-2,3,4,5-tetrahydro-1H-pyrido[4,3-b]indole (1.2 g, 6.0 mmol) in 6 mL DMF, was added sodium hydride (720 mg, 12 mmol) under nitrogen at 0° C. and stirred for 5 min. 2-(3,4-Dimethoxy-phenyl)-oxirane (2.16 g, 18 mmol) was diluted in DMF (2 mL) and added dropwise to the reaction mixture under nitrogen atmosphere. The reaction mixture was stirred at RT for 5 h. After consumption of starting material (TLC and LCMS), the reaction mixture was poured in ice-cold water and extracted with EtOAc (3×50 mL). The combined organic layer was washed with water (5×30 mL) and dried over anhydrous sodium sulfate, concentrated and purified by column chromatography (silica gel 100-200 mesh, eluent: 6% MeOH in DCM) to obtain 590 mg of 1-(3,4-dimethoxy-phenyl)-2-(2,8-dimethyl-1,2,3,4-tetrahydro-pyrido[4,3-b]indol-5-yl)-ethanol. $^1$H NMR (CDCl$_3$, freebase) δ (ppm): 7.19 (m, 2H), 6.98 (d, 1H), 6.83 (m, 2H), 6.78 (s, 1H), 4.98 (t, 1H), 4.1 (m, 2H), 4.83 (s, 3H), 4.8 (s, 3H), 3.6 (dd, 2H), 2.68-2.88 (m, 3H), 2.53 (m, 1H), 2.5 (s, 3H), 2.4 (s, 3H). Separation by chiral HPLC provides enantiomers 66a and 66b.

Example 65

Preparation of Compound Nos. 67, 67a and 67b

To a solution of 4-[2-(2,8-dimethyl-1,2,3,4-tetrahydro-pyrido[4,3-b]indol-5-yl)-1-hydroxy-ethyl]-benzoic acid ethyl ester (800 mg, 2.04 mmol) in 5 mL EtOH was added sodium hydroxide (327 mg, 8.17 mmol, in 5 mL water) and heated to 65° C. After complete conversion of starting material (TLC and LCMS), the EtOH and water were removed under reduced pressure. The crude product was passed through HPLC to yield 600 mg of 4-[2-(2,8-dimethyl-1,2,3,4-tetrahydro-pyrido[4,3-b]indol-5-yl)-1-hydroxy-ethyl]-benzoic acid. $^1$H NMR (DMSO, freebase) δ (ppm): 7.79 (d, 2H), 7.29 (s, 1H), 7.17 (d, 2H), 7.09 (s, 1H), 6.88 (d, 1H), 5.5 b (s, 1H), 4.82 (t, 1H), 4.12 (dd, 1H), 4.06 (dd, 1H), 3.44 (s, 2H), 3.16 (s, 2H), 2.71 (d, 1H), 2.56 (m, 2H), 2.36 s (7H). Separation by chiral HPLC provides enantiomers 67a and 67b.

Example 66

Preparation of Compound No. 68

To a solution of 2,8-dimethyl-2,3,4,5-tetrahydro-1H-pyrido[4,3-b]indole (145 mg, 0.72 mmol) in DMF (2 mL) was added sodium hydride (87 mg, 2.1 mmol). After stirring for 10 min at RT, a solution of 4-(oxiran-2-yl)pyridine-N-oxide (149 mg, 1.08 mmol) was added into the reaction mixture, which was stirred at RT for 16 h. The reaction mixture was cooled to 0° C., quenched with ice water and extracted with EtOAc. The organic layer was washed with water, dried over anhydrous sodium sulfate and evaporated. The residue was triturated with ether to yield the title compound (20 mg). $^1$H NMR (CDCl$_3$, Free base) δ (ppm): 8.2 (d, 2H), 7.71 (d, 2H), 7.25 (d, 1H), 6.99 (s, 2H), 5.22 (s, 2H), 3.64 (s, 2H), 2.85 (t, 2H), 2.7 (t, 2H), 2.56 (s, 3H), 2.42 (s, 3H).

Example 67

Preparation of Compound Nos. 69, 69a and 69b

To a solution of 2-(1,2,3,4-tetrahydro-2,8-dimethylpyrido[4,3-b]indol-5-yl)-1-(pyridin-4-yl) ethanol (450 mg, 2.25 mmol) in DMF (2 mL) was added sodium hydride (270 mg, 6.75 mmol). After stirring for 10 min at RT, a solution of 4-(oxiran-2-yl)pyridine-N-oxide (462 mg, 3.37 mmol) was added into the reaction mixture, and stirred at RT for 16 h. The reaction mixture was cooled to 0° C., quenched with ice water and extracted with EtOAc. The organic layer was washed with water, dried over anhydrous sodium sulfate and evaporated. The aqueous layer was also lyophilized to get crude product, which was submitted for reverse phase HPLC purification. (The organic layer had the keto compound, and the aqueous layer had the hydroxy compound). $^1$H NMR (CDCl$_3$, freebase) δ (ppm): 7.83 (d, 2H), 7.04 (s, 1H), 6.91 (m, 4H), 4.72 (t, 1H), 4.01 (dd, 1H), 3.9 (m, 1H), 3.65 (m, 1H), 3.46 (d, 1H), 3.4 (d, 1H), 2.77(m, 1H), 2.6 (m, 1H), 2.4 (m, 1H), 2.39 (s, 6H). Separation by chiral HPLC provided enantiomers 69a and 69b.

Example 68

Preparation of Compound Nos. 70, 70a, 70b, 70c and 70d

To an ice-cooled stirred solution of 1-(2,3,4,5-tetrahydro-5-(2-hydroxy-2-(pyridin-4-yl)ethyl)-2-methyl-1H-pyrido[4,3-b]indol-8-yl)ethanone (600 mg, 1.72 mmol) in anhydrous THF (10 mL) was portionwise added LAH (163 mg, 4.3 mmol) and stirred at 0° C. for 30 min. The reaction mixture was quenched by adding water, 15% NaOH and again water. The reaction mixture was filtered, and the filtrate was dried over anhydrous sodium sulfate and concentrated under reduced pressure. The residue was purified by reverse phase HPLC to yield the title compound. $^1$H NMR (CDCl$_3$, freebase) δ (ppm): 8.45 (d, 2H), 7.3 (d, 1H), 7.19 (d, 2H), 7.14 (m, 2H), 4.9 (m, 2H), 4.09 (m, 2H), 3.82 (dd, 1H), 3.7 (dd, 1H), 3.07 (m, 2H), 2.9 (m, 1H), 2.7 (d, 1H), 2.57 (s, 3H), 1.51 (d, 3H). Separation by chiral HPLC provides enantiomers 70a, 70b, 70c and 70d.

Example 69

Preparation of Compound Nos. 71, 71a and 71b 2,4,4,8-Tetramethyl-2,3,4,5-tetrahydro-1H-pyrido[4,3-b]indole (1.0 gm, 4.385 mmol) was dissolved in DMF (8 mL) and sodium hydride (0.526 g, 13.15 mmol) was added portionwise under nitrogen. 4-Oxiranyl-pyridine (0.9 g, 7.45 mmol) was diluted in DMF (2 mL) and added dropwise at RT and stirred for 4 h. After consumption of starting material (by monitoring TLC & LCMS), the reaction mixture was poured in to ice water, product was precipitated and filtered, and the residue was washed with water & hexane, dried under

Example 70

Preparation of Compound Nos. 72, 72a and 72b

To a stirred solution of 2-(1,2,3,4-tetrahydro-8-methylpyrido[4,3-b]indol-5-yl)-1-(pyridin-4-yl)ethanol (300 mg, 0.977 mmol) and triethyl amine (0.18 mL, 1.27 mmol) in DCM (6 mL) was added ethyl chloroformate (138 mg, 1.27 mmol), and the reaction mixture stirred at RT for 2 h. The progress of reaction was monitored by TLC and LCMS. The reaction mixture was diluted with DCM and washed with water. The organic layer was dried over anhydrous sodium sulfate and concentrated in vacuo. The residue was purified by silica gel column chromatography (MeOH-DCM) to yield ethyl 3,4-dihydro-5-(2-hydroxy-2-(pyridin-4-yl)ethyl)-8-methyl-1H-pyrido[4,3-b]indole-2(5H)-carboxylate (170 mg). $^1$H NMR (CDCl$_3$, freebase) δ (ppm): 8.4 (d, 2H), 7.21 (m, 4H), 7.0 (d, 1H), 5.03 (t, 1H), 4.6 (m, 2H), 4.21 (m, 4H), 3.78 (m, 2H), 3.6 (m, 1H), 2.75 (m, 1H), 2.4 (s, 3H), 1.28 (t, 3H). Separation by chiral HPLC provides enantiomers 72a and 72b.

Example 71

Preparation of Compound Nos. 73, 73a-73d

To a solution of carboline (1 g, 4.4 mmol) in 10 mL DMF, was added sodium hydride (528 mg, 13.2 mmol) under nitrogen at RT and stirred for 5 min. 4-Oxiranyl-pyridine (803 mg, 6.6 mmol) was diluted in DMF and added dropwise under nitrogen and the reaction mixture stirred at RT for 16 h. After the complete conversion of starting material (TLC and LCMS), the reaction mixture was poured in ice-cold water and extracted with EtOAc (3×40 mL). The combined organic layer was washed with water (6×30 mL) and dried over anhydrous sodium sulfate, concentrated and crude was crystallized in EtOH in ether to obtain 1.2 g of desired product. $^1$H NMR (CDCl$_3$, freebase) δ (ppm): 8.59 (d, 1H), 8.58 (d, 1H), 7.38 (d, 1H), 7.24 (d, 1H), 7.20 (d, 1H), 7.08 (d, 1H), 7.0 (d, 1H), 5.0 (m, 1H), 4.62 (dd, 1H), 4.18 (m, 2H), 4.0 (m, 1H), 2.70 (m, 2H), 2.58 (m, 2H), 2.45 (s, 3H), 2.42 (s, 3H), 2.10 (m, 1H), 1.70 (m, 1H). Separation by chiral HPLC provides enantiomers 73a-73d.

Example 72

Preparation of Compound Nos. 74, 74a and 74b

To a solution of 10-methyl-2,3,5,6,7,11c-hexahydro-1H-pyrido[3',2':4,5]pyrrolo[2,3-g]indolizine (110 mg, 0.484 mmol) in DMF (1 mL) was added a suspension of NaH (60.0 mg, 1.45 mmol) in DMF (1 mL). After stirring for 5 min at RT, a solution of 2-(6-methylpyridin-3-yl)ethyl 4-methylbenzenesulfonate (423 mg, 1.45 mmol) in DMF (1 mL) was added dropwise into the reaction mixture and stirring continued for another 2 h. The progress of reaction was monitored by TLC and LCMS. The reaction mixture was diluted with water (20 mL) and extracted with EtOAc (3×25 mL). The organic layer was washed with water (3×20 mL), dried over anhydrous sodium sulfate and concentrated under reduced pressure to afford crude material, which was purified by reverse phase HPLC to yield 10-methyl-7-(2-(6-methylpyridin-3-yl)ethyl)-2,3,5,6,7,11c-hexahydro-1H-pyrido[3',2':4,5]pyrrolo[2,3-g]indolizine. $^1$H NMR (CD$_3$OD, Tri-HCl salt) δ (ppm): 8.7 (s, 1H), 8.4 (d, 1H), 8.25 (s, 2H), 7.8 (d, 1H), 5.1 (m, 1H), 4.8-4.6 (m, 2H), 3.9-3.7 (m, 3H), 3.4 (m, 2H), 3.4-3.2 (m, 2H), 2.9-2.7 (m, 2H), 2.8 (s, 3H), 2.5 (s, 3H), 2.3-2.15 (m, 3H). Separation by chiral HPLC provided enantiomers 74a and 74b.

Example 73

Preparation of Compound Nos. 75, 75a, 75b, 75c and 75d

To a solution of 2-methyl-6,7,8,9,10,12-hexahydro-5H,6aH-indolo[2,3-b]quinolizine (1.0 g, 4.16 mmol) in 15 mL DMF, was added sodium hydride (500 mg, 12.49 mmol) under nitrogen at RT and stirred for 20 min. 4-Oxiranyl-pyridine (857 mg, 7.08 mmol) was added dropwise under nitrogen and the reaction mixture stirred at RT for 18 h. After the complete conversion of starting material (TLC and LCMS), the reaction mixture was poured in ice-cold water and extracted with EtOAc (3×80 mL). The combined organic layer was washed with water (5×50 mL) and dried over anhydrous sodium sulfate, concentrated and crude was crystallized in EtOH (1 mL) and ether (40 mL) to obtain 800 mg of desired product. $^1$H NMR (CDCl$_3$, freebase) δ (ppm): 8.54 (d, 2H), 7.22 (d, 2H), 7.102 (s, 1H), 7.00 (d, 1H), 6.92 (d, 1H), 4.78 (t, 1H), 4.02 (m, 2H), 3.81 (d, 1H), 3.26 (d, 1H), 2.99 (d, 1H), 2.7 (dd, 1H), 2.5 (d, 1H), 2.43 (s, 3H), 2.23 (m, 2H), 1.89 (d, 1H), 1.81 (d, 1H), 1.69 (m, 2H), 1.5 (q, 1H), 1.35 (t, 1H). This racemate was separated by semi-preparative chiral HPLC separation to give enantiomers 75a, 75b, 75c and 75d.

Example 74

Preparation of Compound Nos. 76, 76a, 76b, 76c and 76d

To a solution of 7-methyl-2,3,5,10,11,11a-hexahydro-1H-indolizino[7,6-b]indole (200 mg, 0.88 mmol) in DMF (2 mL) was added NaH (106 mg, 2.65 mmol). After stirring for 5 min, a solution of 4-(oxiran-2-yl)pyridine (161 mg, 1.32 mmol) in DMF was added into the reaction mixture, which was stirred at RT for 16 h. The reaction mixture was quenched with ice-water and extracted with EtOAc. The organic layer was dried over anhydrous sodium sulfate, concentrated and the residue obtained was purified by reverse phase HPLC to yield the title compound. 76a: $^1$H NMR (CDCl$_3$, freebase) δ (ppm): 8.6 (d, 2H), 7.26 (d, 2H), 7.21 (s, 1H), 7.15 (d, 1H), 7.0 (d, 1H), 5.0 (dd, 1H), 4.2 (m, 3H), 3.29 (m, 2H), 2.7 (s, 2H), 2.42 (s, 3H), 2.4 (q, 1H), 2.1 (m, 1H), 2.0 (m, 1H), 1.85 (m, 1H), 1.62 (m, 2H). 76b: $^1$H NMR (CDCl$_3$, freebase) δ (ppm): 8.53 (d, 2H), 7.24 (d, 2H), 7.17 (s, 1H), 7.14 (d, 1H), 6.97 (d, 1H), 4.95 (d, 1H), 4.10 (m, 3H), 3.28 (m, 2H), 3.0 (d, 1H), 2.49 (m, 2H), 2.44 (s, 3H), 2.37 (q, 1H), 2.11 (m, 1H), 1.97 (m, 1H), 1.87 (m, 1H), 1.63 (m, 1H). 76c: $^1$H NMR (CDCl$_3$, freebase) δ (ppm): 8.5 (d, 2H), 7.17 (d, 2H), 7.06 (s, 1H), 6.97 (d, 1H), 6.9 (d, 1H), 4.76 (t, 1H), 4.0 (m, 2H), 3.9 (d, 1H), 3.19 (d, 1H), 3.13 (t, 1H), 2.67 (q, 2H), 2.42 (s, 3H), 2.39 (m, 1H), 2.28 (q, 1H), 2.08 (t, 1H), 1.93 (m, 1H), 1.86 (m, 1H), 1.64 (m, 1H). 76d: $^1$H NMR (CDCl$_3$, freebase) δ (ppm): 8.53 (d, 2H), 7.24 (d, 2H), 7.17 (s, 1H), 7.14 (d, 1H), 6.97 (d, 1H), 4.95 (d, 1H), 4.10 (m, 3H), 3.28 (m, 2H), 3.0 (d, 1H), 2.49 (m, 2H), 2.44 (s, 3H), 2.37 (q, 1H), 2.11 (m, 1H), 1.97 (m, 1H), 1.87 (m, 1H), 1.63 (m, 1H).

Example 75

Preparation of Compound No. 77

A solution of 5-(2-bromocyclopent-1-enyl)-2,8-dimethyl-2,3,4,5-tetrahydro-1H-pyrido[4,3-b]indole (100 mg, 0.29 mmol), 1H-pyrazole-4-boronic acid (75 mg, 0.580 mmol) and potassium carbonate (120 mg, 0.87 mmol) in 1,2-DME (4 mL)-water (2 mL) was purged with nitrogen. Pd(PPh$_3$)$_4$ (16 mg, 0.0147 mmol) was added and the reaction mixture was heated at 90° C. for 45 min. The reaction mixture concentrated under vacuum, residue diluted with water (20 mL) and extracted with EtOAc (50 mL). The organic layer was dried over anhydrous sodium sulfate, concentrated under vacuum to obtain crude which was purified by reverse phase HPLC to yield 5-(2-(1H-pyrazol-4-yl)cyclopent-1-enyl)-2,8-dimethyl-2,3,4,5-tetrahydro-1H-pyrido[4,3-b]indole. $^1$H NMR (CD$_3$OD, TFA salt) δ (ppm): 7.38 (s, 1H), 7.0 (m, 2H), 6.4 (m, 2H), 4.7 (m, 1H), 4.4 (m, 1H), 3.78 (m, 1H), 3.42 (m, 1H), 3.11 (m, 4H), 2.6-3.0 (m, 5H), 2.4 (s, 3H), 2.2 (m, 2H).

Example 76

Preparation of Compound No. 78

To a degassed solution of 3,6-dimethyl-6,7,8,9-tetrahydro-5H-1,6,9-triaza-fluorene (201 mg, 1.00 mmol), potassium phosphate (466 mg, 2.20 mmol), L-proline (19 mg, 0.10 mmol) and copper iodide (23 mg, 0.20 mmol) in DMF (2 mL) was added 4-(2-bromo-1-methyl-vinyl)-pyridine (424 mg, 2.00 mmol). The reaction mixture was stirred at 120° C. for 20 h. The progress of reaction was monitored by TLC and LCMS. The reaction was monitored by TLC and LCMS. The reaction mixture was diluted with water (20 mL) and extracted with EtOAc (3×10 mL). The organic layer was washed with water (3×20 mL), followed by brine (25 mL), dried over anhydrous sodium sulfate and evaporated to afford crude material, which was purified by reverse phase HPLC. $^1$H NMR (CD$_3$OD, TFA salt) δ (ppm): 9.0 (s, 1H), 8.8 (d, 1H), 8.2 (s, 1H), 8.0 (t, 2H), 7.3 (s, 1H), 4.8 (bs, 1H), 4.4 (bs, 1H), 3.9 (bs, 1H), 3.6 (bs, 1H), 3.2 (bs, 2H), 3.18 (s, 3H), 2.8 (s, 3H), 2.5 (s, 3H), 2.06 (s, 3H).

Example 77

Preparation of Compound No. 79

2-Allyl-8-methyl-5-(2-(pyridin-4-yl)vinyl)-2,3,4,5-tetrahydro-1H-pyrido[4,3-b]indole (50 mg, 0.151 mmol) was dissolved in DCM (2 mL), which was degassed with nitrogen for 15 min. To this was added Pd(PPh$_3$)$_4$ (4 mg, 0.002 mmol) followed by 1,3-dimethyl barbituric acid (71 mg, 0.454 mmol). The reaction mixture was again degassed by nitrogen for 15 min. The resultant mixture was stirred at RT for 1 h. DCM was evaporated in vacuo. EtOAc (20 mL) was added to reaction mixture and was washed with saturated potassium carbonate solution (3×1 mL). The organic layer was dried over anhydrous sodium sulfate, evaporated in vacuo and purified by reverse phase HPLC to obtain 2 mg of 8-methyl-5-(2-(pyridin-4-yl)vinyl)-2,3,4,5-tetrahydro-1H-pyrido[4,3-b]indole. $^1$H NMR (CD$_3$OD, Free base): δ (ppm): 8.45 (d, 2H), 8.0 (d, 1H), 7.7 (d, 1H), 7.58 (d, 2H), 7.3 (s, 1H), 7.19 (d, 1H), 6.8 (d, 1H), 4.29 (s, 2H), 3.42 (m, 2H), 3.2 (m, 2H), 2.4 (s, 3H).

Example 78

Preparation of Compound No. 80

To a degassed solution of trifluoro-methanesulfonic acid 2-(2,8-dimethyl-1,2,3,4-tetrahydro-pyrido[4,3-b]indol-5-yl)-1-methyl-vinylester (200 mg, 0.515 mmol), potassium carbonate (214 mg, 1.550 mmol) and 4-(4,4,5,5-tetramethyl-[1,3,2]dioxaborolan-2-yl)-1H-pyrazole (150 mg, 0.773 mmol) in DME:water (2:1 mL) was added Pd(PPh$_3$)$_4$ (30 mg, 0.025 mmol) and the reaction mixture stirred at 90° C. for 1.5 h. The progress of reaction was monitored by TLC and LCMS. The reaction mixture was diluted with water (25 mL) and extracted with EtOAc (2×25 mL). The organic layer was dried over anhydrous sodium sulfate and concentrated. The residue was purified by silica gel column chromatography followed by reverse phase HPLC to yield the desired product. $^1$H NMR (CD$_3$OD, TFA salt) δ (ppm): 7.3 (s, 1H), 7.08 (d, 1H), 7.0 (d, 1H), 6.92 (s, 2H), 6.5 (s, 1H), 4.76 (d, 1H), 4.39 (d, 1H), 3.75 (m, 1H), 3.43 (m, 1H), 3.05 (s, 3H), 2.9 (m, 2H), 2.41 (s, 3H), 2.25 (s, 3H).

Example 79

Preparation of Compound Nos. 81, 81a and 81b

To a solution of 8-isopropyl-2-methyl-2,3,4,5-tetrahydro-1H-pyrido[4,3-b]indole (1.0 g, 4.38 mmol) in DMF (20 mL) was added sodium hydride (526 mg, 13.14 mmol) and the suspension was stirred at RT for 10 min. A solution of 4-(oxiran-2-yl)pyridine (1.0 g, 8.26 mmol) in DMF (5 mL) was added dropwise, and stirring was continued overnight. The progress of reaction was monitored by TLC and LCMS. The reaction mixture was poured into ice cold water (200 mL) and extracted with EtOAc (3×200 mL). The organic layer was washed with water (4×300 mL), dried over anhydrous sodium sulfate and concentrated. The residue obtained was triturated with diethyl ether (200 mL) to yield the desired product. $^1$H NMR (CDCl$_3$, freebase) δ (ppm): 8.58 (d, 2H), 7.21 (d, 2H), 7.18 (d, 2H), 7.03 (d, 1H), 4.81 (t, 1H), 4.05 (d, 2H), 3.55 (dd, 2H), 3.0 (q, 1H), 2.82 (m, 1H), 2.7 (m, 2H), 2.6 (m, 1H), 2.4 (s, 3H), 1.3 (d, 6H). Separation by chiral HPLC provides enantiomers 81a and 81b.

Example 80

Preparation of Compound Nos. 82, 82a and 82b

To a solution of 2,6-dimethyl-2,3,4,5-tetrahydro-1H-pyrido[4,3-b]indole (1.0 g, 5.00 mmol) in DMF (10 mL) was added sodium hydride (600 mg, 15 mmol) under nitrogen atmosphere at 0° C. and stirred for 10 min. 4-(Oxiran-2-yl)pyridine (1.08 g, 8.92 mmol) was added dropwise under nitrogen atmosphere. The reaction mixture was stirred at RT for 12 h. The progress of reaction was monitored by TLC and LCMS. The reaction mixture was poured in ice-cold water and extracted with EtOAc (2×100 mL). The combined organic layer was washed with water (5×50 mL), dried over anhydrous sodium sulfate and concentrated. The residue was crystallized with diethyl ether to yield 2-(2,6-dimethyl-1,2,3,4-tetrahydro-pyrido[4,3-b]indol-5-yl)-1-pyridin-4-yl-ethanol. $^1$H NMR (CDCl$_3$, freebase) δ (ppm): 8.58 (d, 2H), 7.23 (m, 3H), 7.0 (t, 1H), 6.9 (d, 1H), 4.81 (t, 1H), 4.3-4.4 (m, 2H), 3.5 (dd, 2H), 3.0 (m, 1H), 2.8 (m, 1H), 2.75 (s, 3H), 2.7 (m, 1H), 2.6 (m, 1H), 2.43 (s, 3H). Separation by chiral HPLC provides enantiomers 82a and 82b.

Example 81

Preparation of Compound No. 83

2,8-Dimethyl-2,3,4,5-tetrahydro-1H-pyrido[4,3-b]indole (2 g, 10 mmol) was dissolved in 20 mL of DMF. The resulting solution was cooled in an ice-water bath and sodium hydride (840 mg, 4.2 mmol) was added under nitrogen atmosphere. 2-Bromomethyl-2-phenyl[1,3]dioxolane (2.43 g, 10 mmol) was added and the reaction mixture was heated at 100° C. overnight. Water was added and the product was extracted with EtOAc. The organic layer was washed with water, dried over anhydrous sodium sulfate and concentrated under reduced pressure. The residue was purified by silica gel chromatography eluting with 0-5% MeOH:DCM.

Example 82

Compound Nos. 84, 85, 86, 89, 90, 90a, 90b and 91 were synthesized as described in PCT publication WO-2009/055828; see, for example, synthetic procedures 20, 23, 87, 178 and 274.

Example 83

Compound Nos. 87 and 88 were synthesized as described in PCT publication WO-2009/094668; see, for example, synthetic procedures 71 and 72.

Example 84

Compound Nos. 95,95a-b, 97 and 97a-b were synthesized as described in PCT publication WO-2009/120720; see, for example, synthetic procedures 109 and 115.

Example 85

Compound Nos. 96 and 96a-b were synthesized as described in PCT publication WO-2009/120717; see, for example, synthetic procedure 131.

Example 86

Compound Nos. 93,93a-b, 98,98a-b, 100, 101, 103, 105, 107 and 132 were synthesized as described in PCT publication WO-2010/051501; see, for example, synthetic procedures 45, 131, 199, 241, 273, 329, 341, 354 and 401.

Example 87

Compound Nos. 92, 99 and 106 were synthesized as described in PCT publication WO-2010/051503; see, for example, synthetic procedures 41, 147 and 168.

Example 88

Compound No. 94 was synthesized as described in PCT publication WO-2010/127177; see, for example, synthetic procedure 6.

Example 89

Compound Nos. 102 and 102a-b were synthesized as described in PCT publication WO-2011/019417; see, for example, synthetic procedure 9.

Example 90

Preparation of Compound No. 108

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (50 mg, 0.128 mmol), potassium carbonate (17.8 mg, 0.1287 mmol) and 1-methyl-1H-pyrazole-5-boronic acid pinacol ester (53.5 mg, 0.2574 mmol) in DME-water (2 mL:1 mL) was added Pd(PPh$_3$)$_4$ (7.4 mg, 0.0064) and the reaction mixture was heated to reflux for 2.5 h. The reaction mixture was cooled to RT and the solvent was removed under reduced pressure. The residue was diluted with water and extracted with EtOAc. The organic layer was washed with brine, and concentrated under reduced pressure. The residue was purified by reverse phase HPLC. $^1$H NMR (CD$_3$OD, TFA salt) δ (ppm): 7.58 (d, 1H), 7.26 (d, 1H), 7.18 (m, 2H), 6.93 (s, 1H), 6.45 (s, 1H), 4.78 (d, 1H), 4.39 (d, 1H), 4.02 (s, 3H), 3.86 (m, 1H), 3.59 (m, 1H), 3.23 (m, 1H), 3.18 (m, 4H), 2.42 (s, 3H), 1.87 (s, 3H).

Example 91

Preparation of Compound No. 109

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol), 1-methylpyrazole-4-boronic acid pinacol ester (108 mg, 0.515 mmol) and potassium carbonate (36 mg, 0.257 mmol) in DME-water (4:2 mL) was added Pd(PPh$_3$)$_4$ (15 mg, 0.0128) and the reaction mixture was heated to reflux for 45 min. The reaction mixture was cooled to RT, and the solvent was removed under reduced pressure. The residue was diluted with water and extracted with EtOAc. The organic layer was washed with brine, and concentrated under reduced pressure. The residue was purified by reverse phase HPLC. $^1$H NMR (CD$_3$OD, TFA salt) δ (ppm): 7.92 (s, 1H), 7.89 (s, 1H), 7.26 (s, 1H), 7.16 (m, 2H), 6.98 (s, 1H), 4.78 (d, 1H), 4.37 (d, 1H), 3.85 (s, 3H), 3.82 (m, 1H), 3.58 (m, 1H), 3.18 (s, 3H), 3.13 (m, 2H), 2.43 (s, 3H), 1.82 (s, 3H).

Example 92

Preparation of Compound No. 110

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol), 3,5-dimethylisoxazole-4-boronic acid pinacol ester (115 mg, 0.515 mmol) and potassium carbonate (36 mg, 0.257 mmol) in DME-water (4:2 mL) was added Pd(PPh$_3$)$_4$ (15 mg, 0.0128) and the reaction mixture was heated to reflux for 45 min. The reaction mixture was cooled to RT, and the solvent was removed under reduced pressure. The residue was diluted with water and extracted with EtOAc. The organic layer was washed with brine, and concentrated under reduced pressure. The residue was purified by reverse phase HPLC. $^1$H NMR (CD$_3$OD, TFA salt) δ (ppm): 7.27 (s, 1H), 7.17 (m, 2H), 6.61

(s, 1H), 4.78 (d, 1H), 4.39 (d, 1H), 3.83 (m, 1H), 3.60 (m, 1H), 3.02-3.23 (m, 5H), 2.31-2.60 (m, 9H), 1.81 (s, 3H).

Example 93

Preparation of Compound No. 111

To a solution of [(E,Z)-1-(2,8-dimethyl-3,4-dihydro-1H-pyrido[4,3-b]indol-5(2H)-yl)prop-1-en-2-yl trifluoromethanesulfonate] (100 mg), potassium carbonate (36 mg), and 2-acetamidopyridine-5-boronic acid pinacol ester (135 mg) in DME-water (4:2 mL) was added Pd(PPh$_3$)$_4$ (15 mg) and the reaction mixture was heated to reflux for 45 min. The reaction mixture was cooled to RT, and the solvent was removed under reduced pressure. The residue was diluted with water and extracted with EtOAc. The organic layer was washed with brine, and concentrated under reduced pressure. The residue was purified by reverse phase HPLC. $^1$H NMR (CD$_3$OD, TFA salt) δ (ppm): 7.91 (s, 1H), 7.68 (d, 1H), 7.58 (d, 1H), 7.21 (s, 1H), 7.10 (d, 1H), 6.98 (d, 1H), 6.91 (s, 1H), 4.61 (d, 1H), 4.30 (d, 1H), 3.71 (m, 1H), 3.40 (m, 1H), 3.07 (s, 3H), 2.90 (m, 2H), 2.38 (m, 6H), 2.16 (s, 3H).

Example 94

Preparation of Compound No. 112

To a solution of [(E,Z)-1-(2,8-dimethyl-3,4-dihydro-1H-pyrido[4,3-b]indol-5(2H)-yl)prop-1-en-2-yl trifluoromethanesulfonate] (100 mg), potassium carbonate (36 mg), and 2-acetamidopyridine-5-boronic acid pinacol ester (135 mg) in DME-water (4:2 mL) was added Pd(PPh$_3$)$_4$ (15 mg) and the reaction mixture was heated to reflux for 45 min. The reaction mixture was cooled to RT, and the solvent was removed under reduced pressure. The residue was diluted with water and extracted with EtOAc. The organic layer was washed with brine, and concentrated under reduced pressure. The residue was purified by reverse phase HPLC. $^1$H NMR (CD$_3$OD, TFA salt) δ (ppm): 8.58 (s, 1H), 8.35 (d, 1H), 7.96 (d, 1H), 7.30 (s, 1H), 7.11 (m, 3H), 4.37 (d, 1H), 4.40 (d, 1H), 3.83 (m, 1H), 3.58 (m, 1H), 3.12 (m, 5H), 2.42 (s, 3H), 2.21 (s, 3H), 2.0 (s, 3H).

Example 95

Preparation of Compound No. 113

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol), potassium carbonate (36 mg, 0.257 mmol) and naphthalene-1-boronic acid (88 mg, 0.515 mmol) in DME-water (4:2 mL) was added Pd(PPh$_3$)$_4$ (15 mg, 0.0128 mmol) and the reaction mixture was heated to reflux for 45 min. The reaction mixture was cooled to RT, and the solvent was removed under reduced pressure. The residue was diluted with water and extracted with EtOAc. The organic layer was washed with brine and concentrated under reduced pressure. The residue was purified by reverse phase HPLC. $^1$H NMR (CD$_3$OD, TFA salt) δ (ppm): 8.18 (d, 1H), 7.84-7.98 (m, 2H), 7.51-7.62 (m, 4H), 7.38 (m, 2H), 7.18 (d, 1H), 6.78 (s, 1H), 4.67 (m, 1H), 4.42 (m, 1H), 3.81 (m, 1H), 3.63 (m, 1H), 3.24 (m, 1H), 3.21 (s, 3H), 3.19 (m, 1H), 2.47 (s, 3H), 2.12 (s, 3H).

Example 96

Preparation of Compound No. 114

To a degassed solution of 5-(2-bromocyclopent-1-enyl)-2,8-dimethyl-2,3,4,5-tetrahydro-1H-pyrido[4,3-b]indole (120 mg, 0.348 mmol), 4-pyridineboronic acid (85 mg, 0.69 mmol) and potassium carbonate (144 mg, 1.04 mmol) in DME-water (4:2 mL) was added Pd(PPh$_3$)$_4$ (20 mg, 0.0174 mmol) and the reaction mixture was heated to reflux for 45 min. The reaction mixture was cooled to RT, and the solvent was removed under reduced pressure. The residue was diluted with water and extracted with EtOAc. The organic layer was washed with brine and concentrated under reduced pressure. The residue was purified by reverse phase HPLC. $^1$H NMR (CD$_3$OD, TFA salt) δ (ppm): 8.52 (d, 2H), 7.40 (m, 2H), 7.36 (s, 1H), 6.92-7.15 (m, 2H), 4.78 (d, 1H), 4.40 (d, 1H), 3.80 (m, 1H), 3.51 (m, 1H), 3.20 (m, 6H), 2.80-3.00 (m, 3H), 2.41 (s, 3H), 2.37 (m, 2H).

Example 97

Preparation of Compound No. 115

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg, 0.257 mmol), potassium carbonate (110 mg, 0.77 mmol) and 1H-pyrazole-4-boronic acid (60 mg, 0.540 mmol) in DME-water (2:1 mL) was added Pd(PPh$_3$)$_4$ (20 mg, 0.017 mmol) and the reaction mixture was heated to reflux for 45 min. The reaction mixture was cooled to RT, and the solvent was removed under reduced pressure. The residue was diluted with water and extracted with EtOAc. The organic layer was washed with brine and concentrated under reduced pressure. The residue was purified by reverse phase HPLC.
$^1$H NMR (CD$_3$OD, TFA salt) δ (ppm): 8.0 (s, 2H), 7.27 (s, 1H), 7.0-7.11 (m, 3H), 4.7 (d, 1H), 4.37 (d, 1H), 3.82 (m, 1H), 3.56 (m, 1H), 3.01-3.22 (m, 5H), 2.41 (s, 3H), 1.80 (s, 3H).

Example 98

Preparation of Compound No. 116

To a de-aerated solution of 8-chloro-5-(2-chloroallyl)-2-methyl-2,3,4,5-tetrahydro-1H-pyrido[4,3-b]indole (200 mg, 0.680 mmol) and potassium carbonate (281 mg, 2.039 mmol) in 1,2-dimethoxyethane-water (2:1) were added pyridine-4-boronic acid (167.2 mg, 1.36 mmol) and Pd(PPh$_3$)$_4$ (53 mg, 0.045 mmol). The reaction mixture was stirred at 90° C. for 45 min. The reaction mixture was concentrated under reduced pressure to dryness. The residue obtained was dissolved in EtOAc (50 mL) and washed with water (20 mL). The organic layer was dried over anhydrous sodium sulfate and concentrated under reduced pressure to afford crude product, which was purified by reverse phase HPLC. $^1$H NMR (CDCl$_3$, free-base) δ (ppm): 8.6 (d, 2H), 7.4 (s, 1H), 7.3 (d, 2H), 7.1 (s, 2H), 5.57 (s, 1H), 4.98 (s, 2H), 4.58 (s, 1H), 3.82 (s, 2H), 3.05 (t, 2H), 2.82 (t, 2H), 2.6 (s, 3H).

Example 99

Preparation of Compound No. 117

To a degassed solution of 5-(5-fluoro-pyridin-3-ylethynyl)-2,8-dimethyl-2,3,4,5-tetrahydro-1H-pyrido[4,3-b]indole (60 mg, 0.188 mmol) in MeOH (3 mL) were added 10% dry Pd—C (35 mg) and ammonium formate (59 mg, 0.940 mmol). The reaction mixture was stirred at 75° C. for 1 h. The reaction mass was filtered through Celite and the filtrate concentrated under reduced pressure to afford crude product, which was purified by reverse phase HPLC to yield 5-[2-(5-fluoro-pyridin-3-yl)-ethyl]-2,8-dimethyl-2,3,4,5-tetrahydro- 1H-pyrido[4,3-b]indole. $^1$H NMR (CD$_3$OD, TFA salt) δ (ppm): 8.3 (s, 1H), 7.9 (s, 1H), 7.38 (d, 1H), 7.21 (s, 1H), 7.2 (d, 1H), 7.0 (d, 1H), 4.62 (d, 1H), 4.4 (t, 2H), 4.3 (d, 1H), 3.78 (m, 1H), 3.4 (m, 1H), 3.18 (t, 2H), 3.1 (s, 3H), 2.9 (m, 1H), 2.8 (m, 1H), 2.4 (s, 3H).

Example 100

Preparation of Compound No. 118

A mixture of 5-ethynyl-2,8-dimethyl-2,3,4,5-tetrahydro-1H-pyrido[4,3-b]indole (300 mg, 1.33 mmol), 1H-imidazole (182 mg, 2.66 mmol), TBAF.3H$_2$O (1.2 g, 3.80 mmol) and dichloro bis(triphenylphosphine) palladium (II) (47 mg, 0.06 mmol) was heated at 85° C. for 30 min. The reaction mixture was cooled to RT, diluted with water and extracted with EtOAc (3×25 mL). The organic layer was washed with water (3×25 mL), dried over anhydrous sodium sulfate and concentrated under reduced pressure. The residue was purified by silica gel chromatography (100-200 mesh) eluting with 4% MeOH-DCM to yield 90 mg of 5-(1-imidazol-1-yl-vinyl)-2,8-dimethyl-2,3,4,5-tetrahydro-1H-pyrido[4,3-b]indole. The free base was converted into the di-HCl salt by treatment with ethanolic HCl. $^1$H NMR (CD$_3$OD, D1-HCl salt) δ (ppm): 9.21 (s, 1H), 7.78 (d, 2H), 7.38 (s, 1H), 7.1 (d, 1H), 6.92 (d, 1H), 6.21 (d, 1H), 5.75 (d, 1H), 4.7 (d, 1H), 4.4 (d, 1H), 3.83 (m, 1H), 3.6 (m, 1H), 3.18 (m, 5H), 2.4 (s, 3H).

Example 101

Preparation of Compound No. 119

To a solution of 2-methyl-7-trifluoromethyl-2,3,4,5-tetrahydro-1H-pyrido[4,3-b]indole (100 mg, 0.393 mmol) in DMF (2 mL) were added sodium hydride (60 mg, 1.17 mmol) and 2-(6-methylpyridin-3-yl)ethyl 4-methylbenzenesulfonate (300 mg, 0.98 mmol). The reaction mixture was irradiated in a microwave reactor at 90° C. for 1 h. The reaction mixture was cooled to RT and quenched with water and extracted with EtOAc (3×10 mL). The organic layer was washed with water (10 mL×2), dried over anhydrous sodium sulfate and concentrated under reduced pressure to afford crude product, which was purified by reverse phase HPLC. $^1$H NMR (CD$_3$OD, TFA salt) δ (ppm): 8.21 (s, 1H), 8.07 (d, 1H), 7.6 (dd, 2H), 7.28 (m, 2H), 4.78 (d, 1H), 4.6 (t, 2H), 4.4 (d, 1H), 3.9 (m, 1H), 3.6 (m, 1H), 3.2-3.4 (m, 4H), 3.18 (s, 3H), 2.6 (s, 3H).

Example 102

Preparation of Compound No. 120

To a solution of 2,8-dimethyl-2,3,4,5-tetrahydro-1H-pyrido[4,3-b]indole (200 mg, 1.00 mmol) and 2-aminopyridine (188 mg, 2.00 mmol) in DCM (2 mL) was added powdered KOH (392 mg, 7.00 mmol), and the reaction mixture was stirred at 85° C. for 2 h. The progress of reaction was monitored by TLC and LCMS. DCM was removed under reduced pressure. Water was added to the residue and extracted with EtOAc (2×50 mL). The organic layer was dried over anhydrous sodium sulfate and concentrated to afford crude material, which was purified by reverse phase HPLC to yield (2,8-dimethyl-1,2,3,4-tetrahydro-pyrido[4,3-b]indol-5-ylmethyl)-pyridin-2-yl-amine. $^1$H NMR (CDCl$_3$, freebase) δ (ppm): 8.1 (d, 1H), 7.38 (m, 2H), 7.18 (s, 1H), 7.0 (d, 1H), 6.6 (t, 1H), 6.3 (d, 1H), 5.57 (s, 2H), 5.26 (bs, 1H), 3.8 (s, 2H), 3.1 (t, 2H), 3.0 (t, 2H), 2.6 (s, 3H), 2.4 (s, 3H).

Example 103

Preparation of Compound No. 121

To a de-aerated solution of 5-(2-chloroallyl)-2,8-dimethyl-2,3,4,5-tetrahydro-1H-pyrido[4,3-b]indole (150 mg, 0.547 mmol) and potassium carbonate (226 mg, 1.64 mmol) in 1,2-dimethoxyethane-water (2:1) were added pyridine-4-boronic acid (135 mg, 1.09 mmol) and Pd(PPh$_3$)$_4$ (44 mg, 0.0383 mmol). The reaction mixture was stirred at 90° C. for 45 min. The reaction mixture was cooled to RT and concentrated under reduced pressure to dryness. The residue obtained was dissolved in EtOAc (50 mL) and washed with water (20 mL). The organic layer was dried over anhydrous sodium sulfate and concentrated under reduced pressure to afford crude product, which was purified by reverse phase HPLC as a TFA salt. $^1$H NMR (CD$_3$OD, TFA salt) δ (ppm): 8.8 (d, 2H), 8.2 (d, 2H), 7.3 (m, 2H), 7.05 (d, 1H), 6.0 (s, 1H), 5.3 (d, 2H), 4.8 (s, 1H), 4.7 (d, 1H), 4.37 (d, 1H), 3.86 (m, 1H), 3.6 (m, 1H), 3.17 (m, 2H), 3.1 (s, 3H), 2.43 (s, 3H).

Example 104

Preparation of Compound No. 122

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg, 0.257 mmol) and potassium carbonate (110 mg, 0.796 mmol), in DME (2 mL) and water (1 mL) were added Pd(PPh$_3$)$_4$ (20 mg, 0.017 mmol) and N-methyl-5-(4,4,5,5-tetramethyl-1,3,2-dioxaborolan-2-yl) picolinamide (135 mg, 0.514 mmol) and the reaction mixture was heated to reflux for 45 min. The reaction mixture was cooled to RT, and the solvent was removed under reduced pressure. The residue was diluted with water and extracted with EtOAc. The organic layer was washed with brine and concentrated under reduced pressure. The residue was purified by reverse phase HPLC. $^1$H NMR (CD$_3$OD, TFA salt) δ (ppm): 8.9 (s, 1H), 8.1-8.21 (m, 2H), 7.3 (s, 1H), 7.19 (s, 1H), 7.1 (m, 2H), 4.76 (d, 1H), 4.4 (d, 1H), 3.82 (bs, 1H), 3.6 (bs, 1H), 3.2 (m, 2H), 3.17 (s, 3H), 3.0 (s, 3H), 2.42 (s, 3H), 2.0 (s, 3H).

Example 105

Preparation of Compound No. 124

To a degassed solution of 3,6-dimethyl-6,7,8,9-tetrahydro-5H-1,6,9-triaza-fluorene (201 mg, 1.00 mmol), potassium phosphate (466 mg, 2.20 mmol), L-proline (19 mg, 0.10 mmol) and copper iodide (23 mg, 0.20 mmol) in DMF (2 mL) was added 4-(2-bromo-1-methyl-vinyl)-pyridine (396 mg, 2.00 mmol). The reaction mixture was stirred at 120° C. for 16 h. The progress of reaction was monitored by TLC and LCMS. The reaction mixture was diluted with water (20 mL) and extracted with EtOAc (3×10 mL). The organic layer was washed with water (3×20 mL), followed by brine (25 mL), dried over anhydrous sodium sulfate and evaporated to afford crude material, which was purified by reverse phase HPLC. $^1$H NMR (CD$_3$OD, TFA salt) δ (ppm): 8.8 (bs, 2H), 8.22 (d, 2H), 8.18 (s, 1H), 7.8 (s, 1H), 7.6 (s, 1H), 4.76 (bs, 1H), 4.4 (bs, 1H), 3.82 (bs, 1H), 3.6 (bs, 1H), 3.21 (bs, 2H), 3.1 (s, 3H), 2.42 (s, 3H), 2.1 (s, 3H).

Example 106

Preparation of Compound No. 125

To a stirred solution of (E)-5-(2-(6-(methoxymethyl)pyridin-3-yl)prop-1-en-1-yl)-2,8-dimethyl-2,3,4,5-tetrahydro-1H-pyrido[4,3-b]indole (90 mg, 0.249 mmol) in dry DCM (3 mL) was dropwise addition of solution of BBr$_3$ (0.3 mL, 1.745 mmol) in dry DCM (2 mL) at −78° C. and the reaction mixture was stirred at −78° C. for 2 h. The solvent was removed under reduced pressure. The residue was basified with saturated sodium bicarbonate solution and extracted with DCM (3×20 mL). The organic layer was dried over anhydrous sodium sulfate and concentrated under reduced pressure to afford crude product, which was purified by reverse phase HPLC to yield (E)-(5-(1-(2,8-dimethyl-3,4-dihydro-1H-pyrido[4,3-b]indol-5(2H)-yl)prop-1-en-2-yl)pyridin-2-yl)methanol as the TFA salt. $^1$H NMR (CD$_3$OD, TFA salt) δ (ppm): 8.9 (s, 1H), 8.77 (d, 1H), 8.0 (d, 1H), 7.4 (s, 1H), 7.3 (s, 1H), 7.17 (d, 1H), 7.1 (d, 1H), 5.1 (d, 1H), 5.0 (s, 2H), 4.6 (d, 1H), 4.1 (m, 2H), 3.17 (s, 3H), 3.1 (bs, 2H), 2.42 (s, 3H), 2.1 (s, 3H).

Example 107

Preparation of Compound No. 126

To a degassed solution of (Z)-2,8-dimethyl-5-(2-(4,4,5,5-tetramethyl-1,3,2-dioxaborolan-2-yl)prop-1-en-1-yl)-2,3,4,5-tetrahydro-1H-pyrido[4,3b]indole (271 mg, 0.742 mmol), 5-bromo-2-(methoxymethyl)pyridine (100 mg, 0.495) and potassium carbonate (204 mg, 1.485 mmol) in DME-water (2:1 mL) and was added Pd(PPh$_3$)$_4$ (40.0 mg, 0.034 mmol), and the reaction mixture was heated to reflux for 45 min. The reaction mixture was cooled to RT, and the solvent was removed under reduced pressure. The residue was diluted with water and extracted with EtOAc. The organic layer was washed with brine and concentrated under reduced pressure. The residue was purified by reverse phase HPLC. $^1$H NMR (CD$_3$OD, D1-HCl salt) δ (ppm): 9.0 (s, 1H), 8.84 (d, 1H), 8.05 (d, 1H), 7.42 (s, 1H), 7.3 (s, 1H), 7.15 (d, 1H), 7.1 (d, 1H), 4.9 (s, 2H), 4.78 (d, 1H), 4.4 (d, 1H), 3.82 (bs, 1H), 3.6 (s, 3H), 3.58 (bs, 1H), 3.2 (bs, 2H), 3.1 (s, 3H), 2.43 (s, 3H), 2.1 (s, 3H).

Example 108

Preparation of Compound Nos. 127 and 127a-d

To an ice-cooled stirred suspension of 4-bromopyridine hydrochloride salt (1.0 g, 5.1 mmol) in THF (5 mL) was added isopropyl magnesium chloride (2M in THF, 5 mL, 10.3 mmol) and stirred the reaction at RT for 30 min. A solution of 2-(1,2,3,4-tetrahydro-2,8-dimethylpyrido[4,3-b]indol-5-yl)propanal (300 mg, 1.17 mmol) in THF (3 mL) was added into the brown colored reaction mixture, which was stirred at RT for 1.5 h. The progress of reaction was monitored by TLC and LCMS (45% conversion). The reaction mixture was cooled to 0° C. and quenched with cold saturated ammonium chloride solution (till effervescence stops) and added water, stirred at RT for 15 min and extracted with EtOAc. The organic layer was dried over anhydrous sodium sulfate and evaporated. The residue was purified by reverse phase HPLC. The product was further purified, and enantiomers separated, by chiral preparative HPLC. $^1$H NMR (CDCl$_3$, freebase) δ (ppm): 8.20 (d, 2H), 7.1 (s, 1H), 7.06 (s, 1H), 6.86 (d, 1H), 6.8 (s, 2H), 4.85 (s, 1H), 4.2 (s, 1H), 3.49 (d, 1H), 3.39 (d, 1H), 2.61 (d, 2H), 2.41 (s, 3H), 2.33 (s, 3H), 1.56 (s, 3H). Separation by chiral HPLC provided diastereomers 127a-d.

Example 109

Preparation of Compound Nos. 128 and 128a-b

A solution of tert-butyl 9-(2-hydroxy-2-(pyridin-3-yl)propyl)-6-methyl-3,4-dihydro-1H-pyrido[3,4-b]indole-2(9H)-carboxylate (350 mg) in 3M aqueous HCl solution (10 mL) was stirred at RT for 1 h. The progress of reaction was monitored with TLC and LCMS. The reaction mixture was lyophilized and the solid obtained was washed with diethyl ether (2×30 mL), dried to yield the title compound. The product was further purified, and enantiomers separated, by chiral preparative HPLC. $^1$H NMR (CD$_3$OD, HCl salt) δ (ppm): 8.67 (d, 1H), 8.6 (d, 1H), 8.54 (s, 1H), 7.9 (t, 1H), 7.2 (s, 1H), 6.8 (d, 1H), 6.7 (s, 1H), 4.98 (d, 1H), 4.6 (d, 1H), 4.4 (q, 2H), 3.62 (t, 2H), 3.07 (m, 2H), 2.32 (s. 3H), 1.8 (s, 3H). Separation by chiral HPLC provided enantiomers 128a and 128b.

Example 110

Preparation of Compound Nos. 129 and 129a-d

To a solution of 9-methyl-2,3,4,5,6,10c-hexahydro-1H-3a,6-diaza-cyclopenta[c]fluorene (100 mg, 0.442 mmol) in DMF (2 mL) was added sodium hydride (60%, 53 mg, 1.32 mmol,) at 0° C. After stirring for 5 min, 4-oxiranyl-pyridine (81 mg, 0.669 mmol) was added at 0° C. and the mixture stirred at RT for 12 h. The progress of reaction was monitored by TLC and LCMS. The reaction mixture was poured into ice-cold water and extracted with EtOAc (2×25 mL). The combined organic layer was washed with water (5×25 mL), dried over anhydrous sodium sulfate and concentrated under reduced pressure. The residue was purified by reverse phase HPLC to compound 129 (90 mg), which was separated by chiral prep HPLC to give compounds 129a, 129b, 129c and 129d. Compound 129a: $^1$HNMR (CDCl$_3$, freebase) δ (ppm): 8.58 (d, 2H), 7.25 (m, 4H), 7.04 (d, 1H), 5.08 (t, 1H), 4.3 (bs, 1H), 4.18 (d, 2H), 3.3 (d, 1H), 3.07 (m, 2H), 2.85 (m, 2H), 2.6 (m, 1H), 2.42 (m, 1H), 2.4 (s, 3H), 2.01 (m, 3H), 1.82 (m, 1H). Compound 129b: $^1$HNMR (CDCl$_3$, freebase) δ (ppm): 8.55 (d, 2H), 7.25 (m, 4H), 7.0 (d, 1H), 5.0 (t, 1H), 4.3 (bs, 1H), 4.19 (m, 2H), 3.32 (d, 1H), 3.0 (m, 4H), 2.5 (m, 2H), 2.45 (s, 3H), 2.0 (m, 2H), 1.9 (m, 1H). Compound 129c: $^1$HNMR (CDCl$_3$, freebase) δ (ppm): 8.6 (d, 2H), 7.25 (m, 4H), 7.0 (d, 1H), 5.05 (t, 1H), 4.2 (m, 2H), 3.9 (t, 1H), 3.3 (m, 1H), 2.91 (m, 2H), 2.8 (t, 1H), 2.7 (q, 1H), 2.43 (s, 3H), 2.4 (m, 2H), 1.9 (m, 3H). Compound 129d: $^1$HNMR (CDCl$_3$, freebase) δ (ppm): 8.58 (d, 2H), 7.25 (m, 4H), 7.04 (d, 1H), 5.08 (t, 1H), 4.3 (bs, 1H), 4.18 (d, 2H), 3.3 (d, 1H), 3.07 (m, 2H), 2.85 (m, 2H), 2.6 (m, 1H), 2.42 (m, 1H), 2.4 (s, 3H), 2.01 (m, 3H), 1.82 (m, 1H).

Example 111

Preparation of Compound Nos. 130 and 130a-b

To an ice-cooled stirred solution of 2-(2,8-dimethyl-3,4-dihydro-1H-pyrido[4,3-b]indol-5(2H)-yl)-1-(pyridin-4-yl)ethanol (50 g, 155.76 mmol) in DMF (300 mL) was added NaH (60%, 12.5 g, 312.5 mmol). After stirring at RT for 15 min, pivaloyl chloride (37.38 g, 311.5 mmol) was added dropwise into the reaction mixture, which was stirred at RT for 1 h. The reaction was quenched with EtOH and diluted with ice water. The product was extracted with EtOAc, dried over anhydrous sodium sulfate and concentrated under reduced pressure. The residue was passed through a silica gel filter column to remove excess pivaloyl chloride and yield title compound as yellow solid (22.3 g). The product was further purified by chiral preparative HPLC. $^1$H NMR (CDCl$_3$, freebase) δ (ppm): 8.54 (d, 2H), 7.21 (d, 1H), 7.2 (s, 1H), 7.0 (d, 2H), 6.95 (d, 1H), 6.0 (t, 1H), 4.4 (dd, 1H), 4.1 (dd, 1H), 3.62 (q, 2H), 2.7 (m, 3H), 2.52 (s, 3H), 2.41 (s, 3H), 2.3 (m, 1H), 1.19 (s, 9H).

Example 112

Preparation of Compound Nos. 131 and 131a-b

To solution of 2,3,4,5-tetrahydro-2,8-dimethyl-1H-pyrido[4,3-b]indole (160 mg, 0.8 mmol) in DMF (3 mL) was added NaH (60%, 96 mg, 2.4 mmol). After stirring for 5 min at RT, 1-methyl-4-(oxiran-2-yl)-1H-pyrazole (150 mg, 1.2 mmol) was added into the reaction mixture, which was stirred at RT for 26 h. The progress of reaction was monitored by TLC, NMR and LCMS. The reaction mixture was quenched with ice-water and extracted with EtOAc. The organic layer was washed with water, dried over anhydrous sodium sulfate and concentrated under reduced pressure. The residue was purified by column chromatography (EtOH-Hex) to yield 2-(1,2,3,4-tetrahydro-2,8-dimethylpyrido[4,3-b]indol-5-yl)-1-(1-methyl-1H-pyrazol-4-yl)ethanol. The product was further purified by chiral HPLC separation. $^1$H NMR (CDCl$_3$, freebase) δ (ppm): 7.46 (s, 1H), 7.2 (s, 1H), 7.19 (s, 1H), 7.15 (d, 1H), 6.98 (d, 1H), 5.0 (t, 1H), 4.2 (d, 2H), 3.82 (s, 3H), 3.6 (s, 2H), 2.9 (m, 1H), 2.8 (m, 2H), 2.7 (m, 1H), 2.5 (s. 3H), 2.42 (s, 3H).

Example 113

Preparation of Compound Nos. 133 and 133a-b

To a solution of 2,3,4,5-tetrahydro-2,8-dimethyl-1H-pyrido[4,3-b]indole (100 mg, 0.5 mmol) in DMF (2 mL) was added NaH (60 mg, 1.5 mmol). After stirring for 10 min at RT, a solution of 3-methyl-4-(oxiran-2-yl)pyridine (100 mg, 0.75 mmol) in DMF (1 mL) was added into the reaction mixture, which was stirred at RT for 16 h. The progress of reaction was monitored by TLC, LCMS and NMR. The reaction mixture was quenched with ice-water and extracted with EtOAc. The organic layer was washed with water, dried over anhydrous sodium sulfate and concentrated under reduced pressure. The residue was purified by reverse phase HPLC. $^1$H NMR (CDCl$_3$, freebase) δ (ppm): 8.42 (d, 1H), 8.30 (s, 1H), 7.50 (d, 1H), 7.10 (m, 2H), 6.95 (d, 1H), 5.10 (m, 1H), 4.05 (m, 2H), 3.50 (s, 2H), 2.95-2.60 (m, 4H), 2.42 (s, 6H), 2.20 (s, 3H). Separation by chiral HPLC provided enantiomers 133a and 133b.

Example 114

Preparation of Compound Nos. 134 and 134a-b

A mixture of 9-methyl-2,3,4,5,6,10c-hexahydro-1H-3a,6,7-triaza-cyclopenta[c]fluorene (100 mg, 0.44 mmol), 3-vinyl-pyridine (185 mg, 1.762 mmol), tetrabutylammonium bromide (425 mg, 1.32 mmol) and 50% NaOH solution (6 mL) was stirred at 100° C. for 18 h. The progress of reaction was monitored by TLC and LCMS. The reaction mixture was diluted with water (20 mL) and extracted with EtOAc (2×50 mL). The combined organic layer was washed with brine solution (50 mL), dried over anhydrous sodium sulfate and concentrated under reduced pressure. The residue was purified by silica gel column chromatography to yield 9-methyl-6-(2-pyridin-3-yl-ethyl)-2,3,4,5,6,10c-hexahydro-1H-3a,6,7-triaza-cyclopenta[c]fluorene (58 mg). $^1$H NMR (CDCl$_3$, freebase) δ (ppm): 8.41 (d, 1H), 8.27 (s, 1H), 8.07 (s, 1H), 7.58 (s, 1H), 7.2 (d, 1H), 7.1 (dd, 1H), 4.4 (m, 2 H), 3.99 (bs, 1H), 3.2 (dd, 1H), 3.17 (t, 2H), 2.84-2.7 (m, 3H), 2.5 (m, 1H), 2.41 (s, 3H), 2.2 (dd, 1H), 1.9 (m, 4H). Separation by chiral HPLC provided enantiomers 134a and 134b.

Example 115

Preparation of Compound Nos. 135 and 135a-b

To a solution of 2,3,4,5-tetrahydro-2,8-dimethyl-1H-pyrido[4,3-b]indole (400 mg, 1.61 mmol) in DMF (5 mL) was added NaH (240 mg, 6.0 mmol). After stirring at RT for 15 min, 3-chloro-4-(oxiran-2-yl)pyridine (620 mg, 4.0 mmol) was added into the reaction mixture, which was stirred at RT for 8 h. The progress of reaction was monitored by TLC and LCMS. The reaction mixture was quenched with ice-water and extracted with EtOAc (3×50 mL). The organic layer was washed with water (5×50 mL), dried over anhydrous sodium sulfate and concentrated under reduced pressure. The product was crystallized from ether to yield title compound (430 mg) which was separated by chiral preparative HPLC to obtain 135a and 135b. $^1$H NMR (CDCl$_3$, freebase) δ (ppm): 8.4 (s, 1H), 8.21 (d, 1H), 7.39 (d, 1H), 7.1 (d, 1H), 6.97 (s, 1H), 6.88 (d, 1H), 5.7 (bs, 1H), 5.19 (d, 1H), 4.21 (d, 1H), 3.89 (dd, 1H), 3.23 (dd, 2H), 2.86 (m, 2H), 2.67 (m, 2H), 2.45 (s, 3H), 2.29 (s, 3H).

Example 116

Preparation of Compound Nos. 136 and 136a-b

To a solution of aza carboline (500 mg, 2.48 mmol) in DMF (5 mL) was added NaH (298 mg, 7.46 mmol). After stirring at RT for 10 min, 2-(4-fluorophenyl)oxirane (515 mg, 3.73 mmol) was added into the reaction mixture, which was stirred at RT for 16 h. The progress of reaction was monitored by TLC and LCMS. The reaction mixture was quenched with ice water and extracted with EtOAc. The organic layer was washed thoroughly with water, dried over anhydrous sodium sulfate and concentrated under reduced pressure. The product was recrystallized from ether and further separated by chiral preparative HPLC to obtain 136a and 136b. $^1$H NMR (CDCl$_3$, freebase) δ (ppm): 8.02 (s, 1H), 7.5 (s, 1H), 7.23 (m, 2H), 7.0 (t, 2H), 6.6 (bs, 1H), 5.11 (d, 1H), 4.3 (d, 1H), 4.24 (dd, 1H), 3.56 (dd, 2H), 2.74 (m, 2H), 2.6 (m, 1H), 2.49 (s, 3H), 2.44 (m, 1H), 2.41 (s, 3H).

Example 117

Preparation of Compound Nos. 137 and 137a-b

To a solution of 9-chloro-2,3,4,5,6,10c-hexahydro-1H-3a,6,7-triaza-cyclopenta[c]fluorene (400 mg, 1.61 mmol) in DMF (5 mL) was added sodium hydride (195 mg, 4.87 mmol). After stirring for 10 min at RT, 2-(6-methylpyridin-3-yl)ethyl 4-methylbenzenesulfonate (1.08 g, 3.71 mmol) was added into the reaction mixture, which was stirred at RT for 1 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The residue was purified by silica gel column chromatography followed by reverse phase HPLC to yield the title compound. Separation by chiral HPLC provided enantiomers 133a and 133b. $^1$H NMR (CDCl$_3$, freebase) δ (ppm): 8.2 (s, 1H), 8.19 (s, 1H), 7.7 (s, 1H), 7.1 (d, 1H), 7.0 (d, 1H), 4.38 (m, 2H), 3.8 (bs, 1H), 3.03 (t, 2H), 2.8 (m, 2H), 2.7 (m, 1H), 2.4 (m, 1H), 2.5 (s, 3H), 2.38 (m, 1H), 2.12 (dd, 1H), 1.8 (m, 4H). Separation by chiral HPLC provided enantiomers 137a and 137b.

Example 118

Preparation of Compound Nos. 138 and 138a-b

To a solution of dimethyl-aza carboline (693 mg, 3.4 mmol) in DMF (5 mL) was added NaH (413 mg, 10.3 mmol, 60%). After stirring at RT for 10 min, 2-(4-fluorophenyl)-2-methyloxirane (1.0 g, 6.8 mmol) was added into the reaction mixture, which was stirred at RT for 16 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The residue was purified through reverse phase HPLC to obtain the racemate which was separated by chiral preparative HPLC to obtain 138a and 138b. $^1$H NMR (CDCl$_3$, freebase) δ (ppm): 8.01 (s, 1H), 7.49 (s, 1H), 7.24 (m, 2H), 6.95 (t, 2H), 4.27 (dd, 2H), 3.62 (d, 1H), 3.5 (d, 1H), 2.8 (m, 3H), 2.49 (s, 3H), 2.45 (m, 1H), 2.4 (s, 3H), 1.53 (s, 3H).

Example 119

Preparation of Compound Nos. 139 and 139a-b

A solution of 4-[2-(2,8-dimethyl-1,2,3,4-tetrahydro-pyrido[4,3-b]indol-5-yl)-1-hydroxy-ethyl]-benzoicacid ethyl ester (90 mg, 0.229 mmol) in 25% ammonium hydroxide solution (5 mL) was stirred at 120° C. for 1 h. The progress of reaction was monitored by NMR and LCMS. The reaction mixture was cooled to RT, diluted with water and extracted with EtOAc (3×30 mL). The combined organic layer was dried over anhydrous sodium sulfate and concentrated under reduced pressure. The residue was purified by reverse phase HPLC to yield 4-[2-(2,8-dimethyl-1,2,3,4-tetrahydro-pyrido[4,3-b]indol-5-yl)-1-hydroxy-ethyl]-benzamide (3 mg) which was separated by chiral preparative HPLC to obtain 139a and 139b. $^1$H NMR (CD$_3$OD, TFA salt) δ (ppm): 7.18 (t, 2H), 7.4 (d, 1H), 7.31 (d, 2H), 7.23 (s, 1H), 7.03 (t, 1H), 5.08 (t,1H), 4.64 (dd, 1H), 4.33 (m, 2H), 4.21 (dd, 1H), 3.71 (t, 1H), 3.45 (bs, 1H), 3.12 (m, 1H), 3.09 (d, 3H), 2.6 (d, 1H), 2.41 (s, 3H).

Example 120

Preparation of Compound Nos. 140 and 140a-b

To a degassed solution of 1-(6-bromo-pyridin-3-yl)-2-(2,8-dimethyl-1,2,3,4-tetrahydro-pyrido[4,3-b]indol-5-yl)-ethanol (1 g, 2.5 mmol) in DMF (10 mL) were added Pd(PPh$_3$)$_4$ (0.173 g, 0.15 mmol) and zinc cyanide (585 mg, 5.0 mmol) and the reaction mixture was stirred at 150° C. for 2 h. The reaction mixture was cooled to RT, diluted with EtOAc (250 mL) and filtered. The filtrate was washed with water (3×100 mL). The organic layer was dried over anhydrous sodium sulfate and concentrated. The residue was purified by reverse phase HPLC to yield 5-[2-(2,8-dimethyl-1,2,3,4-tetrahydro-pyrido[4,3-b]indol-5-yl)-1-hydroxy-ethyl]-pyridine-2-carbonitrile (350 mg). $^1$H NMR (CDCl$_3$, freebase) δ (ppm): 8.55 (s, 1H), 7.38 (d, 1H), 7.23 (d, 1H), 6.93 (s, 1H), 6.81 (s 1H), 6.74 (s,1H), 4.96 (m, 1H), 4.11 (dd, 2H), 3.29 (dd, 2H), 2.95 (m, 1H), 2.88 (m 1H), 2.86 (m, 2H), 2.5 (s, 6H). Separation by chiral HPLC provided enantiomers 140a and 140b.

Example 121

Preparation of Compound Nos. 141 and 141a-b

To a solution of 2-(2,8-dimethyl-1,2,3,4-tetrahydro-pyrido[4,3-b]indol-5-yl)-1-pyridin-4-yl-ethanol (2.0 g, 9.04 mmol) in DMF (20 mL) was added sodium hydride (1.0 g, 25 mmol). After stirring at RT for 20 min, a solution of N,N-dimethyl carbamoyl chloride (1.9 g, 17.7 mmol) in DMF (5 mL) was added dropwise into the reaction mixture, which was stirred at RT for 1 h. The progress of reaction was monitored by TLC and LCMS. The reaction mixture was poured into ice water (400 mL) and extracted with EtOAc (3×200 mL). The organic layer was washed with water (3×300 mL), dried over anhydrous sodium sulfate and concentrated under reduced pressure. The residue was purified by silica gel column chromatography (5-7% MeOH in DCM) to yield N,N-dimethyl-carbamic acid 2-(2,8-dimethyl-1,2,3,4-tetrahydro-pyrido[4,3-b]indol-5-yl)-1-pyridin-4-yl-ethyl ester (100 mg). $^1$H NMR (CD$_3$OD, freebase) δ (ppm): 8.5 (d, 2H), 7.34 (d, 2H), 7.31 (d, 1H), 7.21 (s, 1H), 7.00 (d, 1H), 5.96 (t,1H), 4.53 (dd, 1H), 4.45 (dd, 1H), 3.49 (t, 2H), 2.98 (m, 2H), 2.95 (m, 5H), 2.92 (s, 3H), 2.77 (s, 3H), 2.39 (s, 3H). Separation by chiral HPLC provided enantiomers 141a and 141b.

Example 122

Preparation of Compound Nos. 142 and 142a-b

To an ice-cooled stirred solution of 2,3,4,5-tetrahydro-2,8-dimethyl-1H-pyrido[4,3-b]indole (2.6 g, 13.24 mmol) in DMF (12 mL) was added sodium hydride (1.6 g, 39.72 mmol, 60%). After stirring at 0° C. for 10 min, 4-(oxiran-2-yl)benzonitrile (2.4 g, 16.55 mmol) was added into the reaction mixture, which was stirred at RT for 16 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The product was re-crystallized from ether (2.5 g) followed by chiral separation. $^1$H NMR (CDCl$_3$, freebase) δ (ppm): 7.55 (d, 2H), 1.76 (d, 2H), 7.11 (s, 1H), 7.04 (d, 1H), 6.91 (d, 1H), 5.01 (m,1H), 4.1 (dd, 2H), 3.52 (dd, 2H), 2.79 (m, 2H), 2.67 (m, 2H), 2.46 (s, 3H), 2.43 (s, 3H).

Example 123

Preparation of Compound Nos. 143 and 143a-b

A solution of 8-chloro-2,3,4,5-tetrahydro-2-methyl-1H-pyrido[4,3-b]indole (290 mg, 1.31 mmol) and sodium hydride (38 mg, 1.6 mmol) in DMF (6 mL) was stirred at 120° C. for 1 h. The reaction mixture was cooled to 0° C. and 2-(trifluoromethyl)-5-(2-methyloxiran-2-yl)pyridine (400 mg, 1.97 mmol) was added dropwise into the reaction mixture, which was stirred at 120° C. for 2 h. The reaction mixture was cooled to RT and partitioned between EtOAc (60 mL) and water (15 mL). The organic layer was separated and the aqueous layer was extracted with EtOAc (1×20 mL). The combined organic layer was washed with water, followed by brine, dried over anhydrous sodium sulfate and concentrated

Example 124

Preparation of Compound Nos. 144 and 144a-b

To a solution of 5-[2-(2,8-dimethyl-1,2,3,4-tetrahydro-pyrido[4,3-b]indol-5-yl)-1-hydroxy-ethyl]-pyridine-2-carbonitrile (1.5 g, 4.3 mmol) in tert-butanol (30 mL) was added crushed KOH (728 mg, 13 mmol) and the reaction mixture was stirred at 80° C. for 1 h. The progress of reaction was monitored by LCMS. The reaction mixture was concentrated. The residue was diluted with water (50 mL) and extracted with EtOAc (2×100 mL). The combined organic layer was washed with water (2×100 mL), dried over anhydrous sodium sulfate and concentrated. The crude material was purified by reverse phase HPLC to yield 5-[2-(2,8-dimethyl-1,2,3,4-tetrahydro-pyrido[4,3-b]indol-5-yl)-1-hydroxy-ethyl]-pyridine-2-carboxylic acid amide (200 mg). $^1$H NMR (CDCl$_3$, freebase) δ (ppm): 8.45 (d, 1H), 8.12 (t, 1H), 7.78 (s, 2H), 7.05 (m, 2H), 6.94 (t, 1H), 5.57 (bs,1H), 5.03 (m, 1H), 4.13 (s, 2H), 3.63 (m, 2H), 2.79 (m, 2H), 2.78 (bs 1H), 2.66 (d, 1H), 2.53 (d, 3H), 2.42 (s, 3H). Separation by chiral HPLC provided enantiomers 144a and 144b.

Example 125

Preparation of Compound Nos. 145 and 145a-b

To an ice-cooled stirred solution of aza dimethyl-carboline (1.8 g, 8.9 mmol) in DMF (10 mL) was added sodium hydride (1.0 g, 26.86 mmol, 60%). After stirring at 0° C. for 10 min, 4-(oxiran-2-yl)benzonitrile (2.6 g, 17.9 mmol) was added into the reaction mixture, which was stirred at RT for 16 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The product was re-crystallized from EtOH (825 mg). $^1$H NMR (CDCl$_3$, freebase) δ (ppm): 8.03 (s, 1H), 7.58 (d, 2H), 7.51 (s, 1H), 7.39 (d, 2H), 7.1 (s 1H),5.19 (m, 1H), 4.4 (dd, 1H), 4.26 (dd, 1H), 3.55 (dd, 2H), 2.75 (m, 1H), 2.64 (m 1H), 2.49 (s, 3H), 2.42 (s, 3H), 2.38 (m, 1H). Separation by chiral HPLC provides enantiomers 133a and 133b.

Example 126

Preparation of Compound Nos. 146 and 146a-b

To a solution of 1-(1,2,3,4-tetrahydro-2,8-dimethylpyrido [4,3-b]indol-5-yl)-2-(pyridin-3-yl)propan-2-ol (1.0 g, 2.98 mmol) in DMF (10 mL) was added sodium hydride (60%, 0.36 g, 8.95 mmol). After stirring at RT for 10 min, isobutyryl chloride (0.95 g, 8.95 mmol) was added dropwise into the reaction mixture, which was stirred at RT for 15 min. The progress of reaction was monitored by TLC. The reaction mixture was quenched with water (5 mL), basified with sat. aq. sodium bicarbonate and extracted with EtOAc (3×50 mL). The organic layer was washed with water (3×50 mL), dried over anhydrous sodium sulfate and concentrated under reduced pressure. The residue was purified by silica gel flash column chromatography to yield title compound. $^1$H NMR (CDCl$_3$, freebase) δ (ppm): 8.79 (s, 1H), 7.21 (bs, 1H), 6.97 (s, 1H), 6.79 (d, 1H), 6.42 (bs, 2H), 4.15 (d,1H), 4.05 (d, 1H), 3.2 (m, 3H), 2.99 (s, 1H), 2.74 (d, 1H), 2.56 (t, 1H), 2.45 (s, 3H), 1.75 (s, 3H). Separation by chiral HPLC provided enantiomers 143a and 143b.

Example 127

Preparation of Compound Nos. 147 and 147a-b

To a solution of isonicotinic acid (200 mg, 1.626 mmol) in DMF (10 mL) was added potassium carbonate (560 mg, 4.065 mmol) and stirred the solution at 80° C. for 30 min. Methanesulfonic acid 2-(2,8-dimethyl-1,2,3,4-tetrahydro-pyrido[4,3-b]indol-5-yl)-1-pyridin-4-yl-ethyl ester (455 mg, 1.138 mmol) was added portionwise into the reaction mixture, which was stirred at 80° C. 30 min. The progress of reaction was monitored by LCMS and TLC. The reaction mixture was cooled to RT, diluted with water (30 mL) and extracted with EtOAc (2×50 mL). The combined organic layer was washed with water (4×50 mL), dried over anhydrous sodium sulfate and concentrated. The residue was purified by reverse phase HPLC to yield isonicotinic acid 2-(2,8-dimethyl-1,2,3,4-tetrahydro-pyrido[4,3-b]indol-5-yl)-1-pyridin-4-yl-ethylester (30 mg). $^1$H NMR (CDCl$_3$, freebase) δ (ppm): 8.79 (d, 2H), 8.58 (d, 2H), 7.77 (d, 2H), 7.23 (d, 1H), 7.18 (s 1H), 7.12 (d,2H), 7.0 (d, 1H), 6.24 (t, 1H), 4.54 (dd, 1H), 4.35 (dd, 1H), 3.68 (s, 2H), 2.76 (t, 2H), 2.61 (m, 1H), 2.51 (s, 3H), 2.43 (s, 3H), 2.43 (m, 1H). Separation by chiral HPLC provided enantiomers 147a and 147b.

Example 128

Preparation of Compound Nos. 148 and 148a-d

To a solution of 8-aza-10-methyl-2,3,5,6,7,11c-hexahydro-1H-indolizino[7,8-b]indole (500 mg, 2.2 mmol) in DMF (5 mL) was added sodium hydride (264 mg, 6.6 mmol). After stirring for 5 min at RT, 2-methyl-5-(2-methyloxiran-2-yl) pyridine (656 mg, 4.4 mmol) was added into the reaction mixture, which was stirred at RT for 16 h. The progress of reaction was monitored by LCMS. The reaction mixture was quenched with ice-water and extracted with EtOAc. The organic layer was washed with water, dried over anhydrous sodium sulfate and concentrated. The residue was purified by reverse phase HPLC to yield title compound, which was resolved by chiral preparative HPLC. $^1$H NMR (CDCl$_3$, freebase) δ (ppm): 8.48 (s, 1H), 8.03 (s, 1H), 7.55 (d, 1H), 7.53 (s, 1H), 6.98 (d 1H), 4.41 (d,1H), 4.23 (d, 1H), 3.22 (m, 2H), 3.0 (m, 1H), 2.8 m, 2H), 2.6 (m, 1H), 2.46 (s, 3H), 2.41(s, 3H), 2.34 (m, 2H), 1.88 (m, 2H), 1.63 (s, 3H), 1.58 (m, 1H).

Example 129

Preparation of Compound Nos. 149 and 149a-b 5-(2-Azido-2-(pyridin-3-yl)propyl)-2,8-dimethyl-2,3,4,5-tetrahydro-1H-pyrido[4,3-b]indole (Crude) (500 mg, 1.4 mmol) was dissolved in EtOH (4 mL) and water (1 mL). Ammonium chloride (243 mg, 4.5 mmol) followed by zinc dust (293 mg, 4.5 mmol) were added to the reaction mixture and heated at 80° C. for 1 h. The reaction mixture was concentrated to dryness, basified with aqueous ammonia solution and extracted with EtOAc (150 mL). The organic layer was dried over sodium sulfate, evaporated in vacuo and purified by reverse phase HPLC to afford 2 mg of 1-(2,8-dimethyl-3,4-dihydro-1H-pyrido[4,3-b]indol-5(2H)-yl)-2-(pyridin-3-yl)propan-2-amine. $^1$H NMR (CD$_3$OD, freebase): δ (ppm): 8.39 s (1H), 8.3 d (1H), 7.72 d (1H), 7.32 t(1H), 7.11 (1H), 6.91 d (1H), 6.8 d (1H), 4.18 dd (2H), 3.61 dd (2H), 2.7 m (2H), 2.46 s (3H), 2.35 s (3H),2.26 m (2H). Chiral HPLC provided enantiomers 149a and 149b.

Example 130

Preparation of Compound Nos. 150 and 150a-b

A solution of 2-(1,2,3,4-tetrahydro-2,8-dimethylpyrido[4,3-b]indol-5-yl)-1-(pyridin-4-yl)ethyl methanesulfonate (250 mg, 0.62 mmol) in dimethyl amine (3 mL, 40% in water) was stirred at 90° C. for 16 h. The progress of reaction was monitored by LCMS. The reaction mixture was lyophilized and crude material was purified by reverse phase HPLC. The racemate was further separated into optically active forms by chiral preparative HPLC. $^1$H NMR (CDCl$_3$, freebase) δ (ppm): 8.4 (d, 2H), 7.16 (s, 1H), 7.0 (d, 1H), 6.96 (m, 3H), 4.58 (dd, 1H), 4.0 (m, 1H), 3.62 (d, 1H), 3.58 (m, 1H), 3.4 (dd, 1H), 2.7 (t, 2H), 2.6 (t, 2H), 2.42(s, 3H), 2.4 (s, 3H), 2.3 (s, 6H).

Example 131

Preparation of Compound Nos. 151 and 151a-b

A solution of 2-(1,2,3,4-tetrahydro-2,8-dimethylpyrido[4,3-b]indol-5-yl)-1-(pyridin-4-yl)ethyl methanesulfonate (250 mg, 0.62 mmol) in methyl amine (3 mL, 40% in water) was stirred at 90° C. for 12 h. The progress of reaction was monitored by LCMS. The reaction mixture was extracted with EtOAc. The organic layer was dried and concentrated to get the crude product, which was purified by reverse phase HPLC to obtain the 2-(1,2,3,4-tetrahydro-2,8-dimethylpyrido[4,3-b]indol-5-yl)-N-methyl-1-(pyridin-4-yl)ethanamine. $^1$H NMR (CDCl$_3$, freebase): δ (ppm): 8.59 d (2H), 7.3 d (2H), 7.29 d (1H), 7.23 s (1H), 7.03 d (1H), 4.19 m (1H), 4.03 m (2H), 3.66 dd (2H), 2.8 m (3H), 2.6 m (1H), 2.55 s (3H), 2.47 s (3H), 2.18 s (3H). Chiral HPLC provided enantiomers 151a and 151b.

Example 132

Preparation of Compound Nos. 152 and 152a-b

A solution of 2-(1,2,3,4-tetrahydro-2,8-dimethylpyrido[4,3-b]indol-5-yl)-1-(pyridin-4-yl)ethyl methanesulfonate (250 mg, 0.62 mmol) in pyrrolidine (2.5 mL) was irradiated in microwave at 90° C. for 1 h. The progress of reaction was monitored by LCMS. The volatiles were removed under reduced pressure. The residue was diluted with water and extracted with DCM. The organic layer was dried and concentrated under reduced pressure. The crude material was purified by reverse phase HPLC. The racemate was further separated into optically active forms by chiral preparative HPLC. $^1$H NMR (CDCl$_3$, freebase) δ (ppm): 8.39 (d, 2H), 7.16 (s, 1H), 7.0 (d, 1H), 6.97 (m, 3H), 4.6 (dd, 1H), 4.0 (m, 1H), 3.79 (d, 1H), 3.6 (d, 1H), 3.57 (dd, 1H), 2.7-2.6 (m, 4H), 2.46-2.4 (m, 10H), 1.82 (m, 4H).

Example 133

Preparation of Compound Nos. 153 and 153a-b

To a solution of 9-(2-azido-2-(pyridin-4-yl)ethyl)-2,6-dimethyl-2,3,4,9-tetrahydro-1H-pyrido[3,4-b]indole (800 mg, 2.3 mmol) in ethanol-water (9 mL:1 mL) were added zinc dust (600 mg, 9.2 mmol) and ammonium chloride (490 mg, 9.2 mmol) and the reaction mixture stirred at 85° C. for 45 min. The reaction mixture was filtered and the filtrate concentrated. The residue was basified with aqueous ammonia and extracted with EtOAc (2×50 mL). The combined organic layer was dried over anhydrous sodium sulfate and concentrated under reduced pressure. The crude material was purified by reverse phase HPLC to yield 2-(2,6-dimethyl-3,4-dihydro-1H-pyrido[3,4-b]indol-9(2H)-yl)-1-(pyridin-4-yl)ethanamine (25 mg). The racemate can be further separated into the optically active forms by chiral preparative HPLC. $^1$H NMR (CD$_3$OD, TFA salt) δ (ppm): 8.6 (s, 2H), 7.62 (bs, 2H), 7.23 (s, 1H), 7.0 (d, 1H), 6.98 (d, 1H), 4.9 (m, 1H), 4.8-4.58 (m, 3H), 4.0 (bs, 1H), 3.8 (bs, 1H), 3.6-3.4 (m, 2H), 3.1 (bs, 4H), 2.38 (s, 3H).

Example 134

Preparation of Compound Nos. 154 and 154a-b

To a solution of 6-(2-azido-2-(pyridin-4-yl)ethyl)-3,9-dimethyl-1,2,3,4,5,6-hexahydroazepino[4,5-b]indole (188 mg, 0.522 mmol) in ethanol-water (9 mL:1 mL), zinc dust (135 mg, 2.08 mmol) and ammonium chloride (110 mg, 2.08 mmol) were added and the reaction mixture was stirred at 85° C. for 45 min. The reaction mixture was filtered and the filtrate concentrated. The residue was basified with aqueous ammonia and extracted with EtOAc (2×50 mL). The combined organic layer was dried over anhydrous sodium sulfate and concentrated under reduced pressure. The crude material was purified by reverse phase HPLC to yield 2-(3,9-dimethyl-2,3,4,5-tetrahydroazepino[4,5-b]indol-6(1H)-yl)-1-(pyridin-4-yl)ethanamine (45 mg). The racemate can be further separated into the optically active forms by chiral preparative HPLC. $^1$H NMR (CD$_3$OD, TFA salt) δ (ppm): 8.6 (d, 2H), 7.6 (d, 2H), 7.22 (s, 1H), 7.0 (s, 1H), 6.9 (s, 1H), 4.9 (m, 3H), 4.8 (m, 1H), 4.7 (m, 1H), 3.8-3.6 (m, 2H), 3.2 (m, 2H), 3.18-2.97 (m, 4H), 2.8 (bs, 1H), 2.38 (s, 3H).

Example 135

Preparation of Compound Nos. 155 and 155a-d

The azide compound (350 mg, 0.940 mmol) was dissolved in EtOH-water (10 mL: 1 mL). Zinc dust (244 mg, 3.763 mmol) and ammonium chloride (199 mg, 3.763 mmol) were added and the mixture was heated at 85° C. for 45 min. After consumption of starting material, the reaction mixture was filtered through Celite and filtrate was concentrated to obtain the residue. The residue was basified with aq ammonia and extracted with EtOAc (2×70 mL). The combined organic layer was dried over sodium sulfate and concentrated to obtain the crude product, which was crystallized in diethyl ether to obtain 150 mg of desired product. $^1$H NMR (CDCl$_3$, freebase): δ (ppm): 8.55 d (2H), 7.29 d (2H), 7.25 d (1H), 7.2 s (1H), 7.02 d (1H), 4.77 m (2H), 4.49 t (1H), 4.1 m (1H), 4.08 m (2H), 3.51 m (1H), 2.7 dd (1H), 2.46 s (3H), 2.25 s (3H), 2.2 m (1H), 1.86 t (1H), 1.44 t (1H). Chiral HPLC provided enantiomers 155a and 155b.

Example 136

Preparation of Compound Nos. 156 and 156a-b

To a solution of 5-(2-azido-2-(pyridin-4-yl)ethyl)-2,8-dimethyl-6-aza-2,3,4,5-tetrahydro-1H-pyrido[4,3-b]indole (160 mg, 0.461 mmol) in EtOH:water (4:0.4 mL) were added zinc dust (119.8 mg, 1.84 mmol) and ammonium chloride (99.59 mg, 1.84 mmol) and the reaction mixture was stirred at 80° C. for 1 h. The progress of reaction was monitored by NMR. The mixture was filtered and the filtrate concentrated under reduced pressure. The residue was basified with aqueous ammonia and extracted with EtOAc. The organic layer was dried over anhydrous sodium sulfate and concentrated under reduced pressure. The residue was purified by reverse phase HPLC to yield the title compound. The racemate can be further separated into the optically active forms by chiral preparative HPLC. $^1$H NMR (CD$_3$OD, TFA salt) δ (ppm): 8.8 (m, 2H), 8.19 (s, 1H), 7.9 (m, 2H), 7.7 (s,1H), 5.3 (m,1H), 4.8 (m, 2H), 4.63 (d, 1H), 4.25 (d, 1H), 3.85 (m, 1H), 3.5 (m, 1H), 3.2 (m, 2H), 3.17 (s, 3H), 2.4 (s, 3H).

Example 137

Preparation of Compound Nos. 157 and 157a-b

To a solution of 5-[1-amino-2-(2,8-dimethyl-1,2,3,4-tetrahydro-pyrido[4,3-b]indol-5-yl)-ethyl]-pyridine-2-carbonitrile (400 mg, 1.15 mmol) in tert-butanol (20 mL) was added crushed KOH (194 mg, 3.47 mmol) and the reaction mixture was stirred at 80° C. for 1 h. The progress of reaction was monitored by LCMS. The reaction mixture was concentrated to dryness. The residue was diluted with water (50 mL) and extracted with EtOAc (2×100 mL). The combined organic layer was dried over anhydrous sodium sulfate and concentrated under reduced pressure. The residue was purified by reverse phase HPLC to yield 5-[1-amino-2-(2,8-dimethyl-1,2,3,4-tetrahydro-pyrido[4,3-b]indol-5-yl)-ethyl]-pyridine-2-carboxylic acid amide (70 mg). The racemate can be further separated into the optically active forms by chiral preparative HPLC. $^1$H NMR (CDCl$_3$, free base) δ (ppm): 8.5 (s, 1H), 8.2 (d, 1H), 7.9 (d, 1H), 7.2 (m, 2H), 7.0 (d, 1H), 5.6 (bs, 1H), 4.6 (t, 1H), 4.1 (d, 2H), 3.7 (q, 2H), 2.9 (t, 2H), 2.8 (m, 1H), 2.6 (m, 1H), 2.58 (s, 3H), 2.42 (s, 3H).

Example 138

Preparation of Compound Nos. 158 and 158a-b

To a solution of 5-(2-azido-2-(pyridin-4-yl)ethyl)-8-methyl-6-aza-2,3,4,5-tetrahydro-1H-pyrido[4,3-b]indole (730 mg, 2.19 mmol) in EtOH:H2O (15:1.5 mL) were added zinc dust (570 mg, 8.76 mmol) and ammonium chloride (473.5 mg, 8.76 mmol) and the reaction mixture was stirred at 80° C. for 1 h. The progress of reaction was monitored by NMR. The mixture was filtered and the filtrate concentrated under reduced pressure. The residue was basified with aqueous ammonia and extracted with EtOAc. The organic layer was dried over anhydrous sodium sulfate and concentrated under reduced pressure. The residue was purified by reverse phase HPLC to yield the title compound. The racemate can be further separated into the optically active forms by chiral preparative HPLC. $^1$H NMR (CDCl$_3$, free base) δ (ppm): 8.5 (d, 2H), 8.08 (s, 1H), 7.5 (s, 1H), 7.21 (d, 2H), 4.6 (t, 1H), 4.3 (dd, 1H), 4.2(dd, 1H), 4.0 (s, 2H), 3.1 (m, 2H), 2.6 (d, 1H), 2.4 (s, 3H), 2.3 (d, 1H).

Example 139

Preparation of Compound Nos. 159 and 159a-b

To a degassed solution of 4-(1-azido-2-(6-aza-2,8-dimethyl-3,4-dihydro-1H-pyrido[4,3-b]indol-5(2H)-yl)ethyl) benzonitrile (240 mg) in EtOAc:EtOH (7:7 mL) was added 10% Pd—C (100 mg), and hydrogen gas was bubbled into the reaction mixture with stirring at RT for 5 h. The progress of reaction was monitored by LCMS. The reaction mass was filtered through Celite and the filtrate concentrated under reduced pressure. The residue was purified through reverse phase HPLC to yield the racemate (200 mg), which was separated by chiral preparative HPLC. $^1$H NMR (CDCl$_3$, free base) δ (ppm): 8.05 (s, 1H), 7.6 (d, 2H), 7.43 (m, 3H), 4.6 (t, 1H), 4.23 (dd, 2H), 3.7 (dd, 2H), 2.9 (m, 1H), 2.8 (m, 2H), 2.6 (s, 3H), 2.5 (m, 1H), 2.4 (s, 3H).

Example 140

Preparation of Compound Nos. 160 and 160a-b

To a degassed solution of 4-(1-azido-2-(6-aza-8-methyl-3,4-dihydro-1H-pyrido[4,3-b]indol-5(2H)-yl)ethyl)benzonitrile (219 mg) in EtOAc:EtOH (7:7 mL) was added 10% Pd—C (100 mg), and hydrogen gas was bubbled into the reaction mixture with stirring at RT for 5 h. The progress of reaction was monitored by LCMS. The reaction mass was filtered through Celite and the filtrate concentrated under reduced pressure. The residue was purified through reverse phase HPLC to yield the racemate, which was separated by chiral preparative HPLC. $^1$H NMR (CDCl$_3$, free base) δ (ppm): 8.1 (s, 1H), 7.6 (d, 2H), 7.47 (m, 3H), 4.6 (t, 1H), 4.2 (m, 2H), 4.18 (s, 2H), 3.21 (bm, 1H), 2.8 (bm, 1H), 2.7-2.6 (m, 2H), 2.6 (s, 3H).

Example 141

Compound Nos. 161, 161a-d, 162, 162a-d, 163, 163a-d, 164, 164a-d, 165, 165a-b, 166, 166a-b, 167, 167a-b, 171 and 171a-b can be prepared in analogous fashion to Compound Nos. 3 and 3a-b, using appropriately functionalized aromatic-tethered oxiranes as reagents. Compound Nos. 173, 174, 175 and 176 were prepared in analogous fashion to Compound Nos. 3 and 3a-b, using appropriately functionalized aromatic-tethered oxiranes as reagents. Chiral HPLC provided, respectively, Compound Nos. 173a-b, 174a-b, 175a-b and 176a-d.

Example 142

Preparation of Compound Nos. 168 and 168a-d

To a solution of 4-[1-hydroxy-2-(9-methyl-1,2,3,4,5,10c-hexahydro-3a,6-diaza-cyclopenta[c]fluoren-6-yl)-ethyl]-pyridine-2-carbonitrile (68 mg, 0.18 mmol) in 1 mL THF was added NaOH (21 mg, 0.52 mmol) i.e. 0.5 mL 1M NaOH solution and was heated at 80° C. for overnight. The reaction was monitored with LCMS. The solvent was removed under reduced pressure to obtain the crude product that was purified by reverse phase HPLC to obtain pure product as the TFA salt (8 mg). $^1$H NMR (CD$_3$OD, TFA salt): δ (ppm): 8.55 t (1H), 7.95 d (1H), 7.61 d (1H), 7.25 s (1H), 7.2 dd (1H), 7.01 dd (1H), 5.16 m (1H),5.03 m (1H), 4.36 m (2H), 3.61 m (3H), 3.3 m (1H), 2.7 m (2H), 2.4 d (3H), 2.2 m (3H). Chiral HPLC provides diastereomers 168a-d.

Example 143

Preparation of Compound Nos. 169 and 169a-b

A solution of 5-(1-(1,2,3,4-tetrahydro-2,8-dimethylpyrido [4,3-b]indol-5-yl)-2-hydroxypropan-2-yl)pyridine-2-carbonitrile (1.6 g) in ethanol (4 mL) and 10 N NaOH (15 mL) was stirred at 100° C. for 45 min. The progress of reaction was monitored by TLC and LCMS. The reaction mixture was lyophilized and purified with reverse phase HPLC to obtain the 5-(1-(1,2,3,4-tetrahydro-2,8-dimethylpyrido[4,3-b]indol-5-yl)-2-hydroxypropan-2-yl)pyridine-2-carboxylic acid. $^1$H NMR (CD$_3$OD, TFA salt): δ (ppm): 8.6 d (1H), 8.1 s (1H), 8.0 d (1H), 7.19 d (1H), 6.9 d (1H), 6.8 d (1H), 4.7 dd (1H), 4.37 m (2H), 4.3 m (1H), 3.8 m (1H), 3.52 m (2H), 3.15 m (1H), 3.1 s (3H), 2.38 s (3H), 1.7 d (3H). Chiral HPLC provides enantiomers 169a and 169b.

Example 144

Preparation of Compound Nos. 170 and 170a-b

These compounds can be prepared in analogous fashion to Compound Nos. 67 and 67a-b, using ethyl 5-(1-(2,8-dimethyl-3,4-dihydro-1H-pyrido[4,3-b]indol-5(2H)-yl)-2-hydroxypropan-2-yl)nicotinate as starting material. Separation by chiral HPLC provides enantiomers 170a-b.

Example 145

Preparation of Compound Nos. 177 and 177a-d

These compounds can be prepared in analogous fashion to Compound Nos. 67 and 67a-b, using ethyl 4-(1-hydroxy-2-(10-methyl-2,3,5,6-tetrahydro-1H-indolizino[7,8-b]indol-7(11cH)-yl)ethyl)nicotinate as starting material. Separation by chiral HPLC provides diastereomers 177a-d.

Example 146

Preparation of Compound Nos. 178 and 178a-b

These compounds can be prepared in analogous fashion to Compound Nos. 67 and 67a-b, using ethyl 3-(1-(2,8-dimethyl-3,4-dihydro-1H-pyrido[4,3-b]indol-5(2H)-yl)-2-hydroxypropan-2-yl)picolinate as starting material. Separation by chiral HPLC provides enantiomers 178a-b.

Example 147

Preparation of Compound Nos. 179 and 179a-b 3-(1-(2,8-Dimethyl-3,4-dihydro-1H-pyrido[4,3-b]indol-5(2H)-yl)-2-hydroxypropan-2-yl)isonicotinonitrile (200 mg, 0.554 mmol) was dissolved in ethanol and an aqueous solution of sodium hydroxide was added and heated at 100° C. for 1 h. The reaction was monitored by LCMS. After completion of reaction, solvent was removed under reduced pressure and the crude product was purified by reverse phase HPLC (8 mg). $^1$H NMR (CD$_3$OD, freebase): 9.3 s (1H), 8.42 s (1H), 8.3 s (1H), 7.4 d (1H), 7.1 s (1H), 6.8 d (1H), 4.4 s (2H), 4.2 m (2H), 3.58 m (2H), 3.55 m (1H), 3.3 m (1H), 3.1 s (3H), 2.4 s (3H), 1.54 s (3H). Chiral separation provides enantiomers 179a and 179b.

Example 148

Preparation of Compound Nos. 46 and 46a-b

These compounds can be prepared in analogous fashion to Compound Nos. 67 and 67a-b, using ethyl 3-(1-(2,8-dimethyl-3,4-dihydro-1H-pyrido[4,3-b]indol-5(2H)-yl)-2-hydroxypropan-2-yl)picolinate as starting material. Separation by chiral HPLC provides enantiomers 46a-b.

Example 149

Preparation of Compound Nos. 50 and 50a-d

These compounds can be prepared in analogous fashion to Compound Nos. 67 and 67a-b, using ethyl 4-(1-ethoxy-2-(10-methyl-2,3,5,6-tetrahydro-1H-indolizino[7,8-b]indol-7(11cH)-yl)ethyl)nicotinate as starting material. Separation by chiral HPLC provides diastereomers 50a-d.

Example 150

Preparation of Compound Nos. 104 and 104a-b

These compounds can be prepared in analogous fashion to Compound Nos. 67 and 67a-b, using ethyl 4-(2,8-dimethyl-3,4-dihydro-1H-pyrido[4,3-b]indol-5(2H)-yl)-3-hydroxy-3-(pyridin-3-yl)butanoate as starting material. Separation by chiral HPLC provides enantiomers 104a-b.

Example 151

Preparation of Compound Nos. 123 and 123a-b

These compounds can be prepared in analogous fashion to Compound Nos. 67 and 67a-b, using ethyl 5-(1-(2,8-dimethyl-3,4-dihydro-1H-pyrido[4,3-b]indol-5(2H)-yl)-2-hydroxypropan-2-yl)nicotinate as starting material. Separation by chiral HPLC provides enantiomers 123a-b.

Example 152

Preparation of Compound No. 180

2,3,4,5-Tetrahydro-2,8-dimethyl-1H-pyrido[4,3-b]indole (200 mg, 1 mmol), 4-methylstyrene (239 mg, 2.3 mmol) and NaH (120 mg, 60% dispersion in oil, 3 mmol) were heated in DMSO (4 mL) at 120° C. overnight (16 h) after which methanol was added and the contents were concentrated to dryness. The resulting crude product was purified by reverse-phase chromatography (C-18, 500 mm×50 mm, Mobile Phase A=0.05% TFA in water, B=0.05% TFA in acetonitrile, Gradient: 10% B to 80% B in 30 min, injection vol: 5 mL) and/or silica gel (230-400 mesh) chromatography eluting with methanol-dichloromethane gradient to obtain 20 mg (6.2% yield) of 2,3,4,5-tetrahydro-2,8-dimethyl-5-(4-methylphenethyl)-1H-pyrido[4,3-b]indole as a trifluoroacetate salt. $^1$H NMR (CDCl$_3$, TFA salt) δ (ppm): 13.3 (bs, 1H), 7.4-7.0 (m, 5H), 6.80-6.70 (d, 2H), 4.7-4.6 (d, 1H), 4.40-4.22 (m, 1H), 4.20-4.10 (m, 1H), 4.10-4.0 (d, 1H), 3.5-3.4 (t, 1H), 3.20-3.17 (t, 1H), 3.0 (t, 2H), 2.80 (s, 3H), 2.7-2.61 (m, 1H), 2.40 (s, 3H), 2.23 (s, 3H), 2.2-2.1 (m, 1H).

Example 153

Preparation of Compound No. 181

2,3,4,5-Tetrahydro-2-methyl-5-(4-methylphenethyl)-1H-pyrido[4,3-b]indole was prepared from 2,3,4,5-tetrahydro-2-methyl-1H-pyrido[4,3-b]indole (200 mg, 1.07 mmol), 4-methylstyrene (1.41 mL, 10.7 mmol) and NaH (250 mg, 60% dispersion in oil, 6.25 mmol) in DMF (6 mL) at 200° C. for 16 h to obtain 7 mg of 2,3,4,5-tetrahydro-2-methyl-5-(4-methylphenethyl)-1H-pyrido[4,3-b]indole after purification. $^1$H NMR (CDCl₃, TFA salt) δ (ppm): 7.45-7.40 (d, 2H), 7.25-7.16 (m, 2H), 7.1-6.9 (d, 2H), 6.8-6.7 (d, 2H), 4.7 (d, 1H), 4.4-4.3 (m, 1H), 4.20-4.03 (m, 2H), 3.55-3.40 (m, 1H), 3.22-3.10 (m, 1H), 3.09-2.90 (m, 2H), 2.83 (s, 3H), 2.65 (m, 1H), 2.35 (s, 3H), 2.2 (m, 1H).

Example 154

Preparation of Compound No. 182

2,3,4,5-Tetrahydro-2-methyl-5-phenethyl-1H-pyrido[4,3-b]indole was prepared from 2,3,4,5-tetrahydro-2-methyl-1H-pyrido[4,3-b]indole (200 mg, 1.07), styrene (1.23 mL mmol, 10.65) and NaH (250 mg, 6.25 mmol) in DMF (6 mL) at 200° C. for 16 h to obtain 15 mg of 2,3,4,5-tetrahydro-2-methyl-5-phenethyl-1H-pyrido[4,3-b]indole after purification. ¹H NMR (CDCl₃, TFA salt) δ (ppm): 7.5-7.10 (m, 7H), 6.9-6.8 (m, 2H), 4.6 (d, 1H), 4.30-4.19 (m, 2H), 4.05 (d, 1H), 3.62-3.40 (m, 1H), 3.20-3.0 (m, 3H), 2.9 (s, 3H), 2.7-2.6 (t, 1H), 2.2-2.1 (t, 1H).

Example 155

Preparation of Compound Nos. 183 and 183a-b 3,4,5-Tetrahydro-2,8-dimethyl-1H-pyrido[4,3-b]indole (2.2 g, 11 mmol, 1 equiv.), 4-methylstyrene oxide (5.8 g, 44 mmol, 4 equiv.) and NaH (1.3 g, 32.5 mmol, 2.95 eq) were heated in DMF (70 mL) at 120° C. for 16 h (overnight). The contents were quenched by MeOH and evaporated to dryness. The resulting crude product was purified by silica gel chromatography (230-400 mesh) using EtOAc-hexane gradient to obtain 1.3 g of racemic-2-(1,2,3,4-tetrahydro-2,8-dimethylpyrido[4,3-b]indol-5-yl)-1-p-tolylethanol. The free base was converted into its hydrochloride salt by treatment of ethanolic HCl. ¹H NMR (DMSO-d6, HCl salt) δ (ppm): 10.30 (s, 1H), 7.42-7.0 (m, 7H), 5.6 (m, 1H), 4.90-4.80 (m, 1H), 4.60-4.55 (d, 1H), 4.30-4.00 (m, 3H), 3.70 (s, 1H), 3.4 (m, 1H), 3.22-3.10 (d, 1H), 3.00-2.90 (m, 3H), 2.80-2.60 (d, 1H), 2.40 (s, 3H), 2.30 (s, 3H). Separation by chiral HPLC provided enantiomers 183a and 183b.

Example 156

Preparation of Compound No. 184

5-(4-Chlorophenethyl)-2,3,4,5-tetrahydro-2,8-dimethyl-1H-pyrido[4,3-b]indole was prepared from 2,3,4,5-tetrahydro-2,8-dimethyl-1H-pyrido[4,3-b]indole (500 mg, 2.5 mmol), 4-chlorostyrene (3.18 mL, 25 mmol) and NaH (300 mg, 7.5 mmol) in DMF (10 mL) at 180° C. overnight (16 h) to obtain 15 mg of 5-(4-chlorophenethyl)-2,3,4,5-tetrahydro-2,8-dimethyl-1H-pyrido[4,3-b]indole after purification. ¹H NMR (CDCl₃, TFA salt) δ (ppm): 7.30-7.08 (m, 5H), 6.85-6.78 (d, 2H), 4.70-4.60 (d, 1H), 4.40-4.20 (m, 1H), 4.20-4.0 (m, 2H), 3.65-3.50 (m, 1H), 3.10-3.00 (m, 3H), 2.85 (s, 3H), 2.80 (m, 1H), 2.45 (s, 3H), 2.2 (m, 1H).

Example 157

Preparation of Compound No. 185

1-(8-Chloro-1,2,3,4-tetrahydro-2-methylpyrido[4,3-b]indol-5-yl)-2-(pyridin-4-yl)propan-2-ol (1 equiv.) was refluxed with 25% sulfuric acid for 2 h. The reaction mixture was cooled to 5° C. with an ice-water bath. KOH (15% aq. solution) was added dropwise to the reaction mixture until pH 9-10 was achieved. The reaction mixture was extracted with EtOAc. The combined organic layers were washed with water followed by brine, dried over anhydrous sodium sulfate and evaporated under vacuum. The crude product was purified by column chromatography over silica gel (100-200 mesh) using a gradient of MeOH-EtOAc (0-10%) to obtain a mixture of 8-chloro-2,3,4,5-tetrahydro-2-methyl-5-((E)-2-(pyridin-4-yl)prop-1-enyl)-1H-pyrido[4,3-b]indole and 8-chloro-2,3,4,5-tetrahydro-2-methyl-5-(2-(pyridin-4-yl)allyl)-1H-pyrido[4,3-b]indole, which were separated by HPLC. ¹HNMR (DMSO, Oxalate Salt) δ (ppm): 8.60 (d, 2H), 7.62 (m, 3H), 7.40 (s, 1H), 7.30 (d, 1H), 7.20 (d, 1H), 4.40 (m, 2H), 3.10 (m, 4H), 2.99 (s, 3H), 1.90 (s, 3H).

Example 158

Preparation of Compound No. 186

1-(1,2,3,4-Tetrahydro-2,8-dimethylpyrido[4,3-b]indol-5-yl)-2-(6-methylpyridin-3-yl)propan-2-ol (1 equiv.) was refluxed with 25% sulfuric acid for 2 h. The reaction mixture was cooled to 5° C. with an ice-water bath. KOH (15% aq. solution) was added dropwise to the reaction mixture until pH 9-10 was achieved. The reaction mixture was extracted with EtOAc. The combined organic layers were washed with water followed by brine, dried over anhydrous sodium sulfate and evaporated under vacuum. The crude product was purified by column chromatography over silica gel (100-200 mesh) using a gradient of MeOH-EtOAc (0-10%) to obtain a mixture of 2,3,4,5-tetrahydro-2,8-dimethyl-5-4E)-2-(6-methylpyridin-3-yl)prop-1-enyl)-1H-pyrido[4,3-b]indole and 2,3,4,5-tetrahydro-2,8-dimethyl-5-(2-(6-methylpyridin-3-yl)allyl)-1H-pyrido[4,3-b]indole, which were separated by HPLC. ¹HNMR (CD₃OD, TFA salt) δ (ppm) 8.90 (s, 1H), 8.60 (d, 1H), 7.80 (d, 1H), 7.30 (d, 2H), 7.16 (d, 1H), 7.10 (d, 1H), 4.78 (m, 1H), 4.40 (m, 1H), 3.90 (m, 1H), 3.60 (m, 1H), 3.20 (m, 2H), 3.16 (s, 3H), 3.80 (s, 3H), 2.42 (s, 3H), 2.05 (s, 3H).

Example 159

Preparation of Compound No. 187

To a solution of 1-(2,8-dimethyl-3,4-dihydro-1H-pyrido[4,3-b]indol-5(2H)-yl)prop-1-en-2-yl trifluoromethanesulfonate (100 mg, 0.257 mmol) in DME (4 mL) was added Pd(PPh₃)₄ (15 mg, 0.0128 mmol) and the solution was purged with nitrogen for 5 min. Potassium carbonate (36 mg, 0.257 mmol), water (2 mL) and 2-(dimethylamino)-pyrimidine-5-boronic acid pinacol ester (128 mg, 0.515 mmol) were added, the reaction mixture was purged with nitrogen and refluxed for 45 min. The reaction mixture was cooled to RT and the solvent evaporated under reduced pressure. The residue was dissolved in EtOAc and filtered. The filtrate was concentrated under reduced pressure and purified by reverse phase HPLC to obtain the desired product as its TFA salt. ¹H NMR (CD₃OD, TFA salt) δ (ppm): 8.78 (s, 2H), 7.31 (s, 1H), 7.10 (m, 3H), 4.78 (d, 1H), 4.38 (d, 1H), 3.82 (m, 1H), 3.59 (m, 1H), 3.38 (s, 6H), 3.10 (m, 5H), 2.41 (s, 3H), 1.97 (s, 3H).

Example 160

Preparation of Compound No. 188

5-(1-Bromoprop-1-en-2-yl)-2-methylpyridine (254 mg, 1.2 mmol) was dissolved in DMF (2 mL) and potassium phosphate (424 mg, 2 mmol), copper (I) iodide (19 mg, 0.1 mmol) and L-proline (23 mg, 0.2 mmol) were added, followed by 2,3,4,5-tetrahydro-2,6,8-trimethyl-1H-pyrido[4,3-b]indole (214 mg, 1 mmol). The reaction mixture was purged with nitrogen and heated at 140° C. overnight. The reaction mixture was cooled to RT, diluted with ice water and extracted with EtOAc (3×15 mL). The combined organic layer was washed with water (2×10 mL), dried over anhydrous sodium sulfate and concentrated under reduced pressure. The residue was purified by silica gel chromatography (100-200 mesh) eluting with 0-6% MeOH:DCM. The compound was further purified by reverse phase HPLC to obtain 37 mg of product as a freebase. The free base was converted into HCl salt by treatment with ethanolic HCl. $^1$H NMR (CD$_3$OD, HCl salt) δ (ppm): 8.98 (s, 1H), 8.78 (d, 1H), 8.0 (d, 1H), 7.6 (s, 1H), 7.17 (s, 1H), 6.82 (s, 1H), 4.7 (d, 1H), 4.4 (d, 1H), 3.82 (m, 1H), 3.61 (m, 1H), 3.18 (m, 5H), 2.90 (s, 3H), 2.51 (s, 3H), 2.38 (s, 3H), 2.01 (s, 3H).

Example 161

Preparation of Compound No. 189

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol) in DME (4 mL) were added Pd(PPh$_3$)$_4$ (15 mg, 0.0128 mmol), potassium carbonate (36 mg, 0.257 mmol), water (2 mL) and 3-methylthiophene-2-boronic acid pinacol ester (115 mg, 0.515 mmol) followed by nitrogen purging. The reaction mixture was refluxed for 45 min. At that point, TLC showed no starting material remaining. The reaction mixture was cooled to RT and the solvent evaporated under reduced pressure. The residue was dissolved in EtOAc and filtered through a sintered crucible. The filtrate was concentrated under vacuum and the product isolated by reverse phase HPLC. $^1$H NMR, (CD$_3$OD, TFA salt) δ (ppm): 7.32 (m, 2H), 7.13 (m, 2H), 6.97 (d, 1H), 6.79 (s, 1H), 4.67 (d, 1H), 4.40 (d, 1H), 3.83 (m, 1H), 3.58 (m, 1H), 3.14 (m, 5H), 2.40 (s, 6H), 1.87 (s, 3H).

Example 162

Preparation of Compound No. 190

To a degassed solution of 5-(2-bromocyclopent-1-enyl)-2,8-dimethyl-2,3,4,5-tetrahydro-1H-pyrido[4,3-b]indole (100 mg, 0.29 mmol), 5-methylthiophene-2-boronic acid pinacol ester (100 mg, 0.575 mmol) and potassium carbonate (120 mg, 0.87 mmol) in 1,2-DME (4 mL) and water (2 mL) was added Pd(PPh$_3$)$_4$ (17 mg, 0.0147 mmol). The reaction mixture was heated at 90° C. for 45 min. The reaction mixture was concentrated under reduced pressure and the residue diluted with water (20 mL) and extracted with EtOAc (50 mL). The organic layer was dried over anhydrous sodium sulfate and evaporated under reduced pressure. The residue was purified by reverse phase HPLC to yield 2,8-dimethyl-5-(2-(5-methylthiophen-2-yl)cyclopent-1-enyl)-2,3,4,5-tetrahydro-1H-pyrido[4,3-b]indole. $^1$H NMR, (CD$_3$OD, TFA salt) δ (ppm): 7.3 (s, 1H), 7.0 (m, 2H), 6.71 (d, 1H), 6.58 (d, 1H), 4.72 (m, 1H), 4.4 (m, 1H), 3.8 (m, 1H), 3.51 (m, 1H), 3.12 (s, 3H), 3.03 (m, 4H), 2.8 (m, 2H), 2.4 (s, 3H), 2.2-2.3 (m, 5H).

Example 163

Preparation of Compound No. 191

To a degassed solution of 5-(2-bromocyclopent-1-enyl)-2,8-dimethyl-2,3,4,5-tetrahydro-1H-pyrido[4,3-b]indole (100 mg, 0.29 mmol), 1-methylindole-5-boronic acid pinacol ester (149 mg, 0.579 mmol) and potassium carbonate (120 mg, 0.87 mmol) in 1,2-DME (4 mL) and water (2 mL) was added Pd(PPh$_3$)$_4$ (17 mg, 0.0147 mmol). The reaction mixture was heated at 90° C. for 45 min. The reaction mixture was concentrated under reduced pressure. The residue was diluted with water (20 mL) and extracted with EtOAc (50 mL). The organic layer was dried over anhydrous sodium sulfate and evaporated. The residue was purified by reverse phase HPLC to yield 2,8-dimethyl-5-(2-(1-methyl-1H-indol-5-yl)cyclopent-1-enyl)-2,3,4,5-tetrahydro-1H-pyrido[4,3-b]indole. $^1$H NMR, (CD$_3$OD, TFA salt) δ (ppm): 7.21-7.38 (m, 2H), 7.2 (s, 1H), 7.04 (m, 2H), 6.9 (d, 1H), 6.8 (d, 1H), 6.21 (s, 1H), 4.62 (m, 1H), 4.35 (m, 1H), 3.65 (s, 3H), 3.58 (m, 2H), 3.01 (s, 3H), 2.81 (m, 2H), 2.6 (m, 4H), 2.41 (s, 3H), 2.21 (m, 2H).

Example 164

Preparation of Compound Nos. 192 and 192a-d

To a solution of ethyl 4-(1-hydroxy-2-(10-methyl-2,3,5,6-tetrahydro-1H-indolizino[7,8-b]indol-7(11cH)-yl)ethyl)picolinate (1 eq) in EtOH is added sodium hydroxide (4 eq, in water) and heated to 65° C. After conversion of starting material (TLC and LCMS), the EtOH and water are removed under reduced pressure. The crude product is passed through HPLC to yield the title racemic compound. Separation by chiral HPLC provides enantiomers 192a-d.

Example 165

Preparation of Compound Nos. 193 and 193a-b

To a degassed solution of 10-methyl-2,3,5,6,7,11c-hexahydro-1H-indolizino[7,8-b]indole (50 mg, 0.22 mmol), potassium phosphate (93 mg, 0.44 mmol), L-proline (2 mg, 0.01 mmol) and Cu(I)iodide (8 mg, 0.04 mmol) in DMF (1 mL) was added 5-(1-bromoprop-1-en-2-yl)-2-methylpyridine (93 mg, 0.44 mmol). The reaction mixture was stirred at 120° C. for 18 h. The progress of reaction was monitored by TLC and LCMS. The reaction mixture was filtered through Celite and the filtrate was diluted with water (50 mL), extracted with EtOAc (2×50 mL). The organic layer was dried over anhydrous sodium sulfate and concentrated under reduced pressure. The residue was purified by reverse phase HPLC to yield 10-methyl-7-(2-(6-methylpyridin-3-yl)prop-1-enyl)-2,3,5,6,7,11c-hexahydro-1H-indolizino[7,8-b]indole. $^1$H NMR, (CD$_3$OD, formate salt) δ (ppm): 8.65 (s, 1H), 8.0 (d, 1H), 7.4 (d, 1H), 7.35 (s, 1H), 7.15 (d, 1H), 7.08 (d, 2H), 5.0 (t, 1H), 3.6 (m, 3H), 3.4 (m, 1H), 3.09 (q, 2H), 2.85 (m, 1H), 2.6 (s, 3H), 2.42 (s, 3H), 2.2 (m, 3H), 2.0 (s, 3H). Chiral HPLC provided the enantiomers 193a and 193b.

Example 166

Preparation of Compound Nos. 194 and 194a-b

To a degassed solution of 10-methyl-2,3,5,6,7,11c-hexahydro-1H-indolizino[7,8-b]indole (50 mg, 0.22 mmol), potassium phosphate (93 mg, 0.44 mmol), L-proline (2 mg, 0.01 mmol) and Cu(I)iodide (8 mg, 0.04 mmol) in DMF (1 mL) was added 1-(1-bromoprop-1-en-2-yl)-4-fluorobenzene (95 mg, 0.44 mmol). The reaction mixture was stirred at 120° C. for 18 h. The progress of reaction was monitored by TLC and LCMS. The reaction mixture was filtered through Celite. The filtrate was diluted with water (50 mL), extracted with EtOAc (2×50 mL). The organic layer was dried over anhydrous sodium sulfate and concentrated under reduced pressure. The residue was purified by reverse phase HPLC to yield 7-(2-(4-fluorophenyl)prop-1-enyl)-10-methyl-2,3,5,6,7,11c-hexahydro-1H-indolizino[7,8-b]indole. $^1$H NMR, (CD$_3$OD, TFA salt) δ (ppm): 7.65 (t, 2H), 7.35 (s, 1H), 7.19 (t, 2H), 7.1 (m, 2H), 6.95 (s, 1H), 5.1 (t, 1H), 3.79 (m, 1H), 3.62 (m, 2H), 3.41 (m, 1H), 3.1 (m, 2H), 2.75 (m, 1H), 2.41 (s, 3H), 2.28 (m, 3H), 1.95 (s, 3H). Chiral HPLC provided the enantiomers 194a and 194b.

Example 167

Preparation of Compound Nos. 195 and 195a-b

This compound is prepared in analogous fashion to Compound Nos. 30 and 30a-b, using 5-(2-methyloxiran-2-yl)oxazole as the oxirane reagent. Separation by chiral HPLC provides enantiomers 195a-b.

Example 168

Preparation of Compound Nos. 196 and 196a-b

To a stirred solution of 2,3,4,9-tetrahydro-2,6-dimethyl-1H-pyrido[3,4-b]indole (500 mg, 2.5 mmol) in DMF (2 mL) was added NaH (300 mg, 7.5 mmol). After stirring for 5 min, a solution of 2-methyl-5-(2-methyloxiran-2-yl)pyridine (558 mg, 3.7 mmol) in DMF (1 mL) was added and the reaction mixture stirred at RT for 16 h. The progress of reaction was monitored by TLC and LCMS. The reaction mixture was quenched with ice-water and extracted with EtOAc. The organic layer was dried over anhydrous sodium sulfate and concentrated under reduced pressure. The residue was purified by reverse phase HPLC to yield the title compound. The product was further purified by chiral HPLC separation to give enantiomers 196a and 196b. $^1$H NMR, (CDCl$_3$, freebase) δ (ppm): 8.6 (s, 1H), 7.6 (d, 1H), 7.27 (s, 1H), 7.1 (d, 1H), 7.05 (d, 1H), 6.9 (d, 1H), 4.1 (d, 1H), 4.0 (d, 1H), 3.62 (d, 1H), 3.43 (d, 1H), 2.8 (m, 4H), 2.59 (s, 3H), 2.5 (s, 3H), 2.4 (s, 3H), 1.6 (s, 3H).

Example 169

Preparation of Compound Nos. 197 and 197a-b

To a solution of 9-methyl-2,3,4,5,6,10c-hexahydro-1H-3a,6-diaza-cyclopenta[c]fluorene (100 mg, 0.422 mmol) in DMF (1 mL) was added sodium hydride (53 mg, 1.326 mmol). After stirring for 5 min, a solution of toluene-4-sulfonic acid 2-(6-methyl-pyridin-3-yl)-ethyl ester (386 mg, 1.326 mmol) in DMF (1 mL) was added dropwise at 0° C. and the reaction mixture stirred at RT for 6 h. The progress of reaction was monitored by TLC and LCMS. The reaction mixture was poured into ice-cold water and extracted with EtOAc (3×25 mL). The combined organic layer was washed with water (5×20 mL), dried over anhydrous sodium sulfate and concentrated under reduced pressure. The residue was purified by reverse phase HPLC to yield 9-methyl-6-[2-(6-methyl-pyridin-3-yl)-ethyl]-2,3,4,5,6,10c-hexahydro-1H-3a, 6-diaza-cyclopenta[c]fluorene. $^1$H NMR, (CDCl$_3$, freebase) δ (ppm): 8.07 (s, 1H), 7.28 (m, 2H), 7.07 (d, 1H), 7.0 (s, 2H), 4.72 (m, 1H), 4.3 (m, 1H), 4.18 (m, 1H), 3.31 (m, 1H), 3.2 (m, 1H), 3.12 (m, 1H), 3.0 (m, 2H), 2.7 (m, 1H), 2.51 (m, 1H), 2.5 (s, 3H), 2.48 (s, 3H), 2.4 (d, 1H), 2.28 (m, 1H), 2.2 (m, 1H), 2.0 (m, 1H), 1.8 (m, 1H). Chiral HPLC provided enantiomers 197a and 197b.

Example 170

Preparation of Compound Nos. 198 and 198a-d

To a solution of 9-methyl-2,3,4,5,6,10c-hexahydro-1H-3a,6-diaza-cyclopenta[c]fluorene (200 mg, 0.88 mmol) in DMF (10 mL) was added sodium hydride (96 mg, 2.6 mmol). After stirring for 5 min, a solution of 2-methyl-5-oxiranyl-pyridine (175 mg, 1.3 mmol) in DMF (1 mL) was added dropwise into the reaction mixture, which was stirred at RT for 5 h. The progress of reaction was monitored by TLC and LCMS. The reaction mixture was poured into ice-cold water and extracted with EtOAc (3×25 mL). The combined organic layer was washed with water (5×25 mL), dried over anhydrous sodium sulfate and concentrated under reduced pressure. The residue was purified by reverse phase HPLC to yield 2-(9-methyl-1,2,3,4,5,10c-hexahydro-3a,6-diaza-cyclopenta[c]fluoren-6-yl)-1-(6-methyl-pyridin-3-yl)-ethanol. The product was further purified by chiral HPLC separation to give enantiomers 198a and 198b. Enantiomers 198c and 198d are also obtained by this method. $^1$H NMR, (CDCl$_3$, freebase) δ (ppm): 8.45 (s, 1H), 7.6 (dd, 1H), 7.22 (m, 2H), 7.1 (t, 1H), 7.05 (t, 1H), 5.08 (q, 1H), 4.8 (dt, 1H), 3.5 (m, 2H), 3.4 (m, 2H), 3.1 (d, 1H), 3.0 (m, 1H), 2.8 (m, 1H), 2.6 (m, 2H), 2.5 (s, 3H), 2.41 (s, 3H), 2.1 (m, 3H).

Example 171

Preparation of Compound Nos. 199 and 199a-b

To a degassed solution of 11-methyl-1,2,3,4,6,7,8,12c-octahydroindolo[3,2-a]quinolizine (100 mg, 0.41 mmol), copper(I)iodide, L-proline (9.6 mg, 0.08 mmol) and potassium phosphate (176 mg, 0.83 mmol) in DMF was added dropwise 1-(1-bromoprop-1-en-2-yl)-4-fluorobenzene (107 mg, 53 mmol) and the reaction mixture was stirred at 85° C. overnight. The DMF was evaporated under reduced pressure, and the residue was diluted with water and the solid filtered. The solid material was purified by silica gel chromatography (100-200 mesh) eluting with 0-5% MeOH-DCM. The product was further purified by reverse phase HPLC followed by chiral HPLC separation to give enantiomers 199a and 199b. $^1$H NMR, (CDCl$_3$, freebase) δ (ppm): 7.5 (t, 2H), 7.4 (s, 1H), 7.1 (t, 2H), 7.08 (d, 1H), 7.0 (d, 1H), 6.8 (s, 1H), 3.5 (m, 1H), 3.4 (m, 1H), 3.0 (m, 2H), 2.6 (m, 3H), 2.4 (s, 3H), 2.05 (m, 1H), 2.0 (s, 3H), 1.8 (m, 2H), 1.5 (m, 3H).

Example 172

Compound Nos. 200-210, 212-219 and 223 were prepared as described in PCT publication WO2009-055828.

Example 173

Compound Nos. 211, 225 and 231 were prepared as described in PCT publication WO2009-120720.

Example 174

Compound Nos. 224 and 239 were prepared as described in PCT publication WO2009-120717.

Example 175

Compound Nos. 236-237, 243, 250, 252-254, 256-259 and 261-268 were prepared as described in PCT publication WO2010-051501.

Example 176

Compound Nos. 172, 221-222, 226-230, 232-235, 238, 240-242, 244-249 and 251 were prepared as described in PCT publication WO2010-051503.

Example 177

Compound Nos. 255 and 260 were prepared as described in PCT publication WO2010-127177.

Example 178

Preparation of Compound Nos. 220 and 220a-b

This compound is prepared in analogous fashion to Compound Nos. 30 and 30a-b, using 4-(2-methyloxiran-2-yl)oxazole as the oxirane reagent. Separation by chiral HPLC provides enantiomers 220a-b.

Example 179

Preparation of Compound No. 269

To a degassed solution of 2,8-dimethyl-2,3,4,5-tetrahydro-1H-pyrido[4,3-b]indole (0.08 g, 0.0004 mol), potassium tert-butoxide (0.112 g, 0.001 mol), (E/Z)-4-(1-bromoprop-1-en-2-yl)-2-methoxypyridine (0.091 g, 0.0004 mol) and 9,9-dimethyl-4,5-bis(diphenylphosphine) xanthene (0.023 g, 0.00004 mol) in toluene (3 mL) was added $Pd_2(dba)_3$ (0.0219 g, 0.000064 mol) and irradiated the reaction mixture at 80° C. for 30 min. The reaction mixture was diluted with water (30 mL) and extracted with EtOAc (3×20 mL). The organic layer was dried over anhydrous sodium sulfate and concentrated under reduced pressure. The residue was purified by silica gel column chromatography (2% MeOH-DCM) followed by preparative TLC to yield the title compound. $^1H$ NMR ($CD_3OD$, Oxalate salt) δ (ppm): 8.19 (d, 1H), 7.27 (s, 1H), 7.24 (m, 2H), 7.05 (m, 2H), 7.0 (s, 1H), 4.58 (s, 3H), 3.93 (s, 3H), 3.65 (m, 2H), 3.17 (m, 4H), 2.41 (s, 3H), 2.01 (s, 3H).

Example 180

Preparation of Compound No. 270

To a degassed solution of 1-(1,2,3,4-tetrahydro-2,8-dimethylpyrido[4,3-b]indol-5-yl)prop-1-en-2-yl trifluoromethanesulfonate (50 mg, 0.129 mmol), $Pd(PPh_3)_4$ (7.4 mg, 0.0064 mol) in DME (2 mL) were added potassium carbonate (17.8 mg, 0.1287 mmol), water (1 mL) and naphthalene-2-boronic acid (44 mg, 0.258 mmol) and the reaction mixture refluxed for 45 min. The reaction mixture was cooled to RT, and the solvent was removed under reduced pressure. The residue was dissolved in water (10 mL), extracted into EtOAc (3×25 mL) and washed with brine. The organic layer was dried over anhydrous sodium sulfate and concentrated. The residue was purified by silica gel column chromatography (2.5% MeOH-DCM) to yield the title compound. $^1H$ NMR ($CD_3OD$, freebase) δ (ppm): 8.02 (s, 1H), 7.82 (m, 3H), 7.79 (d, 1H), 7.42 (m, 2H), 7.21 (s, 1H), 7.11 (m, 2H), 6.95 (m, 1H), 3.78 (s, 2H), 2.84 (m, 4H), 2.60 (s, 3H), 2.40 (s, 3H), 2.12 (s, 3H).

Example 181

Preparation of Compound No. 271

To a degassed solution of 1-(1,2,3,4-tetrahydro-2,8-dimethylpyrido[4,3-b]indol-5-yl)prop-1-en-2-yl trifluoromethanesulfonate (50 mg, 0.129 mmol) and $Pd(PPh_3)_4$ (7.4 mg, 0.0064) in DME (2 mL) were added potassium carbonate (17.8 mg, 0.1287 mmol), water (1 mL) and naphthalene-2-boronic acid (44 mg, 0.258 mmol), and the reaction mixture refluxed for 45 min. The reaction mixture was cooled to RT, and the solvent was removed under reduced pressure. The residue was dissolved in water (10 mL), extracted into EtOAc (3×25 mL), washed with brine, and concentrated to afford crude material, which was purified by silica gel column chromatography (2.5% MeOH-DCM) to yield the desired compound. $^1H$ NMR ($CD_3OD$, freebase) δ (ppm): 7.64 (m, 3H), 7.34 (m, 1H), 7.29 (m, 2H), 7.18 (m, 2H), 6.97 (m, 1H), 6.82 (m, 2H), 3.67 (s, 2H), 2.63 (d, 2H), 2.38-2.47 (m, 8H), 1.84 (s, 3H).

Example 182

Preparation of Compound Nos. 272 and 272a-b

A solution of 8-chloro-5-(2-(4-fluorophenyl)allyl)-2-methyl-2,3,4,5-tetrahydro-1H-pyrido[4,3-b]indole (150 mg, 0.423 mmol) and 10% Pd/C (10 mg) in MeOH:acetic acid (9 mL, 10:1) was hydrogenated in a Parr shaker at RT and 50 psi for 18 h. The reaction mixture was filtered through a Celite bed and the filtrate concentrated under reduced pressure. The residue was purified by reverse phase HPLC to yield the title compound. The product was further purified by reverse phase HPLC followed by chiral HPLC separation to give enantiomers 272a and 272b. $^1H$ NMR ($CD_3OD$, TFA salt) δ (ppm): 7.41-7.43 (m, 2H), 7.2-6.94 (m, 6H), 4.62 (m, 1H), 4.29 (m, 2H), 4.06 (m, 1H), 3.6 (m, 1H), 3.37 (m, 2H), 3.0-2.9 (m, 5H), 1.45 (m, 3H).

Example 183

Preparation of Compound No. 273

To a degassed solution of 1-(1,2,3,4-tetrahydro-2,8-dimethylpyrido[4,3-b]indol-5-yl)prop-1-en-2-yl trifluoromethanesulfonate (50 mg, 0.128 mmol) and $Pd(PPh_3)_4$ (7.4 mg, 0.0064 mmol) in DME (2 mL) were added potassium carbonate (17.8 mg, 0.1287 mmol), water (1 mL) and 1-methyl-1H-pyrazole-5-boronic acid pinacol ester (53.5 mg, 0.2574 mmol) and the reaction mixture refluxed for 2.5 h. The reaction mixture was cooled to RT, and concentrated to dryness. The residue was extracted into EtOAc, washed with brine, and concentrated under reduced pressure. $^1H$ NMR ($CD_3OD$, TFA salt) δ (ppm): 7.40 (d, 1H), 7.21 (s, 1H), 7.15 (m, 2H), 6.87 (d, 1H), 6.38 (s, 1H), 4.63 (d, 1H), 4.23 (d, 1H), 3.74 (m, 1H), 3.41 (m, 1H), 3.16 (s, 3H), 3.09 (s, 3H), 2.81 (m, 2H), 2.19 (s, 3H), 2.14 (s, 3H).

Example 184

Preparation of Compound Nos. 274 and 274a-b

A solution of 1-(4-allyl-2,4,8-trimethyl-1,2,3,4-tetrahydro-pyrido[4,3-b]indol-5-yl)-2-(4-fluoro-phenyl)-propan-2-ol (300 mg, 0.738 mmol) in 6N HCl (10 mL) was stirred at 80° C. for 2 h. The progress of reaction mass was monitored by TLC and LCMS. The reaction mixture was basified with saturated sodium bicarbonate solution and extracted with EtOAc (3×25 mL). The combined organic layer was dried over anhydrous sodium sulfate and concentrated. The residue was purified by silica gel column chromatography (1% MeOH-DCM) to yield 4-allyl-5-[2-(4-fluoro-phenyl)-propenyl]-2,4,8-trimethyl-2,3,4,5-tetrahydro-1H-pyrido[4,3-b]indole. The product is further purified by reverse phase HPLC followed by chiral HPLC separation to give enantiomers 274a and 274b. $^1$H NMR (CD$_3$OD, HCl salt) δ (ppm): 7.62 (m, 2H), 7.27 (s, 1H), 7.20 (m, 2H), 7.04 (m, 3H), 6.78-6.82 (m, 1H), 5.18 (d, 2H), 4.78 (d, 1H), 4.37 (d, 1H), 3.58 (m,2H), 3.18 (s, 3H), 2.40 (s, 3H), 2.38 (d, 2H), 1.82 (s, 3H), 1.58 (s, 3H).

Example 185

Preparation of Compound No. 275

To a degassed solution of 1-(1,2,3,4-tetrahydro-2,8-dimethylpyrido[4,3-b]indol-5-yl)prop-1-en-2-yl trifluoromethanesulfonate (100 mg, 0.257 mmol) and Pd(PPh$_3$)$_4$ (15 mg, 0.0128) in DME (4 mL) were added 1-methylpyrazole-4-boronic acid pinacol ester (108 mg, 0.515 mmol), potassium carbonate (36 mg, 0.257 mmol) and water (2 mL) and the reaction mixture refluxed for 45 min. The reaction mixture was cooled to RT and the solvent was removed under reduced pressure. $^1$H NMR (CD$_3$OD, TFA salt) δ (ppm): 7.27 (s, 1H), 7.19 (s, 1H), 7.04 (d, 1H), 6.98 (d, 1H), 6.46 (m, 2H), 4.78 (d, 1H), 4.39 (d, 1H), 3.90 (m, 1H), 3.76 (s, 3H), 3.44 (m, 1H), 3.08 (s, 3H), 2.86 (m, 2H), 2.42 (s, 3H), 2.21 (s, 3H).

Example 186

Preparation of Compound No. 276

To a degassed solution of 1-(1,2,3,4-tetrahydro-2,8-dimethylpyrido[4,3-b]indol-5-yl)prop-1-en-2-yl trifluoromethanesulfonate (100 mg, 0.257 mmol) in DME (4 mL) were added Pd(PPh$_3$)$_4$ (15 mg, 0.0128), 2-fluoropyridine-5-boronic acid pinacol ester (115 mg, 0.515 mmol), potassium carbonate (36 mg, 0.257 mmol) and water (2 mL) and the reaction mixture refluxed for 45 min. The reaction mixture was cooled to RT, and the solvent was removed under reduced pressure. $^1$H NMR (CD$_3$OD, TFA salt) δ (ppm): 7.79 (s, 1H), 7.60 (m, 1H), 7.21 (s, 1H), 7.05 (d, 1H), 6.93 (d, 1H), 6.88 (s, 1H), 6.82 (d, 1H), 4.62 (d, 1H), 4.25 (d, 1H), 3.78 (m, 1H), 3.42 (m, 1H), 3.13 (s, 3H), 2.87 (m, 2H), 2.38 (m, 6H).

Example 187

Preparation of Compound No. 277

To a degassed solution of 1-(1,2,3,4-tetrahydro-2,8-dimethylpyrido[4,3-b]indol-5-yl)prop-1-en-2-yl trifluoromethanesulfonate (100 mg, 0.257 mmol) in DME (4 mL) were added Pd(PPh$_3$)$_4$ (15 mg, 0.0128), 5-methylthiophene-2-boronic acid pinacol ester (115 mg, 0.515 mmol), potassium carbonate (36 mg, 0.257 mmol) and water (2 mL) were added followed by nitrogen purging and water (2 mL) and the reaction mixture refluxed for 45 min. The reaction mixture was cooled to RT, and the solvent was removed under reduced pressure. $^1$H NMR (CD$_3$OD, TFA salt) δ (ppm): 7.25 (s, 1H), 7.13 (d, 1H), 7.0 (d, 1H), 6.82 (d, 1H), 6.60 (d, 1H), 6.43 (s, 1H), 4.76 (d, 1H), 4.40 (d, 1H), 3.67 (m, 1H), 3.43 (m, 1H), 3.13 (s, 3H), 2.81-2.93 (m, 2H), 2.30 (s, 3H), 2.25 (s, 3H), 2.20 (s, 3H).

Example 188

Preparation of Compound No. 278

To a degassed solution of 1-(1,2,3,4-tetrahydro-2,8-dimethylpyrido[4,3-b]indol-5-yl)prop-1-en-2-yl trifluoromethanesulfonate (100 mg, 0.257 mmol) in DME (4 mL) were added Pd(PPh$_3$)$_4$ (15 mg, 0.0128), 5-methylthiophene-2-boronic acid pinacol ester (115 mg, 0.515 mmol), potassium carbonate (36 mg, 0.257 mmol) and water (2 mL) and the reaction mixture refluxed for 45 min. The reaction mixture was cooled to RT, and the solvent was removed under reduced pressure. $^1$H NMR (CD$_3$OD, TFA salt) δ (ppm): 7.27 (s, 1H), 7.09 (m, 3H), 6.98 (s, 1H), 6.79 (s, 1H), 4.78 (d, 1H), 4.40 (d, 1H), 3.87 (m, 1H), 3.61 (m, 1H), 3.0-3.20 (m, 5H), 2.45 (s, 3H), 2.40 (s, 3H), 1.89 (s, 3H).

Example 189

Preparation of Compound No. 279

To a degassed solution of 1-(1,2,3,4-tetrahydro-2,8-dimethylpyrido[4,3-b]indol-5-yl)prop-1-en-2-yl trifluoromethanesulfonate (100 mg, 0.257 mmol) in DME (4 mL) were added Pd(PPh$_3$)$_4$ (15 mg, 0.0128 mmol), potassium carbonate (36 mg, 0.257 mmol), water (2 mL) and 2-(dimethylamino)pyrimidine-5-boronic acid pinacol ester (128 mg, 0.515 mmol). The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated and residue purified by reverse phase HPLC. $^1$H NMR (CD$_3$OD, TFA salt) δ (ppm): 7.98 (s, 2H), 7.22 (s. 1H), 7.08 (d, 1H), 6.99 (d, 1H), 6.80 (s, 1H), 4.65 (d, 1H), 4.31 (d, 1H), 3.80 (m, 1H), 3.51 (m, 1H), 3.01-3.81 (m, 11H), 2.40 (s, 3H), 2.37 (s, 3H).

Example 190

Preparation of Compound No. 280

To a solution of (4-(1-bromoprop-1-en-2-yl)phenyl)(methyl)sulfane (132 mg, 0.55 mmol) in DMF (1 mL) were added potassium phosphate (212 mg, 2 mmol), copper(I)iodide (9.5 mg, 0.05 mmol), L-proline (11.5 mg, 0.1 mmol) and 8-chloro-2,3,4,5-tetrahydro-2-methyl-1H-pyrido[4,3-b]indole (110 mg, 0.5 mmol) and the reaction mixture stirred at 85° C. for 16 h. Ice water was added into the reaction mixture and the solid obtained was filtered. The residue was purified by silica gel column chromatography (0-3% MeOH-DCM) to yield the title compound. $^1$H NMR (CD$_3$OD, oxalate salt) δ (ppm): 7.58 (m, 3H), 7.37 (d, 2H), 7.21 (s, 2H), 7.0 (s, 1H), 4.60 (s, 2H), 3.76 (s, 2H), 3.16 (m, 5H), 2.57 (s, 3H), 1.97 (s, 3H).

Example 191

Preparation of Compound No. 281

To a solution of 1-(1-bromoprop-1-en-2-yl)-4-(methylsulfonyl)benzene (150 mg, 0.55 mmol) in DMF (1 mL) were added potassium phosphate (212 mg, 2 mmol), copper(I) iodide (9.5 mg, 0.05 mmol), L-proline (11.5 mg, 0.1 mmol) and 8-chloro-2,3,4,5-tetrahydro-2-methyl-1H-pyrido[4,3-b] indole (110 mg, 0.5 mmol). The reaction mixture was stirred at 85° C. for 16 h. Ice water was added into the reaction mixture and the solid obtained was filtered. The residue was purified by silica gel column chromatography (0-3% MeOH-DCM) to yield the title compound. $^1$H NMR (CD$_3$OD, oxalate salt) δ (ppm): 8.04 (d, 2H), 7.91 (d, 2H), 7.58 (s, 1H), 7.21 (d, 2H), 7.19 (s, 1H), 4.57 (s, 2H), 3.70 (s, 2H), 3.15-3.20 (m, 8H), 2.01 (s, 3H).

Example 192

Preparation of Compound No. 282

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg, 0.257 mmol) in DME (4 mL) were added Pd(PPh$_3$)$_4$ (15 mg, 0.0128 mmol), potassium carbonate (36 mg, 0.257 mmol), water (2 mL) and 1H-benzimidazole-5-boronic acid pinacol ester (125 mg, 0.515 mmol). The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated and the residue was purified by reverse phase HPLC. $^1$H NMR (CD$_3$OD, TFA salt) δ (ppm): 9.37 (s, 1H), 8.02 (s, 1H), 7.90 (m, 2H), 7.37 (s, 1H), 7.16 (m, 3H), 4.76 (bs, 1H), 4.40 (bs, 1H), 3.90 (bs, 1H), 3.60 (bs, 1H), 3.18 (m, 5H), 2.41 (s, 3H), 2.07 (s, 3H).

Example 193

Preparation of Compound No. 283

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg) in DME (4 mL) were added Pd(PPh$_3$)$_4$ (15 mg), potassium carbonate (36 mg), water (1 mL) and 1-methylindole-5-boronic acid pinacol ester (132 mg). The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated and residue was purified by reverse phase HPLC. $^1$H NMR (CD$_3$OD, TFA salt) δ (ppm): 7.80 (d, 1H), 7.42 (d, 1H), 7.39 (d, 1H), 7.31 (s, 1H), 7.20 (s, 1H), 7.18 (d, 1H), 7.10 (d, 1H), 6.91 (s, 1H), 6.43 (d, 1H), 4.73 (d, 1H), 4.38 (d, 1H), 3.81 (s, 4H), 3.60 (m, 1H), 3.17 (m, 5H), 2.42 (s, 3H), 1.98 (s, 3H).

Example 194

Preparation of Compound No. 284

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg) in DME (4 mL) were added Pd(PPh$_3$)$_4$ (15 mg), potassium carbonate (36 mg), water (1 mL) and 1-methylindole-5-boronic acid pinacol ester (132 mg). The reaction mixture was refluxed for 45 min. At that point, TLC showed no starting material. The reaction mixture was cooled to RT and the solvent removed under reduced pressure. The residue was dissolved in EtOAc and filtered through a sintered crucible. The filtrate was concentrated and residue purified by reverse phase HPLC. $^1$H NMR (CD$_3$OD, TFA salt) δ (ppm): 7.31 (d, 2H), 7.20 (s, 1H), 7.05 (m, 3H), 6.80 (d, 1H), 6.76 (s, 1H), 6.21 (d, 1H), 4.51 (d, 1H), 4.20 (d, 1H), 3.70 (s, 3H), 3.52 (m, 2H), 3.19 (m, 2H), 2.80 (s, 3H), 2.40 (s, 3H), 2.38 (s, 3H).

Example 195

Preparation of Compound No. 285

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol) in DME (4 mL) were added Pd(PPh$_3$)$_4$ (15 mg, 0.0128 mmol), potassium carbonate (36 mg, 0.257 mmol), water (2 mL) and 4-methylthiophene-2-boronic acid pinacol ester (115 mg, 0.515 mmol). The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated under vacuum and the residue was purified by reverse phase HPLC. $^1$H NMR (CD$_3$OD, TFA salt) δ (ppm): 7.30 (s, 1H), 7.18 (s, 1H), 7.05 (m, 3H), 6.98 (s, 1H), 4.71 (d, 1H), 4.40 (d, 1H), 3.82 (m, 1H), 3.57 (m, 1H), 3.18 (m, 2H), 3.10 (s, 3H), 2.41 (s, 3H), 2.23 (s, 3H), 1.87 (s, 3H).

Example 196

Preparation of Compound No. 286

To a degassed solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol) in DME (4 mL) were added P(PPh$_3$)$_4$ (15 mg, 0.0128 mmol), potassium carbonate (36 mg, 0.257 mmol), water (2 mL) and naphthalene-1-boronic acid (88 mg, 0.515 mmol). The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated and product isolated by reverse phase HPLC. $^1$H NMR (CD$_3$OD, TFA salt) δ (ppm): 7.92 (d, 1H), 7.78 (d, 1H), 7.67 (m, 1H), 7.29-7.41 (m, 5H), 7.13 (s, 1H), 7.0 (s, 1H), 6.98 (d, 1H), 4.40 (d, 1H), 4.11 (d, 1H), 3.51 (m, 1H), 3.21 (m, 1H), 2.80 (s, 3H), 2.71 (m, 2H), 2.42 (s, 3H), 2.37 (s, 3H).

Example 197

Preparation of Compound No. 287

To a solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol) in DME (4 mL) was added Pd(PPh$_3$)$_4$ (15 mg, 0.0128 mmol) and solution purged with nitrogen for 5 min. Potassium carbonate (36 mg, 0.257 mmol), water (2 mL) and 3-methylthiophene-2-boronic acid pinacol ester (115 mg, 0.515 mmol) were added followed by nitrogen purging. The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated under reduced pressure and residue purified by reverse phase HPLC. $^1$H NMR (CD$_3$OD, TFA salt) δ (ppm): 7.21 (d, 1H), 7.19 (s, 1H), 7.12 (d, 1H), 6.96 (d, 1H), 6.82 (s, 1H), 6.61 (d, 1H), 4.60 (d, 1H), 4.23 (d, 1H), 3.68 (m, 1H), 3.40 (m, 1H), 3.0 (s, 3H), 2.80 (m, 2H), 2.40 (s, 3H), 2.37 (s, 3H), 1.58 (s, 3H).

Example 198

Preparation of Compound Nos. 288 and 288a-b

A solution of 5-(2-(4-fluorophenyl)prop-1-enyl)-2,3,4,5-tetrahydro-2,8-dimethyl-1H-pyrido[4,3-b]indole and 5-(2-(4-fluorophenyl)allyl)-2,3,4,5-tetrahydro-2,8-dimethyl-1H-pyrido[4,3-b]indole (1.8 g, 5.38 mmol) and 10% Pd/C (180 mg) in MeOH-acetic acid (50 mL, 10:1) was hydrogenated in a Parr shaker at RT and 60 psi for 18 h. The reaction mixture was filtered through a Celite bed and the filtrate concentrated under reduced pressure. The residue was diluted with EtOAc (500 mL) and washed with satd. sodium bicarbonate solution (50 mL) and then brine. The organic layer was dried over anhydrous sodium sulfate concentrated under reduced pressure. The residue was purified by silica gel column chromatography (0 to 50% EtOAc in hexanes) to yield the title compound. $^1$HNMR (DMSO, Oxalate salt) δ (ppm):7.38-7.3 (d, 1H), 7.36 (bs, 1H), 7.19 (s, 2H),7.07 (bs, 2H), 6.97-6.95 (d, 1H), 4.53 (m,1H), 4.24-4.12 (m, 3H), 3.86 (m,1H), 3.25 (m, 1H), 3.06 (m, 1H), 2.98 (s, 3H), 2.78 (bs, 1H), 2.62 (bs, 1H), 2.33 (s, 3H), 1.14 (bs, 3H). Separation by chiral HPLC provided enantiomers 288a-b.

Example 199

Preparation of Compound Nos. 289 and 289a-b

A solution of 2,8-dimethyl-5-(2-(6-methylpyridin-3-yl)prop-1-enyl)-2,3,4,5-tetrahydro-1H-pyrido[4,3-b]indole (100 mg) and 10% Pd/C (20 mg) in MeOH (5 mL) was hydrogenated in a Parr shaker at RT and 50 psi for 72 h. The progress of reaction was monitored by LCMS. The reaction mass was filtered through a Celite bed and the filtrate concentrated under reduced pressure. The residue was purified by reverse phase HPLC to yield the title compound. $^1$HNMR (CD$_3$OD, TFA salt) δ (ppm): 8.30 (m, 2H), 7.70 (s, 1H), 7.20 (s, 1H), 7.10 (d, 1H), 6.98 (d, 1H), 4.60 (m, 2H), 4.30 (m, 3H), 3.80 (m, 2H), 3.60 (m, 2H), 3.10 (s, 3H), 2.62 (s, 3H), 2.38 (s, 3H), 1.42 (d, 3H). Separation by chiral HPLC provided enantiomers 289a-b.

Example 200

Preparation of Compound No. 290

To a solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol) in DME (4 mL) was added Pd(PPh$_3$)$_4$ (15 mg, 0.0128 mmol) and solution purged with nitrogen for 5 min. Potassium carbonate (72 mg, 0.515 mmol), water (2 mL) and indazole-4-boronic acid.HCl (102 mg, 0.515 mmol) were added followed by nitrogen purging. The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated under vacuum and the product isolated by reverse phase HPLC. $^1$H NMR (CD$_3$OD, TFA salt) δ (ppm): 7.57 (s, 1H), 7.40 (d, 1H), 7.31 (m, 2H), 7.12 (s, 1H), 7.05 (d, 1H), 7.0 (s, 2H), 4.51 (d, 1H), 4.17 (d, 1H), 3.58 (m, 1H), 3.21 (m, 1H), 2.81 (s, 3H), 2.60 (m, 2H), 2.41 (s, 3H), 2.38 (s, 3H).

Example 201

Preparation of Compound No. 291

To a solution of [(E,Z)-1-(2,8-dimethyl-3,4-dihydro-1H-pyrido[4,3-b]indol-5(2H)-yl)prop-1-en-2-yl trifluoromethanesulfonate] (100 mg, 0.257 mmol) in DME (4 mL) was added Pd(PPh$_3$)$_4$ (15 mg, 0.0128 mmol) and solution purged with nitrogen for 5 min. Potassium carbonate (36 mg, 0.257 mmol), water (2 mL) and 4-methylthiophene-2-boronic acid pinacol ester (115 mg, 0.515 mmol) were added followed by nitrogen purging. The reaction mixture was refluxed for 45 min. At that point, TLC showed no starting material. The reaction mixture was cooled to RT and the solvent evaporated under reduced pressure. The residue was dissolved in EtOAc and filtered through a sintered crucible. The filtrate was concentrated under vacuum and the product isolated by reverse phase HPLC. $^1$H NMR (CD$_3$OD, TFA salt) δ (ppm): 7.23 (s, 1H), 7.08 (d, 1H), 7.00 (d, 1H), 6.85 (s, 1H), 6.78 (s, 1H), 6.55 (s, 1H), 4.73 (d, 1H), 4.38 (d, 1H), 3.71 (m, 1H), 3.42 (m, 1H), 3.05 (s, 3H), 2.97 (m, 1H), 2.80 (m, 1H), 2.42 (s, 3H), 2.38 (s, 3H), 2.20 (s, 3H).

Example 202

Preparation of Compound No. 292

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg, 0.257 mmol) in DME (2 mL) were added Pd(PPh$_3$)$_4$ (20 mg, 0.017 mmol), potassium carbonate (110 mg, 0.77 mmol), water (1 mL) and isoquinoline-4-boronic acid (89 mg, 0.515 mmol). The reaction mixture was refluxed for 45 min. At that point, TLC showed no starting material. The reaction mixture was cooled to RT and diluted with EtOAc. The aqueous layer was extracted with EtOAc (3×6 mL) and the combined organic layer was dried over anhydrous sodium sulfate. The solvent was removed under reduced pressure and residue was purified by reverse phase HPLC. $^1$H NMR (CD$_3$OD, TFA salt) δ (ppm): 9.8 (s, 1H), 8.78 (s, 1H), 8.6 (d, 1H), 8.46 (d, 1H), 8.38 (dd, 1H), 8.17 (dd, 1H), 7.4 (m, 2H), 7.2 (d, 1H), 7.02 (s, 1H), 4.8 (d, 1H), 4.41 (d, 1H), 3.82 (m, 1H), 3.62 (m, 1H), 3.36 (m, 2H), 3.19 (s, 3H), 2.41 (s, 3H), 2.18 (s, 3H).

Example 203

Preparation of Compound No. 293

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg, 0.257 mmol) and potassium carbonate (110 mg, 0.796 mmol), in DME (2 mL)-water (1 mL) were added Pd(PPh$_3$)$_4$ (20 mg, 0.017 mmol) and thianaphthene-2-boronic acid (91.4 mg, 0.514 mmol) followed by nitrogen purging. The reaction mixture was refluxed for 45 min. At that point, TLC showed no starting material. The reaction mixture was cooled to RT and diluted with EtOAc. The aqueous layer was extracted with EtOAc (3×6 mL) and the combined organic layer dried over anhydrous sodium sulfate. The solvent was removed under reduced pressure to afford crude product which was purified by reverse phase HPLC. $^1$H NMR (CD$_3$OD, TFA salt) δ (ppm): 7.78 (d, 1H), 7.52 (d, 1H), 7.5 (s, 1H), 7.32 (s, 1H), 7.2-7.3 (m, 2H), 7.18 (d, 1H), 7.03 (d, 1H), 6.78 (s, 1H), 4.7 (d, 1H), 4.4 (d, 1H), 3.7 (m, 1H), 3.43 (m, 1H), 3.08 (s, 3H), 2.8 (m, 2H), 2.49 (s, 3H), 2.41 (s, 3H).

Example 204

Preparation of Compound No. 294

To a solution of 2,8-dimethyl-2,3,4,5-tetrahydro-1H-pyrido[4,3-b]indole (200 mg, 1.0 mmol) in NMP (1 mL) were added powdered KOH (392 mg, 7.0 mmol) and 3-vinyl-benzo[b]thiophene (320 mg, 2.0 mmol). The reaction mixture was stirred at 90° C. for 5 h. The reaction mixture was diluted with water (15 mL) and extracted with EtOAc (3×20 mL). The combined organic layer was washed with water (5×25 mL), dried over anhydrous sodium sulfate and concentrated. The residue was purified by silica gel column chromatography (3% MeOH-DCM) followed by reverse phase HPLC to yield 5-(2-benzo[b]thiophen-3-yl-ethyl)-2,8-dimethyl-2,3,4,5-tetrahydro-1H-pyrido[4,3-b]indole. $^1$H NMR (CDCl$_3$, freebase) δ (ppm): 7.82 (d, 1H), 7.6 (d, 1H), 7.38 (m, 2H), 7.2 (m, 2H), 7.0 (d, 1H), 6.93 (s, 1H), 4.3 (t, 2H), 3.62 (s, 2H), 3.5 (s, 3H), 3.21 (t, 2H), 2.63 (t, 2H), 2.41 (m, 5H).

Example 205

Preparation of Compound No. 295

To a solution of 3-(1-bromoprop-1-en-2-yl)phenyl)(methyl)sulfane (300 mg, 1.2 mmol) in DMF (2 mL) were added potassium phosphate (424 mg, 2 mmol), copper(I)iodide (19 mg, 0.1 mmol), L-proline (23 mg, 0.2 mmol) and 8-chloro-2,3,4,5-tetrahydro-2-methyl-1H-pyrido[4,3-b]indole (220 mg, 1 mmol). The reaction mixture was stirred at 140° C. for 16 h. Ice water was added to the reaction mixture and extracted with EtOAc (3×15 mL). The combined organic layer was washed with water (2×10 mL), dried and concentrated. The residue was purified by silica gel column chromatography (0-3% MeOH-DCM) followed by reverse phase HPLC to yield the title compound. $^1$H NMR (CD$_3$OD, TFA salt) δ (ppm): 7.57 (d, 1H), 7.5 (d, 1H), 7.38-7.42 (m, 2H), 7.3 (d, 1H), 7.2 (m, 2H), 6.97 (s, 1H), 4.7 (d, 1H), 4.4 (d, 1H), 3.82 (m, 1H), 3.6 (m, 1H), 3.1 (m, 5H), 2.5 (s, 3H), 1.98 (s, 3H).

Example 206

Preparation of Compound No. 296

To a solution of 1-(1-bromoprop-1-en-2-yl)-3-(methylsulfonyl)benzene (297 mg, 1.1 mmol) in DMF (2 mL) were added potassium phosphate (424 mg, 2 mmol), copper(I) iodide (19 mg, 0.1 mmol), L-proline (23 mg, 0.2 mmol) and 8-chloro-2,3,4,5-tetrahydro-2-methyl-1H-pyrido[4,3-b]indole (220 mg, 1 mmol) and purged nitrogen for 2 min and heated at 90° C. for 16 h. Ice water (5 mL) was added and filtered the solid obtained and washed with water (2×10 mL). Product was purified on silica column (100-200 mesh) using 0-3% MeOH:DCM as eluant. The compound was further purified through reverse phase HPLC. Yield: 49.26 mg (freebase). $^1$H NMR (CD$_3$OD, freebase) δ (ppm): 8.2 (s, 1H), 7.98 (m, 2H), 7.7 (dd, 1H), 7.48 (s, 1H), 7.18 (m, 2H), 7.1 (s, 1H), 4.2 (s, 2H), 3.4 (s, 2H), 3.2 (s, 3H), 3.1 (s, 2H), 2.9 (s, 3H), 1.8 (s, 3H).

Example 207

Preparation of Compound No. 297

To a degassed stirred solution of 2,8-dimethyl-5-(6-methyl-pyridin-2-ylethynyl)-2,3,4,5-tetrahydro-1H-pyrido[4,3-b]indole (100 mg, 0.317 mmol) in MeOH (5 mL) was added Pd/C (35 mg, 35% w/w) and purged the reaction mixture with H$_2$ gas at RT for 2 h. The progress of reaction was monitored by TLC and NMR. Reaction mass was filtered through a Celite bed washed with MeOH (3×5 mL). Filtrate was concentrated under reduced pressure and residue was purified by reverse phase HPLC to yield 2,8-dimethyl-5-[2-(6-methyl-pyridin-2-yl)-ethyl]-2,3,4,5-tetrahydro-1H-pyrido[4,3-b]indole. $^1$H NMR (CD$_3$OD, TFA salt) δ (ppm): 8.2 (dd, 1H), 7.63 (d, 1H), 7.57 (d, 1H), 7.21 (d, 1H), 7.02 (d, 1H), 6.96 (d, 1H), 4.7 (d, 1H), 4.58 (t, 2H), 4.37 (d, 1H), 3.82 (m, 1H), 3.57 (m, 1H), 3.4 (t, 2H), 3.2 (m, 2H), 3.18 (s, 3H), 2.61 (s, 3H), 2.4 (s, 3H).

Example 208

Preparation of Compound No. 298

To a solution of 2,8-dimethyl-2,3,4,5-tetrahydro-1H-pyrido[4,3-b]indole (100 mg, 0.5 mmol) was in NMP (1 mL) were added powdered KOH (196 mg, 3.5 mmol) and dimethyl-(3-vinyl-phenyl)-amine (147 mg, 1.0 mmol) and the reaction mixture stirred at 100° C. for 16 h. The progress of reaction was monitored by TLC and LCMS. The reaction mixture was diluted with water (15 mL) and extracted with EtOAc (3×25 mL). The combined organic layer was washed with water (5×20 mL), dried over anhydrous sodium sulfate and concentrated. The residue was purified by silica gel column chromatography (0-3% MeOH-DCM) to yield {3-[2-(2,8-dimethyl-1,2,3,4-tetrahydro-pyrido[4,3-b]indol-5-yl)-ethyl]-phenyl}-dimethyl-amine. $^1$H NMR (CDCl$_3$, freebase) δ (ppm): 7.21 (m, 2H), 7.18 (dd, 1H), 7.0 (d, 1H), 6.6 (d, 1H), 6.43 (d, 1H), 6.21 (s, 1H), 4.2 (t, 2H), 3.71 (s, 2H), 2.90 (t, 2H), 2.85 (s, 3H), 2.80 (m, 4H), 2.57 (s, 6H), 2.41 (s, 3H).

Example 209

Preparation of Compound No. 299

To a degassed stirred solution of 2,8-dimethyl-5-(5-methyl-pyridin-2-ylethynyl)-2,3,4,5-tetrahydro-1H-pyrido[4,3-b]indole (110 mg, 0.349 mmol) in MeOH (5 mL) was added Pd/C (40 mg, 35% w/w) and purged the reaction mixture with H$_2$ gas at RT for 2 h. The progress of reaction was monitored by TLC and NMR. Reaction mass was filtered through a Celite bed washed with MeOH (3×5 mL). Filtrate was concentrated under reduced pressure and residue was purified by reverse phase HPLC to yield 2,8-dimethyl-5-[2-(5-methyl-pyridin-2-yl)-ethyl]-2,3,4,5-tetrahydro-1H-pyrido[4,3-b]indole. $^1$H NMR (CD$_3$OD, TFA salt) δ (ppm): 8.42 (s, 1H), 8.02 (d, 1H), 7.48 (d, 1H), 7.21 (s, 1H), 7.12 (d, 1H), 6.98 (d, 1H), 4.67 (d, 1H), 4.5 (t, 2H), 4.3 (d, 1H), 3.8 (m, 1H), 3.5 (m, 1H), 3.38 (t, 2H), 3.1 (m, 5H), 2.41 (s, 3H), 2.39 (s, 3H).

Example 210

Preparation of Compound No. 300

To a degassed stirred solution of 5-(2-bromocyclopent-1-enyl)-2,8-dimethyl-2,3,4,5-tetrahydro-1H-pyrido[4,3-b]indole (100 mg, 0.29 mmol), 3-pyridinylboronic acid (71 mg, 0.577 mmol) and potassium carbonate (120 mg, 0.87 mmol) in 1,2-dimethoxyethane (4 mL)-water (2 mL) was added Pd(PPh$_3$)$_4$ (16 mg, 0.0147 mmol). The reaction mixture was stirred at 90° C. for 45 min. The reaction mixture concentrated, residue diluted with water (20 mL) and extracted with EtOAc (50 mL). The organic layer was dried over anhydrous sodium sulfate and concentrated under reduced pressure. The residue was purified by reverse phase HPLC to yield 2,8-dimethyl-5-(2-(pyridin-3-yl)cyclopent-1-enyl)-2,3,4,5-tetrahydro-1H-pyrido[4,3-b]indole. $^1$H NMR (CD$_3$OD, TFA salt) δ (ppm): 8.68 (d, 1H), 8.1 (d, 1H), 7.9 (m, 1H), 7.8 (m, 1H), 7.3 (s, 1H), 6.9-7.1 (m, 2H), 4.7 (m, 1H), 4.4 (m, 1H), 3.8 (m, 1H), 3.58 (m, 1H), 2.8-3.3 (m, 9H), 2.22-2.4 (m, 5H).

Example 211

Preparation of Compound No. 301

To a degassed stirred solution of 5-(2-bromocyclopent-1-enyl)-2,8-dimethyl-2,3,4,5-tetrahydro-1H-pyrido[4,3-b]indole (100 mg, 0.29 mmol), 4-fluorophenylboronic acid (81 mg, 0.578 mmol) and potassium carbonate (120 mg, 0.87 mmol) in 1,2-dimethoxyethane (4 mL)-water (2 mL) was added Pd(PPh$_3$)$_4$ (17 mg, 0.0147 mmol). The reaction mixture was stirred at 90° C. for 45 min. The reaction mixture concentrated to dryness, residue diluted with water (20 mL) and extracted with EtOAc (50 mL). The organic layer was dried over anhydrous sodium sulfate, concentrated under reduced pressure. The residue was purified by reverse phase HPLC to yield 5-(2-(4-fluorophenyl)cyclopent-1-enyl)-2,8-dimethyl-2,3,4,5-tetrahydro-1H-pyrido[4,3-b]indole. $^1$H NMR (CD$_3$OD, TFA salt) δ (ppm): 7.3 (s, 1H), 7.17 (d, 1H), 7.02 (d, 1H), 6.8-6.98 (m, 4H), 4.7 (d, 1H), 4.3 (d, 1H), 3.65 (m, 1H), 3.41 (m, 1H), 2.9-3.18 (m, 7H), 2.52-2.77 (m, 2H), 2.45 (s, 3H), 2.21 (m, 2H).

Example 212

Preparation of Compound No. 302

To a degassed stirred solution of 5-(2-bromocyclopent-1-enyl)-2,8-dimethyl-2,3,4,5-tetrahydro-1H-pyrido[4,3-b]indole (100 mg, 0.29 mmol), 3-methylthiophene-2-boronic acid pinacol ester (129 mg, 0.575 mmol) and potassium carbonate (120 mg, 0.87 mmol) in 1,2-dimethoxyethane (4 mL)-water (2 mL) was added Pd(PPh$_3$)$_4$ (16 mg, 0.0147 mmol). The reaction mixture was stirred at 90° C. for 45 min. The solvent was under reduced pressure, residue diluted with water (20 mL) and extracted with EtOAc (50 mL). The organic layer was dried over anhydrous sodium sulfate and concentrated. The residue was purified by reverse phase HPLC to yield 2,8-dimethyl-5-(2-(3-methylthiophen-2-yl)cyclopent-1-enyl)-2,3,4,5-tetrahydro-1H-pyrido[4,3-b]indole. $^1$H NMR (CD$_3$OD, TFA salt) δ (ppm): 7.24 (s, 1H), 7.1-7.2 (m, 2H), 7.0 (dd, 1H), 6.6 (s, 1H), 4.6 (m, 1H), 4.4 (m, 1H), 3.64 (m, 1H), 3.2 (m, 1H), 2.8-3.17 (m, 7H), 2.6 (t, 2H), 2.4 (s, 3H), 2.2 (t, 2H), 1.8 (m, 3H).

Example 213

Preparation of Compound No. 303

To a degassed stirred solution of 5-(2-bromocyclopent-1-enyl)-2,8-dimethyl-2,3,4,5-tetrahydro-1H-pyrido[4,3-b]indole (100 mg, 0.29 mmol), 2-(dimethylamino)pyrimidine-5-boronic acid pinacol ester (129 mg, 0.578 mmol) and potassium carbonate (120 mg, 0.87 mmol) in 1,2-dimethoxyethane (4 mL)-water (2 mL) was added Pd(PPh$_3$)$_4$ (16 mg, 0.0147 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate and concentrated. The residue was purified by reverse phase HPLC to yield 5-(2-(2,8-dimethyl-3,4-dihydro-1H-pyrido[4,3-b]indol-5(2H)-yl)cyclopent-1-enyl)-N,N-dimethylpyrimidin-2-amine. $^1$H NMR (CD$_3$OD, TFA salt) δ (ppm): 7.8 (d, 2H), 7.3 (s, 1H), 6.98-7.1 (m, 2H), 4.7 (m, 1H), 4.38 (m, 1H), 3.8 (m, 1H), 3.5 (m, 1H), 2.78-3.1 (m, 15H), 2.4 (s, 3H), 2.2 (m, 2H).

Example 214

Preparation of Compound No. 304

To a degassed stirred solution of 5-(2-bromocyclopent-1-enyl)-2,8-dimethyl-2,3,4,5-tetrahydro-1H-pyrido[4,3-b]indole (100 mg, 0.29 mmol), 4-methylthiophene-2-boronic acid pinacol ester (129 mg, 0.578 mmol) and potassium carbonate (120 mg, 0.87 mmol) in 1,2-dimethoxyethane (4 mL)-water (2 mL) was purged with nitrogen followed by addition of Pd(PPh$_3$)$_4$ (16 mg, 0.0147 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate and concentrated. The residue was purified by reverse phase HPLC to yield 2,8-dimethyl-5-(2-(4-methylthiophen-2-yl)cyclopent-1-enyl)-2,3,4,5-tetrahydro-1H-pyrido[4,3-b]indole. $^1$H NMR (CD$_3$OD, TFA salt) δ (ppm): 7.3 (s, 1H), 7.0 (m, 3H), 6.78 (s, 1H), 4.7 (m, 1H), 4.4 (m, 1H), 3.8 (m, 1H), 3.5 (m, 1H), 3.37 (s, 3H), 3.03 (m, 2H), 2.83 (m, 2H), 2.61 (m, 2H), 2.4 (s, 3H), 2.2 (m, 2H), 2.17 (s, 3H).

Example 215

Preparation of Compound No. 305

A solution of 5-(2-bromocyclopent-1-enyl)-2,8-dimethyl-2,3,4,5-tetrahydro-1H-pyrido[4,3-b]indole (100 mg, 0.29 mmol), benzo[b]thien-2-ylboronic acid (103 mg, 0.578 mmol) and potassium carbonate (120 mg, 0.87 mmol) in 1,2-dimethoxyethane (4 mL)-water (2 mL) was purged with nitrogen followed by addition of Pd(PPh$_3$)$_4$ (16 mg, 0.0147 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate and concentrated. The residue was purified by reverse phase HPLC to yield 5-(2-(benzo[b]thiophen-2-yl)cyclopent-1-enyl)-2,8-dimethyl-2,3,4,5-tetrahydro-1H-pyrido[4,3-b]indole. $^1$H NMR (CD$_3$OD, TFA salt) δ (ppm): 7.2 (d, 1H), 7.5 (d, 1H), 7.38 (s, 1H), 7.2-7.3 (m, 3H), 7.1 (d, 1H), 7.04 (d, 1H), 4.4 (m, 2H), 3.6 (m, 2H), 3.2 (m, 2H), 3.1 (s, 3H), 2.9 (m, 2H), 2.7 (m, 2H), 2.41 (s, 3H), 2.3 m, 2H).

Example 216

Preparation of Compound No. 306

A solution of 5-(2-bromocyclopent-1-enyl)-2,8-dimethyl-2,3,4,5-tetrahydro-1H-pyrido[4,3-b]indole (100 mg, 0.29 mmol), naphthalene-1-boronic acid (99 mg, 0.575 mmol) and potassium carbonate (120 mg, 0.87 mmol) in mixture of 1,2-dimethoxyethane (4 mL)-water (2 mL) was purged with nitrogen followed by addition of Pd(PPh$_3$)$_4$ (16 mg, 0.0147 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate and concentrated. The residue was purified by reverse phase HPLC to yield 2,8-dimethyl-5-(2-(naphthalen-1-yl)cyclopent-1-enyl)-2,3,4,5-tetrahydro-1H-pyrido[4,3-b]indole. $^1$H NMR (DMSO, TFA salt) δ (ppm): 8.0 (d, 1H), 7.8 (d, 1H), 7.79 (d, 1H), 7.3-7.5 (m, 5H), 7.1 (s, 1H), 6.9 (d, 1H), 4.21 (m, 2H), 3.4 (m, 2H), 2.77-3.0 (m, 9H), 2.3 (m, 5H).

Example 217

Preparation of Compound No. 307

To a solution of 2,8-dimethyl-2,3,4,5-tetrahydro-1H-pyrido[4,3-b]indole (150 mg, 0.75 mmol) in NMP (1 mL) were added powdered KOH (294 mg, 5.25 mmol) and 2-methyl-5-vinyl-thiophene (186 mg, 1.50 mmol), and the reaction mixture stirred at 90° C. for 5 h. The reaction mixture was diluted with water (15 mL) and extracted with EtOAc (3×20 mL). The combined organic layer was washed with water (5×25 mL), dried over anhydrous sodium sulfate and concentrated under reduced pressure. The residue was purified by silica gel column chromatography (3% MeOH-DCM) followed by reverse phase HPLC to yield 2,8-dimethyl-5-[2-(5-methyl-thiophen-2-yl)-ethyl]-2,5-dihydro-1H-pyrido[4,3-b]indole. $^1$H NMR (CD$_3$OD, TFA salt) δ (ppm): 7.3 (d, 1H), 7.22 (s, 1H), 7.08 (d, 1H), 6.5 (d, 1H), 6.3 (d, 1H), 4.6 (d, 1H), 4.2-4.4 (m, 3H), 3.7 (m, 2H), 3.2 (m, 3H), 3.03 (s, 3H), 2.7 (m, 1H), 2.38-2.42 (m, 6H).

Example 218

Preparation of Compound No. 308

To a solution of 2,8-dimethyl-2,3,4,5-tetrahydro-1H-pyrido[4,3-b]indole (250 mg, 1.25 mmol) in NMP (1 mL) were added powdered KOH (490 mg, 8.75 mmol) and 3-methyl-2-vinyl-thiophene (310 mg, 2.25 mmol), and the reaction mixture stirred at 90° C. for 5 h. The reaction mixture was diluted with water (20 mL) and extracted with EtOAc (3×20 mL). The combined organic layer was washed with water (5×25 mL), dried over anhydrous sodium sulfate and concentrated under reduced pressure. The residue was purified by reverse phase HPLC to yield 2,8-dimethyl-5-[2-(3-methyl-thiophen-2-yl)-ethyl]-2,5-dihydro-1H-pyrido[4,3-b]indole. $^1$H NMR (CD$_3$OD, TFA salt) δ (ppm): 7.25 (d, 1H), 7.22 (s, 1H), 7.1 (d, 1H), 7.02 (d, 1H), 6.7 (d, 1H), 4.41 (s, 2H), 4.3 (t, 2H), 2.42 (bs, 2H), 3.2 (t, 2H), 3.0 (s, 3H), 2.61 (bs, 2H), 2.4 (s, 3H), 1.6 (s, 3H).

Example 219

Preparation of Compound No. 309

To a degassed stirred solution of 5-(2-bromocyclopent-1-enyl)-2,8-dimethyl-2,3,4,5-tetrahydro-1H-pyrido[4,3-b]indole (100 mg, 0.29 mmol), 1-methyl-1H-pyrazole-5-boronic acid pinacol ester (81 mg, 0.576 mmol) and potassium carbonate (120 mg, 0.87 mmol) in 1,2-dimethoxyethane (4 mL) and water (2 mL) was added Pd(PPh$_3$)$_4$ (17 mg, 0.0147 mmol). The reaction mixture was stirred at 90° C. for 45 min. The solvent was removed under reduced pressure, residue diluted with water (20 mL) and extracted with EtOAc (50 mL). The organic layer was dried over anhydrous sodium sulfate and concentrated. The residue was purified by reverse HPLC to yield 2,8-dimethyl-5-(2-(1-methyl-1H-pyrazol-5-yl)cyclopent-1-enyl)-2,3,4,5-tetrahydro-1H-pyrido[4,3-b]indole. $^1$H NMR (CDCl$_3$, freebase) δ (ppm): 7.32 (s, 1H), 7.18 (s, 1H), 7.0 (d, 1H), 6.9 (d, 1H), 6.01 (s, 1H), 3.6 (s, 2H), 3.2 (s, 3H), 3.0 (m, 4H), 2.7 (m, 4H), 2.52 (s, 3H), 2.4 (s, 3H), 2.2 (m, 2H).

Example 220

Preparation of Compound No. 310

To a solution of 1-(1-bromoprop-1-en-2-yl)-3-(methylsulfonyl)benzene (148 mg, 0.55 mmol) in DMF (1 mL) were added potassium phosphate (212 mg, 2 mmol), copper(I) iodide (9.5 mg, 0.05 mmol) and L-proline (11.5 mg, 0.1 mmol). The solution was de-aerated by purging nitrogen followed by addition of 2,3,4,5-tetrahydro-2,6,8-trimethyl-1H-pyrido[4,3-b]indole (114.5 mg, 0.5 mmol). The reaction mixture was again purged with nitrogen for two minutes and then stirred at 85° C. overnight. Ice water was poured into the reaction mixture and the solid obtained was filtered. The crude product was purified by column chromatography using 0-3% MeOH:DCM as eluant. The compound was further purified through reverse phase HPLC to yield the title compound. $^1$H NMR (CD$_3$OD, TFA salt) δ (ppm): 8.08 (s, 1H), 8.0 (m, 2H), 7.77 (t, 1H), 7.38 (s, 1H), 7.1 (s, 1H), 6.8 (s, 1H), 4.7 (d, 1H), 4.37 (d, 1H), 3.82 (m, 1H), 3.58 (m, 1H), 3.0-3.2 (m, 8H), 2.73 (s, 3H), 2.38 (s, 3H), 1.97 (s, 3H).

Example 221

Preparation of Compound No. 311

To a degassed solution of (E,Z)-1-(2,8-dimethyl-3,4-dihydro-1H-pyrido[4,3-b]indol-5(2H)-yl)prop-1-en-2-yl trifluoromethanesulfonate (100 mg, 0.257 mmol) and potassium carbonate (110 mg, 0.7 mmol) in DME-water (2:1) were added Pd(PPh$_3$)$_4$ (20 mg, 0.0130 mmol) and 6-(4,4,5,5-tetramethyl-1,3,2-dioxaborolan-2-yl)isoquinoline (100 mg, 0.392 mmol), followed by nitrogen purging for 5 min. The reaction mixture was refluxed for 45 min. At that point, TLC showed no starting material. The reaction mixture was cooled to RT and extracted with EtOAc. The combined organic layer was dried over anhydrous sodium sulfate and concentrated under reduced pressure. The residue was purified by reverse phase HPLC. $^1$H NMR (CD$_3$OD, TFA salt) δ (ppm): 9.77 (s, 1H), 8.6 (d, 1H), 8.44-8.58 (m, 3H), 8.4 (d, 1H), 7.57 (s, 1H), 7.37 (s, 1H), 7.2 (d, 1H), 7.17 (d, 1H), 4.71 (d, 1H), 4.4 (d, 1H), 3.9 (m, 1H), 3.6 (m, 1H), 3.2 (m, 5H), 2.42 (s, 3H), 2.2 (s, 3H).

Example 222

Preparation of Compound No. 312

To a solution of 4-(1-bromoprop-1-en-2-yl)pyridine (238 mg, 1.2 mmol) in DMF (2 mL) were added potassium phosphate (424 mg, 2 mmol), copper(I)iodide (19 mg, 0.1 mmol), L-proline (23 mg, 0.2 mmol) and 2,3,4,5-tetrahydro-2,6,8-trimethyl-1H-pyrido[4,3-b]indole (214 mg, 1 mmol). The reaction mixture was degassed using nitrogen and stirred overnight at 85° C. Ice water (5 mL) was added into the reaction mixture and the solid obtained was filtered. The residue was washed with water (2×10 mL) and purified by column chromatography using neutral alumina and 0-1% MeOH:DCM as eluant to yield the desired compound. $^1$H NMR (CD$_3$OD, HCl salt) δ (ppm): 8.9 (d, 2H), 8.39 (d, 2H), 7.98 (s, 1H), 7.17 (s, 1H), 6.86 (s, 1H), 4.7 (d, 1H), 4.4 (d, 1H), 3.82 (m, 1H), 3.6 (m, 1H), 3.2 (m, 4H), 3.0 (m, 1H), 2.5 (s, 3H), 2.4 (s, 3H), 2.1 (s, 3H).

Example 223

Preparation of Compound No. 313

A mixture of 5-ethynyl-2,8-dimethyl-2,3,4,5-tetrahydro-1H-pyrido[4,3-b]indole (194 mg, 0.866 mmol, 5-bromo-isoquinoline (150 mg, 0.721 mmol, TBAF.3H$_2$O (680 mg, 2.15 mmol) and dichlorobis(triphenylphosphine) palladium(II) (25 mg, 0.035 mmol) was stirred at 85° C. for 5 min. The reaction mixture was diluted with water and extracted with EtOAc (3×40 mL). The organic layer was washed with water (5×30 mL), dried over anhydrous sodium sulfate and concentrated. The crude product was purified by column chromatography using silica (100:200) and 0.5% MeOH-DCM to yield 5-isoquinolin-5-ylethynyl-2,8-dimethyl-2,3,4,5-tetrahydro-1H-pyrido[4,3-b]indole. $^1$H NMR (CDCl$_3$, freebase) δ (ppm): 9.3 (s, 1H), 8.62 (d, 1H), 8.17 (d, 1H), 7.93 (dd, 2H), 7.6 (t, 1H), 7.57 (d, 1H), 7.23 (s, 1H), 7.17 (d, 1H), 3.65 (s, 2H), 3.07 (t, 2H), 2.93 (t, 2H), 2.6 (s, 3H), 2.42 (s, 3H).

Example 224

Preparation of Compound Nos. 314 and 314a-b

To a solution of 2,3,4,9-tetrahydro-2,6-dimethyl-1-phenyl-1H-pyrido[3,4-b]indole (100 mg, 0.362 mmol) in DMF (2 mL) were added sodium hydride (60 mg, 1.08 mmol) and 2-(6-methylpyridin-3-yl)ethyl 4-methylbenzenesulfonate (300 mg, 1.03 mmol). The reaction mixture was irradiated in a microwave reactor at 90° C. for 1 h. The reaction mixture was cooled to RT and quenched with water. The aqueous layer was extracted with EtOAc (3×10 mL). The organic layer was washed with water (2×10 mL), dried over anhydrous sodium sulfate and concentrated under reduced pressure to afford crude product, which was purified by reverse phase HPLC. The product is further purified by reverse phase HPLC followed by chiral HPLC separation to give enantiomers 314a and 314b. $^1$H NMR (CD$_3$OD, TFA salt) δ (ppm): 8.09 (s, 1H), 7.9 (d, 1H), 7.63 (t, 1H), 7.43-7.6 (m, 5H), 7.4 (s, 1H), 7.0 (m, 2H), 6.03 (s, 1H), 4.37 (t, 1H), 4.1 (m, 1H), 3.92 (m, 1H), 3.57-3.65 (m, 2H), 3.18 (t, 1H), 2.9 (bs, 3H), 2.63 (s, 3H), 2.6 (m, 2H), 2.4 (s, 3H). Separation by chiral HPLC provides enantiomers 314a-b.

Example 225

Preparation of Compound No. 315

To a solution of 7-chloro-2-methyl-2,3,4,5-tetrahydro-1H-pyrido[4,3-b]indole (100 mg, 0.453 mmol) in DMF (2 mL) were added sodium hydride (60 mg, 1.359 mmol) and 2-(6-methylpyridin-3-yl)ethyl 4-methylbenzenesulfonate (330 mg, 1.1322 mmol). The reaction mixture was irradiated in a microwave reactor at 90° C. for 1 h. The reaction mixture was cooled to RT and quenched with water. The aqueous layer was extracted with EtOAc (3×10 mL). The organic layer was washed with water (2×10 mL), dried over anhydrous sodium sulfate and concentrated under reduced pressure to afford crude product, which was purified by reverse phase HPLC. $^1$H NMR (CD$_3$OD, TFA salt) δ (ppm): 8.21 (s, 1H), 8.1 (d, 1H), 7.7 (d, 1H), 7.38 (d, 1H), 7.1 (s, 1H), 7.0 (d, 1H), 4.7 (d, 1H), 4.42 (t, 2H), 4.5 (d, 1H), 3.82 (m, 1H), 3.57 (m, 1H), 3.1-3.27 (m, 4H), 3.08 (s, 3H), 2.63 (s, 3H).

Example 226

Preparation of Compound No. 316

To a solution of 5-isoquinolin-5-ylethynyl-2,8-dimethyl-2,3,4,5-tetrahydro-1H-pyrido[4,3-b]indole (90 mg, 0.256 mmol) in MeOH (6 mL) were added 10% dry Pd—C (25 mg) and ammonium formate (81 mg, 1.282 mmol). The reaction mixture was refluxed for 2 h and filtered through Celite. The filtrate was concentrated under reduced pressure to afford crude product, which was purified by reverse phase HPLC to yield 20 mg of 5-(2-isoquinolin-5-yl-vinyl)-2,8-dimethyl-2,3,4,5-tetrahydro-1H-pyrido[4,3-b]indole. $^1$H NMR (CD$_3$OD, TFA salt) δ (ppm): 9.7 (s, 1H), 8.57 (d, 1H), 8.5 (d, 1H), 8.3 (d, 1H), 7.65 (t, 1H), 7.59 (d, 1H), 7.4 (d, 1H), 7.22 (d, 1H), 7.2 (s, 1H), 6.7 (m, 2H), 4.63 (d, 1H), 4.3 (d, 1H), 3.7 (m, 1H), 3.47 (m, 1H), 3.08 (s, 3H), 2.9-3.0 (m, 2H), 2.31 (s, 3H).

Example 227

Preparation of Compound No. 317

To a solution of 5-isoquinolin-5-ylethynyl-2,8-dimethyl-2,3,4,5-tetrahydro-1H-pyrido[4,3-b]indole (80 mg, 0.228 mmol) in MeOH (5 mL) were added 10% dry Pd—C (80 mg) and ammonium formate (72 mg, 1.14 mmol). The reaction mixture was refluxed for 4 h and filtered through Celite. The filtrate was concentrated under reduced pressure to afford crude product, which was purified by reverse phase HPLC to yield 20 mg of 2,8-dimethyl-5-[2-(1,2,3,4-tetrahydro-isoquinolin-5-yl)-ethyl]-2,3,4,5-tetrahydro-1H-pyrido[4,3-b]indole. $^1$H NMR (CD$_3$OD, TFA salt) δ (ppm): 7.21 (d, 1H), 7.18 (m, 2H), 7.1 (d, 1H), 7.0 (d, 1H), 6.93 (d, 1H), 4.7 (d, 1H), 4.2-4.4 (m, 5H), 3.7 (m, 1H), 3.2 (m, 3H), 3.08 (t, 2H), 3.02 (s, 3H), 2.83 (m, 1H), 2.6-2.8 (m, 3H), 2.4 (s, 3H).

Example 228

Preparation of Compound No. 318

To a solution of 2,8-dimethyl-2,3,4,5-tetrahydro-1H-pyrido[4,3-b]indole (250 mg, 1.255 mmol) in NMP (1 mL), was added powdered KOH (490 mg, 8.75 mmol). After stirring for 5 min, 3-methyl-4-vinyl-thiophene (310 mg, 2.50 mmol) was added into the reaction mixture, which was stirred at 85° C. for 16 h. The reaction mixture was diluted with water (15 mL) and extracted with EtOAc (3×20 mL). The organic layer was washed with water (6×30 mL), dried over anhydrous sodium sulfate and concentrated. The crude product was purified by column chromatography using silica (100:200) and 2% MeOH-DCM, followed by reverse phase HPLC to yield 1.10 mg of 2,8-dimethyl-5-[2-(4-methyl-thiophen-3-yl)-ethyl]-2,3,4,5-tetrahydro-1H-pyrido[4,3-b]indole. $^1$H NMR (CD$_3$OD, TFA salt) δ (ppm): 7.3 (d, 1H), 7.24 (s, 1H), 7.07 (d, 1H), 6.92 (s, 1H), 6.78 (s, 1H), 4.6 (d, 1H), 4.3 (m, 3H), 3.62 (m, 1H), 3.3 (m, 3H), 3.0 (m, 4H), 2.8 (m, 1H), 2.4 (s, 3H), 1.95 (s, 3H).

Example 229

Preparation of Compound No. 319

To a solution of 8,9-dichloro-2,3,4,5-tetrahydro-2-methyl-1H-pyrido[4,3-b]indole (100 mg, 0.392 mmol) in DMF (2 mL) were added sodium hydride (60 mg, 1.17 mmol) and 2-(6-methylpyridin-3-yl)ethyl 4-methylbenzenesulfonate (300 mg, 0.98 mmol). The reaction mixture was irradiated in a microwave reactor at 90° C. for 1 h. The reaction mixture was cooled to RT and quenched with water. The aqueous layer was extracted with EtOAc (3×10 mL). The organic layer was washed with water (2×10 mL), dried over anhydrous sodium sulfate and concentrated under reduced pressure to afford crude product, which was purified by reverse phase HPLC. $^1$H NMR (CD$_3$OD, TFA salt) δ (ppm): 8.39 (s, 1H), 8.2 (d, 1H), 7.7 (d, 1H), 7.2 (d, 2H), 5.1 (m, 1H), 4.6 (m, 1H), 4.43 (t, 2H), 3.82 (m, 1H), 3.5 (m, 1H), 3.2-3.3 (m, 4H), 3.1 (m, 3H), 2.7 (s, 3H).

Example 230

Preparation of Compound No. 320

To a degassed solution of 2,8-dimethyl-5-quinolin-3-yl-ethynyl-2,3,4,5-tetrahydro-1H-pyrido[4,3-b]indole (60 mg, 0.170 mmol) in MeOH (5 mL), were added Pd—C (30 mg, 50% w/w) and ammonium formate (54 mg, 0.857 mmol) under nitrogen. The reaction mixture was stirred at 75° C. for 1 h, filtered through a Celite bed and washed with MeOH (10 mL). The filtrate was concentrated under reduced pressure and residue was purified by reverse phase HPLC to yield the desired compound. $^1$H NMR (CD$_3$OD, TFA salt) δ (ppm): 8.6 (s, 2H), 8.02-8.18 (m, 3H), 7.82 (t, 1H), 7.2 (s, 1H), 6.98 (d, 1H), 6.77 (d, 1H), 4.68 (d, 1H), 4.56 (t, 2H), 4.3 (d, 1H), 3.8 (m, 1H), 3.45 (m, 1H), 3.4 (t, 2H), 3.21 (m, 1H), 3.1 (m, 4H), 2.3 (s, 3H).

Example 231

Preparation of Compound No. 321

A mixture of 5-ethynyl-2,8-dimethyl-2,3,4,5-tetrahydro-1H-pyrido[4,3-b]indole (260 mg, 1.160 mmol), 3-bromoquinoline (200 mg, 0.961 mmol), TBAF.3H$_2$O (1.1 g, 3.492 mmol) and dichloro bis(triphenylphosphine) palladium (II) (41 mg, 0.058 mmol) was stirred at 85° C. for 10 min. The reaction mixture was diluted with water and extracted with EtOAc (4×30 mL). The combined organic layer was washed with water (4×30 mL), dried over anhydrous sodium sulfate and concentrated under reduced pressure to afford crude product, which was purified by column chromatography using neutral alumina and 0.5% MeOH-DCM to yield 2,8-dimethyl-5-quinolin-3-ylethynyl-2,3,4,5-tetrahydro-1H-pyrido[4,3-b]indole. $^1$H NMR (CDCl$_3$, freebase) δ (ppm): 9.0 (s, 1H), 8.25 (s, 1H), 8.1 (d, 1H), 7.8 (d, 1H), 7.7 (t, 1H), 7.6 (t, 1H), 7.5 (d, 1H), 7.2 (s, 1H), 7.1 (d, 1H), 3.62 (s, 2H), 3.0 (t, 2H), 2.7 (t, 2H), 2.6 (s, 3H), 2.42 (s, 3H).

Example 232

Preparation of Compound No. 322

To a solution of 7,8-dichloro-2,3,4,5-tetrahydro-2-methyl-1H-pyrido[4,3-b]indole (100 mg, 0.392 mmol) in DMF (2 mL) were added sodium hydride (60 mg, 1.17 mmol) and 2-(6-methylpyridin-3-yl)ethyl 4-methylbenzenesulfonate (300 mg, 0.98 mmol). The reaction mixture was irradiated in a microwave reactor at 90° C. for 1 h. The reaction mixture was cooled to RT and quenched with water. The aqueous layer was extracted with EtOAc (3×10 mL). The organic layer was washed with water (2×10 mL), dried over anhydrous sodium sulfate and concentrated under reduced pressure to afford crude product, which was purified by reverse phase HPLC. $^1$H NMR (CD$_3$OD, TFA salt) δ (ppm): 8.37 (s, 1H), 8.18 (d, 1H), 7.7 (d, 1H), 7.61 (s, 1H), 7.39 (s, 1H), 4.68 (m, 1H), 4.48 (t, 2H), 4.37 (m, 1H), 3.92 (m, 1H), 3.57 (m, 1H), 3.2 (m, 4H), 3.1 (s, 3H), 2.7 (s, 3H).\

Example 233

Preparation of Compound No. 323

To a degassed solution of 2,8-dimethyl-5-quinolin-3-yl-ethynyl-2,3,4,5-tetrahydro-1H-pyrido[4,3-b]indole (60 mg, 0.170 mmol) in MeOH (5 mL), were added Pd—C (30 mg, 50% w/w) and ammonium formate (54 mg, 0.857 mmol) under nitrogen. The reaction mixture was stirred at 75° C. for 1 h, filtered through a Celite bed and washed with MeOH (10 mL). The filtrate was concentrated under reduced pressure to afford crude product, which was purified by reverse phase HPLC to yield the desired compound. $^1$H NMR (CD$_3$OD, TFA salt) δ (ppm): 8.3 (d, 2H), 8.0 (d, 1H), 7.9 (m, 2H), 7.70 (t, 1H), 7.3 (s, 1H), 7.21 (d, 1H), 6.98 (d, 1H), 6.82 (s, 2H), 4.78 (d, 1H), 4.4 (d, 1H), 3.8 (m, 1H), 3.58 (m, 1H), 3.1 (m, 5H), 2.38 (s, 3H).

Example 234

Preparation of Compound No. 324

To a solution of 2,8-dimethyl-2,3,4,5-tetrahydro-1H-pyrido[4,3-b]indole (200 mg, 1.0 mmol) in DCM (4 mL) were added powdered KOH (392 mg, 7.0 mmol) and phenylamine (111 mg, 1.2 mmol). The reaction mixture was stirred at 85° C. for 2 h. The reaction mixture was diluted with water (20 mL) and extracted with DCM (3×20 mL). The combined organic layer was washed with water (3×30 mL), dried over anhydrous sodium sulfate and concentrated under reduced pressure to afford crude material, which was purified by silica gel column chromatography (3% MeOH-DCM), followed by reverse phase HPLC to yield (2,8-dimethyl-1,2,3,4-tetrahydro-pyrido[4,3-b]indol-5-ylmethyl)-phenyl-amine (20 mg). $^1$H NMR (CD$_3$OD, freebase) δ (ppm): 7.4 (d, 1H), 7.07 (s, 1H), 7.0 (t, 2H), 6.97 (d, 1H), 6.67 (d, 2H), 6.6 (t, 1H), 5.42 (s, 2H), 3.7 (s, 2H), 3.07 (t, 2H), 2.9 (t, 2H), 2.58 (s, 3H), 2.4 (s, 3H).

Example 235

Preparation of Compound No. 325

To a solution of 6,9-dichloro-2-methyl-2,3,4,5-tetrahydro-1H-pyrido[4,3-b]indole (100 mg, 0.392 mmol), in DMF (2 mL) were added sodium hydride (60 mg, 1.3 mmol) and 2-(6-methylpyridin-3-yl)ethyl 4-methylbenzenesulfonate (285 mg, 0.980 mmol). The reaction mixture was irradiated in a microwave reactor at 90° C. for 1 h. The reaction mixture was cooled to RT, quenched with water and extracted with EtOAc (3×10 mL). The organic layer was washed with water (2×10 mL), dried over anhydrous sodium sulfate and concentrated under reduced pressure to afford crude product, which was purified by reverse phase HPLC. $^1$H NMR (CD$_3$OD, TFA salt) δ (ppm): 8.41 (s, 1H), 8.18 (d, 1H), 7.78 (d, 1H), 7.1 (d, 1H), 7.06 (d, 1H), 5.1 (m, 1H), 4.8 (t, 2H), 4.6 (m, 1H), 3.8 (m, 1H), 3.57 (m, 1H), 3.22 (m, 4H), 3.18 (s, 3H), 2.7 (s, 3H).

Example 236

Preparation of Compound No. 326

To a stirred solution of 3-(2,8-dimethyl-3,4-dihydro-1H-pyrido[4,3-b]indol-5(2H)-yl)propanethioamide (0.287 g, 1.0 mmol) in EtOH.HCl (3 mL) was added 2-bromo-4'-chloroacetophenone (0.349 g, 1.5 mmol). The reaction mixture was stirred at 82° C. for 16 h. Solvent was removed under reduced pressure. The residue was basified with 1N NaOH solution and extracted with EtOAc (50 mL). The organic layer was dried over anhydrous sodium sulfate and concentrated to afford crude product, which was purified by column chromatography to yield the desired product. $^1$H NMR (CDCl$_3$, freebase) δ (ppm): 7.8 (d, 2H), 7.4 (d, 2H), 7.3 (s, 1H), 7.2 (m, 2H), 6.98 (d, 1H), 4.46 (t, 2H), 3.6 (s, 2H), 3.4 (t, 2H), 2.1-2.78 (m, 4H), 2.53 (s, 3H), 2.4 (s, 3H).

Example 237

Preparation of Compound No. 327

To a de-aerated solution of 6-bromo-2,8-dimethyl-5-(2-(6-methylpyridin-3-yl)ethyl)-2,3,4,5-tetrahydro-1H-pyrido[4,3-b]indole (85 mg, 0.215 mmol) and potassium carbonate (89 mg, 0.642 mmol) in 1,2-dimethoxyethane-water (2:1) were added 3-methylthiophene-2-boronic acid pinacol ester (96 mg, 0.428 mmol) and Pd(PPh$_3$)$_4$ (17 mg, 0.015 mmol). The reaction mixture was stirred at 90° C. for 45 min and concentrated to dryness. The residue was dissolved in EtOAc (50 mL) and washed with water (20 mL). The organic layer was dried over anhydrous sodium sulfate and concentrated under reduced pressure to afford crude product, which was purified by reverse phase HPLC. $^1$H NMR (CD$_3$OD, TFA salt) δ (ppm): 8.0 (s, 1H), 7.77 (s, 2H), 7.47 (s, 1H), 7.38 (s, 1H), 7.02 (s, 1H), 6.9 (s, 1H), 4.78 (m, 1H), 4.38 (m, 1H), 4.1 (bs, 1H), 4.0 (m, 1H), 3.9 (bs, 1H), 3.6 (m, 1H), 3.1-3.27 (m, 5H), 2.8 (t, 2H), 2.7 (s, 3H), 2.4 (s, 3H), 1.99 (s, 3H).

Example 238

Preparation of Compound No. 328

A mixture of 2-bromo-5-methyl-pyridine (250 mg, 1.45 mmol), 5-ethynyl-2,8-dimethyl-2,3,4,5-tetrahydro-1H-pyrido[4,3-b]indole (391 mg, 1.74 mmol), TBAF.3H$_2$O (1.374 g, 4.36 mmol) and dichloro bistriphenylphosphine palladium (II) (51 mg, 0.072 mmol) was stirred at 85° C. for 10 min. The reaction mixture was poured into water and extracted with EtOAc (3×100 mL). The organic layer was washed with water (3×100 mL), dried over anhydrous sodium sulfate and concentrated. The residue was purified by column chromatography (neutral alumina, eluent-0.5% MeOH in DCM) to yield 2,8-dimethyl-5-(5-methyl-pyridin-2-ylethynyl)-2,3,4,5-tetrahydro-1H-pyrido[4,3-b]indole. $^1$H NMR (CDCl$_3$, free-base) δ (ppm): 8.41 (s, 1H), 7.5 (m, 2H), 7.4 (d, 1H), 7.18 (s, 1H), 7.08 (d, 1H), 3.6 (s, 2H), 3.0 (t, 2H), 2.83 (t, 2H), 2.58 (s, 3H), 2.42 (s, 3H), 2.37 (s, 3H).

Example 239

Preparation of Compound No. 329

To a degassed solution of 2,8-dimethyl-5-(2-(4,4,5,5-tetramethyl-1,3,2-dioxaborolan-2-yl)prop-1-en-1-yl)-2,3,4,5-tetrahydro-1H-pyrido[4,3-b]indole (276 mg, 0.753 mmol), 5-bromo-2-propylpyridine (100 mg, 0.502) and potassium carbonate (208 mg, 1.507 mmol) in DME (2 mL) and water (1 mL) was added Pd(PPh$_3$)$_4$ (40.6 mg, 0.035 mmol), followed by nitrogen purging. The reaction mixture was refluxed for 45 min. At that point, TLC showed no starting material. The reaction mixture was cooled to RT and diluted with EtOAc. The aqueous layer was extracted with EtOAc (3×6 mL) and the combined organic layer dried over anhydrous sodium sulfate. The solvent was removed under reduced pressure to afford crude product, which was purified by reverse phase HPLC. $^1$H NMR (CD$_3$OD, TFA salt) δ (ppm): 8.8 (s, 1H), 8.36 (d, 1H), 7.62 (d, 1H), 7.3 (s, 1H), 7.2 (s, 1H), 7.16 (d, 1H), 7.05 (d, 1H), 4.7 (d, 1H), 4.4 (d, 1H), 3.83 (bs, 1H), 3.4 (bs, 1H), 3.18 (m, 2H), 3.1 (s, 3H), 2.9 (t, 2H), 2.4 (s, 3H), 2.0 (s, 3H), 1.8 (m, 2H), 1.0 (t, 3H).

Example 240

Preparation of Compound No. 330

A mixture of 4-bromobenzenesulfonamide (200 mg, 0.84 mmol), 5-ethynyl-2,8-dimethyl-2,3,4,5-tetrahydro-1H-pyrido[4,3-b]indole (391 mg, 1.0 mmol), TBAF.3H$_2$O (793 mg, 2.5 mmol) and dichloro bis(triphenyl phosphine) palladium (II) (29 mg, 0.042 mmol) was stirred at 85° C. for 10 min. The reaction mixture was poured into water and extracted with EtOAc (3×50 mL). The organic layer was washed with water (3×100 mL), dried over anhydrous sodium sulfate and concentrated to afford crude material, which was purified by column chromatography using neutral alumina and 5% MeOH-DCM, followed by reverse phase HPLC to yield 4-(2,8-dimethyl-1,2,3,4-tetrahydro-pyrido[4,3-b]indol-5-ylethynyl)-benzenesulfonamide. $^1$H NMR (CD$_3$OD, HCl salt) δ (ppm): 7.92 (d, 2H), 7.7 (d, 2H), 7.58 (d, 1H), 7.38 (s, 1H), 7.23 (d, 1H), 4.7 (d, 1H), 4.4 (d, 1H), 3.96 (m, 1H), 3.63 (m, 1H), 3.37 (m, 2H), 3.18 (s, 3H), 2.42 (s, 3H).

Example 241

Preparation of Compound No. 331

To a degassed solution of (Z)-2,8-dimethyl-5-(2-(4,4,5,5-tetramethyl-1,3,2-dioxaborolan-2-yl)prop-1-en-1-yl)-2,3,4,5-tetrahydro-1H-pyrido[4,3-b]indole (140 mg, 0.382 mmol), 5-bromo-2-(trifluoromethyl)pyridine (87 mg, 0.382)and potassium carbonate (158 mg, 1.147 mmol) in DME (2 mL) and water (1 mL) was added Pd(PPh$_3$)$_4$ (20 mg, 0.017 mmol), followed by nitrogen purging. The reaction mixture was refluxed for 45 min. At that point, TLC showed no starting material. The reaction mixture was diluted with water and extracted with EtOAc. The combined organic layer dried over anhydrous sodium sulfate and concentrated under reduced pressure to afford crude material, which was purified by reverse phase HPLC. $^1$H NMR (CD$_3$OD, TFA salt) δ (ppm): 9.0 (s, 1H), 8.27 (d, 1H), 7.88 (d, 1H), 7.37 (s, 1H), 7.25 (s, 1H), 7.18 (d, 1H), 7.1 (d, 1H), 4.7 (d, 1H), 4.4 (d, 1H), 3.82 (bs, 1H), 3.6 (m, 1H), 3.37 (m, 1H), 3.2 (m, 1H), 3.6 (s, 3H), 2.42 (s, 3H), 2.01 (s, 3H).

Example 242

Preparation of Compound No. 332

To a de-aerated solution of 2,8-dimethyl-5-naphthalen-2-ylethynyl-2,3,4,5-tetrahydro-1H-pyrido[4,3-b]indole (50 mg, 0.14 mmol) in MeOH (5 mL), palladium hydroxide (25 mg, 50% w/w) and ammonium formate (45 mg, 0.71 mmol) were added. The reaction mixture was stirred at 80° C. for 1 h. The progress of reaction was monitored by TLC and LCMS. The reaction mass was filtered through Celite and washed the residue with MeOH (10 mL). The filtrate was concentrated under reduced pressure to afford crude material, which was purified by reverse phase HPLC to yield 2,8-dimethyl-5-[2-(5,6,7,8-tetrahydro-naphthalen-2-yl)-ethyl]-2,3,4,5-tetrahydro-1H-pyrido[4,3-b]indole. $^1$H NMR (CD$_3$OD, TFA salt) δ (ppm): 7.26 (d, 1H), 7.22 (d, 1H), 7.02 (d, 1H), 6.9 (d, 1H), 6.63 (d, 1H), 6.58 (s, 1H), 4.6 (d, 1H), 4.4 (m, 1H), 4.2 (t, 2H), 3.62 (m, 1H), 3.02 (m, 1H), 2.9 (m, 4H), 3.0 (s, 3H), 2.7 (bs, 2H), 2.6 (bs, 2H), 2.4 (s, 3H), 1.8 (bs, 4H).

Example 243

Preparation of Compound No. 333

A mixture of 4-bromo-benzenesulfonamide (200 mg, 0.84 mmol), 9-ethynyl-2,6-dimethyl-2,3,4,9-tetrahydro-1H-β- carboline (228 mg, 1.01 mmol), TBAF.3H₂O (801 mg, 2.54 mmol) and dichloro bis(triphenylphosphine) palladium(II) (30 mg, 0.042 mmol) was stirred at 85° C. for 10 min. The reaction mixture was poured into water and extracted with EtOAc (3×25 mL). The organic layer was washed with water (3×30 mL), dried over anhydrous sodium sulfate and evaporated to afford crude material, which was purified by reverse phase HPLC to yield 4-(2,6-dimethyl-1,2,3,4-tetrahydro-β-carbolin-9-ylethynyl)-benzenesulfonamide. ¹H NMR (CDCl₃, freebase) δ (ppm): 7.9 (d, 2H), 7.6 (d, 2H), 7.4 (d, 1H), 7.3 (s, 1H), 7.1 (d, 1H), 3.78 (s, 2H), 2.82 (t, 2H), 2.79 (t, 2H), 2.6 (s, 3H), 2.42 (s, 3H).

Example 244

Preparation of Compound No. 334

A mixture of 5-bromo-thiophene-2-sulfonic acid amide (200 mg, 0.8 mmol), 5-ethynyl-2,8-dimethyl-2,3,4,5-tetrahydro-1H-pyrido[4,3-b]indole (222 mg, 0.9 mmol), TBAF.3H₂O (756 mg, 2.4 mmol) and dichloro bis(triphenyl phosphine) palladium (II) (28 mg, 0.04 mmol) was stirred at 85° C. for 10 min. The reaction mixture was poured into water and extracted with EtOAc (3×50 mL). The organic layer was washed with water (3×100 mL), dried over anhydrous sodium sulfate and concentrated to afford crude material, which was purified by column chromatography using neutral alumina and 5% MeOH-DCM, followed by reverse phase HPLC to yield 5-(2,8-dimethyl-1,2,3,4-tetrahydro-pyrido[4,3-b]indol-5-ylethynyl)-thiophene-2-sulfonic acid amide. ¹H NMR (CD₃OD, HCl salt) δ (ppm): 7.57 (d, 1H), 7.46 (d, 1H), 7.36 (m, 2H), 7.21 (d, 1H), 4.42 (s, 2H), 3.71 (s, 2H), 3.3 (m, 2H), 3.1 (s, 3H), 2.42 (s, 3H).

Example 245

Preparation of Compound No. 335

To a degassed solution of 3,6-dimethyl-6,7,8,9-tetrahydro-5H-1,6,9-triaza-fluorene (201 mg, 1.0 mmol), 1-(2-bromo-1-methyl-vinyl)-4-fluoro-benzene (279 mg, 1.3 mmol), potassium phosphate (530 mg, 2.5 mmol) in DMF (4 mL), L-proline (28 mg, 0.25 mmol) and cuprous iodide (47 mg, 0.25 mmol) were added. The reaction mixture was stirred at 120° C. for 8 h. The reaction mixture was cooled to RT, diluted with water (20 mL) and extracted with EtOAc (4×20 mL). The organic layer was washed with water (5×20 mL), dried over anhydrous sodium sulfate and evaporated to afford crude material, which was purified by silica gel flash chromatography to yield 9-[2-(4-fluoro-phenyl)-propenyl]-3,6-dimethyl-6,7,8,9-tetrahydro-5H-1,6,9-triaza-fluorene. ¹H NMR (CDCl₃, freebase) δ (ppm): 8.1 (s, 1H), 7.57 (m, 3H), 7.07 (t, 2H), 6.92 (s, 1H), 3.62 (s, 2H), 2.8 (s, 4H), 2.6 (s, 3H), 2.4 (s, 3H), 2.0 (s, 3H).

Example 246

Preparation of Compound Nos. 336 and 336a-b

To a solution of 8-aza-10-methyl-2,3,5,6,7,11c-hexahydro-1H-indolizino[7,8-b]indole (227 mg, 1.0 mmol) in DMF (5 mL) was added sodium hydride (120 mg, 3.0 mmol). After stirring at RT for 15 min, 4-fluorophenethyl 4-methyl-benzenesulfonate (1.47 g, 3 mmol) was added into the reaction mixture, which was stirred at RT for 12 h. The progress of reaction was monitored by TLC and LCMS. The reaction mixture was quenched with ice-water and extracted with EtOAc (3×50 mL). The organic layer was washed with water (3×100 mL), dried over anhydrous sodium sulfate and concentrated under reduced pressure. The residue was purified by reverse phase HPLC to yield the title compound (125 mg). ¹H NMR (CDCl₃, freebase) δ (ppm): 8.18 (s, 1H), 7.53 (s, 1H), 6.82 (m, 4H), 4.86 (m, 1H), 4.44 (m 1H), 4.26 (m, 1H), 3.47 (m, 1H), 3.3 (m, 2H), 3.12 (m, 2H), 2.89 (q, 1H), 2.56 (m, 1H), 2.49 (m, 1H), 244 (s, 3H), 2.29 (m, 1H), 1.8 (m, 1H). Separation by chiral HPLC provides enantiomers 336a-b.

Example 247

Preparation of Compound Nos. 337 and 337a-b

This compound can be prepared in analogous fashion to Compound Nos. 30 and 30a-b, using 2-(2-methyloxiran-2-yl)oxazole as the oxirane reagent. Separation by chiral HPLC provides enantiomers 337a-b.

Example 248

Preparation of Compound Nos. 338 and 338a-b

To an ice-cooled stirred solution of 2-(2,8-dimethyl-1,2,3,4-tetrahydro-pyrido[4,3-b]indol-5-yl)-1-pyridin-4-yl-ethanol (2.5 g, 7.78 mmol) in DMF (5 mL) was added sodium hydride (373 mg, 15.56 mmol). After stirring for 20 min, heptanoyl chloride (1.9 g, 13.23 mmol) was added into the reaction mixture, which was stirred at 0° C. for 30 min. The progress of reaction was monitored by LCMS and TLC. The reaction mixture was quenched with ice water (200 mL) and extracted with EtOAc (400 mL). The combined organic layer was washed with water, dried over anhydrous sodium sulfate and concentrated. The residue was purified by silica gel column chromatography (6% MeOH-DCM), followed by reverse phase HPLC to yield heptanoic acid 2-(2,8-dimethyl-1,2,3,4-tetrahydro-pyrido[4,3-b]indol-5-yl)-1-pyridin-4-yl-ethyl ester (20 mg). ¹H NMR (CD₃OD, TFA salt) δ (ppm): 8.74 (s, 2H), 7.91 (s, 2H), 7.28 (m, 2H), 7.04 (t, 1H), 6.2 (m 1H), 4.7 (d 1H), 4.59 (m, 2H), 4.3 (m, 1H), 3.5 (t, 1H), 3.34 (m, 1H), 3.31 (m, 2H), 3.12 (s, 3H), 2.4 (s, 3H), 2.3 (m, 2H), 2.1 (m, 1H), 1.35 (m, 2H), 1.22 (m, 2H), 1.15 (m, 3H), 0.86 (t, 3H). Separation by chiral HPLC provides enantiomers 338a-b.

Example 249

Preparation of Compound Nos. 339 and 339a-b

To a solution of 9-chloro-1,2,3,4,5,6-hexahydro-3-methylazepino [4,5-b]indole (1.0 g, 4.27 mmol) in DMF (10 mL) was added potassium tert-butoxide (717.9 mg, 6.41 mmol). After stirring at RT for 15 min, 2-(3,4-difluorophenyl)oxirane (1.33 g, 8.54 mmol) was added into the reaction mixture, which was stirred at RT for 3 h. The progress of reaction was monitored by TLC and LCMS. The reaction mixture was quenched with ice-cold water and extracted with EtOAc. The organic layer was washed with water, dried over anhydrous sodium sulfate and concentrated under reduced pressure. The residue was purified by reverse phase HPLC to yield the title compound, which was resolved by chiral preparative HPLC. ¹H NMR (DMSO, TFA salt) δ (ppm): 7.62-7.50 (t, 1H), 7.50-7.30 (t, 3H), 7.25-7.00 (m, 2H), 4.85-4.75 (m, 1H), 4.30-4.20 (t, 2H), 3.80-3.60 (m, 4H), 3.25-3.10 (m, 4H), 2.90 (s, 3H).

Example 250

Preparation of Compound Nos. 340 and 340a-d

This compound can be prepared in analogous fashion to Compound Nos. 30 and 30a-b, using 5-(oxiran-2-yl)-1H-1,2,3-triazole as the oxirane reagent. Separation by chiral HPLC provides diastereomers 340a-d.

Example 251

Preparation of Compound Nos. 341 and 341a-d

This compound can be prepared in analogous fashion to Compound Nos. 30 and 30a-b, using 5-(oxiran-2-yl)-1H-tetrazole as the oxirane reagent. Separation by chiral HPLC provides diastereomers 341a-d.

Example 252

Preparation of Compound Nos. 342 and 342a-d

This compound can be prepared in analogous fashion to Compound Nos. 30 and 30a-b, using 2-(oxiran-2-yl)-1H-imidazole as the oxirane reagent. Separation by chiral HPLC provides diastereomers 342a-d.

Example 253

Preparation of Compound Nos. II-270 and II-270a-b

These compounds can be synthesized in an analogous fashion to Compound Nos. 55 and 55a-b, using 3,6-dimethyl-6,7,8,9-tetrahydro-5H-1,2,6,9-tetraaza-fluorene as the carboline portion and 4-(2-methyloxiran-2-yl)pyridine as the epoxide. Separation by chiral HPLC provides enantiomers II-270a-b.

Example 254

Preparation of Compound Nos. II-1 and II-1a-b

To a solution of 2-(1,2,3,4-tetrahydro-2,8-dimethylpyrido[4,3-b]indol-5-yl)-1-(pyridin-4-yl)ethanamine (500 mg, 1.56 mmol) in DCM (5 mL) was added pyridine (185 mg, 2.3 mmol). After stirring for 5 min at RT, a solution of acetyl chloride (147.2 mg, 1.88 mmol) in DCM (0.5 mL) was added into the reaction mixture, which was stirred at RT for 16 h. The reaction mixture was diluted with DCM and washed with saturated aq NaHCO$_3$ solution. The organic layer was dried over anhydrous sodium sulfate and concentrated under reduced pressure. The residue was triturated with ether to yield N-(2-(1,2,3,4-tetrahydro-2,8-dimethylpyrido[4,3-b]indol-5-yl)-1-(pyridin-4-yl)ethyl)acetamide (500 mg). $^1$H NMR (CDCl$_3$, Free base) δ (ppm): 8.42 (d, 2H), 7.25 (s, 1H), 7.15 (d, 1H), 6.92 (d, 2H), 6.9 (d, 1H), 6.2 (d, 1H), 5.3 (q, 1H), 4.4 (dd, 1H), 4.25 (dd, 1H), 3.58 (dd, 2H), 2.6 (m, 2H), 2.55 (s, 3H), 2.43 (s, 3H), 2.3 (m, 2H), 2.03 (s, 3H). Separation by chiral HPLC provided enantiomers II-1a-b.

Example 255

Preparation of Compound No. II-2

Crude 2-(2,8-dimethyl-3,4-dihydro-1H-pyrido[4,3-b]indol-5(2H)-yl)-1-(pyridin-4-yl)ethyl methanesulfonate was taken in NMP (5 mL), and KOH powder (873 mg, 15.5 mmol) was added at RT and the mixture stirred at 80° C. for 14 h. The product was detected by LCMS. Water was added to the reaction mixture, which was extracted with EtOAc. The organic layer was dried over anhydrous sodium sulfate and evaporated under reduced pressure. The crude product was chromatographed on silica gel using 5% MeOH-DCM to afford 400 mg of the title compound. $^1$H NMR (DMSO, Formate salt) δ (ppm): 8.55-8.50 (d, 2H), 8.05-8.00 (d, 1H), 7.85-7.80 (d, 1H), 7.65-7.55 (d, 2H), 7.25 (s, 1H), 7.15-7.10 (m, 1H), 6.80-6.75 (d, 1H), 3.58 (s, 2H), 3.05 (t, 2H), 2.78 (t, 2H), 2.41 (s, 3H), 2.38 (s, 3H).

Example 256

Preparation of Compound No. II-3

To a stirred cooled (−70° C.) solution of 2-methyl-5-[2-(6-methyl-pyridin-3-yl)-propenyl]-2,3,4,5-tetrahydro-1H-pyrido[4,3-b]indole-8-carboxylic acid methyl ester (100 mg, 0.26 mmol) in THF (10 mL) was added portionwise LAH (30 mg, 0.79 mmol) and stirring continued at RT for 4 h. The reaction mixture was cooled to −70° C. and quenched with water (0.1 mL), 15% NaOH (0.1 mL) and water (0.2 mL). The solid was filtered and the filtrate concentrated to afford crude material, which was purified by reverse phase HPLC. $^1$H NMR (CD$_3$OD, Formate salt) δ (ppm): 8.67 (s, 1H), 8.0 (d, 1H), 7.5 (s, 1H), 7.4 (d, 1H), 7.27 (d, 1H), 7.23 (d, 1H), 7.1 (s, 1H), 4.7 (s, 2H), 4.42 (s, 2H), 3.6 (t, 2H), 3.1 (t, 2H), 3.05 (s, 3H), 2.6 (s, 3H), 1.28 (s, 3H).

Example 257

Preparation of Compound Nos. II-4 and II-4a-d 6-(2-Azido-2-pyridin-4-yl-ethyl)-9-methyl-2,3,4,5,6,10c-hexahydro-1H-3a,6-diaza-cyclopenta[c]fluorene (400 mg, 1.07 mmol) was dissolved in ethanol-water (10 mL:1 mL). Zinc dust (280 mg, 4.3 mmol) and ammonium chloride (228 mg, 4.3 mmol) were added and the reaction mixture was heated at 80° C. for 1 h. After consumption of starting material, the reaction mixture was filtered through Celite and filtrate was concentrated to obtain the residue. The residue was basified with aq ammonia and extracted with EtOAc (2×100 mL). The combined organic layer was dried over anhydrous sodium sulfate and concentrated to obtain the crude product, which was purified by reverse phase chromatography to obtain 40 mg of 2-(9-methyl-1,2,3,4,5,10c-hexahydro-3a,6-diaza-cyclopenta[c]fluoren-6-yl)-1-pyridin-4-yl-ethylamine as the TFA salt. $^1$H NMR (CDCl$_3$, freebase): δ (ppm): 8.58 (d, 2H), 7.28 (d, 1H), 7.25 (s, 1H), 7.23 (d, 2H), 7.1 (d, 1H), 4.9 (m, 1H), 4.42 (t, 1H), 4.13 (dd, 1H), 3.63 (m, 1H), 3.4 (m, 2H), 3.01 (m, 2H), 2.71 (m, 2H), 2.45 (s, 3H), 2.23 (m, 2H), 2.01 (m, 1H). Chiral HPLC separated the racemate into diastereomers II-4a-d.

Example 258

Preparation of Compound Nos. II-5 and II-5a-d

To a solution of 9-aza-10-methyl-2,3,5,6,7,11c-hexahydro-1H-indolizino[7,8-b]indole (30 mg, 0.13 mmol) in DMF (5 mL) was added NaH (16 mg, 0.4 mmol, 60% dispersion in mineral oil) at 0° C. and the mixture was stirred for 10 min. 3-(2-Methyl-oxiranyl)-pyridine 36 mg, 0.26 mmol) was added and the reaction mixture was stirred overnight at RT. The reaction was monitored by LCMS. The reaction mixture was quenched with MeOH (1 mL), concentrated under reduced pressure to obtain the crude product, which was purified by reverse phase column chromatography to obtain the pure product (3.3 mg) as the free base. $^1$H NMR (CDCl$_3$, freebase): δ (ppm): 9.1 & 8.91 (s, 1H), 8.8 & 8.7 (s, 1H), 8.6 & 8.5 (d, 1H), 7.6 & 7.8 (d, 1H), 7.18 (s, 2H), 4.4 (dd, 1H), 4.2 (m, 2H), 3.32 (m, 2H), 2.7 (dd, 1H), 2.66 (s, 3H), 1.99 (m, 2H), 1.9 (m, 2H), 1.76 & 1.67 (s, 3H), 1.6 (m, 3H). Chiral HPLC separates the racemate into diastereomers II-5a-d.

Example 259

Preparation of Compound Nos. II-6 and II-6a-d 6-(2-Chloro-2-pyrazin-2-yl-propyl)-9-methyl-2,3,4,5,6,10c-hexahydro-1H-3a,6-diaza-cyclopenta[c]fluorene (500 mg, 1.31 mmol) in 40% dimethylamine in water (30 mL) was heated at 100° C. for 3 h. The reaction mixture was cooled at RT and extracted with EtOAc (3×50 mL). The combined organic layer was dried over anhydrous sodium sulfate and concentrated to obtain the crude product, which was purified by reverse phase chromatography to obtain 62 mg of dimethyl-[1-methyl-2-(9-methyl-1,2,3,4,5,10c-hexahydro-3a,6-diaza-cyclopenta[c]fluoren-6-yl)-1-pyrazin-2-yl-ethyl]-amine. $^1$H NMR (CD$_3$OD, TFA salt): δ (ppm): 8.06 (s, 1H), 7.48 (s, 1H), 7.21 (s, 1H), 7.17 (d, 1H), 7.00 (d, 1H), 4.98 (t, 1H), 4.28 (d, 2H), 3.6 (m, 3H), 3.39 (m, 2H), 3.2 (m, 1H), 3.15 (s, 6H), 2.8 (m, 1H), 2.7 (m, 1H), 2.39 (s, 3H), 2.17 (m, 3H). Chiral HPLC separated the racemate into diastereomers II-6a-d.

Example 260

Preparation of Compound Nos. II-7 and II-7a-d

Methanesulfonic acid 2-(9-methyl-1,2,3,4,5,10c-hexahydro-3a,6-diaza-cyclopenta[c]fluoren-6-yl)-1-pyrazin-2-yl-ethyl ester (300 mg, 0.70 mmol) in 40% dimethylamine in water (20 mL) was heated at 90° C. for 1 h. The reaction mixture was cooled to RT and extracted with DCM (12×50 mL)The combined organic layer was dried over anhydrous sodium sulfate and concentrated to obtain the crude product, which was purified by reverse phase chromatography to obtain 60 mg of dimethyl-[2-(9-methyl-1,2,3,4,5,10c-hexahydro-3a,6-diaza-cyclopenta[c]fluoren-6-yl)-1-pyrazin-2-yl-ethyl]-amine. $^1$H NMR (CD$_3$OD, TFA salt): δ (ppm): 8.1 (s, 1H), 7.4 (s, 1H), 7.1 (d, 1H), 5.1 (t, 1H), 4.42 (m, 2H), 3.6 (m, 3H), 3.2 (m, 1H), 3.17 (m, 1H), 3.15 (s, 6H), 2.85 (m, 2H), 2.63 (m, 1H), 2.42 (s, 3H), 2.3 (m, 2H), 2.15 (m, 1H). Chiral HPLC separates the racemate into diastereomers II-7a-d.

Example 261

Preparation of Compound Nos. II-8 and II-8a-b

Methanesulfonicacid-2-(2,8-dimethyl-1,2,3,4-tetrahydropyrido[4,3-b]indol-5-yl)-1-pyridin-4-yl-ethylester (300 mg, 0.75 mmol) in 70% ethylamine in water (15 mL) was heated at 100° C. for 18 h. The reaction mixture was cooled to RT and extracted with EtOAc (2×100 mL). The combined organic layer was washed with water (2×20 mL), dried over anhydrous sodium sulfate and concentrated to obtain the crude product, which was purified by reverse phase chromatography to obtain 55 mg of [2-(2,8-dimethyl-1,2,3,4-tetrahydropyrido[4,3-b]indol-5-yl)-1-pyridin-4-yl-ethyl]-ethyl-amine. $^1$H NMR (DMSO, TFA salt): δ (ppm): 8.5 (d, 2H), 7.3 (d, 1H), 7.2 (m, 3H), 6.9 (d, 1H), 4.7 (m, 2H), 4.43 (m, 2H), 4.1 (d, 1H), 3.3 (m, 1H), 3.0 (m, 2H), 2.85 (d, 6H), 2.8 (m, 1H), 2.5 (m, 2H), 2.3 (s, 3H), 1.22 (s, 3H). Chiral HPLC separates the racemate into enantiomers II-8a-b.

Example 262

Preparation of Compound Nos. II-9 and II-9a-b

Methanesulfonic acid 2-(2,8-dimethyl-1,2,3,4-tetrahydropyrido[4,3-b]indol-5-yl)-1-pyridin-4-yl-ethylester (240 mg, 0.60 mmol) was dissolved in 10 mL of 70% cyclopentylamine solution in water and heated at 100° C. for 18 h. The reaction mixture was cooled to RT and concentrated to obtain the crude product, which was purified by reverse phase chromatography to obtain 11 mg of cyclopentyl-[2-(2,8-dimethyl-1,2,3,4-tetrahydro-pyrido[4,3-b]indol-5-yl)-1-pyridin-4-yl-ethyl]-amine. $^1$H NMR (CDCl$_3$, freebase): δ (ppm): 8.51 (d, 2H), 7.17 (m, 4H), 7.003 (d, 1H), 4.16 (m, 2H), 4.05 (dd, 1H), 3.79 (dd, 2H), 2.9 (m, 1H), 2.83 (m, 2H), 2.55 (s, 3H), 2.44 (s, 3H), 2.39 (m, 1H), 1.99 (s, 2H), 1.7 (m, 2H), 1.5 (m, 2H), 1.4 (m, 1H), 1.9 (m, 2H). Chiral HPLC separates the racemate into enantiomers II-9a-b.

Example 263

Preparation of Compound Nos. II-10 and II-10a-b 2-(2,8-Dimethyl-1,2,3,4-tetrahydro-pyrido[4,3-b]indol-5-yl)-1-pyridin-4-yl-ethylamine (200 mg, 0.62 mmol) was dissolved in 15 mL DCM, acetone (108 mg, 1.87 mmol), acetic acid (0.5 mL) was added and the reaction mixture was stirred at RT overnight. Sodiumcyanoborohydride (117 mg, 1.87 mmol) was added and stirred at for 1 h. The reaction mixture was diluted with DCM (300 mL) and washed with saturated bicarbonate solution (200 mL). The organic layer was dried over anhydrous sodium sulfate and concentrated to obtain the crude product, which was purified by reverse phase chromatography to obtain 120 mg of [2-(2,8-dimethyl-1,2,3,4-tetrahydro-pyrido[4,3-b]indol-5-yl)-1-pyridin-4-yl-ethyl]-isopropyl-amine as the TFA salt. $^1$H NMR (CD$_3$OD, TFA salt): δ (ppm): 8.52 (m, 2H), 7.42 b (s, 2H), 7.30 b (s, 1H), 7.22 (s, 1H), 7.02 (m, 1H), 4.8 (m, 1H), 4.58 (m, 2H), 4.23 (t, 1H), 3.72 (m, 1H), 3.4 (m, 3H), 3.13 (m, 2H), 2.99 (d, 3H), 2.39 (s, 3H), 1.43 (d, 3H), 1.34 (d, 3H). Chiral HPLC separates the racemate into enantiomers II-10a-b.

Example 264

Preparation of Compound Nos. II-11 and II-11a-b

To a solution of 5-(2-azido-2-(4-fluorophenyl)ethyl)-2,8-dimethyl-2,3,4,5-tetrahydro-1H-pyrido[4,3-b]indole (1 g, 2.75 mmol) in ethanol-water (40-5 mL) was added ammonium chloride (590 mg, 11.02 mmol) and zinc dust (716 mg, 11.02 mmol) and heated at 100° C. for 1 h. After complete conversion of starting material (TLC), ethanol was removed under reduced pressure and 50 mL additional water was added and extracted with DCM (3×100 mL). The organic layer was dried over anhydrous sodium sulfate and concentrated under vacuum to obtain the crude product, which was purified by reverse phase HPLC to obtain 2-(2,8-dimethyl-3,4-dihydro-1H-pyrido[4,3-b]indol-5(2H)-yl)-1-(4-fluorophenyl)ethanamine (730 mg) as the TFA salt. $^1$H NMR (CD$_3$OD, TFA salt): δ (ppm): 7.27 (m, 1H), 7.21 (m, 3H), 7.10 (m, 3H), 4.60 (m, 3H), 4.50 (m, 1H), 4.24 (m, 1H), 3.69 (m, 1H), 3.44

(m, 1H), 3.04 (m, 1H), 2.96 (s, 3H), 2.56 (m, 1H), 2.41 (s, 3H). Chiral HPLC separated the racemate into enantiomers II-11a-b.

Example 265

Preparation of Compound Nos. II-12 and II-12a-b 2-(2,8-dimethyl-3,4-dihydro-1H-pyrido[4,3-b]indol-5 (2H)-yl)-1-(4-fluorophenyl)ethyl methane sulfonate (250 mg, 0.6 mmol) in methyl amine (40% solution in water, 5 mL) was heated at 100° C. for 4 h. The progress of the reaction was monitored by TLC and LCMS. 10 mL of water was added to the reaction mixture and then extracted with EtOAc (2×50 mL). The organic layer was dried over anhydrous sodium sulfate and concentrated under vacuum to obtain the crude product, which was purified by reverse phase HPLC to obtain 2-(2,8-dimethyl-3,4-dihydro-1H-pyrido[4,3-b]indol-5(2H)-yl)-1-(4-fluorophenyl)-N-methyl ethanamine (30 mg) as the TFA salt. $^1$H NMR (CDCl$_3$, freebase): δ (ppm): 7.32 (t, 2H), 7.24 (m, 1H), 7.21 (s, 1H), 7.01 (m, 3H), 3.91 (m, 2H), 3.65 (dd, 2H), 2.80 (m, 3H), 2.62 (m, 1H), 2.54 (s, 3H), 2.45 (s, 3H), 2.14 (s, 3H). Chiral HPLC separated the racemate into enantiomers II-12a-b.

Example 266

Preparation of Compound Nos. II-13 and II-13a-b

Methanesulfonicacid2-(2,8-dimethyl-1,2,3,4-tetrahydro-pyrido[4,3-b]indol-5-yl)-1-pyridin-4-yl-ethylester (300 mg, 0.75 mmol) was dissolved in 70% cyclobutylamine in water (6 mL) and heated at 100° C. for 18 h. The reaction mixture was concentrated to obtain the crude product, which was purified by reverse phase chromatography to obtained 90 mg of cyclobutyl-[2-(2,8-dimethyl-1,2,3,4-tetrahydro-pyrido[4,3-b]indol-5-yl)-1-pyridin-4-yl-ethyl]-amine as the TFA salt. $^1$H NMR (CD$_3$OD, TFA salt): δ (ppm): 8.6 (dd, 2H), 7.63 (d, 1H), 7.54 (d, 1H), 7.19 (s, 1H), 7.10 (d, 1H), 6.99 (d, 1H), 4.82 (m, 2H), 4.72 (m, 1H), 4.6 (m, 1H), 4.23 (t, 1H), 3.8 (m, 2H), 3.5 (m, 1H), 3.2 (m, 1H), 3.07 (d, 3H), 2.7 (m, 1H), 2.37 (s, 3H), 2.5 (m, 3H), 2.1 (m, 1H), 1.8 (m, 2H). Chiral HPLC separated the racemate into enantiomers II-13a-b.

Example 267

Preparation of Compound Nos. II-14 and II-14a-b 2-(2,8-dimethyl-3,4-dihydro-1H-pyrido[4,3-b]indol-5 (2H)-yl)-1-(4-fluorophenyl)ethanamine (250 mg, 0.741 mmol), formaldehyde 37-40% solution (5 mL) and formic acid (0.25 mL) was heated at 100° C. for 2 h. After the completion of reaction (TLC and LCMS), the reaction mixture was cooled to RT, neutralized by saturated sodium bicarbonate and extracted into DCM (2×50 mL). The combined organic layer was washed with water (50 mL), dried over anhydrous sodium sulfate and concentrated under reduced pressure to obtain 250 mg of 2-(2,8-dimethyl-3,4-dihydro-1H-pyrido[4,3-b]indol-5(2H)-yl)-1-(4-fluorophenyl)-N,N-dimethylethanamine. $^1$H NMR (CDCl$_3$, freebase): δ (ppm): 7.13 (s, 1H), 7.05 (d, 1H), 7.02 (t, 2H), 6.88 (m, 3H), 4.56 (dd, 1H), 3.99 (m, 1H), 3.64 (d, 1H) 3.54 (dd, 1H), 3.46 (d, 1H), 2.79 (m, 2H), 2.6 (m, 2H), 2.45 (s, 3H), 2.42 (s, 3H), 2.3 (s, 6H), 1.9 (m, 1H). Chiral HPLC separated the racemate into enantiomers II-14a-b.

Example 268

Preparation of Compound Nos. II-15 and II-15a-b 1-(2,8-Dimethyl-1,2,3,4-tetrahydro-pyrido[4,3-b]indol-5-yl)-2-pyridin-3-yl-propan-2-ol (2.0 g, 5.97 mmol) was dissolved in DMF (20 ml), sodium hydride (716 mg, 17.9 mmol) was added and the mixture stirred at RT for 20 min. Acetic anhydride (913 mg, 8.95 mmol) was added dropwise at the same temperature and stirring continued for 1.5 h. The reaction was monitored by TLC and LCMS. The reaction mixture was poured into 250 mL ice water and extracted with EtOAc (3×200 mL), washed with water (3×300 mL), dried over anhydrous sodium sulfate and concentrated to obtain the crude product that was purified by column chromatography (silica gel: 100-200 mesh, eluent: ~6-8% MeOH in DCM) to obtain 110 mg of acetic acid 2-(2,8-dimethyl-1,2,3,4-tetrahydro-pyrido[4,3-b]indol-5-yl)-1-methyl-1-pyridin-3-yl-ethyl ester, which was followed by chiral separation. $^1$H NMR (CD$_3$OD, Free base) δ (ppm): 8.38 (d, 1H), 8.15 (s, 1H), 7.45 (d, 1H), 7.22 (t, 1H), 7.1 (s, 1H), 7.0 (s, 1H), 6.8 (d, 1H), 4.43 (d, 1H), 4.2 (d, 1H), 3.7 (d, 1H), 3.5 (d, 1H), 2.8 (m, 2H), 2.53 (m, 1H), 2.5 (s, 3H), 2.4 (s, 3H), 2.2 (m, 1H), 2.07 (d, 6H). Separation by chiral HPLC provided enantiomers II-15a-b.

Example 269

Preparation of Compound Nos. II-16 and II-16a-b 1-(2,8-Dimethyl-1,2,3,4-tetrahydro-pyrido[4,3-b]indol-5-yl)-2-pyridin-3-yl-propan-2-ol (5.0 g, 14.9 mmol) was dissolved in DMF (100 mL) and sodium hydride (1.8 g, 45 mmol) was added, and the mixture stirred at RT for 15 min. Pivaloyl chloride (3 g, 25 mmol) was added dropwise at the same temperature, and the mixture stirred for 45 min. The reaction was monitored by TLC and LCMS. The reaction mixture was poured into 400 mL ice water to obtain a solid that was filtered. The solid was dissolved in DCM, dried over sodium sulfate and concentrated to obtain the crude product that was purified by column chromatography (silica gel: 100-200 mesh, Eluent: ~4-6% MeOH in DCM) to obtain 1.8 g of 2,2-dimethyl-propionic acid 2-(2,8-dimethyl-1,2,3,4-tetrahydro-pyrido[4,3-b]indol-5-yl)-1-methyl-1-pyridin-3-yl-ethyl ester. The product was further purified by chiral preparative HPLC to give enantiomers II-16a and II-16b. $^1$H NMR (CDCl$_3$, Free base): δ (ppm): 8.55 (d, 1H), 8.5 (s, 1H), 7.2 (d, 1H), 7.18 (m, 3H), 6.9 (d, 1H), 4.3 (dd, 2H), 3.65 (d, 1H), 3.52 (d, 1H), 2.65 (m, 2H), 2.5 (m, 2H), 2.5 (s, 3H), 2.4 (s, 3H), 2.3 (d, 1H), 2.0 (s, 3H), 2.0 (m, 1H), 1.2 (s, 9H).

Example 270

Preparation of Compound Nos. II-17 and II-17a-d

To a solution of 11-aza-10-methyl-2,3,5,6,7,11c-hexahydro-1H-indolizino[7,8-b]indole (120 mg, 0.52 mmol) in DMF (5 mL) was added NaH (31 mg, 1.06 mmol, 60% dispersion in mineral oil) at 0° C. and the reaction mixture was stirred for 10 min. 3-(2-Methyl-oxiranyl)-pyridine 143 mg, 1.06 mmol) was added and the reaction mixture was stirred at RT overnight. The reaction was monitored with LCMS. The reaction mixture was quenched with MeOH (2 mL), concentrated under reduced pressure to obtain the crude product, which was purified by reverse phase column chromatography to obtain the 30 mg of product as the free base. $^1$H NMR (CDCl$_3$, freebase): δ (ppm): 8.72 & 8.69 (s, 1H), 8.25 (t, 1H), 7.62 & 7.6 (d, 1H), 7.43 (t, 1H), 7.22 & 7.19 (m, 1H), 6.86 (t, 1H), 4.25 (m, 2H), 3.2 (m, 1H), 2.99 (m, 1H), 2.85 (t, 2H), 2.7(m, 1H), 2.626 (s, 3H), 2.5 (m, 2H), 2.4 (m, 1H), 2.15 (m, 1H), 1.85 (m, 2H), 1.69 & 1.66 (s, 3H). Chiral HPLC separates the racemate into diastereomers II-17a-d.

Example 271

Preparation of Compound No. II-18

To a solution of 2,6,9-trimethyl-2,3,4,5-tetrahydro-1H-pyrido[4,3-b]indole (100 mg, 0.466 mmol) in DMF (2 mL) were added sodium hydride (60 mg, 1.3 mmol) and 2-(6-methylpyridin-3-yl)ethyl 4-methylbenzenesulfonate (337.5 mg, 1.16 mmol). The reaction mixture was irradiated in a microwave reactor at 90° C. for 1 h. The reaction mixture was cooled to RT, quenched with water and extracted with EtOAc (3×10 mL). The organic layer was washed with water (2×10 mL), dried over anhydrous sodium sulfate and concentrated under reduced pressure to afford the crude product, which was purified by reverse phase HPLC. $^1$H NMR (CD$_3$OD, TFA salt) δ (ppm): 8.1 (m, 2H), 7.7 (d, 1H), 6.6 (d, 2H), 4.98 (m, 1H), 4.5 (m, 1H), 4.4 (t, 2H), 3.82 (bs, 1H), 3.5 (bs, 1H), 3.2 (t, 2H), 3.1 (m, 5H), 2.65 (s, 3H), 2.5 (s, 3H), 2.31 (s, 3H).

Example 272

Preparation of Compound Nos. II-19 and II-19a-b 1-(2,8-Dimethyl-1,2,3,4-tetrahydro-pyrido[4,3-b]indol-5-yl)-2-pyridin-3-yl-propan-2-ol (3.35 g, 10.0 mmol), isonicotinic acid (1.23 g, 10 mmol), DCC (5.0 g, 24.0 mmol) and DMAP (1.2 g, 10 mmol) were suspended in DCM (300 mL) and the resultant mixture was stirred overnight under nitrogen atmosphere. The reaction was monitored by LCMS. The reaction mixture was filtered to remove N,N-dicyclohexyl urea formed during the reaction. The filtrate was washed with water (3×300 mL), dried over anhydrous sodium sulfate and concentrated under reduced pressure to obtain the crude product which was purified by column chromatography (neutral alumina; eluent: 0.5-1% MeOH in DCM) to obtain the product. The product obtained was triturated with diethyl ether (30 mL) to obtain the pure product (400 mg). $^1$H NMR (CDCl$_3$, freebase): δ (ppm): 8.71 (d, 2H), 8.58 (s, 1H), 8.56 (d, 1H), 7.64 (d, 2H), 7.32 (d, 1H), 7.21 (s, 1H), 7.18 (d, 2H), 6.97 (d, 1H), 4.45 (dd, 2H), 3.65 (d, 1H), 3.57 (d, 1H), 2.7 (m, 1H), 2.52 (m, 1H), 2.49 (s, 3H), 2.46 (s, 3H), 2.43 (m, 1H), 2.16 (s, 3H), 2.01 (m, 1H). Separation by chiral HPLC provided enantiomers II-19a-b.

Example 273

Compound Nos. II-21, II-23, II-36, II-56, II-57, II-160, II-188-206, II-233, II-237 and II-254 were synthesized as described in PCT publication WO2009/055828. Compound Nos. II-107 and II-164-165 were synthesized as described in PCT publication WO2009/120720. Compound Nos. II-20, II-48-49, II-52-55, II-156-158 and II-161 were synthesized as described in PCT publication WO2009/120717. Compound Nos. II-47, II-95, II-162-163 and II-166-187 were synthesized as described in PCT publication WO2010/051501. Compound Nos. II-22, II-24-35, II-37-38, II-41-46, II-50-51, II-155 and II-159 were synthesized as described in PCT publication WO2010/051503. Compound No. II-219 was synthesized as described in PCT publication WO2010/127177. Compound Nos. II-207-208, II-216-218 and II-228 were synthesized as described in PCT publication WO2010/019417. Compound No. II-69 was synthesized as described in PCT publication WO2011/038163. Compound Nos. II-79, II-86, II-234-236 and II-238-239 were synthesized as described in PCT publication WO2011/038161. Compound Nos. II-72-74, II-87 and II-214 were synthesized as described in PCT publication WO2011/038162. Compound Nos. II-66 and II-85 were synthesized as described in PCT publication WO2011/038164.

Example 274

Preparation of Compound No. II-39

To a solution of 6-bromo-2,8-dimethyl-2,3,4,5-tetrahydro-1H-pyrido[4,3-b]indole (100 mg, 0.359 mmol), in DMF (2 mL) were added sodium hydride (50 mg, 1.07 mmol) and 2-(6-methylpyridin-3-yl)ethyl 4-methylbenzenesulfonate (262 mg, 0.899 mmol). The reaction mixture was irradiated in a microwave reactor at 90° C. for 1 h. The reaction mixture was cooled to RT, quenched with water and extracted with EtOAc (3×10 mL). The organic layer was washed with water (2×10 mL), dried over anhydrous sodium sulfate and concentrated under reduced pressure to afford crude, which was purified by reverse phase HPLC. $^1$H NMR (CD$_3$OD, TFA salt) δ (ppm): 8.36 (s, 1H), 8.17 (d, 1H), 7.7 (d, 1H), 7.21 (s, 1H), 7.18 (s, 1H), 4.8 (m, 1H), 4.62 (t, 2H), 4.3 (m, 1H), 3.82 (m, 1H), 3.5 (m, 1H), 3.2 (m, 3H), 3.1 (m, 4H), 2.7 (s, 3H), 2.38 (s, 3H).

Example 275

Preparation of Compound No. II-40

A solution of 2,3,4,5-tetrahydro-2,4,4,8-tetramethyl-1H-pyrido[4,3-b]indole (228 mg, 1 mmol) and KOH (448 mg, 8 mmol) in NMP was heated at 100° C. for 15 min. 2-(Trifluoromethyl)-5-vinylpyridine (381 mg, 2.2 mmol) was added dropwise into the reaction mixture and stirring continued at 45° C. for 30 min. The reaction mixture was diluted with water and extracted with EtOAc (3×25 mL). The organic extract was washed with water (3×25 mL), dried over anhydrous sodium sulfate and evaporated in vacuo to afford crude material, which was purified by silica gel column chromatography using 0-5% MeOH-DCM, followed by reverse phase HPLC to yield desired compound as the TFA salt (41 mg). $^1$H NMR (CD$_3$OD, TFA salt) δ (ppm): 8.4 (s, 1H), 7.8 (d, 1H), 7.72 (d, 1H), 7.24 (d, 2H), 7.02 (d, 1H), 4.67 (d, 1H), 4.6 (t, 2H), 4.35 (d, 1H), 3.47 (d, 1H), 3.4 (d, 1H), 3.24 (t, 2H), 3.17 (s, 3H), 2.4 (s, 3H), 1.48 (s, 3H), 1.45 (s, 3H).

Example 276

Preparation of Compound Nos. II-49 and II-49a-b

Sodium hydride (36 mg, 1.5 mmol) was dissolved in THF. 2,6-Dimethyl-2,3,4,9-tetrahydro-1H-pyrido[3,4-b]indole (100 mg, 0.05 mmol) in THF was added dropwise at 0° C. to the NaH solution and the reaction mixture was stirred for 0.5 h. A solution of 2-(2-fluorophenyl) oxirane (103 mg, 0.075 mmol) in THF was added dropwise to the reaction mixture and was stirred at RT for 2 h. The progress of the reaction was monitored by TLC. After completion of the reaction, the reaction was quenched with ice-water, the THF was evaporated and the aqueous layer was extracted with EtOAc. The organic layer was dried over anhydrous sodium sulfate. The crude compound was purified by column chromatography to yield the desired compound (30 mg) which was stirred in ethanolic HCl to yield 2-(2,6-dimethyl-3,4-dihydro-1H-pyrido[3,4-b]indol-9(2H)-yl)-1-(2-fluorophenyl)ethanol hydrochloride salt. $^1$H NMR (CDCl$_3$, Free base) δ (ppm): 7.6 (t, 1H), 7.3 (m, 3H), 7.2 (t, 1H), 7.1 (t, 1H), 7.0 (d, 1H), 5.33 (d, 1H), 4.22 (d, 1H), 3.95 (dd, 1H), 3.8 (d, 1H), 3.5 (d, 1H), 2.8 (m, 4H), 2.5 (s, 3H), 2.4 (s, 3H). Separation by chiral HPLC provided enantiomers II-49a-b.

Example 277

Preparation of Compound Nos. II-57 and II-57a-b 2,8-Dimethyl-2,3,4,5-tetrahydro-1H-pyrido[4,3-b]indole (1.35 g, 6.65 mmol) was taken in DMF (10 mL). NaH (0.9 g, 19.5 mmol) was added to it portionwise at RT and the mixture stirred for 15 min. 2-Methyl-5-(oxiran-2-yl)pyridine (0.9 g, 6.65 mmol) was added to the reaction mixture dropwise at RT. After complete addition, the reaction mixture was stirred at RT for 2 h. The product was detected by LCMS. The reaction mixture was quenched with MeOH and concentrated to dryness. Water (20 mL) was added and the reaction mixture was extracted in EtOAc (2×100 mL), the extracts dried over anhydrous sodium sulfate and concentrated to obtain a dark brown oil. The crude product was purified by reverse phase chromatography to obtain pure material as a TFA salt (310 mg). $^1$H NMR (CDCl$_3$, Free base) δ (ppm): 8.45 (s, 1H), 7.52 (d, 1H), 7.2 (s, 1H), 7.19 (d, 1H), 7.12 (d, 1H), 6.97 (d, 1H), 5.0 (t, 1H), 4.18 (dd, 2H), 3.61 (dd, 2H), 2.9 (m, 1H), 2.82 (m, 2H), 2.65 (m, 1H), 2.50 (s, 3H), 2.48 (s, 3H), 2.41 (s, 3H). Separation by chiral HPLC provided enantiomers II-57a-b.

Example 278

Preparation of Compound Nos. II-58 and II-58a-b 1-(2,8-Dimethyl-1,2,3,4-tetrahydro-pyrido[4,3-b]indol-5-yl)-2-pyridin-4-yl-propan-2-ol (350 mg. 1.0 mmol) was dissolved in 10 mL DCM and metachloro perbenzoic acid (216 mg, 1.2 mmol) was diluted in DCM and added dropwise at RT. After consumption of starting material by monitoring TLC & LCMS, the reaction mixture was concentrated and purified by reverse phase chromatography to obtain 200 mg of 1-(2,8-dimethyl-2-oxy-1,2,3,4-tetrahydro-pyrido[4,3-b]indol-5-yl)-2-pyridin-4-yl-propan-2-ol. $^1$H NMR (CDCl$_3$, Free base) δ (ppm): 8.54 (d, 2H), 7.68 (d, 1H), 7.55 (d, 1H), 7.28 (d, 2H), 7.22 (s, 1H), 7.10 (d, 1H), 6.63 (d, 1H), 4.06 (d, 2H), 3.28 (t, 2H), 2.91 (t, 2H),), 2.46 (s, 3H). Separation by chiral HPLC provides enantiomers II-58a-b.

Example 279

Preparation of Compound No. II-59

To a de-aerated solution of 2-allyl-8-methyl-5-[2-(6-methyl-pyridin-3-yl)-propenyl]-2,3,4,5-tetrahydro-1H-pyrido[4,3-b]indole (750 mg, 2.1 mmol) in DCM (7.5 mL) were added 1,3-dimethylbarbutaric acid (984 mg, 6.302 mmol) and Pd(PPh$_3$)$_4$ (48 mg, 0.042 mmol), and the reaction mixture stirred for 1 h at RT. The reaction mixture was concentrated and the residue diluted with 25% saturated potassium carbonate and extracted with EtOAc (3×30 mL). The combined organic layer was washed with water (2×25 mL), dried over anhydrous sodium sulfate and concentrated to afford crude material, which was purified by column chromatography using neutral alumina and 2% MeOH-DCM followed by reverse phase HPLC to yield 8-methyl-5-[2-(6-methyl-pyridin-3-yl)-propenyl]-2,3,4,5-tetrahydro-1H-pyrido[4,3-b]indole (180 mg). $^1$H NMR (CD$_3$OD, TFA salt) δ (ppm): 8.92 (s, 1H), 8.65 (d, 1H), 7.90 (d, 1H), 7.36 (d, 2H), 7.18 (d, 1H), 7.16 (d, 1H), 4.50 (s, 2H), 3.65 (t, 2H), 3.10 (t, 2H), 2.80 (s, 3H), 2.42 (s, 3H), 2.05 (s, 3H).

Example 280

Preparation of Compound No. II-60 and II-60a-b

To a solution of 5-(2-hydroxy-2-pyridin-4-yl-ethyl)-2-methyl-2,3,4,5-tetrahydro-1H-pyrido[4,3-b]indole-8-carboxylic acid methyl ester (180 mg, 0.493 mmol) in dry THF (12 mL) was portionwise added LAH (56 mg, 1.479 mmol) under nitrogen atmosphere, and the reaction mixture stirred at RT for 2 h. The reaction mixture was cooled to −78° C. and quenched with ice water (0.6 mL), 10% NaOH (0.6 mL) and water (1.8 mL), and the solid filtered. The filtrate was concentrated and the residue was purified by reverse phase HPLC to yield 2-(8-hydroxymethyl-2-methyl-1,2,3,4-tetrahydro-pyrido[4,3-b]indol-5-yl)-1-pyridin-4-yl-ethanol. $^1$H NMR (CD$_3$OD, freebase) δ (ppm): 8.4 (d, 2H), 7.4 (s, 1H), 7.27-7.38 (m, 3H), 7.18 (d, 1H), 5.1 (t, 1H), 4.62 (s, 2H), 4.3 (d, 2H), 4.0 (dd, 2H), 3.2 (m, 1H), 3.1 (m, 2H), 2.73 (m, 1H), 2.7 (s, 3H). Separation by chiral HPLC provides enantiomers II-60a-b.

Example 281

Preparation of Compound No. II-61

To a de-aerated solution of 2,4,4,8-tetramethyl-2,3,4,5-tetrahydro-1H-pyrido[4,3-b]indole (228 mg, 1.00 mmol), potassium phosphate (466 mg, 2.20 mmol), L-proline (19 mg, 0.10 mmol) and copper iodide (I) (23 mg, 0.20 mmol) in DMF (2 mL) was added 5-(1-bromoprop-1-en-2-yl)-2-methylpyridine (424 mg, 2.00 mmol), and the reaction mixture stirred at 120° C. for 20 h. The progress of reaction was monitored by TLC and LCMS. The reaction mixture was diluted with water (20 mL) and extracted with EtOAc (3×10 mL). The combined organic layer was washed with water (3×20 mL), followed by brine (25 mL), dried over anhydrous sodium sulfate and evaporated to afford crude material, which was purified by reverse phase HPLC. $^1$H NMR (CD$_3$OD, TFA salt) δ (ppm): 8.97 (s, 1H), 8.66 (d, 1H), 7.9 (d, 1H), 7.42 (s, 1H), 7.37 (s, 1H), 7.1 (q, 2H), 4.7 (m, 1H), 4.37 (m, 1H), 3.5 (m, 2H), 3.2 (s, 3H), 2.8 (s, 3H), 2.42 (s, 3H), 1.97 (s, 3H), 1.5 (bs, 6H).

Example 282

Preparation of Compound Nos. II-62 and II-62a-b

To a degassed solution of 1-(2-allyl-8-chloro-1,2,3,4-tetrahydro-pyrido[4,3-b]indol-5-yl)-2-pyridin-4-yl-propan-2-ol (300 mg, 0.78 mmol) in DCM (20 mL) were added 1,3-dimethyl barbituric acid (368 mg, 2.3 mmol) and Pd(PPh$_3$)$_4$ (18 mg, 0.015 mmol). After stirring at RT for 30 min, the reaction mixture was diluted with DCM and washed with saturated potassium carbonate solution. The organic layer was dried over anhydrous sodium sulfate and concentrated under reduced pressure. The residue was purified by reverse phase HPLC to yield 1-(8-chloro-1,2,3,4-tetrahydro-pyrido[4,3-b]indol-5-yl)-2-pyridin-4-yl-propan-2-ol. $^1$H NMR (CD$_3$OD, formate salt) δ (ppm): 8.4 (d, 2H), 7.48 (d, 2H), 7.4 (s, 1H), 7.18 (d, 1H), 6.98 (d, 1H), 4.6 (bs, 1H), 4.4 (s, 2H), 4.3 (m, 2H), 3.6 (m, 2H), 3.4 (m, 2H), 3.1 (m, 2H). Separation by chiral HPLC provides enantiomers II-62a-b.

Example 283

Preparation of Compound Nos. II-63 and II-63a-b

To a solution of 2-allyl-2,3,4,5-tetrahydro-8-methyl-1H-pyrido[4,3-b]indole (1000 mg, 4.42 mmol) in DMF (10 mL) was portionwise added sodium hydride (526 mg, 13.26 mmol). After stirring at RT for 5 min., 4-(oxiran-2-yl)pyridine (669 mg, 5.31 mmol) was added dropwise into the reaction mixture, which was stirred at RT for 16 h. Ice water was added into the reaction mixture and the solid mass obtained was filtered, washed with water (2×10 mL), hexane (2×50 mL) and ether to yield 2-(2-allyl-1,2,3,4-tetrahydro-8-methylpyrido[4,3-b]indol-5-yl)-1-(pyridin-4-yl)ethanol. $^1$H NMR (CDCl$_3$, freebase) δ (ppm): 8.6 (d, 2H), 7.24 (s, 1H), 7.2 (d, 2H), 7.0 (d, 2H), 5.98 (m, 1H), 5.2 (dd, 2H), 5.0 (m, 1H), 4.1 (m, 2H), 3.6 (dd, 2H), 3.22 (d, 2H), 2.7-2.9 (m, 3H), 2.6 (m, 1H), 2.4 (s, 3H). Separation by chiral HPLC provides enantiomers II-63a-b.

Example 284

Preparation of Compound Nos. II-64 and II-64a-b

To a solution of 2-(8-methyl-1,2,3,4-tetrahydro-pyrido[4,3-b]indol-5-yl)-1-pyridin-4-yl-ethanol (100 mg, 0.325 mmol) in acetonitrile (3 mL), potassium carbonate (135 mg, 0.977 mmol) and 2-bromoethanol (61 mg, 0.488 mmol) were added and the reaction mixture stirred at 60° C. for 1 h. The progress of reaction was monitored by TLC and LCMS. The reaction mixture was diluted with water (10 mL) and extracted with EtOAc (3×20 mL). The combined organic layer was dried over anhydrous sodium sulfate and concentrated. The residue was purified by reverse phase HPLC to yield 2-[2-(2-hydroxy-ethyl)-8-methyl-1,2,3,4-tetrahydro-pyrido[4,3-b]indol-5-yl]-1-pyridin-4-yl-ethanol. $^1$H NMR (CD$_3$OD, formate salt) δ (ppm): 8.41 (d, 2H), 7.38 (d, 2H), 7.2 (m, 2H), 6.99 (d, 1H), 5.03 (t, 1H), 4.4 (bs, 2H), 4.3 (d, 2H), 3.93 (t, 2H), 3.45-3.62 (m, 2H), 3.2 (m, 2H), 2.9 (m, 2H), 2.4 (s, 3H). Separation by chiral HPLC provides enantiomers II-64a-b.

Example 285

Preparation of Compound Nos. II-65 and II-65a-b

To a solution of 2-(8-methyl-1,2,3,4-tetrahydro-pyrido[4,3-b]indol-5-yl)-1-pyridin-4-yl-ethanol (200 mg, 0.651 mmol) in acetonitrile (4 mL), potassium carbonate (270 mg, 1.953 mmol) and bromo-acetic acid ethyl ester (163 mg, 0.977 mmol) were added and the reaction mixture was stirred at RT for 1 h. The progress of reaction was monitored by TLC and LCMS. The reaction mixture was diluted with water (10 mL) and extracted with EtOAc (3×30 mL). The combined organic layer was dried over anhydrous sodium sulfate and concentrated to yield [5-(2-hydroxy-2-pyridin-4-yl-ethyl)-8-methyl-1,3,4,5-tetrahydro-pyrido[4,3-b]indol-2-yl]-acetic acid ethyl ester (220 mg). To a solution of [5-(2-hydroxy-2-pyridin-4-yl-ethyl)-8-methyl-1,3,4,5-tetrahydro-pyrido[4,3-b]indol-2-yl]-acetic acid ethyl ester (120 mg, 0.305 mmol) in ethanol (2 mL), 1N NaOH (3 mL) was added and the reaction mixture stirred at RT for 1 h. The progress of reaction was monitored by LCMS. The reaction mixture was neutralized with aq HCl. The solvent was removed under reduced pressure and the residue diluted with 90% MeOH in DCM and filtered. The filtrate was concentrated and residue was purified by reverse phase HPLC to yield [5-(2-hydroxy-2-pyridin-4-yl-ethyl)-8-methyl-1,3,4,5-tetrahydro-pyrido[4,3-b]indol-2-yl]-acetic acid. $^1$H NMR (CD$_3$OD, formate salt) δ (ppm): 8.42 (d, 2H), 7.4 (d, 2H), 7.2 (d, 2H), 6.9 (d, 1H), 5.03 (t, 1H), 4.6 (bs, 1H), 4.57 (bs, 2H), 4.3 (m, 2H), 3.8 (s, 2H), 3.7 (bs, 2H), 3.0 (m, 1H), 2.3 (s, 3H). Separation by chiral HPLC provides enantiomers II-65a-b.

Example 286

Preparation of Compound Nos. II-67 and II-67a-b

To a solution of 2-methyl-8-trifluoromethoxy-2,3,4,5-tetrahydro-1H-pyrido[4,3-b]indole (1.0 g, 3.70 mmol) in DMF (10 mL) was added sodium hydride (445 mg, 11.12 mmol) under nitrogen at 0° C. After stirring for 10 min, 4-(oxiran-2-yl)pyridine (806 g, 6.66 mmol) was added dropwise under nitrogen and the reaction mixture was stirred at RT for 12 h. The progress of reaction was monitored by TLC and LCMS. The reaction mixture was poured into ice-cold water and extracted with EtOAc (2×100 mL). The combined organic layer was washed with water (5×50 mL) and dried over anhydrous sodium sulfate, concentrated and re-crystallized in diethyl ether to yield 2-(2-methyl-8-trifluoromethoxy-1,2,3,4-tetrahydro-pyrido[4,3-b]indol-5-yl)-1-pyridin-4-yl-ethanol. $^1$H NMR (CDCl$_3$, freebase) δ (ppm): 8.58 (d, 2H), 7.17-7.21 (m, 4H), 7.0 (d, 1H), 4.6 (m, 1H), 4.0 (m, 2H), 3.38 (dd, 2H), 2.8 (m, 1H), 2.7 (m, 2H), 2.6 (m, 1H), 2.18 (s, 3H). Separation by chiral HPLC provides enantiomers II-67a-b.

Example 287

Preparation of Compound Nos. II-68 and II-68a-b

To a solution of 8-tert-butyl-2-methyl-2,3,4,5-tetrahydro-1H-pyrido[4,3-b]indole (1.0 g, 4.1 mmol) in DMF (6 mL) was added sodium hydride (495 mg, 12.3 mmol) under nitrogen at 0° C. and stirred for 10 min. A solution of 4-(oxiran-2-yl)pyridine (898 mg, 7.4 mmol) in DMF (2 mL) was added dropwise into the reaction mixture at RT and stirred for 12 h. The progress of reaction was monitored by TLC and LCMS. The reaction mass was poured in ice-cold water and extracted with EtOAc (2×100 mL). The combined organic layer was washed with water (5×50 mL), dried over anhydrous sodium sulfate and concentrated. The residue was re-crystallized with hexane to yield 2-(8-tert-butyl-2-methyl-1,2,3,4-tetrahydro-pyrido[4,3-b]indol-5-yl)-1-pyridin-4-yl-ethanol.
$^1$H NMR (CDCl$_3$, freebase) δ (ppm): 8.7 (d, 2H), 7.3 (s, 1H), 7.2 (d, 1H), 7.19 (d, 2H), 7.17 (d, 1H), 4.7 (t, 1H), 4.0 (d, 2H), 3.5 (dd, 2H), 2.82 (m, 1H), 2.7 (m, 2H), 2.58 (m, 1H), 2.4 (s, 3H), 1.4 (s, 9H). Separation by chiral HPLC provides enantiomers II-68a-b.

Example 288

Preparation of Compound No. II-70

A solution of 2-(pyridin-4-yl)-1-(2,4,4,8-tetramethyl-3,4-dihydro-1H-pyrido[4,3-b]indol-5(2H)-yl)propan-2-ol (110 mg) in thionyl chloride (2 mL) was stirred at RT for 20 min. The excess thionyl chloride was removed under reduced pressure, and to the residue were added DMF (2 mL) and powdered KOH (140 mg, 0.303 mmol), followed by stirring at 85° C. for 25 min. The progress of reaction was monitored by LCMS. The reaction mixture was diluted with water (50 mL) and extracted with EtOAc (3×30 mL). The organic layer was washed with water (2×20 mL), dried over anhydrous sodium sulfate and evaporated to afford crude material, which was purified by reverse phase HPLC. $^1$H NMR (CD$_3$OD, TFA salt) δ (ppm): 8.7 (d, 2H), 8.0 (d, 2H), 7.58 (s, 1H), 7.37 (s, 1H), 7.1 (d, 1H), 7.05 (d, 1H), 4.7 (bs, 1H), 4.4 (bs, 1H), 3.5 (d, 2H), 3.18 (s, 3H), 2.42 (s, 3H), 1.97 (s, 3H), 1.57 (bs, 6H).

Example 289

Preparation of Compound Nos. II-71 and II-11a-b

To a solution of 9-chloro-2-methyl-1,2,3,4,5,6-hexahydroazepino[4,3-b]indole (1 g, 4.273 mmol) in DMF was added NaH (512 mg, 12.81 mmol) in portions at 0° C. After stirring the reaction mixture at 0° C. for 15 min, a solution of 4-(oxiran-2-yl)pyridine (775 mg, 6.409 mmol) in DMF (1 mL) was added dropwise into the mixture at the same temperature and stirring continued at RT overnight. The progress of reaction was monitored by TLC and LCMS. After completion, ice water was added into the reaction mixture and extracted with EtOAc (3×50 mL). The organic layer was washed with water (5×50 mL), dried over anhydrous sodium sulfate and concentrated. The residue was purified by silica gel column chromatography using 10% MeOH/DCM as eluent followed by recrystallization with MeOH and acetonitrile to yield 2-(9-chloro-2-methyl-2,3,4,5-tetrahydroazepino[4,3-b]indol-6(1H)-yl)-1-(pyridin-4-yl)ethanol. $^1$H NMR (CDCl$_3$, Free base) δ (ppm): 8.5 (d, 2H), 7.4 (s, 1H), 7.3 (d, 2H), 7.19 (d, 1H), 7.05 (d, 1H), 4.85 (dd, 1H), 4.18 (m, 2H), 3.8 (d, 1H), 3.65 (d, 1H), 3.0 (m, 2H), 2.8 (m, 1H), 2.69 (m, 1H), 2.42 (s, 3H), 1.85 (m, 2H). Separation by chiral HPLC provides enantiomers II-71a-b.

Example 290

Preparation of Compound Nos. II-75 and II-75a-b

To a solution of 3-(3,4-dihydro-8-methyl-1H-pyrido[4,3-b]indol-2(5H)-yl)propan-1-ol (1000 mg, 4.0983 mmol) in DMF (10 mL) was portionwise added sodium hydride (491.8 mg, 12.25 mmol). After stirring at RT for 5 min, 4-(oxiran-2-yl)pyridine (620 mg, 4.92 mmol) was added dropwise into the reaction mixture, which was stirred at RT overnight. Ice water was added into the reaction mixture and the solid mass filtered, washed with water (2×10 mL) and hexane (2×50 mL). The residue was purified by reverse phase HPLC to yield 3-(3,4-dihydro-5-(2-hydroxy-2-(pyridin-4-yl)ethyl)-8-methyl-1H-pyrido[4,3-b]indol-2(5H)-yl)propan-1-ol. $^1$H NMR (CD$_3$OD, formate salt) δ (ppm): 8.43 (bs, 2H), 7.39 (d, 2H), 7.23 (s, 1H), 7.2 (d, 1H), 7.0 (d, 1H), 5.07 (t, 1H), 4.48 (bs, 2H), 4.23 (m, 2H), 3.7 (t, 2H), 3.6 (bs, 2H), 3.4 (t, 2H), 3.2 (m, 1H), 2.95-3.03 (m, 1H), 2.4 (s, 3H), 2.03 (bs, 2H). Separation by chiral HPLC provides enantiomers II-75a-b.

Example 291

Preparation of Compound No. II-76

To a de-aerated solution of (E,Z)-1-(2,8-dimethyl-3,4-dihydro-1H-pyrido[4,3-b]indol-5(2H)-yl)prop-1-en-2-yl trifluoromethanesulfonate (200 mg, 0.515 mmol), 4-methyl-3-(4,4,5,5-tetramethyl-1,3,2-dioxaborolan-2-yl)pyridine (225 mg, 1.03 mmol) and K$_2$CO$_3$ (215 mg, 1.55 mmol) in DME (2 mL) and water (1 mL) was added Pd(PPh$_3$)$_4$ (52 mg, 0.045 mmol). The reaction mixture was stirred at 90° C. for 45 min. The solvent was removed under reduced pressure, and the residue was diluted with water and extracted with EtOAc. The organic layer was dried over anhydrous sodium sulfate and evaporated to afford crude material, which was purified by reverse phase HPLC to yield (E)-2,8-dimethyl-5-(2-(4-methylpyridin-3-yl)prop-1-en-1-yl)-2,3,4,5-tetrahydro-1H-pyrido[4,3-b]indole as the TFA salt. $^1$H NMR (CD$_3$OD, TFA salt) δ (ppm): 8.87 (s, 1H), 8.75 (d, 1H), 8.0 (d, 1H), 7.3 (s, 1H), 7.24 (d, 1H), 7.17 (d, 1H), 6.8 (s, 1H), 4.77 (d, 1H), 4.38 (d, 1H), 3.9 (bs, 1H), 3.4 (bs, 1H), 3.3 (m, 1H), 3.18 (m, 1H), 3.12 (s, 3H), 2.8 (s, 3H), 2.42 (s, 3H), 2.0 (s, 3H).

Example 292

Preparation of Compound No. II-77

To a degassed solution of 2,8-dimethyl-5-(2-(4,4,5,5-tetramethyl-1,3,2-dioxaborolan-2-yl)prop-1-en-1-yl)-2,3,4,5-tetrahydro-1H-pyrido[4,3-b]indole (200 mg, 0.546 mmol), 5-bromo-2-ethylpyridine (50 mg, 0.273 mmol) and K$_2$CO$_3$ (113 mg, 0.819 mmol) in DME (2 mL) and water (1 mL) was added Pd(PPh$_3$)$_4$ (22 mg, 0.019 mmol). The reaction mixture was purged with nitrogen and heated to reflux for 45 min. The reaction mixture was cooled to RT, diluted with water and extracted with EtOAc(3×6 mL). The combined organic layer was dried over anhydrous sodium sulfate. The solvent was removed under reduced pressure to afford crude product which was purified by reverse phase HPLC as a TFA salt. $^1$H NMR (CD$_3$OD, TFA salt) δ (ppm): 8.98 (s, 1H), 8.78 (d, 1H), 8.0 (d, 1H), 7.38 (d, 2H), 7.18 (d, 1H), 7.1 (d, 1H), 4.76 (d, 1H), 4.4 (d, 1H), 3.85 (bs, 1H), 3.6 (bs, 1H), 3.2 (m, 2H), 3.18 (s, 3H), 3.1 (s, 2H), 2.64 (s, 3H), 2.05 (s, 3H), 1.5 (t, 3H).

Example 293

Preparation of Compound Nos. II-78 and II-78a-b

To a solution of 6-methyl-6,7,8,9-tetrahydro-5H-1,6,9-triaza-fluorene (1.0 g, 0.0053 mole) in DMF (15 mL) were added portionwise NaH (60%, 0.634 g, 0.0159 mole) and 4-(oxiran-2-yl)pyridine (0.807 g, 0.0064 mole). The reaction mixture was stirred at RT overnight. The progress of reaction was monitored by LCMS. The reaction mixture was quenched with ice cold water (300 mL) and extracted with EtOAc (3×100 mL). The combined organic layer was washed with water (10×100 mL), brine (2×100 mL), dried over anhydrous sodium sulfate and concentrated. The residue was purified by silica gel column chromatography followed by reverse phase HPLC to yield the title compound. $^1$H NMR (CDCl$_3$, freebase) δ (ppm): 8.5 (d, 2H), 8.2 (d, 1H), 7.7 (d, 1H), 7.23 (d, 2H), 7.9 (m, 1H), 5.08 (m, 1H), 4.5 (d, 1H), 4.3 (d, 1H), 3.6 (dd, 2H), 2.9 (m, 1H), 2.8 (m, 1H), 2.7 (m, 1H), 2.6 (m, 1H), 2.5 (s, 3H). Separation by chiral HPLC provides enantiomers II-78a-b.

Example 294

Preparation of Compound Nos. II-80 and II-80a-b

A solution of 1-(2,8-dimethyl-1,2,3,4-tetrahydro-pyrido[4,3-b]indol-5-yl)-2-(6-methoxy-pyridin-3-yl)-propan-2-ol (100 mg, 0.27 mmol) in 3N HCl (4 mL) was stirred at 100° C. for 4 h. The reaction mixture was concentrated under reduced pressure and the residue was purified by reverse phase HPLC to yield 5-[2-(2,8-dimethyl-1,2,3,4-tetrahydro-pyrido[4,3-b]indol-5-yl)-1-hydroxy-1-methyl-ethyl]-pyridin-2-ol. $^1$H NMR (CD$_3$OD, freebase) δ (ppm): 7.58 (d, 1H), 7.2 (s, 1H), 7.1 (s, 1H), 7.0 (d, 1H), 6.8 (d, 1H), 6.4 (d, 1H), 4.6 (bs, 1H), 4.17 (m, 2H), 4.0 (m, 2H), 3.1-3.25 (m, 2H), 2.97 (m, 1H), 2.8

Example 295

Preparation of Compound Nos. II-81 and II-81a-b

To a solution of 5-(2-hydroxy-2-pyridin-4-yl-ethyl)-2,3,4,5-tetrahydro-1H-pyrido[4,3-b]indole-8-carboxylic acid ethyl ester (200 mg, 0.547 mmol) in dry THF (10 mL) was added portionwise LAH (63 mg, 1.65 mmol) under nitrogen at RT. After stirring for 2 h, the reaction mixture was quenched with water (0.5 mL), NaOH (1 mL). The organic layer was separated and concentrated under reduced pressure. The crude product was purified by reverse phase chromatography to yield 2-(8-hydroxymethyl-1,2,3,4-tetrahydro-pyrido[4,3-b]indol-5-yl)-1-pyridin-4-yl-ethanol. $^1$H NMR (CD$_3$OD, freebase) δ (ppm): 8.41 (d, 2H), 7.42 (s, 1H), 7.39 (d, 2H), 7.3 (d, 1H), 7.19 (d, 1H), 5.08 (t, 1H), 4.66 (s, 2H), 4.4 (s, 2H), 4.3 (m, 2H), 3.5 (m, 2H), 3.2 (m, 1H), 2.9 (m, 1H). Separation by chiral HPLC provides enantiomers II-81a-b.

Example 296

Preparation of Compound No. II-82

5-(2-Bromocyclopent-1-enyl)-2,8-dimethyl-2,3,4,5-tetrahydro-1H-pyrido[4,3-b]indole (100 mg, 0.29 mmol), 2-methyl-5-(4,4,5,5-tetramethyl-1,3,2-dioxaborolan-2-yl) pyridine (127 mg, 0.58 mmol) and K$_2$CO$_3$ (120 mg, 0.87 mmol) were mixed in 1,2-dimethoxyethane (4 mL) and water (2 mL). The reaction mixture was purged with nitrogen, Pd(PPh$_3$)$_4$ (17 mg, 0.0147 mmol) was added and the reaction mixture was heated at 90° C. for 45 min. The reaction mixture was cooled to RT and concentrated under reduced pressure. The residue was diluted with water (20 mL) and extracted with EtOAc (50 mL). The organic layer was dried over anhydrous sodium sulfate and concentrated under reduced pressure. The residue was purified by reverse phase HPLC to yield 26 mg of 2,8-dimethyl-5-(2-(6-methylpyridin-3-yl)cyclopent-1-enyl)-2,3,4,5-tetrahydro-1H-pyrido[4,3-b]indole as the TFA salt. $^1$H NMR (CD$_3$OD, TFA salt) δ (ppm): 8.0 (d, 1H), 7.8 (dd, 1H), 7.61 (d, 1H), 7.31 (s, 1H), 6.95-7.10 (m, 2H), 4.7 (d, 1H), 4.38 (d, 1H), 3.8 (m, 1H), 3.55 (m, 1H), 2.82-3.2 (m, 9H), 2.61 (s, 3H), 2.4 (s, 3H), 2.3 (m, 2H).

Example 297

Preparation of Compound Nos. II-83 and II-83a-d

To a solution of 2-(8-methyl-1,2,3,4-tetrahydro-pyrido[4,3-b]indol-5-yl)-1-pyridin-4-yl-ethanol (200 mg, 0.651 mmol) in acetonitrile (4 mL), potassium carbonate (270 mg, 1.95 mmol) and 1-bromopropan-2-ol (135 mg, 0.977 mmol) were added and stirred the reaction mixture at 100° C. for 2 h. The reaction mixture was diluted with water (10 mL) and extracted with EtOAc (3×20 mL). The combined organic layer was dried over anhydrous sodium sulfate and concentrated under reduced pressure. The residue was purified by reverse phase HPLC to yield 1-[5-(2-hydroxy-2-pyridin-4-yl-ethyl)-8-methyl-1,3,4,5-tetrahydro-pyrido[4,3-b]indol-2-yl]-propan-2-ol. $^1$H NMR, (CDCl$_3$, freebase) δ (ppm): 8.58 (s, 2H), 7.36 (m, 2H), 7.2 (m, 2H), 7.02 (d, 1H), 5.1 (s, 1H), 4.3 (m, 1H), 4.1 (m, 2H), 4.0 (m, 2H), 3.56 (m, 1H), 3.37 (m, 1H), 3.1-3.3 (m, 2H), 2.8 (m, 2H), 2.42 (s, 3H), 1.2 (d, 3H). Separation by chiral HPLC provides diastereomers II-83a-d.

Example 298

Preparation of Compound Nos. II-84 and II-84a-b

To a solution of 2-(8-methyl-1,2,3,4-tetrahydro-pyrido[4,3-b]indol-5-yl)-1-pyridin-4-yl-ethanol (200 mg, 0.651 mmol) in acetonitrile (4 mL), potassium carbonate (270 mg, 1.95 mmol) and 1-chloro-2-methyl-propan-2-ol (105 mg, 0.977 mmol) were added and the reaction mixture was stirred at 100° C. for 12 h. The reaction mixture was diluted with water (10 mL) and extracted with EtOAc (3×20 mL). The combined organic layer was dried over anhydrous sodium sulfate and concentrated under reduced pressure. The residue was purified by column chromatography (Neutral alumina, 1% MeOH-DCM), to yield 1-[5-(2-hydroxy-2-pyridin-4-yl-ethyl)-8-methyl-1,3,4,5-tetrahydro-pyrido[4,3-b]indol-2-yl]-2-methyl-propan-2-ol. $^1$H NMR (CDCl$_3$, freebase) δ (ppm): 8.6 (d, 2H), 7.27 (m, 2H), 7.2 (m, 2H), 7.0 (d, 1H), 5.08 (t, 1H), 4.19 (m, 2H), 3.9 (bs, 2H), 3.0-3.1 (m, 2H), 2.9 (m, 1H), 2.6 (s, 2H), 2.56 (m, 1H), 2.21 (s, 3H), 1.21 (s, 6H). Separation by chiral HPLC provides enantiomers II-84a-b.

Example 299

Preparation of Compound Nos. II-88 and II-88a-b

To a solution of 1-(3,4-Bis-allyloxy-phenyl)-2-(2,8-dimethyl-1,2,3,4-tetrahydro-pyrido[4,3-b]indol-5-yl)-ethanol (500 mg, 1.15 mmol) in 10 mL MeOH was purged with nitrogen for 10 min. 1,3-Dimethylbarbituric acid (903 mg, 5.79 mmol) and Pd(PPh$_3$)$_4$ (80 mg, 0.069 mmol) were added under nitrogen and the mixture stirred for 30 min at RT. After the complete conversion of starting material (TLC and LCMS), the MeOH was removed under reduced pressure. 100 mL of saturated sodium bicarbonate was added and the mixture was extracted with EtOAc (3×100 mL). The combined organic layers were dried over anhydrous sodium sulfate and concentrated. The resultant crude product was purified by HPLC to obtain 160 mg of 4-[2-(2,8-dimethyl-1,2,3,4-tetrahydro-pyrido[4,3-b]indol-5-yl)-1-hydroxy-ethyl]-benzene-1,2-diol. $^1$H NMR (CD$_3$OD, Free base) δ (ppm): 7.3 (d, 1H), 7.2 (s, 1H), 7.05 (dd, 1H), 6.7 (d, 1H), 6.6 (s, 1H), 6.53 (d, 1H), 4.8 (t, 1H), 4.21 (m, 3H), 4.05 (dd, 1H), 3.34 (m, 1H), 3.3 (m, 1H), 2.88 (dt, 1H), 2.81 (s, 3H), 2.5 (dt, 1H), 2.4 (s, 3H). Separation by chiral HPLC provides enantiomers II-88a-b.

Example 300

Preparation of Compound Nos. II-89 and II-89a-b

To a degassed solution of 2-(2-allyl-8-chloro-1,2,3,4-tetrahydro-pyrido[4,3-b]indol-5-yl)-1-pyridin-3-yl-ethanol (1.0 g, 2.7 mmol) in DCM were added 1,3-dimethyl barbituric acid (1.27 g, 8.1 mmol) and Pd(PPh$_3$)$_4$ (63 mg, 0.054 mmol) and the reaction mixture was stirred at RT for 3 h. The solvent was removed under reduced pressure. The residue was dissolved in saturated potassium carbonate solution and extracted with EtOAc (3×50 mL). The combined organic layer was washed with saturated potassium carbonate (6×20 mL), dried over anhydrous sodium sulfate and concentrated. The residue was purified by column chromatography (neutral alumina, 20% methanol in DCM) followed by reverse phase HPLC to yield 2-(8-chloro-1,2,3,4-tetrahydro-pyrido[4,3-b] indol-5-yl)-1-pyridin-3-yl-ethanol. $^1$H NMR (CD$_3$OD, freebase) δ (ppm): 8.4 (d, 1H), 8.37 (s, 1H), 7.8 (d, 1H), 7.4 (d, 1H), 7.39 (m, 1H), 7.2 (d, 1H), 7.02 (d, 1H), 5.1 (t, 1H), 4.33

(d, 2H), 4.3 (s, 2H), 3.38-3.5 (m, 2H), 3.1 (m, 1H), 2.9 (m, 1H). Separation by chiral HPLC provides enantiomers II-89a-b.

Example 301

Preparation of Compound Nos. II-90 and II-90a-b

To a solution of 2,8-dimethyl-2,3,4,5-tetrahydro-1H-pyrido[4,3-b]indole (300 mg, 1.5 mmol) in DMF (5 mL) was added sodium hydride (180 mg, 4.5 mmol) under nitrogen. After stirring at RT for 10 min, 4-(oxiran-2-yl)quinoline (384 mg, 2.25 mmol) was added dropwise under nitrogen into the reaction mixture, which was stirred at RT for 18 h. The progress of reaction was monitored by TLC, LCMS and NMR. The reaction mixture was poured in ice-cold water and extracted with EtOAc (2×50 mL). The combined organic layer was washed with water (3×50 mL), dried over anhydrous sodium sulfate and concentrated under reduced pressure. Re-crystallization with diethyl ether yielded 2-(2,8-dimethyl-3,4-dihydro-1H-pyrido[4,3-b]indol-5(2H)-yl)-1-(quinolin-4-yl)ethanol (140 mg). $^1$H NMR (CDCl$_3$, freebase) δ (ppm): 8.86 (d, 1H), 8.19 (d, 1H), 7.97 (d, 1H), 7.78 (t, 1H), 7.41 (d, 1H), 7.56 (t, 1H), 7.2 (d, 1H), 6.93-7.01 (m, 2H), 5.57 (t, 1H), 4.2 (dd, 1H), 4.1 (dd, 1H), 3.37 (dd, 2H), 2.83 (m, 1H), 2.71 (bs, 3H), 2.4 (s, 3H), 2.38 (s, 3H). Separation by chiral HPLC provides enantiomers II-90a-b.

Example 302

Preparation of Compound Nos. II-91 and II-91a-b

To a solution of 2,8-dimethyl-2,3,4,5-tetrahydro-1H-pyrido[4,3-b]indole (525 mg, 2.6 mmol) in DMF was added sodium hydride (312 mg, 7.8 mmol) at 0° C. After stirring the solution for 15 min, a solution of 2-cyclohexyloxirane (500 mg, 3.9 mmol) was added dropwise into the reaction mixture, which was stirred at RT overnight. The progress of reaction was monitored by TLC, NMR and LCMS. The reaction mixture was quenched with ice-cold water and extracted with EtOAc. The organic layer was thoroughly washed with water, dried over anhydrous sodium sulfate and concentrated. Re-crystallization with ether yielded the desired product (160 mg). $^1$H NMR (CDCl$_3$, Free base) δ (ppm): 7.2 (s, 1H), 7.19 (d, 1H), 6.95 (d, 1H), 4.15 (dd, 1H), 3.92 (dd, 1H), 3.7 (m, 1H), 3.6 (s, 2H), 2.99 (m, 1H), 2.8 (m, 3H), 2.58 (s, 3H), 2.42 (s, 3H), 1.9 (d, 1H), 1.8 (m, 2H), 1.7 (d, 2H), 1.52 (m, 1H), 1.22 (m, 5H). Separation by chiral HPLC provides enantiomers II-91a-b.

Example 303

Preparation of Compound No. II-92 and II-92a-b

A solution of 2-(2,8-dimethyl-1,2,3,4-tetrahydro-pyrido[4,3-b]indol-5-yl)-1-(6-methoxy-pyridin-3-yl)-ethanol (200 mg, 0.569 mmol) in 3N HCl (8 mL) was stirred at 100° C. for 3 h. The reaction mixture was concentrated under reduced pressure and residue was purified by reverse phase HPLC to yield 5-(2-(1,2,3,4-tetrahydro-2,8-dimethylpyrido[4,3-b]indol-5-yl)-1-hydroxyethyl)pyridin-2(1H)-one. $^1$H NMR (CD$_3$OD, TFA salt) δ (ppm): 7.5 (m, 1H), 7.23 (s, 1H), 7.2 (s, 1H), 7.19 (d, 1H), 6.5 (s, 1H), 4.62 (d, 1H), 4.19-4.37 (m, 3H), 3.8 (m, 1H), 3.5 (m, 1H), 3.24 (m, 2H), 3.1 (m, 4H), 2.4 (s, 3H). Separation by chiral HPLC provides enantiomers II-92a-b.

Example 304

Preparation of Compound Nos. II-93 and II-93a-b

To a solution of 2-(8-chloro-1,2,3,4-tetrahydropyrido[4,3-b]indol-5-yl)-1-(pyridin-4-yl)ethanol (600 mg, 1.84 mmol) in acetone (20 mL) were added 2-bromoethanol (341 mg, 2.76 mmol) and K$_2$CO$_3$ (761 mg, 5.52 mmol) and the reaction mixture stirred at 80° C. for 4 h. The progress of reaction was monitored by TLC and LCMS. The reaction mixture was cooled to RT, filtered and the filtrate concentrated under reduced pressure. The residue was diluted with water and extracted with EtOAc. The organic layer was dried over anhydrous sodium sulfate and concentrated. The residue was purified by reverse phase HPLC to yield the title compound. $^1$H NMR (CDCl$_3$, Free base) δ (ppm): 8.41 (d, 2H), 7.31 (s, 1H), 7.18 (m, 4H), 4.79 (t, 1H), 4.0 (m, 2H), 3.68 (m, 3H), 3.56 (d, 1H), 2.8 (m, 3H), 2.65 (m, 2H), 2.58 (m, 1H). Separation by chiral HPLC provided enantiomers II-93a-b.

Example 305

Preparation of Compound Nos. II-94 and II-94a-b

To a solution of 2-(8-chloro-1,2,3,4-tetrahydropyrido[4,3-b]indol-5-yl)-1-(pyridin-3-yl)ethanol (1.0 g, 3.05 mmol) in acetone (30 mL) were added 2-bromoethanol (758 mg, 6.12 mmol) and K$_2$CO$_3$ (1.3 g, 9.43 mmol) and the reaction mixture stirred at 80° C. for 4 h. The progress of reaction was monitored by TLC and LCMS. The reaction mixture was cooled to RT, filtered and the filtrate concentrated under reduced pressure. The residue was diluted with water and extracted with EtOAc. The organic layer was dried over anhydrous sodium sulfate and concentrated. The residue was purified by reverse phase HPLC to yield the title compound. $^1$H NMR (CDCl$_3$, Free base) δ (ppm): 8.39 (d, 1H), 8.2 (s, 1H), 7.6 (d, 1H), 7.27 (s, 1H), 7.2 (m, 2H), 7.16 (d, 1H), 4.8 (m, 1H), 4.1 (dd, 1H), 4.0 (dd, 1H), 3.7 (m, 2H), 3.6 (d, 1H), 3.5 (d, 1H), 2.85 (m, 3H), 2.8 (m, 1H), 2.63 (m, 2H). Separation by chiral HPLC provided enantiomers II-94a-b.

Example 306

Preparation of Compound Nos. II-95 and II-95a-d

Phenyl magnesium bromide (1M solution in THF) (6.24 mL, 6.24 mmol) was added dropwise at −70° C. to a stirred solution of 2-(2,8-dimethyl-1,2,3,4-tetrahydro-pyrido[4,3-b]indol-5-yl)-propionaldehyde (400 mg, 1.56 mmol) in THF (40 mL), the reaction mixture stirred at RT for 16 h, diluted with EtOAc (75 mL) and water (60 mL). The two layers were separated, the aq. layer extracted with EtOAc (2×75 mL), and the combined organic layers dried over anhydrous sodium sulfate and concentrated under reduced pressure. The crude (500 mg) was purified by prep. HPLC to afford 2-(2,8-dimethyl-1,2,3,4-tetrahydro-pyrido[4,3-b]indol-5-yl)1-phenyl-propan-1-ol yielded as the TFA salt (65 mg). $^1$H NMR (CDCl$_3$, Free base) δ (ppm): 7.37 (d, 1H), 7.17 (t, 3H), 7.12 (s, 1H), 7.06 (m, 2H), 6.95 (d, 1H), 5.11 (t, 1H), 4.37 (t, 1H), 3.57 (dd, 1H), 3.46 (d, 1H), 2.67 (m, 2H), 2.51 (m, 1H), 2.43 (s, 3H), 2.41 (s, 3H), 1.68 (d, 3H). Separation by chiral HPLC provides diastereomers II-95a-d.

Example 307

Preparation of Compound No. II-96

To a solution of 1-(2,8-dimethyl-3,4-dihydro-1h-pyrido[4,3-b]indol-5(2h)-yl)prop-1-en-2-yltrifluoromethanesulfonate (100 mg, 0.257 mmol) in DME (4 mL) was added Pd(PPh$_3$)$_4$ (15 mg, 0.0128) and the reaction mixture was purged with N$_2$. 2-Fluoropyridine-5-boronic acid pinacol ester (115 mg, 0.515 mmol), K$_2$CO$_3$ (36 mg, 0.257 mmol) and water (2 mL) were added, the reaction mixture was purged with nitrogen and refluxed for 45 min. The reaction mixture was cooled to RT, and the solvent was removed under reduced pressure. The residue was dissolved in water, extracted with EtOAc, washed with brine, and concentrated to afford crude product which was purified by silica gel chromatography followed by reverse phase HPLC to obtain the products as TFA salts. $^1$H NMR (CD$_3$OD, TFA salt) δ (ppm): 8.42 (s, 1H), 8.21 (m, 1H), 7.28 (s, 1H), 7.02-7.21 (m, 4H), 4.78 (d, 1H), 4.40 (d, 1H), 3.82 (m, 1H), 3.58 (m, 1H), 3.16 (m, 5H), 2.41 (s, 3H), 2.0 (s, 3H).

Example 308

Preparation of Compound Nos. II-97 and II-97a-b

To a solution of 2-(1,2,3,4-tetrahydro-8-methylpyrido[4,3-b]indol-5-yl)-1-(pyridin-4-yl)ethanol (200 mg, 0.652 mmol) and sodium 2-bromoethanesulfonate (164 mg, 0.78 mmol) in DMF (3 mL) and water (0.5 mL), were added sodium bicarbonate (164 mg, 1.95 mmol) and potassium iodide (128 mg, 0.78 mmol) and the reaction mixture was stirred at 90° C. for 2 h. The reaction mixture was diluted with water and extracted with DCM. The aqueous layer was neutralized with aq HCl and the solid obtained was recrystallized from MeOH to yield 2-(3,4-dihydro-5-(2-hydroxy-2-(pyridin-4-yl)ethyl)-8-methyl-1H-pyrido[4,3-b]indol-2(5H)-yl)ethanesulfonic acid as a white solid (80 mg). $^1$H NMR (CD$_3$OD, Free base) δ (ppm): 8.45 (d, 2H), 7.40 (d, 2H), 7.26 (s, 1H), 7.23 (d, 1H), 7.00 (s, 1H), 5.06 (t, 1H), 4.59 (m, 2H), 4.29 (m, 2H), 3.71 (t, 4H), 3.55 (m, 2H), 3.0 (d, 1H), 2.4 (s, 3H). Separation by chiral HPLC provides enantiomers II-97a-b.

Example 309

Preparation of Compound No. II-98 and II-98a-d

To an ice-cooled stirred suspension of 4-bromopyridine hydrochloride salt (1.0 g, 5.1 mmol) in THF (5 mL) was added isopropyl magnesium chloride (2M in THF, 5 mL, 10.3 mmol) and stirred the reaction at RT for 30 min. A solution of 2-(1,2,3,4-tetrahydro-2,8-dimethylpyrido[4,3-b]indol-5-yl) propanal (300 mg, 1.17 mmol) in THF (3 mL) was added into the brown colored reaction mixture, which was stirred at RT for 1.5 h. The progress of reaction was monitored by TLC and LCMS (45% conversion). The reaction mixture was cooled to 0° C. and quenched with cold saturated ammonium chloride solution (till effervescence stopped) and water was added, stirred at RT for 15 min and extracted with EtOAc. The organic layer was dried over anhydrous sodium sulfate and evaporated. The residue was purified by reverse phase HPLC. $^1$H NMR (CDCl$_3$, Free base) δ (ppm): 8.60 (d, 2H), 7.4 (d, 1H), 7.55 (d, 2H), 7.18 (s, 1H), 6.98 (d, 1H), 5.15 (d, 1H), 4.2 (t, 1H), 3.4 (d, 1H), 3.28 (d, 1H), 2.94 (m, 1H), 2.784 (m, 1H), 2.68 (m, 2H), 2.48(s, 3H), 2.43 (s, 3H), 1.37 (s, 3H). Separation by chiral HPLC provides diastereomers II-98a-d.

Example 310

Preparation of Compound Nos. II-99 and II-99a-b

To a solution of 6-aza-2,8-dimethyl carboline (500 mg, 2.5 mmol) in DMF (5 mL) was added NaH (60%, 300 mg, 7.5 mmol). After stirring for 5 min at RT, a solution of 3-(2-methyloxiran-2-yl)pyridine (506.2 mmol, 3.75 mmol) in DMF (1 mL) was added dropwise into the reaction mixture, which was stirred at RT for 12 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The residue was triturated with ether to yield the desired compound (150 mg). $^1$H NMR (CDCl$_3$, Free base) δ (ppm): 8.7 (s, 1H), 8.41 (d, 1H), 8.02 (s, 1H), 7.8 (d, 1H), 7.5 (s, 1H), 7.19 (dd, 1H), 4.3 (dd, 2H), 3.6 (d, 1H), 3.5 (d, 1H), 2.8 (m, 2H), 2.65 (m, 1H), 2.55 (s, 3H), 2.49 (m, 1H), 2.4 (s, 3H), 1.6 (s, 3H). Separation by chiral HPLC provided enantiomers II-99a-b.

Example 311

Preparation of Compound Nos. II-100 and II-100a-b

Aza-dimethyl-carboline (100 mg, 0.497 mmol) was charged in a reaction bottle and N,N-dimethylformamide (2 mL) was added. Sodium hydride (60% suspension in mineral oil) (60 mg, 1.49 mmol) was added portionwise. The reaction mixture was stirred at RT for 5 min and 2-methyl-5-(oxiran-2-yl)pyridine (300 mg, 2.22 mmol) was added dropwise. The reaction mixture was stirred at RT overnight. The reaction was monitored by LCMS. Ice water (5 mL) was added and the organic layer was extracted with EtOAc (2×15 mL). The combined organic layer was washed with water (3×5 mL) and concentrated. The desired product was purified through reverse phase chromatography as a racemate (12.92 mg). $^1$H NMR (CDCl$_3$, Free base) δ (ppm): 8.42 (s, 1H), 8.0 (s, 1H), 7.5 (s, 1H), 7.47 (d, 1H), 7.07 (d, 1H), 5.1 (m, 1H), 4.37 (dd, 1H), 4.26 (dd, 1H), 3.59 (dd, 2H), 2.78 (m, 1H), 2.7 (m, 2H), 2.52 (s, 3H), 2.5 (s, 3H), 2.45 (m, 1H), 2.42 (s, 3H). Separation by chiral HPLC provided enantiomers II-100a-b.

Example 312

Preparation of Compound No. II-101

2,8-Dimethyl-5-(2-pyridin-4-yl-propenyl)-2,3,4,5-tetrahydro-pyrido[4,3-b]indol-1-one (350 mg, 1.057 mmol) was dissolved in dry toluene (6 mL). Methyl magnesium bromide (3M solution in diethyl ether, 1.76 mL, 5.28 mmol) was added and the reaction mixture was heated at 100° C. for 1 h. The reaction mixture was cooled to RT, quenched with ice water and filtered through a Celite bed. The filtrate was extracted with EtOAc (3×70 mL). The combined organic layer was dried over anhydrous sodium sulfate and concentrated under reduced pressure. The residue was purified by column chromatography over neutral alumina followed by reverse phase HPLC to obtain 6.5 mg of 1,1,2,8-tetramethyl-5-(2-pyridin-4-yl-propenyl)-2,3,4,5-tetrahydro-1H-pyrido[4,3-b]indole as a formate salt. $^1$H NMR (CD$_3$OD, formate salt) δ (ppm): 8.60 (d, 2H), 7.70 (d, 2H), 7.50 (s, 1H), 7.30 (s, 1H), 7.12 (m, 2H), 3.70 (t, 2H), 3.10 (t, 2H), 3.02 (s, 3H), 2.44 (s, 3H), 2.02 (s, 3H), 1.90 (s, 6H).

Example 313

Preparation of Compound Nos. II-102 and II-102a-b

To a solution of methyl carboline ethyl ester (500 mg, 1.27 mmol) in THF (30 mL) was added LAH (145 mg, 3.81 mmol) under nitrogen at RT and stirred for 1 h. The progress of reaction was monitored by TLC and LCMS. The reaction mixture was quenched by adding water (0.5 mL), 1N NaOH (1 mL) and water (0.5 mL). The inorganic material was removed by filtration and the filtrate concentrated under reduced pressure. The residue was triturated with ether to yield the title compound (450 mg). $^1$H NMR (CD$_3$OD, Free base) δ (ppm): 8.5 (s, 1H), 8.39 (d, 1H), 7.8 (d, 1H), 7.26 (m, 2H), 7.1 (d, 1H), 7.0 (d, 1H), 4.6 (s,2H), 4.21 (q, 2H), 3.62 (s, 2H), 2.79 (m, 4H), 2.49 (s, 3H), 1.64 (s, 3H). Separation by chiral HPLC provides enantiomers II-102a-b.

Example 314

Preparation of Compound No. II-103

To a stirred solution of 6-methyl-6,7,8,9-tetrahydro-5H-pyrrolo[2,3-b:4,5-c']dipyridine (200 mg, 1.068 mmol) in NMP (3 mL) was added powdered KOH (419 mg, 7.486 mmol). After stirring for 10 min at RT, 2-(trifluoromethyl)-5-vinylpyridine (370 mg, 2.14 mmol) was added to the reaction mixture and stirring continued for another 3 h. The progress of reaction was monitored by TLC and NMR. The reaction mixture was diluted with water (20 mL) and extracted with EtOAc (3×20 mL). The organic layer was washed with water (5×20 mL), dried over anhydrous sodium sulfate and concentrated under reduced pressure to afford crude material, which was purified by reverse phase HPLC to yield 6-methyl-9-(2-(6-(trifluoromethyl)pyridin-3-yl)ethyl)-6,7,8,9-tetrahydro-5H-pyrrolo[2,3-b:4,5-c']dipyridine as the TFA salt (100 mg). $^1$H NMR (CDCl$_3$, TFA salt) δ (ppm): 8.4 (s, 1H), 8.2 (s, 1H), 7.7 (d, 1H), 7.5 (d, 1H), 7.4 (d, 1H), 7.0 (s, 1H), 4.4 (s, 2H), 3.6 (s, 2H), 3.2 (s, 2H), 2.78 (s, 2H), 2.6 (s, 2H), 2.5 (s, 3H).

Example 315

Preparation of Compound Nos. II-104 and II-104a-b

To a solution of methyl carboline ethyl ester (350 mg, 0.92 mmol) in THF (5 mL) was added LAH (175 mg, 4.6 mmol) under nitrogen at RT and stirred for 1 h. The progress of reaction was monitored by TLC and LCMS. The reaction mixture was quenched by adding water (0.5 mL), 1N NaOH (1 mL) and water (0.5 mL). The inorganic material was removed by filtration, and the filtrate concentrated under reduced pressure. The residue was purified through reverse phase HPLC to yield the title compound. $^1$H NMR (CD$_3$OD, Free base) δ (ppm): 8.5 (s, 1H), 8.3 (d, 1H), 7.82 (d, 1H), 7.4 (s, 1H), 7.3 (dd, 1H), 7.0 (m, 2H), 4.6 (s,2H), 4.4 (dd, 2H), 4.41 (d, 1H), 4.2 (d, 1H), 3.5 (m, 2H), 3.21 (m, 1H), 3.0 (m, 1H), 1.64 (s, 3H). Separation by chiral HPLC provides enantiomers II-104a-b.

Example 316

Preparation of Compound Nos. II-105 and II-105a-b 1-(2,8-Dimethyl-1,2,3,4-tetrahydro-pyrido[4,3-b]indol-5-yl)-2-pyridin-3-yl-propan-2-ol (500 mg, 1.49 mmol) was dissolved in 10 mL DCM and m-chloro perbenzoic acid (383 mg, 2.24 mmol) was added and the mixture stirred at RT. After consumption of starting material by monitoring TLC and LCMS, the reaction mixture was concentrated and the crude product was purified by reverse phase chromatography, to obtain 110 mg of 1-(2,8-dimethyl-2-oxy-1,2,3,4-tetrahydro-pyrido[4,3-b]indol-5-yl)-2-pyridin-3-yl-propan-2-ol. $^1$H NMR (CDCl$_3$, Free base) δ (ppm): 8.7 (s, 1H), 8.25 (d, 1H), 7.8 (d, 1H), 7.4 (bs, 1H), 7.27 (d, 1H), 7.2 (m, 2H), 7.0 (d, 1H), 4.79 (d, 1H), 4.6 (d, 1H), 4.2 (d, 1H), 4.05 (d, 1H), 3.85 (m, 1H), 3.6 (m, 1H), 3.4 (m, 1H), 2.64 (m, 1H), 2.4 (s, 3H), 1.6 (s, 3H). Separation by chiral HPLC provides enantiomers II-105a-b.

Example 317

Preparation of Compound Nos. II-106 and II-106a-b 1-(1-(1-Ethoxyethyl)-1H-pyrazol-4-yl)-2-(1,2,3,4-tetrahydro-2,8-dimethylpyrido[4,3-b]indol-5-yl)ethanol (147 mg, 0.3848 mmol) was dissolved in 1,4-dioxane (15 mL) and to it was added 20% aqueous hydrochloride solution (15 mL). The mixture was heated at 55° C. for 1 h. The reaction mixture was neutralized with a saturated solution of sodium bicarbonate and was extracted with EtOAc (3×60 mL). The combined organic layer was washed with water (15 mL) and then brine (2×30 mL). The organic layer was dried over anhydrous sodium sulfate and concentrated under reduced pressure. The crude product was purified by reverse phase chromatography. Yield: 36.6 mg (TFA salt). $^1$H NMR (CDCl$_3$, Free base) δ (ppm): 7.35 (s, 1H), 7.0 (s, 1H), 6.9 (d, 1H), 6.8 (d, 1H), 6.2 (s, 1H), 4.9 (t, 1H), 4.2 (dd, 2H), 3.55 (d,1H), 3.4 (d, 1H), 2.8 (m, 2H), 2.6 (m, 2H), 2.5 (s, 3H), 2.39 (s, 3H). Separation by chiral HPLC provided enantiomers II-106a-b.

Example 318

Preparation of Compound Nos. II-108 and II-108a-b

To a solution of dimethyl-aza carboline (400 mg, 1.99 mmol) in DMF (5 mL) was added NaH (239 mg, 5.97 mmol, 60%). After stirring at RT for 10 min, the epoxide (606 mg, 2.98 mmol) was added into the reaction mixture, which was stirred at RT for 16 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The product was re-crystallized from ether (250 mg). $^1$H NMR (CDCl$_3$, Free base) δ (ppm): 8.81 (s, 1H), 8.0 (m, 2H), 7.6 (d, 1H), 7.52 (s, 1H), 4.23 (q, 2H), 3.6 (d, 1H), 3.5 (d, 1H), 2.8 (m, 1H), 2.72 (m, 3H), 2.5 (s, 3H), 2.4 (m, 1H), 2.4 (s, 3H), 1.6 (s, 3H). Separation by chiral HPLC provided enantiomers II-108a-b.

Example 319

Preparation of Compound Nos. II-109 and II-109a-b

To a solution of 6-aza-8-chloro-2-methyl-2,3,4,5-tetrahydro-1H-pyrido[4,3-b]indole (400 mg, 1.8 mmol) in DMF (5 mL) was added NaH (217 mg, 5.42 mmol, 60%). After stirring at RT for 10 min, the epoxide (552 mg, 2.71 mmol) was added into the reaction mixture, which was stirred at RT for 16 h. The progress of reaction was monitored by TLC and LCMS. The reaction mixture was quenched with ice-water and extracted with EtOAc. The organic layer was washed with water, dried over anhydrous sodium sulfate and concentrated under reduced pressure. The product was re-crystallized from ether (340 mg). $^1$H NMR (CDCl$_3$, Free base) δ (ppm): 8.8 (s, 1H), 8.15 (s, 1H), 8.0 (d, 1H), 7.68 (s, 1H), 7.6 (d, 1H), 4.23 (q, 2H), 3.6 (d, 1H), 3.5 (d, 1H), 2.8 (m, 3H), 2.72 (m, 1H), 2.5 (s, 3H), 2.4 (m, 1H), 1.6 (s, 3H). Separation by chiral HPLC provided enantiomers II-109a-b.

Example 320

Preparation of Compound No. II-110

To a solution of 3,6-dimethyl-6,7,8,9-tetrahydro-5H-pyrrolo[2,3-b:4,5-c']dipyridine (201 mg, 1.0 mmol) in DMF (1 mL) was added a suspension of NaH (128.0 mg, 3.24 mmol) in DMF (1 mL). After stirring for 5 min at RT, a solution of 2-(6-methylpyridin-3-yl)ethyl 4-methylbenzenesulfonate (873 mg, 3.0 mmol) in DMF (1 mL) was added dropwise into the reaction mixture and stirring continued for another 3 h. The progress of reaction was monitored by TLC and NMR. The reaction mixture was diluted with water (20 mL) and extracted with EtOAc (3×25 mL). The organic layer was washed with water (3×20 mL), dried over anhydrous sodium sulfate and concentrated under reduced pressure to afford crude material, which was purified by silica gel flash chromatography and 10% MeOH-DCM to yield 3,6-dimethyl-9-(2-(6-methylpyridin-3-yl)ethyl)-6,7,8,9-tetrahydro-5H-pyrrolo[2,3-b:4,5-c']dipyridine (190 mg). $^1$H NMR (CDCl$_3$, TFA salt) δ (ppm): 8.2 (s, 1H), 8.04 (s, 1H), 7.43 (s, 1H), 7.18 (d, 1H), 7.0 (d, 1H), 4.3 (t, 2H), 3.6 (s, 2H), 3.0 (t, 2H), 2.7 (t, 2H), 2.5 (s, 8H), 2.4 (s, 3H).

Example 321

Preparation of Compound Nos. II-111 and II-111a-b

5-[2-(3,6-Dimethyl-5,6,7,8-tetrahydro-1,6,9-triaza-fluoren-9-yl)-1-hydroxy-ethyl]-pyridine-2-carbonitrile (600 mg, 1.729 mmol) was dissolved in tert-butanol (12 mL), crushed potassium hydroxide (290 mg, 5.187 mmol) was added, and the mixture heated at 80° C. for 1 h. The reaction was monitored by TLC & LCMS. The reaction mixture was allowed to cool to RT, the solvent was removed under vacuum, and the residue was diluted with water (20 ml) and extracted with EtOAc (2×75 mL). The combined organic layer was dried over anhydrous sodium sulfate and concentrated to obtain the crude product that was purified by reverse phase chromatography to afford 100 mg of 5-[2-(3,6-dimethyl-5,6,7,8-tetrahydro-1,6,9-triaza-fluoren-9-yl)-1-hydroxy-ethyl]-pyridine-2-carboxylic acid amide. $^1$H NMR (CD$_3$OD, TFA salt) δ (ppm): 8.62 (s, 1H), 8.1 (s, 1H), 8.05 (d, 1H), 7.95 (d, 1H), 7.8 (s, 1H), 5.23 (t, 1H), 4.7 (d, 1H), 4.53 (d, 1H), 4.4 (m, 2H), 3.83 (m, 1H), 3.6 (m, 1H), 3.4 (m, 2H), 3.2 (s, 3H), 2.43 (s, 3H). Separation by chiral HPLC provides enantiomers II-111a-b.

Example 322

Preparation of Compound Nos. II-112 and II-112a-d 2,6-Dimethyl-1-phenyl-2,3,4,9-tetrahydro-1H-β-carboline (300 mg, 1.08 mmol) was dissolved in DMF (4 mL). Sodium hydride (172 mg, 4.32 mmol) was added and the mixture was stirred at RT for 30 min. 3-(2-Methyl-oxiranyl)-pyridine (733 mg, 5.43 mmol) in 1 mL DMF was added dropwise into the reaction mixture, which was stirred for 5 h at RT. The reaction was monitored by TLC and LCMS. After consumption of starting material, the reaction was quenched with ice and extracted with EtOAc (2×100 mL). The organic layer was washed with water (2×100 mL), dried over anhydrous sodium sulfate and concentrated to obtain the crude that was purified by column chromatography (silica gel 100-200 mesh, Eluent: 6% MeOH in DCM) to obtain 120 mg of 1-(2,6-dimethyl-1-phenyl-1,2,3,4-tetrahydro-β-carbolin-9-yl)-2-pyridin-3-yl-propan-2-ol (racemate) and followed by chiral separation. $^1$H NMR (CD$_3$OD, TFA salt) δ (ppm): 8.25 (s, 1H), 8.2 (d, 1H), 7.6 (d, 1H), 7.4 (m, 3H), 7.2 (s, 1H), 7.19 (m, 3H), 6.65 (d, 1H), 6.4 (d, 1H), 5.5 (s, 1H), 4.0 (d, 1H), 3.43 (d, 1H), 3.2 (m, 1H), 3.0 (m, 3H), 2.6 (s, 3H), 2.3 (s, 3H), 1.6 (s, 3H). Separation by chiral HPLC provided diastereomers II-112a-b.

Example 323

Preparation of Compound Nos. II-113 and II-113a-d 2,6-Dimethyl-1-phenyl-2,3,4,9-tetrahydro-1H-β-carboline (300 mg, 1.08 mmol) was dissolved in DMF (3 mL). Sodium hydride (172 mg, 4.32 mmol) was added and the mixture stirred at RT for 30 min. 4-Oxiranyl-pyridine (657 mg, 5.43 mmol) in 1 mL DMF was added dropwise into the reaction mixture, which was stirred at RT for 5 h. The reaction was monitored by TLC and LCMS. After consumption of starting material, the reaction was quenched with ice and extracted with EtOAc (2×100 mL). The organic layer was washed with water, dried over anhydrous sodium sulfate and concentrated to obtain the crude product that was purified by column chromatography (eluent: 10% MeOH in DCM) to obtain 220 mg of 2-(2,6-dimethyl-1-phenyl-1,2,3,4-tetrahydro-(3-carbolin-9-yl)-1-pyridin-4-yl-ethanol (M6792, racemate) and followed by chiral separation. $^1$H NMR (CD$_3$OD, Free base) δ (ppm): 8.17 (d, 2H), 7.35 (m, 4H), 7.09 (d, 2H), 7.0 (m, 3H), 6.9 (d, 1H), 4.8 (t, 1H), 4.6 (s, 1H), 4.08 (dd, 1H), 3.45 (dd, 1H), 3.0 (m, 1H), 2.8 (m, 2H), 2.6 (m, 1H), 2.4 (s, 3H), 2.2 (s, 3H). Separation by chiral HPLC provided diastereomers II-113a-b.

Example 324

Preparation of Compound Nos. II-114 and II-114a-b 1-(6-Bromo-pyridin-3-yl)-2-(3,6-dimethyl-5,6,7,8-tetrahydro-1,6,9-triaza-fluoren-9-yl)-ethanol (2 g, 4.9 mmol) was dissolved in DMF (20 mL), and the mixture was purged with nitrogen. Zinc cyanide (1.16 g, 9.9 mmol) and Pd(PPh$_3$)$_4$ (339 mg, 0.294 mmol) were added, and the mixture heated at 150° C. for 2 h. The reaction was monitored by LCMS. The reaction mixture was allowed to cool at RT, diluted with EtOAc (250 mL) and filtered. The filtrate was washed with water (3×100 mL). The organic layer was dried over anhydrous sodium sulfate and concentrated to obtain the crude that was purified by reverse phase chromatography to obtain 100 mg of 5-[2-(3,6-dimethyl-5,6,7,8-tetrahydro-1,6,9-triaza-fluoren-9-yl)-1-hydroxy-ethyl]-pyridine-2-carbonitrile. This was followed by chiral separation. $^1$H NMR (CDCl$_3$, Free base) δ (ppm): 8.62 (s, 1H), 8.03 (s, 1H), 7.73 (d, 1H), 7.6 (d, 1H), 7.5 (s, 1H), 5.25 (d, 1H), 4.45 (d, 1H), 4.3 (dd, 1H), 3.55 (dd, 2H), 2.8 (m, 1H), 2.7 (m, 2H), 2.5 (s, 3H), 2.45 (s, 3H), 2.4 (m, 1H). Separation by chiral HPLC provided enantiomers II-114a-b.

Example 325

Preparation of Compound Nos. II-115 and II-115a-d

Compound Nos. II-115 and II-115a-d are prepared in an analogous fashion to Compound Nos. 129 and 129a-d (Example 110), using 2,3,5,6,7,11c-hexahydro-1H-indolizino[7,8-b]indole as the starting material.

Example 326

Preparation of Compound Nos. II-116 and II-116a-b

To a degassed solution of aza-allylcyano alcohol (200 mg, 0.53 mmol) and 1,3-dimethylbarbituric acid (251 mg, 1.61 mmol) in DCM (5 mL) was added Pd(PPh₃)₄ (24 mg, 0.020 mmol) at RT and the reaction mixture was stirred at RT for 45 min. The progress of reaction was monitored by TLC and LCMS. The reaction mixture was diluted with water and the organic layer was separated. The aqueous layer was basified with saturated aq NaHCO₃ and extracted with DCM. The organic layer was dried over anhydrous sodium sulfate and concentrated under reduced pressure. The residue was purified by reverse phase HPLC to yield title compound. $^1$H NMR (CD₃OD, TFA salt) δ (ppm): 8.2 (s, 1H), 8.0 (s, 1H), 7.68 (d, 2H), 7.6 (d, 2H), 5.2 (dd, 1H), 4.5 (dd, 1H), 4.45 (s, 2H), 4.33 (dd, 1H), 3.6 (t, 2H), 3.25 (d, 1H), 3.1 (d, 1H), 2.5 (s, 3H). Separation by chiral HPLC provides enantiomers II-116a-b.

Example 327

Preparation of Compound Nos. II-117 and II-117a-b

Compound Nos. II-117 and II-117a-b are prepared in an analogous fashion to Compound Nos. 5 and 5a-b (Example 5), using 2-fluoro-5-(2-methyloxiran-2-yl)pyridine as the epoxide.

Example 328

Preparation of Compound Nos. II-118 and II-118a-b

To an ice-cooled stirred solution of 8-chloro-2-cyclobutyl-2,3,4,5-tetrahydro-1H-pyrido[4,3-b]indole (1.0 g, 3.84 mmol) in DMF (10 mL) was added sodium hydride (60%, 462 mg, 11.55 mmol). After stirring for 10 min, 3-(2-methyloxiran-2-yl)pyridine (780 mg, 5.77 mmol) was added into the reaction mixture, which was stirred at RT for 16 h. The progress of reaction was monitored by TLC and LCMS. The reaction mixture was quenched with ice-water and extracted with EtOAc (2×100 mL). The organic layer was washed with water (5×100 mL), dried over anhydrous sodium sulfate and concentrated under reduced pressure. The product was crystallized from ether:hexane (50:50) to yield the title compound (1.0 g). The product was further purified by chiral HPLC to give enantiomers II-118a and II-118b. $^1$H NMR (CD₃OD, D1-HCl salt) δ (ppm): 8.7 (m, 3H), 7.79 (d, 1H), 7.43 (d, 1H), 6.9 (m, 2H), 4.7 (d, 1H), 4.4 (dd, 2H), 4.15 (t, 1H), 3.95 (m, 1H), 3.8 (m, 1H), 3.6 (m, 1H), 3.5 (m, 1H), 2.4 (m, 4H), 1.9 (m, 3H), 1.8 (d, 3H).

Example 329

Preparation of Compound No. II-119

To a stirred solution of 3,6-dimethyl-6,7,8,9-tetrahydro-5H-pyrrolo[2,3-b:4,5-c']dipyridine (201 mg, 1.0 mmol) in NMP (3 mL) was added powdered KOH (392 mg, 7.0 mmol). After stirring for 10 min at RT, 2-(trifluoromethyl)-5-vinylpyridine (346 mg, 2.0 mmol) was added to the reaction mixture and stirring continued for another 3 h. The progress of reaction was monitored by TLC and NMR. The reaction mixture was diluted with water (20 mL) and extracted with EtOAc (3×20 mL). The organic layer was washed with water (5×20 mL), dried over anhydrous sodium sulfate and concentrated under reduced pressure to afford crude material, which was purified by reverse phase HPLC to yield 3,6-dimethyl-9-(2-(6-(trifluoromethyl)pyridin-3-yl)ethyl)-6,7,8,9-tetrahydro-5H-pyrrolo[2,3-b:4,5-c']dipyridine (80 mg). $^1$H NMR (CDCl₃, TFA salt) δ (ppm): 8.38 (s, 1H), 8.0 (s, 1H), 7.5 (d, 2H), 7.4 (d, 1H), 4.4 (t, 2H), 3.58 (s, 2H), 3.2 (t, 2H), 2.68 (t, 2H), 2.5 (t, 2H), 2.47 (s, 3H), 2.38 (s, 3H).

Example 330

Preparation of Compound Nos. II-120 and II-120a-d

9-Methyl-2,3,4,5,6,10c-hexahydro-1H-3a,6-diaza-cyclopenta[c]fluorine (250 mg, 1.10 mmol) was dissolved in DMF (3 mL), sodium hydride (221 mg, 5.53 mmol) was added and the mixture stirred at RT for 5 min. 2-(4-Fluoro-phenyl)-oxirane (305 mg, 2.21 mmol) in 2 mL DMF was added dropwise into the reaction mixture and was stirred at RT for 16 h. The reaction was monitored by TLC and LCMS. After completion of reaction, the mixture was quenched with ice cold water (100 mL) and extracted with EtOAc (100 mL). The organic layer was washed with water (5×50 mL), dried over sodium sulfate and concentrated to obtain the crude product that was purified by reverse phase HPLC followed by chiral HPLC to obtain 190 mg of 1-(4-fluoro-phenyl)-2-(9-methyl-1,2,3,4,5,10c-hexahydro-3a,6-diaza-cyclopenta[c]fluoren-6-yl)-ethanol. $^1$H NMR (CD₃OD, HCl salt) δ (ppm): 7.32 (d, 1H), 7.3 (s, 1H), 7.1 (t, 2H), 7.0 (m, 3H), 5.08 (t, 1H), 4.4 (dd, 1H), 4.19 (dd, 1H), 3.6 (m, 2H), 3.45 (m, 1H), 3.0 (d, 1H), 2.6 (m, 2H), 2.4 (s, 3H), 2.2 (m, 2H), 2.0 (m, 1H). Separation by chiral HPLC provided diastereomers II-120a-b.

Example 331

Preparation of Compound Nos. II-121 and II-121a-d

9-Methyl-2,3,4,5,6,10c-hexahydro-1H-3a,6-diaza-cyclopenta[c]fluorene (150 mg, 0.66 mmol) was dissolved in DMF (2 mL), sodium hydride (79 mg, 1.98 mmol) was added and the mixture was stirred at RT for 5 min. 2-(4-Fluoro-phenyl)-2-methyl-oxirane (201 mg, 1.32 mmol) was added dropwise into the reaction mixture and stirred at RT for 18 h. The reaction was monitored by TLC and LCMS. After consumption of starting material, the reaction mixture was quenched with ice cold water (100 mL) and extracted with EtOAc (2×100 mL). The combined organic layer was washed with water (2×100 mL), dried over anhydrous sodium sulfate and concentrated to obtain the crude product, which was purified by column chromatography (neutral alumina) Eluent: ~2% MeOH in DCM followed by chiral HPLC to obtain 77 mg of 2-(4-fluoro-phenyl)-1-(9-methyl-1,2,3,4,5,10c-hexahydro-3a,6-diaza-cyclopenta[c]fluoren-6-yl)-propan-2-ol. $^1$H NMR (CD₃OD, TFA salt) δ (ppm): 7.4 (m, 2H), 7.2 (m, 2H), 7.0 (m, 3H), 5.08 (t, 1H), 4.3 (d, 1H), 4.15 (d, 1H), 3.65 (m, 1H), 3.5 (m, 2H), 3.3 (m, 1H), 2.90 (m, 2H), 2.7 (m, 1H), 2.4 (s, 3H), 2.2 (m, 3H), 1.62 (s, 3H). Separation by chiral HPLC provided diastereomers II-121a-b.

Example 332

Preparation of Compound Nos. II-122 and II-122a-d

To a solution of 11-aza-10-methyl-2,3,5,6,7,11c-hexahydro-1H-indolizino[7,8-b]indole (200 mg, 0.88 mmol) in DMF (5 mL), NaH (105 mg, 2.6 mmol, 60% dispersion in mineral oil) was added at 0° C. and the reaction mixture was stirred for 10 min. 4-oxiranyl-pyridine (213 mg, 1.76 mmol) was added and the reaction mixture was stirred at RT overnight. The reaction was monitored with LCMS. The reaction mixture was quenched with MeOH (2 mL), concentrated under reduced pressure to obtain the product that was purified by reverse phase column chromatography to obtain the 39 mg of product as the free base. ¹H NMR (CD₃OD, freebase) δ (ppm): 8.4 (d, 2H), 7.63 (d, 1H), 7.29 (dd, 2H), 6.95 (t, 1H), 5.0 (t, 1H), 4.3 (m, 3H), 3.21 (m, 1H), 2.9 (m, 4H), 2.7 (m, 1H), 2.57 (s, 3H), 2.52 (m, 1H), 1.9 (m, 3H). Separation by chiral HPLC provides diastereomers II-122a-b.

Example 333

Preparation of Compound Nos. II-123 and II-123a-b

A mixture of 9-chloro-2,8-dimethyl-2,3,4,5-tetrahydro-1H-pyrido[4,3-b]indole and 7-chloro-2,8-dimethyl-2,3,4,5-tetrahydro-1H-pyrido[4,3-b]indole (2.00 g, 8.5 mmol) was dissolved in DMF (15 mL). Sodium hydride (1.708 g, 42.71 mmol) was added at 0-10° C. and stirred at the same temperature for 15 min., 3-(2-methyloxiran-2-yl)pyridine (2.309 g, 17.08 mmol) was added dropwise into the reaction mixture and the mixture was stirred at RT for 16 h. The reaction was monitored by TLC and LCMS. After consumption of starting material, the reaction mixture was quenched with ice cold water (100 mL) and extract with EtOAc (300 mL). The organic layer was washed with water (5×100 mL). The organic layer dried over anhydrous sodium sulfate and concentrated under reduced pressure to obtain the crude. The crude product was purified by reverse phase column chromatography to obtain 350 mg of 1-(7-chloro-2,8-dimethyl-3,4-dihydro-1H-pyrido[4,3-b]indol-5(2H)-yl)-2-(pyridin-3-yl)propan-2-ol. ¹H NMR (CD₃OD, HCl salt) δ (ppm): 8.68 (m, 3H), 7.95 (m, 1H), 7.29 (d, 1H), 6.9 (m, 1H), 4.68 (dd, 1H), 4.38 (m, 2H), 4.32 (dd, 1H), 3.9 (m, 1H), 3.52 (m, 2H), 3.25 (m, 1H), 3.12 (s, 3H), 2.35 (d, 3H), 1.83 (d, 3H). Separation by chiral HPLC provided enantiomers II-123a-b.

Example 334

Preparation of Compound Nos. II-124 and II-124a-b

A mixture of 9-chloro-2,8-dimethyl-2,3,4,5-tetrahydro-1H-pyrido[4,3-b]indole and 7-chloro-2,8-dimethyl-2,3,4,5-tetrahydro-1H-pyrido[4,3-b]indole (2.00 g, 8.5 mmol) was dissolved in DMF (15 mL). Sodium hydride (1.708 g, 42.71 mmol) was added at 0-10° C. and stirred at the same temperature for 15 min., 3-(2-methyloxiran-2-yl)pyridine (2.309 g, 17.08 mmol) was added dropwise into the reaction mixture and the mixture was stirred at RT for 16 h. The reaction was monitored by TLC and LCMS. After consumption of starting material, the reaction mixture was quenched with ice cold water (100 mL) and extract with EtOAc (300 mL). The organic layer was washed with water (5×100 mL). The organic layer dried over anhydrous sodium sulfate and concentrated under reduced pressure to obtain the crude. The crude product was purified by reverse phase column chromatography to obtain 35 mg of 1-(9-chloro-2,8-dimethyl-3,4-dihydro-1H-pyrido[4,3-b]indol-5(2H)-yl)-2-(pyridin-3-yl)propan-2-ol. ¹H NMR (CD₃OD, freebase) δ (ppm): 8.46 (s, 1H), 8.34 (d, 1H), 7.82 (d, 1H), 7.29 (t, 1H), 6.87 (d, 1H), 6.77 (d, 1H), 4.22 (dd, 2H), 3.99 (q, 2H), 2.73 (m, 4H), 2.5 (s, 3H), 2.3 (s, 3H), 1.66 (s, 3H). Separation by chiral HPLC provided enantiomers II-124a-b.

Example 335

Preparation of Compound Nos. II-125 and II-125a-d 8,10-Dimethyl-2,3,5,6,7,11c-hexahydro-1H-indolizino[7,8-b]indole (700 mg, 2.92 mmol) in DMF (20 mL) was stirred at 0° C. for 5 min. NaH (580 mg, 14.60 mmol) was added slowly at 0° C. After 10 min. stirring, 4-(oxiran-2-yl)pyridine (710 mg, 5.87 mmol) was added and the reaction mixture was stirred at RT for 15 h. The reaction mixture was poured in ice-cold water (150 mL) and extracted with EtOAc (3×200 mL). The combined organic layer was washed with water (6×300 mL), dried over anhydrous sodium sulfate and concentrated to obtain semi-solid residue that was washed with hexane (3×20 mL). The residue was suspended in ether (30 mL) stirred for 1 h. The suspension was filtered to give 200 mg of 2-(8,10-dimethyl-2,3,5,6-tetrahydro-1H-indolizino[7,8-b]indol-7(11cH)-yl)-1-(pyridin-4-yl)ethanol. ¹H NMR (CD₃OD, HCl salt) δ (ppm): 8.79 (d, 2H), 8.03 (d, 2H), 7.13 (s, 1H), 6.82 (s, 1H), 5.22 (dd, 1H),5.01 (t, 1H), 4.67 (dd, 1H), 4.48 (dd, 1H), 4.79 (m, 1H), 3.64 (t, 2H), 3.4 (m, 3H), 2.9 (m, 1H), 2.73 (s, 3H), 2.37 (s, 3H), 2.22 (m, 3H). Separation by chiral HPLC provided diastereomers II-125a-b.

Example 336

Preparation of Compound Nos. II-126 and II-126a-b

9-Aza-2-methyl-2,3,4,5-tetrahydro-1H-pyrido[4,3-b]indole (160 mg, 0.88 mmol) was dissolved in DMF (8 mL). Sodium hydride (63 mg, 2.64 mmol) was added at 0-10° C. and stirred at the same temperature for 15 min., 3-(2-methyloxiran-2-yl)pyridine (480 mg, 3.55 mmol) in DMF (2 mL) was added dropwise into the reaction mixture and the mixture was stirred at RT for 16 h. The reaction was monitored by LCMS. After consumption of starting material, the reaction mixture was quenched with ice cold water (4 mL) and solvent was evaporated to obtain the crude product, which was purified by reverse phase column chromatography to obtain 15 mg of product. ¹H NMR (CD₃OD, freebase) δ (ppm): 8.51 (s, 1H), 8.3 (d, 1H), 8.13 (d, 1H), 7.83 (d, 1H), 7.57 (d, 1H),7.31 (t, 1H), 6.99 (t, 1H), 4.33 (dd, 2H), 3.78 (dd, 2H), 3.0 (m, 1H), 2.85 (m, 1H), 2.75 (m, 2H), 2.53 (s, 3H), 1.69 (s, 3H). Separation by chiral HPLC provides enantiomers II-126a-b.

Example 337

Preparation of Compound Nos. II-127 and II-127a-d

9-Methyl-2,3,4,5,6,10c-hexahydro-1H-3a,6-diaza-cyclopenta[c]fluorene (150 mg, 0.66 mmol) was dissolved in DMF (1 mL), sodium hydride (47 mg, 1.98 mmol) was added and the mixture was stirred at RT for 5 min. 3-(2-Methyl-oxiranyl)-pyridine (143 mg, 1.06 mmol) was added dropwise into the reaction mixture and stirred at RT for 2 h. The reaction was monitored by TLC and LCMS. After consumption of starting material, the reaction mixture was quenched with ice cold water (20 mL) and extracted with EtOAc (2×100 mL). The combined organic layer was washed with water (2×100 mL), dried over anhydrous sodium sulfate and concentrated to obtain the crude product, which was purified by column chromatography (silica gel 100-200 mesh, Eluent: −15% MeOH in DCM) to obtain 80 mg of 1-(9-methyl-1,2,3,4,5,10c-hexahydro-3a,6-diaza-cyclopenta[c]fluoren-6-yl)-2-pyridin-3-yl-propan-2-ol. ¹H NMR (CD₃OD, HCl salt) δ (ppm): 8.66 (dd, 2H), 8.56 (s, 1H), 7.92 (t, 1H), 7.20 (s, 1H), 6.77 (t, 2H), 5.04 (t, 1H), 3.75 (dd, 2H),3.72 (m, 2H), 3.6 (m, 1H), 3.44 (m, 2H), 3.22 (d, 1H), 2.75 (m, 1H), 2.73 (s, 3H), 2.16 (m, 3H), 1.8 (s, 3H). Separation by chiral HPLC provided enantiomers II-127a-b.

Example 338

Preparation of Compound Nos. II-128 and II-128a-d

9-Methyl-2,3,4,5,6,10c-hexahydro-1H-3a,6-diaza-cyclopenta[c]fluorene (200 mg, 0.88 mmol) was dissolved in DMF (3 mL), sodium hydride (106 mg, 2.65 mmol) was added and stirred for 15 min. at RT. 2-Methyl-5-(2-methyl-oxiranyl)-pyridine (263 mg, 1.76 mmol) was added dropwise into the reaction mixture and the mixture was stirred at RT for 3 h. The reaction was monitored by TLC and LCMS. After consumption of starting material, the reaction mixture was quenched with ice cold water (20 mL) and extracted with EtOAc (3×30 mL). The combined organic layer was washed with water (2×60 mL), dried over anhydrous sodium sulfate and concentrated to obtain the crude product, which was purified by reverse phase chromatography to obtain 200 mg of 1-(9-methyl-1,2,3,4,5,10c-hexahydro-3a,6-diaza-cyclopenta[c]fluoren-6-yl)-2-(6-methyl-pyridin-3-yl)-propan-2-ol. $^1$H NMR (CD$_3$OD, HCl salt) δ (ppm): 8.5 (d, 1H), 8.3 (s, 1H), 7.79 (d, 1H), 7.22 (s, 1H), 6.82 (s, 2H), 5.03 (t, 1H), 4.38 (dd, 2H), 3.8 (m, 1H), 3.66 (m, 2H),3.46 (m, 2H), 3.2 (m, 2H), 2.7 (m, 1H), 2.67 (s, 3H), 2.36 (s, 3H), 2.22 (m, 2H), 1.77 (s, 3H). Separation by chiral HPLC provided enantiomers II-128a-b.

Example 339

Preparation of Compound Nos. II-129 and II-129a-b

7-Aza-2-methyl-2,3,4,5-tetrahydro-1H-pyrido[4,3-b]indole (160 mg, 0.88 mmol) was dissolved in DMF (8 mL). Sodium hydride (63 mg, 2.64 mmol) was added at 0-10° C. and stirred at the same temperature for 15 min., 3-(2-methyloxiran-2-yl)pyridine (480 mg, 3.55 mmol) in DMF (2 mL) was added dropwise into the reaction mixture and the mixture was stirred at RT for 16 h. The reaction was monitored by LCMS. After consumption of starting material, the reaction mixture was quenched with ice cold water (4 mL) and solvent was evaporated to obtain the crude product, which was purified by reverse phase column chromatography to obtain 3 mg of product as the free base.

$^1$H NMR (CD$_3$OD, freebase) δ (ppm): 8.46 (s, 1H), 8.39 (s, 1H), 8.36 (d, 1H), 7.96 (d, 1H), 7.82 (d, 1H), 7.37 (d, 1H), 7.31 (t, 1H), 4.4 (dd, 2H),3.71 (dd, 2H), 3.0 (m, 1H), 2.9 (m, 1H), 2.72 (m, 1H), 2.62 (m, 1H), 2.52 (s, 3H), 1.72 (s, 3H). Separation by chiral HPLC provides enantiomers II-129a-b.

Example 340

Preparation of Compound Nos. II-130 and II-130a-d

To a stirred solution of 10-chloro-2,3,5,6,7,11c-hexahydro-1H-indolizino[7,8-b]indole (1.0 g, 4.06 mmol) in DMF (50 mL) was added sodium hydride (60%, 406 mg, 10.15 mmol). After stirring for 10 min., 3-(2-methyloxiran-2-yl)pyridine (823 mg, 6.09 mmol) was added to the reaction mixture, which was stirred at RT for 16 h. The progress of reaction was monitored by TLC and LCMS. The reaction mixture was quenched with ice-water and extracted with EtOAc (2×100 mL). The organic layer was washed with water (5×100 mL), dried over anhydrous sodium sulfate and concentrated under reduced pressure to obtain the residue that was crystallized with ethanol-hexane to yield the 1.2 g of 1-(10-chloro-2,3,5,6-tetrahydro-1H-indolizino[7,8-b]indol-7(11cH)-yl)-2-(pyridin-3-yl)propan-2-ol. $^1$H NMR (CDCl$_3$, freebase) δ (ppm): 8.70 (s, 1H), 8.49 (d, 1H), 7.62 (d, 1H), 7.36 (s, 1H), 7.12 (m, 2H), 7.02 (d, 1H), 4.17 (q, 2H), 3.86 (t, 1H), 3.19 (m, 1H), 2.86 (m, 1H), 2.74 (m, 3H), 2.41 (m, 2H), 1.85 (m, 3H), 1.7 (s, 3H). Separation by chiral HPLC provides diastereomers II-130a-d.

Example 341

Preparation of Compound Nos. II-131 and II-131a-d

9-Methyl-2,3,4,5,6,10c-hexahydro-1H-3a,6-diaza-cyclopenta[c]fluorene (200 mg, 0.88 mmol) was dissolved in DMF (3 ml), sodium hydride (106 mg, 2.65 mmol) was added and the mixture was stirred at RT for 15 min. 3-Oxiranyl-pyridine (214 mg, 1.76 mmol) was added dropwise into the reaction mixture and the mixture was stirred at RT for 3 h. The reaction was monitored by TLC and LCMS. After consumption of starting material, the reaction mixture was quenched with ice cold water (20 mL) and extracted with EtOAc (3×30 mL). The combined organic layer was washed with water (2×60 mL), dried over anhydrous sodium sulfate and concentrated to obtain the crude product, which was purified by reverse phase chromatography to obtain 60 mg of 2-(9-Methyl-1,2,3,4,5,10c-hexahydro-3a,6-diaza-cyclopenta[c]fluoren-6-yl)-1-pyridin-3-yl-ethanol as the TFA salt. $^1$H NMR (CD$_3$OD, TFA salt) δ (ppm): 8.7 (d, 1H), 8.53 (s, 1H), 8.4 (d, 1H), 7.85 (t, 1H), 7.25 (s, 1H), 7.08 (t, 1H),6.9 (d, 1H), 5.28 (t, 1H), 5.03 (t, 1H), 4.42 (s, 2H), 3.76 (m, 1H), 3.6 (m, 2H), 3.4 (m, 1H), 3.2 (m, 2H),2.7 (m, 1H), 2.38 (s, 3H), 2.2 (m, 3H). Separation by chiral HPLC provides diastereomers II-131a-d.

Example 342

Preparation of Compound Nos. II-132 and II-132a-d 1-(2-Methoxy-pyridin-4-yl)-2-(9-methyl-1,2,3,4,5,10c-hexahydro-3a,6-diaza-cyclopenta[c]fluoren-6-yl)-ethanol (45 mg, 0.119 mmol) and 47% aqueous HBr (4 mL) and heated at 100° C. for 45 min. The reaction was monitored by TLC and LCMS. After consumption of starting material, the reaction mixture was cooled to RT and basified with ammonia and extracted with EtOAc (2×25 mL). The organic layer was dried over anhydrous sodium sulfate and concentrated and the crude product was purified by reverse phase chromatography to obtain 20 mg of 4-(2-(2,3,5,6-tetrahydro-10-methyl-1H-indolizino[7,8-b]indol-7(11cH)-yl)-1-hydroxyethyl)pyridin-2(1H)-one. $^1$H NMR (CD$_3$OD, TFA salt) δ (ppm): 7.43 (d, 1H), 7.23 (m, 2H), 7.05 (t, 1H), 6.7 (m, 1H), 6.5 (d, 1H),4.79 (m, 1H), 4.3 (m, 2H), 3.9 (m, 2H), 3.8 (m, 1H), 3.6 (m, 1H), 3.4 (m, 2H), 3.1 (m, 1H), 2.6 (m, 1H), 2.4 (s, 3H), 2.3 (m, 2H), 1.9 (m, 1H). Separation by chiral HPLC provided enantiomers II-132a-b.

Example 343

Preparation of Compound No. II-133

To a stirred solution of 6,8,8-trimethyl-6,7,8,9-tetrahydro-5H-pyrrolo[2,3-b:4,5-e]dipyridine (75 mg, 0.348 mmol) in DMF (1.5 mL) was added sodium hydride (42 mg, 1.0465 mmol). After stirring for 10 min at RT, a solution of 2-(6-methylpyridin-3-yl)ethyl trifluoromethanesulfonate (304 mg, 1.046 mmol) in DMF (1.5 mL) was added to the reaction mixture and stirring continued at RT for 16 h. The progress of reaction was monitored by TLC and LCMS. The reaction mixture was diluted with water and extracted with EtOAc (3×25 mL). The organic layer was washed with water (3×25 mL), dried over anhydrous sodium sulfate and concentrated to afford crude mass, which was purified by reverse phase HPLC. $^1$H NMR (CDCl$_3$, TFA salt) δ (ppm): 8.42 (s, 1H), 8.31 (d, 1H), 7.7 (d, 1H), 7.57 (d, 1H), 7.1 (d, 1H), 7.0 (t, 1H), 4.5 (t, 2H), 3.63 (s, 2H), 3.2 (t, 2H), 2.57 (s, 8H), 1.42 (s, 6H).

Example 344

Preparation of Compound Nos. II-134 and II-134a-b

To a solution of 1,2,3,4,5,6-hexahydro-3,9-dimethylazepino[4,5-b]indole (3 g, 14.01 mmol) in DMF (40 mL), NaH (2.8 g, 70 mmol, 60% dispersion in mineral oil) was added slowly at 0° C. The solution was stirred at 0° C. for 10 min. 4-(2-Methyloxiran-2-yl)pyridine (3.8 g, 2.8 mmol) was added and the reaction mixture was stirred at RT for 15 h. The reaction mixture was poured into ice-cold water (300 mL) and extracted with EtOAc (2×200 mL). The organic layer was washed with water (5×200 mL), dried over anhydrous sodium sulfate and concentrated under reduced pressure gave an oily residue that was purified by column chromatography using silica gel (100-200 mesh) and 10 MeOH-DCM as eluting system followed by chiral preparative HPLC to afford the 300 mg of pure product. $^1$H NMR (CDCl$_3$, freebase) δ (ppm): 8.59 (d, 2H), 7.38 (d, 2H), 7.25 (s, 1H), 7.18 (d, 1H), 6.96 (d, 1H), 4.23 (dd, 2H), 2.89 (m, 2H), 2.75 (m, 4H), 2.6 (m, 2H), 2.43 (s, 3H), 2.42 (s, 3H),1.58 (s, 3H). Separation by chiral HPLC provided enantiomers II-134a-b.

Example 345

Preparation of Compound Nos. II-135 and II-135a-b 3,9-Dimethyl-1,2,3,4,5,6-hexahydroazepino[4,5-b]indole (1 g, 4.6 mmol) in DMF (10 mL) was stirred at RT for 5 min. NaH (60%, 933 mg, 23.33 mmol) was added and the reaction mixture was stirred at RT for 10 min. 3-(2-methyloxiran-2-yl)pyridine (1.26 g, 9.34 mmol) was added to the reaction mixture and the mixture was stirred at RT for 16 h. The reaction mixture was poured into ice-water and extracted with EtOAc (200 mL). The organic layer was dried over anhydrous sodium sulfate and concentrated under vacuum to obtain the crude product, which was purified by column chromatography using silica gel: 100-200 mesh and 10% MeOH/DCM/1 mL NH4OH to obtain 600 mg of 1-(3,9-dimethyl-2,3,4,5-tetrahydroazepino[4,5-b]indol-6(1H)-yl)-2-(pyridin-3-yl) propan-2-ol. $^1$H NMR (CDCl$_3$, freebase) δ (ppm): 8.74 (s, 1H), 8.54 (d, 1H), 7.71 (d, 1H), 7.26 (s, 1H), 7.27 (m, 1H), 7.19 (d, 1H), 6.96 (d, 1H), 4.26 (dd, 2H), 2.91 (m, 2H), 2.9 (m, 4H), 2.74 (m, 2H), 2.44 (s, 6H), 1.63 (s, 3H). Separation by chiral HPLC provided enantiomers II-135a-b.

Example 346

Preparation of Compound Nos. II-136 and II-136a-b

A mixture of 5-(1-(2,8-dimethyl-3,4-dihydro-1H-pyrido[4,3-b]indol-5(2H)-yl)-2-hydroxypropan-2-yl)picolinonitrile (300 mg, 0.833 mmol), crushed KOH (140 mg, 2.499 mmol) in 12 mL tert-butanol was heated at 80° C. for 2 h. The reaction was monitored by TLC. The reaction mixture was allowed to cool at RT, diluted with brine (30 mL) and extracted with ethyl acetate (2×100 mL). The combined organic layer was washed with water (3×100 mL), dried over anhydrous sodium sulfate and concentrated to obtain the crude product, which was purified by Preparative HPLC followed by chiral HPLC to obtain 5-(1-(1,2,3,4-tetrahydro-2,8-dimethylpyrido[4,3-b]indol-5-yl)-2-hydroxypropan-2-yl) pyridine-2-carboxamide. $^1$H NMR (CDCl$_3$, freebase) δ (ppm): 8.49 (s, 1H), 8.04 (d, 1H), 7.86 (d, 1H), 7.66 (s, 1H), 7.01 (s, 1H), 6.85 (s, 1H), 6.78 bs (NH), 5.48 s (OH),4.16 (dd, 2H), 3.44 (q, 2H), 2.9 (m, 2H), 2.7 (m, 2H), 2.45 (s, 3H), 2.35 (s, 3H), 2.35 (s, 3H), 1.6 (s, 3H). Separation by chiral HPLC provided enantiomers II-136a-b.

Example 347

Preparation of Compound Nos. II-137 and II-137a-b

These compounds were synthesized in an analogous fashion to Compound Nos. 55 and 55a-b, using 3,6-dimethyl-6,7,8,9-tetrahydro-5H-1,2,6,9-tetraaza-fluorene as the carboline portion. Separation by chiral HPLC provides enantiomers II-137a-b.

Example 348

Preparation of Compound Nos. II-138 and II-138a-d

A solution of benzyl protected fused carboline compound (70 mg, 0.16 mmol) in HPLC grade MeOH (70 mL) was subjected to hydrogenation in H-Cube. The solvent was removed under reduced pressure to afford an oily residue that was purified by preparative HPLC to give 3 mg of desired compound. $^1$H NMR (CD$_3$OD, TFA salt) δ (ppm): 7.67 (s, 2H), 7.28 (m, 3H), 7.04 (d, 1H), 5.21 (m, 1H), 5.04 (t, 1H), 4.39 (m, 2H), 3.67 (m, 3H), 3.25 (m, 2H), 3.03 (m, 1H), 2.68 (m, 1H), 2.41 (s, 3H), 2.19 (m, 3H). Separation by chiral HPLC provides diastereomers II-138a-d.

Example 349

Preparation of Compound Nos. II-139 and II-139a-d

A suspension of 2-(10-methyl-2,3,5,6-tetrahydro-1H-indolizino[7,8-b]indol-7(11cH)-yl)-1-(1-trityl-1H-imidazol-2-yl)ethanol (0.4 g, 0.69 mmol) in MeOH (10 mL), 1N HCl (1 mL) was added and the reaction mixture was stirred at RT for 2 h. The reaction mixture concentrated under vacuum to obtain the crude product that was basified with satd. sodium bicarbonate solution and extracted with EtOAc (50 mL). The organic layer was dried over anhydrous sodium sulfate, and concentrated under vacuum to obtain the crude product, which was purified by reverse HPLC to obtain 11.30 mg 1-(1H-imidazol-2-yl)-2-(10-methyl-2,3,5,6-tetrahydro-1H-indolizino[7,8-b]indol-7(11cH)-yl)ethanol. $^1$H NMR (CD$_3$OD, TFA salt) δ (ppm): 7.44 (s, 2H), 7.27 (s, 1H), 7.13 (d, 1H), 6.99 (d, 1H), 5.37 (t, 1H), 5.1 (m, 1H),4.56 (dd, 1H), 4.46 (dd, 1H), 3.67 (m, 3H), 3.42 (m, 1H), 3.24 (m, 2H), 2.7 (m, 1H), 2.4 (s, 3H), 2.2 (m, 3H).

Example 350

Preparation of Compound Nos. II-140 and II-140a-d

To a stirred solution of compound 2-(10-methyl-2,3,5,6-tetrahydro-1H-indolizino[7,8-b]indol-7(11cH)-yl)-1-(1-trityl-1H-imidazol-5-yl)ethanol (400 mg, 0.69 mmol) in MeOH (10 mL), 1N HCl (1 mL) at 0° C. was added. The reaction mixture was stirred at RT for 2 h. The reaction mixture concentrated under vacuum to obtain the crude product that was basified with sat sodium bicarbonate solution and extracted with EtOAc (50 mL). The organic layer dried on anhydrous sodium sulfate, and concentrated under vacuum to obtain the crude product that was purified by reverse phase HPLC to obtain 1-(1H-imidazol-5-yl)-2-(10-methyl-2,3,5,6-tetrahydro-1H-indolizino[7,8-b]indol-7(11cH)-yl)ethanol (12 mg) as the TFA salt. $^1$H NMR (CD$_3$OD, TFA salt) δ (ppm): 8.79 (s, 1H), 7.4 (s, 1H), 7.27 (s, 1H), 7.2 (dd, 1H), 7.01 (d, 1H), 5.18

(t, 1H), 5.04 (m, 1H), 4.39 (m, 2H), 3.67 (m, 3H), 3.42 (m, 2H), 3.2 (m, 1H), 2.7 (m, 1H), 2.4 (s, 3H), 2.2 (m, 3H). Separation by chiral HPLC provides diastereomers II-140a-d.

Example 351

Preparation of Compound Nos. II-141 and II-141-a-b

To a solution of 2,3,4,5-tetrahydro-2,8-dimethyl-1H-pyrido[4,3-b]indole (90 mg, 0.466 mmol) in DMF (2 mL), sodium hydride (60%, 33 mg, 1.44 mmol) was added. After stirring for 10 min., methyl 5-(2-methyloxiran-2-yl)nicotinate (1.09 g, 12.4 mmol) was added to the reaction mixture, which was stirred at RT for 16 h. The progress of reaction was monitored by TLC and LCMS. The reaction mixture was quenched with ice-water and extracted with EtOAc (2×100 mL). The aqueous layer was lyophilized and purified by reverse phase HPLC purification to obtain the 10 mg of 5-(1-(1,2,3,4-tetrahydro-2,8-dimethylpyrido[4,3-b]indol-5-yl)-2-hydroxypropan-2-yl)pyridine-3-carboxylic acid. $^1$H NMR (CD$_3$OD, TFA salt) δ (ppm): 8.9 (d, 1H), 8.7 (d, 1H), 8.57 (d, 1H), 7.11 (s, 1H), 6.74 (d, 2H), 4.67 (dd, 1H), 4.33 (m, 2H), 4.29 (dd, 1H), 3.9 (t, 1H), 3.6 (m, 2H), 3.2 (m, 1H), 3.11 (s, 3H), 2.3 (s, 3H), 1.79 (d, 3H). Separation by chiral HPLC provides enantiomers II-141a-b.

Example 352

Preparation of Compound Nos. II-142 and II-142a-b 2,8-Dimethyl-2,3,4,5-tetrahydro-1H-pyrido[4,3-b]indole (40 mg, 0.200 mmol) was dissolved in 1 ml DMF. Sodium hydride (24 mg, 0.600 mmol) was added at 0° C. and the reaction mixture was stirred at RT for 10 min. 5-(2-methyloxiran-2-yl)oxazole (35 mg, 0.280 mmol) in DMF (1 mL) was added dropwise over 10 min. and the reaction mixture was stirred at RT for 12 h. The reaction was monitored by TLC and LCMS. Ice cold water was added to the reaction mixture and then extracted with EtOAc (3×20 mL). The combined organic layer was washed with water (4×10 mL), dried over anhydrous sodium sulfate and concentrated to obtain the crude product, which was purified by reverse phase chromatography to obtain the 20 mg of 1-(1,2,3,4-tetrahydro-2,8-dimethylpyrido[4,3-b]indol-5-yl)-2-(oxazol-5-yl)propan-2-ol as the TFA salt. $^1$H NMR (CD$_3$OD, TFA salt) δ (ppm): 8.09 (s, 1H), 7.18 (s, 1H), 6.97 (d, 1H), 6.92 (d, 1H), 6.8 (s, 1H), 4.7 (m, 1H), 4.35 (m, 3H), 3.9 (m, 1H), 3.56 (m, 1H), 3.25 (m, 2H), 3.09 (s, 3H), 2.37 (s, 3H), 1.58 (s, 3H). Separation by chiral HPLC provides enantiomers II-142a-b.

Example 353

Preparation of Compound Nos. II-143 and II-143a-b 2-(2-Chloropyridin-3-yl)-1-(2,8-dimethyl-3,4-dihydro-1H-pyrido[4,3-b]indol-5(2H)-yl)propan-2-ol (100 mg, 0.277 mmol) and crushed potassium hydroxide (106 mg, 1.89 mmol) in 3 mL tert. butanol were heated at 90° C. for 4 h. The reaction mixture was monitored by TLC and LCMS. The reaction mixture was cooled at RT, diluted with 100 mL brine solution and extracted with EtOAc (3×100 mL). The combined organic layer was washed with brine (3×100 mL), dried over anhydrous sodium sulfate and concentrated to obtain the crude product, which was purified by reverse phase chromatography to get the 35 mg of 3-(1-(1,2,3,4-tetrahydro-2,8-dimethylpyrido[4,3-b]indol-5-yl)-2-hydroxypropan-2-yl) pyridin-2(1H)-one as the TFA salt. $^1$H NMR (CD$_3$OD, TFA salt) δ (ppm): 7.79 (d, 1H), 7.35 (m, 2H), 7.17 (s, 1H), 6.93 (d, 1H), 6.34 (t, 1H), 4.61 (d, 2H), 4.3 (d, 2H), 3.9 (m, 1H), 3.8 (m, 1H), 3.36 (m, 2H), 3.1 (s, 3H), 2.37 (s, 3H), 1.51 (s, 3H). Separation by chiral HPLC provides enantiomers II-143a-b.

Example 354

Preparation of Compound No. II-144

To a solution of 6-methyl-6,7,8,9-tetrahydro-5H-pyrrolo[2,3-b:4,5-c']dipyridine (200 mg, 1.068 mmol) in DMF (1 mL) was added a suspension of NaH (128.0 mg, 3.24 mmol) in DMF (1 mL). After stirring for 5 min. at RT, a solution of 2-(6-methylpyridin-3-yl)ethyl 4-methylbenzenesulfonate (932 mg, 3.204 mmol) in DMF (1 mL) was added dropwise into the reaction mixture and stirring continued for another 3 h. The progress of reaction was monitored by TLC and NMR. The reaction mixture was diluted with water (20 mL) and extracted with EtOAc (3×25 mL). The organic layer was washed with water (3×20 mL), dried over anhydrous sodium sulfate and concentrated under reduced pressure to afford crude material, which was purified by silica gel flash chromatography eluting with 10% MeOH-DCM to yield 6-methyl-9-(2-(6-methylpyridin-3-yl)ethyl)-6,7,8,9-tetrahydro-5H-pyrrolo[2,3-b:4,5-c']dipyridine (90 mg) as a free base. The free base was converted into tri-HCl salt by treatment with ethanolic HCl. $^1$H NMR (CD$_3$OD, Tri-HCl salt) δ (ppm): 8.76 (s, 1H), 8.40 (m, 3H), 7.80 (d, 1H), 7.50 (t, 1H), 4.90-4.70 (m, 3H), 4.42 (m, 1H), 3.95 (m, 1H), 3.66 (m, 1H), 3.42-3.30 (m, 4H), 3.15 (s, 3H), 2.76 (s, 3H).

Example 355

Preparation of Compound Nos. II-145 and II-145a-b 2,8,9-Trimethyl-2,3,4,5-tetrahydro-1H-pyrido[4,3-b]indole (400 mg, 1.86 mmol) 4 mL DMF, cooled to 0° C. and sodium hydride (224 mg, 5.60 mmol) was added portionwise at the same temperature. 3-(2-methyloxiran-2-yl)pyridine (504 mg, 3.73 mmol) in DMF (1 mL) was added to the reaction mixture and allowed to stir at RT for 12 h. After complete consumption of starting material, the reaction mixture was poured in to ice water and extracted with EtOAc (3×100 mL). The combined organic layer was washed with water (3×50 mL), dried over anhydrous sodium sulfate and concentrated to obtain the crude product, which was crystallized with ether and hexane to obtain 400 mg of 2-(pyridin-3-yl)-1-(2,8,9-trimethyl-3,4-dihydro-1H-pyrido[4,3-b]indol-5(2H)-yl)propan-2-ol. $^1$H NMR (DMSO, freebase) δ (ppm): 8.59 (s, 1H), 8.42 (d, 1H), 7.73 (d, 1H), 7.31 (t, 1H), 7.1 (d, 1H), 6.73 (d, 1H), 4.11 (dd, 2H), 3.74 (s, 2H), 3.4 (m, 2H), 2.6 (m, 2H), 2.37 (s, 6H), 2.22 (s, 3H), 1.5 (s, 3H). Separation by chiral HPLC provides enantiomers II-145a-b.

Example 356

Preparation of Compound Nos. II-146 and II-146a-d 2,3,8-Trimethyl-2,3,4,5-tetrahydro-1H-pyrido[4,3-b]indole (214 mg, 1 mmol) was dissolved in DMF (3 mL) and NaH (80 mg, 3.33 mmol) was added portionwise at 0° C. The reaction mixture was stirred at 0° C. for 15 min. The solution of 3-(2-methyloxiran-2-yl)pyridine (270 mg, 2 mmol) in DMF (2 mL) was added dropwise at 0° C. and the reaction mixture was stirred at 0° C. for 10 min and at RT for 16 h. Completion of reaction was monitored by LCMS. The reaction mixture was poured onto crushed ice slowly and extracted with EtOAc (3×30 mL). The organic layer was washed with water (7×40 mL), dried over anhydrous sodium sulfate and concentrated under vacuum to obtain the crude product that was purified by reverse HPLC to give 23 mg of 2-(pyridin-3-yl)-1-(2,3,8-trimethyl-3,4-dihydro-1H-pyrido [4,3-b]indol-5(2H)-yl)propan-2-ol. $^1$H NMR (CDCl$_3$, freebase) δ (ppm): 8.73 (s, 1H), 8.47 (d, 1H), 7.2 (d, 1H), 7.11 (s, 1H), 7.04 (d, 2H), 6.90 (d, 1H), 4.15 (dd, 2H), 3.78 (dd, 1H), 3.6 (dd, 1H), 2.9 (m, 2H), 2.7 (dd, 1H), 2.43 (s, 3H), 2.4 (s, 3H), 1.6 (s, 3H), 1.14 (d, 3H). Separation by chiral HPLC provided diastereomers II-146a-d.

Example 357

Preparation of Compound Nos. II-147 and II-147a-d

To a solution of 8-chloro-2,3-dimethyl-2,3,4,5-tetrahydro-1H-pyrido[4,3-b]indole (500 mg, 2.13 mmol) in 4 mL of DMF was added sodium hydride (256 mg, 6.40 mmol) at 0° C., and stirred for 10 min. 3-(2-methyloxiran-2-yl)pyridine (432 mg, 3.20 mmol) was added and the mixture was stirred at RT for 12 h. The reaction was monitored by TLC and LCMS. The reaction mixture was poured into ice cold water and extracted with EtOAc (2×50 mL). The combined organic layer was washed with water (5×25 mL), dried over anhydrous sodium sulfate, concentrated to obtain the crude product, which was crystallized in n-hexane to obtain 350 mg of 1-(8-chloro-2,3-dimethyl-3,4-dihydro-1H-pyrido[4,3-b]indol-5(2H)-yl)-2-(pyridin-3-yl)propan-2-ol. $^1$H NMR (CDCl$_3$, freebase) δ (ppm): 8.72 (s, 1H), 8.47 (d, 1H), 7.52 (d, 1H), 7.23 (s, 1H), 6.94 (m, 3H), 4.10 (dd, 2H), 3.65 (m, 1H), 3.40 (m, 1H), 2.86 (m, 2H), 2.38 (s, 3H), 2.36 (m, 1H), 1.62 (s, 3H), 1.07 (d, 3H). Separation by chiral HPLC provided diastereomers II-147a-b.

Example 358

Preparation of Compound Nos. II-148 and II-148a-b

To a solution of 2,8-dimethyl-2,3,4,5-tetrahydro-1H-pyrido[4,3-b]indole (700 mg, 3.5 mmol) in 3 mL of DMF was added sodium hydride at 0° C. and stirred for 10 min. 4-Chloro-3-(2-methyloxiran-2-yl)pyridine (888 mg, 5.25 mmol) in 2 mL of DMF was added and allowed to stir at RT for 12 h. The reaction was monitored by TLC and LCMS. After completion of reaction, the reaction mixture was poured into ice cold water and extracted with EtOAc (3×50 mL). The combined organic layer was washed with water (5×50 mL), Dried over anhydrous sodium sulfate, concentrated under reduced pressure and crystallized in diethyl ether to get the desired compound (700 mg). $^1$H NMR (CDCl$_3$, freebase) δ (ppm): 9.1 (s, 1H), 8.43 (d, 1H), 7.38 (d, 1H), 7.29 (d, 1H), 7.25 (d, 1H), 6.97 (d, 1H), 4.7 (d, 1H), 4.23 (d, 1H), 3.63 (m, 2H), 2.8 (m, 2H), 2.75 (m, 2H), 2.51 (s, 3H), 2.41 (s, 3H), 1.71 (s, 3H). Separation by chiral HPLC provided enantiomers II-148a-b.

Example 359

Preparation of Compound Nos. II-149 and II-149a-d

9-Methyl-2,3,4,5,6,10c-hexahydro-1H-3a,6,7-triaza-cyclopenta[c]fluorene (700 mg, 3.0 mmol) was dissolved in DMF (7 mL) and sodium hydride (360 mg, 9.0 mmol) was added portionwise at 0° C. and stirred for 10 min. 2-(4-Fluoro-phenyl)-2-methyl-oxirane (720 mg, 4.8 mmol) in 3 mL DMF was added dropwise into the reaction mixture and the mixture was stirred at RT for 18 h. The reaction mixture was quenched with ice cooled water and extracted with EtOAc (3×100 mL). The combined organic layer was washed with water (4×75 mL), dried over anhydrous sodium sulfate and concentrated to obtain the crude product, which was purified by passing through a column of silica gel (100-200 mesh), using the eluent 5% MeOH in DCM to obtain 520 mg of 2-(4-fluoro-phenyl)-1-(9-methyl-1,2,3,4,5,10c-hexahydro-3a,6,7-triaza cyclopenta[c]fluoren-6-yl)-propan-2-ol. $^1$H NMR (CDCl$_3$, freebase) δ (ppm): 8.02 (s, 1H), 7.54 (s, 1H), 7.43 s (OH), 7.37 (t, 2H), 6.93 (t, 2H), 4.37 (d, 1H), 4.22 (d, 1H), 4.04 (t, 1H), 3.23 (dd, 1H), 2.9 (m, 1H), 2.7 (m, 2H), 2.5 (m, 2H), 2.42 (s, 3H), 2.3 (m, 1H), 1.84 (m, 3H), 1.6 (s, 3H). Separation by chiral HPLC provided diastereomers II-149a-d.

Example 360

Preparation of Compound Nos. II-150 and II-150a-d 2-(2,8-Dimethyl-3,4-dihydro-1H-pyrido[4,3-b]indol-5 (2H)-yl)-1-(pyridin-4-yl)ethanol (350 mg, 1 mmol), formaldehyde (37%, 0.89 g, 10 mmol) and formic acid (922 mg, 20 mmol) was stirred at 100° C. for 12 h. The progress of the reaction was monitored by TLC and LCMS. The reaction mixture was washed with saturated sodium bicarbonate and extracted with DCM (2×25 mL). The combined organic layer was washed with water (5×25 mL) dried over anhydrous sodium sulfate and concentrated under vacuum to obtain the crude product, which was subjected to preparative HPLC to obtain 25 mg of 2-(9-(hydroxymethyl)-2,8-dimethyl-3,4-dihydro-1H-pyrido[4,3-b]indol-5(2H)-yl)-1-(pyridin-4-yl) ethanol. $^1$H NMR (CDCl$_3$, freebase) δ (ppm): 8.56 (d, 2H), 7.29 (d, 2H), 7.12 (d, 1H), 6.98 (d, 1H), 4.9 (dd, 1H), 4.79 (q, 2H), 4.13 (m, 2H), 3.78 (d, 1H), 3.72 (d, 1H), 3.0 (m, 1H), 2.8 (m, 1H), 2.67 (m, 2H), 2.49 (s, 3H), 2.32 (s, 3H). Separation by chiral HPLC provided diastereomers II-150a-d.

Example 361

Preparation of Compound Nos. II-151 and II-151a-d 2,8-Dimethyl-2,3,4,5-tetrahydro-1H-pyrido[4,3-b]indol-4-ol (500 mg, 2.314 mmol) in DMF (5.0 mL) was cooled to 0° C. NaH (0.462 mg, 11.57 mmol) was added portionwise and stirred for 5 min. 3-(2-Methyl-oxiranyl)-pyridine (620 mg, 4.629 mmol) was added dropwise and the reaction mixture was stirred at RT for 4 h. The reaction was quenched with ice water and extracted with EtOAc (3×50 mL). The combined organic layer was washed with water (2×25 mL), dried over anhydrous sodium sulfate and concentrated to get 900 mg crude that was purified by reverse phase HPLC to obtain the product. $^1$H NMR (CD$_3$OD, TFA salt) δ (ppm): 8.57 (m, 2H), 8.48 (m, 1H), 7.85 (m, 1H), 7.21 (s, 1H), 6.78 (d, 1H), 6.64 (m, 1H), 5.72 (m, 1H), 4.66 (t, 2H), 4.45 (d, 1H), 4.30 (d, 1H), 3.78 (m, 2H), 3.16 (s, 3H), 2.31 (s, 3H), 1.87 (s, 3H). Separation by chiral HPLC provided diastereomers II-151a-b.

Example 362

Preparation of Compound Nos. II-152 and II-152a-d 1,2,8-Trimethyl-2,3,4,5-tetrahydro-1H-pyrido[4,3-b]indole (500 mg, 2.3 mmol) in DMF (2.5 mL) was stirred at 0° C. for 5 min. NaH (279 mg, 6.97 mmol) was added slowly at 0° C. After 10 min. stirring, 3-(2-methyloxiran-2-yl)pyridine (630 mg, 4.6 mmol) in DMF (2.5 mL) was added and the reaction mixture was stirred at RT for 18 h. The reaction mixture was poured in ice-cold water (50 mL) and extracted with EtOAc (2×50 mL). The combined organic layer was washed with water (6×50 mL), dried over anhydrous sodium sulfate and concentrated to obtain semi-solid residue that was washed with hexane (3×20 mL) to obtain 350 mg of product that was submitted to chiral reverse phase column chromatography. $^1$H NMR (CDCl$_3$, freebase) δ (ppm): 8.74 (s, 1H), 8.49 (d, 1H), 7.60 (d, 1H), 7.20 (s, 1H), 7.07 (m, 2H), 6.90 (d, 1H), 4.16 (dd, 2H), 3.72 (m, 1H), 2.97 (m, 1H), 2.69 (m, 2H), 2.47 (s, 3H), 2.44 (m, 1H), 2.42 (s, 3H), 1.66 (s, 3H), 1.42 (d, 3H). Separation by chiral HPLC provided diastereomers II-152a-d.

Example 363

Preparation of Compound Nos. II-153 and II-153a-b 1-(2,8-Dimethyl-3,4-dihydro-1H-pyrido[4,3-b]indol-5 (2H)-yl)-2-(pyridin-3-yl)propan-2-ol (1 g, 2.99 mmol) in formaldehyde (37%, 5.69 mL, 59.6 mmol) and formic acid (2.25 mL, 59.6 mmol) was stirred at 100° C. for 24 h. The progress of the reaction was monitored by TLC and LCMS. The reaction mixture was concentrated under vacuum to obtain the crude product, which was subjected to preparative HPLC to obtain pure compound (100 mg). $^1$H NMR (CDCl$_3$, freebase) δ (ppm): 8.7 (s, 1H), 8.5 (d, 1H), 7.8 (d, 1H), 7.23 (m, 1H), 7.15 (d, 1H), 6.94 (d, 1H), 4.80 (q, 2H), 4.19 (dd, 2H), 4.17 (m, 2H), 3.0 (m, 4H), 2.6 (s, 3H), 2.47 (s, 3H), 1.6 (s, 3H). Separation by chiral HPLC provides enantiomers II-153a-b.

Example 364

Preparation of Compound Nos. II-154 and II-154a-b 1-(2,8-Dimethyl-3,4-dihydro-1H-pyrido[4,3-b]indol-5 (2H)-yl)-2-(pyridin-3-yl)propan-2-ol (1 g, 2.99 mmol) in formaldehyde (37%, 5.69 mL, 59.6 mmol) and formic acid (2.25 mL, 59.6 mmol) was stirred at 100° C. for 24 h. The progress of the reaction was monitored by TLC and LCMS. The reaction mixture was concentrated under vacuum to obtain the crude product, which was subjected to preparative HPLC to obtain pure compound (100 mg). $^1$H NMR (CDCl$_3$, freebase) δ (ppm): 8.7 (s, 1H), 8.42 (d, 1H), 7.6 (d, 1H), 7.1 (s, 1H), 6.9 b(s, 2H), 4.7 (s, 2H), 4.1 (q, 2H), 3.9 (s, 2H), 2.9 (m, 3H), 2.8 (m, 1H), 2.6 (s, 3H), 2.39 (s, 3H), 1.6 (s, 3H). Separation by chiral HPLC provides enantiomers II-154a-b.

Example 365

Preparation of Compound No. II-209

2-(2,8-Dimethyl-3,4-dihydro-1H-pyrido[4,3-b]indol-5 (2H)-yl)-1-(pyridin-4-yl)ethanone (0.1 g, 0.313 mmol) in 6 mL of DCM was cooled to 0° C., DAST (0.062 mL, 0.47 mmol) was added dropwise and the mixture stirred at RT for 2 h. The reaction was monitored by LCMS. After completion of the reaction, DCM (10 mL) was added, and the reaction was quenched with satd. NaHCO$_3$ solution. The organic layer was separated, dried over anhydrous sodium sulfate and evaporated to dryness. The crude product was purified by preparative HPLC to afford 40 mg of the desired compound as the TFA salt. $^1$H NMR (CDCl$_3$, Free base) δ (ppm): 8.61 (d, 2H), 7.15-7.2 (m, 3H), 6.83-6.95 (m, 2H), 4.5 (t, 2H), 3.6 (s, 2H), 2.78-2.63 (m, 2H), 2.6-2.45 (m, 5H), 2.4 (s, 3H).

Example 366

Preparation of Compound No. II-210 and II-210a-b

To an ice-cooled stirred solution of 1-(2,8-dimethyl-1,2,3, 4-tetrahydro-pyrido(4,3-b)indol-5-yl)-2-(4-fluorophenyl)-propan-2-ol (500 mg, 1.418 mmol) in DCM (50 mL) was added diethylaminosulfur trifluoride (DAST) (0.374 mL, 2.85 mmol) and the reaction mixture was stirred at RT for 1 h. The DCM layer was diluted and washed with aqueous sodium bicarbonate solution. The organic layer was dried over anhydrous sodium sulfate and evaporated. The residue was purified by reverse phase HPLC. $^1$H NMR (DMSO, oxalate salt) δ (ppm): 7.45 (m, 2H), 7.30 (d, 1H), 7.18 (m, 3H), 6.90 (d, 1H), 4.50 (m, 2H), 4.30 (s, 2H), 3.40 (m, 2H), 3.05 (m, 1H), 2.85 (s, 3H), 2.78 (m, 1H), 2.38 (s, 3H), 1.65 (d, 3H). Separation by chiral HPLC provides enantiomers II-210a-b.

Example 367

Preparation of Compound No. II-211 and II-211a-b

To an ice-cooled stirred solution of 1-(8-chloro-1,2,3,4-tetrahydro-2-methylpyrido[4,3-b]indol-5-yl)-2-(4-fluorophenyl)propan-2-ol (500 mg, 1.3 mmol) in DCM (50 mL) was dropwise added DAST (443 mg, 2.6 mmol) and the reaction mixture was stirred at 0° C. for 1 h. The reaction mixture was diluted with DCM (50 mL), washed with saturated sodium bicarbonate solution (3×30 mL), dried over anhydrous sodium sulfate and concentrated. The residue was purified with reverse phase HPLC to yield 8-chloro-5-(2-fluoro-2-(4-fluorophenyl)propyl)-2,3,4,5-tetrahydro-2-methyl-1H-pyrido[4,3-b]indole. $^1$H-NMR (DMSO-d6, oxalate salt) δ (ppm): 7.50 (s, 1H), 7.40 (m, 3H), 7.18 (t, 2H), 7.05 (d, 1H), 4.60 (m, 2H), 4.25 (m, 2H), 3.05 (m, 2H), 2.85 (s, 3H), 2.70 (m, 2H), 1.65 (d, 3H). Separation by chiral HPLC provides enantiomers II-211a-b.

Example 368

Preparation of Compound Nos. II-212 and II-212a-b 1-(2,8-Dimethyl-1,2,3,4-tetrahydro-pyrido[4,3-b]indol-5-yl)-2-pyridin-3-yl-propan-2-ol (500 mg, 1.492 mmol) was dissolved in 20 mL DCM, cooled to 0° C. and diethylaminosulfur trifluoride (720 mg, 4.477 mmol) in DCM (5 mL) was added dropwise at the same temperature and stirred for 1 h. The reaction was monitored by TLC and LCMS. After consumption of starting material, the reaction mixture was quenched with saturated bicarbonate and extracted with DCM. The organic layer was washed with bicarbonate and brine solution, dried over anhydrous sodium sulfate and concentrated to obtain the crude product, which was purified by reverse phase chromatography to obtain 60 mg of 5-(2-Fluoro-2-pyridin-3-yl-propyl)-2,8-dimethyl-2,3,4,5-tetrahydro-1H-pyrido[4,3-b]indole. $^1$H NMR (CDCl$_3$, freebase) δ (ppm): 8.61 (s, 1H), 8.56 (d, 1H), 7.55 (d, 1H), 7.23 (d, 1H), 7.16 (s, 1H), 7.05 (d, 1H), 6.93 (d, 1H), 4.3 (m, 2H), 3.8 (dd, 2H), 2.96 (m, 1H), 2.9 (m, 1H), 2.7 (m, 1H), 2.6 (m, 1H), 2.58 (s, 3H), 2.41 (s, 3H), 1.75 (d, 3H). Separation by chiral HPLC provided enantiomers II-212a-b.

Example 369

Preparation of Compound Nos. II-213 and II-213a-b 1-(8-Hydroxymethyl-2-methyl-1,2,3,4-tetrahydro-pyrido[4,3-b]indol-5-yl)-2-pyridin-3-yl-propan-2-ol (700 mg, 1.99 mmol) was dissolved in 70 mL DCM and cooled to 0° C. Diethylaminosulfur trifluoride (800 mg, 4.9 mmol) in DCM (5 mL) was added dropwise at the same temperature and stirred for 45 min. The reaction was monitored by TLC and LCMS. After consumption of starting material, the reaction mixture was quenched with saturated bicarbonate and extracted with DCM. The organic layer was washed with water and brine solution, dried over anhydrous sodium sulfate and concentrated to obtain the crude product, which was purified by reverse phase chromatography to obtain 14 mg of [5-(2-fluoro-2-pyridin-3-yl-propyl)-2-methyl-2,3,4,5-tetrahydro-1H-pyrido[4,3-b]indol-8-yl]-methanol. $^1$H NMR (CDCl$_3$, freebase) δ (ppm): 8.6 (s, 1H), 8.57 (d, 1H), 7.6 (d, 1H), 7.35 (s, 1H), 7.2 (m, 1H), 7.125 (m, 2H), 4.72 (s, 2H), 4.3 (m, 2H), 3.6 (q, 2H), 2.8 (m, 1H), 2.7 (dd, 2H), 2.6 (m, 1H), 2.52 (s, 3H), 1.75 (d, 3H). Separation by chiral HPLC provides enantiomers II-213a-b.

Example 370

Preparation of Compound No. II-215

To a stirred solution of 6,8,8-trimethyl-6,7,8,9-tetrahydro-5H-pyrrolo[2,3-b:4,5-c']dipyridine (75 mg, 0.348 mmol) in DMF (1.5 mL) was added potassium hydroxide (156 mg, 2.784 mmol). After stirring for 10 min at RT, a solution of 2-(trifluoromethyl)-5-vinylpyridine (181 mg, 1.046 mmol) in DMF (1.5 mL) was added to the reaction mixture and stirring continued at RT for 24 h and then at 80° C. for 48 h. The progress of reaction was monitored by TLC and LCMS. The reaction mixture was diluted with water and extracted with EtOAc (3×30 mL). The organic layer was washed with water (2×20 mL), dried over anhydrous sodium sulfate and concentrated to afford crude product, which was purified by reverse phase HPLC. $^1$H NMR (CD$_3$OD, TFA salt) δ (ppm): 8.48 (s, 1H), 8.3 (d, 1H), 7.97 (d, 1H), 7.9 (d, 1H), 7.7 (d, 1H), 7.2 (t, 1H), 4.6 (m, 3H), 4.3 (m, 1H), 3.5 (d, 2H), 3.38 (bs, 2H), 3.2 (s, 3H), 1.6 (s, 6H).

Example 371

Preparation of Compound Nos. II-220 and II-220a-b 2,7,8-Trimethyl-2,3,4,5-tetrahydro-1H-pyrido[4,3-b]indole (400 mg, 1.86 mmol) was dissolved in DMF (4 mL), cooled to 0° C. and sodium hydride (224 mg, 5.60 mmol) was added portionwise at the same temperature. 3-(2-methyloxiran-2-yl)pyridine (504 mg, 3.73 mmol) in DMF (1 mL) was added to the reaction mixture and allowed to stir at RT for 12 h. After complete consumption of starting material, the reaction mixture was poured in to ice water and extracted with EtOAc (3×100 mL). The combined organic layer was washed with water (3×50 mL), dried over anhydrous sodium sulfate and concentrated to obtain the crude product, which was crystallized with ether and hexane to obtain 400 mg 2-(pyridin-3-yl)-1-(2,7,8-trimethyl-3,4-dihydro-1H-pyrido[4,3-b]indol-5(2H)-yl)propan-2-ol. $^1$H NMR (DMSO, freebase) δ (ppm): 8.60 (s, 1H), 8.4 (d, 1H), 7.7 (m, 1H), 7.28 (t, 1H), 7.06 (s, 1H), 7.01 (s, 1H), 4.11 (dd, 2H), 3.41 (m, 2H), 2.53 (m, 2H), 2.44 (m, 2H), 2.35 (s, 3H), 2.22 (s, 6H), 1.5 (s, 3H). Separation by chiral HPLC provides enantiomers II-220a-b.

Example 372

Preparation of Compound Nos. II-221 and II-221a-b

To a solution of 3-(2,8-dimethyl-1,2,3,4-tetrahydro-pyrido[4,3-b]indol-5-yl)-2-pyridine-4-yl-propionitrile (50 mg, 0.1515 mmol) in anhydrous THF (4 mL) was added LiAlH$_4$ (17 mg, 0.4545 mmol) at 0° C. under nitrogen atmosphere. After the addition, the reaction mixture was stirred at RT for 1 h. The progress of the reaction was monitored by LCMS. After completion of reaction, 0.5 mL of water was added dropwise and then 0.5 mL of NaOH solution to quench the excess LiAlH$_4$. The reaction mixture was evaporated and the crude product purified by preparative HPLC. $^1$H NMR (CDCl$_3$, freebase) δ (ppm): 8.36 (d, 2H), 7.35 (m, 1H), 7.22 (s, 1H), 6.99 (d, 1H), 6.72 b (s, 2H), 4.23 (m, 1H), 3.71 (dd, 1H), 3.59 (m, 3H), 3.15 (dd, 1H), 3.07 (dd, 1H), 2.77 (m, 2H), 2.47 (s, 3H), 2.45 (s, 3H), 2.1 (m, 3H). Separation by chiral HPLC provides enantiomers II-221a-b.

Example 373

Preparation of Compound Nos. II-222 and II-222a-b 4-(2,8-Dimethyl-1,2,3,4-tetrahydro-pyrido[4,3-b]indol-5-yl)-3-pyridin-4-yl-butyricacidmethylester (1.5 g, 3.9 mmol) was dissolved in THF (50 mL) and cooled to −78° C., tert-butyl lithium (16% in pentane) (6 mL, 15.13 mmol) was added dropwise under nitrogen. The reaction mixture was stirred at −78° C. for 90 min. After complete consumption of starting material, the reaction mixture was quenched with ammonium chloride solution and the reaction mixture was allowed to come to RT and extracted with EtOAc (3×100 mL). The combined organic layer was dried over anhydrous sodium sulfate and concentrated to obtain 1.7 g of crude 6-(2,8-dimethyl-1,2,3,4-tetrahydro-pyrido[4,3-b]indol-5-yl)-2,2-dimethyl-5-pyridin-4-yl-hexan-3-one. $^1$H NMR (CDCl$_3$, freebase) δ (ppm): 8.41 (d, 2H), 7.31 (d, 1H), 7.19 (s, 1H), 7.1 (d, 1H), 6.93 (d, 2H), 4.25 (dd, 1H), 3.9 (t, 2H), 3.8 (m, 1H), 3.67 (dd, 1H), 2.87 (m, 3H), 2.71 (m, 2H), 2.51 (s, 3H), 2.42 (s, 3H), 2.1 (m, 1H), 1.21 s (9H). Separation by chiral HPLC provides enantiomers II-222a-b.

Example 374

Preparation of Compound Nos. II-223 and II-223a-b 4-(2,8-Dimethyl-1,2,3,4-tetrahydro-pyrido[4,3-b]indol-5-yl)-3-pyridin-4-yl-but-3-enoicacid methyl ester (100 mg, 0.266 mmol) was dissolved in MeOH (10 mL) and 10% dry Pd/C (50 mg) was added and hydrogen gas was purged in to the reaction mixture at RT for 12 h. The reaction was monitored by TLC and LCMS. After consumption of starting material, the reaction mixture was filtered through Celite. The filtrate was concentrated to obtain the crude product, which was recrystallized in ether-hexane to obtained 50 mg of 4-(2,8-dimethyl-1,2,3,4-tetrahydro-pyrido[4,3-b]indol-5-yl)-3-pyridin-4-yl-butyric acid methyl ester. $^1$H NMR (CDCl$_3$, freebase) δ (ppm): 8.47 (d, 2H), 7.18 (s, 1H), 7.16 (d, 1H), 6.98 (d, 3H), 4.22 (dd, 1H), 4.05 (dd, 1H), 3.7 (m, 2H), 3.57 (s, 3H), 3.5 (dd, 1H), 2.74 (m, 3H), 2.71 (m, 2H), 2.49 (s, 3H), 2.43 (s, 3H), 2.2 (m, 1H). Separation by chiral HPLC provides enantiomers II-223a-b.

Example 375

Preparation of Compound Nos. II-224 and II-224a-b

A solution of 4-(2,8-dimethyl-1,2,3,4-tetrahydro-pyrido[4,3-b]indol-5-yl)-3-pyridin-4-yl-butyric acid methyl ester (300 mg, 0.795 mmol) in THF (5 mL) was added dropwise to a solution of $LiAlH_4$ (93 mg, 2.37 mmol) in THF (10 mL). The reaction mixture was stirred at RT for 30 min. After consumption of starting material, the reaction mixture was cooled to −78° C. 0.2 mL of water and 0.2 mL of 15% NaOH solution was added and the reaction mixture was allowed to come to RT and diluted with THF and filtered. The filtrate was concentrated and the crude product was purified by passing through a column of silica gel (100-200 mesh) by using eluent 2% MeOH in DCM to obtain 69 mg of 4-(2,8-dimethyl-1,2,3,4-tetrahydro-pyrido[4,3-b]indol-5-yl)-3-pyridin-4-yl-butan-1-ol. $^1H$ NMR ($CDCl_3$, freebase) δ (ppm): 8.48 (d, 2H), 7.18 (s, 1H), 7.1 (d, 1H), 7.01 (d, 2H), 6.97 (d, 1H), 4.2 (dd, 1H), 4.15 (dd, 1H), 3.64 (d, 1H), 3.56 (m, 2H), 3.4 (m, 2H), 2.7 (m, 3H), 2.4 (m, 1H), 2.5 (s, 3H), 2.43 (s, 3H), 1.94 (m, 2H). Separation by chiral HPLC provided enantiomers II-224a-b.

Example 376

Preparation of Compound Nos. II-225 and II-225a-b

To a compound 3-(2,8-dimethyl-3,4-dihydro-1H-pyrido[4,3-b]indol-5(2H)-yl)-2-(pyridin-4-yl)propanoic acid (250 mg, 0.7 mmol) in THF was added $LiAlH_4$ (81.6 mg, 2.1 mmol) and the resultant reaction mixture was stirred at RT for 1 h. The progress of the reaction was monitored by TLC and LCMS. The reaction was quenched by NaOH (0.5 mL), water (3 mL) at 0° C. and extracted with DCM (3×25 mL). The combined organic layer was dried on anhydrous sodium sulfate and concentrated under vacuum to obtain the crude product, which was subjected to reverse phase HPLC to obtain pure compound (30 mg). $^1H$ NMR ($CDCl_3$, freebase) δ (ppm): 8.41 (d, 2H), 7.28 b (s, 1H), 7.2 (s, 1H), 7.1 (d, 1H), 6.78 (d, 2H), 4.4 bs (OH), 4.3 (m, 1H), 4.0 (m, 1H), 3.62 (d, 1H), 3.42 (m, 3H), 3.1 (dd, 1H), 2.7 (m, 3H), 2.46 (m, 1H), 2.43 (s, 6H). Separation by chiral HPLC provides enantiomers II-225a-b.

Example 377

Preparation of Compound Nos. II-226 and II-226a-b 4-(2,8-Dimethyl-1,2,3,4-tetrahydro-pyrido[4,3-b]indol-5-yl)-3-pyridin-4-yl-butyricacid methyl ester (400 mg, 1.06 mmol) was dissolved in THF (20 mL) and methyl magnesium chloride (3 M in THF) (2 mL, 6.3 mmol) was added dropwise under nitrogen. The reaction mixture was stirred at 60° C. for 1 h. After consumption of starting material, the reaction mixture was quenched with ammonium chloride solution and the reaction mixture was extracted with EtOAc (3×100 mL). The combined organic layer was dried over anhydrous sodium sulfate and concentrated to obtain 400 mg crude of 5-(2,8-dimethyl-1,2,3,4-tetrahydro-pyrido[4,3-b]indol-5-yl)-2-methyl-4-pyridin-4-yl-pentan-2-ol. $^1H$ NMR ($CDCl_3$, freebase) δ (ppm): 8.43 (d, 2H), 7.16 (s, 1H), 7.14 (d, 1H), 6.99 (d, 3H), 4.3 (dd, 1H), 3.98 (d, 1H), 3.9 (dd, 1H), 3.8 (d, 1H), 3.5 (m, 1H), 3.15 (dd, 1H), 2.84 (m, 3H), 2.59 (s, 3H), 2.42 (s, 3H), 2.3 (dd, 1H), 1.85 (dd, 1H), 1.15 (s, 3H), 1.02 (s, 3H). Separation by chiral HPLC provides enantiomers II-226a-b.

Example 378

Preparation of Compound Nos. II-227 and II-227a-d 6-(2,8-Dimethyl-1,2,3,4-tetrahydro-pyrido[4,3-b]indol-5-yl)-2,2-dimethyl-5-pyridin-4-yl-hexan-3-one (400 mg, 0.99 mmol) was dissolved in MeOH (30 mL). Sodium borohydride (263 mg, 6.9 mmol) was added under nitrogen. The reaction mixture was heated at 60° C. for 8 h. After consumption of starting material, the reaction mixture was concentrated and 2N HCl was added (pH-acidic) and extracted with DCM (2×200 mL) for removing impurities. The aqueous layer was basified with saturated bicarbonate and extracted with DCM. The organic layer was dried over anhydrous sodium sulfate and concentrated to obtain 350 mg of 6-(2,8-dimethyl-1,2,3,4-tetrahydro-pyrido[4,3-b]indol-5-yl)-2,2-dimethyl-5-pyridin-4-yl-hexan-3-ol. $^1H$ NMR ($CDCl_3$, freebase) δ (ppm): 8.44 (d, 2H), 7.15 (s, 1H), 7.0 (d, 1H), 6.94 (d, 1H), 6.92 (d, 2H), 4.25 (dd, 1H), 4.0 (dd, 1H), 3.64 (d, 1H), 3.51 (m, 2H), 2.88 (dd, 1H), 2.73 (t, 1H), 2.58 (m, 1H), 2.48 (s, 3H), 2.42 (s, 3H), 2.2 (m, 1H), 2.02 (t, 1H), 1.71 (t, 2H), 0.837 s (9H). Separation by chiral HPLC provided diastereomers II-227a-b.

Example 379

Preparation of Compound Nos. II-229 and II-229a-b 4-(2,8-Dimethyl-1,2,3,4-tetrahydro-pyrido[4,3-b]indol-5-yl)-3-pyridin-4-yl-butyric acid (175 mg, 0.482 mmol) was dissolved in DCM (5 mL), ammonium chloride (51 mg, 0.964 mmol), PYBOP (300 mg, 0.578 mmol) and triethylamine (0.69 mL, 4.82 mmol) were added and the reaction mixture was stirred at RT for 4 h. The reaction progress was monitored by LC-MS. After completion of the reaction, the reaction mixture was concentrated and the crude product was purified by reverse phase chromatography to obtain 45 mg of 4-(2,8-dimethyl-1,2,3,4-tetrahydro-pyrido[4,3-b]indol-5-yl)-3-pyridin-4-yl-butyramide as the TFA salt. $^1H$ NMR ($CD_3OD$, TFA salt) δ (ppm): 8.6 (d, 2H), 7.8 (d, 2H), 7.25 (s, 1H), 7.15 (d, 1H), 6.9 (d, 1H), 4.63 (t, 1H), 4.5 (m, 1H), 4.4 (m, 1H), 4.3 (dd, 1H), 4.0 (m, 1H), 3.85 (m, 1H), 3.6 (m, 1H), 3.2 (m, 1H), 3.1 (s, 3H), 3.0 (m, 1H), 2.9 (m, 2H), 2.4 (d, 3H). Separation by chiral HPLC provides enantiomers II-229a-b.

Example 380

Preparation of Compound Nos. II-230 and II-230a-b 4-(2,8-Dimethyl-1,2,3,4-tetrahydro-pyrido[4,3-b]indol-5-yl)-3-pyridin-4-yl-butyric acid (130 mg, 0.358 mmol) was dissolved in DCM (5 mL), dimethyl amine hydrochloride (57 mg, 0.716 mmol), PYBOP (223 mg, 0.429 mmol) and triethylamine (0.51 mL, 3.58 mmol) were added and the reaction mixture was stirred at RT for 4 h. The reaction progress was monitored by LC-MS. After completion of the reaction, the reaction mixture was concentrated and the crude product was purified by reverse phase chromatography to obtain 77 mg of 4-(2,8-dimethyl-1,2,3,4-tetrahydro-pyrido[4,3-b]indol-5-yl)-N,N-dimethyl-3-pyridin-4-yl-butyramide as the TFA salt. $^1H$ NMR ($CD_3OD$, TFA salt) δ (ppm): 8.56 (d, 2H), 7.28 (d, 2H), 7.19 (s, 1H), 7.17 (d, 1H), 6.94 (d, 1H), 4.63 (dd, 1H), 4.54 (dd, 1H), 4.39 (d, 1H), 4.37 (t, 1H), 4.0 (m, 1H), 3.8 (m, 1H), 3.6 (m, 1H), 3.45 (m, 1H), 3.3 (m, 1H), 3.1 (s, 6H), 3.0 (d, 3H), 2.9 (m, 2H), 2.8 (d, 3H). Separation by chiral HPLC provides enantiomers II-230a-b.

Example 381

Preparation of Compound Nos. II-231 and II-231a-b

Methanesulfonic acid-4-(2,8-dimethyl-1,2,3,4-tetrahydro-pyrido[4,3-b]indol-5-yl)-3-pyridin-4-yl-butyl ester (200 mg, 0.468 mmol) in 10 mL of aqueous ammonia was heated at 100° C. for 1 h. The progress of reaction was monitored by TLC. After consumption of starting material, the reaction mixture was dried and the crude product was purified by reverse phase chromatography to obtain 33 mg of 4-(2,8-dimethyl-1,2,3,4-tetrahydro-pyrido[4,3-b]indol-5-yl)-3-pyridin-4-yl-butylamine as the TFA salt. $^1$H NMR (CD$_3$OD, TFA salt) δ (ppm): 8.5 (d, 2H), 7.5 (m, 2H), 7.25 (d, 1H), 7.24 (s, 1H), 7.05 (t, 1H), 4.6 (d, 1H), 4.5 (d, 1H), 4.3 (m, 1H), 4.23 (t, 1H), 3.8 (m, 1H), 3.5 (m, 1H), 3.08 (d, 3H), 2.8 (m, 2H), 2.7 (m, 2H), 2.4 (s, 3H), 2.25 (m, 1H), 2.2 (m, 1H). Separation by chiral HPLC provides enantiomers II-231a-b.

Example 382

Preparation of Compound Nos. II-232 and II-232a-b

Methanesulfonic acid-4-(2,8-dimethyl-1,2,3,4-tetrahydro-pyrido[4,3-b]indol-5-yl)-3-pyridin-4-yl-butyl ester (200 mg, 0.468 mmol) in 10 mL of 40% aqueous dimethyl amine was heated at 100° C. for 1 h. The progress of reaction was monitored by TLC. After consumption of starting material, the reaction mixture was dried and the crude product was purified by reverse phase chromatography to obtain 170 mg of [4-(2,8-dimethyl-1,2,3,4-tetrahydro-pyrido[4,3-b]indol-5-yl)-3-pyridin-4-yl-butyl]-dimethyl-amine as the TFA salt. $^1$H NMR (CD$_3$OD, TFA salt) δ (ppm): 8.57 b (s, 2H), 7.65 (dd, 2H), 7.23 (d, 1H), 7.21 (s, 1H), 6.99 (d, 1H), 4.62 (m, 1H), 4.48 (m, 1H), 4.42 (m, 1H), 4.26 (t, 1H), 3.81 (m, 1H), 3.55 (m, 2H), 3.35 (m, 1H), 3.1 (m, 1H), 3.0 (s, 3H), 2.9 (m, 2H), 2.83 (s, 6H), 2.4 (m, 1H), 2.38 (s, 3H), 2.29 (m, 1H). Separation by chiral HPLC provides enantiomers II-232a-b.

Example 383

Preparation of Compound No. II-240

Aza-methylcarboline (50 mg, 0.248 mmol), 4-vinylpyridine (49.6 mg, 0.472 mmol), tetrabutylammoniumbromide (79.8 mg, 0.248 mmol) were charged in 50% solution of sodium hydroxide (2 mL), and the reaction mixture was heated at 95° C. for 1.5 h. The reaction mixture was monitored with TLC and LCMS. The reaction mixture was extracted with EtOAc (2×25 mL). The combined organic layer was washed with water (2×20 mL) and dried over anhydrous sodium sulfate. The organic layer was concentrated and purified through reverse phase chromatography. Yield: 19.20 mg. $^1$H NMR (CD$_3$OD, Free base) δ (ppm): 8.38 (d, 2H), 8.0 (s, 1H), 7.63 (s, 1H), 7.1 (d, 2H), 4.4 (t, 2H), 3.8 (s, 2H), 3.15 (t, 2H), 3.0 (t, 2H), 2.75 (t, 2H), 2.61 (s, 3H), 2.4 (s, 3H).

Example 384

Preparation of Compound Nos. II-241 and II-241a-b

Aza-carboline (100 mg, 0.53 mmol) was dissolved in DMF (8 mL). Sodium hydride (38 mg, 1.59 mmol) was added at 0-10° C. and stirred at the same temperature for 15 min. 4-(oxiran-2-yl)pyridine (254 mg, 2.12 mmol) in DMF (2 mL) was added dropwise into the reaction mixture and the mixture was stirred at RT for 16 h. The reaction was monitored by LCMS. After consumption of starting material, the reaction mixture was quenched with ice cold water (4 mL) and solvent was evaporated to obtain the crude product, which was purified by reverse phase column chromatography to obtain 10 mg of product. $^1$H NMR (CD$_3$OD, freebase) δ (ppm): 8.41 (d, 2H), 8.19 (d, 1H), 7.73 (s, 1H), 7.36 (d, 2H), 7.06 (m, 1H), 5.04 (t, 1H), 4.6 (m, 1H), 4.33 (m, 2H), 3.76 (dd, 2H), 2.9 (m, 4H), 2.5 (s, 3H). Separation by chiral HPLC provides enantiomers II-241a-b.

Example 385

Preparation of Compound No. II-242 and II-242a-b

Aza-carboline (300 mg, 1.60 mmol) was dissolved in DMF (8 mL). Sodium hydride (153 mg, 6.4 mmol) was added at 0-10° C. and stirred at the same temperature for 15 min., 4-(oxiran-2-yl)pyridine (769 mg, 6.41 mmol) in DMF (2 mL) was added dropwise into the reaction mixture and the mixture was stirred at RT for 16 h. The reaction was monitored by LCMS. After consumption of starting material, the reaction mixture was quenched with ice cold water (4 mL) and solvent was evaporated to obtain the crude product, which was purified by reverse phase column chromatography to obtain 8 mg of product. $^1$H NMR (CD$_3$OD, freebase) δ (ppm): 8.5 (s, 1H), 8.43 (d, 2H), 8.01 (d, 1H), 7.4 (d, 1H), 7.38 (d, 2H), 5.07 (t, 1H), 4.4 (m, 2H), 3.68 (s, 2H), 3.3 (s, 2H), 2.85 (m, 4H), 2.45 (s, 3H). Separation by chiral HPLC provides enantiomers II-242a-b.

Example 386

Preparation of Compound Nos. II-243 and II-243a-b

5-[2-(9-Methyl-1,2,3,4,5,10c-hexahydro-3a,6,7-triaza-cyclopenta[c]fluoren-6-yl)-ethyl]-pyridine-2-carboxylic acid (400 mg, 1.063 mmol) was dissolved in 15 mL DCM and cooled at 0° C. Oxalyl chloride (669 mg, 5.315 mmol) and catalytic amount of DMF was added and the reaction mixture was stirred at RT for 1 h. The reaction was monitored by LCMS. The reaction mixture was concentrated and aqueous ammonia was added at 0° C. The reaction mixture was warmed to RT and stirred for 1 h. The reaction mixture was concentrated to obtain the crude product that was purified by reverse phase chromatography to obtain 2.5 mg of 5-[2-(9-methyl-1,2,3,4,5,10c-hexahydro-3a,6,7-triaza-cyclopenta[c]fluoren-6-yl)-ethyl]-pyridine-2-carboxylic acid amide as the TFA salt. $^1$H NMR TFA:—CD$_3$OD: 8.2 (s, 2H), 7.95 (d, 1H), 7.8 (s, 1H), 7.6 (d, 1H), 5.0 (t, 1H), 4.6 (m, 2H), 3.62 (m, 1H), 3.5 (m, 2H), 3.3 (m, 3H), 2.8 (d, 1H), 2.63 (m, 2H), 2.4 (s, 3H), 2.2 (m, 2H), 2.1 (m, 1H). Separation by chiral HPLC provides enantiomers II-243a-b.

Example 387

Preparation of Compound Nos. II-244 and II-244a-b

9-Methyl-2,3,4,5,6,10c-hexahydro-1H-3a,6,7-triaza-cyclopenta[c]fluorene (250 mg, 1.10 mmol), 4-vinyl-pyridine (347 mg, 3.30 mmol), tetrabutyl ammonium bromide (355 mg, 1.10 mmol) were charged in a screw cap bottle and a 60% solution of sodium hydroxide (5 mL) was added and heated to 100° C. for 12 h. The reaction was monitored by TLC and LCMS. The reaction mixture was diluted with 25 mL of water and extracted with EtOAc (2×50 mL). The combined organic extracts were washed with water (25 mL), dried over anhydrous sodium sulfate and concentrated. The resultant crude product was purified by reverse phase chromatography to obtain 85 mg of 9-methyl-6-(2-pyridin-4-yl-ethyl)-2,3,4,5,6,10c-hexahydro-1H-3a,6,7-triaza-cyclopenta[c]fluorene as the formate salt (the product was a racemate which was purified by chiral prep HPLC to obtain product II-244a & product II-244b as the freebase). $^1$H NMR (CDCl$_3$, freebase) δ (ppm): 8.45 (d, 2H), 8.17 (s, 1H), 7.56 (s, 1H), 6.91 (d, 2H), 4.5 (m, 1H), 4.42 (t, 1H), 4.35 (m, 1H), 3.26 (m, 2H), 3.16 (m, 5H), 2.81 (m, 1H), 2.45 (m, 1H), 2.41 (s, 3H), 2.1 (m, 2H), 1.9 (m, 1H). Separation by chiral HPLC provided enantiomers II-244a-b.

Example 388

Preparation of Compound Nos. II-245 and II-245a-b

A suspension of azabicyclic carboline (0.2 g, 0.8 mmol), vinylpyrazine (0.375 g, 3.5 mmol), and tetrabutylammoniumbromide (0.855 g, 2.6 mmol) in 50% NaOH solution (2 mL) was heated at 100° C. for overnight. The reaction mixture diluted with EtOAc (50 mL), organic layer washed with water (20 mL), dried over anhydrous sodium sulfate, and concentrated under vacuum to obtain the crude product that was purified by reverse phase HPLC to obtain 2.4 mg of desired compound. $^1$H NMR (CD$_3$OD, TFA salt) δ (ppm): 8.48 (s, 1H), 8.39 (s, 1H), 8.1 (s, 1H), 8.06 (s, 1H), 7.7 (s, 1H),5.1 (m, 1H), 4.64 (t, 2H), 3.7 (m, 4H), 3.03 (t, 2H), 2.7 (m, 2H), 2.45 (s, 3H), 2.15 (m, 4H). Separation by chiral HPLC provides enantiomers II-245a-b.

Example 389

Preparation of Compound No. II-246

To a solution of 7,10-dichloro-1,2,3,4,5,6-hexahydro-3-methylazepino[4,5-b]indole (200 mg, 0.746 mmol) in DMF (2 mL), sodium hydride (90 mg, 2.25 mmol) was added. After stirring at 60° C. for 30 min., 2-(6-methylpyridin-3-yl)ethyl 4-methylbenzenesulfonate (543 mg, 1.86 mmol) was added to the reaction mixture and the reaction mixture was stirred at the same temperature for 40 min. The progress of reaction was monitored by TLC and LCMS. The reaction mixture was quenched with water and extracted with EtOAc. The organic layer was washed with water, dried over anhydrous sodium sulfate and concentrated to obtain the residue that was purified by reverse phase HPLC to obtain 7,10-dichloro-1,2,3,4,5,6-hexahydro-3-methyl-6-(2-(6-methylpyridin-3-yl)ethyl) azepino [4,5-b]indole. $^1$H NMR TFA:—CD$_3$OD: 8.4 (s, 1H), 8.1 (d, 1H), 7.75 (d, 1H), 7.0 (q, 2H), 4.8 (m, 1H), 4.0 (m, 1H), 3.8 (m, 2H), 3.4 (m, 3H), 3.3 (m, 2H),3.2 (t, 3H),3.0 (s, 3H), 2.7 (s, 3H).

Example 390

Preparation of Compound No. II-247

To a solution of 9-bromo-6-chloro-2,3,4,5-tetrahydro-2-methyl-1H-pyrido[4,3-b]indole (500 mg, 1.67 mmol) in DMF (5 mL), sodium hydride (200 mg, 5.0 mmol) was added. After stirring at 60° C. for 30 min., 2-(6-methylpyridin-3-yl) ethyl 4-methylbenzenesulfonate (1.2 g, 4.2 mmol) was added to the reaction mixture and stirred at the same temperature for 1 h. The progress of reaction was monitored by TLC and LCMS. The reaction mixture was quenched with water and extracted with EtOAc. The organic layer was washed with water, dried over anhydrous sodium sulfate and concentrated to obtain the crude product, which was purified by reverse phase HPLC to obtain the 9-bromo-6-chloro-2,3,4,5-tetrahydro-2-methyl-5-(2-(6-methylpyridin-3-yl)ethyl)-1H-pyrido [4,3-b]indole. $^1$H NMR (CD$_3$OD, TFA salt) δ (ppm): 8.39 (s, 1H), 8.12 (d, 1H), 7.66 (d, 1H), 7.26 (d, 1H), 7.1 (d, 1H),4.67 (m, 4H), 3.7 (m, 2H), 3.27 (t, 2H), 3.18 (m, 2H), 3.15 (s, 3H), 2.69 (s, 3H).

Example 391

Preparation of Compound No. II-248

To a solution of 9-chloro-6-fluoro-2,3,4,5-tetrahydro-2-methyl-1H-pyrido[4,3-b]indole (500 mg, 2.1 mmol) in DMF (5 mL), sodium hydride (252 mg, 6.3 mmol) was added. After stirring at 60° C. for 30 min., 2-(6-methylpyridin-3-yl)ethyl 4-methylbenzenesulfonate (1.5 g, 5.25 mmol) was added to the reaction mixture and stirred at the same temperature for 1 h. The progress of reaction was monitored by TLC and LCMS. The reaction mixture was quenched with water and extracted with EtOAc. The organic layer was washed with water, dried over anhydrous sodium sulfate and concentrated to obtain the crude product, which was purified by reverse phase HPLC to obtain the 9-chloro-6-fluoro-2,3,4,5-tetrahydro-2-methyl-5-(2-(6-methylpyridin-3-yl)ethyl)-1H-pyrido [4,3-b]indole. $^1$H NMR (CD$_3$OD, TFA) δ (ppm): 8.37 (s, 1H), 8.12 (d, 1H), 7.73 (d, 1H), 7.02 (dd, 1H), 6.86 (t, 1H), 5.1 (m, 1H), 4.57 (t, 2H), 4.56 (m, 1H), 3.85 (m, 1H), 3.6 (m, 1H), 3.27 (m, 3H), 3.2 m (2H), 3.1 (s, 3H), 2.69 (s, 3H).

Example 392

Preparation of Compound No. II-249

To a solution of 5,8-dichloro-2,3,4,9-tetrahydro-2-methyl-1H-pyrido[3,4-b]indole (200 mg, 0.78 mmol) in DMF (2 mL), sodium hydride (94 mg, 2.36 mmol) was added. After stirring at 60° C. for 30 min., 2-(6-methylpyridin-3-yl)ethyl 4-methylbenzenesulfonate (572 mg, 1.96 mmol) was added to the reaction mixture and stirred at the same temperature for 40 min. The progress of reaction was monitored by TLC and LCMS. The reaction mixture was quenched with water and extracted with EtOAc. The organic layer was washed with water, dried over anhydrous sodium sulfate and concentrated to get the residue that was purified by reverse phase HPLC to obtain the 5,8-dichloro-2,3,4,9-tetrahydro-2-methyl-9-(2-(6-methylpyridin-3-yl)ethyl)-1H-pyrido[3,4-b]indole.
$^1$H NMR (CD$_3$OD, TFA salt) δ (ppm): 8.43 (s, 1H), 8.18 (d, 1H), 7.74 (d, 1H), 7.09 (d, 1H), 7.04 (d, 1H), 4.79 (t, 2H), 4.65 b(s, 1H), 3.62 b(s, 1H), 3.5 (m, 2H), 3.35 (m, 2H), 3.25 (t, 2H), 3.16 (s, 3H), 2.75 (s, 3H).

Example 393

Preparation of Compound No. II-250

To a solution of 6,9-difluoro-2,3,4,5-tetrahydro-2-methyl-1H-pyrido[4,3-b]indole (550 mg, 2.42 mmol) in DMF (3.5 mL) was added sodium hydride (300 mg, 7.4 mmol). After stirring at 60° C. for 30 min., 2-(6-methylpyridin-3-yl)ethyl 4-methylbenzenesulfonate (1.8 g, 6.1 mmol) was added to the reaction mixture, which was stirred at the same temperature for 1 h. The progress of reaction was monitored by TLC and LCMS. The reaction mixture was quenched with water and extracted with EtOAc. The organic layer was washed with water, dried over anhydrous sodium sulfate and concentrated. The residue was purified by reverse phase HPLC (540 mg, TFA salt). $^1$H NMR (CD$_3$OD, TFA salt) δ (ppm): 8.35 (s, 1H), 8.13 (d, 1H), 7.73 (d, 1H), 6.7 (m, 2H), 4.8 (m, 1H), 4.57 (t, 2H), 4.5 (m, 1H), 3.9 (m, 1H), 3.6 (m, 1H), 3.35 (m, 2H), 3.19 (m, 2H), 3.13 (s, 3H), 2.69 (s, 3H).

Example 394

Preparation of Compound No. II-251

To a solution of 6,9-dibromo-2,3,4,5-tetrahydro-2-methyl-1H-pyrido[4,3-b]indole (800 mg, 2.32 mmol) in DMF (5 mL) was added sodium hydride (0.279 g, 6.9 mmol). After stirring at 60° C. for 30 min., 2-(6-methylpyridin-3-yl)ethyl 4-methylbenzenesulfonate (1.7 g, 5.8 mmol) was added to the reaction mixture, which was stirred at the same temperature for 1 h. The progress of reaction was monitored by TLC and LCMS. The reaction mixture was quenched with water and extracted with EtOAc. The organic layer was washed with water, dried over anhydrous sodium sulfate and concentrated. The residue was purified by reverse phase HPLC (460 mg, TFA salt). $^1$H NMR (CD$_3$OD, TFA salt) δ (ppm): 8.46 (s, 1H), 8.18 (d, 1H), 7.72 (d, 1H), 7.28 (d, 1H), 7.18 (d, 1H), 5.2 (m, 2H), 4.6 (m, 2H), 3.9 (m, 1H), 3.6 (m, 1H), 3.2 (m, 4H), 3.15 (s, 3H), 2.71 (s, 3H).

Example 395

Preparation of Compound No. II-252

To a solution of 6-bromo-9-chloro-2,3,4,5-tetrahydro-2-methyl-1H-pyrido[4,3-b]indole (500 mg, 1.67 mmol) in DMF (4 mL) was added sodium hydride (120 mg, 5.0 mmol). After stirring at 60° C. for 30 min., 2-(6-methylpyridin-3-yl) ethyl 4-methylbenzenesulfonate (1.2 g, 4.19 mmol) was added to the reaction mixture, which was stirred at the same temperature for 1 h. The progress of the reaction was monitored by TLC and LCMS. The reaction mixture was quenched with water and extracted with EtOAc. The organic layer was washed with water, dried over anhydrous sodium sulfate and concentrated. The residue was purified by reverse phase HPLC (279 mg, TFA salt). $^1$H NMR (CD$_3$OD, TFA salt) δ (ppm): 8.43 (s, 1H), 8.14 (d, 1H), 7.7 (d, 1H), 7.35 (d, 1H), 7.03 (d, 1H), 5.0 (m, 2H), 4.6 (m, 2H), 3.8 (m, 1H), 3.6 (m, 1H), 3.27 (t, 2H), 3.22 (t, 2H), 3.14 (s, 3H), 2.7 (s, 3H).

Example 396

Preparation of Compound No. II-253

To a solution of 6-chloro-9-fluoro-2,3,4,5-tetrahydro-2-methyl-1H-pyrido[4,3-b]indole (500 mg, 2.1 mmol) in DMF (5 mL) was added sodium hydride (252 mg, 6.3 mmol). After stirring at 60° C. for 30 min., 2-(6-methylpyridin-3-yl)ethyl 4-methylbenzenesulfonate (1.5 g, 5.25 mmol) was added to the reaction mixture, which was stirred at the same temperature for 1 h. The progress of the reaction was monitored by TLC and LCMS. The reaction mixture was quenched with water and extracted with EtOAc. The organic layer was washed with water, dried over anhydrous sodium sulfate and concentrated. The residue was purified by reverse phase HPLC (463 mg, TFA salt). $^1$H NMR (CD$_3$OD, TFA salt) δ (ppm): 8.42 (s, 1H), 8.15 (d, 1H), 7.7 (d, 1H), 7.1 (dd, 1H), 6.8 (t, 1H), 4.8 (m, 2H), 4.5 (m, 2H), 3.8 (m, 1H), 3.6 (m, 1H), 3.3 (t, 2H), 3.2 (t, 2H), 3.1 (s, 3H), 2.7 (s, 3H).

Example 397

Preparation of Compound Nos. II-255 and II-255a-b 3-(2,8-Dimethyl-3,4-dihydro-1H-pyrido[4,3-b]indol-5 (2H)-yl)-2-hydroxy-2-(pyridin-4-yl)propanenitrile.diHCl salt (500 mg, 1.19 mmol) was dissolved in 500 mL Ethanol. The solution was passed through H-Cube as condition 70 mbar at 70° C. (Ra/Ni as catalyst). The product formation observed by LCMS. The solvent was concentrated under reduced pressure. The crude product was purified by reverse phase column chromatography to obtain 1-amino-3-(2,8-dimethyl-3,4-dihydro-1H-pyrido[4,3-b]indol-5(2H)-yl)-2-(pyridin-4-yl)propan-2-ol (31 mg) as the TFA salt. $^1$H NMR (CDCl$_3$, freebase) δ (ppm): 8.61 (d, 2H), 7.42 (d, 2H), 7.23 (d, 1H), 7.18 (s, 1H), 6.95 (d, 1H), 4.17 (dd, 2H), 3.68 (q, 2H), 3.2 (d, 1H), 3.1 (m, 1H), 2.76 (m, 3H), 2.63 (m, 1H), 2.55 (s, 3H), 2.43 (s, 3H). Separation by chiral HPLC provided enantiomers II-255a-b.

Example 398

Preparation of Compound Nos. II-256 and II-256a-b

A solution of alcohol (2 g, 6.2 mmol) in THF (150 mL) was cooled at −78° C., NaH (0.3 g, 12.4 mmol, 60% dispersion in mineral oil) was added and the reaction mixture was stirred at the same temperature for 30 min. Methyl acrylate (2.1 g, 31.1 mmol) was added slowly and the reaction mixture was stirred at −78° C. for 1 h and at RT for further 2 h. The reaction mixture was quenched with water (60 mL) and extracted with EtOAc (2×60 mL). The combined organic layer was washed with brine (50 mL), dried over anhydrous Sodium sulfate. Removal of solvent under reduced pressure gave crude product that was purified by column chromatography using neutral alumina and 1-2% MeOH-DCM system as eluent to give 0.8 g pure desired ester. To a solution of ester (0.2 g, 0.49 mmol) in MeOH (5 mL) was added 1 N LiOH (1 mL) at RT and the reaction mixture was stirred at 50° C. for 1 h. The reaction mixture was concentrated to dryness under reduce pressure to give crude product which was purified by reverse phase preparative HPLC to give 108 mg pure product. $^1$H NMR (CD$_3$OD, TFA) δ (ppm): 8.66 (d, 2H), 7.8 (d, 2H), 7.23 (s, 1H), 7.1 (d, 1H), 7.0 & 6.9 (d, 1H), 4.8 (m, 1H), 4.7 (m, 1H), 4.4 (m, 3H), 3.85 (m, 1H), 3.6 (m, 2H), 3.45 (m, 1H), 3.24 (m, 4H), 3.12 (s, 3H), 2.4 (s, 3H). Separation by chiral HPLC provides enantiomers II-256a-b.

Example 399

Preparation of Compound Nos. II-257 and II-257a-b

A mixture of 2,8-dimethyl-5-((2-(pyridin-3-yl)oxiran-2-yl)methyl)-2,3,4,5-tetrahydro-1H-pyrido[4,3-b]indole (100 mg, 0.3 mmol) in 20% aq. TFA (2 mL) was stirred at RT overnight. The reaction mixture was neutralized with saturated sodium bicarbonate solution and extracted with EtOAc (2×30 mL) to remove the impurities. The aqueous layer was lyophilized to obtain the crude product that was purified by reverse phase HPLC to obtain 5 mg of 3-(2,8-dimethyl-3,4-dihydro-1H-pyrido[4,3-b]indol-5(2H)-yl)-2-(pyridin-3-yl) propane-1,2-diol as the TFA salt. $^1$H NMR (CD$_3$OD, TFA) δ (ppm): 8.75 (s, 1H), 8.6 (m, 2H), 7.83 (m, 1H), 7.25 (s, 1H), 6.9 (d, 1H), 6.8 (d, 1H), 4.62 (d, 1H), 4.45 (dd, 2H), 4.3 (t, 1H), 4.05 (t, 1H), 3.8 (m, 2H), 3.5 (m, 3H), 3.1 (s, 3H), 2.3 (s, 3H). Separation by chiral HPLC provides enantiomers II-257a-b.

Example 400

Preparation of Compound Nos. II-258 and II-258a-b 3-(2,8-Dimethyl-3,4-dihydro-1H-pyrido[4,3-b]indol-5 (2H)-yl)-2-(pyridin-4-yl)propanoic acid (20 mg, 0.057 mmol) was charged in pyridine (0.5 mL) under nitrogen. DMAP (9.73 mg, 0.08 mmol) and (Boc)₂O (14 mg, 0.069 mmol) were added into it. The reaction mixture was stirred at 60° C. for 30 min and allowed to come to RT. Tert-butanol (84.81 mg, 1.146 mmol) was added dropwise and the reaction mixture was stirred at RT for 1 h. 1M citric acid (5 mL) was added and reaction mixture was then washed with DCM (5 mL). The organic layer was concentrated and the crude product was purified by reverse phase HPLC to obtain tert-butyl 3-(2,8-dimethyl-3,4-dihydro-1H-pyrido[4,3-b]indol-5(2H)-yl)-2-(pyridin-4-yl)propanoate (15.4 mg, TFA salt). $^1$H NMR (CD₃OD, TFA salt) δ (ppm): 8.49 (d, 2H), 7.53 (d, 2H), 7.3 (t, 1H), 7.24 (s, 1H), 7.05 (m, 1H), 5.5 (m, 1H), 4.6 (t, 1H), 4.24 (t, 1H), 3.8 (m, 3H), 3.3 (m, 2H), 3.13 (d, 2H), 2.89 (m, 1H), 2.77 (m, 1H), 2.4 (s, 3H), 1.39 s (9H). Separation by chiral HPLC provides enantiomers II-258a-b.

Example 401

Preparation of Compound Nos. II-259 and II-259a-b 2,8-Dimethyl-5-((2-(pyridin-4-yl)oxiran-2-yl)methyl)-2,3,4,5-tetrahydro-1H-pyrido[4,3-b]indole (100 mg, 0.3 mmol) was added to 2M dimethyl amine solution in THF (5 mL) and the reaction mixture was allowed to stir at 60° C. overnight. The progress of reaction was monitored by LCMS. The solvent was removed under reduced pressure to obtain a crude oily product that was purified by reverse phase HPLC to afford 5 mg of 1-(2,8-dimethyl-3,4-dihydro-1H-pyrido[4,3-b]indol-5(2H)-yl)-3-(dimethylamino)-2-(pyridin-4-yl)propan-2-ol as the TFA salt. $^1$H NMR (CD₃OD, TFA salt) δ (ppm): 8.58 (d, 2H), 7.81 (m, 2H), 7.18 (d, 1H), 7.05 (m, 1H), 6.91 (m, 1H), 4.63 (m, 1H), 4.51 (s, 2H), 4.27 (d, 1H), 4.18 (m, 2H), 3.58 (m, 2H), 3.48 (m, 1H), 3.1 (s, 6H), 2.89 (m, 1H), 2.8 (s, 3H), 2.35 (s, 3H). Separation by chiral HPLC provides enantiomers II-259a-b.

Example 402

Preparation of Compound Nos. II-260 and II-260a-b

Methanesulfonic acid 2-(2,8-dimethyl-1,2,3,4-tetrahydro-pyrido[4,3-b]indol-5-yl)-1-pyridin-4-yl-ethylester (1.0 g, 3.5 mmol) was dissolved in 70% cyclopropylamine in water (50 mL) and heated at 90° C. for 18 h. The reaction mixture was concentrated to obtain the crude product that was purified by reverse phase chromatography to obtain 300 mg of cyclopropyl-[2-(2,8-dimethyl-1,2,3,4-tetrahydro-pyrido[4,3-b]indol-5-yl)-1-pyridin-4-yl-ethyl]-amine. $^1$H NMR (CDCl₃, Free base) δ (ppm): 8.52 (d, 2H), 7.18 (s, 1H), 7.14 (d, 1H), 7.13 (d, 2H), 6.99 (d, 1H), 4.22 (m, 2H), 3.98 (dd, 1H), 3.76 (d, 1H), 3.70 (d, 1H), 2.85 (m, 1H), 2.74 (m, 2H), 2.55 (s, 3H), 2.44 (s, 3H), 2.36 (m, 2H), 0.33 (m, 2H), 0.23 (m, 2H). Separation by chiral HPLC provided enantiomers II-260a-b.

Example 403

Preparation of Compound Nos. II-261 and II-261a-d

Methanesulfonicacid2-(9-methyl-1,2,3,4,5,10c-hexahydro-3a,6-diaza-cyclopenta[c] fluoren-6-yl)-1-pyrazin-2-yl-ethyl ester (280 mg, 0.65 mmol) was dissolved in 3 mL DMF, sodium azide (64 mg, 0.98 mmol) was added and heated at 90° C. for 1 h. The reaction mixture was monitored by LCMS. After consumption of starting material, the reaction mixture was cooled to RT, diluted with water (3 mL) and concentrated to obtain the crude product, which was purified by reverse phase chromatography to obtain 60 mg of 6-(2-azido-2-pyrazin-2-yl-ethyl)-9-methyl-2,3,4,5,6,10c-hexahydro-1H-3a,6-diaza-cyclopenta[c]fluorene. $^1$H NMR (CDCl₃, freebase) δ (ppm): 8.65 (d, 1H), 8.60 (s, 1H), 8.50 (s, 1H), 7.8 (d, 1H), 7.22 (d, 1H), 7.09 (t, 1H), 5.1 (m, 1H), 4.8 (m, 1H), 4.6 (dd, 1H), 4.3 (m, 1H), 3.45 (m, 3H), 2.97 (m, 2H), 2.84 (m, 2H), 2.6 (m, 1H), 2.45 (d, 3H), 2.2 (m, 1H), 1.9 m (1'H). Separation by chiral HPLC provided enantiomers II-261a-b.

Example 404

Preparation of Compound Nos. II-262 and II-262a-b 3-(2,8-dimethyl-3,4-dihydro-1H-pyrido[4,3-b]indol-5(2H)-yl)-2-(pyridin-4-yl)propanenitrile (80 mg, 0.24 mmol) in conc. HCl (2 mL) was heated at 80° C. for 1 h. The reaction mixture was concentrated to obtain a residue that was purified by reverse phase chromatography to obtain 5.3 mg of 3-(2,8-dimethyl-3,4-dihydro-1H-pyrido[4,3-b]indol-5(2H)-yl)-2-(pyridin-4-yl)propanoic acid as the free base. $^1$H NMR (CD₃OD, freebase) δ (ppm): 8.1 (d, 2H), 7.3 (d, 1H), 7.13 (s, 1H), 6.98 (d, 1H), 6.8 (d, 2H), 4.09 (s, 2H), 3.6 (dd, 1H), 3.4 (m, 3H), 2.9 (m, 2H), 2.8 (s, 3H), 2.39 (s, 3H), 2.32 (m, 1H). Chiral HPLC provides enantiomers II-262a and II-262b.

Example 405

Preparation of Compound Nos. II-263 and II-263a-b

To a solution of tert-butanol (4 mL) containing crushed KOH (20.36 mg, 0.363 mmol) was added 3-(2,8-dimethyl-1,2,3,4-tetrahydro-pyrido[4,3-b]indol-5-yl)-2-pyridine-4-yl-propionitrile (40 mg, 0.121 mmol) and the resultant reaction mixture was stirred at 80° C. for 90 min. The progress of the reaction was monitored by TLC and LCMS. After completion of the reaction, the tert-butanol was evaporated under vacuum and resultant reaction mixture was purified by preparative HPLC to obtain the desired compound (15 mg). $^1$H NMR (CDCl₃, freebase): 8.32 (d, 2H), 7.25 (d, 2H), 7.15 (d, 1H), 7.01 (d, 1H), 6.63 (d, 1H), 4.8 (d, 1H), 3.77 (m, 2H), 3.39 (t, 2H), 2.8 (m, 1H), 2.7 (m, 1H), 2.5 (m, 1H), 2.47 (s, 3H), 2.45 (s, 3H), 2.3 (m, 1H). Chiral HPLC provides enantiomers II-263a and II-263b.

Example 406

Preparation of Compound Nos. II-264 and II-264a-b 2,8-Dimethyl-5-((2-(pyridin-3-yl)oxiran-2-yl)methyl)-2,3,4,5-tetrahydro-1H-pyrido[4,3-b]indole (100 mg, 0.3 mmol) was dissolved in MeOH (2 mL) and aq. ammonia (2 mL) and the reaction mixture was allowed to stir at RT for 24 h. The progress of reaction was monitored by LCMS. The volatiles were removed under reduced pressure to obtain a crude oily product that was purified by reverse phase HPLC to afford 7 mg of 1-amino-3-(2,8-dimethyl-3,4-dihydro-1H-pyrido[4,3-b]indol-5(2H)-yl)-2-(pyridin-3-yl)propan-2-ol as TFA salt. $^1$H NMR (CD₃OD, TFA salt) δ (ppm): 8.65 (m, 2H), 8.43 (dd, 1H), 7.75 (m, 1H), 7.18 (d, 1H), 6.88 (m, 2H), 4.67 (d, 1H), 4.55 (m, 2H), 4.29 (t, 1H), 3.90 (m, 2H), 3.69 (m, 1H), 3.5 (m, 2H), 3.1 (m, 1H), 3.11 (s, 3H), 2.34 (s, 3H). Separation by chiral HPLC provides enantiomers II-264a-b.

Example 407

Preparation of Compound Nos. II-265 and II-265a-b 2,8-Dimethyl-5-((2-(pyridin-3-yl)oxiran-2-yl)methyl)-2,3,4,5-tetrahydro-1H-pyrido[4,3-b]indole (200 mg, 0.6 mmol) was added to 2M dimethylamine solution in THF (5 mL) and the reaction mixture was allowed to stir at 40° C. overnight. The progress of reaction was monitored by LCMS. The solvent was removed under reduced pressure to obtain a crude oily product that was purified by reverse phase HPLC to afford 50 mg of 1-(2,8-dimethyl-3,4-dihydro-1H-pyrido[4,3-b]indol-5(2H)-yl)-3-(dimethylamino)-2-(pyridin-3-yl)propan-2-ol as the TFA salt. $^1$H NMR (CDCl$_3$, Free base) δ (ppm): 8.74 (s, 1H), 8.50 (d, 1H), 7.79 (d, 1H), 7.25 (dd, 1H), 7.16 (s, 1H), 7.1 (d, 1H), 6.97 (d, 1H), 4.08 (m, 2H), 3.83 (dd, 2H), 2.98 (m, 4H), 2.74 (d, 2H), 2.70 (s, 3H), 2.42 (s, 3H), 1.98 (s, 6H). Separation by chiral HPLC provided enantiomers II-265a-b.

Example 408

Compounds III-1, III-53 and III-223-224 were synthesized as described in PCT publication WO2009/055828. Compounds III-2-3 were synthesized as described in PCT publication WO2009/120720. Compounds III-4-9 were synthesized as described in PCT publication WO2009/120717. Compounds III-10-46, III-209-220 and III-320-352 were synthesized as described in PCT publication WO2010/051503. Compounds III-47-51 were synthesized as described in PCT publication WO2010/127177. Compounds III-52 and III-225-253 were synthesized as described in PCT publication WO2010/019417. Compounds III-54-58, III-353-355 and III-357 were synthesized as described in PCT publication WO2011/038163. Compounds III-59-61, III-356 and III-358-361 were synthesized as described in PCT publication WO2011/038161. Compounds III-62-98, III-187-197 and III-256-258 were synthesized as described in PCT publication WO2011/038162. Compounds III-99-138, III-198-208, III-221 and III-289-319 were synthesized as described in PCT publication WO2011/038164.

Example 409

Compounds W-2, IV-4-7 and IV-10 were synthesized as described in PCT publication WO2011/038161. Compounds IV-1, IV-3, IV-9, IV-11-92, IV-94-208 and IV-211-244 can be synthesized using similar conditions to those described in both Examples 410-412 below, and in PCT publication WO2011/038161.

Example 410

Preparation of Compound Nos. IV-8 and IV-8a-b

To a solution of 10-methyl-1,2,3,4,5,6,7,11c-octahydro-4a,7,8-triaza-benzo[c]fluorene (150 mg, 0.622 mmol) in DMF (2 mL) were added sodium hydride (75 mg, 1.86 mmol) and a solution of toluene-4-sulfonic acid 2-(6-methyl-pyridin-3-yl)-ethyl ester (544 mg, 1.86 mmol) in DMF (2 mL) at 0° C. The reaction mixture was stirred at RT for 1 h. The progress of reaction was monitored by TLC and LCMS. The reaction mixture was poured into ice-cold water and extracted with EtOAc (2×50 mL). The combined organic layer was washed with water (5×25 mL), dried over anhydrous sodium sulfate and concentrated under reduced pressure. The residue was purified by reverse phase chromatography to yield compound 8 (140 mg). This product was further purified by chiral preparative HPLC to give compounds 8a and 8b. Compound 8a: $^1$HNMR (CDCl$_3$, freebase) δ (ppm): 8.21 (s, 1H), 8.07 (s, 1H), 7.6 (s, 1H), 7.21 (d, 1H), 7.0 (d, 1H), 4.3 (m, 2H), 3.28 (d, 1H), 3.08 (m, 1H), 3.0 (m, 4H), 2.54 (m, 1H), 2.54 (s, 3H), 2.5 (m, 1H), 2.4 (m, 1H), 2.4 (s, 3H), 2.3 (d, 1H), 1.9 (m, 1H), 1.72 (m, 2H), 1.5 (q, 2H). Compound 8b: $^1$HNMR (CDCl$_3$, freebase) δ (ppm): 8.21 (s, 1H), 8.07 (s, 1H), 7.6 (s, 1H), 7.21 (d, 1H), 7.0 (d, 1H), 4.3 (m, 2H), 3.28 (d, 1H), 3.08 (m, 1H), 3.0 (m, 4H), 2.54 (m, 1H), 2.54 (s, 3H), 2.5 (m, 1H), 2.4 (m, 1H), 2.4 (s, 3H), 2.3 (d, 1H), 1.9 (m, 1H), 1.72 (m, 2H), 1.5 (q, 2H).

Example 411

Preparation of Compound Nos. IV-209 and IV-209a-d

9-Methyl-2,3,4,5,6,10c-hexahydro-1H-3a,6,7-triaza-cyclopenta[c]fluorene (600 mg, 2.643 mmol) was dissolved in DMF (18 mL), and cooled to 0° C. Potassium tert-butoxide (444 mg, 3.964 mmol) was added and stirred for 5 min. 4-Oxiranyl-pyridine (639 mg, 5.286 mmol) in DMF (3 mL) was added dropwise into the reaction mixture and the mixture was stirred at RT for 12 h. The reaction was monitored by TLC and LCMS. After consumption of starting material, the reaction mixture was quenched with ice cold water (100 mL) and extracted with EtOAc (2×100 mL). The combined organic layer was washed with water (4×70 mL), dried over anhydrous sodium sulfate and concentrated to obtain the crude product, which was purified by reverse phase chromatography to obtain 400 mg of 2-(9-Methyl-1,2,3,4,5,10c-hexahydro-3a,6,7-triaza-cyclopenta[c]fluoren-6-yl)-1-pyridin-4-yl-ethanol. $^1$H NMR (CD$_3$OD, HCl salt) δ (ppm): 8.8 (d, 2H), 8.2 (d, 2H), 8.1 (s, 1H), 7.9 (s, 1H), 5.38 (m, 1H), 5.09 (t, 1H), 4.68 (dd, 2H), 4.4 (m, 1H), 3.75 (m, 4H), 3.43 (m, 2H), 2.7 (m, 2H), 2.46 (s, 3H), 2.2 (m, 3H). Separation by chiral HPLC provided diastereomers IV-209a-d.

Example 412

Preparation of Compound Nos. IV-210 and IV-210a-d

Chloroaza carboline (500 mg, 2.02 mmol) was dissolved in DMF (8 mL), sodium hydride (404 mg, 10.12 mmol) was added at 0-10° C. and stirred at the same temperature for 15 min. 3-(2-Methyloxiran-2-yl)pyridine (546 g, 4.04 mmol) was added dropwise into the reaction mixture and the mixture was stirred at RT for 16 h. The reaction was monitored by TLC and LCMS. After consumption of starting material, the reaction mixture was quenched with ice cold water (100 mL) and extract with EtOAc (200 mL). The organic layer was washed with water (5×50 mL), dried over anhydrous sodium sulfate and concentrated under reduced pressure to obtain the crude product, which was purified by crystallization using Diethyl ether to obtain 200 mg of product. $^1$H NMR (CD$_3$OD, HCl salt): 8.8 (s, 1H), 8.6 (d, 2H), 7.88 (s, 2H), 7.84 (d, 1H), 4.99 (m, 2H), 4.4 (d, 1H), 3.78 (m, 2H), 3.4 (m, 2H), 3.4 (m, 2H), 2.7 (m, 1H), 2.2 (m, 3H), 1.83 (s, 3H). Separation by chiral HPLC provided diastereomers IV-210a-d.

Example 413

Compound Nos. V-4 to V-13, V-16 to V-17 and V-19 to V-20 can be synthesized using similar conditions to those described in Examples 414-422 below.

Example 414

Preparation of Compound Nos. V-1 and V-1a-b

To a solution of 2-(1,2,3,4-tetrahydro-2,8-dimethylpyrido[4,3-b]indol-5-yl)-1-(pyridin-4-yl)ethyl methanesulfonate (900 mg, 2.18 mmol) in DMF (10 mL) was added sodium azide (212.5 mg, 3.2 mmol) and the reaction mixture was stirred at 100° C. for 1 h. The reaction mixture was diluted with water and extracted with EtOAc. The organic layer was washed with water, dried over anhydrous sodium sulfate and concentrated under reduced pressure to yield 5-(2-azido-2-(pyridin-4-yl)ethyl)-2,3,4,5-tetrahydro-2,8-dimethyl-1H-pyrido[4,3-b]indole (650 mg). The resulting racemate was purified and resolved by chiral preparative HPLC. $^1$H NMR (CD$_3$OD, TFA salt) δ (ppm): 8.8 (d, 2H), 8.0 (d, 2H), 7.31 (d, 1H), 7.3 (s, 1H), 7.04 (d, 1H), 5.45 (m, 1H), 4.7 (d, 1H), 4.59 (t, 1H), 4.4 (m, 2H), 3.9 (d, 1H), 3.6 (m, 1H), 3.4 (m, 1H), 3.2 (m, 1H), 3.1 (s, 3H), 2.4 (s, 3H).

Example 415

Preparation of Compound Nos. V-2 and V-2a-b

To a solution of 2-(2,8-dimethyl-6-aza-3,4-dihydro-1H-pyrido[4,3-b]indol-5(2H)-yl)-1-(pyridin-4-yl)ethyl methanesulfonate (300 mg, 0.724 mmol) in DMF (4 mL) was added sodium azide (70.65 mg, 1.08 mmol) and the reaction mixture was stirred at 100° C. for 1 h. The progress of reaction was monitored by NMR. The reaction mixture was diluted with water and extracted with EtOAc. The organic layer was thoroughly washed with water, dried over anhydrous sodium sulfate and concentrated under reduced pressure to yield 9-(2-azido-2-(pyridin-4-yl)ethyl)-3,6-dimethyl-6,7,8,9-tetrahydro-5H-pyrrolo[2,3-b:4,5-c']dipyridine (160 mg). $^1$H NMR (CDCl$_3$, freebase) δ (ppm): 8.6 (d, 2H), 8.07 (s, 1H), 7.55 (s, 1H), 7.27 (d, 2H), 5.23 (m 1H), 4.37 (dd, 1H), 4.19 (m, 1H), 3.62 (dd, 2H), 2.88 (m, 2H), 2.82 m, 2H), 2.56 (s, 3H), 2.42 (s, 3H). Separation by chiral HPLC provided enantiomers V-2a-b.

Example 416

Preparation of Compound Nos. V-3 and V-3a-b 5-(2-Chloro-2-(pyridin-3-yl)propyl)-2,8-dimethyl-2,3,4,5-tetrahydro-1H-pyrido[4,3-b]indole (crude) (700 mg) was dissolved in DMF (4 mL). Sodium azide (975 mg, 15 mmol) was added and reaction mixture was stirred at 80° C. for 1 h. The reaction mixture was diluted with water, basified with aqueous NaHCO$_3$ solution and was extracted with EtOAc (200 mL). The organic layer was washed with water (6×50 mL), dried over anhydrous sodium sulfate and evaporated in vacuo to obtain the crude product that was purified by reverse phase HPLC to obtain 1 mg of 5-(2-azido-2-(pyridin-3-yl)propyl)-2,8-dimethyl-2,3,4,5-tetrahydro-1H-pyrido[4,3-b]indole as the TFA salt. $^1$H NMR (CD$_3$OD, TFA salt) δ (ppm): 8.56 (m, 2H), 8.11 (dd, 1H), 7.6 (t, 1H), 7.2 (s, 1H), 6.85 (m, 2H), 4.67 (d, 1H), 4.47 (d, 1H), 4.39 (s, 2H), 3.84 (m, 1H), 3.48 (m, 1H), 3.34 (m, 1H), 3.12 (s, 3H), 3.12 (m, 1H), 2.36 (s, 3H), 2.03 (s, 3H). Separation by chiral HPLC provides enantiomers V-3a-b.

Example 417

Preparation of Compound Nos. V-14 and V-14a-b

To a solution of 1-(2,8-dimethyl-3,4-dihydro-1H-pyrido[4,3-b]indol-5(2H)-yl)-2-(pyridin-3-yl)propan-2-ol (200 mg, 0.597 mmol) in DMF (5 mL) was added potassium carbonate (412 mg, 2.98 mmol). After stirring for 5 min at RT, ethyl bromoacetate (200 mg, 1.19 mmol) was added into the reaction mixture, which was stirred at RT for 2 h. The progress of reaction was monitored by LCMS. The reaction was quenched with water and extracted with EtOAc. The aqueous layer was concentrated and residue was purified by reverse HPLC to yield 2-((1-(2,8-dimethyl-3,4-dihydro-1H-pyrido[4,3-b]indol-5(2H)-yl)-2-(pyridin-3-yl)propan-2-yl)oxy) acetic acid (80 mg). The resulting racemate was purified and resolved by chiral preparative HPLC. $^1$H NMR (CD$_3$OD, freebase) δ (ppm): 8.5 (d, 1H), 8.36 (s, 1H), 7.8 (dd, 1H), 7.31 (m, 1H), 7.19 (s, 1H), 7.1 (d, 1H), 6.88 (d, 1H), 4.86 (m, 1H), 4.58 (s, 1H), 4.32 (d, 1H), 4.25 (m, 2H), 3.94 (m, 2H), 3.8 (m, 1H), 3.35 (s, 3H), 3.2 (m, 1H), 3.0 (m, 1H), 2.36 (s, 3H), 1.69 (s, 3H).

Example 418

Preparation of Compound Nos. V-15 and V-15a-d

Ethyl 2-(2-(10-methyl-2,3,5,6-tetrahydro-1H-indolizino[7,8-b]indol-7(11cH)-yl)-1-(pyridin-4-yl)ethoxy)acetate (170 mg, 0.392 mmol) in 2N LiOH solution (5 mL) was stirred at RT for 3 h. The desired product was detected by LCMS. The reaction mixture was concentrated and the crude product was purified by reverse phase chromatography to yield 2-(2-(10-methyl-2,3,5,6-tetrahydro-1H-indolizino[7,8-b]indol-7(11cH)-yl)-1-(pyridin-4-yl)ethoxy)acetic acid (13 mg). $^1$H NMR (CD$_3$OD, freebase) δ (ppm): 8.45 (d, 2H), 7.42 (d, 2H), 7.22 (s, 1H), 7.2 (d, 1H), 7.0 (d, 1H), 5.09 (m, 2H), 4.6 (s, 1H), 4.45 (dd, 1H), 4.29 (m, 2H), 4.19 (m, 1H), 3.96 (m, 2H), 3.81 (d, 1H), 3.7 (t, 1H), 3.2 (d, 1H), 3.1 (m, 1H), 3.82 (m, 1H), 2.4 (s, 3H), 2.34 (m, 1H), 2.09 (m, 1H). Separation by chiral HPLC provides diastereomers V-15a-d.

Example 419

Preparation of Compound Nos. V-18 and V-18a-d 2-(10-Methyl-2,3,5,6-tetrahydro-1H-indolizino[7,8-b]indol-7(11cH)-yl)-1-(pyridin-4-yl)ethanol (350 mg, 1 mmol), succinic acid (118 mg, 1 mmol) and dimethylaminopyridine (122 mg, 1 mmol) in DCM (20 mL) were stirred at RT. Dicyclohexylcarbodiimide (206 mg, 1.6 mmol) in DCM (20 mL) was added dropwise and the reaction mixture was stirred at RT for 2 h. The reaction mixture was concentrated to obtain the crude product that was purified by reverse phase HPLC to yield 4-(2-(10-methyl-2,3,5,6-tetrahydro-1H-indolizino[7,8-b]indol-7(11cH)-yl)-1-(pyridin-4-yl)ethoxy)-4-oxobutanoic acid (96 mg). $^1$H NMR (CD$_3$OD, freebase) δ (ppm): 8.46 (d, 2H), 7.33 (d, 2H), 7.27 (d, 1H), 7.23 (s, 1H), 7.01 (d, 1H), 6.07 (t, 1H), 4.8 (t, 2H), 4.5 (m, 2H), 3.55 (m, 2H), 3.45 (m, 1H), 3.0 (q, 2H), 2.7 (m, 1H), 2.54 (m, 2H), 2.39 (s, 3H), 2.37 (m, 1H), 2.1 (m, 4H). Separation by chiral HPLC provided diastereomers V-18a-d.

Example 420

Preparation of Compound Nos. V-21 and V-21a-b

To a solution of the mesylate compound (2 g, 4.46 mmol) in DMF (25 mL) was added sodium azide (435 mg, 6.69 mmol) and reaction mixture was stirred at 100° C. for 1 h. The progress of reaction was monitored by NMR. The reaction mixture was diluted with water (100 mL) and extracted with EtOAc (2×150 mL). The organic layer was washed with water, dried over anhydrous sodium sulfate and concentrated under reduced pressure to yield 6-(2-azido-2-(2,4-difluorophenyl)ethyl)-3,9-dimethyl-1,2,3,4,5,6-hexahydroazepino[4,5-b]indole (1.6 g). $^1$H NMR (CDCl$_3$, freebase) δ (ppm):

7.4 (q, 1H), 7.2 (s, 1H), 7.18 (d, 1H), 7.01 (d, 1H), 6.99 (d, 1H), 6.92 (d, 1H), 5.13 (dd, 1H), 4.26 (dd, 1H), 4.2 (dd, 1H), 2.9 (d, 1H), 2.93 (m, 2H), 2.8 (m, 1H), 2.83 m (4H), 2.5 (s, 3H), 2.46 (s, 3H). Separation by chiral HPLC provides enantiomers V-21a-b.

Example 421

Preparation of Compound Nos. V-22 and V-22a-b

Methanesulfonic acid-1-(6-carbamoyl-pyridin-3-yl)-2-(2,8-dimethyl-1,2,3,4-tetrahydro-pyrido[4,3-b]indol-5-yl)-ethyl ester (300 mg, 0.678 mmol) was dissolved in 5 mL DMF, and sodium azide (88 mg, 1.357 mmol) was added, and the mixture heated at 100° C. for 1 h. The reaction mixture was monitored by LCMS. After completion of reaction, the reaction mixture was cooled to RT and diluted with water (15 mL) and extracted with EtOAc (3×30 mL). The combined organic layer was washed with water (4×40 mL), dried over anhydrous sodium sulfate and concentrated to obtain the crude product that was purified by reverse phase chromatography to yield 5-[1-azido-2-(2,8-dimethyl-1,2,3,4-tetrahydro-pyrido[4,3-b]indol-5-yl)-ethyl]-pyridine-2-carboxylic acid amide (135 mg). $^1$H NMR (CD$_3$OD, TFA salt) δ (ppm): 8.6 (dd, 1H), 8.1 (t, 1H), 7.9 (t, 1H), 7.33 (dd, 1H), 7.26 (s, 1H), 7.06 (t, 1H), 5.3 (t, 1H), 4.7 (dd, 1H), 4.42 (dd, 1H), 4.4 (dd, 2H), 4.3 (m, 1H), 3.8 (m, 1H), 3.6 (m, 1H), 3.34 (dd, 1H), 3.1 (d, 3H), 2.4 (s, 3H). Separation by chiral HPLC provides enantiomers V-22a-b.

Example 422

Preparation of Compound Nos. V-23 and V-23a-d

A solution of 1-(4-fluorophenyl)-2-(10-methyl-2,3,5,6-tetrahydro-1H-indolizino[7,8-b]indol-7(11cH)-yl)ethyl methanesulfonate (400 mg, 0.9 mmol) and sodium azide (88 mg, 1.3 mmol) in dimethylformamide (10 mL) was stirred at RT for 18 h. The reaction mixture was diluted with ice cooled water (100 mL) and extracted with EtOAc (100 mL). The organic layer was washed with water (5×50 mL), dried over anhydrous sodium sulfate and concentrated to obtain the crude product that was purified by reverse phase HPLC to yield 7-(2-azido-2-(4-fluorophenyl)ethyl)-10-methyl-2,3,5,6,7,11c-hexahydro-1H-indolizino[7,8-b]indole (25 mg). $^1$H NMR (CD$_3$OD, freebase) δ (ppm): 7.32 (m, 3H), 7.26 (s, 1H), 7.13 (m, 2H), 7.09 (d, 1H), 5.09 (t, 1H), 4.8 (m, 1H), 4.32 (m, 2H), 3.44 (m, 2H), 3.3 (m, 1H), 3.1 (m, 1H), 3.0 (d, 1H), 2.8 (m, 1H), 2.6 (m, 1H), 2.4 (s, 3H), 2.18 (m, 2H), 2.0 (m, 1H). Separation by chiral HPLC provides diastereomers V-23a-d.

Example 423

Compounds II-266 to II-269 and II-271 to II-299 can be synthesized in an analogous fashion to other compounds described herein and by reference to the PCT publications listed in the General Methods above.

Example B1: Determination of the Ability of Compounds of the Invention to Bind an Adrenergic Receptor Adrenergic $\alpha_{2B}$ To evaluate in radioligand binding assays the activity of compounds of the invention, human recombinant adrenergic $\alpha_{2B}$ receptor expressed in Chinese hamster ovary (CHO) K1 cells (Uhlen, S. et al, Eur. J. Pharmacol. 343(1):93, 1998) in a modified Tris-HCl buffer (50 mM Tris-HCl, pH 7.4, 12.5 mM MgCl$_2$, 1 mM EDTA, 0.2% BSA) was used. Compounds of the invention were incubated with 2.5 nM [3H]Rauwolscine for 60 min at 25° C. Non-specific binding was estimated in the presence of 10 µM Prazosin. Receptor proteins were filtered and washed, the filters were then counted to determine [3H]Rauwolscine specifically bound. Compounds were screened at 1 µM or lower, using 1% DMSO as vehicle. Compounds of the invention were tested in this biochemical assay and percent inhibition of specific binding was determined. Biochemical assay results are presented as the percent inhibition of specific binding in Table B1.

Adrenergic $\alpha_{2A}$

To evaluate in radioligand binding assays the activity of compounds of the invention, human recombinant adrenergic $\alpha_{2A}$ receptor expressed in insect Sf9 cells (Uhlen, S. et al, J. Pharmacol. Exp. Ther. 271:1558, 1994) in a modified Tris-HCl buffer (50 mM Tris-HCl, pH 7.4, 12.5 mM MgCl$_2$, 2 mM EDTA) was used. Compounds of invention were incubated with 1 nM [$^3$H]MK-912 for 60 min at 25° C. MK912 is (2S-trans)-1,3,4,5',6,6',7,12b-octahydro-1',3'-dimethyl-spiro [2H-benzofuro[2,3-a]quinolizine-2,4'(1'H)-pyrimidin]-2' (3'H)-one hydrochloride. Non-specific binding was estimated in the presence of 10 µM WB-4101 (2-(2,6-Dimethoxyphenoxyethyl)aminomethyl-1,4-benzodioxane hydrochloride). Receptor proteins were filtered and washed, the filters were then counted to determine [$^3$H]MK-912 specifically bound. Compounds were screened at 1 µM or lower, using 1% DMSO as vehicle. Compounds of the invention were tested in this biochemical assay and percent inhibition of specific binding was determined. Biochemical assay results are presented as the percent inhibition of specific binding in Table B1.

Adrenergic $\alpha_{1B}$

To evaluate in radioligand binding assays the activity of compounds of the invention, rat adrenergic $\alpha_{1B}$ receptor obtained from Wistar Rat liver (Garcia-S'ainz, J. et al, Biochem. Biophys. Res. Commun. 186:760, 1992; Michel, A. et al, Br. J. Pharmacol. 98:883, 1989) in a modified Tris-HCl buffer (50 mM Tris-HCl buffer, pH 7.4, 0.5 mM EDTA) was used. Compounds of the invention were incubated with 0.25 nM [$^3$H]Prazosin for 60 min at 25° C. Non-specific binding was estimated in the presence of 10 µM phentolamine. Receptor proteins were filtered and washed, the filters were then counted to determine [$^3$H]Prazosin specifically bound. Compounds were screened at 1 µM or lower, using 1% DMSO as vehicle. Compounds of the invention were tested in this biochemical assay and percent inhibition of specific binding was determined. Biochemical assay results are presented as the percent inhibition of specific binding in Table B1.

Adrenergic $\alpha_{1D}$

To evaluate in radioligand binding assays the activity of compounds of the invention, human recombinant adrenergic $\alpha_{1D}$ receptor expressed in human embryonic kidney (HEK-293) cells (Kenny, B. et al, Br. J. Pharmacol. 115(6):981, 1995) in a 50 mM Tris-HCl buffer, pH 7.4, was used. Compounds were incubated with 0.6 nM [3H]Prazosin for 60 min at 25° C. Non-specific binding was estimated in the presence of 10 µM phentolamine. Receptor proteins were filtered and washed, the filters were then counted to determine [3H]Prazosin specifically bound. Compounds were screened at 1 µM or lower, using 1% DMSO as vehicle. Biochemical assay results are presented as the percent inhibition of specific binding in Table B1.

TABLE B1

Percentage inhibition of ligand binding to aminergic G protein-coupled receptors by compounds of the invention:

| Compound | Adrenergic (0.1 μM)* | | | | Adrenergic (0.03 μM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 1 | 32 | 16 | 6 | 74 | — | — | — | — |
| 2 | 27, 28 | 13 | 4, 19 | 95 | — | — | — | 75 |
| 3 | 51, 54 | 12 | 12, 37 | 100, 103 | 24 | — | 4 | 99 |
| 3a | 12, 44 | — | 16 | 62 | 18 | — | — | 26, 30 |
| 3b | 50, 55, 57, 61 | 18 | 21, 22, 23, 25 | — | 27, 32, 34 | — | 1 | 100, 101, 102, 112 |
| 4 | 51, 60 | 12 | 12, 41 | 101 | — | — | — | 106 |
| 4a | 52, 57 | — | 19, 24 | 104 | 25 | — | 5 | 99, 103 |
| 4b | 58 | — | 7 | — | — | — | — | 46 |
| 5 | 14, 21 | 4 | 13 | 96 | — | — | — | 100 |
| 5a | 18 | — | 0 | 57 | — | — | — | 29, 38 |
| 5b | 23, 30, 33 | 1 | 18, 21, 22 | 82, 100, 107 | 10, 11, 15 | — | 4, 6, 15 | 81, 86, 90, 100 |
| 6 | 8 | — | 2 | — | — | — | — | 62 |
| 7 | 35 | — | 16 | — | — | — | — | 59 |
| 7a | 28 | — | 1 | — | — | — | — | 59 |
| 7b | 37 | — | 25 | — | — | — | — | 74 |
| 8 | 58 | — | 23 | — | — | — | — | 61 |
| 8a | 39 | — | 15 | — | — | — | — | 22 |
| 8b | 61, 63 | — | 8, 12 | 78 | 24 | — | — | 49 |
| 9 | 5 | — | -4 | — | — | — | — | 36 |
| 9a | 11 | — | 4 | — | — | — | — | 23 |
| 9b | 10 | — | 10 | — | — | — | — | 50 |
| 10a | 30 | — | 8 | — | — | — | — | 34 |
| 10b | 28 | — | 15 | — | — | — | — | 91 |
| 11a | 16 | — | -6 | — | — | — | — | 28 |
| 11b | 18 | — | 13 | — | — | — | — | 64 |
| 12a | 23 | — | 3 | — | — | — | — | 24 |
| 12b | 8 | — | 3 | — | — | — | — | 21 |
| 13 | 83 | — | 18 | — | — | — | — | 92 |
| 13a | 75 | — | -2 | — | — | — | — | 37 |
| 13b | 91 | — | -2, 21 | — | 68 | — | — | 100, 102 |
| 14a | 43, 44 | — | 8, 26 | — | 17 | — | — | 97, 98 |
| 14b | 25 | — | -6 | — | — | — | — | 14 |
| 15 | 93 | — | 19 | — | — | — | — | 93 |
| 15a | 81 | — | 6 | — | — | — | — | 65 |
| 15b | 89, 93 | — | 21, 24 | — | 73 | — | — | 103 |
| 16a | 47 | — | 9 | — | — | — | — | 33 |
| 16b | 16 | — | 2 | — | — | — | — | 2 |
| 17 | 18 | — | 19 | — | — | — | — | 37 |
| 17a | 13 | — | 19 | — | — | — | — | 32 |
| 17b | 16 | — | 9 | — | — | — | — | 20 |
| 18a | 55 | — | 50 | — | — | — | — | 54 |
| 18b | 87 | — | 32 | — | — | — | — | 61 |
| 19a | 75 | — | 21 | — | — | — | — | 75 |
| 19b | 62 | — | 9 | — | — | — | — | 27 |
| 20a | 67 | — | 29 | — | — | — | — | 28 |
| 20b | 94 | — | 28 | — | — | — | — | 36 |
| 21a | 5 | — | -1 | — | — | — | — | -2 |
| 21b | -2 | — | -3 | — | — | — | — | 1 |
| 22a | 19 | — | 16 | — | — | — | — | 22 |
| 22b | 9 | — | 0 | — | — | — | — | 30 |
| 23a | -20 | — | 4 | — | — | — | — | 6 |
| 23b | 4 | — | 1 | — | — | — | — | -3 |
| 24a | 8 | — | 8 | — | — | — | — | 63 |
| 24b | 8 | — | 15 | — | — | — | — | 29 |
| 25a | 4 | — | 15 | — | — | — | — | 54 |
| 25b | 12 | — | 18 | — | — | — | — | 75 |
| 26a | 52, 61 | — | 23, 33 | — | 32 | — | 14 | 101, 107 |
| 26b | 15 | — | 12 | 100 | — | — | — | 75, 88 |
| 26c | 1 | — | 19 | — | — | — | — | 1, 7 |
| 26d | -2 | — | 0 | — | — | — | — | 6, 11 |
| 27a | 59, 64 | — | 2, 11 | 94 | 34 | — | — | 76, 83 |
| 27b | 6, 16 | — | 0, 18 | 48 | — | — | — | 30, 36 |
| 28a | 41 | — | 28 | — | — | — | — | 96 |
| 28b | 20 | — | 24 | — | — | — | — | 37 |
| 29 | 24 | 1 | 10 | 100 | — | — | — | — |
| 29a | 32, 38 | — | 35, 39 | — | 19 | — | 16 | 98, 100 |
| 29b | 14 | — | 10 | — | — | — | — | 46 |
| 30 | 86 | 49 | 63 | 91 | — | — | — | — |
| 30a | 57 | — | 19 | — | — | — | — | 79 |
| 30b | 89, 91 | — | 74, 75 | — | 68 | — | 42 | 100, 102 |

TABLE B1-continued

Percentage inhibition of ligand binding to aminergic G protein-coupled receptors by compounds of the invention:

| Compound | Adrenergic (0.1 μM)* | | | | Adrenergic (0.03 μM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 31a | 25, 28 | — | 19, 27 | — | 16 | — | 11 | 93, 97 |
| 31b | 3 | — | 14 | — | — | — | — | 36 |
| 32 | 12 | 7 | 28 | 86 | — | — | — | — |
| 33a | −2 | 23 | 26 | −3 | — | — | — | — |
| 33b | 0 | 14 | −7 | 2 | — | — | — | — |
| 34 | 30 | 2 | 28 | 38 | — | — | — | — |
| 34a | 11 | 19 | 29 | 20 | — | — | — | — |
| 34b | −2 | 13 | 3 | 1 | — | — | — | — |
| 35a | 9 | 6 | 20 | 62 | — | — | — | — |
| 35b | 5 | −13 | 12 | 47 | — | — | — | — |
| 36a | 14 | — | 8 | — | — | — | — | 33 |
| 36b | 11 | — | 0 | — | — | — | — | −1 |
| 37a | −5 | — | 18 | — | — | — | — | 2 |
| 37b | −10 | — | −20 | — | — | — | — | −3 |
| 37c | 2 | — | 6 | — | — | — | — | 0 |
| 37d | 2 | — | 8 | — | — | — | — | −3 |
| 38 | 20 | — | −1 | — | — | — | — | 56 |
| 38a | 11 | — | 14 | — | — | — | — | 35 |
| 38b | 20 | — | −1 | — | — | — | — | 17 |
| 39 | 25 | — | 1 | — | — | — | — | 89 |
| 39a | 38, 33 | — | 13, 15 | 92 | 9 | — | 5 | 86 |
| 39b | 24 | — | 1 | — | — | — | — | 28 |
| 40a | 2 | — | 7 | — | — | — | — | 27 |
| 40b | −2 | — | 13 | — | — | — | — | 29 |
| 41 | 57 | — | 24 | — | — | — | — | 45 |
| 41a | 43 | — | −9 | — | — | — | — | 14 |
| 41b | 50 | — | 8 | — | — | — | — | 50 |
| 42a | 15 | — | 3 | — | — | — | — | 29 |
| 42b | 19 | — | 12 | — | — | — | — | 34 |
| 43 | 21 | — | −1 | — | — | — | — | 24 |
| 43a | 33 | — | 9 | — | — | — | — | 51 |
| 43b | 46 | — | 13 | — | — | — | — | 27 |
| 44 | −3 | — | −1 | — | — | — | — | 56 |
| 44a | 12 | — | 11 | — | — | — | — | 33 |
| 44b | 18 | — | 1 | — | — | — | — | 75 |
| 45a | 23 | — | −4 | — | — | — | — | 54 |
| 45b | 24 | — | 16 | — | — | — | — | 96 |
| 47a | 58 | — | 10 | — | — | — | — | 40 |
| 47b | 70 | — | 41 | — | — | — | — | 119 |
| 47c | 6 | — | 4 | — | — | — | — | 53 |
| 47d | 5 | — | −3 | — | — | — | — | 30 |
| 48a | 16 | — | 12 | — | — | — | — | 58 |
| 48b | 14 | — | 17 | — | — | — | — | 86 |
| 49a | 4 | — | 1 | — | — | — | — | 18 |
| 49b | 5 | — | 6 | — | — | — | — | 19 |
| 51 | 43 | — | 20 | — | — | — | — | 82 |
| 51a | 8 | — | 11 | — | — | — | — | 21 |
| 51b | 36 | — | 26 | — | — | — | — | 90 |
| 52a | 9 | — | 5 | — | — | — | — | 21 |
| 52b | 73 | — | 29 | — | — | — | — | 93 |
| 53a | 12 | — | 10 | — | — | — | — | 37 |
| 53b | 14 | — | 12 | — | — | — | — | 85 |
| 54a | 39 | — | 30 | — | — | — | — | 105 |
| 54b | 71 | — | 66 | — | — | — | — | 106 |
| 55 | 37 | — | 13 | — | — | — | — | 63 |
| 55a | 28 | — | 11 | — | — | — | — | 14 |
| 55b | 57 | — | 7 | — | — | — | — | 67 |
| 56a | 1 | — | 11 | — | — | — | — | 20 |
| 56b | 6 | — | 17 | — | — | — | — | 28 |
| 57a | 3 | — | 22 | — | — | — | — | 16 |
| 57b | 9 | — | 24 | — | — | — | — | 84 |
| 58 | 21 | — | −1 | — | — | — | — | 26 |
| 58a | 7 | — | 9 | — | — | — | — | 5 |
| 58b | 24 | — | 0 | — | — | — | — | 39 |
| 59a | 11 | — | 18 | — | — | — | — | 15 |
| 59b | 7 | — | 12 | — | — | — | — | 31 |
| 60 | 65 | 35 | 26 | 93 | — | — | — | 66 |
| 61 | 60 | 37 | 30 | 85, 94 | 28 | 14 | — | 65, 80 |
| 62 | 16 | — | 1 | — | — | — | — | 76 |
| 63a | 10 | — | 16 | — | — | — | — | 83 |
| 63b | −5 | — | 3 | — | — | — | — | 41 |
| 64 | 25 | — | 12 | — | — | — | — | 62 |

TABLE B1-continued

Percentage inhibition of ligand binding to aminergic G protein-coupled receptors by compounds of the invention:

| Compound | Adrenergic (0.1 µM)* | | | | Adrenergic (0.03 µM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 65 | −13 | — | −3 | — | — | — | — | 64 |
| 66 | 48 | — | 15 | — | — | — | — | 69 |
| 67 | 12 | — | −7 | — | — | — | — | 17 |
| 68 | 2 | — | 1 | — | — | — | — | 4 |
| 69a | 4 | — | 11 | — | — | — | — | 10 |
| 69b | 8 | — | 7 | — | — | — | — | 19 |
| 70 | 8 | — | 10 | — | — | — | — | 26 |
| 71 | 11 | — | 11 | — | — | — | — | 9 |
| 72 | 6 | — | −2 | — | — | — | — | 12 |
| 73 | 17 | — | 15 | — | — | — | — | 61 |
| 74 | 81 | 57 | 6 | 104 | — | — | — | — |
| 74a | 91, 96 | 61 | 22, 27 | 101 | 81 | 42 | — | 93 |
| 74b | 28 | — | 14 | — | — | — | — | 27 |
| 75a | 61 | — | 11 | — | — | — | — | 77 |
| 75b | 16 | — | 5 | — | — | — | — | 43 |
| 75c | 59 | — | −2 | — | — | — | — | 11 |
| 75d | 26 | — | 49 | — | — | — | — | 102 |
| 76a | 78 | — | 21 | — | — | — | — | 92 |
| 76b | 71 | — | 18 | — | — | — | — | 34 |
| 76c | 33 | — | 5 | — | — | — | — | 35 |
| 76d | 51 | — | 40 | — | — | — | — | 91 |
| 77 | 5, 6 | 10 | −1, 22 | 91 | — | — | — | 84 |
| 78 | 11, 12 | 22 | −7, 18 | 87 | — | — | — | 67 |
| 79 | 34 | — | 19 | — | — | — | — | 77 |
| 80 | 49 | — | 12 | — | — | — | — | 81 |
| 81 | 25 | — | 26 | — | — | — | — | 96 |
| 82 | 16 | — | 5 | — | — | — | — | 79 |
| 83 | 9, 15 | 13 | 21, 29 | 78 | — | — | — | 63 |
| 84 | 69 | 36 | 27 | 84 | — | — | — | — |
| 85 | 26 | 17 | 12 | 60 | −3 | — | — | 40 |
| 86 | 62 | 62 | 27 | 77 | — | — | — | — |
| 87 | 5 | 24 | 14 | 66 | — | — | — | — |
| 88 | 10 | 36 | 2 | 90 | — | — | — | — |
| 89 | 79 | 68 | 23 | 57, 79 | — | — | — | 25 |
| 90 | 57 | 20 | 22 | 91 | — | — | — | — |
| 90a | 74 | — | 71 | — | — | — | — | 97 |
| 90b | 81 | — | 82 | — | — | — | — | 97 |
| 91 | 52, 53, 58 | 25, 30, 32 | 5 | 82, 83, 87 | 25, 28, 32 | 7, 11, 21 | 6 | 53, 56 |
| 92 | 77 | 46 | 30 | 77 | — | — | — | — |
| 93 | 25 | 6 | 21 | 87 | — | — | — | — |
| 93a | 37 | — | 25, 36 | — | 13 | — | 14 | 63, 102 |
| 93b | 1 | — | −5 | — | — | — | — | 26 |
| 94 | 40 | 10 | 11 | 66 | — | — | — | — |
| 95 | 52 | 29 | 9 | 105 | — | — | — | — |
| 96 | 25 | 3 | 29 | 71 | — | — | — | — |
| 97 | 3 | −7 | −12 | 88 | — | — | — | — |
| 98 | 81, 83 | 31, 35 | 26, 32 | 96, 103 | — | — | — | — |
| 99 | 69 | 34 | 29 | 85 | — | — | — | — |
| 100 | 73 | 47 | 20 | 72 | — | — | — | — |
| 101 | 61, 79 | 45, 48 | 14, 15 | 63, 76 | — | — | — | — |
| 102 | 40 | 21 | 21 | 77 | — | — | — | — |
| 103 | 49 | 20 | 19 | 80 | — | — | — | — |
| 105 | 57 | 36 | 14 | 68 | — | — | — | — |
| 106 | 65 | 45 | 6 | 79 | — | — | — | — |
| 107 | 56 | 63 | 10 | 85 | — | — | — | — |
| 108 | 42 | 21 | 20 | 88 | — | — | — | — |
| 109 | 13 | 21 | 25 | 69 | — | — | — | — |
| 110 | 5 | 35 | 27 | 62 | — | — | — | — |
| 111 | 56 | 77 | 0 | 65 | — | — | — | — |
| 112 | 44 | 40 | 26 | 79 | — | — | — | — |
| 113 | 12 | 3 | 29 | 87 | — | — | — | — |
| 114 | 15 | 15 | 21 | 58, 71 | — | — | — | 42 |
| 115 | 19 | 24 | 21 | 94 | — | — | — | — |
| 116 | 23 | 26 | 22 | 75 | — | — | — | — |
| 117 | 59 | — | 18 | 68 | — | — | — | — |
| 118 | 35 | 7 | 19 | 60 | — | — | — | — |
| 119 | 14 | −6 | 14 | 60 | — | — | — | — |
| 120 | 21, 22 | 14, 26 | 45, 48 | 55, 70 | 4 | 3 | 25 | 39 |
| 121 | 6 | 44 | 16 | 88 | — | — | — | — |
| 122 | 51 | 84 | 13 | 96 | — | — | — | — |
| 124 | 19 | 12 | −2 | 63 | — | — | — | — |

TABLE B1-continued

Percentage inhibition of ligand binding to aminergic G protein-coupled receptors by compounds of the invention:

| Compound | Adrenergic (0.1 µM)* | | | | Adrenergic (0.03 µM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 125 | −3 | 1 | −4 | 68 | — | — | — | — |
| 126 | 30 | 46 | 12 | 82 | — | — | — | — |
| 127a | 26 | — | 9 | 74 | — | — | — | 43 |
| 127b | 13 | — | 4 | — | — | — | — | 1 |
| 128a | 37, 45 | — | 31, 34 | 104 | 14 | — | 9 | 97, 100 |
| 128b | 45 | — | 22 | — | — | — | — | 54 |
| 129a | 73 | — | 46 | — | — | — | — | 86 |
| 129b | 69 | — | 55 | — | — | — | — | 89 |
| 129c | 94, 96 | — | 29, 35 | — | 86 | — | 14 | 100 |
| 129d | 94, 99 | — | 90, 96 | — | 93 | — | 87 | 97, 104 |
| 130a | 66, 68 | — | 82, 89 | 107 | 32 | — | 56 | 100, 104 |
| 130b | 8, 11 | — | 31, 44 | 93 | 2 | — | 13 | 89, 92 |
| 131a | 24 | — | 10 | — | — | — | — | 30 |
| 131b | 36 | — | 11 | 90 | — | — | — | 53, 63 |
| 132 | 28 | — | 19 | — | — | — | — | 91 |
| 133a | 57 | — | 13 | — | — | — | — | 52 |
| 133b | 40, 42 | — | 34, 39 | 94 | 16 | — | 27 | 87, 88 |
| 134a | 27 | — | 4 | — | — | — | — | 42 |
| 134b | 93, 95 | — | 23, 29 | — | 78 | — | — | 102, 103 |
| 135a | 60 | — | 4 | — | — | — | — | 42 |
| 135b | 30 | — | 22 | — | — | — | — | 68 |
| 136a | 54 | — | 16 | — | — | — | — | 34 |
| 136b | 90 | — | 21 | — | — | — | — | 69 |
| 137a | 94 | — | 19 | — | — | — | — | 104 |
| 137b | 23 | — | 6 | — | — | — | — | 30 |
| 138a | 61 | — | −8 | — | — | — | — | 63 |
| 138b | 22 | — | 4 | — | — | — | — | 25 |
| 139 | 72 | — | −2 | 87 | 46 | — | — | 59, 83 |
| 139a | 17 | — | 16 | — | — | — | — | 88, 101 |
| 139b | 11 | — | 6 | — | — | — | — | 59 |
| 140 | 37 | — | −2 | — | — | — | — | 49 |
| 140a | 59 | — | 11 | — | — | — | — | 76 |
| 140b | 18 | — | 3 | — | — | — | — | 52 |
| 141 | 23 | — | 5 | — | — | — | — | 76 |
| 141a | 25 | — | −5 | — | — | — | — | 70 |
| 141b | 28 | — | 19 | — | — | — | — | 79, 86 |
| 142a | 68 | — | 19 | 95 | — | — | — | 71 |
| 142b | 83 | — | 63 | — | — | — | — | 99 |
| 143a | 43 | — | 19 | — | — | — | — | 77 |
| 143b | 17 | — | 0 | — | — | — | — | 49 |
| 144a | 57 | — | 1 | — | — | — | — | 40 |
| 144b | 53, 60, 66 | — | 3, 4 | 100, 102 | 28, 36 | — | — | 83, 85, 87 |
| 145 | 49 | — | 6 | — | — | — | — | 61 |
| 146a | 41 | — | −1 | — | — | — | — | 37 |
| 146b | 11 | — | 21 | — | — | — | — | 63 |
| 147 | 7 | — | 19 | — | — | — | — | 91, 102 |
| 147a | 33 | — | 3 | — | — | — | — | 72 |
| 147b | 82 | — | 36 | — | — | — | — | 93 |
| 148a | 23 | — | −5 | — | — | — | — | 52 |
| 148b | 71, 74 | — | 37 | 106 | 35 | — | — | 105 |
| 148c | 6 | — | −1 | — | — | — | — | 16 |
| 148d | 19 | — | −11 | — | — | — | — | 11 |
| 149a | 12 | — | −4 | — | — | — | — | 16 |
| 149b | 16 | — | 19 | — | — | — | — | 32 |
| 150a | 16 | — | 16 | 100 | — | — | — | 88, 96 |
| 150b | 7 | — | 5 | — | — | — | — | 9 |
| 151a | 11 | — | 15 | — | — | — | — | 93 |
| 151b | 9 | — | 8 | — | — | — | — | 37 |
| 152a | 20 | — | 17 | — | — | — | — | 20 |
| 152b | 7 | — | 10 | — | — | — | — | 19 |
| 153 | 17 | — | 6 | — | — | — | — | 17 |
| 154 | 86 | — | 15 | — | — | — | — | 58 |
| 154a | 39 | — | 4 | — | — | — | — | 31 |
| 154b | 95 | — | 5 | 95 | 80 | — | — | 80, 83 |
| 155 | 15 | — | 14 | — | — | — | — | 36 |
| 155a | 9 | — | −1 | — | — | — | — | 10 |
| 155b | 1 | — | 5 | — | — | — | — | 5 |
| 156 | 21 | — | 1 | — | — | — | — | 6 |
| 157 | 57 | — | 6 | — | — | — | — | 43 |
| 158 | 8 | — | −1 | — | — | — | — | 43 |
| 159a | −2 | — | 10 | — | — | — | — | 37 |
| 159b | 53 | — | −12 | — | — | — | — | 52 |

TABLE B1-continued

Percentage inhibition of ligand binding to aminergic G protein-coupled receptors by compounds of the invention:

| Compound | Adrenergic (0.1 μM)* | | | | Adrenergic (0.03 μM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 160a | 35 | — | −12 | — | — | — | — | 43 |
| 160b | 65 | — | 5 | — | — | — | — | 41 |
| 168 | 23 | — | 16 | — | — | — | — | 32 |
| 169 | 2 | — | 15 | — | — | — | — | 20 |
| 172a | 54 | — | 18 | — | — | — | — | 65 |
| 172b | 92 | — | 46 | — | — | — | — | 93 |
| 173a | 5 | — | 15 | 82 | — | — | — | 61, 68 |
| 173b | 8 | — | −2 | — | — | — | — | 28 |
| 174a | 13 | — | 22 | 86 | — | — | — | 62, 71 |
| 174b | 11 | — | 6 | — | — | — | — | 15 |
| 175a | 11 | — | 11 | 90 | — | — | — | 69, 73 |
| 175b | 4 | — | 7 | — | — | — | — | 4 |
| 176a | 79 | — | 32 | 105 | 52 | — | — | 93, 98, 100 |
| 176b | 41 | — | 12 | — | — | — | — | 67 |
| 179 | 6 | — | 6 | — | — | — | — | 8 |
| 180 | 87 | 74 | 95 | 99 | 70 | — | — | 91 |
| 181 | 30 | 32 | 89 | 92 | −4 | — | — | 70 |
| 182 | 29 | 16 | 69 | 91 | 13 | — | — | 83 |
| 183 | 71 | 36 | 93 | 80 | 50 | — | — | 68 |
| 183a | 77 | — | 56 | — | — | — | — | 82 |
| 183b | 93 | — | 93, 97 | — | — | — | 84 | 98 |
| 184 | — | — | 93 | — | 60 | 24 | — | 95 |
| 185 | 86 | 58 | 62 | 94, 97 | 63 | 47 | 37 | 73, 77 |
| 186 | 53, 55 | 51, 55 | 54, 72 | 100, 101 | 24 | 31 | 53 | 94, 97 |
| 187 | 71 | 83 | 63, 84 | 84, 98 | — | — | 41 | 78 |
| 188 | 60 | 48 | 66, 90 | 105 | — | — | 35 | — |
| 189 | 31, 55 | 16 | 81, 86 | 104, 107 | 26 | — | 71 | 96 |
| 190 | 14, 15 | 31 | 70, 89 | 84, 99 | 9 | — | 49 | 88 |
| 191 | 10, 20 | 43 | 89, 98 | 89, 99 | 2 | — | 85 | 84 |
| 193 | 93 | 88 | 77 | 103 | — | — | — | — |
| 193a | 89 | — | 85 | — | — | — | — | 98 |
| 193b | 91 | — | 83 | — | — | — | — | 104 |
| 194a | 100 | — | 98 | — | — | — | — | 106 |
| 194b | 100 | — | 94 | — | — | — | — | 103 |
| 196a | 54.6 | — | 58, 71 | — | 30 | — | 37 | 93, 103 |
| 196b | 37 | — | 19 | — | — | — | — | −2 |
| 197a | 82 | — | 31 | — | — | — | — | 81 |
| 197b | 96 | — | 56, 77 | — | 89 | — | 50 | 101, 105 |
| 198a | 24 | — | 10 | — | — | — | — | 47 |
| 198b | 84 | — | 44 | — | — | — | — | 103 |
| 199a | 82 | — | 96 | — | — | — | — | 94 |
| 199b | 88 | — | 61 | — | — | — | — | 27 |
| 200 | 83 | 69 | 92 | — | 63 | — | 81 | — |
| 201 | 50 | 18 | 67 | 36 | 22 | — | — | 16 |
| 202 | 52 | 52 | 92 | 22 | 29 | — | — | 7 |
| 203 | 71 | 47 | 88 | 41 | 37 | — | — | 23 |
| 203a | 76 | — | 71 | — | — | — | — | 36 |
| 203b | 47 | — | 31 | — | — | — | — | 24 |
| 204 | — | — | 87 | 107 | — | — | — | — |
| 205 | — | — | 69 | 70 | — | — | — | — |
| 206 | — | — | 86 | 102 | 46 | 42 | — | — |
| 207 | — | — | 90 | 106 | 49 | 39 | — | — |
| 208 | — | — | 101 | 97 | 60 | 41 | — | — |
| 209 | — | — | 80 | 84 | — | — | — | — |
| 210 | — | — | 88 | 63 | — | — | — | — |
| 211 | — | — | 88 | 108 | 63 | 44 | — | — |
| 212 | — | — | 66 | 64 | — | — | — | — |
| 213 | — | — | 98 | 68, 97 | 53 | 53 | — | 26 |
| 214 | 18 | — | 58, 64 | 80 | — | — | 37 | 48 |
| 215 | — | — | 97 | 102 | — | — | — | — |
| 216 | 65 | — | 76, 98 | 103, 106 | 34, 47 | 38 | 58 | 98 |
| 217 | 62 | — | 74 | 102 | — | — | — | — |
| 218 | — | — | — | — | 79 | 60 | 85 | 110 |
| 219 | — | — | — | — | — | 3 | 69 | — |
| 221 | 65 | 16 | 56 | 80 | — | — | — | — |
| 222 | 95 | 101 | 96 | 104 | — | — | — | — |
| 223 | 21 | — | 69 | — | — | — | — | 47 |
| 224 | 70 | 26 | 52 | 69 | — | — | — | — |
| 225 | 27 | 12 | 75 | 80 | — | — | — | — |
| 226 | 88 | 48 | 85 | 83 | — | — | — | — |
| 227 | 21 | −2 | 66 | 98 | — | — | — | — |
| 228 | 64 | 19 | 77 | 42 | — | — | — | — |

TABLE B1-continued

Percentage inhibition of ligand binding to aminergic G protein-coupled receptors by compounds of the invention:

| Compound | Adrenergic (0.1 μM)* | | | | Adrenergic (0.03 μM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 229 | 17 | 8 | 53 | 90 | — | — | — | — |
| 230 | 94 | 58 | 87 | 93 | — | — | — | — |
| 231 | 48 | 26 | 65 | 87 | — | — | — | — |
| 232 | 87 | 43 | 87 | 102 | — | — | — | — |
| 233 | 73 | 28 | 80 | 103 | — | — | — | — |
| 235 | 48 | 11 | 80 | 96 | — | — | — | — |
| 236 | 94 | 85 | 99 | 98 | — | — | — | — |
| 237 | 80 | 52 | 98 | 99 | — | — | — | — |
| 238 | 67 | 25 | 94 | 98 | — | — | — | — |
| 239 | 19 | −11 | 52 | 30 | — | — | — | — |
| 240 | 74, 75 | 44, 47 | 82, 87 | 83, 97 | — | — | — | — |
| 241 | 81, 82 | 47, 49 | 75, 78 | 91, 93 | — | — | — | — |
| 242 | 53 | 37 | 50 | 98 | — | — | — | — |
| 243 | 58 | 45 | 90, 98 | 105 | — | — | 73 | — |
| 244 | 78 | 42 | 76 | 99 | — | — | — | — |
| 245 | 69 | 35 | 65 | 96 | — | — | — | — |
| 246 | 82 | 68 | 86 | 101 | — | — | — | — |
| 247 | 95 | 81 | 96 | 89 | — | — | — | — |
| 248 | 76 | 31 | 90 | 95 | — | — | — | — |
| 249 | 95 | 82 | 98 | 98 | — | — | — | — |
| 250 | 37 | 22 | 62 | 105 | — | — | — | — |
| 251 | 89 | 53 | 85 | 101 | — | — | — | — |
| 252 | 36 | 13 | 66 | 52 | — | — | — | — |
| 253 | 54, 55 | 18, 24 | 44, 64 | 64, 86 | — | — | — | — |
| 254a | 75 | 36 | 58 | 85 | — | — | — | — |
| 254b | 63 | 22 | 57 | 79 | — | — | — | — |
| 255 | 55 | 43 | 63 | 96 | — | — | — | — |
| 256 | 47 | 23 | 55 | 58 | — | — | — | — |
| 257 | 51 | 24 | 84 | 100 | — | — | — | — |
| 258 | 93 | 74 | 94 | 99 | — | — | — | — |
| 259 | 71 | 53 | 82 | 98 | — | — | — | — |
| 260 | 45 | 26 | 54 | 92 | — | — | — | — |
| 261 | 50 | 30 | 84 | 84 | — | — | — | — |
| 262 | 52 | 35 | 87 | 74 | — | — | — | — |
| 263 | 1 | 6 | 61 | 54 | — | — | — | — |
| 264 | 79 | 46 | 81 | 82 | — | — | — | — |
| 265 | 50 | 30 | 67 | 70 | — | — | — | — |
| 266 | 63 | 72 | 62 | 92 | — | — | — | — |
| 267 | 7 | 26 | 63 | 85 | — | — | — | — |
| 268 | 57 | 39 | 90 | 94 | — | — | — | — |
| 269 | 36 | 44 | 61 | 83 | — | — | — | — |
| 270 | 50 | 66 | 96 | 76 | — | — | — | — |
| 271 | 65 | 83 | 97 | 71 | — | — | — | — |
| 272a | 27 | 12 | 33 | −10 | — | — | — | — |
| 272b | 30 | 36 | 68 | 72 | — | — | — | — |
| 273 | 88 | 71 | 67 | 89 | — | — | — | — |
| 274 | 28 | 25 | 68 | 27 | — | — | — | — |
| 275 | 75 | 61 | 51 | 94 | — | — | — | — |
| 276 | 86 | 81 | 71 | 101 | — | — | — | — |
| 277 | 71 | 84 | 98 | 97 | — | — | — | — |
| 278 | 62 | 44 | 93 | 98 | — | — | — | — |
| 279 | 79 | 93 | 90 | 92 | — | — | — | — |
| 280 | 76 | 65 | 97 | 98 | — | — | — | — |
| 281 | 67 | 47 | 72 | 90 | — | — | — | — |
| 282 | 33 | 30 | 75 | 101 | — | — | — | — |
| 283 | 63 | 46 | 90 | 89 | — | — | — | — |
| 284 | 83 | 81 | 97 | 76 | — | — | — | — |
| 285 | 63 | 71 | 98 | 97 | — | — | — | — |
| 286 | 26 | 19 | 80 | 60 | — | — | — | — |
| 287 | 81 | 69 | 99 | 98 | — | — | — | — |
| 288a | 89 | 88 | 98 | 104 | — | — | — | — |
| 288b | 39 | 17 | 67 | 84 | — | — | — | — |
| 289a | 51 | 57 | 60 | 90 | — | — | — | — |
| 289b | 12 | −2 | 53 | 54 | — | — | — | — |
| 290 | 90 | 79 | 80 | 96 | — | — | — | — |
| 291 | 88 | 85 | 102 | 105 | — | — | — | — |
| 292 | 13 | 23 | 58 | 104 | — | — | — | — |
| 293 | 73 | 82 | 96 | 93 | — | — | — | — |
| 294 | 76 | 39 | 94 | 41 | — | — | — | — |
| 295 | 15 | 7 | 69 | 79 | — | — | — | — |
| 296 | 20 | 33 | 60 | 70 | — | — | — | — |
| 297 | 69 | 36 | 50 | 46 | — | — | — | — |

TABLE B1-continued

Percentage inhibition of ligand binding to aminergic G protein-coupled receptors by compounds of the invention:

| Compound | Adrenergic (0.1 µM)* | | | | Adrenergic (0.03 µM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| 298 | 60 | 17 | 54 | 51 | — | — | — | — |
| 299 | 78 | 47 | 52 | 54 | — | — | — | — |
| 300 | 14 | 29 | 67 | 86 | — | — | — | — |
| 301 | 29 | 36 | 87 | 84 | — | — | — | — |
| 302 | 23 | 17 | 81 | 35 | — | — | — | — |
| 303 | 16 | 51 | 62 | 71 | — | — | — | — |
| 304 | 15 | 27 | 79 | 81 | — | — | — | — |
| 305 | 20 | 41 | 93 | 79 | — | — | — | — |
| 306 | 18 | 12 | 78 | 14 | — | — | — | — |
| 307 | 93 | 81 | 93 | 98 | — | — | — | — |
| 308 | 79 | 56 | 86 | 97 | — | — | — | — |
| 309 | 23 | 40 | 57 | 37 | — | — | — | — |
| 310 | 63 | 47 | 69 | 87 | — | — | — | — |
| 311 | 87 | 79 | 91 | 97 | — | — | — | — |
| 312 | 71 | 50 | 56 | 93 | — | — | — | — |
| 313 | 92 | 53 | 73 | 73 | — | — | — | — |
| 314 | 92 | 71 | 91 | 50 | — | — | — | — |
| 315 | 4 | 3 | 59 | 48 | — | — | — | — |
| 316 | 93 | 81 | 90 | 45 | — | — | — | — |
| 317 | 89 | 71 | 61 | 7 | — | — | — | — |
| 318 | 94 | 60 | 95 | 103 | — | — | — | — |
| 319 | 13 | 8 | 63 | 4 | — | — | — | — |
| 320 | 61 | 56 | 66 | 18 | — | — | — | — |
| 321 | 94 | 66 | 59 | 90 | — | — | — | — |
| 322 | 59 | 22 | 58 | 49 | — | — | — | — |
| 323 | 85 | 69 | 92 | 95 | — | — | — | — |
| 324 | 63 | 31 | 67 | 99 | — | — | — | — |
| 325 | −1 | 1 | 81, 84 | −6 | — | — | 53 | — |
| 326 | 33 | 35 | 51 | 93 | — | — | — | — |
| 327 | −5 | 4 | 58 | −4 | — | — | — | — |
| 328 | 95 | 80 | 76 | 93 | — | — | — | — |
| 329 | 68 | 78 | 60 | 104 | — | — | — | — |
| 330 | 98 | 72 | 58 | 99 | — | — | — | — |
| 331 | 53 | 70 | 53 | 99 | — | — | — | — |
| 332 | 41 | 51 | 94 | 86 | — | — | — | — |
| 333 | 65 | 16 | 52 | 88 | — | — | — | — |
| 334 | 91 | 72 | 55 | 82 | — | — | — | — |
| 335 | 82 | 73 | 60 | 99 | — | — | — | — |
| 336 | 98 | — | 66 | — | — | — | — | 104 |
| 338 | 16 | — | 60 | — | — | — | — | 102 |
| 339a | 13 | — | 37 | — | — | — | — | 86 |
| 339b | 10 | — | 64 | — | — | — | — | 87 |
| II-1a | 6 | — | 15 | — | — | — | — | 14 |
| II-1b | −7 | — | 1 | — | — | — | — | 32 |
| II-2 | 74 | — | 49 | — | — | — | — | 96 |
| II-4a | 72 | — | 35 | — | — | — | — | 79 |
| II-4b | 98 | — | 57 | — | — | — | — | 100 |
| II-5 | 2 | — | 9 | — | — | — | — | 4 |
| II-6a | 66 | — | 45 | — | — | — | — | 85 |
| II-6b | 91 | — | 81 | — | — | — | — | 102 |
| II-7 | 95 | — | 52 | — | — | — | — | 100 |
| II-8 | 6 | — | 9 | — | — | — | — | 70 |
| II-9 | 30 | — | 7 | — | — | — | — | 78 |
| II-10 | 7 | — | 10 | — | — | — | — | 47 |
| II-11 | 63 | — | 25 | — | — | — | — | 70 |
| II-11a | 9 | — | 22 | — | — | — | — | 53 |
| II-11b | 76 | — | 43 | — | — | — | — | 89 |
| II-12 | 18 | — | 11 | — | — | — | — | 65 |
| II-12a | 26 | — | 25 | — | — | — | — | 89 |
| II-12b | 11 | — | 15 | — | — | — | — | 65 |
| II-13 | 9 | — | 9 | — | — | — | — | 73 |
| II-14a | 30 | — | 34 | — | — | — | — | 88 |
| II-14b | 8 | — | 17 | — | — | — | — | 33 |
| II-15a | 61 | — | 7 | — | — | — | — | 47 |
| II-15b | 5 | — | 18 | — | — | — | — | 40 |
| II-16a | 20 | — | 11 | — | — | — | — | 39 |
| II-16b | 32, 46 | — | 32 | 88 | 16 | — | — | 65, 73 |
| II-17 | 8 | — | 4 | — | — | — | — | 7 |
| II-18 | −7 | −9 | 14 | −15 | — | — | — | — |
| II-19 | 8 | — | 8 | — | — | — | — | 21 |
| II-39 | 16 | 13 | 27 | −14 | — | — | — | — |
| II-40 | — | — | — | 36 | — | — | — | — |

TABLE B1-continued

Percentage inhibition of ligand binding to aminergic G protein-coupled receptors by compounds of the invention:

| Compound | Adrenergic (0.1 µM)* | | | | Adrenergic (0.03 µM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| II-48 | 27 | 8 | 26 | 0 | — | — | — | — |
| II-49a | 47 | — | 34 | — | — | — | — | 43 |
| II-49b | 69 | — | 18 | — | — | — | — | 50 |
| II-56 | 54 | 11 | 31 | 78 | — | — | — | — |
| II-57a | 20 | — | 22 | — | — | — | — | 38 |
| II-57b | 31 | — | 31 | — | — | — | — | 45 |
| II-58 | 16 | — | 16 | — | — | — | — | 58 |
| II-60 | 11 | — | 9 | — | — | — | — | 54 |
| II-61 | — | — | — | 47 | — | — | — | — |
| II-62 | 14 | — | 5 | — | — | — | — | 37 |
| II-63 | 55 | — | 39 | — | — | — | — | 90 |
| II-64 | 23 | — | −3 | — | — | — | — | 54 |
| II-65 | 10 | — | 12 | — | — | — | — | 25 |
| II-66 | 27 | — | 0 | — | — | — | — | 46 |
| II-67 | 7 | — | −11 | — | — | — | — | 43 |
| II-68 | 12 | — | 5 | — | — | — | — | 17 |
| II-69 | 45 | — | 11 | — | — | — | — | 14 |
| II-70 | — | — | — | 34 | — | — | — | — |
| II-71 | 3 | — | −3 | — | — | — | — | 11 |
| II-72 | 30 | — | 25 | — | — | — | — | 47 |
| II-73 | 34 | — | 28 | — | — | — | — | 33 |
| II-74 | 11 | — | 10 | — | — | — | — | 18 |
| II-75 | 8 | — | 15 | — | — | — | — | 35 |
| II-76 | — | — | — | 103 | — | — | — | — |
| II-77 | 54 | 66 | 43 | 108 | — | — | — | — |
| II-78 | −11 | — | 1 | — | — | — | — | −9 |
| II-79 | 7 | — | 0 | — | — | — | — | 59 |
| II-80 | 4 | — | 3 | — | — | — | — | 9 |
| II-81 | −1 | — | 15 | — | — | — | — | −9 |
| II-82 | 13 | 23 | 45 | 48, 53 | — | — | — | 35 |
| II-83 | 12 | — | 2 | — | — | — | — | 24 |
| II-84 | 2 | — | 11 | — | — | — | — | −11 |
| II-85 | −7 | — | 15 | — | — | — | — | −2 |
| II-86 | 44 | — | 27 | — | — | — | — | 35 |
| II-87 | 11 | — | 1 | — | — | — | — | 24 |
| II-88 | 68 | — | −2 | — | — | — | — | 48 |
| II-89 | 13 | — | −5 | — | — | — | — | 35 |
| II-90 | 62 | — | 19 | — | — | — | — | 55 |
| II-91 | 16 | — | −2 | — | — | — | — | 25 |
| II-92 | 13 | — | 0 | — | — | — | — | 25 |
| II-93a | 6 | — | 7 | — | — | — | — | 24 |
| II-93b | 18 | — | 4 | — | — | — | — | 56 |
| II-94a | 10 | — | 0 | — | — | — | — | 8 |
| II-94b | 7 | — | −5 | — | — | — | — | 24 |
| II-95a | 32 | — | 16 | — | — | — | — | 53 |
| II-95b | −1 | — | −1 | — | — | — | — | 12 |
| II-96 | 39 | 31 | 49 | 95 | — | — | — | — |
| II-97 | −4 | — | 4 | — | — | — | — | 24 |
| II-98a | 33 | — | 12 | — | — | — | — | 10 |
| II-98b | 10 | — | 19 | — | — | — | — | 5 |
| II-99a | 12 | — | 24 | — | — | — | — | 49 |
| II-99b | 5 | — | 16 | — | — | — | — | 7 |
| II-100a | 10 | — | 7 | — | — | — | — | 12 |
| II-100b | 24 | — | 4 | — | — | — | — | 1 |
| II-102 | 2 | — | 10 | — | — | — | — | 49 |
| II-103 | 1 | 8 | −5 | 35 | — | — | — | — |
| II-104 | 3 | — | 10 | — | — | — | — | 21 |
| II-105 | 5 | — | 7, 18 | 27 | — | — | — | 5, 30 |
| II-106a | 25 | — | 18 | — | — | — | — | 20 |
| II-106b | 31 | — | 8 | — | — | — | — | 36 |
| II-108a | 13 | — | −2 | — | — | — | — | 27 |
| II-108b | −2 | — | −6 | — | — | — | — | 11 |
| II-109a | 27 | — | 2 | — | — | — | — | 41 |
| II-109b | 5 | — | −10 | — | — | — | — | 2 |
| II-110 | 25, 36 | 17 | 1, 2 | 47 | — | — | — | 11 |
| II-111 | 42 | — | 3 | — | — | — | — | 35 |
| II-112a | 5 | — | 10 | — | — | — | — | 36 |
| II-112b | 10 | — | 3 | — | — | — | — | 31 |
| II-113a | 9 | — | −3 | — | — | — | — | 39 |
| II-113b | 5 | — | 19 | — | — | — | — | 38 |
| II-114a | 45 | — | 12 | — | — | — | — | 40 |
| II-114b | 7 | — | −5 | — | — | — | — | 40 |

TABLE B1-continued

Percentage inhibition of ligand binding to aminergic G protein-coupled receptors by compounds of the invention:

| Compound | Adrenergic (0.1 µM)* | | | | Adrenergic (0.03 µM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| II-116 | 4 | — | 3 | — | — | — | — | 43 |
| II-118a | 18 | — | 3 | — | — | — | — | 27 |
| II-118b | 11 | — | 5 | — | — | — | — | -3 |
| II-119 | 23 | 53 | -4 | 27 | — | — | — | — |
| II-120a | 99 | — | 65 | — | — | — | — | 101 |
| II-120b | 100 | — | 98 | — | — | — | — | 98 |
| II-121a | 97, 98 | — | 91, 92 | — | 90 | — | 65 | 103, 104 |
| II-121b | 93, 96 | — | 80, 85 | — | 77 | — | 54 | 100, 103 |
| II-122 | -2 | — | -10 | — | — | — | — | 47 |
| II-123a | 41 | — | 16 | — | — | — | — | 62 |
| II-123b | 61 | — | 75 | — | — | — | — | 93 |
| II-124a | -2 | — | 23 | — | — | — | — | 26 |
| II-124b | 10 | — | 7 | — | — | — | — | 18 |
| II-125a | 92 | — | 62 | — | — | — | — | 100 |
| II-125b | 97, 102 | — | 97, 98 | — | 89 | — | 89 | 103, 106 |
| II-125c | 42 | — | 9 | — | — | — | — | 67 |
| II-125d | 64 | — | 71 | — | — | — | — | 88 |
| II-126 | -4 | — | 4 | — | — | — | — | 4 |
| II-127a | 83 | — | 79 | — | — | — | — | 105 |
| II-127b | 65 | — | 54 | — | — | — | — | 104 |
| II-128a | 61 | — | 34 | — | — | — | — | 97 |
| II-128b | 84, 86 | — | 74, 77 | — | 56 | — | 50 | 102, 106 |
| II-129 | 2 | — | 12 | — | — | — | — | 1 |
| II-130 | 43 | — | 41 | — | — | — | — | 97 |
| II-130a | 92 | — | 86 | — | — | — | — | 103 |
| II-130b | 3 | — | 15 | — | — | — | — | 33 |
| II-131 | 90 | — | 85 | — | — | — | — | 103 |
| II-132a | 33 | — | 8 | — | — | — | — | 40 |
| II-132b | 68 | — | 22 | — | — | — | — | 70 |
| II-133 | — | — | — | -5 | — | — | — | — |
| II-134a | 86 | — | 19 | — | — | — | — | 89 |
| II-134b | 65 | — | 6 | — | — | — | — | 79 |
| II-135a | 48 | — | -3 | — | — | — | — | 34 |
| II-135b | 60, 70 | — | 40 | 105 | 26 | — | — | 103, 105 |
| II-136a | 60 | — | 7 | — | — | — | — | 36 |
| II-136b | 31 | — | 5 | — | — | — | — | 32 |
| II-138 | 57 | — | 9 | — | — | — | — | 77 |
| II-139 | 34 | — | 7 | — | — | — | — | 72 |
| II-140 | 53 | — | 3 | — | — | — | — | 72 |
| II-141 | 7 | — | -2 | — | — | — | — | 22 |
| II-142 | 5 | — | -4 | — | — | — | — | 23 |
| II-143 | 13 | — | -3 | — | — | — | — | 22 |
| II-146a | 23 | — | 47 | — | — | — | — | 102 |
| II-146b | 13 | — | 5 | — | — | — | — | 43 |
| II-146c | 17 | — | 8 | — | — | — | — | 42 |
| II-146d | 13 | — | 3 | — | — | — | — | 16 |
| II-147a | 32 | — | 57 | — | — | — | — | 102 |
| II-147b | 20 | — | 15 | — | — | — | — | 66 |
| II-147c | 7 | — | 3 | — | — | — | — | 38 |
| II-147d | 10 | — | 4 | — | — | — | — | 13 |
| II-148 | 21 | — | 27 | — | — | — | — | 93 |
| II-149a | 90 | — | 53 | — | — | — | — | 104 |
| II-149b | 59 | — | 27 | — | — | — | — | 96 |
| II-149c | 49 | — | 5 | — | — | — | — | 41 |
| II-149d | 41 | — | 7 | — | — | — | — | 44 |
| II-150 | 14 | — | 5 | — | — | — | — | 30 |
| II-151a | 11 | — | 1 | — | — | — | — | 27 |
| II-151b | 13 | — | 11 | — | — | — | — | 78 |
| II-152a | 19 | — | 9 | — | — | — | — | 93 |
| II-152b | 2 | — | 6 | — | — | — | — | 61 |
| II-152c | 6 | — | 1 | — | — | — | — | 14 |
| II-152d | 5 | — | 8 | — | — | — | — | 9 |
| II-153 | 2 | — | 2 | — | — | — | — | 7 |
| II-154 | 2 | — | 11 | — | — | — | — | 73 |
| II-160 | 7, 14 | 15 | 17, 37 | 35 | — | — | — | 39 |
| II-161 | 7 | 2 | 7 | 13 | — | — | — | — |
| II-163 | 66 | 28 | 41 | 86 | — | — | — | — |
| II-164 | 12 | 0 | 15 | 40 | — | — | — | — |
| II-171 | 95 | 55 | 96 | 94 | — | — | — | — |
| II-187 | 54 | — | 10 | — | — | — | — | 27 |
| II-212 | 29 | — | 19 | — | — | — | — | 73 |
| II-213 | -3 | — | 12 | — | — | — | — | 11 |

TABLE B1-continued

Percentage inhibition of ligand binding to aminergic G protein-coupled receptors by compounds of the invention:

| Compound | Adrenergic (0.1 μM)* | | | | Adrenergic (0.03 μM)* | | | |
|---|---|---|---|---|---|---|---|---|
| | $\alpha_{1B}$ | $\alpha_{1D}$ | $\alpha_{2A}$ | $\alpha_{2B}$ | $\alpha_{1B}$ | $\alpha_{1D}$ | $\alpha_{2A}$ | $\alpha_{2B}$ |
| II-215 | — | — | — | −5 | — | — | — | — |
| II-221 | −1 | — | 10 | — | — | — | — | 0 |
| II-222 | 19 | — | 26 | — | — | — | — | 99 |
| II-223 | 9 | — | 8 | — | — | — | — | 88 |
| II-224 | 13 | — | 22 | — | — | — | — | 68 |
| II-225 | 9 | — | −1 | — | — | — | — | 8 |
| II-226 | 15 | — | 4 | — | — | — | — | 40 |
| II-227a | 25 | — | 15 | — | — | — | — | 86 |
| II-227b | 8 | — | 6 | — | — | — | — | 18 |
| II-227c | 20 | — | 24 | — | — | — | — | 94 |
| II-227d | 12 | — | 6 | — | — | — | — | 26 |
| II-228 | −2 | — | 3 | — | — | — | — | 10 |
| II-229 | 3 | — | 6 | — | — | — | — | 12 |
| II-230 | −2 | — | 1 | — | — | — | — | 22 |
| II-231 | 11 | — | 9 | — | — | — | — | −2 |
| II-232 | 3 | — | 3 | — | — | — | — | 28 |
| II-234 | −8 | −1 | 7 | 33 | — | — | — | — |
| II-235 | 58 | 28 | 3 | 45 | — | — | — | — |
| II-236 | — | — | — | −4 | — | — | — | — |
| II-238 | — | — | — | 98 | — | — | — | — |
| II-239 | — | — | — | 17 | — | — | — | — |
| II-240 | 57 | — | 7 | — | — | — | — | 53 |
| II-241 | 5 | — | −1 | — | — | — | — | −1 |
| II-242 | 4 | — | 2 | — | — | — | — | 3 |
| II-243 | 91, 93 | — | 19 | 82 | 79 | — | — | 58, 61 |
| II-244a | 95 | — | 22 | — | — | — | — | 102 |
| II-244b | 12 | — | 2 | — | — | — | — | 16 |
| II-245 | 27 | — | 7 | — | — | — | — | 44 |
| II-246 | −2 | — | 47 | — | — | — | — | 5 |
| II-247 | 3 | — | 83 | — | — | — | — | 19 |
| II-248 | 4 | — | 88 | — | — | — | — | 5 |
| II-249 | 6 | — | 74 | — | — | — | — | 4 |
| II-250 | −5 | — | 57 | — | — | — | — | 6 |
| II-251 | −7 | — | 81 | — | — | — | — | −4 |
| II-252 | −1 | — | 91 | — | — | — | — | 1 |
| II-253 | 9 | — | 54 | — | — | — | — | 16 |
| II-261 | 71 | — | 70 | — | — | — | — | 103 |
| II-262 | 3 | — | 10 | — | — | — | — | 11 |
| II-263 | 2 | — | 10 | — | — | — | — | 10 |
| IV-2 | — | — | — | 50 | — | — | — | — |
| IV-4 | 2 | 15 | −3 | 56 | — | — | — | — |
| IV-8a | 49 | — | 7 | — | — | — | — | 4 |
| IV-8b | 5 | — | 22 | — | — | — | — | 3 |
| IV-93a | 7 | — | 18 | — | — | — | — | 52 |
| IV-93b | 65 | — | −1 | — | — | — | — | 44 |
| IV-209a | 89 | — | 6 | — | — | — | — | 72 |
| IV-209b | 11 | — | 10 | — | — | — | — | 13 |
| IV-209c | 98 | — | 59 | — | — | — | — | 102 |
| IV-209d | 54 | — | 8 | — | — | — | — | 79 |
| IV-210a | 70, 75 | — | 37 | — | 43 | — | — | 101, 103 |
| IV-210b | 10 | — | 8 | — | — | — | — | 29 |
| IV-210c | −4 | — | 1 | — | — | — | — | 10 |
| IV-210d | 19 | — | 13 | — | — | — | — | 87 |
| V-1 | 15 | — | 35 | — | — | — | — | 102 |
| V-1a | 20 | — | 36 | — | — | — | — | 88 |
| V-1b | 57 | — | 29 | — | — | — | — | 102 |
| V-2 | 49 | — | 2 | — | — | — | — | 61 |
| V-3 | 22 | — | 40 | — | — | — | — | 71 |
| V-14a | 0 | — | 18 | — | — | — | — | 7 |
| V-14b | 2 | — | 3 | — | — | — | — | 0 |
| V-15 | 4 | — | 7 | — | — | — | — | 20 |
| V-18a | 78 | — | 13 | — | — | — | — | 57 |
| V-18b | 95 | — | 57 | — | — | — | — | 98 |
| V-21a | 68 | — | 62 | — | — | — | — | 98 |
| V-21b | 34 | — | 43 | — | — | — | — | 93 |
| V-22 | 28 | — | 18 | — | — | — | — | 90 |
| V-23 | 94 | — | 109 | — | — | — | — | 105 |

*Where shown, some compounds were tested in repeat assays, each datapoint is shown.

TABLE B2

Ki values of compounds of the invention:

| Compound No. | $\alpha_{2B}$ (nM) | $\alpha_{2A}$ (nM) | $\alpha_{1B}$ (nM) | $\alpha_{1D}$ (nM) |
|---|---|---|---|---|
| 3 | 0.64 | 0.26 | — | — |
| 3a | 27.41 | — | — | — |
| 3b | 0.26, 0.28, 0.46 | 139, 166, 222 | 51 | 258 |
| 4a | 0.64 | 176 | — | — |
| 5a | 35 | — | — | — |
| 5b | 0.95, 1.06, 4.53 | 152, 192, 195 | 184 | — |
| 8b | 11.65 | 2104 | — | — |
| 13b | 0.62 | 199 | — | — |
| 14a | 1.92 | 123 | — | — |
| 15b | 0.64 | 112 | — | — |
| 26a | 0.56 | 113 | — | — |
| 26b | 3.06 | — | — | — |
| 27a | 4.32 | 1101 | — | — |
| 27b | 43.43 | 3713 | — | — |
| 29a | 1.09 | 77.23 | — | — |
| 30b | 1.13 | 14.25 | — | — |
| 31a | 1.58 | 167 | — | — |
| 39a | 2.50 | 1659 | — | — |
| 74a | 1.42 | 234 | 4.72 | — |
| 60 | 5.84 | — | — | — |
| 61 | 5.89 | — | — | — |
| 89 | 32 | — | — | — |
| 91 | 9.84, 10.68, 11.97 | — | — | — |
| 93a | 1.14 | 90.50 | — | — |
| 114 | 17.38 | — | — | — |
| 120 | 20.52 | 65.83 | — | — |
| 127a | 15.14 | — | — | — |
| 128a | 0.97 | 98.62 | — | — |
| 129c | 0.77 | 88.55 | — | — |
| 129d | 0.35 | 1.87 | — | — |
| 130a | 1.66 | 6.91 | — | — |
| 130b | 2.52 | 72.60 | — | — |
| 131b | 7.95 | — | — | — |
| 133b | 2.42 | 59.45 | — | — |
| 134b | 0.43 | 102 | — | — |
| 139a | 2.36 | — | — | — |
| 139 | 8.12 | 390 | — | — |
| 141b | 3.44 | — | — | — |
| 144b | 1.70, 2.36 | — | — | — |
| 148b | 0.43 | — | — | — |
| 147 | 1.49 | — | — | — |
| 150a | 1.57 | — | — | — |
| 154b | 3.33 | — | — | — |
| 173a | 8.77 | — | — | — |
| 174a | 7.91 | — | — | — |
| 175a | 4.42 | — | — | — |
| 176a | 0.53 | — | — | — |
| 183b | — | 2.72 | — | — |
| 184 | — | 184 | — | — |
| 185 | 3.80 | 20.97 | — | — |
| 186 | 0.52 | 11.04 | — | — |
| 187 | 4.43 | 17.89 | — | — |
| 189 | 0.86 | 2.86 | — | — |
| 190 | 2.26 | 12.83 | — | — |
| 191 | 3.23 | 2.10 | — | — |
| 196a | 1.83 | 16.80 | — | — |
| 197b | 0.78 | 11.90 | — | — |
| 200 | — | 1.63, 3.21 | — | — |
| 204 | — | 2.48 | — | — |
| 206 | — | 1.12, 6.79 | — | — |
| 207 | — | 1.16 | — | — |
| 213 | 26.30 | — | — | — |
| 214 | 12.91 | 22.67 | — | — |
| 216 | 0.95 | 9.59 | — | — |
| 243 | — | 3.86 | — | — |
| 325 | 206 | 9.88 | — | — |
| II-16b | 5.58 | — | — | — |
| II-82 | 26.76 | — | — | — |
| II-105 | 152 | — | — | — |
| II-121a | — | 4.52 | — | — |
| II-121b | 0.22 | 9.18 | — | — |
| II-125b | 0.16 | 1.21 | — | — |
| II-128b | 0.49 | 13.07 | — | — |
| II-135b | 0.53 | — | — | — |
| II-243 | 9.44 | — | — | — |
| IV-210a | 0.33 | — | — | — |
| V-1 | 0.51 | — | — | — |

Example B2. Functional Activity on Recombinant Adrenergic $\alpha_{1B}$, Adrenergic $\alpha_{2A}$, Adrenergic $\alpha_{2B}$ and Adrenergic $\alpha_{1D}$ Receptors Using Aequorin and GTPγS Functional Assays To study the functional activity of compounds of the invention on the human recombinant adrenergic $\alpha_{2B}$, adrenergic $\alpha_{2A}$, adrenergic $\alpha_{1B}$ or adrenergic $\alpha_{1D}$ with Aequorin functional assays and on the human recombinant adrenergic $\alpha_{2B}$ receptor with GTPγS assay, CHO-K1 cell lines expressing adrenergic $\alpha_{2B}$, adrenergic $\alpha_{2A}$, adrenergic $\alpha_{1B}$ or adrenergic $\alpha_{1D}$ recombinant receptor, mitochondrial apoaequorin and Gα16 were used for the Aequorin assay. CHO-K1 cell line expressing the recombinant $\alpha_{2B}$ receptor was amplified to prepare membranes used for the GTPγS assay.

The following reference agonists were used as both the reference ligand in agonist mode and as the agonist that needs to be inhibited in antagonist mode.

| Assay | $\alpha_{1B}$ (aeq) | $\alpha_{1D}$ (aeq) | $\alpha_{2A}$ (aeq) | $\alpha_{2B}$ (aeq) | $\alpha_{2B}$ (GTPgS) |
|---|---|---|---|---|---|
| Agonist ligand | Cirazoline | Cirazoline | UK 14304 | Oxymetazoline | Guanfacine |

Figure 3:
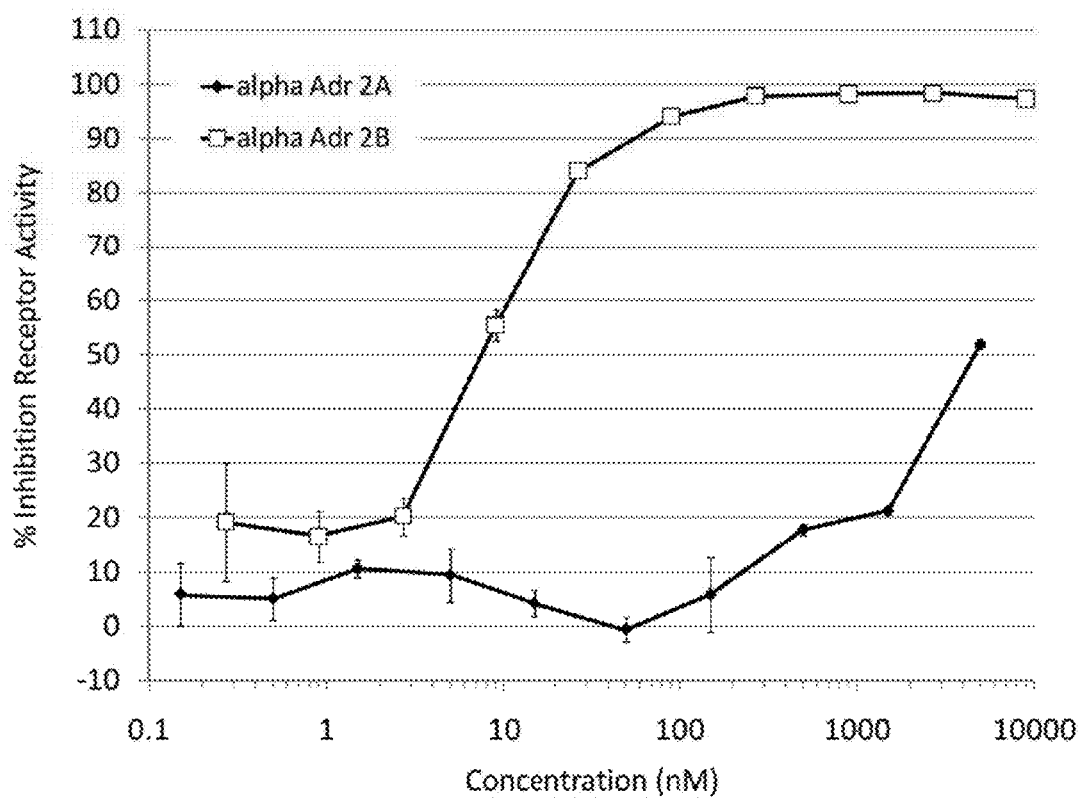
FIG. 3 illustrates the binding activity of Compound No. 3b in the $\alpha_{2A}$ and $\alpha_{2B}$ receptor assays.
Figure 5:
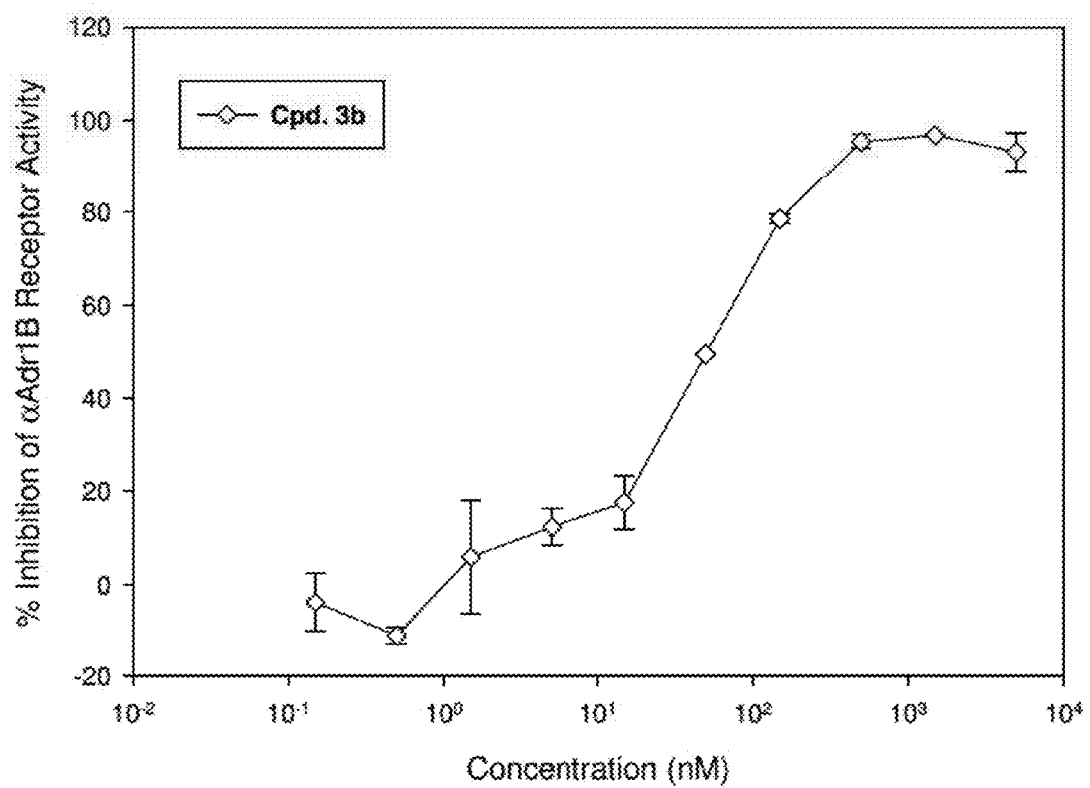
FIG. 5 illustrates the $\alpha_{1B}$ antagonist activity of Compound No. 3b in the Aequorin Antagonist Activity Assay.
Figure 6:
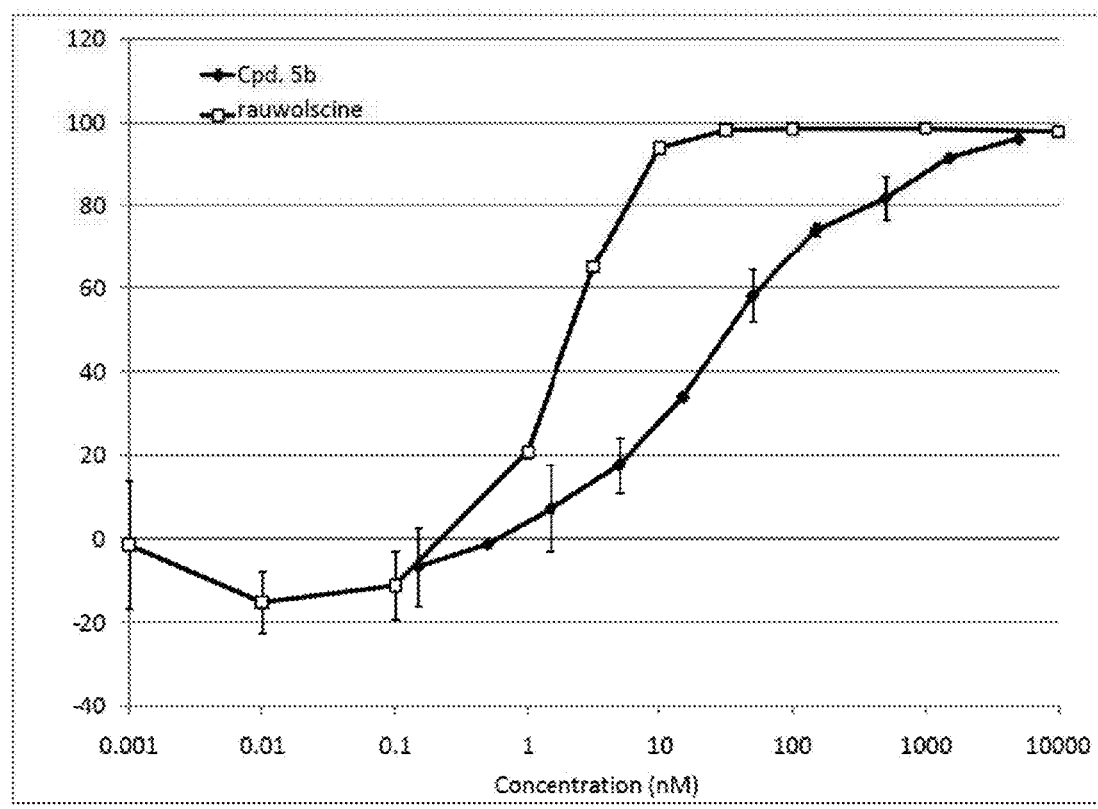
FIG. 6 illustrates the inhibitory effects of Compound No. 5b in a $\alpha_{2B}$ receptor in a cell-based activity assay.

Aequorin Assay Procedure:

Aequorin adrenergic $\alpha_{1B}$ (FAST-008A) (FIG. 5), adrenergic $\alpha_{2A}$ (FAST-006A) (FIG. 3) or adrenergic $\alpha_{2B}$ (FAST-007A) (FIGS. 1, 2, 3, 6) cells were grown 18 h prior to the test in media without antibiotics. They were then detached by gentle flushing with PBS-EDTA (5 mM EDTA), recovered by centrifugation and re-suspended in "assay buffer" (DMEM/HAM's F12 with HEPES+0.1% BSA protease free). Cells were incubated at RT for at least 4 h with Coelenterazine h (Molecular Probes). Dose response curves with reference compounds were performed before testing the compounds of the invention. The $\alpha_{1B}$ reference agonist and antagonist were cirazoline and qinazoline, respectively. The $\alpha_{2A}$ reference agonist and antagonist were UK14,304 and rauwolscine, respectively. The $\alpha_{2B}$ reference agonist and antagonist were oxymetazoline and rauwolscine, respectively.

For agonist testing, 50 μL of cell suspension were injected on 50 μL of test compound or reference agonist plated in a 96-well plate. The resulting emission of light was recorded using the Hamamatsu Functional Drug Screening System 6000 (FDSS 6000). For antagonist testing, following an incubation of 15 min. after the first injection, 100 μL of reference agonist at a concentration corresponding to its $EC_{80}$ was injected on the 100 μL of the mixture of cell suspension and test compound. The resulting emission of light was recorded using the same luminometer as for agonist testing. To standardize the emission of recorded light (determination of the "100% signal") across plates and across different experiments, some of the wells contained 100 μM digitonin or a saturating concentration of ATP (20 μM). Plates also contained the reference agonist at a concentration equivalent to the $EC_{80}$ obtained during the test validation.

Agonist activity of test compound was expressed as a percentage of the activity of the reference agonist at its $EC_{100}$ concentration. Antagonist activity of test compound was expressed as a percentage of the inhibition of reference agonist activity at its $EC_{80}$ concentration.

Compounds were tested for agonist & antagonist activity at the human adrenergic $\alpha_{1B}$ (FAST-008A), adrenergic $\alpha_{2A}$ (FAST-006A) or adrenergic $\alpha_{2B}$ (FAST-007A) at the following nanomolar concentrations, in duplicate: Agonist (nM): 0.3, 1, 3, 10, 30, 100, 300, 1000, 3000, 10000; Antagonist (nM): 0.15, 0.5, 1.5, 5, 15, 50, 150, 500, 1500, 5000.

GTPγS Assay Procedure:

The procedure was carried out with the following: assay buffer [20 mM HEPES pH 7.4; 100 mM NaCl, 10 μg/mL saponin, 1 mM $MgCl_2$]; membranes [Recombinant CHO-K1-adrenergic $\alpha_{2B}$ membrane extracts thawed on ice and diluted in assay buffer to give 10 μg/well and kept on ice]; GDP [diluted in assay buffer to give 3 μM final concentration]; beads [PVT-WGA (Amersham, RPNQ0001), diluted in assay buffer at 0.5 mg/well]; GTPγ$^{35}$S [(PerkinElmer NEG030X), diluted in assay buffer to give 0.1 nM final concentration]; ligand [Guanfacine (Tocris, 1030) as reference agonist and Rauwolscine (Tocris, 891) as reference antagonist, diluted in assay buffer]. Membranes were mixed with GDP (volume:volume) and incubated for at least 15 min. on ice. In parallel, GTPγ[$^{35}$S] was mixed with the beads (volume:volume) just before starting the reaction.

For agonist testing, the following reagents were successively added in the wells of an Optiplate (Perkin Elmer): 50 μL of test or reference ligand, 20 μL of the membranes:GDP mix, 10 μL of assay buffer and 20 μL of the GTPγ[$^{35}$S]:beads mix. For antagonist testing, the following reagents were successively added in the wells of an Optiplate (Perkin Elmer): 50 μL of test or reference ligand, 20 μL of the membranes:GDP mix, and then after an incubation of 15 min. at RT, 10 μL of reference ligand at historical $EC_{80}$ concentration and 20 μL of the GTPγ[$^{35}$S]:beads mix.

The plates were covered with a top seal, mixed on an orbital shaker for 2 min, and then incubated for 1 h at RT. Then the plates were centrifuged for 10 min. at 2000 rpm, incubated at $R_T$ 4 h and counted for 1 min/well with a Perkin Elmer TopCount reader.

Figure 4:
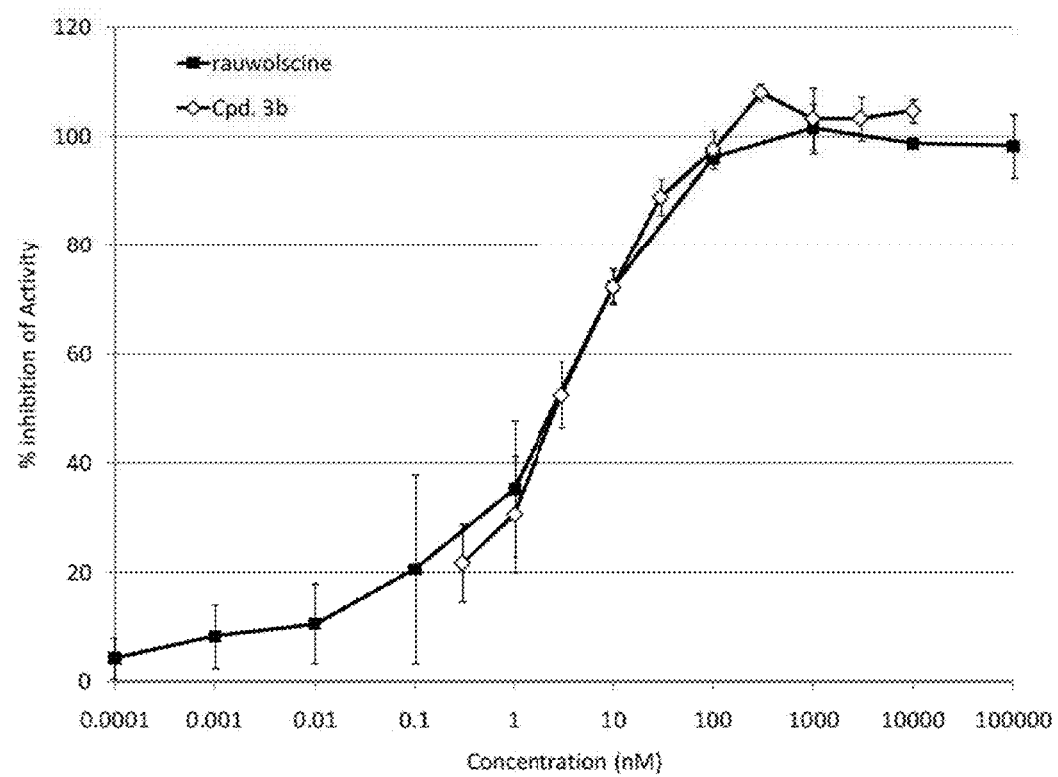
FIG. 4 illustrates the inhibitory effects of Compound No. 3b in a human $\alpha_{2B}$ cell membrane-based GTPgS binding activity assay (24 nM cirazoline (EC80)).

Compounds were tested for antagonist activity at the human adrenergic $\alpha_{2B}$ receptor (FAST-007G) (FIG. 4) at the following nanomolar concentrations, in duplicate: Agonist and antagonist (nM): 0.3, 1, 3, 10, 30, 100, 300, 1000, 3000, 10000.

Inverse Agonist Activity

Figure 28:
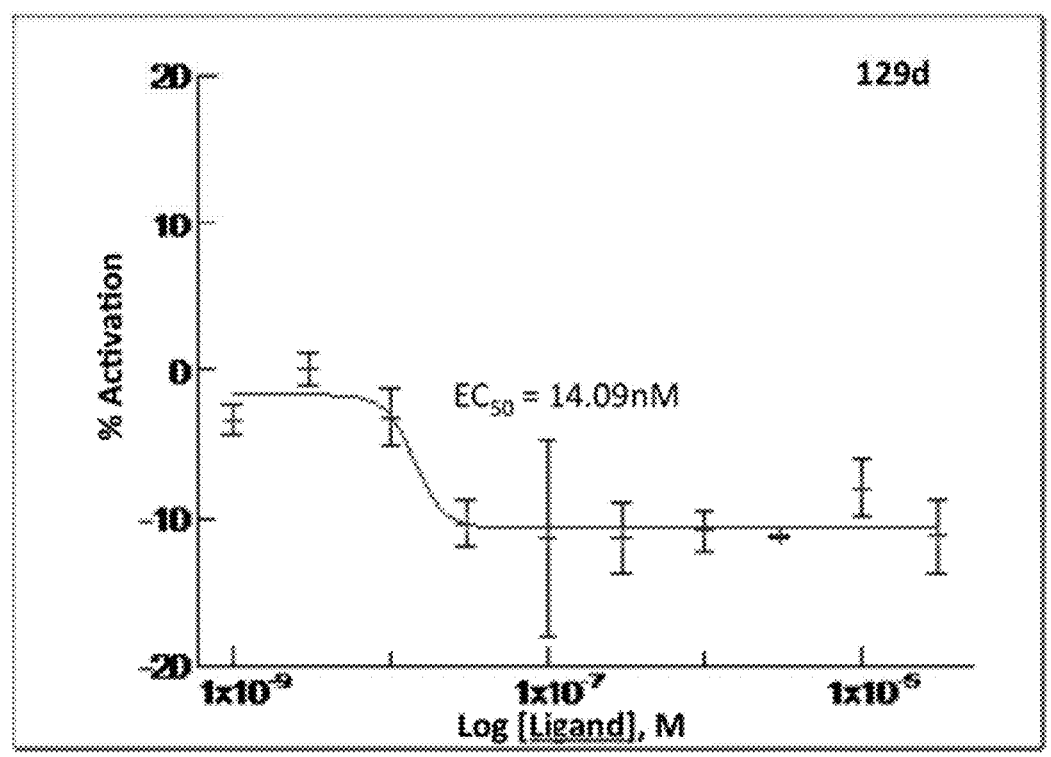
FIG. 28 illustrates Compound No. 129d in a human adrenergic $\alpha_{2A}$ receptor inverse agonist activity assay (using GTPg35S binding functional assay).

SPA 35S-GTPgS and Radioligand Binding experiments were conducted with Euroscreen membrane preparations. Compound was tested for inverse agonist activity at the human Adrenergic a2A receptor using GTPg35S binding functional assay (FAST-006G) in dose-response and in duplicates. As shown in the FIG. 28, Compound 129d showed inverse agonist activity to adrenergic $\alpha_{2A}$ receptor.

Example B3 Cell Culture and Cell Viability Assay

Figure 17A:
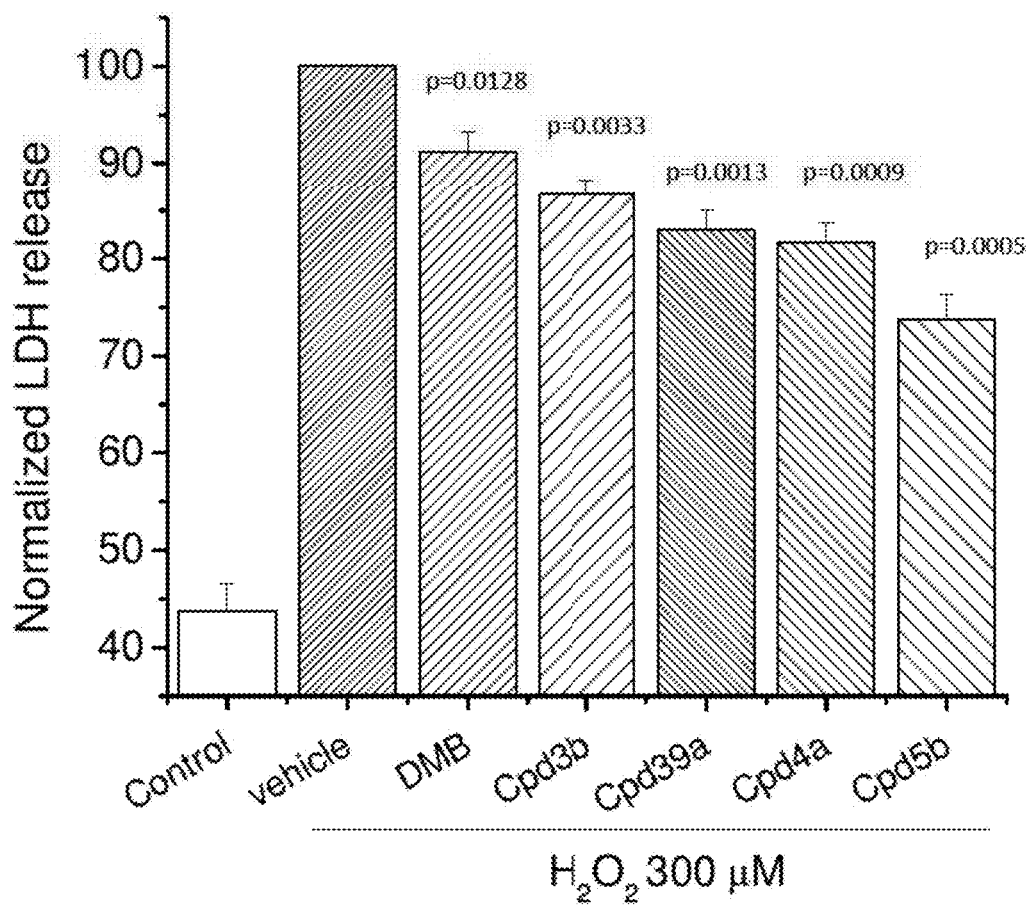
FIG. 17A illustrates the mitochondrial effects of Compound Nos. 3b, 4a, 5b and 39a and dimebon when subjected to hydrogen peroxide toxicity. The word "Dimebon" may be abbreviated as "DMB" in the figures.

SH-SY5Y cells cultured in DMEM/F12 media supplemented with 10% FBS were seeded in 96-well microplates at 150,000 cells/cm$^2$. After 24 h, cells were depleted from FBS and kept in culture for 24 h before the experiment. Cells were then treated with 4-Br-A23187 (2 μM), hydrogen peroxide (300 μM) or the mitochondrial toxin rotenone (25 μM) in the presence of vehicle or Compound of the Invention for 24 h. Cell death was determined by measurements of LDH release according to the Cytotoxicity Detection KitPlus (Roche, Mannheim, Germany). Cell viability was determined by measuring the capacity of cells to metabolize MTS tetrazolium (MTS) according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA). Compounds were screened at 10 nM, using DMSO as vehicle. Assay results for the experiments with hydrogen peroxide are presented as the LDH release (cell death) of untreated cells (control), hydrogen peroxide-treated cells (vehicle), and co-incubation of hydrogen peroxide with Compounds of the Invention treated cells normalized to the vehicle (FIG. 17A). This assay assesses the ability of the test compounds to protect against cell death that is mediated by mitochondrial dysfunction. In the assay, the calcium ionophore 4-Br-A23187 is used to challenge the cells, causing calcium levels to rise in mitochondria, which leads to depolarization and cell death. Test compounds are assessed for their ability to prevent cell death in response to challenge with 4-Br-A23187.

TABLE B3

Relative Cell Death protection of compounds of the invention

| Compound No. | Relative cell death protection | SE | p value |
|---|---|---|---|
| Control | 43.78 | 2.72 | <0.0001 |
| Vehicle | 100 | 0 | — |
| Dimebon (DMB) | 91.15 | 2.07 | 0.0128 |
| 3b | 86.70 | 1.55 | 0.0033 |
| 39a | 82.94 | 2.11 | 0.0013 |
| 4a | 81.64 | 2.06 | 0.0009 |
| 5b | 73.73 | 2.55 | 0.0005 |

Figure 17B:
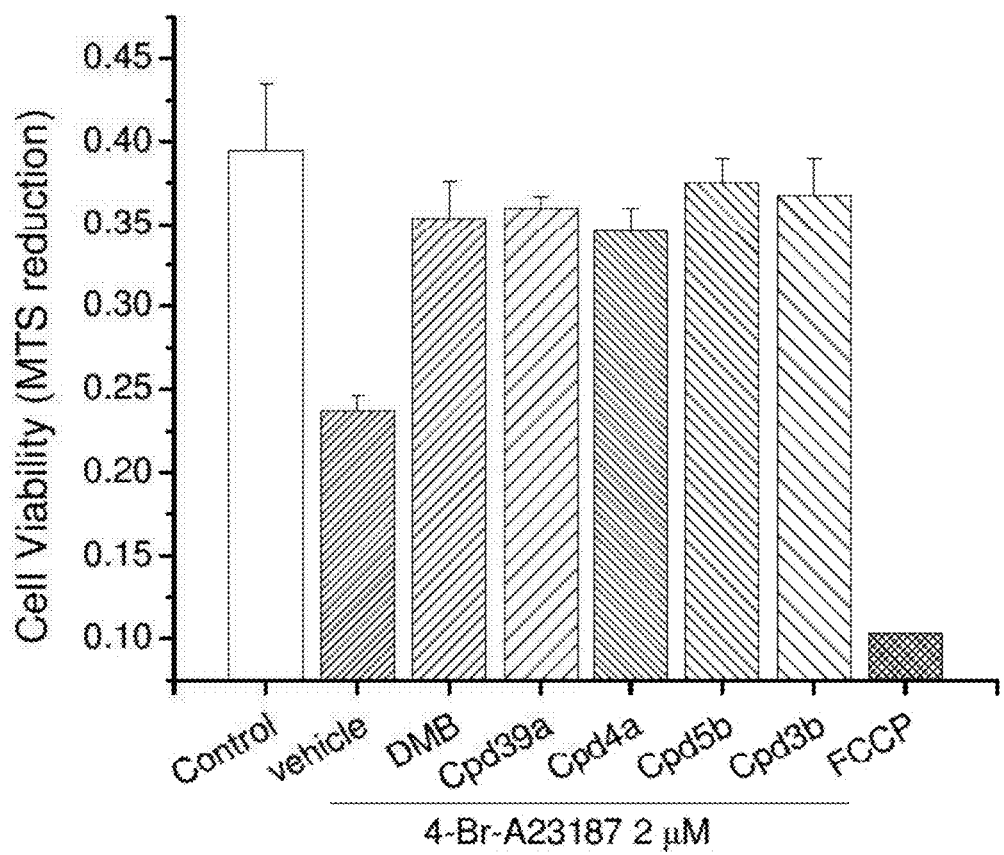
FIG. 17B illustrates the mitochondrial effects of Compound Nos. 3b, 4a, 5b and 39a and dimebon when subjected to calcium overload toxicity.

Assay results for the experiments with Br-A23187 are presented as the MTS reduction capacity (cell viability) of untreated cells (control), 4-Br-A23187-treated cells (vehicle), and co-incubation of Br-A23187 with Compounds of the Invention treated cells and using p-trifluoromethoxyphenylhydrazone (FCCP) at 10 μM for 30 min as a control (FIG. 17B)

TABLE B4

Relative cell viability protection of compounds of the invention

| Compound No. | Relative cell viability protection | SE | p value |
|---|---|---|---|
| Control | 0.3945 | 0.04025 | — |
| Vehicle | 0.23688 | 0.00966 | 0.0034 |
| Dimebon (DMB) | 0.35375 | 0.02209 | ns. |
| 39$^a$ | 0.36 | 0.00668 | ns. |
| 4$^a$ | 0.34625 | 0.01367 | ns. |
| 5b | 0.37475 | 0.01533 | ns. |
| 3b | 0.36725 | 0.0224 | ns. |
| FCCP | 0.1035 | 2.89E−04 | <0.0001 |

Example B4. Cell Culture and Cell Viability Assay

Cell Culture. SH-SY5Y cells stably transfected with a doxycyline-inducible wild-type α-synuclein (α-syn) gene along with control SH-SY5Y cells over-expressing the β-galactosidase (β-gal) gene (a gift from L. Stefanis, Division of Basic Neurosciences, Biomedical Research Foundation of the Academy of Athens, Athens, Greece) are cultured as described by Vekrellis et al. (Vekrellis K, Xilouri M, Emmanouilidou E, Stefanis L. (2009). Inducible over-expression of α-syn in human neuronal cells leads to caspase-dependent non-apoptotic death. J Neurochem 109, 1348-1362). In accordance with this method, cells are cultured and maintained in RPMI 1640, 10% fetal bovine serum supplemented with 250 μg/mL G418 and 50 μg/mL Hygromycin B. Expression of α-syn is switched off in stock cultures with doxycycline (2 μg/mL). For experimental procedures, cells are plated at (4–8×10⁴ cells/cm²) and differentiated in absence of doxycycline and in the presence of 20 μM all-trans retinoic acid (RA) (Sigma, St Louis, Mo., USA).

Viability Assay: Cells are cultured in 96-well plates. After 24 h, cells are treated with RA and Compounds of Invention at 0.1 and 10 nM in the absence of doxycyline. Culture medium with RA and drugs is fully replaced after 7 days. Cell viability is measured by the release of lactate dehydrogenase (LDH) from necrotic cells into the culture medium and by measuring the capacity of cells to metabolize MTS tetrazolium (MTS) after 14 days in culture. LDH leakage is assessed according to the Cytotoxicity Detection KitPlus (Roche, Mannheim, Germany) and MTS reduction is assessed by the CellTiter 96® AQueous One Solution Cell Proliferation assay (Promega Corporation, Madison, Wis., USA).

Figure 18A:
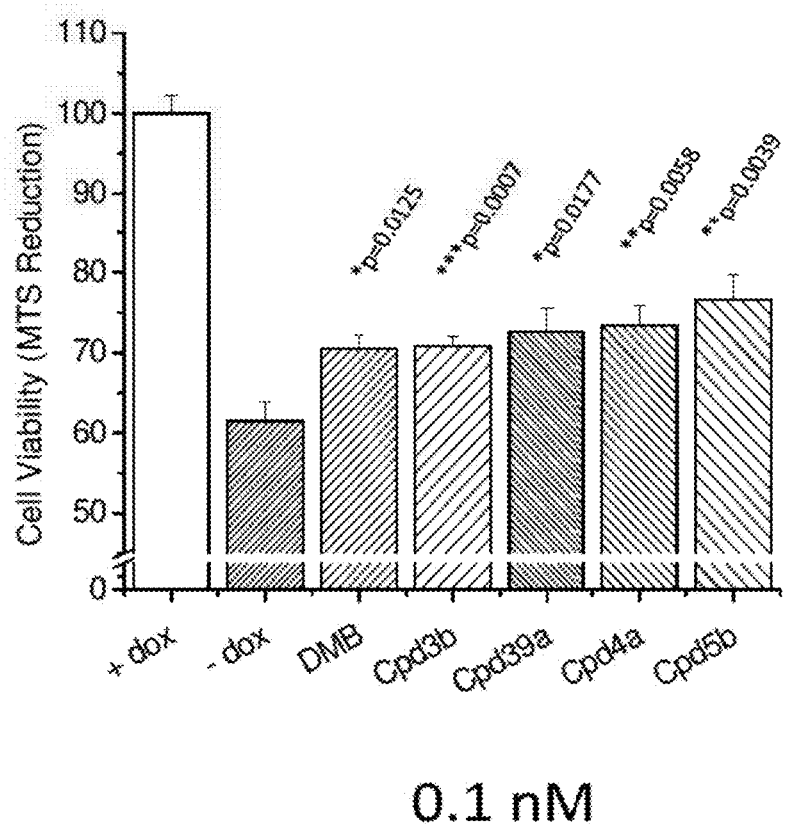
FIGS. 18A and 18B illustrate the cytoprotective effects of Compound Nos. 3b, 4a, 5b and 39a and dimebon from α-Synuclein (α-syn) toxicity.
Figure 18B:
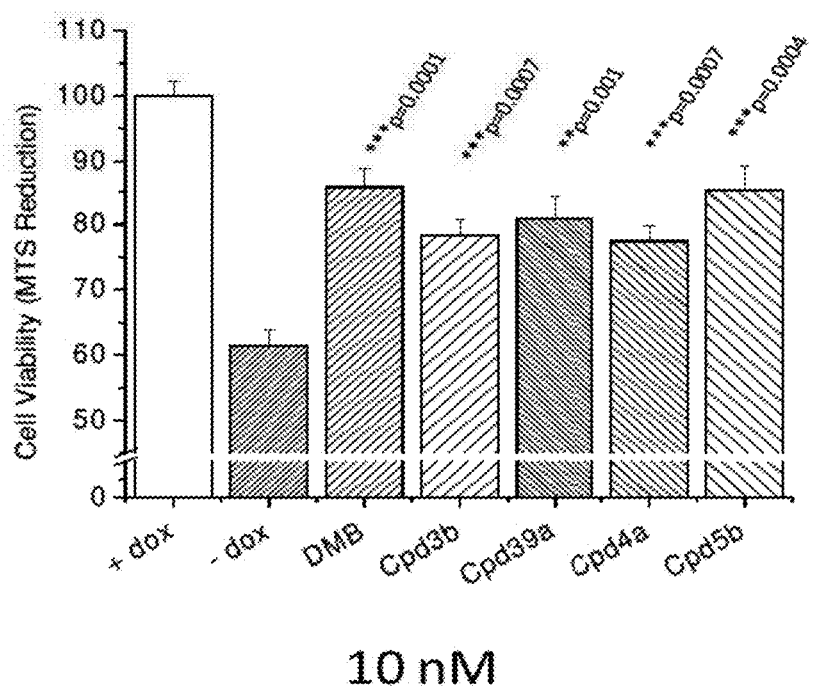

Assay results for the experiments with α-syn over-expression are presented as the MTS reduction capacity (cell viability) of control cells (+dox), cells over-expressing α-syn (−dox), and cells over-expressing α-syn incubated with Compounds of the Invention at 0.1 nM (FIG. 18A) or 10 nM (FIG. 18B).

TABLE B5

Relative cell viability protection of compounds of the invention at 0.1 nM (FIG. 17A)

| Compound No. | Relative cell viability protection | SE | p value |
|---|---|---|---|
| +dox (control) | 100 | 2.32 | |
| −dox | 61.46 | 2.42 | |
| Dimebon (DMB) | 70.53 | 1.74 | 0.0125 |
| 3b | 70.84 | 1.25 | 0.0007 |
| 39a | 72.53 | 3.07 | 0.0177 |
| 4a | 73.39 | 2.41 | 0.0058 |
| 5b | 76.52 | 3.24 | 0.0039 |

TABLE B6

Relative cell viability protection of compounds of the invention at 10 nM (FIG. 17B)

| Compound No. | Relative cell viability protection | SE | p value |
|---|---|---|---|
| +dox (control) | 100 | 2.32 | |
| −dox | 61.46 | 2.42 | |
| DMB | 85.70 | 3.10 | <0.0001 |
| Cpd3b | 78.32 | 2.54 | 0.0007 |
| Cpd39a | 80.85 | 3.48 | 0.001 |
| Cpd4a | 77.46 | 2.28 | 0.0007 |
| Cpd5b | 85.29 | 3.92 | 0.0004 |

Immunoblotting of α-Synuclein and α-Synuclein Aggregates: Cells stably expressing α-synuclein are cultured in 6-well plates at a density of 4×10⁴ cells/cm² cells per well. Cells are differentiated and treated with Compound of the Invention at 10 nM in absence of dox after 24 h of plating. Drug treatments are repeated after 7 days in freshly prepared medium containing RA. After 14 days, cells are washed twice with cold PBS and lysed in lysis buffer containing 1% Triton X-100, 20 mM HEPES, 150 mM NaCl, 10% glycerol, 1 mM EGTA, 1.5 mM MgCl$_2$, 1 mM PMSF pH 7.4, and 1× protease inhibitor mixture (Roche, Mannheim, Germany). Lysates are homogenized and subjected to four successive freeze-thaw cycles to disrupt membranes. Triton soluble fractions and triton insoluble pellets are obtained by ultracentrifugation at 100,000×g for 30 min at 4° C. The concentration of protein in each fraction is determined by BCA assay (Thermo Scientific). Samples from total, soluble and triton insoluble fractions, are boiled in 1× sample buffer (20 mM Tris, 1% glycerol, 180 mM (3-mercaptoethanol, 0.003% bromophenol blue, and 2% SDS, pH 6.8), loaded on 12% SDS-PAGE gels, and transferred to polyvinylidene difluoride (PVDF) membranes (0.2 μM-pore immobilon Biorad). Membranes are blocked in 1X TBS-Tween (20 mM Tris, pH 7.4, 150 mM NaCl, and 0.2% Tween 20) containing 5% milk for 1 h and incubated overnight at 4° C. with the following primary antibodies in blocking solution at the indicated dilutions: monoclonal anti-α-synuclein α-syn-1 (1:1000; BD Transduction Laboratories). (Perrin, R. J., Payton, J. E., Barnett, D. H., Wraight, C. L., Woods, W. S., Ye, L., and George, J. M. (2003). Epitope mapping and specificity of the anti-α-_synuclein monoclonal antibody Syn-1 in mouse brain and cultured cell lines. Neurosci Lett 349, 133-135), and monoclonal vimentin (1:1000; BD PharMingen). Primary antibodies are detected with secondary anti-mouse antibodies conjugated to HRP (1:5000).

Isolation of RNA and RT-quantitative PCR (RT-qPCR): SH-SY5Y cells stably over-expressing α-syn are treated with Compound of the Invention (10 nM). Total RNA from these cells as well as control cells not treated with Compound is extracted using the E.Z.N.A RNA extraction Kit (OMEGA-biotek, Norcross, Ga.). 1 μg of RNA is reverse transcribed to cDNA using the M-Mulv reverse transcriptase enzyme (Promega Corporation, Madison, Wis., USA). RT-qPCR of cDNA templates is carried out using TAQMAN probes for human α-synuclein (Hs00240906_M1) and TAQMAN masterMix (Applied Biosystems) and a Mx3005P real-time PCR system (Agilent Technologies Inc., Santa Clara, Calif.). Levels of alpha-tubulin mRNA are used to normalize the amounts of total RNA between samples. Fold changes are calculated as described by (Pfaffl, M. W. (2001). A new mathematical model for relative quantification in real-time RT-PCR. Nucleic Acids Res 29, e45).

Example B5. α$_{2B}$ Pharmacology: Studies in Spontaneously Hypertensive Rat (SHR) Model of Hypertension Male spontaneously hypertensive rats (SHR), approximately 3 months of age and weighting approximately 250 grams were utilized. Free access to standard lab chow for rats and reverse osmosis (RO) water was granted. All aspects of this work, including housing, experimentation and disposal of animals were performed in general accordance with the Guide for the Care and Use of Laboratory Animals (National Academy Press, Washington, D.C., 1996).

The animals were anaesthetized with sodium pentobarbital (50 mg/kg IP). The left carotid artery when compound dosed orally (PO) or subcutaneously (SC); and both left carotid and femoral artery when compound dosed intravenous (i.v.) were cannulated with a polyethylene catheter (38 cm in length; PE60, Portex, Ltd.) connected with a polyurethane tubing (12 cm in length; PU-40, Cat. #BB520-40, Scientific Commodities, Inc.), which was tunneled under the skin and exited through the nape of the neck. The arterial cannula was connected to a pressure transducer through a swivel system, allowing free roaming during continuous recording of mean arterial pressure and heart rate. The animals were housed individually with food and water freely available during recovery. On the following day, the arterial cannula was connected via a Statham (P 23×L) pressure transducer to a NEC/San-Ei amplifier and data acquisition and analysis system (Power Lab 8/SP) for direct mean arterial pressure and heart rate measurements.

The test compounds, dissolved in sterile saline, were administered subcutaneously (SC) or orally (PO), or by intravenous (i.v.) bolus administration in two minutes or the escalating doses of compound administration in every 30 minutes, with each dose and its strength delivered over 2 minutes as shown in the respective figures; the internal standard phentolamine was given by oral gavage. The control group received vehicle alone. Immediately before (−10 min and −5 min) and at 15 min, 30 min, 1 hr, 1.5 hr, 2 hr, 2.5 hr, 3 hr, 3.5 hr, and 4 hr post-dosing, systolic pressure blood pressure values were recorded.

Figure 7:
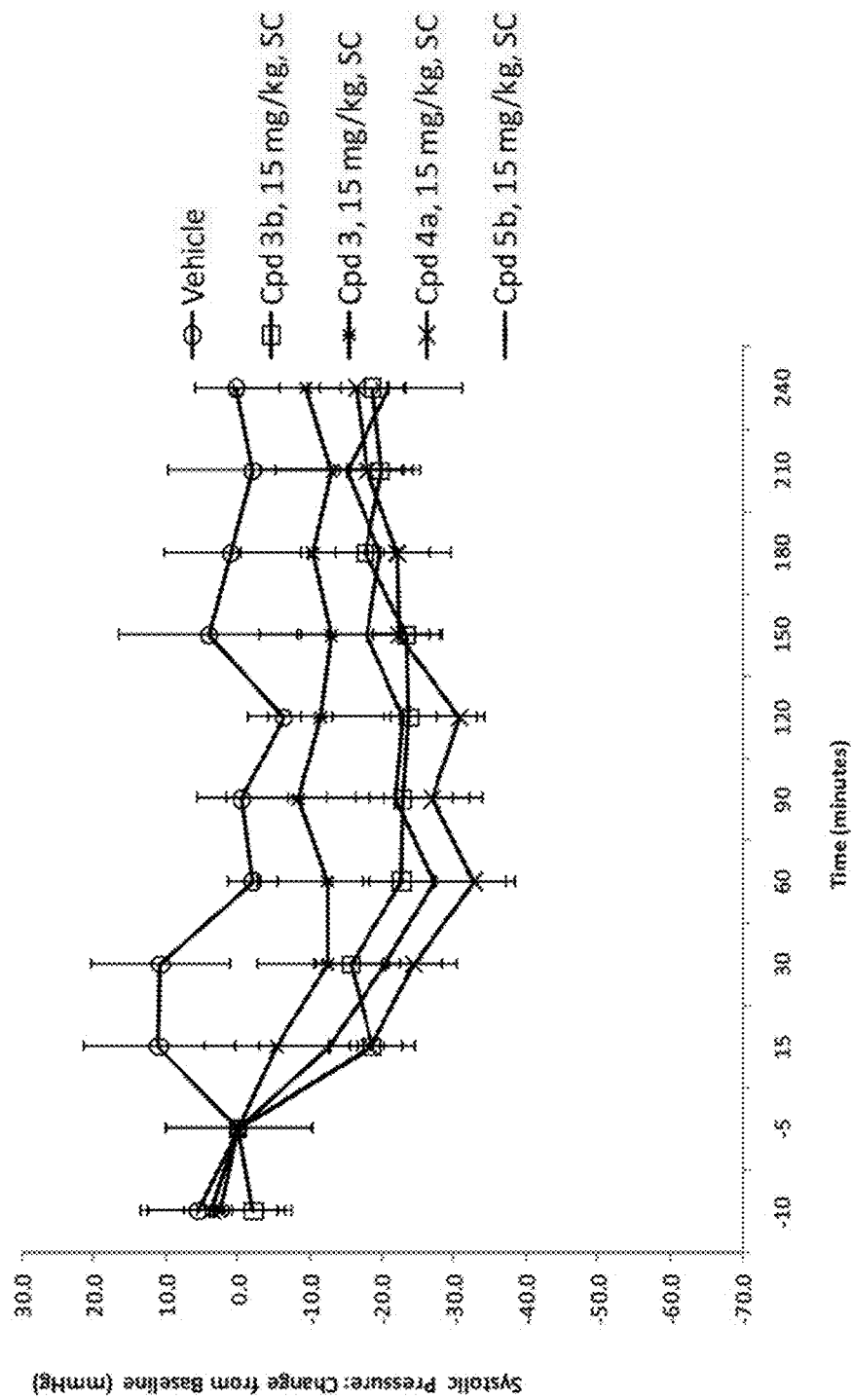
FIG. 7 illustrates the effects of Compound Nos. 3, 3b, 4a and 5b on Systolic Blood Pressure in a SHR model.
Figure 8:
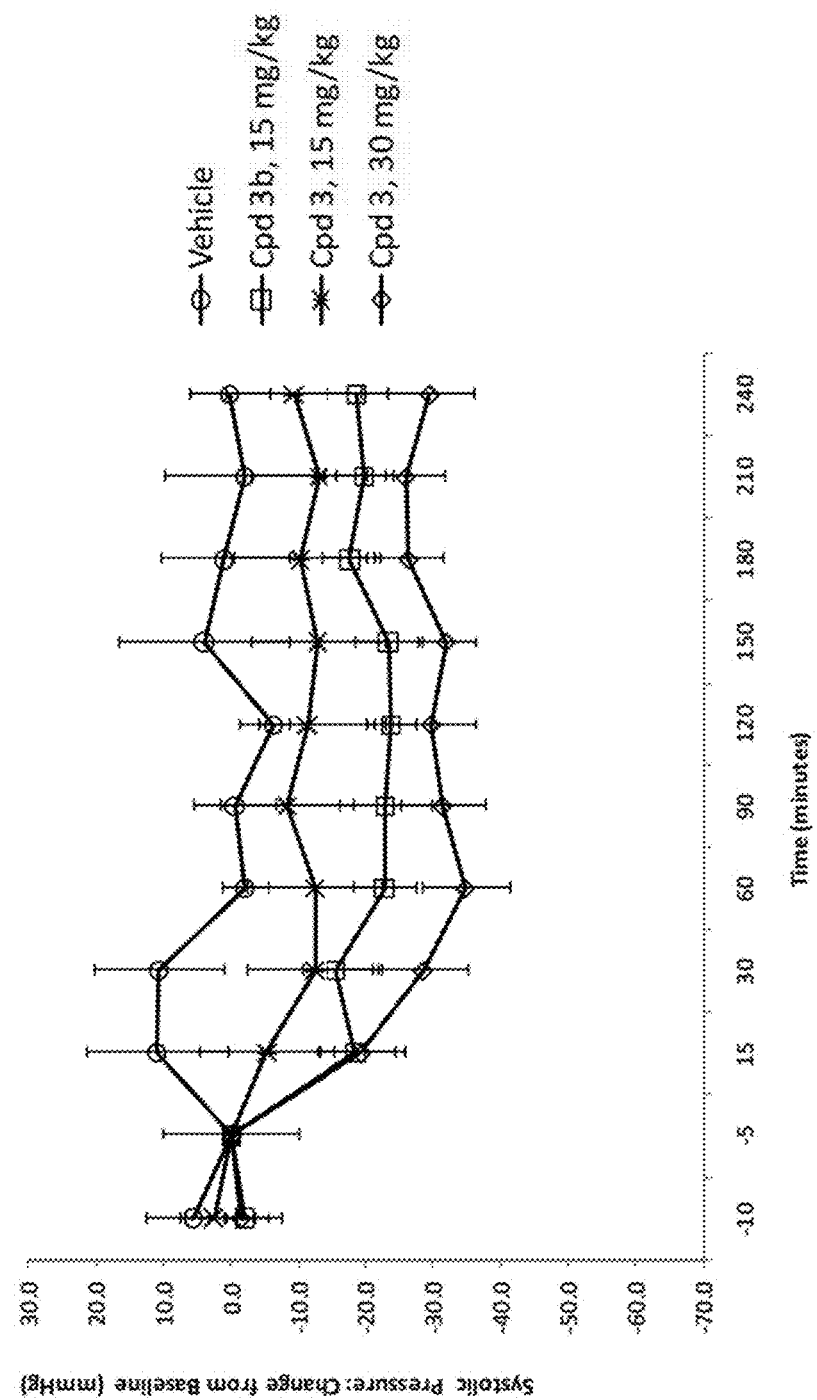
FIG. 8 illustrates the effects of Compound Nos. 3 and 3b (SC Treatment) on Systolic Blood Pressure in a SHR model.
Figure 9:
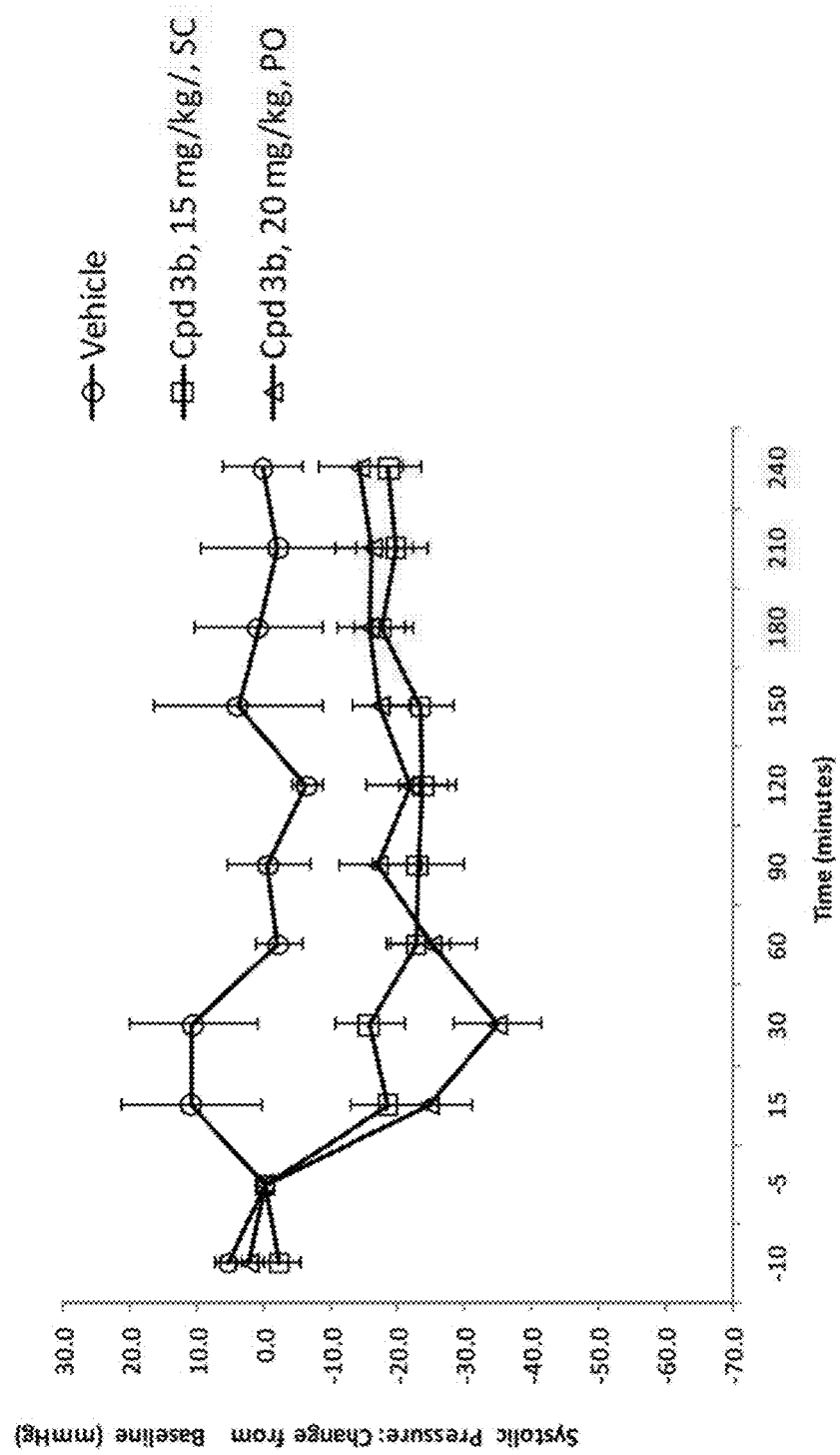
FIG. 9 illustrates the effects of Compound No. 3b on Systolic Blood Pressure in SHR model (administration: 15 mg/kg SC vs. 20 mg/kg PO).
Figure 10:
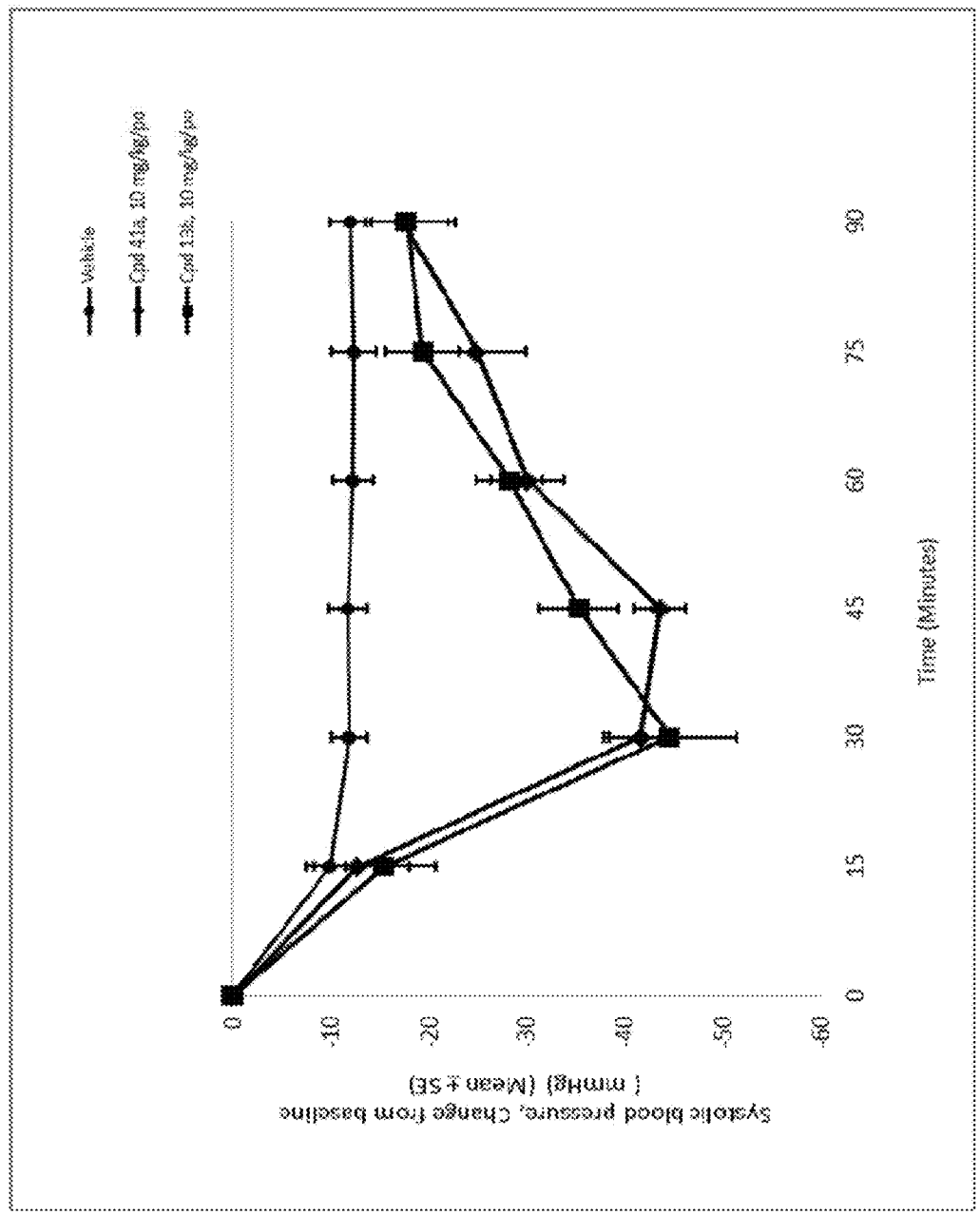
FIG. 10 illustrates the effects of Compound Nos. 13b and 41a on Systolic Blood Pressure in a SHR model.
Figure 19:
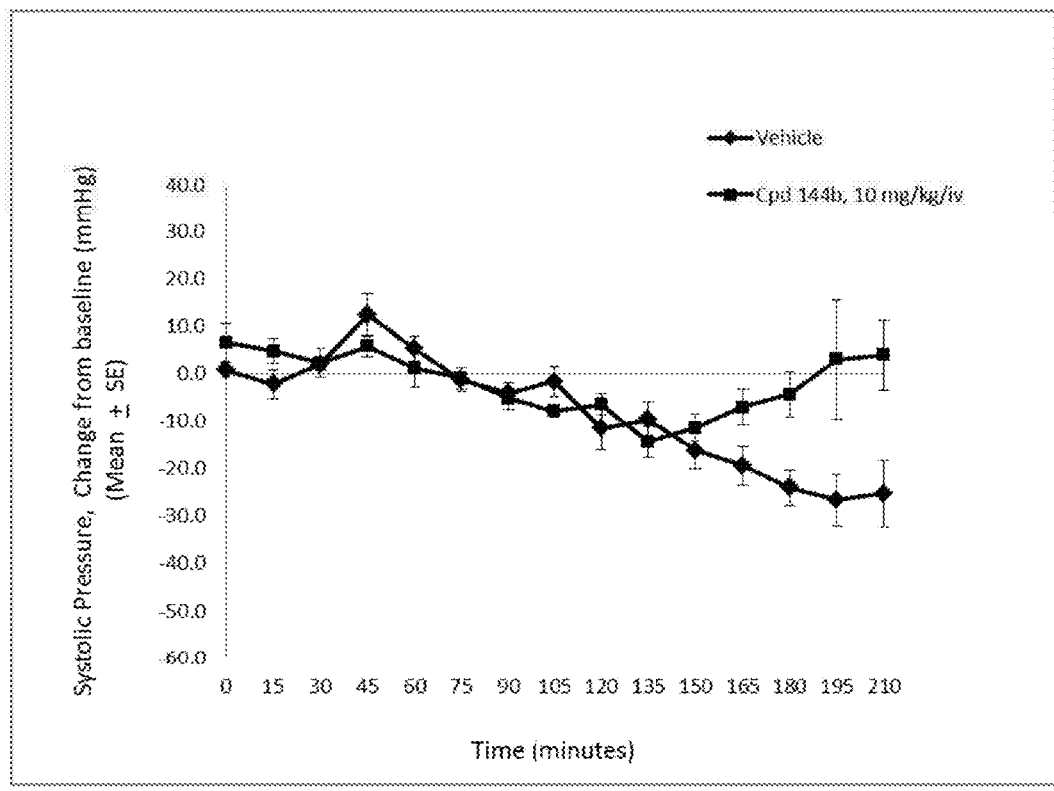
FIG. 19 illustrates the effects of Compound No. 144b (10 mg/kg, i.v.) in SHR model on Systolic Blood Pressure (Change from baseline).
Figure 20:
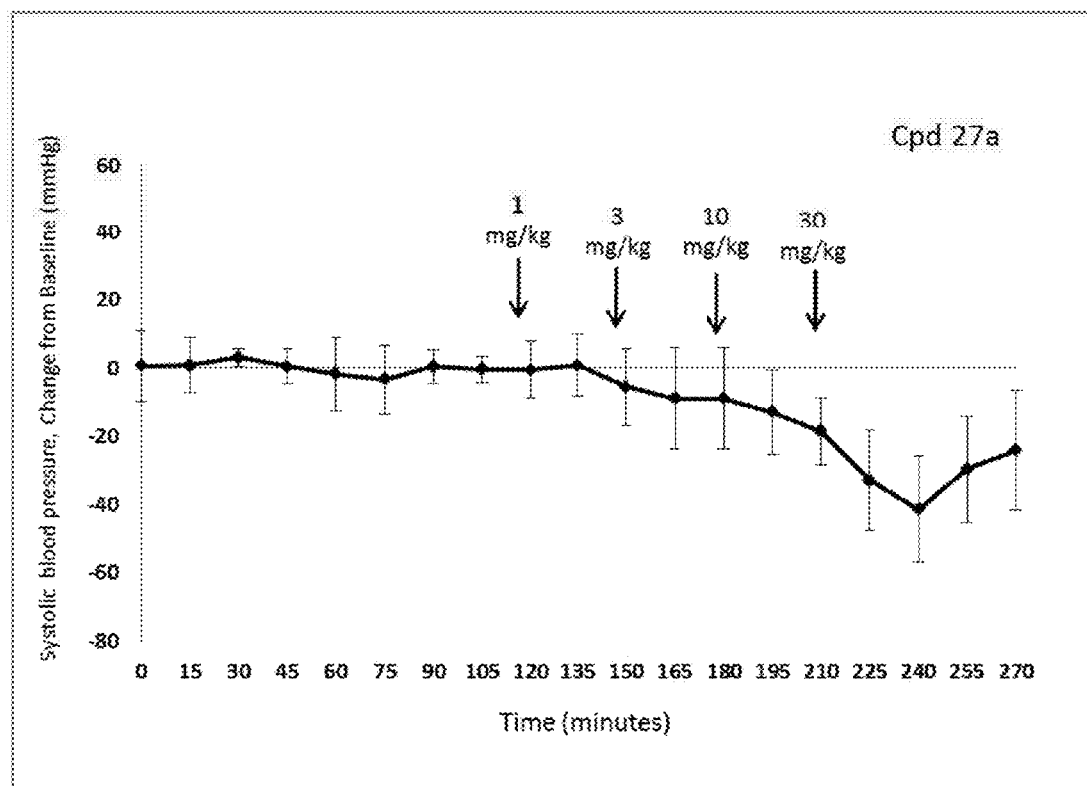
FIG. 20 illustrates the effects of Compound No. 27a in SHR on Systolic Blood Pressure in an i.v. dose escalation model (Change from baseline).
Figure 21:
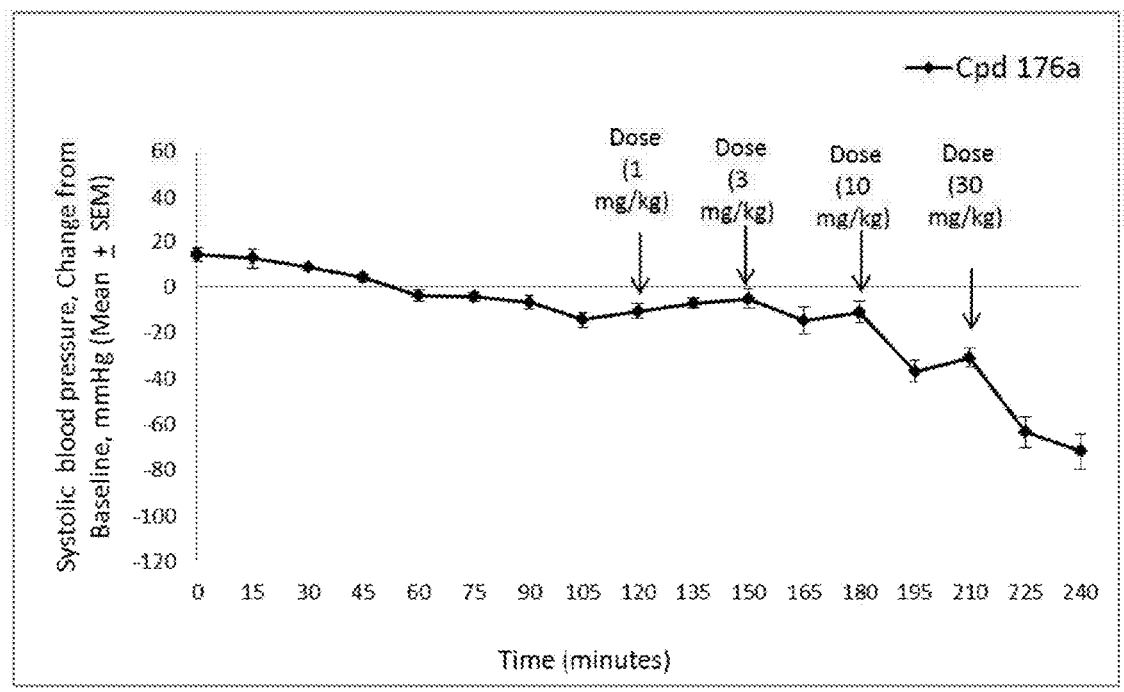
FIG. 21 illustrates the effects of Compound No. 176a in SHR on Systolic Blood Pressure in an i.v. dose escalation model (Change from baseline).
Figure 22:
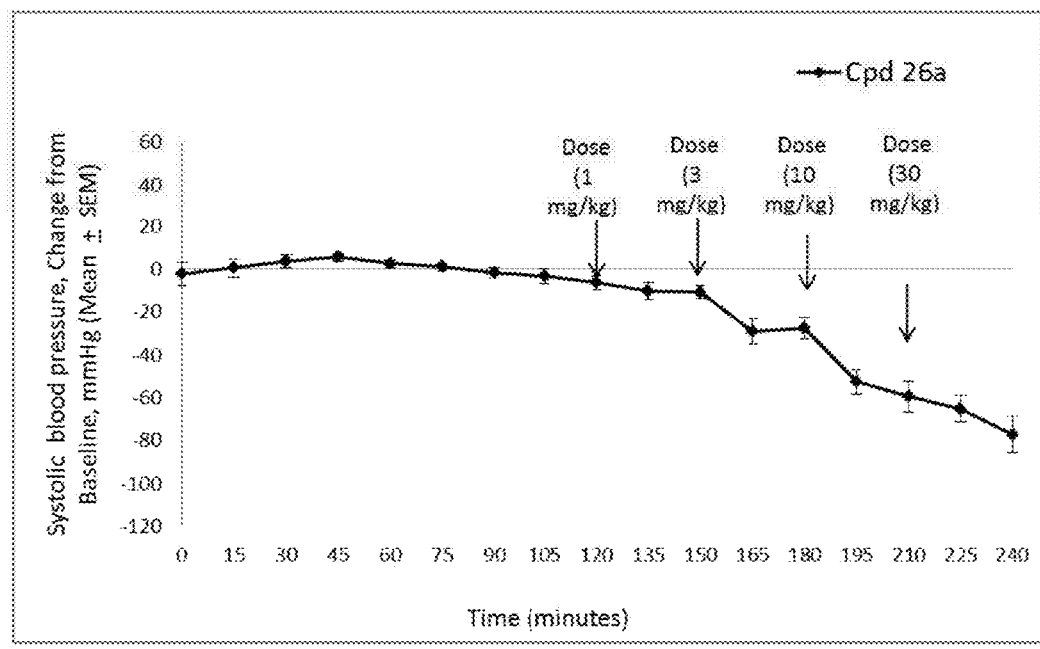
FIG. 22 illustrates the effects of Compound No. 26a in SHR on Systolic Blood Pressure in an i.v. dose escalation model (Change from baseline).

Certain compounds of the invention, when they were administered SC route or PO, remarkably lowered systolic blood pressure from 15 minutes through 2.5 hours and the effect was still evident throughout the 4 hour study period (See FIG. 7). In addition, compound 3 was associated with a dose-dependent reduction in systolic blood pressure throughout the 4 hour study period (FIG. 8). As illustrated, compound 3b (FIG. 9) and compound 13b (FIG. 10) lowered systolic blood pressure in SHR rats. Compound 41a, a mixed inhibitor of $\alpha_{2B}$ and $\alpha_{1B}$ markedly lowered blood pressure in SHR rats (FIG. 10). When Compound 144b was tested i.v. bolus in 2 minutes, a marked reduction in systolic blood pressure was found (FIG. 19). Compound 27a, Compound 176a and Compound 26a were tested escalating doses (1, 3, 10 and 30 mg/kg/iv for every 30 minutes), their systolic blood pressure lowering effects were robust (FIG. 20, FIG. 21, and FIG. 22 respectively). Compound 27a had a neutral effect on heart rate when systolic blood pressure falls suggesting a peripheral effect (data not shown).

Example B6. $\alpha_{2B}$ Pharmacology: Studies in Healthy Dogs and Dexmedetomidine (DEX) Induced Beagle Dog Model of Hypertension These studies were conducted in both acute and chronic modes.

Four adult beagle dogs of both sex and weighted around 10 kg were chosen for the acute studies after a preliminary qualitative electrocardiogram/ECG, clinical pathology and physical examination. Upon arrival at the laboratory, the dogs were weighed and acclimated for a period of one week. Lab Diet certified canine diet #5007, PMI Nutrition International Inc was made available ad libitum to all dogs except during fasting periods. The dogs were surgically implanted with a pressure transducer equipped telemetry transmitter under sodium pentobarbitone anesthesia. The transmitter assembly was secured internally, the fluid-filled catheter was placed into an appropriate artery.

In the acute studies, the test compounds 3b and 5b at different doses (dosing sequences provided in Table B7 for compound 3b and Table B8 for compound 5b) was administered by oral gavage, 30 minutes prior to intravenous dexmedetomidine (5 µg/kg) challenge. Dexmedetomidine administration was enabled by prior placement of a peripheral intravenous line. The same four dogs were received all four treatments in the order noted in the table below, with at least a 3-day washout period between treatments.

TABLE B7

Acute dosing sequence for Compound 3b

| Compound 3b - 30 minute Pretreatment (mg/kg, p.o.) | Dexmedetomidine Challenge (µg/kg, i.v.) | Number of Dogs |
|---|---|---|
| 18 | 0 | 4 |
| 18 | 5 | 4 |
| 6 | 5 | 4 |
| 2 | 5 | 4 |

TABLE B8

Acute dosing sequence for Compound 5b

| Compound 5b - 30 minute Pretreatment (mg/kg, p.o.) | Dexmedetomidine Challenge (µg/kg, i.v.) | Number of Dogs |
|---|---|---|
| 0 | 5 | 4 |
| 2 | 5 | 4 |
| 6 | 5 | 4 |
| 18 | 5 | 4 |
| 2 | 0 | 4 |
| 6 | 0 | 4 |
| 18 | 0 | 4 |

In another acute study with compound 41a, the test agent was administered a dose of 6 mg/kg by oral gavage to 4 healthy dogs; and the blood pressure monitored for a period of 4 hours.

For the chronic study mode (see Table B9), the test compound 3b at 3 doses was administered by oral gavage once on day 1 and then twice/day on days 2 to 14, and finally once on day 15. The dexmedetomidine was administered on day-4 to check its effectiveness in inducing blood pressure, and once following the morning dose of compound 3b or vehicle on days 2, 7 and 14. Blood pressure and heart rate data were collected 1 h prior & 4 h post-morning dose on days 1, 2, 7, 14 and 15 to allow the appropriate data comparisons. Blood aliquots were saved at 4 h post-morning dose for exposure determination.

TABLE B9

Chronic dosing sequence and study design for Compound 3b

| Compound 3b—30 minute Pretreatment (mg/kg, p.o.) with b.i.d. regimen for 14 days | Dexmedeto- midine Challenge (µg/kg, i.v.) | Number of Dogs |
|---|---|---|
| 0 | 5 | 6 |
| 6 | 5 | 6 |
| 18 | 5 | 6 |

| | Day | | | | |
|---|---|---|---|---|---|
| | −4 | 1 | 2 | 7 | 14 | 15 |
| Compound dosed on | — | am | am/pm | from day 2 am/pm | to day 14 am/pm | am |
| DEX* | am | — | am | am | am | — |

*DEX administered 30 min following am dose of compound 3b.

In both acute and chronic studies, dogs were weighed before dosing. Cardiovascular evaluations at each dose of test compound were collected with animals gently restrained in a sling. Dogs were placed in the sling at least 1 hour prior to dose administration, and after at least 30 minutes of stable baseline data collection. The dogs were monitored continuously for 3-4 hours subsequent to test compound administration and summarized in 5-minute bins. The systolic blood pressure was collected. Data was reported as mean±SEM or mean as presented in the Figures.

Figure 11:
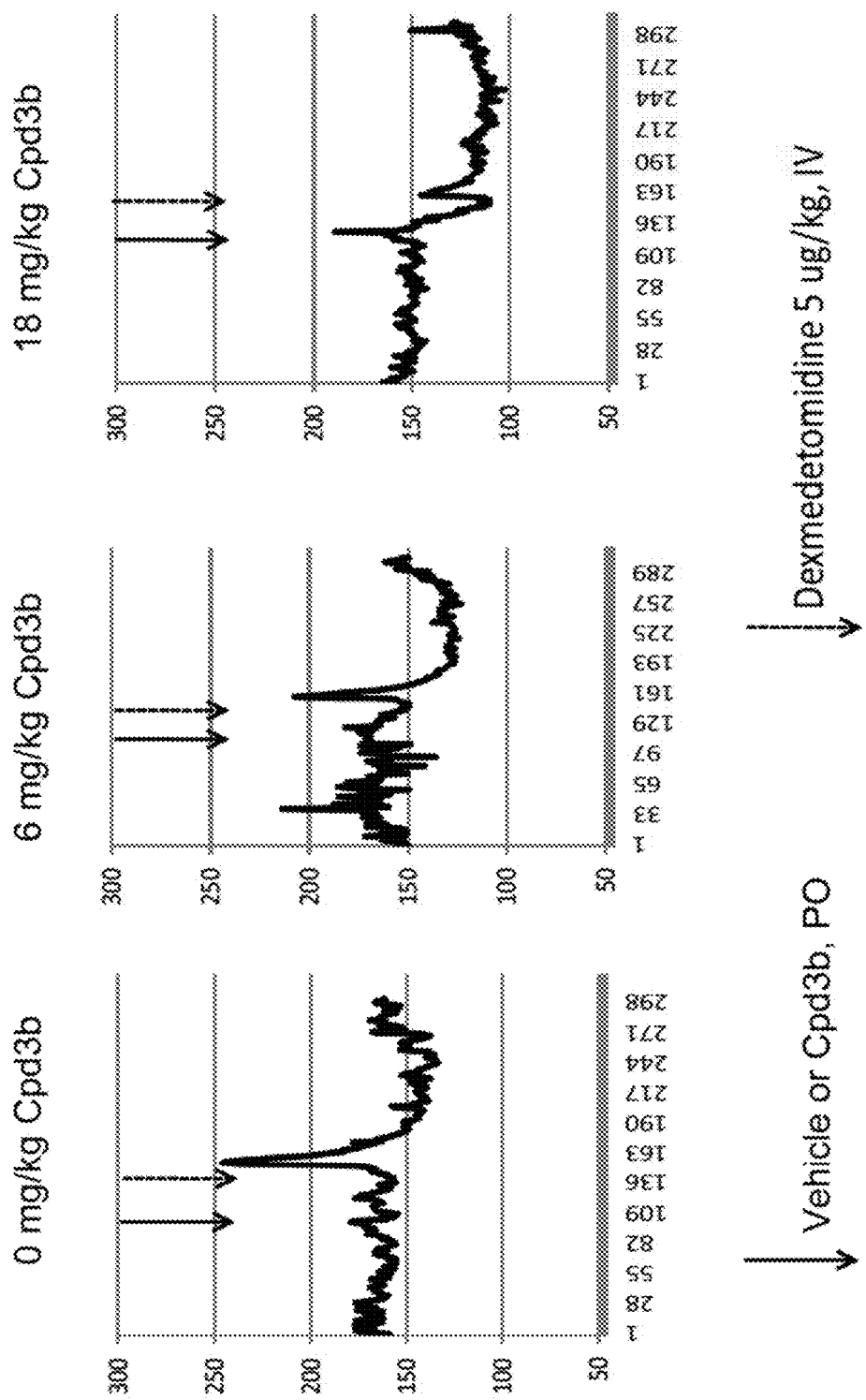
FIG. 11 illustrates the effect of Compound No. 3b on Systolic Blood Pressure in a dexmedetomidine induced dog model of hypertension.
Figure 12:
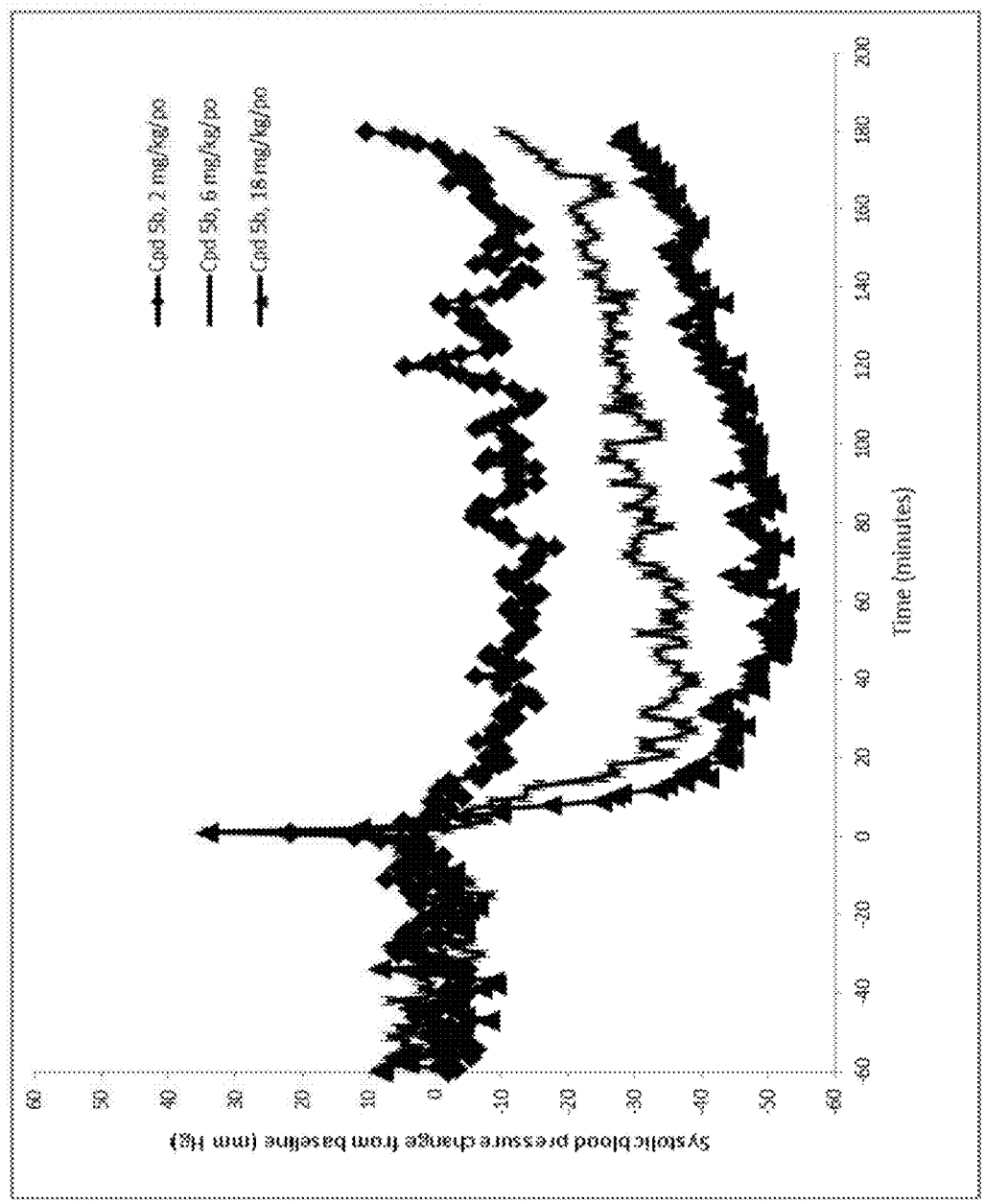
FIG. 12 illustrates the effect of Compound No. 5b on Systolic Blood Pressure in a dexmedetomidine induced dog model of hypertension.
Figure 13:
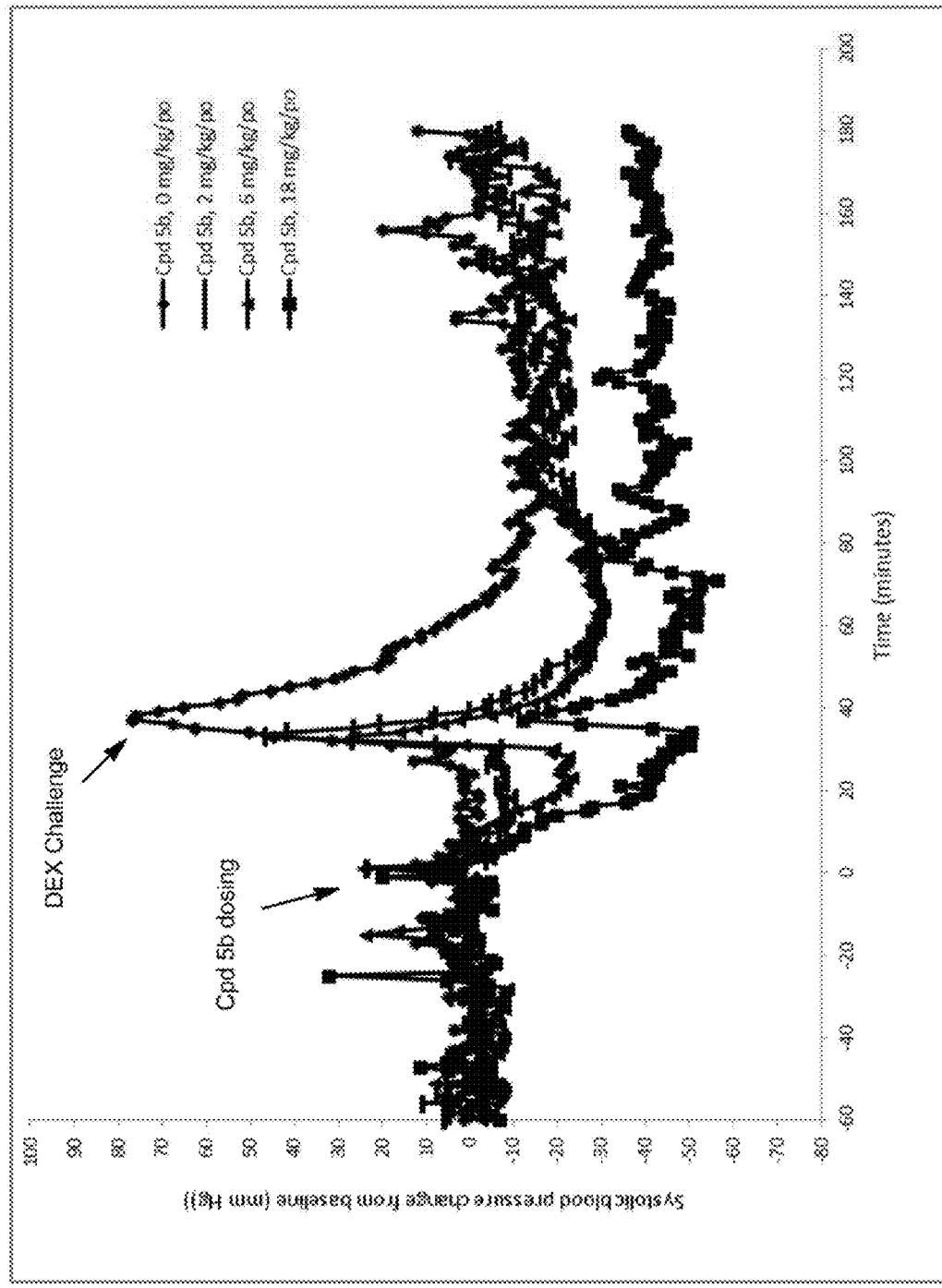
FIG. 13 illustrates the effect of Compound No. 5b on Systolic Blood Pressure in a dexmedetomidine induced dog model of hypertension, with DEX challenge.
Figure 14:
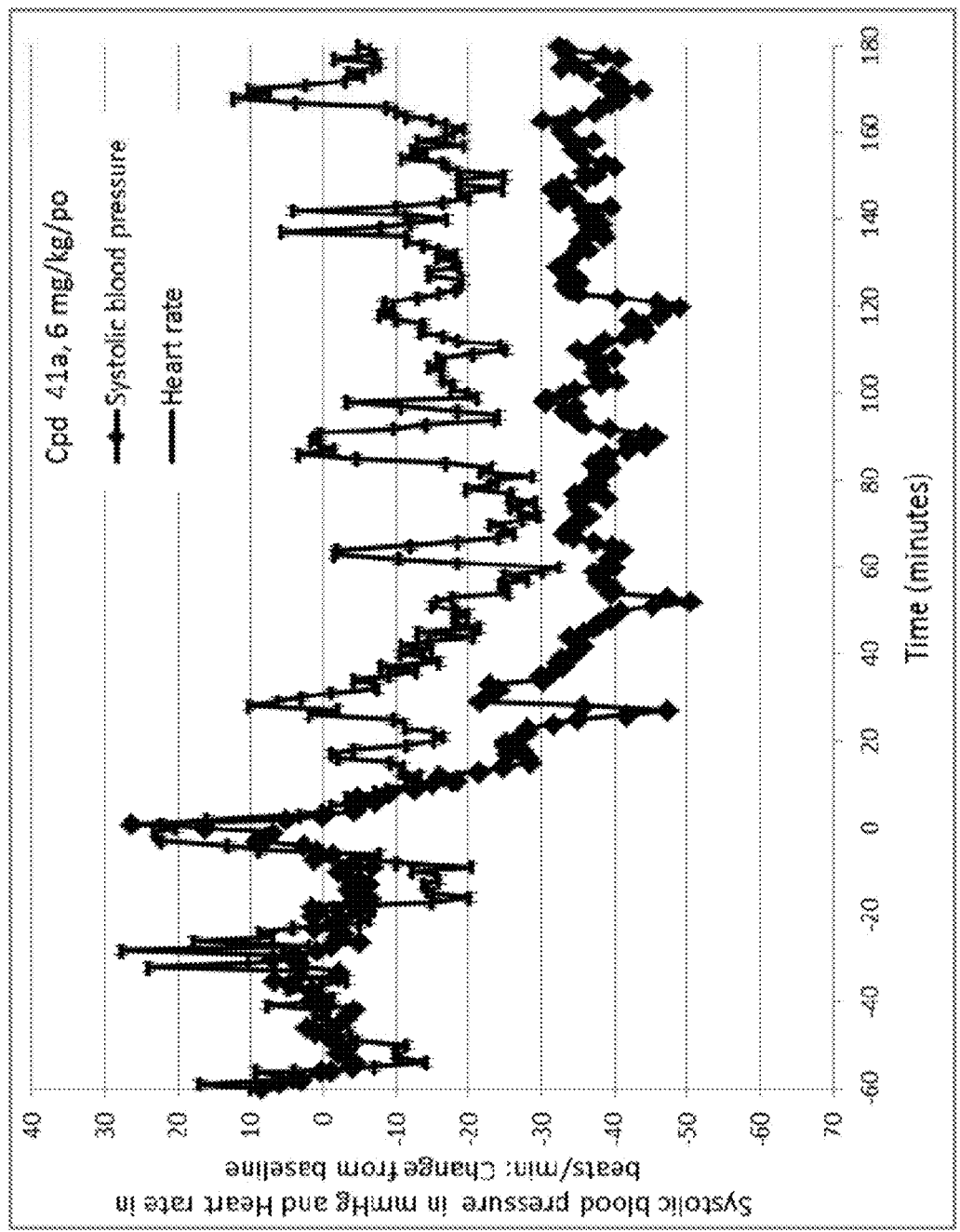
FIG. 14 illustrates the effect of Compound No. 41a on Systolic Blood Pressure in a dexmedetomidine induced dog model of hypertension.

In acute studies, oral administration of compound 3b dose-dependently reduced systolic blood pressure in both healthy and dexmedetomidine induced dogs that were tested in the acute mode. Data on dexmedetomidine induced dogs is presented in FIG. 11. Compound 5b as well dose-dependently reduced systolic blood pressure (FIG. 12) in both healthy and dexmedetomidine induced (FIG. 13) dogs tested. Compound 41a, mixed inhibitor of $\alpha_{2B}$ and $\alpha_{1B}$ caused a robust and long lasting reduction in systolic blood pressure (FIG. 14) in all the 4 healthy dogs, with a slight decrease or neutral effect but not with an expected raise on heart rate, i.e., blocking compensatory tachycardia when blood pressure falls suggests a peripheral mode of action. Compound 41a effects on several cardiovascular parameters and body temperature are also comparable with that of the same class (A1B) of marketed drug prazosin.

Figure 15:
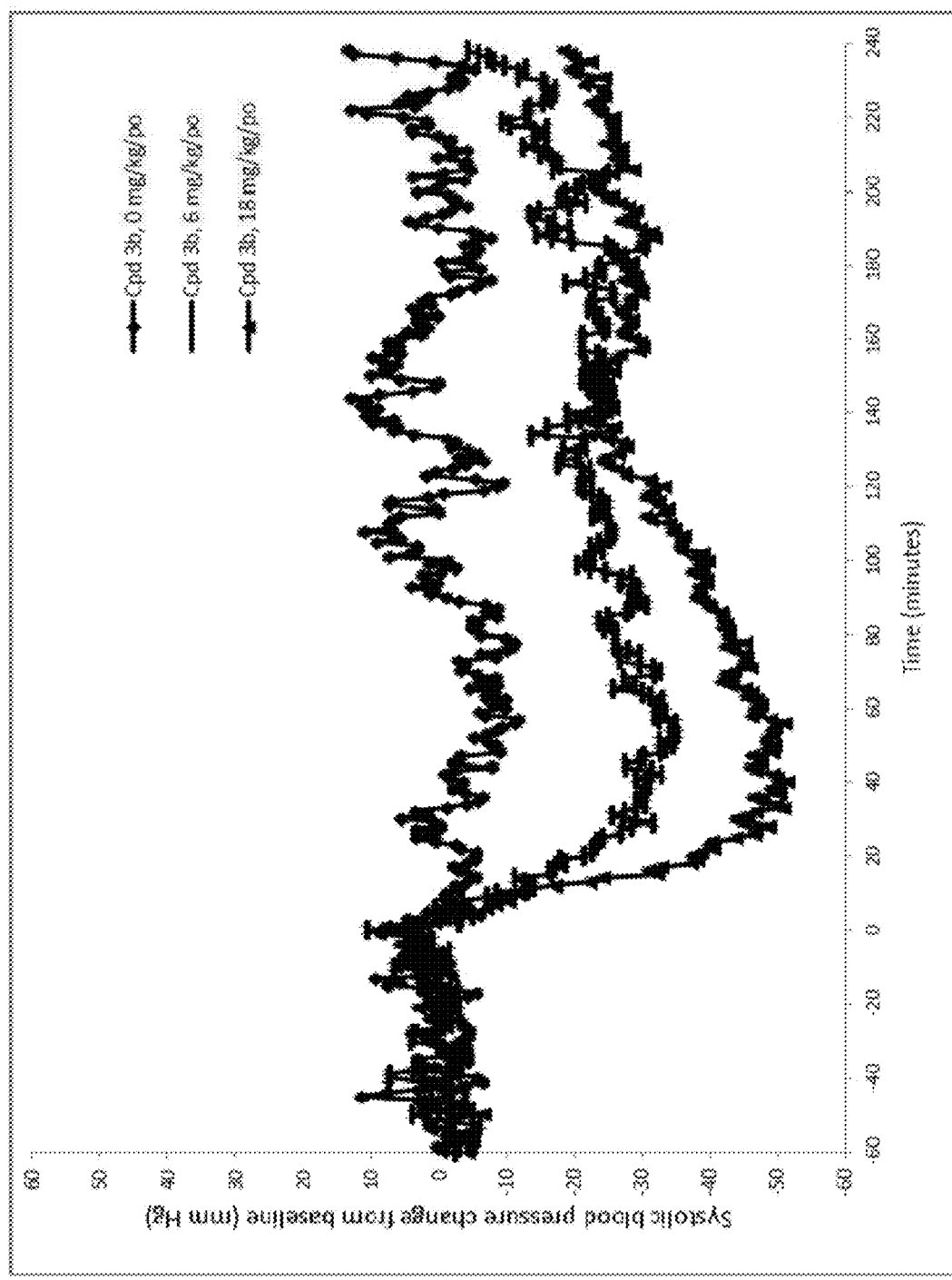
FIG. 15 illustrates the effect of Compound No. 3b on Systolic Blood Pressure in a dexmedetomidine induced dog model of hypertension—chronic mode, day 1.
Figure 16:
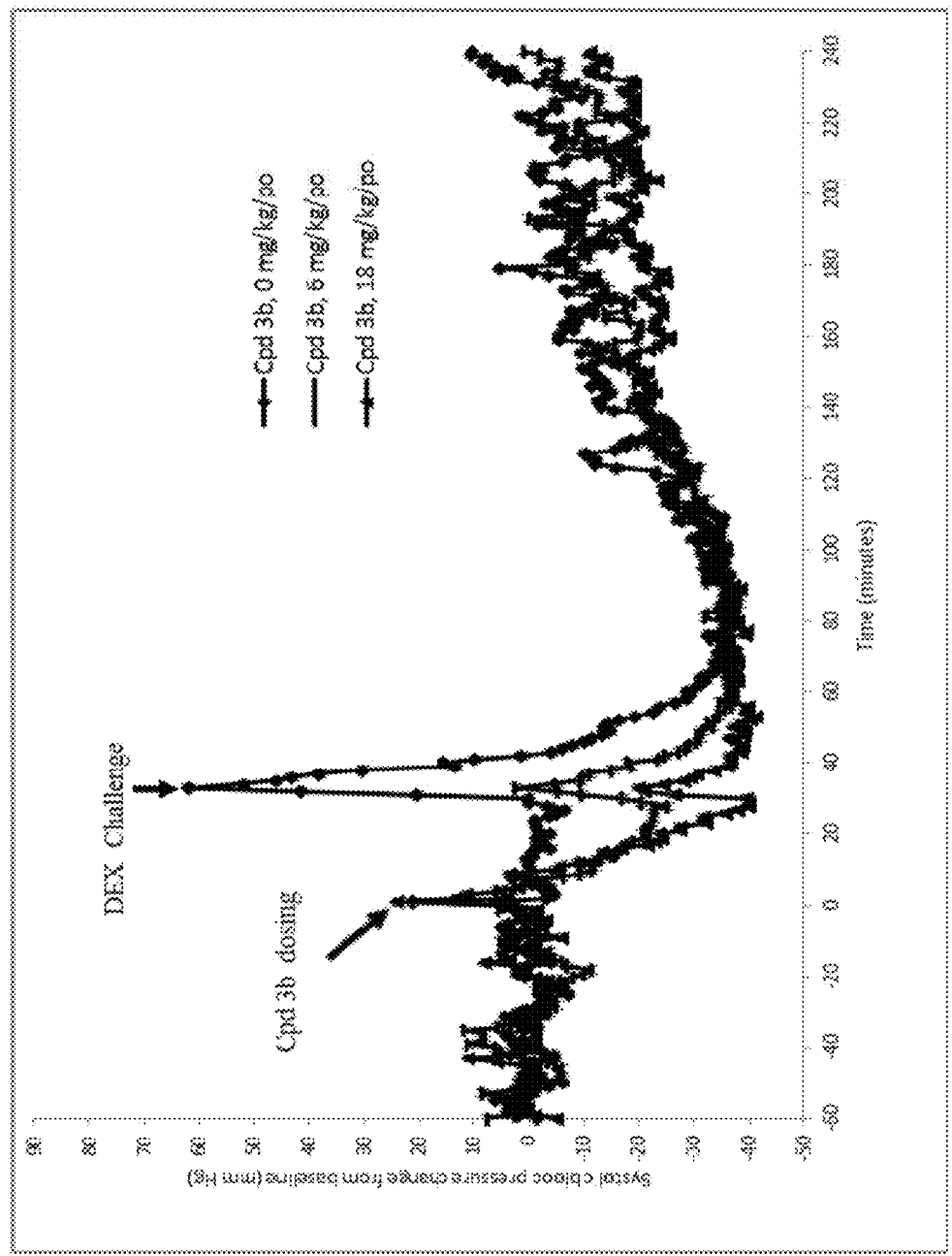
FIG. 16 illustrates the effect of Compound No. 3b on Systolic Blood Pressure in a dexmedetomidine induced dog model of hypertension—chronic mode, day 2.

In chronic studies, oral administration of compound 3b dose dependently reduced systolic blood pressure on day 1 and 15 in healthy dogs; and dexmedetomidine induced dogs on day, 2, 7 and 14 of the 15-day study. Data on systolic blood pressure on day 1 in healthy dogs and dexmedetomidine induced dogs on day 2 are shown in the FIG. 15 and FIG. 16, respectively.

Figure 23:
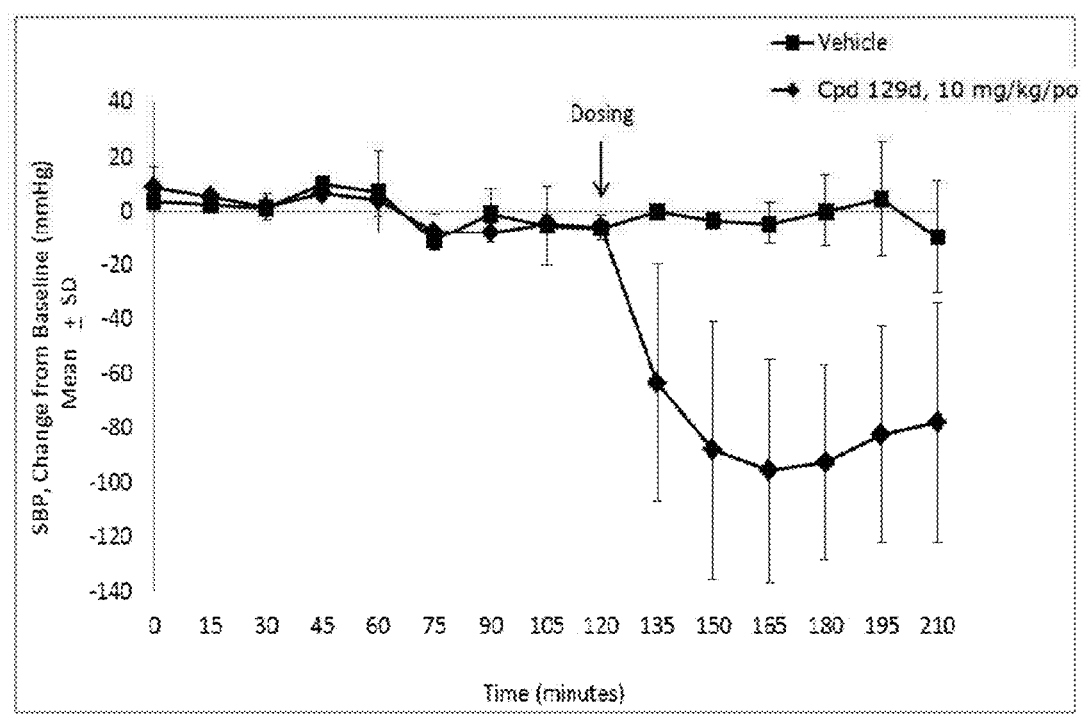
FIG. 23 illustrates the effect of Compound No. 129d (PO) on Systolic blood pressure in SHR rats.
Figure 24:
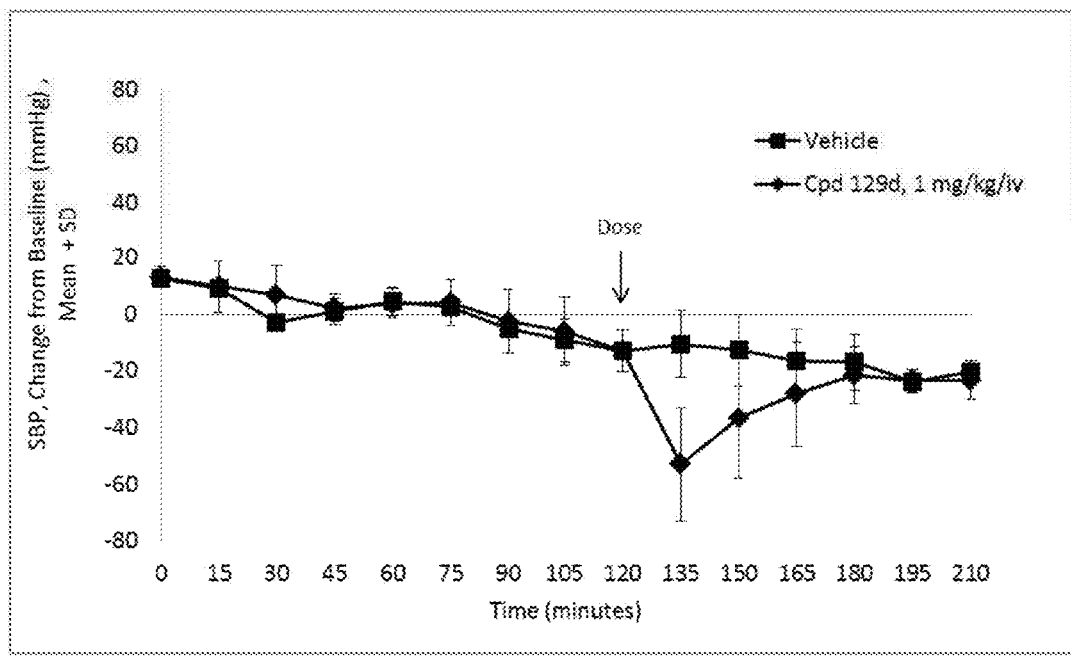
FIG. 24 illustrates the effect of Compound No. 129d (i.v., Bolus) on Systolic blood pressure in SHR rats.
Figure 25:
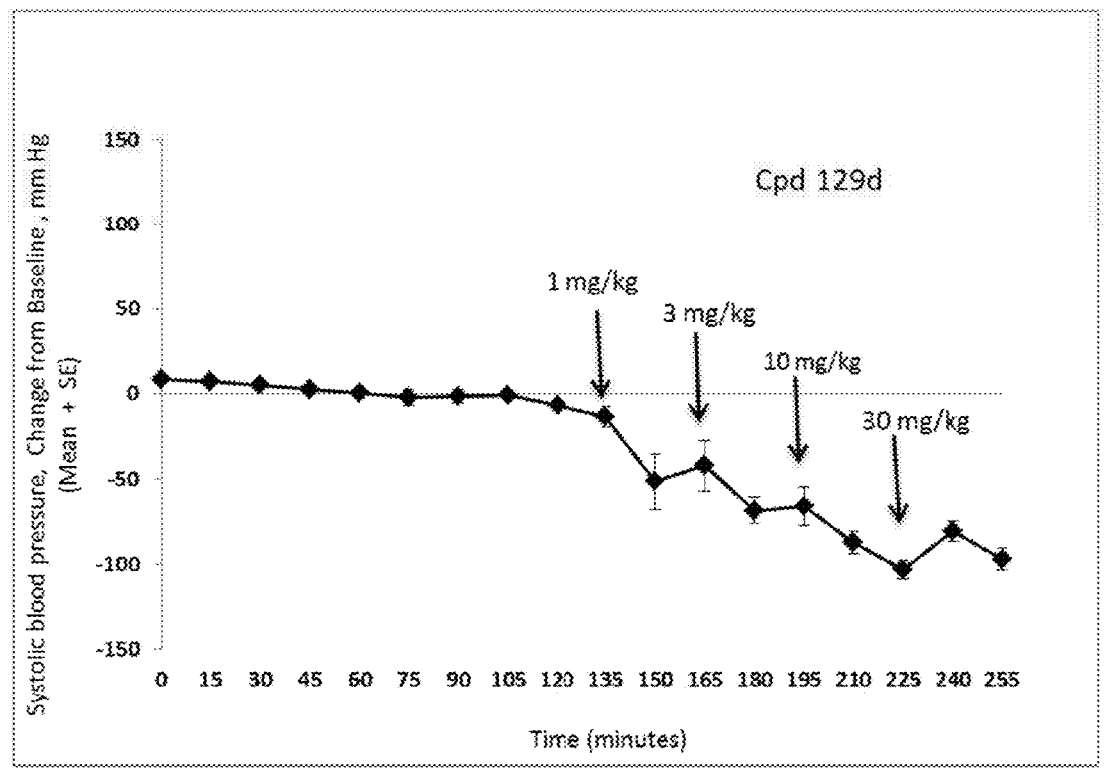
FIG. 25 illustrates the effect of Compound No. 129d (i.v., Escalating Doses) on Systolic blood pressure in SHR rats.

Adrenergic receptors $\alpha_{2B}$ and $\alpha_{2A}$ mixed inhibitor's pharmacology —Studies in Spontaneously Hypertensive Rat (SHR) Model of Hypertension: Similar to dosing regimen for selective antagonists of adrenergic receptor $\alpha_{2B}$, the mixed inhibitors (e.g., Compound 129d) was dosed orally (PO) or intravenous (i.v bolus or escalating doses) to SHR rats. When compound 129d was tested oral or iv bolus or i.v. escalating does, its effects on systolic blood pressure is robust (see FIG. 23, FIG. 24 and FIG. 25) with tachycardia; and it is a perfect example that a compound that is an adrenergic receptor $\alpha_{2B}$ antagonist also showing adrenergic receptor $\alpha_{2A}$ antagonist and/or inverse agonist activity may find use reducing blood pressure in an individual with hypertension who is also suffering from metabolic syndrome.

Example B7. Peripheral and Central Effects of Compound 3d on Blood Pressure in Conscious Rabbits Methods: Four adult New Zealand White rabbits of both sexes were chosen for these studies. The experiments were conducted in accordance with the Australian code of Practice for the Care and use of Animals for Scientific Purposes and approval was sought from the Animal Experimental Committee of Alfred Hospital, Baker IDI, Melbourne, Australia. The conscious rabbits were implanted with an intravenous catheter in marginal ear vein or by centrally by intracisternal catheter interfaced to a pressure transducer connected to a suitable recorder. To unveil peripheral effects of Compound 3b, two sets of acute studies were conducted in rabbits. In the first set of studies, Compound 3b was dosed to rabbit intravenously for a dose-response study with cumulative doses starting 0 (Ringer's Lock solution as a vehicle), 0.1, 0.3, 1, 3.2 and 10 mg/kg where each dose was tested on a separate day. A single intravenous bolus dose at 3 mg/kg was given and a time-course study was conducted in the second set of studies. Systolic, diastolic, mean and diastolic blood pressures were recorded in both the studies. Data collections were made for 3 hours in the second set of studies. Heart rate (HR) was derived electronically using an algorithm to determine HR from pulse interval. In a separate set of studies, Clonidine (positive control) was tested where all experimental procedures including dose-regimen were identical to that of the studies with Compound 3d.

Figure 26:
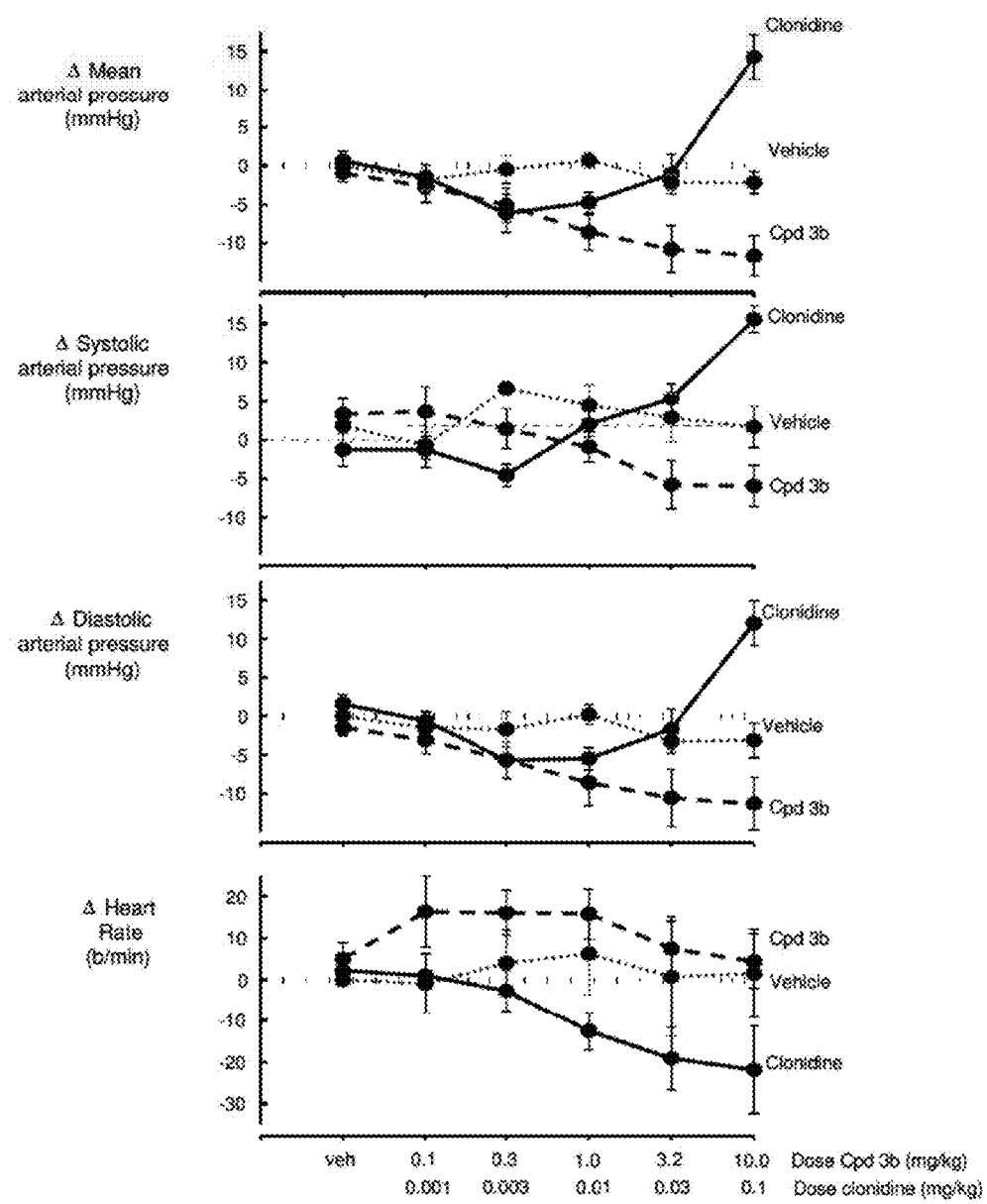
FIG. 26 illustrates the dose-response effects of Compound No. 3b, clonidine and vehicle on mean arterial blood pressure, systolic blood pressure, diastolic blood pressure and heart rate in rabbits.
Figure 27:
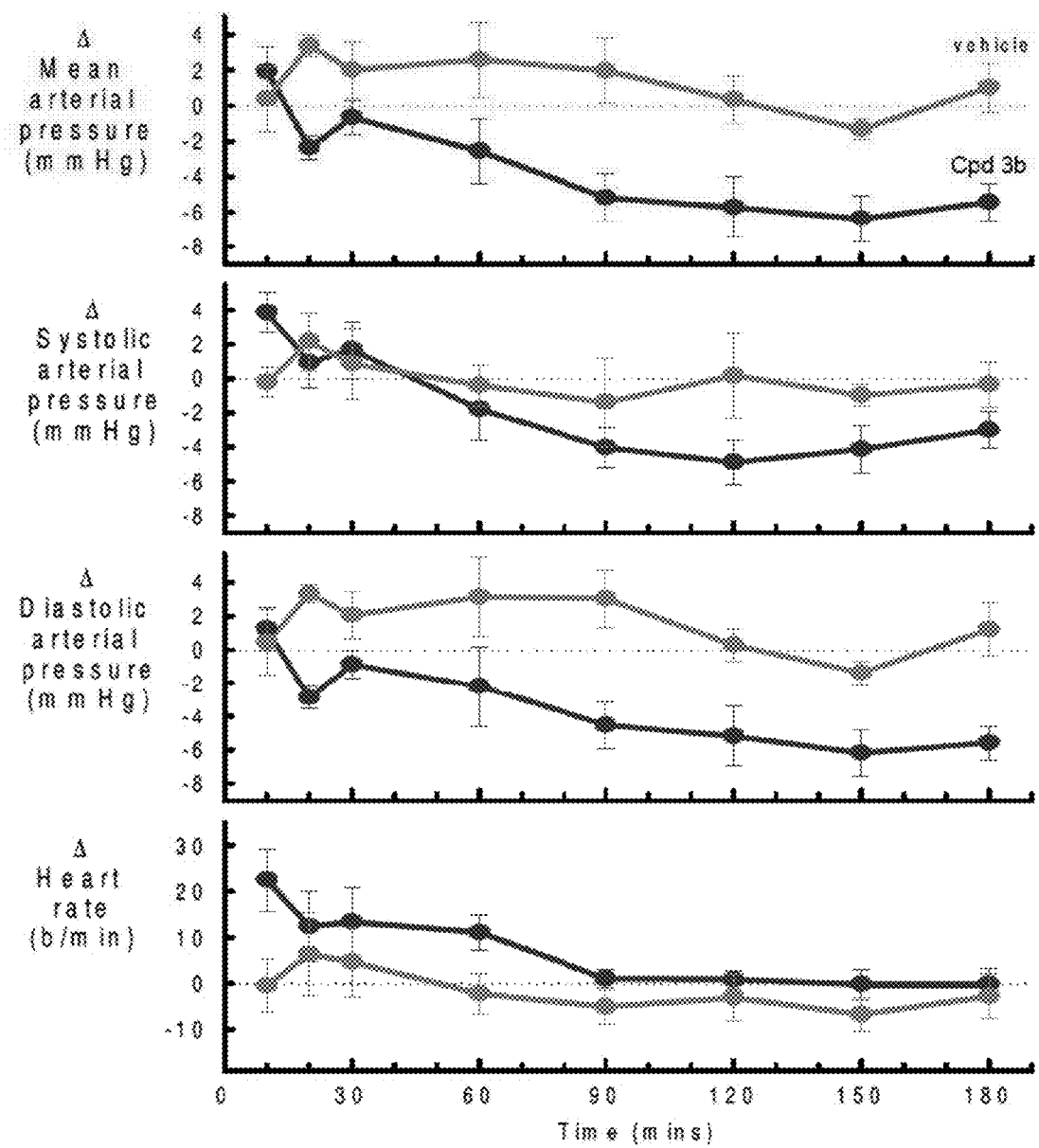
FIG. 27 illustrates the time-course effect of Compound No. 3b at 3 mg/kg and vehicle on mean arterial blood pressure, systolic blood pressure, diastolic blood pressure and heart rate in rabbits.

Results: The mean arterial pressure responses to Compound 3d are dose-dependent in the dose-response study with cumulative doses (FIG. 26, first panel). Compound 3b caused a maximum arterial blood drop of −11.6 mmHg at a dose of 10 mg/kg. This effect is similar to the effect on diastolic blood pressure and greater than on systolic blood pressure (FIG. 26, second and third panels). The dose that produced 80% of the maximum drop in blood pressure is 3 mg/kg. The reduction in blood pressure is associated with tachycardia (FIG. 26, fourth panel). Clonidine produced a maximum drop of arterial blood pressure of −6 mmHg before the blood pressure reversed back (FIG. 26, first panel). In a single bolus dose at 3 mg/kg time-course study, Compound 3b produced relatively −6 mmHg drop in arterial blood pressure and it is stable from 90 to 180 minutes and no indication of reversal of the effect (FIG. 27, first panel). Identical effects were seen with systolic and diastolic blood pressures (FIG. 27, second and third panels). These findings suggest that Compound 3b dose-dependently lowers blood pressure, most prominently mean arterial blood pressure, and these effects are stable for a period for 3 hours when it is administered intravenously.

In addition to studying the effect of Compound 3b on blood pressure and heart rate when the compound is administered intravenously, the blood pressure and heart rate effect of Compound 3b will also be measured following infusion of the compound directly into the brain with the cannula delivering the compound placed directly into the 4th ventrical of the brain. Several doses will be tested for cardiovascular effects following direct brain infusion. Comparison of the blood pressure effects following intravenous and ventricular infusion will determine whether the compound exerts its cardiovascular actions by the brain.

The long duration of blood pressure effect of Compound 3b suggests a reduction in blood volume that might result from diueresis and/or the movement of fluid from the vascular space to the extravascular space. This will be studied further by measuring the effect of Compound 3b as well as other $\alpha_{2B}$ antagonists on hematocrit as agents that reduce blood volume should increase hematocrit. Characterization of the effect of $\alpha_{2B}$ antagonists on renal function will also be studied by measuring urine volume, urine sodium and urine potassium using methods described by Burke et al. (Effects of chronic sympatho-inhibition on renal excretory function in renovascular hypertension Sandra L. Burke, Roger G. Evans and Geoffrey A. Head. Journal of Hypertens 29:945-952 (2011).

Example B8. Human Clinical Studies

The compound is studied in a clinical trial of hypertensive patients who have not reached their blood pressure goals on current therapy. The target patient population are patients with refractory hypertension that have not reached their blood pressure goals despite use of at least 3 different blood pressure agents. The study compares the active compound against a matched placebo compound with the primary objective of comparing mean blood pressure change from baseline to the end of the study between the active compound and placebo.

All references throughout, such as publications, patents, patent applications and published patent applications, are incorporated herein by reference in their entireties.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

What is claimed is:
1. A method of lowering blood pressure in an individual in need thereof comprising administering to the individual an effective amount of a compound of the formula (A-III):

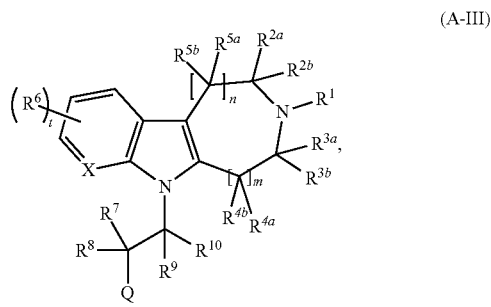

(A-III)

or a salt, solvate or N-oxide thereof, wherein:
$R^1$ is H; $C_1$-$C_5$ alkyl optionally substituted with 1 to 3 substituents independently selected from the group consisting of halo, hydroxyl, carboxyl and perhaloalkyl;

$C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{3a}$ to form a propylene (—$CH_2CH_2CH_2$—) moiety or a butylene (—$CH_2CH_2CH_2CH_2$—) moiety; or is taken together with $R^{4a}$ or $R^{5a}$, where present, to form an ethylene (—$CH_2CH_2$—) moiety or a propylene (—$CH_2CH_2CH_2$—) moiety;

each n and m is 1, or n is 0 and m is 1, or n is 1 and m is 0;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—$CH_2CH_2CH_2$—) moiety or a butylene (—$CH_2CH_2CH_2CH_2$—) moiety; or is taken together with $R^{3a}$ to form an ethylene (—$CH_2CH_2$—) moiety or a propylene (—$CH_2CH_2CH_2$—) moiety; or is taken together with $R^{4a}$, where present, to form a methylene (—$CH_2$—) moiety or an ethylene (—$CH_2CH_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—$CH_2CH_2CH_2$—) moiety or a butylene (—$CH_2CH_2CH_2CH_2$—) moiety; or is taken together with $R^{2a}$ to form an ethylene (—$CH_2CH_2$—) moiety or a propylene (—$CH_2CH_2CH_2$—) moiety; or is taken together with $R^{5a}$, where present, to form a methylene (—$CH_2$—) moiety or an ethylene (—$CH_2CH_2$—) moiety;

$R^{4a}$ is H; optionally substituted $C_1$-$C_5$ alkyl; optionally substituted $C_2$-$C_5$ alkenyl; or optionally substituted aryl; or is taken together with $R^{3a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{2a}$ to form a methylene (—$CH_2$—) moiety or an ethylene (—$CH_2CH_2$—) moiety; or is taken together with $R^{5a}$, where present, to form a methylene (—$CH_2$—) moiety;

$R^{5a}$ is H; optionally substituted $C_1$-$C_5$ alkyl; optionally substituted $C_2$-$C_5$ alkenyl; or optionally substituted aryl; or is taken together with $R^{2a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{3a}$ to form a methylene (—$CH_2$—) moiety or an ethylene (—$CH_2CH_2$—) moiety; or is taken together with $R^{4a}$, where present, to form a methylene (—$CH_2$—) moiety;

each $R^{2b}$, $R^{3b}$, $R^{4b}$ and $R^{5b}$ is independently H, optionally substituted $C_1$-$C_5$ alkyl, optionally substituted $C_2$-$C_5$ alkenyl, or optionally substituted aryl;

X is N or $CR^{6a}$;

t is 1, 2 or 3;

each $R^6$ and $R^{6a}$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; N($R^{11}$)$R^{12}$; $SR^{13}$; S(O)$R^{13}$; $SO_2R^{13}$; —OC(O)N($R^{14}$)$R^{15}$; —OC(O)-aryl; —OC(O)-heteroaryl; or —OC(O)$C_1$-$C_5$ alkyl optionally substituted with amino; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl; or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl; or is taken together with $R^8$ to form a bond;

each $R^{11}$ and $R^{12}$ is independently H or optionally substituted $C_1$-$C_5$ alkyl; or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

2. The method of claim 1, wherein the method reduces systolic blood pressure of the individual.

3. The method of claim 1, wherein the method reduces diastolic blood pressure of the individual.

4. The method of claim 2, wherein the method reduces (i) mean arterial blood pressure, or (ii) pulse pressure, of the individual.

5. The method of any one of claims 2 to 4, wherein the method does not substantially increase heart rate of the individual.

6. The method of claim 1, wherein the individual has one or more risk factors for developing high blood pressure.

7. A method of (i) increasing renal blood flow, and/or (ii) decreasing sodium reabsorption, in an individual in need thereof comprising administering to the individual an effective amount of a compound of the formula (A-III):

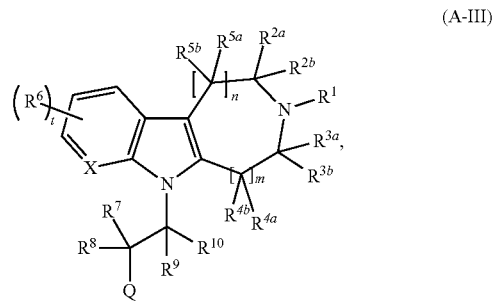

(A-III)

or a salt, solvate or N-oxide thereof, wherein:

$R^1$ is H; $C_1$-$C_5$ alkyl optionally substituted with 1 to 3 substituents independently selected from the group consisting of halo, hydroxyl, carboxyl and perhaloalkyl;

$C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{1a}$ to form a propylene (—$CH_2CH_2CH_2$—) moiety or a butylene (—$CH_2CH_2CH_2CH_2$—) moiety; or is taken together with $R^{4a}$ or $R^{ya}$, where present, to form an ethylene (—$CH_2CH_2$—) moiety or a propylene (—$CH_2CH_2CH_2$—) moiety;

each n and m is 1, or n is 0 and m is 1, or n is 1 and m is 0;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—$CH_2CH_2CH_2$—) moiety or a butylene (—$CH_2CH_2CH_2CH_2$—) moiety; or is taken together with $R^{3a}$ to form an ethylene (—$CH_2CH_2$—) moiety or a propylene (—$CH_2CH_2CH_2$—) moiety; or is taken together with $R^{4a}$, where present, to form a methylene (—$CH_2$—) moiety or an ethylene (—$CH_2CH_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—$CH_2CH_2CH_2$—) moiety or a butylene (—$CH_2CH_2CH_2CH_2$—) moiety; or is taken together with $R^{2a}$ to form an ethylene (—$CH_2CH_2$—) moiety or a propylene (—$CH_2CH_2CH_2$—) moiety; or is taken together with $R^{5a}$, where present, to form a methylene (—$CH_2$—) moiety or an ethylene (—$CH_2CH_2$—) moiety;

$R^{4a}$ is H; optionally substituted $C_1$-$C_5$ alkyl; optionally substituted $C_2$-$C_5$ alkenyl; or optionally substituted aryl; or is taken together with $R^{3a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{2a}$ to form a methylene (—$CH_2$—) moiety or an ethylene (—$CH_2CH_2$—) moiety; or is taken together with $R^{5a}$, where present, to form a methylene (—$CH_2$—) moiety;

$R^{5a}$ is H; optionally substituted $C_1$-$C_5$ alkyl; optionally substituted $C_2$-$C_5$ alkenyl; or optionally substituted aryl; or is taken together with $R^{2a}$ to form a propylene (—$CH_2CH_2CH_2$—) moiety or a butylene (—$CH_2CH_2CH_2CH_2$—) moiety; or is taken together with $R^1$ to form an ethylene (—$CH_2CH_2$—) moiety or a propylene (—$CH_2CH_2CH_2$—) moiety; or is taken together with $R^{3a}$ to form a methylene (—$CH_2$—) moiety or an ethylene (—$CH_2CH_2$—) moiety; or is taken together with $R^{4a}$, where present, to form a methylene (—$CH_2$—) moiety;

each $R^{2b}$, $R^{3b}$, $R^{4b}$ and $R^{5b}$ is independently H, optionally substituted $C_1$-$C_5$ alkyl, optionally substituted $C_2$-$C_5$ alkenyl, or optionally substituted aryl;

X is N or $CR^{6a}$;

t is 1, 2 or 3;

each $R^6$ and $R^{6a}$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; N($R^{11}$)$R^{12}$; S$R^{13}$; S(O)$R^{13}$; $SO_2R^{13}$; —OC(O)N($R^{14}$)$R^{15}$; —OC(O)-aryl; —OC(O)-heteroaryl; or —OC(O)$C_1$-$C_5$ alkyl optionally substituted with amino; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl; or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl; or is taken together with $R^8$ to form a bond;

each $R^{11}$ and $R^{12}$ is independently H or optionally substituted $C_1$-$C_5$ alkyl; or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

8. The method of claim 7, wherein the method results in increase in urine sodium content and/or increase in urine volume.

9. The method of claim 7, wherein the method results in any one or more of: (i) reducing edema, (ii) reducing elevated blood urea nitrogen to creatinine (BUN/Cr) ratio, and (iii) decreasing creatinine levels.

10. The method of claim 1, wherein the individual has or is at risk of developing acute or chronic congestive heart failure, acute decompensated congestive heart failure, acute or chronic renal failure, or acute or chronic renal failure due to renal insufficiency.

11. A method of treating a disease or condition that is responsive to any one or more of: (i) a decrease in blood pressure; (ii) an increase in renal blood flow; and (iii) a decrease of sodium reabsorption, comprising administering to an individual in need thereof an effective amount of a compound of the formula (A-III):

(A-III)

or a salt, solvate or N-oxide thereof, wherein:

$R^1$ is H; $C_1$-$C_5$ alkyl optionally substituted with 1 to 3 substituents independently selected from the group consisting of halo, hydroxyl, carboxyl and perhaloalkyl;

$C_3$-$C_8$ cycloalkyl optionally substituted with 1 to 3 substituents independently selected from the group consisting of halo, hydroxyl, carboxyl and perhaloalkyl; $C_2$-$C_5$ alkenyl optionally substituted with 1 to 3 substituents independently selected from the group consisting of halo, hydroxyl, carboxyl and perhaloalkyl; or —C(O)O—$C_1$-$C_5$ alkyl; or is taken together with $R^{2a}$ or $R^{1a}$ to form a propylene (—CH$_2$CH$_2$CH$_2$—) moiety or a butylene (—CH$_2$CH$_2$CH$_2$CH$_2$—) moiety; or is taken together with $R^{4a}$ or $R^{5a}$, where present, to form an ethylene (—CH$_2$CH$_2$—) moiety or a propylene (—CH$_2$CH$_2$CH$_2$—) moiety;

each n and m is 1, or n is 0 and m is 1, or n is 1 and m is 0;

$R^{2a}$ is H; optionally substituted $C_1$-$C_5$ alkyl; optionally substituted $C_2$-$C_5$ alkenyl; or optionally substituted aryl; or is taken together with $R^1$ or $R^{5a}$, where present, to form a propylene (—CH$_2$CH$_2$CH$_2$—) moiety or a butylene (—CH$_2$CH$_2$CH$_2$CH$_2$—) moiety; or is taken together with $R^{3a}$ to form an ethylene (—CH$_2$CH$_2$—) moiety or a propylene (—CH$_2$CH$_2$CH$_2$—) moiety; or is taken together with $R^{4a}$, where present, to form a methylene (—CH$_2$—) moiety or an ethylene (—CH$_2$CH$_2$—) moiety;

$R^{3a}$ is H; optionally substituted $C_1$-$C_5$ alkyl; optionally substituted $C_2$-$C_5$ alkenyl; or optionally substituted aryl; or is taken together with $R^1$ or $R^{4a}$, where present, to form a propylene (—CH$_2$CH$_2$CH$_2$—) moiety or a butylene (—CH$_2$CH$_2$CH$_2$CH$_2$—) moiety; or is taken together with $R^{2a}$ to form an ethylene (—CH$_2$CH$_2$—) moiety or a propylene (—CH$_2$CH$_2$CH$_2$—) moiety; or is taken together with $R^{5a}$, where present, to form a methylene (—CH$_2$—) moiety or an ethylene (—CH$_2$CH$_2$—) moiety;

$R^{4a}$ is H; optionally substituted $C_1$-$C_5$ alkyl; optionally substituted $C_2$-$C_5$ alkenyl; or optionally substituted aryl; or is taken together with $R^{3a}$ to form a propylene (—CH$_2$CH$_2$CH$_2$—) moiety or a butylene (—CH$_2$CH$_2$CH$_2$CH$_2$—) moiety; or is taken together with $R^1$ to form an ethylene (—CH$_2$CH$_2$—) moiety or a propylene (—CH$_2$CH$_2$CH$_2$—) moiety; or is taken together with $R^{2a}$ to form a methylene (—CH$_2$—) moiety or an ethylene (—CH$_2$CH$_2$—) moiety; or is taken together with $R^{5a}$, where present, to form a methylene (—CH$_2$—) moiety;

$R^{5a}$ is H; optionally substituted $C_1$-$C_5$ alkyl; optionally substituted $C_2$-$C_5$ alkenyl; or optionally substituted aryl; or is taken together with $R^{2a}$ to form a propylene (—CH$_2$CH$_2$CH$_2$—) moiety or a butylene (—CH$_2$CH$_2$CH$_2$CH$_2$—) moiety; or is taken together with $R^1$ to form an ethylene (—CH$_2$CH$_2$—) moiety or a propylene (—CH$_2$CH$_2$CH$_2$—) moiety; or is taken together with $R^{3a}$ to form a methylene (—CH$_2$—) moiety or an ethylene (—CH$_2$CH$_2$—) moiety; or is taken together with $R^{4a}$, where present, to form a methylene (—CH$_2$—) moiety;

each $R^{2b}$, $R^{3b}$, $R^{4b}$ and $R^{5b}$ is independently H, optionally substituted $C_1$-$C_5$ alkyl, optionally substituted $C_2$-$C_5$ alkenyl, or optionally substituted aryl;

X is N or $CR^{6a}$;

t is 1, 2 or 3;

each $R^6$ and $R^{6a}$ is independently H; hydroxyl; halo; $C_1$-$C_5$ alkyl optionally substituted with 1 to 3 substituents independently selected from the group consisting of halo, hydroxyl, carboxyl and perhaloalkyl; $C_2$-$C_5$ alkenyl; optionally substituted $C_1$-$C_5$ alkoxy; or optionally substituted —C(O)$C_1$-$C_5$ alkyl;

$R^7$ is H; halo; optionally substituted $C_1$-$C_5$ alkyl; or optionally substituted aryl; or is taken together with $R^8$ and the carbon atom to which they are attached to form a dioxolane ring or a carbonyl moiety; or is taken together with $R^9$ to form a $C_3$-$C_5$ alkylene when $R^8$ and $R^{10}$ are taken together to form a bond;

$R^8$ is H; halo; hydroxyl; $N(R^{11})R^{12}$; $SR^{13}$, $S(O)R^{13}$; $SO_2R^{13}$; —OC(O)N($R^{14}$)$R^{15}$; —OC(O)-aryl; —OC(O)-heteroaryl; or —OC(O)$C_1$-$C_5$ alkyl optionally substituted with amino; or is taken together with $R^7$ and the carbon atom to which they are attached to form a dioxolane ring or a carbonyl moiety; or is taken together with $R^{10}$ to form a bond;

$R^9$ is H or optionally substituted $C_1$-$C_5$ alkyl; or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl; or is taken together with $R^8$ to form a bond;

each $R^{11}$ and $R^{12}$ is independently H or optionally substituted $C_1$-$C_5$ alkyl; or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl; or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

12. The method of claim 11, wherein the disease or condition is hypertension.

13. The method of claim 12, wherein the disease or condition is treatment-resistant hypertension.

14. The method of claim 11, wherein the disease or condition is hypertensive emergency.

15. The method of claim 11, wherein the disease or condition is a cardiac or renal disease or condition.

16. The method of any one of claims 1, 7 and 11, wherein X is $CR^{6a}$, wherein $R^{6a}$ is H, halo or $C_1$-$C_5$ alkyl; and each $R^6$ is independently H, halo or $C_1$-$C_5$ alkyl.

17. The method of any one of claims 1, 7 and 11, wherein X is N.

18. The method of any one of claims 1, 7 and 11, wherein $R^1$ is H or $C_1$-$C_5$ alkyl.

19. The method of any one of claims 1, 7 and 11, wherein $R^7$ is H or $C_1$-$C_5$ alkyl, and $R^8$ is H, hydroxyl, $N(R^{11})R^{12}$ or —OC(O)$C_1$-$C_5$ alkyl.

20. The method of any one of claims 1, 7 and 11, wherein $R^7$ is H or $C_1$-$C_5$ alkyl, and $R^8$ is H or hydroxyl.

21. The method of any one of claims 1, 7 and 11, wherein $R^7$ is H or $C_1$-$C_5$ alkyl, and $R^8$ is hydroxyl.

22. The method of any one of claims 1, 7 and 11, wherein $R^7$ is H, $R^8$ is hydroxyl, n is zero and m is 1.

23. The method of any one of claims 1, 7 and 11, wherein $R^7$ is methyl, $R^8$ is hydroxyl, n is zero and m is 1.

24. The method of any one of claims 1, 7 and 11, wherein Q is:
unsubstituted pyridyl;
unsubstituted pyrimidyl;

unsubstituted pyrazinyl;
unsubstituted phenyl;
unsubstituted imidazolyl;
unsubstituted triazolyl;
pyridyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl;
pyrimidyl substituted with 1 to 3 sub stituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl;
pyrazinyl substituted with 1 to 3 sub stituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl;
phenyl substituted with 1 to 3 sub stituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl;
imidazolyl substituted with 1 to 3 sub stituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl; or
triazolyl substituted with 1 to 3 substituents independently selected form the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl.

25. The method of any one of claims 1, 7 and 11, wherein:
X is CR$^{6a}$, wherein R$^{6a}$ is H, halo or $C_1$-$C_5$ alkyl;
each R$^6$ is independently H, halo or $C_1$-$C_5$ alkyl;
R$^7$ is H or $C_1$-$C_5$ alkyl;
R$^8$ is H, hydroxyl, N(R$^{11}$)R$^{12}$ or —OC(O)$C_1$-$C_5$ alkyl;
each R$^9$ and R$^{10}$ is hydrogen; and
Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl.

26. The method of claim 25, wherein n is 0 and m is 1; R$^7$ is H or CH$_3$; and R$^8$ is H or hydroxyl.

27. The method of any one of claims 1, 7 and 11, wherein:
X is N;
R$^7$ is H or $C_1$-$C_5$ alkyl;
R$^8$ is H, hydroxyl, N(R$^{11}$)R$^{12}$ or —OC(O)$C_1$-$C_5$ alkyl;
each R$^9$ and R$^{10}$ is hydrogen; and
Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl.

28. The method of claim 27, wherein n is 0 and m is 1; R$^7$ is H or CH$_3$; and R$^8$ is H or hydroxyl.

29. The method of any one of claims 1, 7 and 11, wherein:
n is 0 and m is 1;
R$^1$ is taken together with R$^{2a}$ to form a propylene (—CH$_2$CH$_2$CH$_2$—) moiety;
X is CR$^{6a}$, wherein R$^{6a}$ is H, halo or $C_1$-$C_5$ alkyl;
each R$^6$ is independently H, halo or $C_1$-$C_5$ alkyl;
R$^7$ is H or $C_1$-$C_5$ alkyl;
R$^8$ is H, hydroxyl, N(R$^{11}$)R$^{12}$ or —OC(O)$C_1$-$C_5$ alkyl;
each R$^9$ and R$^{10}$ is hydrogen; and
Q is unsubstituted pyridyl; or pyridyl substituted with 1 to 3 substituents independently selected from the group consisting of halo, $C_1$-$C_5$ alkyl, halo-substituted $C_1$-$C_5$ alkyl, carboxyl and —C(O)NR$^{16}$R$^{17}$, wherein each R$^{16}$ and R$^{17}$ is independently H or optionally substituted $C_1$-$C_5$ alkyl.

30. The method of claim 29, wherein R$^7$ is H or CH$_3$; and R$^8$ is H or hydroxyl.

31. The method of any one of claims 1, 7 and 11, wherein the compound is Compound No. 3a, 3b, 39a, 4a, 5b, 13b, 14a, 41a, 74a, 26a, 26b, 27a, 29b, 31a, 127a, 129d, 134b, 144b, 148, 173a, 174a, 150a, 176a, IV-210a, 151a, II-4b, II-132b, 148b, 141b, 154b, II-135b, II-138, II-139, 11-140, II-244a, II-7, II-146a, II-152a, II-227c, II-220, II-148a, II-13a, II-212a, II-260a or II-260b, or a salt, solvate or N-oxide thereof.

32. The method any one of claims 1, 7 and 11, wherein the compound is an adrenergic receptor α$_{2B}$ antagonist.

33. The method of claim 32, wherein the compound is also an adrenergic receptor α$_{1B}$ antagonist.

34. The method of claim 33, wherein the compound is also an adrenergic receptor α$_{1D}$ antagonist.

35. A method of lowering blood pressure in an individual in need thereof comprising administering to the individual an effective amount of a compound of the formula (A-IIIA):

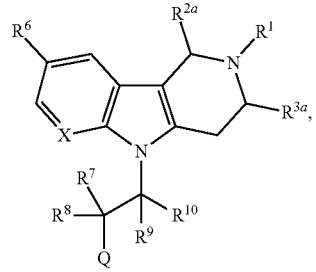

(A-IIIA)

or a salt, solvate or N-oxide thereof, wherein:
R$^1$ is H; $C_1$-$C_5$ alkyl optionally substituted with 1 to 3 substituents independently selected from halo, hydroxyl, carboxyl and perhaloalkyl; $C_3$-$C_8$ cycloalkyl optionally substituted with 1 to 3 substituents independently selected from halo, hydroxyl, carboxyl and perhaloalkyl; $C_2$-$C_5$ alkenyl optionally substituted with 1 to 3 substituents independently selected from halo, hydroxyl, carboxyl and perhaloalkyl; or —C(O)O—$C_1$-$C_5$ alkyl, or is taken together with R$^{2a}$ or R$^{1a}$ to form a propylene (—CH$_2$CH$_2$CH$_2$—) moiety or a butylene (—CH$_2$CH$_2$CH$_2$CH$_2$—) moiety;
R$^{2a}$ is H, optionally substituted $C_1$-$C_5$ alkyl, optionally substituted alkenyl or optionally substituted aryl, or is taken together with R$^1$ to form a propylene (—CH$_2$CH$_2$CH$_2$—) moiety or a butylene (—CH$_2$CH$_2$CH$_2$CH$_2$—) moiety;
R$^{3a}$ is H, optionally substituted $C_1$-$C_5$ alkyl, optionally substituted alkenyl or optionally substituted aryl, or is taken together with R$^1$ to form a propylene (—CH$_2$CH$_2$CH$_2$—) moiety or a butylene (—CH$_2$CH$_2$CH$_2$CH$_2$—) moiety;
X is N or CR$^{6a}$;
each R$^6$ and R$^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, —$OC(O)N(R^{14})R^{15}$, —$OC(O)$-aryl, —$OC(O)$-heteroaryl, or —$OC(O)C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

36. The method of claim 35, wherein the method reduces systolic blood pressure of the individual.

37. The method of claim 35, wherein the method reduces diastolic blood pressure of the individual.

38. The method of claim 36, wherein the method reduces (i) mean arterial blood pressure, or (ii) pulse pressure, of the individual.

39. The method of any one of claims 36 to 38, wherein the method does not substantially increase heart rate of the individual.

40. The method of claim 35, wherein the individual has one or more risk factors for developing high blood pressure.

41. A method of (i) increasing renal blood flow, and/or (ii) decreasing sodium reabsorption, in an individual in need thereof comprising administering to the individual an effective amount of a compound of the formula (A-IIIA):

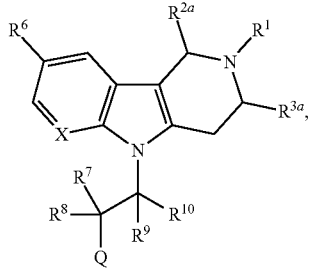

(A-IIIA)

or a salt, solvate or N-oxide thereof, wherein:

$R^1$ is H; $C_1$-$C_5$ alkyl optionally substituted with 1 to 3 substituents independently selected from halo, hydroxyl, carboxyl and perhaloalkyl; $C_3$-$C_8$ cycloalkyl optionally substituted with 1 to 3 substituents independently selected from halo, hydroxyl, carboxyl and perhaloalkyl; $C_2$-$C_5$ alkenyl optionally substituted with 1 to 3 substituents independently selected from halo, hydroxyl, carboxyl and perhaloalkyl; or —$C(O)O$—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —$C(O)C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, $N(R^{11})R^{12}$, $SR^{13}$, $S(O)R^{13}$, $SO_2R^{13}$, —$OC(O)N(R^{14})R^{15}$, —$OC(O)$-aryl, —$OC(O)$-heteroaryl, or —$OC(O)C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

42. The method of claim 41, wherein the method results in increase in urine sodium content and/or increase in urine volume.

43. The method of claim 41, wherein the method results in any one or more of: (i) reducing edema, (ii) reducing elevated blood urea nitrogen to creatinine (BUN/Cr) ratio, and (iii) decreasing creatinine levels.

44. The method of claim 35, wherein the individual has or is at risk of developing acute or chronic congestive heart failure, acute decompensated congestive heart failure, acute or chonic renal failure, or acute or chronic renal failure due to renal insufficiency.

45. A method of treating a disease or condition that is responsive to any one or more of: (i) a decrease in blood pressure; (ii) an increase in renal blood flow; and (iii) a decrease of sodium reabsorption, comprising administering to an individual in need thereof an effective amount of a compound of the formula (A-IIIA):

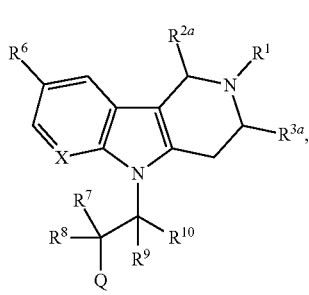

(A-IIIA)

or a salt, solvate or N-oxide thereof, wherein:

$R^1$ is H; $C_1$-$C_5$ alkyl optionally substituted with 1 to 3 substituents independently selected from halo, hydroxyl, carboxyl and perhaloalkyl; $C_3$-$C_8$ cycloalkyl optionally substituted with 1 to 3 substituents independently selected from halo, hydroxyl, carboxyl and perhaloalkyl; $C_2$-$C_5$ alkenyl optionally substituted with 1 to 3 substituents independently selected from halo, hydroxyl, carboxyl and perhaloalkyl; or —C(O)O—$C_1$-$C_5$ alkyl, or is taken together with $R^{2a}$ or $R^{3a}$ to form a propylene (—$CH_2CH_2CH_2$—) moiety or a butylene (—$CH_2CH_2CH_2CH_2$—) moiety;

$R^{2a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

$R^{3a}$ is H, optionally substituted $C_1$-$C_5$ alkyl, optionally substituted alkenyl or optionally substituted aryl, or is taken together with $R^1$ to form a propylene (—$CH_2CH_2CH_2$—) moiety or a butylene (—$CH_2CH_2CH_2CH_2$—) moiety;

X is N or $CR^{6a}$;

each $R^6$ and $R^{6a}$ is independently H, hydroxyl, halo, $C_1$-$C_5$ alkyl optionally substituted with 1 to 3 substituents independently selected from halo, hydroxyl, carboxyl and perhaloalkyl, optionally substituted $C_1$-$C_5$ alkoxy or optionally substituted —C(O)$C_1$-$C_5$ alkyl;

$R^7$ is H, halo, optionally substituted $C_1$-$C_5$ alkyl, or optionally substituted aryl, or is taken together with $R^8$ and the carbon atom to which they are attached to form a dioxolane ring or a carbonyl moiety, or is taken together with $R^9$ to form a $C_3$-$C_5$ alkylene when $R^8$ and $R^{10}$ are taken together to form a bond;

$R^8$ is H, halo, hydroxyl, N($R^{11}$)$R^{12}$, $SR^{13}$, S(O)$R^{13}$, $SO_2R^{13}$, —OC(O)N($R^{14}$)$R^{15}$, —OC(O)-aryl, —OC(O)-heteroaryl, or —OC(O)$C_1$-$C_5$ alkyl optionally substituted with amino, or is taken together with $R^7$ and the carbon atom to which they are attached to form a dioxolane ring or a carbonyl moiety, or is taken together with $R^{10}$ to form a bond;

$R^9$ is H or optionally substituted $C_1$-$C_5$ alkyl, or is taken together with $R^7$ to form a $C_3$-$C_5$ alkylene when $R^8$ and $R^{10}$ are taken together to form a bond;

$R^{10}$ is H or optionally substituted $C_1$-$C_5$ alkyl, or is taken together with $R^8$ to form a bond;

each $R^{11}$ and $R^{12}$ is independently H or optionally substituted $C_1$-$C_5$ alkyl, or $R^{11}$ and $R^{12}$ are taken together to form $C_3$-$C_5$ alkylene;

$R^{13}$ is H or optionally substituted $C_1$-$C_5$ alkyl;

each $R^{14}$ and $R^{15}$ is independently H or optionally substituted $C_1$-$C_5$ alkyl, or $R^{14}$ and $R^{15}$ are taken together to form a $C_3$-$C_5$ alkylene; and Q is unsubstituted aryl; unsubstituted heteroaryl; aryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino; or heteroaryl substituted with 1 to 3 substituents independently selected from the group consisting of halo, $C_1$-$C_5$ alkyl, $C_3$-$C_8$ cycloalkyl, halo-substituted $C_1$-$C_5$ alkyl, halo-substituted $C_3$-$C_8$ cycloalkyl, $C_1$-$C_5$ alkoxy, $C_3$-$C_8$ cycloalkoxy, cyano, carboxyl, aminoacyl and acylamino.

46. The method of claim 45, wherein the disease or condition is hypertension.

47. The method of claim 46, wherein the disease or condition is treatment-resistant hypertension.

48. The method of claim 45, wherein the disease or condition is hypertensive emergency.

49. The method of claim 45, wherein the disease or condition is a cardiac or renal disease or condition.

50. The method of any one of claims 35, 41 and 45, wherein X is CH.

51. The method of any one of claims 35, 41 and 45, wherein X is N.

52. The method of any one of claims 35, 41 and 45, wherein $R^1$ is H or $CH_3$.

53. The method of any one of claims 35, 41 and 45, wherein $R^{2a}$ is H or is taken together with $R^1$ to form a propylene (—$CH_2CH_2CH_2$—) moiety.

54. The method of any one of claims 35, 41 and 45, wherein each $R^6$ and $R^{6a}$ is independently H, halo or $C_1$-$C_5$ alkyl.

55. The method of any one of claims 35, 41 and 45, wherein $R^7$ is H or $CH_3$.

56. The method of any one of claims 35, 41 and 45, wherein $R^8$ is hydroxyl.

57. The method of any one of claims 35, 41 and 45, wherein Q is:

unsubstituted pyridyl;
unsubstituted pyrimidyl;
unsubstituted pyrazinyl;
unsubstituted phenyl;
unsubstituted imidazolyl;
unsubstituted triazolyl;
pyridyl substituted with halo, $CH_3$, $CF_3$, $CONH_2$, OH, or $OCH_3$;
pyrimidyl substituted with halo, $CH_3$, $CF_3$, $CONH_2$, OH, or $OCH_3$;
pyrazinyl substituted with halo, $CH_3$, $CF_3$, $CONH_2$, OH, or $OCH_3$; or
phenyl substituted with halo, $CH_3$, $CF_3$, $CONH_2$, OH, or $OCH_3$.

58. The method of any one of claims 35, 41 and 45, wherein:

X is CH;
each $R^6$ is independently H, halo or $C_1$-$C_5$ alkyl;

$R^7$ is H or $CH_3$;

$R^8$ is hydroxyl; and

Q is unsubstituted pyridyl, or pyridyl substituted with halo, $CH_3$, $CF_3$, $CONH_2$, OH, or $OCH_3$.

59. The method of any one of claims 35, 41 and 45, wherein the compound is Compound No. 3a, 3b, 39a, 4a, 5b, 74a, 26a, 26b, 27a, 29b, 31a, 127a, 129d, 134b, 144b, 148, 173a, 174a, 150a, 176a, IV-210a, 151a, II-4b, II-132b, 148b, 141b, II-135b, II-138, II-139, II-140, II-244a, II-7, II-146a, II-151b, II-152a, II-227c, II-220, II-148a, II-13a, II-212a, II-260a and II-260b, or a salt, solvate or N-oxide thereof.

60. The method any one of claims 35, 41 and 45, wherein the compound is an adrenergic receptor $\alpha_{2B}$ antagonist.

61. The method of claim 60, wherein the compound is also an adrenergic receptor $\alpha_{1B}$ antagonist.

62. The method of claim 61, wherein the compound is also an adrenergic receptor $\alpha_{1D}$ antagonist.

* * * * *